(12) United States Patent
Burnett et al.

(10) Patent No.: US 9,771,378 B2
(45) Date of Patent: Sep. 26, 2017

(54) FUSED MORPHOLINOPYRIMIDINES AND METHODS OF USE THEREOF

(71) Applicant: Denali Therapeutics, Inc., South San Francisco, CA (US)

(72) Inventors: Duane A. Burnett, Wayland, MA (US); Matthew Gregory Bursavich, Needham, MA (US); Andrew J. McRiner, Winchester, MA (US)

(73) Assignee: DENALI THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 15/210,927

(22) Filed: Jul. 15, 2016

(65) Prior Publication Data

US 2017/0044182 A1 Feb. 16, 2017

Related U.S. Application Data

(63) Continuation of application No. PCT/US2015/011631, filed on Jan. 15, 2015.

(60) Provisional application No. 62/022,328, filed on Jul. 9, 2014, provisional application No. 61/927,909, filed on Jan. 15, 2014.

(51) Int. Cl.

| C07D 498/10 | (2006.01) |
|---|---|
| C07D 498/04 | (2006.01) |
| C07D 498/20 | (2006.01) |
| A61K 31/5383 | (2006.01) |
| C07D 498/14 | (2006.01) |

(52) U.S. Cl.
CPC ......... *C07D 498/04* (2013.01); *C07D 498/10* (2013.01); *C07D 498/14* (2013.01); *C07D 498/20* (2013.01)

(58) Field of Classification Search
None
See application file for complete search history.

(56) References Cited

U.S. PATENT DOCUMENTS

| 2008/0176881 A1 | 7/2008 | Michellys et al. |
| 2009/0325992 A1 | 12/2009 | Hanada et al. |

FOREIGN PATENT DOCUMENTS

| EP | 0184752 A2 | 6/1986 | |
|---|---|---|---|
| EP | 1847524 A1 | 10/2007 | |
| EP | 1849762 A1 | 10/2007 | |
| WO | 2004074232 | 9/2004 | |
| WO | 2004110350 | 12/2004 | |
| WO | 2005054193 | 6/2005 | |
| WO | 2005108362 | 11/2005 | |
| WO | 2005115990 | 12/2005 | |
| WO | 2007110667 | 10/2007 | |
| WO | 2007116228 | 10/2007 | |
| WO | 2007124394 | 11/2007 | |
| WO | 2007125364 | 11/2007 | |
| WO | 2009086277 | 7/2009 | |
| WO | 2010056758 | 5/2010 | |
| WO | 2010117425 | 10/2010 | |
| WO | WO 2010117425 A1 * | 10/2010 | ........... C07D 487/02 |

OTHER PUBLICATIONS

Asberom, et al., "Discovery of γ-secretese inhibitors efficacious in a transgenic animal model of Alzheimer's disease", Bioorganic & Medicinal Chemistry Letters 17, 511-516 (2007).
De Strooper, "Aph-1, Pen-2, and Nicastrin with Presenilin generate an active garnma-Secretase complex", Neuron (1), 9-12 (2003).
Patent Cooperation Treaty, International Searching Authority, Search Report and Written Opinion for PCT/US2015/11631, 9 pages, dated Apr. 10, 2015.
Peretto, et al., "Synthesis and Biological Activity of Flurbiprofen Analogues as Selective Inhibitors of β-Amyloid1-42 Secretion", J Med Chem 48 (18), 5705-5720 (2005).
Stock, et al., "The geminal dimethyl analogue of Flurbiprofen as a novel Abeta42 inhibitor and potential Alzheimer's disease modifying agent", Bioorg Med Chem Lett 16 (8), 2219-2223 (2006).
Thompson, et al., "Synthesis and evaluation of succinoyl-caprolactam gamma-secretase inhibtors", Bioorg Med Chem Lett 16, 2357-2363 (2006).

* cited by examiner

*Primary Examiner* — Michael Barker
(74) *Attorney, Agent, or Firm* — Viksins Harris Padys Malen LLP

(57) ABSTRACT

The present disclosure relates to Fused Morpholinopyrimidines, pharmaceutical compositions comprising an effective amount of a Fused Morpholinopyrimidine and methods for using a Fused Morpholinopyrimidine in the treatment of a neurodegenerative disease, comprising administering to a subject in need thereof an effective amount of a Fused Morpholinopyrimidine.

20 Claims, No Drawings

FUSED MORPHOLINOPYRIMIDINES AND METHODS OF USE THEREOF

1. RELATED APPLICATIONS

This application is a continuation of International Application No. PCT/US2015/011631, filed Jan. 15, 2015, which claims priority under 35 U.S.C. §119(e) to U.S. Provisional Application Ser. No. 62/022,328, filed Jul. 9, 2014 and to U.S. Provisional Application Ser. No. 61/927,909, filed Jan. 15, 2014, the entire disclosures of which are incorporated by reference herein in their entirety.

2. FIELD

This disclosure relates generally to fused morpholinopyrimidine compounds. More specifically, the disclosure relates to the use of the fused morpholinopyrimidine compounds for the treatment of neurological disease.

3. BACKGROUND

Alzheimer's disease (AD) is the most prevalent form of dementia. It is a neurodegenerative disease that is associated (though not exclusively) with aging. The disease is clinically characterized by a progressive loss of memory, cognition, reasoning and judgment that leads to an extreme mental deterioration and ultimately death. The disease is pathologically characterized by the deposition of extracellular plaques and the presence of neurofibrillary tangles. The plaques are considered to play an important role in the pathogenesis of the disease. They mainly consist of fibrillar aggregates of β-amyloid peptide (Aβ), which are products of the amyloid precursor protein (APP). APP is initially processed by β-secretase forming a secreted peptide and a membrane bound C99 fragment. The C99 fragment is subsequently processed by the proteolytic activity of γ-secretase. Multiple sites of proteolysis on the C99 fragment lead to the production of a range of smaller peptides (Aβ37-42 amino acids). N-terminal truncations can also be found e.g., Aβ (4-42). For convenience, notations Aβ40 and Aβ42, as used herein, include these N-terminal truncated peptides. Upon secretion, the Aβ peptides initially form soluble aggregates which ultimately lead to the formation of insoluble deposits and plaques. Aβ42 is believed to be the most neurotoxic; the shorter peptides have less propensity to aggregate and form plaques. AP plaques in the brain are also associated with cerebral amyloid angiopathy, hereditary cerebral hemorrhage with amyloidosis, multi infarct dementia, dementia pugilistisca and Down's Syndrome.

γ-secretase is an association of four proteins: Aph1, nicastrin, presenilin and Pen-2 (review De Strooper, *Neuron* 38:9-12 (2003)). Subjects carrying particular mutations in one of these components, presenilin, show increased Aβ42/Aβ40 ratio. These mutations are correlated with early onset familial AD Inhibition of γ-secretase resulting in the lowering of Aβ42 has been investigated by the pharmaceutical community, and numerous inhibitors have been found. See, e.g., Thompson et al. (*Bioorg. Med. Chem. Lett.* 2006, 16, 2357-63), Shaw et al. (*Bioorg. Med. Chem. Lett.* 2006, 17, 511-16) and Asberom et al. (*Bioorg. Med. Chem. Lett.* 2007, 15, 2219-2223) Inhibition of γ-secretase, though, is not without side-effects, some of which are due to the γ-secretase complex processing substrates other than C99, e.g., Notch. A more desirable approach is to modulate the proteolytic activity of the γ-secretase complex in a manner that lowers Aβ42 in favor of shorter peptides without significantly affecting the activity of γ-secretase on substrates such as Notch.

Compounds that have shown modulation of γ-secretase include certain non-steroidal, anti-inflammatory drugs (NSAIDs), for example Flurbiprofen, (Stock et al., *Bioorg. Med. Chem. Lett.* 2006, 16, 2219-2223). Other publications that disclose agents said to reduce Aβ42 through the modulation of γ-secretase include: WO 2004/074232, WO 2005/054193, Perreto et al., *Journal of Medicinal Chemistry* 2005, 48:5705-20, WO 2005/108362, WO 2006/008558, WO 2006/021441, WO 2006/041874, WO 2006/045554, WO 2004/110350, WO 2006/043964, WO 2005/115990, EP 1847524, WO 2007/116228, WO 2007/110667, WO 2007/124394, EP 184752, EP 1849762, WO 2007/125364, WO 2009/086277.

4. SUMMARY

It is understood that any of the embodiments described below can be combined in any desired way, and that any embodiment or combination of embodiments can be applied to each of the aspects described below, unless the context indicates otherwise.

A compound of Formula (I), Formula (II) or a pharmaceutically acceptable salt thereof (also referred to herein as a "Fused Morpholinopyrimidine") is useful for treating, preventing or ameliorating symptoms of a neurodegenerative disease.

In one aspect, the invention provides a compound of Formula (I)

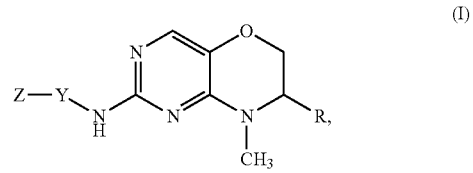

(I)

or a pharmaceutically acceptable salt thereof, wherein:
R is phenyl, —$C_1$-$C_4$ alkylene-phenyl, oxetanyl, —$C_1$-$C_6$ alkyl, —$C_3$-$C_8$ monocyclic cycloalkyl, —$C_1$-$C_4$ alkylene-$C_3$-$C_8$ monocyclic cycloalkyl, 3- to 7-membered monocyclic heterocycle, —$C_1$-$C_4$ alkylene 3- to 7-membered monocyclic heterocycle, each of which is unsubstituted or substituted with one or more substituents independently selected from the group consisting of -halo, —CN, —$NH_2$, —OH, oxo, —$C_1$-$C_4$ alkyl, halo-substituted $C_1$-$C_4$ alkyl, amino-substituted $C_1$-$C_4$ alkyl, —NH—$C_1$-$C_4$ alkyl, —NHC(O)—$C_1$-$C_4$ alkyl, —C(O)NH—$C_1$-$C_4$ alkyl, —C(O)N($C_1$-$C_4$ alkyl)$_2$, hydroxy-substituted $C_1$-$C_4$ alkyl, —S(O)$_2$—$C_1$-$C_4$ alkyl, —S(O)$_2$-halo-substituted $C_1$-$C_4$ alkyl, —S(O)$_2$—NH—$C_1$-$C_4$ alkyl, —S(O)$_2$—N($C_1$-$C_4$ alkyl)$_2$, —NH—S(O)$_2$—$C_1$-$C_4$ alkyl, —N($C_1$-$C_4$ alkyl)-S(O)$_2$—$C_1$-$C_4$ alkyl, —$C_1$-$C_4$ alkoxy, halo-substituted $C_1$-$C_4$ alkoxy, 3- to 7-membered monocyclic heterocycle, —$C_3$-$C_8$ monocyclic cycloalkyl, —C(O)$NH_2$ and -phenoxy, provided that phenyl is not substituted with one or more oxo; Y is phenyl or pyridinyl which is unsubstituted or substituted with one or more substituents independently selected from the group consisting of -halo, —$C_1$-$C_4$ alkoxy, halo-substituted $C_1$-$C_4$ alkoxy, —$C_1$-$C_4$ alkyl, halo-substituted $C_1$-$C_4$ alkyl, amino-substituted $C_1$-$C_4$ alkoxy, —CN, ($C_1$-$C_4$ alkyl)$_2$ N—$C_1$-$C_4$ alkoxy, —NH—$C_1$-$C_4$ alkyl, —OH and —$NH_2$; and Z is —CN or nitrogen-containing 3- to 7-membered monocyclic heterocycle which is unsubstituted or substituted with one or more substituents independently selected from the group consisting of -halo, —CN, —NH$_2$, —OH, —C$_1$-C$_4$ alkyl, halo-substituted C$_1$-C$_4$ alkyl, —C$_1$-C$_4$ alkoxy, —OCF$_3$ and 3- to 7-membered monocyclic heterocycle.

In some embodiments, R is phenyl, —C$_1$-C$_4$ alkylene-phenyl, oxetanyl, —C$_1$-C$_6$ alkyl, —C$_3$-C$_8$ monocyclic cycloalkyl, 3- to 7-membered monocyclic heterocycle, —C$_1$-C$_4$ alkylene 3- to 7-membered monocyclic heterocycle or —C$_1$-C$_4$ alkylene-C$_3$-C$_8$ monocyclic cycloalkyl, each of which is unsubstituted or substituted with one or more substituents independently selected from the group consisting of -halo, —CN, —NH$_2$, —OH, —C$_1$-C$_4$ alkyl, halo-substituted C$_1$-C$_4$ alkyl, amino-substituted C$_1$-C$_4$ alkyl, —NH—C$_1$-C$_4$ alkyl, —NHC(O)—C$_1$-C$_4$ alkyl, —C(O)NH—C$_1$-C$_4$ alkyl, —C(O)N(C$_1$-C$_4$ alkyl)$_2$, hydroxy-substituted C$_1$-C$_4$ alkyl, —S(O)$_2$—C$_1$-C$_4$ alkyl, —S(O)$_2$-halo-substituted C$_1$-C$_4$ alkyl, —S(O)$_2$—NH—C$_1$-C$_4$ alkyl, —S(O)$_2$—N(C$_1$-C$_4$ alkyl)$_2$, —NH—S(O)$_2$—C$_1$-C$_4$ alkyl, —N(C$_1$-C$_4$ alkyl)-S(O)$_2$—C$_1$-C$_4$ alkyl, —C$_1$-C$_4$ alkoxy, halo-substituted C$_1$-C$_4$ alkoxy, 3- to 7-membered monocyclic heterocycle, —C$_3$-C$_8$ monocyclic cycloalkyl, —C(O)NH$_2$; Y is phenyl which is unsubstituted or substituted with one or more substituents independently selected from the group consisting of -halo, —C$_1$-C$_4$ alkoxy, halo-substituted C$_1$-C$_4$ alkoxy, —C$_1$-C$_4$ alkyl, halo-substituted C$_1$-C$_4$ alkyl, amino-substituted C$_1$-C$_4$ alkoxy, —CN, (C$_1$-C$_4$ alkyl)$_2$N—C$_1$-C$_4$ alkoxy, —NH—C$_1$-C$_4$ alkyl, —OH and —NH$_2$; and Z is pyridinyl or imidazolyl, each of which is unsubstituted or substituted with one or more substituents independently selected from the group consisting of -halo, —NH$_2$, —OH, —C$_1$-C$_4$ alkyl, halo-substituted C$_1$-C$_4$ alkyl, —C$_1$-C$_4$ alkoxy, —OCF$_3$ and 3- to 7-membered monocyclic heterocycle.

In some embodiments, R is phenyl, —C$_1$-C$_4$ alkylene-phenyl, oxetanyl, —C$_1$-C$_6$ alkyl, —C$_3$-C$_8$ monocyclic cycloalkyl, nitrogen containing 3- to 7-membered monocyclic heterocycle, —C$_1$-C$_4$ alkylene nitrogen-containing 3- to 7-membered monocyclic heterocycle or —C$_1$-C$_4$ alkylene-C$_3$-C$_8$ monocyclic cycloalkyl, each of which is unsubstituted or substituted with one or more substituents independently selected from the group consisting of -halo, —CN, —NH$_2$, —OH, —C$_1$-C$_4$ alkyl, halo-substituted C$_1$-C$_4$ alkyl, amino-substituted C$_1$-C$_4$ alkyl, —NH—C$_1$-C$_4$ alkyl, —NHC(O)—C$_1$-C$_4$ alkyl, —C(O)NH—C$_1$-C$_4$ alkyl, —C(O)N(C$_1$-C$_4$ alkyl)$_2$, hydroxy-substituted C$_1$-C$_4$ alkyl, —S(O)$_2$—C$_1$-C$_4$ alkyl, —S(O)$_2$-halo-substituted C$_1$-C$_4$ alkyl, —S(O)$_2$—NH—C$_1$-C$_4$ alkyl, —S(O)$_2$—N(C$_1$-C$_4$ alkyl)$_2$, —NH—S(O)$_2$—C$_1$-C$_4$ alkyl, —N(C$_1$-C$_4$ alkyl)-S(O)$_2$—C$_1$-C$_4$ alkyl, —C$_1$-C$_4$ alkoxy, halo-substituted C$_1$-C$_4$ alkoxy, 3- to 7-membered monocyclic heterocycle, —C$_3$-C$_8$ monocyclic cycloalkyl, —C(O)NH$_2$.

In some embodiments, R is phenyl, tetrahydropyranyl, —C$_1$-C$_4$ alkyl, —C$_1$-C$_4$ alkylene-phenyl or oxetanyl, each of which is unsubstituted or substituted with one or more substituents independently selected from the group consisting of halo, —C$_1$-C$_4$ alkyl, halo-substituted C$_1$-C$_4$ alkyl, —C$_1$-C$_4$ alkoxy and halo-substituted C$_1$-C$_4$ alkoxy.

In some embodiments, Y is phenyl which is unsubstituted or substituted with one or more substituents independently selected from the group consisting of halo and —C$_1$-C$_4$ alkoxy.

In some embodiments, Z is pyridinyl or imidazolyl, each of which is unsubstituted or substituted with one or more —C$_1$-C$_4$ alkyl or halo.

In some embodiments, R is phenyl, tetrahydropyranyl, —C$_1$-C$_4$ alkyl, —C$_1$-C$_4$ alkylene-phenyl, each of which is unsubstituted or substituted with one or more substituents independently selected from the group consisting of halo, —C$_1$-C$_4$ alkyl, halo-substituted C$_1$-C$_4$ alkyl and halo-substituted C$_1$-C$_4$ alkoxy; Y is phenyl which is unsubstituted or substituted with one or more substituents independently selected from the group consisting of halo and —C$_1$-C$_4$ alkoxy; and Z is pyridinyl or imidazolyl, each of which is substituted with one —C$_1$-C$_4$ alkyl or halo.

In some embodiments, R is phenyl which is unsubstituted or substituted with one or more substituents independently selected from the group consisting of halo and —C$_1$-C$_4$ alkyl; Y is phenyl substituted with one or more substituents independently selected from the group consisting of halo and —C$_1$-C$_4$ alkoxy; and Z is imidazolyl substituted with methyl or halo.

In some embodiments, R is phenyl which is unsubstituted or substituted with one or more substituents independently selected from the group consisting of halo and —C$_1$-C$_4$ alkyl; Y is phenyl substituted with one or more substituents independently selected from the group consisting of halo and —C$_1$-C$_4$ alkoxy; and Z is pyridinyl substituted with methyl or chloro.

In some embodiments, R is phenyl which is unsubstituted.

In some embodiments, R is phenyl substituted with two to three —F.

In some embodiments, R is phenyl substituted with one methyl.

In some embodiments, R is tetrahydropyranyl which is unsubstituted; Y is phenyl substituted with one or more substituents independently selected from the group consisting of halo and —C$_1$-C$_4$ alkoxy; and Z is imidazolyl substituted with —C$_1$-C$_4$ alkyl.

In some embodiments, R is phenyl substituted with one —C$_1$-C$_4$ alkyl.

In some embodiments, each —C$_1$-C$_4$ alkyl is methyl.

In some embodiments, each —C$_1$-C$_4$ alkoxy is methoxy.

In some embodiments, Y is phenyl which is unsubstituted or substituted with one or more substituents independently selected from the group consisting of halo and —C$_1$-C$_4$ alkoxy.

In some embodiments, Y is phenyl which is unsubstituted.

In some embodiments, Y is phenyl substituted with one —F.

In some embodiments, Y is phenyl substituted with one methoxy.

In some embodiments, Z is pyridinyl, which is unsubstituted or substituted with one to three —C$_1$-C$_4$ alkyl.

In some embodiments, Z is pyridinyl substituted with one to three methyl.

In some embodiments, Z is pyridinyl substituted with one methyl.

In some embodiments, Z is imidazolyl, which is unsubstituted or substituted with one to three —C$_1$-C$_4$ alkyl.

In some embodiments, Z is imidazolyl substituted with one to three methyl.

In some embodiments, Z is imidazolyl substituted with one methyl.

In some embodiments, R is phenyl, —C$_1$-C$_4$ alkylene-phenyl, oxetanyl, —C$_1$-C$_6$ alkyl, —C$_3$-C$_8$ monocyclic cycloalkyl, —C$_1$-C$_4$ alkylene-C$_3$-C$_8$ monocyclic cycloalkyl, 3- to 7-membered monocyclic heterocycle, —C$_1$-C$_4$ alkylene-3- to 7-membered monocyclic heterocycle, each of which is unsubstituted or substituted with one or more substituents independently selected from the group consisting of -halo, —CN, —NH$_2$, —OH, oxo, —C$_1$-C$_4$ alkyl, halo-substituted $C_1$-$C_4$ alkyl, amino-substituted $C_1$-$C_4$ alkyl, —NH—$C_1$-$C_4$ alkyl, —NHC(O)—$C_1$-$C_4$ alkyl, —C(O)NH—$C_1$-$C_4$ alkyl, —C(O)N($C_1$-$C_4$ alkyl)$_2$, hydroxy-substituted $C_1$-$C_4$ alkyl, —S(O)$_2$—$C_1$-$C_4$ alkyl, —S(O)$_2$-halo-substituted $C_1$-$C_4$ alkyl, —S(O)$_2$—NH—$C_1$-$C_4$ alkyl, —S(O)$_2$—N($C_1$-$C_4$ alkyl)$_2$, —NH—S(O)$_2$—$C_1$-$C_4$ alkyl, —N($C_1$-$C_4$ alkyl)-S(O)$_2$—$C_1$-$C_4$ alkyl, —$C_1$-$C_4$ alkoxy, halo-substituted $C_1$-$C_4$ alkoxy, 3- to 7-membered monocyclic heterocycle, —$C_3$-$C_8$ monocyclic cycloalkyl, —C(O)NH$_2$ and -phenoxy, provided that phenyl is not substituted with one or more oxo.

In some embodiments, R is phenyl, oxetanyl, —$C_1$-$C_6$ alkyl, —$C_3$-$C_8$ monocyclic cycloalkyl, —$C_1$-$C_4$ alkylene-$C_3$-$C_8$ monocyclic cycloalkyl or 3- to 7-membered monocyclic heterocycle, each of which is unsubstituted or substituted with one or more substituents independently selected from the group consisting of -halo, —OH, oxo, —$C_1$-$C_4$ alkyl, halo-substituted $C_1$-$C_4$ alkyl, —$C_1$-$C_4$ alkoxy, halo-substituted $C_1$-$C_4$ alkoxy and -phenoxy, provided that phenyl is not substituted with one or more oxo.

In some embodiments, R is phenyl, —$C_1$-$C_6$ alkyl, —$C_3$-$C_8$ monocyclic cycloalkyl, —$C_1$-$C_4$ alkylene-$C_3$-$C_8$ monocyclic cycloalkyl, each of which is unsubstituted or substituted with one or more substituents independently selected from the group consisting of -halo, —$C_1$-$C_4$ alkyl, halo-substituted $C_1$-$C_4$ alkyl, —$C_1$-$C_4$ alkoxy and -phenoxy.

In some embodiments, R is phenyl substituted with one to three substituents independently selected from the group consisting of -halo, —$C_1$-$C_4$ alkyl, halo-substituted $C_1$-$C_4$ alkyl and —$C_1$-$C_4$ alkoxy.

In some embodiments, R is —$C_1$-$C_6$ alkyl, monocyclic cycloalkyl, alkylene-$C_3$-$C_8$ monocyclic cycloalkyl, each of which is unsubstituted or substituted with one or more substituents independently selected from the group consisting of -halo, —$C_1$-$C_4$ alkyl, halo-substituted $C_1$-$C_4$ alkyl and -phenoxy.

In some embodiments, Y is phenyl or pyridinyl, each of which is unsubstituted or substituted with one or more substituents independently selected from the group consisting of -halo, —$C_1$-$C_4$ alkoxy, halo-substituted $C_1$-$C_4$ alkoxy, —$C_1$-$C_4$ alkyl, halo-substituted $C_1$-$C_4$ alkyl, amino-substituted $C_1$-$C_4$ alkoxy, —CN, ($C_1$-$C_4$ alkyl)$_2$N—$C_1$-$C_4$ alkoxy, —NH—$C_1$-$C_4$ alkyl, —OH and —NH$_2$.

In some embodiments, Y is phenyl or pyridinyl which is unsubstituted or substituted with one or more substituents independently selected from the group consisting of -halo, —$C_1$-$C_4$ alkoxy, halo-substituted $C_1$-$C_4$ alkoxy, halo-substituted $C_1$-$C_4$ alkyl and —CN.

In some embodiments, Y is phenyl or pyridinyl, each of which is substituted with one substituent independently selected from the group consisting of -halo, —$C_1$-$C_4$ alkoxy and —CN.

In some embodiments, Y is phenyl which is substituted with -halo, —$C_1$-$C_4$ alkoxy or —CN.

In some embodiments, Y is pyridinyl which is substituted with -halo or —$C_1$-$C_4$ alkoxy.

In some embodiments, Z is —CN or nitrogen-containing 3- to 7-membered monocyclic heterocycle which is unsubstituted or substituted with one or more substituents independently selected from the group consisting of -halo, —CN, —NH$_2$, —OH, —$C_1$-$C_4$ alkyl, halo-substituted $C_1$-$C_4$ alkyl, —$C_1$-$C_4$ alkoxy, —OCF$_3$ and 3- to 7-membered monocyclic heterocycle.

In some embodiments, Z is —CN or nitrogen-containing 3- to 7-membered monocyclic heterocycle which is unsubstituted or substituted with one or more substituents independently selected from the group consisting of -halo, —CN, —$C_1$-$C_4$ alkyl and halo-substituted $C_1$-$C_4$ alkyl.

In some embodiments, Z is nitrogen-containing 3- to 7-membered monocyclic heterocycle which is unsubstituted or substituted with one or more substituents independently selected from the group consisting of -halo, —CN, —$C_1$-$C_4$ alkyl and halo-substituted $C_1$-$C_4$ alkyl.

In some embodiments, Z is nitrogen-containing 3- to 7-membered monocyclic heterocycle which is substituted with one or more substituents independently selected from the group consisting of -halo, —$C_1$-$C_4$ alkyl and halo-substituted $C_1$-$C_4$ alkyl.

In some embodiments, Z is imidazolyl, pyrimidinyl, pyrazolyl, triazolyl, each of which is unsubstituted or substituted with one or more substituents independently selected from the group consisting of -halo, —CN, —$C_1$-$C_4$ alkyl and halo-substituted $C_1$-$C_4$ alkyl.

In some embodiments, Z is imidazolyl or triazolyl, each of which is substituted with one substituent independently selected from the group consisting of -halo, —CN, —$C_1$-$C_4$ alkyl and halo-substituted $C_1$-$C_4$ alkyl.

In some embodiments, Z is imidazolyl or triazolyl, each of which is substituted with one substituent independently selected from the group consisting of -halo, —$C_1$-$C_4$ alkyl and halo-substituted $C_1$-$C_4$ alkyl.

In some embodiments, Z is imidazolyl substituted with one substituent independently selected from the group consisting of -halo, —$C_1$-$C_4$ alkyl and halo-substituted $C_1$-$C_4$ alkyl.

In some embodiments, Z is triazolyl substituted with one —$C_1$-$C_4$ alkyl.

In one aspect, the compound of Formula (I) is selected from the group consisting of: (S)—N-(3-methoxy-4-(4-methyl-1H-imidazol-1-yl)phenyl)-8-methyl-7-phenyl-7,8-dihydro-6H-pyrimido[5,4-b][1,4]oxazin-2-amine; (S)—N-(3-methoxy-4-(2-methylpyridin-4-yl)phenyl)-8-methyl-7-phenyl-7,8-dihydro-6H-pyrimido[5,4-b][1,4]oxazin-2-amine; (R)—N-(3-methoxy-4-(4-methyl-1H-imidazol-1-yl)phenyl)-8-methyl-7-phenyl-7,8-dihydro-6H-pyrimido[5,4-b][1,4]oxazin-2-amine; (R)—N-(3-methoxy-4-(2-methylpyridin-4-yl)phenyl)-8-methyl-7-phenyl-7,8-dihydro-6H-pyrimido[5,4-b][1,4]oxazin-2-amine; difluorophenyl)-8-methyl-N-(4-(4-methyl-1H-imidazol-1-yl)phenyl)-7,8-dihydro-6H-pyrimido[5,4-b][1,4]oxazin-2-amine; (+)-7-(3, 5-difluorophenyl)-8-methyl-N-(4-(4-methyl-1H-imidazol-1-yl) phenyl)-7, 8-dihydro-6H-pyrimido [5, 4-b] [1, 4] oxazin-2-amine; 8-methyl-N-(4-(2-methylpyridin-4-yl)phenyl)-7-phenyl-7,8-dihydro-6H-pyrimido[5,4-b][1,4]oxazin-2-amine; (+)-8-methyl-N-(4-(2-methylpyridin-4-yl)phenyl)-7-phenyl-7,8-dihydro-6H-pyrimido[5,4-b][1,4]oxazin-2-amine; N-(3-fluoro-4-(4-methyl-1H-imidazol-1-yl)phenyl)-8-methyl-7-phenyl-7,8-dihydro-6H-pyrimido[5,4-b][1,4]oxazin-2-amine; (+)-N-(3-fluoro-4-(4-methyl-1H-imidazol-1-yl)phenyl)-8-methyl-7-phenyl-7,8-dihydro-6H-pyrimido[5,4-b][1,4]oxazin-2-amine; 8-methyl-N-(4-(4-methyl-1H-imidazol-1-yl)phenyl)-7-phenyl-7,8-dihydro-6H-pyrimido[5,4-b][1,4] oxazin-2-amine; (+)-8-methyl-N-(4-(4-methyl-1H-imidazol-1-yl)phenyl)-7-phenyl-7,8-dihydro-6H-pyrimido [5,4-b][1,4]oxazin-2-amine; 7-(3,5-difluorophenyl)-8-methyl-N-(4-(2-methylpyridin-4-yl)phenyl)-7,8-dihydro-6H-pyrimido[5,4-b][1,4]oxazin-2-amine; (+)-7-(3,5-difluorophenyl)-8-methyl-N-(4-(2-methylpyridin-4-yl) phenyl)-7,8-dihydro-6H-pyrimido[5,4-b][1,4]oxazin-2-amine; (+)-8-methyl-N-(4-(2-methylpyridin-4-yl)phenyl)-7-(o-tolyl)-7,8-dihydro-6H-pyrimido[5,4-b][1,4]oxazin-2-amine; 7-(3,5-difluorophenyl)-N-(3-methoxy-4-(4-methyl- 1H-imidazol-1-yl)phenyl)-8-methyl-7,8-dihydro-6H-pyrimido[5,4-b][1,4]oxazin-2-amine; (−)-7-(3,5-difluorophenyl)-N-(3-methoxy-4-(4-methyl-1H-imidazol-1-yl)phenyl)-8-methyl-7,8-dihydro-6H-pyrimido[5,4-b][1,4]oxazin-2-amine; (+)-7-(3,5-difluorophenyl)-N-(3-methoxy-4-(4-methyl-1H-imidazol-1-yl)phenyl)-8-methyl-7,8-dihydro-6H-pyrimido[5,4-b][1,4]oxazin-2-amine; N-(3-methoxy-4-(4-methyl-1H-imidazol-1-yl)phenyl)-8-methyl-7-(o-tolyl)-7,8-dihydro-6H-pyrimido[5,4-b][1,4]oxazin-2-amine; (−)-N-(3-methoxy-4-(4-methyl-1H-imidazol-1-yl)phenyl)-8-methyl-7-(o-tolyl)-7,8-dihydro-6H-pyrimido[5,4-b][1,4]oxazin-2-amine; (+)-N-(3-methoxy-4-(4-methyl-1H-imidazol-1-yl)phenyl)-8-methyl-7-(o-tolyl)-7,8-dihydro-6H-pyrimido[5,4-b][1,4]oxazin-2-amine; N-(3-fluoro-4-(2-methylpyridin-4-yl)phenyl)-8-methyl-7-(o-tolyl)-7,8-dihydro-6H-pyrimido[5,4-b][1,4]oxazin-2-amine; (+)-N-(3-fluoro-4-(2-methylpyridin-4-yl)phenyl)-8-methyl-7-(o-tolyl)-7,8-dihydro-6H-pyrimido[5,4-b][1,4]oxazin-2-amine; 7-(3,5-difluorophenyl)-N-(3-fluoro-4-(4-methyl-1H-imidazol-1-yl)phenyl)-8-methyl-7,8-dihydro-6H-pyrimido[5,4-b][1,4]oxazin-2-amine; (+)-7-(3,5-difluorophenyl)-N-(3-fluoro-4-(4-methyl-1H-imidazol-1-yl)phenyl)-8-methyl-7,8-dihydro-6H-pyrimido[5,4-b][1,4]oxazin-2-amine; N-(3-fluoro-4-(4-methyl-1H-imidazol-1-yl)phenyl)-8-methyl-7-(o-tolyl)-7,8-dihydro-6H-pyrimido[5,4-b][1,4]oxazin-2-amine; (+)-N-(3-fluoro-4-(4-methyl-1H-imidazol-1-yl)phenyl)-8-methyl-7-(o-tolyl)-7,8-dihydro-6H-pyrimido[5,4-b][1,4]oxazin-2-amine; N-(3-methoxy-4-(2-methylpyridin-4-yl)phenyl)-8-methyl-7-(o-tolyl)-7,8-dihydro-6H-pyrimido[5,4-b][1,4]oxazin-2-amine; (+)-N-(3-methoxy-4-(2-methylpyridin-4-yl)phenyl)-8-methyl-7-(o-tolyl)-7,8-dihydro-6H-pyrimido[5,4-b][1,4]oxazin-2-amine; N-(3-fluoro-4-(2-methylpyridin-4-yl)phenyl)-8-methyl-7-(3,4,5-trifluorophenyl)-7,8-dihydro-6H-pyrimido[5,4-b][1,4]oxazin-2-amine; (+)-N-(3-fluoro-4-(2-methylpyridin-4-yl)phenyl)-8-methyl-7-(3,4,5-trifluorophenyl)-7,8-dihydro-6H-pyrimido[5,4-b][1,4]oxazin-2-amine; 8-methyl-N-(4-(2-methylpyridin-4-yl)phenyl)-7-(3,4,5-trifluorophenyl)-7,8-dihydro-6H-pyrimido[5,4-b][1,4]oxazin-2-amine; (+)-8-methyl-N-(4-(2-methylpyridin-4-yl)phenyl)-7-(3,4,5-trifluorophenyl)-7,8-dihydro-6H-pyrimido[5,4-b][1,4]oxazin-2-amine; N-(3-fluoro-4-(4-methyl-1H-imidazol-1-yl)phenyl)-8-methyl-7-(3,4,5-trifluorophenyl)-7,8-dihydro-6H-pyrimido[5,4-b][1,4]oxazin-2-amine; N-(3-methoxy-4-(2-methylpyridin-4-yl)phenyl)-8-methyl-7-(3,4,5-trifluorophenyl)-7,8-dihydro-6H-pyrimido[5,4-b][1,4]oxazin-2-amine; (+)-N-(3-methoxy-4-(2-methylpyridin-4-yl)phenyl)-8-methyl-7-(3,4,5-trifluorophenyl)-7,8-dihydro-6H-pyrimido[5,4-b][1,4]oxazin-2-amine; N-(3-methoxy-4-(4-methyl-1H-imidazol-1-yl)phenyl)-8-methyl-7-(3,4,5-trifluorophenyl)-7,8-dihydro-6H-pyrimido[5,4-b][1,4]oxazin-2-amine; (+)-N-(3-methoxy-4-(4-methyl-1H-imidazol-1-yl)phenyl)-8-methyl-7-(3,4,5-trifluorophenyl)-7,8-dihydro-6H-pyrimido[5,4-b][1,4]oxazin-2-amine; 7-(3,5-difluorophenyl)-N-(3-fluoro-4-(2-methylpyridin-4-yl)phenyl)-8-methyl-7,8-dihydro-6H-pyrimido[5,4-b][1,4]oxazin-2-amine; (+)-7-(3,5-difluorophenyl)-N-(3-fluoro-4-(2-methylpyridin-4-yl)phenyl)-8-methyl-7,8-dihydro-6H-pyrimido[5,4-b][1,4]oxazin-2-amine; 7-(3,5-difluorophenyl)-N-(3-methoxy-4-(2-methylpyridin-4-yl)phenyl)-8-methyl-7,8-dihydro-6H-pyrimido[5,4-b][1,4]oxazin-2-amine; (+)-7-(3,5-difluorophenyl)-N-(3-methoxy-4-(2-methylpyridin-4-yl)phenyl)-8-methyl-7,8-dihydro-6H-pyrimido[5,4-b][1,4]oxazin-2-amine; 8-methyl-N-(4-(4-methyl-1H-imidazol-1-yl)phenyl)-7-(o-tolyl)-7,8-dihydro-6H-pyrimido[5,4-b][1,4]oxazin-2-amine; (+)-8-methyl-N-(4-(4-methyl-1H-imidazol-1-yl)phenyl)-7-(o-tolyl)-7,8-dihydro-6H-pyrimido[5,4-b][1,4]oxazin-2-amine; 8-methyl-N-(4-(4-methyl-1H-imidazol-1-yl)phenyl)-7-(3,4,5-trifluorophenyl)-7,8-dihydro-6H-pyrimido[5,4-b][1,4]oxazin-2-amine; N-(3-methoxy-4-(4-methyl-1H-imidazol-1-yl)phenyl)-8-methyl-7-phenyl-7,8-dihydro-6H-pyrimido[5,4-b][1,4]oxazin-2-amine; N-(3-methoxy-4-(2-methylpyridin-4-yl)phenyl)-8-methyl-7-phenyl-7,8-dihydro-6H-pyrimido[5,4-b][1,4]oxazin-2-amine; 7-benzyl-N-(3-methoxy-4-(4-methyl-1H-imidazol-1-yl) phenyl)-8-methyl-7,8-dihydro-6H-pyrimido[5,4-b][1,4]oxazin-2-amine; (+)-7-benzyl-N-(3-methoxy-4-(4-methyl-1H-imidazol-1-yl) phenyl)-8-methyl-7,8-dihydro-6H-pyrimido[5,4-b][1,4]oxazin-2-amine; (−)-7-benzyl-N-(3-methoxy-4-(4-methyl-1H-imidazol-1-yl) phenyl)-8-methyl-7,8-dihydro-6H-pyrimido[5,4-b][1,4]oxazin-2-amine; 7-(2,4-difluorophenyl)-N-(3-methoxy-4-(4-methyl-1H-imidazol-1-yl) phenyl)-8-methyl-7,8-dihydro-6H-pyrimido[5,4-b][1,4]oxazin-2-amine; (+)-7-(2,4-difluorophenyl)-N-(3-methoxy-4-(4-methyl-1H-imidazol-1-yl) phenyl)-8-methyl-7,8-dihydro-6H-pyrimido[5,4-b][1,4]oxazin-2-amine; 7-(4-fluorophenyl)-N-(3-methoxy-4-(4-methyl-1H-imidazol-1-yl) phenyl)-8-methyl-7,8-dihydro-6H-pyrimido[5,4-b][1,4]oxazin-2-amine; (−)-7-(4-fluorophenyl)-N-(3-methoxy-4-(4-methyl-1H-imidazol-1-yl) phenyl)-8-methyl-7,8-dihydro-6H-pyrimido[5,4-b][1,4]oxazin-2-amine; (+)-7-(4-fluorophenyl)-N-(3-methoxy-4-(4-methyl-1H-imidazol-1-yl) phenyl)-8-methyl-7,8-dihydro-6H-pyrimido[5,4-b][1,4]oxazin-2-amine; N-(3-methoxy-4-(4-methyl-1H-imidazol-1-yl) phenyl)-8-methyl-7-(tetrahydro-2H-pyran-4-yl)-7,8-dihydro-6H-pyrimido[5,4-b][1,4]oxazin-2-amine; 7-(2-chlorophenyl)-N-(3-methoxy-4-(4-methyl-1H-imidazol-1-yl) phenyl)-8-methyl-7,8-dihydro-6H-pyrimido[5,4-b][1,4]oxazin-2-amine; (−)-7-(2-chlorophenyl)-N-(3-methoxy-4-(4-methyl-1H-imidazol-1-yl) phenyl)-8-methyl-7,8-dihydro-6H-pyrimido[5,4-b][1,4]oxazin-2-amine; (+)-7-(2-chlorophenyl)-N-(3-methoxy-4-(4-methyl-1H-imidazol-1-yl) phenyl)-8-methyl-7,8-dihydro-6H-pyrimido[5,4-b][1,4]oxazin-2-amine; N-(3-methoxy-4-(4-methyl-1H-imidazol-1-yl) phenyl)-7,8-dimethyl-7,8-dihydro-6H-pyrimido[5,4-b][1,4]oxazin-2-amine; 7-(2-chloro-4-fluorophenyl)-N-(3-methoxy-4-(4-methyl-1H-imidazol-1-yl) phenyl)-8-methyl-7,8-dihydro-6H-pyrimido[5,4-b][1,4]oxazin-2-amine; 7-(4-fluoro-2-methylphenyl)-N-(3-methoxy-4-(4-methyl-1H-imidazol-1-yl) phenyl)-8-methyl-7,8-dihydro-6H-pyrimido[5,4-b][1,4]oxazin-2-amine; N-(3-methoxy-4-(4-methyl-1H-imidazol-1-yl) phenyl)-8-methyl-7-(2-(trifluoromethyl) phenyl)-7,8-dihydro-6H-pyrimido[5,4-b][1,4]oxazin-2-amine; (−)-N-(3-methoxy-4-(4-methyl-1H-imidazol-1-yl) phenyl)-8-methyl-7-(2-(trifluoromethyl) phenyl)-7,8-dihydro-6H-pyrimido[5,4-b][1,4]oxazin-2-amine; (+)-N-(3-methoxy-4-(4-methyl-1H-imidazol-1-yl) phenyl)-8-methyl-7-(2-(trifluoromethyl) phenyl)-7,8-dihydro-6H-pyrimido[5,4-b][1,4]oxazin-2-amine; (+)-N-(3-fluoro-4-(2-methylpyridin-4-yl) phenyl)-7-(4-fluorophenyl)-8-methyl-7,8-dihydro-6H-pyrimido[5,4-b][1,4]oxazin-2-amine; (+)-7-benzyl-N-(3-fluoro-4-(2-methylpyridin-4-yl) phenyl)-8-methyl-7,8-dihydro-6H-pyrimido[5,4-b][1,4]oxazin-2-amine; (+)-N-(3-fluoro-4-(4-methyl-1H-imidazol-1-yl) phenyl)-7-(4-fluorophenyl)-8-methyl-7,8-dihydro-6H-pyrimido[5,4-b][1,4]oxazin-2-amine; (+)-7-benzyl-N-(3-fluoro-4-(4-methyl-1H-imidazol-1-yl) phenyl)-8-methyl-7,8-dihydro-6H-pyrimido[5,4-b][1,4]oxazin-2-amine; (−)-N-(3-methoxy-4-(4-methyl-1H-imidazol-1-yl) phenyl)-8-methyl-7-(2-(trifluoromethoxy) phenyl)-7,8-dihydro-6H-pyrimido[5,4-b][1,4]oxazin-2-amine; (+)-N-(3-methoxy-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine; (+)-7-(4-fluorophenyl)-N-(3-methoxy-4-(2-methylpyridin-4-yl) phenyl)-8-methyl-7, 8-dihydro-6H-pyrimido [5, 4-b] [1, 4] oxazin-2-amine; (+)-N-(3-methoxy-4-(2-methylpyridin-4-yl) phenyl)-8-methyl-7-(2-(trifluoromethoxy) phenyl)-7, 8-dihydro-6H-pyrimido [5, 4-b] [1, 4] oxazin-2-amine; (+)-7-(2, 4-difluorophenyl)-N-(3-methoxy-4-(2-methylpyridin-4-yl) phenyl)-8-methyl-7, 8-dihydro-6H-pyrimido [5, 4-b] [1, 4] oxazin-2-amine; N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine; (+)-7-(2-chlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine; (+)-7-benzyl-N-(3-methoxy-4-(2-methylpyridin-4-yl) phenyl)-8-methyl-7, 8-dihydro-6H-pyrimido [5, 4-b] [1, 4] oxazin-2-amine; (−)-7-benzyl-N-(3-methoxy-4-(2-methylpyridin-4-yl) phenyl)-8-methyl-7, 8-dihydro-6H-pyrimido [5, 4-b] [1, 4] oxazin-2-amine; (+)-7-(2, 4-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine; (+)-N-(3-methoxy-4-(2-methylpyridin-4-yl) phenyl)-8-methyl-7-(2-(trifluoromethyl) phenyl)-7; 8-dihydro-6H-pyrimido [5, 4-b] [1, 4] oxazin-2-amine; (+)-N-(3-fluoro-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine; (+)-2-(2-chlorophenyl)-N-(3-methoxy-4-(2-methylpyridin-4-yl) phenyl)-1-methyl-2, 3-dihydro-1H-pyrido [3, 4-b] [1, 4] oxazin-7-amine; 7-(2-chloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; 7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; 7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; 7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; 7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; 7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; 7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (−)-7-(2-chloro-4-fluorophenyl)-N-(3-methoxy-4-(4-methyl-1H-imidazol-1-yl) phenyl)-8-methyl-7,8-dihydro-6H-pyrimido [5, 4-b] [1,4] oxazin-2-amine; (+)-7-(2-chloro-4-fluorophenyl)-N-(3-methoxy-4-(4-methyl-1H-imidazol-1-yl) phenyl)-8-methyl-7,8-dihydro-6H-pyrimido [5, 4-b] [1,4] oxazin-2-amine; (−)-7-(4-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(4-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (−)-7-(2, 4-dichlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(2, 4-dichlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(2, 4-dichlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine; (−)-N-(3-methoxy-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine; (+)-N-(3-methoxy-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine; (+)-N-(3-fluoro-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine; (+)-7-(4-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine; (+)-7-(5-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine; (+)-7-(2-chloro-4-fluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine; (+)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine; (−)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine; (+)-7-(5-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine; (−)-7-(5-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(5-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(4-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine; (+)-7-(4-chloro-2-(trifluoromethyl) phenyl)-N-(3-methoxy-4-(2-methylpyridin-4-yl) phenyl)-8-methyl-7, 8-dihydro-6H-pyrimido [5, 4-b] [1, 4] oxazin-2-amine; (+)-N-(3-fluoro-4-(4-methyl-1H-imidazol-1-yl) phenyl)-7, 8-dimethyl-7, 8-dihydro-6H-pyrimido [5, 4-b] [1, 4] oxazin-2-amine; (+)-N-(3-fluoro-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine; (−)-N-(3-methoxy-4-(2-methylpyridin-4-yl) phenyl)-7, 8-dimethyl-7, 8-dihydro-6H-pyrimido [5, 4-b] [1, 4] oxazin-2-amine; (+)-N-(3-methoxy-4-(2-methylpyridin-4-yl) phenyl)-7, 8-dimethyl-7, 8-dihydro-6H-pyrimido [5, 4-b] [1, 4] oxazin-2-amine; (S)—N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine; (−)-7-(4-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(4-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-N-(3-methoxy-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine; (+)-8-methyl-N-(4-(4-methyl-1H-imidazol-1-yl) phenyl)-7-(3, 4, 5-trifluorophenyl)-7, 8-dihydro-6H-pyrimido [5, 4-b] [1, 4] oxazin-2-amine; (−)-N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine; (+)-N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine; (−)-7-(4-fluoro-2-methylphenyl)-N-(3-methoxy-4-(4-methyl-1H-imidazol-1-yl) phenyl)-8-methyl- 7, 8-dihydro-6H-pyrimido [5, 4-b] [1, 4] oxazin-2-amine; (+)-7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine; (+)-7-(5-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (−)-7-(5-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (−)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (−)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine; (+)-N-(5-methoxy-6-(4-methyl-1H-imidazol-1-yl) pyridin-3-yl)-8-methyl-7-(o-tolyl)-7, 8-dihydro-6H-pyrimido [5, 4-b] [1, 4] oxazin-2-amine; (−)-N-(5-methoxy-6-(4-methyl-1H-imidazol-1-yl) pyridin-3-yl)-8-methyl-7-(o-tolyl)-7, 8-dihydro-6H-pyrimido [5, 4-b] [1, 4] oxazin-2-amine; (−)-N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine; (+)-N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine; (+)-7-(2-chloro-5-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine; (−)-7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (−)-7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(4, 5-difluoro-2-(trifluoromethyl) phenyl)-N-(1-(2-methoxypyridin-4-yl) piperidin-4-yl)-8-methyl-7, 8-dihydro-6H-pyrimido [5, 4-b] [1, 4] oxazin-2-amine; (−)-7-(4, 5-difluoro-2-(trifluoromethyl) phenyl)-N-(1-(2-methoxypyridin-4-yl) piperidin-4-yl)-8-methyl-7, 8-dihydro-6H-pyrimido [5, 4-b] [1, 4] oxazin-2-amine; (+)-N-(5-methoxy-6-(4-methyl-1H-imidazol-1-yl) pyridin-3-yl)-8-methyl-7-(2, 4, 5-trifluorophenyl)-7, 8-dihydro-6H-pyrimido [5, 4-b] [1, 4] oxazin-2-amine; (+)-N-(5-methoxy-6-(4-methyl-1H-imidazol-1-yl) pyridin-3-yl)-8-methyl-7-(3, 4, 5-trifluorophenyl)-7, 8-dihydro-6H-pyrimido [5, 4-b] [1, 4] oxazin-2-amine; (−)-N-(5-methoxy-6-(4-methyl-1H-imidazol-1-yl) pyridin-3-yl)-8-methyl-7-(3, 4, 5-trifluorophenyl)-7, 8-dihydro-6H-pyrimido [5, 4-b] [1, 4] oxazin-2-amine; (+)-N-(5-methoxy-6-(4-methyl-1H-imidazol-1-yl) pyridin-3-yl)-7, 8-dimethyl-7, 8-dihydro-6H-pyrimido [5, 4-b] [1, 4] oxazin-2-amine; (+)-7-(2, 4-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (−)-N-(3-methoxy-4-(4-methyl-1H-imidazol-1-yl) phenyl)-8-methyl-7-(trifluoromethyl)-7, 8-dihydro-6H-pyrimido [5, 4-b] [1, 4] oxazin-2-amine; (+)-7-(3, 5-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (−)-N-(5-methoxy-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine; (+)-N-(5-methoxy-6-(4-methyl-1H-imidazol-1-yl) pyridin-3-yl)-7, 7, 8-trimethyl-7, 8-dihydro-6H-pyrimido [5, 4-b] [1, 4] oxazin-2-amine; (+)-7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (−)-7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (S)—N-(3-methoxy-4-(4-methyl-1H-imidazol-1-yl) phenyl)-8-methyl-7-(phenoxymethyl)-7, 8-dihydro-6H-pyrimido [5, 4-b] [1, 4] oxazin-2-amine; (R)—N-(3-methoxy-4-(4-methyl-1H-imidazol-1-yl) phenyl)-8-methyl-7-(phenoxymethyl)-7, 8-dihydro-6H-pyrimido [5, 4-b] [1, 4] oxazin-2-amine; (−)-N-(4-(4-chloro-1H-imidazol-1-yl)-3-methoxyphenyl)-7, 8-dimethyl-7, 8-dihydro-6H-pyrimido [5, 4-b] [1, 4] oxazin-2-amine; (+)-N-(4-(4-chloro-1H-imidazol-1-yl)-3-methoxyphenyl)-7, 8-dimethyl-7, 8-dihydro-6H-pyrimido [5, 4-b] [1, 4] oxazin-2-amine; (+)-5-((7-(3, 5-difluorophenyl)-8-methyl-7, 8-dihydro-6H-pyrimido [5, 4-b] [1, 4] oxazin-2-yl) amino)-2-(4-methyl-1H-imidazol-1-yl) benzonitrile; (−)-5-((7-(3, 5-difluorophenyl)-8-methyl-7, 8-dihydro-6H-pyrimido [5, 4-b] [1, 4] oxazin-2-yl) amino)-2-(4-methyl-1H-imidazol-1-yl) benzonitrile; (+)-N-(4-(4-chloro-1H-imidazol-1-yl)-3-methoxyphenyl)-7-(3, 5-difluorophenyl)-8-methyl-7, 8-dihydro-6H-pyrimido [5, 4-b] [1, 4] oxazin-2-amine; (+)-5-((7, 8-dimethyl-7, 8-dihydro-6H-pyrimido [5, 4-b] [1, 4] oxazin-2-yl) amino)-2-(4-methyl-1H-imidazol-1-yl) benzonitrile; (+)-7-(3, 5-difluorophenyl)-N-(5-methoxy-6-(4-(trifluoromethyl)-1H-imidazol-1-yl) pyridin-3-yl)-8-methyl-7, 8-dihydro-6H-pyrimido [5, 4-b] [1, 4] oxazin-2-amine; (+)-7-(5-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (−)-7-(5-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (+)-7-(2-chloro-5-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (−)-7-(2-chloro-5-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (+)-7-(2-chloro-4-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (−)-7-(2-chloro-4-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (+)-N-(5-chloro-6-(4-methyl-1H-imidazol-1-yl) pyridin-3-yl)-7-(3, 5-difluorophenyl)-8-methyl-7, 8-dihydro-6H-pyrimido [5, 4-b] [1, 4] oxazin-2-amine; (+)-1-(5-((7-(3, 5-difluorophenyl)-8-methyl-7, 8-dihydro-6H-pyrimido [5, 4-b] [1, 4] oxazin-2-yl) amino)-3-methoxypyridin-2-yl)-1H-imidazole-4-carbonitrile; (+)-7-(3, 3-difluorocyclobutyl)-N-(3-methoxy-4-(4-methyl-1H- imidazol-1-yl) phenyl)-8-methyl-7, 8-dihydro-6H-pyrimido [5, 4-b] [1, 4] oxazin-2-amine; (+)-7-(4-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (−)-7-(4-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (+)-7-(4, 4-difluorocyclohexyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (S)-7-(cyclopropylmethyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (S)-7-(cyclopropylmethyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (+)-7-(3, 3-difluorocyclobutyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (+)-7-(3, 5-difluorophenyl)-N-(4-methoxy-5-(4-methyl-1H-imidazol-1-yl) pyridin-2-yl)-8-methyl-7, 8-dihydro-6H-pyrimido [5, 4-b] [1, 4] oxazin-2-amine; (+)-7-(4, 4-difluorocyclohexyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (S)-7-cyclopropyl-N-(3-methoxy-4-(4-methyl-1H-imidazol-1-yl) phenyl)-8-methyl-7, 8-dihydro-6H-pyrimido [5, 4-b] [1, 4] oxazin-2-amine; (S)-7-cyclopropyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (S)-7-cyclobutyl-N-(3-methoxy-4-(4-methyl-1H-imidazol-1-yl) phenyl)-8-methyl-7, 8-dihydro-6H-pyrimido [5, 4-b] [1, 4] oxazin-2-amine; (−)-N-(4-(4-chloro-1H-imidazol-1-yl)-3-methoxyphenyl)-8-methyl-7-(trifluoromethyl)-7, 8-dihydro-6H-pyrimido [5, 4-b] [1, 4] oxazin-2-amine; (−)-N-(5-chloro-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine; (−)-2-(4-methyl-1H-imidazol-1-yl)-5-((8-methyl-7-(trifluoromethyl)-7, 8-dihydro-6H-pyrimido [5, 4-b] [1, 4] oxazin-2-yl) amino) benzonitrile; (S)-7-cyclobutyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (−)-N-(4-methoxy-5-(4-methyl-1H-imidazol-1-yl) pyridin-2-yl)-8-methyl-7-(trifluoromethyl)-7, 8-dihydro-6H-pyrimido [5, 4-b] [1, 4] oxazin-2-amine; (+)-4-((7-(3, 5-difluorophenyl)-8-methyl-7, 8-dihydro-6H-pyrimido [5, 4-b] [1, 4] oxazin-2-yl) amino)-2-methoxybenzonitrile; (+)-N-(5-methoxy-6-(4-methyl-1H-imidazol-1-yl) pyridin-3-yl)-8-methyl-7-(2, 2, 2-trifluoroethyl)-7, 8-dihydro-6H-pyrimido [5, 4-b] [1, 4] oxazin-2-amine; (S)-7-(tert-butyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (−)-N-(3-methoxy-4-(3-methyl-1H-1, 2, 4-triazol-1-yl) phenyl)-8-methyl-7-(trifluoromethyl)-7, 8-dihydro-6H-pyrimido [5, 4-b] [1, 4] oxazin-2-amine; (+)-7-(3, 5-difluorophenyl)-N-(3-methoxy-4-(3-methyl-1H-1, 2, 4-triazol-1-yl) phenyl)-8-methyl-7, 8-dihydro-6H-pyrimido [5, 4-b] [1, 4] oxazin-2-amine; (−)-N-(3-methoxy-4-(4-methyl-1H-imidazol-1-yl) phenyl)-8-methyl-7-(1-(trifluoromethyl) cyclopropyl)-7, 8-dihydro-6H-pyrimido [5, 4-b] [1, 4] oxazin-2-amine; (+)-N-(3-methoxy-4-(4-methyl-1H-imidazol-1-yl) phenyl)-8-methyl-7-(1-(trifluoromethyl) cyclopropyl)-7, 8-dihydro-6H-pyrimido [5, 4-b] [1, 4] oxazin-2-amine; (S)-7-(tert-butyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (S)—N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine; (−)-N-(5-methoxy-6-(4-methyl-1H-imidazol-1-yl) pyridin-3-yl)-8-methyl-7-(1-(trifluoromethyl) cyclopropyl)-7, 8-dihydro-6H-pyrimido [5, 4-b] [1, 4] oxazin-2-amine; and (+)-N-(5-methoxy-6-(4-methyl-1H-imidazol-1-yl) pyridin-3-yl)-8-methyl-7-(1-(trifluoromethyl) cyclopropyl)-7, 8-dihydro-6H-pyrimido [5, 4-b] [1, 4] oxazin-2-amine; or a pharmaceutically acceptable salt thereof.

In some embodiments, the compound of Formula (I) is selected from the group consisting of: (S)—N-(3-methoxy-4-(4-methyl-1H-imidazol-1-yl)phenyl)-8-methyl-7-phenyl-7,8-dihydro-6H-pyrimido[5,4-b][1,4]oxazin-2-amine; (S)—N-(3-methoxy-4-(2-methylpyridin-4-yl)phenyl)-8-methyl-7-phenyl-7,8-dihydro-6H-pyrimido[5,4-b][1,4]oxazin-2-amine; 7-(3,5-difluorophenyl)-8-methyl-N-(4-(4-methyl-1H-imidazol-1-yl)phenyl)-7,8-dihydro-6H-pyrimido[5,4-b][1,4]oxazin-2-amine; (+)-7-(3, 5-difluorophenyl)-8-methyl-N-(4-(4-methyl-1H-imidazol-1-yl) phenyl)-7, 8-dihydro-6H-pyrimido [5, 4-b] [1, 4] oxazin-2-amine; (+)-N-(3-fluoro-4-(4-methyl-1H-imidazol-1-yl)phenyl)-8-methyl-7-phenyl-7,8-dihydro-6H-pyrimido[5,4-b][1,4]oxazin-2-amine; (+)-8-methyl-N-(4-(4-methyl-1H-imidazol-1-yl)phenyl)-7-phenyl-7,8-dihydro-6H-pyrimido[5,4-b][1,4]oxazin-2-amine; 7-(3,5-difluorophenyl)-N-(3-methoxy-4-(4-methyl-1H-imidazol-1-yl)phenyl)-8-methyl-7,8-dihydro-6H-pyrimido[5,4-b][1,4]oxazin-2-amine; (+)-7-(3,5-difluorophenyl)-N-(3-methoxy-4-(4-methyl-1H-imidazol-1-yl)phenyl)-8-methyl-7,8-dihydro-6H-pyrimido[5,4-b][1,4]oxazin-2-amine; N-(3-methoxy-4-(4-methyl-1H-imidazol-1-yl)phenyl)-8-methyl-7-(o-tolyl)-7,8-dihydro-6H-pyrimido[5,4-b][1,4]oxazin-2-amine; (+)-N-(3-methoxy-4-(4-methyl-1H-imidazol-1-yl)phenyl)-8-methyl-7-(o-tolyl)-7,8-dihydro-6H-pyrimido[5,4-b][1,4]oxazin-2-amine; 7-(3, 5-difluorophenyl)-N-(3-fluoro-4-(4-methyl-1H-imidazol-1-yl)phenyl)-8-methyl-7,8-dihydro-6H-pyrimido[5,4-b][1,4]oxazin-2-amine; (+)-7-(3,5-difluorophenyl)-N-(3-fluoro-4-(4-methyl-1H-imidazol-1-yl)phenyl)-8-methyl-7,8-dihydro-6H-pyrimido[5,4-b][1,4]oxazin-2-amine; N-(3-fluoro-4-(4-methyl-1H-imidazol-1-yl)phenyl)-8-methyl-7-(o-tolyl)-7,8-dihydro-6H-pyrimido[5,4-b][1,4]oxazin-2-amine; (+)-N-(3-fluoro-4-(4-methyl-1H-imidazol-1-yl)phenyl)-8-methyl-7-(o-tolyl)-7,8-dihydro-6H-pyrimido[5,4-b][1,4]oxazin-2-amine; (+)-N-(3-methoxy-4-(2-methylpyridin-4-yl)phenyl)-8-methyl-7-(o-tolyl)-7,8-dihydro-6H-pyrimido[5,4-b][1,4]oxazin-2-amine; N-(3-fluoro-4-(4-methyl-1H-imidazol-1-yl)phenyl)-8-methyl-7-(3,4,5-trifluorophenyl)-7,8-dihydro-6H-pyrimido[5,4-b][1,4]oxazin-2-amine; N-(3-methoxy-4-(2-methylpyridin-4-yl)phenyl)-8-methyl-7-(3,4,5-trifluorophenyl)-7,8-dihydro-6H-pyrimido[5,4-b][1,4]oxazin-2-amine; (+)-N-(3-methoxy-4-(2-methylpyridin-4-yl)phenyl)-8-methyl-7-(3,4,5-trifluorophenyl)-7,8-dihydro-6H-pyrimido[5,4-b][1,4]oxazin-2-amine; N-(3-methoxy-4-(4-methyl-1H-imidazol-1-yl)phenyl)-8-methyl-7-(3,4,5-trifluorophenyl)-7,8-dihydro-6H-pyrimido[5,4-b][1,4]oxazin-2-amine; (+)-N-(3-methoxy-4-(4-methyl-1H-imidazol-1-yl)phenyl)-8-methyl-7-(3,4,5-trifluorophenyl)-7,8-dihydro-6H-pyrimido[5,4-b][1,4]oxazin-2-amine; 7-(3, 5-difluorophenyl)-N-(3-methoxy-4-(2-methylpyridin-4-yl) phenyl)-8-methyl-7,8-dihydro-6H-pyrimido[5,4-b][1,4]oxazin-2-amine; (+)-7-(3,5-difluorophenyl)-N-(3-methoxy-4-(2-methylpyridin-4-yl)phenyl)-8-methyl-7,8-dihydro-6H-pyrimido[5,4-b][1,4]oxazin-2-amine; (+)-8-methyl-N-(4-(4-methyl-1H-imidazol-1-yl)phenyl)-7-(o-tolyl)-7,8-dihydro-6H-pyrimido[5,4-b][1,4]oxazin-2-amine; N-(3-methoxy-4-(2-methylpyridin-4-yl)phenyl)-8-methyl-7-phenyl-7,8-dihydro-6H-pyrimido[5,4-b][1,4]oxazin-2-amine; 7-benzyl-N-(3-methoxy-4-(4-methyl-1H-imidazol-1-yl) phenyl)-8- methyl-7, 8-dihydro-6H-pyrimido [5, 4-b] [1, 4] oxazin-2-amine; (+)-7-benzyl-N-(3-methoxy-4-(4-methyl-1H-imidazol-1-yl) phenyl)-8-methyl-7, 8-dihydro-6H-pyrimido [5, 4-b] [1, 4] oxazin-2-amine; 7-(2, 4-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(2, 4-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; 7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; 7-(2-chlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (−)-7-(2-chlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; 7-(2-chloro-4-fluorophenyl)-N-(3-methoxy-4-(4-methyl-1H-imidazol-1-yl) phenyl)-8-methyl-7,8-dihydro-6H-pyrimido [5, 4-b] [1,4] oxazin-2-amine; N-(3-methoxy-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine; (+)-N-(3-fluoro-4-(4-methyl-1H-imidazol-1-yl) phenyl)-7-(4-fluorophenyl)-8-methyl-7, 8-dihydro-6H-pyrimido [5, 4-b] [1, 4] oxazin-2-amine; (+)-7-benzyl-N-(3-methoxy-4-(2-methylpyridin-4-yl) phenyl)-8-methyl-7; 8-dihydro-6H-pyrimido [5, 4-b] [1, 4] oxazin-2-amine; 7-(2-chloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; 7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; 7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; 7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; 7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; 7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(2-chloro-4-fluorophenyl)-N-(3-methoxy-4-(4-methyl-1H-imidazol-1-yl) phenyl)-8-methyl-7,8-dihydro-6H-pyrimido [5, 4-b] [1,4] oxazin-2-amine; (+)-7-(4-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(2, 4-dichlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-N-(3-methoxy-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine; (+)-N-(3-fluoro-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine; (+)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine; (+)-7-(5-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(4-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-8-methyl-N-(4-(4-methyl-1H-imidazol-1-yl) phenyl)-7-(3, 4, 5-trifluorophenyl)-7, 8-dihydro-6H-pyrimido [5, 4-b] [1, 4] oxazin-2-amine; (+)-N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine; (+)-7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine; (+)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine; (+)-N-(5-methoxy-6-(4-methyl-1H-imidazol-1-yl) pyridin-3-yl)-8-methyl-7-(o-tolyl)-7, 8-dihydro-6H-pyrimido [5, 4-b] [1, 4] oxazin-2-amine; (+)-N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine; (+)-7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(4, 5-difluoro-2-(trifluoromethyl) phenyl)-N-(1-(2-methoxypyridin-4-yl) piperidin-4-yl)-8-methyl-7, 8-dihydro-6H-pyrimido [5, 4-b] [1, 4] oxazin-2-amine; (+)-N-(5-methoxy-6-(4-methyl-1H-imidazol-1-yl) pyridin-3-yl)-8-methyl-7-(2, 4, 5-trifluorophenyl)-7, 8-dihydro-6H-pyrimido [5, 4-b] [1, 4] oxazin-2-amine; (+)-N-(5-methoxy-6-(4-methyl-1H-imidazol-1-yl) pyridin-3-yl)-8-methyl-7-(3, 4, 5-trifluorophenyl)-7, 8-dihydro-6H-pyrimido [5, 4-b] [1, 4] oxazin-2-amine; (+)-7-(2, 4-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (−)-N-(3-methoxy-4-(4-methyl-1H-imidazol-1-yl) phenyl)-8-methyl-7-(trifluoromethyl)-7, 8-dihydro-6H-pyrimido [5, 4-b] [1, 4] oxazin-2-amine; (+)-7-(3, 5-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (−)-N-(5-methoxy-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine; (+)-7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (S)—N-(3-methoxy-4-(4-methyl-1H-imidazol-1-yl) phenyl)-8-methyl-7-(phenoxymethyl)-7, 8-dihydro-6H-pyrimido [5, 4-b] [1, 4] oxazin-2-amine; (+)-N-(4-(4-chloro-1H-imidazol-1-yl)-3-methoxyphenyl)-7, 8-dimethyl-7, 8-dihydro-6H-pyrimido [5, 4-b] [1, 4] oxazin-2-amine; (+)-5-((7-(3, 5-difluorophenyl)-8-methyl-7, 8-dihydro-6H-pyrimido [5, 4-b] [1, 4] oxazin-2-yl) amino)-2-(4-methyl-1H-imidazol-1-yl) benzonitrile; (+)-N-(4-(4-chloro-1H-imidazol-1-yl)-3-methoxyphenyl)-7-(3, 5-difluorophenyl)-8-methyl-7, 8-dihydro-6H-pyrimido [5, 4-b] [1, 4] oxazin-2-amine; (+)-7-(3, 5-difluorophenyl)-N-(5-methoxy-6-(4-(trifluoromethyl)-1H-imidazol-1-yl) pyridin-3-yl)-8-methyl-7, 8-dihydro-6H-pyrimido [5, 4-b] [1, 4] oxazin-2- amine; (+)-7-(5-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (+)-7-(2-chloro-5-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (+)-7-(2-chloro-4-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (−)-7-(2-chloro-4-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (+)-N-(5-chloro-6-(4-methyl-1H-imidazol-1-yl) pyridin-3-yl)-7-(3, 5-difluorophenyl)-8-methyl-7, 8-dihydro-6H-pyrimido [5, 4-b] [1, 4] oxazin-2-amine; (+)-7-(3, 3-difluorocyclobutyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(4-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (+)-7-(4, 4-difluorocyclohexyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (S)-7-(cyclopropylmethyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (S)-7-(cyclopropylmethyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (+)-7-(3, 3-difluorocyclobutyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (+)-7-(3, 5-difluorophenyl)-N-(4-methoxy-5-(4-methyl-1H-imidazol-1-yl) pyridin-2-yl)-8-methyl-7, 8-dihydro-6H-pyrimido [5, 4-b] [1, 4] oxazin-2-amine; (+)-7-(4, 4-difluorocyclohexyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (S)-7-cyclopropyl-N-(3-methoxy-4-(4-methyl-1H-imidazol-1-yl) phenyl)-8-methyl-7, 8-dihydro-6H-pyrimido [5, 4-b] [1, 4] oxazin-2-amine; (S)-7-cyclopropyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (S)-7-cyclobutyl-N-(3-methoxy-4-(4-methyl-1H-imidazol-1-yl) phenyl)-8-methyl-7, 8-dihydro-6H-pyrimido [5, 4-b] [1, 4] oxazin-2-amine; (−)-N-(4-(4-chloro-1H-imidazol-1-yl)-3-methoxyphenyl)-8-methyl-7-(trifluoromethyl)-7, 8-dihydro-6H-pyrimido [5, 4-b] [1, 4] oxazin-2-amine; (−)-2-(4-methyl-1H-imidazol-1-yl)-5-((8-methyl-7-(trifluoromethyl)-7, 8-dihydro-6H-pyrimido [5, 4-b] [1, 4] oxazin-2-yl) amino) benzonitrile; (S)-7-cyclobutyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; (+)-N-(5-methoxy-6-(4-methyl-1H-imidazol-1-yl) pyridin-3-yl)-8-methyl-7-(2, 2, 2-trifluoroethyl)-7, 8-dihydro-6H-pyrimido [5, 4-b] [1, 4] oxazin-2-amine; (S)-7-(tert-butyl)-N-(3-methoxy-4-(4-methyl-1H-imidazol-1-yl) phenyl)-8-methyl-7, 8-dihydro-6H-pyrimido [5, 4-b] [1, 4] oxazin-2-amine; (+)-7-(3, 5-difluorophenyl)-N-(3-methoxy-4-(3-methyl-1H-1, 2, 4-triazol-1-yl) phenyl)-8-methyl-7, 8-dihydro-6H-pyrimido [5, 4-b] [1, 4] oxazin-2-amine; (+)-N-(3-methoxy-4-(4-methyl-1H-imidazol-1-yl) phenyl)-8-methyl-7-(1-(trifluoromethyl) cyclopropyl)-7, 8-dihydro-6H-pyrimido [5, 4-b] [1, 4] oxazin-2-amine; (S)-7-(tert-butyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; and (+)-N-(5-methoxy-6-(4-methyl-1H-imidazol-1-yl) pyridin-3-yl)-8-methyl-7-(1-(trifluoromethyl) cyclopropyl)-7, 8-dihydro-6H-pyrimido [5, 4-b] [1, 4] oxazin-2-amine; or a pharmaceutically acceptable salt thereof.

In one aspect, the invention provides a pharmaceutical composition comprising a pharmaceutically acceptable carrier or vehicle and an effective amount of a compound of Formula (I) or a pharmaceutically acceptable salt thereof.

In one aspect, the invention provides a method for treating a neurodegenerative disease, comprising administering to a subject in need thereof an effective amount of a compound or a pharmaceutically acceptable salt of a compound of Formula (I).

In some embodiments, the neurodegenerative disease is panic disorder, obsessive compulsive disorder, delusional disorder, drug-induced psychosis, post-traumatic stress disorder, age-related cognitive decline, attention deficit/hyperactivity disorder, personality disorder of the paranoid type, personality disorder of the schizoid type, dyskinesia, choreiform condition, psychosis associated with Parkinson's disease, psychotic symptoms associated with Alzheimer's disease, mood disorder, or dementia.

In one aspect, the invention provides a method for treating Alzheimer's disease, comprising administering to a subject in need thereof an effective amount of a compound or a pharmaceutically acceptable salt of a compound of Formula (I).

In one aspect, the invention provides a method for improving an impaired cognitive function, comprising administering to a subject having impaired cognitive function an effective amount of a compound or a pharmaceutically acceptable salt of a compound of Formula (I).

In one aspect, the invention provides a method for ameliorating a symptom of Alzheimer's disease, comprising administering to a subject in need thereof an effective amount of a compound or a pharmaceutically acceptable salt of a compound of Formula (I).

In some embodiments, Alzheimer's disease is early onset Alzheimer's disease.

In some embodiments, the subject is a human.

In one embodiment, the symptom is progressive loss of memory, progressive loss of cognition, progressive loss of reasoning and/or progressive loss of judgment.

A compound of Formula (I) or a pharmaceutically acceptable salt thereof (also referred to herein as a "Fused Morpholinopyrimidine") is useful for treating, preventing or ameliorating one or more symptoms of a neurodegenerative disease.

Exemplary neurodegenerative diseases include, but are not limited to Alzheimer's disease, early onset Alzheimer's disease, panic disorder, obsessive compulsive disorder, delusional disorder, drug-induced psychosis, post-traumatic stress disorder, age-related cognitive decline, attention deficit/hyperactivity disorder, personality disorder of the paranoid type, personality disorder of the schizoid type, dyskinesia, choreiform condition, psychosis associated with Parkinson's disease, psychotic symptoms associated with Alzheimer's disease, mood disorder, dementia, cognitive impairment, myclonus, seizures, Parkinsonism, extrapyramidal signs (EPS), apraxia, dystonia, dementia with Lewy bodies (DLB), aphasia, visual agnosia, and ataxia.

In some embodiments, the cognitive function impaired is one or more of attention, learning, delayed memory, working memory, visual learning, speed of processing, vigilance, verbal learning, visual motor function, social cognition, long term memory or executive function.

In some embodiments, the subject is 65 years old or older. In other embodiments, the subject is 55 years old or older.

In still other embodiments, the subject is 55 years old or younger, or 50 years old or younger.

A pharmaceutical composition comprising an effective amount of a Fused Morpholinopyrimidine of Formula (I) and a pharmaceutically acceptable carrier or vehicle is useful for treating or preventing a neurodegenerative disease.

In another aspect, the invention provides a compound of Formula (II)

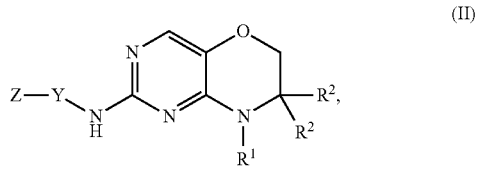

(II)

or a pharmaceutically acceptable salt thereof, wherein:
$R^1$ is —$C_1$-$C_4$ alkyl which is unsubstituted or substituted with one or more -halo; each $R^2$ is independently —$C_1$-$C_6$ alkyl, or $R^1$ and one $R^2$ together with the intervening atoms form a nitrogen-containing 4- to 6-membered nonaromatic heterocycle and the other $R^2$ is hydrogen or —$C_1$-$C_4$ alkyl, or both $R^2$ together with the intervening atom form a —$C_3$-$C_8$ monocyclic cycloalkyl or an oxygen-containing 3- to 6-membered nonaromatic heterocycle, wherein the nitrogen-containing 4- to 6-membered nonaromatic heterocycle, the —$C_3$-$C_8$ monocyclic cycloalkyl or the oxygen-containing 3- to 6-membered nonaromatic heterocycle is unsubstituted or substituted with one or more substituents independently selected from the group consisting of -halo, —CN, —$C_1$-$C_4$ alkyl, halo-substituted $C_1$-$C_4$ alkyl, —$C_1$-$C_4$ alkoxy and oxo; Y is phenyl or pyridinyl, each of which is unsubstituted or substituted with one or more substituents independently selected from the group consisting of -halo, —$C_1$-$C_4$ alkoxy, halo-substituted $C_1$-$C_4$ alkoxy, —$C_1$-$C_4$ alkyl and halo-substituted $C_1$-$C_4$ alkyl; and Z is imidazolyl or pyrazolyl, each of which is unsubstituted or substituted with one or more substituents independently selected from the group consisting of -halo and —$C_1$-$C_4$ alkyl.

In some embodiments, $R^1$ and one $R^2$ together with the intervening atoms form a nitrogen-containing 4- to 6-membered nonaromatic heterocycle which is unsubstituted or substituted with one or more substituents independently selected from the group consisting of -halo, —CN, —$C_1$-$C_4$ alkyl, halo-substituted $C_1$-$C_4$ alkyl, —$C_1$-$C_4$ alkoxy and oxo, and the other $R^2$ is hydrogen or —$C_1$-$C_4$ alkyl.

In some embodiments, both $R^2$ together with the intervening atom form a —$C_3$-$C_8$ monocyclic cycloalkyl or an oxygen-containing 3- to 6-membered nonaromatic heterocycle, wherein the —$C_3$-$C_8$ monocyclic cycloalkyl or the oxygen-containing 3- to 6-membered nonaromatic heterocycle is unsubstituted or substituted with one or more substituents independently selected from the group consisting of -halo, —CN, —$C_1$-$C_4$ alkyl, halo-substituted $C_1$-$C_4$ alkyl, —$C_1$-$C_4$ alkoxy and oxo.

In some embodiments, $R^2$ is independently —$C_1$-$C_6$ alkyl, or $R^1$ and one $R^2$ together with the intervening atoms form a nitrogen-containing 4- to 6-membered nonaromatic heterocycle and the other $R^2$ is hydrogen or —$C_1$-$C_4$ alkyl, or both $R^2$ together with the intervening atom form a —$C_3$-$C_8$ monocyclic cycloalkyl or an oxygen-containing 3- to 6-membered nonaromatic heterocycle, wherein the nitrogen-containing 4- to 6-membered nonaromatic heterocycle, the —$C_3$-$C_8$ monocyclic cycloalkyl or the oxygen-containing 3- to 6-membered nonaromatic heterocycle is unsubstituted or substituted with one or more substituents independently selected from the group consisting of -halo, —CN, —$C_1$-$C_4$ alkyl, halo-substituted $C_1$-$C_4$ alkyl, —$C_1$-$C_4$ alkoxy and oxo.

In some embodiments, $R^1$ and one $R^2$ together with the intervening atoms form a nitrogen-containing 4- to 6-membered nonaromatic heterocycle and the other $R^2$ is hydrogen or —$C_1$-$C_4$ alkyl, or both $R^2$ together with the intervening atom form a —$C_3$-$C_8$ monocyclic cycloalkyl or an oxygen-containing 3- to 6-membered nonaromatic heterocycle, wherein the nitrogen-containing 4- to 6-membered nonaromatic heterocycle, the —$C_3$-$C_8$ monocyclic cycloalkyl or the oxygen-containing 3- to 6-membered nonaromatic heterocycle is unsubstituted or substituted with one or more substituents independently selected from the group consisting of -halo, —CN, —$C_1$-$C_4$ alkyl, halo-substituted $C_1$-$C_4$ alkyl, —$C_1$-$C_4$ alkoxy and oxo.

In some embodiments, Y is phenyl or pyridinyl, each of which is unsubstituted or substituted with one or more substituents independently selected from the group consisting of -halo, —$C_1$-$C_4$ alkoxy, halo-substituted $C_1$-$C_4$ alkoxy, —$C_1$-$C_4$ alkyl and halo-substituted $C_1$-$C_4$ alkyl.

In some embodiments, Z is imidazolyl or pyrazolyl, each of which is unsubstituted or substituted with one or more substituents independently selected from the group consisting of -halo and —$C_1$-$C_4$ alkyl.

In some embodiments, $R^1$ is methyl; $R^2$ is independently —$C_1$-$C_6$ alkyl, or $R^1$ and one $R^2$ together with the intervening atoms form a nitrogen-containing 4- to 6-membered nonaromatic heterocycle and the other $R^2$ is hydrogen or —$C_1$-$C_4$ alkyl, or both $R^2$ together with the intervening atom form a —$C_3$-$C_8$ monocyclic cycloalkyl or an oxygen-containing 3- to 6-membered nonaromatic heterocycle, wherein the nitrogen-containing 4- to 6-membered nonaromatic heterocycle, the —$C_3$-$C_8$ monocyclic cycloalkyl or the oxygen-containing 3- to 6-membered nonaromatic heterocycle is unsubstituted or substituted with one or more substituents independently selected from the group consisting of -halo and oxo; Y is phenyl or pyridinyl, each of which is substituted with one or more substituent independently selected from the group consisting of -halo and —$C_1$-$C_4$ alkoxy; and Z is imidazolyl or pyrazolyl, each of which is substituted with one or more substituents independently selected from the group consisting of -halo and —$C_1$-$C_4$ alkyl.

In some embodiments, $R^1$ is methyl; $R^2$ is independently —$C_1$-$C_6$ alkyl, or $R^1$ and one $R^2$ together with the intervening atoms form a nitrogen-containing 4- to 6-membered nonaromatic heterocycle and the other $R^2$ is hydrogen or —$C_1$-$C_4$ alkyl, or both $R^2$ together with the intervening atom form a —$C_3$-$C_8$ monocyclic cycloalkyl or an oxygen-containing 3- to 6-membered nonaromatic heterocycle, wherein the nitrogen-containing 4- to 6-membered nonaromatic heterocycle, the —$C_3$-$C_8$ monocyclic cycloalkyl or the oxygen-containing 3- to 6-membered nonaromatic heterocycle is unsubstituted or substituted with one or more -halo; Y is phenyl or pyridinyl, each of which is substituted with one or more substituents independently selected from the group consisting of -halo and —$C_1$-$C_4$ alkoxy; and Z is imidazolyl or pyrazolyl, each of which is substituted with one or more substituents independently selected from the group consisting of -halo and —$C_1$-$C_4$ alkyl.

In some embodiments, $R^1$ and one $R^2$ together with the intervening atoms form a nitrogen-containing 4- to 6-membered nonaromatic heterocycle and the other $R^2$ is hydrogen or —$C_1$-$C_4$ alkyl, or both $R^2$ together with the intervening atom form a —$C_3$-$C_8$ monocyclic cycloalkyl or an oxygen-containing 3- to 6-membered nonaromatic heterocycle, wherein the nitrogen-containing 4- to 6-membered nonaromatic heterocycle, the —$C_3$-$C_8$ monocyclic cycloalkyl or the oxygen-containing 3- to 6-membered nonaromatic heterocycle is unsubstituted or substituted with two -halo.

In some embodiments, $R^1$ and one $R^2$ together with the intervening atoms form a nitrogen-containing 4- to 6-membered nonaromatic heterocycle and the other $R^2$ is hydrogen or —$C_1$-$C_4$ alkyl, or both $R^2$ together with the intervening atom form a —$C_3$-$C_8$ monocyclic cycloalkyl or an oxygen-containing 3- to 6-membered nonaromatic heterocycle, wherein the nitrogen-containing 4- to 6-membered nonaromatic heterocycle, the —$C_3$-$C_8$ monocyclic cycloalkyl or the oxygen-containing 3- to 6-membered nonaromatic heterocycle is unsubstituted or substituted with two —F.

In some embodiments, each $R^2$ is independently —$C_1$-$C_6$ alkyl.

In some embodiments, each $R^2$ is independently methyl.

In some embodiments, $R^1$ and one $R^2$ together with the intervening atoms form a nitrogen-containing 4- to 6-membered nonaromatic heterocycle and the other $R^2$ is hydrogen or —$C_1$-$C_4$ alkyl, wherein the nitrogen-containing 4- to 6-membered nonaromatic heterocycle is unsubstituted or substituted with two -halo.

In some embodiments, $R^1$ and one $R^2$ together with the intervening atoms form a nitrogen-containing 4- to 6-membered nonaromatic heterocycle and the other $R^2$ is hydrogen or —$C_1$-$C_4$ alkyl, wherein the nitrogen-containing 4- to 6-membered nonaromatic heterocycle is unsubstituted or substituted with two —F.

In some embodiments, both $R^2$ together with the intervening atom form a —$C_3$-$C_8$ monocyclic cycloalkyl or an oxygen-containing 3- to 6-membered nonaromatic heterocycle.

In some embodiments, both $R^2$ together with the intervening atom form a —$C_3$-$C_8$ monocyclic cycloalkyl or an oxygen-containing 3- to 6-membered nonaromatic heterocycle, each of which is unsubstituted or substituted with two —F.

In some embodiments, Y is phenyl or pyridinyl, each of which is unsubstituted or substituted with one or more substituents independently selected from the group consisting of -halo and —$C_1$-$C_4$ alkoxy.

In some embodiments, Y is phenyl substituted with one -halo.

In some embodiments, Y is phenyl substituted with one —F.

In some embodiments, Y is phenyl substituted with one —$C_1$-$C_4$ alkoxy.

In some embodiments, Y is phenyl substituted with one methoxy.

In some embodiments, Y is pyridinyl substituted with one —$C_1$-$C_4$ alkoxy.

In some embodiments, Y is pyridinyl substituted with one methoxy.

In some embodiments, Z is imidazolyl, which is unsubstituted or substituted with one -halo or —$C_1$-$C_4$ alkyl.

In some embodiments, Z is imidazolyl substituted with one -halo.

In some embodiments, Z is imidazolyl substituted with one —Cl.

In some embodiments, Z is imidazolyl substituted with one —$C_1$-$C_4$ alkyl.

In some embodiments, Z is imidazolyl substituted with one methyl.

In one aspect, the compound of Formula (II) is selected from the group consisting of:

N-(3-methoxy-4-(4-methyl-1H-imidazol-1-yl) phenyl)-7, 7, 8-trimethyl-7, 8-dihydro-6H-pyrimido [5, 4-b] [1, 4] oxazin-2-amine; N-(3-fluoro-4-(4-methyl-1H-imidazol-1-yl) phenyl)-7, 7, 8-trimethyl-7, 8-dihydro-6H-pyrimido [5, 4-b] [1, 4] oxazin-2-amine; N-(3-methoxy-4-(4-methyl-1H-imidazol-1-yl) phenyl)-8'-methyl-6'H, 8'H-spiro [cyclopropane-1, 7'-pyrimido [5, 4-b] [1, 4] oxazin]-2'-amine; N-(3-fluoro-4-(4-methyl-1H-imidazol-1-yl) phenyl)-8'-methyl-6'H, 8'H-spiro [cyclopentane-1, 7'-pyrimido [5, 4-b] [1, 4] oxazin]-2'-amine; N-(5-methoxy-6-(4-methyl-1H-imidazol-1-yl) pyridin-3-yl)-8'-methyl-6'H, 8'H-spiro [cyclopentane-1, 7'-pyrimido [5, 4-b] [1, 4] oxazin]-2'-amine; N-(5-methoxy-6-(4-methyl-1H-imidazol-1-yl) pyridin-3-yl)-8'-methyl-6'H, 8'H-spiro [cyclopropane-1, 7'-pyrimido [5, 4-b] [1, 4] oxazin]-2'-amine; N-(5-methoxy-6-(4-methyl-1H-imidazol-1-yl) pyridin-3-yl)-7, 7, 8-trimethyl-7, 8-dihydro-6H-pyrimido [5, 4-b] [1, 4] oxazin-2-amine; N-(3-methoxy-4-(1-methyl-1H-pyrazol-4-yl) phenyl)-8'-methyl-6'H, 8'H-spiro [cyclopentane-1, 7'-pyrimido [5, 4-b] [1, 4] oxazin]-2'-amine; N-(3-methoxy-4-(4-methyl-1H-imidazol-1-yl) phenyl)-8'-methyl-2, 3, 5, 6-tetrahydro-6'H, 8'H-spiro [pyran-4, 7'-pyrimido [5, 4-b] [1, 4] oxazin]-2'-amine; 3, 3-difluoro-N-(3-methoxy-4-(4-methyl-1H-imidazol-1-yl) phenyl)-8'-methyl-6'H, 8'H-spiro [cyclobutane-1, 7'-pyrimido [5, 4-b] [1, 4] oxazin]-2'-amine; N-(4-(4-chloro-1H-imidazol-1-yl)-3-methoxyphenyl)-3, 3-difluoro-8'-methyl-6'H, 8'H-spiro [cyclobutane-1, 7'-pyrimido [5, 4-b] [1, 4] oxazin]-2'-amine; 3, 3-difluoro-N-(5-methoxy-6-(4-methyl-1H-imidazol-1-yl) pyridin-3-yl)-8'-methyl-6'H, 8'H-spiro [cyclobutane-1, 7'-pyrimido [5, 4-b] [1, 4] oxazin]-2'-amine; (+)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine; (−)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine; (−)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine; (+)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine; (S)—N-(3-methoxy-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine; (R)—N-(3-fluoro-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine; (R)—N-(3-methoxy-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine; (S)-8, 8-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine; (S)-8, 8-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine; (R)-8, 8-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine; (+)-7, 7-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine; and (+)-7, 7-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine; or a pharmaceutically acceptable salt thereof.

In some embodiments, the compound of Formula (II) is selected from the group consisting of: N-(3-methoxy-4-(4- methyl-1H-imidazol-1-yl) phenyl)-7, 7, 8-trimethyl-7, 8-dihydro-6H-pyrimido [5, 4-b] [1, 4] oxazin-2-amine; N-(3-fluoro-4-(4-methyl-1H-imidazol-1-yl) phenyl)-7, 7, 8-trimethyl-7, 8-dihydro-6H-pyrimido [5, 4-b] [1, 4] oxazin-2-amine; N-(3-methoxy-4-(4-methyl-1H-imidazol-1-yl) phenyl)-8'-methyl-6'H, 8'H-spiro [cyclopropane-1, 7'-pyrimido [5, 4-b] [1, 4] oxazin]-2'-amine; and 3, 3-difluoro-N-(3-methoxy-4-(4-methyl-1H-imidazol-1-yl) phenyl)-8'-methyl-6'H, 8'H-spiro [cyclobutane-1, 7'-pyrimido [5, 4-b] [1, 4] oxazin]-2'-amine; or a pharmaceutically acceptable salt thereof.

In one aspect, the invention provides a pharmaceutical composition comprising a pharmaceutically acceptable carrier or vehicle and an effective amount of a compound of Formula (II) or a pharmaceutically acceptable salt thereof.

In one aspect, the invention provides a method for treating a neurodegenerative disease, comprising administering to a subject in need thereof an effective amount of a compound or a pharmaceutically acceptable salt of a compound of Formula (II).

In one aspect, the invention provides a method for treating Alzheimer's disease, comprising administering to a subject in need thereof an effective amount of a compound or a pharmaceutically acceptable salt of a compound of Formula (II).

In one aspect, the invention provides a method for improving an impaired cognitive function, comprising administering to a subject having impaired cognitive function an effective amount of a compound or a pharmaceutically acceptable salt of a compound of Formula (II). In one embodiment, the subject has impaired cognitive function relative to a healthy subject, for example a healthy subject of the same age.

In one aspect, the invention provides a method for ameliorating a symptom of Alzheimer's disease, comprising administering to a subject in need thereof an effective amount of a compound or a pharmaceutically acceptable salt of a compound of Formula (II).

In some embodiments, the symptom of Alzheimer's disease is progressive loss of memory, progressive loss of cognition, progressive loss of reasoning and/or progressive loss of judgment.

In some embodiments, Alzheimer's disease is early onset Alzheimer's disease. In some embodiments, the subject is a human.

Exemplary neurodegenerative disease include Alzheimer's disease, early onset Alzheimer's disease, panic disorder, obsessive compulsive disorder, delusional disorder, drug-induced psychosis, post-traumatic stress disorder, age-related cognitive decline, attention deficit/hyperactivity disorder, personality disorder of the paranoid type, personality disorder of the schizoid type, dyskinesia, choreiform condition, psychosis associated with Parkinson's disease, psychotic symptoms associated with Alzheimer's disease, mood disorder, dementia, cognitive impairment, myclonus, seizures, Parkinsonism, extrapyramidal signs (EPS), apraxia, dystonia, dementia with Lewy bodies (DLB), aphasia, visual agnosia, and ataxia.

In some embodiments, the cognitive function impaired is one or more of attention, learning, delayed memory, working memory, visual learning, speed of processing, vigilance, verbal learning, visual motor function, social cognition, long term memory or executive function.

In some embodiments, the subject is 65 years old or older. In other embodiments, the subject is 55 years old or older. In still other embodiments, the subject is 55 years old or younger, or 50 years old or younger.

A pharmaceutical composition comprising an effective amount of a Fused Morpholinopyrimidine of Formula (II) and a pharmaceutically acceptable carrier or vehicle is useful for treating or preventing a neurodegenerative disease.

The details of the invention are set forth in the accompanying description below.

All patents and publications cited in this specification are hereby incorporated by reference in their entirety.

5. DETAILED DESCRIPTION

5.1 Definitions and Abbreviations

The following are definitions of terms used in the present specification. The initial definition provided for a group or term herein applies to that group or term throughout the present specification individually or as part of another group, unless otherwise indicated. Unless otherwise defined, all technical and scientific terms used herein have the same meaning as commonly understood by one of ordinary skill in the art.

The term "—$C_1$-$C_4$ alkyl" as used herein, refers to a straight chain or branched non-cyclic hydrocarbon having from 1 to 4 carbon atoms, wherein one of the hydrocarbon's hydrogen atoms has been replaced by a single bond. Representative straight chain —$C_1$-$C_4$ alkyls include -methyl, -ethyl, -n-propyl and -n-butyl. Representative branched —$C_1$-$C_4$ alkyls include -isopropyl, -sec-butyl, -isobutyl and -tert-butyl.

The term "—$C_1$-$C_6$ alkyl" as used herein, refers to a straight chain or branched non-cyclic hydrocarbon having from 1 to 6 carbon atoms, wherein one of the hydrocarbon's hydrogen atoms has been replaced by a single bond. Representative straight chain —$C_1$-$C_6$ alkyls include -methyl, -ethyl, -n-propyl, -n-butyl, -n-pentyl and -n-hexyl. Representative branched —$C_1$-$C_6$ alkyls include -isopropyl, -sec-butyl, -isobutyl, -tert-butyl, -isopentyl, -neopentyl, -1-methylbutyl, -isohexyl, -neohexyl, -2-methylbutyl, -3-methylbutyl, -1,1-dimethylpropyl and -1,2-dimethylpropyl.

The term "—$C_3$-$C_8$ monocyclic cycloalkyl" as used herein, refers to a saturated cyclic hydrocarbon having from 3 to 8 carbon atoms. Representative —$C_3$-$C_8$ monocyclic cycloalkyls include -cyclopropyl, -cyclobutyl, -cyclopentyl, -cyclohexyl, -cycloheptyl and -cyclooctyl.

The term "$C_1$-$C_4$ alkylene" as used herein, refers to a straight or branched chain saturated hydrocarbon containing 1-4 carbon atoms, wherein two of the hydrocarbon's hydrogen atoms have been replaced by a single a bond. Representative $C_1$-$C_4$ alkylene groups include, methylene, ethylene, n-propylene, isopropylene, n-butylene and isobutylene.

The term "$C_1$-$C_4$ alkoxy" as used herein, refers to a $C_1$-$C_4$ alkyl-O— group wherein the $C_1$-$C_4$ alkyl is as defined above. Examples of $C_1$-$C_4$ alkoxy include, but are not limited to, methoxy, trifluoromethoxy, ethoxy, propoxy or butoxy.

The term "halo-substituted $C_1$-$C_4$ alkoxy" as used herein, refers to a $C_1$-$C_4$ alkoxy group, as defined above, wherein one or more of the $C_1$-$C_4$ alkoxy group's hydrogen atoms have been replaced with —F, —Cl, —Br or —I. Examples of a halo-substituted $C_1$-$C_4$ alkoxy include, but are not limited to, —O—$CH_2F$, —O—$CCl_3$, —O—$CF_3$, —O—$CH_2Cl$, —O—$CH_2CH_2Br$, —O—$CH_2CH_2I$, —O—$CF_2CF_3$, —O—$CH_2CH_2F$, —O—$CH_2CH_2CH_2Cl$, —O—$CH_2CH_2CH_2Br$, —O—$CH_2CH_2CH_2I$, —O—$CH_2CH(Br)CH_3$, —O—CH$_2$CH(Cl)CH$_2$CH$_3$, —O—CH(F)CH$_2$CH$_3$, —OCH$_2$CF$_3$ and —O—C(CH$_3$)$_2$(CH$_2$Cl).

The term "amino-substituted C$_1$-C$_4$ alkoxy" as used herein, refers to a C$_1$-C$_4$ alkoxy group, as defined above, wherein one or more of the C$_1$-C$_4$ alkoxy group's hydrogen atoms have been replaced with —NH$_2$. Examples of amino-substituted C$_1$-C$_4$ alkoxy include, but are not limited to, —O—CH$_2$NH$_2$, —O—CH$_2$CH$_2$NH$_2$, —O—CH(NH$_2$)CH$_3$, —O—CH$_2$CH$_2$CH$_2$NH$_2$, —O—CH$_2$CH$_2$CH$_2$CH$_2$NH$_2$, —O—CH$_2$CH(NH$_2$)CH$_3$, —O—CH(NH$_2$)CH$_2$CH$_3$ and —O—C(CH$_3$)$_2$(CH$_2$NH$_2$).

The term "nitrogen containing 3- to 7-membered monocyclic heterocycle" as used herein, refers to a monocyclic 3- to 7-membered aromatic or non-aromatic monocyclic cycloalkyl group in which one of the cycloalkyl group's ring carbon atoms has been replaced with a nitrogen atom and 0-4 of the cycloalkyl group's remaining ring carbon atoms are independently replaced with a N, O or S atom. The nitrogen-containing 3- to 7-membered monocyclic heterocycles can be attached via a nitrogen or carbon atom. Representative examples of nitrogen-containing 3- to 7-membered monocyclic heterocycles include, but are not limited to, piperidinyl, piperazinyl, pyrrolyl, piperidonyl, oxazinyl, thiazinyl, diazinyl, triazinyl, tetrazinyl, imidazolyl, tetrazolyl, pyrrolidinyl, isoxazolyl, pyridinyl, oxazolyl, thiazolyl, pyrazolyl, triazolyl, pyrimidinyl, morpholinyl, furuzanyl, pyrrolinyl, imidazolinyl, imidazolidinyl, pyrazolinyl, isothiazolyl, oxadiazolyl, thiadiazolyl, pyridazinyl, pyrazinyl, azetidine, aziridine, pyrazolidinyl and thiomorpholinyl. In one embodiment, the nitrogen-containing 3- to 7-membered monocyclic heterocycle is fully saturated or partially saturated.

A "nitrogen-containing 4- to 6-membered nonaromatic heterocycle" refers to a monocyclic 4- to 6-membered nonaromatic monocyclic cycloalkyl group in which one of the cycloalkyl group's ring carbon atoms has been replaced with a nitrogen atom and 0-3 of the cycloalkyl group's remaining ring carbon atoms are independently replaced with a N, O or S atom. The nitrogen-containing 4- to 6-membered nonaromatic heterocycles can be attached via a nitrogen or carbon atom. Representative examples of nitrogen-containing 4- to 6-membered nonaromatic heterocycles include, but are not limited to, azetidinyl, piperidinyl, piperazinyl, pyrrolinyl, oxazinyl, morpholinyl, imidazolidinyl, pyrazolidinyl and thiomorpholinyl.

An "oxygen-containing 3- to 6-membered nonaromatic heterocycle" refers to a monocyclic 3- to 6-membered nonaromatic monocyclic cycloalkyl group in which one of the cycloalkyl group's ring carbon atoms has been replaced with a oxygen atom and 0-3 of the cycloalkyl group's remaining ring carbon atoms are independently replaced with a N, O or S atom. Representative examples of oxygen-containing 3- to 6-membered nonaromatic heterocycles include, but are not limited to, oxiranyl, oxetanyl, furanyl, tetrahydrofuranyl, dihydrofuranyl, pyranyl, dihydropyranyl, tetrahydropyranyl, dioxanyl, dioxolanyl, trioxanyl and trioxolanyl.

The term "oxo" refers to =O group.

The term "3- to 7-membered monocyclic heterocycle" as used herein, refers to a monocyclic 3- to 7-membered aromatic or non-aromatic monocyclic cycloalkyl in which 1-4 of the ring carbon atoms have been independently replaced with a N, O or S atom. The 3- to 7-membered monocyclic heterocycles can be attached via a nitrogen or carbon atom. Representative examples of a 3- to 7-membered monocyclic heterocycle group include, but are not limited to, nitrogen-containing 3- to 7-membered monocyclic heterocycles discussed above, tetrahydrofuranyl, dihydrofuranyl, pyranyl, dihydropyranyl, tetrahydropyranyl, thiopyranyl, dihydrothiopyranyl, tetrahydrothiopyranyl, dioxanyl, dithianyl, trithianyl, dioxolanyl, furanyl and thiophenyl. In one embodiment, the 3- to 7-membered monocyclic heterocycle is a nitrogen-containing 3- to 7-membered monocyclic heterocycle. In another embodiment, the 3- to 7-membered monocyclic heterocycle is fully saturated or partially saturated.

The terms "halogen" or "halo" as used herein, refer to chlorine, bromine, fluorine or iodine.

The term "halo-substituted C$_1$-C$_4$ alkyl" as used herein, refers to a C$_1$-C$_4$ alkyl group, as defined above, wherein one or more of the C$_1$-C$_4$ alkyl group's hydrogen atoms have been replaced with —F, —Cl, —Br or —I. Examples of a halo-substituted C$_1$-C$_4$ alkyl include, but are not limited to, —CH$_2$F, —CCl$_3$, —CF$_3$, —CH$_2$Cl, —CH$_2$CH$_2$Br, —CH$_2$CH$_2$I, —CF$_2$CF$_3$, —CH$_2$CH$_2$CH$_2$F, —CH$_2$CH$_2$CH$_2$Cl, —CH$_2$CH$_2$CH$_2$CH$_2$Br, —CH$_2$CH$_2$CH$_2$CH$_2$I, —CH$_2$CH(Br)CH$_3$, —CH$_2$CH(Cl)CH$_2$CH$_3$, —CH(F)CH$_2$CH$_3$, —CH$_2$CF$_3$ and —C(CH$_3$)$_2$(CH$_2$Cl).

The term "amino-substituted C$_1$-C$_4$ alkyl" as used herein, refers to a C$_1$-C$_4$ alkyl group, as defined above, wherein one or more of the C$_1$-C$_4$ alkyl group's hydrogen atoms have been replaced with —NH$_2$. Examples of amino-substituted C$_1$-C$_4$ alkyl include, but are not limited to, —CH$_2$NH$_2$, —CH$_2$CH$_2$NH$_2$, —CH(NH$_2$)CH$_3$, —CH$_2$CH$_2$CH$_2$NH$_2$, —CH$_2$CH(NH$_2$)CH$_3$, —CH$_2$CH(NH$_2$)CH$_2$CH$_3$, —CH(NH$_2$)CH$_2$CH$_3$ and —C(CH$_3$)$_2$(CH$_2$NH$_2$).

The term "halo-substituted phenyl" as used herein, refers to a phenyl group, wherein one or more of the phenyl group's hydrogen atoms have been replaced with —F, —Cl, —Br or —I. The one or more —F, —Cl, —Br or —I can be in ortho, mew and/or para position. Representative examples of halo-substituted phenyl include, but are not limited to, —C$_6$H$_4$F, —C$_6$H$_3$ClF, —C$_6$H$_3$Cl$_2$, —C$_6$H$_2$F$_3$, —C$_6$HCl$_4$, —C$_6$H$_2$FCll and —C$_6$F$_5$.

The term "C$_1$-C$_4$ alkylene-phenyl" as used herein, refers to a C$_1$-C$_4$ alkyl group, as defined above, wherein one of the C$_1$-C$_4$ alkyl group's hydrogen atoms has been replaced with phenyl.

The term "hydroxy-substituted C$_1$-C$_4$ alkyl" as used herein, refers to a C$_1$-C$_4$ alkyl group, as defined above, wherein one or more of the C$_1$-C$_4$ alkyl group's hydrogen atoms have been replaced with —OH. Representative examples of a hydroxy-substituted C$_1$-C$_4$ alkyl include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH(OH)CH$_3$, —CH$_2$CH(OH)CH$_2$CH$_3$, —CH(OH)CH$_2$CH$_3$ and —C(CH$_3$)$_2$(CH$_2$OH).

Unless otherwise indicated, any heteroatom with unsatisfied valences is assumed to have hydrogen atoms sufficient to satisfy the valences.

The phrase "pharmaceutically acceptable carrier or vehicle" as used herein, refers to a pharmaceutically acceptable material, composition or vehicle, such as a liquid or solid filler, diluent, excipient, solvent or encapsulating material, involved in carrying or transporting the Fused Morpholinopyrimidine from one organ, or portion of the body, to another organ, or portion of the body. Each carrier or vehicle must be "acceptable" in the sense of being compatible with the other ingredients of the formulation and not injurious to the subject. Some examples of materials which can serve as pharmaceutically acceptable carriers or vehicles include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as butylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The compounds described herein may form salts which are also within the scope of this invention. Reference to a compound described herein is understood to include reference to salts thereof, unless otherwise indicated. The term "salt(s)", as employed herein, denotes acidic and/or basic salts formed with inorganic and/or organic acids and bases. In addition, when a compound described herein contains both a basic moiety, such as, but not limited to, amine, pyridine or imidazole and an acidic moiety, such as, but not limited to, a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds described herein may be formed, for example, by reacting a compound with an amount of acid or base, such as an equivalent amount, in a medium, such as one in which the salt precipitates or in an aqueous medium followed by lyophilization.

The compounds described herein which contain a basic moiety, such as, but not limited to, an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates, such as tosylates, undecanoates and the like.

The compounds described herein which contain an acidic moiety, such as, but not limited to, a carboxylic acid, may form salts with a variety of organic and inorganic bases. Exemplary basic salts include ammonium salts, alkali metal salts, such as sodium, lithium and potassium salts, alkaline earth metal salts, such as calcium and magnesium salts, salts with organic bases (for example, organic amines), such as benzathines, dicyclohexylamines, hydrabamines (formed with N,N-bis(dehydroabietyl) ethylenediamine), N-methyl-D-glucamines, N-methyl-D-glycamides, t-butyl amines and salts with amino acids, such as arginine, lysine and the like. Basic nitrogen-containing groups may be quaternized with agents, such as lower alkyl halides (e.g., methyl, ethyl, propyl and butyl chlorides, bromides and iodides), dialkyl sulfates (e.g., dimethyl, diethyl, dibutyl and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds described herein are also contemplated herein. The term "prodrug" as employed herein denotes a compound that, upon administration to a subject, undergoes chemical conversion by metabolic or chemical processes to yield a compound described herein, or a salt and/or solvate thereof. Solvates of the compounds described herein include, for example, hydrates.

Compounds described herein are, subsequent to their preparation, preferably isolated and purified to afford a composition containing an amount by weight equal to or greater than 90%, for example, equal to or greater than 95%, equal to or greater than 97%, equal to or greater than 98%, or equal to or greater than 99% of the compounds ("substantially pure" compounds), which is then used or formulated as described herein. Such "substantially pure" compounds described herein are also contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds described herein may, for example, be substantially free of other isomers (e.g., as a pure or substantially pure optical isomer having a specified activity), or may be admixed, for example, as racemates or with all other, or other selected, stereoisomers. The chiral centers of the compounds described herein may have the S or R configuration as defined by the International Union of Pure and Applied Chemistry (IUPAC) 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

If, for instance, a particular enantiomer of a compound described herein is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

All configurational isomers of the compounds described herein are contemplated, either in admixture or in pure or substantially pure form. Certain compounds described herein may exist in particular geometric or stereoisomeric forms. The present invention contemplates all such compounds, including cis- and trans-isomers, cis (Z) and trans (E) alkene isomers R- and S-enantiomers, diastereomers, (D)-isomers, (L)-isomers, the racemic mixtures thereof, and other mixtures thereof, as falling within the scope of the invention. Additional asymmetric carbon atoms may be present in a substituent, such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

Throughout the specifications, groups and substituents thereof may be chosen to provide stable moieties and compounds. Compounds useful in the treatment, for example, are neurodegenerative disorders. The term "stable", as used herein, refers to compounds which possess stability sufficient to allow manufacture and which maintain the integrity of the compound for a sufficient period of time to be detected and preferably for a sufficient period of time to be useful for the purposes detailed herein.

Definitions of specific functional groups and chemical terms are described in more detail above. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999, the entire contents of which are incorporated herein by reference.

In some embodiments, the present invention also includes isotopically labeled compounds, which are identical to the compounds disclosed herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorous, sulfur, fluorine and chlorine, such as $^2$H, $^3$H, $^{13}$C, $^{11}$C, $^{14}$C, $^{15}$N, $^{18}$O, $^{17}$O, $^{31}$P, $^{32}$P, $^{35}$S, $^{18}$F and $^{36}$Cl, respectively. Compounds described herein, or an enantiomer, diastereomer, tautomer, or pharmaceutically acceptable salt or solvate thereof, which contain the aforementioned isotopes and/or other isotopes of other atoms, are within the scope of this invention. Certain isotopically labeled compounds described herein, for example those into which radioactive isotopes, such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes, such as deuterium, i.e., $^2$H, can afford certain therapeutic advantages resulting from greater metabolic stability, for example increased in vivo half-life or reduced dosage requirements, and hence, may be preferred in some circumstances. Isotopically labeled compounds can generally be prepared by carrying out the procedures disclosed in the Schemes and/or in the Examples below, by substituting a readily available isotopically labeled reagent for a non-isotopically labeled reagent.

When more than one position in any given structure may be substituted with more than one substituent selected from a specified group, the substituent may be either the same or different at every position.

As used herein, "effective amount" refers to any amount that is necessary or sufficient for achieving or promoting a desired outcome, e.g., for treating, preventing, or ameliorating a symptom of a neurodegenerative disease. In some instances an effective amount is a therapeutically effective amount. A therapeutically effective amount is any amount that is necessary or sufficient for promoting or achieving a desired biological response in a subject. The effective amount for any particular application can vary depending on such factors as the disease or condition being treated, the particular agent being administered, the size of the subject, or the severity of the disease or condition.

As used herein, "treat" or "treating" includes reducing or ameliorating a symptom of a neurodegenerative disease, for example, improving cognitive function.

As used herein, the term "subject" refers to a vertebrate animal. In one embodiment the subject is a mammal. In one embodiment the subject is a human. In other embodiments the subject is a non-human vertebrate animal, including, without limitation, non-human primates, laboratory animals, livestock, domesticated animals and non-domesticated animals. Non-limiting examples of subject include a mammal, e g, a human, mouse, rat, guinea pig, dog, cat, horse, cow, pig, and non-human primate, such as a monkey, chimpanzee, baboon or rhesus. In one embodiment, the subject is a human.

Practitioners of the art will recognize that certain chemical groups may exist in multiple tautomeric forms (for example, as an amide or imino ether). The scope of this disclosure is meant to include all such tautomeric forms. For example, a tetrazole may exist in two tautomeric forms, 1-H tetrazole and a 2-H tetrazole. This is depicted in the figure below. This example is not meant to be limiting in the scope of tautomeric forms.

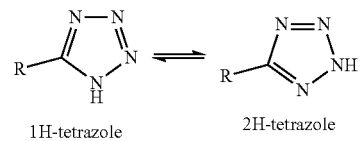

1H-tetrazole    2H-tetrazole

Practitioners of the art will recognize that certain electrophilic ketones, may exist in a hydrated form. The scope of this disclosure is to include all such hydrated forms. For example, a trifluoromethyl ketone may exist in a hydrated form via addition of water to the carbonyl group. This is depicted in the figure below. This example is not meant to be limiting in the scope of hydrated forms.

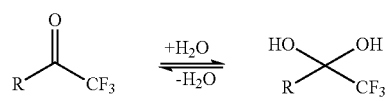

ABBREVIATIONS

Abbreviations used in the following examples and preparations include:

| | |
|---|---|
| Aβ | Amyloid-beta |
| Ac | Acyl (Me-C(O)-) |
| AD | Alzheimer's Disease |
| APP | Amyloid Precursor Protein |
| Aq | Aqueous |

-continued

| | |
|---|---|
| BINAP | 2,2'-Bis(diphenylphosphino)-1,1'-binaphthyl |
| Boc | Tert-butyloxycarbonyl |
| Bn | Benzyl |
| BSA | Bovine Serum Albumin |
| Bu | Butyl |
| c | Cyclo |
| cBu | Cylcobutyl |
| CBZ | Carboxybenzyl |
| Conc. | Concentrated |
| cPr | Cyclopropyl |
| CSF | Cerebrospinal Fluid |
| DAPT | N-[N-(3,5-Difluorophenacetyl-L-alanyl)]-(S)-phenylglycine t-butyl ester |
| DAST | Diethylaminosulfur Trifluoride |
| dba | Dibenzylideneacetone |
| DBU | 1,8-Diazabicyclo[5.4.0]undec-7-ene |
| DCC | Dicyclohexylcarbodiimide |
| DCE | 1, 2-Dichloroethane |
| DEA | Di-ethylamine |
| DIAD | Diisopropyl Azodicarboxylate |
| DIPEA | N, N-Diisopropylethylamine |
| DME | 1,2-Dimethoxyethane |
| DMF | Dimethylformamide |
| DMP | Dess-Martin Periodinane |
| DMSO | Dimethyl Sulfoxide |
| DPPA | Diphenylphosphorylazide |
| dppf | 1,1'-Bis(diphenylphosphino)ferrocene |
| ELISA | Enzyme-Linked Immuno Sorbent Assay |
| Et | Ethyl |
| Et₃N | Triethylamine |
| Eq. | Equivalent |
| g | grams(s) |
| HPLC | High Pressure Liquid Chromatography |
| h | Hour(s) |
| IPA | Isopropyl alcohol |
| i.v. or IV | Intravenous |
| LAH | Lithium Aluminum Hydride |
| LCMS | Liquid Chromatography-Mass Spectrometry |
| LG | Leaving Group |
| m | Multiplet |
| Me | Methyl |
| MeOH | Methyl Alcohol or Methanol |
| min | Minute(s) |
| mmol | Millimoles |
| μl | Microliter |
| ul | Microliter |
| Ms | Mesylate |
| MS | Mass Spectrometry |
| MW | Molecular Weight (all values are ±0.05) |
| n | Normal |
| N | Normal |
| NBS | N-Bromosuccinimide |
| NMP | 1-Methylpyrrolidin-2-one |
| NMR | Nuclear Magnetic Resonance |
| NSAIDS | Non-Steroidal Anti-Inflammatory Drugs |
| o/n | Overnight |
| PMB | Para-methoxybenzyl |
| PBS | Phosphate Buffered Saline |
| Py | Pyridine |
| Ra-Ni | Raney Nickel |
| RT (or rt) | Room Temperature (about 20-25°C.) |
| s | Singlet |
| sat. | Saturated |
| t | Triplet |
| TBAF | Tetra-N-butylammonium Fluoride |
| TBS | Tert-butyldimethylsilyl |
| t-Bu | Tertiary Butyl |
| tert | Tertiary |
| Tf | Triflate |
| TFA | Trifluoroacetic Acid |
| THF | Tetrahydrofuran |
| TLC | Thin Layer Chromatography |
| TMS | Trimethylsilyl |
| TPP | Triphenylphosphine |
| Ts | Tosylate |
| v/v | Volume/volume |
| wt/v | Weight/volume |

5.2 Fused Morpholinopyrimidines

Described below are Fused Morpholinopyrimidines, i.e., compounds according to Formula (I) and Formula (II) and pharmaceutically acceptable salts thereof, as well as methods for preparing the compounds and using the compounds to treat one or more neurodegenerative diseases, e.g., reducing a symptom of Alzheimer's disease (such as improving cognitive function). The compounds of the disclosure are believed to be gamma secretase modulators (GSMs), i.e., compounds that act to shift the relative levels of Aβ peptides produced by γ-secretase. In some embodiments, the compounds alter the relative levels of Aβ peptides produced by γ-secretase, for example the level of Aβ42 peptide, without significantly changing the total level of Aβ peptides produced.

In one aspect, described herein are compounds according to Formula (I), below:

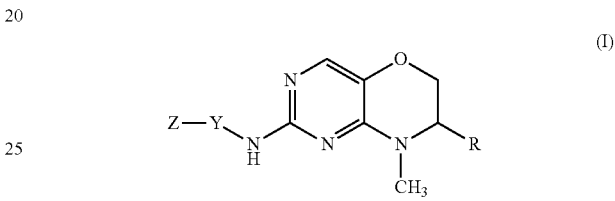

(I)

and pharmaceutically-acceptable salts thereof, wherein R, Y and Z are as defined above for the compounds of Formula (I).

In some embodiments, R is phenyl, —$C_1$-$C_4$ alkylene-phenyl, oxetanyl, —$C_1$-$C_6$ alkyl, —$C_3$-$C_8$ monocyclic cycloalkyl, —$C_1$-$C_4$ alkylene-$C_3$-$C_8$ monocyclic cycloalkyl, 3- to 7-membered monocyclic heterocycle, —$C_1$-$C_4$ alkylene 3- to 7-membered monocyclic heterocycle, each of which is unsubstituted or substituted with one or more substituents independently selected from the group consisting of -halo, —CN, —$NH_2$, —OH, oxo, —$C_1$-$C_4$ alkyl, halo-substituted $C_1$-$C_4$ alkyl, amino-substituted $C_1$-$C_4$ alkyl, —NH—$C_1$-$C_4$ alkyl, —NHC(O)—$C_1$-$C_4$ alkyl, —C(O)NH—$C_1$-$C_4$ alkyl, —C(O)N($C_1$-$C_4$ alkyl)$_2$, hydroxy-substituted $C_1$-$C_4$ alkyl, —S(O)$_2$—$C_1$-$C_4$ alkyl, —S(O)$_2$-halo-substituted $C_1$-$C_4$ alkyl, —S(O)$_2$—NH—$C_1$-$C_4$ alkyl, —S(O)$_2$—N($C_1$-$C_4$ alkyl)$_2$, —NH—S(O)$_2$—$C_1$-$C_4$ alkyl, —N($C_1$-$C_4$ alkyl)-S(O)$_2$—$C_1$-$C_4$ alkyl, —$C_1$-$C_4$ alkoxy, halo-substituted $C_1$-$C_4$ alkoxy, 3- to 7-membered monocyclic heterocycle, —$C_3$-$C_8$ monocyclic cycloalkyl, —C(O)NH$_2$ and -phenoxy, provided that phenyl is not substituted with one or more oxo; Y is phenyl or pyridinyl which is unsubstituted or substituted with one or more substituents independently selected from the group consisting of -halo, —$C_1$-$C_4$ alkoxy, halo-substituted $C_1$-$C_4$ alkoxy, —$C_1$-$C_4$ alkyl, halo-substituted $C_1$-$C_4$ alkyl, amino-substituted $C_1$-$C_4$ alkoxy, —CN, ($C_1$-$C_4$ alkyl)$_2$N—$C_1$-$C_4$ alkoxy, —NH—$C_1$-$C_4$ alkyl, —OH and —$NH_2$; and Z is —CN or nitrogen-containing 3- to 7-membered monocyclic heterocycle which is unsubstituted or substituted with one or more substituents independently selected from the group consisting of -halo, —CN, —$NH_2$, —OH, —$C_1$-$C_4$ alkyl, halo-substituted $C_1$-$C_4$ alkyl, —$C_1$-$C_4$ alkoxy, —$OCF_3$ and 3- to 7-membered monocyclic heterocycle.

In some embodiments, R is phenyl, —$C_1$-$C_4$ alkylene-phenyl, oxetanyl, —$C_1$-$C_6$ alkyl, —$C_3$-$C_8$ monocyclic cycloalkyl, nitrogen containing 3- to 7-membered monocyclic heterocycle, —$C_1$-$C_4$ alkylene-nitrogen-containing 3- to 7-membered monocyclic heterocycle or —$C_1$-$C_4$ alkylene- $C_3$-$C_8$ monocyclic cycloalkyl, each of which is unsubstituted or substituted with one or more substituents independently selected from the group consisting of -halo, —CN, —NH$_2$, —OH, —$C_1$-$C_4$ alkyl, halo-substituted $C_1$-$C_4$ alkyl, amino-substituted $C_1$-$C_4$ alkyl, —NH—$C_1$-$C_4$ alkyl, —NHC(O)—$C_1$-$C_4$ alkyl, —C(O)NH—$C_1$-$C_4$ alkyl, —C(O)N($C_1$-$C_4$ alkyl)$_2$, hydroxy-substituted $C_1$-$C_4$ alkyl, —S(O)$_2$—$C_1$-$C_4$ alkyl, —S(O)$_2$-halo-substituted $C_1$-$C_4$ alkyl, —S(O)$_2$—NH—$C_1$-$C_4$ alkyl, —S(O)$_2$—N($C_1$-$C_4$ alkyl)$_2$, —NH—S(O)$_2$—$C_1$-$C_4$ alkyl, —N($C_1$-$C_4$ alkyl)-S(O)$_2$—$C_1$-$C_4$ alkyl, —$C_1$-$C_4$ alkoxy, halo-substituted $C_1$-$C_4$ alkoxy, 3- to 7-membered monocyclic heterocycle, —$C_3$-$C_8$ monocyclic cycloalkyl and —C(O)NH$_2$.

In some embodiments, R is phenyl, —$C_1$-$C_4$ alkylene-phenyl, oxetanyl, —$C_1$-$C_6$ alkyl, —$C_3$-$C_8$ monocyclic cycloalkyl, nitrogen containing 3- to 7-membered monocyclic heterocycle, —$C_1$-$C_4$ alkylene nitrogen-containing 3- to 7-membered monocyclic heterocycle or —$C_1$-$C_4$ alkylene-$C_3$-$C_8$ monocyclic cycloalkyl, each of which is unsubstituted or substituted with one or more substituents independently selected from the group consisting of -halo, —CN, —NH$_2$, —OH, —$C_1$-$C_4$ alkyl, halo-substituted $C_1$-$C_4$ alkyl, amino-substituted $C_1$-$C_4$ alkyl, —NH—$C_1$-$C_4$ alkyl, —NHC(O)—$C_1$-$C_4$ alkyl, —C(O)NH—$C_1$-$C_4$ alkyl, —C(O)N($C_1$-$C_4$ alkyl)$_2$, hydroxy-substituted $C_1$-$C_4$ alkyl, —S(O)$_2$—$C_1$-$C_4$ alkyl, —S(O)$_2$-halo-substituted $C_1$-$C_4$ alkyl, —S(O)$_2$—NH—$C_1$-$C_4$ alkyl, —S(O)$_2$—N($C_1$-$C_4$ alkyl)$_2$, —NH—S(O)$_2$—$C_1$-$C_4$ alkyl, —N($C_1$-$C_4$ alkyl)-S(O)$_2$—$C_1$-$C_4$ alkyl, —$C_1$-$C_4$ alkoxy, halo-substituted $C_1$-$C_4$ alkoxy, 3- to 7-membered monocyclic heterocycle, —$C_3$-$C_8$ monocyclic cycloalkyl, —C(O)NH$_2$.

In some embodiments, R is phenyl, tetrahydropyranyl, —$C_1$-$C_4$ alkyl, —$C_1$-$C_4$ alkylene-phenyl or oxetanyl, each of which is unsubstituted or substituted with one or more substituents independently selected from the group consisting of halo, —$C_1$-$C_4$ alkyl, halo-substituted $C_1$-$C_4$ alkyl, —$C_1$-$C_4$ alkoxy and halo-substituted $C_1$-$C_4$ alkoxy.

In some embodiments, Y is phenyl which is unsubstituted or substituted with one or more substituents independently selected from the group consisting of halo and —$C_1$-$C_4$ alkoxy.

In some embodiments, Z is pyridinyl or imidazolyl, each of which is unsubstituted or substituted with one or more —$C_1$-$C_4$ alkyl or halo.

In some embodiments, R is phenyl, tetrahydropyranyl, —$C_1$-$C_4$ alkyl, —$C_1$-$C_4$ alkylene-phenyl, each of which is unsubstituted or substituted with one or more substituents independently selected from the group consisting of halo, —$C_1$-$C_4$ alkyl, halo-substituted $C_1$-$C_4$ alkyl and halo-substituted $C_1$-$C_4$ alkoxy; Y is phenyl which is unsubstituted or substituted with one or more substituents independently selected from the group consisting of halo and —$C_1$-$C_4$ alkoxy; and Z is pyridinyl or imidazolyl, each of which is substituted with one —$C_1$-$C_4$ alkyl or halo.

In some embodiments, R is phenyl which is unsubstituted or substituted with one or more substituents independently selected from the group consisting of halo and —$C_1$-$C_4$ alkyl; Y is phenyl substituted with one or more substituents independently selected from the group consisting of halo and —$C_1$-$C_4$ alkoxy; and Z is imidazolyl substituted with methyl or halo.

In some embodiments, R is phenyl which is unsubstituted or substituted with one or more substituents independently selected from the group consisting of halo and —$C_1$-$C_4$ alkyl; Y is phenyl substituted with one or more substituents independently selected from the group consisting of halo and —$C_1$-$C_4$ alkoxy; and Z is pyridinyl substituted with methyl or chloro.

In some embodiments, R is phenyl which is unsubstituted.

In some embodiments, R is phenyl substituted with two to three —F.

In some embodiments, R is phenyl substituted with one methyl.

In some embodiments, R is tetrahydropyranyl which is unsubstituted; Y is phenyl substituted with one or more substituents independently selected from the group consisting of halo and —$C_1$-$C_4$ alkoxy; and Z is imidazolyl substituted with —$C_1$-$C_4$ alkyl.

In some embodiments, R is phenyl substituted with one —$C_1$-$C_4$ alkyl.

In some embodiments, each —$C_1$-$C_4$ alkyl is methyl.

In some embodiments, each —$C_1$-$C_4$ alkoxy is methoxy.

In some embodiments, Y is phenyl which is unsubstituted or substituted with one or more substituents independently selected from the group consisting of halo and —$C_1$-$C_4$ alkoxy.

In some embodiments, Y is phenyl which is unsubstituted.

In some embodiments, Y is phenyl substituted with one —F.

In some embodiments, Y is phenyl substituted with one methoxy.

In some embodiments, Z is pyridinyl, which is unsubstituted or substituted with one to three —$C_1$-$C_4$ alkyl.

In some embodiments, Z is pyridinyl substituted with one to three methyl.

In some embodiments, Z is pyridinyl substituted with one methyl.

In some embodiments, Z is imidazolyl, which is unsubstituted or substituted with one to three —$C_1$-$C_4$ alkyl.

In some embodiments, Z is imidazolyl substituted with one to three methyl.

In some embodiments, Z is imidazolyl substituted with one methyl.

In some embodiments, R is phenyl, —$C_1$-$C_4$ alkylene-phenyl, oxetanyl, —$C_1$-$C_6$ alkyl, —$C_3$-$C_8$ monocyclic cycloalkyl, —$C_1$-$C_4$ alkylene-$C_3$-$C_8$ monocyclic cycloalkyl, 3- to 7-membered monocyclic heterocycle, —$C_1$-$C_4$ alkylene-3- to 7-membered monocyclic heterocycle, each of which is unsubstituted or substituted with one or more substituents independently selected from the group consisting of -halo, —CN, —NH$_2$, —OH, oxo, —$C_1$-$C_4$ alkyl, halo-substituted $C_1$-$C_4$ alkyl, amino-substituted $C_1$-$C_4$ alkyl, —NH—$C_1$-$C_4$ alkyl, —NHC(O)—$C_1$-$C_4$ alkyl, —C(O)NH—$C_1$-$C_4$ alkyl, —C(O)N($C_1$-$C_4$ alkyl)$_2$, hydroxy-substituted $C_1$-$C_4$ alkyl, —S(O)$_2$—$C_1$-$C_4$ alkyl, —S(O)$_2$-halo-substituted $C_1$-$C_4$ alkyl, —S(O)$_2$—NH—$C_1$-$C_4$ alkyl, —S(O)$_2$—N($C_1$-$C_4$ alkyl)$_2$, —NH—S(O)$_2$—$C_1$-$C_4$ alkyl, —N($C_1$-$C_4$ alkyl)-S(O)$_2$—$C_1$-$C_4$ alkyl, —$C_1$-$C_4$ alkoxy, halo-substituted $C_1$-$C_4$ alkoxy, 3- to 7-membered monocyclic heterocycle, —$C_3$-$C_8$ monocyclic cycloalkyl, —C(O)NH$_2$ and -phenoxy, provided that phenyl is not substituted with one or more oxo.

In some embodiments, R is phenyl, oxetanyl, —$C_1$-$C_6$ alkyl, —$C_3$-$C_8$ monocyclic cycloalkyl, —$C_1$-$C_4$ alkylene-$C_3$-$C_8$ monocyclic cycloalkyl or 3- to 7-membered monocyclic heterocycle, each of which is unsubstituted or substituted with one or more substituents independently selected from the group consisting of -halo, —OH, oxo, —$C_1$-$C_4$ alkyl, halo-substituted $C_1$-$C_4$ alkyl, —$C_1$-$C_4$ alkoxy, halo-substituted $C_1$-$C_4$ alkoxy and -phenoxy, provided that phenyl is not substituted with one or more oxo.

In some embodiments, R is phenyl, —C$_1$-C$_6$ alkyl, —C$_3$-C$_8$ monocyclic cycloalkyl, —C$_1$-C$_4$ alkylene-C$_3$-C$_8$ monocyclic cycloalkyl, each of which is unsubstituted or substituted with one or more substituents independently selected from the group consisting of -halo, —C$_1$-C$_4$ alkyl, halo-substituted C$_1$-C$_4$ alkyl, —C$_1$-C$_4$ alkoxy and -phenoxy.

In some embodiments, R is phenyl substituted with one to three substituents independently selected from the group consisting of -halo, —C$_1$-C$_4$ alkyl, halo-substituted C$_1$-C$_4$ alkyl and —C$_1$-C$_4$ alkoxy.

In some embodiments, R is —C$_1$-C$_6$ alkyl, —C$_3$-C$_8$ monocyclic cycloalkyl, —C$_1$-C$_4$ alkylene-C$_3$-C$_8$ monocyclic cycloalkyl, each of which is unsubstituted or substituted with one or more substituents independently selected from the group consisting of -halo, —C$_1$-C$_4$ alkyl, halo-substituted C$_1$-C$_4$ alkyl and -phenoxy.

In some embodiments, Y is phenyl or pyridinyl, each of which is unsubstituted or substituted with one or more substituents independently selected from the group consisting of -halo, —C$_1$-C$_4$ alkoxy, halo-substituted C$_1$-C$_4$ alkoxy, —C$_1$-C$_4$ alkyl, halo-substituted C$_1$-C$_4$ alkyl, amino-substituted C$_1$-C$_4$ alkoxy, —CN, (C$_1$-C$_4$ alkyl)$_2$N—C$_1$-C$_4$ alkoxy, —NH—C$_1$-C$_4$ alkyl, —OH and —NH$_2$.

In some embodiments, Y is phenyl or pyridinyl which is unsubstituted or substituted with one or more substituents independently selected from the group consisting of -halo, —C$_1$-C$_4$ alkoxy, halo-substituted C$_1$-C$_4$ alkoxy, halo-substituted C$_1$-C$_4$ alkyl and —CN.

In some embodiments, Y is phenyl or pyridinyl, each of which is substituted with one substituent independently selected from the group consisting of -halo, —C$_1$-C$_4$ alkoxy and —CN.

In some embodiments, Y is phenyl which is substituted with -halo, —C$_1$-C$_4$ alkoxy or —CN.

In some embodiments, Y is pyridinyl which is substituted with -halo or —C$_1$-C$_4$ alkoxy.

In some embodiments, Z is —CN or nitrogen-containing 3- to 7-membered monocyclic heterocycle which is unsubstituted or substituted with one or more substituents independently selected from the group consisting of -halo, —CN, —NH$_2$, —OH, —C$_1$-C$_4$ alkyl, halo-substituted C$_1$-C$_4$ alkyl, —C$_1$-C$_4$ alkoxy, —OCF$_3$ and 3- to 7-membered monocyclic heterocycle.

In some embodiments, Z is —CN or nitrogen-containing 3- to 7-membered monocyclic heterocycle which is unsubstituted or substituted with one or more substituents independently selected from the group consisting of -halo, —CN, —C$_1$-C$_4$ alkyl and halo-substituted C$_1$-C$_4$ alkyl.

In some embodiments, Z is nitrogen-containing 3- to 7-membered monocyclic heterocycle which is unsubstituted or substituted with one or more substituents independently selected from the group consisting of -halo, —CN, —C$_1$-C$_4$ alkyl and halo-substituted C$_1$-C$_4$ alkyl.

In some embodiments, Z is nitrogen-containing 3- to 7-membered monocyclic heterocycle which is substituted with one or more substituents independently selected from the group consisting of -halo, —C$_1$-C$_4$ alkyl and halo-substituted C$_1$-C$_4$ alkyl.

In some embodiments, Z is imidazolyl, pyrimidinyl, pyrazolyl, triazolyl, each of which is unsubstituted or substituted with one or more substituents independently selected from the group consisting of -halo, —CN, —C$_1$-C$_4$ alkyl and halo-substituted C$_1$-C$_4$ alkyl.

In some embodiments, Z is imidazolyl or triazolyl, each of which is substituted with one substituent independently selected from the group consisting of -halo, —CN, —C$_1$-C$_4$ alkyl and halo-substituted C$_1$-C$_4$ alkyl.

In some embodiments, Z is imidazolyl or triazolyl, each of which is substituted with one substituent independently selected from the group consisting of -halo, —C$_1$-C$_4$ alkyl and halo-substituted C$_1$-C$_4$ alkyl.

In some embodiments, Z is imidazolyl substituted with one substituent independently selected from the group consisting of -halo, —C$_1$-C$_4$ alkyl and halo-substituted C$_1$-C$_4$ alkyl.

In some embodiments, Z is triazolyl substituted with one —C$_1$-C$_4$ alkyl.

In some embodiments, the compound of Formula (I) is a compound selected from the compounds in Table I.

TABLE I

Exemplary Fused Morpholinopyrimidines of Formula (I)

| Compound of Example | Structure | Name |
|---|---|---|
| 21A | 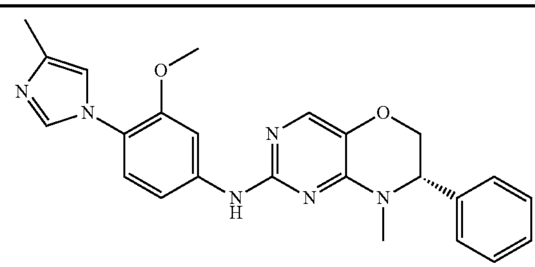 | (S)-N-(3-methoxy-4-(4-methyl-1H-imidazol-1-yl)phenyl)-8-methyl-7-phenyl-7,8-dihydro-6H-pyrimido[5,4-b][1,4]oxazin-2-amine |
| 21B | 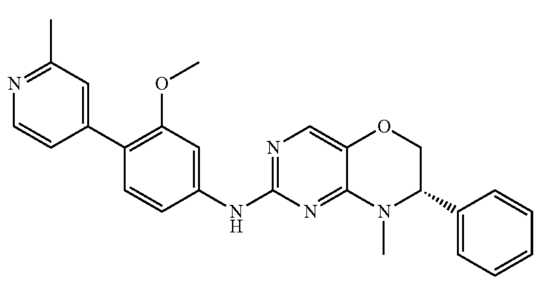 | (S)-N-(3-methoxy-4-(2-methylpyridin-4-yl)phenyl)-8-methyl-7-phenyl-7,8-dihydro-6H-pyrimido[5,4-b][1,4]oxazin-2-amine |

TABLE I-continued

Exemplary Fused Morpholinopyrimidines of Formula (I)

| Compound of Example | Structure | Name |
|---|---|---|
| 22A | 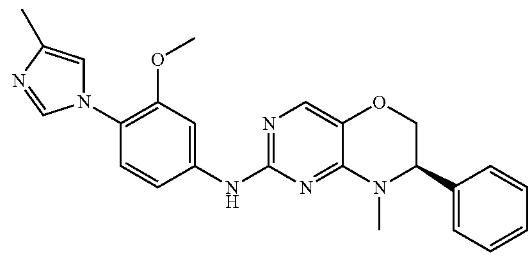 [SMILES: COc1cc(Nc2ncc3c(n2)N(C)[C@H](c2ccccc2)CO3)ccc1-n1cnc(C)c1] | (R)-N-(3-methoxy-4-(4-methyl-1H-imidazol-1-yl)phenyl)-8-methyl-7-phenyl-7,8-dihydro-6H-pyrimido [5,4-b][1,4]oxazin-2- amine |
| 22B | 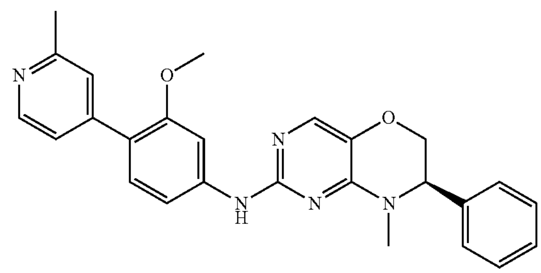 [SMILES: COc1cc(Nc2ncc3c(n2)N(C)[C@H](c2ccccc2)CO3)ccc1-c1ccnc(C)c1] | (R)-N-(3-methoxy-4-(2-methylpyridin-4-yl)phenyl)-8-methyl-7-phenyl-7,8-dihydro-6H-pyrimido [5,4-b][1,4]oxazin-2-amine |
| 23 | 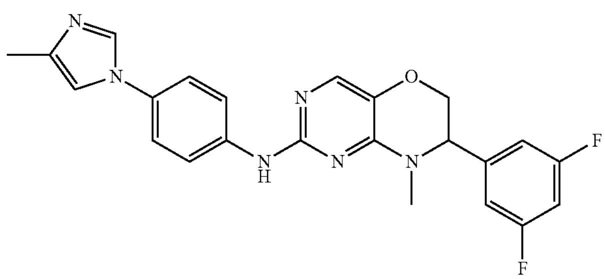 [SMILES: Cc1cn(-c2ccc(Nc3ncc4c(n3)N(C)C(c3cc(F)cc(F)c3)CO4)cc2)cn1] | 7-(3,5-difluorophenyl)-8-methyl-N-(4-(4-methyl-1H-imidazol-1-yl)phenyl)-7,8-dihydro-6H-pyrimido[5,4-b][1,4]oxazin-2-amine (racemic) |
| 23A | 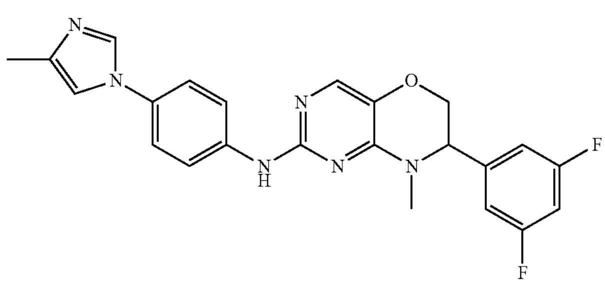 [SMILES: Cc1cn(-c2ccc(Nc3ncc4c(n3)N(C)C(c3cc(F)cc(F)c3)CO4)cc2)cn1] | (−)-7-(3, 5-difluorophenyl)-8-methyl-N-(4-(4-methyl-1H-imidazol-1-yl) phenyl)-7, 8-dihydro-6H-pyrimido [5, 4-b] [1, 4]oxazin-2-amine |
| 23B | 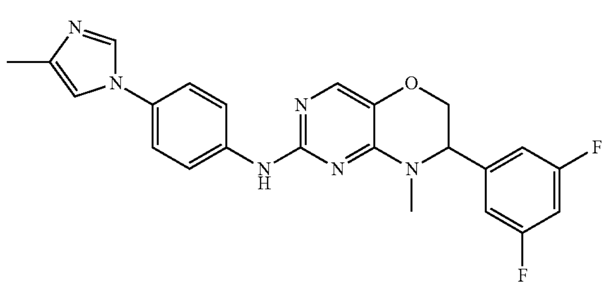 [SMILES: Cc1cn(-c2ccc(Nc3ncc4c(n3)N(C)C(c3cc(F)cc(F)c3)CO4)cc2)cn1] | (+)-7-(3, 5-difluorophenyl)-8-methyl-N-(4-(4-methyl-1H-imidazol-1-yl) phenyl)-7, 8-dihydro-6H-pyrimido[5, 4-b] [1, 4]oxazin-2-amine |

TABLE I-continued

Exemplary Fused Morpholinopyrimidines of Formula (I)

| Compound of Example | Structure | Name |
|---|---|---|
| 24 | 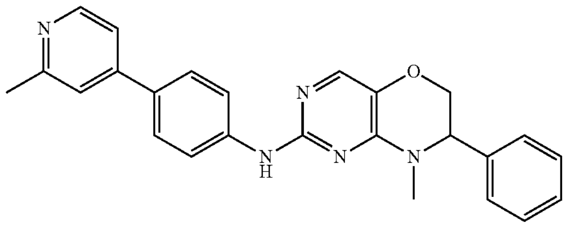 [SMILES: Cc1cc(-c2ccc(Nc3ncc4c(n3)N(C)C(c3ccccc3)CO4)cc2)ccn1] | 8-methyl-N-(4-(2-methylpyridin-4-yl)phenyl)-7-phenyl-7,8-dihydro-6H-pyrimido[5,4-b][1,4]oxazin-2-amine (racemic) |
| 24A | 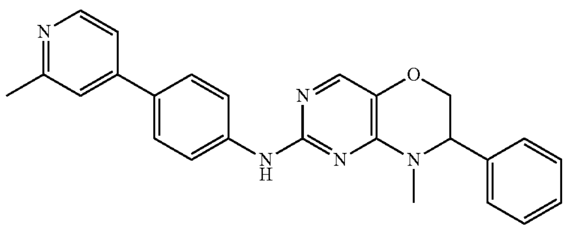 [SMILES: Cc1cc(-c2ccc(Nc3ncc4c(n3)N(C)C(c3ccccc3)CO4)cc2)ccn1] | (+)-8-methyl-N-(4-(2-methylpyridin-4-yl)phenyl)-7-phenyl-7,8-dihydro-6H-pyrimido[5,4-b][1,4]oxazin-2-amine |
| 24B | 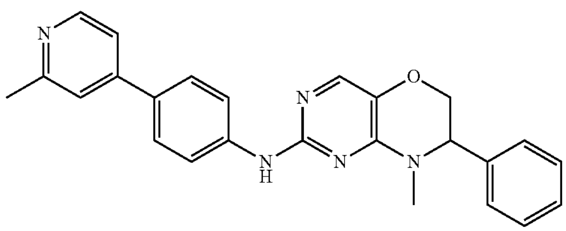 [SMILES: Cc1cc(-c2ccc(Nc3ncc4c(n3)N(C)C(c3ccccc3)CO4)cc2)ccn1] | (−)-8-methyl-N-(4-(2-methylpyridin-4-yl)phenyl)-7-phenyl-7,8-dihydro-6H-pyrimido[5,4-b][1,4]oxazin-2-amine |
| 25 | 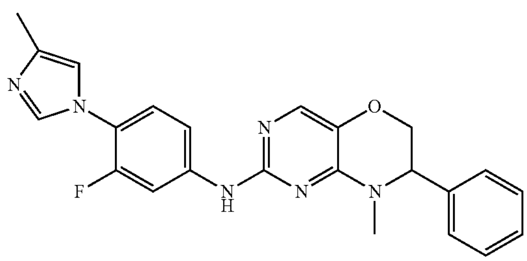 [SMILES: Cc1cn(-c2ccc(Nc3ncc4c(n3)N(C)C(c3ccccc3)CO4)cc2F)cn1] | N-(3-fluoro-4-(4-methyl-1H-imidazol-1-yl)phenyl)-8-methyl-7-phenyl-7,8-dihydro-6H-pyrimido[5,4-b][1,4]oxazin-2-amine (racemic) |
| 25A | 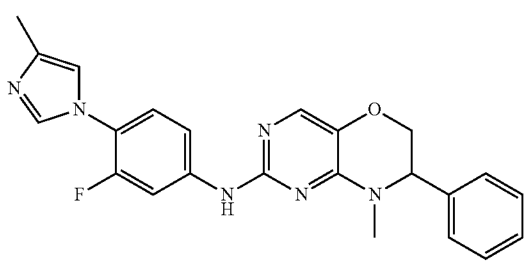 [SMILES: Cc1cn(-c2ccc(Nc3ncc4c(n3)N(C)C(c3ccccc3)CO4)cc2F)cn1] | (+)-N-(3-fluoro-4-(4-methyl-1H-imidazol-1-yl)phenyl)-8-methyl-7-phenyl-7,8-dihydro-6H-pyrimido[5,4-b][1,4]oxazin-2-amine |
| 25B | 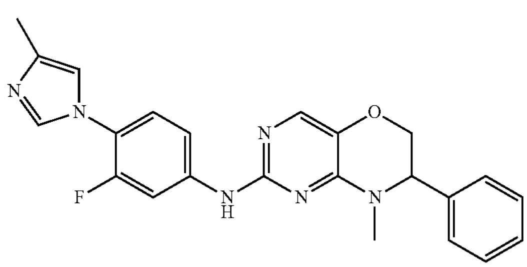 [SMILES: Cc1cn(-c2ccc(Nc3ncc4c(n3)N(C)C(c3ccccc3)CO4)cc2F)cn1] | (−)-N-(3-fluoro-4-(4-methyl-1H-imidazol-1-yl)phenyl)-8-methyl-7-phenyl-7,8-dihydro-6H-pyrimido[5,4-b][1,4]oxazin-2-amine |

TABLE I-continued

Exemplary Fused Morpholinopyrimidines of Formula (I)

| Compound of Example | Structure | Name |
|---|---|---|
| 26 | 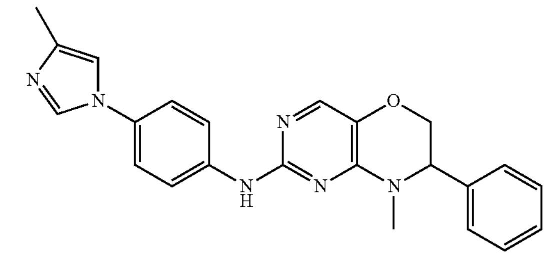 [SMILES: Cc1cn(-c2ccc(Nc3ncc4c(n3)N(C)C(c3ccccc3)CO4)cc2)cn1] | 8-methyl-N-(4-(4-methyl-1H-imidazol-1-yl)phenyl)-7-phenyl-7,8-dihydro-6H-pyrimido[5,4-b][1,4]oxazin-2-amine (racemic) |
| 26A | 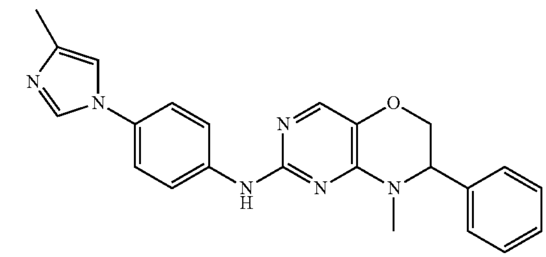 [SMILES: Cc1cn(-c2ccc(Nc3ncc4c(n3)N(C)C(c3ccccc3)CO4)cc2)cn1] | (+)-8-methyl-N-(4-(4-methyl-1H-imidazol-1-yl)phenyl)-7-phenyl-7,8-dihydro-6H-pyrimido[5,4-b][1,4]oxazin-2-amine |
| 26B | 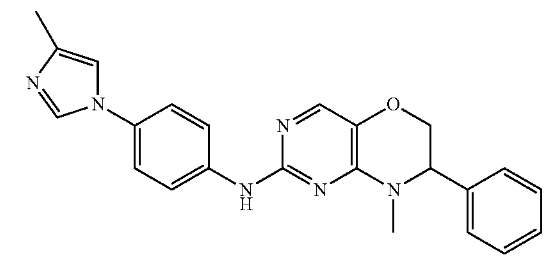 [SMILES: Cc1cn(-c2ccc(Nc3ncc4c(n3)N(C)C(c3ccccc3)CO4)cc2)cn1] | (−)-8-methyl-N-(4-(4-methyl-1H-imidazol-1-yl)phenyl)-7-phenyl-7,8-dihydro-6H-pyrimido[5,4-b][1,4]oxazin-2-amine |
| 27 | | N-(3-fluoro-4-(2-methylpyridin-4-yl)phenyl)-8-methyl-7-phenyl-7,8-dihydro-6H-pyrimido[5,4-b][1,4]oxazin-2-amine (racemic) |
| 27A | 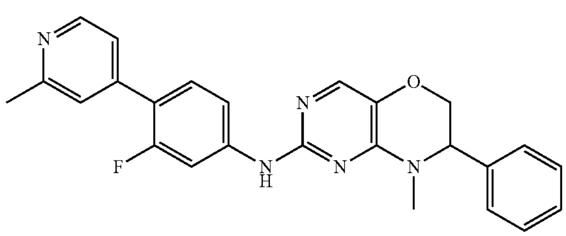 [SMILES: Cc1cc(-c2ccc(Nc3ncc4c(n3)N(C)C(c3ccccc3)CO4)cc2F)ccn1] | (+)-N-(3-fluoro-4-(2-methylpyridin-4-yl)phenyl)-8-methyl-7-phenyl-7,8-dihydro-6H-pyrimido[5,4-b][1,4]oxazin-2-amine |
| 27B | 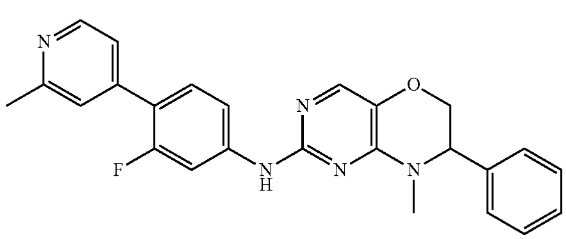 [SMILES: Cc1cc(-c2ccc(Nc3ncc4c(n3)N(C)C(c3ccccc3)CO4)cc2F)ccn1] | (−)-N-(3-fluoro-4-(2-methylpyridin-4-yl)phenyl)-8-methyl-7-phenyl-7,8-dihydro-6H-pyrimido[5,4-b][1,4]oxazin-2-amine |

TABLE I-continued

Exemplary Fused Morpholinopyrimidines of Formula (I)

| Compound of Example | Structure | Name |
| --- | --- | --- |
| 28 | 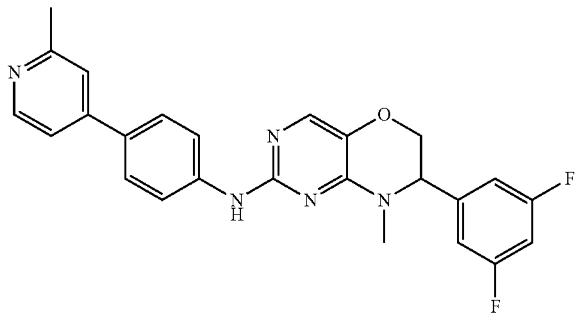 [SMILES: Cc1cc(-c2ccc(Nc3ncc4c(n3)N(C)C(c3cc(F)cc(F)c3)CO4)cc2)ccn1] | 7-(3,5-difluorophenyl)-8-methyl-N-(4-(2-methylpyridin-4-yl)phenyl)-7,8-dihydro-6H-pyrimido[5,4-b][1,4]oxazin-2-amine (racemic) |
| 28A | 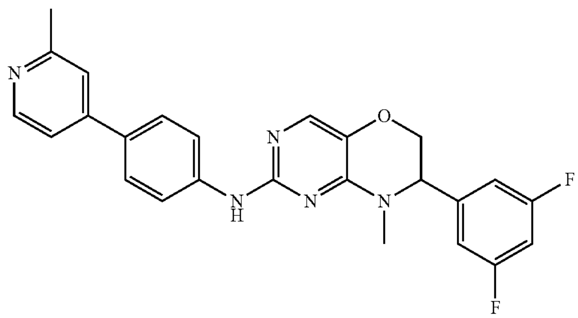 [SMILES: Cc1cc(-c2ccc(Nc3ncc4c(n3)N(C)C(c3cc(F)cc(F)c3)CO4)cc2)ccn1] | (−)-7-(3,5-difluorophenyl)-8-methyl-N-(4-(2-methylpyridin-4-yl)phenyl)-7,8-dihydro-6H-pyrimido[5,4-b][1,4]oxazin-2-amine |
| 28B | 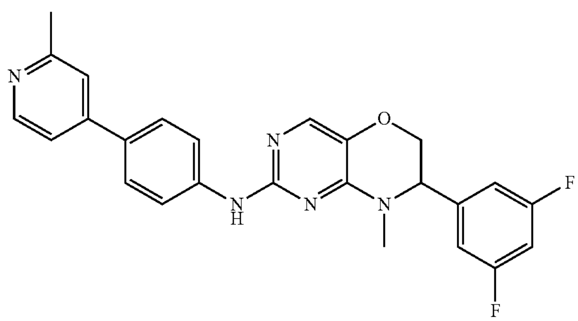 [SMILES: Cc1cc(-c2ccc(Nc3ncc4c(n3)N(C)C(c3cc(F)cc(F)c3)CO4)cc2)ccn1] | (+)-7-(3,5-difluorophenyl)-8-methyl-N-(4-(2-methylpyridin-4-yl)phenyl)-7,8-dihydro-6H-pyrimido[5,4-b][1,4]oxazin-2-amine |
| 29 | 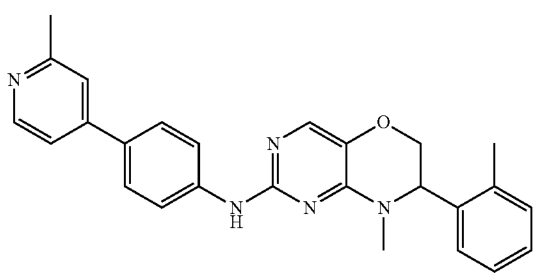 [SMILES: Cc1cc(-c2ccc(Nc3ncc4c(n3)N(C)C(c3ccccc3C)CO4)cc2)ccn1] | 8-methyl-N-(4-(2-methylpyridin-4-yl)phenyl)-7-(o-tolyl)-7,8-dihydro-6H-pyrimido[5,4-b][1,4]oxazin-2-amine (racemic) |
| 29A | 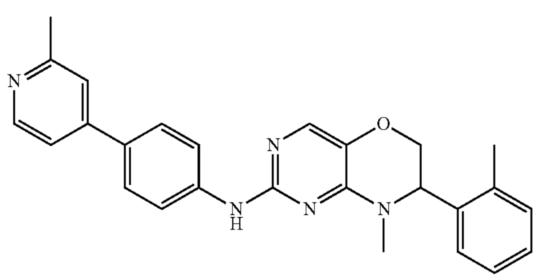 [SMILES: Cc1cc(-c2ccc(Nc3ncc4c(n3)N(C)C(c3ccccc3C)CO4)cc2)ccn1] | (−)-8-methyl-N-(4-(2-methylpyridin-4-yl)phenyl)-7-(o-tolyl)-7,8-dihydro-6H-pyrimido[5,4-b][1,4]oxazin-2-amine |

TABLE I-continued

Exemplary Fused Morpholinopyrimidines of Formula (I)

| Compound of Example | Structure | Name |
|---|---|---|
| 29B | 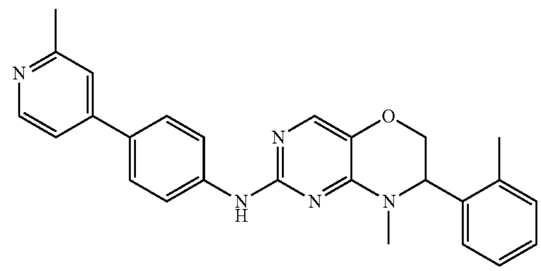 [SMILES: Cc1cc(-c2ccc(Nc3ncc4c(n3)N(C)C(c3ccccc3C)CO4)cc2)ccn1] | (+)-8-methyl-N-(4-(2-methylpyridin-4-yl)phenyl)-7-(o-tolyl)-7,8-dihydro-6H-pyrimido[5,4-b][1,4]oxazin-2-amine |
| 30 | 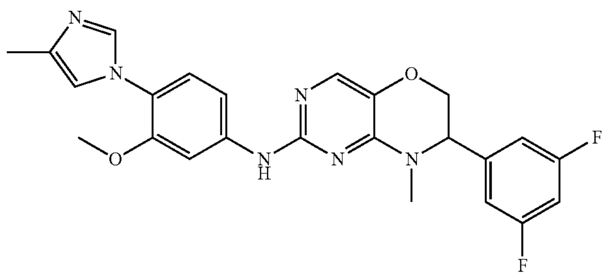 [SMILES: COc1cc(Nc2ncc3c(n2)N(C)C(c2cc(F)cc(F)c2)CO3)ccc1-n1cnc(C)c1] | 7-(3,5-difluorophenyl)-N-(3-methoxy-4-(4-methyl-1H-imidazol-1-yl)phenyl)-8-methyl-7,8-dihydro-6H-pyrimido[5,4-b][1,4]oxazin-2-amine (racemic) |
| 30A | 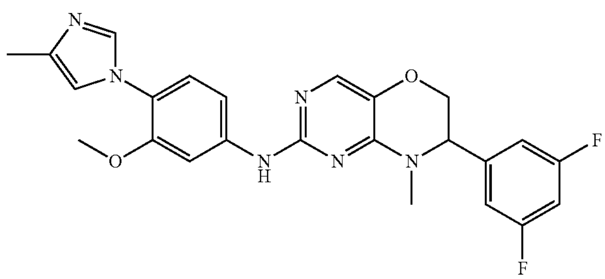 [SMILES: COc1cc(Nc2ncc3c(n2)N(C)C(c2cc(F)cc(F)c2)CO3)ccc1-n1cnc(C)c1] | (−)-7-(3,5-difluorophenyl)-N-(3-methoxy-4-(4-methyl-1H-imidazol-1-yl)phenyl)-8-methyl-7,8-dihydro-6H-pyrimido[5,4-b][1,4]oxazin-2-amine |
| 30B | 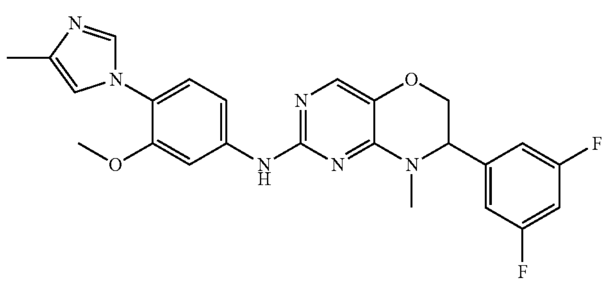 [SMILES: COc1cc(Nc2ncc3c(n2)N(C)C(c2cc(F)cc(F)c2)CO3)ccc1-n1cnc(C)c1] | (+)-7-(3,5-difluorophenyl)-N-(3-methoxy-4-(4-methyl-1H-imidazol-1-yl)phenyl)-8-methyl-7,8-dihydro-6H-pyrimido[5,4-b][1,4]oxazin-2-amine |
| 31 | 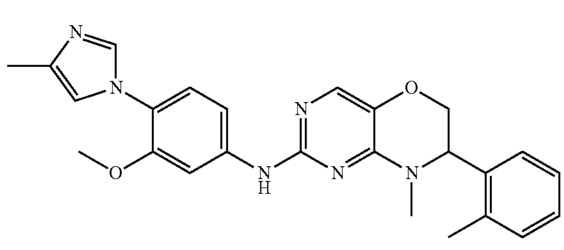 [SMILES: COc1cc(Nc2ncc3c(n2)N(C)C(c2ccccc2C)CO3)ccc1-n1cnc(C)c1] | N-(3-methoxy-4-(4-methyl-1H-imidazol-1-yl)phenyl)-8-methyl-7-(o-tolyl)-7,8-dihydro-6H-pyrimido[5,4-b][1,4]oxazin-2-amine (racemic) |

TABLE I-continued

Exemplary Fused Morpholinopyrimidines of Formula (I)

| Compound of Example | Structure | Name |
|---|---|---|
| 31A | 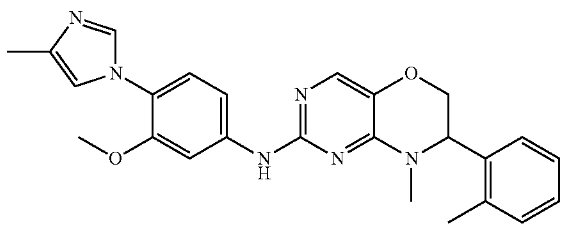 [SMILES: COc1cc(Nc2ncc3c(n2)N(C)C(c2ccccc2C)CO3)ccc1-n1cnc(C)c1] | (−)-N-(3-methoxy-4-(4-methyl-1H-imidazol-1-yl)phenyl)-8-methyl-7-(o-tolyl)-7,8-dihydro-6H-pyrimido[5,4-b][1,4]oxazin-2-amine |
| 31B | 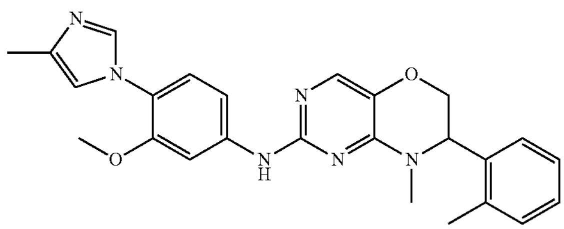 [SMILES: COc1cc(Nc2ncc3c(n2)N(C)C(c2ccccc2C)CO3)ccc1-n1cnc(C)c1] | (+)-N-(3-methoxy-4-(4-methyl-1H-imidazol-1-yl)phenyl)-8-methyl-7-(o-tolyl)-7,8-dihydro-6H-pyrimido[5,4-b][1,4]oxazin-2-amine |
| 32 | 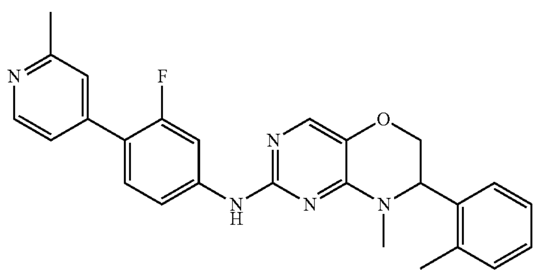 [SMILES: Cc1cc(-c2ccc(Nc3ncc4c(n3)N(C)C(c3ccccc3C)CO4)cc2F)ccn1] | N-(3-fluoro-4-(2-methylpyridin-4-yl)phenyl)-8-methyl-7-(o-tolyl)-7,8-dihydro-6H-pyrimido[5,4-b][1,4]oxazin-2-amine (racemic) |
| 32A | 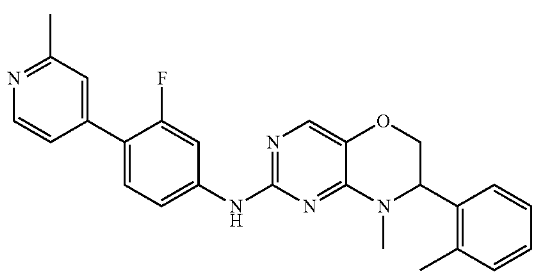 [SMILES: Cc1cc(-c2ccc(Nc3ncc4c(n3)N(C)C(c3ccccc3C)CO4)cc2F)ccn1] | (−)-N-(3-fluoro-4-(2-methylpyridin-4-yl)phenyl)-8-methyl-7-(o-tolyl)-7,8-dihydro-6H-pyrimido[5,4-b][1,4]oxazin-2-amine |
| 32B | 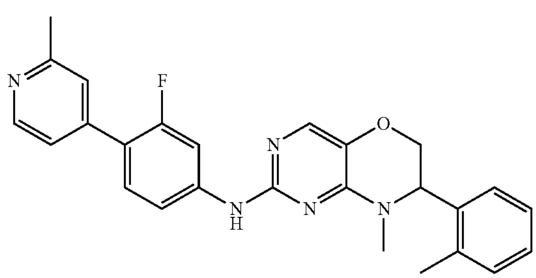 [SMILES: Cc1cc(-c2ccc(Nc3ncc4c(n3)N(C)C(c3ccccc3C)CO4)cc2F)ccn1] | (+)-N-(3-fluoro-4-(2-methylpyridin-4-yl)phenyl)-8-methyl-7-(o-tolyl)-7,8-dihydro-6H-pyrimido[5,4-b][1,4]oxazin-2-amine |

TABLE I-continued

Exemplary Fused Morpholinopyrimidines of Formula (I)

| Compound of Example | Structure | Name |
|---|---|---|
| 33 | 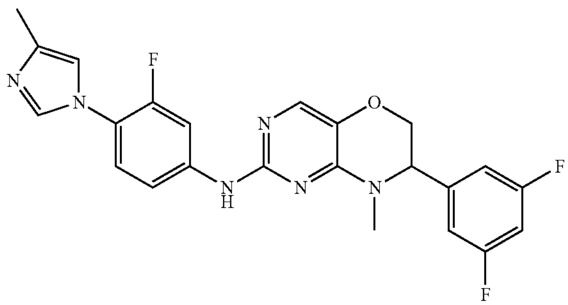 [SMILES: Cc1cn(-c2ccc(Nc3ncc4c(n3)N(C)C(c3cc(F)cc(F)c3)CO4)cc2F)cn1] | 7-(3,5-difluorophenyl)-N-(3-fluoro-4-(4-methyl-1H-imidazol-1-yl)phenyl)-8-methyl-7,8-dihydro-6H-pyrimido[5,4-b][1,4]oxazin-2-amine (racemic) |
| 33A | 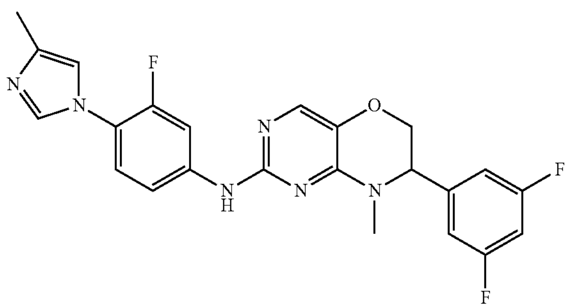 [SMILES: Cc1cn(-c2ccc(Nc3ncc4c(n3)N(C)C(c3cc(F)cc(F)c3)CO4)cc2F)cn1] | (+)-7-(3,5-difluorophenyl)-N-(3-fluoro-4-(4-methyl-1H-imidazol-1-yl)phenyl)-8-methyl-7,8-dihydro-6H-pyrimido[5,4-b][1,4]oxazin-2-amine |
| 33B | 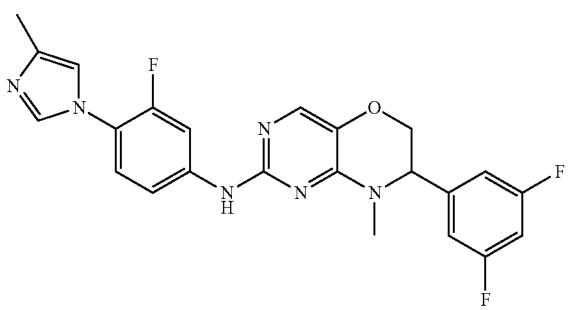 [SMILES: Cc1cn(-c2ccc(Nc3ncc4c(n3)N(C)C(c3cc(F)cc(F)c3)CO4)cc2F)cn1] | (−)-7-(3,5-difluorophenyl)-N-(3-fluoro-4-(4-methyl-1H-imidazol-1-yl)phenyl)-8-methyl-7,8-dihydro-6H-pyrimido[5,4-b][1,4]oxazin-2-amine |
| 34 | 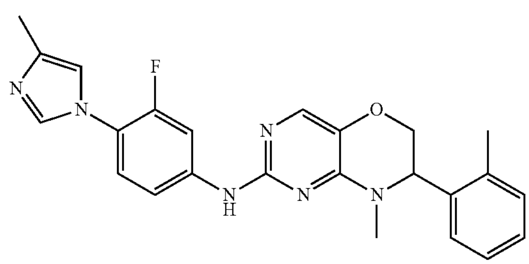 [SMILES: Cc1cn(-c2ccc(Nc3ncc4c(n3)N(C)C(c3ccccc3C)CO4)cc2F)cn1] | N-(3-fluoro-4-(4-methyl-1H-imidazol-1-yl)phenyl)-8-methyl-7-(o-tolyl)-7,8-dihydro-6H-pyrimido[5,4-b][1,4]oxazin-2-amine (racemic) |
| 34A | 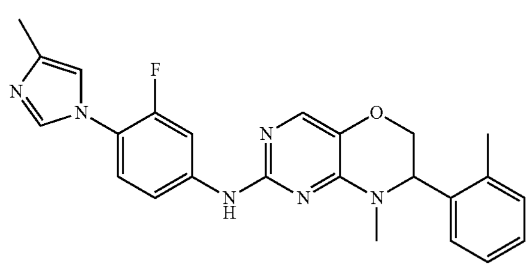 [SMILES: Cc1cn(-c2ccc(Nc3ncc4c(n3)N(C)C(c3ccccc3C)CO4)cc2F)cn1] | (+)-N-(3-fluoro-4-(4-methyl-1H-imidazol-1-yl)phenyl)-8-methyl-7-(o-tolyl)-7,8-dihydro-6H-pyrimido[5,4-b][1,4]oxazin-2-amine |

TABLE I-continued

Exemplary Fused Morpholinopyrimidines of Formula (I)

| Compound of Example | Structure | Name |
|---|---|---|
| 34B | 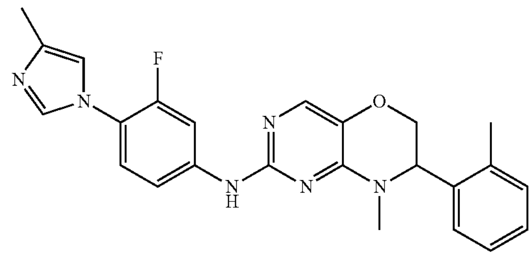 [SMILES: Cc1cn(-c2ccc(Nc3ncc4c(n3)N(C)C(c3ccccc3C)CO4)cc2F)cn1] | (−)-N-(3-fluoro-4-(4-methyl-1H-imidazol-1-yl)phenyl)-8-methyl-7-(o-tolyl)-7,8-dihydro-6H-pyrimido[5,4-b][1,4]oxazin-2-amine |
| 35 | 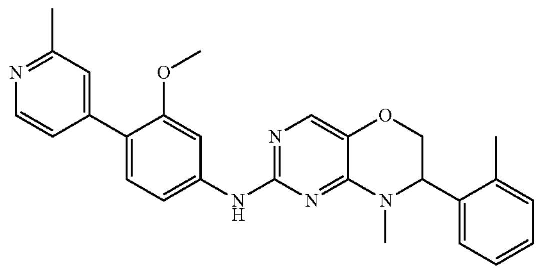 [SMILES: COc1cc(Nc2ncc3c(n2)N(C)C(c2ccccc2C)CO3)ccc1-c1ccnc(C)c1] | N-(3-methoxy-4-(2-methylpyridin-4-yl)phenyl)-8-methyl-7-(o-tolyl)-7,8-dihydro-6H-pyrimido[5,4-b][1,4]oxazin-2-amine (racemic) |
| 35A | 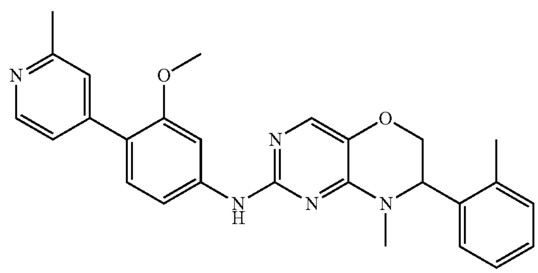 [SMILES: COc1cc(Nc2ncc3c(n2)N(C)C(c2ccccc2C)CO3)ccc1-c1ccnc(C)c1] | (−)-N-(3-methoxy-4-(2-methylpyridin-4-yl)phenyl)-8-methyl-7-(o-tolyl)-7,8-dihydro-6H-pyrimido[5,4-b][1,4]oxazin-2-amine |
| 35B | 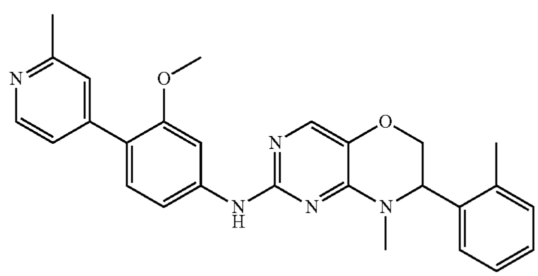 [SMILES: COc1cc(Nc2ncc3c(n2)N(C)C(c2ccccc2C)CO3)ccc1-c1ccnc(C)c1] | (+)-N-(3-methoxy-4-(2-methylpyridin-4-yl)phenyl)-8-methyl-7-(o-tolyl)-7,8-dihydro-6H-pyrimido[5,4-b][1,4]oxazin-2-amine |
| 36 | 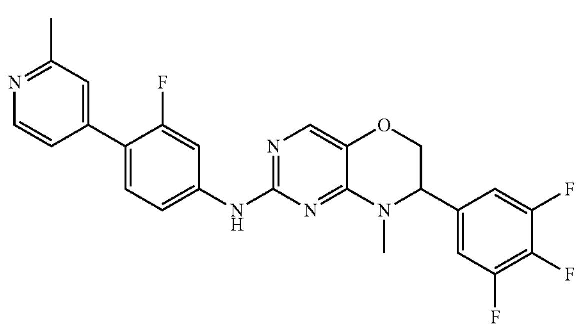 [SMILES: Cc1cc(-c2ccc(Nc3ncc4c(n3)N(C)C(c3cc(F)c(F)c(F)c3)CO4)cc2F)ccn1] | N-(3-fluoro-4-(2-methylpyridin-4-yl)phenyl)-8-methyl-7-(3,4,5-trifluorophenyl)-7,8-dihydro-6H-pyrimido[5,4-b][1,4]oxazin-2-amine (racemic) |

TABLE I-continued

Exemplary Fused Morpholinopyrimidines of Formula (I)

| Compound of Example | Structure | Name |
|---|---|---|
| 36A | 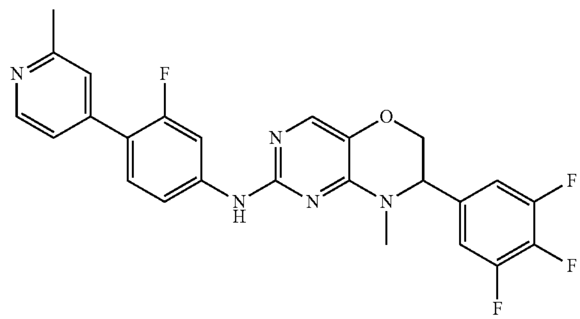 [SMILES: Cc1cc(-c2ccc(Nc3ncc4c(n3)N(C)C(c3cc(F)c(F)c(F)c3)CO4)cc2F)ccn1] | (+)-N-(3-fluoro-4-(2-methylpyridin-4-yl)phenyl)-8-methyl-7-(3,4,5-trifluorophenyl)-7,8-dihydro-6H-pyrimido[5,4-b][1,4]oxazin-2-amine |
| 36B | 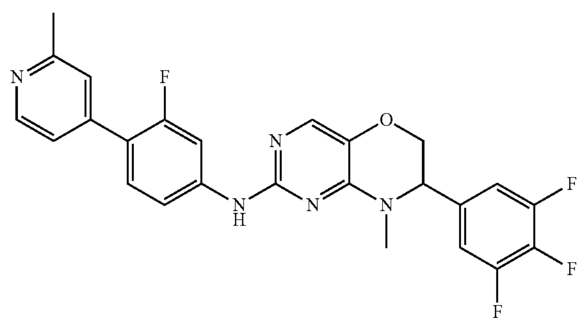 [SMILES: Cc1cc(-c2ccc(Nc3ncc4c(n3)N(C)C(c3cc(F)c(F)c(F)c3)CO4)cc2F)ccn1] | (−)-N-(3-fluoro-4-(2-methylpyridin-4-yl)phenyl)-8-methyl-7-(3,4,5-trifluorophenyl)-7,8-dihydro-6H-pyrimido[5,4-b][1,4]oxazin-2-amine |
| 37 | 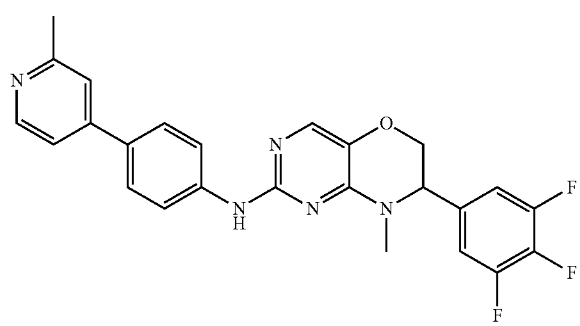 [SMILES: Cc1cc(-c2ccc(Nc3ncc4c(n3)N(C)C(c3cc(F)c(F)c(F)c3)CO4)cc2)ccn1] | 8-methyl-N-(4-(2-methylpyridin-4-yl)phenyl)-7-(3,4,5-trifluorophenyl)-7,8-dihydro-6H-pyrimido[5,4-b][1,4]oxazin-2-amine (racemic) |
| 37A | 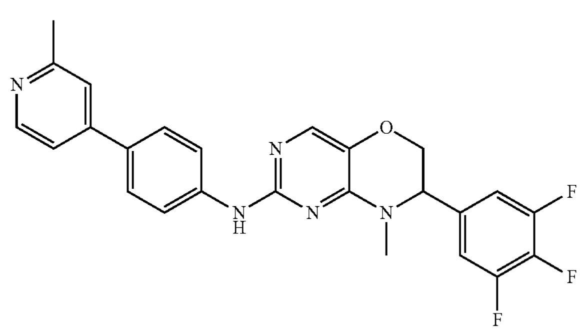 [SMILES: Cc1cc(-c2ccc(Nc3ncc4c(n3)N(C)C(c3cc(F)c(F)c(F)c3)CO4)cc2)ccn1] | (+)-8-methyl-N-(4-(2-methylpyridin-4-yl)phenyl)-7-(3,4,5-trifluorophenyl)-7,8-dihydro-6H-pyrimido[5,4-b][1,4]oxazin-2-amine |

TABLE I-continued

Exemplary Fused Morpholinopyrimidines of Formula (I)

| Compound of Example | Structure | Name |
|---|---|---|
| 37B | 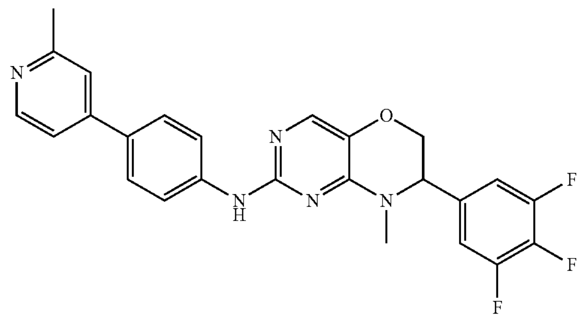 [SMILES: Cc1cc(-c2ccc(Nc3ncc4c(n3)N(C)C(c3cc(F)c(F)c(F)c3)CO4)cc2)ccn1] | (−)-8-methyl-N-(4-(2-methylpyridin-4-yl)phenyl)-7-(3,4,5-trifluorophenyl)-7,8-dihydro-6H-pyrimido[5,4-b][1,4]oxazin-2-amine |
| 38 | 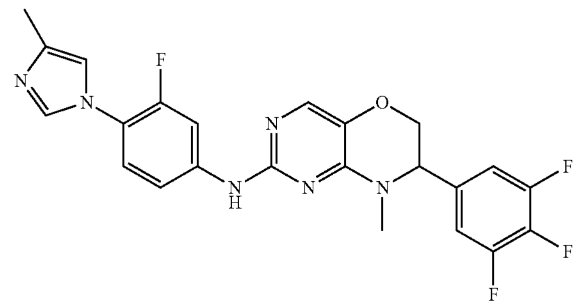 [SMILES: Cc1cn(-c2ccc(Nc3ncc4c(n3)N(C)C(c3cc(F)c(F)c(F)c3)CO4)cc2F)cn1] | N-(3-fluoro-4-(4-methyl-1H-imidazol-1-yl)phenyl)-8-methyl-7-(3,4,5-trifluorophenyl)-7,8-dihydro-6H-pyrimido[5,4-b][1,4]oxazin-2-amine (racemic) |
| 39 | 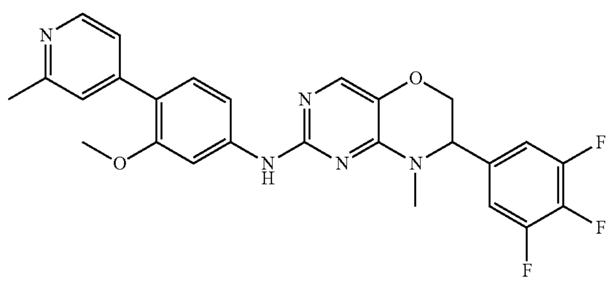 [SMILES: COc1cc(Nc2ncc3c(n2)N(C)C(c2cc(F)c(F)c(F)c2)CO3)ccc1-c1ccnc(C)c1] | N-(3-methoxy-4-(2-methylpyridin-4-yl)phenyl)-8-methyl-7-(3,4,5-trifluorophenyl)-7,8-dihydro-6H-pyrimido[5,4-b][1,4]oxazin-2-amine (racemic) |
| 39A | 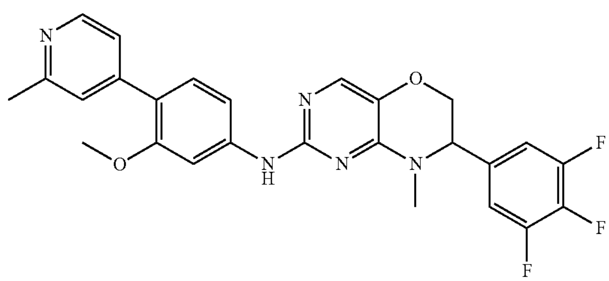 [SMILES: COc1cc(Nc2ncc3c(n2)N(C)C(c2cc(F)c(F)c(F)c2)CO3)ccc1-c1ccnc(C)c1] | (+)-N-(3-methoxy-4-(2-methylpyridin-4-yl)phenyl)-8-methyl-7-(3,4,5-trifluorophenyl)-7,8-dihydro-6H-pyrimido[5,4-b][1,4]oxazin-2-amine |
| 39B | 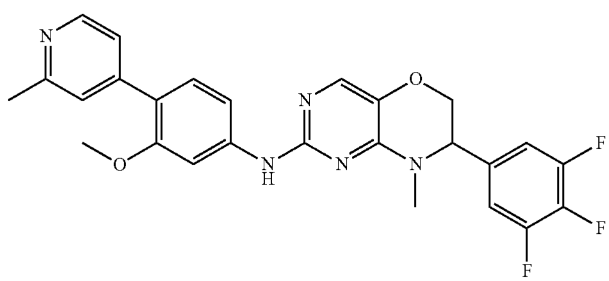 [SMILES: COc1cc(Nc2ncc3c(n2)N(C)C(c2cc(F)c(F)c(F)c2)CO3)ccc1-c1ccnc(C)c1] | (−)-N-(3-methoxy-4-(2-methylpyridin-4-yl)phenyl)-8-methyl-7-(3,4,5-trifluorophenyl)-7,8-dihydro-6H-pyrimido[5,4-b][1,4]oxazin-2-amine |

TABLE I-continued

Exemplary Fused Morpholinopyrimidines of Formula (I)

| Compound of Example | Structure | Name |
|---|---|---|
| 40 | 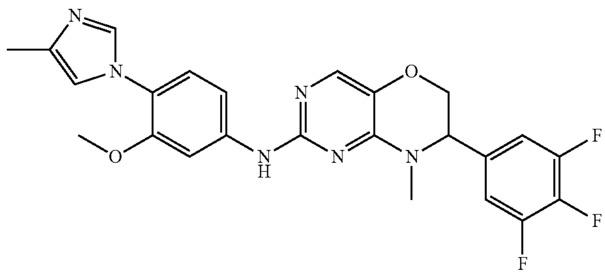 [SMILES: COc1cc(Nc2ncc3c(n2)N(C)C(c2cc(F)c(F)c(F)c2)CO3)ccc1-n1cnc(C)c1] | N-(3-methoxy-4-(4-methyl-1H-imidazol-1-yl)phenyl)-8-methyl-7-(3,4,5-trifluorophenyl)-7,8-dihydro-6H-pyrimido[5,4-b][1,4]oxazin-2-amine (racemic) |
| 40A | 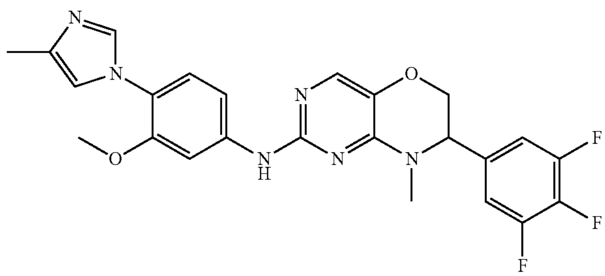 [SMILES: COc1cc(Nc2ncc3c(n2)N(C)C(c2cc(F)c(F)c(F)c2)CO3)ccc1-n1cnc(C)c1] | (−)-N-(3-methoxy-4-(4-methyl-1H-imidazol-1-yl)phenyl)-8-methyl-7-(3,4,5-trifluorophenyl)-7,8-dihydro-6H-pyrimido[5,4-b][1,4]oxazin-2-amine |
| 40B | 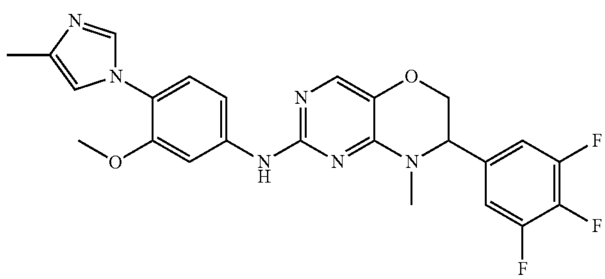 [SMILES: COc1cc(Nc2ncc3c(n2)N(C)C(c2cc(F)c(F)c(F)c2)CO3)ccc1-n1cnc(C)c1] | (+)-N-(3-methoxy-4-(4-methyl-1H-imidazol-1-yl)phenyl)-8-methyl-7-(3,4,5-trifluorophenyl)-7,8-dihydro-6H-pyrimido[5,4-b][1,4]oxazin-2-amine |
| 41 | 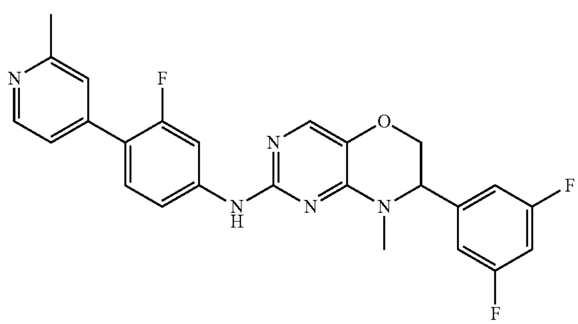 [SMILES: Cc1cc(-c2ccc(Nc3ncc4c(n3)N(C)C(c3cc(F)cc(F)c3)CO4)cc2F)ccn1] | 7-(3,5-difluorophenyl)-N-(3-fluoro-4-(2-methylpyridin-4-yl)phenyl)-8-methyl-7,8-dihydro-6H-pyrimido[5,4-b][1,4]oxazin-2-amine (racemic) |
| 41A | 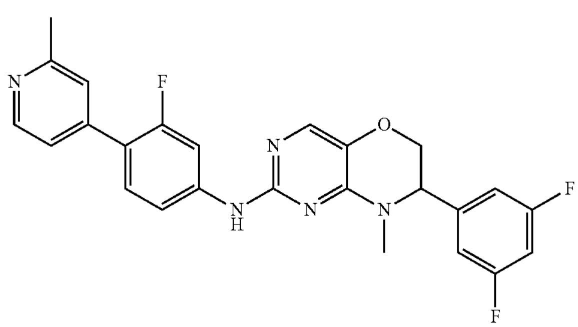 [SMILES: Cc1cc(-c2ccc(Nc3ncc4c(n3)N(C)C(c3cc(F)cc(F)c3)CO4)cc2F)ccn1] | (+)-7-(3,5-difluorophenyl)-N-(3-fluoro-4-(2-methylpyridin-4-yl)phenyl)-8-methyl-7,8-dihydro-6H-pyrimido[5,4-b][1,4]oxazin-2-amine |

TABLE I-continued

Exemplary Fused Morpholinopyrimidines of Formula (I)

| Compound of Example | Structure | Name |
|---|---|---|
| 41B | 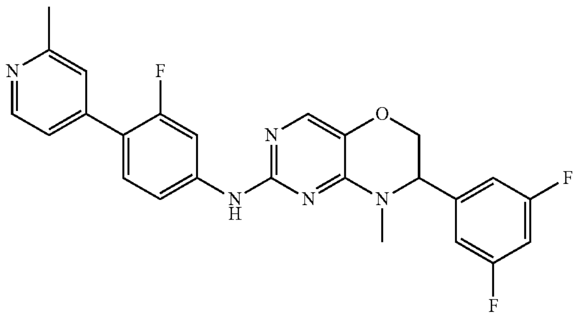 [SMILES: Cc1cc(-c2ccc(Nc3ncc4c(n3)N(C)C(c3cc(F)cc(F)c3)CO4)cc2F)ccn1] | (−)-7-(3,5-difluorophenyl)-N-(3-fluoro-4-(2-methylpyridin-4-yl)phenyl)-8-methyl-7,8-dihydro-6H-pyrimido [5,4-b][1,4]oxazin-2-amine |
| 42 | 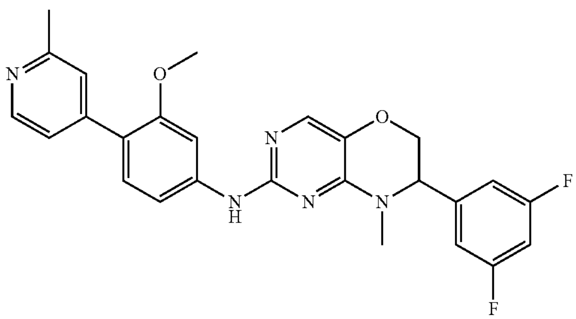 [SMILES: COc1cc(Nc2ncc3c(n2)N(C)C(c2cc(F)cc(F)c2)CO3)ccc1-c1ccnc(C)c1] | 7-(3,5-difluorophenyl)-N-(3-methoxy-4-(2-methylpyridin-4-yl)phenyl)-8-methyl-7,8-dihydro-6H-pyrimido[5,4-b][1,4]oxazin-2-amine (racemic) |
| 42A | 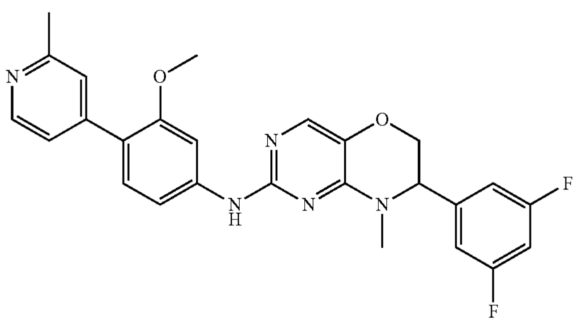 [SMILES: COc1cc(Nc2ncc3c(n2)N(C)C(c2cc(F)cc(F)c2)CO3)ccc1-c1ccnc(C)c1] | (+)-7-(3,5-difluorophenyl)-N-(3-methoxy-4-(2-methylpyridin-4-yl)phenyl)-8-methyl-7,8-dihydro-6H-pyrimido[5,4-b][1,4]oxazin-2-amine |
| 42B | 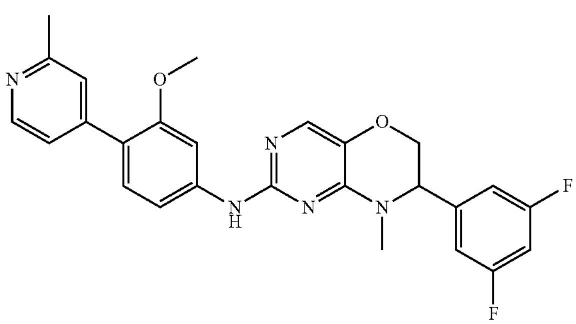 [SMILES: COc1cc(Nc2ncc3c(n2)N(C)C(c2cc(F)cc(F)c2)CO3)ccc1-c1ccnc(C)c1] | (−)-7-(3,5-difluorophenyl)-N-(3-methoxy-4-(2-methylpyridin-4-yl)phenyl)-8-methyl-7,8-dihydro-6H-pyrimido[5,4-b][1,4]oxazin-2-amine |
| 43 | 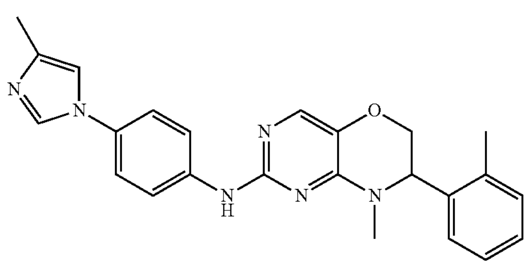 [SMILES: Cc1cn(-c2ccc(Nc3ncc4c(n3)N(C)C(c3ccccc3C)CO4)cc2)cn1] | 8-methyl-N-(4-(4-methyl-1H-imidazol-1-yl)phenyl)-7-(o-tolyl)-7,8-dihydro-6H-pyrimido[5,4-b][1,4]oxazin-2-amine (racemic) |

TABLE I-continued

Exemplary Fused Morpholinopyrimidines of Formula (I)

| Compound of Example | Structure | Name |
|---|---|---|
| 43A | 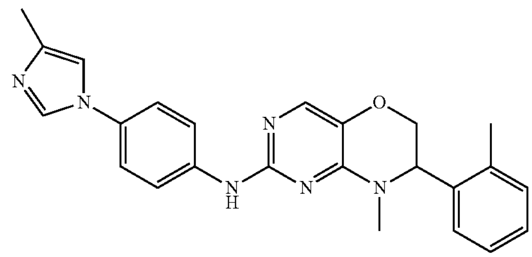 [SMILES: Cc1cn(-c2ccc(Nc3ncc4c(n3)N(C)C(c3ccccc3C)CO4)cc2)cn1] | (+)-8-methyl-N-(4-(4-methyl-1H-imidazol-1-yl)phenyl)-7-(o-tolyl)-7,8-dihydro-6H-pyrimido[5,4-b][1,4]oxazin-2-amine |
| 43B | 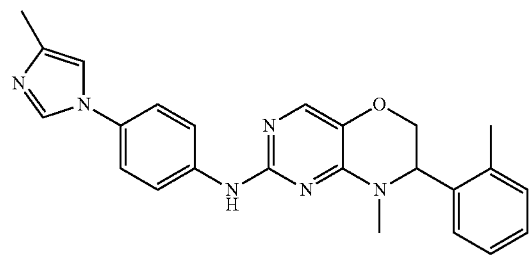 [SMILES: Cc1cn(-c2ccc(Nc3ncc4c(n3)N(C)C(c3ccccc3C)CO4)cc2)cn1] | (−)-8-methyl-N-(4-(4-methyl-1H-imidazol-1-yl)phenyl)-7-(o-tolyl)-7,8-dihydro-6H-pyrimido[5,4-b][1,4]oxazin-2-amine |
| 44 | 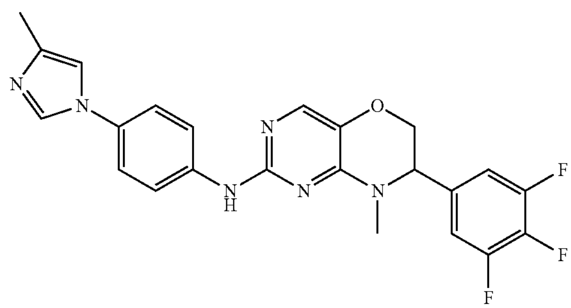 [SMILES: Cc1cn(-c2ccc(Nc3ncc4c(n3)N(C)C(c3cc(F)c(F)c(F)c3)CO4)cc2)cn1] | 8-methyl-N-(4-(4-methyl-1H-imidazol-1-yl)phenyl)-7-(3,4,5-trifluorophenyl)-7,8-dihydro-6H-pyrimido[5,4-b][1,4]oxazin-2-amine (racemic) |
| 45 | 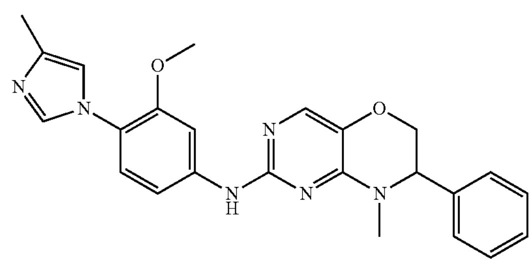 [SMILES: COc1cc(Nc2ncc3c(n2)N(C)C(c2ccccc2)CO3)ccc1-n1cnc(C)c1] | N-(3-methoxy-4-(4-methyl-1H-imidazol-1-yl)phenyl)-8-methyl-7-phenyl-7,8-dihydro-6H-pyrimido[5,4-b][1,4]oxazin-2-amine (racemic) |
| 46 | 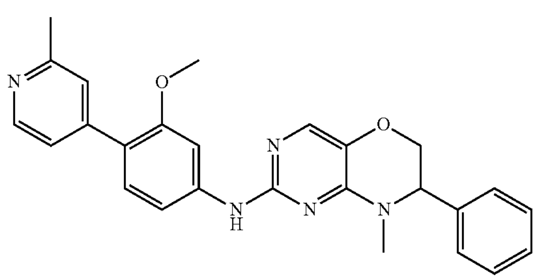 [SMILES: COc1cc(Nc2ncc3c(n2)N(C)C(c2ccccc2)CO3)ccc1-c1ccnc(C)c1] | N-(3-methoxy-4-(2-methylpyridin-4-yl)phenyl)-8-methyl-7-phenyl-7,8-dihydro-6H-pyrimido[5,4-b][1,4]oxazin-2-amine (racemic) |

TABLE I-continued

Exemplary Fused Morpholinopyrimidines of Formula (I)

| Compound of Example | Structure | Name |
|---|---|---|
| 47 | 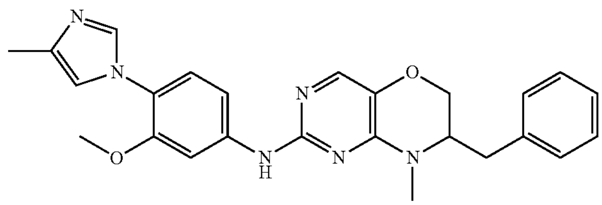 [SMILES: COc1cc(Nc2ncc3c(n2)N(C)C(Cc2ccccc2)CO3)ccc1-n1cnc(C)c1] | 7-benzyl-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) |
| 47A | 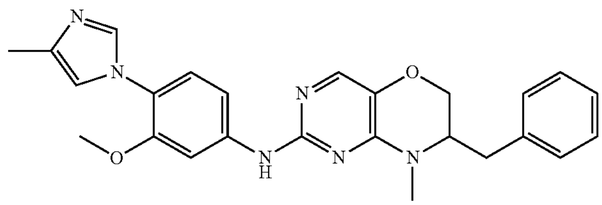 [SMILES: COc1cc(Nc2ncc3c(n2)N(C)C(Cc2ccccc2)CO3)ccc1-n1cnc(C)c1] | (+)-7-benzyl-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 47B | 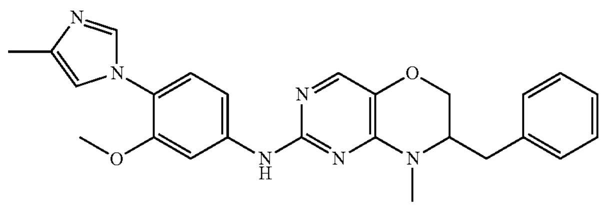 [SMILES: COc1cc(Nc2ncc3c(n2)N(C)C(Cc2ccccc2)CO3)ccc1-n1cnc(C)c1] | (−)-7-benzyl-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 48 | 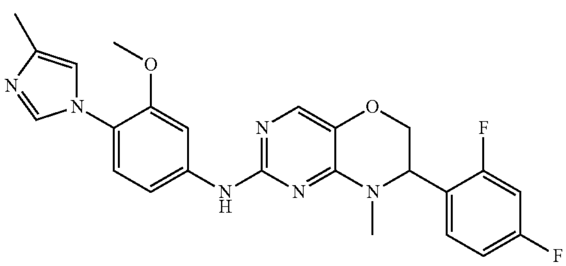 [SMILES: COc1cc(Nc2ncc3c(n2)N(C)C(c2ccc(F)cc2F)CO3)ccc1-n1cnc(C)c1] | 7-(2, 4-difluorophenyl)-N-(3-methoxy-4-(4-methyl-1H-imidazol-1-yl) phenyl)-8-methyl-7,8-dihydro-6H-pyrimido [5, 4-b] [1, 4] oxazin-2-amine (racemic) |
| 48A | 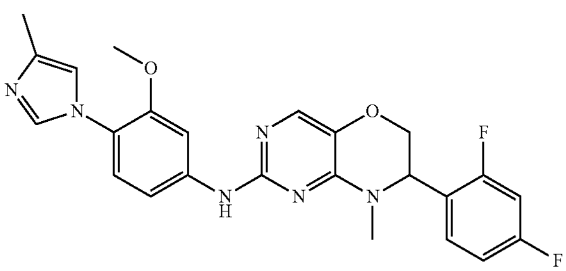 [SMILES: COc1cc(Nc2ncc3c(n2)N(C)C(c2ccc(F)cc2F)CO3)ccc1-n1cnc(C)c1] | (−)-7-(2, 4-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 48B | 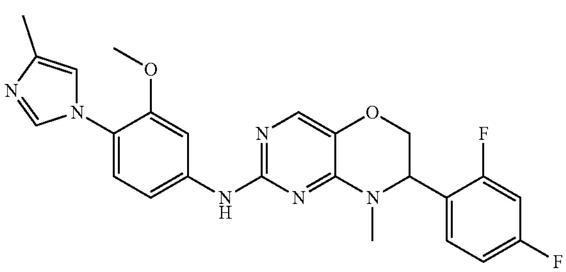 [SMILES: COc1cc(Nc2ncc3c(n2)N(C)C(c2ccc(F)cc2F)CO3)ccc1-n1cnc(C)c1] | (+)-7-(2, 4-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 49 | 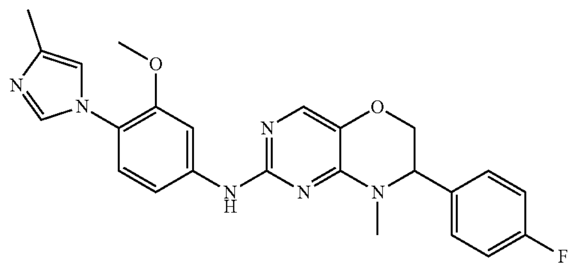 [SMILES: COc1cc(Nc2ncc3c(n2)N(C)C(c2ccc(F)cc2)CO3)ccc1-n1cnc(C)c1] | 7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) |
| 49A | 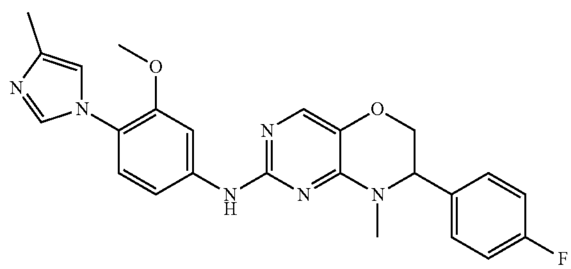 [SMILES: COc1cc(Nc2ncc3c(n2)N(C)C(c2ccc(F)cc2)CO3)ccc1-n1cnc(C)c1] | (−)-7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 49B | 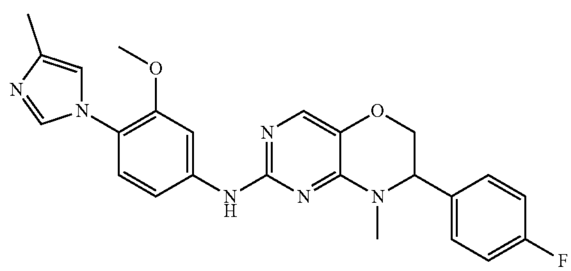 [SMILES: COc1cc(Nc2ncc3c(n2)N(C)C(c2ccc(F)cc2)CO3)ccc1-n1cnc(C)c1] | (+)-7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 50 | 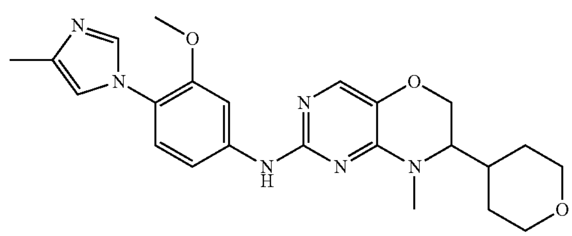 [SMILES: COc1cc(Nc2ncc3c(n2)N(C)C(C2CCOCC2)CO3)ccc1-n1cnc(C)c1] | N-(3-methoxy-4-(4-methyl-1H-imidazol-1-yl) phenyl)-8-methyl-7-fletrahydro-2H-pyran-4-yl)-7, 8-dihydro-6H-pyrimido [5, 4-b] [1, 4] oxazin-2-amine (racemic) |
| 51 | 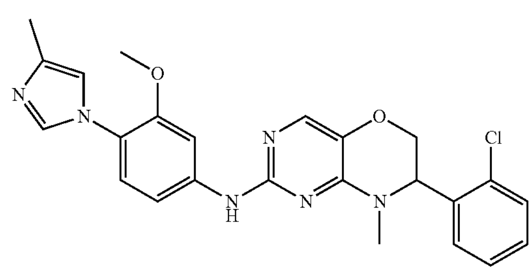 [SMILES: COc1cc(Nc2ncc3c(n2)N(C)C(c2ccccc2Cl)CO3)ccc1-n1cnc(C)c1] | 7-(2-chlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) |

TABLE I-continued

Exemplary Fused Morpholinopyrimidines of Formula (I)

| Compound of Example | Structure | Name |
|---|---|---|
| 51A | 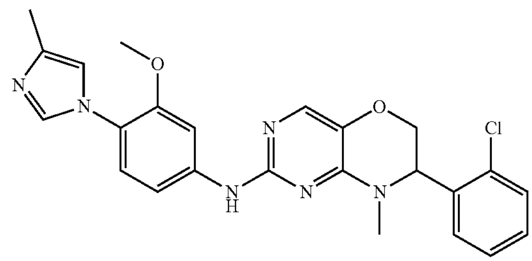 [SMILES: COc1cc(Nc2ncc3c(n2)N(C)C(c2ccccc2Cl)CO3)ccc1-n1cnc(C)c1] | (−)-7-(2-chlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 51B | 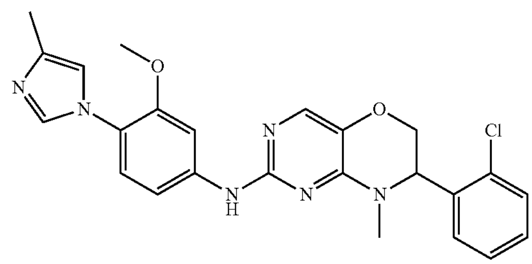 [SMILES: COc1cc(Nc2ncc3c(n2)N(C)C(c2ccccc2Cl)CO3)ccc1-n1cnc(C)c1] | (+)-7-(2-chlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 52 | 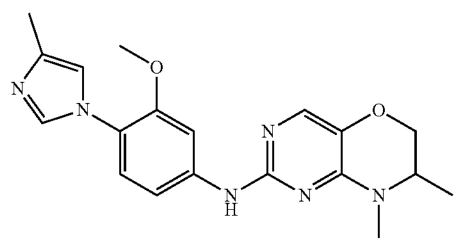 [SMILES: COc1cc(Nc2ncc3c(n2)N(C)C(C)CO3)ccc1-n1cnc(C)c1] | N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine (racemic) |
| 53 | 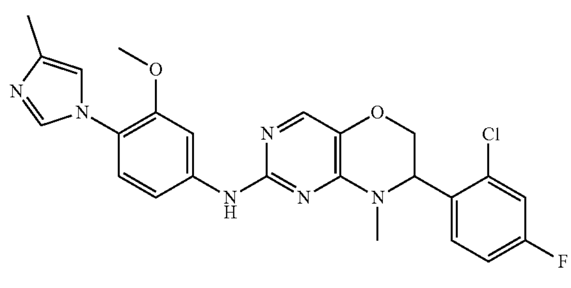 [SMILES: COc1cc(Nc2ncc3c(n2)N(C)C(c2ccc(F)cc2Cl)CO3)ccc1-n1cnc(C)c1] | 7-(2-chloro-4-fluorophenyl)-N-(3-methoxy-4-(4-methyl-1H-imidazol-1-yl) phenyl)-8-methyl-7,8-dihydro-6H-pyrimido [5, 4-b][1,4]oxazin-2-amine (racemic) |
| 54 | 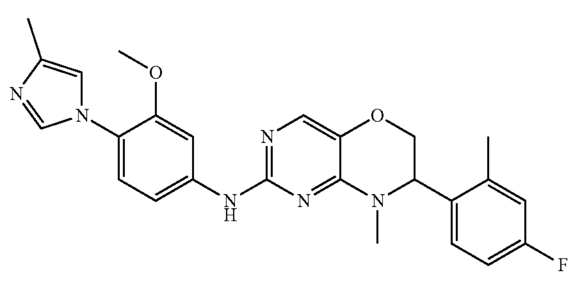 [SMILES: COc1cc(Nc2ncc3c(n2)N(C)C(c2ccc(F)cc2C)CO3)ccc1-n1cnc(C)c1] | 7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) |

TABLE I-continued

Exemplary Fused Morpholinopyrimidines of Formula (I)

| Compound of Example | Structure | Name |
| --- | --- | --- |
| 55 | 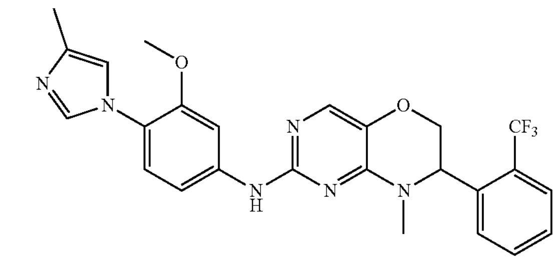 | N-(3-methoxy-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine (racemic) |
| 55A | 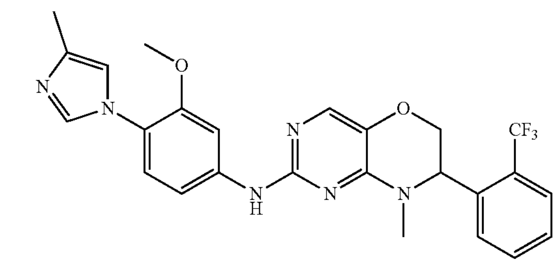 | (−)-N-(3-methoxy-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine |
| 55B | 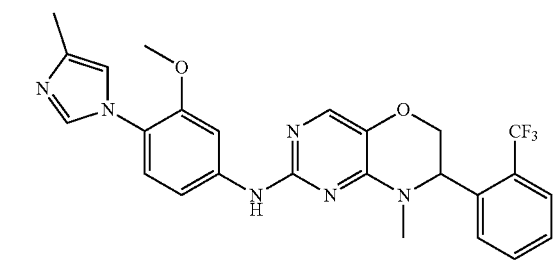 [SMILES: COc1cc(Nc2ncc3c(n2)N(C)C(c2ccccc2C(F)(F)F)CO3)ccc1-n1cnc(C)c1] | (+)-N-(3-methoxy-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine |
| 56A | 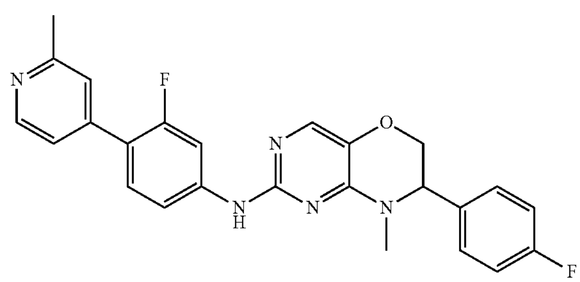 [SMILES: Cc1cc(-c2ccc(Nc3ncc4c(n3)N(C)C(c3ccc(F)cc3)CO4)cc2F)ccn1] | (+)-N-(3-fluoro-4-(2-methylpyridin-4-yl) phenyl)-7-(4-fluorophenyl)-8-methyl-7, 8-dihydro-6H-pyrimido [5, 4-b] [1, 4]oxazin-2-amine |
| 56B | 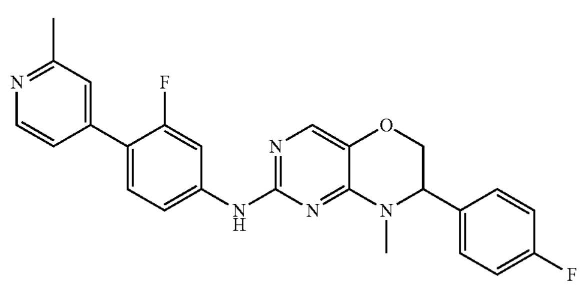 [SMILES: Cc1cc(-c2ccc(Nc3ncc4c(n3)N(C)C(c3ccc(F)cc3)CO4)cc2F)ccn1] | (−)-N-(3-fluoro-4-(2-methylpyridin-4-yl) phenyl)-7-(4-fluorophenyl)-8-methyl-7, 8-dihydro-6H-pyrimido [5, 4-b] [1, 4]oxazin-2-amine |

TABLE I-continued

Exemplary Fused Morpholinopyrimidines of Formula (I)

| Compound of Example | Structure | Name |
|---|---|---|
| 57A | 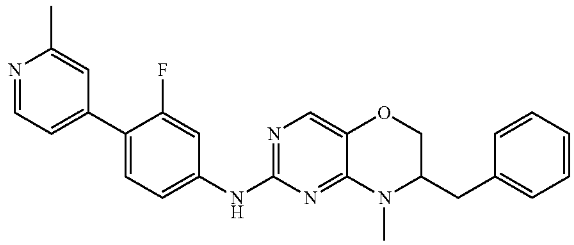 [SMILES: Cc1cc(-c2ccc(Nc3ncc4c(n3)N(C)C(Cc3ccccc3)CO4)cc2F)ccn1] | (+)-7-benzyl-N-(3-fluoro-4-(2-methylpyridin-4-yl) phenyl)-8-methyl-7, 8-dihydro-6H-pyrimido [5, 4-b] [1, 4] oxazin-2-amine |
| 57B | 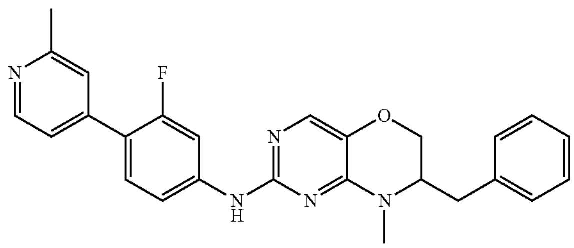 [SMILES: Cc1cc(-c2ccc(Nc3ncc4c(n3)N(C)C(Cc3ccccc3)CO4)cc2F)ccn1] | (−)-7-benzyl-N-(3-fluoro-4-(2-methylpyridin-4-yl) phenyl)-8-methyl-7, 8-dihydro-6H-pyrimido [5, 4-b] [1, 4] oxazin-2-amine |
| 58A | 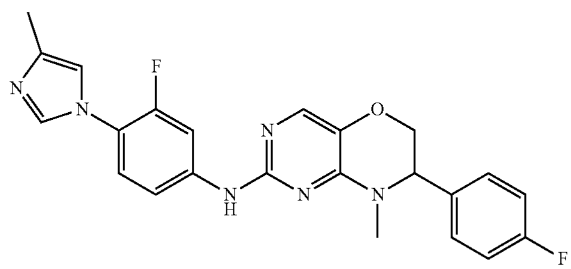 [SMILES: Cc1cn(-c2ccc(Nc3ncc4c(n3)N(C)C(c3ccc(F)cc3)CO4)cc2F)cn1] | (+)-N-(3-fluoro-4-(4-methyl-1H-imidazol-1-yl) phenyl)-7-(4-fluorophenyl)-8-methyl-7, 8-dihydro-6H-pyrimido [5, 4-b] [1, 4]oxazin-2-amine |
| 58B | 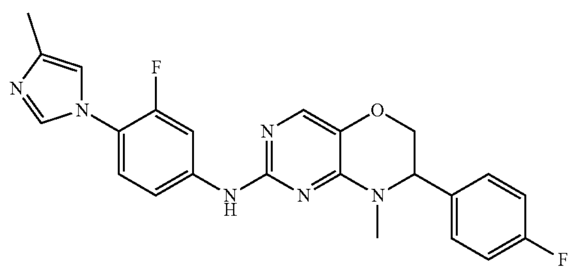 [SMILES: Cc1cn(-c2ccc(Nc3ncc4c(n3)N(C)C(c3ccc(F)cc3)CO4)cc2F)cn1] | (−)-N-(3-fluoro-4-(4-methyl-1H-imidazol-1-yl) phenyl)-7-(4-fluorophenyl)-8-methyl-7, 8-dihydro-6H-pyrimido [5, 4-b] [1, 4]oxazin-2-amine |
| 59A | 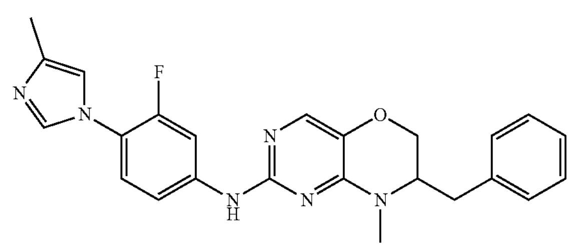 [SMILES: Cc1cn(-c2ccc(Nc3ncc4c(n3)N(C)C(Cc3ccccc3)CO4)cc2F)cn1] | (+)-7-benzyl-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 59B | 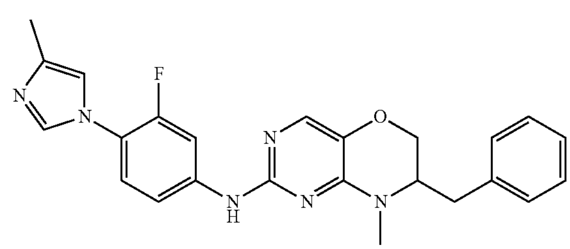 [SMILES: Cc1cn(-c2ccc(Nc3ncc4c(n3)N(C)C(Cc3ccccc3)CO4)cc2F)cn1] | (−)-7-benzyl-N-(3-fluoro-4-(4-methyl-1H-imidazol-1-yl) phenyl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 60A | 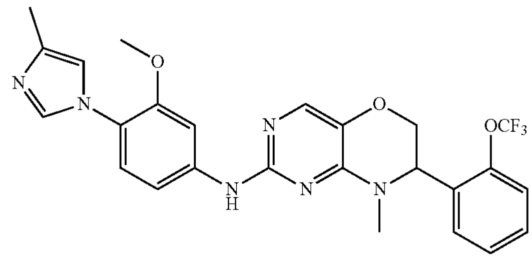 [SMILES: COc1cc(Nc2ncc3c(n2)N(C)C(c2ccccc2OC(F)(F)F)CO3)ccc1-n1cnc(C)c1] | (−)-N-(3-methoxy-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine |
| 60B | 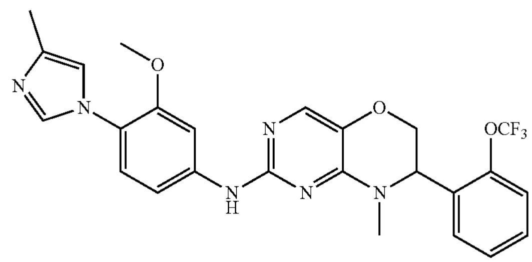 [SMILES: COc1cc(Nc2ncc3c(n2)N(C)C(c2ccccc2OC(F)(F)F)CO3)ccc1-n1cnc(C)c1] | (+)-N-(3-methoxy-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine |
| 61A | 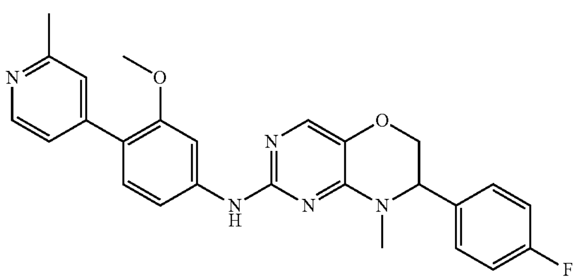 [SMILES: COc1cc(Nc2ncc3c(n2)N(C)C(c2ccc(F)cc2)CO3)ccc1-c1ccnc(C)c1] | (−)-7-(4-fluorophenyl)-N-(3-methoxy-4-(2-methylpyridin-4-yl) phenyl)-8-methyl-7, 8-dihydro-6H-pyrimido [5, 4-b] [1, 4]oxazin-2-amine |
| 61B | 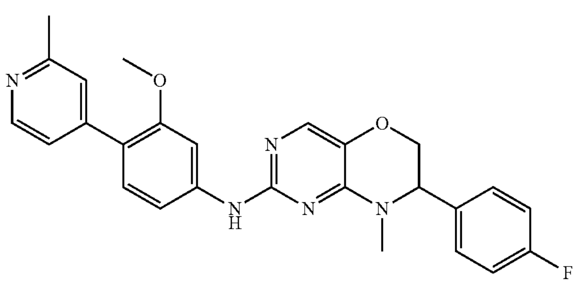 [SMILES: COc1cc(Nc2ncc3c(n2)N(C)C(c2ccc(F)cc2)CO3)ccc1-c1ccnc(C)c1] | (+)-7-(4-fluorophenyl)-N-(3-methoxy-4-(2-methylpyridin-4-yl) phenyl)-8-methyl-7, 8-dihydro-6H-pyrimido [5, 4-b] [1, 4]oxazin-2-amine |
| 62A | 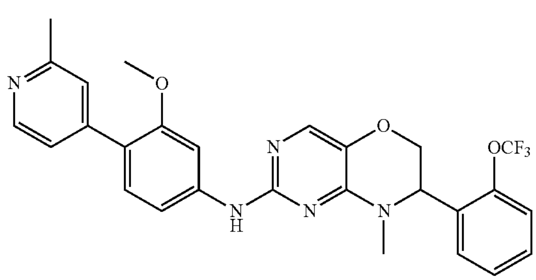 | (−)-N-(3-methoxy-4-(2-methylpyridin-4-yl) phenyl)-8-methyl-7-(2-(trifluoromethoxy) phenyl)-7, 8-dihydro-6H pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 62B | 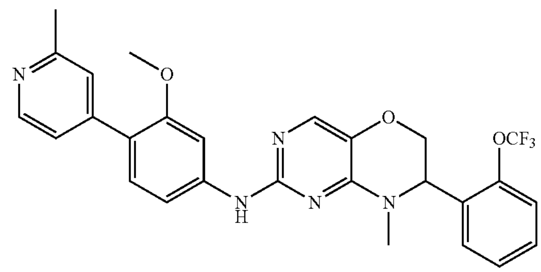 | (+)-N-(3-methoxy-4-(2-methylpyridin-4-yl) phenyl)-8-methyl-7-(2-(trifluoromethoxy) phenyl)-7, 8-dihydro-6H-pyrimido [5, 4-b] [1, 4] oxazin-2-amine |
| 63A | 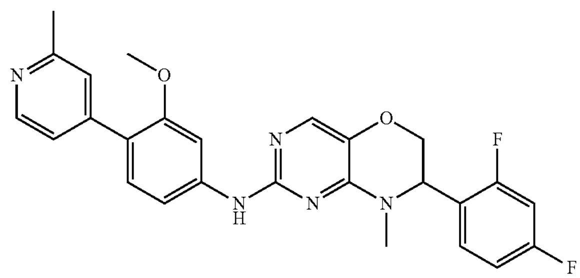 [SMILES: COc1cc(Nc2ncc3c(n2)N(C)C(c2ccc(F)cc2F)CO3)ccc1-c1ccnc(C)c1] | (−)-7-(2, 4-difluorophenyl)-N-(3-methoxy-4-(2-methylpyridin-4-yl) phenyl)-8-methyl-7, 8-dihydro-6H-pyrimido [5, 4-b] [1, 4] oxazin-2-amine |
| 63B | 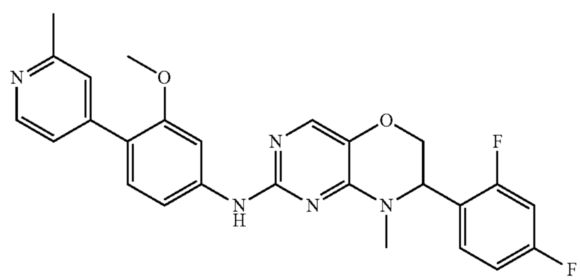 [SMILES: COc1cc(Nc2ncc3c(n2)N(C)C(c2ccc(F)cc2F)CO3)ccc1-c1ccnc(C)c1] | (+)-7-(2, 4-difluorophenyl)-N-(3-methoxy-4-(2-methylpyridin-4-yl) phenyl)-8-methyl-7, 8-dihydro-6H-pyrimido [5, 4-b] [1, 4] oxazin-2-amine |
| 64A | 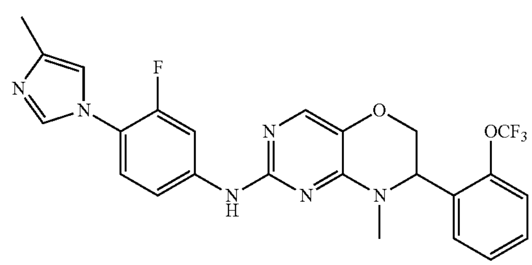 | (+)-N-(3-fluoro-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine |
| 64B | 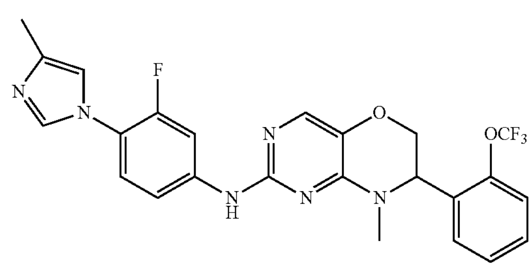 | (−)-N-(3-fluoro-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 65 | 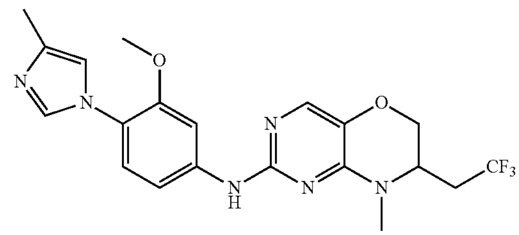 [SMILES: COc1cc(Nc2ncc3c(n2)N(C)C(CC(F)(F)F)CO3)ccc1-n1cnc(C)c1] | N-(3-methoxy-4-(4-methyl-1H-imidazol-1-yl) phenyl)-1-methyl-2-(2, 2, 2-trifluoroethyl)-2, 3-dihydro-1H-pyrido [3, 4-b][1, 4] oxazin-7-amine (racemic) |
| 66A | 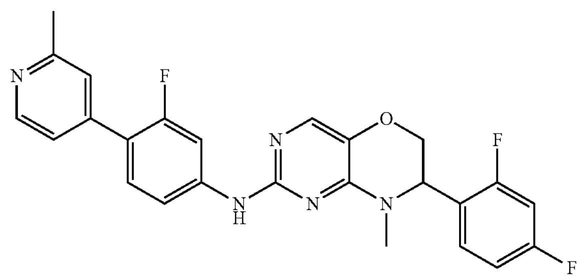 | (+)-7-(2, 4-difluorophenyl)-N-(3-fluoro-4-(2-methylpyridin-4-yl) phenyl)-8-methyl-7, 8-dihydro-6H-pyrimido [5, 4-b] [1, 4] oxazin-2-amine |
| 66B | 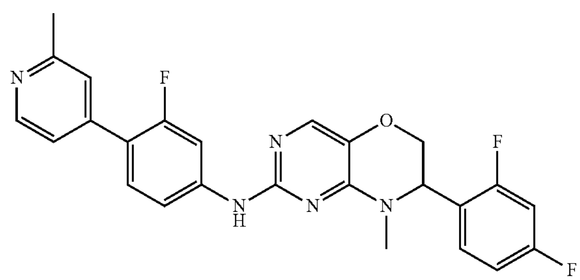 | (−)-7-(2, 4-difluorophenyl)-N-(3-fluoro-4-(2-methylpyridin-4-yl) phenyl)-8-methyl-7, 8-dihydro-6H-pyrimido [5, 4-b] [1, 4] oxazin-2-amine |
| 67A | 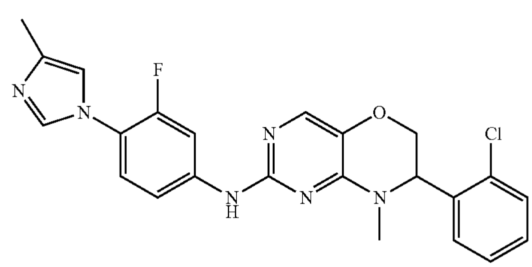 | (+)-7-(2-chlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 67B | 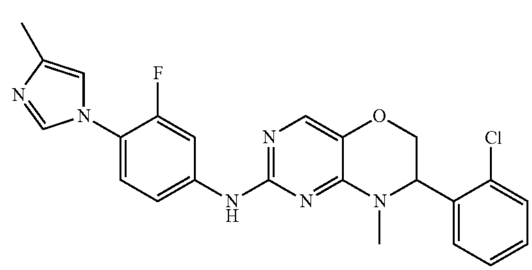 | (−)-7-(2-chlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 68A | 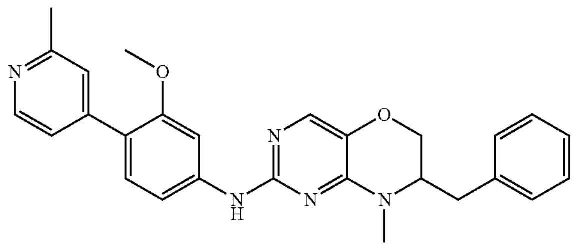 [SMILES: COc1cc(Nc2ncc3c(n2)N(C)C(Cc2ccccc2)CO3)ccc1-c1ccnc(C)c1] | (+)-7-benzyl-N-(3-methoxy-4-(2-methylpyridin-4-yl) phenyl)-8-methyl-7, 8-dihydro-6H-pyrimido [5, 4-b] [1, 4] oxazin-2-amine |
| 68B | 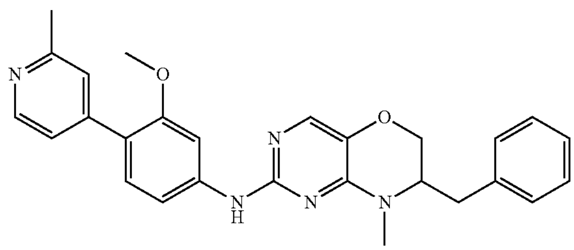 [SMILES: COc1cc(Nc2ncc3c(n2)N(C)C(Cc2ccccc2)CO3)ccc1-c1ccnc(C)c1] | (−)-7-benzyl-N-(3-methoxy-4-(2-methylpyridin-4-yl) phenyl)-8-methyl-7, 8-dihydro-6H-pyrimido [5, 4-b] [1, 4] oxazin-2-amine |
| 69A | 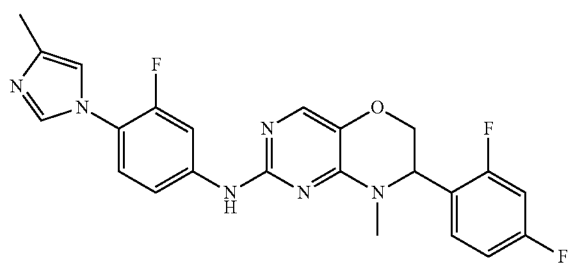 [SMILES: Cc1cn(-c2ccc(Nc3ncc4c(n3)N(C)C(c3ccc(F)cc3F)CO4)cc2F)cn1] | (+)-7-(2, 4-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 69B | 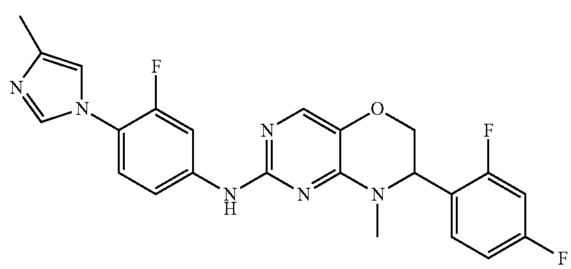 [SMILES: Cc1cn(-c2ccc(Nc3ncc4c(n3)N(C)C(c3ccc(F)cc3F)CO4)cc2F)cn1] | (−)-7-(2, 4-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 70A | 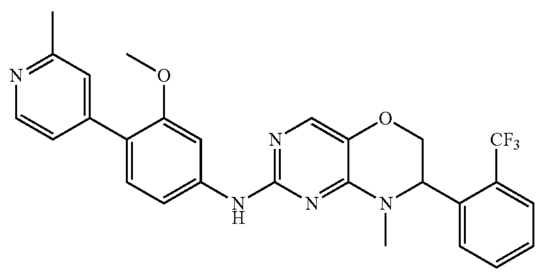 [SMILES: COc1cc(Nc2ncc3c(n2)N(C)C(c2ccccc2C(F)(F)F)CO3)ccc1-c1ccnc(C)c1] | (−)-N-(3-methoxy-4-(2-methylpyridin-4-yl) phenyl)-8-methyl-7-(2-(trifluoromethyl) phenyl)-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 70B | 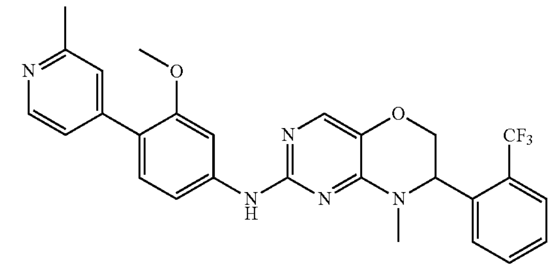 [SMILES: COc1cc(Nc2ncc3c(n2)N(C)C(c2ccccc2C(F)(F)F)CO3)ccc1-c1ccnc(C)c1] | (+)-N-(3-methoxy-4-(2-methylpyridin-4-yl) phenyl)-8-methyl-7-(2-(trifluoromethyl) phenyl)-7, 8-dihydro-6H-pyrimido [5, 4-b] [1, 4] oxazin-2-amine |
| 84A | 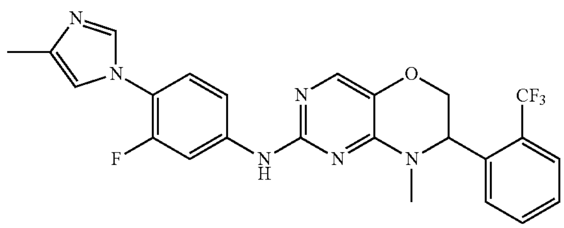 [SMILES: Cc1cn(-c2ccc(Nc3ncc4c(n3)N(C)C(c3ccccc3C(F)(F)F)CO4)cc2F)cn1] | (+)-N-(3-fluoro-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine |
| 84B | 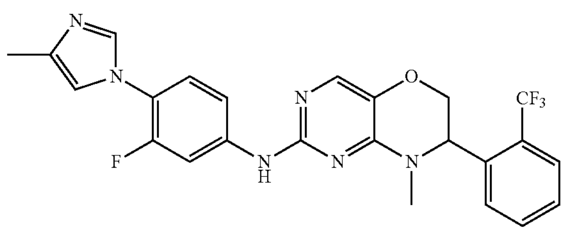 [SMILES: Cc1cn(-c2ccc(Nc3ncc4c(n3)N(C)C(c3ccccc3C(F)(F)F)CO4)cc2F)cn1] | (−)-N-(3-fluoro-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine |
| 85A | 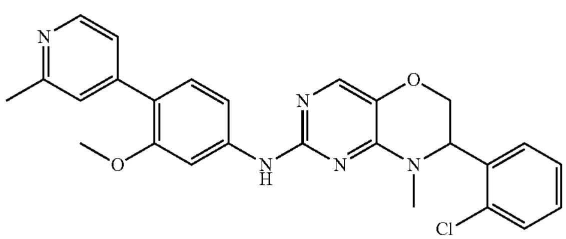 [SMILES: COc1cc(Nc2ncc3c(n2)N(C)C(c2ccccc2Cl)CO3)ccc1-c1ccnc(C)c1] | (−)-2-(2-chlorophenyl)-N-(3-methoxy-4-(2-methylpyridin-4-yl) phenyl)-1-methyl-2, 3-dihydro-1H-pyrido [3, 4-b][1, 4]oxazin-7-amine |
| 85B | 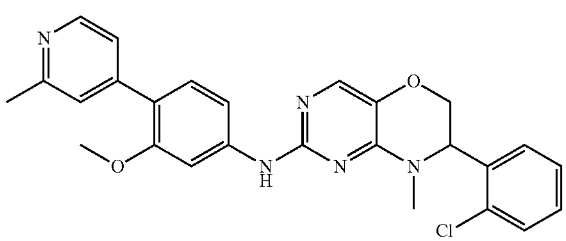 [SMILES: COc1cc(Nc2ncc3c(n2)N(C)C(c2ccccc2Cl)CO3)ccc1-c1ccnc(C)c1] | (+)-2-(2-chlorophenyl)-N-(3-methoxy-4-(2-methylpyridin-4-yl) phenyl)-1-methyl-2, 3-dihydro-1H-pyrido [3, 4-b][1, 4]oxazin-7-amine |
| 86 | 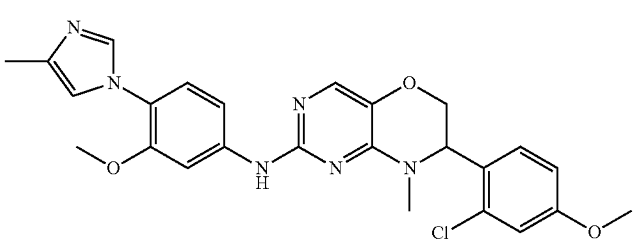 | 7-(2-chloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) |

TABLE I-continued

Exemplary Fused Morpholinopyrimidines of Formula (I)

| Compound of Example | Structure | Name |
|---|---|---|
| 87 | 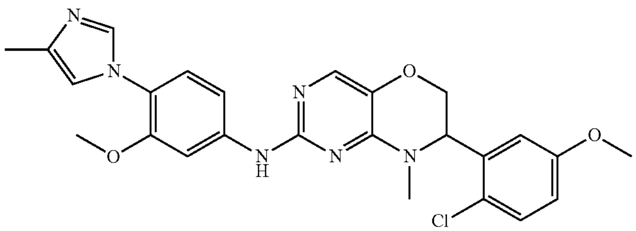 | 7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) |
| 88 | 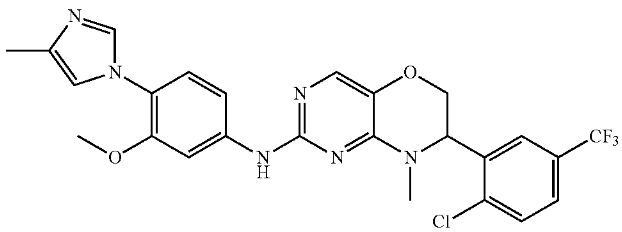 [SMILES: COc1cc(Nc2ncc3c(n2)N(C)C(c2cc(C(F)(F)F)ccc2Cl)CO3)ccc1-n1cnc(C)c1] | 7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) |
| 88A | 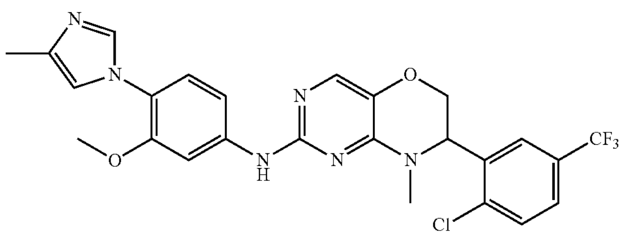 [SMILES: COc1cc(Nc2ncc3c(n2)N(C)C(c2cc(C(F)(F)F)ccc2Cl)CO3)ccc1-n1cnc(C)c1] | (+)-7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 88B | 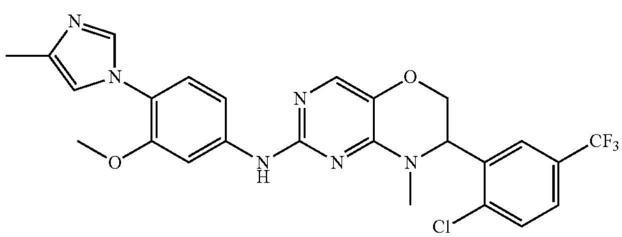 [SMILES: COc1cc(Nc2ncc3c(n2)N(C)C(c2cc(C(F)(F)F)ccc2Cl)CO3)ccc1-n1cnc(C)c1] | (−)-7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 89 | 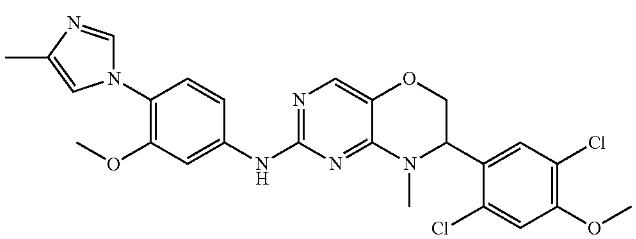 | 7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) |
| 90 | 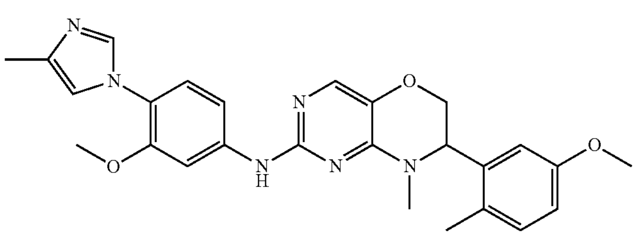 | 7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) |

TABLE I-continued

Exemplary Fused Morpholinopyrimidines of Formula (I)

| Compound of Example | Structure | Name |
|---|---|---|
| 91 | 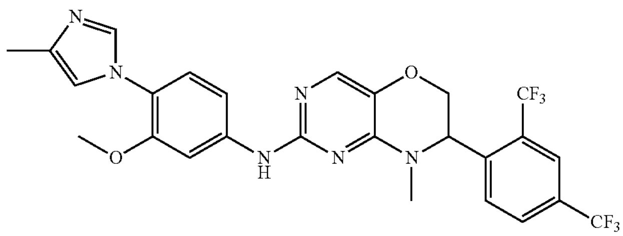 [SMILES: COc1cc(Nc2ncc3c(n2)N(C)C(c2ccc(C(F)(F)F)cc2C(F)(F)F)CO3)ccc1-n1cnc(C)c1] | 7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) |
| 92 | 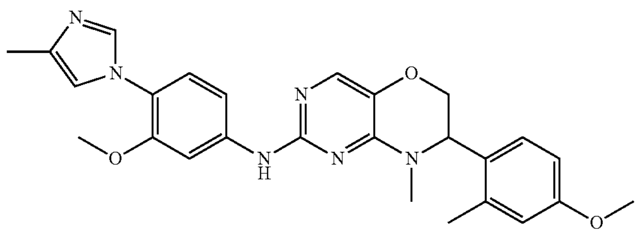 | 7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) |
| 93A | 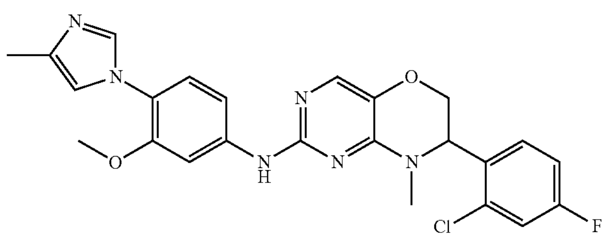 [SMILES: COc1cc(Nc2ncc3c(n2)N(C)C(c2ccc(F)cc2Cl)CO3)ccc1-n1cnc(C)c1] | (−)-7-(2-chloro-4-fluorophenyl)-N-(3-methoxy-4-(4-methyl-1H-imidazol-1-yl) phenyl)-8-methyl-7,8-dihydro-6H-pyrimido [5, 4-b][1,4] oxazin-2-amine |
| 93B | 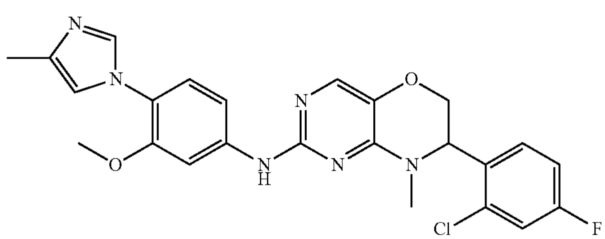 [SMILES: COc1cc(Nc2ncc3c(n2)N(C)C(c2ccc(F)cc2Cl)CO3)ccc1-n1cnc(C)c1] | (+)-7-(2-chloro-4-fluorophenyl)-N-(3-methoxy-4-(4-methyl-1H-imidazol-1-yl) phenyl)-8-methyl-7,8-dihydro-6H-pyrimido [5, 4-b][1,4] oxazin-2-amine |
| 94A | 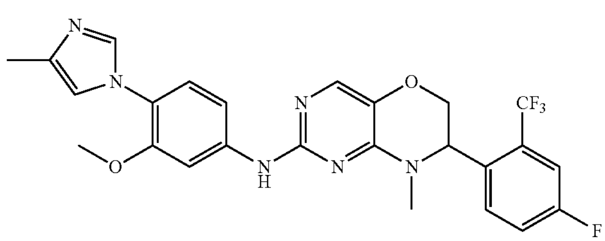 [SMILES: COc1cc(Nc2ncc3c(n2)N(C)C(c2ccc(F)cc2C(F)(F)F)CO3)ccc1-n1cnc(C)c1] | (−)-7-(4-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 94B | 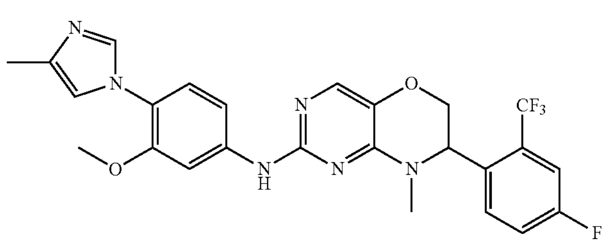 [SMILES: COc1cc(Nc2ncc3c(n2)N(C)C(c2ccc(F)cc2C(F)(F)F)CO3)ccc1-n1cnc(C)c1] | (+)-7-(4-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 95A | 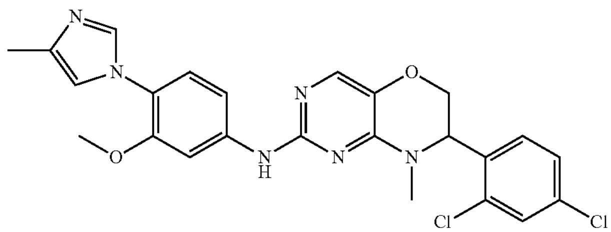 [SMILES: COc1cc(Nc2ncc3c(n2)N(C)C(c2ccc(Cl)cc2Cl)CO3)ccc1-n1cnc(C)c1] | (−)-7-(2, 4-dichlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 95B | 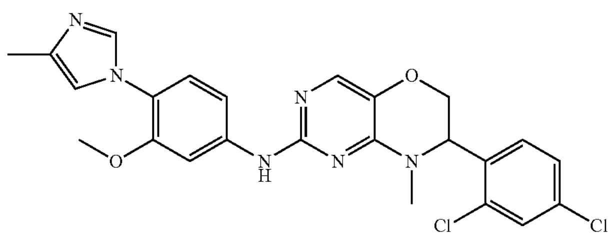 [SMILES: COc1cc(Nc2ncc3c(n2)N(C)C(c2ccc(Cl)cc2Cl)CO3)ccc1-n1cnc(C)c1] | (+)-7-(2, 4-dichlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 96A | 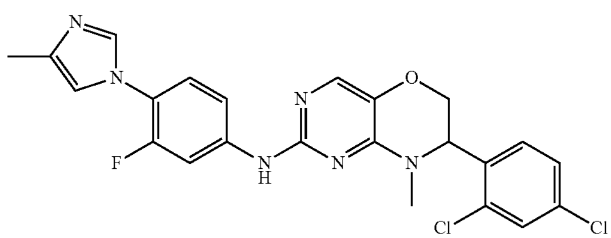 [SMILES: Cc1cn(-c2ccc(Nc3ncc4c(n3)N(C)C(c3ccc(Cl)cc3Cl)CO4)cc2F)cn1] | (+)-7-(2, 4-dichlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 96B | 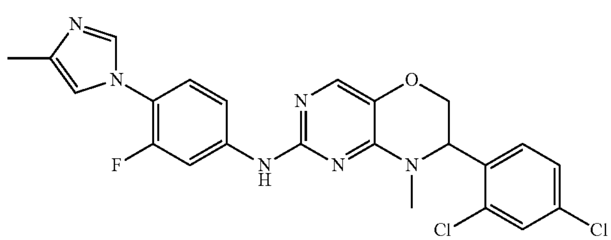 [SMILES: Cc1cn(-c2ccc(Nc3ncc4c(n3)N(C)C(c3ccc(Cl)cc3Cl)CO4)cc2F)cn1] | (−)-7-(2, 4-dichlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 97A | 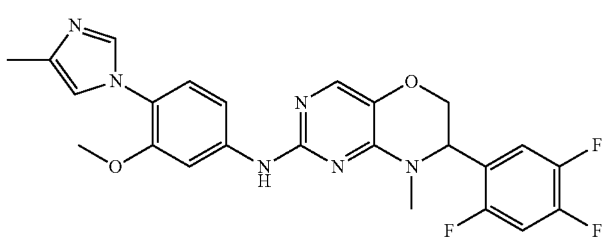 [SMILES: COc1cc(Nc2ncc3c(n2)N(C)C(c2cc(F)c(F)cc2F)CO3)ccc1-n1cnc(C)c1] | (−)-N-(3-methoxy-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine |
| 97B | 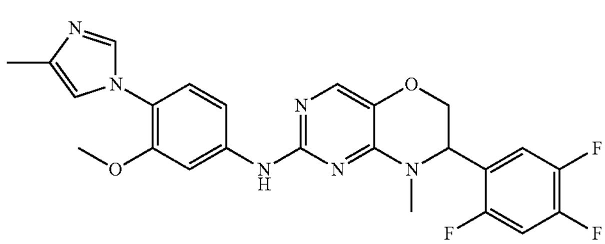 | (+)-N-(3-methoxy-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 98A | 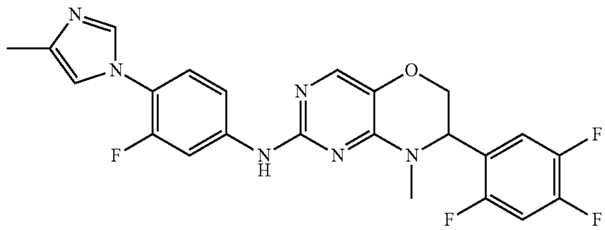 [SMILES: Cc1cn(-c2ccc(Nc3ncc4c(n3)N(C)C(c3cc(F)c(F)cc3F)CO4)cc2F)cn1] | (+)-N-(3-fluoro-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine |
| 98B | 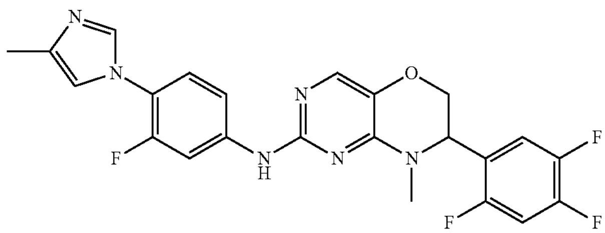 [SMILES: Cc1cn(-c2ccc(Nc3ncc4c(n3)N(C)C(c3cc(F)c(F)cc3F)CO4)cc2F)cn1] | (−)-N-(3-fluoro-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine |
| 99A | 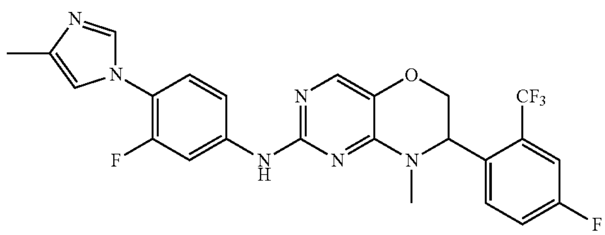 [SMILES: Cc1cn(-c2ccc(Nc3ncc4c(n3)N(C)C(c3ccc(F)cc3C(F)(F)F)CO4)cc2F)cn1] | (+)-7-(4-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 99B | 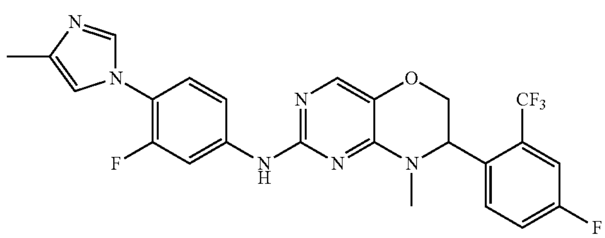 [SMILES: Cc1cn(-c2ccc(Nc3ncc4c(n3)N(C)C(c3ccc(F)cc3C(F)(F)F)CO4)cc2F)cn1] | (−)-7-(4-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 100A | 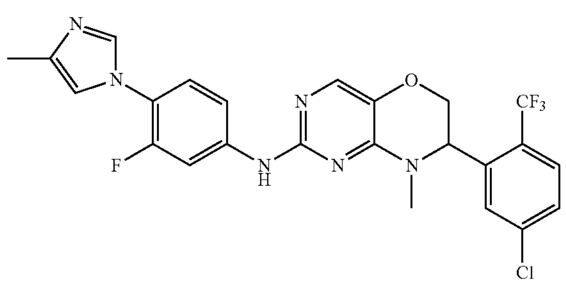 [SMILES: Cc1cn(-c2ccc(Nc3ncc4c(n3)N(C)C(c3cc(Cl)ccc3C(F)(F)F)CO4)cc2F)cn1] | (+)-7-(5-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 100B | 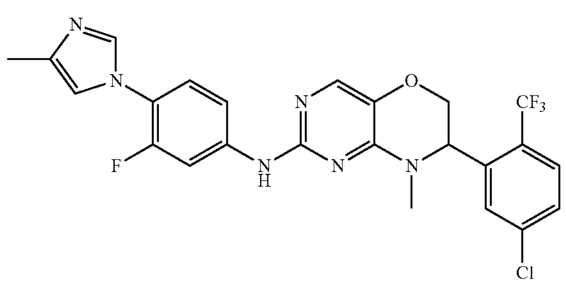 [SMILES: Cc1cn(-c2ccc(Nc3ncc4c(n3)N(C)C(c3cc(Cl)ccc3C(F)(F)F)CO4)cc2F)cn1] | (−)-7-(5-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 101A | 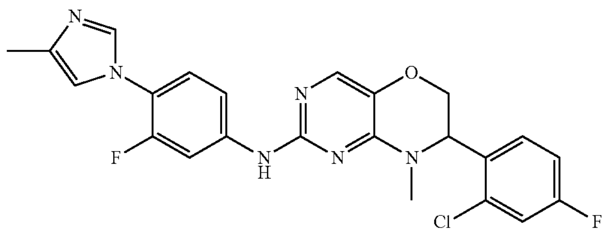 [SMILES: Cc1cn(-c2ccc(Nc3ncc4c(n3)N(C)C(c3ccc(F)cc3Cl)CO4)cc2F)cn1] | (+)-7-(2-chloro-4-fluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 101B | 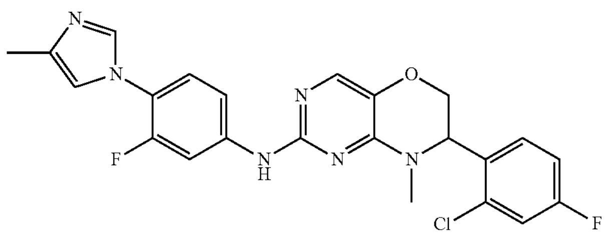 [SMILES: Cc1cn(-c2ccc(Nc3ncc4c(n3)N(C)C(c3ccc(F)cc3Cl)CO4)cc2F)cn1] | (−)-7-(2-chloro-4-fluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 102A | 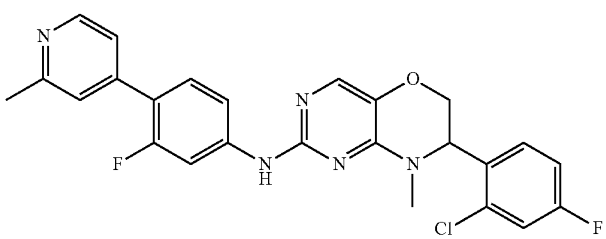 [SMILES: Cc1cc(-c2ccc(Nc3ncc4c(n3)N(C)C(c3ccc(F)cc3Cl)CO4)cc2F)ccn1] | (+)-7-(2-chloro-4-fluorophenyl)-N-(3-fluoro-4-(2-methylpyridin-4-yl) phenyl)-8-methyl-7, 8-dihydro-6H-pyrimido [5, 4-b] [1, 4] oxazin-2-amine |
| 102B | 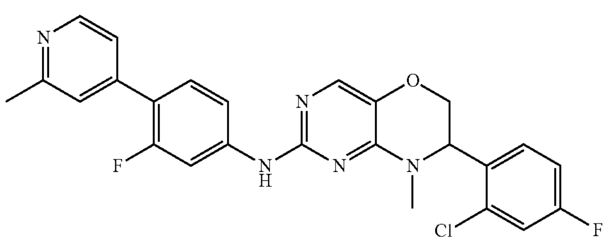 [SMILES: Cc1cc(-c2ccc(Nc3ncc4c(n3)N(C)C(c3ccc(F)cc3Cl)CO4)cc2F)ccn1] | (−)-7-(2-chloro-4-fluorophenyl)-N-(3-fluoro-4-(2-methylpyridin-4-yl) phenyl)-8-methyl-7, 8-dihydro-6H-pyrimido [5, 4-b] [1, 4] oxazin-2-amine |
| 103A | 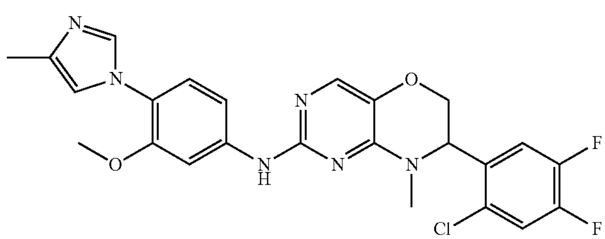 [SMILES: COc1cc(Nc2ncc3c(n2)N(C)C(c2cc(F)c(F)cc2Cl)CO3)ccc1-n1cnc(C)c1] | (+)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 103B | 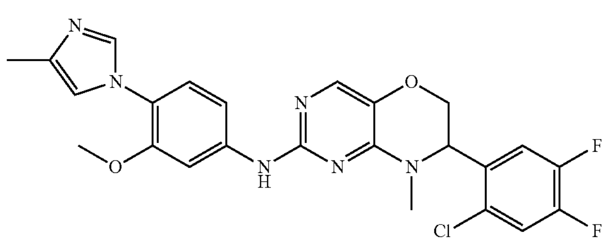 [SMILES: COc1cc(Nc2ncc3c(n2)N(C)C(c2cc(F)c(F)cc2Cl)CO3)ccc1-n1cnc(C)c1] | (−)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 104A | 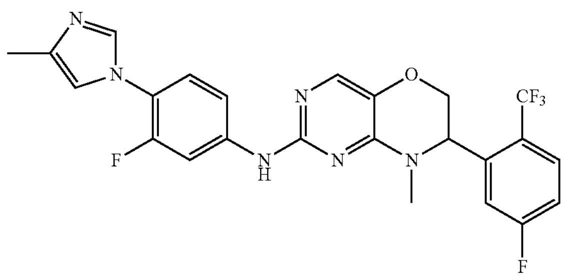 [SMILES: Cc1cn(-c2ccc(Nc3ncc4c(n3)N(C)C(c3cc(F)ccc3C(F)(F)F)CO4)cc2F)cn1] | (−)-7-(5-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 104B | 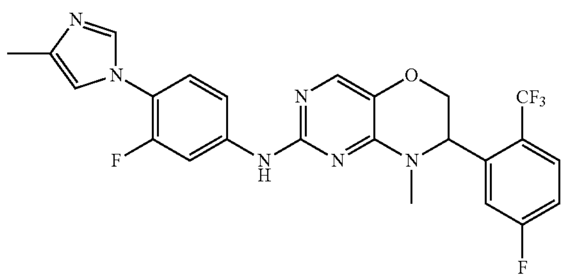 [SMILES: Cc1cn(-c2ccc(Nc3ncc4c(n3)N(C)C(c3cc(F)ccc3C(F)(F)F)CO4)cc2F)cn1] | (+)-7-(5-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 105A | 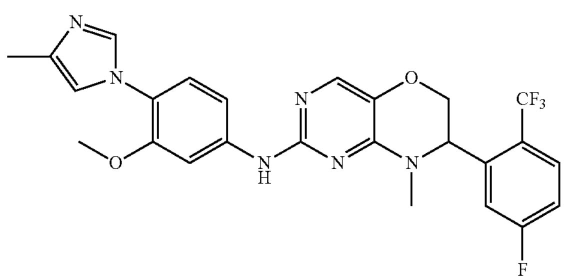 [SMILES: COc1cc(Nc2ncc3c(n2)N(C)C(c2cc(F)ccc2C(F)(F)F)CO3)ccc1-n1cnc(C)c1] | (−)-7-(5-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 105B | 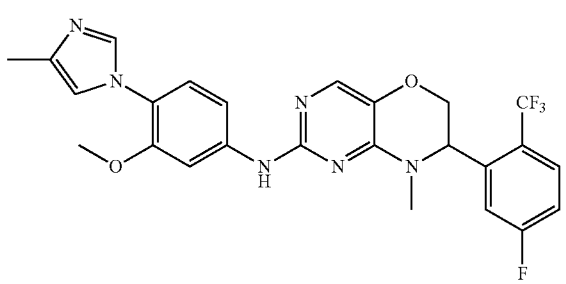 [SMILES: COc1cc(Nc2ncc3c(n2)N(C)C(c2cc(F)ccc2C(F)(F)F)CO3)ccc1-n1cnc(C)c1] | (+)-7-(5-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 106A | 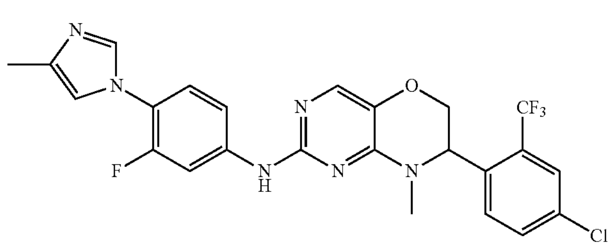 [SMILES: Cc1cn(-c2ccc(Nc3ncc4c(n3)N(C)C(c3ccc(Cl)cc3C(F)(F)F)CO4)cc2F)cn1] | (+)-7-(4-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 106B | 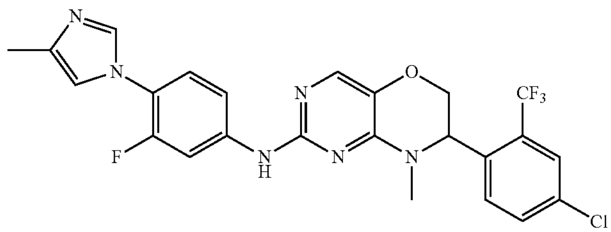 [SMILES: Cc1cn(-c2ccc(Nc3ncc4c(n3)N(C)C(c3ccc(Cl)cc3C(F)(F)F)CO4)cc2F)cn1] | (−)-7-(4-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 107A | 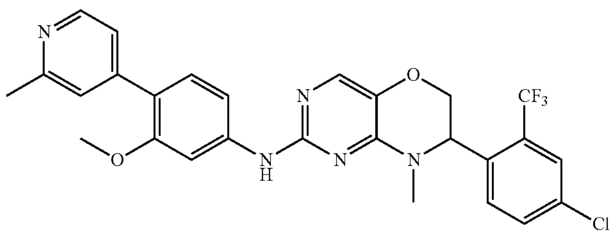 [SMILES: COc1cc(Nc2ncc3c(n2)N(C)C(c2ccc(Cl)cc2C(F)(F)F)CO3)ccc1-c1ccnc(C)c1] | (−)-7-(4-chloro-2-(trifluoromethyl) phenyl)-N-(3-methoxy-4-(2-methylpyridin-4-yl) phenyl)-8-methyl-7, 8-dihydro-6H-pyrimido [5, 4-b] [1, 4]oxazin-2-amine |
| 107B | 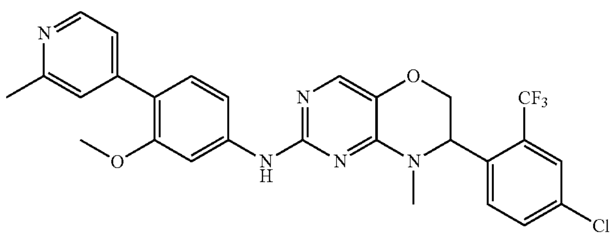 [SMILES: COc1cc(Nc2ncc3c(n2)N(C)C(c2ccc(Cl)cc2C(F)(F)F)CO3)ccc1-c1ccnc(C)c1] | (+)-7-(4-chloro-2-(trifluoromethyl) phenyl)-N-(3-methoxy-4-(2-methylpyridin-4-yl) phenyl)-8-methyl-7, 8-dihydro-6H-pyrimido [5, 4-b] [1, 4]oxazin-2-amine |
| 108A | 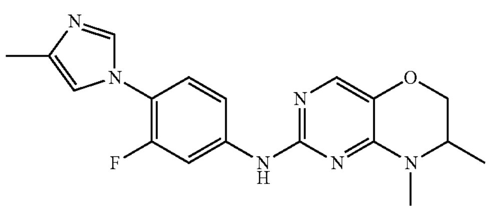 | (−)-N-(3-fluoro-4-(4-methyl-1H-imidazol-1-yl) phenyl)-7, 8-dimethyl-7, 8-dihydro-6H-pyrimido [5, 4-b] [1, 4] oxazin-2-amine |
| 108B | 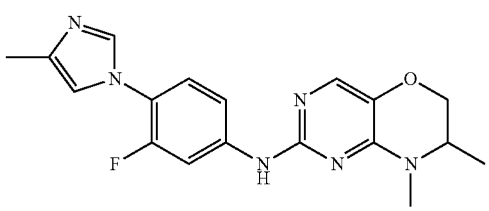 | (+)-N-(3-fluoro-4-(4-methyl-1H-imidazol-1-yl) phenyl)-7, 8-dimethyl-7, 8-dihydro-6H-pyrimido [5, 4-b] [1, 4] oxazin-2-amine |
| 109A | 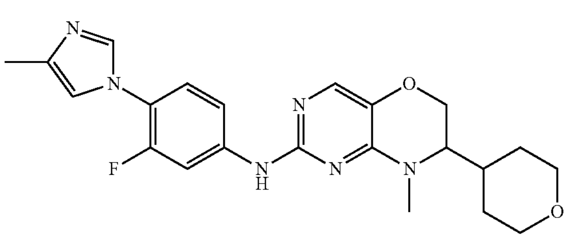 [SMILES: Cc1cn(-c2ccc(Nc3ncc4c(n3)N(C)C(C3CCOCC3)CO4)cc2F)cn1] | (+)-N-(3-fluoro-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 109B | 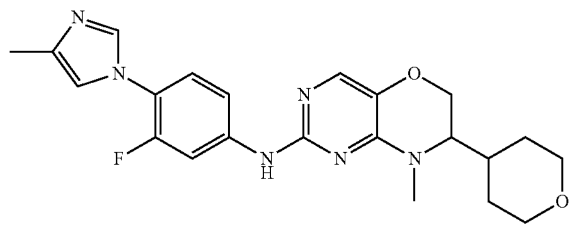 [SMILES: Cc1cn(-c2ccc(Nc3ncc4c(n3)N(C)C(C3CCOCC3)CO4)cc2F)cn1] | (−)-N-(3-fluoro-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine |
| 110A | 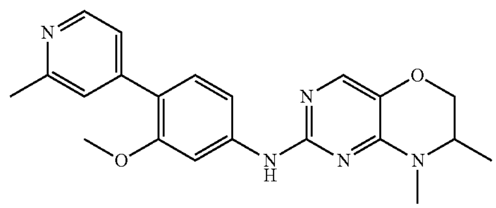 | (−)-N-(3-methoxy-4-(2-methylpyridin-4-yl) phenyl)-7, 8-dimethyl-7, 8-dihydro-6H-pyrimido [5, 4-b] [1, 4] oxazin-2-amine |
| 110B | 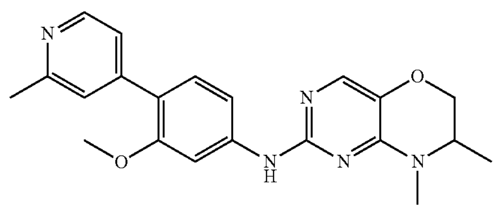 | (+)-N-(3-methoxy-4-(2-methylpyridin-4-yl) phenyl)-7, 8-dimethyl-7, 8-dihydro-6H-pyrimido [5, 4-b] [1, 4] oxazin-2-amine |
| 111 | 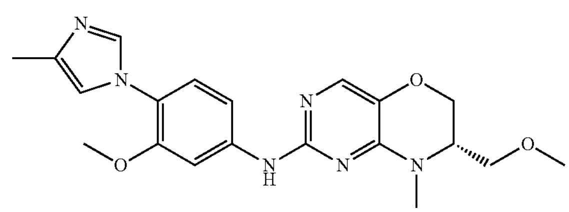 | (S)-N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine |
| 112A | 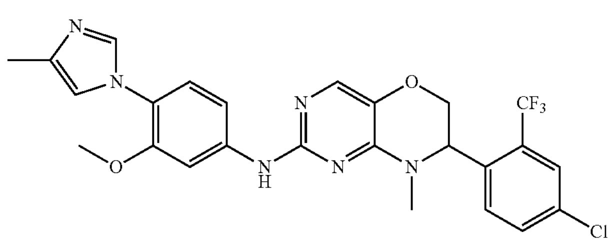 | (−)-7-(4-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4]oxazin-2-amine |
| 112B | 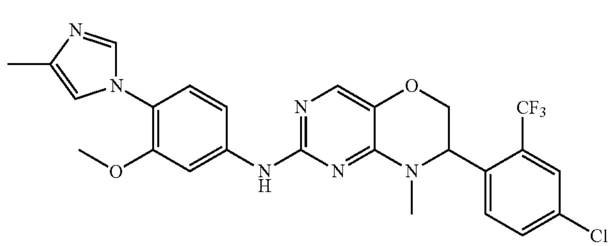 [SMILES: COc1cc(Nc2ncc3c(n2)N(C)C(c2ccc(Cl)cc2C(F)(F)F)CO3)ccc1-n1cnc(C)c1] | (+)-7-(4-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 113 | 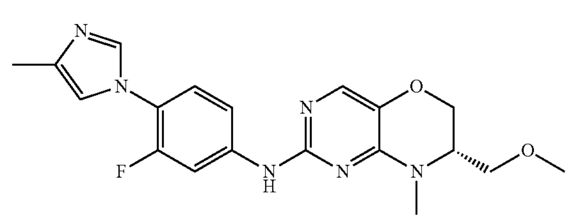 | (S)-N-(3-fluoro-4-(4-methyl-1H-imidazol-1-yl) phenyl)-7-(methoxymethyl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 114A | 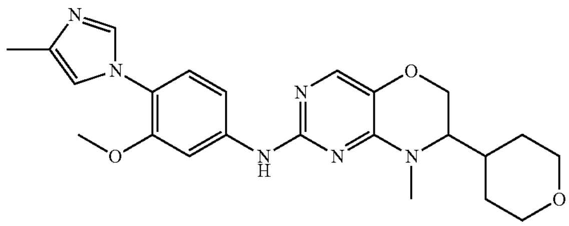 [SMILES: COc1cc(Nc2ncc3c(n2)N(C)C(C2CCOCC2)CO3)ccc1-n1cnc(C)c1] | (−)-N-(3-methoxy-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine |
| 114B | 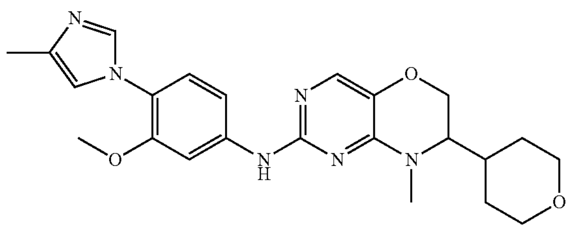 [SMILES: COc1cc(Nc2ncc3c(n2)N(C)C(C2CCOCC2)CO3)ccc1-n1cnc(C)c1] | (+)-N-(3-methoxy-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine |
| 115A | 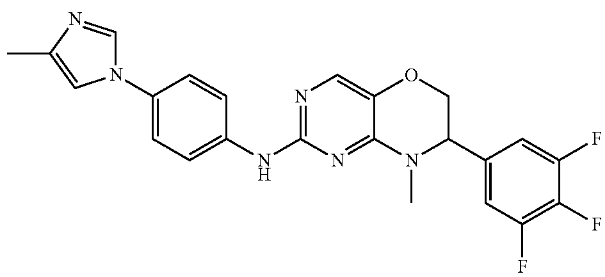 [SMILES: Cc1cn(-c2ccc(Nc3ncc4c(n3)N(C)C(c3cc(F)c(F)c(F)c3)CO4)cc2)cn1] | (−)-8-methyl-N-(4-(4-methyl-1H-imidazol-1-yl) phenyl)-7-(3, 4, 5-trifluorophenyl)-7, 8-dihydro-6H-pyrimido [5, 4-b] [1, 4]oxazin-2-amine |
| 115B | 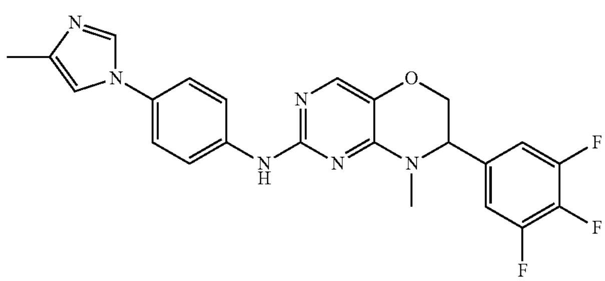 [SMILES: Cc1cn(-c2ccc(Nc3ncc4c(n3)N(C)C(c3cc(F)c(F)c(F)c3)CO4)cc2)cn1] | (+)-8-methyl-N-(4-(4-methyl-1H-imidazol-1-yl) phenyl)-7-(3, 4, 5-trifluorophenyl)-7, 8-dihydro-6H-pyrimido [5, 4-b] [1, 4]oxazin-2-amine |
| 116A | 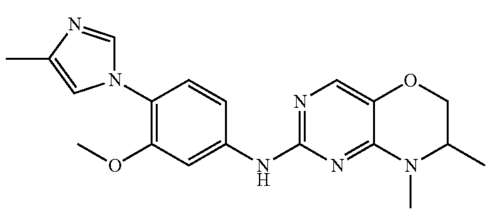 | (−)-N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine |
| 116B | 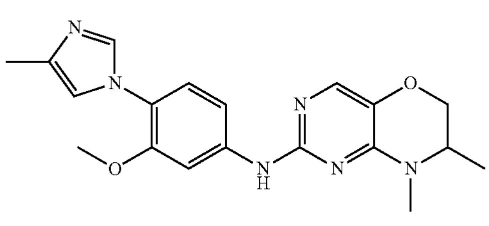 | (+)-N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 117A | 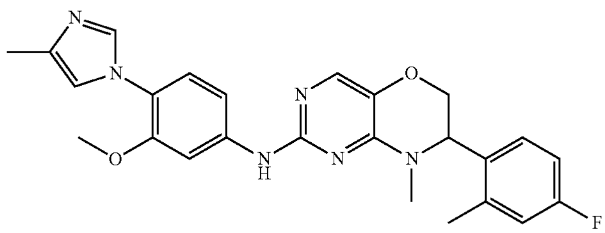 [SMILES: COc1cc(Nc2ncc3c(n2)N(C)C(c2ccc(F)cc2C)CO3)ccc1-n1cnc(C)c1] | (−)-7-(4-fluoro-2-methylphenyl)-N-(3-methoxy-4-(4-methyl-1H-imidazol-1-yl)phenyl)-8-methyl-7,8-dihydro-6H-pyrimido [5, 4-b] [1, 4] oxazin-2-amine |
| 117B | 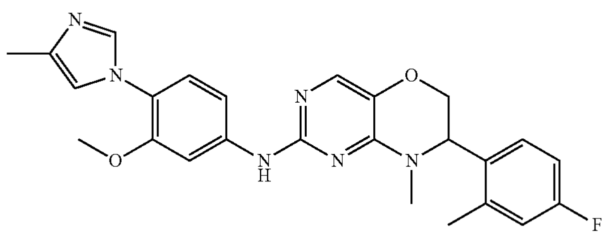 [SMILES: COc1cc(Nc2ncc3c(n2)N(C)C(c2ccc(F)cc2C)CO3)ccc1-n1cnc(C)c1] | (+)-7-(4-fluoro-2-methylphenyl)-N-(3-methoxy-4-(4-methyl-1H-imidazol-1-yl)phenyl)-8-methyl-7,8-dihydro-6H-pyrimido [5, 4-b] [1, 4] oxazin-2-amine |
| 118A | 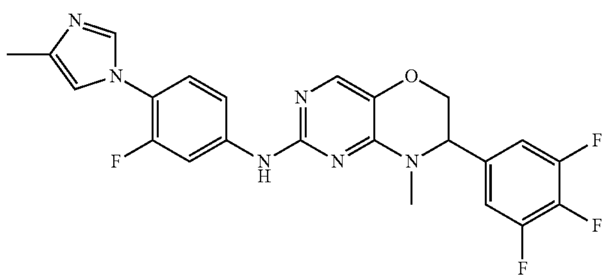 [SMILES: Cc1cn(-c2ccc(Nc3ncc4c(n3)N(C)C(c3cc(F)c(F)c(F)c3)CO4)cc2F)cn1] | (+)-N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine |
| 118B | 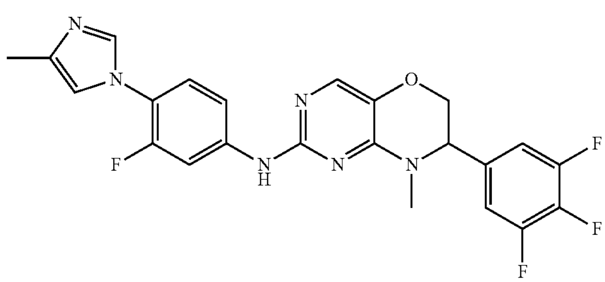 [SMILES: Cc1cn(-c2ccc(Nc3ncc4c(n3)N(C)C(c3cc(F)c(F)c(F)c3)CO4)cc2F)cn1] | (−)-N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine |
| 164 | 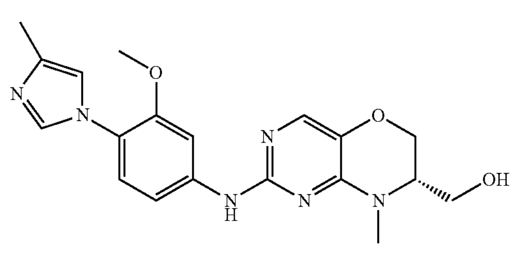 [SMILES: COc1cc(Nc2ncc3c(n2)N(C)[C@@H](CO)CO3)ccc1-n1cnc(C)c1] | (S)-N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 165A | 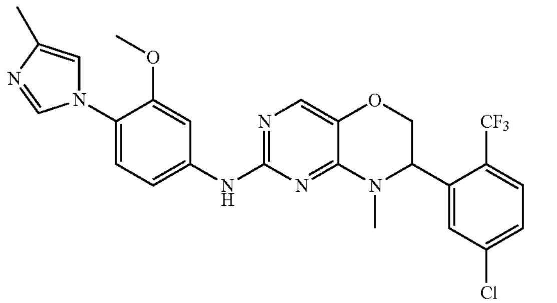 | (+)-7-(5-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 165B | 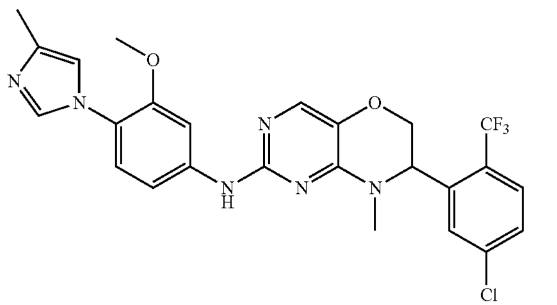 | (−)-7-(5-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 166A | 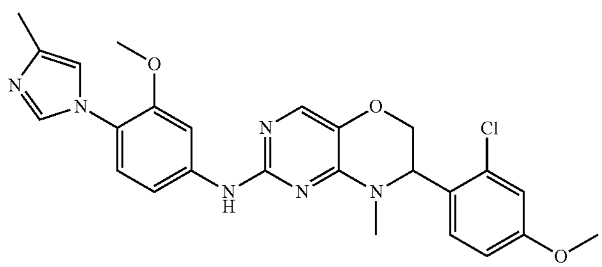 | (+)-7-(2-chloro-5-methoxyphenyl)-N-(3-methoxy-4-(4-methyl-1H-imidazol-1-yl) phenyl)- 8-methyl-7, 8-dihydro-6H-pyrimido [5, 4-b] [1, 4] oxazin-2-amine |
| 166B | 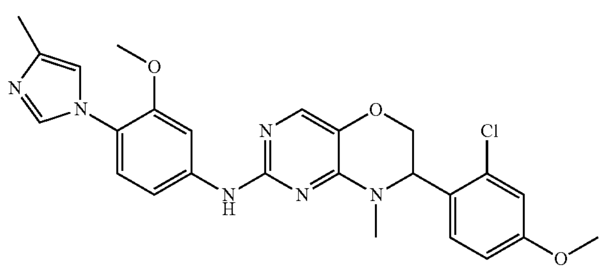 | (−)-7-(2-chloro-5-methoxyphenyl)-N-(3-methoxy-4-(4-methyl-1H-imidazol-1-yl) phenyl)- 8-methyl-7, 8-dihydro-6H-pyrimido [5, 4-b] [1, 4] oxazin-2-amine |
| 167A | 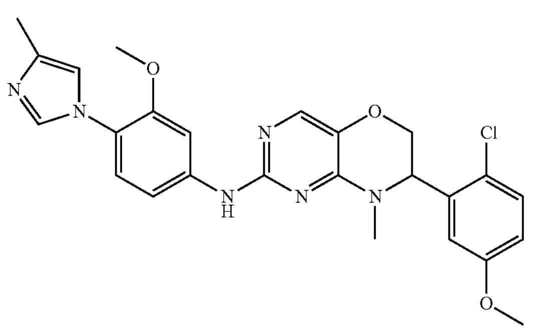 | (+)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 167B | 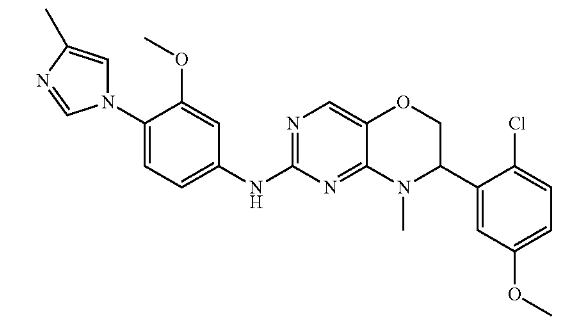 | (−)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 168A | 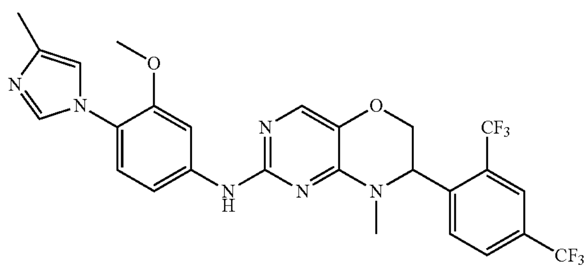 [SMILES: COc1cc(Nc2ncc3c(n2)N(C)C(c2ccc(C(F)(F)F)cc2C(F)(F)F)CO3)ccc1-n1cnc(C)c1] | (−)-7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 168B | 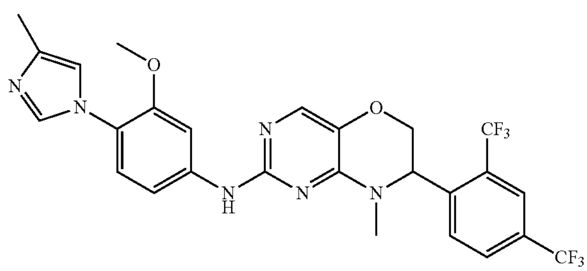 [SMILES: COc1cc(Nc2ncc3c(n2)N(C)C(c2ccc(C(F)(F)F)cc2C(F)(F)F)CO3)ccc1-n1cnc(C)c1] | (+)-7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 169A | 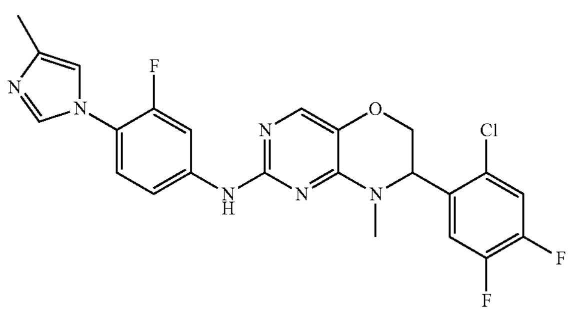 [SMILES: Cc1cn(-c2ccc(Nc3ncc4c(n3)N(C)C(c3cc(F)c(F)cc3Cl)CO4)cc2F)cn1] | (+)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 169B | 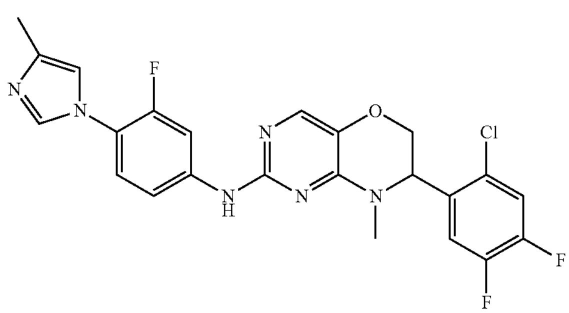 [SMILES: Cc1cn(-c2ccc(Nc3ncc4c(n3)N(C)C(c3cc(F)c(F)cc3Cl)CO4)cc2F)cn1] | (−)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4]oxazin-2-amine |

TABLE I-continued

Exemplary Fused Morpholinopyrimidines of Formula (I)

| Compound of Example | Structure | Name |
| --- | --- | --- |
| 170 | 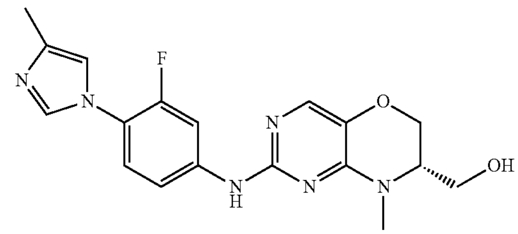 [SMILES: Cc1cn(-c2ccc(Nc3ncc4c(n3)N(C)[C@@H](CO)CO4)cc2F)cn1] | (S)-(2-((3-fluoro-4-(4-methyl-1H-imidazol-1-yl) phenyl) amino)-8-methyl-7, 8-dihydro-6H-pyrimido [5, 4-b] [1, 4] oxazin-7-yl) methanol |
| 171A | 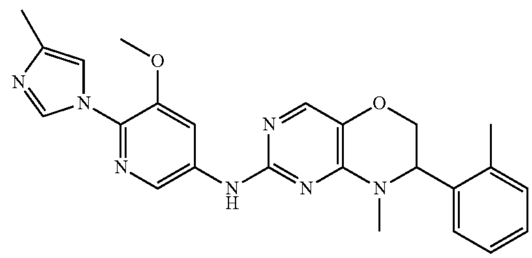 [SMILES: COc1cc(Nc2ncc3c(n2)N(C)C(c2ccccc2C)CO3)cnc1-n1cnc(C)c1] | (+)-N-(5-methoxy-6-(4-methyl-1H-imidazol-1-yl) pyridin-3-yl)-8-methyl-7-(o-tolyl)-7, 8-dihydro-6H-pyrimido [5, 4-b] [1, 4] oxazin-2-amine |
| 171B | 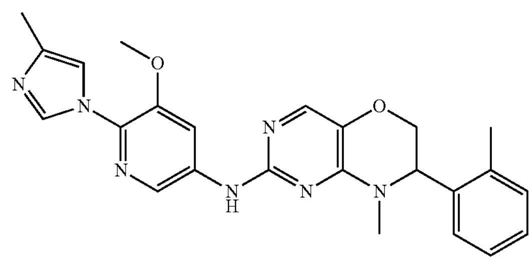 [SMILES: COc1cc(Nc2ncc3c(n2)N(C)C(c2ccccc2C)CO3)cnc1-n1cnc(C)c1] | (−)-N-(5-methoxy-6-(4-methyl-1H-imidazol-1-yl) pyridin-3-yl)-8-methyl-7-(o-tolyl)-7, 8-dihydro-6H-pyrimido [5, 4-b] [1, 4] oxazin-2-amine |
| 172A | 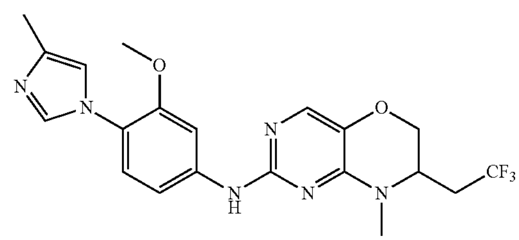 [SMILES: COc1cc(Nc2ncc3c(n2)N(C)C(CC(F)(F)F)CO3)ccc1-n1cnc(C)c1] | (−)-N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine |
| 172B | 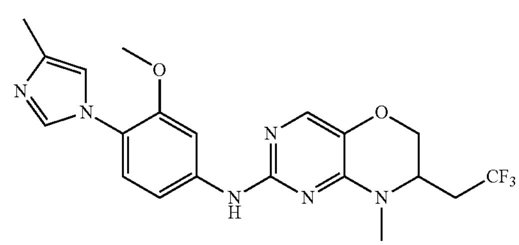 [SMILES: COc1cc(Nc2ncc3c(n2)N(C)C(CC(F)(F)F)CO3)ccc1-n1cnc(C)c1] | (+)-N-(3-methoxy-4-(4-methyl-1H-imidazol-1-yl) phenyl)-1-methyl-2-(2, 2, 2-trifluoroethyl)-2, 3-dihydro-1H-pyrido [3, 4-b][1, 4] oxazin-7-amine |
| 173A | 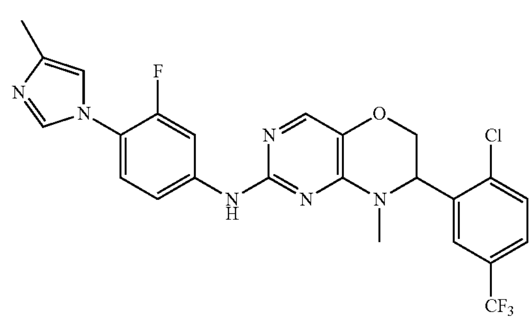 [SMILES: Cc1cn(-c2ccc(Nc3ncc4c(n3)N(C)C(c3cc(C(F)(F)F)ccc3Cl)CO4)cc2F)cn1] | (+)-7-(2-chloro-5-(trifluoromethyl) phenyl)-N-(3-fluoro-4-(4-methyl-1H-imidazol-1-yl) phenyl)- 8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 173B | 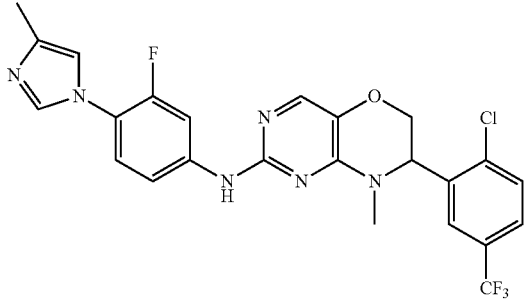 [SMILES: Cc1cn(-c2ccc(Nc3ncc4c(n3)N(C)C(c3cc(C(F)(F)F)ccc3Cl)CO4)cc2F)cn1] | (−)-7-(2-chloro-5-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine |
| 174A | 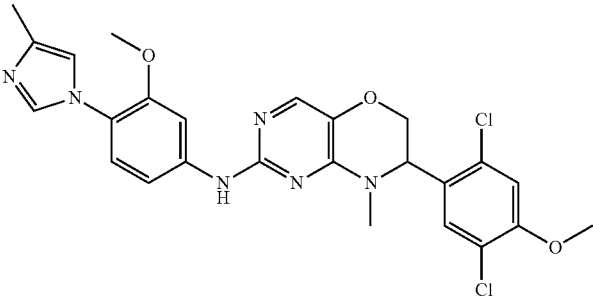 [SMILES: COc1cc(Cl)c(C2COc3cnc(Nc4ccc(-n5cnc(C)c5)c(OC)c4)nc3N2C)cc1Cl] | (−)-7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 174B | 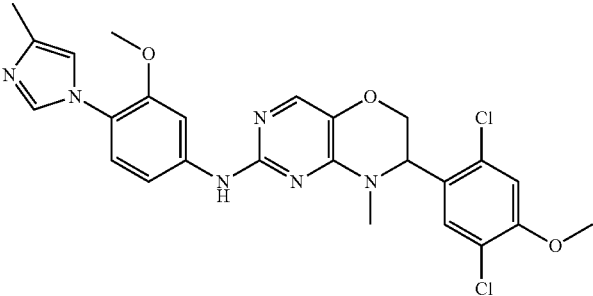 [SMILES: COc1cc(Cl)c(C2COc3cnc(Nc4ccc(-n5cnc(C)c5)c(OC)c4)nc3N2C)cc1Cl] | (+)-7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 175A | 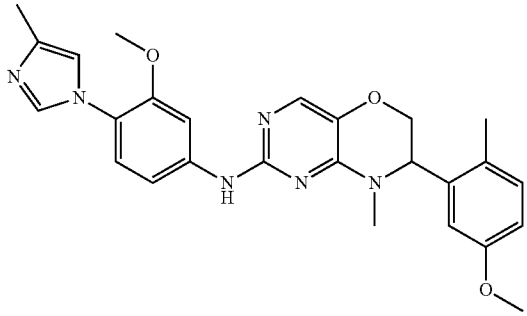 | (+)-7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 175B | 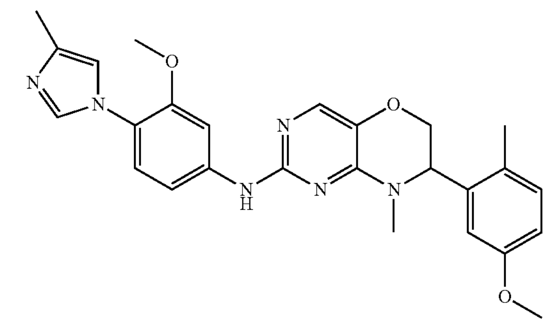 [SMILES: COc1ccc(C)c(C2COc3cnc(Nc4ccc(-n5cnc(C)c5)c(OC)c4)nc3N2C)c1] | (−)-7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 176 | 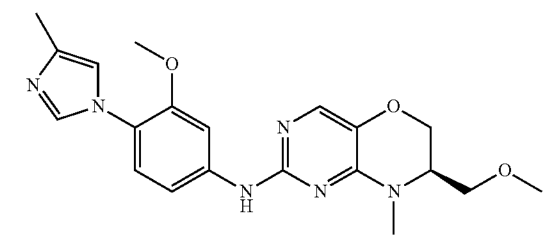 [SMILES: COC[C@@H]1COc2cnc(Nc3ccc(-n4cnc(C)c4)c(OC)c3)nc2N1C] | (R)-N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine |
| 177 | 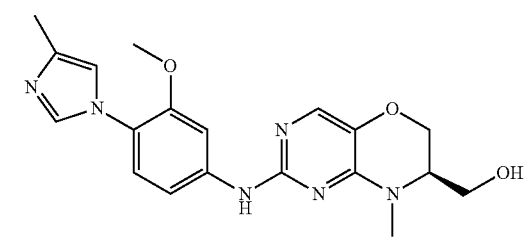 [SMILES: COc1cc(Nc2ncc3c(n2)N(C)[C@H](CO)CO3)ccc1-n1cnc(C)c1] | (R)-(2-((3-methoxy-4-(4-methyl-1H-imidazol-1-yl) phenyl) amino)-8-methyl-7, 8-dihydro-6H-pyrimido [5, 4-b] [1, 4]oxazin-7-yl) methanol |
| 178A | 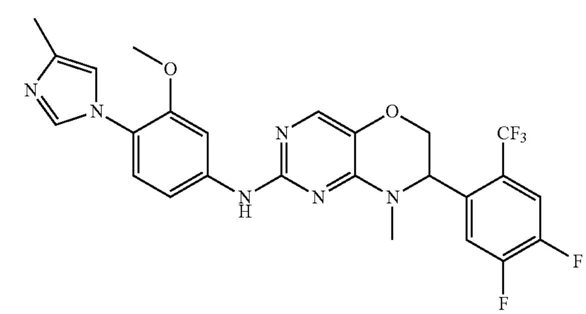 [SMILES: COc1cc(Nc2ncc3c(n2)N(C)C(c2cc(F)c(F)cc2C(F)(F)F)CO3)ccc1-n1cnc(C)c1] | (+)-7-(4, 5-difluoro-2-(trifluoromethyl) phenyl)-N-(1-(2-methoxypyridin-4-yl) piperidin-4-yl)-8-methyl-7, 8-dihydro-6H-pyrimido [5, 4-b] [1, 4] oxazin-2-amine |
| 178B | 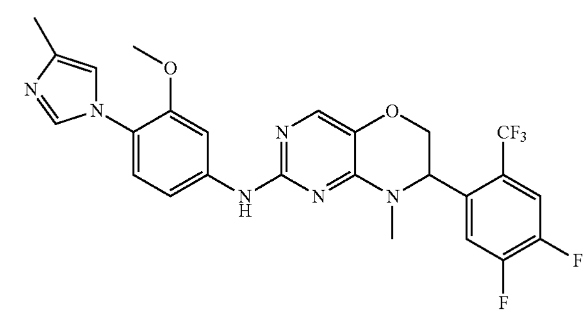 [SMILES: COc1cc(Nc2ncc3c(n2)N(C)C(c2cc(F)c(F)cc2C(F)(F)F)CO3)ccc1-n1cnc(C)c1] | (−)-7-(4, 5-difluoro-2-(trifluoromethyl) phenyl)-N-(1-(2-methoxypyridin-4-yl) piperidin-4-yl)-8-methyl-7, 8-dihydro-6H-pyrimido [5, 4-b] [1, 4]oxazin-2-amine |

TABLE I-continued

Exemplary Fused Morpholinopyrimidines of Formula (I)

| Compound of Example | Structure | Name |
|---|---|---|
| 179A | 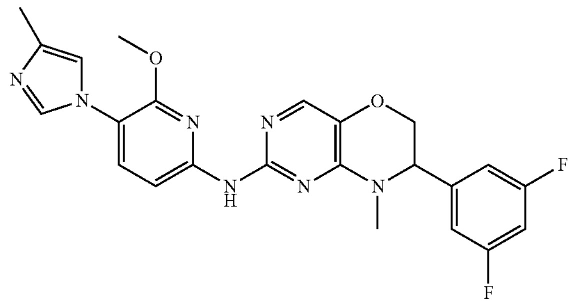 [SMILES: COc1nc(Nc2ncc3c(n2)N(C)C(c2cc(F)cc(F)c2)CO3)ccc1-n1cnc(C)c1] | (−)-7-(3, 5-difluorophenyl)-N-(6-methoxy-5-(4-methyl-1H-imidazol-1-yl) pyridin-2-yl)-8-methyl-7, 8-dihydro-6H-pyrimido [5, 4-b] [1, 4] oxazin-2-amine |
| 179B | 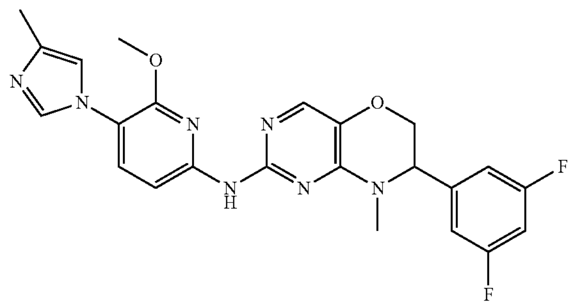 [SMILES: COc1nc(Nc2ncc3c(n2)N(C)C(c2cc(F)cc(F)c2)CO3)ccc1-n1cnc(C)c1] | (+)-7-(3, 5-difluorophenyl)-N-(6-methoxy-5-(4-methyl-1H-imidazol-1-yl) pyridin-2-yl)-8-methyl-7, 8-dihydro-6H-pyrimido [5, 4-b] [1, 4] oxazin-2-amine |
| 180A | 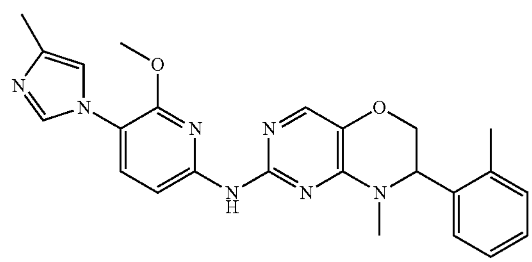 | (−)-N-(6-methoxy-5-(4-methyl-1H-imidazol-1-yl) pyridin-2-yl)-8-methyl-7-(o-tolyl)-7, 8-dihydro-6H-pyrimido [5, 4-b] [1, 4] oxazin-2-amine |
| 180B | 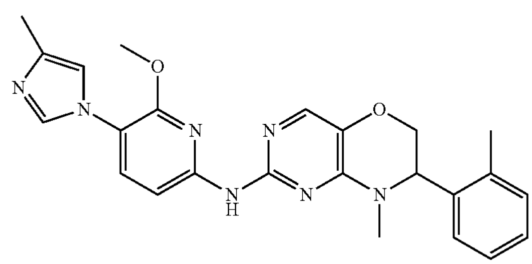 | (+)-N-(6-methoxy-5-(4-methyl-1H-imidazol-1-yl) pyridin-2-yl)-8-methyl-7-(o-tolyl)-7, 8-dihydro-6H-pyrimido [5, 4-b] [1, 4] oxazin-2-amine |
| 181A | 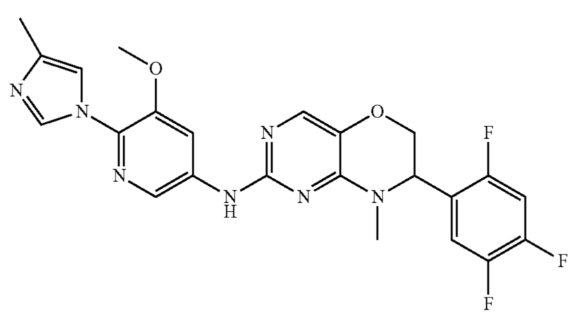 [SMILES: COc1cc(Nc2ncc3c(n2)N(C)C(c2cc(F)c(F)cc2F)CO3)cnc1-n1cnc(C)c1] | (−)-N-(5-methoxy-6-(4-methyl-1H-imidazol-1-yl) pyridin-3-yl)-8-methyl-7-(2, 4, 5-trifluorophenyl)-7, 8-dihydro-6H-pyrimido [5, 4-b] [1, 4]oxazin-2-amine |

TABLE I-continued

Exemplary Fused Morpholinopyrimidines of Formula (I)

| Compound of Example | Structure | Name |
|---|---|---|
| 181B | 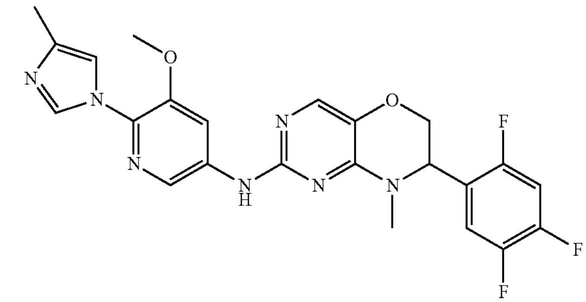 [SMILES: COc1cc(Nc2ncc3c(n2)N(C)C(c2cc(F)c(F)cc2F)CO3)cnc1-n1cnc(C)c1] | (+)-N-(5-methoxy-6-(4-methyl-1H-imidazol-1-yl)pyridin-3-yl)-8-methyl-7-(2, 4, 5-trifluorophenyl)-7, 8-dihydro-6H-pyrimido [5, 4-b] [1, 4]oxazin-2-amine |
| 182A | 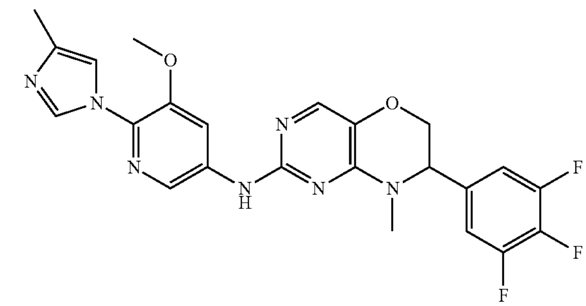 [SMILES: COc1cc(Nc2ncc3c(n2)N(C)C(c2cc(F)c(F)c(F)c2)CO3)cnc1-n1cnc(C)c1] | (+)-N-(5-methoxy-6-(4-methyl-1H-imidazol-1-yl)pyridin-3-yl)-8-methyl-7-(3, 4, 5-trifluorophenyl)-7, 8-dihydro-6H-pyrimido [5, 4-b] [1, 4] oxazin-2-amine |
| 182B | 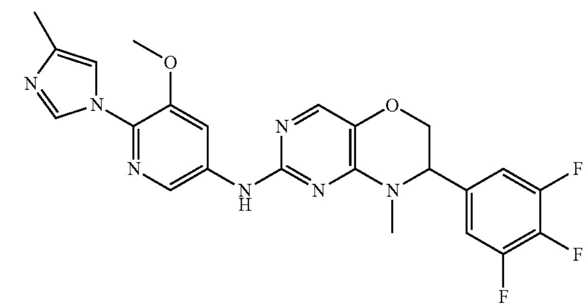 [SMILES: COc1cc(Nc2ncc3c(n2)N(C)C(c2cc(F)c(F)c(F)c2)CO3)cnc1-n1cnc(C)c1] | (−)-N-(5-methoxy-6-(4-methyl-1H-imidazol-1-yl)pyridin-3-yl)-8-methyl-7-(3, 4, 5-trifluorophenyl)-7, 8-dihydro-6H-pyrimido [5, 4-b] [1, 4] oxazin-2-amine |
| 183A | 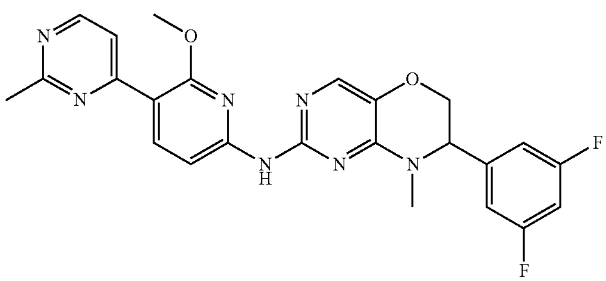 [SMILES: COc1nc(Nc2ncc3c(n2)N(C)C(c2cc(F)cc(F)c2)CO3)ccc1-c1ccnc(C)n1] | (+)-7-(3, 5-difluorophenyl)-N-(6-methoxy-5-(2-methylpyrimidin-4-yl)pyridin-2-yl)-8-methyl-7, 8-dihydro-6H-pyrimido [5, 4-b][1, 4] oxazin-2-amine |
| 183B | 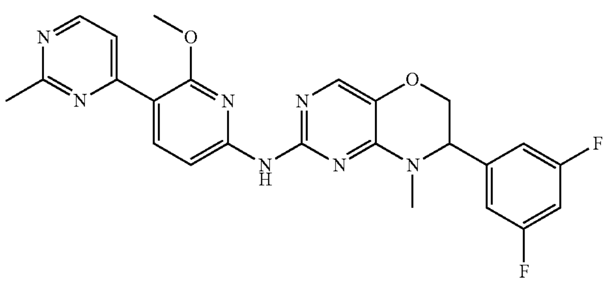 [SMILES: COc1nc(Nc2ncc3c(n2)N(C)C(c2cc(F)cc(F)c2)CO3)ccc1-c1ccnc(C)n1] | (−)-7-(3, 5-difluorophenyl)-N-(6-methoxy-5-(2-methylpyrimidin-4-yl)pyridin-2-yl)-8-methyl-7, 8-dihydro-6H-pyrimido [5, 4-b][1, 4] oxazin-2-amine |

TABLE I-continued

Exemplary Fused Morpholinopyrimidines of Formula (I)

| Compound of Example | Structure | Name |
|---|---|---|
| 184A | 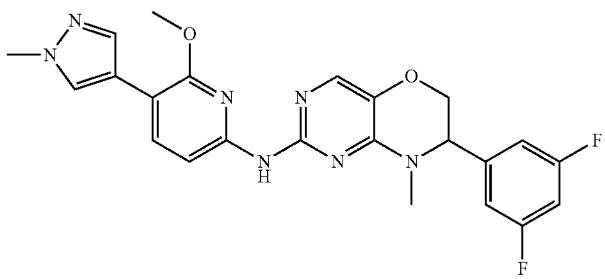 [SMILES: COc1nc(Nc2ncc3c(n2)N(C)C(c2cc(F)cc(F)c2)CO3)ccc1-c1cnn(C)c1] | (−)-7-(3, 5-difluorophenyl)-N-(6-methoxy-5-(1-methyl-1H-pyrazol-4-yl) pyridin-2-yl)-8-methyl-7, 8-dihydro-6H-pyrimido [5, 4-b] [1, 4] oxazin-2-amine |
| 184B | 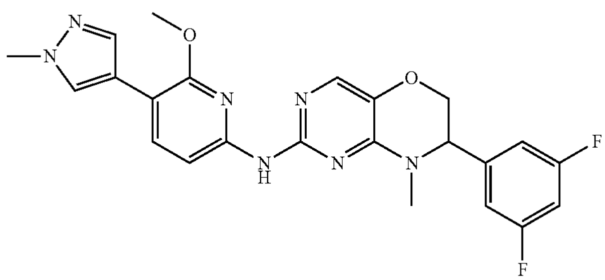 [SMILES: COc1nc(Nc2ncc3c(n2)N(C)C(c2cc(F)cc(F)c2)CO3)ccc1-c1cnn(C)c1] | (+)-7-(3, 5-difluorophenyl)-N-(6-methoxy-5-(1-methyl-1H-pyrazol-4-yl) pyridin-2-yl)-8-methyl-7, 8-dihydro-6H-pyrimido [5, 4-b] [1, 4] oxazin-2-amine |
| 185A | 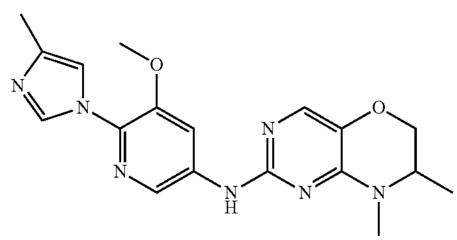 | (+)-N-(5-methoxy-6-(4-methyl-1H-imidazol-1-yl) pyridin-3-yl)-7, 8-dimethyl-7, 8-dihydro-6H-pyrimido [5, 4-b] [1, 4] oxazin-2-amine |
| 185B | 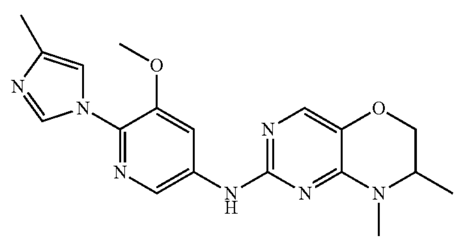 | (−)-N-(5-methoxy-6-(4-methyl-1H-imidazol-1-yl) pyridin-3-yl)-7, 8-dimethyl-7, 8-dihydro-6H-pyrimido [5, 4-b] [1, 4] oxazin-2-amine |
| 186A | 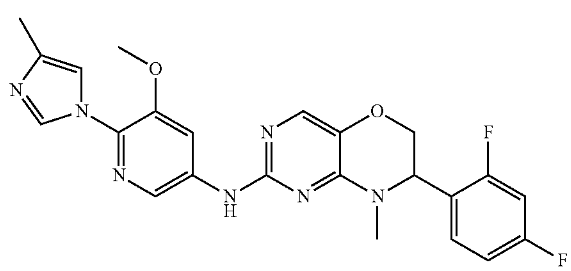 [SMILES: COc1cc(Nc2ncc3c(n2)N(C)C(c2ccc(F)cc2F)CO3)cnc1-n1cnc(C)c1] | (+)-7-(2, 4-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 186B | 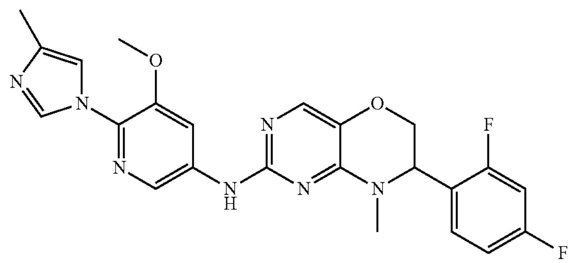 [SMILES: COc1cc(Nc2ncc3c(n2)N(C)C(c2ccc(F)cc2F)CO3)cnc1-n1cnc(C)c1] | (−)-7-(2, 4-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |
| 187A | 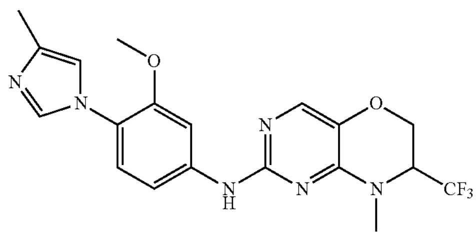 [SMILES: COc1cc(Nc2ncc3c(n2)N(C)C(C(F)(F)F)CO3)ccc1-n1cnc(C)c1] | (+)-N-(3-methoxy-4-(4-methyl-1H-imidazol-1-yl) phenyl)-8-methyl-7-(trifluoromethyl)-7, 8-dihydro-6H-pyrimido [5, 4-b] [1, 4] oxazin-2-amine |
| 187B | 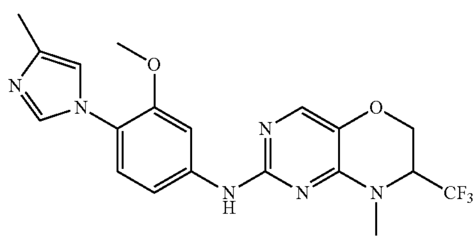 [SMILES: COc1cc(Nc2ncc3c(n2)N(C)C(C(F)(F)F)CO3)ccc1-n1cnc(C)c1] | (−)-N-(3-methoxy-4-(4-methyl-1H-imidazol-1-yl) phenyl)-8-methyl-7-(trifluoromethyl)-7, 8-dihydro-6H-pyrimido [5, 4-b] [1, 4]oxazin-2-amine |
| 188A | 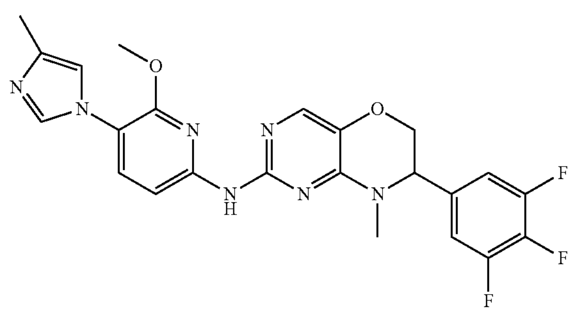 [SMILES: COc1nc(Nc2ncc3c(n2)N(C)C(c2cc(F)c(F)c(F)c2)CO3)ccc1-n1cnc(C)c1] | (−)-N-(6-methoxy-5-(4-methyl-1H-imidazol-1-yl) pyridin-2-yl)-8-methyl-7-(3, 4, 5-trifluorophenyl)-7, 8-dihydro-6H-pyrimido [5, 4-b] [1, 4]oxazin-2-amine |
| 188B | 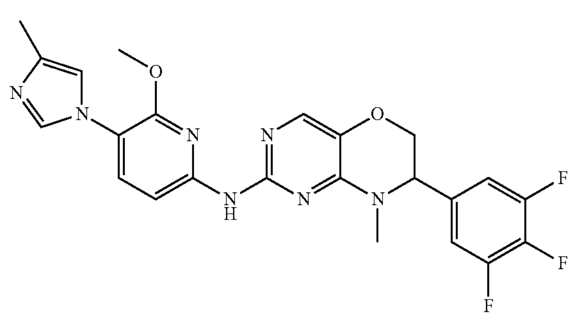 [SMILES: COc1nc(Nc2ncc3c(n2)N(C)C(c2cc(F)c(F)c(F)c2)CO3)ccc1-n1cnc(C)c1] | (+)-N-(6-methoxy-5-(4-methyl-1H-imidazol-1-yl) pyridin-2-yl)-8-methyl-7-(3, 4, 5-trifluorophenyl)-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 189A | 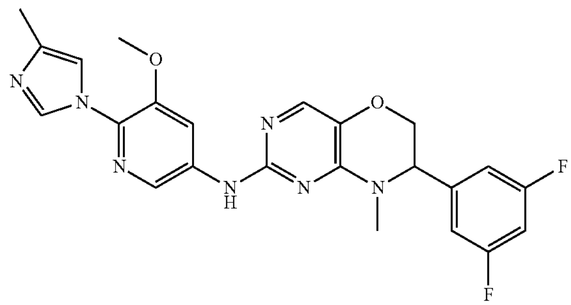 [SMILES: COc1cc(Nc2ncc3c(n2)N(C)C(c2cc(F)cc(F)c2)CO3)cnc1-n1cnc(C)c1] | (+)-7-(3, 5-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |
| 189B | 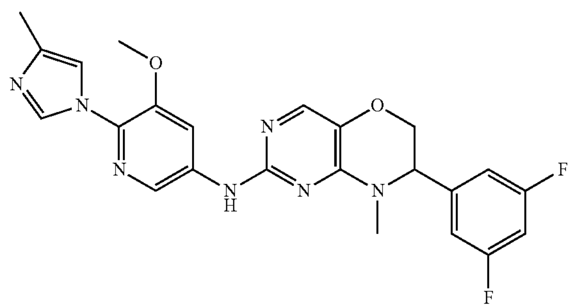 [SMILES: COc1cc(Nc2ncc3c(n2)N(C)C(c2cc(F)cc(F)c2)CO3)cnc1-n1cnc(C)c1] | (−)-7-(3, 5-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |
| 190 | 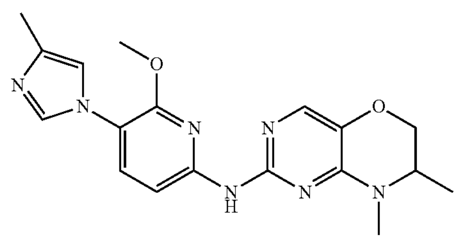 [SMILES: COc1nc(Nc2ncc3c(n2)N(C)C(C)CO3)ccc1-n1cnc(C)c1] | N-(6-methoxy-5-(4-methyl-1H-imidazol-1-yl) pyridin-2-yl)-7, 8-dimethyl-7, 8-dihydro-6H-pyrimido [5, 4-b] [1, 4]oxazin-2-amine (racemic) |
| 191 | 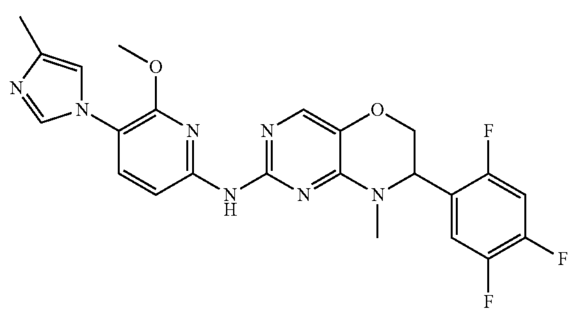 [SMILES: COc1nc(Nc2ncc3c(n2)N(C)C(c2cc(F)c(F)cc2F)CO3)ccc1-n1cnc(C)c1] | N-(6-methoxy-5-(4-methyl-1H-imidazol-1-yl) pyridin-2-yl)-8-methyl-7-(2, 4, 5-trifluorophenyl)-7, 8-dihydro-6H-pyrimido [5, 4-b] [1, 4] oxazin-2-amine (racemic) |
| 192A | 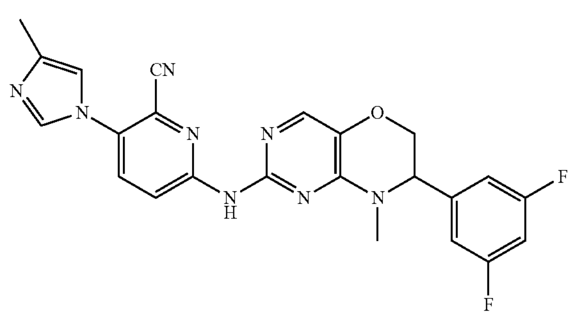 [SMILES: Cc1cn(-c2ccc(Nc3ncc4c(n3)N(C)C(c3cc(F)cc(F)c3)CO4)nc2C#N)cn1] | (−)-6-((7-(3, 5-difluorophenyl)-8-methyl-7, 8-dihydro-6H-pyrimido [5, 4-b] [1, 4] oxazin-2-yl) amino)-3-(4-methyl-1H-imidazol-1-yl) picolinonitrile |

TABLE I-continued

Exemplary Fused Morpholinopyrimidines of Formula (I)

| Compound of Example | Structure | Name |
|---|---|---|
| 192B | 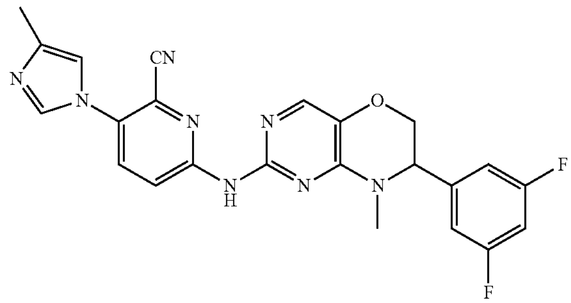 [SMILES: Cc1cn(-c2ccc(Nc3ncc4c(n3)N(C)C(c3cc(F)cc(F)c3)CO4)nc2C#N)cn1] | (+)-6-((7-(3, 5-difluorophenyl)-8-methyl-7, 8-dihydro-6H-pyrimido [5, 4-b] [1, 4] oxazin-2-yl) amino)-3-(4-methyl-1H-imidazol-1-yl) picolinonitrile |
| 193A | 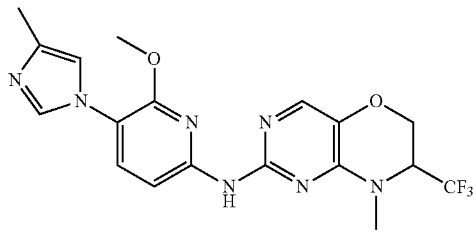 [SMILES: COc1nc(Nc2ncc3c(n2)N(C)C(C(F)(F)F)CO3)ccc1-n1cnc(C)c1] | (+)-N-(5-methoxy-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine |
| 193B | 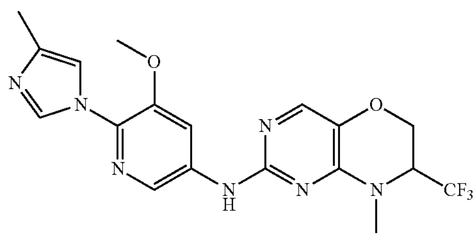 [SMILES: COc1cc(Nc2ncc3c(n2)N(C)C(C(F)(F)F)CO3)cnc1-n1cnc(C)c1] | (−)-N-(5-methoxy-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine |
| 194A | 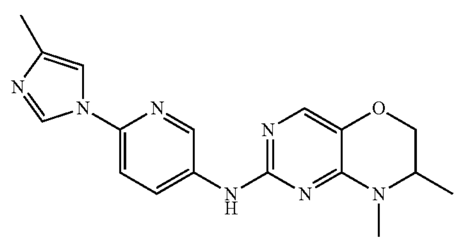 [SMILES: Cc1cn(-c2ccc(Nc3ncc4c(n3)N(C)C(C)CO4)cn2)cn1] | (+)-7, 8-dimethyl-N-(6-(4-methyl-1H-imidazol-1-yl) pyridin-3-yl)-7, 8-dihydro-6H-pyrimido [5, 4-b] [1, 4] oxazin-2-amine |
| 194B | 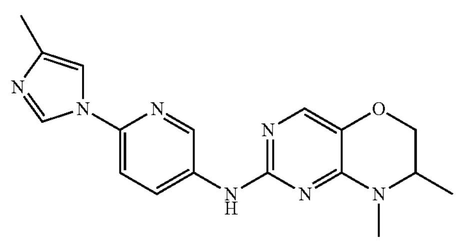 [SMILES: Cc1cn(-c2ccc(Nc3ncc4c(n3)N(C)C(C)CO4)cn2)cn1] | (−)-7, 8-dimethyl-N-(6-(4-methyl-1H-imidazol-1-yl) pyridin-3-yl)-7, 8-dihydro-6H-pyrimido [5, 4-b] [1, 4] oxazin-2-amine |
| 195 | 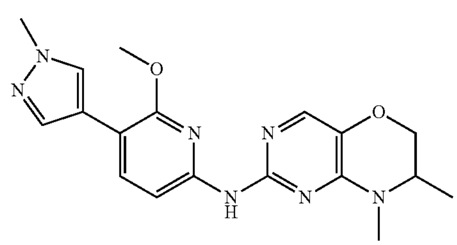 [SMILES: COc1nc(Nc2ncc3c(n2)N(C)C(C)CO3)ccc1-c1cnn(C)c1] | N-(6-methoxy-5-(1-methyl-1H-pyrazol-4-yl) pyridin-2-yl)-7, 8-dimethyl-7, 8-dihydro-6H-pyrimido [5, 4-b] [1, 4] oxazin-2-amine (racemic) |

TABLE I-continued

Exemplary Fused Morpholinopyrimidines of Formula (I)

| Compound of Example | Structure | Name |
|---|---|---|
| 196 | 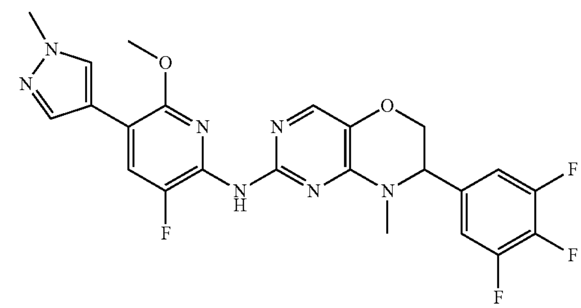 [SMILES: COc1nc(Nc2ncc3c(n2)N(C)C(c2cc(F)c(F)c(F)c2)CO3)c(F)cc1-c1cnn(C)c1] | N-(3-fluoro-6-methoxy-5-(1-methyl-1H-pyrazol-4-yl) pyridin-2-yl)-8-methyl-7-(3, 4, 5-trifluorophenyl)-7, 8-dihydro-6H-pyrimido [5, 4-b] [1, 4] oxazin-2-amine (racemic) |
| 197 | 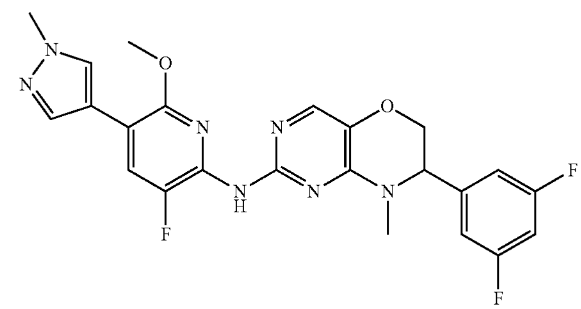 [SMILES: COc1nc(Nc2ncc3c(n2)N(C)C(c2cc(F)cc(F)c2)CO3)c(F)cc1-c1cnn(C)c1] | 7-(3, 5-difluorophenyl)-N-(3-fluoro-6-methoxy-5-(1-methyl-1H-pyrazol-4-yl) pyridin-2-yl)-8-methyl-7, 8-dihydro-6H-pyrimido [5, 4-b] [1, 4] oxazin-2-amine (racemic) |
| 198A | 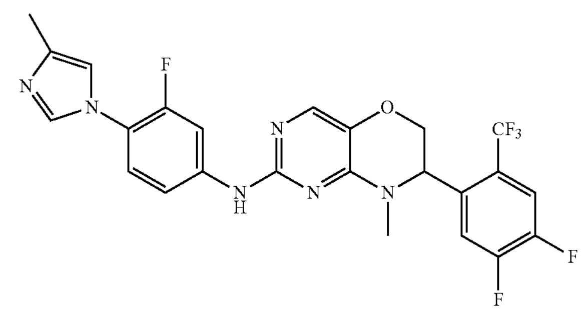 [SMILES: Cc1cn(-c2ccc(Nc3ncc4c(n3)N(C)C(c3cc(F)c(F)cc3C(F)(F)F)CO4)cc2F)cn1] | (−)-N-(5-methoxy-6-(4-methyl-1H-imidazol-1-yl) pyridin-3-yl)-7, 7, 8-trimethyl-7, 8-dihydro-6H-pyrimido [5, 4-b] [1, 4] oxazin-2-amine |
| 198B | 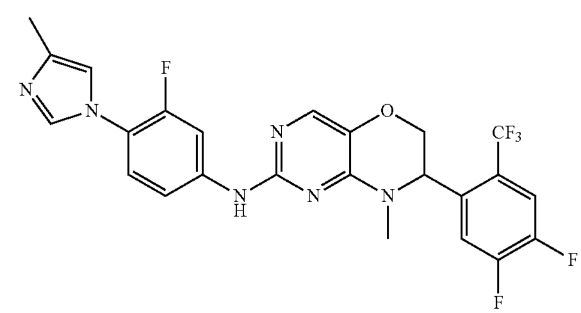 [SMILES: Cc1cn(-c2ccc(Nc3ncc4c(n3)N(C)C(c3cc(F)c(F)cc3C(F)(F)F)CO4)cc2F)cn1] | (+)-N-(5-methoxy-6-(4-methyl-1H-imidazol-1-yl) pyridin-3-yl)-7, 7, 8-trimethyl-7, 8-dihydro-6H-pyrimido [5, 4-b] [1, 4] oxazin-2-amine |
| 199A | 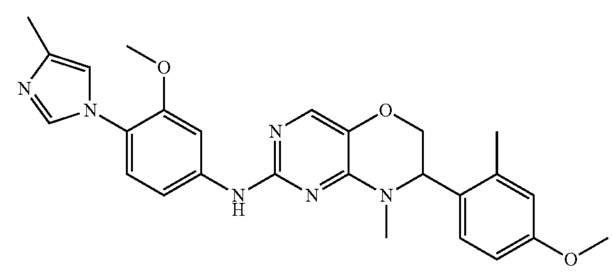 [SMILES: COc1ccc(C2COc3cnc(Nc4ccc(-n5cnc(C)c5)c(OC)c4)nc3N2C)c(C)c1] | (+)-7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 199B | 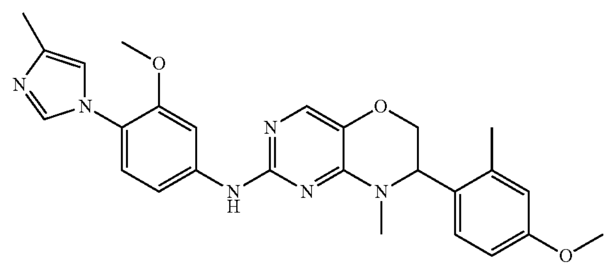 | (−)-7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 200 | 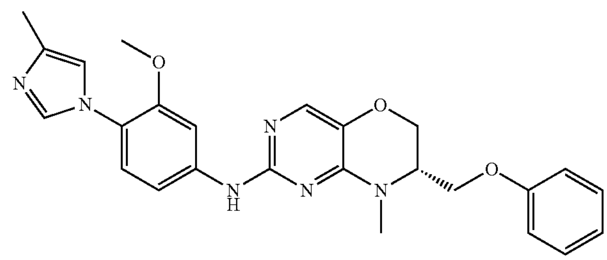 [SMILES: COc1cc(Nc2ncc3c(n2)N(C)[C@@H](COc2ccccc2)CO3)ccc1-n1cnc(C)c1] | (S)-N-(3-methoxy-4-(4-methyl-1H-imidazol-1-yl) phenyl)-8-methyl-7-(phenoxymethyl)-7, 8-dihydro-6H-pyrimido [5, 4-b] [1, 4] oxazin-2-amine |
| 201 | 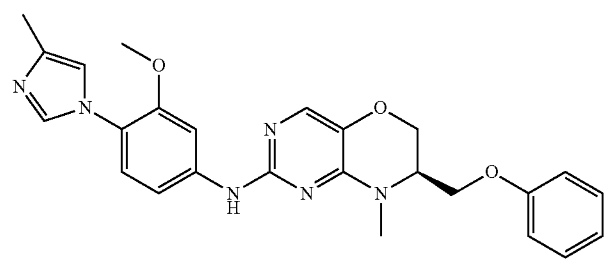 [SMILES: COc1cc(Nc2ncc3c(n2)N(C)[C@H](COc2ccccc2)CO3)ccc1-n1cnc(C)c1] | (R)-N-(3-methoxy-4-(4-methyl-1H-imidazol-1-yl) phenyl)-8-methyl-7-(phenoxymethyl)-7, 8-dihydro-6H-pyrimido [5, 4-b] [1, 4] oxazin-2-amine |
| 202A | 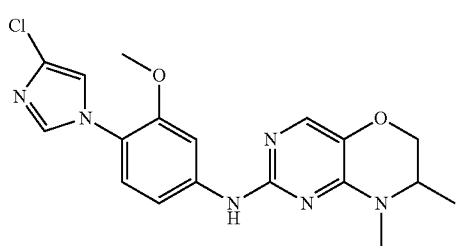 [SMILES: COc1cc(Nc2ncc3c(n2)N(C)C(C)CO3)ccc1-n1cnc(Cl)c1] | (−)-N-(4-(4-chloro-1H-imidazol-1-yl)-3-methoxyphenyl)-7, 8-dimethyl-7, 8-dihydro-6H-pyrimido [5, 4-b] [1, 4] oxazin-2-amine |
| 202B | 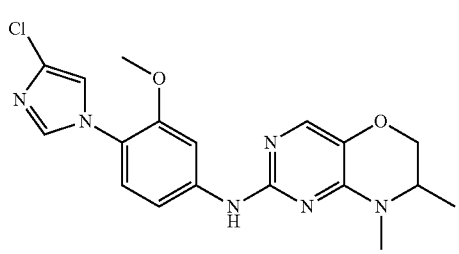 [SMILES: COc1cc(Nc2ncc3c(n2)N(C)C(C)CO3)ccc1-n1cnc(Cl)c1] | (+)-N-(4-(4-chloro-1H-imidazol-1-yl)-3-methoxyphenyl)-7, 8-dimethyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 203A | 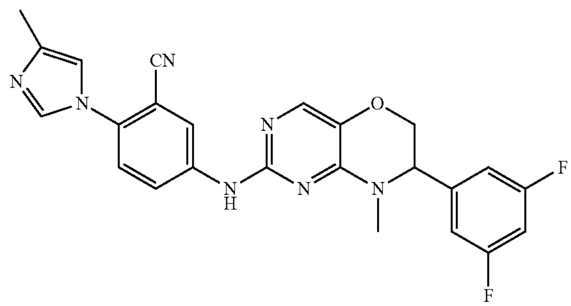 [SMILES: Cc1cn(-c2ccc(Nc3ncc4c(n3)N(C)C(c3cc(F)cc(F)c3)CO4)cc2C#N)cn1] | (+)-5-((7-(3, 5-difluorophenyl)-8-methyl-7, 8-dihydro-6H-pyrimido [5, 4-b] [1, 4] oxazin-2-yl) amino)-2-(4-methyl-1H-imidazol-1-yl) benzonitrile |
| 203B | 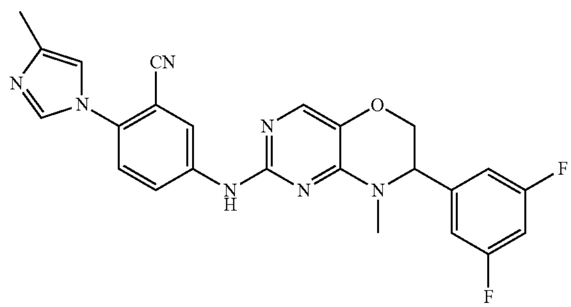 [SMILES: Cc1cn(-c2ccc(Nc3ncc4c(n3)N(C)C(c3cc(F)cc(F)c3)CO4)cc2C#N)cn1] | (−)-5-((7-(3, 5-difluorophenyl)-8-methyl-7, 8-dihydro-6H-pyrimido [5, 4-b] [1, 4] oxazin-2-yl) amino)-2-(4-methyl-1H-imidazol-1-yl) benzonitrile |
| 204A | 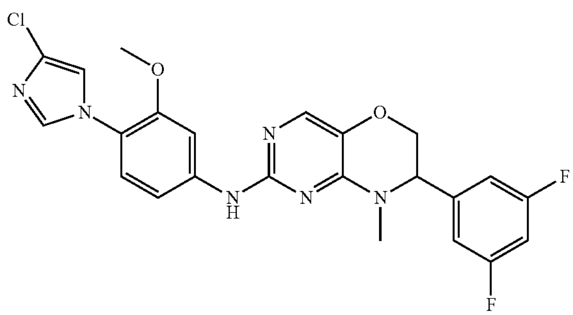 [SMILES: COc1cc(Nc2ncc3c(n2)N(C)C(c2cc(F)cc(F)c2)CO3)ccc1-n1cnc(Cl)c1] | (−)-N-(4-(4-chloro-1H-imidazol-1-yl)-3-methoxyphenyl)-7-(3, 5-difluorophenyl)-8-methyl-7, 8-dihydro-6H-pyrimido [5, 4-b] [1, 4] oxazin-2-amine |
| 204B | 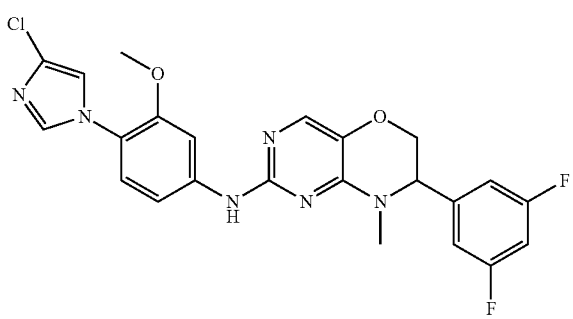 [SMILES: COc1cc(Nc2ncc3c(n2)N(C)C(c2cc(F)cc(F)c2)CO3)ccc1-n1cnc(Cl)c1] | (+)-N-(4-(4-chloro-1H-imidazol-1-yl)-3-methoxyphenyl)-7-(3, 5-difluorophenyl)-8-methyl-7, 8-dihydro-6H-pyrimido [5, 4-b] [1, 4] oxazin-2-amine |
| 205A | 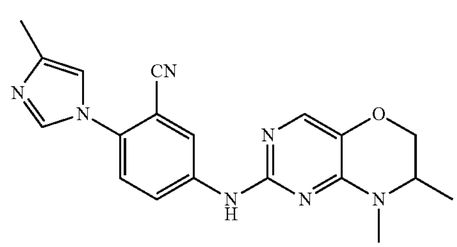 [SMILES: Cc1cn(-c2ccc(Nc3ncc4c(n3)N(C)C(C)CO4)cc2C#N)cn1] | (+)-5-((7, 8-dimethyl-7, 8-dihydro-6H-pyrimido [5, 4-b] [1, 4] oxazin-2-yl) amino)-2-(4-methyl-1H-imidazol-1-yl) benzonitrile |

TABLE I-continued

Exemplary Fused Morpholinopyrimidines of Formula (I)

| Compound of Example | Structure | Name |
|---|---|---|
| 205B | 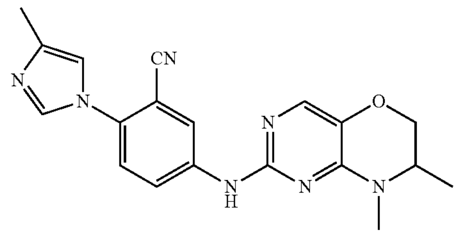 [SMILES: Cc1cn(-c2ccc(Nc3ncc4c(n3)N(C)C(C)CO4)cc2C#N)cn1] | (−)-5-((7, 8-dimethyl-7, 8-dihydro-6H-pyrimido [5, 4-b] [1, 4]oxazin-2-yl) amino)-2-(4-methyl-1H-imidazol-1-yl) benzonitrile |
| 206A | 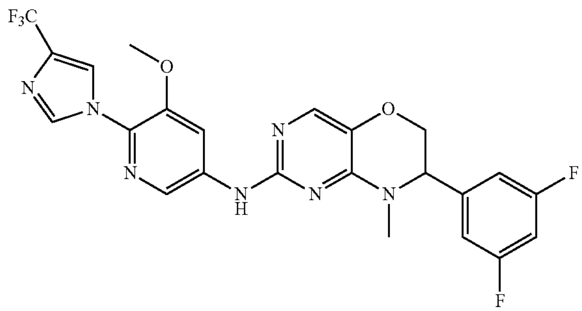 [SMILES: COc1cc(Nc2ncc3c(n2)N(C)C(c2cc(F)cc(F)c2)CO3)cnc1-n1cnc(C(F)(F)F)c1] | (+)-7-(3, 5-difluorophenyl)-N-(5-methoxy-6-(4-(trifluoromethyl)-1H-imidazol-1-yl) pyridin-3-yl)-8-methyl-7, 8-dihydro-6H-pyrimido [5, 4-b] [1, 4] oxazin-2-amine |
| 206B | 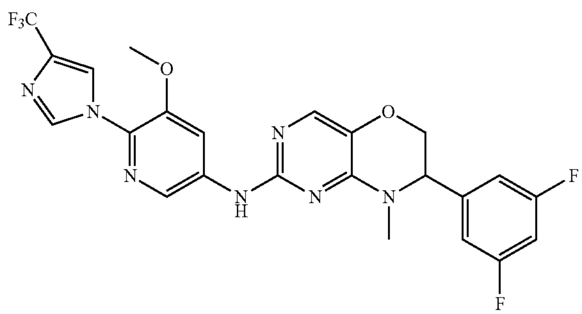 [SMILES: COc1cc(Nc2ncc3c(n2)N(C)C(c2cc(F)cc(F)c2)CO3)cnc1-n1cnc(C(F)(F)F)c1] | (−)-7-(3, 5-difluorophenyl)-N-(5-methoxy-6-(4-(trifluoromethyl)-1H-imidazol-1-yl) pyridin-3-yl)-8-methyl-7, 8-dihydro-6H-pyrimido [5, 4-b] [1, 4] oxazin-2-amine |
| 207A | 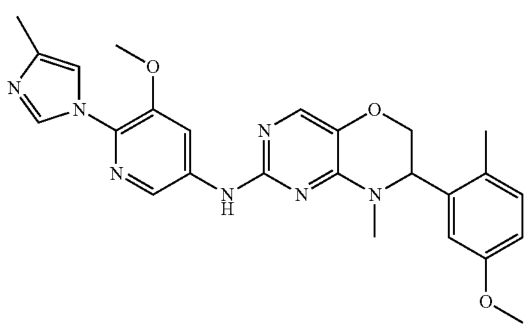 [SMILES: COc1ccc(C)c(C2COc3cnc(Nc4cnc(-n5cnc(C)c5)c(OC)c4)nc3N2C)c1] | (+)-7-(5-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |
| 207B | 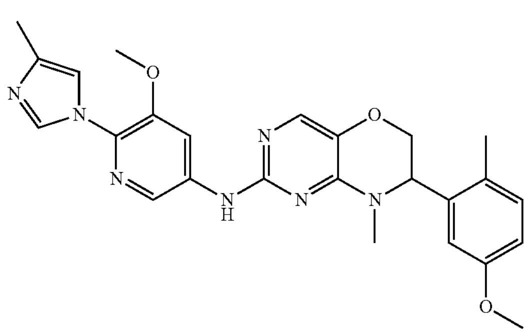 | (−)-7-(5-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
| --- | --- | --- |
| 208A | 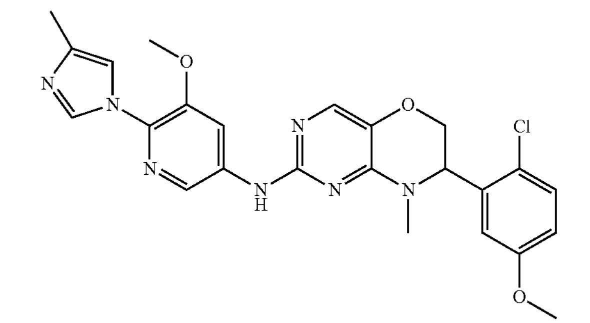 | (+)-7-(2-chloro-5-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |
| 208B | 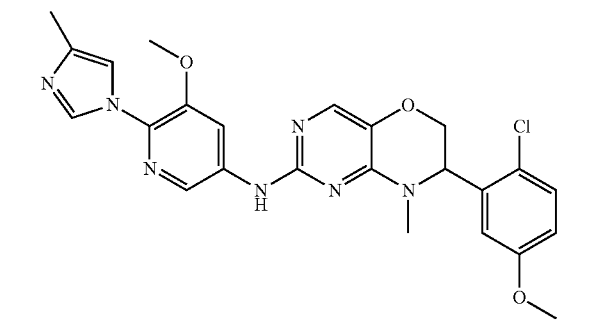 | (−)-7-(2-chloro-5-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |
| 209A | 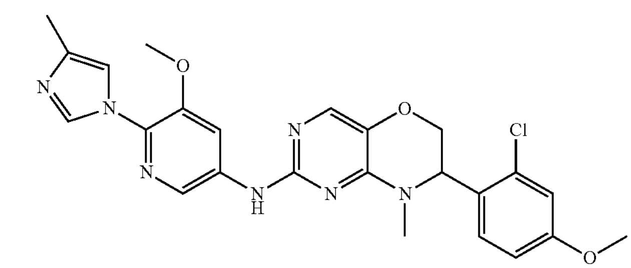 | (+)-7-(2-chloro-4-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |
| 209B | 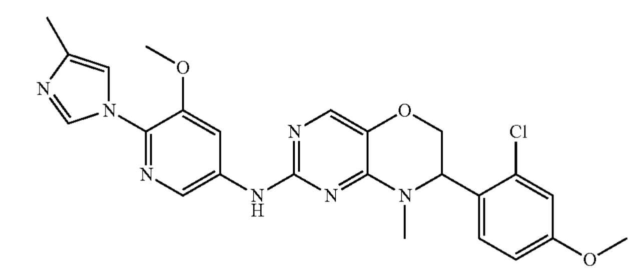 | (−)-7-(2-chloro-4-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |
| 210A | 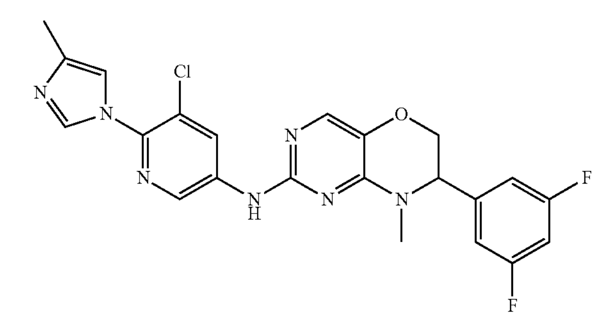 [SMILES: Cc1cn(-c2ncc(Nc3ncc4c(n3)N(C)C(c3cc(F)cc(F)c3)CO4)cc2Cl)cn1] | (+)-N-(5-chloro-6-(4-methyl-1H-imidazol-1-yl) pyridin-3-yl)-7-(3, 5-difluorophenyl)-8-methyl-7, 8-dihydro-6H-pyrimido [5, 4-b][1, 4]oxazin-2-amine |

TABLE I-continued

Exemplary Fused Morpholinopyrimidines of Formula (I)

| Compound of Example | Structure | Name |
|---|---|---|
| 210B | 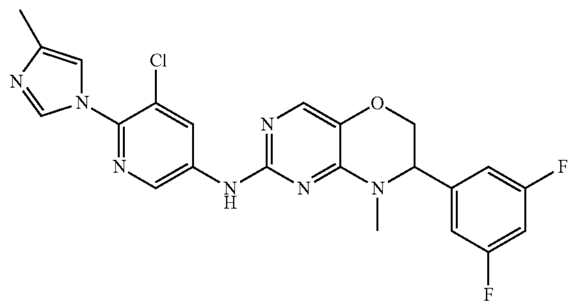 | (−)-N-(5-chloro-6-(4-methyl-1H-imidazol-1-yl) pyridin-3-yl)-7-(3, 5-difluorophenyl)-8-methyl-7, 8-dihydro-6H-pyrimido [5, 4-b] [1, 4] oxazin-2-amine |
| 211A | 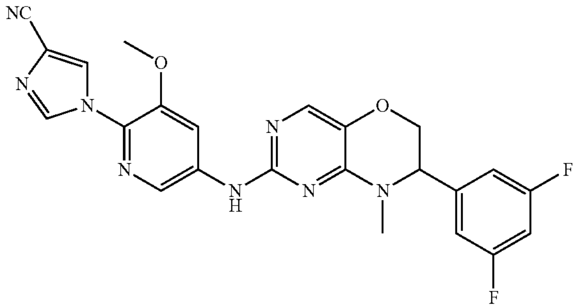 [SMILES: COc1cc(Nc2ncc3c(n2)N(C)C(c2cc(F)cc(F)c2)CO3)cnc1-n1cnc(C#N)c1] | (+)-1-(5-((7-(3, 5-difluorophenyl)-8-methyl-7, 8-dihydro-6H-pyrimido [5, 4-b][1, 4]oxazin-2-yl) amino)-3-methoxypyridin-2-yl)-1H-imidazole-4-carbonitrile |
| 211B | 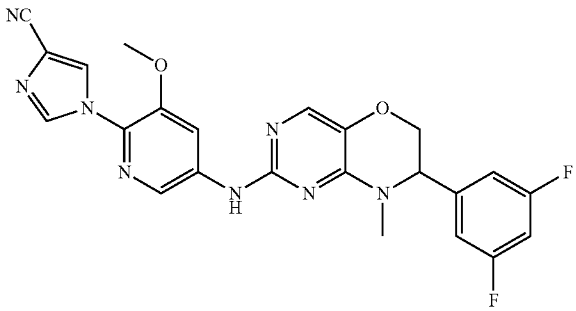 [SMILES: COc1cc(Nc2ncc3c(n2)N(C)C(c2cc(F)cc(F)c2)CO3)cnc1-n1cnc(C#N)c1] | (−)-1-(5-((7-(3, 5-difluorophenyl)-8-methyl-7, 8-dihydro-6H-pyrimido [5, 4-b][1, 4]oxazin-2-yl) amino)-3-methoxypyridin-2-yl)-1H-imidazole-4-carbonitrile |
| 212A | 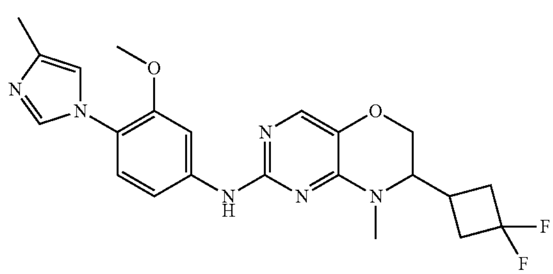 [SMILES: COc1cc(Nc2ncc3c(n2)N(C)C(C2CC(F)(F)C2)CO3)ccc1-n1cnc(C)c1] | (−)-7-(3, 3-difluorocyclobutyl)-N-(3-methoxy-4-(4-methyl-1H-imidazol-1-yl) phenyl)-8-methyl-7, 8-dihydro-6H-pyrimido[5, 4-b] [1, 4] oxazin-2-amine |
| 212B | 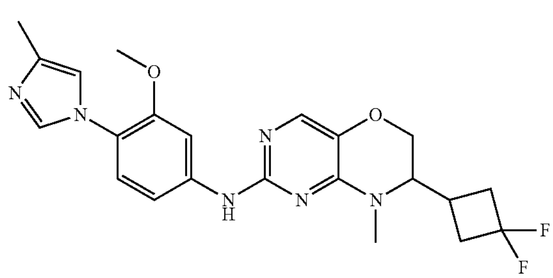 [SMILES: COc1cc(Nc2ncc3c(n2)N(C)C(C2CC(F)(F)C2)CO3)ccc1-n1cnc(C)c1] | (+)-7-(3, 3-difluorocyclobutyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 213A | 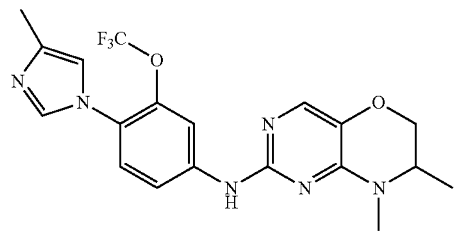 [SMILES: Cc1cn(-c2ccc(Nc3ncc4c(n3)N(C)C(C)CO4)cc2OC(F)(F)F)cn1] | (−)-7, 8-dimethyl-N-(4-(4-methyl-1H-imidazol-1-yl)-3-(trifluoromethoxy) phenyl)-7, 8-dihydro-6H-pyrimido [5, 4-b] [1, 4]oxazin-2-amine |
| 213B | 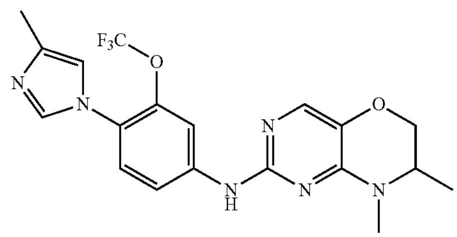 [SMILES: Cc1cn(-c2ccc(Nc3ncc4c(n3)N(C)C(C)CO4)cc2OC(F)(F)F)cn1] | (+)-7, 8-dimethyl-N-(4-(4-methyl-1H-imidazol-1-yl)-3-(trifluoromethoxy) phenyl)-7, 8-dihydro-6H-pyrimido [5, 4-b] [1, 4] oxazin-2-amine |
| 214A | 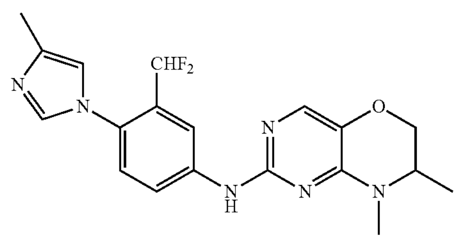 | (+)-N-(3-(difluoromethyl)-4-(4-methyl-1H-imidazol-1-yl) phenyl)-7, 8-dimethyl-7, 8-dihydro-6H-pyrimido [5, 4-b] [1, 4]oxazin-2-amine |
| 214B | 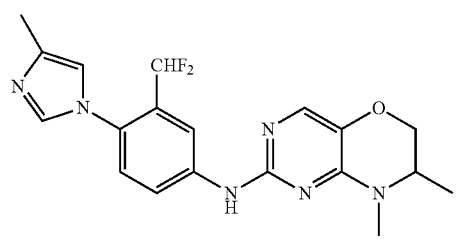 | (−)-N-(3-(difluoromethyl)-4-(4-methyl-1H-imidazol-1-yl) phenyl)-7, 8-dimethyl-7, 8-dihydro-6H-pyrimido [5, 4-b] [1, 4] oxazin-2-amine |
| 215A | 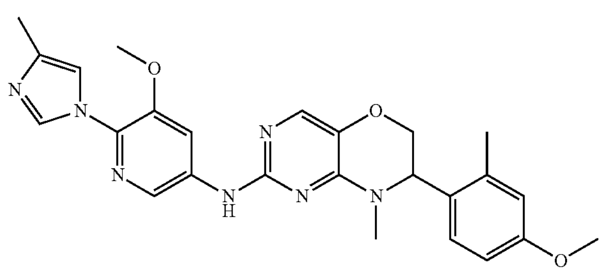 | (+)-7-(4-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |
| 215B | 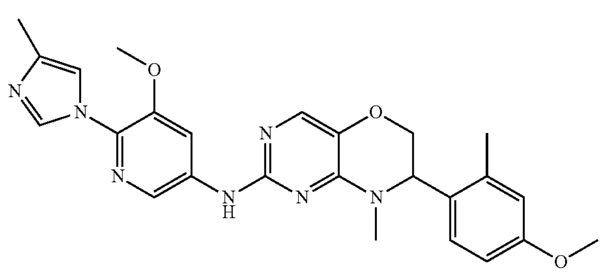 | (−)-7-(4-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 216A | 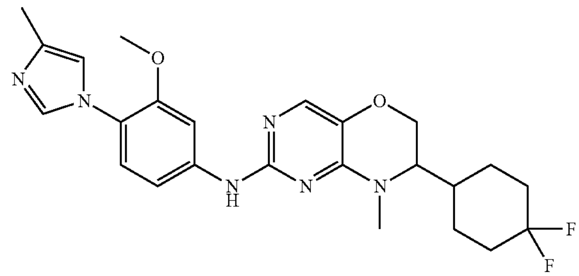 [SMILES: COc1cc(Nc2ncc3c(n2)N(C)C(C2CCC(F)(F)CC2)CO3)ccc1-n1cnc(C)c1] | (−)-7-(4, 4-difluorocyclohexyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 216B | 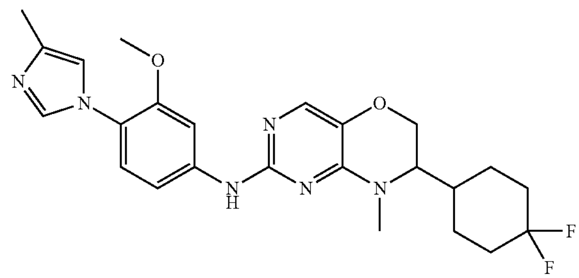 [SMILES: COc1cc(Nc2ncc3c(n2)N(C)C(C2CCC(F)(F)CC2)CO3)ccc1-n1cnc(C)c1] | (+)-7-(4, 4-difluorocyclohexyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 217 | 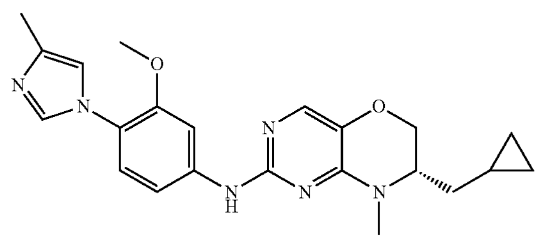 [SMILES: COc1cc(Nc2ncc3c(n2)N(C)[C@@H](CC2CC2)CO3)ccc1-n1cnc(C)c1] | (S)-7-(cyclopropylmethyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 218 | 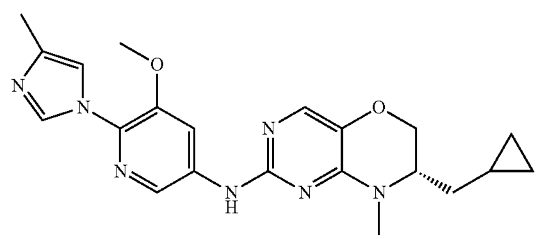 [SMILES: COc1cc(Nc2ncc3c(n2)N(C)[C@@H](CC2CC2)CO3)cnc1-n1cnc(C)c1] | (S)-7-(cyclopropylmethyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |
| 219A | 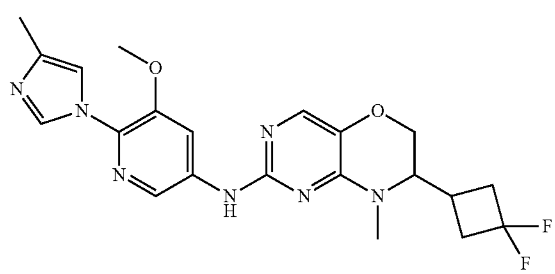 | (+)-7-(3, 3-difluorocyclobutyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 219B | 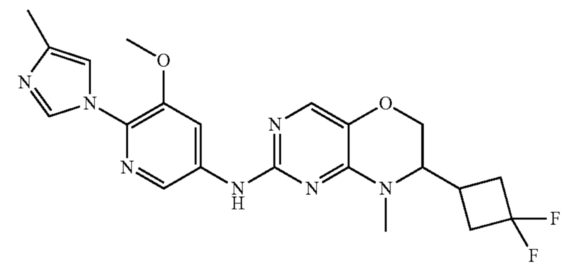 | (−)-7-(3, 3-difluorocyclobutyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |
| 220A | 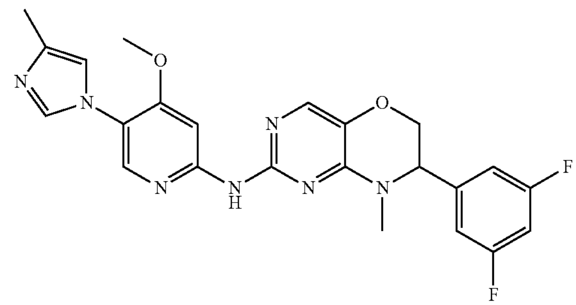 [SMILES: COc1cc(Nc2ncc3c(n2)N(C)C(c2cc(F)cc(F)c2)CO3)ncc1-n1cnc(C)c1] | (−)-7-(3, 5-difluorophenyl)-N-(4-methoxy-5-(4-methyl-1H-imidazol-1-yl) pyridin-2-yl)-8-methyl-7, 8-dihydro-6H-pyrimido [5, 4-b] [1, 4] oxazin-2-amine |
| 220B | 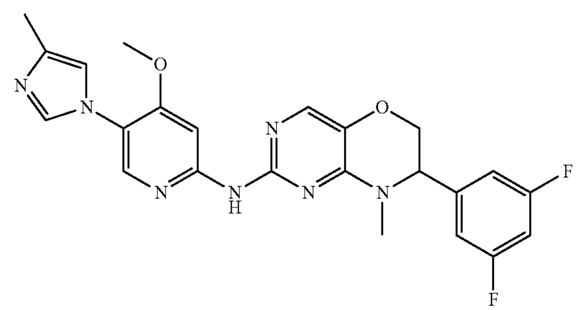 [SMILES: COc1cc(Nc2ncc3c(n2)N(C)C(c2cc(F)cc(F)c2)CO3)ncc1-n1cnc(C)c1] | (+)-7-(3, 5-difluorophenyl)-N-(4-methoxy-5-(4-methyl-1H-imidazol-1-yl) pyridin-2-yl)-8-methyl-7, 8-dihydro-6H-pyrimido [5, 4-b] [1, 4] oxazin-2-amine |
| 221A | 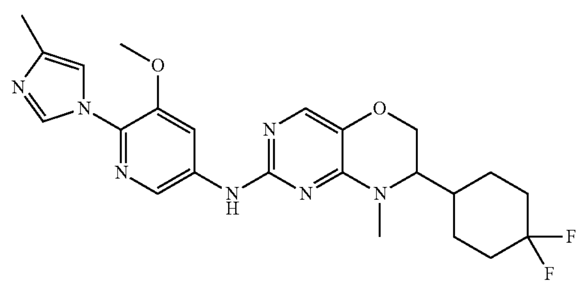 [SMILES: COc1cc(Nc2ncc3c(n2)N(C)C(C2CCC(F)(F)CC2)CO3)cnc1-n1cnc(C)c1] | (+)-7-(4, 4-difluorocyclohexyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |
| 221B | 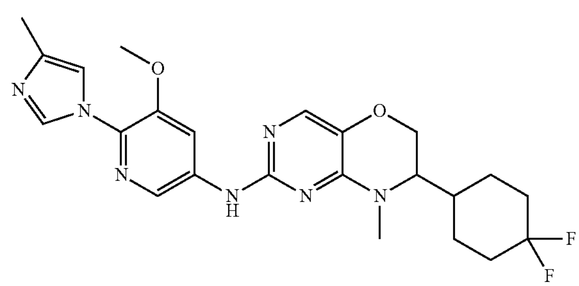 | (−)-7-(4, 4-difluorocyclohexyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 222A | 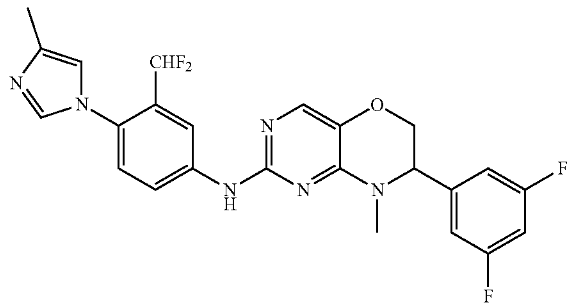 | (+)-N-(3-(difluoromethyl)-4-(4-methyl-1H-imidazol-1-yl) phenyl)-7-(3, 5-difluorophenyl)-8-methyl-7, 8-dihydro-6H-pyrimido [5, 4-b] [1, 4] oxazin-2-amine |
| 222B | 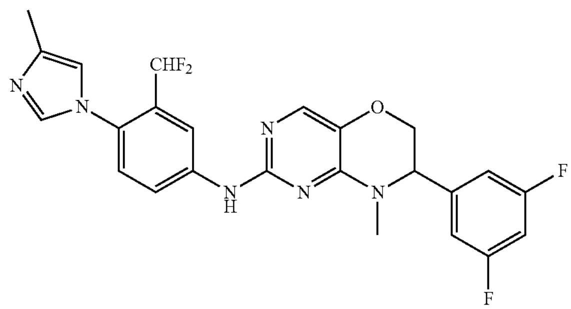 | (−)-N-(3-(difluoromethyl)-4-(4-methyl-1H-imidazol-1-yl) phenyl)-7-(3, 5-difluorophenyl)-8-methyl-7, 8-dihydro-6H-pyrimido [5, 4-b][1, 4] oxazin-2-amine |
| 223A | 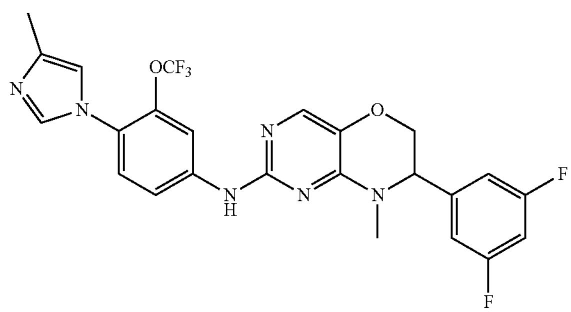 [SMILES: Cc1cn(-c2ccc(Nc3ncc4c(n3)N(C)C(c3cc(F)cc(F)c3)CO4)cc2OC(F)(F)F)cn1] | (−)-7-(3, 5-difluorophenyl)-8-methyl-N-(4-(4-methyl-1H-imidazol-1-yl)-3-(trifluoromethoxy) phenyl)-7, 8-dihydro-6H-pyrimido [5, 4-b] [1, 4]oxazin-2-amine |
| 223B | 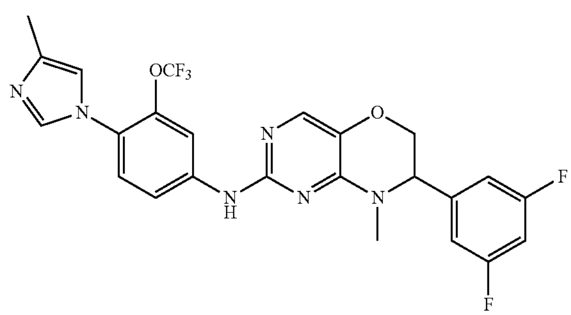 | (+)-7-(3, 5-difluorophenyl)-8-methyl-N-(4-(4-methyl-1H-imidazol-1-yl)-3-(trifluoromethoxy) phenyl)-7, 8-dihydro-6H-pyrimido [5, 4-b] [1, 4]oxazin-2-amine |
| 224 | 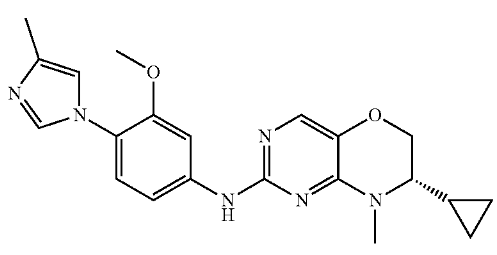 | (S)-7-cyclopropyl-N-(3-methoxy-4-(4-methyl-1H-imidazol-1-yl) phenyl)- 8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 225 | 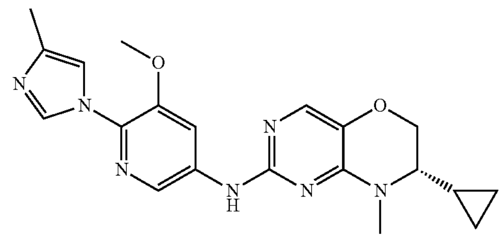 [SMILES: COc1cc(Nc2ncc3c(n2)N(C)[C@@H](C2CC2)CO3)ccc1-n1cnc(C)c1] | (S)-7-cyclopropyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |
| 226A | 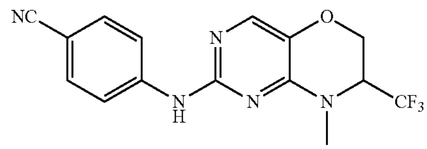 [SMILES: CN1c2nc(Nc3ccc(C#N)cc3)ncc2OCC1C(F)(F)F] | (+)-4-((8-methyl-7-(trifluoromethyl)-7, 8-dihydro-6H-pyrimido [5, 4-b][1, 4]oxazin-2-yl) amino) benzonitrile |
| 226B | 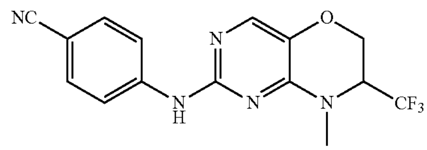 [SMILES: CN1c2nc(Nc3ccc(C#N)cc3)ncc2OCC1C(F)(F)F] | (−)-4-((8-methyl-7-(trifluoromethyl)-7, 8-dihydro-6H-pyrimido [5, 4-b] [1, 4] oxazin-2-yl) amino) benzonitrile |
| 227 | 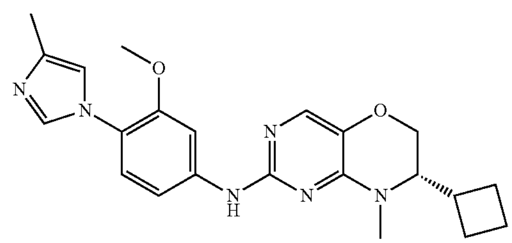 [SMILES: COc1cc(Nc2ncc3c(n2)N(C)[C@@H](C2CCC2)CO3)ccc1-n1cnc(C)c1] | (S)-7-cyclobutyl-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 228A | 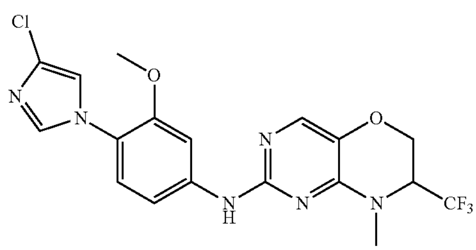 [SMILES: COc1cc(Nc2ncc3c(n2)N(C)C(C(F)(F)F)CO3)ccc1-n1cnc(Cl)c1] | (+)-N-(4-(4-chloro-1H-imidazol-1-yl)-3-methoxyphenyl)-8-methyl-7-(trifluoromethyl)-7, 8-dihydro-6H-pyrimido [5, 4-b] [1, 4]oxazin-2-amine |
| 228B | 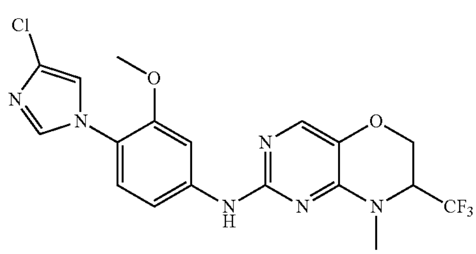 [SMILES: COc1cc(Nc2ncc3c(n2)N(C)C(C(F)(F)F)CO3)ccc1-n1cnc(Cl)c1] | (−)-N-(4-(4-chloro-1H-imidazol-1-yl)-3-methoxyphenyl)-8-methyl-7-(trifluoromethyl)-7, 8-dihydro-6H-pyrimido [5, 4-b] [1, 4]oxazin-2-amine |
| 229A | 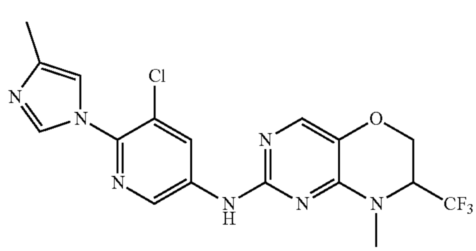 [SMILES: Cc1cn(-c2ncc(Nc3ncc4c(n3)N(C)C(C(F)(F)F)CO4)cc2Cl)cn1] | (−)-N-(5-chloro-6-(4-methyl-1H-imidazol-1-yl) pyridin-3-yl)-8-methyl-7-(trifluoromethyl)-7, 8-dihydro-6H-pyrimido [5, 4-b] [1, 4]oxazin-2-amine |

TABLE I-continued

Exemplary Fused Morpholinopyrimidines of Formula (I)

| Compound of Example | Structure | Name |
|---|---|---|
| 229B | 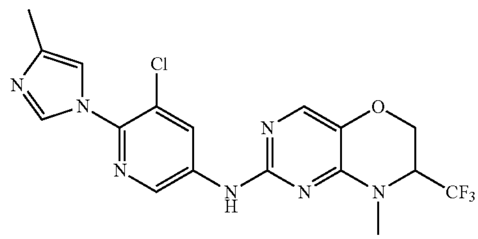 [SMILES: Cc1cn(-c2ncc(Nc3ncc4c(n3)N(C)C(C(F)(F)F)CO4)cc2Cl)cn1] | (+)-N-(5-chloro-6-(4-methyl-1H-imidazol-1-yl) (trifluoromethyl)-7, 8-dihydro-6H-pyrimido [5, 4-b] [1, 4] oxazin-2-amine |
| 230A | 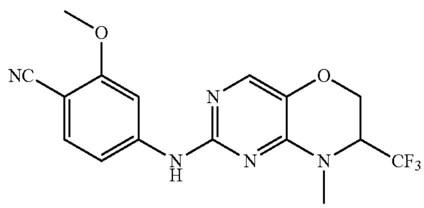 [SMILES: COc1cc(Nc2ncc3c(n2)N(C)C(C(F)(F)F)CO3)ccc1C#N] | (+)-2-methoxy-4-((8-methyl-7-(trifluoromethyl)-7, 8-dihydro-6H-pyrimido [5, 4-b][1, 4]oxazin-2-yl) amino) benzonitrile |
| 230B | 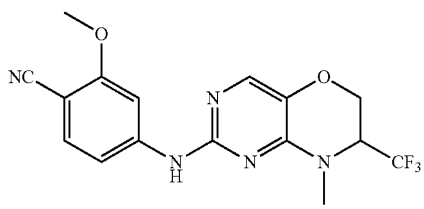 [SMILES: COc1cc(Nc2ncc3c(n2)N(C)C(C(F)(F)F)CO3)ccc1C#N] | (−)-2-methoxy-4-((8-methyl-7-(trifluoromethyl)-7, 8-dihydro-6H-pyrimido [5, 4-b] [1, 4]oxazin-2-yl) amino) benzonitrile |
| 231A | 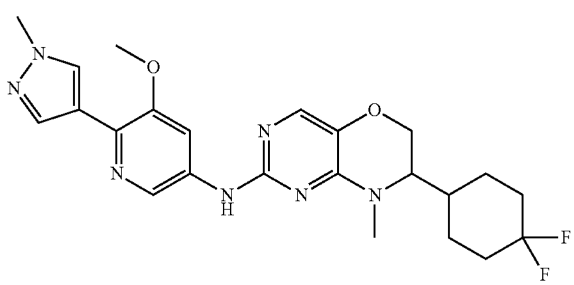 [SMILES: COc1cc(Nc2ncc3c(n2)N(C)C(C2CCC(F)(F)CC2)CO3)cnc1-c1cnn(C)c1] | (+)-7-(4, 4-difluorocyclohexyl)-N-(5-methoxy-6-(1-methyl-1H-pyrazol-4-yl) pyridin-3-yl)-8-methyl-7, 8-dihydro-6H-pyrimido [5, 4-b] [1, 4] oxazin-2-amine |
| 231B | 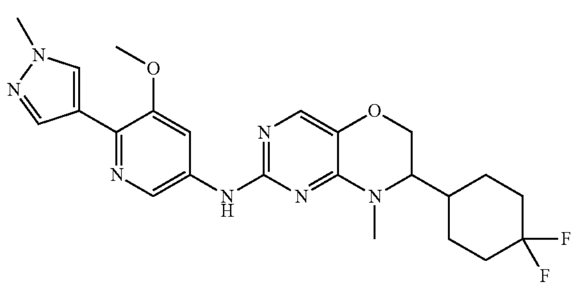 [SMILES: COc1cc(Nc2ncc3c(n2)N(C)C(C2CCC(F)(F)CC2)CO3)cnc1-c1cnn(C)c1] | (−)-7-(4, 4-difluorocyclohexyl)-N-(5-methoxy-6-(1-methyl-1H-pyrazol-4-yl) pyridin-3-yl)-8-methyl-7, 8-dihydro-6H-pyrimido [5, 4-b] [1, 4] oxazin-2-amine |
| 232A | 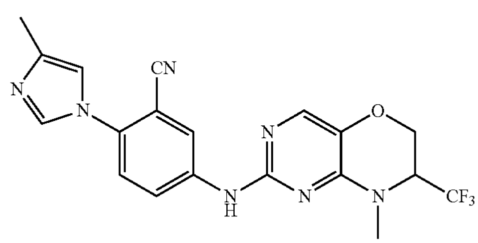 [SMILES: Cc1cn(-c2ccc(Nc3ncc4c(n3)N(C)C(C(F)(F)F)CO4)cc2C#N)cn1] | (+)-2-(4-methyl-1H-imidazol-1-yl)-5-((8-methyl-7-(trifluoromethyl)-7, 8-dihydro-6H-pyrimido [5, 4-b] [1, 4]oxazin-2-yl) amino) benzonitrile |

US 9,771,378 B2

149                                                              150

TABLE I-continued

Exemplary Fused Morpholinopyrimidines of Formula (I)

| Compound of Example | Structure | Name |
|---|---|---|
| 232B | 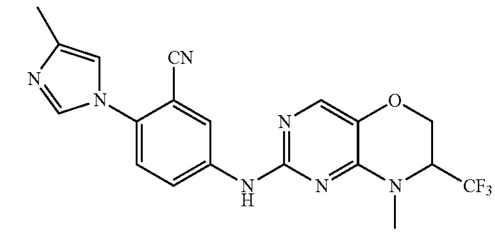 [SMILES: Cc1cn(-c2ccc(Nc3ncc4c(n3)N(C)C(C(F)(F)F)CO4)cc2C#N)cn1] | (−)-2-(4-methyl-1H-imidazol-1-yl)-5-((8-methyl-7-(trifluoromethyl)-7, 8-dihydro-6H-pyrimido [5, 4-b] [1, 4] oxazin-2-yl) amino) benzonitrile |
| 233A | 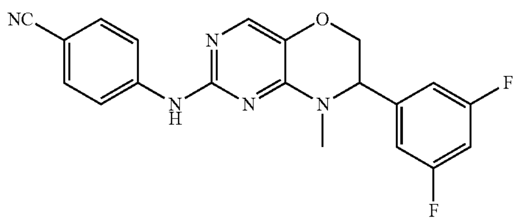 [SMILES: CN1c2nc(Nc3ccc(C#N)cc3)ncc2OCC1c1cc(F)cc(F)c1] | (+)-4-((7-(3, 5-difluorophenyl)-8-methyl-7, 8-dihydro-6H-pyrimido [5, 4-b] [1, 4]oxazin-2-yl) amino) benzonitrile |
| 233B | 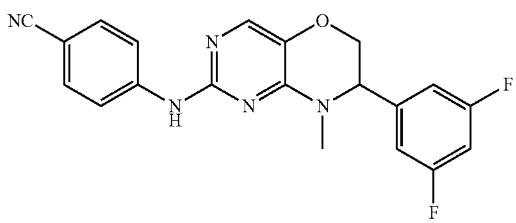 [SMILES: CN1c2nc(Nc3ccc(C#N)cc3)ncc2OCC1c1cc(F)cc(F)c1] | (−)-4-((7-(3, 5-difluorophenyl)-8-methyl-7, 8-dihydro-6H-pyrimido [5, 4-b] [1, 4] oxazin-2-yl) amino) benzonitrile |
| 234 | 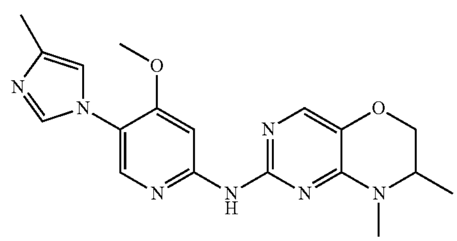 [SMILES: COc1cc(Nc2ncc3c(n2)N(C)C(C)CO3)ncc1-n1cnc(C)c1] | N-(4-methoxy-5-(4-methyl-1H-imidazol-1-yl) pyridin-2-yl)-7, 8-dimethyl-7, 8-dihydro-6H-pyrimido [5, 4-b] [1, 4]oxazin-2-amine (racemic) |
| 235 | 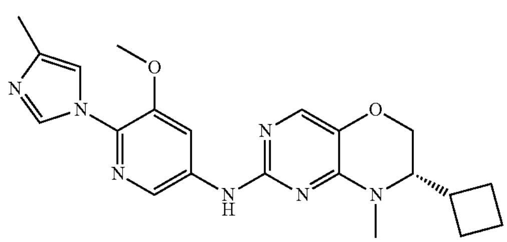 [SMILES: COc1cc(Nc2ncc3c(n2)N(C)[C@@H](C2CCC2)CO3)cnc1-n1cnc(C)c1] | (S)-7-cyclobutyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |
| 236A | 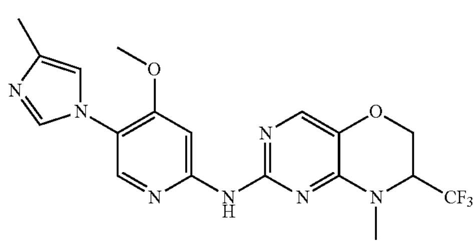 [SMILES: COc1cc(Nc2ncc3c(n2)N(C)C(C(F)(F)F)CO3)ncc1-n1cnc(C)c1] | (+)-N-(4-methoxy-5-(4-methyl-1H-imidazol-1-yl) pyridin-2-yl)-8-methyl-7-(trifluoromethyl)-7, 8-dihydro-6H-pyrimido [5, 4-b] [1, 4]oxazin-2-amine |

TABLE I-continued

Exemplary Fused Morpholinopyrimidines of Formula (I)

| Compound of Example | Structure | Name |
|---|---|---|
| 236B | 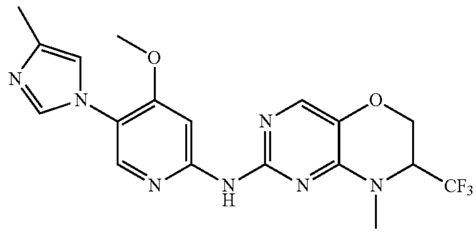 [SMILES: COc1cc(Nc2ncc3c(n2)N(C)C(C(F)(F)F)CO3)ncc1-n1cnc(C)c1] | (−)-N-(4-methoxy-5-(4-methyl-1H-imidazol-1-yl)pyridin-2-yl)-8-methyl-7-(trifluoromethyl)-7, 8-dihydro-6H-pyrimido [5, 4-b] [1, 4]oxazin-2-amine |
| 237A | 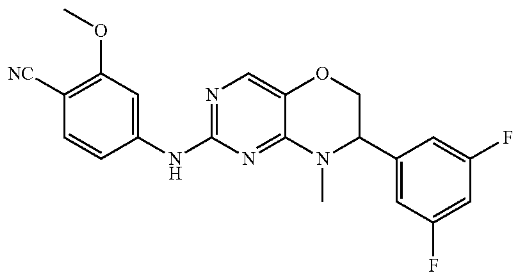 [SMILES: COc1cc(Nc2ncc3c(n2)N(C)C(c2cc(F)cc(F)c2)CO3)ccc1C#N] | (−)-4-((7-(3, 5-difluorophenyl)-8-methyl-7, 8-dihydro-6H-pyrimido [5, 4-b] [1, 4] oxazin-2-yl) amino)-2-methoxybenzonitrile |
| 237B | 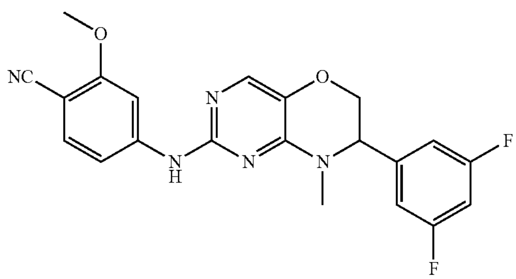 [SMILES: COc1cc(Nc2ncc3c(n2)N(C)C(c2cc(F)cc(F)c2)CO3)ccc1C#N] | (+)-4-((7-(3, 5-difluorophenyl)-8-methyl-7, 8-dihydro-6H-pyrimido [5, 4-b] [1, 4] oxazin-2-yl) amino)-2-methoxybenzonitrile |
| 238A | 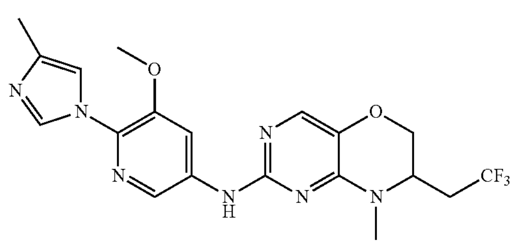 [SMILES: COc1cc(Nc2ncc3c(n2)N(C)C(CC(F)(F)F)CO3)cnc1-n1cnc(C)c1] | (−)-N-(5-methoxy-6-(4-methyl-1H-imidazol-1-yl)pyridin-3-yl)-8-methyl-7-(2, 2, 2-trifluoroethyl)-7, 8-dihydro-6H-pyrimido [5, 4-b] [1, 4]oxazin-2-amine |
| 238B | 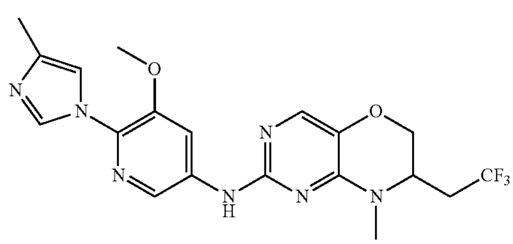 [SMILES: COc1cc(Nc2ncc3c(n2)N(C)C(CC(F)(F)F)CO3)cnc1-n1cnc(C)c1] | (+)-N-(5-methoxy-6-(4-methyl-1H-imidazol-1-yl)pyridin-3-yl)-8-methyl-7-(2, 2, 2-trifluoroethyl)-7, 8-dihydro-6H-pyrimido [5, 4-b] [1, 4]oxazin-2-amine |

TABLE I-continued

Exemplary Fused Morpholinopyrimidines of Formula (I)

| Compound of Example | Structure | Name |
|---|---|---|
| 239A | 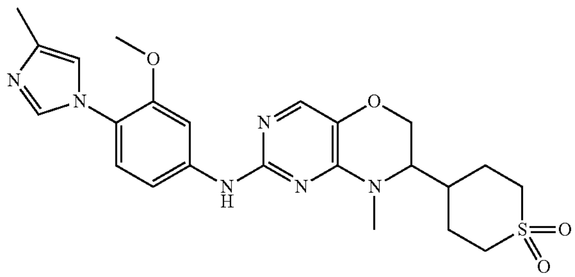 [SMILES: COc1cc(Nc2ncc3c(n2)N(C)C(C2CCS(=O)(=O)CC2)CO3)ccc1-n1cnc(C)c1] | (−)-4-(2-((3-methoxy-4-(4-methyl-1H-imidazol-1-yl) phenyl) amino)-8-methyl-7, 8-dihydro-6H-pyrimido [5, 4-b] [1, 4] oxazin-7-yl) tetrahydro-2H-thiopyran 1, 1-dioxide |
| 239B | 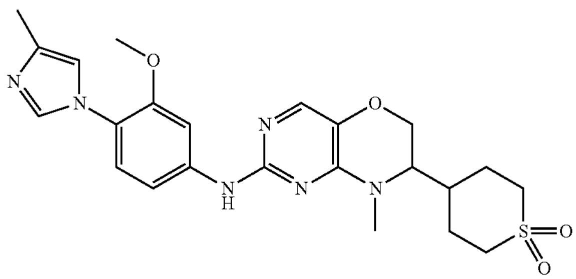 [SMILES: COc1cc(Nc2ncc3c(n2)N(C)C(C2CCS(=O)(=O)CC2)CO3)ccc1-n1cnc(C)c1] | (+)-4-(2-((3-methoxy-4-(4-methyl-1H-imidazol-1-yl) phenyl) amino)-8-methyl-7, 8-dihydro-6H-pyrimido [5, 4-b] [1, 4] oxazin-7-yl) tetrahydro-2H-thiopyran 1, 1-dioxide |
| 240 | 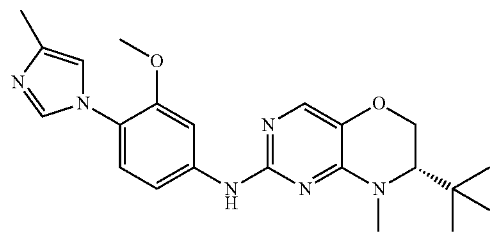 [SMILES: COc1cc(Nc2ncc3c(n2)N(C)[C@@H](C(C)(C)C)CO3)ccc1-n1cnc(C)c1] | (S)-7-(tert-butyl)-N-(3-methoxy-4-(4-methyl-1H-imidazol-1-yl) phenyl)-8-methyl-7, 8-dihydro-6H-pyrimido [5, 4-b] [1, 4] oxazin-2-amine |
| 241A | 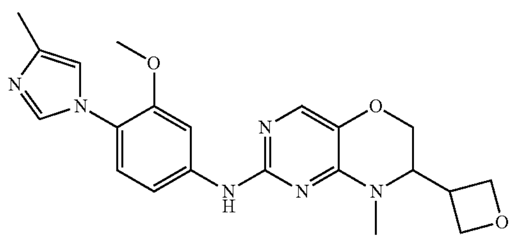 | (−)-N-(3-methoxy-4-(4-methyl-1H-imidazol-1-yl) phenyl)-8-methyl-7-(oxetan-3-yl)-7, 8-dihydro-6H-pyrimido [5, 4-b] [1, 4] oxazin-2-amine |
| 241B | 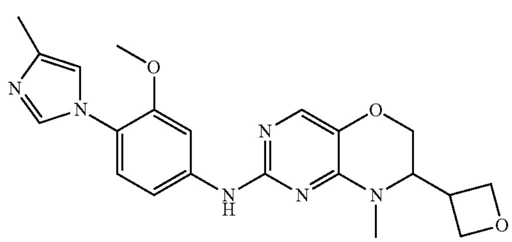 | (+)-N-(3-methoxy-4-(4-methyl-1H-imidazol-1-yl) phenyl)-8-methyl-7-(oxetan-3-yl)-7, 8-dihydro-6H-pyrimido [5, 4-b] [1, 4] oxazin-2-amine |
| 242A | 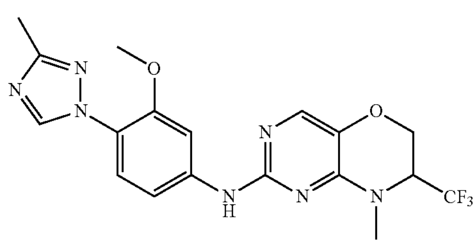 [SMILES: COc1cc(Nc2ncc3c(n2)N(C)C(C(F)(F)F)CO3)ccc1-n1cnc(C)n1] | (−)-N-(3-methoxy-4-(3-methyl-1H-1, 2, 4-triazol-1-yl) phenyl)-8-methyl-7-(trifluoromethyl)-7, 8-dihydro-6H-pyrimido [5, 4-b] [1, 4]oxazin-2-amine |

TABLE I-continued

Exemplary Fused Morpholinopyrimidines of Formula (I)

| Compound of Example | Structure | Name |
|---|---|---|
| 242B | 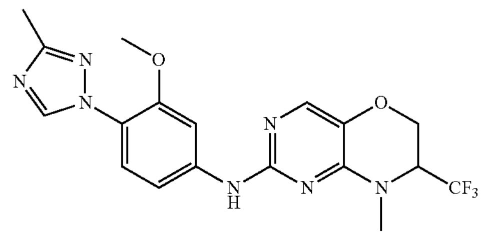 [SMILES: COc1cc(Nc2ncc3c(n2)N(C)C(C(F)(F)F)CO3)ccc1-n1cnc(C)n1] | (+)-N-(3-methoxy-4-(3-methyl-1H-1, 2, 4-triazol-1-yl) phenyl)-8-methyl-7-(trifluoromethyl)-7, 8-dihydro-6H-pyrimido [5, 4-b] [1, 4]oxazin-2-amine |
| 243A | 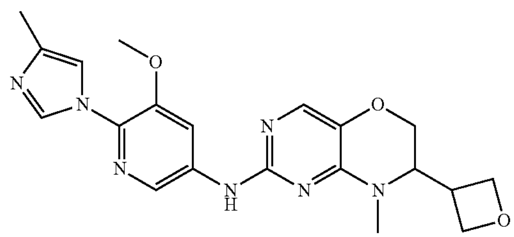 [SMILES: COc1cc(Nc2ncc3c(n2)N(C)C(C2COC2)CO3)cnc1-n1cnc(C)c1] | (+)-N-(5-methoxy-6-(4-methyl-1H-imidazol-1-yl) pyridin-3-yl)-8-methyl-7-(oxetan-3-yl)-7, 8-dihydro-6H-pyrimido [5, 4-b] [1, 4] oxazin-2-amine |
| 243B | 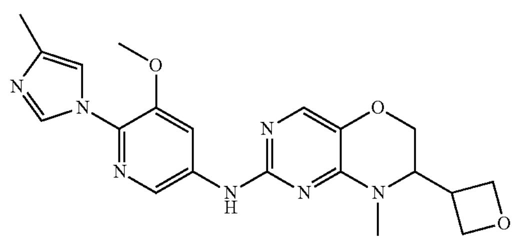 [SMILES: COc1cc(Nc2ncc3c(n2)N(C)C(C2COC2)CO3)cnc1-n1cnc(C)c1] | (−)-N-(5-methoxy-6-(4-methyl-1H-imidazol-1-yl) pyridin-3-yl)-8-methyl-7-(oxetan-3-yl)-7, 8-dihydro-6H-pyrimido [5, 4-b] [1, 4] oxazin-2-amine |
| 244A | 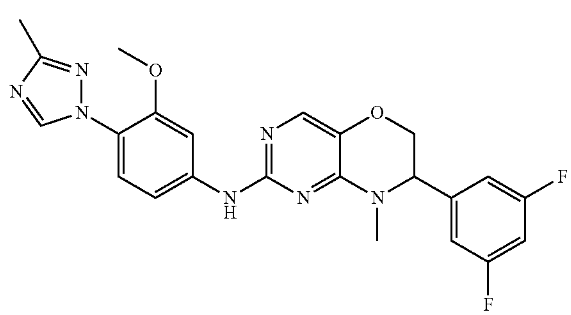 [SMILES: COc1cc(Nc2ncc3c(n2)N(C)C(c2cc(F)cc(F)c2)CO3)ccc1-n1cnc(C)n1] | (+)-7-(3, 5-difluorophenyl)-N-(3-methoxy-4-(3-methyl-1H-1, 2, 4-triazol-1-yl) phenyl)-8-methyl-7, 8-dihydro-6H-pyrimido [5, 4-b] [1, 4]oxazin-2-amine |
| 244B | 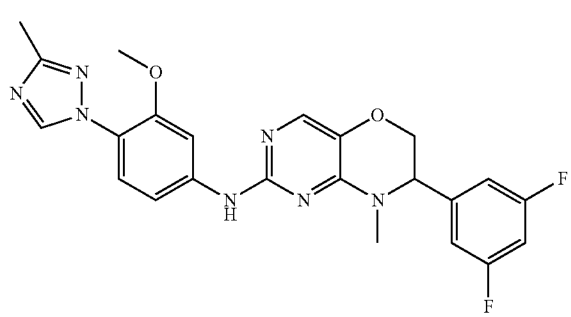 [SMILES: COc1cc(Nc2ncc3c(n2)N(C)C(c2cc(F)cc(F)c2)CO3)ccc1-n1cnc(C)n1] | (−)-7-(3, 5-difluorophenyl)-N-(3-methoxy-4-(3-methyl-1H-1, 2, 4-triazol-1-yl) phenyl)-8-methyl-7, 8-dihydro-6H-pyrimido [5, 4-b] [1, 4] oxazin-2-amine |

TABLE I-continued

Exemplary Fused Morpholinopyrimidines of Formula (I)

| Compound of Example | Structure | Name |
|---|---|---|
| 245A | 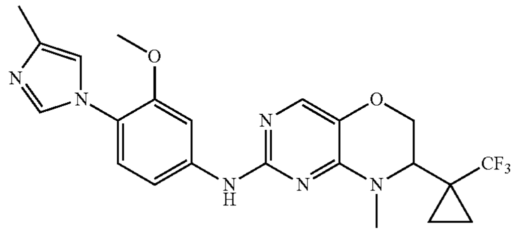 [SMILES: COc1cc(Nc2ncc3c(n2)N(C)C(C2(C(F)(F)F)CC2)CO3)ccc1-n1cnc(C)c1] | (−)-N-(3-methoxy-4-(4-methyl-1H-imidazol-1-yl) phenyl)-8-methyl-7-(1-(trifluoromethyl) cyclopropyl)-7, 8-dihydro-6H-pyrimido [5, 4-b] [1, 4] oxazin-2-amine |
| 245B | 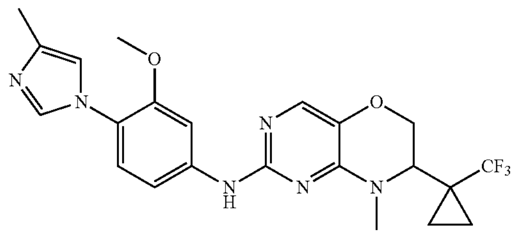 | (+)-N-(3-methoxy-4-(4-methyl-1H-imidazol-1-yl) phenyl)-8-methyl-7-(1-(trifluoromethyl) cyclopropyl)-7, 8-dihydro-6H-pyrimido [5, 4-b] [1, 4] oxazin-2-amine |
| 246 | 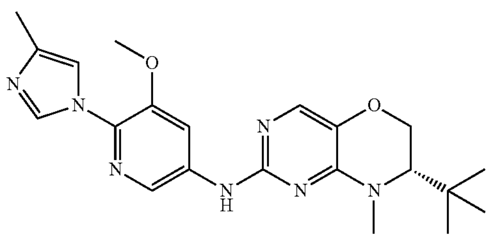 | (S)-7-(tert-butyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine |
| 247A | 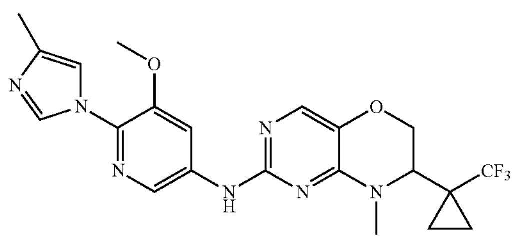 [SMILES: COc1cc(Nc2ncc3c(n2)N(C)C(C2(C(F)(F)F)CC2)CO3)cnc1-n1cnc(C)c1] | (−)-N-(5-methoxy-6-(4-methyl-1H-imidazol-1-yl) pyridin-3-yl)-8-methyl-7-(1-(trifluoromethyl) cyclopropyl)-7, 8-dihydro-6H-pyrimido [5, 4-b] [1, 4] oxazin-2-amine |
| 247B | 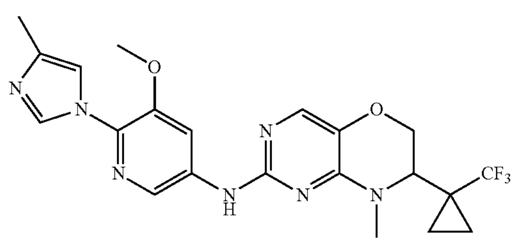 | (+)-N-(5-methoxy-6-(4-methyl-1H-imidazol-1-yl) pyridin-3-yl)-8-methyl-7-(1-(trifluoromethyl) cyclopropyl)-7, 8-dihydro-6H-pyrimido [5, 4-b] [1, 4] oxazin-2-amine |

In another aspect, the invention provides a compound of Formula (II)

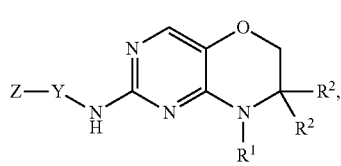

(II)

or a pharmaceutically acceptable salt thereof, wherein:

$R^1$ is —$C_1$-$C_4$ alkyl which is unsubstituted or substituted with one or more -halo;

each $R^2$ is independently —$C_1$-$C_6$ alkyl, or $R^1$ and one $R^2$ together with the intervening atoms form a nitrogen-containing 4- to 6-membered nonaromatic heterocycle and the other $R^2$ is hydrogen or —$C_1$-$C_4$ alkyl, or both $R^2$ together with the intervening atom form a —$C_3$-$C_8$ monocyclic cycloalkyl or an oxygen-containing 3- to 6-membered nonaromatic heterocycle, wherein the nitrogen-containing 4- to 6-membered nonaromatic heterocycle, the —$C_3$-$C_8$ monocyclic cycloalkyl or the oxygen-containing 3- to 6-membered nonaromatic heterocycle is unsubstituted or substituted with one or more substituents independently selected from the group consisting of -halo, —CN, —$C_1$-$C_4$ alkyl, halo-substituted $C_1$-$C_4$ alkyl, —$C_1$-$C_4$ alkoxy and oxo; Y is phenyl or pyridinyl, each of which is unsubstituted or substituted with one or more substituents independently selected from the group consisting of -halo, —$C_1$-$C_4$ alkoxy, halo-substituted $C_1$-$C_4$ alkoxy, —$C_1$-$C_4$ alkyl and halo-substituted $C_1$-$C_4$ alkyl; and Z is imidazolyl or pyrazolyl, each of which is unsubstituted or substituted with one or more substituents independently selected from the group consisting of -halo and —$C_1$-$C_4$ alkyl.

In some embodiments, $R^1$ and one $R^2$ together with the intervening atoms form a nitrogen-containing 4- to 6-membered nonaromatic heterocycle which is unsubstituted or substituted with one or more substituents independently selected from the group consisting of -halo, —CN, —$C_1$-$C_4$ alkyl, halo-substituted $C_1$-$C_4$ alkyl, —$C_1$-$C_4$ alkoxy and oxo, and the other $R^2$ is hydrogen or —$C_1$-$C_4$ alkyl.

In some embodiments, both $R^2$ together with the intervening atom form a —$C_3$-$C_8$ monocyclic cycloalkyl or an oxygen-containing 3- to 6-membered nonaromatic heterocycle, wherein the —$C_3$-$C_8$ monocyclic cycloalkyl or the oxygen-containing 3- to 6-membered nonaromatic heterocycle is unsubstituted or substituted with one or more substituents independently selected from the group consisting of -halo, —CN, —$C_1$-$C_4$ alkyl, halo-substituted $C_1$-$C_4$ alkyl, —$C_1$-$C_4$ alkoxy and oxo.

In some embodiments, $R^2$ is independently —$C_1$-$C_6$ alkyl, or $R^1$ and one $R^2$ together with the intervening atoms form a nitrogen-containing 4- to 6-membered nonaromatic heterocycle and the other $R^2$ is hydrogen or —$C_1$-$C_4$ alkyl, or both $R^2$ together with the intervening atom form a —$C_3$-$C_8$ monocyclic cycloalkyl or an oxygen-containing 3- to 6-membered nonaromatic heterocycle, wherein the nitrogen-containing 4- to 6-membered nonaromatic heterocycle, the —$C_3$-$C_8$ monocyclic cycloalkyl or the oxygen-containing 3- to 6-membered nonaromatic heterocycle is unsubstituted or substituted with one or more substituents independently selected from the group consisting of -halo, —CN, —$C_1$-$C_4$ alkyl, halo-substituted $C_1$-$C_4$ alkyl, —$C_1$-$C_4$ alkoxy and oxo.

In some embodiments, $R^1$ and one $R^2$ together with the intervening atoms form a nitrogen-containing 4- to 6-membered nonaromatic heterocycle and the other $R^2$ is hydrogen or —$C_1$-$C_4$ alkyl, or both $R^2$ together with the intervening atom form a —$C_3$-$C_8$ monocyclic cycloalkyl or an oxygen-containing 3- to 6-membered nonaromatic heterocycle, wherein the nitrogen-containing 4- to 6-membered nonaromatic heterocycle, the —$C_3$-$C_8$ monocyclic cycloalkyl or the oxygen-containing 3- to 6-membered nonaromatic heterocycle is unsubstituted or substituted with one or more substituents independently selected from the group consisting of -halo, —CN, —$C_1$-$C_4$ alkyl, halo-substituted $C_1$-$C_4$ alkyl, —$C_1$-$C_4$ alkoxy and oxo.

In some embodiments, Y is phenyl or pyridinyl, each of which is unsubstituted or substituted with one or more substituents independently selected from the group consisting of -halo, —$C_1$-$C_4$ alkoxy, halo-substituted $C_1$-$C_4$ alkoxy, —$C_1$-$C_4$ alkyl and halo-substituted $C_1$-$C_4$ alkyl.

In some embodiments, Z is imidazolyl or pyrazolyl, each of which is unsubstituted or substituted with one or more substituents independently selected from the group consisting of -halo and —$C_1$-$C_4$ alkyl.

In some embodiments, $R^1$ is methyl; $R^2$ is independently —$C_1$-$C_6$ alkyl, or $R^1$ and one $R^2$ together with the intervening atoms form a nitrogen-containing 4- to 6-membered nonaromatic heterocycle and the other $R^2$ is hydrogen or —$C_1$-$C_4$ alkyl, or both $R^2$ together with the intervening atom form a —$C_3$-$C_8$ monocyclic cycloalkyl or an oxygen-containing 3- to 6-membered nonaromatic heterocycle, wherein the nitrogen-containing 4- to 6-membered nonaromatic heterocycle, the —$C_3$-$C_8$ monocyclic cycloalkyl or the oxygen-containing 3- to 6-membered nonaromatic heterocycle is unsubstituted or substituted with one or more substituents independently selected from the group consisting of -halo and oxo; Y is phenyl or pyridinyl, each of which is substituted with one or more substituent independently selected from the group consisting of -halo and —$C_1$-$C_4$ alkoxy; and Z is imidazolyl or pyrazolyl, each of which is substituted with one or more substituents independently selected from the group consisting of -halo and —$C_1$-$C_4$ alkyl.

In some embodiments, $R^1$ is methyl; $R^2$ is independently —$C_1$-$C_6$ alkyl, or $R^1$ and one $R^2$ together with the intervening atoms form a nitrogen-containing 4- to 6-membered nonaromatic heterocycle and the other $R^2$ is hydrogen or —$C_1$-$C_4$ alkyl, or both $R^2$ together with the intervening atom form a —$C_3$-$C_8$ monocyclic cycloalkyl or an oxygen-containing 3- to 6-membered nonaromatic heterocycle, wherein the nitrogen-containing 4- to 6-membered nonaromatic heterocycle, the —$C_3$-$C_8$ monocyclic cycloalkyl or the oxygen-containing 3- to 6-membered nonaromatic heterocycle is unsubstituted or substituted with one or more -halo; Y is phenyl or pyridinyl, each of which is substituted with one or more substituents independently selected from the group consisting of -halo and —$C_1$-$C_4$ alkoxy; and Z is imidazolyl or pyrazolyl, each of which is substituted with one or more substituents independently selected from the group consisting of -halo and —$C_1$-$C_4$ alkyl.

In some embodiments, $R^1$ and one $R^2$ together with the intervening atoms form a nitrogen-containing 4- to 6-membered nonaromatic heterocycle and the other $R^2$ is hydrogen or —$C_1$-$C_4$ alkyl, or both $R^2$ together with the intervening atom form a —$C_3$-$C_8$ monocyclic cycloalkyl or an oxygen-containing 3- to 6-membered nonaromatic heterocycle, wherein the nitrogen-containing 4- to 6-membered nonaromatic heterocycle, the —$C_3$-$C_3$ monocyclic cycloalkyl or the oxygen-containing 3- to 6-membered nonaromatic heterocycle is unsubstituted or substituted with two -halo.

In some embodiments, $R^1$ and one $R^2$ together with the intervening atoms form a nitrogen-containing 4- to 6-membered nonaromatic heterocycle and the other $R^2$ is hydrogen or —$C_1$-$C_4$ alkyl, or both $R^2$ together with the intervening atom form a —$C_3$-$C_8$ monocyclic cycloalkyl or an oxygen-containing 3- to 6-membered nonaromatic heterocycle, wherein the nitrogen-containing 4- to 6-membered nonaromatic heterocycle, the —$C_3$-$C_3$ monocyclic cycloalkyl or the oxygen-containing 3- to 6-membered nonaromatic heterocycle is unsubstituted or substituted with two —F.

In some embodiments, each $R^2$ is independently —$C_1$-$C_6$ alkyl.

In some embodiments, each $R^2$ is independently methyl.

In some embodiments, $R^1$ and one $R^2$ together with the intervening atoms form a nitrogen-containing 4- to 6-membered nonaromatic heterocycle and the other $R^2$ is hydrogen or —$C_1$-$C_4$ alkyl, wherein the nitrogen-containing 4- to 6-membered nonaromatic heterocycle is unsubstituted or substituted with two -halo.

In some embodiments, $R^1$ and one $R^2$ together with the intervening atoms form a nitrogen-containing 4- to 6-membered nonaromatic heterocycle and the other $R^2$ is hydrogen or —$C_1$-$C_4$ alkyl, wherein the nitrogen-containing 4- to 6-membered nonaromatic heterocycle is unsubstituted or substituted with two —F.

In some embodiments, both R² together with the intervening atom form a —C₃-C₈ monocyclic cycloalkyl or an oxygen-containing 3- to 6-membered nonaromatic heterocycle.

In some embodiments, both R² together with the intervening atom form a —C₃-C₈ monocyclic cycloalkyl or an oxygen-containing 3- to 6-membered nonaromatic heterocycle, each of which is unsubstituted or substituted with two —F.

In some embodiments, Y is phenyl or pyridinyl, each of which is unsubstituted or substituted with one or more substituents independently selected from the group consisting of -halo and —C₁-C₄ alkoxy.

In some embodiments, Y is phenyl substituted with one -halo.

In some embodiments, Y is phenyl substituted with one —F.

In some embodiments, Y is phenyl substituted with one —C₁-C₄ alkoxy.

In some embodiments, Y is phenyl substituted with one methoxy.

In some embodiments, Y is pyridinyl substituted with one —C₁-C₄ alkoxy.

In some embodiments, Y is pyridinyl substituted with one methoxy.

In some embodiments, Z is imidazolyl, which is unsubstituted or substituted with one -halo or —C₁-C₄ alkyl.

In some embodiments, Z is imidazolyl substituted with one -halo.

In some embodiments, Z is imidazolyl substituted with one —Cl.

In some embodiments, Z is imidazolyl substituted with one —C₁-C₄ alkyl.

In some embodiments, Z is imidazolyl substituted with one methyl.

In some embodiments, the compound of Formula (II) is a compound selected from the compounds in Table II.

TABLE II

Exemplary Fused Morpholinopyrimidines of Formula (II)

| Compound of Example | Structure | Name |
| --- | --- | --- |
| 254 | 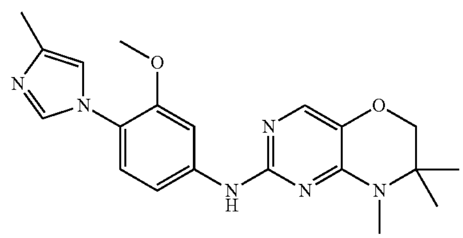 [SMILES: COc1cc(Nc2ncc3c(n2)N(C)C(C)(C)CO3)ccc1-n1cnc(C)c1] | N-(3-methoxy-4-(4-methyl-1H-imidazol-1-yl) phenyl)-7, 7, 8-trimethyl-7, 8-dihydro-6H-pyrimido [5, 4-b] [1, 4] oxazin-2-amine |
| 255 | 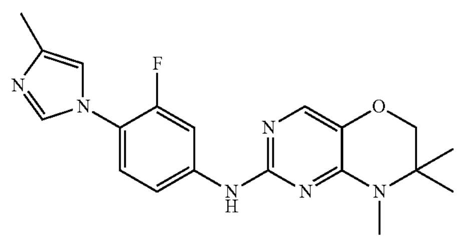 [SMILES: Cc1cn(-c2ccc(Nc3ncc4c(n3)N(C)C(C)(C)CO4)cc2F)cn1] | N-(3-fluoro-4-(4-methyl-1H-imidazol-1-yl) phenyl)-7, 7, 8-trimethyl-7, 8-dihydro-6H-pyrimido [5, 4-b] [1, 4] oxazin-2-amine |
| 256 | 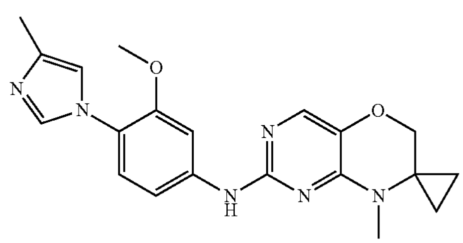 [SMILES: COc1cc(Nc2ncc3c(n2)N(C)C2(CC2)CO3)ccc1-n1cnc(C)c1] | N-(3-fluoro-4-(4-methyl-1H-imidazol-1-yl) phenyl)-7, 7, 8-trimethyl-7, 8-dihydro-6H-pyrimido [5, 4-b] [1, 4] oxazin-2-amine |
| 257 | 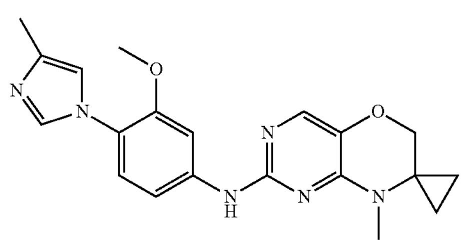 | N-(3-methoxy-4-(4-methyl-1H-imidazol-1-yl) phenyl)-8'-methyl-6'H, 8'H-spiro [cyclopropane-1, 7'-pyrimido [5, 4-b] [1, 4] oxazin]-2'-amine |

TABLE II-continued

Exemplary Fused Morpholinopyrimidines of Formula (II)

| Compound of Example | Structure | Name |
|---|---|---|
| 258 | 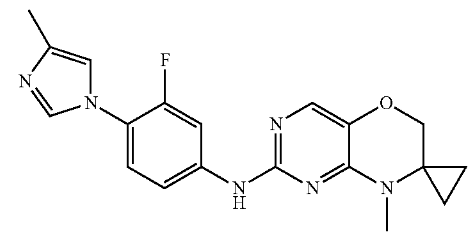 [SMILES: Cc1cn(-c2ccc(Nc3ncc4c(n3)N(C)C3(CC3)CO4)cc2F)cn1] | N-(3-fluoro-4-(4-methyl-1H-imidazol-1-yl) phenyl)-8'-methyl-6'H, 8'H-spiro [cyclopropane-1, 7'-pyrimido [5, 4-b] [1, 4] oxazin]-2'-amine |
| 259 | 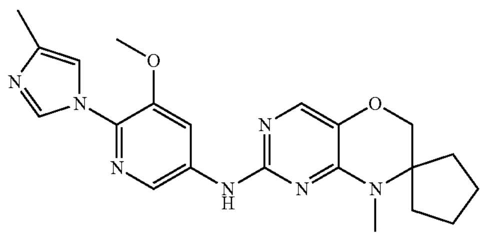 [SMILES: COc1cc(Nc2ncc3c(n2)N(C)C2(CCCC2)CO3)cnc1-n1cnc(C)c1] | N-(5-methoxy-6-(4-methyl-1H-imidazol-1-yl) pyridin-3-yl)-8-methyl-6'H, 8'H-spiro [cyclopentane-1, 7'-pyrimido [5, 4-b] [1, 4] oxazin]-2'-amine |
| 260 | 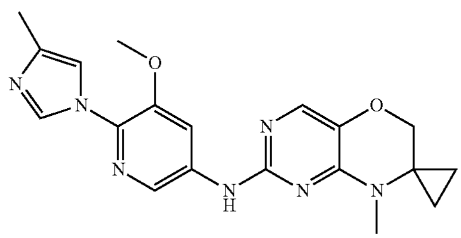 [SMILES: COc1cc(Nc2ncc3c(n2)N(C)C2(CC2)CO3)cnc1-n1cnc(C)c1] | N-(5-methoxy-6-(4-methyl-1H-imidazol-1-yl) pyridin-3-yl)-8'-methyl-6'H, 8'H-spiro [cyclopropane-1, 7'-pyrimido [5, 4-b] [1, 4] oxazin]-2'-amine |
| 261 | 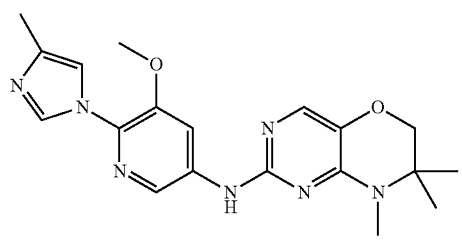 [SMILES: COc1cc(Nc2ncc3c(n2)N(C)C(C)(C)CO3)cnc1-n1cnc(C)c1] | N-(5-methoxy-6-(4-methyl-1H-imidazol-1-yl) pyridin-3-yl)-7, 7, 8-trimethyl-7, 8-dihydro-6H-pyrimido [5, 4-b] [1, 4] oxazin-2-amine |
| 262 | 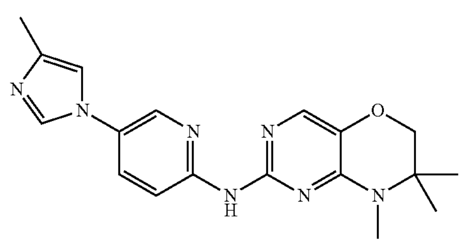 [SMILES: Cc1cn(-c2ccc(Nc3ncc4c(n3)N(C)C(C)(C)CO4)nc2)cn1] | 7, 7, 8-trimethyl-N-(5-(4-methyl-1H-imidazol-1-yl) pyridin-2-yl)-7, 8-dihydro-6H-pyrimido [5, 4-b] [1, 4] oxazin-2-amine |
| 263 | 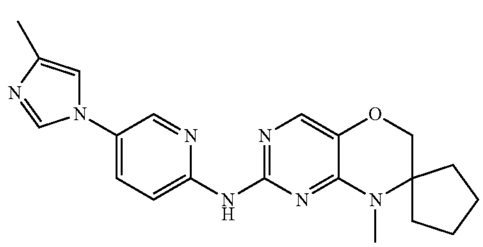 [SMILES: Cc1cn(-c2ccc(Nc3ncc4c(n3)N(C)C3(CCCC3)CO4)nc2)cn1] | 8'-methyl-N-(5-(4-methyl-1H-imidazol-1-yl) pyridin-2-yl)-6'H, 8'H-spiro [cyclopentane-1, 7'-pyrimido [5, 4-b] [1, 4] oxazin]-2'-amine |

TABLE II-continued

Exemplary Fused Morpholinopyrimidines of Formula (II)

| Compound of Example | Structure | Name |
|---|---|---|
| 264 | 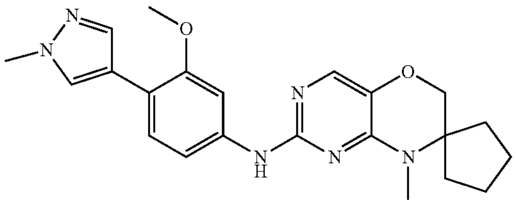 [SMILES: COc1cc(Nc2ncc3c(n2)N(C)C2(CCCC2)CO3)ccc1-c1cnn(C)c1] | N-(3-methoxy-4-(1-methyl-1H-pyrazol-4-yl) phenyl)-8'-methyl-6'H, 8'H-spiro [cyclopentane-1, 7'-pyrimido [5, 4-b] [1, 4] oxazin]-2'-amine |
| 265 | 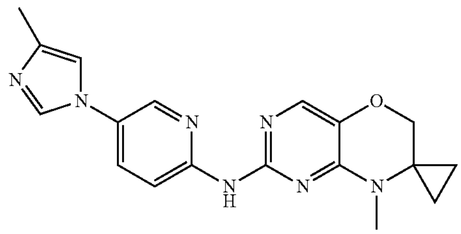 [SMILES: Cc1cn(-c2ccc(Nc3ncc4c(n3)N(C)C3(CC3)CO4)nc2)cn1] | N-(5-(4-methyl-1H-imidazol-1-yl) pyridin-2-yl)-6'H, 8'H-spiro [cyclopropane-1, 7'-pyrimido [5, 4-b] [1, 4] oxazin]-2'-amine |
| 266 | 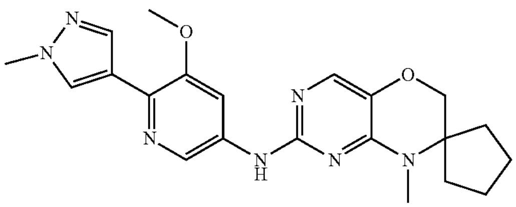 | N-(5-methoxy-6-(1-methyl-1H-pyrazol-4-yl) pyridin-3-yl)-8'-methyl-6'H, 8'H-spiro [cyclopentane-1, 7'-pyrimido [5, 4-b] [1, 4] oxazin]-2'-amine |
| 267 | 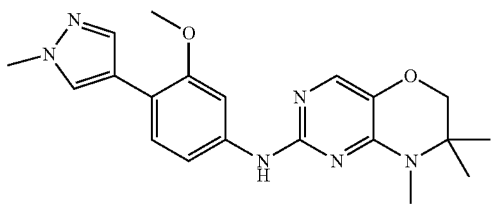 | N-(3-methoxy-4-(1-methyl-1H-pyrazol-4-yl phenyl)-7, 7, 8-trimethyl-7, 8-dihydro-6H-pyrimido [5, 4-b] [1, 4] oxazin-2-amine |
| 268 | 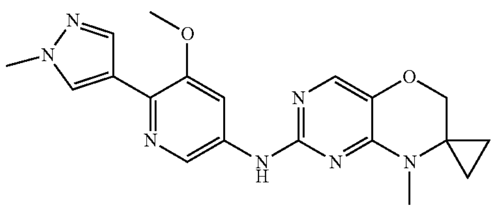 | N-(5-methoxy-6-(1-methyl-1H-pyrazol-4-yl) pyridin-3-yl)-8-methyl-6'H, 8'H-spiro [cyclopropane-1, 7'-pyrimido [5, 4-b] [1, 4] oxazin]-2'-amine |
| 269 | 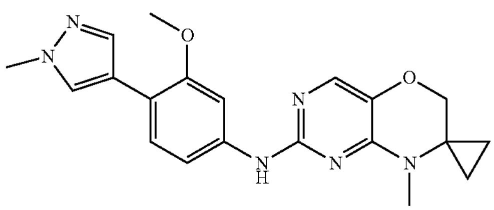 [SMILES: COc1cc(Nc2ncc3c(n2)N(C)C2(CC2)CO3)ccc1-c1cnn(C)c1] | N-(3-methoxy-4-(1-methyl-1H-pyrazol-4-yl) phenyl)-8'-methyl-6'H, 8'H-spiro [cyclopropane-1, 7'-pyrimido [5, 4-b] [1, 4] oxazin]-2'-amine |
| 270 | 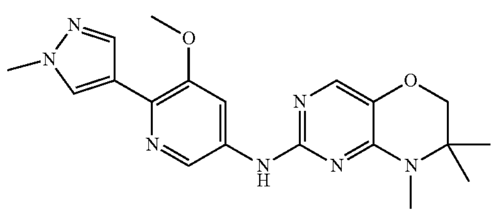 | N-(5-methoxy-6-(1-methyl-1H-pyrazol-4-yl) pyridin-3-yl)-7, 7, 8-trimethyl-7, 8-dihydro-6H-pyrimido [5, 4-b] [1, 4] oxazin-2-amine |

TABLE II-continued

Exemplary Fused Morpholinopyrimidines of Formula (II)

| Compound of Example | Structure | Name |
|---|---|---|
| 271 | 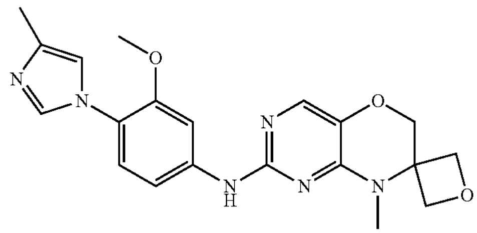 [SMILES: COc1cc(Nc2ncc3c(n2)N(C)C2(COC2)CO3)ccc1-n1cnc(C)c1] | N-(3-methoxy-4-(4-methyl-1H-imidazol-1-yl) phenyl)-8'-methyl-6'H, 8'H-spiro [oxetane-3, 7'-pyrimido 5, 4-b] [1, 4] oxazin]-2'-amine |
| 272 | 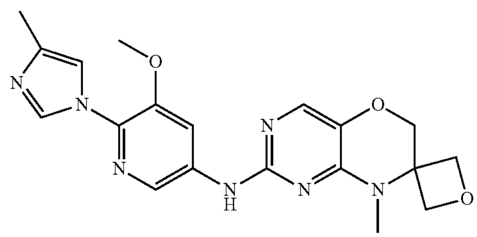 [SMILES: COc1cc(Nc2ncc3c(n2)N(C)C2(COC2)CO3)cnc1-n1cnc(C)c1] | N-(5-methoxy-6-(4-methyl-1H-imidazol-1-yl) pyridin-3-yl)-8'-methyl-6'H, 8'H-spiro [oxetane-3,7'-pyrimido [5, 4-b] [1,4] oxazin]-2'-amine |
| 273 | 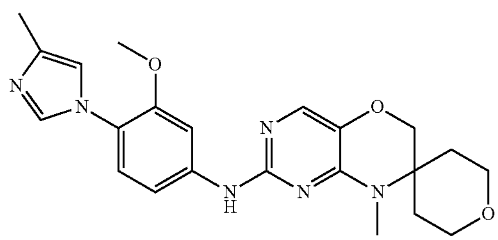 [SMILES: COc1cc(Nc2ncc3c(n2)N(C)C2(CCOCC2)CO3)ccc1-n1cnc(C)c1] | N-(3-methoxy-4-(4-methyl-1H-imidazol-1-yl) phenyl)-8'-methyl-2, 3, 5, 6-tetrahydro-6'H, 8'H-spiro [pyran-4, 7'-pyrimido [5, 4-b] [1, 4] oxazin]-2'-amine |
| 274 | 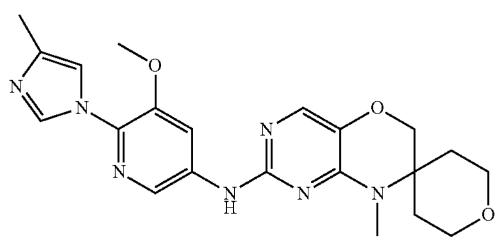 [SMILES: COc1cc(Nc2ncc3c(n2)N(C)C2(CCOCC2)CO3)cnc1-n1cnc(C)c1] | N-(5-methoxy-6-(4-methyl-1H-imidazol-1-yl) pyridin-3-yl)-8'-methyl-2, 3, 5, 6-tetrahydro-6'H, 8'H-spiro pyran-4, 7'-pyrimido [5, 4-b] [1, 4] oxazin1-2'-amine |
| 275 | 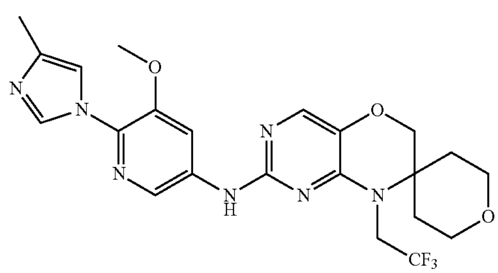 [SMILES: COc1cc(Nc2ncc3c(n2)N(CC(F)(F)F)C2(CCOCC2)CO3)cnc1-n1cnc(C)c1] | N-(3-methoxy-4-(4-methyl-1H-imidazol-1-yl) phenyl)-8'-(2, 2, 2-trifluoroethyl)-2, 3, 5, 6-tetrahydro-6'H, 8'H-spiro [pyran-4, 7'-pyrimido [5, 4-b] [1, 4] oxazin]-2'-amine |
| 276 | 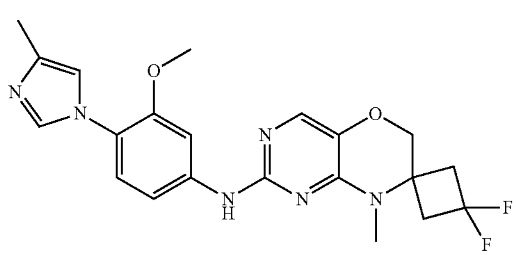 [SMILES: COc1cc(Nc2ncc3c(n2)N(C)C2(CO3)CC(F)(F)C2)ccc1-n1cnc(C)c1] | 3, 3-difluoro-N-(3-methoxy-4-(4-methyl-1H-imidazol-1-yl) phenyl)-8'-methyl-6'H, 8'H-spiro [cyclobutane-1, 7'-pyrimido [5, 4-b] [1, 4] oxazin]-2'-amine |

TABLE II-continued

Exemplary Fused Morpholinopyrimidines of Formula (II)

| Compound of Example | Structure | Name |
|---|---|---|
| 277 | 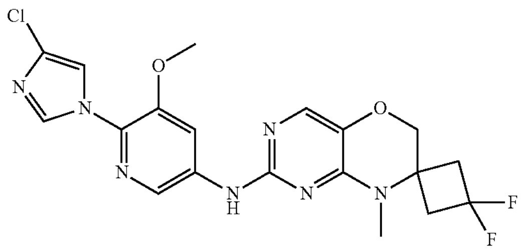 | N-(4-(4-chloro-1H-imidazol-1-yl)-3-methoxyphenyl)-3,3-difluoro-8'-methyl-6'H,8'H-spiro [cyclobutane-1, 7'-pyrimido [5, 4-b] [1, 4] oxazin1-2'-amine |
| 278 | 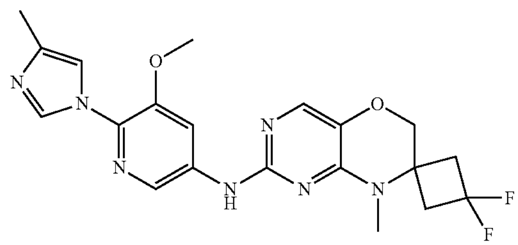 [SMILES: COc1cc(Nc2ncc3c(n2)N(C)C2(CO3)CC(F)(F)C2)cnc1-n1cnc(C)c1] | 3, 3-difluoro-N-(5-methoxy-6-(4-methyl-1H-imidazol-1-yl) pyridin-3-yl)-8'-methyl-6'H, 8'H-spiro [cyclobutane-1, 7'-pyrimido [5, 4-b] [1, 4] oxazin]-2'-amine |
| 279 | 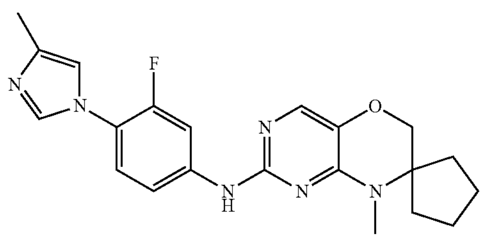 [SMILES: Cc1cn(-c2ccc(Nc3ncc4c(n3)N(C)C3(CCCC3)CO4)cc2F)cn1] | N-(3-fluoro-4-(4-methyl-1H-imidazol-1-yl) phenyl)-8'-methyl-6H, 8'H-spiro [cyclopentane-1, 7'-pyrimido [5, 4-b] [1, 4] oxazin]-2'-amine |
| 289A | 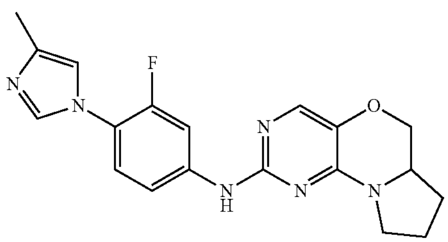 [SMILES: Cc1cn(-c2ccc(Nc3ncc4c(n3)N3CCCC3CO4)cc2F)cn1] | (+)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine |
| 289B | 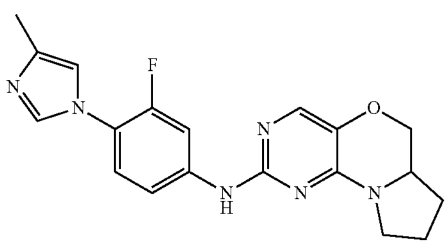 | (−)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine |
| 290A | 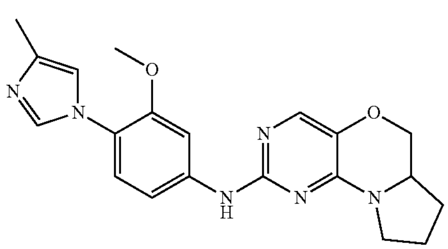 [SMILES: COc1cc(Nc2ncc3c(n2)N2CCCC2CO3)ccc1-n1cnc(C)c1] | (−)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine |

TABLE II-continued

Exemplary Fused Morpholinopyrimidines of Formula (II)

| Compound of Example | Structure | Name |
|---|---|---|
| 290B | 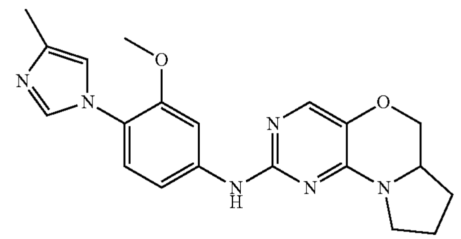 [SMILES: COc1cc(Nc2ncc3c(n2)N2CCCC2CO3)ccc1-n1cnc(C)c1] | (+)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine |
| 291 | 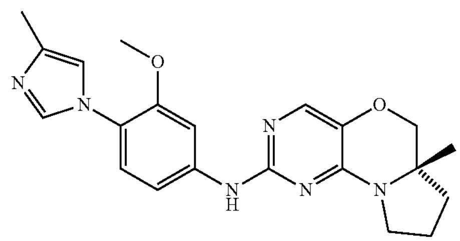 | (S)-N-(3-methoxy-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine |
| 292 | 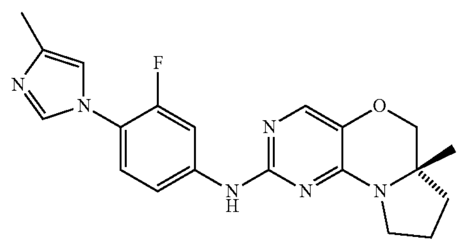 | (S)-N-(3-fluoro-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine |
| 293 | 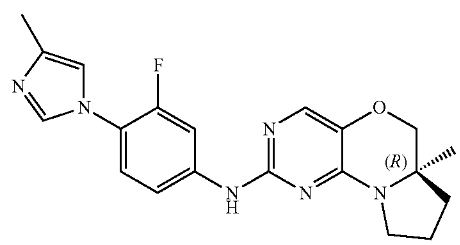 | (R)-N-(3-fluoro-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine |
| 294 | 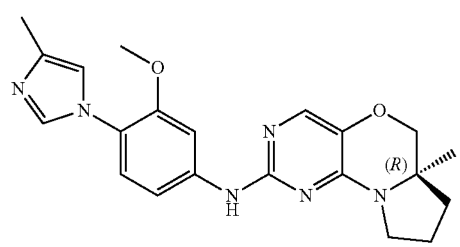 | (R)-N-(3-methoxy-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine |
| 295 | 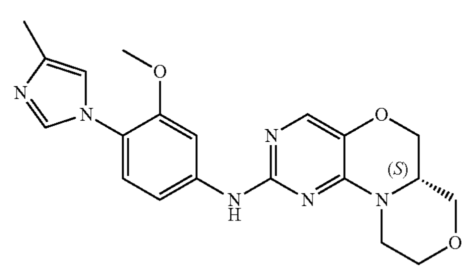 | (S)-N-(3-methoxy-4-(4-methyl-1H-imidazol-1-yl) phenyl)-6a, 7, 9, 10-tetrahydro-6H-[1, 4] oxazino [4, 3-d] pyrimido [5, 4-b] [1, 4] oxazin-2-amine |

TABLE II-continued

Exemplary Fused Morpholinopyrimidines of Formula (II)

| Compound of Example | Structure | Name |
|---|---|---|
| 296 | 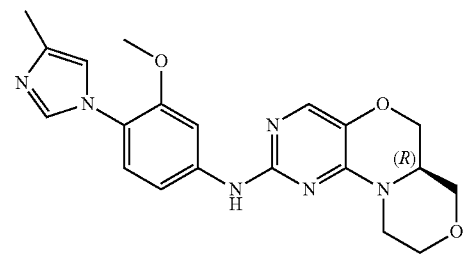 | (R)-N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine |
| 297 | 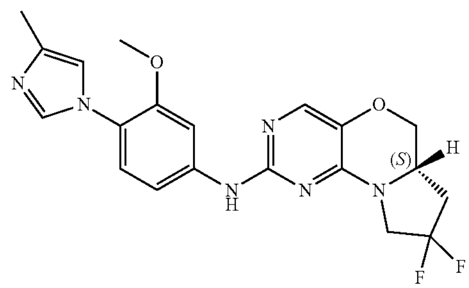 | (S)-8, 8-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine |
| 298 | 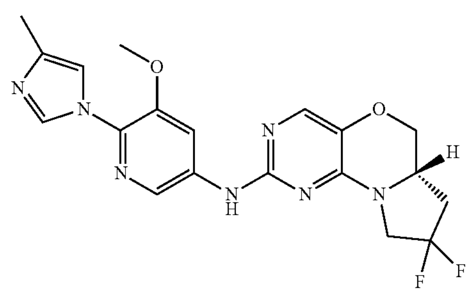 [SMILES: COc1cc(Nc2ncc3c(n2)N2CC(F)(F)C[C@H]2CO3)cnc1-n1cnc(C)c1] | (S)-8, 8-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine |
| 299 | 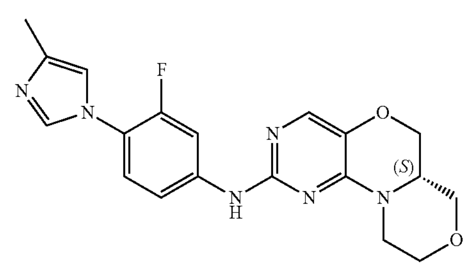 | (S)-N-(3-fluoro-4-(4-methyl-1H-imidazol-1-yl) phenyl)-6a, 7, 9, 10-tetrahydro-6H-[1, 4] oxazino [4, 3-d] pyrimido [5, 4-b] [1, 4] oxazin-2-amine |
| 300 | 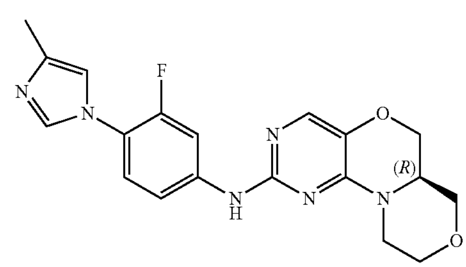 | (R)-N-(3-fluoro-4-(4-methyl-1H-imidazol-1-yl) phenyl)-6a, 7, 9, 10-tetrahydro-6H-[1, 4] oxazino [4, 3-d] pyrimido [5, 4-b] [1, 4] oxazin-2-amine |

TABLE II-continued

Exemplary Fused Morpholinopyrimidines of Formula (II)

| Compound of Example | Structure | Name |
|---|---|---|
| 301A | 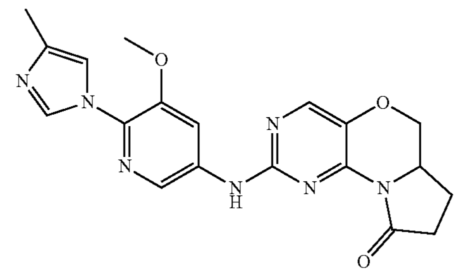 [SMILES: COc1cc(Nc2ncc3c(n2)N2C(=O)CCC2CO3)cnc1-n1cnc(C)c1] | (+)-N-(5-methoxy-6-(4-methyl-1H-imidazol-1-yl) pyridin-3-yl)-8'-methyl-2, 3, 5, 6-tetrahydro-6'H, 8'H-spiro [pyran-4, 7'-pyrimido [5, 4-b] [1, 4] oxazin]-2'-amine |
| 301B | 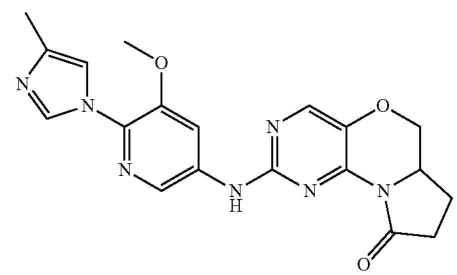 | (−)-N-(5-methoxy-6-(4-methyl-1H-imidazol-1-yl) pyridin-3-yl)-8'-methyl-2, 3, 5, 6-tetrahydro-6'H, 8'H-spiro [pyran-4, 7'-pyrimido [5, 4-b] [1, 4] oxazin]-2'-amine |
| 302A | 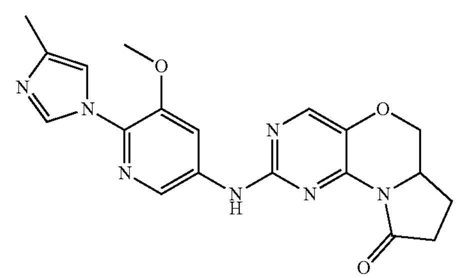 [SMILES: COc1cc(Nc2ncc3c(n2)N2C(=O)CCC2CO3)cnc1-n1cnc(C)c1] | (+)-2-((5-methoxy-6-(4-methyl-1H-imidazol-1-yl) pyridin-3-yl) amino)-6, 6a, 7, 8-tetrahydro-9H-pyrimido [5, 4-b] pyrrolo [1, 2-d] [1, 4] oxazin-9-one |
| 302B | 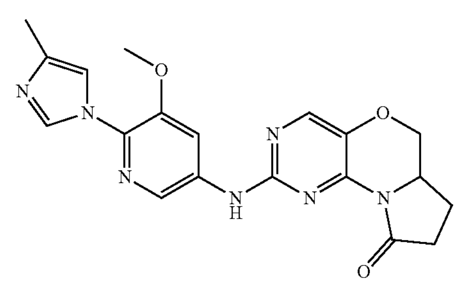 | (−)-2-((5-methoxy-6-(4-methyl-1H-imidazol-1-yl) pyridin-3-yl) amino)-6, 6a, 7, 8-tetrahydro-9H-pyrimido [5, 4-b] pyrrolo [1, 2-d] [1, 4] oxazin-9-one |
| 303 | 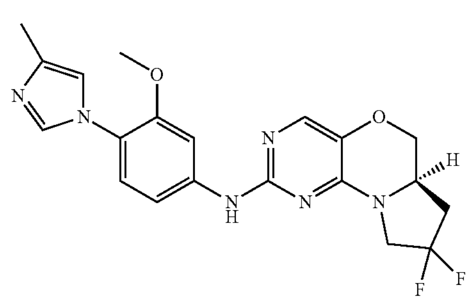 [SMILES: COc1cc(Nc2ncc3c(n2)N2CC(F)(F)C[C@@H]2CO3)ccc1-n1cnc(C)c1] | (R)-8, 8-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine |

TABLE II-continued

Exemplary Fused Morpholinopyrimidines of Formula (II)

| Compound of Example | Structure | Name |
|---|---|---|
| 304A | 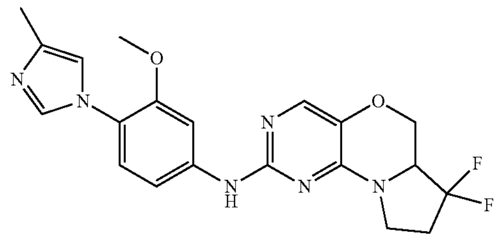 [SMILES: COc1cc(Nc2ncc3c(n2)N2CCC(F)(F)C2CO3)ccc1-n1cnc(C)c1] | (−)-7, 7-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine |
| 304B | 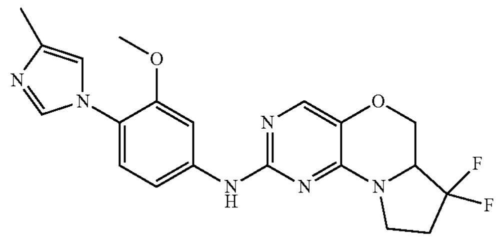 [SMILES: COc1cc(Nc2ncc3c(n2)N2CCC(F)(F)C2CO3)ccc1-n1cnc(C)c1] | (+)-7, 7-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine |
| 305A | 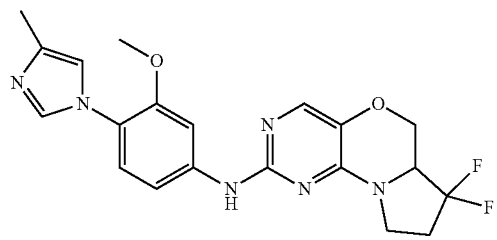 [SMILES: COc1cc(Nc2ncc3c(n2)N2CCC(F)(F)C2CO3)ccc1-n1cnc(C)c1] | (+)-7, 7-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine |
| 305B | 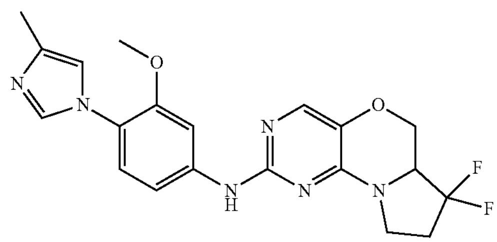 [SMILES: COc1cc(Nc2ncc3c(n2)N2CCC(F)(F)C2CO3)ccc1-n1cnc(C)c1] | (−)-7, 7-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine |

5.3 Methods for Making Fused Morpholinopyrimidines

Methods useful for making the Fused Morpholinopyrimidines are set forth in the Examples below and generalized in Schemes 1-10.

Schemes 1-10 represent general synthetic schemes for manufacturing Fused Morpholinopyrimidines. These schemes are illustrative and are not meant to limit the possible techniques one skilled in the art may use to manufacture compounds disclosed herein. Different methods will be evident to those skilled in the art. Additionally, the various steps in the synthesis may be performed in an alternate sequence or order to give the desired compound(s).

Various modifications to these methods may be envisioned by those skilled in the art to achieve similar results to that of the inventors provided below. For example, optional protecting groups can be used as described, for example, in Greene et al., *Protective Groups in Organic Synthesis* (3$^{rd}$ ed. 1999).

Scheme 1

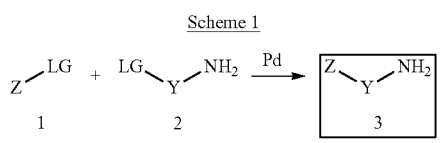

As shown in Scheme 1, a compound of formula 1 is reacted with the compound of formula 2 using Pd-catalyzed coupling conditions to provide a compound of formula 3.

Scheme 2

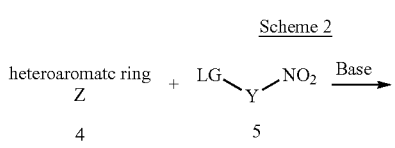

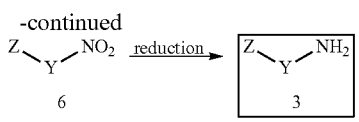

As shown in Scheme 2, alternatively, a compound of formula 4 is reacted with the compound of formula 5 under basic conditions to provide a compound of formula 6. The compound of formula 6 is reduced to provide a compound of formula 3.

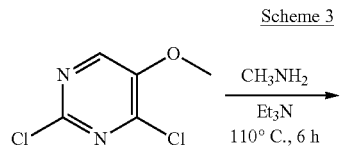

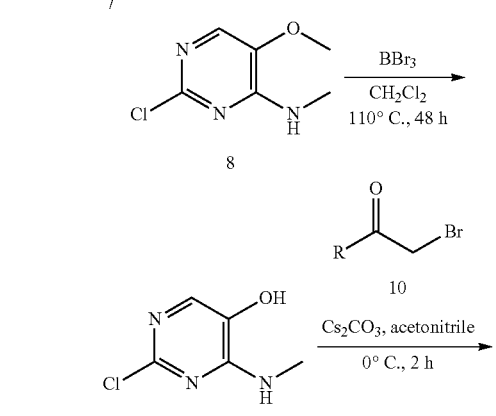

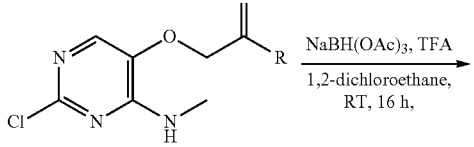

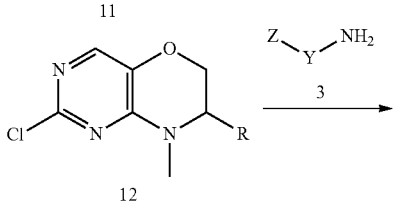

As shown in Scheme 3, a compound of formula 7 is reacted with methyl amine under basic conditions to provide a compound of formula 8. The compound of formula 8 is then reacted with BBr₃ to provide a compound of formula 9. The compound of formula 9 is reacted using, for example, a compound of formula 10, to provide a compound of formula 11. The compound of formula 11 is then cyclized to from a compound of formula 12. The compound of formula 12 is reacted with a compound of formula 3 to provide a Fused Morpholinopyrimidine.

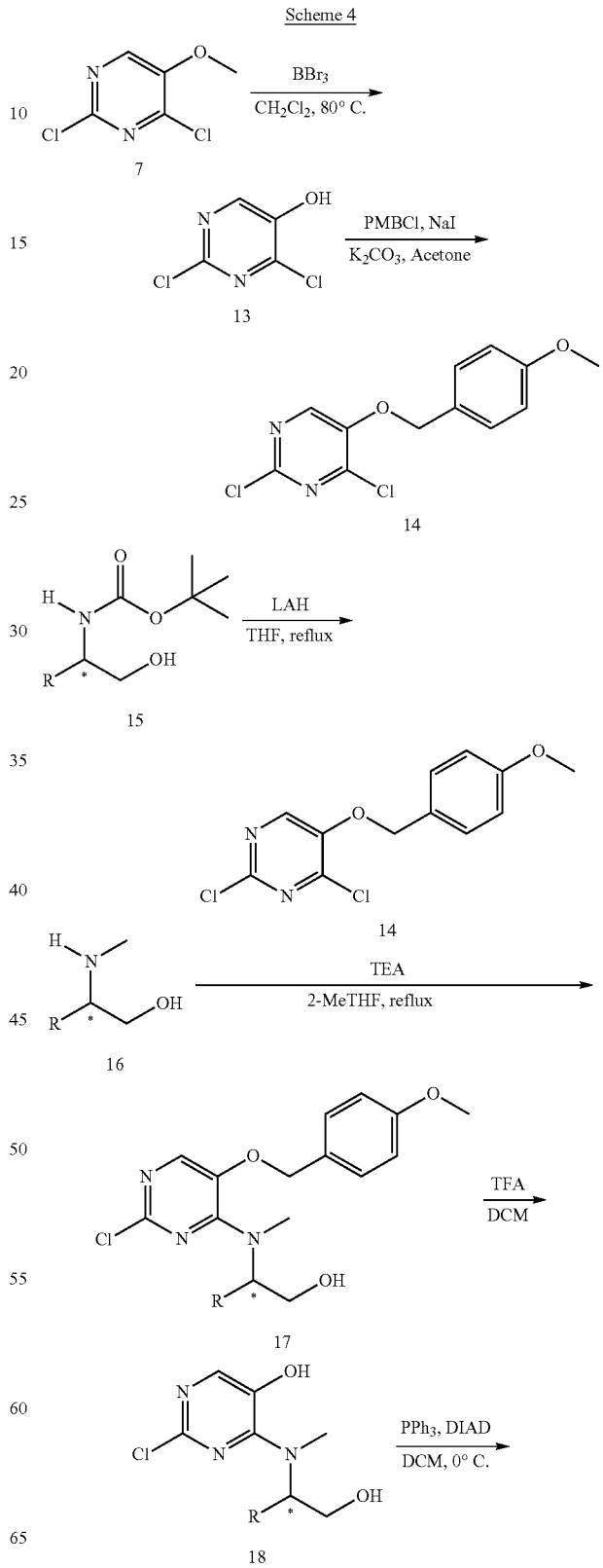

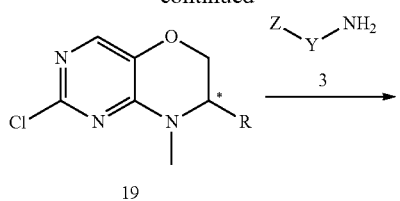

19

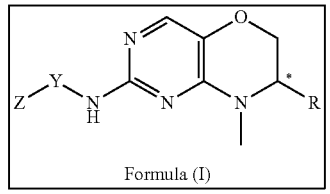

Formula (I)

As shown in Scheme 4, a compound of formula 7 is reacted with BBr₃ to provide a compound of formula 13. The compound of formula 13 is then protected to form compound 14. Enantio-pure compound of formula 15 is reduced with LAH to provide a compound of formula 16. The compound of formula 16 is then reacted with compound 14 to form compound 17. The compound of formula 17 is then deprotected under acidic conditions to provide a compound of formula 18. The compound of formula 18 is then cyclized to form a compound of formula 19. The compound of formula 19 is reacted with a compound of formula 3 to provide an enantiomerically-pure Fused Morpholinopyrimidine at the chiral carbon atom (marked with *).

Scheme 5

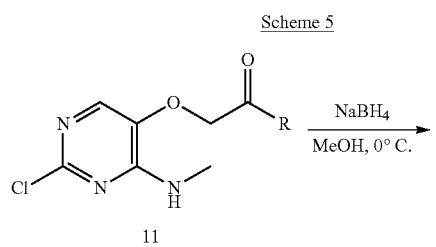

11

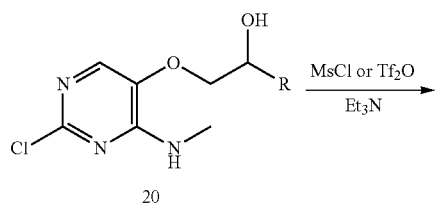

20

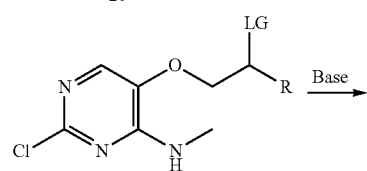

21

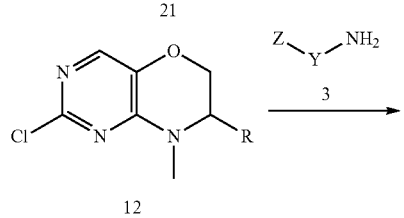

12

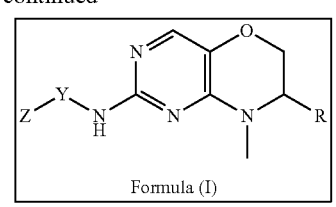

Formula (I)

As shown in Scheme 5, a compound of formula 11 is reduced with sodium borohydride to provide a compound of formula 20. The compound of formula 20 is then reacted with MsCl or Tf₂O to provide a compound of formula 21. The compound of formula 21 is cyclized under basic conditions to provide a compound of formula 12. The compound of formula 12 is reacted with a compound of formula 3 to provide a Fused Morpholinopyrimidine.

Scheme 6

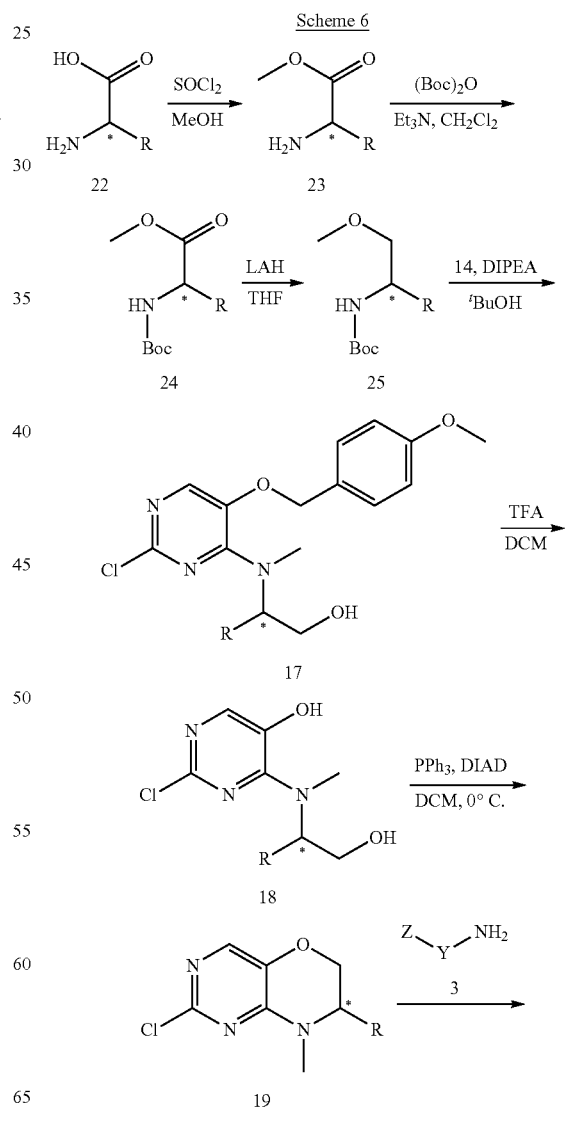

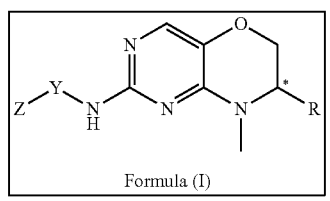

Formula (I)

As shown in Scheme 6, Enantio-pure compound of formula 22 is reacted with SOCl$_2$ to provide a compound of formula 23. The compound of formula 23 is then protected to form compound 24. The compound of formula 24 is reduced with LAH to provide a compound of formula 25. The compound of formula 25 is then reacted with compound 14 to form compound 17. The compound of formula 17 is then deprotected under acidic conditions to provide a compound of formula 18. The compound of formula 18 is then cyclized to provide a compound of formula 19. The compound of formula 19 is reacted with a compound of formula 3 to provide an enantiomerically-pure Fused Morpholinopyrimidine at the chiral carbon atom (marked with *).

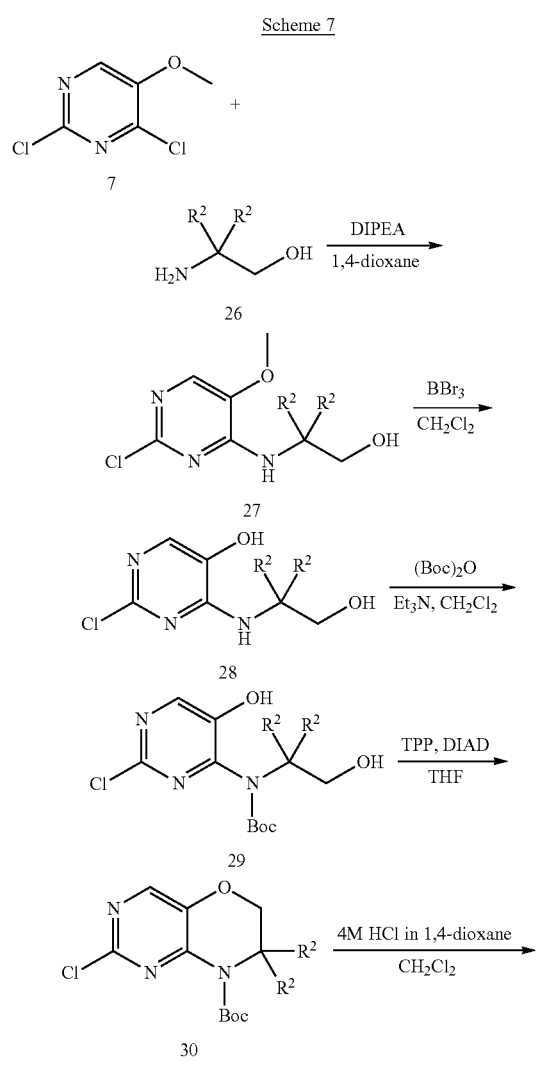

Scheme 7

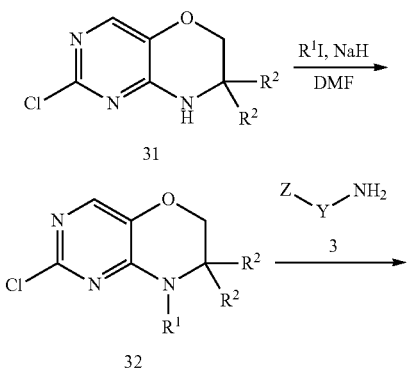

Formula (II)

As shown in Scheme 7, a compound of formula 7 is reacted with a compound of formula 26 under basic conditions to provide a compound of formula 27. The compound of formula 27 is then reacted with BBr$_3$ to provide a compound of formula 28. The compound of formula 28 is then protected to form compound 29. The compound of formula 29 is then cyclized to form a compound of formula 30. The compound of formula 30 is then deprotected under acidic conditions to provide a compound of formula 31. The compound of formula 31 is then alkylated to provide a compound of formula 32. The compound of formula 32 is reacted with a compound of formula 3 to provide a Fused Morpholinopyrimidine.

Scheme 8

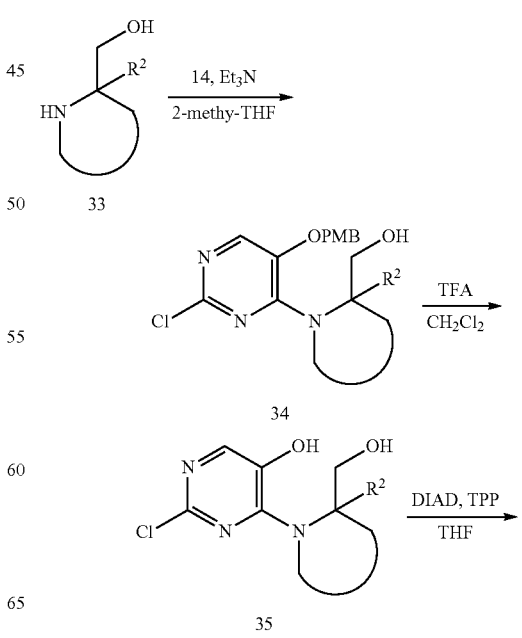

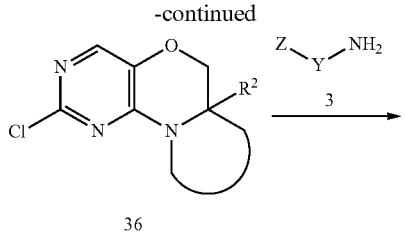

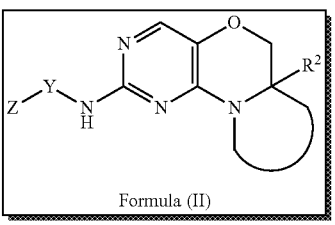

As shown in Scheme 8, The compound of formula 33 is coupled with compound 14 to form compound 34. The compound of formula 34 is then deprotected under acidic conditions to provide a compound of formula 35. The compound of formula 35 is then cyclized to provide a compound of formula 36. The compound of formula 36 is reacted with a compound of formula 3 to provide a Fused Morpholinopyrimidine.

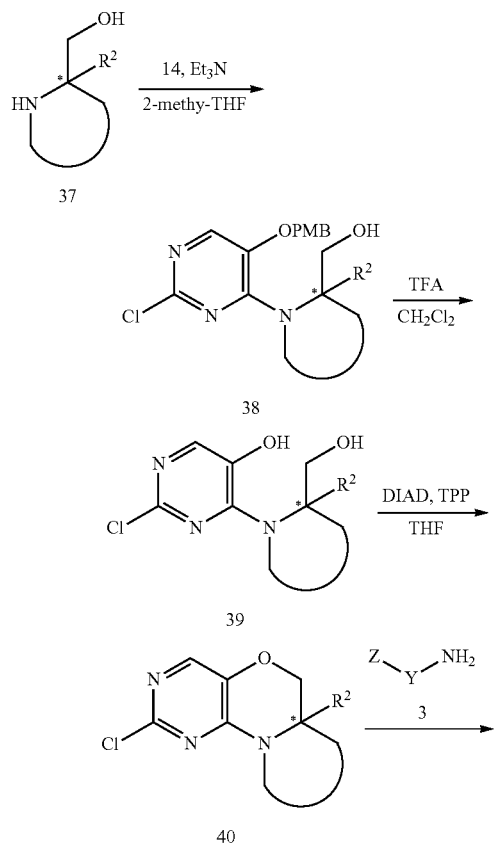

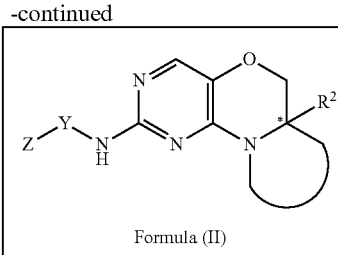

As shown in Scheme 9, Enantio-pure compound of formula 37 is reacted with compound 14 to form compound 38. The compound of formula 38 is then deprotected under acidic conditions to provide a compound of formula 39. The compound of formula 39 is then cyclized to provide a compound of formula 40. The compound of formula 40 is reacted with a compound of formula 3 to provide an enantiomerically-pure Fused Morpholinopyrimidine at the chiral carbon atom (marked with *).

As shown in Scheme 10, a compound of formula 41 is reacted with iodine to provide a compound of formula 42. The compound of formula 42 is reacted with a compound of formula 13 to provide a compound of formula 31. The compound of formula 31 is then alkylated to provide a compound of formula 32. The compound of formula 32 is reacted with a compound of formula 3 to provide a Fused Morpholinopyrimidine.

5.4 Pharmaceutical Compositions Comprising a Fused Morpholinopyrimidine

In another aspect, the present disclosure provides pharmaceutical compositions for treating, preventing, or ameliorating a symptom of a neurodegenerative disease in a subject having a neurodegenerative disease, wherein the pharmaceutical composition comprises a therapeutically effective amount of a Fused Morpholinopyrimidine, and a pharmaceutically acceptable carrier or vehicle.

As set out above, in some embodiments, Fused Morpholinopyrimidines are provided in the form of pharmaceutically acceptable salts. These salts can be prepared in situ during the final isolation and purification of the compounds described herein, or by separately reacting a purified compound described herein in its free base or acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, laurylsulphonate, ammonium, amine salts and the like. See, for example, Berge, et al., (1977) "Pharmaceutical Salts", *J. Pharm. Sci.* 66:1-19.

The pharmaceutically acceptable salts of Fused Morpholinopyrimidines include the conventional nontoxic salts or acid salts of the compounds, e.g., from non-toxic organic or inorganic acids. For example, such conventional nontoxic salts include those derived from inorganic acids, such as hydrochloride, hydrobromic, sulfuric, sulfamic, phosphoric, nitric, and the like; and the salts prepared from organic acids, such as acetic, butionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic and the like.

In general, a suitable dose of a Fused Morpholinopyrimidine will be in the range of 0.01 to 100 mg per kilogram body weight of the recipient per day or in the range of 0.2 to 10 mg per kilogram body weight per day. The desired dose can be administered once daily, but may be dosed as two, three, four, five, six or more sub-doses administered at appropriate intervals throughout the day.

The concentration of compounds included in compositions used in the methods described herein can range from about 1 nM to about 100 µM. Effective doses are believed to range from about 10 picomole/kg to about 100 micromole/kg.

A Fused Morpholinopyrimidine can be administered as the sole active agent, or in combination with other known therapeutics to be beneficial in the treatment of neurodegenerative diseases. In any event, the administering physician can provide a method of treatment that is prophylactic or therapeutic by adjusting the amount and timing of drug administration on the basis of observations of one or more symptoms (e.g., motor or cognitive function as measured by standard clinical scales or assessments) of the disease being treated.

Details on techniques for formulation and administration are well described in the scientific and patent literature, see, e.g., Remington: The Science and Practice of Pharmacy (2 Volumes), (22nd Edition, 2012), Pharmaceutical Press ("Remington's"). After a pharmaceutical composition has been formulated in an acceptable carrier, it can be placed in an appropriate container and labeled for treatment of an indicated condition. For administration of a Fused Morpholinopyrimidine, such labeling would include, e.g., instructions concerning the amount, frequency, and method of administration.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient, which can be combined with a carrier or vehicle material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

The compounds and pharmaceutical compositions described herein can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved.

Methods of preparing these formulations or compositions include the step of bringing into association a compound described herein with the carrier and, optionally, one or more accessory ingredients. In general, the formulations are prepared by uniformly and intimately bringing into association a compound described herein with liquid carriers, or finely divided solid carriers, or both, and then, if necessary, shaping the product.

When a Fused Morpholinopyrimidine is administered as pharmaceuticals to humans or animals, it can be given per se or as a pharmaceutical composition containing, for example, 0.1% to 99.5% (more preferably, 0.5% to 90%) of active ingredient in combination with a pharmaceutically acceptable carrier.

The pharmaceutical compositions described herein can be administered in a variety of dosage forms including, but not limited to, a solid dosage form, a liquid dosage form, an oral dosage form, a parenteral dosage form, an intranasal dosage form, a suppository, a lozenge, a troche, a buccal dosage form, a controlled release dosage form, a pulsed release dosage form, an immediate release dosage form, an intravenous solution, a suspension or combinations thereof.

Oral Formulations and Administration

Pharmaceutical formulations described herein suitable for oral administration can be in the form of capsules, cachets, pills, tablets, caplet, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound described herein as an active ingredient. The dosage can be an oral dosage form that is a controlled release dosage form. A Fused Morpholinopyrimidine can also be administered as a bolus, electuary or paste.

In solid dosage forms described herein for oral administration (capsules, tablets, pills, dragees, powders, granules and the like), the active ingredient is mixed with one or more pharmaceutically acceptable carriers and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polybutylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols and the like.

A tablet can be made by compression or molding, optionally with one or more accessory ingredients. Compressed tablets can be prepared using a binder (for example, gelatin or hydroxybutylmethyl cellulose), lubricant, inert diluent, preservative, disintegrant (for example, sodium starch glycolate or cross-linked sodium carboxymethyl cellulose), surface-active or dispersing agent. Molded tablets can be made by molding in a suitable machine a mixture of the powdered compound moistened with an inert liquid diluent.

Tablets, and other solid dosage forms of the pharmaceutical compositions described herein, such as dragees, capsules, pills and granules, can optionally be scored or prepared with coatings and shells, such as enteric coatings and other coatings well known in the pharmaceutical-formulating art. They can also be formulated so as to provide slow or controlled release of the active ingredient therein using, for example, hydroxybutylmethyl cellulose in varying proportions to provide the desired release profile, other polymer matrices, liposomes and/or microspheres. They can be sterilized by, for example, filtration through a bacteria-retaining filter, or by incorporating sterilizing agents in the form of sterile solid compositions, which can be dissolved in sterile water, or some other sterile injectable medium immediately before use. These compositions can also optionally contain opacifying agents and may be of a composition that they release the active ingredient(s) only, or preferentially, in a certain portion of the gastrointestinal tract, optionally, in a delayed manner Examples of embedding compositions which can be used include polymeric substances and waxes. The active ingredient can also be in micro-encapsulated form, if appropriate, with one or more of the above-described excipients.

Capsules for oral use include hard gelatin capsules in which the active ingredient is mixed with a solid diluent, and soft gelatin capsules, wherein the active ingredients is mixed with water or an oil, such as peanut oil, liquid paraffin or olive oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Liquid dosage forms for oral administration of the compounds described herein include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isobutyl alcohol, ethyl carbonate, ethyl acetate, benzyl alcohol, benzyl benzoate, butylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxybutyl-β-cyclodextrin, may be used to solubilize compounds.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar and tragacanth, and mixtures thereof.

Besides inert diluents, the oral compositions can also include adjuvants, such as wetting agents, emulsifying and suspending agents, sweetening, flavoring, coloring, perfuming and preservative agents.

Pharmaceutical preparations for oral use can be obtained through combination of a Fused Morpholinopyrimidine with a solid excipient, optionally grinding a resulting mixture, and processing the mixture of granules, after adding suitable additional compounds, if desired, to obtain tablets or dragee cores. Suitable solid excipients in addition to those previously mentioned are carbohydrate or protein fillers that include, but are not limited to, sugars, including lactose, sucrose, mannitol, or sorbitol; starch from corn, wheat, rice, potato, or other plants; cellulose, such as methyl cellulose, hydroxypropylmethyl-cellulose or sodium carboxymethylcellulose; and gums including arabic and tragacanth; as well as proteins, such as gelatin and collagen. If desired, disintegrating or solubilizing agents can be added, such as the cross-linked polyvinyl pyrrolidone, agar, alginic acid, or a salt thereof, such as sodium alginate.

Pharmaceutical preparations for oral use can be presented as aqueous or liposome formulations. Aqueous suspensions can contain a Fused Morpholinopyrimidine in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents, such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives, such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a Fused Morpholinopyrimidine in a vegetable oil, such as arachis oil, olive oil, sesame oil or coconut oil, or in a mineral oil, such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant, such as ascorbic acid. As an example of an injectable oil vehicle, see Minto, *J. Pharmacol. Exp. Ther.* 281:93-102, 1997. The pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Parenteral Formulations and Administration

In another embodiment, a Fused Morpholinopyrimidine can be administered parenterally, such as intravenous (IV) or intramuscular (IM) administration. The formulations for administration will commonly comprise a solution of a Fused Morpholinopyrimidine dissolved in a pharmaceutically acceptable carrier. Administration of a Fused Morpholinopyrimidine to any of the above mentioned sites can be achieved by direct injection of the pharmaceutical composition comprising the Fused Morpholinopyrimidine or by the use of infusion pumps. The pharmaceutical compositions can be formulated in solid form and re-dissolved or suspended immediately prior to use. Lyophilized forms are also included. The injection can be, for example, in the form of a bolus injection or continuous infusion (e.g., using infusion pumps) of pharmaceutical composition.

Pharmaceutical compositions suitable for parenteral administration comprise one or more compounds described herein in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Among the acceptable vehicles and solvents that can be employed for formulation and/or reconstitution are water (e.g., water for injection) and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, fatty acids, such as oleic acid can likewise be used in the preparation of injectables. These solutions are sterile and generally free of undesirable matter. These formulations may be sterilized by conventional, well known sterilization techniques such as gamma-radiation or electron beam sterilization. The formulations can contain pharmaceutically acceptable auxiliary substances as required to approximate physiological conditions, such as pH adjusting and buffering agents, toxicity adjusting agents, e.g., sodium acetate, sodium chloride, potassium chloride, calcium chloride, sodium lactate and the like. The concentration of a Fused Morpholinopyrimidine in these formulations can vary widely, and will be selected primarily based on fluid volumes, viscosities, body weight, and the like, in accordance with the particular mode of administration selected and the subject's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In some embodiments, a Fused Morpholinopyrimidine can be administered by introduction into the central nervous system of the subject, e.g., into the cerebrospinal fluid of the subject. The formulations for administration will commonly comprise a solution of the Fused Morpholinopyrimidine dissolved in a pharmaceutically acceptable carrier. In certain aspects, the Fused Morpholinopyrimidine is introduced intrathecally, e.g., into a cerebral ventricle, the lumbar region, or the cisterna magna.

In some embodiments, the pharmaceutical composition comprising a Fused Morpholinopyrimidine is administered into a subject intrathecally. As used herein, the term "intrathecal administration" is intended to include delivering a pharmaceutical composition comprising a Fused Morpholinopyrimidine directly into the cerebrospinal fluid of a subject, by techniques including lateral cerebroventricular injection through a borehole or cisternal or lumbar puncture or the like (described in Lazorthes et al., Advances in Drug Delivery Systems and Applications in Neurosurgery, 1991, 18:143-192 and Omaya et al., Cancer Drug Delivery, 1984, 1:169-179, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. In some embodiments, the pharmaceutical composition is administered by injection into the cisterna magna, or lumbar area of a subject.

Depot Formulations and Administration

A Fused Morpholinopyrimidine can be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle. One strategy for depot injections includes the use of polyethylene oxide-polybutylene oxide copolymers, wherein the vehicle is fluid at room temperature and solidifies at body temperature.

Injectable depot forms can be made by forming microencapsule matrices of the subject compounds in biodegradable polymers, such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations can also be prepared by entrapping the drug in liposomes or microemulsions, which are compatible with body tissue.

Intranasal Formulations and Administration

For administration by inhalation, the compounds are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base, such as lactose or starch.

Other Formulations and Modes of Administration

For transmucosal administration (e.g., buccal, rectal, nasal, ocular, etc.), penetrants appropriate to the barrier to be permeated are used in the formulation. Such penetrants are generally known in the art.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid and polyanhydrides. Microcapsules of the foregoing polymers containing drugs are described in, for example, U.S. Pat. No. 5,075,109. Delivery systems also include non-polymer systems that are: lipids including sterols, such as cholesterol, cholesterol esters and fatty acids or neutral fats, such as mono-, di- and triglycerides; hydrogel release systems; silastic systems; peptide based systems; wax coatings; compressed tablets using conventional binders and excipients; partially fused implants; and the like. Specific examples include, but are not limited to: (a) erosional systems in which an agent described herein is contained in a form within a matrix, such as those described in U.S. Pat. Nos. 4,452,775, 4,675,189, and 5,736,152, and (b) diffusional systems in which an active component permeates at a controlled rate from a polymer, such as described in U.S. Pat. Nos. 3,854,480, 5,133,974 and 5,407,686. In addition, pump-based hardware delivery systems can be used, some of which are adapted for implantation.

5.5 Treatment, Prevention or Amelioration of Symptoms of a Neurodegenerative Disease In another aspect, a method for treating a neurodegenerative disease is described, comprising administering to a subject an effective amount a pharmaceutical composition comprising an effective amount of a Fused Morpholinopyrimidine.

In some embodiments, the method for treating a neurodegenerative disease is a method for reducing or ameliorating a symptom of the neurodegenerative disease.

In some embodiments, a method for reducing or ameliorating a symptom of a neurological disease is described, comprising administering to a subject in need thereof an effective amount of a Fused Morpholinopyrimidine. Ameliorating or reducing the symptoms can be manifested in a variety of ways, for example by improvement in cognitive function can be assessed relative to the cognitive function of the subject prior to being treated or being administered a Fused Morpholinopyrimidine or a pharmaceutical composition comprising an effective amount of a Fused Morpholinopyrimidine.

Exemplary symptoms of neurological disease that can be reduced or ameliorated by administration of a Fused Morpholinopyrimidine are loss of memory, loss of cognition, loss of reasoning and/or loss of judgment. The loss of each of memory, cognition, reasoning and/or judgment can be progressive or sudden. Dementia is an exemplary symptom of neurodegenerative disease. Administration of a Fused Morpholinopyrimidine can reduce or improve one or more of these symptoms.

Exemplary cognitive functions that can be improved by administration of a Fused Morpholinopyrimidine are attention, learning, delayed memory, working memory, visual learning, speed of processing, vigilance, verbal learning, visual motor function, social cognition, long term memory or executive function.

In one embodiment, the neurodegenerative disease is Alzheimer's disease. In some embodiments, the neurodegenerative disease is early onset Alzheimer's disease. In some embodiments, the early onset Alzheimer's disease is autosomal dominant early onset Alzheimer's disease.

In some embodiments, the subject is 65 years or older. In some embodiments, the subject is 55 years old or younger, or 50 years old or younger. In some embodiments, the subject is older than 55 years and younger than 65 years. In some embodiments, the subject is older than 55 years.

In some embodiments, the neurodegenerative disease is panic disorder, obsessive compulsive disorder, delusional disorder, drug-induced psychosis, post-traumatic stress disorder, age-related cognitive decline, attention deficit/hyperactivity disorder, personality disorder of the paranoid type, personality disorder of the schizoid type, dyskinesia, choreiform condition, psychosis associated with Parkinson's disease, psychotic symptoms associated with Alzheimer's disease, mood disorder, or dementia.

In some embodiments, the neurodegenerative disease is cognitive impairment, myclonus, seizures, Parkinsonism, extrapyramidal signs (EPS), apraxia, dystonia, dementia with Lewy bodies (DLB), aphasia, visual agnosia, or ataxia.

In some embodiments, the subject has impaired cognitive function including one or more of attention, learning, delayed memory, working memory, visual learning, speed of processing, vigilance, verbal learning, visual motor function, social cognition, long term memory or executive function.

In some embodiments, the subject has a mutation in at least one gene selected from PSEN1, PSEN2 and APP. In some embodiments, the mutation in PSEN1, PSEN2 or APP is a missense mutation.

In some embodiments, the invention provides a method for treating or ameliorating a symptom of neurodegenerative disease (e g, Alzheimer's disease) in a subject with an increased level of A$\beta$42 in cerebrospinal fluid, the method comprising administering to a subject in need thereof an effective amount of a Fused Morpholinopyrimidine. In such subject, the increased level of A$\beta$42 in cerebrospinal fluid can be detected relative to the level of A$\beta$42 in cerebrospinal fluid of a healthy subject.

In some embodiments, the invention provides a method for lowering A$\beta$42 concentration in a subject, the method comprising administering to a subject in need thereof an effective amount of a Fused Morpholinopyrimidine. In some embodiments, the subject has an elevated A$\beta$42 concentration relative to a healthy subject.

In some embodiments, the invention provides a method for preventing increase of Aβ42 concentration in a subject, the method comprising administering to a subject in need thereof an effective amount of a Fused Morpholinopyrimidine.

5.6 Kits

Described herein are kits that can simplify the administration of an Fused Morpholinopyrimidine to a subject. The kit can comprise one or more containers filled with one or more of the ingredients of the pharmaceutical compositions described herein. Optionally associated with such container(s) can be a notice in the form prescribed by a governmental agency regulating the manufacture, use or sale of pharmaceuticals or biological products, which notice reflects approval by the agency of manufacture, use or sale for human administration.

A typical kit comprises a unit dosage form of a Fused Morpholinopyrimidine. In one embodiment, the unit dosage form is a container, which can be sterile, containing an effective amount of a Fused Morpholinopyrimidine and a pharmaceutically acceptable carrier or vehicle. The kit can further comprise a label or printed instructions instructing the use of the Fused Morpholinopyrimidine to treat or prevent a neurodegenerative disease. The kit can also further comprise a unit dosage form of another prophylactic or therapeutic agent, for example, a container containing an effective amount of the other prophylactic or therapeutic agent. In one embodiment, the kit comprises a container containing an effective amount of a Fused Morpholinopyrimidine and an effective amount of another prophylactic or therapeutic agent. Examples of other prophylactic or therapeutic agents include, but are not limited to, those listed above.

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain additional information, exemplification and guidance which can be adapted to the practice of this invention in its various embodiments and equivalents thereof. The examples do not limit the scope of the invention described in the claims.

6. EXAMPLES

Example 1

Synthesis of 4-(2-methylpyridin-4-yl)aniline

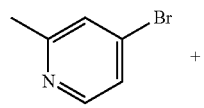

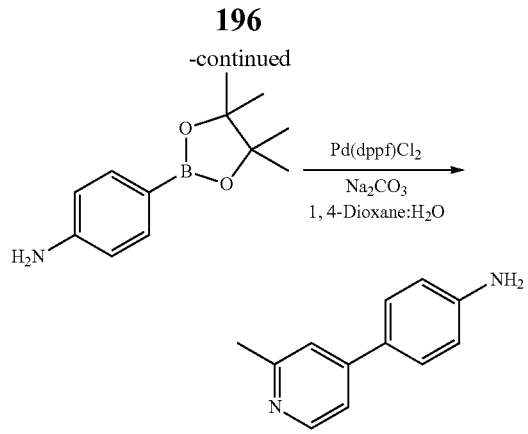

To stirred solution of 4-bromo-2-methylpyridine (2 g, 12.00 mmol) in 1, 4-dioxane (50 mL) and water (12 mL), under an argon atmosphere were added sodium carbonate (3.08 g, 29.00 mmol), 4-(4,4,5,5-tetramethyl-1,3,2-dioxaborolan-2-yl)aniline (3.05 g, 14.00 mmol) and Pd(dppf)Cl$_2$ (0.25 g, 0.3 mmol) at room temperature and purged under an argon atmosphere for 10 minutes. The reaction mixture was stirred at 100° C. for 8 h. After consumption of the starting material (monitored by TLC), the reaction was filtered through celite and the filtrate was concentrated in vacuo. The crude material was purified through silica gel column chromatography using EtOAc to afford 4-(2-methylpyridin-4-yl)aniline (2 g, 92%) as an off-white solid. $^1$H-NMR (DMSO-d$_6$, 400 MHz): δ 8.34 (d, 1H), 7.52 (d, 2H), 7.46 (s, 1H), 7.43 (d, 1H), 6.62 (d, 2H), 5.48 (s, 2H), 2.47 (s, 3H); LCMS: 184.9 [M$^+$+1] at 2.31 RT (98.49%); TLC: 100% EtOAc (R$_f$: 0.3).

Example 2

Synthesis of 3-methoxy-4-(2-methylpyridin-4-yl)aniline

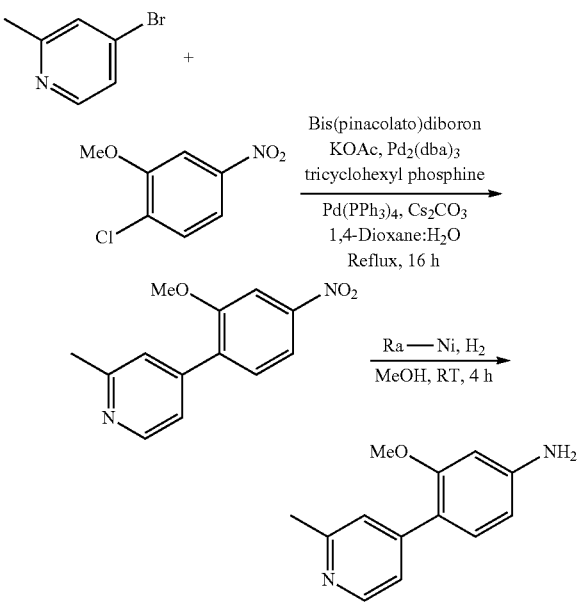

Synthesis of 4-(2-methoxy-4-nitrophenyl)-2-methylpyridine

To a stirred solution of 4-bromo-2-methylpyridine (2.5 g, 14.53 mmol) in 1,4-dioxane (50 mL) under an argon atmosphere were added bis (pinacolato) diborane ester (4.04 g, 15.98 mmol), potassium acetate (2.84 g, 29.06 mmol), tricyclohexylphosphine (0.61 g, 21.81 mmol) and purged for 30 min. To this was added $Pd_2(dba)_3$ (0.66 g, 0.726 mmol) and stirred at reflux for 4 h. After consumption of 4-bromo-2-methylpyridine (monitored by TLC), the reaction mixture was cooled to RT, then added 4-bromo-2-methylpyridine (2.71 g, 14.49 mmol), cesium carbonate (21.2 g, 65.21 mmol), $Pd(PPh_3)_4$ (1.68 g, 14.49 mmol), 1,4-dioxane (50 mL), water (10 mL) and stirred for 30 min. The reaction mixture was heated to reflux and stirred for 16 h. After consumption of 1-chloro-2-methoxy-4-nitrobenzene (monitored by TLC), the reaction was cooled to RT and filtered through celite. The filtrate was concentrated in vacuo to afford the crude product. The crude was purified through silica gel column chromatography to afford 4-(2-methoxy-4-nitrophenyl)-2-methylpyridine (3.0 g, 85%) as a colorless semisolid. $^1$H-NMR (CDCl$_3$, 400 MHz): δ 8.56 (d, 1H), 7.94 (d, 1H), 7.87 (s, 1H), 7.71-7.68 (m, 1H), 7.28 (s, 1H), 7.24-7.21 (m, 1H), 3.94 (s, 3H), 2.62 (s, 3H); Mass (ESI): 245 [M+1], 279 [M+Na]; TLC: 30% EtOAc:hexane (R$_f$: 0.9).

Synthesis of 3-methoxy-4-(2-methylpyridin-4-yl) aniline

To a stirred solution of 4-(2-methoxy-4-nitrophenyl)-2-methylpyridine (3.0 g, 12.29 mmol) in MeOH (50 mL) was added Raney Ni (500 mg) under an argon atmosphere and stirred at room temperature for 4 h under H$_2$ atmosphere (balloon pressure). After consumption of the starting material (monitored by TLC), the reaction was filtered through celite and the filtrate was concentrated in vacuo to afford 3-methoxy-4-(2-methylpyridin-4-yl) aniline (2.0 g, 76%) used without further purification. $^1$H-NMR (DMSO-d$_6$, 400 MHz): δ 8.32 (d, 1H), 7.28 (s, 1H), 7.24-7.21 (m, 1H), 7.12-7.08 (m, 1H), 6.24 (s, 1H), 6.24 (d, 1H), 5.42 (br s, 2H), 3.74 (s, 3H), 2.43 (s, 3H); Mass (ESI): 215 [M+1]; TLC: 100% EtOAc (R$_f$: 0.4).

Example 3

Synthesis of 3-fluoro-4-(2-methylpyridin-4-yl) aniline

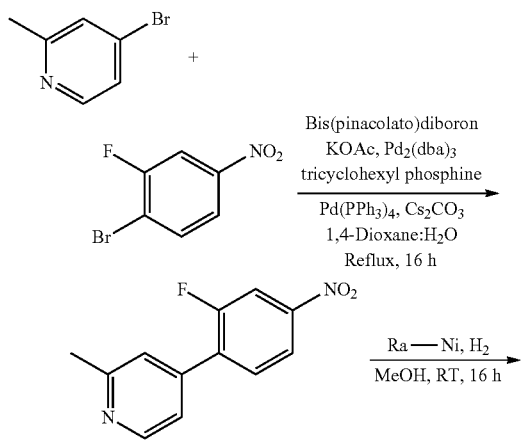

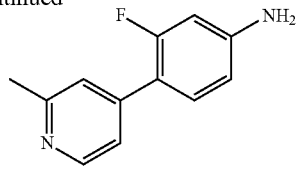

Synthesis of 4-(2-fluoro-4-nitrophenyl)-2-methylpyridine

To a stirred solution of 4-bromo-2-methylpyridine (3 g, 17.44 mmol) in 1,4-dioxane (150 mL) under an argon atmosphere were added Bis (pinacolato) diboron (4.87 g, 19.18 mmol), tricyclohexyl phosphine (732 mg, 2.61 mmol), potassium acetate (3.4 g, 34.88 mmol), Pd$_2$(dba)$_3$ (798 mg, 0.87 mmol). The reaction was purged under an argon atmosphere for 10 min at room temperature, heated to 100° C. and stirred for 3 h. After the disappearance of 4-bromo-2-methylpyridine (monitored by TLC) the reaction mixture was cooled to room temperature, 1-bromo-2-fluoro-4-nitrobenzene (3.8 g, 17.43 mmol), cesium carbonate (25.49 g, 78.43 mmol) and Pd(PPh$_3$)$_4$ (2.01 g, 1.74 mmol) were added and refluxed for 16 h. After consumption of 1-bromo-2-fluoro-4-nitrobenzene (monitored by TLC), the volatile components were evaporated in vacuo to afford the crude material which was purified through silica gel column chromatography (20% EtOAc:hexanes) to afford 4-(2-fluoro-4-nitrophenyl)-2-methylpyridine (2.4 g, 59%) as a pale yellow solid. $^1$H-NMR (DMSO-d$_6$, 500 MHz): δ 8.60 (d, 1H), 8.29-8.26 (m, 1H), 8.20-8.18 (m, 1H), 7.91 (t, 1H), 7.51 (s, 1H), 7.44 (d, 1H), 2.56 (s, 3H); LC-MS: 232.9 (M+1); (column; X-Bridge C-18 (50×3.0 mm, 3.5 μm); RT 2.28 min. 0.05% aq TFA: ACN; 0.80 mL/min); TLC: 40% EtOAc:hexanes (R$_f$: 0.2).

Synthesis of 3-fluoro-4-(2-methylpyridin-4-yl) aniline

To a stirred solution of 4-(2-fluoro-4-nitrophenyl)-2-methylpyridine (2.4 g, 10.33 mmol) in MeOH (45 mL) under an argon atmosphere was added Raney nickel (300 mg) at room temperature and stirred for 4 h under a hydrogen atmosphere (balloon pressure). After consumption of the starting material (monitored by TLC), the reaction was filtered through celite and the filtrate was concentrated in vacuo to afford 3-fluoro-4-(2-methylpyridin-4-yl) aniline (1.8 g, 86%) as a pale red solid. $^1$H-NMR (DMSO-d$_6$, 500 MHz): δ 8.38 (d, 1H), 7.31-7.28 (m, 2H), 7.24-7.23 (m, 1H), 6.48 (d, 1H), 6.45-6.38 (m, 1H), 5.75 (s, 2H), 2.47 (s, 3H); LC-MS: 203 (M+1); (column; X-Bridge C-18 (50×3.0 mm, 3.5 μm); RT 1.88 min. 0.05% aq TFA: ACN; 0.80 mL/min); TLC: 40% EtOAc:hexanes (R$_f$: 0.3).

Example 4

Synthesis of 4-(4-methyl-1H-imidazol-1-yl) aniline

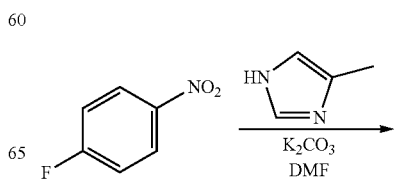

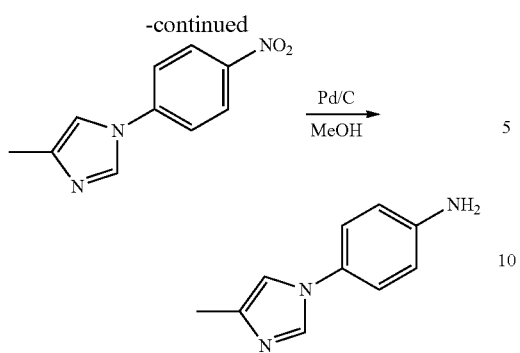

Synthesis of 4-methyl-1-(4-nitrophenyl)-1H-imidazole

To a stirred solution of 1-fluoro-4-nitrobenzene (2.0 g, 14.18 mmol) in DMF (50 mL) under an argon atmosphere were added 4-methyl-1H-imidazole (1.16 g, 14.18 mmol) and $K_2CO_3$ (1.95 g, 14.18 mmol) at RT. The reaction mixture was stirred at 110° C. for 12 h. After consumption of the starting materials (monitored by TLC), the reaction was diluted with water (50 mL) and filtered to afford a solid which was washed with hexane and dried in vacuo to afford 4-methyl-1-(4-nitrophenyl)-1H-imidazole (1.7 g, 59%) as a brown solid. $^1$H-NMR (DMSO-$d_6$, 400 MHz): δ 8.39 (s, 1H), 8.34-8.32 (m, 2H), 7.94 (d, 2H), 7.67 (s, 1H), 2.16 (s, 3H); Mass (ESI): 204 [M+1]; TLC: 100% EtOAc ($R_f$: 0.3).

Synthesis of 4-(4-methyl-M-imidazol-1-yl) aniline

To a stirred solution of 4-methyl-1-(4-nitrophenyl)-1H-imidazole (1.7 g, 8.37 mmol) in MeOH (50 mL) under an argon atmosphere was added 10% Pd/C (0.3 g) and stirred at RT for 16 h under $H_2$ atmosphere (balloon pressure). The reaction was filtered through celite, washed with MeOH (15 mL), and concentrated in vacuo to afford 4-(4-methyl-1H-imidazol-1-yl) aniline (1.2 g, 83%) as a brown solid used without further purification. $^1$H-NMR (DMSO-$d_6$, 500 MHz): δ 7.81 (s, 1H), 7.21-7.18 (m, 3H), 6.62 (d, 2H), 5.23 (br, s, 2H), 2.14 (s, 3H); Mass (ESI): 174 [M+1]; TLC: 10% MeOH:$CH_2Cl_2$ ($R_f$ 0.4).

Example 5

Synthesis of 3-methoxy-4-(4-methyl-1H-imidazol-1-yl)aniline

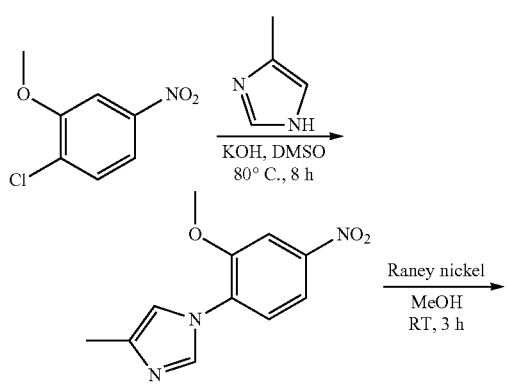

Synthesis of 1-(2-Methoxy-4-nitrophenyl)-4-methyl-1H-imidazole

To a stirred solution of 2-chloro-5-nitroanisole (3 g, 16.0 mmol) in DMSO (15 mL) under an argon atmosphere were added 4-methyl imidazole (5.2 g, 64.0 mmol), KOH (1.34 g, 24.0 mmol) at RT. The reaction mixture was stirred at 80° C. for 8 h. After the completion of the starting material (monitored by TLC), the reaction was diluted with water (50 mL) to afford the solid which was filtered and dried in vacuo to afford 1-(2-Methoxy-4-nitrophenyl)-4-methyl-1H-imidazole (3.2 g, 85%) as a yellow solid. $^1$H-NMR (DMSO-$d_6$, 400 MHz): δ 7.98-7.95 (m, 3H), 7.72-7.67 (m, 1H), 7.28 (s, 1H), 3.98 (s, 3H), 2.16 (s, 3H); TLC: 100% EtOAc ($R_f$: 0.3).

Synthesis of 3-methoxy-4-(4-methyl-1H-imidazol-1-yl)aniline

To a stirred solution of 1-(2-Methoxy-4-nitrophenyl)-4-methyl-1H-imidazole (3.2 g, 13.7 mmol) in MeOH (40 mL) was added Raney-Ni (510 mg) under an argon atmosphere and stirred at room temperature for 3 h under $H_2$ atmosphere (balloon pressure). After consumption of the starting material (monitored by TLC), the reaction was filtered through celite, washed with methanol (20 mL) and the filtrate was concentrated in vacuo to afford 3-methoxy-4-(4-methyl-1H-imidazol-1-yl)aniline (1.8 g, 64%) as a yellow solid. $^1$H-NMR (DMSO-$d_6$, 500 MHz): δ 7.43 (s, 1H), 6.94 (d, 1H), 6.89 (s, 1H), 6.34 (s, 1H), 6.18 (d, 1H), 5.34 (s, 2H), 3.72 (s, 3H), 2.13 (s, 3H). TLC: 10% MeOH:DCM ($R_f$: 0.5).

Example 6

Synthesis of 4-(4-chloro-1H-imidazol-1-yl)-3-methoxyaniline

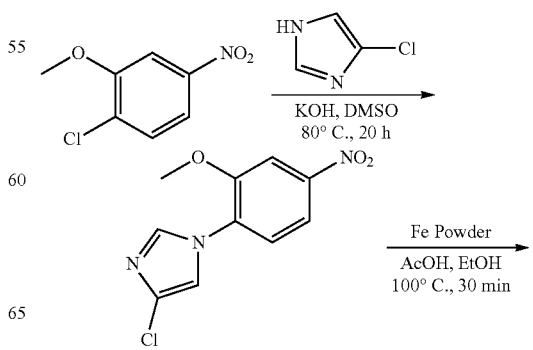

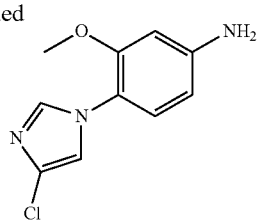

Synthesis of 4-chloro-1-(2-methoxy-4-nitrophenyl)-1H-imidazole

To a stirred solution of 1-chloro-2-methoxy-4-nitrobenzene (4 g, 39.21 mmol) in DMSO (40 mL) under an argon atmosphere were added 4-chloro-1H-imidazole (7.3 g, 39.21 mmol) and potassium hydroxide (2.2 g, 39.21 mmol) at RT. The reaction mixture was stirred at 80° C. for 20 h. After consumption of the starting material (monitored by TLC), the reaction was diluted with water (600 mL), filtered, washed with water (2×50 mL) and dried in vacuo to afford 4-chloro-1-(2-methoxy-4-nitrophenyl)-1H-imidazole (3.8 g, 70%) as a brown solid which was used without further purification. $^1$H-NMR (CDCl$_3$, 400 MHz): δ 7.98-7.94 (m, 2H), 7.75 (s, 1H), 7.44 (d, 1H), 7.19 (s, 1H), 4.01 (s, 3H); LC-MS: 254.1 (M+1); (column; X-Bridge C-18 (50×3.0 mm, 3.5 μm); RT 3.05 min. 0.05% aq TFA: ACN; 0.80 mL/min); TLC: 30% EtOAc:hexanes (R$_f$: 0.5).

Synthesis of 4-(4-chloro-1H-imidazol-1-yl)-3-methoxyaniline

To a stirred solution of 4-chloro-1-(2-methoxy-4-nitrophenyl)-1H-imidazole (3.8 g, 15.01 mmol) in EtOH (80 mL) under an argon atmosphere were added Fe powder (3.4 g, 63.24 mmol) and AcOH (40 mL) at RT. The reaction mixture was stirred at 100° C. for 30 min. After consumption of the starting material (monitored by TLC), the reaction was basified with a 1 N NaOH solution to pH 8 and extracted with EtOAc (2×100 mL). The combined organic extracts were dried over sodium sulfate, filtered and concentrated in vacuo to afford 4-(4-chloro-1H-imidazol-1-yl)-3-methoxyaniline (3 g, 89%) as an off-white solid.

$^1$H-NMR (DMSO-d$_6$, 400 MHz): δ 7.62 (s, 1H), 7.31 (s, 1H), 6.98 (d, 1H), 6.36 (s, 1H), 6.18 (d, 1H), 5.45 (br s, 2H), 3.69 (s, 3H); LC-MS: 224.3 (M+1); (column; X-Bridge C-18 (50×3.0 mm, 3.5 μm); RT 2.25 min. 0.05% aq TFA: ACN; 0.80 mL/min); TLC: 50% EtOAc:hexanes (R$_f$: 0.2).

Example 7

Synthesis of 3-fluoro-4-(4-methyl-1H-imidazol-1-yl) aniline

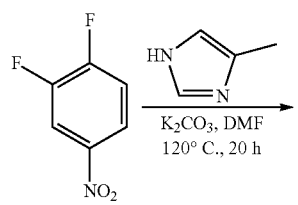

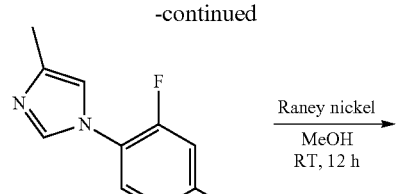

Synthesis of 1-(2-fluoro-4-nitrophenyl)-4-methyl-1H-imidazole

To a stirred solution of 1, 2-difluoro-4-nitrobenzene (5 g, 31.44 mmol) in DMF (50 mL) under an argon atmosphere were added 4-methyl-1H-imidazole (3.09 g, 37.73 mmol) and potassium carbonate (5.2 g, 37.73 mmol) at room temperature. The reaction mixture was stirred at 120° C. for 20 h. After consumption of the starting material (monitored by TLC), the reaction was filtered through celite and the filtrate was concentrated in vacuo. The residue was diluted with water (200 mL) and extracted with EtOAc (2×100 mL). The combined organic extracts were dried over sodium sulfate, filtered and concentrated in vacuo. The crude material was purified through silica gel column chromatography using 30% EtOAc:hexanes to afford 1-(2-fluoro-4-nitrophenyl)-4-methyl-1H-imidazole (2.5 g, 36%) as a pale yellow solid. $^1$H-NMR (DMSO-d$_6$, 500 MHz): δ 8.19-8.15 (m, 2H), 7.87-7.86 (m, 1H), 7.59-7.55 (m, 1H), 7.07 (s, 1H), 2.32 (s, 3H); LC-MS: 222.1 (M+1); (column; X-Bridge C-18 (50× 3.0 mm, 3.5 μm); RT 3.11 min. 5 mM NH$_4$OAc: ACN; 0.80 mL/min); TLC: EtOAc (R$_f$: 0.5).

Synthesis of 3-fluoro-4-(4-methyl-M-imidazol-1-yl) aniline

To a stirred solution of 1-(2-fluoro-4-nitrophenyl)-4-methyl-1H-imidazole (2.5 g, 11.31 mmol) in MeOH (30 mL) under an argon atmosphere at RT, Raney nickel (300 mg) was added and stirred under H$_2$ atmosphere (balloon pressure) for 12 h. After consumption of the starting material (monitored by TLC), the reaction was filtered through celite and the filtrate was concentrated in vacuo to afford 3-fluoro-4-(4-methyl-1H-imidazol-1-yl) aniline (2 g) as a brown solid which was used without further purification. $^1$H-NMR (DMSO-d$_6$, 500 MHz): δ 7.62 (s, 1H), 7.12 (t, 1H), 7.00 (s, 1H), 6.50-6.47 (m, 1H), 6.43 (d, 1H), 5.63 (s, 2H), 2.13 (s, 3H); LC-MS: 192.1 (M+1); (column; X-Bridge C-18 (50× 3.0 mm, 3.5 μm); RT 3.26 min. 5 mM NH$_4$OAc: ACN; 0.80 mL/min) TLC: EtOAc (R$_f$: 0.5).

Example 8

Synthesis of 2-chloro-8-methyl-7-phenyl-7,8-dihydro-6H-pyrimido[5,4-b][1,4]oxazine

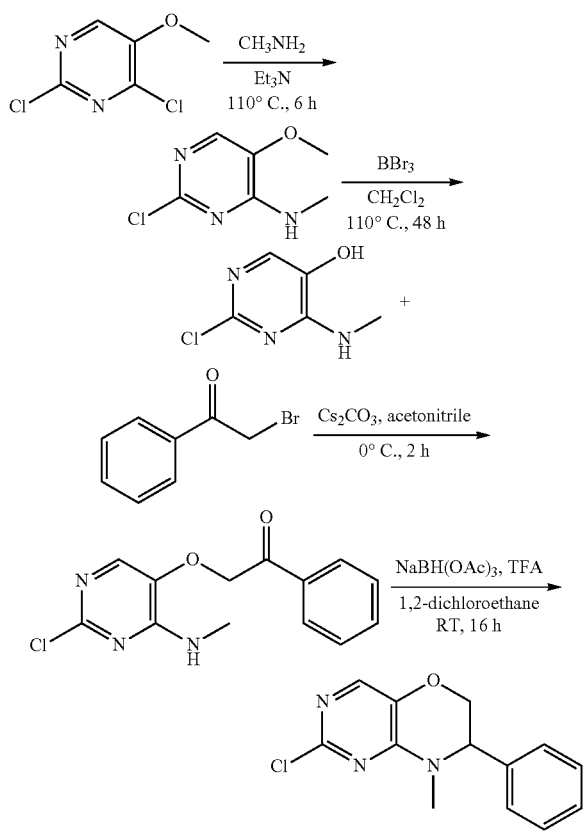

Synthesis of 2-chloro-5-methoxy-N-methylpyrimidin-4-amine

To a stirred solution of 2,4-dichloro-5-methoxypyrimidine (5 g, 28.0 mmol) in triethylamine (7.8 mL) under an argon atmosphere was added methyl amine (33% in ethanol, 3.9 mL, 42.1 mmol) in a sealed tube at RT and heated to 110° C. for 6 h. After consumption of the starting material (monitored by TLC), the reaction was diluted with water. The obtained solid was filtered, washed with cold water and dried to afford 2-chloro-5-methoxy-N-methylpyrimidin-4-amine (3.85 g, 79%) as a white crystalline solid. LC-MS: 173.8 (M+1); (column; X-Select CSH C-18 (50×3.0 mm, 3.5 µm); RT 1.51 min. 0.05% Aq TFA: ACN; 0.80 ml/min); TLC: 80% EtOAc:hexanes ($R_f$: 0.3).

Synthesis of 2-chloro-4-(methylamino) pyrimidin-5-ol

To a stirred solution of 2-chloro-5-methoxy-N-methylpyrimidin-4-amine (6 g, 34.68 mmol) in $CH_2Cl_2$ (600 mL) under an argon atmosphere at 0° C. was added 1M $BBr_3$ in $CH_2Cl_2$ (49.2 mL, 520 mmol). The reaction mixture was warmed to RT and stirred for 48 h. After consumption of the starting material (monitored by TLC), the reaction was quenched with methanol (100 mL) and concentrated in vacuo. To the resultant residue a saturated sodium bicarbonate solution (100 mL) was added and extracted with EtOAc (3×200 mL). The combined organic extracts were dried over sodium sulfate, filtered and concentrated in vacuo to afford 2-chloro-4-(methylamino) pyrimidin-5-ol (5 g, 92%) as an off-white solid which was used without further purification. $^1$H-NMR (DMSO-$d_6$, 400 MHz): δ 10.2 (brs, 1H), 7.39 (s, 1H), 7.21 (br s, 1H), 2.80 (s, 3H); LC-MS: 159.8 (M+1); (column; X-Select CSH C-18 (50×3.0 mm, 3.5 µm); RT 0.93 min. 0.05% Aq TFA: ACN; 0.80 ml/min); TLC: 90% EtOAc:hexanes ($R_f$: 0.3).

Synthesis of 2-((2-chloro-4-(methylamino) pyrimidin-5-yl) oxy)-1-phenylethan-1-one To a stirred solution of 2-chloro-4-(methylamino) pyrimidin-5-ol (2.0 g, 12.57 mmol) in acetonitrile (35 mL) under an argon atmosphere at 0° C. were added cesium carbonate (8.2 g, 25.14 mmol) and 2-bromo-1-phenylethan-1-one (2.75 g, 13.8 mmol) and stirred for 2 h. After completion of the reaction (monitored by TLC), the reaction was diluted with water (100 mL) and extracted with EtOAc (2×150 mL). The combined organic extracts were dried over sodium sulfate, filtered and concentrated in vacuo. The crude material was purified by silica gel column chromatography using 20-30% EtOAc:hexanes to afford 2-((2-chloro-4-(methylamino) pyrimidin-5-yl) oxy)-1-phenylethan-1-one (2.3 g, 66%) as an off-white solid. $^1$H-NMR (DMSO-$d_6$, 400 MHz): δ 7.81 (s, 1H), 7.41-7.36 (m, 5H), 7.09 (s, 1H), 4.13 (d, 1H), 4.00 (d, 1H), 2.78 (s, 3H); LC-MS: 277.9 (M+1); (column; X-Bridge C-18 (50×3.0 mm, 3.5 µm); RT 3.25 min. 0.05% TFA in water: ACN; 0.80 ml/min); TLC: 80% EtOAc:hexanes ($R_f$: 0.5).

Synthesis of 2-chloro-7-(3, 5-difluorophenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-phenylethan-1-one (2.0 g, 7.22 mmol) in 1, 2-dichloroethane (40 mL) under an argon atmosphere were added $NaBH(OAc)_3$ (3.06 g, 14.44 mmol) and trifluoroacetic acid (0.55 mL, 7.22 mmol) at RT and stirred for 16 h. After completion of the reaction (monitored by TLC), the mixture was diluted with a 1N sodium hydroxide solution (50 mL) and extracted with $CH_2Cl_2$ (2×75 mL). The combined organic extracts were dried over sodium sulfate, filtered and concentrated in vacuo. The crude material was purified by silica gel column chromatography using 20-30% EtOAc:hexanes to afford 2-chloro-7-(phenyl)-8-methyl-7, 8-dihydro-6H-pyrimido [5, 4-b] [1, 4] oxazine. $^1$H-NMR (CDCl$_3$, 500 MHz): δ 7.70 (s, 1H), 7.40-7.36 (m, 3H), 7.19 (d, 2H), 4.60-4.58 (m, 1H), 4.23 (d, 1H), 4.19 (d, 1H), 3.08 (s, 3H); LC-MS: 262.3 (M+1); (column; X-Bridge C-18 (50×3.0 mm, 3.5 µm); RT 4.02 min. 0.05% Aq TFA: ACN; 0.80 ml/min); TLC: 60% EtOAc:hexanes ($R_f$: 0.4).

Example 9

Synthesis of 2-chloro-7-(3, 5-difluorophenyl)-8-methyl-7, 8-dihydro-6H-pyrimido [5, 4-b] [1, 4] oxazine

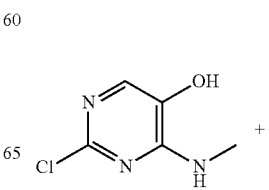

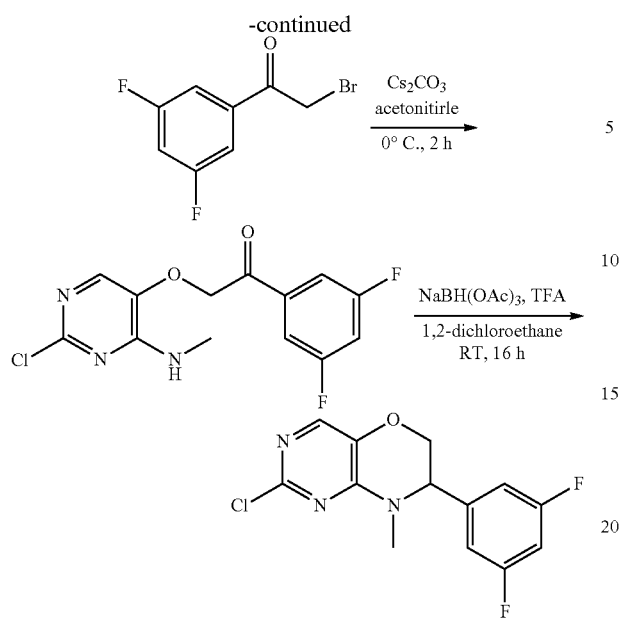

Synthesis of 2-((2-chloro-4-(methylamino) pyrimidin-5-yl) oxy)-1-(3, 5-difluorophenyl) ethan-1-one To a stirred solution of 2-chloro-4-(methylamino) pyrimidin-5-ol (400 mg, 2.51 mmol) in acetonitrile (8 mL) under an argon atmosphere at 0° C. was added cesium carbonate (1.64 g, 5.02 mmol) and 2-bromo-1-(3, 5-difluorophenyl) ethan-1-one (650 mg, 2.76 mmol) and stirred for 2 h. After completion of the reaction (monitored by TLC), the mixture was diluted with water (100 mL) and extracted with EtOAc (2×100 mL). The combined organic extracts were dried over sodium sulfate, filtered and concentrated in vacuo. The crude material was purified by silica gel column chromatography using 20-30% EtOAc:hexanes to afford 2-((2-chloro-4-(methylamino) pyrimidin-5-yl) oxy)-1-(3, 5-difluorophenyl) ethan-1-one (420 mg, 54%) as an off-white solid. $^1$H-NMR (DMSO-$d_6$, 500 MHz): δ 7.83 (s, 1H), 7.30-7.27 (m, 2H), 7.19-7.17 (m, 2H), 4.20 (d, 1H), 4.00 (d, 1H), 2.78 (s, 3H). LC-MS: 314.3 (M+1); (column; X-Bridge C-18 (50×3.0 mm, 3.5 μm); RT 4.17 min. 0.05% Aq TFA: ACN; 0.80 ml/min); TLC: 60% EtOAc:hexanes ($R_f$: 0.5).

Synthesis of 2-chloro-7-(3, 5-difluorophenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(3, 5-difluorophenyl) ethan-1-one (500 mg, 1.59 mmol) in 1, 2-dichloroethane (10 mL) under an argon atmosphere was added NaBH(OAc)$_3$ (684 mg, 3.18 mmol) and trifluoroacetic acid (0.122 mL, 1.59 mmol) at RT and stirred for 16 h. After consumption of the starting material (monitored by TLC), the mixture was diluted with a 1N sodium hydroxide solution (50 mL) and extracted with CH$_2$Cl$_2$ (2×100 mL). The combined organic extracts were dried over sodium sulfate, filtered and concentrated in vacuo to afford 2-chloro-7-(3, 5-difluorophenyl)-8-methyl-7, 8-dihydro-6H-pyrimido [5, 4-b] [1, 4] oxazine (370 mg, 78%) as a pale yellow solid. $^1$H-NMR (CDCl$_3$, 400 MHz): δ 7.71 (s, 1H), 6.81 (t, 1H), 6.70 (d, 2H), 4.55-4.54 (m, 1H), 4.25-4.19 (m, 2H), 3.10 (s, 3H); LC-MS: 298 (M+1); (column; X-Select CSH C-18 (50×3.0 mm, 3.5 μm); RT 4.13 min. 0.05% Aq TFA: ACN; 0.80 ml/min); TLC: 60% EtOAc:hexanes ($R_f$: 0.4).

Example 10

Synthesis of 2-chloro-8-methyl-7-(3, 4, 5-trifluorophenyl)-7, 8-dihydro-6H-pyrimido [5, 4-b] [1, 4] oxazine

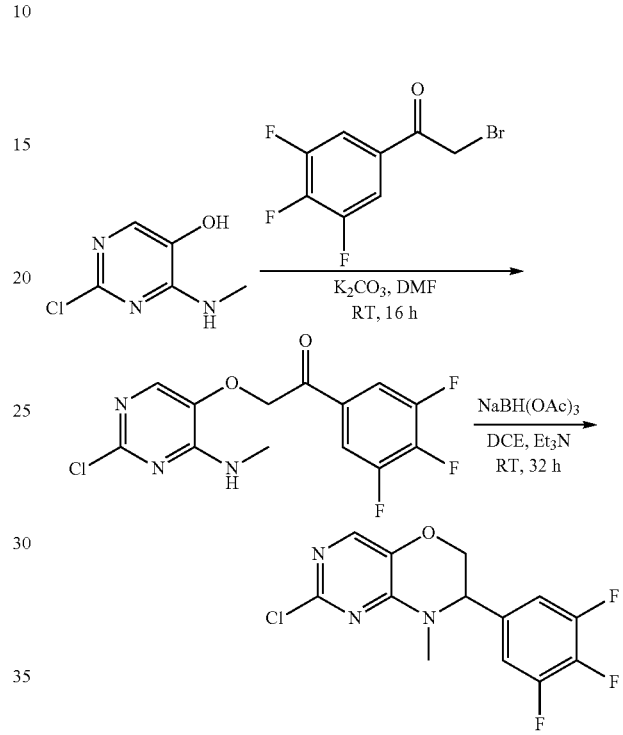

Synthesis of 2-((2-chloro-4-(methylamino) pyrimidin-5-yl) oxy)-1-(3, 4, 5-trifluorophenyl) ethan-1-one To a stirred solution of 2-chloro-4-(methylamino) pyrimidin-5-ol (630 mg, 3.95 mmol) in DMF (5 mL) under an argon atmosphere at 0° C. were added K$_2$CO$_3$ (1.4 g, 4.13 mmol) and 2-bromo-1-(3, 4, 5-trifluorophenyl) ethan-1-one (1.1 g, 4.3 mmol) and stirred for 2 h. After completion of the reaction (monitored by TLC), the reaction was diluted with water (50 mL) and extracted with EtOAc (2×50 mL). The combined organic extracts were washed with water (50 mL), dried over sodium sulfate, filtered and concentrated in vacuo. The crude material was purified by silica gel column chromatography using 15% EtOAc:hexanes to afford 2-((2-chloro-4-(methylamino) pyrimidin-5-yl) oxy)-1-(3, 4, 5-trifluorophenyl) ethan-1-one (430 mg, 66%) as an off-white solid. $^1$H-NMR (DMSO-$d_6$, 400 MHz): δ 7.82 (s, 1H), 7.42-7.35 (m, 2H), 7.30 (s, 1H), 4.20 (d, 1H), 4.01 (d, 1H), 2.70 (s, 3H); TLC: 30% EtOAc:hexanes ($R_f$: 0.5).

Synthesis of 2-chloro-8-methyl-7-(3, 4, 5-trifluorophenyl)-7, 8-dihydro-6H-pyrimido [5, 4-b] [1, 4] oxazine To a stirred solution of 2-((2-chloro-4-(methylamino) pyrimidin-5-yl) oxy)-1-(3, 4, 5-trifluorophenyl) ethan-1-one (480 mg, 1.45 mmol) in 1,2-dichloroethane (8 mL) under an argon atmosphere were added NaBH(OAc)₃ (614 mg, 2.90 mmol) and trifluoroacetic acid (0.11 mL, 1.45 mmol) at 0° C. The reaction mixture was warmed to RT and stirred for 32 h. After consumption of the starting material (monitored by TLC), the reaction was quenched with a 1N sodium hydroxide solution (20 mL) and extracted with CH₂Cl₂ (2×20 mL). The combined organic extracts were dried over sodium sulfate, filtered and concentrated in vacuo. The crude material was washed with ether (2×10 mL) to afford 2-chloro-8-methyl-7-(3, 4, 5-trifluorophenyl)-7, 8-dihydro-6H-pyrimido [5, 4-b] [1, 4] oxazine (300 mg, 66%) as an off-white solid. ¹H-NMR (CDCl₃, 400 MHz): δ 7.74 (s, 1H), 6.84-6.80 (m, 2H), 4.52-4.51 (m, 1H), 4.25-4.16 (m, 2H), 3.12 (s, 3H); LC-MS: 316.2 (M+1); (column; X-Select CSH C-18 (50×3.0 mm, 3.5 μm); RT 4.31 min. 0.05% Aq TFA: ACN; 0.80 ml/min); TLC: 30% EtOAc:hexanes (R$_f$: 0.3).

Example 11

Synthesis of 2-chloro-8-methyl-7-(o-tolyl)-7,8-dihydro-6H-pyrimido[5,4-b][1,4]oxazine

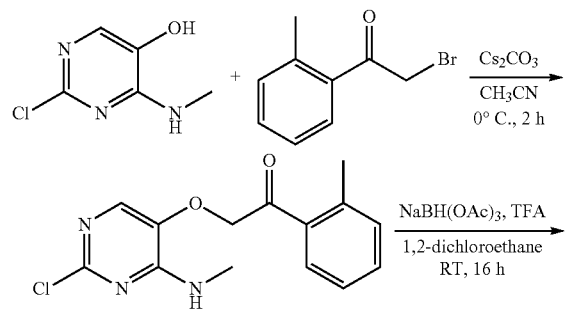

Synthesis of 2-((2-chloro-4-(methylamino) pyrimidin-5-yl) oxy)-1-(o-tolyl) ethan-1-one To a stirred solution of 2-chloro-4-(methylamino) pyrimidin-5-ol (100 mg, 0.62 mmol) in CH₃CN (2 mL) under an argon atmosphere at 0° C. were added cesium carbonate (409 mg, 1.25 mmol) and 2-bromo-1-(o-tolyl) ethan-1-one (120 mg, 0.69 mmol) and stirred for 2 h. After consumption of the starting material (monitored by TLC), the mixture was diluted with a saturated sodium bicarbonate solution (20 mL) and extracted with EtOAc (2×50 mL). The combined organic extracts were dried over sodium sulfate, filtered and concentrated in vacuo. The crude material was purified by silica gel column chromatography using 20-50% EtOAc: hexanes to afford 2-((2-chloro-4-(methylamino) pyrimidin-5-yl) oxy)-1-(o-tolyl) ethan-1-one (120 mg, 66%) as an off-white solid. ¹H-NMR (DMSO-d₆, 400 MHz): δ 7.87 (s, 1H), 7.52 (d, 1H), 7.30-7.19 (m, 3H), 7.08 (s, 1H), 4.25 (d, 1H), 3.95 (d, 1H), 2.79 (s, 3H), 2.30 (s, 3H); TLC: 60% EtOAc:hexanes (R$_f$: 0.4).

Synthesis of 2-chloro-8-methyl-7-(o-tolyl)-7, 8-dihydro-6H-pyrimido [5, 4-b] [1, 4] oxazine To a stirred solution of 2-((2-chloro-4-(methylamino) pyrimidin-5-yl) oxy)-1-(o-tolyl) ethan-1-one (1 g, 3.43 mmol) in 1, 2-dichloroethane (20 mL) under an argon atmosphere were added NaBH(OAc)₃ (1.45 g, 6.87 mmol) and trifluoroacetic acid (0.26 mL, 3.43 mmol) at RT and stirred for 16 h. After completion of reaction (monitored by TLC), the mixture was diluted with a 1N sodium hydroxide solution (100 mL) and extracted with CH₂Cl₂ (2×100 mL). The combined organic extracts were dried over sodium sulfate, filtered and concentrated in vacuo. The crude material was purified by silica gel column chromatography using 10-20% EtOAc:hexanes to afford 2-chloro-8-methyl-7-(o-tolyl)-7, 8-dihydro-6H-pyrimido [5, 4-b] [1, 4] oxazine (700 mg, 74%) as a pale yellow solid. ¹H-NMR (CDCl₃, 400 MHz): δ 7.80 (s, 1H), 7.25-7.19 (m, 3H), 6.97 (d, 1H), 4.88-4.86 (m, 1H), 4.27-4.23 (m, 1H), 4.12-4.09 (m, 1H), 3.03 (s, 3H), 2.40 (s, 3H); LC-MS: 276.3 (M+1); (column; X-Bridge C-18 (50×3.0 mm, 3.5 μm); RT 4.28 min. 0.05% Aq TFA:ACN; 0.80 ml/min); TLC: 60% EtOAc:hexanes (R$_f$: 0.5).

Example 12

Synthesis of 2-chloro-7-(4-fluorophenyl)-8-methyl-7, 8-dihydro-6H-pyrimido [5, 4-b] [1, 4] oxazine

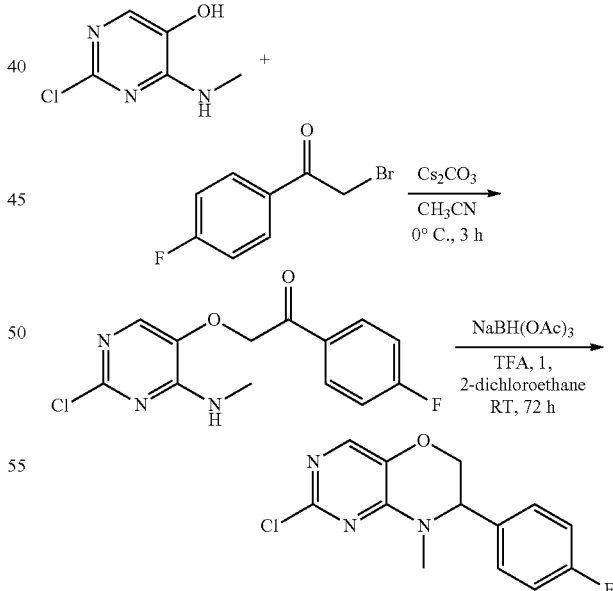

Synthesis of 2-((2-chloro-4-(methylamino) pyrimidin-5-yl) oxy)-1-(4-fluorophenyl) ethan-1-one To a stirred solution of 2-chloro-4-(methylamino) pyrimidin-5-ol (1.5 g, 9.43 mmol) in CH₃CN (20 mL) was added cesium carbonate (6.1 g, 18.86 mmol) and stirred for 10 min at 0° C. 2-Bromo-1-(4-fluorophenyl) ethan-1-one (2.25 g, 10.37 mmol) was added and the reaction mixture was stirred for 3 h. After consumption of the starting material (monitored by TLC), the mixture was diluted with water (30 mL) and extracted with EtOAc (2×30 mL). The combined organic layers were washed with water (30 mL), dried over sodium sulfate, filtered and concentrated in vacuo. The residue was washed with ether: n-hexane (1:1, 2×5 mL) to afford 2-((2-chloro-4-(methylamino) pyrimidin-5-yl) oxy)-1-(4-fluorophenyl) ethan-1-one (2 g, 71%) as an off-white solid. TLC: 40% EtOAc/hexanes ($R_f$: 0.6).

Synthesis of 2-chloro-7-(4-fluorophenyl)-8-methyl-7,8-dihydro-6H-pyrimido [5, 4-b] [1, 4] oxazine To a stirred solution of 2-((2-chloro-4-(methylamino) pyrimidin-5-yl) oxy)-1-(4-fluorophenyl) ethan-1-one (2 g, 6.75 mmol) in 1, 2-dichloroethane (20 mL) was added trifluoroacetic acid (770 mg, 6.75 mmol) and stirred for 10 min. Sodium triacetoxyborohydride (2.86 g, 13.51 mmol) was added and the reaction mixture was stirred for 72 h. After consumption of the starting material (monitored by TLC), the reaction was quenched with a 1N sodium hydroxide solution (30 mL) and extracted with $CH_2Cl_2$ (2×30 mL). The combined organic extracts were dried over sodium sulfate, filtered and concentrated in vacuo. The crude material was purified by silica gel column chromatography using 20% EtOAc:hexanes to afford 2-chloro-7-(4-fluorophenyl)-8-methyl-7, 8-dihydro-6H-pyrimido [5, 4-b] [1, 4] oxazine (1.8 g, 96%) as a pale yellow oil. $^1$H-NMR ($CDCl_3$, 400 MHz): δ 7.70 (s, 1H), 7.18-7.02 (m, 4H), 4.53-4.51 (m, 1H), 4.22-4.20 (m, 1H), 4.12-4.08 (m, 1H), 3.08 (s, 3H); LC-MS: 279.8 (M+1); (column; X-Select CSH C-18 (50×3.0 mm, 3.5 µm); RT 3.53 min. 0.05% Aq TFA: ACN; 0.8 mL/min); TLC: 40% EtOAc:hexanes ($R_f$: 0.6).

Example 13

Synthesis of 7-benzyl-2-chloro-8-methyl-7,8-dihydro-6H-pyrimido [5, 4-b] [1, 4] oxazine

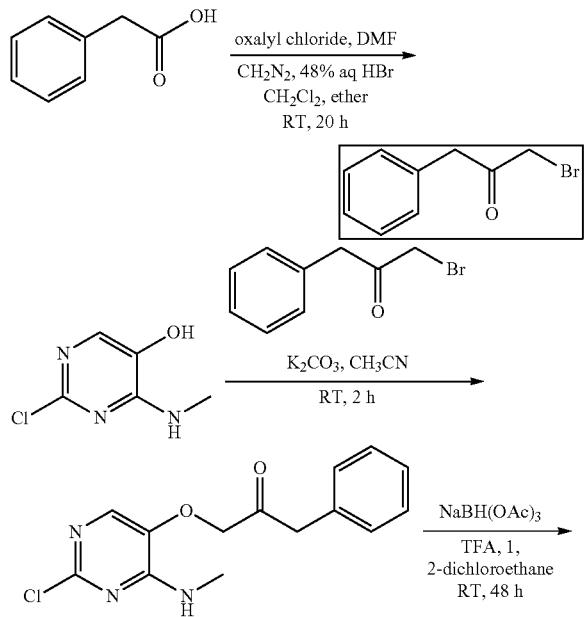

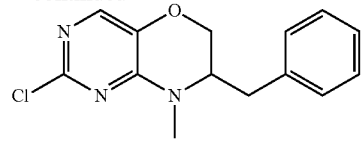

Synthesis of 1-bromo-3-phenylpropan-2-one

To a stirred solution of 2-phenylacetic acid (5 g, 36.76 mmol) in $CH_2Cl_2$ (50 mL) was added oxalyl chloride (4.6 g, 36.76 mmol) and DMF (2 drops) at 0° C. The reaction mixture was warmed to room temperature and continued to stir for 2 h. After consumption of acid (monitored by TLC), the mixture was concentrated in vacuo. The crude material was dissolved in ether and cooled to 0° C. A solution of $CH_2N_2$ in ether was added and the reaction mixture was warmed to room temperature and stirred for 2 h. After consumption of the starting material (monitored by TLC), the mixture was concentrated in vacuo. To a stirred solution of the crude material in THF (20 mL) was added a solution of 48% aq HBr (5 mL) at 0° C. The reaction mixture was warmed to room temperature and stirred for 16 h. After consumption of the starting material (monitored by TLC), the reaction was quenched with a sodium bicarbonate solution (100 mL) and extracted with EtOAc (2×100 mL). The combined organic extracts were washed successively with a sodium bicarbonate solution (50 mL) and water (50 mL). The organic layer was dried over sodium sulfate, filtered and concentrated in vacuo to afford 1-bromo-3-phenylpropan-2-one (6 g, 76%) as a viscous oil.
$^1$H-NMR ($CDCl_3$, 400 MHz): δ 7.38-7.30 (m, 3H), 7.27-7.20 (m, 2H), 3.92 (s, 2H), 3.89 (s, 2H); TLC: 10% EtOAc: hexanes ($R_f$: 0.6).

Synthesis of 1-((2-chloro-4-(methylamino) pyrimidin-5-yl) oxy)-3-phenylpropan-2-one To a stirred solution of 2-chloro-4-(methylamino) pyrimidin-5-ol (3 g, 18.8 mmol) in acetonitrile (30 mL) was added potassium carbonate (12.2 g, 37.60 mmol) followed by 1-bromo-3-phenylpropan-2-one (4.4 g 20.70 mmol) at 0° C. The reaction mixture was warmed to room temperature and stirred for 2 h. After consumption of the starting material (monitored by TLC), the reaction was quenched with ice cold water (20 mL) and extracted with $CH_2Cl_2$ (2×20 mL). The combined organic extracts were dried over sodium sulfate, filtered and concentrated in vacuo. The crude material was triturated with n-hexane:$CH_2Cl_2$ (1:1, 2×50 mL) to afford 1-((2-chloro-4-(methylamino) pyrimidin-5-yl) oxy)-3-phenylpropan-2-one (3 g, 55%) as a pale brown solid.
$^1$H-NMR ($CDCl_3$, 500 MHz): δ 7.70 (s, 1H), 7.39-7.30 (m, 3H), 7.29-7.27 (m, 2H), 4.02 (d, 1H), 2.62 (d, 1H), 3.21 (d, 1H), 3.19 (s, 3H), 2.96 (d, 1H); LC-MS: 291.9 (M$^+$); (column; X-Select CSH C-18 (50×3.0 mm, 3.5 µm); RT 3.37 min. 0.05% Aq TFA: ACN; 0.8 mL/min); TLC: 30% EtOAc: hexanes ($R_f$: 0.8).

Synthesis of 7-benzyl-2-chloro-8-methyl-7,8-dihydro-6H-pyrimido [5, 4-b] [1, 4] oxazine To a stirred solution of 1-((2-chloro-4-(methylamino) pyrimidin-5-yl) oxy)-3-phenylpropan-2-one (3 g, 10.3 mmol) in 1, 2-dichloroethane (30 mL) was added trifluoroacetic acid (1.1 g, 10.31 mmol) at 0° C. and stirred for 10 min. Sodium triacetoxyborohydride (4.3 g, 20.62 mmol) was added and the reaction mixture was stirred for 48 h. After consumption of the starting material (monitored by TLC), the reaction was quenched with a 1 N sodium hydroxide solution (50 mL) and extracted with CH$_2$Cl$_2$ (2×50 mL). The combined organic extracts were dried over sodium sulfate, filtered and concentrated in vacuo. The crude material was purified by silica gel column chromatography using 20% EtOAc:hexanes to afford 7-benzyl-2-chloro-8-methyl-7, 8-dihydro-6H-pyrimido [5, 4-b] [1, 4] oxazine (1.6 g, 57%) as a white solid. $^1$H-NMR (CDCl$_3$, 500 MHz): δ 7.70 (s, 1H), 7.38-7.34 (m, 2H), 7.32-7.28 (m, 1H), 7.28 (d, 2H), 4.10 (d, 1H), 3.81 (d, 1H), 3.60-3.58 (m, 1H), 3.14 (s, 3H), 3.10-3.07 (m, 1H), 2.81-2.78 (m, 1H); LC-MS: 275.8 (M+1); (column; X-Select CSH C-18 (50×3.0 mm, 3.5 μm); RT 3.61 min. 0.05% Aq TFA: ACN; 0.8 mL/min); TLC: 30% EtOAc:hexanes (R$_f$ 0.5).

Example 14

Synthesis of 2-chloro-8-methyl-7-(2-(trifluoromethyl) phenyl)-7, 8-dihydro-6H-pyrimido [5, 4-b] [1, 4] oxazine

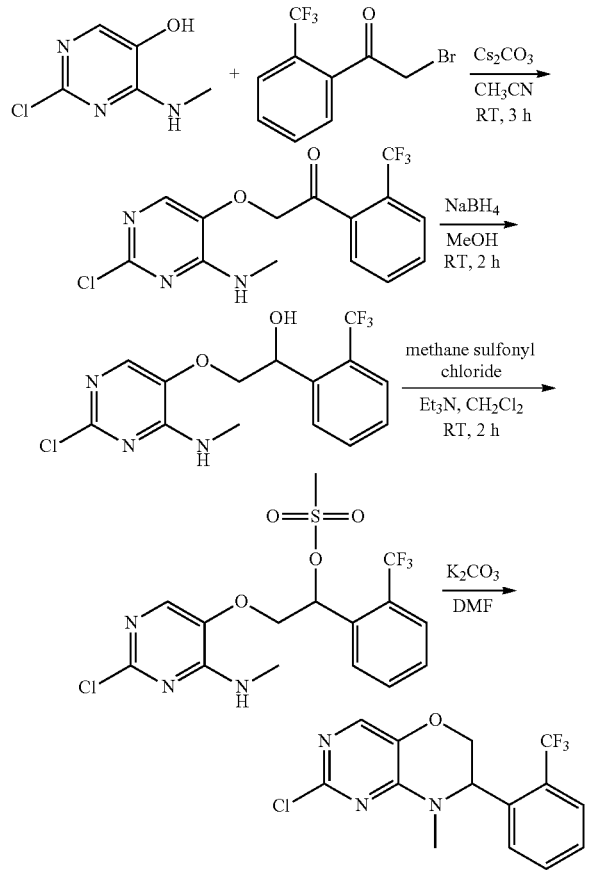

Synthesis of 2-((2-chloro-4-(methylamino) pyrimidin-5-yl) oxy)-1-(2-(trifluoromethyl) phenyl) ethan-1-one To a stirred solution of 2-chloro-4-(methylamino) pyrimidin-5-ol (100 mg, 0.62 mmol) in CH$_3$CN (2 mL) was added cesium carbonate (409 mg, 1.25 mmol) and 2-bromo-1-(2-(trifluoromethyl) phenyl) ethan-1-one (184 mg, 0.69 mmol) and the reaction mixture was stirred for 3 h. After consumption of the starting material (monitored by TLC), the mixture was diluted with water (50 mL) and extracted with EtOAc (2×50 mL). The combined organic extracts were dried over sodium sulfate, filtered and concentrated in vacuo. The crude material was purified by silica gel column chromatography using 10% EtOAc:hexanes to afford 2-((2-chloro-4-(methylamino) pyrimidin-5-yl) oxy)-1-(2-(trifluoromethyl) phenyl) ethan-1-one (100 mg, 46%) as an off-white solid. $^1$H-NMR (DMSO-d$_6$, 400 MHz): δ 8.03 (d, 1H), 7.90 (d, 1H), 7.89-7.79 (m, 2H), 7.69 (s, 1H), 7.48-7.40 (m, 1H), 5.55 (s, 2H), 2.83 (d, 3H); LC-MS: 345.8 (M+1); (column; X-Select CSH C-18 (50×3.0 mm, 3.5 μm); RT 3.41 min. 0.05% Aq TFA: ACN; 0.80 mL/min); TLC: 50% EtOAc: hexanes (R$_f$: 0.7).

Synthesis of 2-((2-chloro-4-(methylamino) pyrimidin-5-yl) oxy)-1-(2-(trifluoromethyl) phenyl) ethan-1-ol To a stirred solution of 2-((2-chloro-4-(methylamino) pyrimidin-5-yl) oxy)-1-(2-(trifluoromethyl) phenyl) ethan-1-one (400 mg, 1.15 mmol) in MeOH (4 mL) was added sodium borohydride (64 mg, 1.73 mmol) at 0° C. The reaction mixture was warmed to room temperature and stirred for 2 h. After consumption of the starting material (monitored by TLC), the mixture was diluted with water (50 mL) and extracted with EtOAc (2×50 mL). The combined organic extracts were dried over sodium sulfate, filtered and concentrated in vacuo. The crude material was purified by silica gel column chromatography using 10% EtOAc: hexanes to afford 2-((2-chloro-4-(methylamino) pyrimidin-5-yl) oxy)-1-(2-(trifluoromethyl) phenyl) ethan-1-ol (250 mg, 62%) as an off-white solid. LC-MS: 347.8 (M+1); (column; X-Select CSH C-18 (50×3.0 mm, 3.5 μm); RT 3.30 min. 0.05% Aq TFA: ACN; 0.80 mL/min); TLC: 30% EtOAc:hexanes (R$_f$: 0.6).

Synthesis of 2-((2-chloro-4-(methylamino) pyrimidin-5-yl) oxy)-1-(2-(trifluoromethyl) phenyl) ethyl methanesulfonate To a stirred solution of 2-((2-chloro-4-(methylamino) pyrimidin-5-yl) oxy)-1-(2-(trifluoromethyl) phenyl) ethan-1-ol (550 mg, 1.58 mmol) in CH$_2$Cl$_2$ (6 mL) was added successively triethylamine (0.26 mL, 1.90 mmol) and methane sulfonyl chloride (180 mg, 1.58 mmol) at 0° C. The reaction mixture was warmed to room temperate and stirred for 2 h. After consumption of the starting material (monitored by TLC), the mixture was filtered. The filtrate was diluted with water (20 mL) and extracted with CH$_2$Cl$_2$ (2×20 mL). The combined organic extracts were dried over sodium sulfate, filtered and concentrated in vacuo. The crude material was recrystallized from diisopropylether (2×5 mL) to afford 2-((2-chloro-4-(methylamino) pyrimidin-5-yl) oxy)-1-(2-(trifluoromethyl) phenyl) ethyl methanesulfonate (500 mg, 74%) as an off-white solid. LC-MS: 425.7 (M+1); (column; X-Select CSH C-18 (50×3.0 mm, 3.5 μm); RT 3.63 min. 0.05% Aq TFA: ACN; 0.80 mL/min); TLC: 40% EtOAc:hexanes (R$_f$: 0.6).

Synthesis of 2-chloro-8-methyl-7-(2-(trifluoromethyl) phenyl)-7, 8-dihydro-6H-pyrimido [5, 4-b] [1, 4] oxazine To a stirred solution of 2-((2-chloro-4-(methylamino) pyrimidin-5-yl) oxy)-1-(2-(trifluoromethyl) phenyl) ethyl methanesulfonate (650 mg, 1.52 mmol) in DMF (6 mL) was added potassium carbonate (316 mg, 2.29 mmol). The reaction mixture was heated to 80° C. and stirred for 2 h. After consumption of the starting material (monitored by TLC), the mixture was concentrated in vacuo. The crude material was dissolved in water (50 mL) and extracted with ether (2×50 mL). The combined organic extracts were dried over sodium sulfate, filtered and concentrated in vacuo. The crude material was purified by silica gel column chromatography using 10% EtOAc:hexanes to afford 2-chloro-8-methyl-7-(2-(trifluoromethyl) phenyl)-7, 8-dihydro-6H-pyrimido [5, 4-b] [1, 4] oxazine (100 mg, 19%) as an off-white solid. $^1$H-NMR (CDCl$_3$, 400 MHz): δ 7.77-7.71 (m, 2H), 7.59-7.51 (m, 1H), 7.49-7.45 (m, 1H), 7.19 (d, 1H), 5.02-5.00 (m, 1H), 4.30-4.25 (m, 1H), 4.18-4.12 (m, 1H), 3.02 (s, 3H); LC-MS: 330.1 (M+1); (column; X-Select CSH C-18 (50×3.0 mm, 3.5 µm); RT 4.55 min. 0.05% Aq TFA: ACN; 0.80 mL/min); TLC: 40% EtOAc:hexanes (R$_f$: 0.7).

Example 15

Synthesis of 2-chloro-7,8-dimethyl-7,8-dihydro-6H-pyrimido[5,4-b][1,4]oxazine

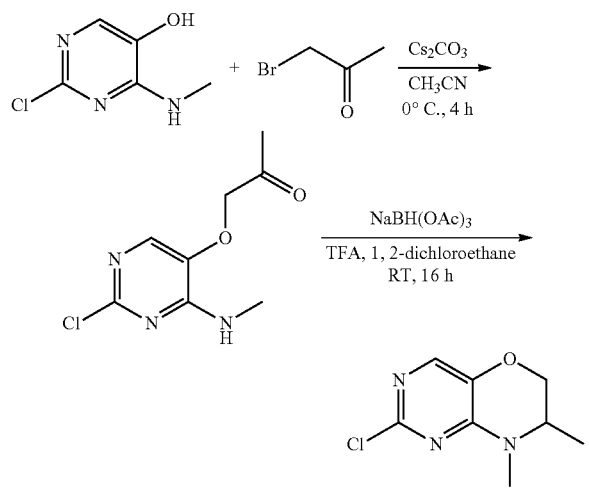

Synthesis of 1-((2-chloro-4-(methylamino) pyrimidin-5-yl) oxy) propan-2-one

To a stirred solution of 2-chloro-4-(methylamino) pyrimidin-5-ol (200 mg, 1.25 mmol) in CH$_3$CN (4 mL) was added successively 1-bromopropan-2-one (243 mg, 1.38 mmol) and cesium carbonate (815 mg, 2.50 mmol) at 0° C. and stirred for 4 h. After consumption of the starting material (monitored by TLC), the mixture was diluted with a saturated sodium carbonate solution (20 mL) and extracted with EtOAc (2×20 mL). The combined organic extracts were dried over sodium sulfate, filtered and concentrated in vacuo. The crude material was purified by silica gel column chromatography using 15-20% EtOAc:hexanes to afford 1-((2-chloro-4-(methylamino) pyrimidin-5-yl) oxy) propan-2-one (220 mg, 82%) as an off-white solid. $^1$H-NMR (DMSO-d$_6$, 400 MHz): δ 7.70 (s, 1H), 6.41 (s, 1H), 4.01 (d, 1H), 3.89 (d, 1H), 3.00 (s, 3H), 1.38 (s, 3H); LC-MS: 216 (M+1); (column; X-Select CSH C-18 (50×3.0 mm, 3.5 µm); RT 2.18 min. 0.05% Aq TFA: ACN; 0.8 mL/min); TLC: 60% EtOAc:hexanes (R$_f$: 0.2).

Synthesis of 2-chloro-7,8-dimethyl-7,8-dihydro-6H-pyrimido[5,4-b] [1,4]oxazine

To a stirred solution of 1-((2-chloro-4-(methylamino) pyrimidin-5-yl) oxy) propan-2-one (200 mg, 0.93 mmol) in 1, 2-dichloroethane (4 mL) was added sodium triacetoxyborohydride (395 mg, 1.86 mmol) followed by trifluoroacetic acid (0.07 mL, 0.93 mmol) and stirred for 16 h. After consumption of the starting material (monitored by TLC), the mixture was diluted with a 1 N sodium hydroxide solution (20 mL) and extracted with CH$_2$Cl$_2$ (2×20 mL). The combined organic extracts were dried over sodium sulfate, filtered and concentrated in vacuo. The crude material was purified by silica gel column chromatography using 10-15% EtOAc:hexanes to afford 2-chloro-7,8-dimethyl-7,8-dihydro-6H-pyrimido[5,4-b][1,4]oxazine (110 mg, 59%) as an off-white solid. $^1$H-NMR (CDCl$_3$, 400 MHz): δ 7.63 (s, 1H), 4.01 (s, 2H), 3.61-3.58 (m, 1H), 3.14 (s, 3H), 1.31 (d, 3H); LC-MS: 200 (M+1); (column; X-Select CSH C-18 (50×3.0 mm, 3.5 µm); RT 2.49 min. 0.05% Aq TFA: ACN; 0.8 mL/min); TLC: 60% EtOAc:hexanes (R$_f$: 0.4).

Example 16

Synthesis of 2-chloro-7-(4-fluoro-2-methylphenyl)-8-methyl-7, 8-dihydro-6H-pyrimido [5, 4-b] [1, 4] oxazine

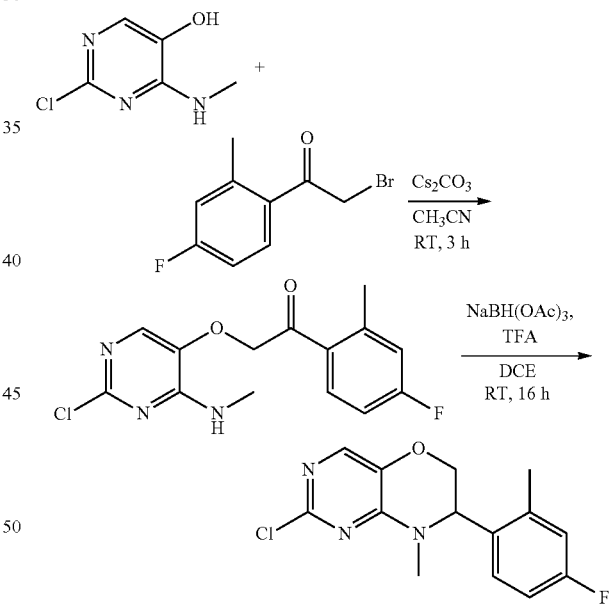

Synthesis of 2-((2-chloro-4-(methylamino) pyrimidin-5-yl) oxy)-1-(4-fluoro-2-methylphenyl) ethan-1-one To a stirred solution of 2-chloro-4-(methylamino) pyrimidin-5-ol (100 mg, 0.62 mmol) in CH$_3$CN (2 mL) was added cesium carbonate (409 mg, 1.25 mmol) followed by 2-bromo-1-(4-fluoro-2-methylphenyl) ethan-1-one (159 mg, 0.69 mmol) and stirred for 3 h. After consumption of the starting material (monitored by TLC), the mixture was diluted with water (20 mL) and extracted with EtOAc (2×20 mL). The combined organic extracts were dried over sodium sulfate, filtered and concentrated in vacuo to afford 2-((2-chloro-4-(methylamino) pyrimidin-5-yl) oxy)-1-(4-fluoro-2-methylphenyl) ethan-1-one (120 mg, 62%) as an off-white solid. LC-MS: 309.8 (M+1); (column; X-Select CSH C-18 (50×3.0 mm, 3.5 µm); RT 3.35 min. 0.05% Aq TFA: ACN; 0.80 mL/min); TLC: 30% EtOAc:hexanes ($R_f$: 0.7).

Synthesis of 2-chloro-7-(4-fluoro-2-methylphenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(4-fluoro-2-methylphenyl) ethan-1-one (150 mg, 0.48 mmol) in 1, 2-dichloroethane (2 mL) was added sodium triacetoxyborohydride (205 mg, 0.97 mmol) followed by trifluoroacetic acid (0.1 mL, 0.48 mmol) at 0° C. The reaction mixture was warmed to room temperature and stirred for 16 h. After consumption of the starting material (monitored by TLC), the mixture was diluted with 1N sodium hydroxide solution (20 mL) and extracted with $CH_2Cl_2$ (2×20 mL). The combined organic extracts were dried over sodium sulfate, filtered and concentrated in vacuo to afford 2-chloro-7-(4-fluoro-2-methylphenyl)-8-methyl-7, 8-dihydro-6H-pyrimido [5, 4-b] [1, 4] oxazine LC-MS: 294 (M+1); (column; X-Select CSH C-18 (50×3.0 mm, 3.5 µm); RT 4.31 min. 0.05% Aq TFA: ACN; 0.80 mL/min); TLC: 30% EtOAc:hexanes ($R_f$: 0.3).

Example 17

Synthesis of 7-chloro-1-methyl-2-(2, 2, 2-trifluoroethyl)-2, 3-dihydro-1H-pyrido [3, 4-b] [1, 4] oxazine

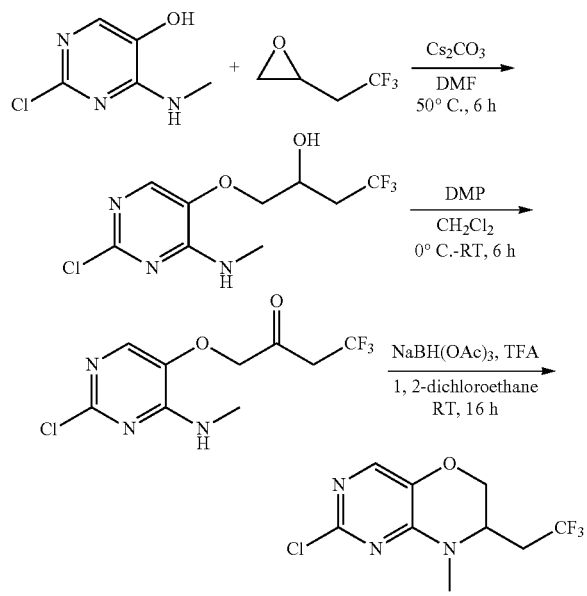

Synthesis of 1-((2-chloro-4-(methylamino) pyrimidin-5-yl) oxy)-4, 4, 4-trifluorobutan-2-ol To a stirred solution of 2-chloro-4-(methylamino) pyrimidin-5-ol (200 mg, 1.25 mmol) in DMF (5 mL) was added cesium carbonate (810 mg, 0.50 mmol) followed by 2-(2, 2, 2-trifluoroethyl) oxirane (160 mg, 1.25 mmol). The reaction mixture was heated to 50° C. and stirred for 6 h. After consumption of the starting material (monitored by TLC), the mixture was diluted with water (20 mL) and extracted with EtOAc (2×20 mL). The combined organic extracts were dried over sodium sulfate, filtered and concentrated in vacuo. The crude material was purified by silica gel column chromatography using 20-30% EtOAc:hexanes to afford 1-((2-chloro-4-(methylamino) pyrimidin-5-yl) oxy)-4, 4, 4-trifluorobutan-2-ol (220 mg, 62%) as an off-white solid. $^1$H-NMR (CDCl$_3$, 500 MHz): δ 7.53 (s, 1H), 5.68 (br s, 1H), 4.43-4.39 (m, 1H), 4.02-3.99 (m, 2H), 3.04 (s, 3H), 2.90 (br s, 1H), 2.54-2.38 (m, 2H); LC-MS: 285.8 (M+1); (column; X-Select CSH C-18 (50×3.0 mm, 3.5 µm); RT 2.63 min. 0.05% Aq TFA: ACN; 0.8 mL/min); TLC: 20% EtOAc: hexanes ($R_f$: 0.6).

Synthesis of 1-((2-chloro-4-(methylamino) pyrimidin-5-yl) oxy)-4, 4, 4-trifluorobutan-2-one To a stirred solution of 1-((2-chloro-4-(methylamino) pyrimidin-5-yl) oxy)-4, 4, 4-trifluorobutan-2-ol (400 mg, 1.40 mmol) in CH$_2$Cl$_2$ (5 mL) was added Dess-Martin Periodinane (893 mg, 2.10 mmol) at 0° C. The reaction mixture was warmed to room temperature and stirred for 6 h. After consumption of the starting material (monitored by TLC), the mixture was diluted with a saturated sodium bicarbonate solution (20 mL) and extracted with CH$_2$Cl$_2$ (2×20 mL). The combined organic extracts were washed with a sodium thoisulfate solution (20 mL), dried over sodium sulfate, filtered and concentrated in vacuo. The crude material was purified by silica gel column chromatography using 30% EtOAc:hexanes to afford 1-((2-chloro-4-(methylamino) pyrimidin-5-yl) oxy)-4, 4, 4-trifluorobutan-2-one (220 mg, 55%) as a pale yellow solid. $^1$H-NMR (CDCl$_3$, 400 MHz): δ 7.70 (s, 1H), 4.31 (d, 1H), 4.00 (d, 1H), 3.18 (s, 3H), 2.78-2.63 (m, 2H); LC-MS: 284.1 (M+1); (column; X-Select CSH C-18 (50×3.0 mm, 3.5 µm); RT 3.60 min. 0.05% Aq TFA: ACN; 0.8 mL/min); TLC: 40% EtOAc: hexanes ($R_f$: 0.4).

Synthesis of 7-chloro-1-methyl-2-(2, 2, 2-trifluoroethyl)-2, 3-dihydro-1H-pyrido [3, 4-b] [1, 4] oxazine To a stirred solution of 1-((2-chloro-4-(methylamino) pyrimidin-5-yl) oxy)-4, 4, 4-trifluorobutan-2-one (200 mg, 0.70 mmol) in 1, 2-dichloroethane (4 mL) was added sodium triacetoxyborohydride (300 mg, 1.41 mmol) followed by trifluoroacetic acid (80 mg, 0.70 mmol) at and stirred for 16 h. After consumption of the starting material (monitored by TLC), the mixture was diluted with a 1N sodium hydroxide solution (20 mL) and extracted with CH$_2$Cl$_2$ (2×20 mL). The combined organic extracts were dried over sodium sulfate, filtered and concentrated in vacuo. The crude material was purified by silica gel column chromatography using 15-20% EtOAc:hexanes to afford 7-chloro-1-methyl-2-(2, 2, 2-trifluoroethyl)-2, 3-dihydro-1H-pyrido [3, 4-b] [1, 4] oxazine (90 mg, 48%) as an off-white solid. $^1$H-NMR (CDCl$_3$, 400 MHz): δ 7.72 (s, 1H), 4.32 (d, 1H), 4.02 (d, 1H), 3.83-3.79 (m, 1H), 3.21 (s, 3H), 2.60-2.40 (m, 2H); LC-MS: 268 (M+1); (column; X-Select CSH C-18 (50×3.0 mm, 3.5 µm); RT 3.77 min. 0.05% Aq TFA: ACN; 0.8 mL/min); TLC: 50% EtOAc:hexanes ($R_f$: 0.4).

Example 18

Synthesis of 2-chloro-8-methyl-7-(2-(trifluoromethoxy) phenyl)-7, 8-dihydro-6H-pyrimido [5, 4-b] [1, 4] oxazine

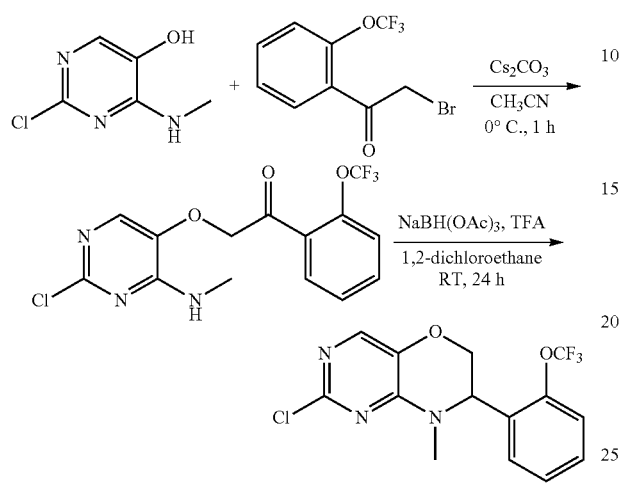

Synthesis of 2-((2-chloro-4-(methylamino) pyrimidin-5-yl) oxy)-1-(2-(trifluoromethoxy) phenyl) ethan-1-one To a stirred solution of 2-chloro-4-(methylamino) pyrimidin-5-ol (300 mg, 1.88 mmol) in CH₃CN (10 mL) was added cesium carbonate (1.22 g, 0.37 mmol) followed by 2-bromo-1-(2-(trifluoromethoxy) phenyl) ethan-1-one (580 mg, 0.20 mmol) at 0° C. and stirred for 1 h. After consumption of the starting material (monitored by TLC), the mixture was diluted with water (20 mL) and extracted with EtOAc (2×20 mL). The combined organic extracts were dried over sodium sulfate, filtered and concentrated in vacuo. The crude material was purified by silica gel column chromatography using 10% EtOAc:hexanes to afford 2-((2-chloro-4-(methylamino) pyrimidin-5-yl) oxy)-1-(2-(trifluoromethoxy) phenyl) ethan-1-one (350 mg, 51%) as an off white solid. ¹H-NMR (DMSO-d₆, 500 MHz): δ 7.88 (s, 1H), 7.77 (d, 1H), 7.58 (d, 1H), 7.46 (t, 1H), 7.41 (d, 1H), 7.50 (s, 1H), 4.21 (d, 1H), 4.11 (d, 1H), 2.79 (s, 3H); LC-MS: 362.1 (M+1); (column; X-Select CSH C-18 (50×3.0 mm, 3.5 μm); RT 4.25 min. 0.05% Aq TFA: ACN; 0.80 ml/min); TLC: 40% EtOAc:hexanes (R_f: 0.7).

Synthesis of 2-chloro-8-methyl-7-(2-(trifluoromethoxy) phenyl)-7, 8-dihydro-6H-pyrimido [5, 4-b] [1, 4] oxazine To a stirred solution of 2-((2-chloro-4-(methylamino) pyrimidin-5-yl) oxy)-1-(2-(trifluoromethoxy) phenyl) ethan-1-one (350 mg, 0.96 mmol) in 1,2-dichloroethane (10 mL) was added sodium triacetoxyborohydride (400 mg, 1.93 mmol) followed by trifluoroacetic acid (0.1 mL, 0.96 mmol) at 0° C. The reaction mixture was warmed to room temperature and stirred for 24 h. After consumption of the starting material (monitored by TLC), the reaction was quenched with 1N sodium hydroxide (20 mL) and extracted with CH₂Cl₂ (2×20 mL). The combined organic extracts were dried over sodium sulfate, filtered and concentrated in vacuo. The crude material was triturated with EtOAc (2×10 mL) to afford 2-chloro-8-methyl-7-(2-(trifluoromethoxy) phenyl)-7, 8-dihydro-6H-pyrimido [5, 4-b] [1, 4] oxazine (220 mg, 66%) as an off white solid. ¹H-NMR (CDCl₃, 400 MHz): δ 7.71 (s, 1H), 7.45-7.30 (m, 3H), 7.08-7.03 (m, 1H), 5.00 (s, 1H), 4.24 (s, 2H), 3.11 (s, 3H); LC-MS: 346.1 (M+1); (column; X-Select CSH C-18 (50×3.0 mm, 3.5 μm); RT 4.51 min. 0.05% Aq TFA: ACN; 0.80 ml/min); TLC: 30% EtOAc:hexanes (R_f: 0.7).

Example 19

Synthesis of 2-chloro-8-methyl-7-(tetrahydro-2H-pyran-4-yl)-7, 8-dihydro-6H-pyrimido [5, 4-b] [1, 4] oxazine

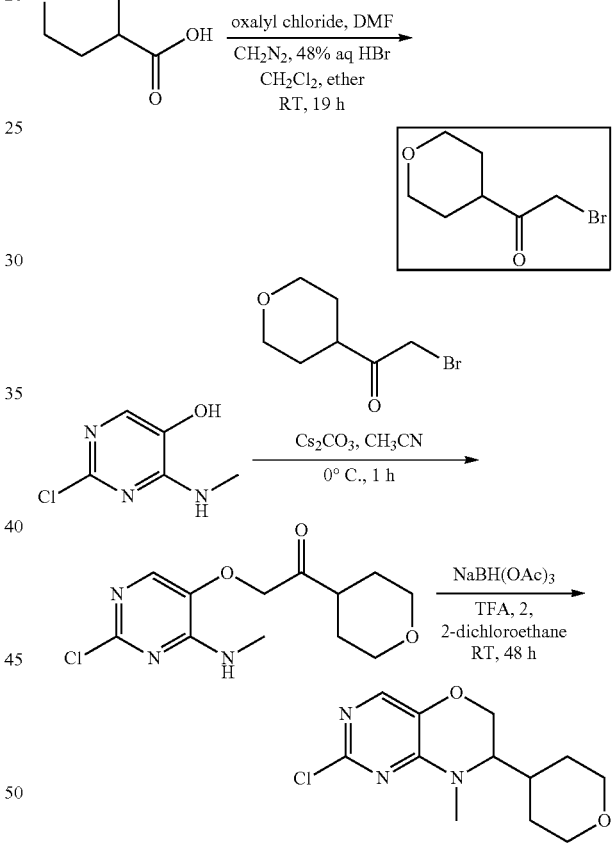

Synthesis of 2-bromo-1-(tetrahydro-2H-pyran-4-yl) ethan-1-one

To a stirred solution of tetrahydro-2H-pyran-4-carboxylic acid (1.5 g, 0.01 mmol) in CH₂Cl₂ (10 mL) was added oxalyl chloride (1.6 g, 0.01 mmol) and DMF (1 drop) at 0° C. The reaction mixture was warmed to room temperature and stirred for 2 h. After consumption of acid (monitored by TLC), the mixture was concentrated in vacuo. The crude material was dissolved in ether and cooled to −10° C. A solution of CH₂N₂ in ether (20 mL) was added and the reaction mixture was warmed to room temperature and stirred for 16 h. After consumption of the starting material (monitored by TLC), the mixture was concentrated in vacuo. To a stirred solution of the crude material in $CH_2Cl_2$ (20 mL) was added a solution of 48% aq HBr (5 mL) at −10° C. The reaction mixture was warmed to room temperature and stirred for 1 h. After consumption of the starting material (monitored by TLC), the reaction was quenched with a sodium bicarbonate solution (50 mL) and extracted with $CH_2Cl_2$ (2×50 mL). The combined organic extracts were washed successively with a sodium bicarbonate solution (20 mL) and water (20 mL). The organic layer was dried over sodium sulfate, filtered and concentrated in vacuo to afford 2-bromo-1-(tetrahydro-2H-pyran-4-yl) ethan-1-one (2 g) as a yellow solid. $^1$H-NMR (DMSO-$d_6$, 500 MHz): δ 4.49 (s, 2H), 3.83 (d, 2H), 3.33 (t, 2H), 2.90-2.80 (m, 1H), 1.80-1.70 (m, 2H), 1.57-1.44 (m, 2H); TLC: 30% EtOAc:hexanes ($R_f$: 0.7).

Synthesis of 2-((2-chloro-4-(methylamino) pyrimidin-5-yl)oxy)-1-(tetrahydro-2H-pyran-4-yl) ethan-1-one To a stirred solution of the 2-chloro-4-(methylamino) pyrimidin-5-ol (3 g, 18.8 mmol) in $CH_3CN$ (60 mL) was added cesium carbonate (12.2 g, 37.70 mmol) followed by 2-bromo-1-(tetrahydro-2H-pyran-4-yl) ethan-1-one (3.9 g 18.8 mmol) at 0° C. and stirred for 1 h. After consumption of the starting material (monitored by TLC), the reaction was quenched with a sodium carbonate solution (20 mL) and extracted with EtOAc (2×20 mL). The combined organic extracts were dried over sodium sulfate, filtered and concentrated in vacuo to afford 2-((2-chloro-4-(methylamino) pyrimidin-5-yl) oxy)-1-(tetrahydro-2H-pyran-4-yl) ethan-1-one (2.5 g) as a yellow solid and used without further purification. LC-MS: 286.1 (M$^+$); (column; X-Select CSH C-18 (50×3.0 mm, 3.5 μm); RT 2.86 min. 0.05% Aq TFA: ACN; 0.8 mL/min); TLC: 30% EtOAc:hexanes ($R_f$: 0.5).

Synthesis of 2-chloro-8-methyl-7-(tetrahydro-2H-pyran-4-yl)-7, 8-dihydro-6H-pyrimido [5, 4-b] [1, 4] oxazine To a stirred solution of 2-((2-chloro-4-(methylamino) pyrimidin-5-yl) oxy)-1-(tetrahydro-2H-pyran-4-yl) ethan-1-one (2.5 g, 8.70 mmol) in 1, 2-dichloroethane (50 mL) was added trifluoroacetic acid (1 mL) followed by sodium triacetoxyborohydride (3.7 g, 17.50 mmol) and stirred for 48 h. After consumption of the starting material (monitored by TLC), the reaction was quenched with 1N sodium hydroxide (50 mL) (pH>9) and extracted with $CH_2Cl_2$ (2×50 mL). The combined organic extracts were dried over sodium sulfate, filtered and concentrated in vacuo. The crude material was purified by silica gel column chromatography using 20-30% EtOAc:hexanes to afford 2-chloro-8-methyl-7-(tetrahydro-2H-pyran-4-yl)-7, 8-dihydro-6H-pyrimido [5, 4-b] [1, 4] oxazine (2 g, 86%) as a pale yellow solid. LC-MS: 270.2 (M+1); (column; X-Select CSH C-18 (50×3.0 mm, 3.5 μm); RT 3.10 min. 0.05% Aq TFA: ACN; 0.8 mL/min); UPLC (column; Acquity UPLC BEH C-18, 2.1×50 mm, 1.7 μm); RT 1.63 min. ACN: 0.025% TFA (Aq); 0.50 ml/min; TLC: 50% EtOAc:hexanes ($R_f$: 0.3).

Example 20

Synthesis of 7-(2-chlorophenyl)-8-methyl-7, 8-dihydro-6H-pyrimido [5, 4-b] [1, 4] oxazin

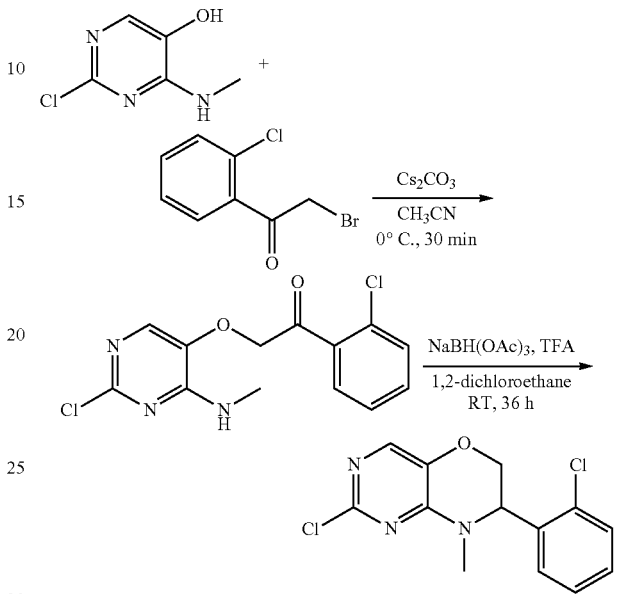

Synthesis of 2-((2-chloro-4-(methylamino) pyrimidin-5-yl) oxy)-1-(2-chlorophenyl) ethan-1-one To a stirred solution of 2-chloro-4-(methylamino) pyrimidin-5-ol (4 g, 25.15 mmol) in $CH_3CN$ (100 mL) was added cesium carbonate (16.25 g, 50.31 mmol) followed by 2-bromo-1-(2-chlorophenyl) ethan-1-one (12 g, 37.7 mmol) at 0° C. and stirred for 30 min. After consumption of the starting material (monitored by TLC), the mixture was diluted with water (100 mL) and extracted with EtOAc (2×100 mL). The combined organic extracts were dried over sodium sulfate, filtered and concentrated in vacuo. The crude material was purified by silica gel column chromatography using 6% EtOAc:hexanes to afford 2-((2-chloro-4-(methylamino) pyrimidin-5-yl) oxy)-1-(2-chlorophenyl) ethan-1-one (4.3 g, 55%) as a white solid. $^1$H-NMR (DMSO-$d_6$, 500 MHz): δ 7.95-7.88 (m, 2H), 7.59-7.41 (m, 3H), 7.38 (s, 1H), 4.37 (d, 1H), 4.05 (d, 1H), 2.78 (s, 3H); TLC: 20% EtOAc:hexanes ($R_f$: 0.7).

Synthesis of 2-chloro-7-(2-chlorophenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(2-chlorophenyl) ethan-1-one (4.3 g, 13.78 mmol) in 1, 2-dichloroethane (100 mL) was added sodium triacetoxyborohydride (6.1 g, 28.94 mmol) followed by trifluoroacetic acid (1.1 mL, 13.78 mmol) and stirred for 36 h. After consumption of the starting material (monitored by TLC), the reaction was quenched with a 5% sodium bicarbonate solution (100 mL) and extracted with $CH_2Cl_2$ (2×100 mL). The combined organic extracts were dried over sodium sulfate, filtered and concentrated in vacuo. The crude material was purified by silica gel column chromatography using 12% EtOAc:hexanes to afford 2-chloro-7-

(2-chlorophenyl)-8-methyl-7, 8-dihydro-6H-pyrimido [5,4-b] [1, 4] oxazine (1.8 g, 45%) as an off white solid.

¹H-NMR (DMSO-d₆, 500 MHz): δ 7.77 (s, 1H), 7.55 (d, 1H), 7.40 (t, 1H), 7.36 (t, 1H), 6.98 (d, 1H), 5.23 (s, 1H), 4.34 (s, 2H), 3.01 (s, 3H); LC-MS: 296.1 (M+1); (column; X-Select CSH C-18 (50×3.0 mm, 3.5 µm); RT 4.30 min. 0.05% Aq TFA: ACN; 0.80 ml/min); TLC: 20% EtOAc: hexanes (R$_f$: 0.7).

Example 21

Synthesis of (S)-2-chloro-8-methyl-7-phenyl-7,8-dihydro-6H-pyrimido[5,4-b][1,4]oxazine

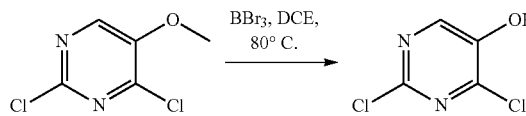

Synthesis of 2,4-Dichloropyrimidin-5-ol

To a solution of 2,4-dichloro-5-methoxypyrimidine (5.30 g, 29.6 mmol) in 1,2-dichloroethane (75 mL) at 0° C. was slowly added BBr₃ (14 mL, 148 mmol). The reaction mixture was heated to 80° C. for 16 h and monitored by LC/MS until completion of the reaction. The reaction mixture was cooled to 0° C. and basified with a 1N NaOH solution. The mixture was stirred for 1 h at room temperature and then acidified with NH₄Cl. The pH was adjusted between pH 6-7 using AcOH. The layers were separated and the aqueous layer was extracted 3 times with ethyl acetate. The combined organic extracts were dried over Na₂SO₄, filtered and concentrated in vacuo. The crude material was triturated with DCM:hexanes and filtered to afford pure 2,4-dichloropyrimidin-5-ol (2.03 g, 73%) as a solid. ¹H NMR (CDCl₃, 400 MHz): δ 8.35 (s, 1H), 5.73 (s, 1H); LRMS (ESpos) calcd for $C_4H_2Cl_2N_2O$ [M+H]+: 164.95. found: 165.13.

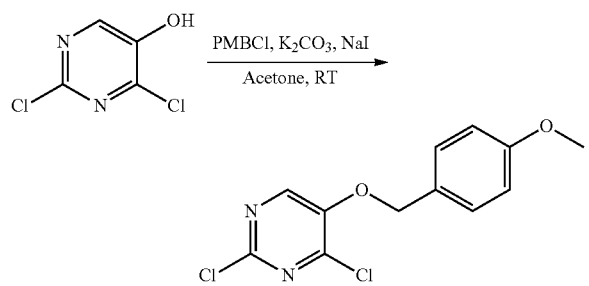

Synthesis of 2,4-dichloro-5-(4-methoxybenzyloxy)pyrimidine

To a solution of 2,4-dichloropyrimidin-5-ol (3.58 g, 21.7 mmol), K₂CO₃ (7.5 g, 54.3 mmol) and NaI (325 mg, 2.2 mmol) in acetone (45 mL) at RT was added PMBCl (4.41 mL, 32.5 mmol). The reaction was stirred for 16 h. When the reaction was complete (by LC/MS), the mixture was partitioned between ethyl acetate and water. The layers were separated and the aqueous was extracted 3 times with ethyl acetate. The combined organic extracts were dried over Na₂SO₄, filtered and concentrated in vacuo. The crude material was purified by silica gel column chromatography (gradient 0-30% EtOAc/hexanes) to afford pure 2,4-dichloro-5-(4-methoxybenzyloxy)pyrimidine (4.48 g, 72%) as a white solid. ¹H NMR (CDCl₃, 400 MHz): δ 8.18 (s, 1H), 7.34 (d, J=8.8 Hz, 2H), 6.93 (d, J=8.7 Hz, 2H), 5.17 (s, 2H), 3.82 (s, 3H).

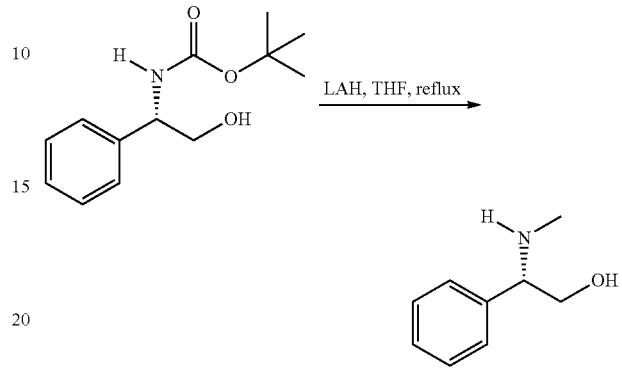

Synthesis of (S)-2-(methylamino)-2-phenylethanol

To a dry flask under a N₂ atmosphere was added LAH (956 mg, 25.2 mmol), followed by THF (42 mL) and (S)-tert-butyl 2-hydroxy-1-phenylethylcarbamate (3.0 g, 12.6 mmol). The reaction mixture was heated to reflux for 16 h. When the reaction was complete (by LC/MS), a 10% NaOH aqueous solution was added slowly at 0° C. until no gas evolution was observed. The reaction mixture was stirred at RT for 15 minutes and Na₂SO₄ was added. The reaction mixture was stirred vigorously for 15 min, filtered and washed with THF. The filtrate was concentrated in vacuo to afford (S)-2-(methylamino)-2-phenylethanol (1.91 g) as a light yellow gum which solidified upon standing. ¹H NMR (CDCl₃, 400 MHz): δ 7.38-7.33 (m, 2H), 7.31-7.26 (m, 3H), 3.72 (dd, J=10.4, 4.4 Hz, 1H), 3.65 (dd, J=8.3, 4.4 Hz, 1H), 3.55 (dd, J=10.4, 8.3 Hz, 1H), 2.35 (s, 3H).

Synthesis of (S)-2-((2-chloro-5-(4-methoxybenzyloxy)pyrimidin-4-yl)(methyl)amino)-2-phenylethanol To a mixture of 2,4-dichloro-5-(4-methoxybenzyloxy) pyrimidine (2.04 g, 7.15 mmol) and (S)-2-(methylamino)-2-phenylethanol (1.91 g, 7.49 mmol) in 2-methyl tetrahydrofuran (18 mL) was added triethylamine (2.5 mL, 17.9 mmol). The reaction mixture was stirred at reflux for 16 h. When the reaction was complete (by LC/MS), the mixture was diluted with ethyl acetate. The solution was washed twice with water, brine, dried over $Na_2SO_4$, filtered and concentrated in vacuo. The crude material was purified by silica gel column chromatography (gradient 10-80% EtOAc:hexanes) to afford of (S)-2-((2-chloro-5-(4-methoxybenzyloxy)pyrimidin-4-yl)(methyl)amino)-2-phenylethanol (2.14 g, 75%) as a yellow gummy solid. $^1$H NMR ($CDCl_3$, 400 MHz): δ7.80 (s, 1H), 7.35-7.27 (m, 3H), 7.22 (dd, J=14.3, 7.9 Hz, 4H), 6.88-6.84 (m, 2H), 6.09 (dd, J=8.9, 5.6 Hz, 1H), 4.96 (s, J=11.1 Hz, 2H), 4.22-4.15 (m, 2H), 3.80 (s, 3H), 2.93 (s, 3H), 2.15 (s, 1H); LRMS (ESpos) calcd for $C_{21}H_{22}ClN_3O_3$ [M+H]+: 400.13. found: 400.53.

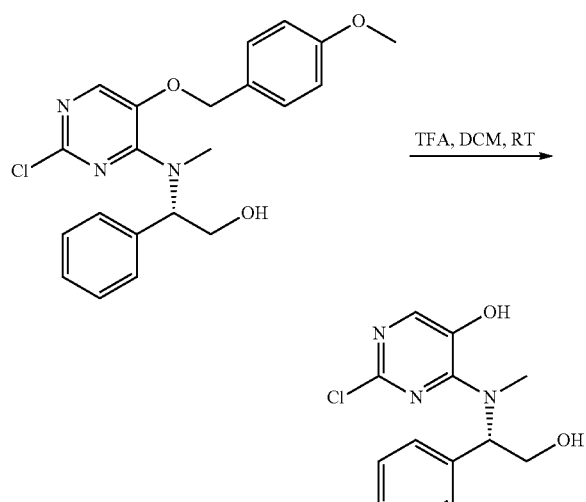

Synthesis of (S)-2-chloro-4-((2-hydroxy-1-phenylethyl)(methyl)amino)pyrimidin-5-ol To a mixture of (S)-2-(2-chloro-5-(4-methoxybenzyloxy) pyrimidin-4-yl)(methyl)amino)-2-phenylethanol (2.14 g, 5.35 mmol) at 0° C. in DCM (35 mL) was added trifluoroacetic acid (15 mL). When the reaction was completed (by LC/MS), the reaction was concentrated to dryness and co-evaporated several times with toluene. The crude material was partitioned between ethyl acetate and a sodium bicarbonate solution. The layers were separated and the aqueous layer was extracted with ethyl acetate twice. The combined organic layers were dried over $Na_2SO_4$, filtered and concentrated in vacuo. The residue was purified by silica gel column chromatography (gradient 0-10% MeOH:DCM) to afford (S)-2-chloro-4-((2-hydroxy-1-phenylethyl)(methyl)amino)pyrimidin-5-ol as a white foam (1.19 g, 80%).

$^1$H NMR ($CDCl_3$, 400 MHz): δ 7.83 (s, 1H), 7.33 (dq, J=14.2, 7.0 Hz, 4H), 7.11 (d, J=7.1 Hz, 2H), 5.71 (d, J=10.9 Hz, 1H), 4.36 (t, J=10.7 Hz, 1H), 4.27 (dd, J=10.7, 3.8 Hz, 1H), 3.42 (s, 1H), 2.72 (s, 3H); LRMS (ESpos) calcd for $C_{13}H_{14}ClN_3O_2$ [M+H]+: 280.08. found: 280.46.

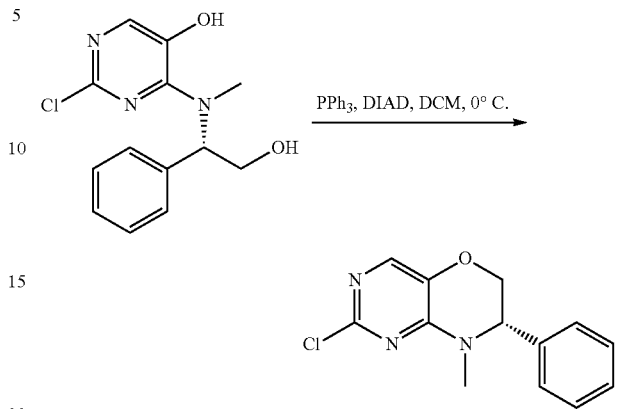

Synthesis of (S)-2-chloro-8-methyl-7-phenyl-7,8-dihydro-6H-pyrimido[5,4-b] [1,4] oxazine To a mixture of (S)-2-chloro-4-((2-hydroxy-1-phenylethyl)(methyl)amino)pyrimidin-5-ol (600 mg, 2.14 mmol) and triphenylphosphine (616 mg, 2.35 mmol) at 0° C. in DCM (11 mL) was added DIAD (0.46 mL, 2.35 mmol) drop-wise. The reaction was shown to be completed after 30 min (by LC/MS). The mixture was concentrated to dryness and purified by silica gel column chromatography (gradient 0-70% methyl tert-butylether (MTBE):hexanes) to afford (S)-2-chloro-8-methyl-7-phenyl-7,8-dihydro-6H-pyrimido[5,4-b][1,4]oxazine (0.2 g, 36%) as a colourless oil. $^1$H NMR ($CDCl_3$, 400 MHz): δ 7.71 (s, 1H), 7.41-7.34 (m, 3H), 7.17 (dd, J=7.7, 1.6 Hz, 2H), 4.57 (t, J=3.6 Hz, 1H), 4.27 (dd, J=11.2, 3.3 Hz, 1H), 4.18 (dd, J=11.2, 4.0 Hz, 1H), 3.08 (s, 3H); LRMS (ESpos) calcd for $C_{13}H_{12}ClN_3O$ [M+H]+: 262.07. found: 262.42.

Example 21A

Synthesis of (S)—N-(3-methoxy-4-(4-methyl-1H-imidazol-1-yl)phenyl)-8-methyl-7-phenyl-7,8-dihydro-6H-pyrimido[5,4-b][1,4]oxazin-2-amine

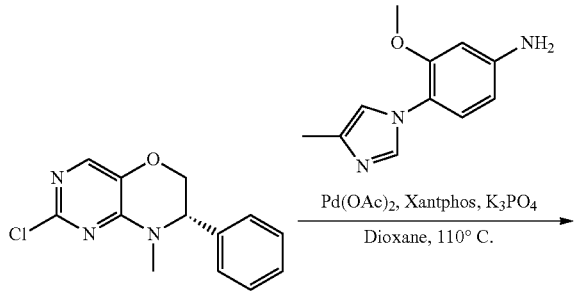

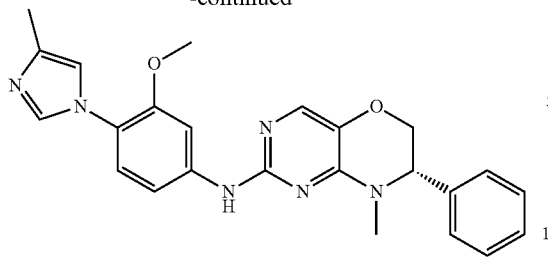

Synthesis of (S)—N-(3-methoxy-4-(4-methyl-1H-imidazol-1-yl)phenyl)-8-methyl-7-phenyl-7,8-dihydro-6H-pyrimido[5,4-b][1,4]oxazin-2-amine To a mixture of (S)-2-chloro-8-methyl-7-phenyl-7,8-dihydro-6H-pyrimido[5,4-b][1,4]oxazine (100 mg, 0.382 mmol), K₃PO₄ (202 mg, 0.955 mmol) and 3-methoxy-4-(4-methyl-1H-imidazol-1-yl)aniline (85 mg, 0.420 mmol) under N₂ in degassed dioxane (1.9 mL) at RT was added a 15 min premixed solution of Xantphos (44.2 mg, 0.076 mmol) and Pd(OAc)₂ (8.5 mg, 0.038 mmol) in dioxane at RT. The reaction mixture was heated to 110° C. and stirred for 16 h. When the reaction was complete (by LC/MS), the mixture was diluted with ethyl acetate, washed successively with water, brine, dried over Na₂SO₄, filtered and concentrated in vacuo. The crude material was purified by silica gel column chromatography (100% Ethyl Acetate, then gradient 0-10% MeOH:EtOAc) followed by C18 column chromatography (gradient 5-90% MeCN+0.1% HCOOH:H₂O) to afford (S)—N-(3-methoxy-4-(4-methyl-1H-imidazol-1-yl)phenyl)-8-methyl-7-phenyl-7,8-dihydro-6H-pyrimido[5,4-b][1,4]oxazin-2-amine (36.0 mg, 22%) as a solid. HPLC analysis on a chiral stationary phase (ChiralPak OD 250×4.6 mm, 40% (iPrOH+0.1% Et₂NH) in (hexane+0.1% Et₂NH), 1.0 mLmin⁻¹, DAD 254 nm) t$_r$=8.73 min. ¹H NMR (CDCl₃, 400 MHz): δ 7.69 (d, J=2.2 Hz, 1H), 7.68 (s, 1H), 7.61 (d, J=1.2 Hz, 1H), 7.42-7.33 (m, 3H), 7.24-7.20 (m, 2H), 7.13 (d, J=8.5 Hz, 1H), 7.08-7.01 (m, 2H), 6.86 (s, 1H), 4.56 (t, J=3.6 Hz, 1H), 4.26 (dd, J=11.1, 3.3 Hz, 1H), 4.15 (dd, J=11.1, 4.0 Hz, 1H), 3.84 (s, 3H), 3.11 (s, 3H), 2.29 (d, J=0.8 Hz, 3H); LRMS (ESpos) calcd for C₂₄H₂₄N₆O₂ [M+H]+: 429.20. found: 429.57.

Example 21B

Synthesis of (S)—N-(3-methoxy-4-(2-methylpyridin-4-yl)phenyl)-8-methyl-7-phenyl-7,8-dihydro-6H-pyrimido[5,4-b][1,4]oxazin-2-amine

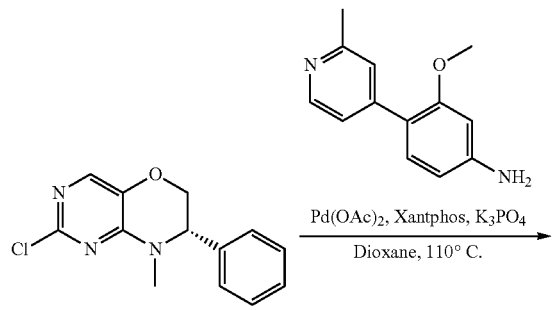

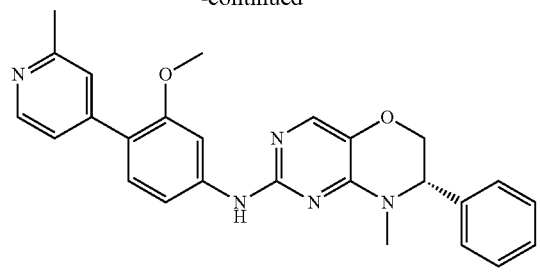

Synthesis of (S)—N-(3-methoxy-4-(2-methylpyridin-4-yl)phenyl)-8-methyl-7-phenyl-7,8-dihydro-6H-pyrimido[5,4-b][1,4]oxazin-2-amine To a mixture of (S)-2-chloro-8-methyl-7-phenyl-7,8-dihydro-6H-pyrimido[5,4-b][1,4]oxazine (85 mg, 0.325 mmol), K₃PO₄ (172.3 mg, 0.818 mmol) and 3-methoxy-4-(2-methylpyridin-4-yl)aniline (76.4 mg, 0.357 mmol) under N₂ in degassed dioxane (1.1 mL) at RT was added a premixed solution of Xantphos (37.6 mg, 0.065 mmol) and Pd(OAc)₂ (7.2 mg, 0.032 mmol) in dioxane at RT. The reaction mixture was heated to 110° C. and stirred for 16 h. When the reaction was complete (by LC/MS), the mixture was diluted with ethyl acetate, washed successively with water, brine, dried over Na₂SO₄, filtered and concentrated in vacuo. The crude material was purified by silica gel column chromatography (100% EtOAc, then gradient 0-10% MeOH:EtOAc) then C18 column chromatography (gradient 5-90% MeCN+0.1% HCOOH:H₂O) to afford (S)—N-(3-methoxy-4-(2-methylpyridin-4-yl)phenyl)-8-methyl-7-phenyl-7,8-dihydro-6H-pyrimido[5,4-b][1,4]oxazin-2-amine (36.0 mg, 25%) as a solid. HPLC analysis on a chiral stationary phase (ChiralPak AD 250×4.6 mm, 40% (iPrOH+0.1% Et₂NH) in (hexane+0.1% Et₂NH), 1.0 mLmin⁻¹, DAD 254 nm) t$_r$=3.78 min. ¹H NMR (CDCl₃, 400 MHz): δ 8.47 (d, J=5.2 Hz, 1H), 7.67 (s, 1H), 7.64 (d, J=2.0 Hz, 1H), 7.43-7.33 (m, 5H), 7.31 (d, J=5.2 Hz, 1H), 7.28 (s, J=6.8 Hz, 1H), 7.24-7.20 (m, 2H), 7.12 (dd, J=8.3, 2.0 Hz, 1H), 4.57 (t, J=3.5 Hz, 1H), 4.26 (dd, J=11.1, 3.3 Hz, 1H), 4.15 (dd, J=11.1, 3.9 Hz, 1H), 3.86 (s, 3H), 3.13 (s, 3H), 2.59 (s, 3H); LRMS (ESpos) calcd for C₂₆H₂₅N₅O₂ [M+H]+: 440.20. found: 440.60.

Example 22

Synthesis of (R)-2-chloro-8-methyl-7-phenyl-7,8-dihydro-6H-pyrimido[5,4-b][1,4]oxazine

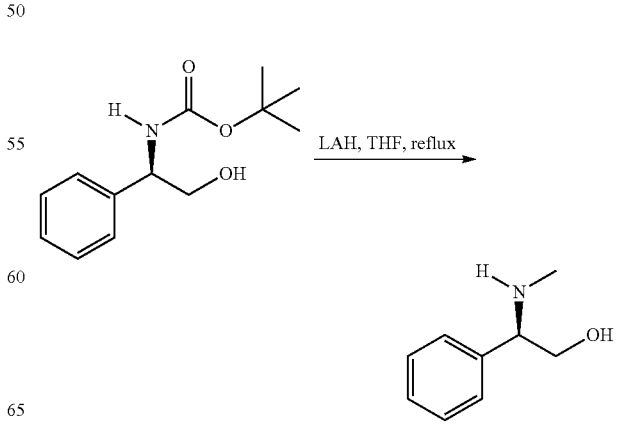

Synthesis of (R)-2-(methylamino)-2-phenylethanol

To a dry flask under nitrogen was charged with LAH (943 mg, 24.9 mmol), was added tetrahydrofuran (THF) (40 mL) and (R)-tert-butyl 2-hydroxy-1-phenylethylcarbamate (2.95 g, 12.4 mmol). The reaction mixture was heated to reflux for 16 h. When the reaction was shown to be complete by LC/MS, a 10% NaOH aqueous solution was added slowly at 0° C. until no more gas evolution was observed. The reaction mixture was stirred at RT for 15 minutes and $Na_2SO_4$ was added. The reaction was vigorously stirred for 15 min, filtered and washed with THF. The volatile components were evaporated to afford (R)-2-(methylamino)-2-phenylethanol as a light yellow gum which solidifies upon standing (1.85 g, 98%). $^1$H NMR (CDCl$_3$, 400 MHz): δ 7.38-7.33 (m, 2H), 7.31-7.26 (m, 3H), 3.72 (dd, J=10.4, 4.4 Hz, 1H), 3.65 (dd, J=8.3, 4.4 Hz, 1H), 3.55 (dd, J=10.4, 8.3 Hz, 1H), 2.35 (s, 3H).

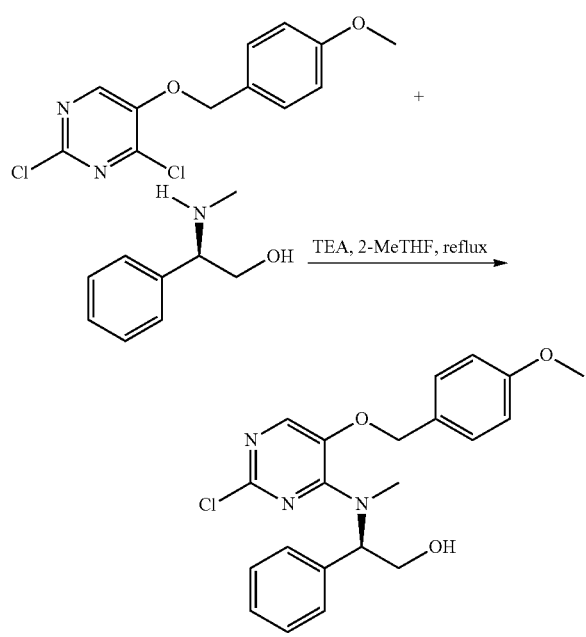

Synthesis of (R)-2-((2-chloro-5-(4-methoxybenzyloxy)pyrimidin-4-yl)(methyl)amino)-2-phenylethanol To a mixture of 2,4-dichloro-5-(4-methoxybenzyloxy)pyrimidine (1.2 g, 4.21 mmol) and (R)-2-(methylamino)-2-phenylethanol (0.67 g, 4.42 mmol) in 2-methyl tetrahydrofuran (10 mL) was added triethylamine (1.5 mL, 10.5 mmol). The reaction mixture was stirred at reflux for 16 h. The reaction was diluted with ethyl acetate, washed twice with water, brine, dried over $Na_2SO_4$, filtered and concentrated. The crude material was purified by silica gel column chromatography (gradient 10-80% EtOAc:hexanes) to afford (R)-2-((2-chloro-5-(4-methoxybenzyloxy)pyrimidin-4-yl)(methyl)amino)-2-phenylethanol as a yellow gummy solid (852 mg, 51%). $^1$H NMR (CDCl$_3$, 400 MHz): δ 7.80 (s, 1H), 7.35-7.27 (m, 3H), 7.22 (dd, J=14.3, 7.9 Hz, 4H), 6.88-6.84 (m, 2H), 6.09 (dd, J=8.9, 5.6 Hz, 1H), 4.96 (s, J=11.1 Hz, 2H), 4.22-4.15 (m, 2H), 3.80 (s, 3H), 2.93 (s, 3H), 2.15 (s, 1H); LRMS (ESpos) calcd for $C_{21}H_{22}ClN_3O_3$ [M+H]+: 400.13. found: 400.53.

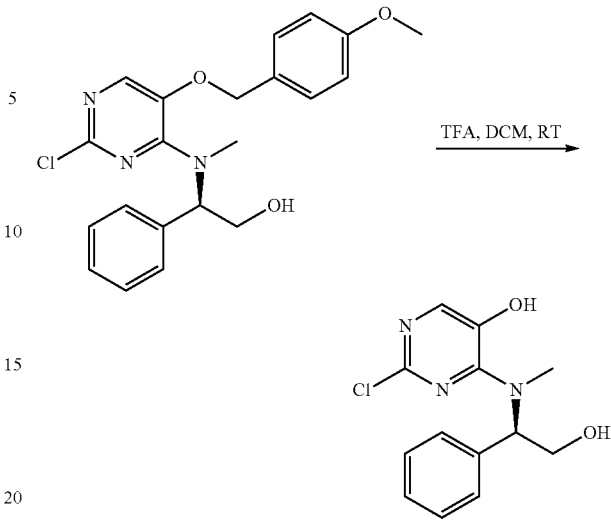

Synthesis of (R)-2-chloro-4-((2-hydroxy-1-phenylethyl)(methyl)amino)pyrimidin-5-ol To a mixture of (R)-2-((2-chloro-5-(4-methoxybenzyloxy)pyrimidin-4-yl)(methyl)amino)-2-phenylethanol (850 mg, 2.13 mmol) at 0° C. in dichloromethane (13.5 mL) was added trifluoroacetic acid (6.5 mL). When the reaction was shown to be complete by LC/MS, the mixture was concentrated to dryness and co-evaporated several times with toluene. The crude material was partitioned between ethyl acetate and a $NaHCO_3$ solution. The layers were separated and the aqueous layer was extracted with ethyl acetate twice. The combined organic layers were dried over $Na_2SO_4$, filtered and concentrated in vacuo. The residue was triturated in DCM:hexanes mixture, filtered and dried in vacuo to afford (R)-2-chloro-4-((2-hydroxy-1-phenylethyl)(methyl)amino)pyrimidin-5-ol as a white solid (327 mg, 55%). $^1$H NMR (CDCl$_3$, 400 MHz): δ 7.83 (s, 1H), 7.33 (dq, J=14.2, 7.0 Hz, 4H), 7.11 (d, J=7.1 Hz, 2H), 5.71 (d, J=10.9 Hz, 1H), 4.36 (t, J=10.7 Hz, 1H), 4.27 (dd, J=10.7, 3.8 Hz, 1H), 3.42 (s, 1H), 2.72 (s, 3H); LRMS (ESpos) calcd for $C_{13}H_{14}ClN_3O_2$ [M+H]+: 280.08. found: 280.46.

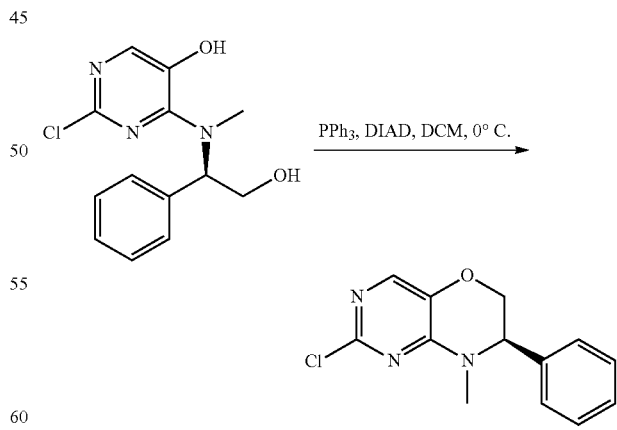

Synthesis of (R)-2-chloro-8-methyl-7-phenyl-7,8-dihydro-6H-pyrimido[5,4-b][1,4]oxazine To a mixture of (R)-2-chloro-4-((2-hydroxy-1-phenylethyl)(methyl)amino)pyrimidin-5-ol (325 mg, 1.16 mmol)

and triphenylphosphine (335 mg, 1.28 mmol) at 0° C. in dichloromethane (11 mL) was added DIAD (0.25 mL, 1.28 mmol) drop-wise. When the reaction was shown to be complete by LC/MS, the mixture was concentrated to dryness. The crude material was purified by silica gel column chromatography (gradient 0-70% methyl tert-butylether (MTBE):hexanes) to afford (R)-2-chloro-8-methyl-7-phenyl-7,8-dihydro-6H-pyrimido[5,4-b][1,4]oxazine as a colourless oil (0.13 g, 43%). $^1$H NMR (CDCl$_3$, 400 MHz): δ 7.71 (s, 1H), 7.41-7.34 (m, 3H), 7.17 (dd, J=7.7, 1.6 Hz, 2H), 4.57 (t, J=3.6 Hz, 1H), 4.27 (dd, J=11.2, 3.3 Hz, 1H), 4.18 (dd, J=11.2, 4.0 Hz, 1H), 3.08 (s, 3H); LRMS (ESpos) calcd for C$_{13}$H$_{12}$ClN$_3$O [M+H]+: 262.07. found: 262.42.

Example 22A

Synthesis of (R)—N-(3-methoxy-4-(4-methyl-1H-imidazol-1-yl)phenyl)-8-methyl-7-phenyl-7,8-dihydro-6H-pyrimido[5,4-b][1,4]oxazin-2-amine

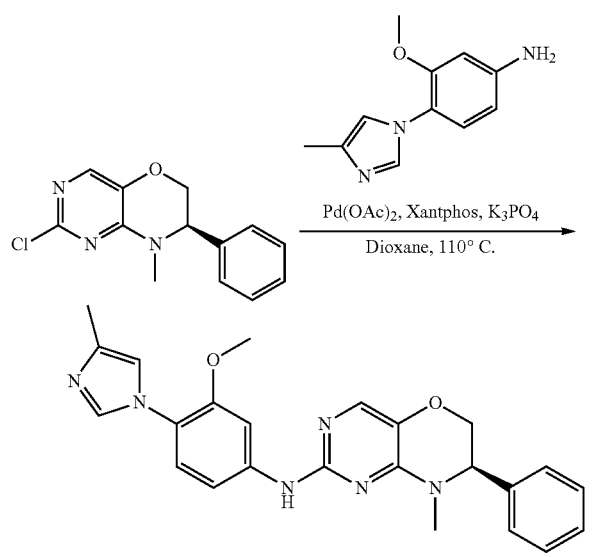

Synthesis of (R)—N-(3-methoxy-4-(4-methyl-1H-imidazol-1-yl)phenyl)-8-methyl-7-phenyl-7,8-dihydro-6H-pyrimido[5,4-b][1,4]oxazin-2-amine To a mixture of (R)-2-chloro-8-methyl-7-phenyl-7,8-dihydro-6H-pyrimido[5,4-b][1,4]oxazine (99 mg, 0.38 mmol), K$_3$PO$_4$ (201 mg, 0.955 mmol) and 3-methoxy-4-(4-methyl-1H-imidazol-1-yl)aniline (85 mg, 0.420 mmol) under N$_2$ in degassed dioxane (3.8 mL) was added a premixed solution of Xantphos (44.0 mg, 0.076 mmol) and Pd(OAc)$_2$ (8.5 mg, 0.038 mmol) in dioxane. The reaction mixture was heated to 110° C. and stirred for 16 h. When the reaction was shown to be complete by LC/MS, the mixture was diluted with ethyl acetate, washed successively with water, brine, dried over Na$_2$SO$_4$, filtered and concentrated in vacuo. The crude material was purified by silica gel column chromatography (100% EtOAc, then gradient 0-10% MeOH:EtOAc) then C18 column chromatography (gradient 5-90% MeCN+0.1% HCOOH:H$_2$O) to afford (R)—N-(3-methoxy-4-(4-methyl-1H-imidazol-1-yl)phenyl)-8-methyl-7-phenyl-7,8-dihydro-6H-pyrimido[5,4-b][1,4]oxazin-2-amine as a solid (46.0 mg, 28%). HPLC analysis on a chiral stationary phase (ChiralPak OD 250×4.6 mm, 40% (iPrOH+0.1% Et$_2$NH) in (hexane+0.1% Et$_2$NH), 1.0 mL·min$^{-1}$, DAD 254 nm) t$_r$=14.60 min. $^1$H NMR (CDCl$_3$, 400 MHz): δ 7.69 (d, J=2.2 Hz, 1H), 7.68 (s, 1H), 7.61 (d, J=1.2 Hz, 1H), 7.42-7.33 (m, 3H), 7.24-7.20 (m, 2H), 7.13 (d, J=8.5 Hz, 1H), 7.08-7.01 (m, 2H), 6.86 (s, 1H), 4.56 (t, J=3.6 Hz, 1H), 4.26 (dd, J=11.1, 3.3 Hz, 1H), 4.15 (dd, J=11.1, 4.0 Hz, 1H), 3.84 (s, 3H), 3.11 (s, 3H), 2.29 (d, J=0.8 Hz, 3H); LRMS (ESpos) calcd for C$_{24}$H$_{24}$N$_6$O$_2$[M+H]+: 429.20. found: 429.57.

Example 22B

Synthesis of (R)—N-(3-methoxy-4-(2-methylpyridin-4-yl)phenyl)-8-methyl-7-phenyl-7,8-dihydro-6H-pyrimido[5,4-b][1,4]oxazin-2-amine

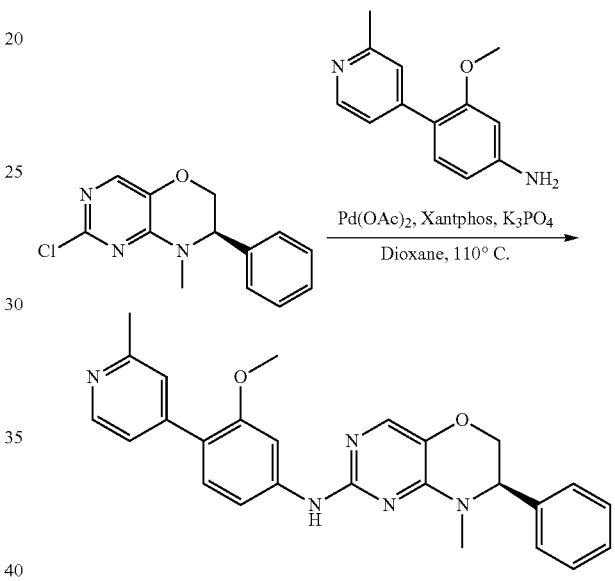

Synthesis of (R)—N-(3-methoxy-4-(2-methylpyridin-4-yl)phenyl)-8-methyl-7-phenyl-7,8-dihydro-6H-pyrimido[5,4-b][1,4]oxazin-2-amine To a mixture of (R)-2-chloro-8-methyl-7-phenyl-7,8-dihydro-6H-pyrimido[5,4-b][1,4]oxazine (28 mg, 0.325 mmol), K$_3$PO$_4$ (45.4 mg, 0.214 mmol) and 3-methoxy-4-(2-methylpyridin-4-yl)aniline (25.2 mg, 0.118 mmol) under N$_2$ in degassed dioxane (1.1 mL) was added a premixed solution of Xantphos (12.4 mg, 0.02 mmol) and Pd(OAc)$_2$ (2.4 mg, 0.032 mmol) in dioxane. The reaction mixture was heated to 110° C. and stirred for 16 h. When the reaction was shown to be completed by LC/MS, the mixture was diluted with ethyl acetate, washed successively with water, brine, dried over Na$_2$SO$_4$, filtered and concentrated in vacuo. The crude material was purified by silica gel column chromatography (100% EtOAc, then gradient 0-10% MeOH:EtOAc) and C18 column chromatography (gradient 5-90% MeCN+0.1% HCOOH:H$_2$O) to afford (R)—N-(3-methoxy-4-(2-methylpyridin-4-yl)phenyl)-8-methyl-7-phenyl-7,8-dihydro-6H-pyrimido[5,4-b][1,4]oxazin-2-amine as a solid (11.4 mg, 24%). HPLC analysis on a chiral stationary phase (ChiralPak AD 250×4.6 mm, 40% (iPrOH+0.1% Et$_2$NH) in (hexane+0.1% Et$_2$NH), 1.0 mL·min$^{-1}$, DAD 254 nm) t$_r$=9.70 min. $^1$H NMR (CDCl$_3$, 400 MHz): δ 8.47 (d, J=5.2 Hz, 1H), 7.67 (s, 1H), 7.64 (d, J=2.0 Hz, 1H), 7.43-7.33 (m, 5H), 7.31 (d, J=5.2 Hz, 1H), 7.28 (s, J=6.8 Hz, 1H), 7.24-7.20 (m, 2H), 7.12 (dd, J=8.3, 2.0 Hz, 1H), 4.57 (t, J=3.5 Hz, 1H), 4.26 (dd, J=11.1, 3.3 Hz, 1H), 4.15 (dd, J=11.1, 3.9 Hz, 1H), 3.86 (s, 3H), 3.13 (s, 3H), 2.59 (s, 3H); LRMS (ESpos) calcd for $C_{26}H_{25}N_5O_2$ [M+H]+: 440.20. found: 440.50.

Example 23

Synthesis of 7-(3, 5-difluorophenyl)-8-methyl-N-(4-(4-methyl-1H-imidazol-1-yl) phenyl)-7, 8-dihydro-6H-pyrimido [5, 4-b] [1, 4] oxazin-2-amine

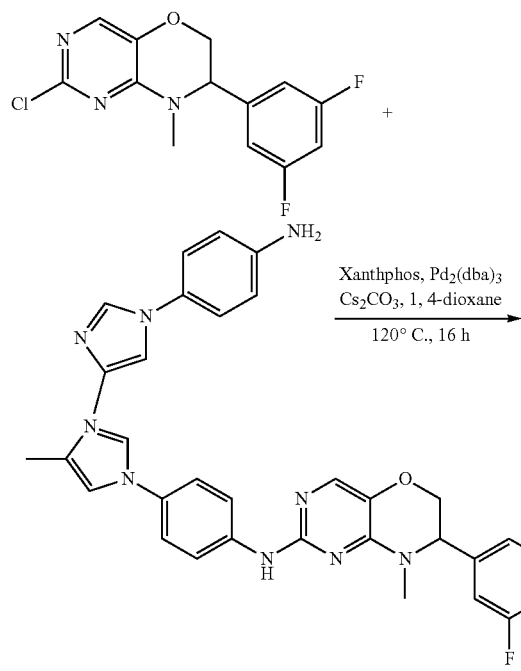

Synthesis of 7-(3, 5-difluorophenyl)-8-methyl-N-(4-(4-methyl-1H-imidazol-1-yl) phenyl)-7, 8-dihydro-6H-pyrimido [5, 4-b] [1, 4] oxazin-2-amine To a dry vial was added a suspension of Pd$_2$(dba)$_3$ (7 mg, 0.008 mmol) and Xantphos (14 mg, 0.02 mmol) in 1, 4-dioxane (0.25 mL). The suspension was degassed, heated to 120° C. and stirred for 3 min. A mixture of 2-chloro-7-(3, 5-difluorophenyl)-8-methyl-7, 8-dihydro-6H-pyrimido [5, 4-b] [1, 4] oxazine (50 mg, 0.16 mmol), 4-(4-methyl-1H-imidazol-1-yl) aniline (58 mg, 0.33 mmol) and cesium carbonate (76 mg, 0.02 mmol) in 1, 4-dioxane (0.25 mL) was degassed and the catalyst premix was added. The reaction mixture was heated to 120° C. and stirred for 16 h in a sealed tube. After consumption of the starting material (monitored by TLC and LCMS), the mixture was diluted with water (10 mL) and extracted with CH$_2$Cl$_2$ (2×10 mL). The combined organic extracts were washed with brine (20 mL), dried over sodium sulfate, filtered and concentrated in vacuo. The crude material was purified by preparative HPLC [acentis-C18 (250×21 2 mm×10 um) (30 mg loading; CH$_3$CN; 0.05% Aq TFA (0.01/95, 2/95, 3/80, 15/65, 15.1/0, 25/0, 35/95) as the mobile phase with a Flow rate=15 mL/min] to afford 7-(3, 5-difluorophenyl)-8-methyl-N-(4-(4-methyl-1H-imidazol-1-yl) phenyl)-7, 8-dihydro-6H-pyrimido [5, 4-b] [1, 4] oxazin-2-amine (20 mg, 27%) as an off-white solid. $^1$H-NMR (CD$_3$OD, 400 MHz): δ 7.89 (s, 1H), 7.79 (d, 2H), 7.60 (s, 1H), 7.40 (d, 2H), 7.19 (s, 1H), 6.91-6.80 (m, 3H), 4.73 (s, 1H), 4.20 (s, 2H), 3.13 (s, 3H), 2.21 (s, 3H); Mass (ESI): 435.6 [M+1]; LC-MS: 435.6 (M+1); (column; X-Select CSH C-18 (50×3.0 mm, 3.5 μm); RT 2.76 min 0.05% Aq TFA: ACN; 0.80 mL/min); UPLC: (column; Acquity BEH C-18 50×2.1 mm, 1.7 μm); RT 1.55 min. ACN: 0.025% Aq TFA; 0.5 mL/min. TLC: 10% MeOH:CH$_2$Cl$_2$ (R$_f$; 0.3).

Racemic compound of Example 23 was separated using a Chiralpak IA (250×20 mm, 5 μm (25 mg loading; 0.1% DEA in n-hexane: CH$_2$Cl$_2$:MeOH (50:50); (75:25) as the mobile phase) to provide the compound of Example 23A (Fraction I (−)) and the compound of Example 23B (Fraction II (+)).

Example 23A

Synthesis of (−)-7-(3, 5-difluorophenyl)-8-methyl-N-(4-(4-methyl-1H-imidazol-1-yl) phenyl)-7, 8-dihydro-6H-pyrimido [5, 4-b] [1, 4] oxazin-2-amine

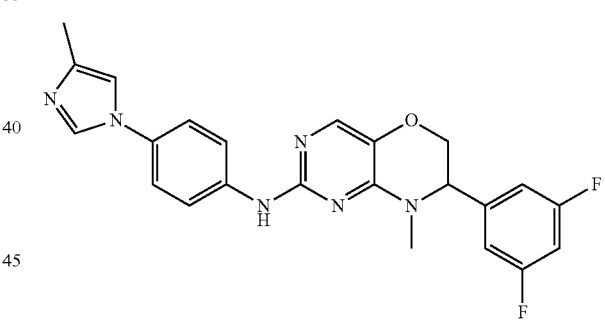

The compound of Example 23A was produced as described in Example 23. Analytical data for product Fraction I (−): $^1$H-NMR (CD$_3$OD, 400 MHz): δ 7.89 (s, 1H), 7.79 (d, 2H), 7.59 (s, 1H), 7.39 (d, 2H), 7.19 (s, 1H), 6.94-6.82 (m, 3H), 4.75 (s, 1H), 4.20 (d, 2H), 3.15 (s, 3H), 2.23 (s, 3H); Mass (ESI): 435.4 [M+1]; LC-MS: 434.9 (M+1); (column; X-Select CSH C-18 (50×3.0 mm, 3.5 μm); RT 2.32 min. 0.05% Aq TFA: ACN; 0.80 ml/min); UPLC (column; Acquity BEH C-18, 50×2.1 mm, 1.7 μm); RT 1.50 min. ACN: 0.025% TFA (Aq); 0.50 ml/min; Chiral HPLC: RT=18.54 min (CHIRALPAK-IA (250×4.6 mm, 5 μm; mobile phase (A) 0.1% DEA in n-hexane (B) CH$_2$Cl$_2$: MeOH (50:50) (A:B: 75:25; flow Rate: 1.0 mL/min); Optical rotation $[α]_D^{20.00}$: −137.37 (c=0.25, DCM).

Example 23B

Synthesis of (+)-7-(3, 5-difluorophenyl)-8-methyl-N-(4-(4-methyl-1H-imidazol-1-yl) phenyl)-7, 8-dihydro-6H-pyrimido [5, 4-b] [1, 4] oxazin-2-amine

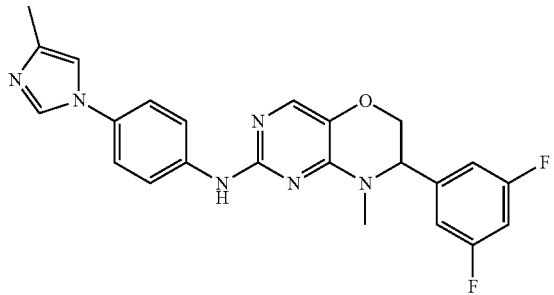 [SMILES: Cc1cn(-c2ccc(Nc3ncc4c(n3)N(C)C(c3cc(F)cc(F)c3)CO4)cc2)cn1]

The compound of Example 23B was produced as described in Example 23. Analytical data for product Fraction II (+): $^1$H-NMR (CD$_3$OD, 400 MHz): δ 7.89 (s, 1H), 7.79 (d, 2H), 7.59 (s, 1H), 7.39 (d, 2H), 7.19 (s, 1H), 6.94-6.82 (m, 3H), 4.75 (s, 1H), 4.20 (d, 2H), 3.15 (s, 3H), 2.23 (s, 3H); Mass (ESI): 435.4 [M+1]; LC-MS: 434.9 (M+1); (column; X-Select CSH C-18 (50×3.0 mm, 3.5 µm); RT 2.33 min. 0.05% Aq TFA: ACN; 0.80 ml/min); UPLC (column; Acquity BEH C-18, 50×2.1 mm, 1.7 µm); RT 1.51 min. ACN: 0.025% TFA (Aq); 0.50 ml/min; Chiral HPLC: RT=21.64 min (CHIRALPAK-IA (250×4.6 mm, 5 µm; mobile phase (A) 0.1% DEA in n-hexane (B) CH$_2$Cl$_2$:MeOH (50:50) (A:B: 75:25; flow Rate: 1.0 mL/min); Optical rotation $[α]_D^{20.01}$: +121.55 (c=0.25, DCM).

Example 24

Synthesis of 8-methyl-N-(4-(2-methylpyridin-4-yl) phenyl)-7-phenyl-7, 8-dihydro-6H-pyrimido [5, 4-b] [1, 4] oxazin-2-amine

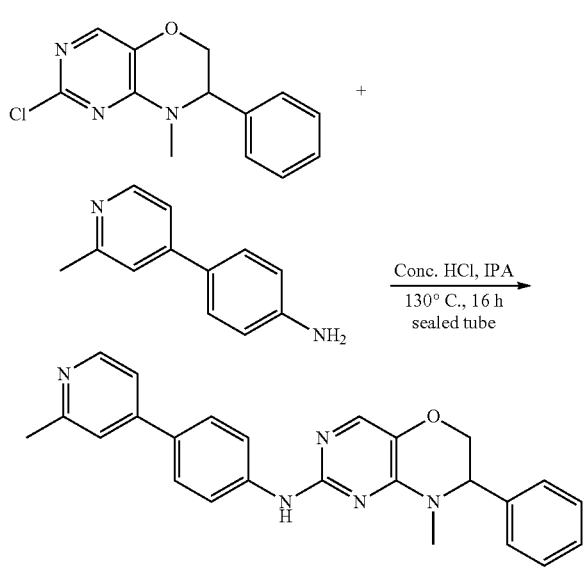

Synthesis of 8-methyl-N-(4-(2-methylpyridin-4-yl) phenyl)-7-phenyl-7, 8-dihydro-6H-pyrimido [5, 4-b] [1, 4] oxazin-2-amine To a stirred solution of 2-chloro-8-methyl-7-phenyl-7, 8-dihydro-6H-pyrimido [5, 4-b] [1, 4] oxazine (50 mg, 0.19 mmol) in isopropanol (0.5 mL) under an argon atmosphere were added 4-(2-methylpyridin-4-yl) aniline (70 mg, 0.38 mmol) and concentrated hydrochloric acid (catalytic amount) at room temperature. The reaction mixture was stirred at 130° C. for 16 h in a sealed tube. After completion of reaction (monitored by TLC), the reaction was diluted with a saturated sodium bicarbonate solution (30 mL) and extracted with EtOAc (3×25 mL). The combined organic extracts were dried over sodium sulfate, filtered and concentrated in vacuo. The crude material was purified by silica gel column chromatography using 2% MeOH:CH$_2$Cl$_2$ to afford 8-methyl-N-(4-(2-methylpyridin-4-yl) phenyl)-7-phenyl-7, 8-dihydro-6H-pyrimido [5, 4-b] [1, 4] oxazin-2-amine (15 mg, 19%) as an off-white solid. $^1$H-NMR (CD$_3$OD, 400 MHz): δ 8.37-8.36 (m, 1H), 7.81 (d, 2H), 7.69 (d, 2H), 7.58-7.56 (m, 2H), 7.50-7.49 (m, 1H), 7.40-7.37 (m, 2H), 7.34-7.31 (m, 1H), 7.25 (d, 2H), 4.71-4.69 (m, 1H), 4.27-4.16 (m, 2H), 3.13 (s, 3H), 2.57 (s, 3H); Mass (ESI): 410.4 [M+1]; LC-MS: 410.4 (M+1); (column; X select CSH C-18 (50×3.0 mm, 3.5 µm); RT 3.07 min. 0.05% Aq TFA: ACN; 0.80 mL/min); UPLC: (column; Acquity UPLC BEH C-18 2.1×50 mm, 1.7 µm); RT 1.58 min. ACN: 0.025% TFA (Aq); 0.50 mL/min. TLC: 5% MeOH:CH$_2$Cl$_2$ (R$_f$: 0.2).

Racemic compound of Example 24 was separated using a Chiralpak IA column (250×4.6 mm, 5 µm; mobile phase (A) 0.1% DEA in n-hexane (B) CH$_2$Cl$_2$:MeOH (20:80) (A:B: 80:20) to provide the compound of Example 24A (Fraction I (+)) and the compound of Example 24B (Fraction II (−)).

Example 24A

Synthesis of (+)-8-methyl-N-(4-(2-methylpyridin-4-yl) phenyl)-7-phenyl-7, 8-dihydro-6H-pyrimido [5, 4-b] [1, 4] oxazin-2-amine

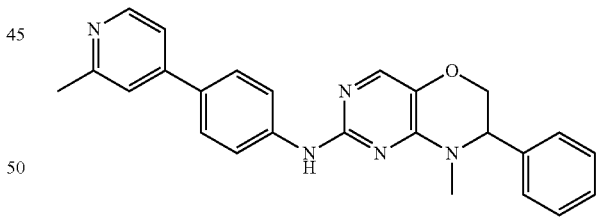

The compound of Example 24A was produced as described in Example 24. Analytical data for Fraction I (+): $^1$H NMR (CD$_3$OD, 400 MHz): δ 8.38 (d, 1H), 7.80 (d, 2H), 7.68 (d, 2H), 7.56 (s, 2H), 7.48 (d, 1H), 7.40-7.35 (m, 3H), 7.24 (d, 2H), 4.70 (s, 1H), 4.26-4.17 (m, 2H), 3.14 (s, 3H), 2.60 (s, 3H); Mass (ESI): 410.6 [M+1]; LC-MS: 410.5 (M+1); (column; X-Select CSH C-18 (50×3.0 mm, 3.5 µm); RT 2.80 min. 0.05% Aq TFA: ACN; 0.80 ml/min); UPLC: (column; Acquity BEH C-18, 50×2.1 mm, 1.7 µm); RT 1.60 min. ACN: 0.025% TFA (Aq); 0.50 ml/min. Chiral HPLC: RT=16.14 min (Chiralpak IC (250×4.6 mm, 5 µm; mobile phase (A) 0.1% DEA in n-hexane (B) DCM:MeOH (50:50); flow Rate: 1.0 mL/min); Optical rotation $[α]_D^{19.96}$: +206.38 (c=0.25, DCM); TLC: 5% MeOH:CH$_2$Cl$_2$ (R$_f$: 0.3).

Example 24B

Synthesis of (−)-8-methyl-N-(4-(2-methylpyridin-4-yl) phenyl)-7-phenyl-7, 8-dihydro-6H-pyrimido [5, 4-b] [1, 4] oxazin-2-amine

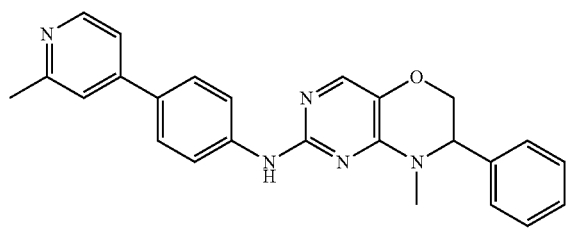 [SMILES: Cc1cc(-c2ccc(Nc3ncc4c(n3)N(C)C(c3ccccc3)CO4)cc2)ccn1]

The compound of Example 24B was produced as described in Example 24. Analytical data for Fraction II (−): $^1$H NMR (CD$_3$OD, 400 MHz): δ 8.38 (d, 1H), 7.82 (d, 2H), 7.70 (d, 2H), 7.54 (s, 2H), 7.50 (d, 1H), 7.36 (d, 2H), 7.32 (d, 1H), 7.24 (d, 2H), 4.70 (s, 1H), 4.26-4.16 (d, 2H), 3.12 (s, 3H), 2.50 (s, 3H). Mass (ESI): 410.6 [M+1]; LC-MS: 410.5 (M+1); (column; X-select CSH C-18 (50×3.0 mm, 3.5 µm); RT 2.80 min. 0.05% Aq TFA: ACN; 0.80 ml/min); UPLC: (column; Acquity BEH C-18, 50×2.1 mm, 1.7 µm); RT 1.60 min. ACN: 0.025% TFA (Aq); 0.50 ml/min. Chiral HPLC: RT=17.89 min (Chiralpak IC (250×4.6 mm, 5 µm; mobile phase (A) 0.1% DEA in n-hexane (B) DCM:MeOH (50:50); flow Rate: 1.0 mL/min); Optical rotation [α]$_D^{19.97}$: −195.32 (c=0.25, DCM); TLC: 5% MeOH:CH$_2$Cl$_2$ (R$_f$: 0.3).

Example 25

Synthesis of N-(3-fluoro-4-(4-methyl-1H-imidazol-1-yl) phenyl)-8-methyl-7-phenyl-7, 8-dihydro-6H-pyrimido [5, 4-b] [1, 4] oxazin-2-amine

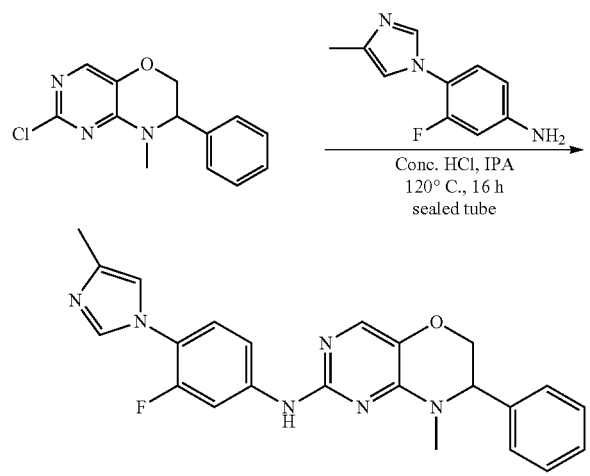

Synthesis of N-(3-fluoro-4-(4-methyl-1H-imidazol-1-yl) phenyl)-8-methyl-7-phenyl-7, 8-dihydro-6H-pyrimido [5, 4-b] [1, 4] oxazin-2-amine To a stirred solution of 2-chloro-8-methyl-7-phenyl-7, 8-dihydro-6H-pyrimido [5, 4-b] [1, 4] oxazine (100 mg, 0.38 mmol) in isopropanol (1 mL) under an argon atmosphere were added 3-fluoro-4-(4-methyl-1H-imidazol-1-yl) aniline (146 mg, 0.76 mmol) and concentrated hydrochloric acid (catalytic amount) at room temperature. The reaction mixture was stirred at 120° C. for 16 h in a sealed tube. After consumption of the starting material (monitored by TLC), the volatile components were evaporated in vacuo. The residue was basified with a saturated sodium bicarbonate solution (20 mL) and extracted with 10% MeOH: CH$_2$Cl$_2$ (2×20 mL). The combined organic extracts were dried over sodium sulfate, filtered and concentrated in vacuo. The crude material was purified by silica gel column chromatography using 5% MeOH: CH$_2$Cl$_2$ to afford 85 mgs further purified by preparative HPLC [kromasil-C18 (250×21.2 mm×10 um) (65 mg loading; CH$_3$CN; 0.05% Aq TFA (0.01/90, 15/50, 25/10, 35/10) as the mobile phase with a Flow rate=15 mL/min] to afford N-(3-fluoro-4-(4-methyl-1H-imidazol-1-yl) phenyl)-8-methyl-7-phenyl-7, 8-dihydro-6H-pyrimido [5, 4-b] [1, 4] oxazin-2-amine (45 mg, 28%) as a yellow solid. $^1$H-NMR (CD3OD, 400 MHz): δ 9.03 (s, 1H), 8.05-8.02 (m, 1H), 7.62 (s, 1H), 7.57-7.53 (m, 3H), 7.43-7.34 (m, 3H), 7.28-7.27 (m, 2H), 4.86-4.84 (s, 1H), 4.35-4.24 (m, 2H), 3.19 (s, 3H), 2.42 (s, 3H); Mass (ESI): 417.3 [M+1]; LC-MS: 417.3 (M+1); (column; X select CSH C-18 (50×3.0 mm, 3.5 µm); RT 3.04 min. 0.05% Aq TFA: ACN; 0.80 mL/min); UPLC: (column; Acquity UPLC BEH C-18 2.1×50 mm, 1.7µ); RT 1.58 min. ACN: 0.025% Aq TFA; 0.5 mL/min. TLC: 5% MeOH:CH$_2$Cl$_2$ (R$_f$: 0.2).

Racemic compound of Example 25 was separated using a Chiralpak IA (250×20 mm, 5 µm (50 mg loading; 0.1% DEA in n-hexane: CH$_2$Cl$_2$:MeOH (50:50); (80:20) as the mobile phase) to provide the compound of Example 25A (Fraction I (+)) and the compound of Example 25B (Fraction II (−)).

Example 25A

Synthesis of (+)-N-(3-fluoro-4-(4-methyl-1H-imidazol-1-yl) phenyl)-8-methyl-7-phenyl-7, 8-dihydro-6H-pyrimido [5, 4-b] [1, 4] oxazin-2-amine

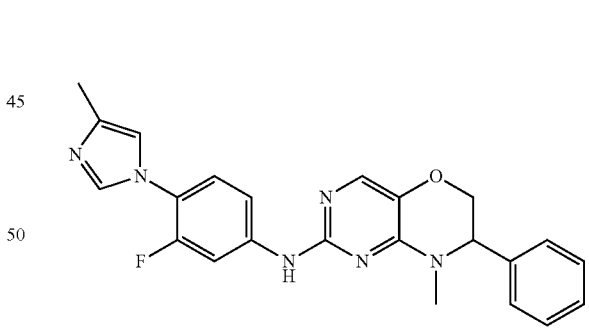

The compound of Example 25A was produced as described in Example 25. Analytical data for Fraction I (+): $^1$H NMR (CD$_3$OD, 400 MHz): δ 8.00-7.98 (m, 1H), 7.75 (s, 1H), 7.58 (s, 1H), 7.41-7.32 (m, 5H), 7.23 (d, 2H), 7.08 (s, 1H), 4.60-4.59 (m, 1H), 4.27-4.20 (m, 2H), 3.10 (s, 3H), 2.22 (s, 3H); (Mass (ESI): 417.7 [M+1]; LC-MS: 417.4 (M+1); (column; X-Select CSH C-18 (50×3.0 mm, 3.5 µm); RT 2.79 min. 0.05% Aq TFA: ACN; 0.80 ml/min); UPLC: (column; Acquity BEH C-18, 50×2.1 mm, 1.7 µm); RT 1.59 min. ACN: 0.025% TFA (Aq); 0.50 ml/min. Chiral HPLC: RT=17.25 min (Chiralpak IA (250×4.6 mm, 5 µm; mobile phase (A) 0.1% DEA in n-hexane: CH$_2$Cl$_2$:EtOH (50:50);

Example 25B

Synthesis of (−)-N-(3-fluoro-4-(4-methyl-1H-imidazol-1-yl) phenyl)-8-methyl-7-phenyl-7, 8-dihydro-6H-pyrimido [5, 4-b] [1, 4] oxazin-2-amine

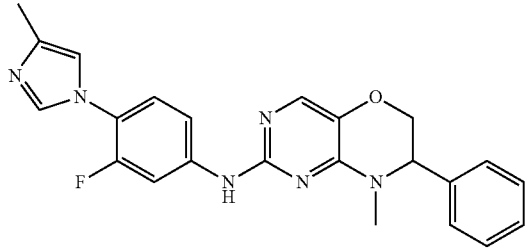 [SMILES: Cc1cn(-c2ccc(Nc3ncc4c(n3)N(C)C(c3ccccc3)CO4)cc2F)cn1]

The compound of Example 25B was produced as described in Example 25. Analytical data for Fraction II (−): $^1$H NMR (CD$_3$OD, 400 MHz): δ 8.00-7.98 (m, 1H), 7.79 (s, 1H), 7.59 (s, 1H), 7.40-7.30 (m, 5H), 7.24 (d, 2H), 7.08 (s, 1H), 4.71-4.69 (m, 1H), 4.25-4.17 (m, 2H), 3.11 (s, 3H), 2.22 (s, 3H); Mass (ESI): 417.7 [M+1]; LC-MS: 417.4 (M+1); (column; X-select CSH C-18 (50×3.0 mm, 3.5 μm); RT 2.79 min. 0.05% Aq TFA: ACN; 0.80 ml/min); UPLC: (column; Acquity BEH C-18, 50×2.1 mm, 1.7 μm); RT 1.58 min. ACN: 0.025% TFA (Aq); 0.50 ml/min. Chiral HPLC: RT=22.95 min (Chiralpak IA (250×4.6 mm, 5 μm; mobile phase (A) 0.1% DEA in n-hexane: CH$_2$Cl$_2$:MeOH (50:50); flow Rate: 1.0 mL/min); Optical rotation [α]$_D^{20.01}$: −151.16 (c=0.25, DCM); TLC: 5% MeOH:CH$_2$Cl$_2$ (R$_f$: 0.2).

Example 26

Synthesis of 8-methyl-N-(4-(4-methyl-1H-imidazol-1-yl) phenyl)-7-phenyl-7, 8-dihydro-6H-pyrimido [5, 4-b] [1, 4] oxazin-2-amine

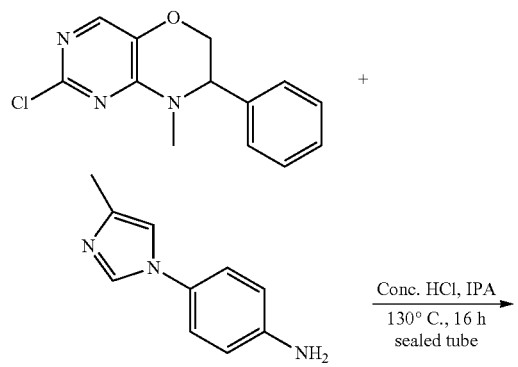

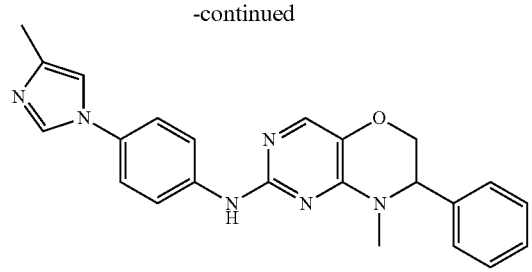

Synthesis of 8-methyl-N-(4-(4-methyl-1H-imidazol-1-yl) phenyl)-7-phenyl-7, 8-dihydro-6H-pyrimido [5, 4-b] [1, 4] oxazin-2-amine To a stirred solution of 2-chloro-8-methyl-7-phenyl-7, 8-dihydro-6H-pyrimido [5, 4-b] [1, 4] oxazine (50 mg, 0.19 mmol) in isopropanol (0.5 mL) under an argon atmosphere were added 4-(4-methyl-1H-imidazol-1-yl) aniline (66 mg, 0.38 mmol) and concentrated hydrochloric acid (catalytic amount) at room temperature. The reaction mixture was stirred at 130° C. for 16 h in a sealed tube. After consumption of the starting material (monitored by TLC), the reaction was diluted with a saturated sodium bicarbonate solution (25 mL) and extracted with EtOAc (3×25 mL). The combined organic extracts were dried over sodium sulfate, filtered and concentrated in vacuo. The crude material was purified by silica gel column chromatography using 2% MeOH:CH$_2$Cl$_2$ to afford 8-methyl-N-(4-(4-methyl-1H-imidazol-1-yl) phenyl)-7-phenyl-7, 8-dihydro-6H-pyrimido [5, 4-b] [1, 4] oxazin-2-amine (20 mg, 26%) as an off-white solid. $^1$H-NMR (CD$_3$OD, 400 MHz): δ 7.89 (s, 1H), 7.78 (d, 2H), 7.50 (s, 1H), 7.40-7.32 (m, 5H), 7.23-7.20 (m, 3H), 4.70-4.68 (m, 1H), 4.23-4.18 (m, 2H), 3.10 (s, 3H), 2.20 (s, 3H); Mass (ESI): 399.3 [M+1]; LC-MS: 399.3 (M+1); (column; X-select C-18 (50×3.0 mm, 3.5 μm); RT 2.98 min 0.05% Aq TFA: ACN; 0.80 mL/min); HPLC: (column; Eclipse XDB C-18 150×4.6 mm, 5.0 μm); RT 7.67 min. ACN: 5 mM Aq NH$_4$OAc; 1.0 mL/min. TLC: 5% MeOH: CH$_2$Cl$_2$ (R$_f$: 0.3).

Racemic compound of Example 26 was separated using a Chiralpak IA (250×20 mm, 5 μm (30 mg loading; A) 0.1% DEA in n-hexane B) CH$_2$Cl$_2$:MeOH (50:50) (A:B: 75:25) to provide the compound of Example 26A (Fraction I (+)) and the compound of Example 26B (Fraction II (−)).

Example 26A

Synthesis of (+)-8-methyl-N-(4-(4-methyl-1H-imidazol-1-yl) phenyl)-7-phenyl-7, 8-dihydro-6H-pyrimido [5, 4-b] [1, 4] oxazin-2-amine

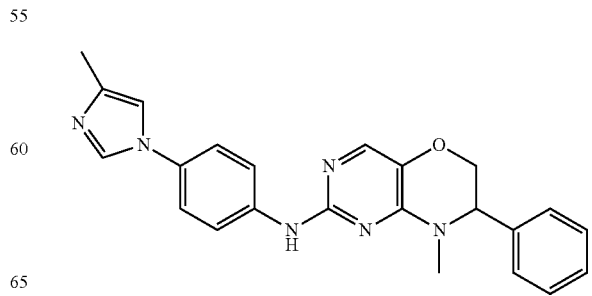

The compound of Example 26A was produced as described in Example 26. Analytical data for Fraction I (+): 1H-NMR (CD3OD, 500 MHz): δ 7.96 (s, 1H), 7.80 (d, 2H), 7.58 (s, 1H), 7.46-7.36 (m, 5H), 7.24 (d, 2H), 7.20 (s, 1H), 4.70-4.68 (m, 1H), 4.23-4.18 (m, 2H), 3.14 (s, 3H), 2.22 (s, 3H); Mass (ESI): 399.4 [M+1]; LC-MS: 399.3 (M+1); (column; X-select CSH C-18 (50×3.0 mm, 3.5 μm); RT 2.64 min. 0.05% Aq TFA: ACN; 0.80 mL/min); HPLC: (column; Eclipse XDB C-18 150×4.6 mm, 5.0 μm); RT 10.43 min. ACN: 5 mM Aq NH4OAc; 1.0 mL/min. Chiral HPLC: RT=15.85 min (Chiralpak IA (250×4.6 mm, 5 μm; mobile phase (A) 0.1% DEA in n-hexane (B) CH2Cl2:MeOH (50:50) (75:25); flow Rate: 1.0 mL/min); Optical rotation [α]$_D^{20.01}$: +117.84 (c=0.25, DCM); TLC: 5% MeOH: CH2Cl2 (R$_f$: 0.3).

Example 26B

Synthesis of (−)-8-methyl-N-(4-(4-methyl-1H-imidazol-1-yl) phenyl)-7-phenyl-7, 8-dihydro-6H-pyrimido [5, 4-b] [1, 4] oxazin-2-amine

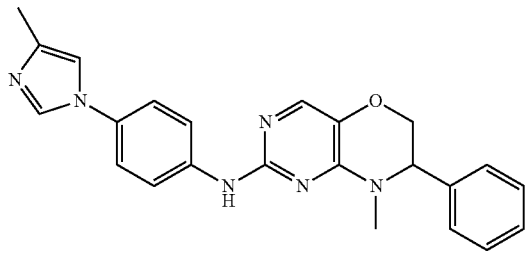 [SMILES: Cc1cn(-c2ccc(Nc3ncc4c(n3)N(C)C(c3ccccc3)CO4)cc2)cn1]

The compound of Example 26B was produced as described in Example 26. Analytical data for Fraction II (−): 1H-NMR (CD3OD, 500 MHz): δ 7.92 (s, 1H), 7.80 (d, 2H), 7.58 (s, 1H), 7.44-7.32 (m, 5H), 7.24 (d, 2H), 7.20 (s, 1H), 4.70-4.68 (m, 1H), 4.23-4.18 (m, 2H), 3.14 (s, 3H), 2.24 (s, 3H); Mass (ESI): 399.4 [M+1]; LC-MS: 399.3 (M+1); (column; X-select C-18 (50×3.0 mm, 3.5 μm); RT 2.64 min 0.05% Aq TFA: ACN; 0.80 mL/min); HPLC: (column; Eclipse XDB C-18 150×4.6 mm, 5.0 μm); RT 10.40 min. ACN: 5 mM Aq NH4OAc; 1.0 mL/min. Chiral HPLC: RT=19.10 min (Chiralpak IA (250×4.6 mm, 5 μm; mobile phase (A) 0.1% DEA in n-hexane (B) CH2Cl2:MeOH (50:50) (75:25); flow Rate: 1.0 mL/min); Optical rotation [α]$_D^{20.01}$: −124.14 (c=0.25, DCM); TLC: 5% MeOH: CH2Cl2 (R$_f$: 0.3).

Example 27

Synthesis of N-(3-fluoro-4-(2-methylpyridin-4-yl) phenyl)-8-methyl-7-phenyl-7, 8-dihydro-6H-pyrimido [5, 4-b] [1, 4] oxazin-2-amine

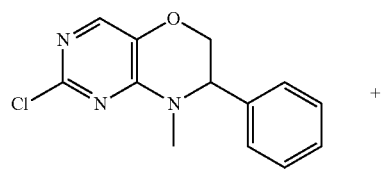

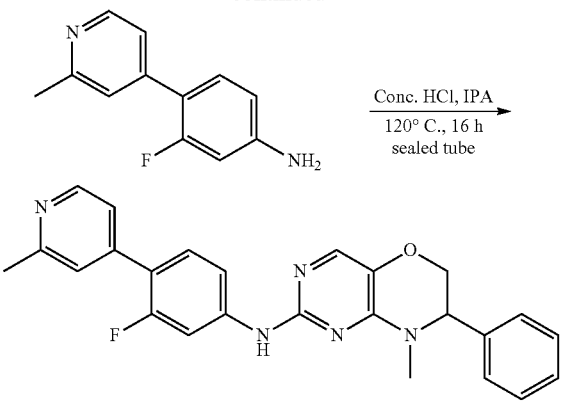

Synthesis of N-(3-fluoro-4-(2-methylpyridin-4-yl) phenyl)-8-methyl-7-phenyl-7, 8-dihydro-6H-pyrimido [5, 4-b] [1, 4] oxazin-2-amine To a stirred solution of 2-chloro-8-methyl-7-phenyl-7, 8-dihydro-6H-pyrimido [5, 4-b] [1, 4] oxazine (100 mg, 0.38 mmol) in isopropanol (1 mL) under an argon atmosphere were added 3-fluoro-4-(2-methylpyridin-4-yl) aniline (155 mg, 0.76 mmol) and concentrated hydrochloric acid (catalytic amount) at room temperature. The reaction mixture was stirred at 120° C. for 16 h in a sealed tube. After completion of reaction (monitored by TLC), the mixture was diluted with water (30 mL) and extracted with EtOAc (2×30 mL). The combined organic extracts were dried over sodium sulfate, filtered and concentrated in vacuo. The crude material was purified by silica gel column chromatography using 0-4% MeOH: CH2Cl2 to afford 90 mgs further purified by preparative HPLC [kromasil-C18 (250×21.2 mm×10 um) (70 mg loading; CH3CN; 0.05% Aq TFA (0.01/90, 15/50, 25/10, 35/10) as the mobile phase with a Flow rate=15 mL/min] to afford N-(3-fluoro-4-(2-methylpyridin-4-yl) phenyl)-8-methyl-7-phenyl-7, 8-dihydro-6H-pyrimido [5, 4-b] [1, 4] oxazin-2-amine (18 mg, 11%) as a yellow solid. 1H-NMR (CD3OD, 400 MHz): δ 8.40-8.39 (m, 1H), 7.93-7.88 (m, 1H), 7.59 (s, 1H), 7.51-7.33 (m, 7H), 7.25 (d, 2H), 4.72-4.70 (m, 1H), 4.24-4.16 (m, 2H), 3.14 (s, 3H), 2.57 (s, 3H); Mass (ESI): 428.4 [M+1]; LC-MS: 428.4 (M+1); (column; X-Select CSH C-18 (50×3.0 mm, 3.5 μm); RT 3.20 min. 0.05% Aq TFA: ACN; 0.80 mL/min); UPLC: (column; Acquity UPLC BEH C-18 2.1×50 mm, 1.7 μm); RT 1.62 min. ACN: 0.025% Aq TFA; 0.50 mL/min. TLC: 5% MeOH:CH2Cl2 (R$_f$: 0.1).

Racemic compound of Example 27 was separated using a Chiralpak IA (250×20 mm, 5 μm (35 mg loading; 0.1% DEA in n-hexane: EtOH (80:20) as the mobile phase to provide the compound of Example 27A (Fraction I (+)) and the compound of Example 27B (Fraction II (−)).

Example 27A

Synthesis of (+)-N-(3-fluoro-4-(2-methylpyridin-4-yl) phenyl)-8-methyl-7-phenyl-7, 8-dihydro-6H-pyrimido [5, 4-b] [1, 4] oxazin-2-amine

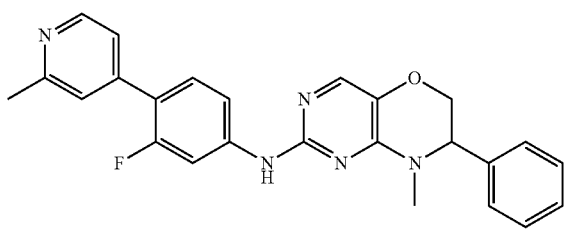 [SMILES: Cc1cc(-c2ccc(Nc3ncc4c(n3)N(C)C(c3ccccc3)CO4)cc2F)ccn1]

The compound of Example 27A was produced as described in Example 27. Analytical data for Fraction I (+): $^1$H NMR (CD$_3$OD, 400 MHz): δ 8.40 (d, 1H), 7.90 (d, 1H), 7.60 (s, 1H), 7.50-7.33 (m, 7H), 7.28 (d, 2H), 4.70 (s, 1H), 4.22-4.17 (m, 2H), 3.12 (s, 3H), 2.60 (s, 3H); (Mass (ESI): 428.6 [M+1]; LC-MS: 428.6 (M+1); (column; X-Select CSH C-18 (50×3.0 mm, 3.5 µm); RT 2.90 min. 0.05% Aq TFA: ACN; 0.80 ml/min); UPLC: (column; Acquity BEH C-18, 50×2.1 mm, 1.7 µm); RT 1.60 min. ACN: 0.025% TFA (Aq); 0.50 ml/min. Chiral HPLC: RT=13.17 min (Chiralpak IA (250×4.6 mm, 5 µm; mobile phase (A) 0.1% DEA in n-hexane: EtOH (75:25); flow Rate: 1.0 mL/min); Optical rotation $[α]_D^{20.02}$: +174.75 (c=0.25, DCM); TLC: 5% MeOH:CH$_2$Cl$_2$ (R$_f$: 0.3).

Example 27B

Synthesis of (−)-N-(3-fluoro-4-(2-methylpyridin-4-yl) phenyl)-8-methyl-7-phenyl-7, 8-dihydro-6H-pyrimido [5, 4-b] [1, 4] oxazin-2-amine

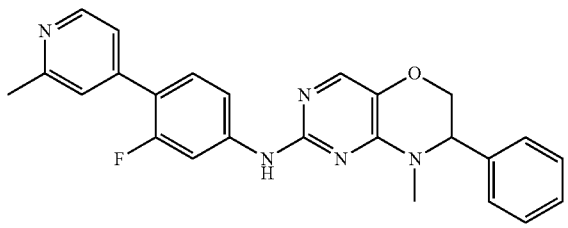 [SMILES: Cc1cc(-c2ccc(Nc3ncc4c(n3)N(C)C(c3ccccc3)CO4)cc2F)ccn1]

The compound of Example 27B was produced as described in Example 27. Analytical data for Fraction II (−): $^1$H NMR (CD$_3$OD, 400 MHz): δ 8.40 (d, 1H), 7.90 (d, 1H), 7.60 (s, 1H), 7.50-7.32 (m, 7H), 7.28 (d, 2H), 4.70 (s, 1H), 4.22-4.17 (m, 2H), 3.12 (s, 3H), 2.60 (s, 3H); Mass (ESI): 428.6 [M+1]; LC-MS: 428.6 (M+1); (column; X-select CSH C-18 (50×3.0 mm, 3.5 µm); RT 2.90 min. 0.05% Aq TFA: ACN; 0.80 ml/min); UPLC: (column; Acquity BEH C-18, 50×2.1 mm, 1.7 µm); RT 1.60 min. ACN: 0.025% TFA (Aq); 0.50 ml/min. Chiral HPLC: RT=16.02 min (Chiralpak IA (250×4.6 mm, 5 µm; mobile phase (A) 0.1% DEA in n-hexane: EtOH (75:25); flow Rate: 1.0 mL/min); Optical rotation $[α]_D^{20.01}$: −170.96 (c=0.25, DCM); TLC: 5% MeOH:CH$_2$Cl$_2$ (R$_f$: 0.3).

Example 28

Synthesis of 7-(3, 5-difluorophenyl)-8-methyl-N-(4-(2-methylpyridin-4-yl) phenyl)-7, 8-dihydro-6H-pyrimido [5, 4-b] [1, 4] oxazin-2-amine

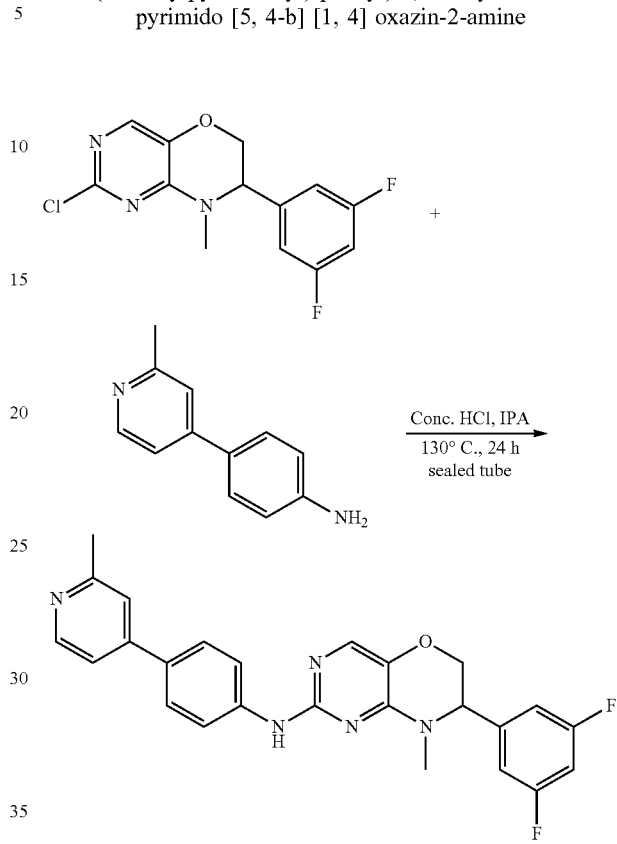

Synthesis of 7-(3, 5-difluorophenyl)-8-methyl-N-(4-(2-methylpyridin-4-yl) phenyl)-7, 8-dihydro-6H-pyrimido [5, 4-b] [1, 4] oxazin-2-amine To a stirred solution of 2-chloro-7-(3, 5-difluorophenyl)-8-methyl-7, 8-dihydro-6H-pyrimido [5, 4-b] [1, 4] oxazine (100 mg, 0.33 mmol) in isopropyl alcohol (1 mL) under an argon atmosphere were added concentrated hydrochloric acid (catalytic amount) and 4-(2-methylpyridin-4-yl) aniline (124 mg, 0.67 mmol) at room temperature. The reaction mixture was stirred at 130° C. for 24 h in a sealed tube. After completion of the reaction (monitored by TLC), the reaction was diluted with a saturated sodium bicarbonate solution (10 mL) and extracted with EtOAc (2×30 mL). The combined organic extracts were dried over sodium sulfate, filtered and concentrated in vacuo. The crude was purified by silica gel column chromatography using 0-5% MeOH:CH$_2$Cl$_2$ to afford 7-(3, 5-difluorophenyl)-8-methyl-N-(4-(2-methylpyridin-4-yl) phenyl)-7, 8-dihydro-6H-pyrimido [5, 4-b] [1, 4] oxazin-2-amine (149 mg, 18%) as an off-white solid. $^1$H-NMR (CD$_3$OD, 400 MHz): δ 8.38 (d, 1H), 7.82 (d, 2H), 7.70 (d, 2H), 7.60 (d, 2H), 7.48 (d, 1H), 6.96-6.89 (m, 3H), 4.78 (s, 1H), 4.21 (d, 2H), 3.19 (s, 3H), 2.60 (s, 3H); Mass (ESI): 446.4 [M+1] LC-MS: 446.5 (M+1); (column; X-Bridge C-18 (50×3.0 mm, 3.5 µm); RT 3.25 min 0.05% Aq TFA: ACN; 0.80 mL/min); HPLC: (column; Acquity BEH C-18 50×2.1 mm, 1.7 µm); RT 1.66 min. ACN: water; 0.50 mL/min. TLC: 5% MeOH:CH$_2$Cl$_2$ (R$_f$: 0.2).

Racemic compound of Example 28 was separated using a Chiralpak-ADH (250×20 mm, 5 µm (35 mg loading; 0.1% DEA in n-hexane: EtOH:MeOH (50:50); (A:B: 75:25) as the mobile phase) to provide the compound of Example 28A (Fraction I (−)) and the compound of Example 28B (Fraction II (+)).

Example 28A

Synthesis of (−)-7-(3, 5-difluorophenyl)-8-methyl-N-(4-(2-methylpyridin-4-yl) phenyl)-7, 8-dihydro-6H-pyrimido [5, 4-b] [1, 4] oxazin-2-amine

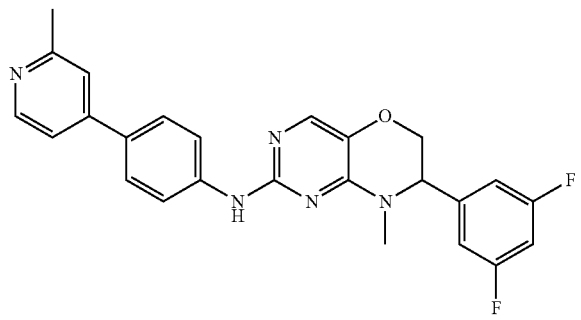 [SMILES: Cc1cc(-c2ccc(Nc3ncc4c(n3)N(C)C(c3cc(F)cc(F)c3)CO4)cc2)ccn1]

The compound of Example 28A was produced as described in Example 28. Analytical data for product Fraction I (−): $^1$H-NMR (CD$_3$OD, 400 MHz): δ 8.37 (d, 1H), 7.81 (d, 2H), 7.68 (d, 2H), 7.60 (s, 1H), 7.57 (s, 1H), 7.48 (d, 1H), 6.93-6.83 (m, 3H), 4.75-4.73 (m, 1H), 4.21 (s, 2H), 3.15 (s, 3H), 2.54 (s, 3H); Mass (ESI): 446.4 [M+1]; LC-MS: 446.4 (M+1); (column; X-Select CSH C-18 (50× 3.0 mm, 3.5 µm); RT 2.95 min. 0.05% Aq TFA: ACN; 0.80 ml/min); UPLC: (column; Acquity UPLC BEH C-18, 2.1× 50 mm, 1.7 µm); RT 1.60 min. ACN: 0.025% TFA (Aq); 0.50 ml/min; Chiral HPLC: RT=17.95 min (CHIRALPAK-AD-H (250×4.6 mm, 5 µm; mobile phase (A) 0.1% DEA in n-hexane (B) EtOH:MeOH (50:50) (A:B: 70:30; flow Rate: 1.0 mL/min); Optical rotation [α]$_D^{20.00}$: −168.86 (c 0.25, DCM).

Example 28B

Synthesis of (+)-7-(3, 5-difluorophenyl)-8-methyl-N-(4-(2-methylpyridin-4-yl) phenyl)-7, 8-dihydro-6H-pyrimido [5, 4-b] [1, 4] oxazin-2-amine

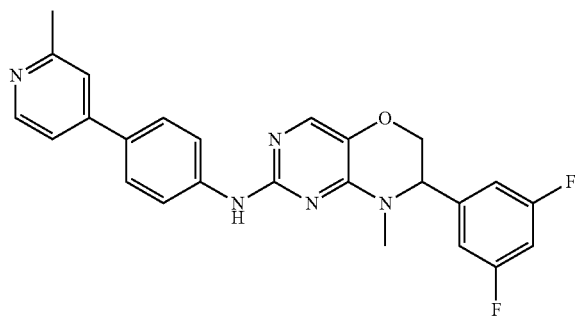 [SMILES: Cc1cc(-c2ccc(Nc3ncc4c(n3)N(C)C(c3cc(F)cc(F)c3)CO4)cc2)ccn1]

The compound of Example 28B was produced as described in Example 28. Analytical data for product Fraction II (+): $^1$H-NMR (CD$_3$OD, 400 MHz): δ 8.37 (d, 1H), 7.81 (d, 2H), 7.68 (d, 2H), 7.60 (s, 1H), 7.57 (s, 1H), 7.48 (d, 1H), 6.93-6.83 (m, 3H), 4.75-4.73 (m, 1H), 4.21 (s, 2H), 3.15 (s, 3H), 2.54 (s, 3H); Mass (ESI): 446.4 [M+1]; LC-MS: 446.3 (M+1); (column; X-Select CSH C-18 (50× 3.0 mm, 3.5 µm); RT 2.94 min. 0.05% Aq TFA: ACN; 0.80 ml/min); UPLC: (column; Acquity UPLC BEH C-18, 2.1× 50 mm, 1.7 µm); RT 1.60 min. ACN: 0.025% TFA (Aq); 0.50 ml/min; Chiral HPLC: RT=24.77 min (CHIRALPAK-AD-H (250×4.6 mm, 5 µm; mobile phase (A) 0.1% DEA in n-hexane (B) EtOH:MeOH (50:50) (A:B: 70:30; flow Rate: 1.0 mL/min); Optical rotation [α]$_D^{20.02}$: +174.17 (c 0.25, DCM).

Example 29

Synthesis of 8-methyl-N-(4-(2-methylpyridin-4-yl) phenyl)-7-(o-tolyl)-7, 8-dihydro-6H-pyrimido [5, 4-b] [1, 4] oxazin-2-amine

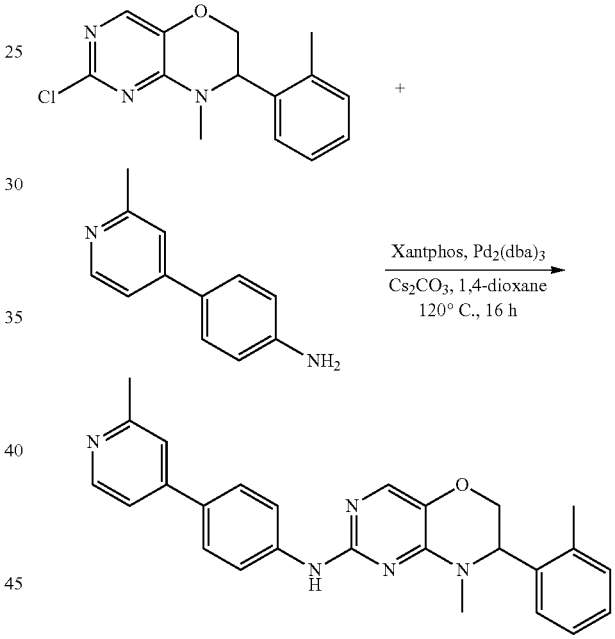

Synthesis of 8-methyl-N-(4-(2-methylpyridin-4-yl) phenyl)-7-(o-tolyl)-7, 8-dihydro-6H-pyrimido [5, 4-b] [1, 4] oxazin-2-amine To a dry vial was added a suspension of Pd$_2$(dba)$_3$ (4 mg, 0.004 mmol) and Xantphos (7 mg, 0.013 mmol) in 1, 4-dioxane (0.75 mL). The suspension was degassed, heated to 120° C. and stirred for 3 min. A mixture of 2-chloro-8-methyl-7-(o-tolyl)-7, 8-dihydro-6H-pyrimido [5, 4-b] [1, 4] oxazine (80 mg, 0.29 mmol), 4-(2-methylpyridin-4-yl) aniline (107 mg, 0.58 mmol) and cesium carbonate (133 mg, 0.40 mmol) in 1, 4-dioxane (0.75 mL) was degassed and the catalyst premix was added. The reaction mixture was heated to 110° C. and stirred for 16 h in a sealed tube. After consumption of the starting material (monitored by TLC and LCMS), the mixture was concentrated in vacuo. The crude material was treated with a saturated sodium carbonate solution (30 mL) and extracted with EtOAc (2×50 mL). The combined organic extracts were dried over sodium sulfate, filtered and concentrated in vacuo. The crude material was purified by silica gel column chromatography using 0-5% MeOH:CH$_2$Cl$_2$ to afford 8-methyl-N-(4-(2-methylpyridin-4-yl) phenyl)-7-(o-tolyl)-7, 8-dihydro-6H-pyrimido [5, 4-b] [1, 4] oxazin-2-amine (20 mg, 16%) as an off-white solid. $^1$H-NMR (CD$_3$OD, 400 MHz): δ 8.38 (s, 1H), 7.82 (d, 2H), 7.69 (d, 2H), 7.57-7.53 (m, 2H), 7.49-7.47 (m, 1H), 7.24-7.18 (m, 3H), 7.00-6.99 (m, 1H), 5.01-4.99 (m, 1H), 4.25-4.20 (m, 1H), 4.11-4.09 (m, 1H), 3.10 (s, 3H), 2.57 (s, 3H), 2.41 (s, 3H); Mass (ESI): 424.6 [M+1]; LC-MS: 424.7 (M+1); (column; X-Select CSH C-18 (50×3.0 mm, 3.5 µm); RT 2.92 min 0.05% Aq TFA: ACN; 0.80 mL/min); UPLC: (column; Acquity BEH C-18 2.1×50 mm, 1.7 µm); RT 1.69 min. ACN: 0.025% TFA (Aq); 0.50 mL/min. TLC: 5% MeOH:CH$_2$Cl$_2$ (R$_f$; 0.3).

Racemic compound of Example 29 was separated using a Chiralpak IA (250×20 mm, 5 µm (20 mg loading; A) 0.1% DEA in n-hexane B) CH$_2$Cl$_2$:MeOH (50:50) (A:B: 80:20) to provide the compound of Example 29A (Fraction I (−)) and the compound of Example 29B (Fraction II (+)).

Example 29A

Synthesis of (−)-8-methyl-N-(4-(2-methylpyridin-4-yl) phenyl)-7-(o-tolyl)-7, 8-dihydro-6H-pyrimido [5, 4-b] [1, 4] oxazin-2-amine

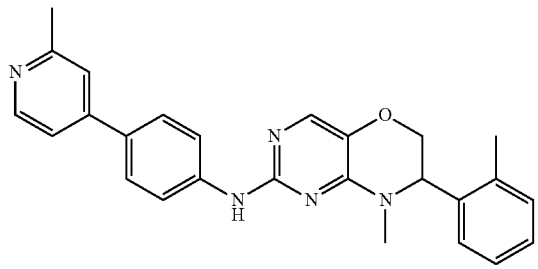 [SMILES: Cc1cc(-c2ccc(Nc3ncc4c(n3)N(C)C(c3ccccc3C)CO4)cc2)ccn1]

The compound of Example 29A was produced as described in Example 29. Analytical data for product Fraction I (−): $^1$H-NMR (CD$_3$OD, 500 MHz): δ 8.38 (d, 1H), 7.84 (d, 2H), 7.72 (d, 2H), 7.58 (s, 2H), 7.50 (d, 1H), 7.28 (t, 1H), 7.24-7.25 (m, 1H), 7.18 (t, 1H), 7.02 (d, 1H), 5.04-4.98 (m, 1H), 4.24-4.16 (m, 2H), 3.12 (s, 3H), 2.58 (s, 3H), 2.42 (s, 3H); Mass (ESI): 424.4 [M+1]; LC-MS: 424.3 (M+1); (column; X-Select CSH C-18 (50×3.0 mm, 3.5 µm); RT 2.84 min 0.05% Aq TFA: ACN; 0.80 mL/min); UPLC (column; Acquity BEH C-18 2.1×50 mm, 1.7 µm); RT 1.64 min. ACN: 0.025% TFA (Aq); 0.50 mL/min; Chiral HPLC: RT=11.92 min (Chiralpak IA (250×4.6 mm, 5 µm; mobile phase (A) 0.1% DEA in n-hexane (B) CH$_2$Cl$_2$:MeOH (50:50) (80:20); flow Rate: 1.0 mL/min); Optical rotation [α]$_D^{20.02}$: −202.41 (c 0.25, DCM).

Example 29B

Synthesis of (+)-8-methyl-N-(4-(2-methylpyridin-4-yl) phenyl)-7-(o-tolyl)-7, 8-dihydro-6H-pyrimido [5, 4-b] [1, 4] oxazin-2-amine

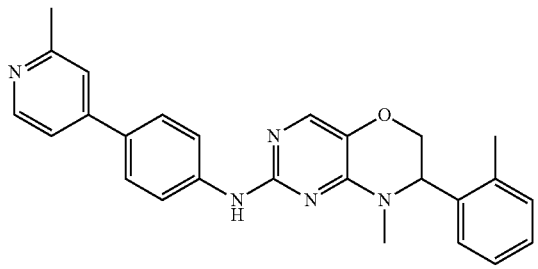

The compound of Example 29B was produced as described in Example 29. Analytical data for product Fraction II (+): $^1$H-NMR (CD$_3$OD, 500 MHz): δ 8.40 (d, 1H), 7.82 (d, 2H), 7.70 (d, 2H), 7.58-7.56 (m, 2H), 7.50 (d, 1H), 7.30-7.18 (m, 3H), 7.02 (d, 1H), 5.04-4.98 (m, 1H), 4.27-4.17 (m, 2H), 3.12 (s, 3H), 2.60 (s, 3H), 2.42 (s, 3H); Mass (ESI): 424.4 [M+1]; LC-MS: 424.4 (M+1); (column; X-Select CSH C-18 (50×3.0 mm, 3.5 µm); RT 2.83 min 0.05% Aq TFA: ACN; 0.80 mL/min); UPLC (column; Acquity BEH C-18 2.1×50 mm, 1.7 µm); RT 1.63 min. ACN: 0.025% TFA (Aq); 0.50 mL/min; Chiral HPLC: RT=13.35 min (Chiralpak IA (250×4.6 mm, 5 µm; mobile phase (A) 0.1% DEA in n-hexane (B) CH$_2$Cl$_2$:MeOH (50:50) (80:20); flow Rate: 1.0 mL/min); Optical rotation [α]$_D^{20.02}$: +215.53 (c 0.25, DCM).

Example 30

Synthesis of 7-(3, 5-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

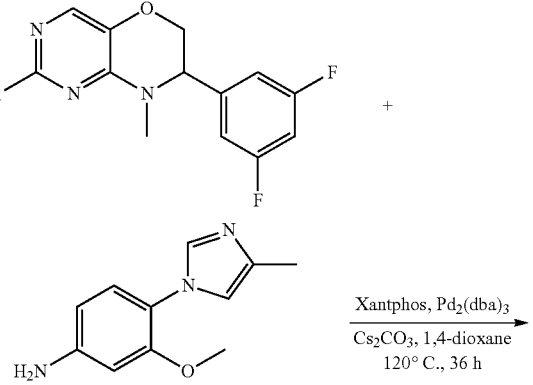

-continued

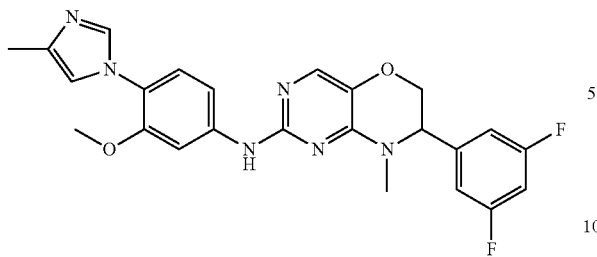

Synthesis of 7-(3, 5-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a dry vial was added a suspension of Pd$_2$(dba)$_3$ (4 mg, 0.004 mmol) and Xantphos (7 mg, 0.01 mmol) in 1, 4-dioxane (0.75 mL). The suspension was degassed, heated to 120° C. and stirred for 3 min. A mixture of 2-chloro-7-(3, 5-difluorophenyl)-8-methyl-7, 8-dihydro-6H-pyrimido [5, 4-b][1, 4] oxazine (80 mg, 0.26 mmol), 3-methoxy-4-(4-methyl-1H-imidazol-1-yl) aniline (109 mg, 0.53 mmol) and cesium carbonate (132 mg, 0.37 mmol) in 1, 4-dioxane (0.75 mL) was degassed and the catalyst premix was added. The reaction mixture was heated to 120° C. and stirred for 36 h in a sealed tube. After consumption of the starting material (monitored by TLC and LCMS), the mixture was diluted with water (10 mL) and extracted with EtOAc (2×10 mL). The combined organic extracts were dried over sodium sulfate, filtered and concentrated in vacuo. The crude material was purified by silica gel column chromatography using 2% MeOH:CH$_2$Cl$_2$ to afford 100 mgs further purified by preparative HPLC [Chiralpak-IC (250×20 mm×5 um) (30 mg loading; 0.1% DEA in n-hexane; CH2Cl2:MeOH (50:50); (80:20) as the mobile phase with a Flow rate=15 mL/min] to afford 7-(3, 5-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (35 mg, 28%) as an off-white solid. $^1$H-NMR (DMSO-d$_6$, 400 MHz): δ 9.20 (s, 1H), 7.87-7.86 (m, 1H), 7.66-7.63 (m, 2H), 7.33-7.30 (m, 1H), 7.24-7.15 (m, 2H), 7.00 (s, 1H), 6.97-6.95 (m, 2H), 4.89 (s, 1H), 4.29-4.25 (m, 1H), 4.21-4.17 (m, 1H), 3.77 (s, 3H), 3.11 (s, 3H), 2.13 (s, 3H); Mass (ESI): 465.5 [M+1]; LC-MS: 465.6 (M+1); (column; X-Select CSH C-18 (50×3.0 mm, 3.5 μm); RT 2.86 min. 0.05% Aq TFA: ACN; 0.80 mL/min); UPLC: (column; Acquity BEH C-18 50×2.1 mm, 1.7 μm); RT 1.69 min. ACN: 0.025% Aq TFA; 0.5 mL/min. TLC: 10% MeOH:CH$_2$Cl$_2$ (R$_f$: 0.5).

Racemic compound of Example 30 was separated using a Chiralpak IC (250×20 mm, 5 μm (30 mg loading; 0.1% DEA in n-hexane: CH$_2$Cl$_2$:MeOH (50:50) (80:20) as the mobile phase to provide the compound of Example 30A (Fraction I (−)) and the compound of Example 30B (Fraction II (+)).

Example 30A

Synthesis of (−)-7-(3, 5-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

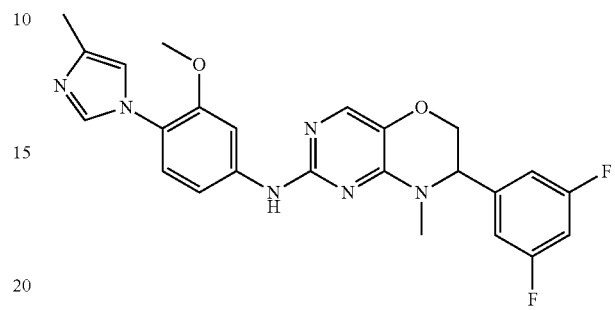

The compound of Example 30A was produced as described in Example 30. Analytical data for product Fraction I (−): $^1$H NMR (DMSO-d$_6$, 500 MHz): δ 9.21 (s, 1H), 7.87 (s, 1H), 7.64 (d, 2H), 7.33 (d, 1H), 7.22 (t, 1H), 7.19 (d, 1H), 7.01 (s, 1H), 6.96 (d, 2H), 4.88 (s, 1H), 4.26-4.24 (m, 1H), 4.20-4.18 (m, 1H), 3.88 (s, 3H), 3.12 (s, 3H), 2.14 (s, 3H); Mass (ESI): 465.4[M+1]; LC-MS: 465.4 (M+1); (column; X-Select CSH C-18 (50×3.0 mm, 3.5 μm); RT 2.94 min. 0.05% Aq TFA: ACN; 0.80 ml/min); UPLC (column; Acquity UPLC BEH C-18, 2.1×50 mm, 1.7 μm); RT 1.60 min. ACN: 0.025% TFA (Aq); 0.50 ml/min; Chiral HPLC: RT=13.58 min (Chiralpak ADH (250×4.6 mm, 5 μm; mobile phase (A) 0.1% DEA in n-hexane (B) EtOH:MeOH (50:50) (A:B; 70:30); flow Rate: 1.0 mL/min); Optical rotation [α]$_D^{20.00}$: −153.31 (c 0.25, DCM).

Example 30B

Synthesis of (+)-7-(3, 5-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine


The compound of Example 30B was produced as described in Example 30. Analytical data for product Fraction I (+): $^1$H NMR (DMSO-d$_6$, 500 MHz): δ 9.21 (s, 1H), 7.87 (s, 1H), 7.64 (d, 2H), 7.33 (d, 1H), 7.22 (t, 1H), 7.19 (d, 1H), 7.01 (s, 1H), 6.96 (d, 2H), 4.88 (s, 1H), 4.26-4.24 (m, 1H), 4.20-4.18 (m, 1H), 3.88 (s, 3H), 3.12 (s, 3H), 2.14 (s, 3H); Mass (ESI): 465.4[M+1]; LC-MS: 465.4 (M+1); (column; X-Select CSH C-18 (50×3.0 mm, 3.5 μm); RT 2.94 min. 0.05% Aq TFA: ACN; 0.80 ml/min); UPLC (column; Acquity UPLC BEH C-18, 2.1×50 mm, 1.7 μm); RT 1.60 min. ACN: 0.025% TFA (Aq); 0.50 ml/min; Chiral HPLC: RT=19.51 min (Chiralpak ADH (250×4.6 mm, 5 μm; mobile phase (A) 0.1% DEA in n-hexane (B) EtOH:MeOH (50:50) (A:B; 70:30); flow Rate: 1.0 mL/min); Optical rotation $[\alpha]_D^{19.98}$: +135.88 (c 0.25, DCM).

Example 31

Synthesis of N-(3-methoxy-4-(4-methyl-1H-imidazol-1-yl) phenyl)-8-methyl-7-(o-tolyl)-7, 8-dihydro-6H-pyrimido [5, 4-b] [1, 4] oxazin-2-amine

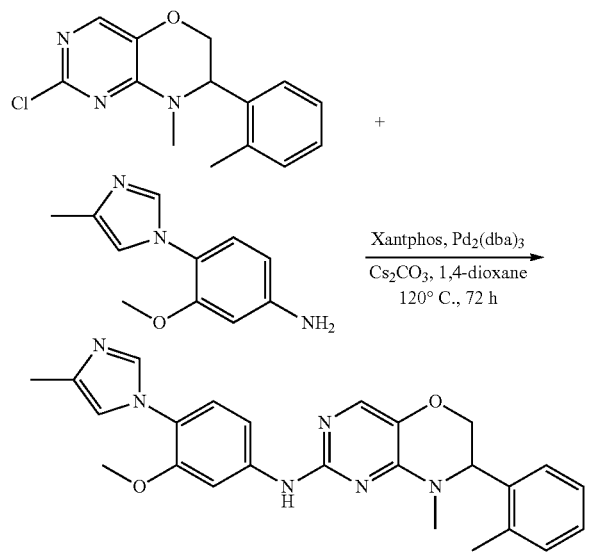

Synthesis of N-(3-methoxy-4-(4-methyl-1H-imidazol-1-yl) phenyl)-8-methyl-7-(o-tolyl)-7, 8-dihydro-6H-pyrimido [5, 4-b] [1, 4] oxazin-2-amine To a dry vial was added a suspension of Pd$_2$(dba)$_3$ (4 mg, 0.004 mmol) and Xantphos (7 mg, 0.01 mmol) in 1, 4-dioxane (0.75 mL). The suspension was degassed, heated to 120° C. and stirred for 3 min. A mixture of 2-chloro-8-methyl-7-(o-tolyl)-7, 8-dihydro-6H-pyrimido [5, 4-b] [1, 4] oxazine (80 mg, 0.29 mmol), 3-methoxy-4-(4-methyl-1H-imidazol-1-yl) aniline (118 mg, 0.58 mmol) and cesium carbonate (132 mg, 0.40 mmol) in 1, 4-dioxane (0.75 mL) was degassed and the catalyst premix was added. The reaction mixture was heated to 120° C. and stirred for 72 h in a sealed tube. After consumption of the starting material (monitored by TLC and LCMS), the mixture was diluted with water (10 mL) and extracted with EtOAc (2×10 mL). The combined organic extracts were dried over sodium sulfate, filtered and concentrated in vacuo. The crude material was purified by silica gel column chromatography using 2-4% MeOH: CH$_2$Cl$_2$ to afford 70 mgs further purified by preparative TLC using 70% EtOAc:hexanes to afford N-(3-methoxy-4-(4-methyl-1H-imidazol-1-yl) phenyl)-8-methyl-7-(o-tolyl)-7, 8-dihydro-6H-pyrimido [5, 4-b] [1, 4] oxazin-2-amine (30 mg, 23%) as an off-white solid. $^1$H-NMR (CD$_3$OD, 400 MHz): δ 7.77 (s, 1H), 7.76 (s, 1H), 7.68 (s, 1H), 7.26-7.17 (m, 5H), 7.00-6.97 (m, 2H), 5.00-4.99 (m, 1H), 4.25-4.22 (m, 1H), 4.14-4.10 (m, 1H), 3.84 (s, 3H), 3.10 (s, 3H), 2.41 (s, 3H), 2.23 (s, 3H); Mass (ESI): 443.7 [M+1]; LC-MS: 443.5 (M+1); (column; X-Select CSH C-18 (50×3.0 mm, 3.5 μm); RT 2.93 min. 0.05% Aq TFA: ACN; 0.80 mL/min); UPLC: (column; Acquity BEH C-18 50×2.1 mm, 1.7 μm); RT 1.61 min. ACN: 0.025% Aq TFA; 0.5 mL/min. TLC: 10% MeOH:CH$_2$Cl$_2$ (R$_f$: 0.4).

Racemic compound of Example 31 was separated using a Chiralpak ADH (250×20 mm, 5 μm (40 mg loading; A) 0.1% DEA in n-hexane B) EtOH (A:B: 75:25) to provide the compound of Example 31A (Fraction I (−)) and the compound of Example 31B (Fraction II (+)).

Example 31A

Synthesis of (−)-N-(3-methoxy-4-(4-methyl-1H-imidazol-1-yl) phenyl)-8-methyl-7-(o-tolyl)-7, 8-dihydro-6H-pyrimido [5, 4-b] [1, 4] oxazin-2-amine

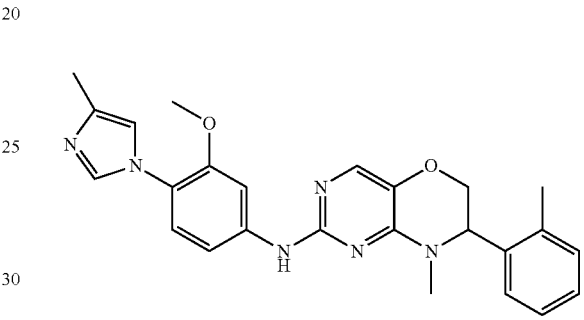

The compound of Example 31A was produced as described in Example 31. Analytical data for product Fraction I (−): $^1$H NMR (CD$_3$OD, 400 MHz): δ 7.78 (s, 1H), 7.68 (s, 1H), 7.58 (s, 1H), 7.28-7.16 (m, 5H), 6.98-6.94 (m, 2H), 5.01 (s, 1H), 4.22 (d, 1H), 4.12 (d, 1H), 3.82 (s, 3H), 3.10 (s, 3H), 2.40 (s, 3H), 2.22 (s, 3H); Mass (ESI): 443.6 [M+1]; LC-MS: 443.6 (M+1); (column; X-Select CSH C-18 (50× 3.0 mm, 3.5 μm); RT 2.92 min. 0.05% Aq TFA: ACN; 0.80 ml/min); UPLC: (column; Acquity BEH C-18, 50×2.1 mm, 1.7 μm); RT 1.65 min. ACN: 0.025% TFA (Aq); 0.50 ml/min; Chiral HPLC: RT=21.10 min (Chiralpak ADH (250×4.6 mm, 5 μm; mobile phase (A) 0.1% DEA in n-hexane (B) EtOH (75:25); flow Rate: 1.0 mL/min); Optical rotation $[\alpha]_D^{19.99}$: −188.80 (c 0.25, DCM).

Example 31B

Synthesis of (+)-N-(3-methoxy-4-(4-methyl-1H-imidazol-1-yl) phenyl)-8-methyl-7-(o-tolyl)-7, 8-dihydro-6H-pyrimido [5, 4-b] [1, 4] oxazin-2-amine

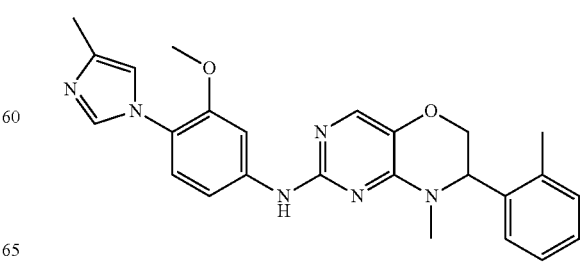

The compound of Example 31B was produced as described in Example 31. Analytical data for product Fraction II (+): $^1$H-NMR (CD$_3$OD, 400 MHz): δ 7.78 (s, 1H), 7.70 (s, 1H), 7.58 (s, 1H), 7.30-7.18 (m, 5H), 7.01-6.99 (m, 2H), 5.03-5.01 (m, 1H), 4.26 (d, 1H), 4.14 (d, 1H), 3.88 (s, 3H), 3.10 (s, 3H), 2.40 (s, 3H), 2.22 (s, 3H); Mass (ESI): 443.6 [M+1]; LC-MS: 443.6 (M+1); (column; X-Select CSH C-18 (50×3.0 mm, 3.5 μm); RT 2.93 min. 0.05% Aq TFA: ACN; 0.80 ml/min); UPLC (column; Acquity BEH C-18, 50×2.1 mm, 1.7 μm); RT 1.65 min. ACN: 0.025% TFA (Aq); 0.50 ml/min; Chiral HPLC: RT=28.68 min (Chiralpak ADH (250×4.6 mm, 5 μm; mobile phase (A) 0.1% DEA in n-hexane (B) EtOH (75:25); flow Rate: 1.0 mL/min); Optical rotation $[α]_D^{20.00}$: +203.29 (c 0.25, DCM).

Example 32

Synthesis of N-(3-fluoro-4-(2-methylpyridin-4-yl) phenyl)-8-methyl-7-(o-tolyl)-7, 8-dihydro-6H-pyrimido [5, 4-b] [1, 4] oxazin-2-amine

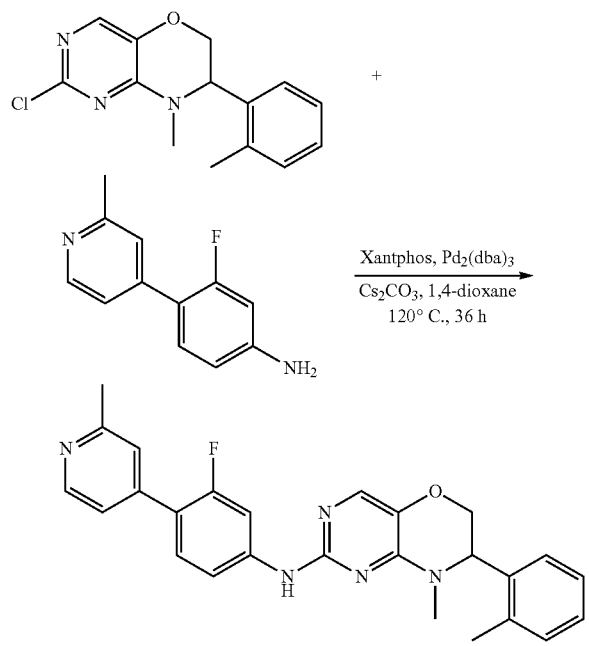

Synthesis of N-(3-fluoro-4-(2-methylpyridin-4-yl) phenyl)-8-methyl-7-(o-tolyl)-7, 8-dihydro-6H-pyrimido [5, 4-b] [1, 4] oxazin-2-amine To a dry vial was added a suspension of Pd$_2$(dba)$_3$ (4 mg, 0.004 mmol) and Xantphos (7 mg, 0.01 mmol) in 1, 4-dioxane (0.75 mL). The suspension was degassed, heated to 120° C. and stirred for 3 min. A mixture of 2-chloro-8-methyl-7-(o-tolyl)-7, 8-dihydro-6H-pyrimido [5, 4-b] [1, 4] oxazine (80 mg, 0.29 mmol), 3-fluoro-4-(2-methylpyridin-4-yl) aniline (117 mg, 0.58 mmol) and cesium carbonate (132 mg, 0.40 mmol) in 1, 4-dioxane (0.75 mL) was degassed and the catalyst premix was added. The reaction mixture was heated to 120° C. and stirred for 36 h in a sealed tube. After consumption of the starting material (monitored by TLC and LCMS), the reaction was diluted with water (10 mL) and extracted with EtOAc (2×10 mL). The combined organic extracts were dried over sodium sulfate, filtered and concentrated in vacuo. The crude material was purified by silica gel column chromatography using 1.5-2% MeOH: CH$_2$Cl$_2$ to afford 75 mgs further purified by preparative HPLC [Kromasil C18 (250×21.2 mm 10 um) (30 mg loading; n-hexane; CH2Cl2:MeOH (50:50); (90:10) as the mobile phase with a Flow rate=15 mL/min] to afford N-(3-fluoro-4-(2-methylpyridin-4-yl) phenyl)-8-methyl-7-(o-tolyl)-7, 8-dihydro-6H-pyrimido [5, 4-b] [1, 4] oxazin-2-amine (10 mg, 8%) as an off-white solid. $^1$H-NMR (CD$_3$OD, 400 MHz): δ 8.40-8.39 (m, 1H), 7.93-7.89 (m, 1H), 7.60-7.58 (m, 1H), 7.51-7.42 (m, 4H), 7.26-7.16 (m, 3H), 6.99 (d, 1H), 5.01-5.00 (m, 1H), 4.26-4.22 (m, 1H), 4.15-4.11 (m, 1H), 3.10 (s, 3H), 2.57 (s, 3H), 2.42 (s, 3H); (Mass ESI): 442.6 [M+1]; LC-MS: 442.6 (M+1); (column; X-Select CSH C-18 (50×3.0 mm, 3.5 μm); RT 3.00 min. 0.05% Aq TFA: ACN; 0.80 mL/min); UPLC: (column; Acquity BEH C-18 50×2.1 mm, 1.7 μm); RT 1.66 min. ACN: 0.025% Aq TFA; 0.5 mL/min. TLC: 70% EtOAc:hexanes (R$_f$ 0.3).

Racemic compound of Example 32 was separated using a Chiralcel A-DH (250×4.6 mm, 5 μm (40 mg loading; A) CO$_2$B) MeOH:EtOH (50:50) (A:B: 70:30) to provide the compound of Example 32A (Fraction I (−)) and the compound of Example 32B (Fraction II (+)).

Example 32A

Synthesis of (−)-N-(3-fluoro-4-(2-methylpyridin-4-yl) phenyl)-8-methyl-7-(o-tolyl)-7, 8-dihydro-6H-pyrimido [5, 4-b] [1, 4] oxazin-2-amine

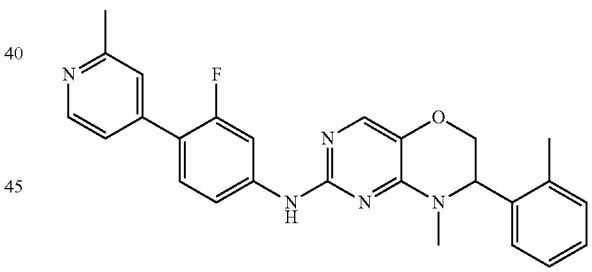

The compound of Example 32A was produced as described in Example 32. Analytical data for product Fraction I (−): $^1$H-NMR (CD$_3$OD, 400 MHz): δ 8.40-8.38 (m, 1H), 7.92 (d, 1H), 7.60 (s, 1H), 7.50-7.42 (m, 4H), 7.24-7.14 (m, 3H), 7.00 (d, 1H), 5.03-5.01 (m, 1H), 4.26-4.21 (m, 1H), 4.19-4.16 (m, 1H), 3.10 (s, 3H), 2.56 (s, 3H), 2.42 (s, 3H); Mass (ESI): 442.4 [M+1]; LC-MS: 442 (M+1); (column; X-Select CSH C-18 (50×3.0 mm, 3.5 μm); RT 2.44 min. 0.05% Aq TFA: ACN; 0.80 ml/min); UPLC (column; Acquity BEH C-18, 50×2.1 mm, 1.7 μm); RT 1.64 min. ACN: 0.025% TFA (Aq); 0.50 ml/min; Chiral HPLC: RT=11.23 min (Chiralpak ADH (250×4.6 mm, 5 μm; mobile phase (A) CO$_2$ (B) MeOH; EtOH (70:30); flow Rate: 3.0 mL/min); Optical rotation $[α]_D^{25.00}$: −162.04 (c 0.25, DCM).

Example 32B

Synthesis of (+)-N-(3-fluoro-4-(2-methylpyridin-4-yl) phenyl)-8-methyl-7-(o-tolyl)-7, 8-dihydro-6H-pyrimido [5, 4-b] [1, 4] oxazin-2-amine

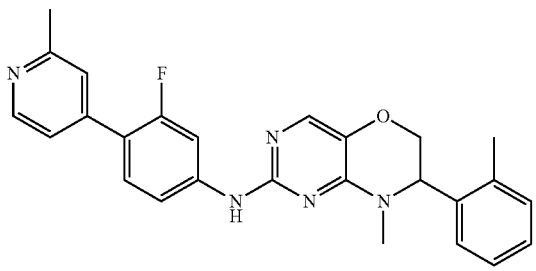 [SMILES: Cc1cc(-c2ccc(Nc3ncc4c(n3)N(C)C(c3ccccc3C)CO4)cc2F)ccn1]

The compound of Example 32B was produced as described in Example 32. Analytical data for product Fraction II (+): $^1$H-NMR (CD$_3$OD, 400 MHz): δ 8.40-8.38 (m, 1H), 7.92 (d, 1H), 7.60 (s, 1H), 7.50-7.42 (m, 4H), 7.24-7.14 (m, 3H), 7.00 (d, 1H), 5.03-5.01 (m, 1H), 4.26-4.21 (m, 1H), 4.19-4.16 (m, 1H), 3.10 (s, 3H), 2.56 (s, 3H), 2.42 (s, 3H); Mass (ESI): 442.4 [M+1]; LC-MS: 442 (M+1); (column; X-Select CSH C-18 (50×3.0 mm, 3.5 µm); RT 2.44 min. 0.05% Aq TFA: ACN; 0.80 ml/min); UPLC (column; Acquity BEH C-18, 50×2.1 mm, 1.7 µm); RT 1.64 min. ACN: 0.025% TFA (Aq); 0.50 ml/min; Chiral HPLC: RT=14.16 min (Chiralpak ADH (250×4.6 mm, 5 µm; mobile phase (A) CO$_2$ (B) MeOH; EtOH (70:30); flow Rate: 3.0 mL/min); Optical rotation $[α]_D^{25.01}$: +142.49 (c 0.25, DCM).

Example 33

Synthesis of 7-(3, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

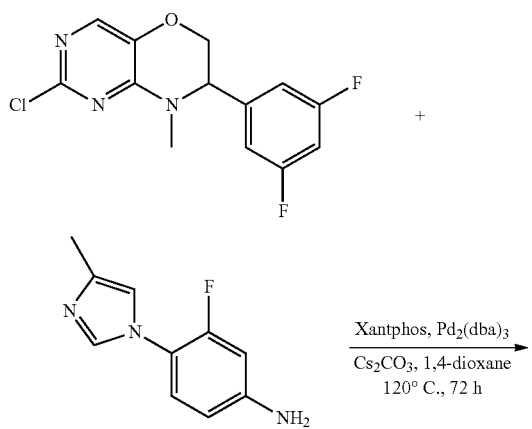

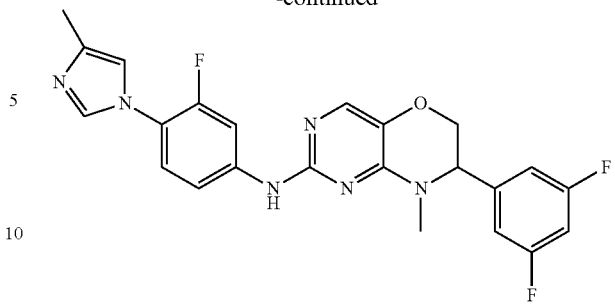

Synthesis of 7-(3, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine To a dry vial was added a suspension of Pd$_2$(dba)$_3$ (2 mg, 0.002 mmol) and Xantphos (4.3 mg, 0.007 mmol) in 1, 4-dioxane (0.5 mL). The suspension was degassed, heated to 120° C. and stirred for 3 min. A mixture of 2-chloro-7-(3, 5-difluorophenyl)-8-methyl-7, 8-dihydro-6H-pyrimido [5, 4-b] [1, 4] oxazine (50 mg, 0.16 mmol), 3-fluoro-4-(4-methyl-1H-imidazol-1-yl) aniline (64 mg, 0.33 mmol). and cesium carbonate (76 mg, 0.23 mmol) in 1, 4-dioxane (0.5 mL) was degassed and the catalyst premix was added. The reaction mixture was heated to 120° C. and stirred for 72 h in a sealed tube. After consumption of staring material (monitored by TLC and LCMS), the mixture was diluted with water (10 mL) and extracted with EtOAc (2×10 mL). The combined organic extracts were dried over sodium sulfate, filtered and concentrated in vacuo. The crude material was purified by silica gel column chromatography using 2% MeOH:CH$_2$Cl$_2$ to afford 60 mgs further purified by preparative HPLC [Kromasil C18 (250×21.2 mm 10 um) (20 mg loading; n-hexane; CH$_2$Cl$_2$:MeOH (50:50); (85:15) as the mobile phase with a Flow rate=15 mL/min] to afford 7-(3, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine (15 mg, 20%) as an off-white solid. $^1$H-NMR (CD$_3$OD, 400 MHz): δ 8.02-8.01 (m, 1H), 7.76 (s, 1H), 7.63 (s, 1H), 7.44-7.41 (m, 2H), 7.08-7.09 (m, 1H), 6.95-6.85 (m, 3H), 4.77-4.76 (m, 1H), 4.23 (s, 2H), 3.16 (s, 3H), 2.24 (s, 3H); Mass (ESI): 453.4 [M+1]; LC-MS: 453.6 (M+1); (column; X-Select CSH C-18 (50× 3.0 mm, 3.5 µm); RT 2.92 min. 0.05% Aq TFA: ACN; 0.80 mL/min); UPLC: (column; Acquity BEH C-18 50×2.1 mm, 1.7 µm); RT 1.61 min. ACN: 0.025% Aq TFA; 0.5 mL/min. TLC: 10% MeOH:CH$_2$Cl$_2$ (R$_f$: 0.3).

Racemic compound of Example 33 was separated using a Chiralpak IA (250×20 mm, 5 µm (35 mg loading; 0.1% TFA in n-hexane: CH$_2$Cl$_2$:MeOH (15:85) (A:B; 80:20) as the mobile phase) to provide the compound of Example 33A (Fraction I (+)) and the compound of Example 33B (Fraction II (−)).

Example 33A

Synthesis of (+)-7-(3, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

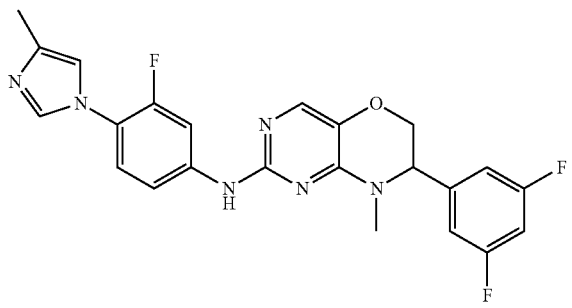 [SMILES: Cc1cn(-c2ccc(Nc3ncc4c(n3)N(C)C(c3cc(F)cc(F)c3)CO4)cc2F)cn1]

The compound of Example 33A was produced as described in Example 33. Analytical data for product Fraction I (+): $^1$H-NMR (CD$_3$OD, 400 MHz): δ 8.02-8.01 (m, 1H), 7.79 (s, 1H), 7.61 (s, 1H), 7.41-7.39 (m, 2H), 7.07 (s, 1H), 6.93-6.81 (m, 3H), 4.77-4.75 (m, 1H), 4.21 (s, 2H), 3.14 (s, 3H), 2.23 (s, 3H); Mass (ESI): 453.4 [M+1]; LC-MS: 453.3 (M+1); (column; X-Select CSH C-18 (50×3.0 mm, 3.5 μm); RT 3.19 min. 0.05% Aq TFA: ACN; 0.80 ml/min); UPLC (column; Acquity BEH C-18, 2.1×50 mm, 1.7 μm); RT 1.61 min. ACN: 0.025% TFA (Aq); 0.50 ml/min; Chiral HPLC: RT=14.62 min (CHIRALPAK-AD-H (250×4.6 mm, 5 μm; mobile phase (A) 0.1% DEA in n-hexane (B) EtOH:MeOH (50:50) (A:B: 60:40; flow Rate: 1.0 mL/min); Optical rotation $[α]_D^{19.99}$: +130.22 (c 0.25, DCM).

Example 33B

Synthesis of (−)-7-(3, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

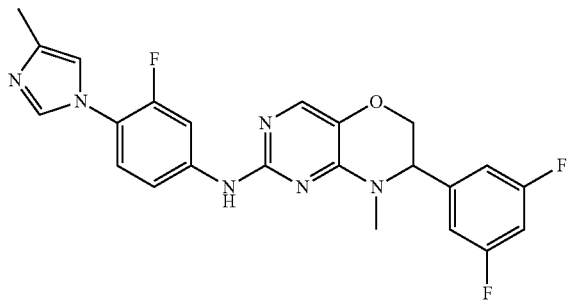 [SMILES: Cc1cn(-c2ccc(Nc3ncc4c(n3)N(C)C(c3cc(F)cc(F)c3)CO4)cc2F)cn1]

The compound of Example 33B was produced as described in Example 33. Analytical data for product Fraction II (−): $^1$H-NMR (CD$_3$OD, 400 MHz): δ 8.02-8.01 (m, 1H), 7.79 (s, 1H), 7.61 (s, 1H), 7.41-7.39 (m, 2H), 7.07 (s, 1H), 6.93-6.81 (m, 3H), 4.77-4.75 (m, 1H), 4.21 (s, 2H), 3.12 (s, 3H), 2.21 (s, 3H); Mass (ESI): 453.4 [M+1]; LC-MS: 453.3 (M+1); (column; X-Select CSH C-18 (50×3.0 mm, 3.5 μm); RT 3.17 min. 0.05% Aq TFA: ACN; 0.80 ml/min); UPLC (column; Acquity BEH C-18, 50×2.1 mm, 1.7 μm); RT 1.61 min. ACN: 0.025% TFA (Aq); 0.50 ml/min; Chiral HPLC: RT=37.11 min (CHIRALPAK-AD-H (250×4.6 mm, 5 μm; mobile phase (A) 0.1% DEA in n-hexane (B) EtOH:MeOH (50:50) (A:B: 60:40; flow Rate: 1.0 mL/min); Optical rotation $[α]_D^{20.02}$: −124.49 (c 0.25, DCM).

Example 34

Synthesis of N-(3-fluoro-4-(4-methyl-1H-imidazol-1-yl) phenyl)-8-methyl-7-(o-tolyl)-7, 8-dihydro-6H-pyrimido [5, 4-b] [1, 4] oxazin-2-amine

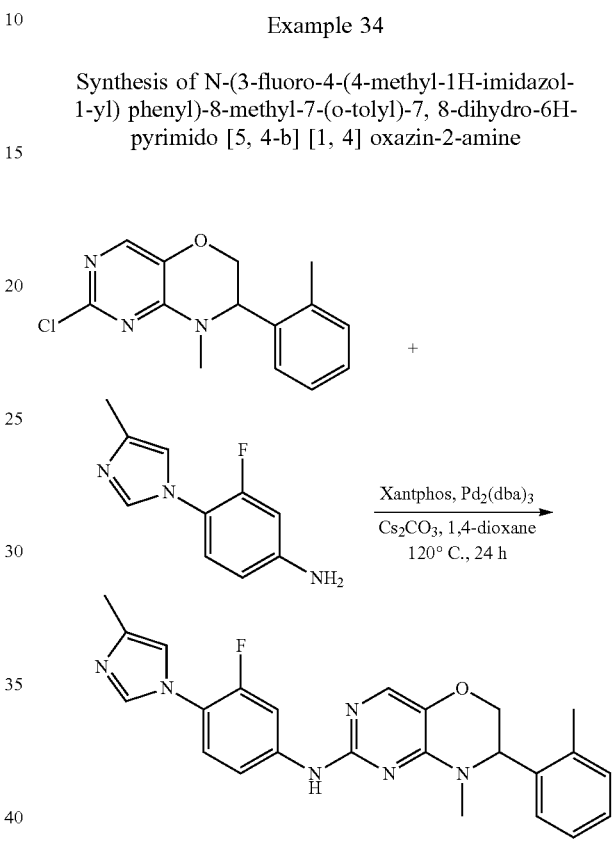

Synthesis of N-(3-fluoro-4-(4-methyl-1H-imidazol-1-yl) phenyl)-8-methyl-7-(o-tolyl)-7, 8-dihydro-6H-pyrimido [5, 4-b] [1, 4] oxazin-2-amine To a dry vial added a suspension of Pd$_2$(dba)$_3$ (13 mg, 0.01 mmol) and Xantphos (25 mg, 0.04 mmol) in 1, 4-dioxane (0.75 mL). The suspension was degassed, heated to 120° C. and stirred for 3 min. A mixture of 2-chloro-8-methyl-7-(o-tolyl)-7, 8-dihydro-6H-pyrimido [5, 4-b] [1, 4] oxazine [5, 4-b] [1, 4] oxazine (80 mg, 0.29 mmol), 3-fluoro-4-(4-methyl-1H-imidazol-1-yl) aniline (111 mg, 0.58 mmol) and cesium carbonate (132 mg, 0.40 mmol) in 1, 4-dioxane (0.5 mL) was degassed and the catalyst premix was added. The reaction mixture was heated to 120° C. and stirred for 24 h in a sealed tube. After consumption of the starting material (monitored by TLC and LCMS), the mixture was diluted with water (20 mL) and extracted with EtOAc (2×20 mL). The combined organic extracts were dried over sodium sulfate, filtered and concentrated in vacuo. The crude material was purified by silica gel column chromatography using 2% MeOH:CH$_2$Cl$_2$ to afford 90 mg of compound further washed with ACN (2×1 mL), ether (2×1 mL) and pentane (2×1 mL) to afford N-(3-fluoro-4-(4-methyl-1H-imidazol-1-yl) phenyl)-8-methyl-7-(o-tolyl)-

7,8-dihydro-6H-pyrimido [5, 4-b] [1, 4] oxazin-2-amine (30 mg, 24%) as an off-white solid. ¹H-NMR (CD₃OD, 400 MHz): δ 8.02-7.98 (m, 1H), 7.76 (s, 1H), 7.56 (s, 1H), 7.43-7.41 (m, 1H), 7.36-7.32 (m, 1H), 7.26-7.17 (m, 3H), 7.08-7.09 (m, 1H), 6.98 (d, 1H), 5.01-4.99 (m, 1H), 4.26-4.22 (m, 1H), 4.14-4.11 (m, 1H), 3.08 (s, 3H), 2.42 (s, 3H), 2.24 (s, 3H); Mass (ESI): 431.4 [M+1]; LC-MS: 431.7 (M+1); (column; X-Select CSH C-18 (50×3.0 mm, 3.5 μm); RT 2.92 min. 0.05% Aq TFA: ACN; 0.80 mL/min); UPLC: (column; Acquity BEH C-18 50×2.1 mm, 1.7 μm); RT 1.65 min. ACN: 0.025% Aq TFA; 0.5 mL/min. TLC: 70% EtOAc:hexanes (R$_f$: 0.3).

Racemic compound of Example 34 was separated using a Chiralpak IA (250×20 mm, 5 μm (25 mg loading; 0.1% DEA in n-hexane: CH₂Cl₂:MeOH (50:50); (75:25) as the mobile phase) to provide the compound of Example 34A (Fraction I (+)) and the compound of Example 34B (Fraction II (−)).

Example 34A

Synthesis of (+)-N-(3-fluoro-4-(4-methyl-1H-imidazol-1-yl) phenyl)-8-methyl-7-(o-tolyl)-7, 8-dihydro-6H-pyrimido [5, 4-b] [1, 4] oxazin-2-amine

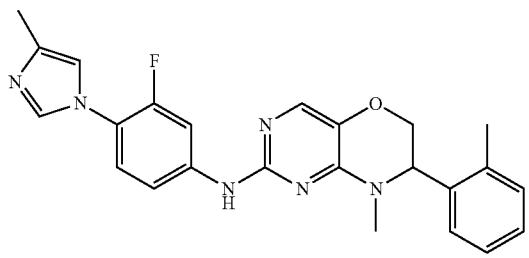 [SMILES: Cc1cn(-c2ccc(Nc3ncc4c(n3)N(C)C(c3ccccc3C)CO4)cc2F)cn1]

The compound of Example 34A was produced as described in Example 34. Analytical data for Fraction I (+): ¹H-NMR (CD₃OD, 400 MHz): δ 8.00-7.98 (m, 1H), 7.74 (s, 1H), 7.57 (s, 1H), 7.41-7.39 (m, 1H), 7.37-7.30 (m, 1H), 7.28-7.15 (m, 3H), 7.09-7.08 (m, 1H), 6.98 (d, 1H), 5.00-4.98 (m, 1H), 4.27-4.20 (m, 1H), 4.14-4.09 (m, 1H), 3.08 (s, 3H), 2.40 (s, 3H), 2.21 (s, 3H); Mass (ESI): 431.4 [M+1]; LC-MS: 430.9 (M+1); (column; X-Select CSH C-18 (50×3.0 mm, 3.5 μm); RT 2.41 min. 0.05% Aq TFA: ACN; 0.80 ml/min); UPLC (column; Acquity BEH C-18, 50×2.1 mm, 1.7 μm); RT 1.62 min. ACN: 0.025% TFA (Aq); 0.50 ml/min; Chiral HPLC: RT=10.88 min (CHIRALPAK-IA (250×4.6 mm, 5 μm; mobile phase (A) 0.1% DEA in n-hexane (B) CH₂Cl₂:MeOH (50:50) (A:B: 75:25; flow Rate: 1.0 mL/min); Optical rotation [α]$_D^{19.99}$: +180.78 (c 0.25, DCM).

Example 34B

Synthesis of (−)-N-(3-fluoro-4-(4-methyl-1H-imidazol-1-yl) phenyl)-8-methyl-7-(o-tolyl)-7, 8-dihydro-6H-pyrimido [5, 4-b] [1, 4] oxazin-2-amine

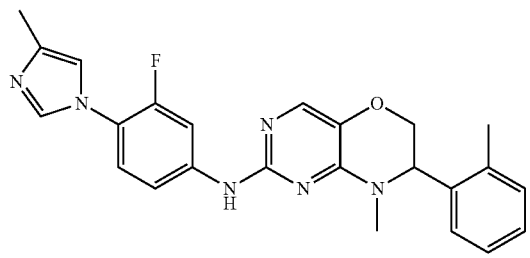 [SMILES: Cc1cn(-c2ccc(Nc3ncc4c(n3)N(C)C(c3ccccc3C)CO4)cc2F)cn1]

The compound of Example 34B was produced as described in Example 34. Analytical data for Fraction II (−): ¹H-NMR (CD₃OD, 400 MHz): δ 8.00-7.98 (m, 1H), 7.74 (s, 1H), 7.57 (s, 1H), 7.41-7.39 (m, 1H), 7.37-7.30 (m, 1H), 7.28-7.15 (m, 3H), 7.09-7.08 (m, 1H), 6.98 (d, 1H), 5.00-4.98 (m, 1H), 4.27-4.20 (m, 1H), 4.14-4.09 (m, 1H), 3.08 (s, 3H), 2.40 (s, 3H), 2.21 (s, 3H); Mass (ESI): 431.5 [M+1]; LC-MS: 431 (M+1); (column; X-Select CSH C-18 (50×3.0 mm, 3.5 μm); RT 2.41 min. 0.05% Aq TFA: ACN; 0.80 ml/min); UPLC (column; Acquity BEH C-18, 50×2.1 mm, 1.7 μm); RT 1.62 min. ACN: 0.025% TFA (Aq); 0.50 ml/min; Chiral HPLC: RT=13.75 min (CHIRALPAK-IA (250×4.6 mm, 5 μm; mobile phase (A) 0.1% DEA in n-hexane (B) CH₂Cl₂:MeOH (50:50) (A:B: 75:25; flow Rate: 1.0 mL/min); Optical rotation [α]$_D^{19.97}$: −178.49 (c 0.25, DCM).

Example 35

Synthesis of N-(3-methoxy-4-(2-methylpyridin-4-yl) phenyl)-8-methyl-7-(o-tolyl)-7, 8-dihydro-6H-pyrimido [5, 4-b] [1, 4] oxazin-2-amine

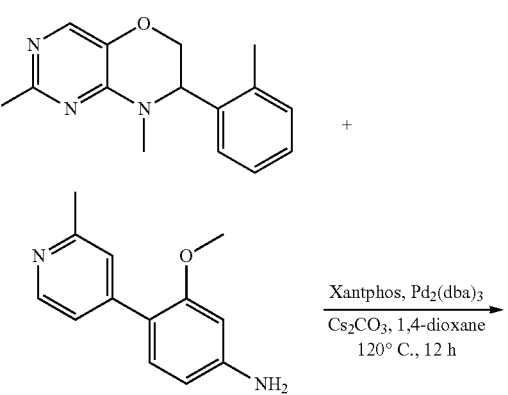

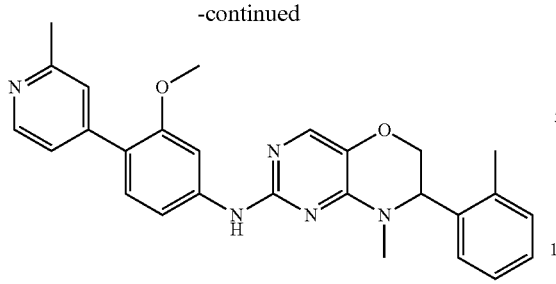

Synthesis of N-(3-methoxy-4-(2-methylpyridin-4-yl) phenyl)-8-methyl-7-(o-tolyl)-7, 8-dihydro-6H-pyrimido [5, 4-b] [1, 4] oxazin-2-amine To a dry vial was added a suspension of $Pd_2(dba)_3$ (13 mg, 0.01 mmol) and Xantphos (25 mg, 0.04 mmol) in 1, 4-dioxane (0.75 mL). The suspension was degassed, heated to 120° C. and stirred for 3 min. A mixture of 2-chloro-8-methyl-7-(o-tolyl)-7, 8-dihydro-6H-pyrimido [5, 4-b] [1, 4] oxazine (80 mg, 0.29 mmol), 3-methoxy-4-(2-methylpyridin-4-yl) aniline (124 mg, 0.58 mmol) and cesium carbonate (132 mg, 0.40 mmol) in 1, 4-dioxane (0.5 mL) was degassed and the catalyst premix was added. The reaction mixture was heated to 120° C. and stirred for 12 h in a sealed tube. After consumption of the starting material (monitored by TLC and LCMS), the mixture was diluted with water (20 mL) and extracted with EtOAc (2×25 mL). The combined organic extracts were dried over sodium sulfate, filtered and concentrated in vacuo. The crude material was purified by silica gel column chromatography using 1.5-2% MeOH:$CH_2Cl_2$ to afford 100 mgs further purified by preparative TLC using 60% EtOAc:hexanes to afford N-(3-methoxy-4-(2-methylpyridin-4-yl) phenyl)-8-methyl-7-(o-tolyl)-7, 8-dihydro-6H-pyrimido [5, 4-b] [1, 4] oxazin-2-amine (30 mg, 23%) as an off-white solid. $^1$H-NMR (CD$_3$OD, 400 MHz): δ 8.32-8.31 (m, 1H), 7.71-7.70 (m, 1H), 7.57 (br s, 1H), 7.46 (s, 1H), 7.41 (d, 1H), 7.31-7.15 (m, 5H), 7.00 (d, 1H), 5.00-4.99 (m, 1H), 4.25-4.22 (m, 1H), 4.14-4.10 (m, 1H), 3.85 (s, 3H), 3.11 (s, 3H), 2.53 (s, 3H), 2.41 (s, 3H); Mass (ESI): 454.5 [M+1]; LC-MS: 454.7 (M+1); (column; X-Select CSH C-18 (50×3.0 mm, 3.5 μm); RT 3.00 min. 0.05% Aq TFA: ACN; 0.80 mL/min); UPLC: (column; Acquity BEH C-18 50×2.1 mm, 1.7 μm); RT 1.70 min. ACN: 0.025% Aq TFA; 0.5 mL/min. TLC: 70% EtOAc:hexanes ($R_f$: 0.2).

Racemic compound of Example 35 was separated using a Chiralpak IA (250×20 mm, 5 μm (30 mg loading; 0.1% DEA in n-hexane: THF:MeOH (80:20); (80:20) as the mobile phase to provide the compound of Example 35A (Fraction I (−)) and the compound of Example 35B (Fraction II (+)).

Example 35A

Synthesis of (−)-N-(3-methoxy-4-(2-methylpyridin-4-yl) phenyl)-8-methyl-7-(o-tolyl)-7, 8-dihydro-6H-pyrimido [5, 4-b] [1, 4] oxazin-2-amine

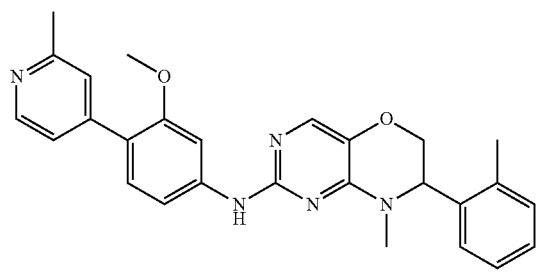

The compound of Example 35A was produced as described in Example 35. Analytical data for Fraction I (−): $^1$H-NMR (CD$_3$OD, 400 MHz): δ 8.32-8.30 (m, 1H), 7.71-7.70 (m, 1H), 7.57 (s, 1H), 7.49 (s, 1H), 7.45 (d, 1H), 7.33-7.13 (m, 5H), 7.00 (d, 1H), 5.02-5.00 (m, 1H), 4.26-4.21 (m, 1H), 4.16-4.11 (m, 1H), 3.87 (s, 3H), 3.12 (s, 3H), 2.58 (s, 3H), 2.41 (s, 3H); Mass (ESI): 454.4 [M+1]; LC-MS: 454 (M+1); (column; X-Select CSH C-18 (50×3.0 mm, 3.5 μm); RT 2.48 min. 0.05% Aq TFA: ACN; 0.80 ml/min); UPLC (column; Acquity BEH C-18, 50×2.1 mm, 1.7 μm); RT 1.64 min. ACN: 0.025% TFA (Aq); 0.50 ml/min; Chiral HPLC: RT=14.96 min (CHIRALPAK-IA (250×4.6 mm, 5 μm; mobile phase (A) 0.1% DEA in n-hexane (B) THF:MeOH (80:20) (A:B: 80:20; flow Rate: 1.0 mL/min); Optical rotation $[α]_D^{20.01}$: −184.73 (c 0.25, DCM).

Example 35B

Synthesis of (+)-N-(3-methoxy-4-(2-methylpyridin-4-yl) phenyl)-8-methyl-7-(o-tolyl)-7, 8-dihydro-6H-pyrimido [5, 4-b] [1, 4] oxazin-2-amine

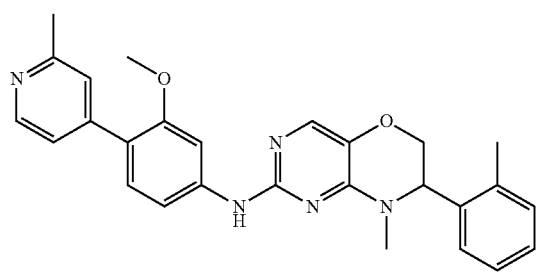 [SMILES: COc1cc(Nc2ncc3c(n2)N(C)C(c2ccccc2C)CO3)ccc1-c1ccnc(C)c1]

The compound of Example 35B was produced as described in Example 35. Analytical data for Fraction II (+): $^1$H-NMR (CD$_3$OD, 400 MHz): δ 8.32-8.30 (m, 1H), 7.71-7.70 (m, 1H), 7.57 (s, 1H), 7.49 (s, 1H), 7.45 (d, 1H), 7.33-7.13 (m, 5H), 7.00 (d, 1H), 5.02-5.00 (m, 1H), 4.26-4.21 (m, 1H), 4.16-4.11 (m, 1H), 3.87 (s, 3H), 3.12 (s, 3H), 2.58 (s, 3H), 2.41 (s, 3H); Mass (ESI): 454.4 [M+1]; LC-MS: 454 (M+1); (column; X-Select CSH C-18 (50×3.0 mm, 3.5 μm); RT 2.46 min. 0.05% Aq TFA: ACN; 0.80 ml/min); UPLC (column; Acquity BEH C-18, 50×2.1 mm, 1.7 μm); RT 1.65 min. ACN: 0.025% TFA (Aq); 0.50 ml/min; Chiral HPLC: RT=17.63 min (CHIRALPAK-IA (250×4.6 mm, 5 μm; mobile phase (A) 0.1% DEA in n-hexane (B) THF:MeOH (80:20) (A:B: 80:20; flow Rate: 1.0 mL/min); Optical rotation [α]$_D^{20.00}$: +188.46 (c 0.25, DCM).

Example 36

Synthesis of N-(3-fluoro-4-(2-methylpyridin-4-yl) phenyl)-8-methyl-7-(3, 4, 5-trifluorophenyl)-7, 8-dihydro-6H-pyrimido [5, 4-b] [1, 4] oxazin-2-amine

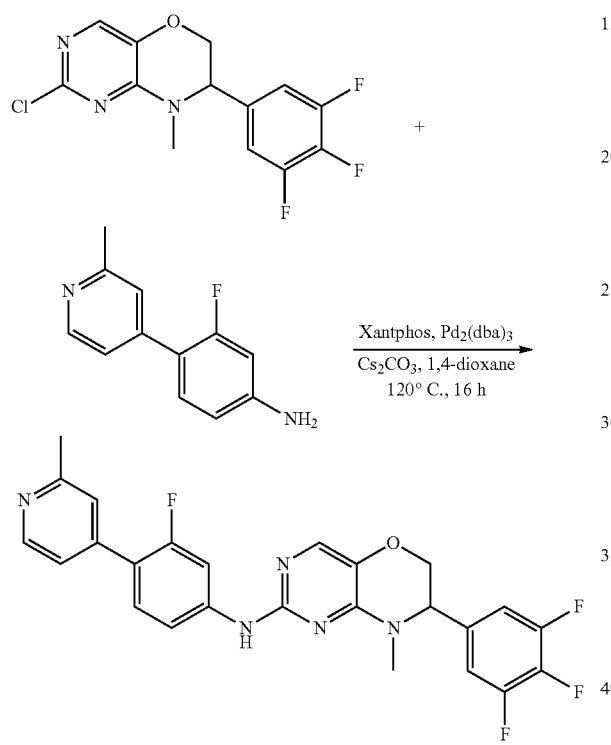

Synthesis of N-(3-fluoro-4-(2-methylpyridin-4-yl) phenyl)-8-methyl-7-(3, 4, 5-trifluorophenyl)-7, 8-dihydro-6H-pyrimido [5, 4-b] [1, 4] oxazin-2-amine To a dry vial was added a suspension of Pd$_2$(dba)$_3$ (7 mg, 0.007 mmol) and Xantphos (14 mg, 0.02 mmol) in 1, 4-dioxane (0.5 mL). The suspension was degassed, heated to 120° C. and stirred for 3 min. A mixture of 2-chloro-8-methyl-7-(3, 4, 5-trifluorophenyl)-7, 8-dihydro-6H-pyrimido [5, 4-b] [1, 4] oxazine (50 mg, 0.15 mmol), 3-fluoro-4-(2-methylpyridin-4-yl) aniline (64 mg, 0.31 mmol) and cesium carbonate (73 mg, 0.23 mmol) in 1, 4-dioxane (0.5 mL) was degassed and the catalyst premix was added. The reaction mixture was heated to 120° C. and stirred for 16 h in a sealed tube. After consumption of the starting material (monitored by TLC and LCMS), the mixture was diluted with water (20 mL) and extracted with EtOAc (2×20 mL). The combined organic extracts were dried over sodium sulfate, filtered and concentrated in vacuo. The crude material was purified by preparative TLC using 60% EtOAc: hexanes to afford 60 mgs further purified by preparative HPLC [Kromasil-silica (250×21.2 mm×10 um) (30 mg loading; n-hexane; CH$_2$Cl$_2$:CH$_3$OH (50:50); (80:20) as the mobile phase with a Flow rate=15 mL/min] to afford N-(3-fluoro-4-(2-methylpyridin-4-yl) phenyl)-8-methyl-7-(3, 4, 5-trifluorophenyl)-7, 8-dihydro-6H-pyrimido [5, 4-b] [1, 4] oxazin-2-amine (10 mg, 13%) as an off-white solid. $^1$H-NMR (CD$_3$OD, 400 MHz): δ 8.40-8.39 (m, 1H), 7.92-7.88 (m, 1H), 7.64 (s, 1H), 7.51-7.41 (m, 4H), 7.04 (t, 2H), 4.75-4.73 (m, 1H), 4.22-4.21 (m, 2H), 3.17 (s, 3H), 2.57 (s, 3H); Mass (ESI): 482.5 [M+1]; LC-MS: 482.6 (M+1); (column; X-Select CSH C-18 (50×3.0 mm, 3.5 μm); RT 3.09 min. 0.05% Aq TFA:ACN; 0.80 mL/min); UPLC: (column; Acquity BEH C-18 50×2.1 mm, 1.7 μm); RT 1.79 min. ACN: 0.025% Aq TFA; 0.5 mL/min. TLC: 70% EtOAc: hexanes (R$_f$; 0.2).

Racemic compound of Example 36 was separated using a Chiralpak IA (250×20 mm, 5 μm (25 mg loading; 0.1% TFA in n-hexane: CH$_2$Cl$_2$:MeOH (50:50); (75:15) as the mobile phase) to provide the compound of Example 36A (Fraction I (+)) and the compound of Example 36B (Fraction II (−)).

Example 36A

Synthesis of (+)-N-(3-fluoro-4-(2-methylpyridin-4-yl) phenyl)-8-methyl-7-(3, 4, 5-trifluorophenyl)-7, 8-dihydro-6H-pyrimido [5, 4-b] [1, 4] oxazin-2-amine

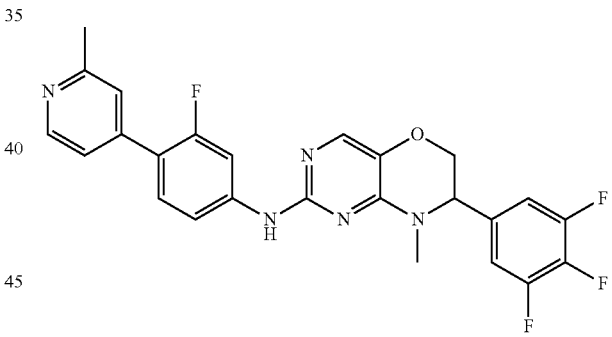

The compound of Example 36A was produced as described in Example 36. Analytical data for product Fraction I (+): $^1$H-NMR (CD$_3$OD, 400 MHz): δ 8.40-8.38 (m, 1H), 7.91-7.86 (m, 1H), 7.61 (s, 1H), 7.50-7.39 (m, 4H), 7.03 (t, 2H), 4.73-4.70 (m, 1H), 4.22-4.20 (m, 2H), 3.19 (s, 3H), 2.58 (s, 3H); Mass (ESI): 482.3 [M+1]; LC-MS: 482.4 (M+1); (column; X-Select CSH C-18 (50×3.0 mm, 3.5 μm); RT 3.32 min. 0.05% Aq TFA: ACN; 0.80 ml/min); UPLC (column; Acquity BEH C-18, 2.1×50 mm, 1.7 μm); RT 1.76 min. ACN: 0.025% TFA (Aq); 0.50 ml/min; Chiral HPLC: RT=11.63 min (CHIRALPAK-IA (250×4.6 mm, 5 μm; mobile phase (A) 0.1% TFA in n-hexane (B) CH$_2$Cl$_2$:MeOH (50:50) (A:B: 75:25; flow Rate: 1.0 mL/min); Optical rotation [α]$_D^{20.01}$: +138.36 (c 0.25, DCM).

Example 36B

Synthesis of (−)-N-(3-fluoro-4-(2-methylpyridin-4-yl) phenyl)-8-methyl-7-(3, 4, 5-trifluorophenyl)-7, 8-dihydro-6H-pyrimido [5, 4-b] [1, 4] oxazin-2-amine

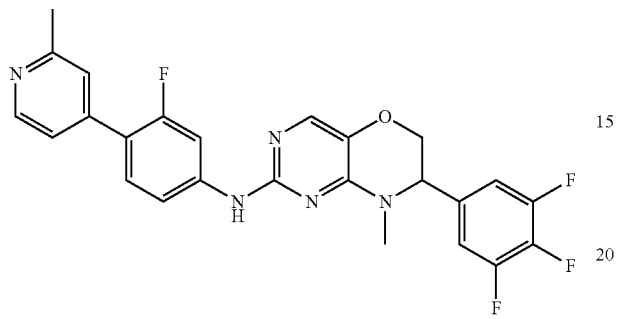

The compound of Example 36B was produced as described in Example 36. Analytical data for product Fraction I (−): $^1$H-NMR (CD$_3$OD, 400 MHz): δ 8.40-8.38 (m, 1H), 7.91-7.86 (m, 1H), 7.61 (s, 1H), 7.50-7.39 (m, 4H), 7.03 (t, 2H), 4.73-4.70 (m, 1H), 4.22-4.20 (m, 2H), 3.19 (s, 3H), 2.58 (s, 3H); Mass (ESI): 482.3 [M+1]; LC-MS: 482.3 (M+1); (column; X-Select CSH C-18 (50×3.0 mm, 3.5 μm); RT 3.32 min. 0.05% Aq TFA: ACN; 0.80 ml/min); UPLC (column; Acquity BEH C-18, 50×2.1 mm, 1.7 μm); RT 1.76 min. ACN: 0.025% TFA (Aq); 0.50 ml/min; Chiral HPLC: RT=14.43 min (CHIRALPAK-IA (250×4.6 mm, 5 μm; mobile phase (A) 0.1% TFA in n-hexane (B) CH$_2$Cl$_2$:MeOH (50:50) (A:B: 75:25; flow Rate: 1.0 mL/min); Optical rotation $[α]_D^{20.02}$: −139.28 (c 0.25, DCM).

Example 37

Synthesis of 8-methyl-N-(4-(2-methylpyridin-4-yl) phenyl)-7-(3, 4, 5-trifluorophenyl)-7, 8-dihydro-6H-pyrimido [5, 4-b] [1, 4] oxazin-2-amine

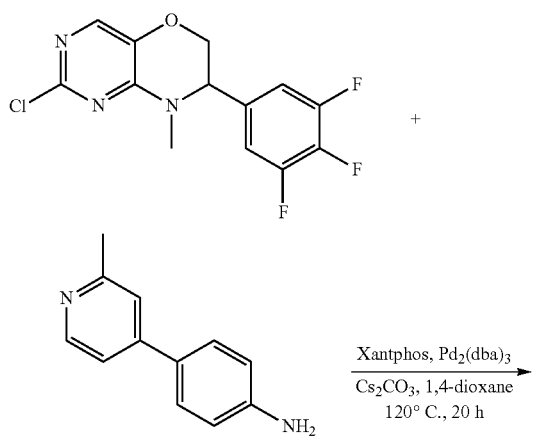

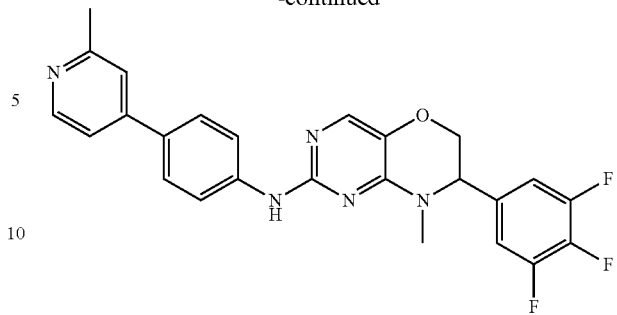

Synthesis of 8-methyl-N-(4-(2-methylpyridin-4-yl) phenyl)-7-(3, 4, 5-trifluorophenyl)-7, 8-dihydro-6H-pyrimido [5, 4-b] [1, 4] oxazin-2-amine To a dry vial added a suspension of Pd$_2$(dba)$_3$ (7 mg, 0.008 mmol) and Xantphos (14 mg, 0.02 mmol) in 1, 4-dioxane (0.5 mL). The suspension was degassed, heated to 120° C. and stirred for 3 min. A mixture of 2-chloro-8-methyl-7-(3, 4, 5-trifluorophenyl)-7, 8-dihydro-6H-pyrimido [5, 4-b] [1, 4] oxazine (50 mg, 0.15 mmol), 4-(2-methylpyridin-4-yl) aniline (58 mg, 0.31 mmol) and cesium carbonate (72 mg, 0.22 mmol) in 1, 4-dioxane (0.5 mL) was degassed and the catalyst premix was added. The reaction mixture was heated to 120° C. and stirred for 20 h in a sealed tube. After consumption of the starting material (monitored by TLC and LCMS), the mixture was diluted with water (20 mL) and extracted with EtOAc (2×20 mL). The combined organic extracts were dried over sodium sulfate, filtered and concentrated in vacuo. The crude material was purified by silica gel column chromatography using 60% EtOAc: hexanes to afford 50 mgs further purified by preparative TLC using 50% EtOAc:hexanes to afford 8-methyl-N-(4-(2-methylpyridin-4-yl) phenyl)-7-(3, 4, 5-trifluorophenyl)-7, 8-dihydro-6H-pyrimido [5, 4-b] [1, 4] oxazin-2-amine (10 mg, 14%) as an off-white solid. $^1$H-NMR (CD$_3$OD, 400 MHz): δ 8.38-8.36 (m, 1H), 7.81 (d, 2H), 7.69 (d, 2H), 7.61 (s, 1H), 7.57 (s, 1H), 7.50-7.48 (m, 1H), 7.04 (t, 2H), 4.74-4.72 (m, 1H), 4.21-4.20 (m, 2H), 3.16 (s, 3H), 2.57 (s, 3H); Mass (ESI): 464.5 [M+1]; LC-MS: 464.5 (M+1); (column; X-Select CSH C-18 (50×3.0 mm, 3.5 μm); RT 3.03 min. 0.05% Aq TFA: ACN; 0.80 mL/min); UPLC: (column; Acquity BEH C-18 50×2.1 mm, 1.7 μm); RT 1.68 min. ACN: 0.025% Aq TFA; 0.5 mL/min. TLC: 50% EtOAc: hexanes (R$_f$: 0.3).

Racemic compound of Example 37 was separated using a Chiralpak IA (250×20 mm, 5 μm (25 mg loading; 0.1% DEA in n-hexane: EtOH:MeOH (50:50); (70:30) as the mobile phase) to provide the compound of Example 37A (Fraction I (+)) and the compound of Example 37B (Fraction II (−)).

Example 37A

Synthesis of (+)-8-methyl-N-(4-(2-methylpyridin-4-yl) phenyl)-7-(3, 4, 5-trifluorophenyl)-7, 8-dihydro-6H-pyrimido [5, 4-b] [1, 4] oxazin-2-amine

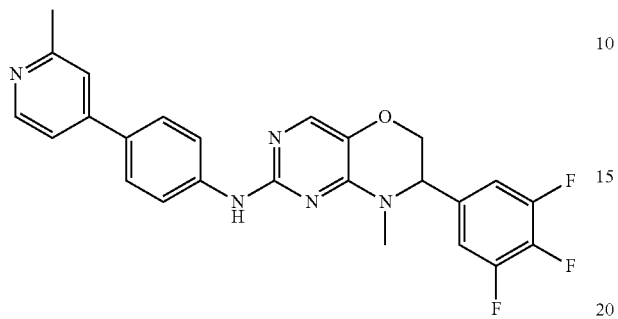

The compound of Example 37A was produced as described in Example 37. Analytical data for product Fraction I (+): $^1$H NMR (CD$_3$OD, 400 MHz): δ 8.39-8.35 (m, 1H), 7.78 (d, 2H), 7.64 (d, 2H), 7.59 (s, 1H), 7.58 (s, 1H), 7.46-7.44 (m, 1H), 7.04-7.00 (m, 2H), 4.72-4.70 (m, 1H), 4.20 (s, 2H), 3.11 (s, 3H), 2.52 (s, 3H); LC-MS: 464.4 (M+1); (column; X-Select CSH C-18 (50×3.0 mm, 3.5 µm); RT 2.98 min. 0.05% Aq TFA: ACN; 0.80 ml/min); UPLC (column; Acquity BEH C-18, 50×2.1 mm, 1.7 µm); RT 1.62 min. ACN: 0.025% TFA (Aq); 0.50 ml/min; Chiral HPLC: RT=11.02 min (Chiralpak IA (250×4.6 mm, 5 µm; mobile phase (A) 0.1% TFA in n-hexane (B) EtOH:MeOH (50:50) (70:30); flow Rate: 1.0 mL/min); Optical rotation [α]$_D^{24.98}$: +143.56 (c 0.25%, DCM); TLC: 5% MeOH:CH$_2$Cl$_2$ (R$_f$: 0.3).

Example 37B

Synthesis of (−)-8-methyl-N-(4-(2-methylpyridin-4-yl) phenyl)-7-(3, 4, 5-trifluorophenyl)-7, 8-dihydro-6H-pyrimido [5, 4-b] [1, 4] oxazin-2-amine

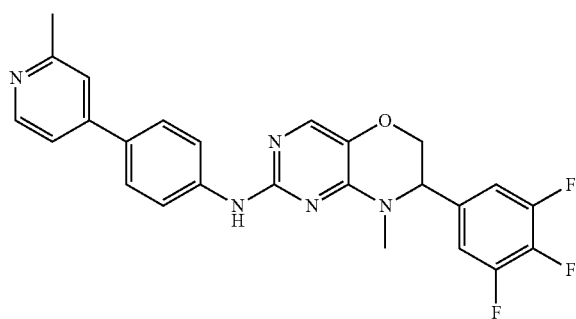 [SMILES: Cc1cc(-c2ccc(Nc3ncc4c(n3)N(C)C(c3cc(F)c(F)c(F)c3)CO4)cc2)ccn1]

The compound of Example 37B was produced as described in Example 37. Analytical data for product Fraction II (−): $^1$H NMR (CD$_3$OD, 400 MHz): δ 8.40-8.38 (m, 1H), 7.80 (d, 2H), 7.64 (d, 2H), 7.60 (s, 1H), 7.58 (s, 1H), 7.50-7.48 (m, 1H), 7.01 (t, 2H), 4.73-4.70 (m, 1H), 4.21 (s, 2H), 3.18 (s, 3H), 2.55 (s, 3H); Mass (ESI): 464.4 [M+1]; LC-MS: 464.3 (M+1); (column; X-Select CSH C-18 (50×3.0 mm, 3.5 µm); RT 2.98 min. 0.05% Aq TFA: ACN; 0.80 ml/min); UPLC (column; Acquity BEH C-18, 50×2.1 mm, 1.7 µm); RT 1.62 min. ACN: 0.025% TFA (Aq); 0.50 ml/min. Chiral HPLC: RT=13.29 min (Chiralpak IA (250×4.6 mm, 5 µm; mobile phase (A) 0.1% TFA in n-hexane (B) EtOH:MeOH (50:50) (70:30); flow Rate: 1.0 mL/min); Optical rotation [α]$_D^{25.01}$: −148.27 (c 0.25%, DCM).

Example 38

Synthesis of N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine

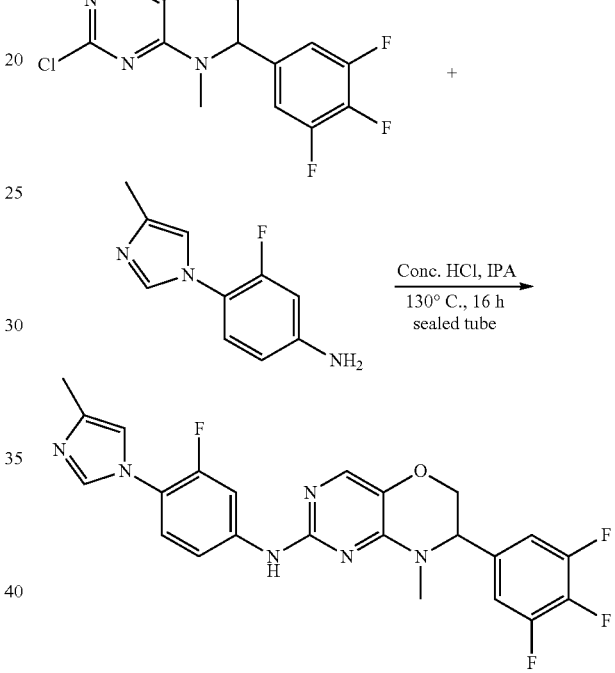

Synthesis of N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine To a stirred solution of 2-chloro-8-methyl-7-(3, 4, 5-trifluorophenyl)-7, 8-dihydro-6H-pyrimido [5, 4-b] [1, 4] oxazine (80 mg, 0.29 mmol) in isopropanol (0.8 mL) under an argon atmosphere were added concentrated hydrochloric acid (catalytic amount) and 3-fluoro-4-(4-methyl-1H-imidazol-1-yl) aniline (97 mg, 0.50 mmol) at room temperature. The reaction mixture was stirred at 130° C. for 16 h in a sealed tube. After consumption of the starting material (monitored by TLC), the reaction was diluted with a saturated sodium carbonate solution (20 mL) and extracted with EtOAc (2×20 mL). The combined organic extracts were dried over sodium sulfate, filtered and concentrated in vacuo. The crude material was purified by silica gel column chromatography using 3% MeOH: CH$_2$Cl$_2$ to afford N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine (12 mg, 10%) as an off-white solid.

¹H-NMR (CD₃OD, 400 MHz): δ 8.00-7.99 (m, 1H), 7.73 (s, 1H), 7.60 (s, 1H), 7.40-7.39 (m, 1H), 7.30 (t, 1H), 7.07-7.00 (m, 3H), 4.71 (s, 1H), 4.21 (s, 2H), 3.13 (s, 3H), 2.23 (s, 3H); Mass (ESI): 471.4 [M+1]; LC-MS: 471.6 (M+1); (column; X-Selected CSH C-18 (50×3.0 mm, 3.5 μm); RT 2.99 min 0.05% Aq TFA: ACN; 0.80 mL/min); UPLC: (column; Acquity BEH C-18 50×2.1 mm, 1.7 μm); RT 1.75 min. ACN: 0.025% TFA (Aq); 0.50 mL/min. TLC: 5% MeOH:CH₂Cl₂ (R$_f$: 0.2).

Example 39

Synthesis of N-(3-methoxy-4-(2-methylpyridin-4-yl) phenyl)-8-methyl-7-(3, 4, 5-trifluorophenyl)-7, 8-dihydro-6H-pyrimido [5, 4-b] [1, 4] oxazin-2-amine

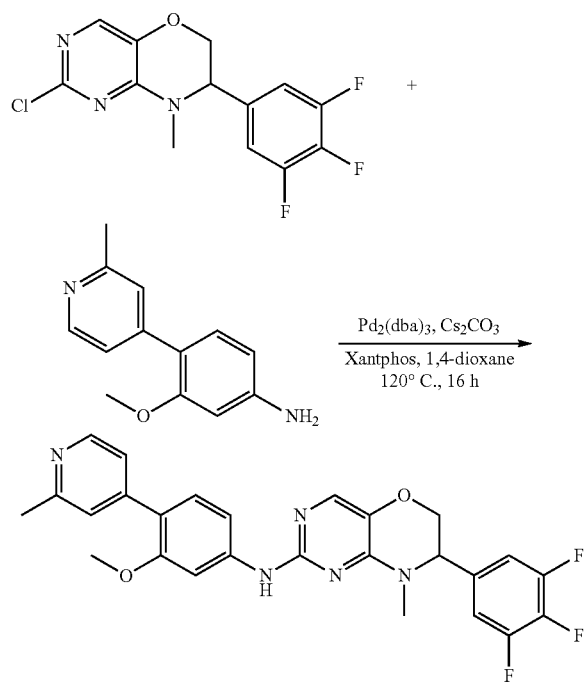

Synthesis of N-(3-methoxy-4-(2-methylpyridin-4-yl) phenyl)-8-methyl-7-(3, 4, 5-trifluorophenyl)-7, 8-dihydro-6H-pyrimido [5, 4-b] [1, 4] oxazin-2-amine To a dry vial was added a suspension of Pd₂(dba)₃ (2 mg, 0.002 mmol) and Xantphos (4 mg, 0.006 mmol) in 1,4-dioxane (0.3 mL). The suspension was degassed, heated to 120° C. and stirred for 3 min. A mixture of 2-chloro-8-methyl-7-(3, 4, 5-trifluorophenyl)-7, 8-dihydro-6H-pyrimido [5, 4-b] [1, 4] oxazine (50 mg, 0.15 mmol), 3-methoxy-4-(2-methylpyridin-4-yl) aniline (68 mg, 0.31 mmol) and cesium carbonate (72 mg, 0.21 mmol) in 1, 4-dioxane (0.3 mL) was degassed and the catalyst premix was added. The reaction mixture was heated to 120° C. and stirred for 16 h in a sealed tube. After consumption of the starting material (monitored by TLC and LCMS), the mixture was concentrated in vacuo. The crude material was diluted with water (20 mL) and extracted with CH₂Cl₂ (2×20 mL). The combined organic extracts were dried over sodium sulfate, filtered and concentrated in vacuo. The crude material was purified by preparative HPLC [Kromasil C18 (250× 21.2 mm 10 um) (50 mg loading; CH₃CN; 0.05% TFA Aq (0.1/90, 2/80, 15/60, 25/10, 35/10) as the mobile phase with a Flow rate=15 mL/min] to afford N-(3-methoxy-4-(2-methylpyridin-4-yl) phenyl)-8-methyl-7-(3, 4, 5-trifluorophenyl)-7, 8-dihydro-6H-pyrimido [5, 4-b] [1, 4] oxazin-2-amine (20 mg, 25%) as a yellow solid. ¹H-NMR (CD₃OD, 500 MHz): δ 8.35-8.34 (m, 1H), 7.71 (s, 1H), 7.64 (s, 1H), 7.49 (s, 1H), 7.44-7.43 (m, 1H), 7.34-7.30 (m, 2H), 7.07 (t, 2H), 4.78. 4.76 (m, 1H), 4.23 (d, 2H), 3.88 (s, 3H), 3.20 (s, 3H), 2.56 (s, 3H); Mass (ESI): 494.6 [M+1]; LC-MS: 494.7 (M+1); (column; X-Select CSH C-18 (50×3.0 mm, 3.5 μm); RT 3.02 min. 0.05% Aq TFA: ACN; 0.80 mL/min); UPLC: (column; Acquity BEH C-18 (50×2.1 mm, 1.7 μm); RT 1.78 min. ACN: 0.025% Aq TFA; 0.5 mL/min. TLC: 50% EtOAc:hexanes (R$_f$: 0.2).

Racemic compound of Example 39 was separated using a Chiralpak IB (250×20 mm, 5 μm (20 mg loading; A) 0.1% DEA in n-hexane B) EtOH (A:B: 90:10) to provide the compound of Example 39A (Fraction I (+)) and the compound of Example 39B (Fraction II (−))

Example 39A

Synthesis of (+)-N-(3-methoxy-4-(2-methylpyridin-4-yl) phenyl)-8-methyl-7-(3, 4, 5-trifluorophenyl)-7, 8-dihydro-6H-pyrimido [5, 4-b] [1, 4] oxazin-2-amine

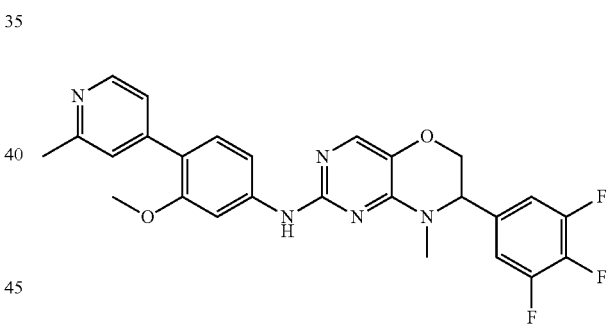

The compound of Example 39A was produced as described in Example 39. Analytical data for Fraction I (+): ¹H NMR (CD₃OD, 400 MHz): δ 8.32 (br s, 1H), 7.71 (s, 1H), 7.64 (s, 1H), 7.49 (s, 1H), 7.44-7.43 (m, 1H), 7.32-7.25 (m, 2H), 7.01-6.99 (m, 2H), 4.82-4.80 (m, 1H), 4.20-4.19 (m, 2H), 3.87 (s, 3H), 3.19 (s, 3H), 2.52 (s, 3H); Mass (ESI): 494.4 [M+1]; LC-MS: 494.4 (M+1); (column; X-Select C-18 (50×3.0 mm, 3.5 μm); RT 3.00 min. 0.05% Aq TFA: ACN; 0.80 ml/min); UPLC: (column; Acquity BEH C-18, 50×2.1 mm, 1.7 μm); RT 1.75 min. ACN: 0.025% TFA (Aq); 0.50 ml/min. Chiral HPLC: RT=21.16 min (Chiralpak IB (250×4.6 mm, 5 μm; mobile phase (A) 0.1% DEA in n-hexane (B) EtOH (90:10); flow Rate: 1.0 mL/min); Optical rotation [α]$_D^{19.98}$: +160.80 (c=0.25, DCM); TLC: 5% MeOH:CH₂Cl₂ (R$_f$: 0.3).

Example 39B

Synthesis of (−)-N-(3-methoxy-4-(2-methylpyridin-4-yl) phenyl)-8-methyl-7-(3, 4, 5-trifluorophenyl)-7, 8-dihydro-6H-pyrimido [5, 4-b] [1, 4] oxazin-2-amine

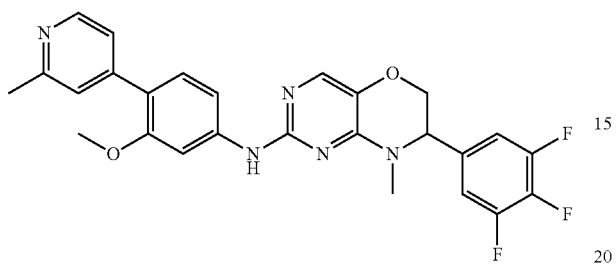

The compound of Example 39B was produced as described in Example 39. Analytical data for Fraction II (−): $^1$H-NMR (CD$_3$OD, 400 MHz): δ 8.30-8.29 (m, 1H), 7.69 (s, 1H), 7.60 (s, 1H), 7.46 (s, 1H), 7.41-7.39 (m, 1H), 7.30-7.27 (m, 2H), 7.01-6.99 (m, 2H), 4.71-4.69 (m, 1H), 4.20 (s, 2H), 3.82 (s, 3H), 3.14 (s, 3H), 2.51 (s, 3H); Mass (ESI): 494.4 [M+1]; LC-MS: 494.4 (M+1); (column; X-Select CSH C-18 (50×3.0 mm, 3.5 μm); RT 2.99 min. 5 mM NH$_4$OAc: ACN; 0.80 ml/min); UPLC: (column; Acquity BEH C-18, 50×2.1 mm, 1.7 μm); RT 1.75 min. ACN: 0.025% TFA (Aq); 0.50 ml/min. Chiral HPLC: RT=24.64 min (Chiralpak IB (250×4.6 mm, 5 μm; mobile phase (A) 0.1% DEA in n-hexane (B) EtOH (90:10) 0:30); flow Rate: 1.0 mL/min); Optical rotation $[α]_D^{19.99}$: −150.80 (c=0.25, DCM); TLC: 5% MeOH: CH$_2$Cl$_2$ (R$_f$: 0.3).

Example 40

Synthesis of N-(3-methoxy-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine

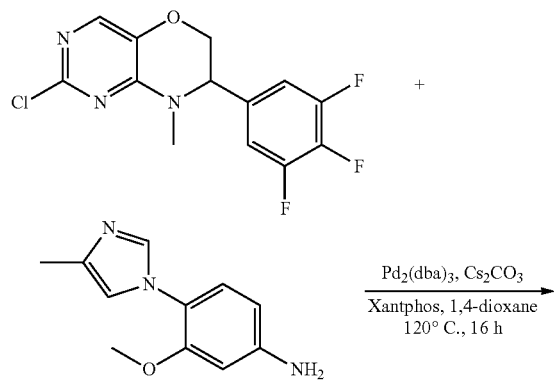

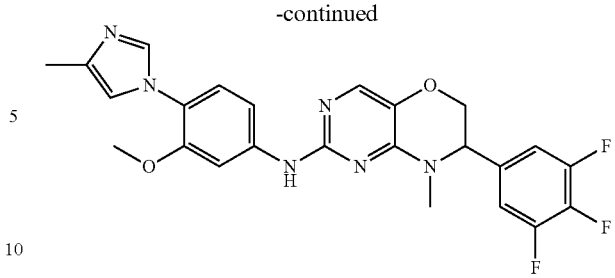

Synthesis of N-(3-methoxy-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine To a dry vial was added a suspension of Pd$_2$(dba)$_3$ (2 mg, 0.002 mmol) and Xantphos (4 mg, 0.006 mmol) in 1, 4-dioxane (0.3 mL). The suspension was degassed, heated to 120° C. and stirred for 3 min. A mixture of 2-chloro-8-methyl-7-(3, 4, 5-trifluorophenyl)-7, 8-dihydro-6H-pyrimido [5, 4-b] [1, 4] oxazine (50 mg, 0.15 mmol), 3-methoxy-4-(4-methyl-1H-imidazol-1-yl) aniline (64 mg, 0.31 mmol) and cesium carbonate (73 mg, 0.21 mmol) in 1, 4-dioxane (0.3 mL) was degassed and the catalyst premix was added. The reaction mixture was heated to 120° C. and stirred for 16 h in a sealed tube. After consumption of the starting material (monitored by TLC and LCMS), the mixture was concentrated in vacuo. The crude material was diluted with water (20 mL) and extracted with CH$_2$Cl$_2$ (2×20 mL). The combined organic extracts were dried over sodium sulfate, filtered and concentrated in vacuo. The crude material was purified by preparative HPLC [Kromasil C18 (250×21.2 mm 10 um) (50 mg loading; CH3CN; 0.05% TFA Aq (0.1/90, 2/80, 15/60, 25/10, 35/10) as the mobile phase with a Flow rate=15 mL/min] to afford N-(3-methoxy-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine (27 mg, 35%) as a brown solid. $^1$H-NMR (CD$_3$OD, 400 MHz): δ 7.75 (s, 1H), 7.68 (s, 1H), 7.61 (s, 1H), 7.25 (d, 1H), 7.18 (d, 1H), 7.06-7.02 (m, 2H), 6.97 (s, 1H), 4.74-4.73 (m, 1H), 4.21-4.20 (m, 2H), 3.85 (s, 3H), 3.17 (s, 3H), 2.23 (s, 3H); Mass (ESI): 483.5 [M+1]; LC-MS: 483.6 (M+1); (column; X-Select CSH C-18 (50×3.0 mm, 3.5 μm); RT 2.95 min. 0.05% Aq TFA: ACN; 0.80 mL/min); UPLC: (column; Eclipse XDB C-18 150×4.6 mm, 5.0 μm); RT 7.76 min. ACN: 0.05% Aq TFA; 1.0 mL/min. TLC: 70% EtOAc:hexanes (R$_f$: 0.2).

Racemic compound of Example 40 was separated using a Chiralcel A-DH (250×4.6 mm, 5 μm (30 mg loading; A) CO$_2$B) 0.1% DEA in MeOH (A:B: 70:30) to provide the compound of Example 40A (Fraction I (−)) and the compound of Example 40B (Fraction II (+)).

Example 40A

Synthesis of (−)-N-(3-methoxy-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine

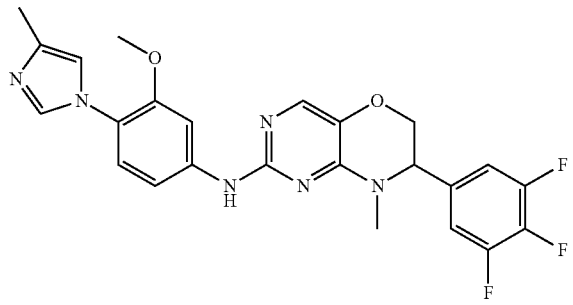 [SMILES: COc1cc(Nc2ncc3c(n2)N(C)C(c2cc(F)c(F)c(F)c2)CO3)ccc1-n1cnc(C)c1]

The compound of Example 40A was produced as described in Example 40. Analytical data for product Fraction I (−): $^1$H-NMR (CD$_3$OD, 400 MHz): δ 7.73 (s, 1H), 7.65 (s, 1H), 7.60 (s, 1H), 7.22 (d, 1H), 7.18 (d, 1H), 7.09-7.00 (m, 2H), 6.97 (s, 1H), 4.72-4.70 (m, 1H), 4.20 (s, 2H), 3.82 (s, 3H), 3.19 (s, 3H), 2.21 (s, 3H); Mass (ESI): 483.4 [M+1]; LC-MS: 483 (M+1); (column; X-Select CSH C-18 (50×3.0 mm, 3.5 μm); RT 2.45 min. 0.05% Aq TFA: ACN; 0.80 ml/min); UPLC (column; Acquity BEH C-18, 50×2.1 mm, 1.7 μm); RT 1.64 min. ACN: 0.025% TFA (Aq); 0.50 ml/min; Chiral HPLC: RT=6.89 min (Chiralcel AD-H (250×4.6 mm, 5 μm; mobile phase (A) 0.1% DEA in Methanol (70:30); flow Rate: 3.0 mL/min); Optical rotation $[\alpha]_D^{25.01}$: −137.42 (c 0.25, DCM).

Example 40B

Synthesis of (+)-N-(3-methoxy-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine

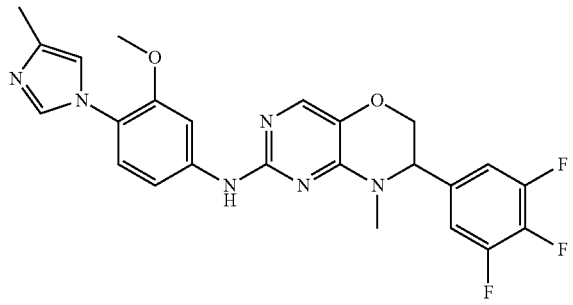 [SMILES: COc1cc(Nc2ncc3c(n2)N(C)C(c2cc(F)c(F)c(F)c2)CO3)ccc1-n1cnc(C)c1]

The compound of Example 40B was produced as described in Example 40. Analytical data for product Fraction II (+): $^1$H-NMR (CD$_3$OD, 400 MHz): δ 7.73 (s, 1H), 7.65 (s, 1H), 7.60 (s, 1H), 7.22 (d, 1H), 7.18 (d, 1H), 7.09-7.00 (m, 2H), 6.97 (s, 1H), 4.72-4.70 (m, 1H), 4.20 (s, 2H), 3.82 (s, 3H), 3.19 (s, 3H), 2.21 (s, 3H); Mass (ESI): 483.4 [M+1]; LC-MS: 483 (M+1); (column; X-Select CSH C-18 (50×3.0 mm, 3.5 μm); RT 2.45 min 0.05% Aq TFA: ACN; 0.80 ml/min); UPLC (column; Acquity BEH C-18, 50×2.1 mm, 1.7 μm); RT 1.64 min. ACN: 0.025% TFA (Aq); 0.50 ml/min; Chiral HPLC: RT=8.83 min (Chiralcel AD-H (250×4.6 mm, 5 μm; mobile phase (A) 0.1% DEA in Methanol (70:30); flow Rate: 3.0 mL/min); Optical rotation $[\alpha]_D^{25.01}$: +146.03 (c 0.25, DCM).

Example 41

Synthesis of 7-(3, 5-difluorophenyl)-N-(3-fluoro-4-(2-methylpyridin-4-yl) phenyl)-8-methyl-7, 8-dihydro-6H-pyrimido [5, 4-b] [1, 4] oxazin-2-amine

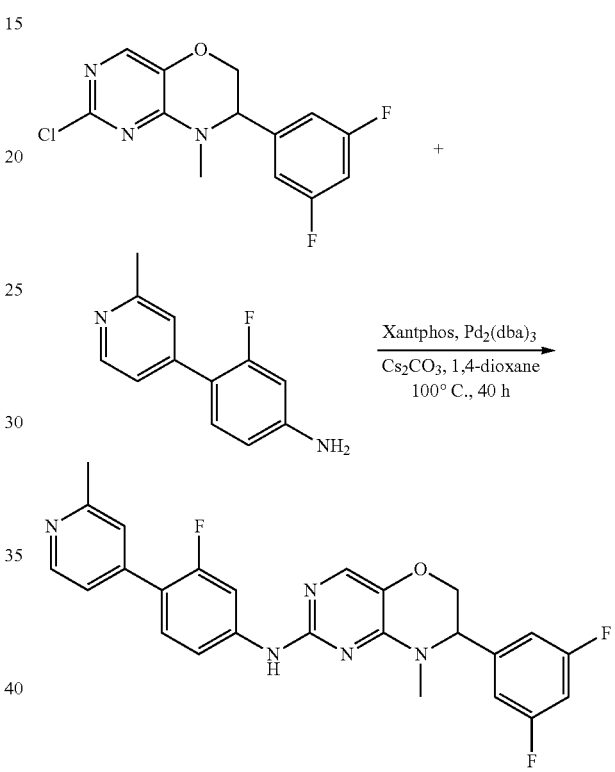

Synthesis of 7-(3, 5-difluorophenyl)-N-(3-fluoro-4-(2-methylpyridin-4-yl) phenyl)-8-methyl-7, 8-dihydro-6H-pyrimido [5, 4-b] [1, 4] oxazin-2-amine To a dry vial was added a suspension of Pd$_2$(dba)$_3$ (2.3 mg, 0.002 mmol) and Xantphos (4.3 mg, 0.007 mmol) in 1, 4-dioxane (0.3 mL). The suspension was degassed, heated to 100° C. and stirred for 3 min. A mixture of 2-chloro-7-(3, 5-difluorophenyl)-8-methyl-7, 8-dihydro-6H-pyrimido [5, 4-b] [1, 4] oxazine (50 mg, 0.16 mmol), 3-fluoro-4-(2-methylpyridin-4-yl) aniline (68 mg, 0.33 mmol) and cesium carbonate (76 mg, 0.23 mmol) in 1, 4-dioxane (0.3 mL) was degassed and the catalyst premix was added. The reaction mixture was heated to 100° C. and stirred for 40 h in a sealed tube. After consumption of the starting material (monitored by TLC and LCMS), the mixture was concentrated in vacuo. The crude material was diluted with water (20 mL) and extracted with CH$_2$Cl$_2$ (2×20 mL). The combined organic extracts were dried over sodium sulfate, filtered and concentrated in vacuo. The crude material was purified by silica gel column chromatography using 60% EtOAc:hexanes to afford 70 mgs further purified by preparative HPLC [Kromasil C18 (250×21.2 mm 10 um) (30 mg loading; n-hexane; CH2Cl2:MeOH (50:50); (90:10) as the mobile phase with a Flow rate=15 mL/min] to afford 7-(3, 5-difluorophenyl)-N-(3-fluoro-4-(2-methylpyridin-4-yl) phenyl)-8-methyl-7, 8-dihydro-6H-pyrimido [5, 4-b] [1, 4] oxazin-2-amine (12 mg, 15%) as an off-white solid. $^1$H-NMR (CD$_3$OD, 400 MHz): δ 8.40 (d, 1H), 7.92-7.88 (m, 1H), 7.63 (s, 1H), 7.51-7.42 (m, 4H), 6.95-6.86 (m, 3H), 4.78-4.77 (m, 1H), 4.23 (d, 2H), 3.18 (s, 3H), 2.57 (s, 3H); LC-MS: 464.5 (M+1); (column; X-Select CSH C-18 (50×3.0 mm, 3.5 μm); RT 2.99 min. 0.05% Aq TFA: ACN; 0.80 mL/min); UPLC: (column; Acquity BEH C-18 50×2.1 mm, 1.7 μm); RT 1.69 min. ACN: 0.025% Aq TFA; 0.5 mL/min. TLC: 50% EtOAc:hexanes (R$_f$: 0.4).

Racemic compound of Example 41 was separated using a Chiralpak IA (250×4.6 mm, 5 μm; mobile phase (A) 0.1% DEA in n-hexane (B) CH$_2$Cl$_2$:MeOH (20:80) (A:B: 80:20) to provide the compound of Example 41A (Fraction I (+)) and the compound of Example 41B (Fraction II (−)).

Example 41A

Synthesis of (+)-7-(3, 5-difluorophenyl)-N-(3-fluoro-4-(2-methylpyridin-4-yl) phenyl)-8-methyl-7, 8-dihydro-6H-pyrimido [5, 4-b] [1, 4] oxazin-2-amine

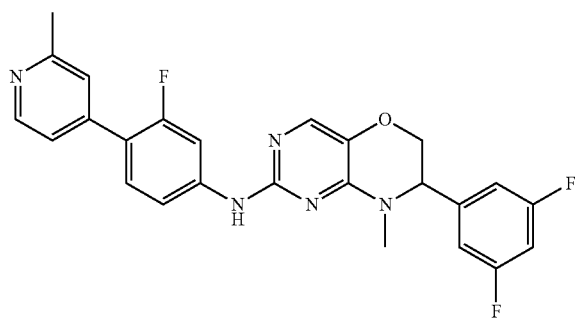 [SMILES: Cc1cc(-c2ccc(Nc3ncc4c(n3)N(C)C(c3cc(F)cc(F)c3)CO4)cc2F)ccn1]

The compound of Example 41A was produced as described in Example 41. Analytical data for Fraction I (+): $^1$H-NMR (CD$_3$OD, 400 MHz): δ 8.40-8.39 (m, 1H), 7.90-7.88 (m, 1H), 7.60 (s, 1H), 7.49-7.39 (m, 4H), 6.91-6.81 (m, 3H), 4.78-4.77 (m, 1H), 4.23 (d, 2H), 3.13 (s, 3H), 2.52 (s, 3H); Mass (ESI): 464.4 [M+1]; LC-MS: 464.3 (M+1); (column; X-Select C-18 (50×3.0 mm, 3.5 μm); RT 2.92 min. 0.05% Aq TFA: ACN; 0.80 ml/min); UPLC: (column; Acquity BEH C-18, 50×2.1 mm, 1.7 μm); RT 1.66 min. ACN: 0.025% TFA (Aq); 0.50 ml/min. Chiral HPLC: RT=14.45 min (Chiralpak IA (250×4.6 mm, 5 μm; mobile phase (A) 0.1% DEA in n-hexane (B) CH$_2$Cl$_2$:MeOH (20:80) (80:20); flow Rate: 1.0 mL/min); Optical rotation $[α]_D^{20.01}$: +172.01 (c=0.25, DCM); TLC: 5% MeOH/CH$_2$Cl$_2$ (R$_f$: 0.3).

Example 41B

Synthesis of (−)-7-(3, 5-difluorophenyl)-N-(3-fluoro-4-(2-methylpyridin-4-yl) phenyl)-8-methyl-7, 8-dihydro-6H-pyrimido [5, 4-b] [1, 4] oxazin-2-amine

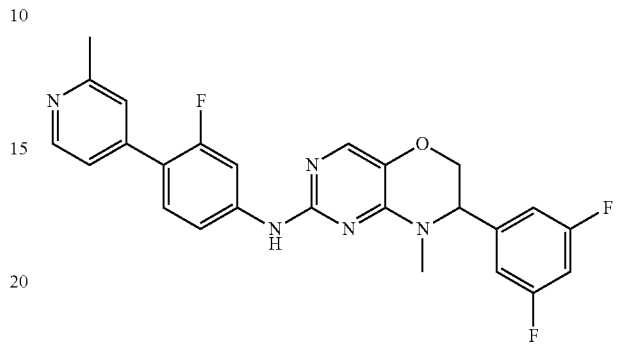

The compound of Example 41B was produced as described in Example 41. Analytical data for Fraction II (−): $^1$H-NMR (CD$_3$OD, 400 MHz): δ 8.40-8.38 (m, 1H), 7.91-7.89 (m, 1H), 7.61 (s, 1H), 7.49-7.30 (m, 4H), 6.93-6.80 (m, 3H), 4.78-4.77 (m, 1H), 4.23 (d, 2H), 3.12 (s, 3H), 2.56 (s, 3H); Mass (ESI): 464.4 [M+1]; LC-MS: 464.3 (M+1); (column; X-Select C-18 (50×3.0 mm, 3.5 μm); RT 2.92 min. 0.05% Aq TFA: ACN; 0.80 ml/min); UPLC: (column; Acquity BEH C-18, 50×2.1 mm, 1.7 μm); RT 1.66 min. ACN: 0.025% TFA (Aq); 0.50 ml/min. Chiral HPLC: RT=16.71 min (Chiralpak IA (250×4.6 mm, 5 μm; mobile phase (A) 0.1% DEA in n-hexane (B) CH$_2$Cl$_2$:MeOH (20:80) (80:20); flow Rate: 1.0 mL/min); Optical rotation $[α]_D^{20.01}$: −154.78 (c=0.25, DCM); TLC: 5% MeOH/CH$_2$Cl$_2$ (R$_f$: 0.3).

Example 42

Synthesis of 7-(3, 5-difluorophenyl)-N-(3-methoxy-4-(2-methylpyridin-4-yl) phenyl)-8-methyl-7, 8-dihydro-6H-pyrimido [5, 4-b] [1, 4] oxazin-2-amine

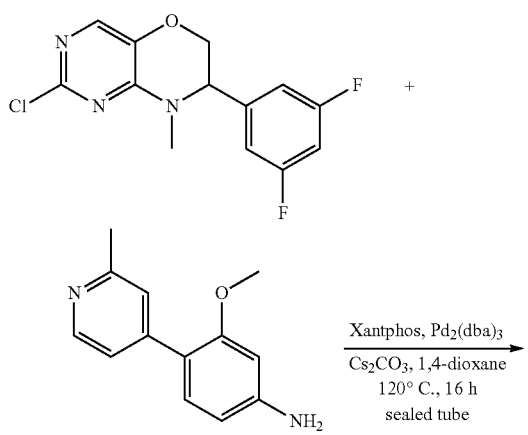

275

-continued

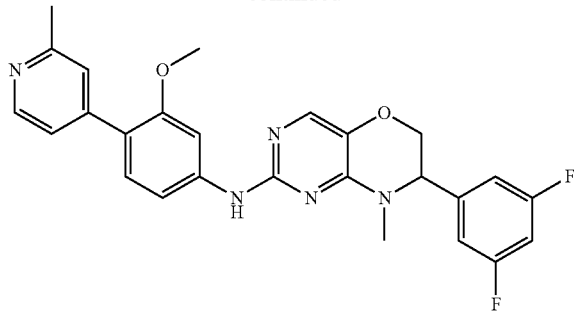 [SMILES: COc1cc(Nc2ncc3c(n2)N(C)C(c2cc(F)cc(F)c2)CO3)ccc1-c1ccnc(C)c1]

Synthesis of 7-(3, 5-difluorophenyl)-N-(3-methoxy-4-(2-methylpyridin-4-yl) phenyl)-8-methyl-7, 8-dihydro-6H-pyrimido [5, 4-b] [1, 4] oxazin-2-amine To a dry vial was added a suspension of $Pd_2(dba)_3$ (12 mg, 0.01 mmol) and Xantphos (23 mg, 0.04 mmol) in 1, 4-dioxane (0.75 mL). The suspension was degassed, heated to 120° C. and stirred for 3 min. A mixture of 2-chloro-7-(3, 5-difluorophenyl)-8-methyl-7, 8-dihydro-6H-pyrimido [5, 4-b] [1, 4] oxazine (80 mg, 0.27 mmol), 3-methoxy-4-(2-methylpyridin-4-yl) aniline (115 mg, 0.53 mmol) and cesium carbonate (123 mg, 0.37 mmol) in 1, 4-dioxane (0.75 mL) was degassed and the catalyst premix was added. The reaction mixture was heated to 120° C. and stirred for 16 h in a sealed tube. After consumption of the starting material (monitored by TLC and LCMS), the mixture was diluted with water (50 mL) and extracted with EtOAc (2×50 mL). The combined organic extracts were dried over sodium sulfate, filtered and concentrated in vacuo. The crude material was purified by silica gel column chromatography using 5% MeOH: $CH_2Cl_2$ and further purified by preparative HPLC [Kromasil C18 (250×21.2 mm 10 um) (25 mg loading; n-hexane; CH2Cl2:MeOH (50:50); (85:15) as the mobile phase with a Flow rate=15 mL/min] to afford 7-(3, 5-difluorophenyl)-N-(3-methoxy-4-(2-methylpyridin-4-yl) phenyl)-8-methyl-7, 8-dihydro-6H-pyrimido [5, 4-b] [1, 4] oxazin-2-amine (20 mg, 16%) as an off-white solid.

$^1$H-NMR ($CD_3OD$, 500 MHz): δ 8.36 (d, 1H), 7.72 (s, 1H), 7.62 (s, 1H), 7.50 (s, 1H), 7.44 (d, 1H), 7.32-7.28 (m, 2H), 6.96 (t, 2H), 6.90 (d, 1H), 4.80 (s, 1H), 4.22 (s, 2H), 3.84 (s, 3H), 3.20 (s, 3H), 2.56 (s, 3H)); Mass (ESI): 476.6 [M+1]; LC-MS: 476.6 (M+1); (column; X-Select CSH C-18 (50×3.0 mm, 3.5 μm); RT 2.98 min. 0.05% Aq TFA: ACN; 0.80 mL/min); UPLC (column; Acquity BEH C-18 50×2.1 mm, 1.7 μm); RT 1.72 min. ACN: 0.025% Aq TFA; 0.5 mL/min. TLC: 70% EtOAc:hexanes ($R_f$: 0.2).

Racemic compound of Example 42 was separated using a Chiralcel-ADH (250×20 mm, 5 μm (25 mg loading; 0.1% DEA in n-hexane: EtOH:MeOH (50:50); (90:10) as the mobile phase) to provide the compound of Example 42A (Fraction I (+)) and the compound of Example 42B (Fraction II (−)).

276

Example 42A

Synthesis of (+)-7-(3, 5-difluorophenyl)-N-(3-methoxy-4-(2-methylpyridin-4-yl) phenyl)-8-methyl-7, 8-dihydro-6H-pyrimido [5, 4-b] [1, 4] oxazin-2-amine

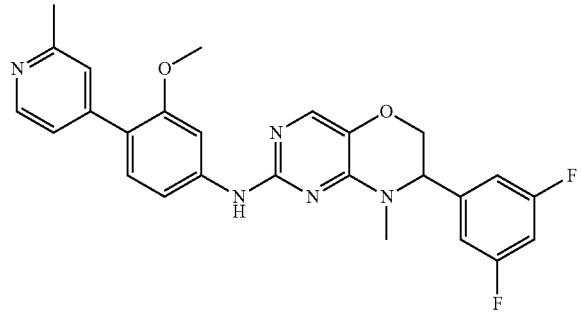 [SMILES: COc1cc(Nc2ncc3c(n2)N(C)C(c2cc(F)cc(F)c2)CO3)ccc1-c1ccnc(C)c1]

The compound of Example 42A was produced as described in Example 42. Analytical data for product Fraction I (+): $^1$H-NMR ($CD_3OD$, 500 MHz): δ 8.34 (d, 1H), 7.72 (s, 1H), 7.63 (s, 1H), 7.49 (s, 1H), 7.43 (d, 1H), 7.34-7.28 (m, 2H), 6.99-6.89 (m, 3H), 4.78 (s, 1H), 4.24 (s, 2H), 3.88 (s, 3H), 3.20 (s, 3H), 2.58 (s, 3H)); Mass (ESI): 476.4 [M+1]; LC-MS: 475.9 (M+1); (column; X-Select CSH C-18 (50×3.0 mm, 3.5 μm); RT 2.45 min. 0.05% Aq TFA: ACN; 0.80 ml/min); UPLC (column; Acquity BEH C-18, 50×2.1 mm, 1.7 μm); RT 1.64 min. ACN: 0.025% TFA (Aq); 0.50 ml/min; Chiral HPLC: RT=25.73 min (Chiralcel-OD-H (250×4.6 mm, 5 μm; mobile phase (A) 0.1% DEA in n-hexane (B) EtOH:MeOH (50:50) (90:10); flow Rate: 1.0 mL/min); Optical rotation $[\alpha]_D^{20.02}$: +178.27 (c 0.25, DCM).

Example 42B

Synthesis of (−)-7-(3, 5-difluorophenyl)-N-(3-methoxy-4-(2-methylpyridin-4-yl) phenyl)-8-methyl-7, 8-dihydro-6H-pyrimido [5, 4-b] [1, 4] oxazin-2-amine

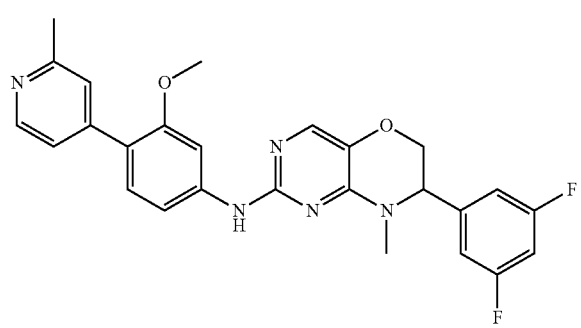

The compound of Example 42B was produced as described in Example 42. Analytical data for product Fraction II (−): $^1$H-NMR ($CD_3OD$, 500 MHz): δ 8.34 (d, 1H), 7.72 (s, 1H), 7.63 (s, 1H), 7.49 (s, 1H), 7.43 (d, 1H), 7.34-7.28 (m, 2H), 6.99-6.89 (m, 3H), 4.78 (s, 1H), 4.24 (s, 2H), 3.88 (s, 3H), 3.20 (s, 3H), 2.58 (s, 3H)); Mass (ESI):

476.4 [M+1]; LC-MS: 476 (M+1); (column; X-Select CSH C-18 (50×3.0 mm, 3.5 μm); RT 2.46 min. 0.05% Aq TFA: ACN; 0.80 ml/min); UPLC (column; Acquity BEH C-18, 50×2.1 mm, 1.7 μm); RT 1.63 min. ACN: 0.025% TFA (Aq); 0.50 ml/min; Chiral HPLC: RT=29.71 min (Chiralcel-OD-H (250×4.6 mm, 5 μm; mobile phase (A) 0.1% DEA in n-hexane (B) EtOH:MeOH (50:50) (90:10); flow Rate: 1.0 mL/min); Optical rotation $[\alpha]_D^{20.01}$: −171.66 (c 0.25, DCM).

Example 43

Synthesis of 8-methyl-N-(4-(4-methyl-1H-imidazol-1-yl) phenyl)-7-(o-tolyl)-7, 8-dihydro-6H-pyrimido [5, 4-b] [1, 4] oxazin-2-amine

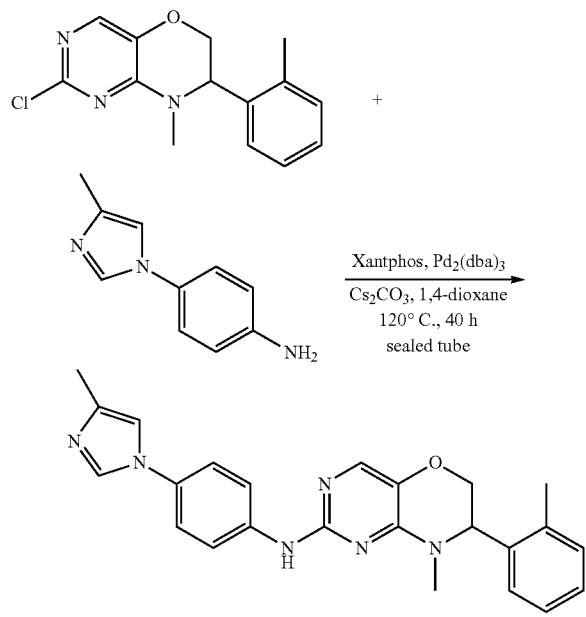

Synthesis of 8-methyl-N-(4-(4-methyl-1H-imidazol-1-yl) phenyl)-7-(o-tolyl)-7, 8-dihydro-6H-pyrimido [5, 4-b] [1, 4] oxazin-2-amine To a dry vial was added a suspension of Pd$_2$(dba)$_3$ (8 mg, 0.009 mmol) and Xantphos (16 mg, 0.02 mmol) in 1, 4-dioxane (0.5 mL). The suspension was degassed, heated to 120° C. and stirred for 3 min. A mixture of 2-chloro-8-methyl-7-(o-tolyl)-7, 8-dihydro-6H-pyrimido [5, 4-b] [1, 4] oxazine (50 mg, 0.18 mmol), 4-(4-methyl-1H-imidazol-1-yl) aniline (63 mg, 0.36 mmol) and cesium carbonate (84 mg, 0.85 mmol) in 1, 4-dioxane (0.5 mL) was degassed and the catalyst premix was added. The reaction mixture was heated to 120° C. and stirred for 40 h in a sealed tube. After consumption of the starting material (monitored by TLC and LCMS), the mixture was diluted with water (25 mL) and extracted with EtOAc (2×25 mL). The combined organic extracts were dried over sodium sulfate, filtered and concentrated in vacuo. The crude material was purified by silica gel column chromatography using 3-4% MeOH: CH$_2$Cl$_2$ which was further washed with ACN: pentane (1:1, 10 mL) to afford 8-methyl-N-(4-(4-methyl-1H-imidazol-1-yl) phenyl)-7-(o-tolyl)-7, 8-dihydro-6H-pyrimido [5, 4-b] [1, 4] oxazin-2-amine (20 mg, 26%) as an off-white solid. $^1$H-NMR (CD$_3$OD, 400 MHz): δ 7.89 (s, 1H), 7.79 (d, 2H), 7.54 (s, 1H), 7.39 (d, 2H), 7.26-7.15 (m, 4H), 6.99 (d, 1H), 5.00-4.98 (m, 1H), 4.25-4.21 (m, 1H), 4.13-4.10 (m, 1H), 3.08 (s, 3H), 2.41 (s, 3H), 2.24 (s, 3H); Mass (ESI): 413.5 [M+1]; LC-MS: 413.1 (M+1); (column; X-Select CSH C-18 (50×3.0 mm, 3.5 μm); RT 2.33 min 0.05% Aq TFA: ACN; 0.80 mL/min); UPLC: (column; Acquity BEH C-18 50×2.1 mm, 1.7 μm); RT 1.55 min. ACN: 0.025% Aq TFA; 0.5 mL/min. TLC: 50% EtOAc:hexanes (R$_f$: 0.7).

Racemic compound of Example 43 was separated using a Chiralpak IB (250×20 mm, 5 μm (30 mg loading; 0.1% DEA in n-hexane: DCM:MeOH (50:50); (90:10) as the mobile phase) to provide the compound of Example 43A (Fraction I (+)) and the compound of Example 43B (Fraction II (−)).

Example 43A

Synthesis of (+)-8-methyl-N-(4-(4-methyl-1H-imidazol-1-yl) phenyl)-7-(o-tolyl)-7, 8-dihydro-6H-pyrimido [5, 4-b] [1, 4] oxazin-2-amine

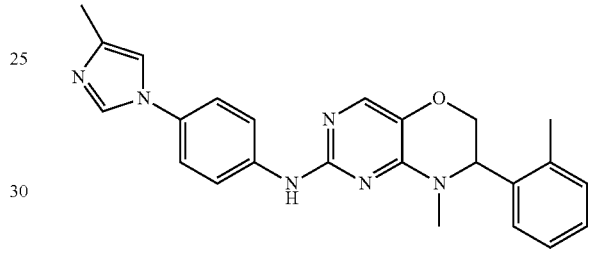

The compound of Example 43A was produced as described in Example 43. Analytical data for product Fraction I (+): $^1$H-NMR (CD$_3$OD, 400 MHz): δ 7.89 (s, 1H), 7.79 (d, 2H), 7.52 (s, 1H), 7.40 (d, 2H), 7.28-7.17 (m, 4H), 7.00 (d, 1H), 5.00-4.99 (m, 1H), 4.25-4.20 (m, 1H), 4.13-4.10 (m, 1H), 3.08 (s, 3H), 2.41 (s, 3H), 2.24 (s, 3H); Mass (ESI): 413.4 [M+1]; LC-MS: 413.3 (M+1); (column; X-Select CSH C-18 (50×3.0 mm, 3.5 μm); RT 2.76 min. 0.05% Aq TFA: ACN; 0.80 ml/min); UPLC (column; Acquity UPLC BEH C-18, 50×2.1 mm, 1.7 μm); RT 1.56 min. ACN: 0.025% TFA (Aq); 0.50 ml/min; Chiral HPLC: RT=17.91 min (CHIRALPAK-IB (250×4.6 mm, 5 μm; mobile phase (A) 0.1% DEA in n-hexane (B) CH$_2$Cl$_2$:MeOH (50:50) (A:B: 90:10); flow Rate: 1.0 mL/min); Optical rotation $[\alpha]_D^{20.02}$: +182.24 (c 0.25, DCM).

Example 43B

Synthesis of (−)-8-methyl-N-(4-(4-methyl-1H-imidazol-1-yl) phenyl)-7-(o-tolyl)-7, 8-dihydro-6H-pyrimido [5, 4-b] [1, 4] oxazin-2-amine

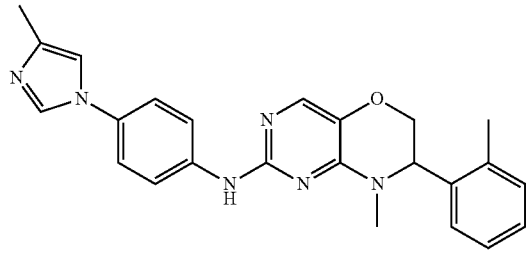 [SMILES: Cc1cn(-c2ccc(Nc3ncc4c(n3)N(C)C(c3ccccc3C)CO4)cc2)cn1]

The compound of Example 43B was produced as described in Example 43. Analytical data for product Fraction II (−): ¹H-NMR (CD₃OD, 400 MHz): δ 7.89 (s, 1H), 7.79 (d, 2H), 7.52 (s, 1H), 7.40 (d, 2H), 7.28-7.17 (m, 4H), 7.00 (d, 1H), 5.00-4.99 (m, 1H), 4.25-4.20 (m, 1H), 4.13-4.10 (m, 1H), 3.08 (s, 3H), 2.41 (s, 3H), 2.24 (s, 3H); Mass (ESI): 413.4 [M+1]; LC-MS: 413.3 (M+1); (column; X-Select CSH C-18 (50×3.0 mm, 3.5 μm); RT 2.76 min. 0.05% TFA in water: ACN; 0.80 ml/min); UPLC (column; Acquity UPLC BEH C-18, 2.1×50 mm, 1.7 μm); RT 1.57 min. ACN: 0.025% TFA (Aq); 0.50 ml/min; Chiral HPLC: RT=21.30 min (CHIRALPAK-IB (250×4.6 mm, 5 μm; mobile phase (A) 0.1% DEA in n-hexane (B) CH₂Cl₂:MeOH (50:50) (A:B: 90:10); flow Rate: 1.0 mL/min); Optical rotation [α]$_D^{20.00}$: −165.79 (c 0.25, DCM).

Example 44

Synthesis of 8-methyl-N-(4-(4-methyl-1H-imidazol-1-yl) phenyl)-7-(3, 4, 5-trifluorophenyl)-7, 8-dihydro-6H-pyrimido [5, 4-b] [1, 4] oxazin-2-amine

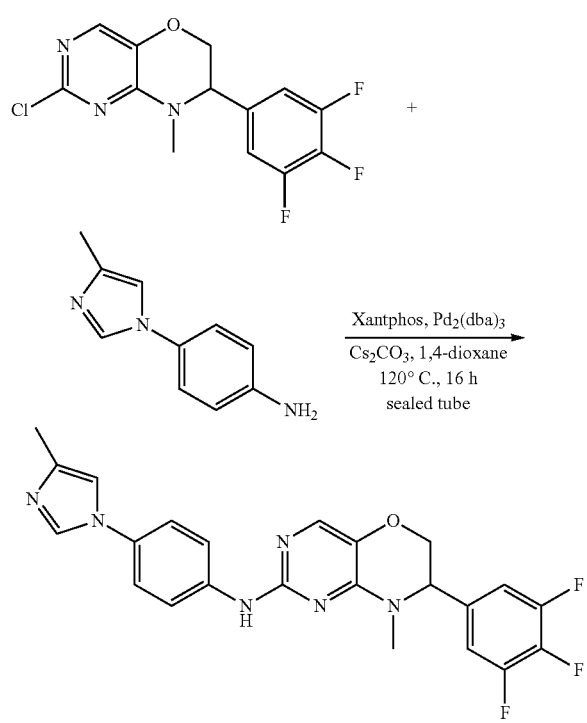

Synthesis of 8-methyl-N-(4-(4-methyl-1H-imidazol-1-yl) phenyl)-7-(3, 4, 5-trifluorophenyl)-7, 8-dihydro-6H-pyrimido [5, 4-b] [1, 4] oxazin-2-amine To a dry vial was added a suspension of Pd₂(dba)₃ (7 mg, 0.007 mmol) and Xantphos (14 mg, 0.02 mmol) in 1,4-dioxane (0.25 mL). The suspension was degassed, heated to 120° C. and stirred for 3 min. A mixture of 2-chloro-8-methyl-7-(3, 4, 5-trifluorophenyl)-7, 8-dihydro-6H-pyrimido [5, 4-b] [1, 4] oxazine (50 mg, 0.15 mmol), 4-(4-methyl-1H-imidazol-1-yl) aniline (55 mg, 0.31 mmol) and cesium carbonate (72 mg, 0.22 mmol) in 1, 4-dioxane (0.25 mL) was degassed and the catalyst premix was added. The resultant mixture was heated to 120° C. and stirred for 16 h in a sealed tube. After consumption of the starting material (monitored by TLC and LCMS), the mixture was diluted with water (5 mL) and extracted with EtOAc (2×5 mL). The combined organic extracts were dried over sodium sulfate, filtered and concentrated in vacuo. The crude material was purified by preparative [Kromasil C18 (250×21.2 mm 10 um) (45 mg loading; CH3CN; 0.05% TFA (0.1/90, 15/70, 25/10, 40/10) as the mobile phase with a Flow rate=15 mL/min] to afford 8-methyl-N-(4-(4-methyl-1H-imidazol-1-yl) phenyl)-7-(3, 4, 5-trifluorophenyl)-7, 8-dihydro-6H-pyrimido [5, 4-b] [1, 4] oxazin-2-amine (10 mg, 14%) as an off-white solid. ¹H-NMR (CD₃OD, 400 MHz): δ 7.92 (s, 1H), 7.78 (d, 2H), 7.60 (s, 1H), 7.40 (d, 2H), 7.20 (s, 1H), 7.08-7.02 (m, 2H), 4.70-4.68 (m, 1H), 4.23 (d, 2H), 3.14 (s, 3H), 2.26 (s, 3H); Mass (ESI): 453.4 [M+1]; LC-MS: 453.5 (M+1); (column; X-Select CSH C-18 (50×3.0 mm, 3.5 μm); RT 3.44 min 5 mM NH₄OAc: ACN; 0.80 mL/min); UPLC: (column; Acquity BEH C-18 50×2.1 mm, 1.7 μm); RT 1.59 min. ACN: 0.025% Aq TFA; 0.5 mL/min. TLC: 5% MeOH/DCM (R$_f$: 0.3).

Example 45

Synthesis of N-(3-methoxy-4-(4-methyl-1H-imidazol-1-yl)phenyl)-8-methyl-7-phenyl-7,8-dihydro-6H-pyrimido[5,4-b][1,4]oxazin-2-amine

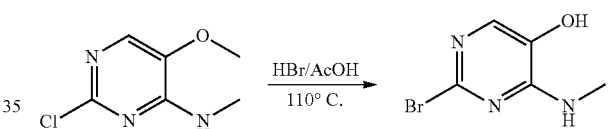

Synthesis of 2-Bromo-4-(methylamino)pyrimidin-5-ol

2-Chloro-5-methoxy-N-methylpyrimidin-4-amine (295 mg, 1.69 mmol) and HBr/AcOH 30% (3.4 mL) were charged in a reaction flask and heated to 110° C. After LCMS analysis showed complete conversion, the volatile components were evaporated and the residue diluted with water. The aqueous layer was basified using a saturated solution of sodium bicarbonate (pH~6-7) and then extracted with ethyl acetate several times. The combined organic fractions were dried over Na₂SO₄, filtered and concentrated to afford 2-Bromo-4-(methylamino)pyrimidin-5-ol used crude in the next step (108 mg, 31%). ¹H NMR (DMSO-d6, 400 MHz): δ 10.18 (s, 1H), 7.35 (s, 1H), 7.24 (s, 1H), 2.77 (d, J=4.8 Hz, 3H); LRMS (ESpos) calcd for C₅H₆BrN₃O [M+1]+: 203.97. found: 204.27.

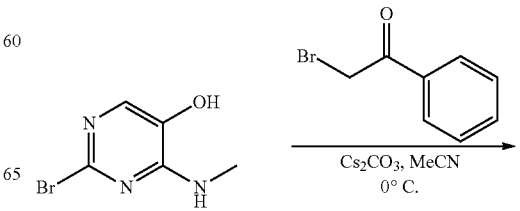

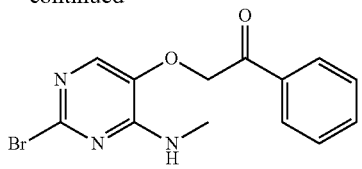

Synthesis of 2-(2-Bromo-4-(methylamino)pyrimidin-5-yloxy)-1-phenylethanone

2-Bromo-4-(methylamino)pyrimidin-5-ol (100 mg, 0.49 mmol) was dissolved in MeCN (2.0 mL) and cooled to 0° C. To this solution was added Cs$_2$CO$_3$ (355 mg, 1.03 mmol) followed by 2-bromo-1-phenylethanone (107 mg, 0.54 mmol). After LCMS analysis showed complete conversion, the mixture was partitioned between ethyl acetate and a saturated sodium bicarbonate solution. The layers were separated and the aqueous was extracted with ethyl acetate twice. The combined organic fractions were dried over Na$_2$SO$_4$, filtered and concentrated in vacuo. The residue was purified by trituration in CH$_2$Cl$_2$:hexanes to afford 2-(2-Bromo-4-(methylamino)pyrimidin-5-yloxy)-1-phenylethanone (117 mg, 74%).

$^1$H NMR (DMSO-d6, 400 MHz): δ 7.80 (s, 1H), 7.46-7.35 (m, 5H), 7.11 (s, 1H), 4.16 (d, J=11.2 Hz, 1H), 4.01 (d, J=11.2 Hz, 1H), 2.75 (s, 3H); LRMS (ESpos) calcd for C$_{13}$H$_{12}$BrN$_3$O$_2$ [M+1]+: 322.01. found: 322.46.

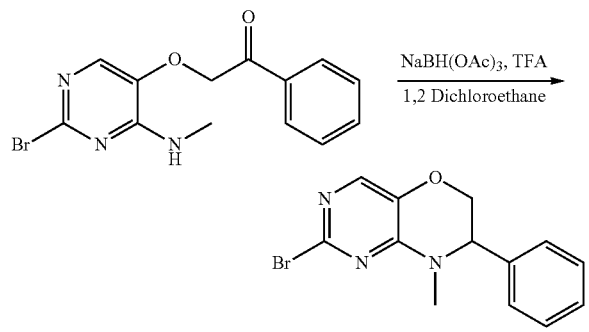

Synthesis of 2-Bromo-8-methyl-7-phenyl-7,8-dihydro-6H-pyrimido[5,4-b] [1,4] oxazine To a solution of 2-(2-Bromo-4-(methylamino)pyrimidin-5-yloxy)-1-phenylethanone (112 mg, 0.35 mmol) in 1,2-dichloroethane (1.8 mL) was added NaBH(OAc)$_3$ (148 mg, 0.7 mmol) was added, followed by TFA (27 μL, 0.35 mmol). After LCMS analysis showed complete conversion, the mixture was partitioned between CH$_2$Cl$_2$ and a 1N sodium hydroxide solution. The layers were separated and the aqueous was extracted with CH$_2$Cl$_2$ twice. The combined organic fractions were dried over Na$_2$SO$_4$, filtered and concentrated. The residue was purified by normal phase chromatography on silica (gradient 0-5% MeOH/CH$_2$Cl$_2$) to afford 2-Bromo-8-methyl-7-phenyl-7,8-dihydro-6H-pyrimido[5,4-b][1,4]oxazine (72 mg, 67%). $^1$H NMR (CDCl$_3$, 400 MHz): δ 7.66 (s, 1H), 7.42-7.27 (m, 3H), 7.20-7.14 (m, 2H), 4.57 (t, J=3.6 Hz, 1H), 4.26 (dd, J=11.2, 3.3 Hz, 1H), 4.17 (dd, J=11.2, 3.9 Hz, 1H), 3.08 (s, 3H); LRMS (ESpos) calcd for C$_{13}$H$_{12}$BrN$_3$O [M+1]+: 306.02. found: 306.52.

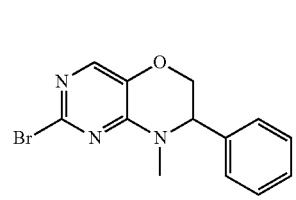

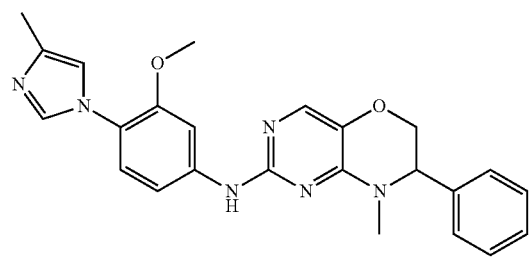

Synthesis of N-(3-methoxy-4-(4-methyl-1H-imidazol-1-yl)phenyl)-8-methyl-7-phenyl-7,8-dihydro-6H-pyrimido[5,4-b] [1,4] oxazin-2-amine To a flask containing 2-Bromo-8-methyl-7-phenyl-7,8-dihydro-6H-pyrimido[5,4-b][1,4]oxazine (20 mg, 0.07 mmol), 3-methoxy-4-(4-methyl-1H-imidazol-1-yl)aniline (15 mg, 0.07 mmol) in 1-methylpyrrolidin-2-one (0.28 mL) were added 4N HCl in dioxane (70 μL, 1:5 ratio to 1-methylpyrrolidin-2-one). The reaction mixture was stirred at 110° C. for 16 h and water was added, followed by a 1N NaOH solution and ethyl acetate. The layers were separated and the aqueous was extracted with ethyl acetate twice, the combined organic fractions were washed with water, brine, dried over Na$_2$SO$_4$, filtered and concentrated in vacuo. The residue was purified by normal phase chromatography on silica (gradient 0-5% MeOH/CH$_2$Cl$_2$) and C18 column chromatography (gradient 0-95% MeCN+0.1% HCOOH/H$_2$O) to afford N-(3-methoxy-4-(4-methyl-1H-imidazol-1-yl)phenyl)-8-methyl-7-phenyl-7,8-dihydro-6H-pyrimido[5,4-b][1,4]oxazin-2-amine as a white solid (13 mg, 46%). HPLC analysis on a chiral stationary phase (ChiralPak AD 250×4.6 mm, 40% (iPrOH+0.1% Et$_2$NH) in (hexane+0.1% Et$_2$NH), 1.0 mLmin$^{-1}$, DAD 254 nm) t$_r$=9.69 min and 12.52 min. $^1$H NMR (CDCl$_3$, 400 MHz) δ 7.70-7.64 (m, 3H), 7.43-7.35 (m, 3H), 7.24-7.18 (m, 3H), 7.14 (d, J=8.5 Hz, 1H), 7.05 (dd, J=8.5, 2.3 Hz, 1H), 6.87 (s, 1H), 4.57 (t, J=3.5 Hz, 1H), 4.26 (dd, J=11.1, 3.3 Hz, 1H), 4.15 (dd, J=11.1, 3.9 Hz, 1H), 3.84 (s, 3H), 3.12 (s, 3H), 2.31 (d, J=0.9 Hz, 3H); LRMS (ESpos) calcd for C$_{24}$H$_{24}$N$_6$O$_2$ [M+1-1]+: 429.20. found: 429.76.

Example 46

Synthesis of N-(3-methoxy-4-(2-methylpyridin-4-yl)phenyl)-8-methyl-7-phenyl-7,8-dihydro-6H-pyrimido[5,4-b][1,4]oxazin-2-amine

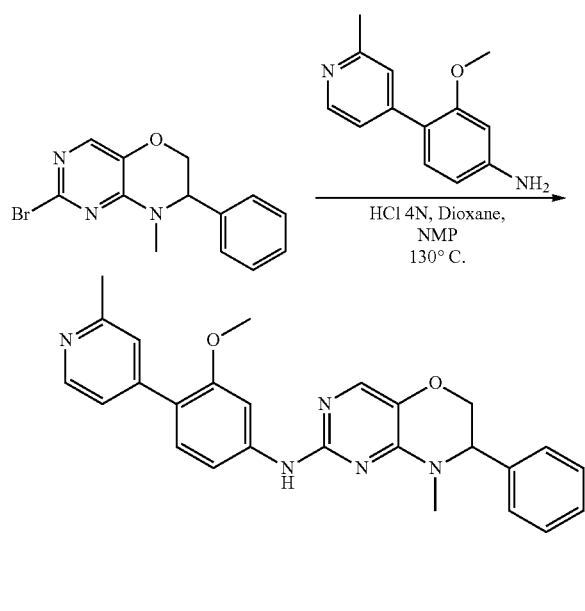

Synthesis of N-(3-methoxy-4-(2-methylpyridin-4-yl)phenyl)-8-methyl-7-phenyl-7,8-dihydro-6H-pyrimido[5,4-b][1,4]oxazin-2-amine To a reaction flask containing 2-Bromo-8-methyl-7-phenyl-7,8-dihydro-6H-pyrimido[5,4-b][1,4]oxazine (20 mg, 0.07 mmol), 3-methoxy-4-(2-methylpyridin-4-yl)aniline (15 mg, 0.07 mmol) in 1-methylpyrrolidin-2-one (0.30 mL) was added 4N HCl in dioxane (70 μL, 1:5 ratio to 1-methylpyrrolidin-2-one) was added. The reaction mixture was stirred at 130° C. for 16 h and water was added, followed by a 1N NaOH solution and ethyl acetate twice. The layers were separated and the aqueous was extracted with ethyl acetate twice. The combined organic fractions were washed with water, brine, dried over Na$_2$SO$_4$, filtered and concentrated. The residue was purified by silica gel column chromatography (gradient 0-5% MeOH/CH$_2$Cl$_2$) and C18 column chromatography (gradient 0-95% MeCN+0.1% HCOOH/H$_2$O) to afford N-(3-methoxy-4-(2-methylpyridin-4-yl)phenyl)-8-methyl-7-phenyl-7,8-dihydro-6H-pyrimido[5,4-b][1,4]oxazin-2-amine as a yellow solid (29 mg, 27%). HPLC analysis on a chiral stationary phase (ChiralPak AD 250×4.6 mm, 40% (iPrOH+0.1% Et$_2$NH) in (hexane+0.1% Et$_2$NH), 1.0 mLmin$^{-1}$, DAD 254 nm) t$_r$=10.17 min and 14.34 min. $^1$H NMR (CDCl$_3$, 400 MHz) δ 8.46 (s, 1H), 7.93 (s, 1H), 7.71-7.58 (m, 2H), 7.44-7.34 (m, 5H), 7.29 (d, J=8.3 Hz, 1H), 7.22 (dd, J=7.8, 1.5 Hz, 2H), 7.17 (dd, J=8.3, 1.8 Hz, 1H), 4.60 (t, J=3.5 Hz, 1H), 4.28 (dd, J=11.1, 3.3 Hz, 1H), 4.17 (dd, J=11.1, 3.8 Hz, 1H), 3.86 (s, 3H), 3.15 (s, 3H), 2.62 (s, 3H); LRMS (ESpos) calcd for C$_{26}$H$_{25}$N$_5$O$_2$ [M+H]+: 440.20 found: 440.6.

Example 47

Synthesis of 7-benzyl-N-(3-methoxy-4-(4-methyl-1H-imidazol-1-yl) phenyl)-8-methyl-7, 8-dihydro-6H-pyrimido [5, 4-b] [1, 4] oxazin-2-amine

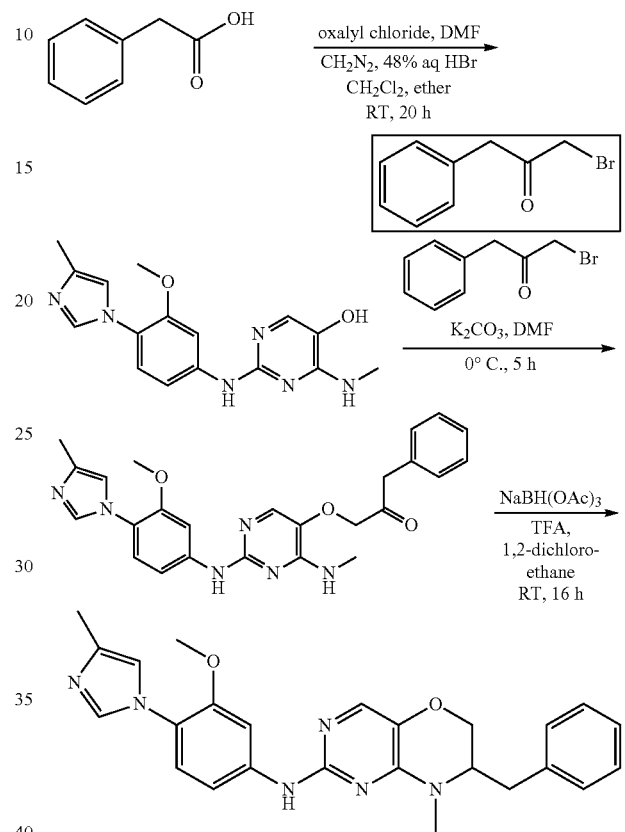

Synthesis of 1-bromo-3-phenylpropan-2-one

To a stirred solution of 2-phenylacetic acid (5 g, 36.76 mmol) in CH$_2$Cl$_2$ (50 mL) was added oxalyl chloride (4.6 g, 36.76 mmol) and DMF (2 drops) at 0° C. The reaction mixture was warmed to room temperature and stirred for 2 h. After consumption of acid (monitored by TLC), the mixture was concentrated in vacuo. The crude material was dissolved in ether and a solution of CH$_2$N$_2$ in ether was added at 0° C. The reaction mixture was warmed to room temperature and stirred for 2 h. After consumption of the starting material (monitored by TLC), the mixture was concentrated in vacuo. To a stirred solution of crude material in THF (20 mL) was added a solution of 48% aq HBr (5 mL) at 0° C. The reaction mixture was warmed to room temperature and stirred for 16 h. After consumption of the starting material (monitored by TLC), the reaction was quenched with a sodium bicarbonate solution (100 mL) and extracted with EtOAc (2×100 mL). The combined organic extracts were washed successively with a sodium bicarbonate solution (50 mL) and water (50 mL). The organic layer was dried over sodium sulfate, filtered and concentrated in vacuo to afford 1-bromo-3-phenylpropan-2-one (6 g, 76%) as a viscous oil. $^1$H-NMR (CDCl$_3$, 400 MHz): δ 7.38-7.30

(m, 3H), 7.27-7.20 (m, 2H), 3.92 (s, 2H), 3.89 (s, 2H); TLC: 10% EtOAc:hexanes (R$_f$: 0.6).

Synthesis of 1-((2-((3-methoxy-4-(4-methyl-1H-imidazol-1-yl) phenyl) amino)-4-(methylamino) pyrimidin-5-yl) oxy)-3-phenylpropan-2-one To a stirred solution of 2-((3-methoxy-4-(4-methyl-1H-imidazol-1-yl)phenyl)amino)-4-(methylamino)pyrimidin-5-ol (200 mg, 0.61 mmol) in DMF (2 mL) was added potassium carbonate (169 mg, 1.22 mmol) followed by 1-bromo-3-phenylpropan-2-one (196 mg, 9.20 mmol) at 0° C. and stirred for 5 h. After consumption of the starting material (monitored by TLC), the reaction was quenched with ice cold water (20 mL) and extracted with EtOAc (2×20 mL). The combined organic extracts were dried over sodium sulfate, filtered and concentrated in vacuo to afford 1-((2-((3-methoxy-4-(4-methyl-1H-imidazol-1-yl) phenyl) amino)-4-(methylamino) pyrimidin-5-yl) oxy)-3-phenylpropan-2-one (180 mg) as a pale brown solid. LC-MS: 441.0 (M+1); (column; X-Select CSH C-18 (50×3.0 mm, 3.5 µm); RT 2.36 min. 0.05% Aq TFA: ACN; 0.8 mL/min); TLC: EtOAc (R$_f$: 0.6).

Synthesis of 7-benzyl-N-(3-methoxy-4-(4-methyl-M-imidazol-1-yl) phenyl)-8-methyl-7, 8-dihydro-6H-pyrimido [5, 4-b][1,4] oxazin-2-amine To a stirred solution of 1-((2-((3-methoxy-4-(4-methyl-1H-imidazol-1-yl) phenyl) amino)-4-(methylamino) pyrimidin-5-yl) oxy)-3-phenylpropan-2-one (100 mg, 0.21 mmol) in 1, 2-dichloroethane (2 mL) was added trifluoroacetic acid (0.21 mmol) followed by sodium triacetoxyborohydride (92 mg, 0.43 mmol) and stirred for 16 h. After consumption of the starting material (monitored by TLC), the reaction was quenched with 1N sodium hydroxide (10 mL) and extracted with CH$_2$Cl$_2$ (2×10 mL). The combined organic extracts were dried over sodium sulfate, filtered and concentrated in vacuo. The crude material was purified by silica gel column chromatography using 20% EtOAc:hexanes to afford 7-benzyl-N-(3-methoxy-4-(4-methyl-1H-imidazol-1-yl) phenyl)-8-methyl-7, 8-dihydro-6H-pyrimido [5, 4-b][1, 4] oxazin-2-amine (40 mg, 61%) as a white solid. $^1$H-NMR (CD$_3$OD, 400 MHz): δ 7.78 (s, 1H), 7.70 (s, 1H), 7.54 (s, 1H), 7.36-7.26 (m, 5H), 7.19-7.12 (m, 2H), 6.91 (s, 1H), 4.08 (d, 1H), 3.88 (s, 3H), 3.86-3.84 (m, 1H), 3.75-3.71 (m, 1H), 3.14 (s, 3H), 3.10-3.09 (m, 1H), 2.90-2.88 (m, 1H), 2.22 (s, 3H); Mass (ESI): 443.4 [M+1]; LC-MS: 443 (M+1); (column; X-Select CSH C-18 (50×3.0 mm, 3.5 µm); RT 2.39 min. 0.05% Aq TFA: ACN; 0.8 mL/min); UPLC (column; Acquity BEH C-18, 50×2.1 mm, 1.7 µm); RT 1.57 min. ACN: 0.025% TFA (Aq); 0.50 ml/min TLC: 50% EtOAc: hexanes (R$_f$: 0.5).

Racemic compound of Example 47 was separated using a Chiralpak IA (250×20 mm, 5 µm (45 mg loading; 0.1% DEA in n-hexane: EtOH:MeOH (50:50); (70:30) as the mobile phase) to provide the compound of Example 47A (Fraction I (+)) and the compound of Example 47B (Fraction II (−)).

Example 47A

Synthesis of (+)-7-benzyl-N-(3-methoxy-4-(4-methyl-1H-imidazol-1-yl) phenyl)-8-methyl-7, 8-dihydro-6H-pyrimido [5, 4-b] [1, 4] oxazin-2-amine

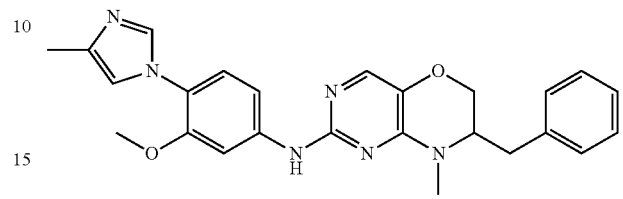

The compound of Example 47A was produced as described in Example 47. Analytical data for product Fraction I (+): $^1$H-NMR (CD$_3$OD, 400 MHz): δ 7.75 (s, 1H), 7.64 (s, 1H), 7.53 (s, 1H), 7.37-7.21 (m, 5H), 7.19-7.12 (m, 2H), 6.91 (s, 1H), 4.08 (d, 1H), 3.85 (s, 3H), 3.84-3.80 (m, 1H), 3.75-3.70 (m, 1H), 3.12 (s, 3H), 3.11-3.09 (m, 1H), 2.87-2.83 (m, 1H), 2.21 (s, 3H); Mass (ESI): 443.5 [M+1]; LC-MS: 443.5 (M+1); (column; X-Select CSH C-18 (50× 3.0 mm, 3.5 µm); RT 2.85 min. 0.05% Aq TFA: ACN; 0.8 mL/min); (column; Acquity BEH C-18, 50×2.1 mm, 1.7 µm); RT 1.58 min. ACN: 0.025% TFA (Aq); 0.50 ml/min; Chiral HPLC: RT=13.96 min (Chiralpak-IA (250×4.6 mm, 5 µm; mobile phase (A) 0.1% DEA in n-hexane (B) EtOH: MeOH (50:50) (70:30); flow Rate: 1.0 mL/min); Optical rotation [α]$_D^{19.98}$: +69.28 (c 0.25, DCM).

Example 47B

Synthesis of (−)-7-benzyl-N-(3-methoxy-4-(4-methyl-1H-imidazol-1-yl) phenyl)-8-methyl-7, 8-dihydro-6H-pyrimido [5, 4-b] [1, 4] oxazin-2-amine

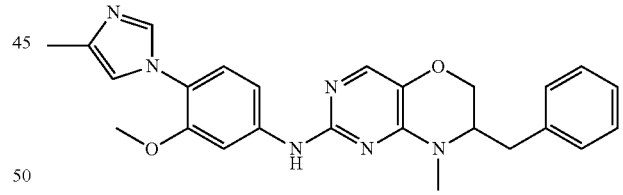

The compound of Example 47B was produced as described in Example 47. Analytical data for product Fraction II (−): $^1$H-NMR (CD$_3$OD, 400 MHz): δ 7.75 (s, 1H), 7.64 (s, 1H), 7.53 (s, 1H), 7.37-7.21 (m, 5H), 7.19-7.12 (m, 2H), 6.91 (s, 1H), 4.08 (d, 1H), 3.85 (s, 3H), 3.84-3.80 (m, 1H), 3.75-3.70 (m, 1H), 3.12 (s, 3H), 3.11-3.09 (m, 1H), 2.87-2.83 (m, 1H), 2.21 (s, 3H); Mass (ESI): 443.4 [M+1]; LC-MS: 443.4 (M+1); (column; X-Select CSH C-18 (50× 3.0 mm, 3.5 µm); RT 2.85 min. 0.05% Aq TFA: ACN; 0.8 mL/min); UPLC (column; Acquity BEH C-18, 50×2.1 mm, 1.7 µm); RT 1.59 min. ACN: 0.025% TFA (Aq); 0.50 ml/min; Chiral HPLC: RT=25.86 min (Chiralpak-IA (250× 4.6 mm, 5 µm; mobile phase (A) 0.1% DEA in n-hexane (B) EtOH:MeOH (50:50) (70:30); flow Rate: 1.0 mL/min); Optical rotation [α]$_D^{20.00}$: −62.46 (c 0.25, DCM).

Example 48

Synthesis of 7-(2, 4-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

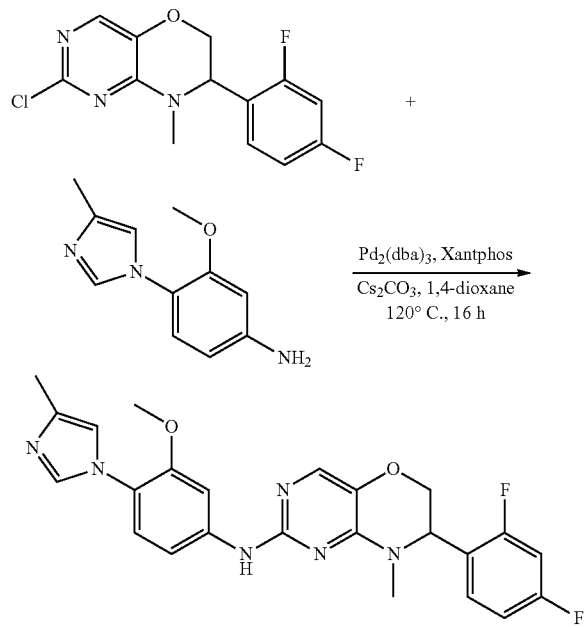

Synthesis of 7-(2, 4-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a dry vial was added a suspension of Pd₂(dba)₃ (27 mg, 0.03 mmol) and Xantphos (52 mg, 0.09 mmol) in 1, 4-dioxane (2 mL). The mixture was degassed, heated to 120° C. and stirred for 3 min. A mixture of 2-chloro-7-(2,4-difluorophenyl)-8-methyl-7, 8-dihydro-6H-pyrimido [5, 4-b] [1, 4] oxazine (180 mg, 0.60 mmol), 3-methoxy-4-(4-methyl-1H-imidazol-1-yl) aniline (246 mg, 1.21 mmol), cesium carbonate (275 mg, 0.84 mmol) in 1, 4-dioxane (1 mL) was degassed and the catalyst premix was added. The reaction mixture was heated to 120° C. and stirred for 16 h in a sealed tube. After consumption of the starting material (monitored by TLC and LCMS), the mixture was diluted with a sodium bicarbonate solution (20 mL) and extracted with EtOAc (2×25 mL). The combined organic extracts were dried over sodium sulfate, filtered and concentrated in vacuo. The crude material was purified by silica gel column chromatography using 3% MeOH:CH₂Cl₂ to afford 7-(2,4-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (45 mg, 16%) as an off-white solid. ¹H-NMR (CD₃OD, 500 MHz): δ 7.78 (s, 1H), 7.69 (s, 1H), 7.60 (s, 1H), 7.28-7.25 (m, 1H), 7.21 (s, 1H), 7.17-7.15 (m, 1H), 7.12-7.06 (m, 1H), 6.98 (s, 2H), 5.03-5.01 (m, 1H), 4.23 (s, 2H), 3.93 (s, 3H), 3.19 (s, 3H), 2.21 (s, 3H); Mass (ESI): 465.4 [M+1]; LC-MS: 464.9 (M+1); (column; X-Select CSH C-18 (50×3.0 mm, 3.5 μm); RT 2.36 min. 0.05% Aq TFA: ACN; 0.80 ml/min); UPLC (column; Acquity BEH C-18, 50×2.1 mm, 1.7 μm); RT 1.57 min. ACN: 0.025% TFA (Aq); 0.50 ml/min; TLC: 5% MeOH:CH₂Cl₂ ($R_f$: 0.4).

Racemic compound of Example 48 was separated using a Chiralpak-IA (250×20 mm, 5 μm (40 mg loading; 0.1% DEA in n-hexane: CH₂Cl₂:MeOH (50:50); (A:B: 85:15) as the mobile phase) to provide the compound of Example 48A (Fraction I (−)) and the compound of Example 48B (Fraction II (+)).

Example 48A

Synthesis of (−)-7-(2, 4-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

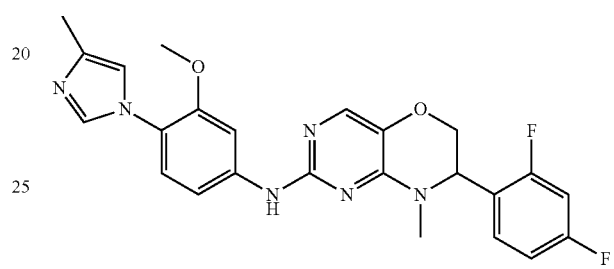

The compound of Example 48A was produced as described in Example 48. Analytical data for product Fraction I (−): ¹H-NMR (CD₃OD, 400 MHz): δ 7.74 (s, 1H), 7.65 (s, 1H), 7.57 (s, 1H), 7.26-7.20 (m, 1H), 7.19 (s, 1H), 7.17-7.00 (m, 2H), 6.96 (s, 2H), 5.02-5.00 (m, 1H), 4.22 (s, 2H), 3.83 (s, 3H), 3.18 (s, 3H), 2.21 (s, 3H); Mass (ESI): 465.4 [M+1]; LC-MS: 465.3 (M+1); (column; X-Select CSH C-18 (50×3.0 mm, 3.5 μm); RT 2.90 min. 0.05% Aq TFA: ACN; 0.80 ml/min); UPLC (column; Acquity UPLC BEH C-18, 2.1×50 mm, 1.7 μm); RT 1.62 min. ACN: 0.025% TFA (Aq); 0.50 ml/min; Chiral HPLC: RT=16.49 min (CHIRALPAK-ADH (250×4.6 mm, 5 μm; mobile phase (A) 0.1% DEA in n-hexane (B) EtOH:MeOH (50:50) (A:B: 75:25; flow Rate: 1.0 mL/min); Optical rotation $[\alpha]_D^{20.00}$: −149.21 (c 0.25, DCM).

Example 48B

Synthesis of (+)-7-(2, 4-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

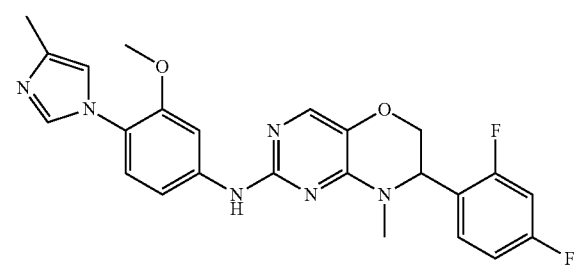

The compound of Example 48B was produced as described in Example 48. Analytical data for product Fraction II (+): $^1$H-NMR (CD$_3$OD, 400 MHz): δ 7.74 (s, 1H), 7.65 (s, 1H), 7.57 (s, 1H), 7.23-7.20 (m, 1H), 7.19 (s, 1H), 7.17-7.00 (m, 2H), 6.96 (s, 2H), 5.02-5.00 (m, 1H), 4.22 (s, 2H), 3.83 (s, 3H), 3.18 (s, 3H), 2.21 (s, 3H); Mass (ESI): 465.4 [M+1]; LC-MS: 465.4 (M+1); (column; X-Select CSH C-18 (50×3.0 mm, 3.5 µm); RT 2.91 min. 0.05% Aq TFA: ACN; 0.80 ml/min); UPLC (column; Acquity UPLC BEH C-18, 2.1×50 mm, 1.7 µm); RT 1.64 min. ACN: 0.025% TFA (Aq); 0.50 ml/min; Chiral HPLC: 100% RT=25.61 min (CHIRALPAK-ADH (250×4.6 mm, 5 µm; mobile phase (A) 0.1% DEA in n-hexane (B) EtOH:MeOH (50:50) (A:B: 75:25; flow Rate: 1.0 mL/min); Optical rotation $[α]_D^{20.00}$: +155.31 (c 0.25, DCM).

Example 49

Synthesis of 7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

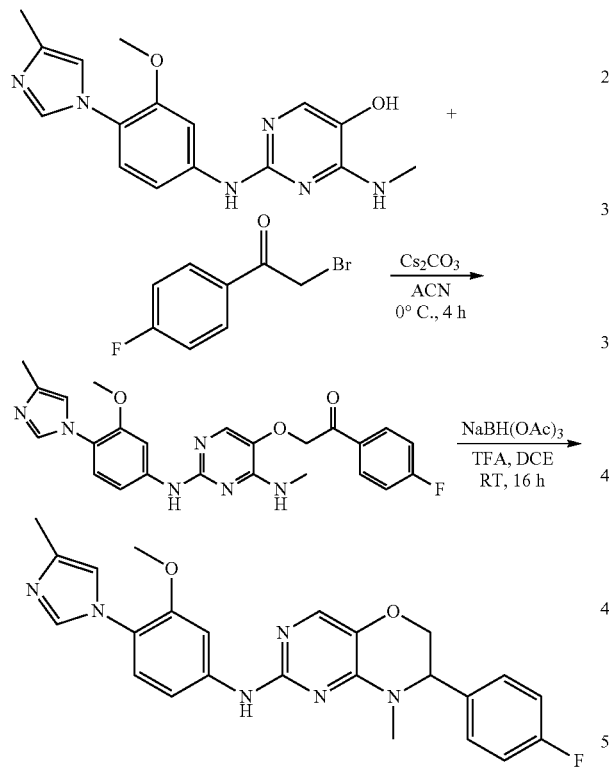

Synthesis of 1-(4-fluorophenyl)-2-((2-((3-methoxy-4-(4-methyl-1H-imidazol-1-yl) phenyl) amino)-4-(methylamino) pyrimidin-5-yl) oxy) ethan-1-one To a stirred solution of 2-((3-methoxy-4-(4-methyl-1H-imidazol-1-yl) phenyl) amino)-4-(methylamino) pyrimidin-5-ol (200 mg, 0.61 mmol) in acetonitrile (4 mL) was added cesium carbonate (399 mg, 1.22 mmol) at 0° C. and stirred for 5 min. 2-Bromo-1-(4-fluorophenyl) ethan-1-one (145 mg, 0.67 mmol) was added and the reaction mixture was stirred for 4 h. After consumption of the starting material (monitored by TLC), the mixture was diluted with water (20 mL) and extracted with EtOAc (2×20 mL). The combined organic extracts were dried over sodium sulfate, filtered and concentrated in vacuo to afford 1-(4-fluorophenyl)-2-((2-((3-methoxy-4-(4-methyl-1H-imidazol-1-yl) phenyl) amino)-4-(methylamino) pyrimidin-5-yl) oxy) ethan-1-one (250 mg) as an off-white solid. The crude material was used without further purification. TLC: 10% MeOH:CH$_2$Cl$_2$ (R$_f$: 0.7).

Synthesis of 7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a stirred solution of 1-(4-fluorophenyl)-2-((2-((3-methoxy-4-(4-methyl-1H-imidazol-1-yl) phenyl) amino)-4-(methylamino) pyrimidin-5-yl) oxy) ethan-1-one (250 mg, 0.54 mmol) in 1, 2-dichloroethane (5 mL) was added sodium triacetoxyborohydride (229 mg, 1.08 mmol) followed by trifluoroacetic acid (0.54 mmol) and stirred for 16 h. After consumption of the starting material (monitored by TLC), the mixture was diluted with a 1N sodium hydroxide solution (20 mL). Water (20 mL) was added and the mixture was extracted with CH$_2$Cl$_2$ (2×25 mL). The combined organic extracts were dried over sodium sulfate, filtered and concentrated in vacuo. The crude material was purified by silica gel column chromatography using 5% MeOH:CH$_2$Cl$_2$ to afford 7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (120 mg, 50%) as an off-white solid. $^1$H-NMR (CD$_3$OD, 400 MHz): δ 7.67 (s, 1H), 7.55 (s, 1H), 7.49 (s, 1H), 7.20-7.10 (m, 3H), 7.09 (d, 2H), 7.01-6.99 (m, 1H), 6.87 (s, 1H), 4.60-4.50 (m, 1H), 4.13-4.06 (m, 1H), 3.09-3.07 (m, 1H), 3.72 (s, 3H), 3.00 (s, 3H), 2.11 (s, 3H); Mass (ESI): 447.4 [M+1]; LC-MS: 446.9 (M+1); (column; X-Select CSH C-18 (50×3.0 mm, 3.5 µm); RT 2.34 min. 0.05% Aq TFA: ACN; 0.80 mL/min); UPLC (column; Acquity BEH C-18 50×2.1 mm, 1.7 µm); RT 1.53 min. ACN: 0.025% TFA (Aq); 0.50 mL/min; TLC: 5% MeOH: CH$_2$Cl$_2$ (R$_f$: 0.3).

Racemic compound of Example 49 was separated using a Chiralcel-ODH (250×20 mm, 5 µm (30 mg loading; 0.1% DEA in n-hexane: EtOH:MeOH (50:50); (85:15) as the mobile phase) to provide the compound of Example 49A (Fraction I (−)) and the compound of Example 49B (Fraction II (+)).

Example 49A

Synthesis of (−)-7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

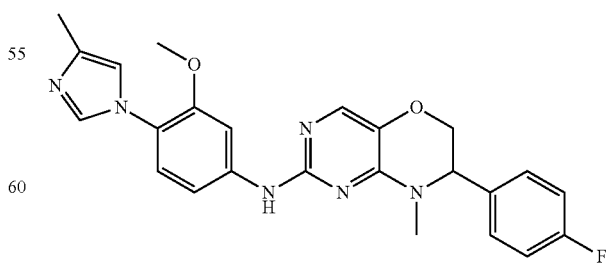

The compound of Example 49A was produced as described in Example 49. Analytical data for product Fraction I (−): $^1$H-NMR (CD$_3$OD, 400 MHz): δ 7.77 (s, 1H), 7.70 (s, 1H), 7.59 (s, 1H), 7.30-7.08 (m, 6H), 6.98 (s, 1H), 4.71-4.70 (m, 1H), 4.22 (d, 1H), 4.18 (d, 1H), 3.86 (s, 3H), 3.14 (s, 3H), 2.20 (s, 3H); Mass (ESI): 447.4 [M+1]; LC-MS: 446.9 (M+1); (column; X-Select CSH C-18 (50× 3.0 mm, 3.5 µm); RT 2.35 min. 0.05% Aq TFA: ACN; 0.80 ml/min); UPLC (column; Acquity UPLC BEH C-18, 2.1×50 mm, 1.7 µm); RT 1.53 min. ACN: 0.025% TFA (Aq); 0.50 ml/min; Chiral HPLC: RT=16.58 min (Chiralcel-OD-H (250×4.6 mm, 5 µm; mobile phase (A) 0.1% DEA in n-hexane (B) EtOH:MeOH (50:50) (85:15); flow Rate: 1.0 mL/min); Optical rotation $[\alpha]_D^{20.00}$: −131.96 (c 0.25, DCM).

Example 49B

Synthesis of (+)-7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

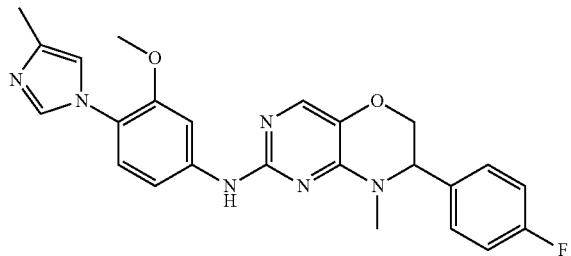 [SMILES: COc1cc(Nc2ncc3c(n2)N(C)C(c2ccc(F)cc2)CO3)ccc1-n1cnc(C)c1]

The compound of Example 49B was produced as described in Example 49. Analytical data for product Fraction II (+): $^1$H-NMR (CD$_3$OD, 400 MHz): δ 7.77 (s, 1H), 7.70 (s, 1H), 7.59 (s, 1H), 7.30-7.08 (m, 6H), 6.98 (s, 1H), 4.71-4.70 (m, 1H), 4.22 (d, 1H), 4.18 (d, 1H), 3.86 (s, 3H), 3.14 (s, 3H), 2.20 (s, 3H); Mass (ESI): 447.4 [M+1]; LC-MS: 447 (M+1); (column; X-Select CSH C-18 (50×3.0 mm, 3.5 µm); RT 2.35 min. 0.05% Aq TFA: ACN; 0.80 ml/min); UPLC (column; Acquity UPLC BEH C-18, 2.1×50 mm, 1.7 µm); RT 1.53 min. ACN: 0.025% TFA (Aq); 0.50 ml/min; Chiral HPLC: RT=19.21 min (Chiralcel-OD-H (250×4.6 mm, 5 µm; mobile phase (A) 0.1% DEA in n-hexane (B) EtOH:MeOH (50:50) (85:15); flow Rate: 1.0 mL/min); Optical rotation $[\alpha]_D^{19.99}$: +128.06 (c 0.25, DCM).

Example 50

Synthesis of N-(3-methoxy-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine

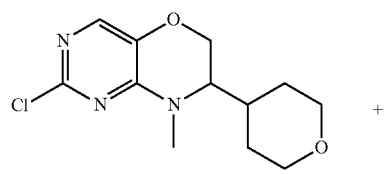

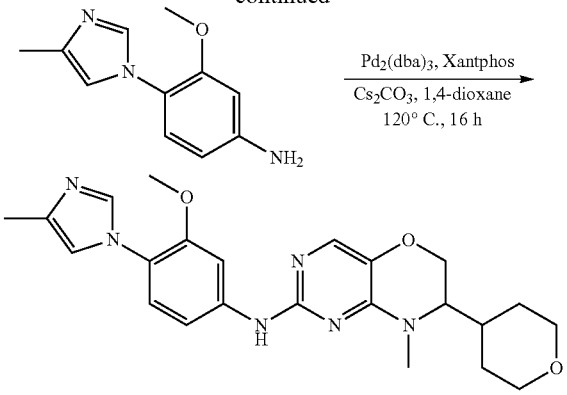

Synthesis of N-(3-methoxy-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine To a dry vial was added a suspension of Pd$_2$(dba)$_3$ (25 mg, 0.02 mmol) and Xantphos (48 mg, 0.08 mmol) in 1, 4-dioxane (1.5 mL). The mixture was degassed, heated to 120° C. and stirred for 3 min. A mixture of 2-chloro-8-methyl-7-(tetrahydro-2H-pyran-4-yl)-7, 8-dihydro-6H-pyrimido [5, 4-b] [1, 4] oxazine (150 mg, 0.55 mmol), 3-methoxy-4-(4-methyl-1H-imidazol-1-yl) aniline (226 mg, 1.11 mmol), cesium carbonate (253 mg, 0.78 mmol) in 1, 4-dioxane (1.5 mL) was degassed and the catalyst premix was added. The reaction mixture was heated to 120° C. and stirred for 16 h in a sealed tube. After consumption of the starting material (monitored by TLC and LCMS), the mixture was diluted with water (10 mL) and extracted with EtOAc (2×10 mL). The combined organic extracts were dried over sodium sulfate, filtered and concentrated in vacuo. The crude material was purified by preparative HPLC (Kromacil silica (250×21.2 mm, 10 µm (50 mg loading; CH$_3$CN: 0.05% TFA (0.1/95, 15/70, 25/10, 35/10) to afford N-(3-methoxy-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine (35 mg, 14%) as a yellow solid. $^1$H-NMR (CD$_3$OD, 500 MHz): δ 7.79-7.77 (m, 1H), 7.75 (s, 1H), 7.53 (s, 1H), 7.26-7.18 (m, 2H), 7.02 (s, 1H), 4.43-4.42 (m, 1H), 4.00 (t, 2H), 3.89 (s, 3H), 3.86-3.82 (m, 1H), 3.44-3.40 (m, 3H), 3.39-3.36 (m, 3H), 2.25 (s, 3H), 2.10-2.03 (m, 1H), 1.69-1.58 (m, 4H); Mass (ESI): 437.4 [M+1]; LC-MS: 437 (M+1); (column; X-Select CSH C-18 (50×3.0 mm, 3.5 µm); RT 1.99 min. 0.05% Aq TFA: ACN; 0.80 mL/min); UPLC (column; Acquity BEH C-18, 50×2.1 mm, 1.7 µm); RT 1.27 min. ACN: 0.025% TFA (Aq); 0.50 ml/min; TLC: 5% MeOH:CH$_2$Cl$_2$ (R$_f$: 0.4).

Example 51

Synthesis of 7-(2-chlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

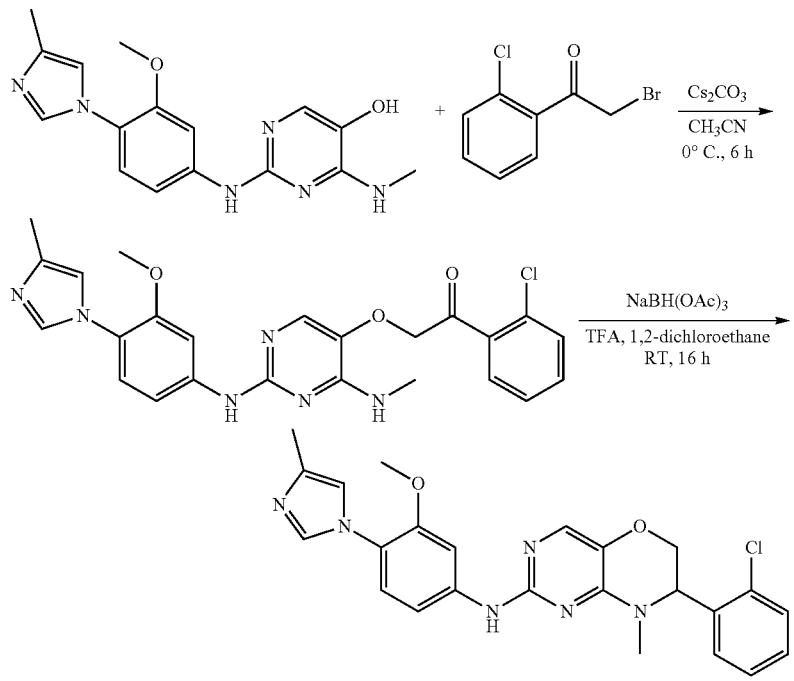

Synthesis of 1-(2-chlorophenyl)-2-((2-((3-methoxy-4-(4-methyl-1H-imidazol-1-yl) phenyl) amino)-4-(methylamino) pyrimidin-5-yl) oxy) ethan-1-one To a stirred solution of 2-((3-methoxy-4-(4-methyl-1H-imidazol-1-yl) phenyl) amino)-4-(methylamino) pyrimidin-5-ol (150 mg, 0.46 mmol) in acetonitrile (3 mL) was added cesium carbonate (300 mg, 0.92 mmol) at 0° C. and stirred for 5 min. 2-Bromo-1-(2-chlorophenyl) ethan-1-one (118 mg, 0.50 mmol) was added and the reaction mixture was stirred for 6 h. After consumption of the starting material (monitored by TLC), the mixture was diluted with a saturated sodium bicarbonate solution (20 mL) and extracted with EtOAc (3×25 mL). The combined organic extracts were dried over sodium sulfate, filtered and concentrated in vacuo to afford 1-(2-chlorophenyl)-2-((2-((3-methoxy-4-(4-methyl-1H-imidazol-1-yl) phenyl) amino)-4-(methylamino) pyrimidin-5-yl) oxy) ethan-1-one (130 mg) as an off-white solid and used in the next step without further purification. TLC: 10% MeOH:CH$_2$Cl$_2$ (R$_f$: 0.4).

Synthesis of 7-(2-chlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a stirred solution of 1-(2-chlorophenyl)-2-((2-((3-methoxy-4-(4-methyl-1H-imidazol-1-yl) phenyl) amino)-4-(methylamino) pyrimidin-5-yl) oxy) ethan-1-one (130 mg, 0.27 mmol) in 1, 2-dichloroethane (3 mL) was added sodium triacetoxyborohydride (115 mg, 0.54 mmol) followed by trifluoroacetic acid (21 µL) and stirred for 16 h. After consumption of the starting material (monitored by TLC), the mixture was diluted with a 1N sodium hydroxide solution (20 mL) and extracted with CH$_2$Cl$_2$ (2×25 mL). The combined organic extracts were dried over sodium sulfate, filtered and concentrated in vacuo. The crude material was purified by silica gel column chromatography using 5% MeOH:CH$_2$Cl$_2$ to afford 70 mg of compound which was further purified by preparative HPLC to afford 7-(2-chlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (35 mg, 18%) as a pale yellow solid. $^1$H-NMR (CD$_3$OD, 400 MHz): δ 7.75 (s, 1H), 7.68 (s, 1H), 7.59 (s, 1H), 7.48 (d, 1H), 7.33-7.29 (m, 3H), 7.20-7.17 (m, 1H), 7.07 (d, 1H), 6.97 (s, 1H), 5.20-5.18 (m, 1H), 4.30-4.21 (m, 2H), 3.86 (s, 3H), 3.17 (s, 3H), 2.21 (s, 3H); Mass (ESI): 463.4 [M+1]; LC-MS: 463 (M+1); (column; X-Select CSH C-18 (50×3.0 mm, 3.5 µm); RT 2.40 min. 0.05% Aq TFA: ACN; 0.80 mL/min); UPLC (column; Acquity BEH C-18 50×2.1 mm, 1.7 µm); RT 1.62 min. ACN: 0.025% TFA (Aq); 0.50 mL/min; TLC: 80% EtOAc:hexanes (R$_f$: 0.4).

Racemic compound of Example 51 was separated using a Chiralpak IB (250×20 mm, 5 µm (30 mg loading; 0.1% DEA in n-hexane: CH$_2$Cl$_2$:MeOH (50:50); (90:10) as the mobile phase to provide the compound of Example 51A (Fraction I (−)) and the compound of Example 51B (Fraction II (+)).

Example 51A

Synthesis of (−)-7-(2-chlorophenyl)-N-(3-methoxy-4-(4-methyl-1H-imidazol-1-yl) phenyl)-8-methyl-7,8-dihydro-6H-pyrimido [5, 4-b] [1, 4] oxazin-2-amine

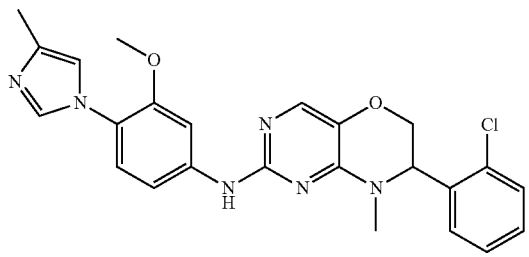 [SMILES: COc1cc(Nc2ncc3c(n2)N(C)C(c2ccccc2Cl)CO3)ccc1-n1cnc(C)c1]

The compound of Example 51A was produced as described in Example 51. Analytical data for product Fraction I (−): $^1$H-NMR (CD$_3$OD, 400 MHz): δ 7.74 (s, 1H), 7.65 (s, 1H), 7.56 (s, 1H), 7.48 (d, 1H), 7.34-7.28 (m, 2H), 7.25-7.20 (m, 1H), 7.18 (d, 1H), 7.08 (d, 1H), 6.93 (s, 1H), 5.20-5.18 (m, 1H), 4.30-4.20 (m, 2H), 3.82 (s, 3H), 3.14 (s, 3H), 2.22 (s, 3H); Mass (ESI): 463.5 [M+1]; LC-MS: 463.4 (M+1); (column; X-Select CSH C-18 (50×3.0 mm, 3.5 μm); RT 2.99 min. 0.05% Aq TFA: ACN; 0.80 ml/min); UPLC (column; Acquity UPLC BEH C-18, 2.1×50 mm, 1.7 μm); RT 1.66 min. ACN: 0.025% TFA (Aq); 0.50 ml/min; Chiral HPLC: RT=20.65 min (Chiralpak-IB (250×4.6 mm, 5 μm; mobile phase (A) 0.1% DEA in n-hexane (B) CH$_2$Cl$_2$: MeOH (50:50) (90:10); flow Rate: 1.0 mL/min); Optical rotation $[α]_D^{20.00}$: −161.36 (c 0.25, DCM).

Example 51B

Synthesis of (+)-7-(2-chlorophenyl)-N-(3-methoxy-4-(4-methyl-1H-imidazol-1-yl) phenyl)-8-methyl-7,8-dihydro-6H-pyrimido [5, 4-b] [1, 4] oxazin-2-amine

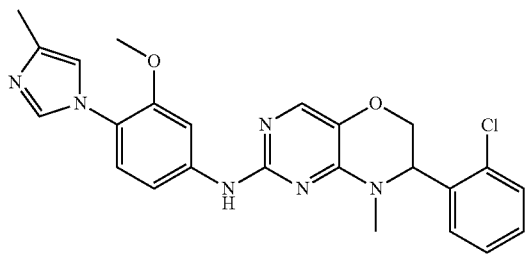 [SMILES: COc1cc(Nc2ncc3c(n2)N(C)C(c2ccccc2Cl)CO3)ccc1-n1cnc(C)c1]

The compound of Example 51B was produced as described in Example 51. Analytical data for product Fraction II (+): $^1$H-NMR (CD$_3$OD, 400 MHz): δ 7.74 (s, 1H), 7.65 (s, 1H), 7.56 (s, 1H), 7.48 (d, 1H), 7.34-7.28 (m, 2H), 7.25-7.20 (m, 1H), 7.18 (d, 1H), 7.08 (d, 1H), 6.93 (s, 1H), 5.20-5.18 (m, 1H), 4.30-4.20 (m, 2H), 3.82 (s, 3H), 3.14 (s, 3H), 2.22 (s, 3H); Mass (ESI): 463.4 [M+1]; LC-MS: 463.4 (M+1); (column; X-Select CSH C-18 (50×3.0 mm, 3.5 μm); RT 2.99 min. 0.05% Aq TFA: ACN; 0.80 ml/min); UPLC (column; Acquity UPLC BEH C-18, 2.1×50 mm, 1.7 μm); RT 1.66 min. ACN: 0.025% TFA (Aq); 0.50 ml/min; Chiral HPLC: RT=24.50 min (Chiralpak-IB (250×4.6 mm, 5 μm; mobile phase (A) 0.1% DEA in n-hexane (B) CH$_2$Cl$_2$: MeOH (50:50) (90:10); flow Rate: 1.0 mL/min); Optical rotation $[α]_D^{19.98}$: +176.78 (c 0.25, DCM).

Example 52

Synthesis of N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine

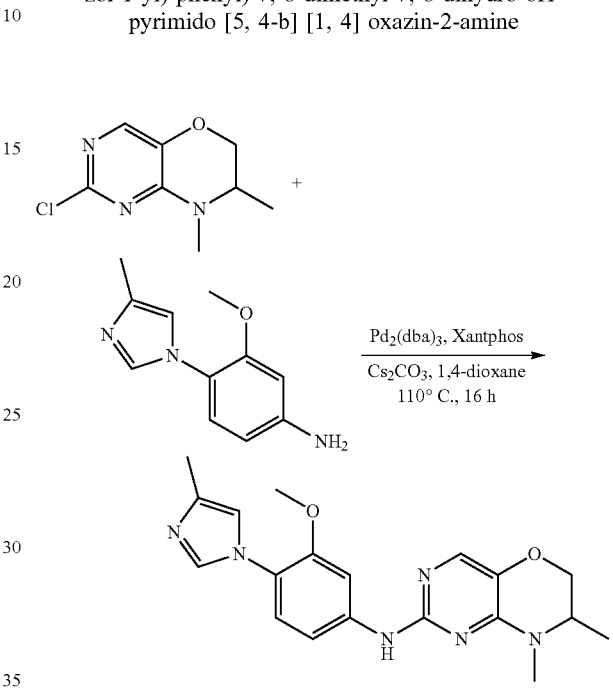

Synthesis of N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine To a dry vial was added a suspension of Pd$_2$(dba)$_3$ (23 mg, 0.02 mmol) and Xantphos (43 mg, 0.07 mmol) in 1, 4-dioxane (1 mL). The suspension was degassed, heated to 110° C. and stirred for 3 min. A mixture of 2-chloro-7, 8-dimethyl-7, 8-dihydro-6H-pyrimido [5, 4-b] [1, 4] oxazine (100 mg, 0.50 mmol), 3-methoxy-4-(4-methyl-1H-imidazol-1-yl) aniline (204 mg, 1.00 mmol), cesium carbonate (228 mg, 0.70 mmol) in 1, 4-dioxane (1 mL) was degassed and the catalyst premix was added. The reaction mixture was heated to 110° C. and stirred for 16 h in a sealed tube. After consumption of the starting material (monitored by TLC and LCMS), the mixture was diluted with a saturated sodium carbonate solution (20 mL) and extracted with EtOAc (2×20 mL). The combined organic extracts were dried over sodium sulfate, filtered and concentrated in vacuo. The crude material was purified by silica gel column chromatography using 0-5% MeOH:CH$_2$Cl$_2$ to afford N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine (30 mg, 16%) as an off-white solid. $^1$H-NMR (CD$_3$OD, 400 MHz): δ 7.73 (d, 2H), 7.50 (s, 1H), 7.20 (s, 2H), 7.00 (s, 1H), 4.01-3.99 (m, 2H), 3.83 (s, 3H), 3.68-3.59 (m, 1H), 3.19 (s, 3H), 2.21 (s, 3H), 1.31 (d, 3H); Mass (ESI): 367.3 [M+1]; LC-MS: 366.9 (M+1); (column; X-Select CSH C-18 (50×3.0 mm, 3.5 μm); RT 1.97 min. 0.05% Aq TFA: ACN; 0.8 mL/min); UPLC (column; Acquity UPLC HSS-T-3, 100×2.1 mm, 1.8µ); RT 3.22 min. ACN: 0.025% TFA (Aq); 0.30 ml/min; TLC: 5% MeOH:CH$_2$Cl$_2$ (R$_f$ 0.2).

Example 53

Synthesis of 7-(2-chloro-4-fluorophenyl)-N-(3-methoxy-4-(4-methyl-1H-imidazol-1-yl) phenyl)-8-methyl-7,8-dihydro-6H-pyrimido [5, 4-b] [1,4] oxazin-2-amine

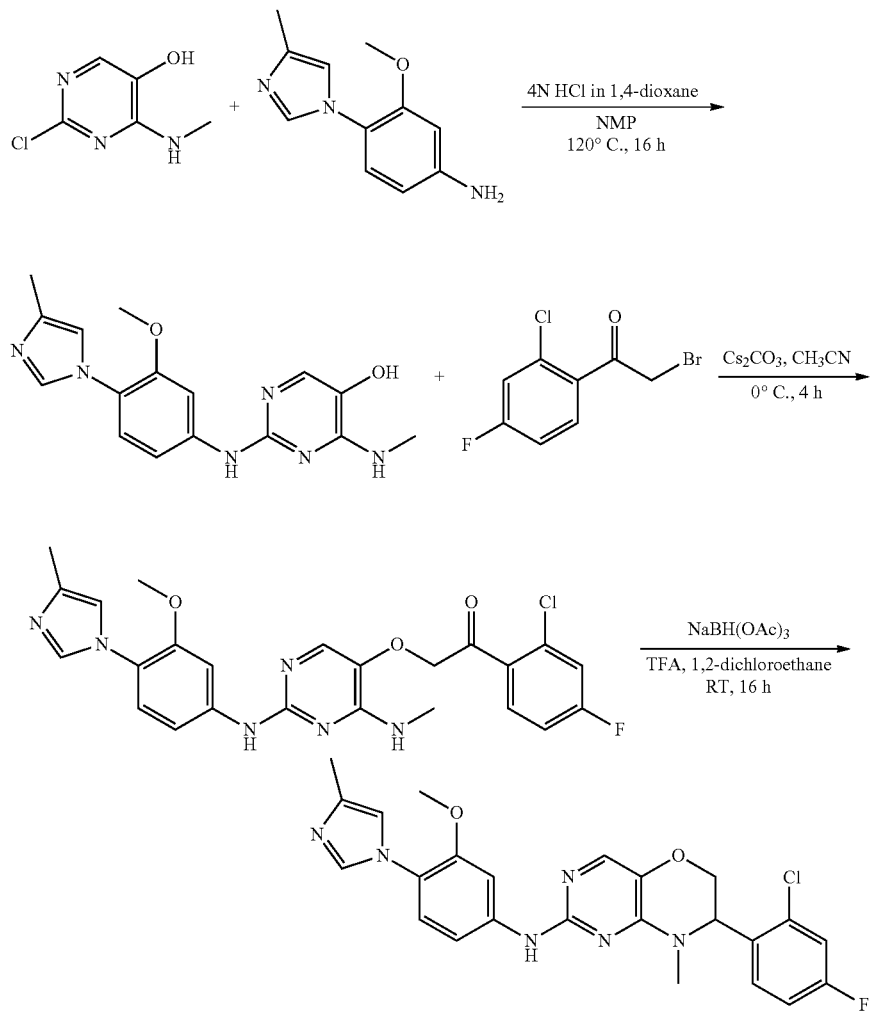

(2×1 mL) to afford 2-((3-methoxy-4-(4-methyl-1H-imidazol-1-yl) phenyl) amino)-4-(methylamino) pyrimidin-5-ol (70 mg, 69%) as a brown solid. $^1$H-NMR (DMSO-d$_6$, 400 MHz): δ 9.00 (br s, 1H), 8.80 (s, 1H), 7.89 (s, 1H), 7.59 (s, 1H), 7.40 (s, 1H), 7.27 (d, 1H), 7.09 (d, 1H), 6.95 (s, 1H), 6.71-6.68 (m, 1H), 3.73 (s, 3H), 2.87 (s, 3H), 2.12 (s, 3H); LC-MS: 327.4 (M+1); (column; X-Select CSH C-18 (50× 3.0 mm, 3.5 µm); RT 2.53 min. 5 mM Aq NH$_4$OAc: ACN; 0.80 ml/min); TLC: 80% EtOAc:hexanes (R$_f$ 0.1).

Synthesis of 2-((3-methoxy-4-(4-methyl-M-imidazol-1-yl) phenyl) amino)-4-(methylamino) pyrimidin-5-ol To a stirred solution of 2-chloro-4-(methylamino) pyrimidin-5-ol (50 mg, 0.31 mmol) in N-methyl-2-pyrrolidinone (1.3 mL) was added 3-methoxy-4-(4-methyl-1H-imidazol-1-yl) aniline (69 mg, 0.34 mmol) and 4N HCl in 1, 4-dioxane (0.3 mL). The reaction mixture was heated to 120° C. and stirred for 16 h. After consumption of the starting material (monitored by TLC), the mixture was diluted with a saturated sodium bicarbonate solution (20 mL), filtered, washed with water (2×5 mL) and dried in vacuo. The crude material was washed successively with ether (2×1 mL) and n-pentane Synthesis of 1-(2-chloro-4-fluorophenyl)-2-((2-((3-methoxy-4-(4-methyl-1H-imidazol-1-yl) phenyl) amino)-4-(methylamino) pyrimidin-5-yl) oxy) ethan-1-one To a stirred solution of 2-((3-methoxy-4-(4-methyl-1H-imidazol-1-yl) phenyl) amino)-4-(methylamino) pyrimidin-5-ol (150 mg, 0.46 mmol) in CH$_3$CN (3 mL) was added cesium carbonate (300 mg, 0.92 mmol) and stirred for 15 min. 2-Bromo-1-(2-chloro-4-fluorophenyl) ethan-1-one (127 mg, 0.50 mmol) was added at 0° C. and the reaction mixture was stirred for 4 h. After consumption of the starting material (monitored by TLC), the mixture was diluted with water (20 mL) and extracted with EtOAc (2×20 mL). The combined organic extracts were dried over sodium sulfate, filtered and concentrated in vacuo to afford 1-(2-chloro-4-fluorophenyl)-2-((2-((3-methoxy-4-(4-methyl-1H-imidazol-1-yl) phenyl) amino)-4-(methylamino) pyrimidin-5-yl) oxy) ethan-1-one (170 mg, 74%) as a yellow solid. TLC: 10% MeOH:CH$_2$Cl$_2$ (R$_f$: 0.4).

Synthesis of 7-(2-chloro-4-fluorophenyl)-N-(3-methoxy-4-(4-methyl-1H-imidazol-1-yl)phenyl)-8-methyl-7,8-dihydro-6H-pyrimido[5,4-b][1,4]oxazin-2-amine To a stirred solution of 1-(2-chloro-4-fluorophenyl)-2-((2-((3-methoxy-4-(4-methyl-1H-imidazol-1-yl) phenyl) amino)-4-(methylamino) pyrimidin-5-yl) oxy) ethan-1-one (120 mg, 0.24 mmol) in 1, 2-dichloroethane (3 mL) was added trifluoroacetic acid (0.24 mmol) and sodium triacetoxyborohydride (103 mg, 0.48 mmol) and the reaction mixture was stirred for 16 h. After consumption of the starting material (monitored by TLC), the reaction was quenched with 1N sodium hydroxide (50 mL) and extracted with CH$_2$Cl$_2$ (2×50 mL). The combined organic extracts were dried over sodium sulfate, filtered and concentrated in vacuo. The crude material was purified by silica gel column chromatography using 0-5% MeOH:CH$_2$Cl$_2$ to afford 7-(2-chloro-4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (30 mg, 26%) as an off-white solid. $^1$H-NMR (CD$_3$OD, 400 MHz): δ 7.72 (s, 1H), 7.65 (s, 1H), 7.59 (s, 1H), 7.31 (d, 1H), 7.24 (d, 1H), 7.19 (d, 1H), 7.10-7.06 (m, 2H), 6.92-6.90 (m, 1H), 5.19-5.17 (m, 1H), 4.30-4.20 (m, 2H), 3.82 (s, 3H), 3.14 (s, 3H), 2.20 (s, 3H); Mass (ESI): 481.4 [M+1]; LC-MS: 480.9 (M+1); (column; X-Select CSH C-18 (50×3.0 mm, 3.5 μm); RT 2.49 min. 0.05% Aq TFA: ACN; 0.80 ml/min); UPLC (column; Acquity BEH C-18, 50×2.1 mm, 1.7 μm); RT 1.69 min. ACN: 0.025% TFA (Aq); 0.50 ml/min; TLC: 80% EtOAc: hexanes (R$_f$: 0.4).

Example 54

Synthesis of 7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

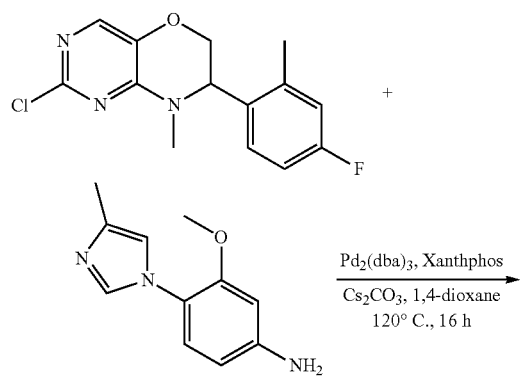

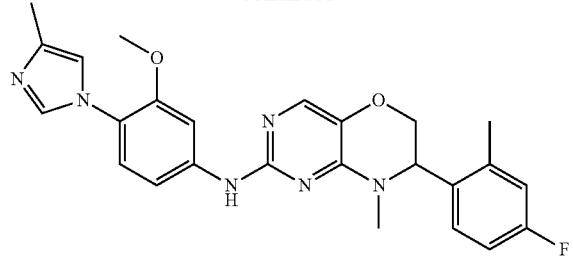

Synthesis of 7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a dry vial was added a suspension of Pd$_2$(dba)$_3$ (15 mg, 0.01 mmol) and Xantphos (29 mg, 0.05 mmol) in 1, 4-dioxane (1 mL). The suspension was degassed, heated to 120° C. and stirred for 3 min. A mixture of 2-chloro-7-(4-fluoro-2-methylphenyl)-8-methyl-7, 8-dihydro-6H-pyrimido [5, 4-b] [1, 4] oxazine (100 mg, 0.34 mmol), 3-methoxy-4-(4-methyl-1H-imidazol-1-yl) aniline (138 mg, 0.68 mmol), cesium carbonate (155 mg, 0.47 mmol) in 1, 4-dioxane (0.5 mL) was degassed and the catalyst premix was added. The reaction mixture was heated to 120° C. and stirred for 16 h in a sealed tube. After consumption of the starting material (monitored by TLC and LCMS), the mixture was diluted with an aqueous sodium carbonate solution (20 mL) and extracted with EtOAc (2×20 mL). The combined organic extracts were dried over sodium sulfate, filtered and concentrated in vacuo. The crude material was purified by silica gel column chromatography using 30% EtOAc:hexanes to afford 7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (20 mg, 12%) as an off-white solid. $^1$H-NMR (CD$_3$OD, 400 MHz): δ 7.72 (s, 1H), 7.61 (s, 1H), 7.54 (s, 1H), 7.28-7.18 (m, 2H), 7.04-6.90 (m, 4H), 4.99-6.90 (m, 1H), 4.24-4.10 (m, 2H), 3.82 (s, 3H), 3.09 (s, 3H), 2.41 (s, 3H), 2.20 (s, 3H); Mass (ESI): 461.4 [M+1]; LC-MS: 461.6 (M+1); (column; X-Select CSH C-18 (50×3.0 mm, 3.5 μm); RT 3.75 min. 5 μm NH$_4$OAc: ACN; 0.80 mL/min); HPLC (column; Eclipse XDB C-18, 150×4.6 mm, 5 μm); RT 10.86 min. ACN: 5 mM Aq NH$_4$OAc; 1.0 ml/min; TLC: 30% EtOAc:hexanes (R$_f$: 0.4).

Example 55

Synthesis of N-(3-methoxy-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine

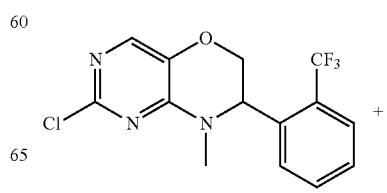

-continued

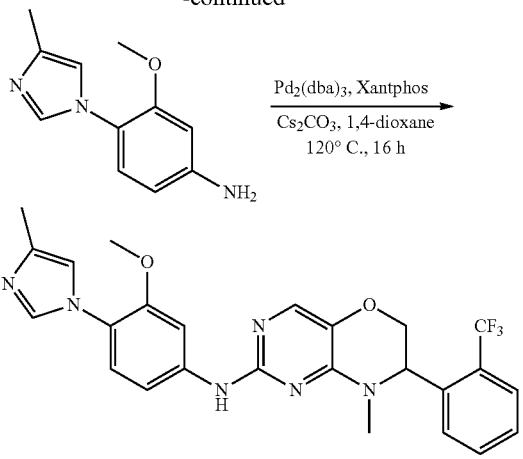

Synthesis of N-(3-methoxy-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine To a dry vial was added a suspension of Pd$_2$(dba)$_3$ (14 mg, 0.01 mmol) and Xantphos (26 mg, 0.04 mmol) in 1, 4-dioxane (0.5 mL). The suspension was degassed, heated to 120° C. and stirred for 3 min. A mixture 2-chloro-8-methyl-7-(2-(trifluoromethyl)phenyl)-7, 8-dihydro-6H-pyrimido [5, 4-b] [1, 4] oxazine (100 mg, 0.30 mmol), 3-methoxy-4-(4-methyl-1H-imidazol-1-yl) aniline (123 mg, 0.60 mmol), cesium carbonate (138 mg, 0.42 mmol) in 1, 4-dioxane (0.5 mL) was degassed and the catalyst premix was added. The reaction mixture was heated to 120° C. and stirred for 16 h in a sealed tube. After consumption of staring material (monitored by TLC and LCMS), the reaction was diluted with an aqueous sodium carbonate solution (20 mL) and extracted with EtOAc (2×20 mL). The combined organic extracts were dried over sodium sulfate, filtered and concentrated in vacuo. The crude material was purified by silica gel column chromatography using 80% EtOAc:hexanes to afford N-(3-methoxy-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine (40 mg, 26%) as an off-white solid. $^1$H-NMR (CD$_3$OD, 400 MHz): δ 7.79 (d, 1H), 7.72 (s, 1H), 7.67-7.60 (m, 3H), 7.54 (t, 1H), 7.34 (d, 1H), 7.25 (d, 1H), 7.19-7.17 (m, 1H), 6.95 (s, 1H), 5.04-4.99 (m, 1H), 4.31-4.29 (m, 1H), 4.11-4.09 (m, 1H), 3.82 (s, 3H), 3.09 (s, 3H), 2.20 (s, 3H); Mass (ESI): 497.3 [M+1]; LC-MS: 497.5 (M+1); (column; X-Select CSH C-18 (50× 3.0 mm, 3.5 µm); RT 3.94 min. 5 mM NH$_4$OAc: ACN; 0.80 mL/min); HPLC (column; Eclipse XDB C-18, 150×4.6 mm, 5 µm); RT 11.53 min. ACN: 5 mM Aq NH$_4$OAc; 1.0 ml/min); TLC: 50% EtOAc:hexanes (R$_f$: 0.4).

Racemic compound of Example 55 was separated using a Chiralpak IA (250×20 mm, 5 µm (40 mg loading; 0.1% DEA in n-hexane: CH$_2$Cl$_2$:MeOH (50:50); (85:15) as the mobile phase) to provide the compound of Example 55A (Fraction I (−)) and the compound of Example 55B (Fraction II (+)).

Example 55A

Synthesis of (−)-N-(3-methoxy-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine

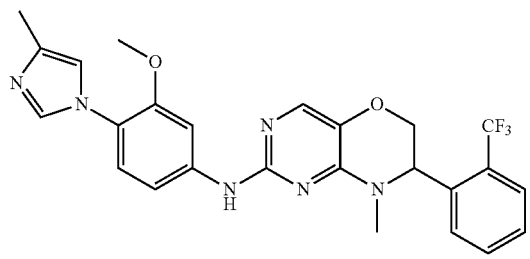 [SMILES: COc1cc(Nc2ncc3c(n2)N(C)C(c2ccccc2C(F)(F)F)CO3)ccc1-n1cnc(C)c1]

The compound of Example 55A was produced as described in Example 55. Analytical data for product Fraction I (−): $^1$H-NMR (CD$_3$OD, 400 MHz): δ 7.80 (d, 1H), 7.74 (s, 1H), 7.65-7.60 (m, 3H), 7.52 (t, 1H), 7.33 (d, 1H), 7.23 (d, 1H), 7.19-7.17 (m, 1H), 6.98 (s, 1H), 5.01-4.99 (m, 1H), 4.31-4.28 (m, 1H), 4.11-4.08 (m, 1H), 3.81 (s, 3H), 3.08 (s, 3H), 2.21 (s, 3H); Mass (ESI): 497.5 [M+1]; LC-MS: 497.6 (M+1); (column; X-Select CSH C-18 (50× 3.0 mm, 3.5 µm); RT 3.96 min. 5 mM NH$_4$OAc: ACN; 0.80 ml/min); HPLC (column; Eclipse XDB-C-18, 150×4.6 mm, 5 µm); RT 11.47 min. ACN: 5 mM Aq NH$_4$OAc % TFA (Aq); 1.0 ml/min; Chiral HPLC: RT=14.24 min (Chiralpak-IA (250×4.6 mm, 5 µm; mobile phase (A) 0.1% DEA in n-hexane (B) CH$_2$Cl$_2$:MeOH (50:50) (85:15); flow Rate: 1.0 mL/min); Optical rotation $[\alpha]_D^{20.01}$: −105.80 (c 0.25, DCM).

Example 55B

Synthesis of (+)-N-(3-methoxy-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine

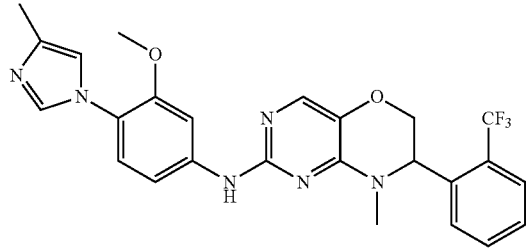 [SMILES: COc1cc(Nc2ncc3c(n2)N(C)C(c2ccccc2C(F)(F)F)CO3)ccc1-n1cnc(C)c1]

The compound of Example 55B was produced as described in Example 55. Analytical data for product Fraction II (+): $^1$H-NMR (CD$_3$OD, 400 MHz): δ 7.80 (d, 1H), 7.74 (s, 1H), 7.65-7.60 (m, 3H), 7.52 (t, 1H), 7.33 (d, 1H), 7.23 (d, 1H), 7.19-7.17 (m, 1H), 6.98 (s, 1H), 5.01-4.99 (m, 1H), 4.31-4.28 (m, 1H), 4.11-4.08 (m, 1H), 3.81 (s, 3H), 3.08 (s, 3H), 2.21 (s, 3H); Mass (ESI): 497.4 [M+1]; LC-MS: 497.5 (M+1); (column; X-Select CSH C-18 (50× 3.0 mm, 3.5 µm); RT 3.96 min. 5 mM NH$_4$OAc: ACN; 0.80 ml/min); HPLC (column; Eclipse XDB-C-18, 150×4.6 mm, 5 µm); RT 11.52 min. ACN: 5 mM Aq NH₄OAc % TFA (Aq); 1.0 ml/min; Chiral HPLC: RT=17.95 min (Chiralpak-IA (250×4.6 mm, 5 µm; mobile phase (A) 0.1% DEA in n-hexane (B) CH₂Cl₂:MeOH (50:50) (85:15); flow Rate: 1.0 mL/min); Optical rotation $[α]_D^{20.00}$: +95.61 (c 0.25, DCM).

Example 56

Synthesis of N-(3-fluoro-4-(2-methylpyridin-4-yl) phenyl)-7-(4-fluorophenyl)-8-methyl-7, 8-dihydro-6H-pyrimido [5, 4-b] [1, 4] oxazin-2-amine

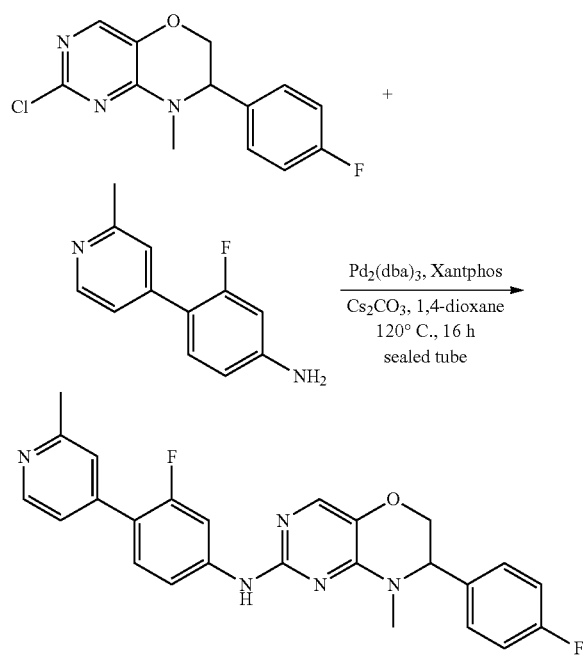

Synthesis of N-(3-fluoro-4-(2-methylpyridin-4-yl) phenyl)-7-(4-fluorophenyl)-8-methyl-7, 8-dihydro-6H-pyrimido [5, 4-b] [1, 4] oxazin-2-amine To a dry vial was added a suspension of Pd₂(dba)₃ (41 mg, 0.04 mmol) and Xantphos (77 mg, 0.13 mmol) in 1, 4-dioxane (1.25 mL). The suspension was degassed, heated to 120° C. and stirred for 3 min. A mixture of 2-chloro-7-(4-fluorophenyl)-8-methyl-7, 8-dihydro-6H-pyrimido [5, 4-b] [1, 4] oxazine (250 mg, 0.89 mmol), 3-fluoro-4-(2-methylpyridin-4-yl) aniline (362 mg, 1.79 mmol), cesium carbonate (408 mg, 1.25 mmol) in 1, 4-dioxane (1.25 mL) was degassed and the catalyst premix was added. The reaction mixture was heated to 120° C. and stirred for 16 h in a sealed tube. After consumption of the starting material (monitored by TLC and LCMS), the mixture was filtered. The filtrate was washed with water (20 mL), dried over sodium sulfate, filtered and concentrated in vacuo. The crude material was purified by silica gel column chromatography using 80% EtOAc:hexanes to afford N-(3-fluoro-4-(2-methylpyridin-4-yl) phenyl)-7-(4-fluorophenyl)-8-methyl-7, 8-dihydro-6H-pyrimido [5, 4-b] [1, 4] oxazin-2-amine (180 mg, 45%) as a pale yellow solid. UPLC (column; Acquity BEH C-18, 50×2.1 mm, 1.7 µm); RT 1.67 min. ACN: 0.025% TFA (Aq); 0.50 ml/min, TLC: 50% EtOAc:hexanes ($R_f$: 0.7).

Racemic compound of Example 56 was separated using a Chiralpak IA (250×20 mm, 5 µm (30 mg loading; 0.1% DEA in n-hexane: CH₂Cl₂:MeOH (50:50); (A:B: 85:15) as the mobile phase) to provide the compound of Example 56A (Fraction I (+)) and the compound of Example 56B (Fraction II (−)).

Example 56A

Synthesis of (+)-N-(3-fluoro-4-(2-methylpyridin-4-yl) phenyl)-7-(4-fluorophenyl)-8-methyl-7, 8-dihydro-6H-pyrimido [5, 4-b] [1, 4] oxazin-2-amine

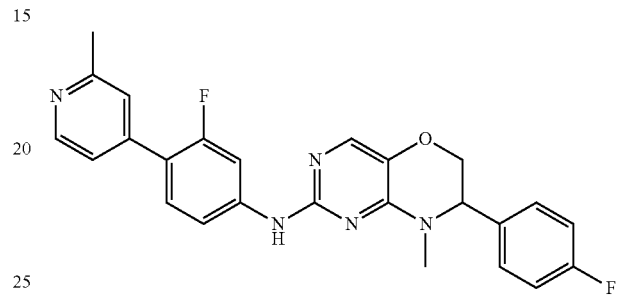

The compound of Example 56A was produced as described in Example 56. Analytical data for product Fraction I (+): ¹H-NMR (CD₃OD, 400 MHz): δ 8.40-8.38 (m, 1H), 7.90-7.88 (m, 1H), 7.59 (s, 1H), 7.50-7.40 (m, 4H), 7.29-7.26 (m, 2H), 7.10 (t, 2H), 4.71-4.69 (m, 1H), 4.22-4.17 (m, 2H), 3.11 (s, 3H), 2.55 (s, 3H); Mass (ESI): 446.3 [M+1]; LC-MS: 446.3 (M+1); (column; X-Select CSH C-18 (50×3.0 mm, 3.5 µm); RT 2.85 min. 0.05% Aq TFA: ACN; 0.80 ml/min); UPLC (column; Acquity BEH C-18, 50×2.1 mm, 1.7 µm); RT 1.63 min. ACN: 0.025% TFA (Aq); 0.50 ml/min; Chiral HPLC: RT=23.95 min (CHIRALPAK-IA (250×4.6 mm, 5 µm; mobile phase (A) 0.1% DEA in n-hexane (B) CH₂Cl₂:MeOH (50:50) (A:B: 85:15); flow Rate: 1.0 mL/min); Optical rotation $[α]_D^{19.98}$: +142.43 (c 0.25, DCM).

Example 56B

Synthesis of (−)-N-(3-fluoro-4-(2-methylpyridin-4-yl) phenyl)-7-(4-fluorophenyl)-8-methyl-7, 8-dihydro-6H-pyrimido [5, 4-b] [1, 4] oxazin-2-amine

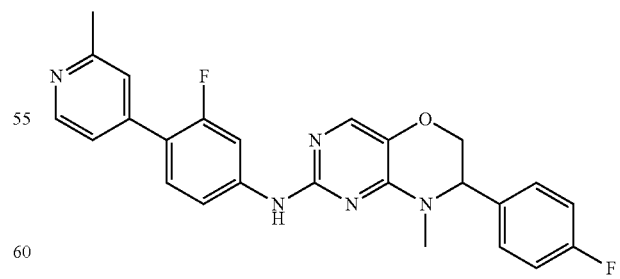

The compound of Example 56B was produced as described in Example 56. Analytical data for product Fraction I (−): ¹H-NMR (CD₃OD, 400 MHz): δ 8.40-8.38 (m, 1H), 7.91-7.89 (m, 1H), 7.59 (s, 1H), 7.50-7.40 (m, 4H), 7.29-7.26 (m, 2H), 7.10 (t, 2H), 4.71-4.69 (m, 1H), 4.22-

4.17 (m, 2H), 3.11 (s, 3H), 2.55 (s, 3H); Mass (ESI): 446.3 [M+1]; LC-MS: 446.3 (M+1); (column; X-Select CSH C-18 (50×3.0 mm, 3.5 μm); RT 2.86 min. 0.05% Aq TFA: ACN; 0.80 ml/min; UPLC (column; Acquity BEH C-18, 50×2.1 mm, 1.7 μm); RT 1.63 min. ACN: 0.025% TFA (Aq); 0.50 ml/min; Chiral HPLC: RT=26.52 min (CHIRALPAK-IA (250×4.6 mm, 5 μm; mobile phase (A) 0.1% DEA in n-hexane (B) $CH_2Cl_2$:MeOH (50:50) (A:B: 85:15); flow Rate: 1.0 mL/min); Optical rotation $[\alpha]_D^{20.00}$: −134.38 (c 0.25, DCM).

Example 57

Synthesis of 7-benzyl-N-(3-fluoro-4-(2-methylpyridin-4-yl) phenyl)-8-methyl-7, 8-dihydro-6H-pyrimido [5, 4-b] [1, 4] oxazin-2-amine

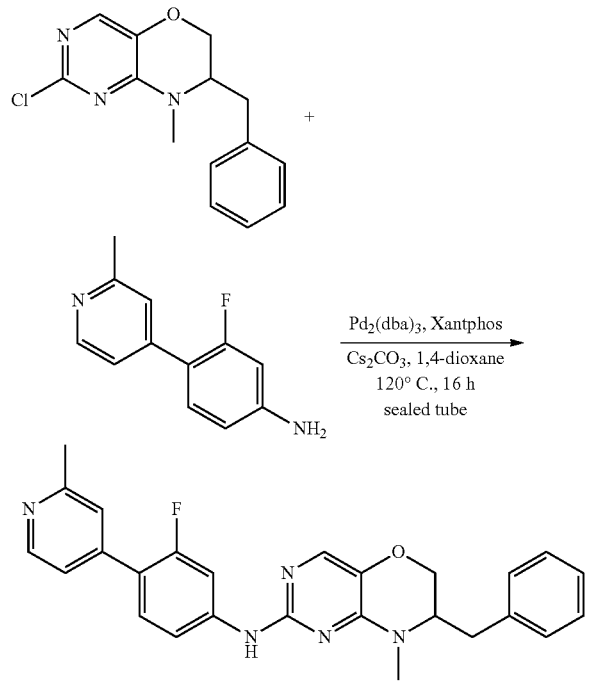

Synthesis of 7-benzyl-N-(3-fluoro-4-(2-methylpyridin-4-yl) phenyl)-8-methyl-7, 8-dihydro-6H-pyrimido [5, 4-b] [1, 4] oxazin-2-amine To a dry vial was added a suspension of $Pd_2(dba)_3$ (33 mg, 0.03 mmol) and Xantphos (63 mg, 0.10 mmol) in 1, 4-dioxane (1 mL). The suspension was degassed, heated to 120° C. and stirred for 3 min. A mixture of 7-benzyl-2-chloro-8-methyl-7, 8-dihydro-6H-pyrimido [5, 4-b] [1, 4] oxazine (200 mg, 0.72 mmol), 3-fluoro-4-(2-methylpyridin-4-yl) aniline (293 mg, 1.45 mmol) and cesium carbonate (330 mg, 1.01 mmol) in 1, 4-dioxane (1 mL) was degassed and the catalyst premix was added. The reaction mixture was heated to 120° C. and stirred for 16 h in a sealed tube. After consumption of the starting material (monitored by TLC and LCMS), the reaction was diluted with water (20 mL) and extracted with $CH_2Cl_2$ (2×25 mL). The combined organic extracts were dried over sodium sulfate, filtered and concentrated in vacuo. The crude material was purified by silica gel column chromatography using 2-5% MeOH:$CH_2Cl_2$ to afford 7-benzyl-N-(3-fluoro-4-(2-methylpyridin-4-yl) phenyl)-8-methyl-7, 8-dihydro-6H-pyrimido [5, 4-b] [1, 4] oxazin-2-amine (95 mg, 29%) as a yellow solid. LC-MS: 442.3 (M+1); (column; X-Select CSH C-18 (50×3.0 mm, 3.5 μm); RT 2.93 min. 0.05% Aq TFA: ACN; 0.80 ml/min); UPLC (column; Acquity BEH C-18, 50×2.1 mm, 1.7 μm); RT 1.68 min. ACN: 0.025% TFA (Aq); 0.50 ml/min. TLC: 5% MeOH:$CH_2Cl_2$ ($R_f$: 0.5).

Racemic compound of Example 57 was separated using a Chiralpak IA (250×20 mm, 5 μm (70 mg loading; 0.1% DEA in n-hexane: $CH_2Cl_2$:MeOH (50:50); (75:25) as the mobile phase) to provide the compound of Example 57A (Fraction I (+)) and the compound of Example 57B (Fraction II (−)).

Example 57A

Synthesis of (+)-7-benzyl-N-(3-fluoro-4-(2-methylpyridin-4-yl) phenyl)-8-methyl-7, 8-dihydro-6H-pyrimido [5, 4-b] [1, 4] oxazin-2-amine

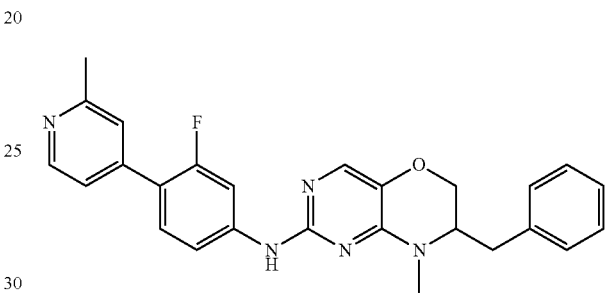

The compound of Example 57A was produced as described in Example 57. Analytical data for product Fraction I (+): $^1$H-NMR (CD$_3$OD, 400 MHz): δ 8.40 (d, 1H), 7.90-7.86 (m, 1H), 7.55 (s, 1H), 7.49-7.47 (m, 2H), 7.46-7.38 (m, 2H), 7.36-7.30 (m, 2H), 7.29-7.20 (m, 3H), 4.10-4.07 (m, 1H), 3.83-3.80 (m, 1H), 3.78-3.70 (m, 1H), 3.11 (s, 3H), 3.10-3.09 (m, 1H), 2.87-2.83 (m, 1H), 2.55 (s, 3H); Mass (ESI): 442.4 [M+1]; LC-MS: 442.4 (M+1); (column; X-Select CSH C-18 (50×3.0 mm, 3.5 μm); RT 2.90 min. 0.05% Aq TFA: ACN; 0.80 ml/min); UPLC (column; Acquity BEH C-18, 50×2.1 mm, 1.7 μm); RT 1.64 min. ACN: 0.025% TFA (Aq); 0.50 ml/min; Chiral HPLC: RT=12.43 min (CHIRALPAK-IA (250×4.6 mm, 5 μm; mobile phase (A) 0.1% DEA in n-hexane (B) $CH_2Cl_2$:MeOH (50:50) (A:B: 75:25); flow Rate: 1.0 mL/min); Optical rotation $[\alpha]_D^{19.99}$: +63.29 (c=0.25, DCM).

Example 57B

Synthesis of (−)-7-benzyl-N-(3-fluoro-4-(2-methylpyridin-4-yl) phenyl)-8-methyl-7, 8-dihydro-6H-pyrimido [5, 4-b] [1, 4] oxazin-2-amine

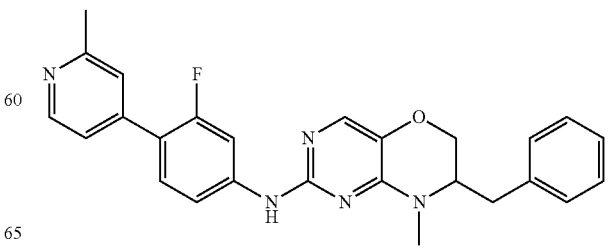

The compound of Example 57B was produced as described in Example 57. Analytical data for product Fraction II (−): $^1$H-NMR (CD$_3$OD, 400 MHz): δ 8.41 (d, 1H), 7.90-7.85 (m, 1H), 7.55 (s, 1H), 7.49-7.47 (m, 2H), 7.46-7.38 (m, 2H), 7.36-7.31 (m, 2H), 7.29-7.20 (m, 3H), 4.10-4.07 (m, 1H), 3.83-3.80 (m, 1H), 3.78-3.70 (m, 1H), 3.11 (s, 3H), 3.10-3.08 (m, 1H), 2.87-2.83 (m, 1H), 2.55 (s, 3H); Mass (ESI): 442.4 [M+1]; LC-MS: 442.3 (M+1); (column; X-Select CSH C-18 (50×3.0 mm, 3.5 μm); RT 2.91 min. 0.05% Aq TFA: ACN; 0.80 ml/min); UPLC (column; Acquity BEH C-18, 50×2.1 mm, 1.7 μm); RT 1.64 min. ACN: 0.025% TFA (Aq); 0.50 ml/min; Chiral HPLC: RT=21.38 min (CHIRALPAK-IA (250×4.6 mm, 5 μm; mobile phase (A) 0.1% DEA in n-hexane (B) CH$_2$Cl$_2$: MeOH (50:50) (A:B: 75:25); flow Rate: 1.0 mL/min); Optical rotation $[\alpha]_D^{19.99}$: −77.24 (c=0.25, DCM).

Example 58

Synthesis of N-(3-fluoro-4-(4-methyl-1H-imidazol-1-yl) phenyl)-7-(4-fluorophenyl)-8-methyl-7, 8-dihydro-6H-pyrimido [5, 4-b] [1, 4] oxazin-2-amine

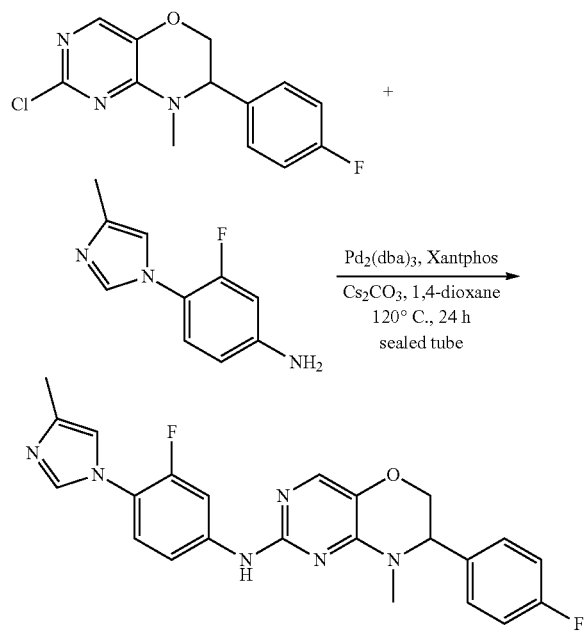

Synthesis of N-(3-fluoro-4-(4-methyl-1H-imidazol-1-yl) phenyl)-7-(4-fluorophenyl)-8-methyl-7, 8-dihydro-6H-pyrimido [5, 4-b] [1, 4] oxazin-2-amine To a dry vial was added a suspension of Pd$_2$(dba)$_3$ (40 mg, 0.09 mmol) and Xantphos (76 mg, 0.13 mmol) in 1, 4-dioxane (2.5 mL). The suspension was degassed, heated to 120° C. and stirred for 3 min. A mixture of 2-chloro-7-(4-fluorophenyl)-methyl-7, 8-dihydro-6H-pyrimido [5, 4-b] [1, 4] oxazine (250 mg, 0.89 mmol), 3-fluoro-4-(4-methyl-1H-imidazol-1-yl) aniline (188 mg, 0.98 mmol), cesium carbonate (407 mg, 1.25 mmol) in 1, 4-dioxane (2.5 mL) was degassed and the catalyst premix was added. The reaction mixture was heated to 120° C. and stirred for 24 h in a sealed tube. After consumption of the starting material (monitored by TLC and LCMS), the mixture was filtered and concentrated in vacuo. The crude material was purified by silica gel column chromatography using 2% MeOH: CH$_2$Cl$_2$ to afford N-(3-fluoro-4-(4-methyl-1H-imidazol-1-yl) phenyl)-7-(4-fluorophenyl)-8-methyl-7, 8-dihydro-6H-pyrimido [5, 4-b] [1, 4] oxazin-2-amine GSM-NS-570 (150 mg, 40%) as an off-white solid. LC-MS: 435.3 (M+1); (column; X-Select CSH C-18 (50×3.0 mm, 3.5 μm); RT 2.82 min. 0.05% Aq TFA: ACN; 0.80 ml/min); HPLC (column; Eclipse-XDB-C-18, 150×4.6 mm, 5μ); RT 10.86 min. ACN: 5 mM Aq NH$_4$OAc (Aq); 1.0 ml/min; TLC: 5% MeOH: CH$_2$Cl$_2$ (R$_f$: 0.3).

Racemic compound of Example 58 was separated using a Chiralpak IA (250×20 mm, 5 μm (20 mg loading; 0.1% DEA in n-hexane: CH$_2$Cl$_2$:MeOH (50:50); (80:20) as the mobile phase to provide the compound of Example 58A (Fraction I (+)) and the compound of Example 58B (Fraction II (−)).

Example 58A

Synthesis of (+)-N-(3-fluoro-4-(4-methyl-1H-imidazol-1-yl) phenyl)-7-(4-fluorophenyl)-8-methyl-7, 8-dihydro-6H-pyrimido [5, 4-b] [1, 4] oxazin-2-amine

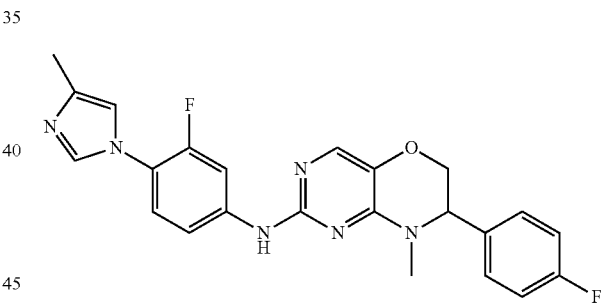

The compound of Example 58A was produced as described in Example 58. Analytical data for product Fraction I (+): $^1$H-NMR (CD$_3$OD, 400 MHz): δ 8.01-7.98 (m, 1H), 7.78 (s, 1H), 7.60 (s, 1H), 7.41-7.21 (m, 4H), 7.12-7.08 (m, 3H), 4.71-4.70 (m, 1H), 4.25-4.21 (m, 1H), 4.19-4.17 (m, 1H), 3.11 (s, 3H), 2.25 (s, 3H); Mass (ESI): 435.4 [M+1]; LC-MS: 435.4 (M+1); (column; X-Select CSH C-18 (50×3.0 mm, 3.5 μm); RT 2.79 min. 0.05% Aq TFA: ACN; 0.80 ml/min); UPLC (column; Acquity UPLC BEH C-18, 2.1×50 mm, 1.7 μm); RT 1.57 min. ACN: 0.025% TFA (Aq); 0.50 ml/min; Chiral HPLC: RT=23.38 min (CHIRALPAK-IA (250×4.6 mm, 5 μm; mobile phase (A) 0.1% DEA in n-hexane (B) CH$_2$Cl$_2$:MeOH (50:50) (A:B 80:20); flow Rate: 1.0 mL/min); Optical rotation $[\alpha]_D^{19.99}$: +137.53 (c 0.25, DCM).

Example 58B

Synthesis of (−)-N-(3-fluoro-4-(4-methyl-1H-imidazol-1-yl) phenyl)-7-(4-fluorophenyl)-8-methyl-7, 8-dihydro-6H-pyrimido [5, 4-b] [1, 4] oxazin-2-amine

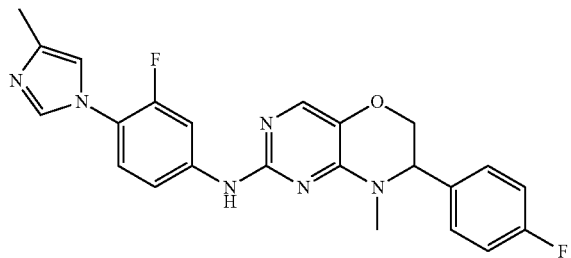 [SMILES: Cc1cn(-c2ccc(Nc3ncc4c(n3)N(C)C(c3ccc(F)cc3)CO4)cc2F)cn1]

The compound of Example 58B was produced as described in Example 58. Analytical data for product Fraction II (−): $^1$H-NMR (CD$_3$OD, 400 MHz): δ 8.01-7.98 (m, 1H), 7.78 (s, 1H), 7.60 (s, 1H), 7.41-7.21 (m, 4H), 7.12-7.08 (m, 3H), 4.71-4.70 (m, 1H), 4.25-4.21 (m, 1H), 4.19-4.17 (m, 1H), 3.11 (s, 3H), 2.25 (s, 3H); Mass (ESI): 435.4 [M+1]; LC-MS: 435.3 (M+1); (column; X-Select CSH C-18 (50×3.0 mm, 3.5 µm); RT 2.80 min. 0.05% Aq TFA: ACN; 0.80 ml/min); UPLC (column; Acquity UPLC BEH C-18, 2.1×50 mm, 1.7 µm); RT 1.57 min. ACN: 0.025% TFA (Aq); 0.50 ml/min; Chiral HPLC: RT=29.71 min (CHIRALPAK-IA (250×4.6 mm, 5 µm; mobile phase (A) 0.1% DEA in n-hexane (B) CH$_2$Cl$_2$:MeOH (50:50) (A:B: 80:20); flow Rate: 1.0 mL/min); Optical rotation [α]$_D^{20.01}$: −129.13 (c 0.25, DCM).

Example 59

Synthesis of 7-benzyl-N-(3-fluoro-4-(4-methyl-1H-imidazol-1-yl) phenyl)-8-methyl-7, 8-dihydro-6H-pyrimido [5, 4-b] [1, 4] oxazin-2-amine

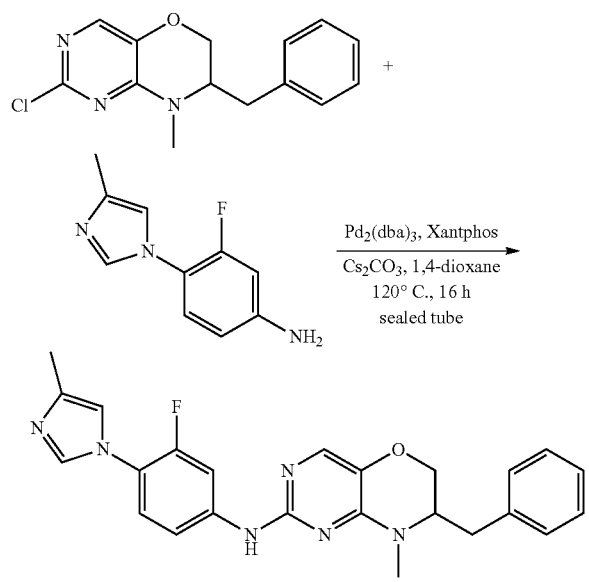

Synthesis of 7-benzyl-N-(3-fluoro-4-(4-methyl-1H-imidazol-1-yl) phenyl)-8-methyl-7, 8-dihydro-6H-pyrimido [5, 4-b] [1, 4] oxazin-2-amine To a dry vial was added a suspension of Pd$_2$(dba)$_3$ (33 mg, 0.03 mmol) and Xantphos (63 mg, 0.10 mmol) in 1, 4-dioxane (1 mL). The suspension was degassed, heated to 120° C. and stirred for 3 min. A mixture of 7-benzyl-2-chloro-8-methyl-7, 8-dihydro-6H-pyrimido [5, 4-b] [1, 4] oxazine (200 mg, 0.72 mmol), 3-fluoro-4-(4-methyl-1H-imidazol-1-yl) aniline (277 mg, 1.45 mmol) and cesium carbonate (330 mg, 1.01 mmol) in 1, 4-dioxane (1 mL) was degassed and the catalyst premix was added. The reaction mixture was heated to 120° C. and stirred for 16 h in a sealed tube. After consumption of the starting material (monitored by TLC and LCMS), the mixture was diluted with water (20 mL) and extracted with CH$_2$Cl$_2$ (2×25 mL). The combined organic extracts were dried over sodium sulfate, filtered and concentrated in vacuo. The crude material was purified by silica gel column chromatography using 2-5% MeOH:CH$_2$Cl$_2$ to afford 7-benzyl-N-(3-fluoro-4-(4-methyl-1H-imidazol-1-yl) phenyl)-8-methyl-7, 8-dihydro-6H-pyrimido [5, 4-b] [1, 4] oxazin-2-amine (95 mg, 30%) as an off-white solid. UPLC (column; Acquity BEH C-18, 50×2.1 mm, 1.7 µm); RT 1.59 min. ACN: 0.025% TFA (Aq); 0.50 ml/min; TLC: 5% MeOH:CH$_2$Cl$_2$ (R$_f$: 0.5).

Racemic compound of Example 59 was separated using a Chiralpak IA (250×20 mm, 5 µm (40 mg loading; 0.1% DEA in n-hexane: CH$_2$Cl$_2$:MeOH (50:50); (70:30) as the mobile phase) to provide the compound of Example 59A (Fraction I (+)) and the compound of Example 59B (Fraction II (−)).

Example 59A

Synthesis of (+)-7-benzyl-N-(3-fluoro-4-(4-methyl-1H-imidazol-1-yl) phenyl)-8-methyl-7, 8-dihydro-6H-pyrimido [5, 4-b] [1, 4] oxazin-2-amine

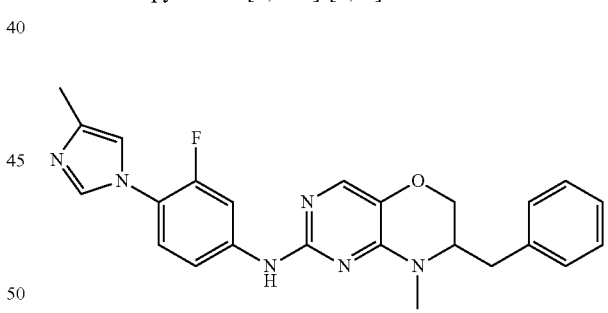

The compound of Example 59A was produced as described in Example 59. Analytical data for product Fraction I (+): $^1$H-NMR (CD$_3$OD, 400 MHz): δ 8.00-7.95 (m, 1H), 7.74 (s, 1H), 7.52 (s, 1H), 7.38-7.20 (m, 7H), 7.07-7.05 (m, 1H), 4.09-4.06 (m, 1H), 3.82-3.80 (m, 1H), 3.74-3.70 (m, 1H), 3.10 (s, 3H), 3.09-3.07 (m, 1H), 2.90-2.86 (m, 1H), 2.23 (s, 3H); Mass (ESI): 431.4 [M+1]; LC-MS: 431.3 (M+1); (column; X-Select CSH C-18 (50×3.0 mm, 3.5 µm); RT 2.81 min. 0.05% Aq TFA: ACN; 0.80 ml/min); UPLC (column; Acquity BEH C-18, 50×2.1 mm, 1.7 µm); RT 1.61 min. ACN: 0.025% TFA (Aq); 0.50 ml/min; Chiral HPLC: RT=14.29 min (CHIRALPAK-IA (250×4.6 mm, 5 µm; mobile phase (A) 0.1% DEA in n-hexane (B) CH$_2$Cl$_2$: MeOH (50:50) (A:B: 70:30); flow Rate: 1.0 mL/min); Optical rotation [α]$_D^{24.25}$: +67.32 (c=0.25, DCM).

Example 59B

Synthesis of (−)-7-benzyl-N-(3-fluoro-4-(4-methyl-1H-imidazol-1-yl) phenyl)-8-methyl-7, 8-dihydro-6H-pyrimido [5, 4-b] [1, 4] oxazin-2-amine

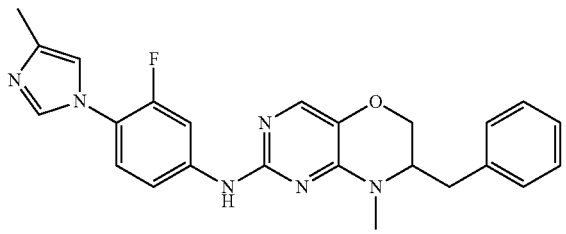 [SMILES: Cc1cn(-c2ccc(Nc3ncc4c(n3)N(C)C(Cc3ccccc3)CO4)cc2F)cn1]

The compound of Example 59B was produced as described in Example 59. Analytical data for product Fraction II (−): ¹H-NMR (CD₃OD, 400 MHz): δ 8.00-7.95 (m, 1H), 7.74 (s, 1H), 7.52 (s, 1H), 7.38-7.20 (m, 7H), 7.07-7.05 (m, 1H), 4.09-4.06 (m, 1H), 3.82-3.80 (m, 1H), 3.74-3.70 (m, 1H), 3.10 (s, 3H), 3.09-3.07 (m, 1H), 2.90-2.86 (m, 1H), 2.23 (s, 3H); Mass (ESI): 431.4 [M+1]; LC-MS: 431.3 (M+1); (column; X-Select CSH C-18 (50×3.0 mm, 3.5 μm); RT 2.82 min. 0.05% Aq TFA: ACN; 0.80 ml/min); UPLC (column; Acquity BEH C-18, 50×2.1 mm, 1.7 μm); RT 1.62 min. ACN: 0.025% TFA (Aq); 0.50 ml/min; Chiral HPLC: RT=22.68 min (CHIRALPAK-IA (250×4.6 mm, 5 μm; mobile phase (A) 0.1% DEA in n-hexane (B) CH₂Cl₂: MeOH (50:50) (A:B): 70:30); flow Rate: 1.0 mL/min); Optical rotation $[\alpha]_D^{24.42}$: −69.34 (c=0.25, DCM).

Example 60

Synthesis of N-(3-methoxy-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine

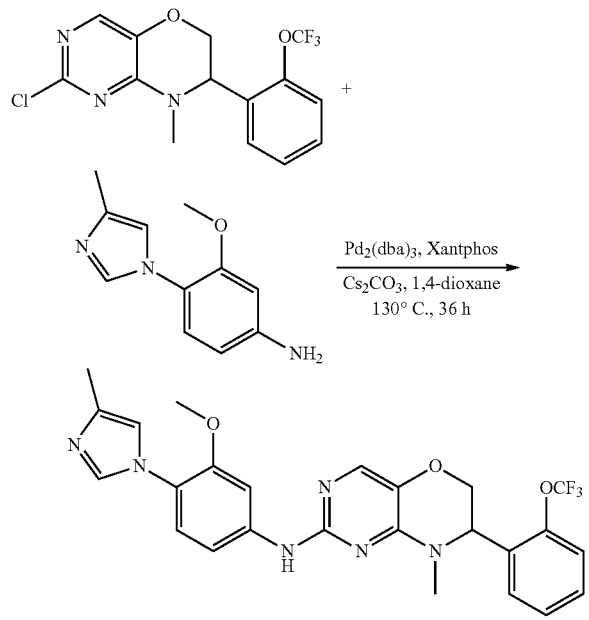

Synthesis of N-(3-methoxy-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine To a dry vial was added a suspension of Pd₂(dba)₃ (33 mg, 0.03 mmol) and Xantphos (62 mg, 0.10 mmol) in 1, 4-dioxane (2.5 mL). The suspension was degassed, heated 120° C. and stirred for 3 min. A mixture of 2-chloro-8-methyl-7-(2-(trifluoromethoxy) phenyl)-7, 8-dihydro-6H-pyrimido [5, 4-b] [1, 4] oxazine (250 mg, 0.72 mmol), 3-methoxy-4-(4-methyl-1H-imidazol-1-yl) aniline (290 mg, 0.14 mmol), cesium carbonate (320 mg, 1.01 mmol) in 1, 4-dioxane (2.5 mL) was degassed and the catalyst premix was added. The reaction mixture was heated to 130° C. and stirred for 36 h in a sealed tube. After consumption of the starting material (monitored by TLC and LCMS), the mixture was concentrated in vacuo. The crude material was purified by silica gel column chromatography using 5% MeOH:CH₂Cl₂ to afford N-(3-methoxy-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine (160 mg, 43%) as a brown liquid. LC-MS: 513.4 (M+1); (column; X-Select CSH C-18 (50×3.0 mm, 3.5 μm); RT 3.11 min. 0.05% Aq TFA: ACN; 0.80 ml/min); UPLC (column; Acquity UPLC BEH C-18, 2.1×50 mm, 1.7 μm); RT 1.76 min. ACN: 0.025% TFA (Aq); 0.50 ml/min.

Racemic compound of Example 60 was separated using a Chiralpak-IA (250×4.6 mm, 5 μm (35 mg loading; 0.1% DEA in n-hexane: CH₂Cl₂:MeOH (50:50); (A:B): 95:15) as the mobile phase) to provide the compound of Example 60A (Fraction I (−)) and the compound of Example 60B (Fraction II (+)).

Example 60A

Synthesis of (−)-N-(3-methoxy-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine

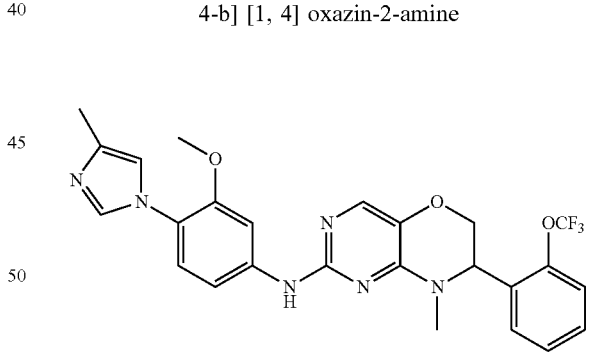

The compound of Example 60A was produced as described in Example 60. Analytical data for product Fraction I (−): ¹H-NMR (DMSO-d₆, 400 MHz): δ 9.20 (s, 1H), 7.83 (s, 1H), 7.68 (s, 1H), 7.62 (s, 1H), 7.50-7.41 (m, 2H), 7.40 (t, 1H), 7.31 (d, 1H), 7.13 (t, 2H), 7.00 (s, 1H), 5.09-5.07 (m, 1H), 4.27-4.23 (m, 1H), 4.17-4.11 (m, 1H), 3.75 (s, 3H), 3.07 (s, 3H), 2.11 (s, 3H); Mass (ESI): 513.4 [M+1]; LC-MS: 513.4 (M+1); (column; X-Select CSH C-18 (50×3.0 mm, 3.5 μm); RT 3.15 min. 0.05% Aq TFA: ACN; 0.80 ml/min); UPLC (column; Acquity UPLC BEH C-18, 2.1×50 mm, 1.7 μm); RT 1.77 min. ACN: 0.025% TFA (Aq); 0.50 ml/min; Chiral HPLC: RT=14.20 min (CHIRALPAK-IA (250×4.6 mm, 5 μm; mobile phase (A) 0.1% DEA in n-hexane (B) CH₂Cl₂:MeOH (50:50) (A:B 85:15); flow Rate: 1.0 mL/min); Optical rotation $[\alpha]_D^{19.99}$: −148.24 (c 0.25, DCM).

Example 60B

Synthesis of (+)-N-(3-methoxy-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine

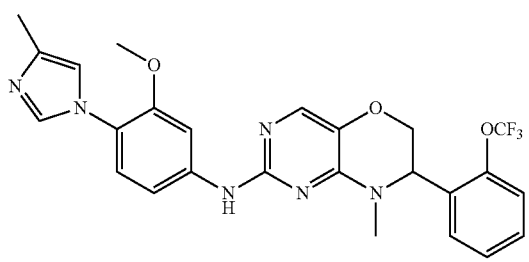

The compound of Example 60B was produced as described in Example 60. Analytical data for product Fraction I (+): ¹H-NMR (DMSO-d₆, 400 MHz): δ 9.20 (s, 1H), 7.83 (s, 1H), 7.68 (s, 1H), 7.62 (s, 1H), 7.50-7.41 (m, 2H), 7.40 (t, 1H), 7.31 (d, 1H), 7.13 (t, 2H), 7.00 (s, 1H), 5.09-5.07 (m, 1H), 4.27-4.23 (m, 1H), 4.17-4.11 (m, 1H), 3.75 (s, 3H), 3.07 (s, 3H), 2.11 (s, 3H); Mass (ESI): 513.5 [M+1]; LC-MS: 513.4 (M+1); (column; X-Select CSH C-18 (50×3.0 mm, 3.5 μm); RT 3.04 min. 0.05% Aq TFA: ACN; 0.80 ml/min); UPLC (column; Acquity UPLC BEH C-18, 2.1×50 mm, 1.7 μm); RT 1.75 min. ACN: 0.025% TFA (Aq); 0.50 ml/min; Chiral HPLC: RT=20.31 min (CHIRALPAK-IA (250×4.6 mm, 5 μm; mobile phase (A) 0.1% DEA in n-hexane (B) CH₂Cl₂:MeOH (50:50) (A:B: 85:15); flow Rate: 1.0 mL/min); Optical rotation $[\alpha]_D^{19.99}$: +157.20 (c 0.25, DCM).

Example 61

Synthesis of 7-(4-fluorophenyl)-N-(3-methoxy-4-(2-methylpyridin-4-yl) phenyl)-8-methyl-7, 8-dihydro-6H-pyrimido [5, 4-b] [1, 4] oxazin-2-amine

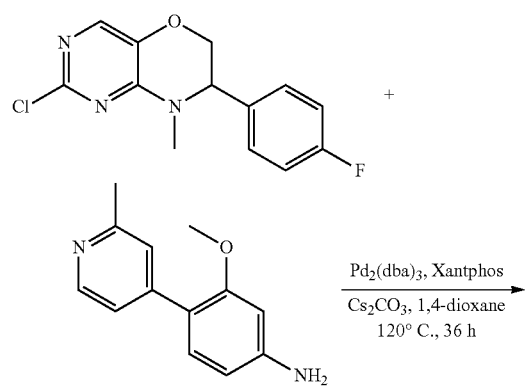

-continued

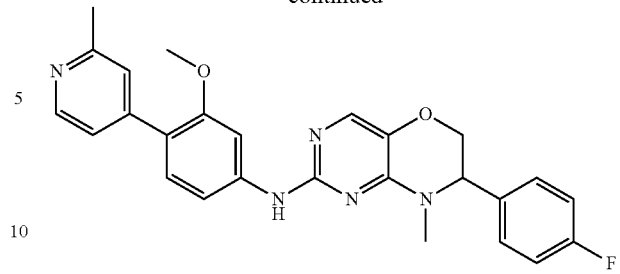

Synthesis of 7-(4-fluorophenyl)-N-(3-methoxy-4-(2-methylpyridin-4-yl) phenyl)-8-methyl-7, 8-dihydro-6H-pyrimido [5, 4-b] [1, 4] oxazin-2-amine To a dry vial was added a suspension of Pd₂(dba)₃ (41 mg, 0.04 mmol) and Xantphos (77 mg, 0.13 mmol) in 1, 4-dioxane (1.25 mL). The suspension was degassed, heated to 120° C. and stirred for 3 min. A mixture of 2-chloro-7-(4-fluorophenyl)-8-methyl-7, 8-dihydro-6H-pyrimido [5, 4-b] [1, 4] oxazine (250 mg, 0.89 mmol), 3-methoxy-4-(2-methylpyridin-4-yl) aniline (383 mg, 1.79 mmol) and cesium carbonate (408 mg, 1.25 mmol) in 1, 4-dioxane (1.25 mL) was degassed and the catalyst premix was added. The reaction mixture was heated to 120° C. and stirred for 16 h in a sealed tube. After consumption of the starting material (monitored by TLC and LCMS), the mixture was filtered and concentrated in vacuo. The crude material was purified by silica gel column chromatography using 1-5% MeOH: CH₂Cl₂ to afford 7-(4-fluorophenyl)-N-(3-methoxy-4-(2-methylpyridin-4-yl) phenyl)-8-methyl-7, 8-dihydro-6H-pyrimido [5, 4-b] [1, 4] oxazin-2-amine (120 mg, 29%) as an off-white solid. UPLC (column; Acquity BEH C-18, 50×2.1 mm, 1.7 μm); RT 1.61 min. ACN: 0.025% TFA (Aq); 0.50 ml/min.

Racemic compound of Example 61 was separated using a Chiralpak-ADH (250×20 mm, 5 μm (25 mg loading; 0.1% DEA in n-hexane: EtOH:MeOH (50:50); (A:B: 75:25) as the mobile phase) to provide the compound of Example 61A (Fraction I (−)) and the compound of Example 61B (Fraction II (+)).

Example 61A

Synthesis of (−)-7-(4-fluorophenyl)-N-(3-methoxy-4-(2-methylpyridin-4-yl) phenyl)-8-methyl-7, 8-dihydro-6H-pyrimido [5, 4-b] [1, 4] oxazin-2-amine

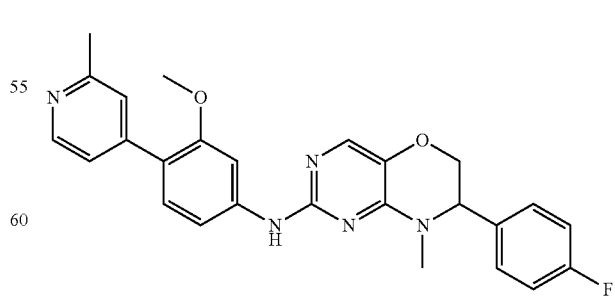

The compound of Example 61A was produced as described in Example 61. Analytical data for product Fraction I (−): ¹H-NMR (CD₃OD, 400 MHz): δ 8.31 (d, 1H), 7.90-7.69 (m, 1H), 7.59 (s, 1H), 7.47 (s, 1H), 7.40 (d, 1H), 7.29-7.22 (m, 4H), 7.11 (t, 2H), 4.70-4.69 (m, 1H), 4.21-4.10 (m, 2H), 3.84 (s, 3H), 3.12 (s, 3H), 2.51 (s, 3H); Mass (ESI): 458.5 [M+1]; LC-MS: 458.3 (M+1); (column; X-Select CSH C-18 (50×3.0 mm, 3.5 μm); RT 2.96 min. 0.05% Aq TFA: ACN; 0.80 ml/min); UPLC (column; Acquity UPLC BEH C-18, 2.1×50 mm, 1.7 μm); RT 1.61 min. ACN: 0.025% TFA (Aq); 0.50 ml/min; Chiral HPLC: RT=15.45 min (CHIRALPAK AD-H (250×4.6 mm, 5μ; mobile phase (A) 0.1% DEA in n-hexane (B) EtOH (A:B: 65:35); flow Rate: 1.0 mL/min); Optical rotation $[\alpha]_D^{20.00}$: −159.72 (c=0.25, DCM); TLC: 50% EtOAc:hexanes ($R_f$: 0.7).

Example 61B

Synthesis of (+)-7-(4-fluorophenyl)-N-(3-methoxy-4-(2-methylpyridin-4-yl) phenyl)-8-methyl-7, 8-dihydro-6H-pyrimido [5, 4-b] [1, 4] oxazin-2-amine

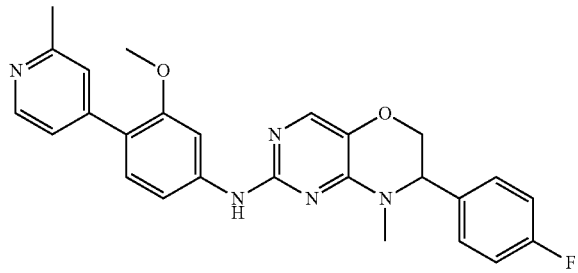 [SMILES: COc1cc(Nc2ncc3c(n2)N(C)C(c2ccc(F)cc2)CO3)ccc1-c1ccnc(C)c1]

The compound of Example 61B was produced as described in Example 61. Analytical data for product Fraction II (+): $^1$H-NMR (CD$_3$OD, 400 MHz): δ 8.31 (d, 1H), 7.90-7.69 (m, 1H), 7.59 (s, 1H), 7.47 (s, 1H), 7.40 (d, 1H), 7.29-7.22 (m, 4H), 7.11 (t, 2H), 4.70-4.69 (m, 1H), 4.21-4.10 (m, 2H), 3.84 (s, 3H), 3.12 (s, 3H), 2.51 (s, 3H); Mass (ESI): 458.5 [M+1]; LC-MS: 458.4 (M+1); (column; X-Select CSH C-18 (50×3.0 mm, 3.5 μm); RT 2.96 min. 0.05% Aq TFA: ACN; 0.80 ml/min); UPLC (column; Acquity UPLC BEH C-18, 2.1×50 mm, 1.7 μm); RT 1.62 min. ACN: 0.025% TFA (Aq); 0.50 ml/min; Chiral HPLC: RT=29.19 min (CHIRALPAK AD-H (250×4.6 mm, 5μ; mobile phase (A) 0.1% DEA in n-hexane (B) EtOH (A:B: 65:35); flow Rate: 1.0 mL/min); Optical rotation $[\alpha]_D^{19.97}$: +166.08 (c=0.25, DCM); TLC: 50% EtOAc:hexanes ($R_f$: 0.7).

Example 62

Synthesis of N-(3-methoxy-4-(2-methylpyridin-4-yl) phenyl)-8-methyl-7-(2-(trifluoromethoxy) phenyl)-7, 8-dihydro-6H-pyrimido [5, 4-b] [1, 4] oxazin-2-amine

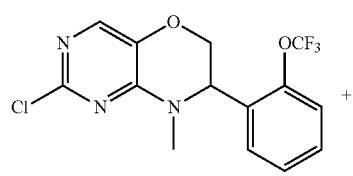

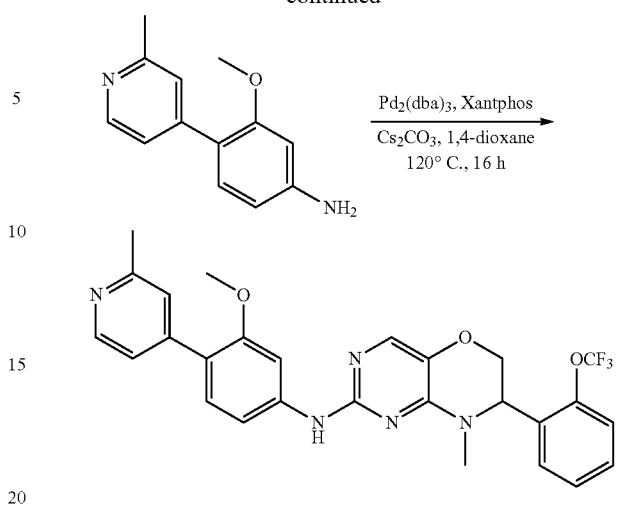

Synthesis of N-(3-methoxy-4-(2-methylpyridin-4-yl) phenyl)-8-methyl-7-(2-(trifluoromethoxy) phenyl)-7, 8-dihydro-6H-pyrimido [5, 4-b] [1, 4] oxazin-2-amine To a dry vial was added a suspension of Pd$_2$(dba)$_3$ (33 mg, 0.03 mmol) and Xantphos (63 mg, 0.10 mmol) in 1, 4-dioxane (1.25 mL). The suspension was degassed, heated to 120° C. and stirred for 3 min. A mixture of 2-chloro-8-methyl-7-(2-(trifluoromethoxy) phenyl)-7, 8-dihydro-6H-pyrimido [5, 4-b] [1, 4] oxazine (250 mg, 0.72 mmol), 3-methoxy-4-(2-methylpyridin-4-yl) aniline (310 mg, 1.44 mmol) and cesium carbonate (329 mg, 1.00 mmol) in 1, 4-dioxane (1.25 mL) was degassed and the catalyst premix was added. The reaction mixture was heated to 120° C. and stirred for 16 h in a sealed tube. After consumption of the starting material (monitored by TLC and LCMS), the mixture was diluted with water (20 mL) and extracted with EtOAc (2×20 mL). The combined organic extracts were dried over sodium sulfate, filtered and concentrated in vacuo. The crude material was purified by silica gel column chromatography using 8% MeOH:CH$_2$Cl$_2$ to afford N-(3-methoxy-4-(2-methylpyridin-4-yl) phenyl)-8-methyl-7-(2-(trifluoromethoxy) phenyl)-7, 8-dihydro-6H-pyrimido [5, 4-b] [1, 4] oxazin-2-amine (130 mg, 34%) as a pale yellow solid. TLC: 50% EtOAc:hexanes ($R_f$: 0.7). LC-MS: 524.5 (M+1); (column; X-Select CSH C-18 (50×3.0 mm, 3.5 μm); RT 3.13 min. 0.05% Aq TFA: ACN; 0.80 ml/min).

Racemic compound of Example 62 was separated using a Chiralpak IA (250×20 mm: 5 μm; (25 mg loading; 0.1% DEA in n-hexane: CH$_2$Cl$_2$:MeOH (80:20); (A:B: 85:15) as the mobile phase) to provide the compound of Example 62A (Fraction I (−)) and the compound of Example 62B (Fraction II (+)).

Example 62A

Synthesis of (−)-N-(3-methoxy-4-(2-methylpyridin-4-yl) phenyl)-8-methyl-7-(2-(trifluoromethoxy) phenyl)-7, 8-dihydro-6H-pyrimido [5, 4-b] [1, 4] oxazin-2-amine

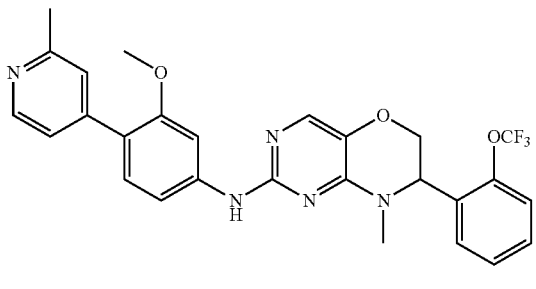

The compound of Example 62A was produced as described in Example 62. Analytical data for product Fraction I (−): $^1$H-NMR (CD$_3$OD, 400 MHz): δ 8.31 (d, 1H), 7.69 (s, 1H), 7.59 (s, 1H), 7.48-7.38 (m, 4H), 7.35-7.30 (m, 1H), 7.29-7.25 (m, 2H), 7.18 (d, 1H), 5.10-5.08 (m, 1H), 4.30-4.18 (m, 2H), 3.87 (s, 3H), 3.15 (s, 3H), 2.53 (s, 3H); Mass (ESI): 524.5 [M+1]; LC-MS: 524.4 (M+1); (column; X-Select CSH C-18 (50×3.0 mm, 3.5 μm); RT 3.20 min. 0.05% Aq TFA: ACN; 0.80 ml/min); HPLC (column; Eclipse-XDB-C-18, 150×4.6 mm, 5 μm); RT 12.46 min. ACN: 5 mM Aq NH$_4$OAc; 1.0 ml/min; Chiral HPLC: RT=14.91 min (CHIRALPAK-IA (250×4.6 mm, 5 μm; mobile phase (A) 0.1% DEA in n-hexane (B) CH$_2$Cl$_2$:MeOH (80:20) (A:B: 85:15); flow Rate: 1.0 mL/min); Optical rotation $[α]_D^{19.98}$: −166.54 (c=0.25, DCM).

Example 62B

Synthesis of (+)-N-(3-methoxy-4-(2-methylpyridin-4-yl) phenyl)-8-methyl-7-(2-(trifluoromethoxy) phenyl)-7, 8-dihydro-6H-pyrimido [5, 4-b] [1, 4] oxazin-2-amine

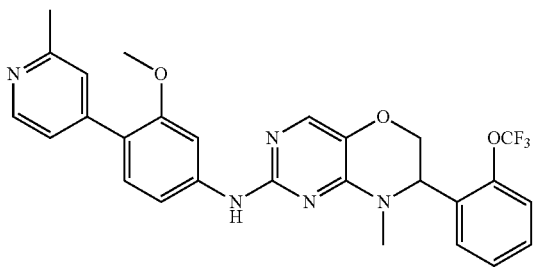 [SMILES: COc1cc(Nc2ncc3c(n2)N(C)C(c2ccccc2OC(F)(F)F)CO3)ccc1-c1ccnc(C)c1]

The compound of Example 62B was produced as described in Example 62. Analytical data for product Fraction II (+): $^1$H-NMR (CD$_3$OD, 400 MHz): δ 8.30 (d, 1H), 7.69 (s, 1H), 7.59 (s, 1H), 7.48-7.38 (m, 4H), 7.35-7.25 (m, 3H), 7.18 (d, 1H), 5.10-5.08 (m, 1H), 4.30-4.18 (m, 2H), 3.87 (s, 3H), 3.15 (s, 3H), 2.53 (s, 3H); Mass (ESI): 524.4 [M+1]; LC-MS: 524.5 (M+1); (column; X-Select CSH C-18 (50×3.0 mm, 3.5 μm); RT 3.19 min. 0.05% Aq TFA: ACN; 0.80 ml/min); HPLC (column; Eclipse-XDB-C-18, 150×4.6 mm, 5 μm); RT 12.46 min. ACN: 5 mM Aq NH$_4$OAc; 1.0 ml/min; Chiral HPLC: RT=17.23 min (CHIRALPAK-IA (250×4.6 mm, 5 μm; mobile phase (A) 0.1% DEA in n-hexane (B) CH$_2$Cl$_2$:MeOH (80:20) (A:B: 85:15); flow Rate: 1.0 mL/min); Optical rotation $[α]_D^{20.00}$: +167.80 (c=0.25, DCM).

Example 63

Synthesis of 7-(2, 4-difluorophenyl)-N-(3-methoxy-4-(2-methylpyridin-4-yl) phenyl)-8-methyl-7, 8-dihydro-6H-pyrimido [5, 4-b] [1, 4] oxazin-2-amine

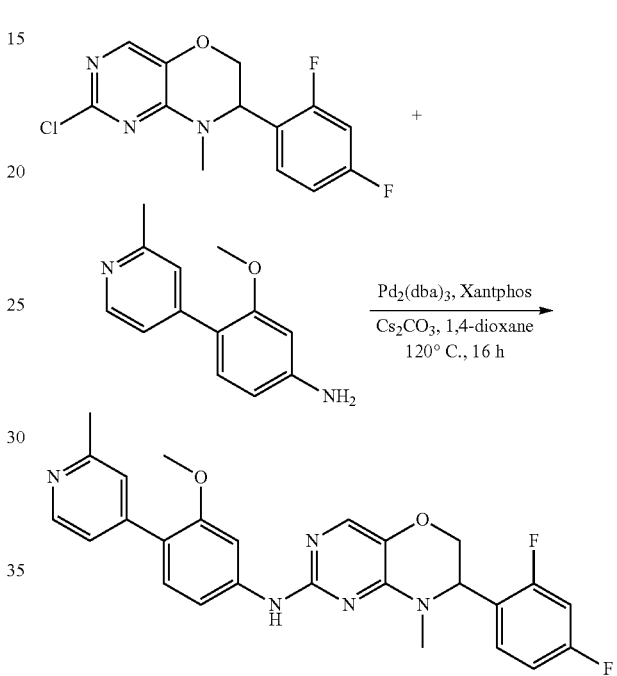

Synthesis of 7-(2, 4-difluorophenyl)-N-(3-methoxy-4-(2-methylpyridin-4-yl) phenyl)-8-methyl-7, 8-dihydro-6H-pyrimido [5, 4-b] [1, 4] oxazin-2-amine To a dry vial was added a suspension of Pd$_2$(dba)$_3$ (38 mg, 0.04 mmol) and Xantphos (73 mg, 0.12 mmol) in 1, 4-dioxane (1 mL). The suspension was degassed, heated to 120° C. and stirred for 3 min. A mixture of 2-chloro-7-(2, 4-difluorophenyl)-8-methyl-7, 8-dihydro-6H-pyrimido [5, 4-b] [1, 4] oxazine (250 mg, 0.84 mmol), 3-methoxy-4-(2-methylpyridin-4-yl) aniline (360 mg, 1.68 mmol) and cesium carbonate (383 mg, 1.17 mmol) in 1, 4-dioxane (1 mL) was degassed and the catalyst premix was added. The reaction mixture was heated to 120° C. and stirred for 16 h in a sealed tube. After consumption of the starting material (monitored by TLC and LCMS), the reaction was filtered, washed with water (10 mL) and extracted with EtOAc (2×10 mL). The combined organic extracts were dried over sodium sulfate, filtered and concentrated in vacuo. The crude material was purified by silica gel column chromatography using 1-5% MeOH:CH$_2$Cl$_2$ to afford 7-(2, 4-difluorophenyl)-N-(3-methoxy-4-(2-methylpyridin-4-yl) phenyl)-8-methyl-7, 8-dihydro-6H-pyrimido [5, 4-b] [1, 4] oxazin-2-amine (120 mg, 30%) as an off-white solid. TLC: 40% EtOAc:hexanes (R$_f$: 0.2). LC-MS: 476.3 (M+1); (column; X-Select CSH C-18 (50×3.0 mm, 3.5 μm); RT 2.89 min. 0.05% Aq TFA;

ACN; 0.80 ml/min: HPLC (column; Acquity BEH C-18, 50×2.1 mm, 1.7 µm); RT 1.62 min. ACN: 0.025% Aq TFA; 0.5 ml/min.

Racemic compound of Example 63 was separated using a Chiralpak ADH (250×20 mm: 5 µm; (40 mg loading; 0.1% DEA in n-hexane: EtOH (70:30) as the mobile phase to provide the compound of Example 63A (Fraction I (−)) and the compound of Example 63B (Fraction II (+)).

Example 63A

Synthesis of (−)-7-(2, 4-difluorophenyl)-N-(3-methoxy-4-(2-methylpyridin-4-yl) phenyl)-8-methyl-7, 8-dihydro-6H-pyrimido [5, 4-b] [1, 4] oxazin-2-amine

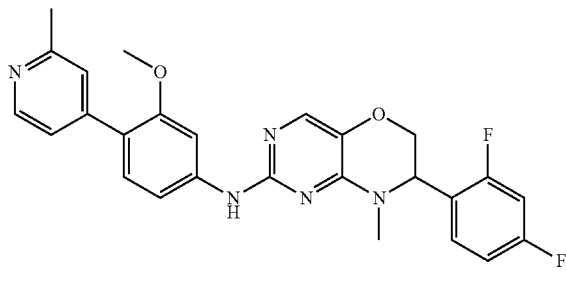

The compound of Example 63A was produced as described in Example 63. Analytical data for product Fraction I (−): $^1$H-NMR (CD$_3$OD, 400 MHz): δ 8.31 (d, 1H), 7.70 (s, 1H), 7.60 (s, 1H), 7.48 (s, 1H), 7.43-7.40 (m, 1H), 7.30-7.23 (m, 2H), 7.18-7.05 (m, 2H), 6.98-6.95 (m, 1H), 5.02-5.00 (m, 1H), 4.24 (d, 2H), 3.86 (s, 3H), 3.20 (s, 3H), 2.53 (s, 3H); Mass (ESI): 476.4 [M+1]; LC-MS: 476.4 (M+1); (column; X-Select CSH C-18 (50×3.0 mm, 3.5 µm); RT 2.98 min. 0.05% Aq TFA: ACN; 0.80 ml/min); HPLC (column; Acquity-UPLC BEH C-18, 2.1×50 mm, 1.7 µm); RT 1.65 min. ACN: 0.025% Aq TFA; 0.5 ml/min; Chiral HPLC: RT=17.34 min (CHIRALPAK-IA (250×4.6 mm, 5 µm; mobile phase (A) 0.1% DEA in n-hexane (B) CH$_2$Cl$_2$: MeOH (50:50) (A:B: 85:15); flow Rate: 1.0 mL/min); Optical rotation $[α]_D^{19.98}$: −188.14 (c=0.25, DCM).

Example 63B

Synthesis of (+)-7-(2, 4-difluorophenyl)-N-(3-methoxy-4-(2-methylpyridin-4-yl) phenyl)-8-methyl-7, 8-dihydro-6H-pyrimido [5, 4-b] [1, 4] oxazin-2-amine

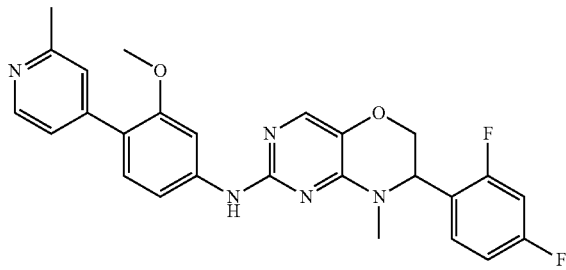 [SMILES: COc1cc(Nc2ncc3c(n2)N(C)C(c2ccc(F)cc2F)CO3)ccc1-c1ccnc(C)c1]

The compound of Example 63B was produced as described in Example 63. Analytical data for product Fraction II (+): $^1$H-NMR (CD$_3$OD, 400 MHz): δ 8.31 (d, 1H), 7.70 (s, 1H), 7.60 (s, 1H), 7.48 (s, 1H), 7.43-7.40 (m, 1H), 7.30-7.23 (m, 2H), 7.18-7.05 (m, 2H), 6.98-6.95 (m, 1H), 5.02-5.00 (m, 1H), 4.24 (d, 2H), 3.86 (s, 3H), 3.20 (s, 3H), 2.53 (s, 3H); Mass (ESI): 476.4 [M+1]; LC-MS: 476.4 (M+1); (column; X-Select CSH C-18 (50×3.0 mm, 3.5 µm); RT 2.99 min. 0.05% Aq TFA: ACN; 0.80 ml/min); HPLC (column; Acquity-UPLC BEH C-18, 2.1×50 mm, 1.7 µm); RT 1.65 min. ACN: 0.025% Aq TFA; 0.5 ml/min; Chiral HPLC: RT=18.96 min (CHIRALPAK-IA (250×4.6 mm, 5 µm; mobile phase (A) 0.1% DEA in n-hexane (B) CH$_2$Cl$_2$: MeOH (50:50) (A:B: 85:15); flow Rate: 1.0 mL/min); Optical rotation $[α]_D^{19.98}$: +180.92 (c=0.25, DCM).

Example 64

Synthesis of N-(3-fluoro-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine

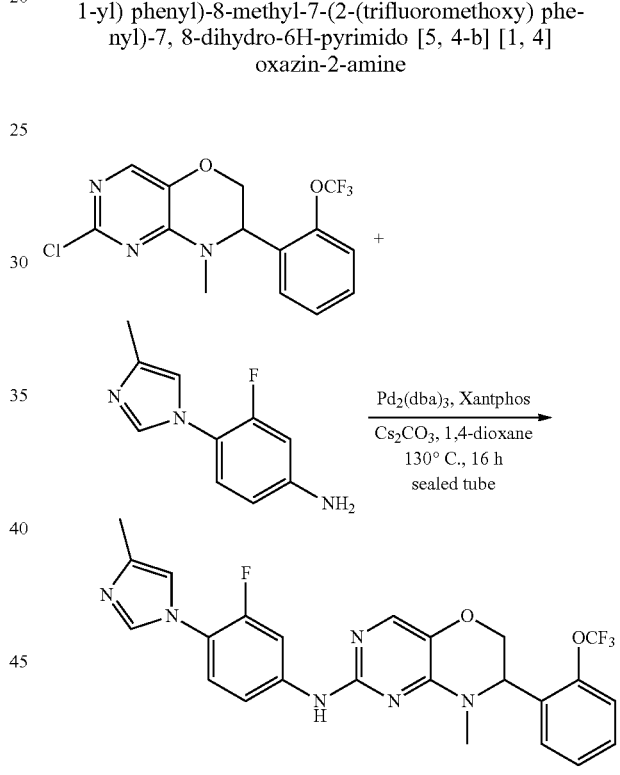

Synthesis of N-(3-fluoro-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine To a dry vial was added a suspension of Pd$_2$(dba)$_3$ (33 mg, 0.03 mmol) and Xantphos (63 mg, 0.10 mmol) in 1, 4-dioxane (1.25 mL). The suspension was degassed, heated to 130° C. and stirred for 3 min. A mixture of 2-chloro-8-methyl-7-(2-(trifluoromethoxy) phenyl)-7, 8-dihydro-6H-pyrimido [5, 4-b] [1, 4] oxazine (250 mg, 0.72 mmol), 3-fluoro-4-(4-methyl-1H-imidazol-1-yl) aniline (276 mg, 1.44 mmol) and cesium carbonate (330 mg, 1.01 mmol) in 1, 4-dioxane (1.25 mL) was degassed and the catalyst premix was added. The reaction mixture was heated to 130° C. and stirred for 16 h in a sealed tube. After consumption of the starting material (monitored by TLC and LCMS), the reaction was filtered. The filtrate was washed with water (10 mL) and extracted with EtOAc (2×10 mL). The combined organic extracts were dried over sodium sulfate, filtered and concentrated in vacuo. The crude material was purified by silica gel column chromatography using 90% EtOAc: hexanes to afford N-(3-fluoro-4-(4-methyl-1H-imidazol-1-yl) phenyl)-8-methyl-7-(2-(trifluoromethoxy) phenyl)-7,8-dihydro-6H-pyrimido [5, 4-b] [1, 4] oxazin-2-amine (110 mg, 25%) as an off-white solid. TLC: 70% EtOAc:hexanes ($R_f$: 0.5). HPLC (column; Acquity-UPLC BEH C-18, 2.1×50 mm, 1.7 μm); RT 1.78 min. ACN: 0.025% Aq TFA; 0.5 ml/min.

Racemic compound of Example 64 was separated using a Chiralpak IA (250×20 mm: 5 μm; (30 mg loading; 0.1% DEA in n-hexane: $CH_2Cl_2$:MeOH (50:50); (A:B: 85:15) as the mobile phase) to provide the compound of Example 64A (Fraction I (+)) and the compound of Example 64B (Fraction II (−)).

Example 64A

Synthesis of (+)-N-(3-fluoro-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine

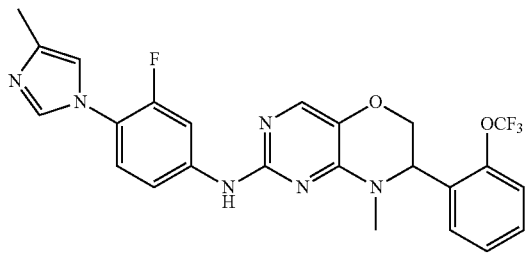 [SMILES: Cc1cn(-c2ccc(Nc3ncc4c(n3)N(C)C(c3ccccc3OC(F)(F)F)CO4)cc2F)cn1]

The compound of Example 64A was produced as described in Example 64. Analytical data for product Fraction I (+): $^1$H-NMR ($CD_3OD$, 400 MHz): δ 8.01-7.99 (m, 1H), 7.77 (s, 1H), 7.61 (s, 1H), 7.49-7.40 (m, 3H), 7.38-7.31 (m, 2H), 7.27 (d, 1H), 7.09 (s, 1H), 5.10-5.08 (m, 1H), 4.26-4.22 (m, 1H), 4.20-4.18 (m, 1H), 3.12 (s, 3H), 2.22 (s, 3H); Mass (ESI): 501.4 [M+1]; LC-MS: 501.4 (M+1); (column; X-Select CSH C-18 (50×3.0 mm, 3.5 μm); RT 3.13 min. 0.05% Aq TFA: ACN; 0.80 ml/min); HPLC (column; Acquity-UPLC BEH C-18, 2.1×50 mm, 1.7 μm); RT 1.80 min. ACN: 0.025% Aq TFA; 0.5 ml/min; Chiral HPLC: RT=15.71 min (CHIRALPAK-IA (250×4.6 mm, 5 μm; mobile phase (A) 0.1% DEA in n-hexane (B) $CH_2Cl_2$: MeOH (50:50) (A:B: 85:15); flow Rate: 1.0 mL/min); Optical rotation $[α]_D^{20.00}$: +131.53 (c=0.25, DCM).

Example 64B

Synthesis of (−)-N-(3-fluoro-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine

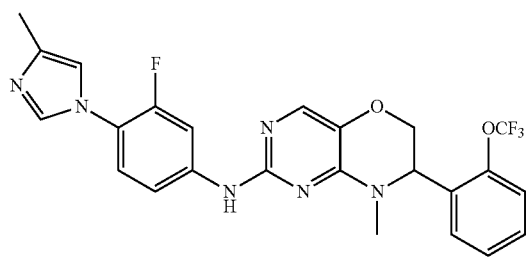

The compound of Example 64B was produced as described in Example 64. Analytical data for product Fraction II (−): $^1$H-NMR ($CD_3OD$, 400 MHz): δ 8.01-7.99 (m, 1H), 7.77 (s, 1H), 7.61 (s, 1H), 7.49-7.40 (m, 3H), 7.38-7.31 (m, 2H), 7.27 (d, 1H), 7.09 (s, 1H), 5.10-5.08 (m, 1H), 4.26-4.22 (m, 1H), 4.20-4.18 (m, 1H), 3.12 (s, 3H), 2.22 (s, 3H); Mass (ESI): 501.4 [M+1]; LC-MS: 501.4 (M+1); (column; X-Select CSH C-18 (50×3.0 mm, 3.5 μm); RT 3.13 min. 0.05% Aq TFA: ACN; 0.80 ml/min); HPLC (column; Acquity-UPLC BEH C-18, 2.1×50 mm, 1.7 μm); RT 1.80 min. ACN: 0.025% Aq TFA; 0.5 ml/min; Chiral HPLC: RT=20.03 min (CHIRALPAK-IA (250×4.6 mm, 5 μm; mobile phase (A) 0.1% DEA in n-hexane (B) $CH_2Cl_2$: MeOH (50:50) (A:B: 85:15); flow Rate: 1.0 mL/min); Optical rotation $[α]_D^{20.01}$: −115.52 (c=0.25, DCM).

Example 65

Synthesis of N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine

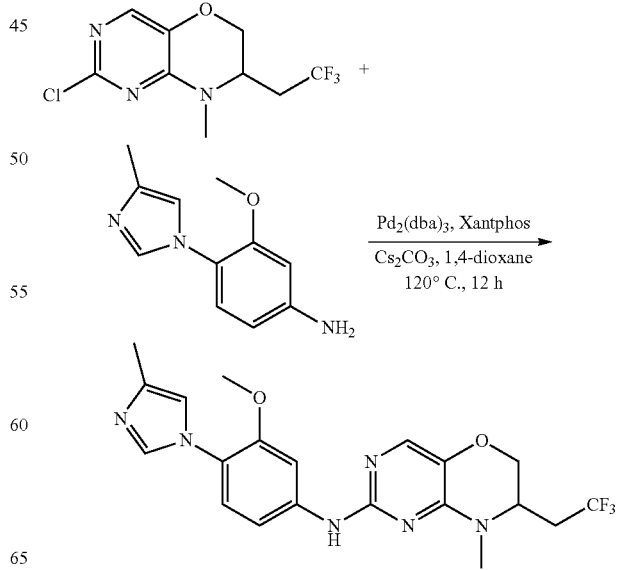

323

Synthesis of N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine To a dry vial was added a suspension of $Pd_2(dba)_3$ (14 mg, 0.01 mmol) and Xantphos (27 mg, 0.04 mmol) in 1, 4-dioxane (1 mL). The suspension was degassed, heated 120° C. and stirred for 3 min. A mixture of 2-chloro-8-methyl-7-(2, 2, 2-trifluoroethyl)-7, 8-dihydro-6H-pyrimido [5, 4-b] [1, 4] oxazine (90 mg, 0.30 mmol), 3-methoxy-4-(4-methyl-1H-imidazol-1-yl) aniline (123 mg, 0.60 mmol) and cesium carbonate (137 mg, 0.42 mmol) in 1, 4-dioxane (1 mL) was degassed and the catalyst premix was added. The reaction mixture was heated to 120° C. and stirred for 32 h in a sealed tube. After consumption of the starting material (monitored by TLC and LCMS), the reaction was diluted with water (20 mL) and extracted with EtOAc (2×20 mL). The combined organic extracts were dried over sodium sulfate, filtered and concentrated in vacuo. The crude material was purified by silica gel column chromatography using 5% $MeOH:CH_2Cl_2$ to afford N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine (10 mg, 8%) as an off-white solid. $^1$H-NMR ($CD_3OD$, 400 MHz): δ 7.72 (s, 2H), 7.59 (s, 1H), 7.22-7.19 (m, 2H), 6.99 (br s, 1H), 4.29-4.26 (m, 1H), 3.99-3.91 (m, 2H), 3.82 (s, 3H), 3.21 (s, 3H), 2.66-2.57 (m, 2H), 2.21 (s, 3H); Mass (ESI): 435.4 [M+1]; LC-MS: 435.4 (M+1); (column; X-Select CSH C-18 (50×3.0 mm, 3.5 μm); RT 2.50 min. 0.05% Aq TFA: ACN; 0.8 mL/min); HPLC (column; Acquity UPLC BEH C-18, 2.1×50 mm, 1.7 μm); RT 1.43 min. ACN: 0.025% Aq TFA; 0.5 ml/min; TLC: 5% $MeOH/CH_2Cl_2$ ($R_f$: 0.3).

Example 66

Synthesis of 7-(2, 4-difluorophenyl)-N-(3-fluoro-4-(2-methylpyridin-4-yl) phenyl)-8-methyl-7, 8-dihydro-6H-pyrimido [5, 4-b] [1, 4] oxazin-2-amine

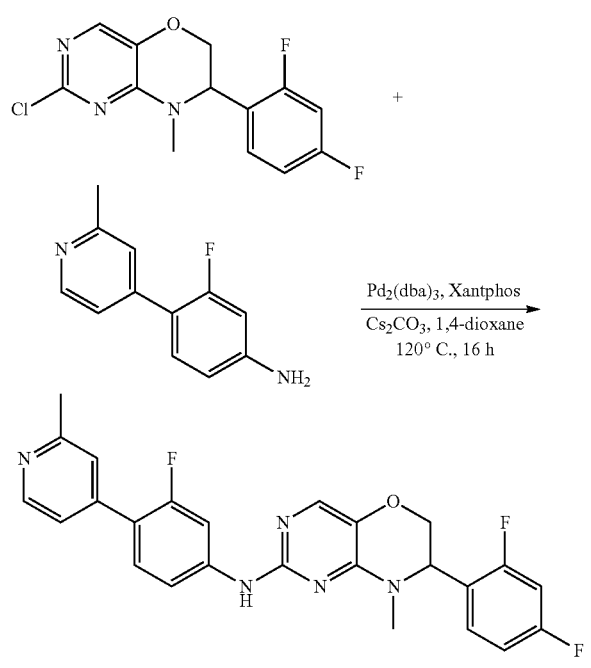

324

Synthesis of 7-(2, 4-difluorophenyl)-N-(3-fluoro-4-(2-methylpyridin-4-yl) phenyl)-8-methyl-7, 8-dihydro-6H-pyrimido [5, 4-b] [1, 4] oxazin-2-amine To a dry vial was added a suspension of $Pd_2(dba)_3$ (38 mg, 0.04 mmol) and Xantphos (73 mg, 0.12 mmol) in 1, 4-dioxane (1 mL). The suspension was degassed, heated to 120° C. and stirred for 3 min. A mixture of 2-chloro-7-(2, 4-difluorophenyl)-8-methyl-7, 8-dihydro-6H-pyrimido [5, 4-b] [1, 4] oxazine (250 mg, 0.84 mmol), 3-fluoro-4-(2-methylpyridin-4-yl) aniline (340 mg, 1.68 mmol) and cesium carbonate (383 mg, 1.17 mmol) in 1, 4-dioxane (1 mL) was degassed and the catalyst premix was added. The reaction mixture was heated to 120° C. and stirred for 16 h in a sealed tube. After consumption of the starting material (monitored by TLC and LCMS), the mixture was filtered. The filtrate was washed with water (10 mL), dried over sodium sulfate, filtered and concentrated in vacuo. The crude material was purified by silica gel column chromatography using 1% $MeOH:CH_2Cl_2$ to afford 7-(2, 4-difluorophenyl)-N-(3-fluoro-4-(2-methylpyridin-4-yl) phenyl)-8-methyl-7, 8-dihydro-6H-pyrimido [5, 4-b] [1, 4] oxazin-2-amine (120 mg, 31%) as an off-white solid. HPLC (column; Eclipse-XDB C-18, 150×4.6 mm, 5 μm); RT 12.11 min. ACN: 5 mM Aq $NH_4OAc$; 1.0 ml/min; TLC: 5% $MeOH/CH_2Cl_2$ ($R_f$: 0.3).

Racemic compound of Example 66 was separated using a Chiralpak IA (250×20 mm: 5 μm; (20 mg loading; 0.1% DEA in n-hexane: $CH_2Cl_2$:MeOH (50:50) (A:B: 90:10) as the mobile phase) to provide the compound of Example 66A (Fraction I (+)) and the compound of Example 66B (Fraction II (−)).

Example 66A

Synthesis of (+)-7-(2, 4-difluorophenyl)-N-(3-fluoro-4-(2-methylpyridin-4-yl) phenyl)-8-methyl-7, 8-dihydro-6H-pyrimido [5, 4-b] [1, 4] oxazin-2-amine

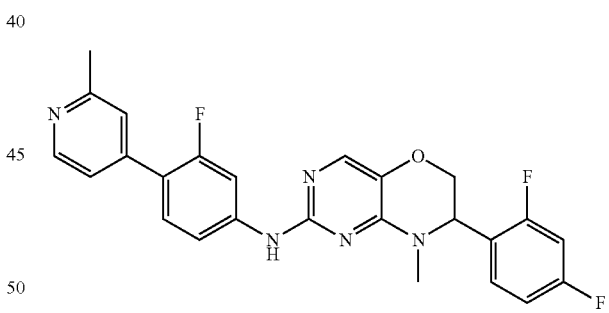

The compound of Example 66A was produced as described in Example 66. Analytical data for product Fraction I (+): $^1$H-NMR ($CD_3OD$, 400 MHz): δ 8.40 (d, 1H), 7.92-7.89 (m, 1H), 7.60 (s, 1H), 7.50-7.40 (m, 4H), 7.12-7.00 (m, 2H), 6.96-6.92 (m, 1H), 5.06-5.02 (m, 1H), 4.21 (d, 2H), 3.17 (s, 3H), 2.58 (s, 3H); Mass (ESI): 464.4 [M+1]; LC-MS: 464.4 (M+1); (column; X-Select CSH C-18 (50×3.0 mm, 3.5 μm); RT 2.96 min. 0.05% Aq TFA: ACN; 0.80 ml/min); HPLC (column; Acquity-UPLC BEH C-18, 2.1×50 mm, 1.7 μm); RT 1.66 min. ACN: 0.025% Aq TFA; 0.5 ml/min; Chiral HPLC: RT=26.61 min (CHIRALPAK-IA (250×4.6 mm, 5 μm; mobile phase (A) 0.1% DEA in n-hexane (B) $CH_2Cl_2$:MeOH (50:50) (A:B: 90:10); flow Rate: 1.0 mL/min); Optical rotation $[α]_D^{20.00}$: +172.89 (c=0.25, DCM).

Example 66B

Synthesis of (−)-7-(2, 4-difluorophenyl)-N-(3-fluoro-4-(2-methylpyridin-4-yl) phenyl)-8-methyl-7, 8-dihydro-6H-pyrimido [5, 4-b] [1, 4] oxazin-2-amine

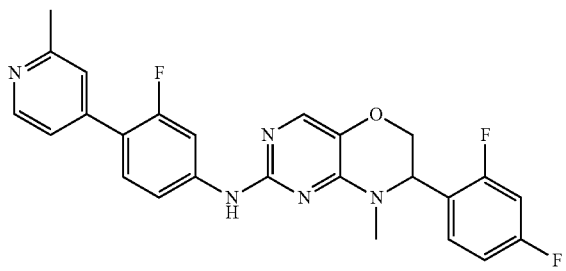

The compound of Example 66B was produced as described in Example 66. Analytical data for product Fraction II (−): $^1$H-NMR (CD$_3$OD, 400 MHz): δ 8.48 (d, 1H), 7.90-7.88 (m, 1H), 7.60 (s, 1H), 7.50-7.40 (m, 4H), 7.19-6.90 (m, 2H), 6.96-6.90 (m, 1H), 5.06-5.02 (m, 1H), 4.22 (d, 2H), 3.15 (s, 3H), 2.59 (s, 3H); Mass (ESI): 464.4 [M+1]; LC-MS: 464.4 (M+1); (column; X-Select CSH C-18 (50× 3.0 mm, 3.5 μm); RT 2.94 min. 0.05% Aq TFA: ACN; 0.80 ml/min); HPLC (column; Acquity-UPLC BEH C-18, 2.1×50 mm, 1.7 μm); RT 1.66 min. ACN: 0.025% Aq TFA; 0.5 ml/min; Chiral HPLC RT=31.53 min (CHIRALPAK-AD-H (250×4.6 mm, 5 μm; mobile phase (A) 0.1% DEA in n-hexane (B) EtOH:MeOH (50:50) (A:B: 75:25); flow Rate: 1.0 mL/min); Optical rotation $[α]_D^{20.00}$: −158.67 (c=0.25, DCM).

Example 67

Synthesis of 7-(2-chlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

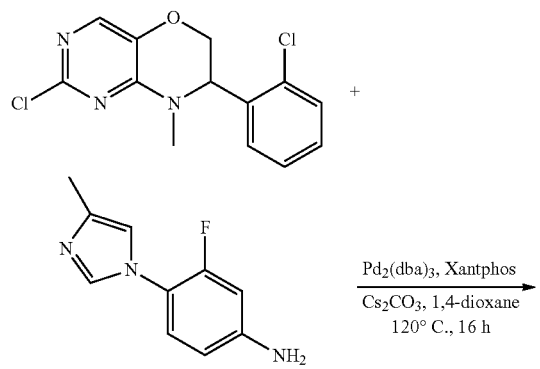

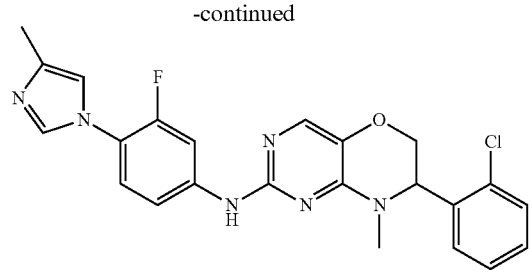

Synthesis of 7-(2-chlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine To a dry vial was added a suspension of Pd$_2$(dba)$_3$ (36 mg, 0.04 mmol) and Xantphos (69 mg, 0.12 mmol) in 1, 4-dioxane (0.5 mL). The suspension was degassed, heated to 120° C. and stirred for 3 min. A mixture of 2-chloro-7-(2-chlorophenyl)-8-methyl-7, 8-dihydro-6H-pyrimido [5, 4-b] [1, 4] oxazine (250 mg, 0.80 mmol), 3-fluoro-4-(4-methyl-1H-imidazol-1-yl)aniline (168 mg, 0.88 mmol) and cesium carbonate (364 mg, 1.12 mmol) in 1, 4-dioxane (0.5 mL) was degassed and the catalyst premix was added. The reaction mixture was heated to 120° C. and stirred for 16 h in a sealed tube. After consumption of the starting material (monitored by TLC and LCMS), the reaction was filtered and concentrated in vacuo. The crude material was purified by silica gel column chromatography using 2% MeOH: CH$_2$Cl$_2$ to afford 7-(2-chlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine (150 mg, 39%) as an off-white solid. LC-MS: 451.3 (M+1); (column; X-Select CSH C-18 (50×3.0 mm, 3.5 μm); RT 3.00 min. 0.05% Aq TFA: ACN; 0.80 ml/min); HPLC (column; Acquity-UPLC BEH C-18, 2.1×50 mm, 1.7 μm); RT 1.66 min. ACN: 0.025% Aq TFA; 0.5 ml/min; TLC: 5% MeOH/CH$_2$Cl$_2$ (R$_f$: 0.3).

Racemic compound of Example 67 was separated using a Chiralpak IB (250×20 mm: 5 μm; (25 mg loading; 0.1% DEA in n-hexane: CH$_2$Cl$_2$:MeOH (50:50); (A:B: 90:10) as the mobile phase) to provide the compound of Example 67A (Fraction I (+)) and the compound of Example 67B (Fraction II (−)).

Example 67A

Synthesis of (+)-7-(2-chlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

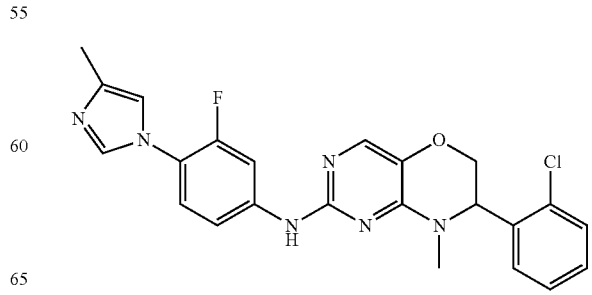

The compound of Example 67A was produced as described in Example 67. Analytical data for product Fraction I (+): $^1$H-NMR (CD$_3$OD, 400 MHz): δ 8.01-7.99 (m, 1H), 7.79 (s, 1H), 7.59 (s, 1H), 7.51 (d, 1H), 7.44-7.40 (m, 1H), 7.38-7.30 (m, 3H), 7.10-7.05 (m, 2H), 5.20-5.18 (m, 1H), 4.32-4.22 (m, 2H), 3.14 (s, 3H), 2.23 (s, 3H); Mass (ESI): 451.4 [M+1]; LC-MS: 451.3 (M+1); (column; X-Select CSH C-18 (50×3.0 mm, 3.5 μm); RT 2.93 min. 0.05% Aq TFA: ACN; 0.80 ml/min); HPLC (column; Acquity UPLC BEH C-18, 2.1×50 mm, 1.7 μm); RT 1.66 min. ACN: 5 mM Aq TFA; 0.5 ml/min; Chiral HPLC: RT=14.36 min (CHIRALPAK-IB (250×4.6 mm, 5 μm; mobile phase (A) 0.1% DEA in n-hexane (B) CH$_2$Cl$_2$:MeOH (50:50) (A:B: 90:10); flow Rate: 1.0 mL/min); Optical rotation $[\alpha]_D^{19.99}$: +176.20 (c=0.25, DCM).

Example 67B

Synthesis of (−)-7-(2-chlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

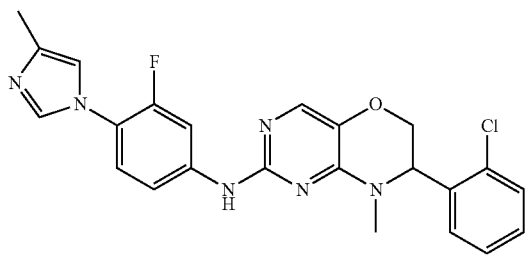 [SMILES: Cc1cn(-c2ccc(Nc3ncc4c(n3)N(C)C(c3ccccc3Cl)CO4)cc2F)cn1]

The compound of Example 67B was produced as described in Example 67. Analytical data for product Fraction II (−): $^1$H-NMR (CD$_3$OD, 400 MHz): δ 8.01-7.99 (m, 1H), 7.79 (s, 1H), 7.59 (s, 1H), 7.51 (d, 1H), 7.44-7.40 (m, 1H), 7.38-7.30 (m, 3H), 7.10-7.05 (m, 2H), 5.20-5.18 (m, 1H), 4.32-4.22 (m, 2H), 3.14 (s, 3H), 2.23 (s, 3H); Mass (ESI): 451.4 [M+1]; LC-MS: 451.3 (M+1); (column; X-Select CSH C-18 (50×3.0 mm, 3.5 μm); RT 2.92 min. 0.05% Aq TFA: ACN; 0.80 ml/min); HPLC (column; Acquity-UPLC BEH C-18, 2.1×50 mm, 1.7 μm); RT 1.66 min. ACN: 0.025% Aq TFA; 0.5 ml/min; Chiral HPLC: RT=16.22 min (CHIRALPAK-IB (250×4.6 mm, 5 μm; mobile phase (A) 0.1% DEA in n-hexane (B) CH$_2$Cl$_2$:MeOH (50:50) (A:B: 90:10); flow Rate: 1.0 mL/min); Optical rotation $[\alpha]_D^{20.00}$: 153.56 (c=0.25, DCM).

Example 68

Synthesis of 7-benzyl-N-(3-methoxy-4-(2-methyl-pyridin-4-yl) phenyl)-8-methyl-7, 8-dihydro-6H-pyrimido [5, 4-b] [1, 4] oxazin-2-amine

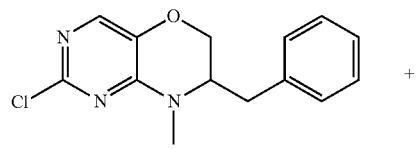

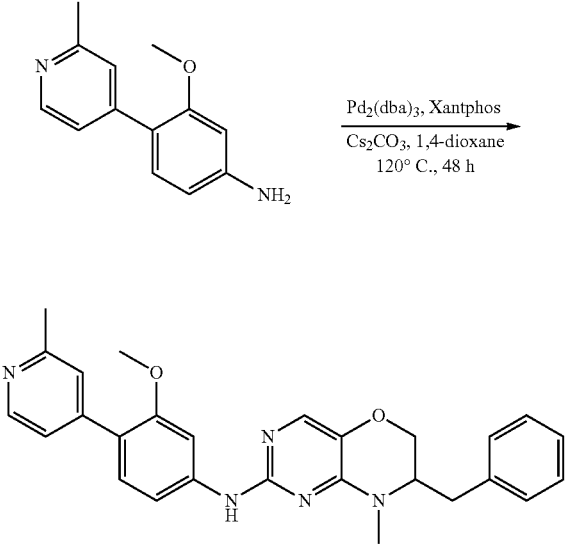

Synthesis of 7-benzyl-N-(3-methoxy-4-(2-methyl-pyridin-4-yl) phenyl)-8-methyl-7, 8-dihydro-6H-pyrimido [5, 4-b] [1, 4] oxazin-2-amine To a dry vial was added a suspension of Pd$_2$(dba)$_3$ (41 mg, 0.04 mmol) and Xantphos (78 mg, 0.13 mmol) in 1, 4-dioxane (0.25 mL). The suspension was degassed, heated to 120° C. and stirred for 3 min. A mixture of 7-benzyl-2-chloro-8-methyl-7, 8-dihydro-6H-pyrimido [5, 4-b] [1, 4] oxazine (250 mg, 0.90 mmol), 3-methoxy-4-(2-methylpyridin-4-yl) aniline (212 mg, 0.99 mmol) and cesium carbonate (409 mg, 1.26 mmol) in 1, 4-dioxane (0.5 mL) was degassed and the catalyst premix was added. The reaction mixture was heated to 120° C. and stirred for 48 h in a sealed tube. After consumption of the starting material (monitored by TLC and LCMS), the mixture was filtered and concentrated in vacuo. The crude material was purified by silica gel column chromatography using 2% MeOH:CH$_2$Cl$_2$ to afford 7-benzyl-N-(3-methoxy-4-(2-methylpyridin-4-yl) phenyl)-8-methyl-7, 8-dihydro-6H-pyrimido [5, 4-b] [1, 4] oxazin-2-amine (150 mg, 36%) as an off-white solid. TLC: 5% MeOH:CH$_2$Cl$_2$ (R$_f$: 0.3). LC-MS: 454.4 (M+1); (column; X-Select CSH C-18 (50×3.0 mm, 3.5 μm); RT 2.89 min. 0.05% Aq TFA: ACN; 0.80 ml/min); HPLC (column; Acquity-UPLC BEH C-18, 2.1×50 mm, 1.7 μm); RT 1.66 min. ACN: 0.025% Aq TFA; 0.5 ml/min.

Racemic compound of Example 68 was separated using a Chiralpak IB (250×20 mm: 5 μm; (20 mg loading; 0.1% DEA in n-hexane: CH$_2$Cl$_2$:MeOH (50:50) (A:B: 90:10) as the mobile phase) to provide the compound of Example 68A (Fraction I (+)) and the compound of Example 68B (Fraction II (−)).

Example 68A

Synthesis of (+)-7-benzyl-N-(3-methoxy-4-(2-methylpyridin-4-yl) phenyl)-8-methyl-7, 8-dihydro-6H-pyrimido [5, 4-b] [1, 4] oxazin-2-amine

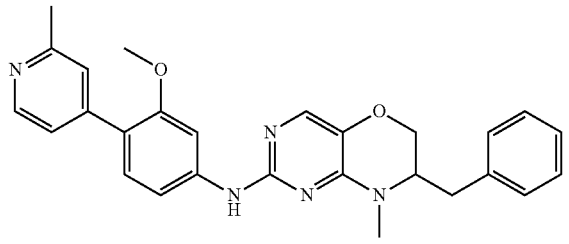 [SMILES: COc1cc(Nc2ncc3c(n2)N(C)C(Cc2ccccc2)CO3)ccc1-c1ccnc(C)c1]

The compound of Example 68A was produced as described in Example 68. Analytical data for product Fraction I (+): $^1$H-NMR (CD$_3$OD, 400 MHz): δ 8.31 (d, 1H), 7.69 (s, 1H), 7.53 (s, 1H), 7.47 (s, 1H), 7.41 (d, 1H), 7.36-7.20 (m, 7H), 4.09 (d, 1H), 3.85 (s, 3H), 3.84-3.80 (m, 1H), 3.77-3.70 (m, 1H), 3.13 (s, 3H), 3.10-3.08 (m, 1H), 2.90-2.83 (m, 1H), 2.53 (s, 3H); Mass (ESI): 454.5 [M+1]; LC-MS: 454.4 (M+1); (column; X-Select CSH C-18 (50× 3.0 mm, 3.5 μm); RT 2.94 min. 0.05% Aq TFA: ACN; 0.80 ml/min); HPLC (column; Acquity-UPLC BEH C-18, 2.1×50 mm, 1.7 μm); RT 1.64 min. ACN: 0.025% Aq TFA; 0.5 ml/min; Chiral HPLC: RT=18.03 min (CHIRALPAK-IB (250×4.6 mm, 5 μm; mobile phase (A) 0.1% DEA in n-hexane (B) CH$_2$Cl$_2$:MeOH (50:50) (A:B: 90:10); flow Rate: 1.0 mL/min); Optical rotation $[α]_D^{19.98}$: +80.17 (c=0.25, DCM).

Example 68B

Synthesis of (−)-7-benzyl-N-(3-methoxy-4-(2-methylpyridin-4-yl) phenyl)-8-methyl-7, 8-dihydro-6H-pyrimido [5, 4-b] [1, 4] oxazin-2-amine

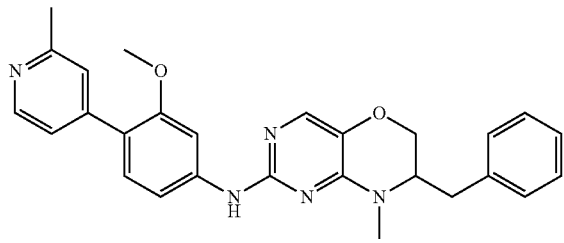 [SMILES: COc1cc(Nc2ncc3c(n2)N(C)C(Cc2ccccc2)CO3)ccc1-c1ccnc(C)c1]

The compound of Example 68B was produced as described in Example 68. Analytical data for product Fraction II (−): $^1$H-NMR (CD$_3$OD, 400 MHz): δ 8.31 (d, 1H), 7.69 (s, 1H), 7.53 (s, 1H), 7.47 (s, 1H), 7.41 (d, 1H), 7.36-7.20 (m, 7H), 4.09 (d, 1H), 3.85 (s, 3H), 3.84-3.80 (m, 1H), 3.77-3.70 (m, 1H), 3.13 (s, 3H), 3.10-3.08 (m, 1H), 2.90-2.83 (m, 1H), 2.53 (s, 3H); Mass (ESI): 454.5 [M+1]; LC-MS: 454.4 (M+1); (column; X-Select CSH C-18 (50× 3.0 mm, 3.5 μm); RT 2.93 min. 0.05% Aq TFA: ACN; 0.80 ml/min); HPLC (column; Acquity-UPLC BEH C-18, 2.1×50 mm, 1.7 μm); RT 1.64 min. ACN: 0.025% Aq TFA; 0.5 ml/min; Chiral HPLC: RT=19.97 min (CHIRALPAK-IB (250×4.6 mm, 5 μm; mobile phase (A) 0.1% DEA in n-hexane (B) CH$_2$Cl$_2$:MeOH (50:50) (A:B: 90:10); flow Rate: 1.0 mL/min); Optical rotation $[α]_D^{20.01}$: −58.54 (c=0.25, DCM).

Example 69

Synthesis of 7-(2, 4-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

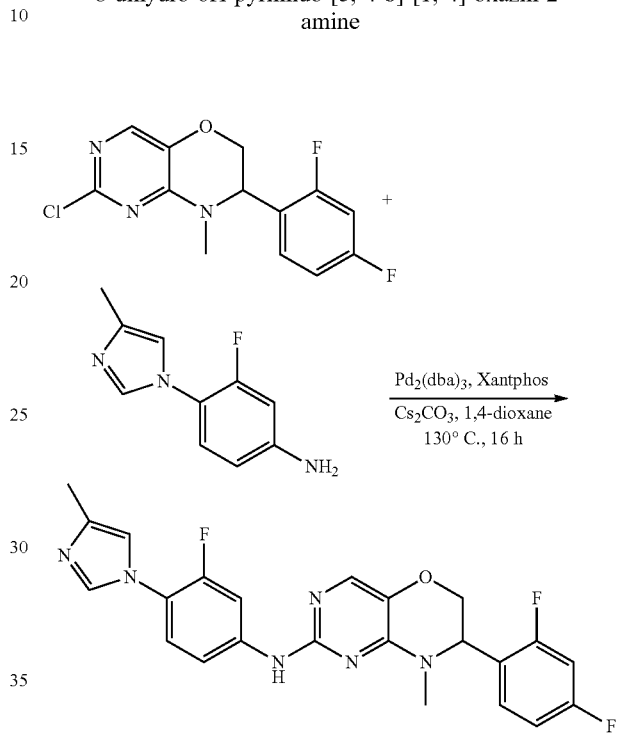

Synthesis of 7-(2, 4-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine To a dry vial was added a suspension of Pd$_2$(dba)$_3$ (38 mg, 0.04 mmol) and Xantphos (72 mg, 0.12 mmol) in 1, 4-dioxane (2.5 mL). The suspension was degassed, heated to 120° C. and stirred for 3 min. A mixture of 2-chloro-7-(2, 4-difluorophenyl)-8-methyl-7, 8-dihydro-6H-pyrimido [5, 4-b] [1, 4] oxazine (250 mg, 0.84 mmol), 3-fluoro-4-(4-methyl-1H-imidazol-1-yl) aniline (160 mg, 0.84 mmol) and cesium carbonate (382 mg, 1.10 mmol) in 1, 4-dioxane (2.5 mL) was degassed and the catalyst premix was added. The reaction mixture was heated to 130° C. and stirred for 16 h in a sealed tube. After consumption of the starting material (monitored by TLC and LCMS), the mixture was diluted with water (20 mL) and extracted with EtOAc (2×20 mL). The combined organic extracts were dried over sodium sulfate, filtered and concentrated in vacuo. The crude material was purified by silica gel column chromatography using 8% MeOH:CH$_2$Cl$_2$ to afford 7-(2, 4-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine (220 mg, 58%) as a colorless oil. LC-MS: 453.5 (M+1); (column; X-Select CSH C-18 (50×3.0 mm, 3.5 μm); RT 3.84 min. 5 Mm Aq NH$_4$OAc: ACN; 0.80 ml/min); HPLC (column;

Eclipse-XDB C-18, 150×4.6 mm, 5 μm); RT 10.95 min. ACN: 5 mM Aq NH₄OAc; 1.0 ml/min.

Racemic compound of Example 69 was separated using a Chiralpak IA (250×20 mm: 5 μm; (40 mg loading; 0.1% DEA in n-hexane: CH₂Cl₂:MeOH (50:50); (A:B: 80:20) as the mobile phase) to provide the compound of Example 69A (Fraction I (+)) and the compound of Example 69B (Fraction II (−)).

Example 69A

Synthesis of (+)-7-(2, 4-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

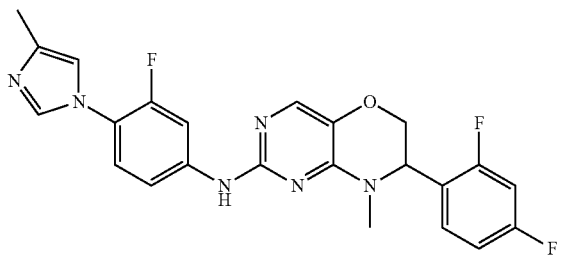 [SMILES: Cc1cn(-c2ccc(Nc3ncc4c(n3)N(C)C(c3ccc(F)cc3F)CO4)cc2F)cn1]

The compound of Example 69A was produced as described in Example 69. Analytical data for product Fraction I (+): ¹H-NMR (CD₃OD, 400 MHz): δ 8.01-7.99 (m, 1H), 7.76 (s, 1H), 7.60 (s, 1H), 7.42 (d, 1H), 7.35 (t, 1H), 7.18-7.01 (m, 3H), 7.00-6.96 (m, 1H), 5.07-5.05 (m, 1H), 4.23 (d, 2H), 3.17 (s, 3H), 2.25 (s, 3H); Mass (ESI): 453.4 [M+1]; LC-MS: 453.5 (M+1); (column; X-Select CSH C-18 (50×3.0 mm, 3.5 μm); RT 3.81 min. 5 mM Aq NH₄OAc: ACN; 0.80 ml/min); HPLC (column; Eclipse-XDB C-18, 150×4.6 mm, 5 μm); RT 10.93 min. ACN: 5 mM Aq NH₄OAc; 1.0 ml/min; Chiral HPLC: RT=16.14 min (CHIRALPAK-IA (250×4.6 mm, 5 μm; mobile phase (A) 0.1% DEA in n-hexane (B) CH₂Cl₂:MeOH (50:50) (A:B: 75:25); flow Rate: 1.0 mL/min); Optical rotation $[\alpha]_D^{19.99}$: +170.03 (c=0.25, DCM).

Example 69B

Synthesis of (−)-7-(2, 4-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

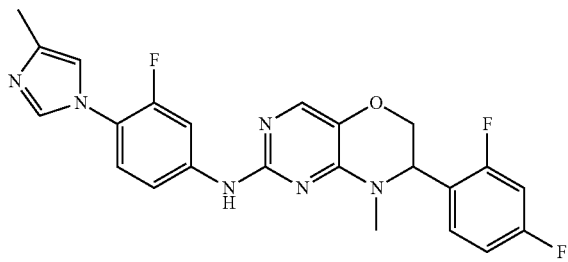 [SMILES: Cc1cn(-c2ccc(Nc3ncc4c(n3)N(C)C(c3ccc(F)cc3F)CO4)cc2F)cn1]

The compound of Example 69B was produced as described in Example 69. Analytical data for product Fraction I (−): ¹H-NMR (CD₃OD, 400 MHz): δ 8.01-7.99 (m, 1H), 7.76 (s, 1H), 7.60 (s, 1H), 7.42 (d, 1H), 7.35 (t, 1H), 7.18-7.01 (m, 3H), 7.00-6.96 (m, 1H), 5.07-5.05 (m, 1H), 4.23 (d, 2H), 3.17 (s, 3H), 2.25 (s, 3H); Mass (ESI): 453.4 [M+1]; LC-MS: 453.5 (M+1); (column; X-Select CSH C-18 (50×3.0 mm, 3.5 μm); RT 3.82 min. 5 mM Aq NH₄OAc: ACN; 0.80 ml/min); HPLC (column; Eclipse-XDB C-18, 150×4.6 mm, 5 μm); RT 11.01 min. ACN: 5 mM Aq NH₄OAc; 1.0 ml/min; Chiral HPLC: RT=32.30 min (CHIRALPAK-IA (150×4.6 mm, 5 μm; mobile phase (A) 0.1% DEA in n-hexane (B) CH₂Cl₂:MeOH (50:50) (A:B: 80:20); flow Rate: 1.0 mL/min); Optical rotation $[\alpha]_D^{19.99}$: −140.54 (c=0.25, DCM).

Example 70

Synthesis of N-(3-methoxy-4-(2-methylpyridin-4-yl) phenyl)-8-methyl-7-(2-(trifluoromethyl) phenyl)-7, 8-dihydro-6H-pyrimido [5, 4-b] [1, 4] oxazin-2-amine

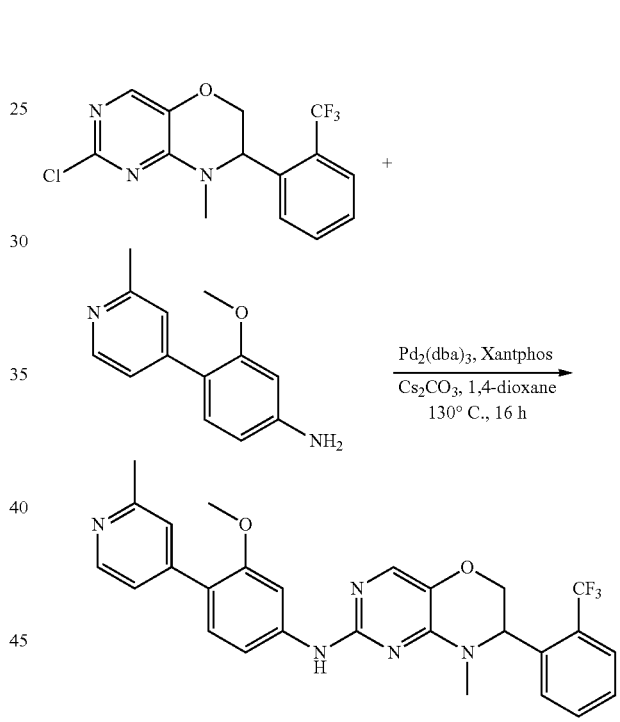

Synthesis of N-(3-methoxy-4-(2-methylpyridin-4-yl) phenyl)-8-methyl-7-(2-(trifluoromethyl) phenyl)-7, 8-dihydro-6H-pyrimido [5, 4-b] [1, 4] oxazin-2-amine To a dry vial was added a suspension of Pd₂(dba)₃ (37 mg, 0.04 mmol) and Xantphos (70 mg, 0.12 mmol) in 1, 4-dioxane (1.3 mL). The suspension was degassed, heated to 120° C. and stirred for 3 min. A mixture of 2-chloro-8-methyl-7-(2-(trifluoromethyl) phenyl)-7, 8-dihydro-6H-pyrimido [5, 4-b] [1, 4] oxazine (266 mg, 0.80 mmol), 3-methoxy-4-(2-methylpyridin-4-yl) aniline (346 mg, 1.61 mmol), cesium carbonate (367 mg, 1.13 mmol) in 1, 4-dioxane (1.3 mL) was degassed and the catalyst premix was added. The reaction mixture was heated to 130° C. and stirred for 16 h in a sealed tube. After consumption of the starting material (monitored by TLC and LCMS), the reaction was filtered and the filtrate was washed with water (20 mL). The organic layer was separated, dried over sodium sulfate, filtered and concentrated in vacuo. The crude material was purified by silica gel column chromatography using 90% EtOAc:hexane to afford N-(3-methoxy-4-(2-methylpyridin-4-yl) phenyl)-8-methyl-7-(2-(trifluoromethyl) phenyl)-7, 8-dihydro-6H-pyrimido [5, 4-b] [1, 4] oxazin-2-amine (120 mg, 29%) as a yellow solid. LC-MS: 508.5 (M+1); (column; X-Select CSH C-18 (50×3.0 mm, 3.5 μm); RT 3.14 min. 0.05% Aq TFA:ACN; 0.80 ml/min); TLC: 70% EtOAc:hexane ($R_f$: 0.6).

Racemic compound of Example 70 was separated using a Chiralpak-AD-H (250×20 mm: 5 μm; (30 mg loading; 0.1% DEA in n-hexane: EtOH:MeOH (50:50); (A:B: 75:25) as the mobile phase) to provide the compound of Example 70A (Fraction I (−)) and the compound of Example 70B (Fraction II (+)).

Example 70A

Synthesis of (−)-N-(3-methoxy-4-(2-methylpyridin-4-yl) phenyl)-8-methyl-7-(2-(trifluoromethyl) phenyl)-7, 8-dihydro-6H-pyrimido [5, 4-b] [1, 4] oxazin-2-amine

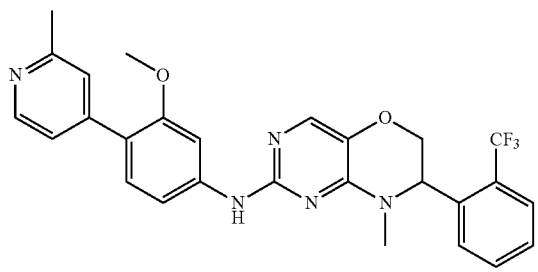

The compound of Example 70A was produced as described in Example 70. Analytical data for product Fraction I (−): $^1$H-NMR (CD$_3$OD, 400 MHz): δ 8.31 (d, 1H), 7.82 (d, 1H), 7.70 (s, 1H), 7.68 (s, 2H), 7.54 (t, 1H), 7.46 (s, 1H), 7.40 (d, 1H), 7.35 (d, 1H), 7.29-7.27 (m, 2H), 5.10 (br s, 1H), 4.30 (d, 1H), 4.12 (d, 1H), 3.88 (s, 3H), 3.10 (s, 3H), 2.52 (s, 3H); Mass (ESI): 508.5 [M+1]; LC-MS: 508.5 (M+1); (column; X-Select CSH C-18 (50×3.0 mm, 3.5 μm); RT 3.18 min. 0.05% Aq TFA:ACN; 0.80 ml/min); HPLC (column; Acquity-UPLC BEH C-18, 2.1×50 mm, 1.7 μm); RT 1.78 min. ACN: 0.025% Aq TFA; 0.5 ml/min; Chiral HPLC: RT=9.92 min (CHIRALPAK-AD H (250×4.6 mm, 5 μm; mobile phase (A) 0.1% DEA in n-hexane (B) EtOH: MeOH (50:50) (A:B: 75:25); flow Rate: 1.0 mL/min); Optical rotation $[α]_D^{20.01}$: −117.74 (c 0.25, DCM).

Example 70B

Synthesis of (+)-N-(3-methoxy-4-(2-methylpyridin-4-yl) phenyl)-8-methyl-7-(2-(trifluoromethyl) phenyl)-7, 8-dihydro-6H-pyrimido [5, 4-b] [1, 4] oxazin-2-amine

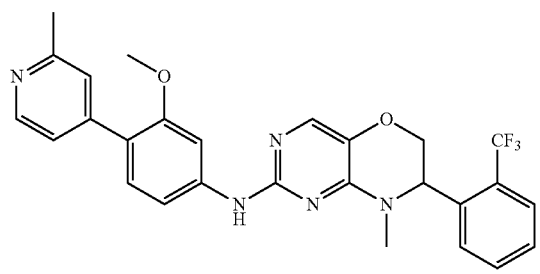

The compound of Example 70B was produced as described in Example 70. Analytical data for product Fraction II (+): $^1$H-NMR (CD$_3$OD, 400 MHz): δ 8.31 (d, 1H), 7.82 (d, 1H), 7.70 (s, 1H), 7.68 (s, 2H), 7.54 (t, 1H), 7.46 (s, 1H), 7.40 (d, 1H), 7.35 (d, 1H), 7.29-7.27 (m, 2H), 5.10 (br s, 1H), 4.30 (d, 1H), 4.12 (d, 1H), 3.88 (s, 3H), 3.10 (s, 3H), 2.52 (s, 3H); Mass (ESI): 508.5 [M+1]; LC-MS: 508.5 (M+1); (column; X-Select CSH C-18 (50×3.0 mm, 3.5 μm); RT 3.18 min. 0.05% Aq TFA:ACN; 0.80 ml/min); HPLC (column; Acquity-UPLC BEH C-18, 2.1×50 mm, 1.7 μm); RT 1.78 min. ACN: 0.025% Aq TFA; 0.5 ml/min; Chiral HPLC: RT=15.06 min (CHIRALPAK-AD H (250×4.6 mm, 5 μm; mobile phase (A) 0.1% DEA in n-hexane (B) EtOH: MeOH (50:50) (A:B: 75:25); flow Rate: 1.0 mL/min); Optical rotation $[α]_D^{20.00}$: +125.23 (c 0.25, DCM).

Example 71

Synthesis of 2-chloro-7-(2, 4-difluorophenyl)-8-methyl-7, 8-dihydro-6H-pyrimido [5, 4-b] [1, 4] oxazine

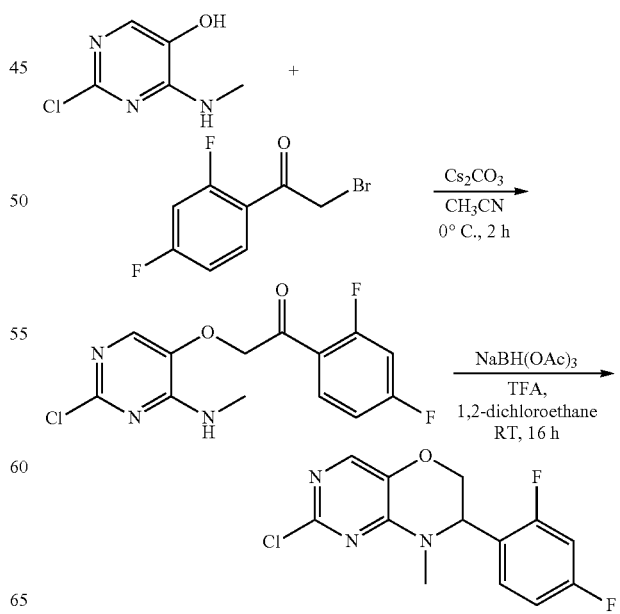

Synthesis of 2-((2-chloro-4-(methylamino) pyrimidin-5-yl) oxy)-1-(2, 4-difluorophenyl) ethan-1-one To a stirred solution of 2-chloro-4-(methylamino) pyrimidin-5-ol (500 mg, 3.14 mmol) in CH$_3$CN (10 mL) under an argon atmosphere were added cesium carbonate (2 g, 6.28 mmol) at 0° C. After stirring 5 min, 2-bromo-1-(2, 4-difluorophenyl) ethan-1-one (812 mg, 3.46 mmol) was added at 0° C. and stirred for 2 h. After consumption of the starting material (monitored by TLC), water (20 mL) was added to the reaction and extracted with EtOAc (2×20 mL). The combined organic extracts were dried over sodium sulfate, filtered and concentrated in vacuo. The crude compound was purified by column chromatography using 15-20% EtOAc: hexanes to afford 2-((2-chloro-4-(methylamino) pyrimidin-5-yl) oxy)-1-(2, 4-difluorophenyl) ethan-1-one (620 mg, 63%) an off-white solid. $^1$H-NMR (DMSO-d$_6$, 400 MHz): δ 7.85 (s, 1H), 7.70-7.67 (m, 1H), 7.39 (s, 1H), 7.30 (t, 1H), 7.19 (t, 1H), 4.15 (d AB q, 1H), 4.08 (d AB q, 1H), 2.80 (s, 3H); LC-MS: 313.8 (M+1); (column; X-Select CSH C-18 (50×3.0 mm, 3.5 μm); RT 3.43 min. 0.05% Aq TFA: ACN; 0.8 mL/min); TLC: 50% EtOAc:hexanes (R$_f$: 0.3).

Synthesis of 2-chloro-7-(2, 4-difluorophenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(2, 4-difluorophenyl) ethan-1-one (600 mg, 1.91 mmol) in 1, 2-dichloroethane (12 mL) under an argon atmosphere were added sodium triacetoxyborohydride (812 mg, 3.83 mmol) and trifluoroacetic acid (147 mL, 1.91 mmol) at room temperature. The reaction mixture was stirred at room temperature for 16 h. After consumption of the starting material (monitored by TLC), the reaction was basified with a 1N sodium hydroxide solution (20 mL) and extracted with CH$_2$Cl$_2$ (2×20 mL). The combined organic extracts were dried over sodium sulfate, filtered and concentrated in vacuo. The crude compound was purified by column chromatography using 10-15% EtOAc:hexanes to afford 2-chloro-7-(2,4-difluorophenyl)-8-methyl-7,8-dihydro-6H-pyrimido [5, 4-b] [1, 4] oxazine (500 mg, 87%) as pale yellow solid.

$^1$H-NMR (CDCl$_3$, 400 MHz): δ 7.70 (s, 1H), 6.99-6.81 (m, 3H), 4.92-4.90 (m, 1H), 4.24-4.20 (m, 2H), 3.10 (s, 3H); LC-MS: 298.1 (M+1); (column; X-Select CSH C-18 (50× 3.0 mm, 3.5 μm); RT 4.20 min. 0.05% Aq TFA: ACN; 0.8 mL/min); TLC: 50% EtOAc:hexanes (R$_f$: 0.6).

Example 72

Synthesis of 2-chloro-7-(2-chloro-5-(trifluoromethyl) phenyl)-8-methyl-7, 8-dihydro-6H-pyrimido [5, 4-b] [1, 4] oxazine

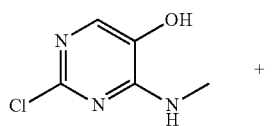

+

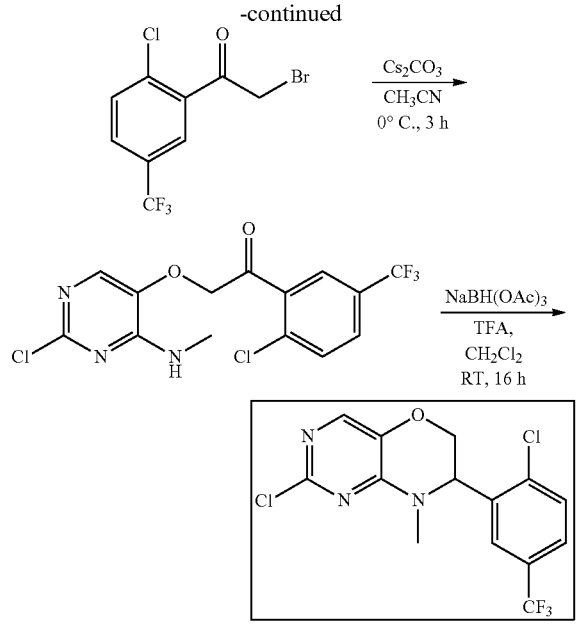

Synthesis of 2-((2-chloro-4-(methylamino) pyrimidin-5-yl) oxy)-1-(2-chloro-5-(trifluoromethyl) phenyl) ethan-1-one To a stirred solution of 2-chloro-4-(methylamino) pyrimidin-5-ol (1 g, 6.28 mmol) in CH$_3$CN (10 mL) under an argon atmosphere were added 2-bromo-1-(2-chloro-5-(trifluoromethyl) phenyl) ethan-1-one (2 g, 6.91 mmol) and cesium carbonate (4 g, 12.57 mmol) at 0° C. The reaction mixture was stirred at 0° C. for 3 h. After consumption of the starting material (monitored by TLC), the reaction was diluted with water (20 mL) and extracted with EtOAc (2×20 mL). The combined organic extracts were dried over sodium sulfate, filtered and concentrated in vacuo. The crude material was recrystallized from CH$_2$Cl$_2$: pentane (1:1, 2×10 mL) to afford 2-((2-chloro-4-(methylamino) pyrimidin-5-yl) oxy)-1-(2-chloro-5-(trifluoromethyl) phenyl) ethan-1-one (1.45 g, 63%) as an off-white solid.

$^1$H-NMR (DMSO-d$_6$, 500 MHz): δ 8.24-8.22 (m, 1H), 7.95 (s, 1H), 7.89-7.86 (m, 1H), 7.80 (d, 1H), 7.68 (br s, 1H), 4.33-4.29 (m, 1H), 4.14-4.11 (m, 1H), 2.73 (s, 3H); LCMS: 379.8 (M+1); (column; X-Select CSH C-18 (50×3.0 mm, 3.5 μm); RT 3.76 min. 0.05% Aq TFA: ACN; 0.8 mL/min); TLC: 40% EtOAc:hexanes (R$_f$: 0.6).

Synthesis of 2-chloro-7-(2-chloro-5-(trifluoromethyl) phenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(2-chloro-5-(trifluoromethyl) phenyl) ethan-1-one (1.4 g, 3.68 mmol) in 1, 2-dichloroethane (10 mL) under an argon atmosphere was added sodium triacetoxyborohydride (1.6 g, 7.73 mmol) followed by trifluoroacetic acid (281 mL, 3.68 mmol) at room temperature. The reaction mixture was stirred at room temperature for 16 h. After consumption of the starting material (monitored by TLC), the reaction was quenched with a 1 N sodium hydroxide solution (20 mL) and extracted with CH$_2$Cl$_2$ (2×20 mL). The combined organic extracts were dried over sodium sulfate, filtered and concentrated in vacuo. The crude material was purified by column chromatography using 10% EtOAc:hexanes to afford 2-chloro-7-(2-chloro-5-(trifluoromethyl) phenyl)-8-methyl-7, 8-dihydro-6H-pyrimido [5, 4-b] [1, 4] oxazine (800 mg, 58%) as an off-white solid. $^1$H-NMR (DMSO-$d_6$, 500 MHz): δ 7.88-7.80 (m, 1H), 7.23 (s, 1H), 5.31-5.29 (m, 1H), 4.39-4.30 (m, 2H), 3.01 (s, 3H); LCMS: 365.6 (M+1); (column; X-Select CSH C-18 (50×3.0 mm, 3.5 μm); RT 3.84 min. 0.05% Aq TFA: ACN; 0.8 mL/min); TLC: 25% EtOAc:hexanes ($R_f$: 0.5).

Example 73

Synthesis of 2-chloro-7-(5-chloro-2-(trifluoromethyl) phenyl)-8-methyl-7, 8-dihydro-6H-pyrimido [5, 4-b] [1, 4] oxazine

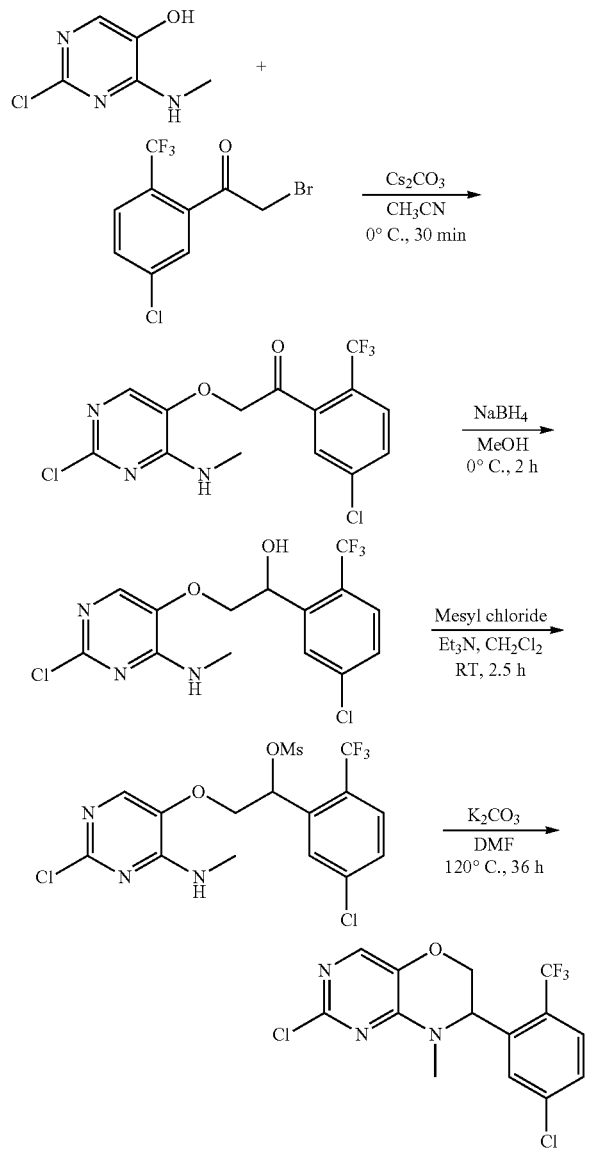

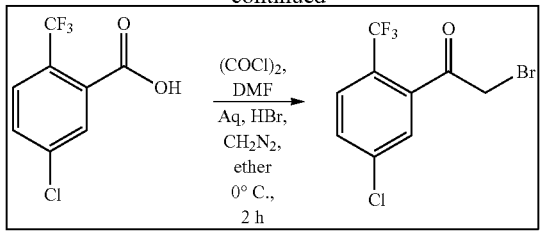

Synthesis of 2-bromo-1-(5-chloro-2-(trifluoromethyl) phenyl) ethan-1-one

To a stirred solution of 5-chloro-2-(trifluoromethyl) benzoic acid (4 g, 17.85 mmol) in $CH_2Cl_2$ (100 mL) under an argon atmosphere was added oxalyl chloride (2 mL, 19.64 mmol) and DMF (0.2 mL) at 0° C. The reaction mixture was stirred at 0° C. for 2 h. After consumption of acid (monitored by TLC), the volatile components were evaporated in vacuo, the obtained residue was dissolved in ether and a $CH_2N_2$ in ether solution was added at 0° C. The reaction mixture was stirred at 0° C. for 2 h. After consumption of the starting material (monitored by TLC), the reaction was quenched with a 48% Aq HBr solution (40 mL) at 0° C. and stirred for 2 h. After consumption of the starting material (monitored by TLC), the reaction was quenched with water (800 mL) and extracted with $CH_2Cl_2$ (2×100 mL). The combined organic extracts were washed with a sodium bicarbonate solution (50 mL), water (50 mL), dried over sodium sulfate, filtered and concentrated in vacuo to afford 2-bromo-1-(5-chloro-2-(trifluoromethyl) phenyl) ethan-1-one (5 g, 93%) as a pale yellow liquid. $^1$H-NMR (CDCl$_3$, 400 MHz): δ 7.79 (d, 1H), 7.59 (d, 1H), 7.49 (s, 1H), 4.33 (s, 2H); LCMS: 301 (M-2); (column; X-Select CSH C-18 (50×3.0 mm, 3.5 μm); RT 3.86 min. 5 mM Aq NH$_4$OAc: ACN; 0.8 mL/min); TLC: 20% EtOAc:hexanes ($R_f$: 0.7).

Synthesis of 1-(5-chloro-2-(trifluoromethyl) phenyl)-2-((2-chloro-4-(methylamino) pyrimidin-5-yl) oxy) ethan-1-one To a stirred solution of 2-chloro-4-(methylamino) pyrimidin-5-ol (2.7 g, 16.98 mmol) in CH$_3$CN (110 mL) under an argon atmosphere was added cesium carbonate (16 g, 33.96 mmol) at 0° C. After stirring 5 min, 2-bromo-1-(5-chloro-2-(trifluoromethyl) phenyl) ethan-1-one (6.4 g, 21.22 mmol) was added and stirred for 30 min. After consumption of the starting material (monitored by TLC), the reaction was diluted with water (20 mL) and extracted with EtOAc (2×20 mL). The combined organic extracts were dried over sodium sulfate, filtered and concentrated in vacuo. The crude material was washed with hexane (2×10 mL) to afford 1-(5-chloro-2-(trifluoromethyl) phenyl)-2-((2-chloro-4-(methylamino) pyrimidin-5-yl) oxy) ethan-1-one (5.5 g, 86%) as pale yellow solid. LCMS: 380.4 (M+1); (column; X-Select CSH C-18 (50×3.0 mm, 3.5 μm); RT 4.29 min. 0.05% Aq TFA: ACN; 0.8 mL/min); TLC: 30% EtOAc:hexanes ($R_f$: 0.5).

Synthesis of 1-(5-chloro-2-(trifluoromethyl)phenyl)-2-((2-chloro-4-(methylamino)pyrimidin-5-yl)oxy) ethan-1-ol)

To a stirred solution of 1-(5-chloro-2-(trifluoromethyl) phenyl)-2-((2-chloro-4-(methylamino) pyrimidin-5-yl) oxy)

ethan-1-one (5.5 g, 14.43 mmol) in MeOH (110 mL) under an argon atmosphere was added sodium borohydride (1.1 g, 28.86 mmol) at 0° C. The reaction mixture was stirred at 0° C. for 2 h. After consumption of the starting material (monitored by TLC), the reaction was quenched with cold water and volatile components were evaporated in vacuo, saturated ammonium chloride solution (100 mL) was added and extracted with EtOAc (2×100 mL). The combined organic extracts were dried over sodium sulfate, filtered and concentrated in vacuo to afford 1-(5-chloro-2-(trifluoromethyl)phenyl)-2-((2-chloro-4-(methylamino)pyrimidin-5-yl)oxy) ethan-1-ol) (5.5 g) as an off-white solid. $^1$H-NMR (DMSO-$d_6$, 500 MHz): δ 7.93 (s, 1H), 7.77 (d, 1H), 7.70-7.60 (m, 2H), 7.50-7.43 (m, 1H), 6.13 (d, 1H), 5.27-5.20 (m, 1H), 4.11-4.10 (m, 2H), 2.88 (d, 3H); LCMS: 383.1 (M+1); (column; X-Select CSH C-18 (50×3.0 mm, 3.5 μm); RT 4.23 min. 0.05% Aq TFA: ACN; 0.8 mL/min); TLC: 30% EtOAc:hexanes (R$_f$: 0.4).

Synthesis of 1-(5-chloro-2-(trifluoromethyl) phenyl)-2-((2-chloro-4-(methylamino) pyrimidin-5-yl) oxy) ethyl methanesulfonate To a stirred solution of 1-(5-chloro-2-(trifluoromethyl) phenyl)-2-((2-chloro-4-(methylamino)pyrimidin-5-yl) oxy) ethan-1-ol) (5.3 g, 14.00 mmol) in CH$_2$Cl$_2$ (100 mL) under an argon atmosphere was added triethylamine (6.82 mL, 49.00 mmol) followed by mesyl chloride (2.2 mL, 28.00 mmol) at 0° C. The reaction mixture was warmed to room temperature and stirred for 2.5 h. After consumption of the starting material (monitored by TLC), the reaction was neutralized with a 5% sodium bicarbonate solution (100 mL) and extracted with CH$_2$Cl$_2$ (2×100 mL). The combined organic extracts were dried over sodium sulfate, filtered and concentrated in vacuo to afford 1-(5-chloro-2-(trifluoromethyl) phenyl)-2-((2-chloro-4-(methylamino) pyrimidin-5-yl) oxy) ethyl methanesulfonate (5 g, 78%) as an off-white solid. $^1$H-NMR (DMSO-$d_6$, 400 MHz): δ 7.99 (s, 1H), 7.83 (d, 1H), 7.75-7.71 (m, 2H), 7.43-7.40 (m, 1H), 6.10 (d, 1H), 4.62-4.58 (m, 1H), 4.23-4.20 (m, 1H), 3.30 (s, 3H), 2.87 (d, 3H); LCMS: 461.2 (M+1); (column; X-Select CSH C-18 (50×3.0 mm, 3.5 μm); RT 4.44 min. 0.05% Aq TFA: ACN; 0.8 mL/min); UPLC (column; Acquity UPLC-BEH-C18 2.1×50 mm, 1.7 μm); RT 2.49 min. ACN: 0.025% Aq TFA; 0.5 mL/min; TLC: 30% EtOAc:hexanes (R$_f$: 0.5).

Synthesis of 2-chloro-7-(5-chloro-2-(trifluoromethyl) phenyl)-8-methyl-7, 8-dihydro-6H-pyrimido [5, 4-b] [1, 4] oxazine To a stirred solution of 1-(5-chloro-2-(trifluoromethyl) phenyl)-2-((2-chloro-4-(methylamino) pyrimidin-5-yl) oxy) ethyl methanesulfonate (900 mg, 1.95 mmol) in DMF (30 mL) under an argon atmosphere was added potassium carbonate (808 mg, 5.85 mmol) at room temperature. The reaction mixture was stirred at 120° C. for 36 h. After consumption of the starting material (monitored by TLC), the reaction was quenched with water (50 mL) and extracted with EtOAc (2×50 mL). The combined organic extracts were dried over sodium sulfate, filtered and concentrated in vacuo. The crude material was purified by column chromatography using 15% EtOAc:hexanes to afford 2-chloro-7-(5-chloro-2-(trifluoromethyl) phenyl)-8-methyl-7, 8-dihydro-6H-pyrimido [5, 4-b] [1, 4] oxazine (300 mg, 42%) as a pale yellow solid. $^1$H-NMR (DMSO-$d_6$, 400 MHz): δ 7.90-7.84 (m, 2H), 7.80 (d, 1H), 7.30 (s, 1H), 5.01-4.99 (m, 1H), 4.33-4.30 (m, 1H), 4.21-4.18 (m, 1H), 2.95 (s, 3H); LCMS: 365.1 (M+1); (column; X-Select CSH C-18 (50×3.0 mm, 3.5 μm); RT 4.75 min 0.05% Aq TFA: ACN; 0.8 mL/min); UPLC (column; Acquity UPLC-BEH-C18 2.1×50 mm, 1.7 μm); RT 2.73 min. ACN: 0.025% Aq TFA; 0.5 mL/min; TLC: 30% EtOAc:hexanes (R$_f$: 0.7).

Example 74

Synthesis of 7-(2, 4-bis (trifluoromethyl) phenyl)-2-chloro-8-methyl-7, 8-dihydro-6H-pyrimido [5, 4-b] [1, 4] oxazine

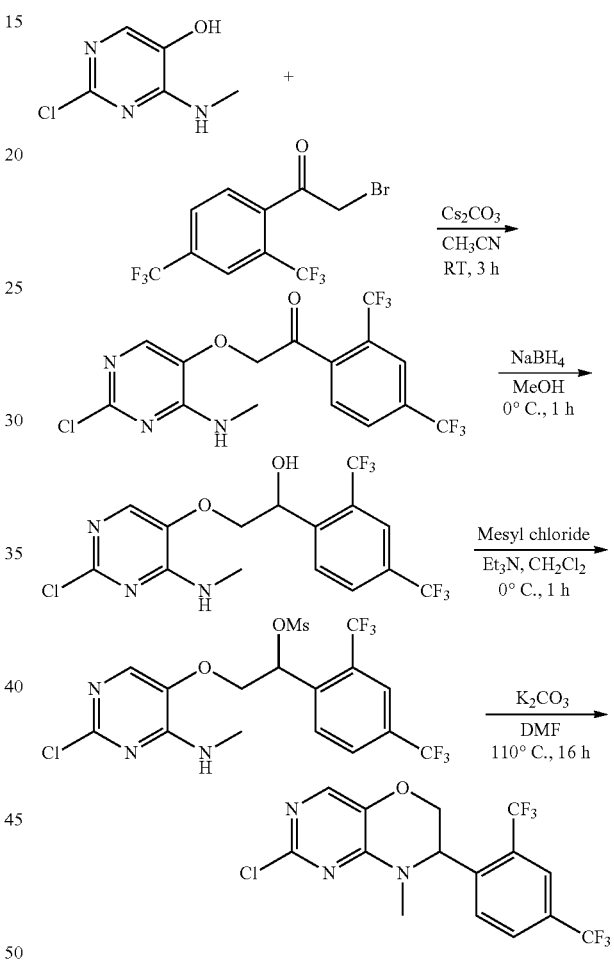

Synthesis of 1-(2, 4-bis (trifluoromethyl) phenyl)-2-((2-chloro-4-(methylamino) pyrimidin-5-yl) oxy) ethan-1-one To a stirred solution of 2-chloro-4-(methylamino) pyrimidin-5-ol (600 mg, 3.77 mmol) in CH$_3$CN (6 mL) under an argon atmosphere were added cesium carbonate (2.4 g, 7.54 mmol) and 1-(2, 4-bis (trifluoromethyl) phenyl)-2-bromoethan-1-one (1.4 g, 4.15 mmol) at room temperature. The reaction mixture was stirred at room temperature for 3 h. After consumption of the starting material (monitored by TLC), the reaction was diluted with water (50 mL) and extracted with EtOAc (2×50 mL). The combined organic extracts were dried over sodium sulfate, filtered and concentrated in vacuo. The crude material was purified by column chromatography using 20% EtOAc:hexane to afford 1-(2, 4-bis (trifluoromethyl) phenyl)-2-((2-chloro-4-(methylamino) pyrimidin-5-yl) oxy) ethan-1-one (500 mg, 33%) as an off-white solid. $^1$H-NMR (DMSO-d$_6$, 500 MHz): δ 8.30 (s, 2H), 8.27 (s, 1H), 7.71 (s, 1H), 7.46-7.42 (m, 1H), 5.59 (s, 2H), 2.85 (d, 3H); LCMS: 413.8 (M+1); (column; X-Select CSH C-18 (50×3.0 mm, 3.5 μm); RT 3.83 min. 0.05% Aq TFA: ACN; 0.80 mL/min); TLC: 50% EtOAc: hexanes (R$_f$: 0.6).

Synthesis of 1-(2, 4-bis (trifluoromethyl) phenyl)-2-((2-chloro-4-(methylamino) pyrimidin-5-yl) oxy) ethan-1-ol To a stirred solution of 1-(2, 4-bis (trifluoromethyl) phenyl)-2-((2-chloro-4-(methylamino) pyrimidin-5-yl) oxy) ethan-1-one (1.5 g, 3.63 mmol) in MeOH (15 mL) under an argon atmosphere was added sodium borohydride (201 mg, 5.44 mmol) at 0° C. The reaction mixture was stirred at 0° C. for 1 h. After consumption of the starting material (monitored by TLC), the volatile components were evaporated in vacuo, water (50 mL) was added and extracted with EtOAc (2×50 mL). The combined organic extracts were dried over sodium sulfate, filtered and concentrated in vacuo. The crude material was purified by column chromatography using 20% EtOAc:hexane to afford 1-(2, 4-bis-(trifluoromethyl) phenyl)-2-((2-chloro-4-(methylamino) pyrimidin-5-yl) oxy) ethan-1-ol (1.1 g, 73%) as an off-white solid. $^1$H-NMR (CDCl$_3$, 500 MHz): δ 8.02 (d, 1H), 7.96 (s, 1H), 7.92 (d, 1H), 7.51 (s, 1H), 5.62-5.59 (m, 2H), 4.15-4.12 (m, 1H), 4.03 (t, 1H), 3.03 (d, 3H); LCMS: 415.8 (M+1); (column; X-Select CSH C-18 (50×3.0 mm, 3.5 μm); RT 3.74 min. 0.05% Aq TFA: ACN; 0.80 mL/min); TLC: 30% EtOAc:hexanes (R$_f$: 0.4).

Synthesis of 1-(2, 4-bis (trifluoromethyl) phenyl)-2-((2-chloro-4-(methylamino) pyrimidin-5-yl) oxy) ethyl methanesulfonate To a stirred solution of 1-(2, 4-bis-(trifluoromethyl) phenyl)-2-((2-chloro-4-(methylamino) pyrimidin-5-yl) oxy) ethan-1-ol (1.2 g, 2.89 mmol) in CH$_2$Cl$_2$ (12 mL) under an argon atmosphere were added triethylamine (0.5 mL, 3.46 mmol) followed by mesyl chloride (329 mg, 2.89 mmol) at 0° C. The reaction mixture was stirred at 0° C. for 1 h. After consumption of the starting material (monitored by TLC), the reaction was neutralized with water (50 mL) and extracted with CH$_2$Cl$_2$ (2×50 mL). The combined organic extracts were dried over sodium sulfate, filtered and concentrated in vacuo. The crude material was purified by column chromatography using 30% EtOAc:hexane to afford 1-(2, 4-bis (trifluoromethyl) phenyl)-2-((2-chloro-4-(methylamino) pyrimidin-5-yl) oxy) ethyl methanesulfonate (1 g, 71%) as an off-white solid. $^1$H-NMR (CDCl$_3$, 400 MHz): δ 8.02 (d, 1H), 8.00-7.98 (m, 1H), 7.91 (d, 1H), 7.40 (s, 1H), 6.10-6.08 (m, 1H), 4.22-4.10 (m, 2H), 3.68 (s, 1H), 3.07 (d, 3H), 3.00 (s, 3H); LCMS: 493.9 (M+1); (column; X-Select CSH C-18 (50×3.0 mm, 3.5 μm); RT 3.89 min. 0.05% Aq TFA: ACN; 0.80 mL/min); TLC: 40% EtOAc:hexanes (R$_f$: 0.4).

Synthesis of 7-(2, 4-bis (trifluoromethyl) phenyl)-2-chloro-8-methyl-7, 8-dihydro-6H-pyrimido [5, 4-b] [1, 4] oxazine To a stirred solution of 1-(2, 4-bis-(trifluoromethyl) phenyl)-2-((2-chloro-4-(methylamino) pyrimidin-5-yl) oxy) ethyl methanesulfonate (1 g, 2.02 mmol) in DMF (10 mL) under an argon atmosphere was added potassium carbonate (419 mg, 3.04 mmol) at room temperature. The reaction mixture was heated at 110° C. for 16 h. After consumption of the starting material (monitored by TLC), the volatile components were evaporated in vacuo. The reaction was diluted with cold water (50 mL) and extracted with ether (2×50 mL). The combined organic extracts were washed with water (50 mL), dried over sodium sulfate, filtered and concentrated in vacuo. The crude material was purified by column chromatography using 5% EtOAc:hexane to afford 7-(2, 4-bis (trifluoromethyl) phenyl)-2-chloro-8-methyl-7, 8-dihydro-6H-pyrimido [5, 4-b] [1, 4] oxazine (200 mg, 25%) as an off-white solid. $^1$H-NMR (CDCl$_3$, 500 MHz): δ 8.00 (s, 1H), 7.81 (d, 1H), 7.80 (s, 1H), 7.34 (d, 1H), 5.10-5.08 (m, 1H), 4.31-4.29 (m, 1H), 4.20-4.16 (m, 1H), 3.08 (s, 3H); LCMS: 397.8 (M+1); (column; X-Select CSH C-18 (50×3.0 mm, 3.5 μm); RT 4.20 min. 0.05% Aq TFA: ACN; 0.80 mL/min); TLC: 30% EtOAc:hexanes (R$_f$: 0.6).

Example 75

Synthesis of 2-chloro-7-(4-methoxy-2-methylphenyl)-7, 8-dihydro-6H-pyrimido [5, 4-b] [1, 4] oxazine

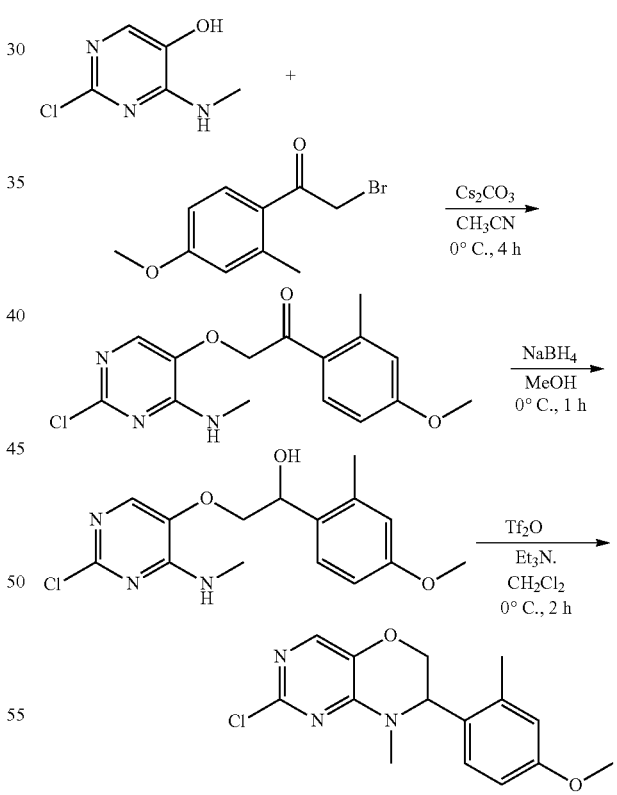

Synthesis of 2-bromo-1-(4-methoxy-2-methylphenyl) ethan-1-one

To a stirred solution of 2-chloro-4-(methylamino) pyrimidin-5-ol (1 g, 6.28 mmol) in CH$_3$CN (20 mL) under an argon atmosphere was added cesium carbonate (1.68 g, 6.92 mmol) at 0° C. After stirring 5 min, 2-bromo-1-(4-methoxy-2-methylphenyl) ethan-1-one (1.7 g, 6.92 mmol) was added to the reaction mixture and stirred for 4 h. After consumption of the starting material (monitored by TLC), the reaction was diluted with water (100 mL) and extracted with EtOAc (2×50 mL). The combined organic extracts were dried over sodium sulfate, filtered and concentrated in vacuo. The crude material was purified by column chromatography using 15-20% EtOAc:hexane to afford 2-bromo-1-(4-methoxy-2-methylphenyl) ethan-1-one (1.3 g, 65%) as an off-white solid. $^1$H-NMR (DMSO-$d_6$, 400 MHz): δ 7.92 (d, 1H), 7.58 (s, 1H), 7.49-7.43 (m, 1H), 6.90 (s, 1H), 6.89-6.87 (m, 1H), 5.50 (s, 2H), 3.83 (s, 3H), 2.86 (d, 3H), 2.45 (s, 3H); LCMS: 322.4 (M+1); (column; X-Select CSH C-18 (50×3.0 mm, 3.5 μm); RT 3.92 min 0.05% Aq TFA: ACN; 0.80 mL/min); TLC: 50% EtOAc:hexanes ($R_f$: 0.5).

Synthesis of 2-((2-chloro-4-(methylamino) pyrimidin-5-yl) oxy)-1-(4-methoxy-2-methylphenyl) ethan-1-ol To a stirred solution of 2-bromo-1-(4-methoxy-2-methylphenyl) ethan-1-one (1.1 g, 3.40 mmol) in MeOH (20 mL) under an argon atmosphere was added sodium borohydride (194 mg, 5.14 mmol) at 0° C. The reaction mixture was stirred at 0° C. for 1 h. After consumption of the starting material (monitored by TLC), volatile components were evaporated, water (50 mL) was added and extracted with EtOAc (2×50 mL). The combined organic extracts were dried over sodium sulfate, filtered and concentrated in vacuo. The crude material was purified by column chromatography using 20-40% EtOAc:hexane to afford 2-((2-chloro-4-(methylamino) pyrimidin-5-yl) oxy)-1-(4-methoxy-2-methylphenyl) ethan-1-ol (800 mg, 73%) as an off-white solid. TLC: 40% EtOAc:hexanes ($R_f$: 0.2).

Synthesis of 2-chloro-7-(4-methoxy-2-methylphenyl)-7, 8-dihydro-6H-pyrimido [5, 4-b] [1, 4] oxazine To a stirred solution of 2-((2-chloro-4-(methylamino) pyrimidin-5-yl) oxy)-1-(4-methoxy-2-methylphenyl) ethan-1-ol (50 mg, 0.15 mmol) in $CH_2Cl_2$ (3 mL) under an argon atmosphere were added triethylamine (0.04 mL, 0.31 mmol) and triflic anhydride (55 mg, 0.19 mmol) at 0° C. The reaction mixture was stirred at 0° C. for 2 h. After consumption of the starting material (monitored by TLC), the reaction was basified with a saturated sodium bicarbonate solution (50 mL) and extracted with $CH_2Cl_2$ (2×50 mL). The combined organic extracts were dried over sodium sulfate, filtered and concentrated in vacuo. The crude material was purified by column chromatography using 20-30% EtOAc:hexane to afford 2-chloro-7-(4-methoxy-2-methylphenyl)-7, 8-dihydro-6H-pyrimido [5, 4-b] [1, 4] oxazine (14 mg, 30%) as a white solid. $^1$H-NMR (CDCl$_3$, 400 MHz): δ 7.70 (s, 1H), 6.90 (d, 1H), 6.79-6.73 (m, 2H), 4.80 (t, 1H), 4.20 (d, 1H), 4.09 (d, 1H), 3.80 (s, 3H), 3.01 (s, 3H), 2.35 (s, 3H); LCMS: 306.3 (M+1); (column; X-Select CSH C-18 (50×3.0 mm, 3.5 μm); RT 4.78 min 0.05% Aq TFA: ACN; 0.80 mL/min); TLC: 50% EtOAc:hexanes ($R_f$: 0.5).

Example 76

Synthesis of 2-chloro-7-(4-fluoro-2-(trifluoromethyl) phenyl)-8-methyl-7, 8-dihydro-6H-pyrimido [5, 4-b] [1, 4] oxazine

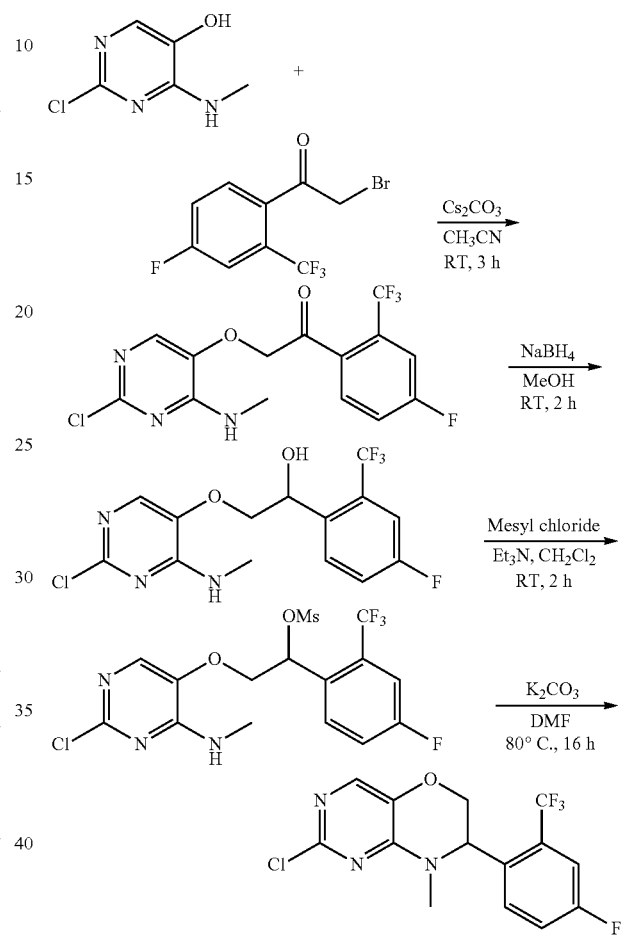

Synthesis of 2-((2-chloro-4-(methylamino) pyrimidin-5-yl) oxy)-1-(4-fluoro-2-(trifluoromethyl) phenyl) ethan-1-one To a stirred solution of 2-chloro-4-(methylamino) pyrimidin-5-ol (600 mg, 3.77 mmol) in $CH_3CN$ (6 mL) under an argon atmosphere were added cesium carbonate (2.4 g, 7.54 mmol) and 2-bromo-1-(4-fluoro-2-(trifluoromethyl) phenyl) ethan-1-one (1.1 g, 4.15 mmol) at room temperature. The reaction mixture was stirred at room temperature for 3 h. After consumption of the starting material (monitored by TLC), the reaction was diluted with water (50 mL) and extracted with EtOAc (2×50 mL). The combined organic extracts were dried over sodium sulfate, filtered and concentrated in vacuo. The crude material was purified by column chromatography using 20% EtOAc:hexane to afford 2-((2-chloro-4-(methylamino) pyrimidin-5-yl) oxy)-1-(4-fluoro-2-(trifluoromethyl) phenyl) ethan-1-one (500 mg, 36%) as an off-white solid. $^1$H-NMR (CDCl$_3$, 500 MHz): δ 7.56-7.50 (m, 3H), 7.40 (t, 1H), 5.75 (br s, 1H), 5.05 (s, 2H), 3.09 (d, 3H); TLC: 30% EtOAc:hexanes ($R_f$: 0.4).

Synthesis of 2-((2-chloro-4-(methylamino) pyrimidin-5-yl) oxy)-1-(4-fluoro-2-(trifluoromethyl) phenyl) ethan-1-ol To a stirred solution of 2-((2-chloro-4-(methylamino) pyrimidin-5-yl) oxy)-1-(4-fluoro-2-(trifluoromethyl) phenyl) ethan-1-one (500 mg, 1.37 mmol) in MeOH (2 mL) under an argon atmosphere was added sodium borohydride (76 mg, 2.06 mmol) at 0° C. The reaction mixture was warmed to room temperature and stirred for 2 h. After consumption of the starting material (monitored by TLC), volatile components were evaporated, water (50 mL) was added and extracted with EtOAc (2×50 mL). The combined organic extracts were dried over sodium sulfate, filtered and concentrated in vacuo to afford 2-((2-chloro-4-(methylamino) pyrimidin-5-yl) oxy)-1-(4-fluoro-2-(trifluoromethyl) phenyl) ethan-1-ol (450 mg, 89%) as an off-white solid.

$^1$H-NMR (DMSO-$d_6$, 400 MHz): δ 7.94-7.90 (m, 1H), 7.66-7.60 (m, 3H), 7.45-7.40 (m, 1H), 6.00 (s, 1H), 5.23-5.20 (m, 1H), 4.09-4.00 (m, 1H), 3.99-3.91 (m, 1H), 2.88 (d, 3H); LCMS: 366.2 (M+1); (column; X-Select CSH C-18 (50×3.0 mm, 3.5 μm); RT 3.97 min. 0.05% Aq TFA: ACN; 0.80 mL/min); TLC: 40% EtOAc:hexanes ($R_f$: 0.5).

Synthesis of 2-((2-chloro-4-(methylamino) pyrimidin-5-yl) oxy)-1-(4-fluoro-2-(trifluoromethyl) phenyl) ethyl methanesulfonate To a stirred solution of 2-((2-chloro-4-(methylamino) pyrimidin-5-yl) oxy)-1-(4-fluoro-2-(trifluoromethyl) phenyl) ethan-1-ol (450 mg, 1.23 mmol) in dichloroethane (2 mL) under an argon atmosphere were added triethylamine (0.2 mL, 1.47 mmol) and mesyl chloride (140 mg, 1.23 mmol) at 0° C. The reaction mixture was warmed to room temperature and stirred for 2 h. After consumption of the starting material (monitored by TLC), the reaction was diluted with water (50 mL) and extracted with CH$_2$Cl$_2$ (2×50 mL). The combined organic extracts were dried over sodium sulfate, filtered and concentrated in vacuo to afford 2-((2-chloro-4-(methylamino) pyrimidin-5-yl) oxy)-1-(4-fluoro-2-(trifluoromethyl) phenyl) ethyl methanesulfonate (500 mg) as an off-white solid. $^1$H-NMR (CDCl$_3$, 500 MHz): δ 7.79-7.74 (m, 1H), 7.50-7.45 (m, 1H), 7.45-7.40 (m, 2H), 6.10 (br s, 1H), 4.20-4.10 (m, 2H), 3.13 (s, 1H), 3.08 (d, 3H), 2.99 (s, 3H); LCMS: 444.3 (M+1); (column; X-Select CSH C-18 (50×3.0 mm, 3.5 μm); RT 3.69 min 5 mM Aq NH$_4$OAc: ACN; 0.80 mL/min); TLC: 30% EtOAc:hexanes ($R_f$: 0.4).

Synthesis of 2-chloro-7-(4-fluoro-2-(trifluoromethyl) phenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(4-fluoro-2-(trifluoromethyl) phenyl) ethyl methanesulfonate (500 mg, 1.12 mmol) in DMF (5 mL) under an argon atmosphere was added potassium carbonate (233 mg, 1.69 mmol) at room temperature. The reaction mixture was heated at 80° C. for 16 h. After consumption of the starting material (monitored by TLC), the volatile components were evaporated in vacuo. The reaction was diluted with ice cold water (50 mL) and extracted with ether (2×50 mL). The combined organic extracts were dried over sodium sulfate, filtered and concentrated in vacuo. The crude material was purified by column chromatography using 15% EtOAc:hexane to afford 2-chloro-7-(4-fluoro-2-(trifluoromethyl) phenyl)-8-methyl-7, 8-dihydro-6H-pyrimido [5, 4-b] [1, 4] oxazine (120 mg, 30%) as an off-white solid. $^1$H-NMR (CD$_3$OD, 500 MHz): δ 7.75 (s, 1H), 7.70 (d, 1H), 7.46-7.40 (m, 1H), 7.37-7.30 (m, 1H), 5.16-5.13 (m, 1H), 4.35-4.30 (m, 1H), 4.20-4.18 (m, 1H), 3.03 (s, 3H); LCMS: 348.2 (M+1); (column; X-Select CSH C-18 (50×3.0 mm, 3.5 μm); RT 4.66 min 0.05% Aq TFA: ACN; 0.80 mL/min); TLC: 30% EtOAc: hexanes ($R_f$: 0.7).

Example 77

Synthesis of 2-chloro-7-(2, 4-dichlorophenyl)-8-methyl-7, 8-dihydro-6H-pyrimido [5, 4-b] [1, 4] oxazine

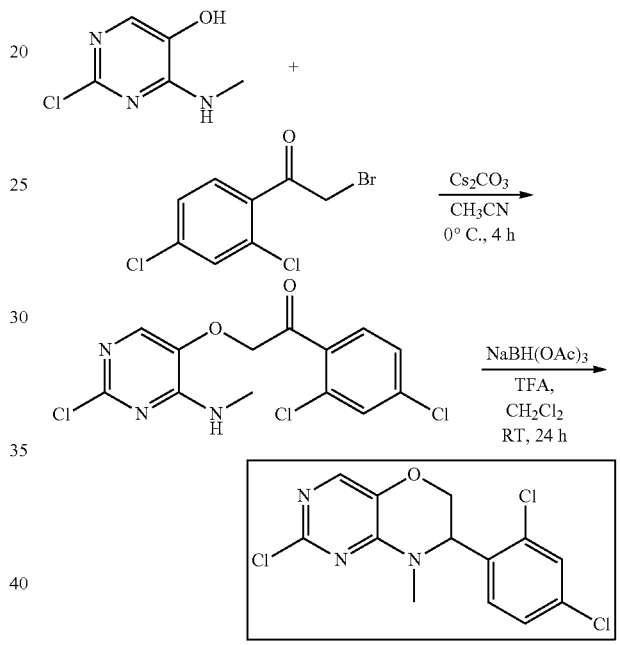

Synthesis of 2-((2-chloro-4-(methylamino) pyrimidin-5-yl) oxy)-1-(2, 4-dichlorophenyl) ethan-1-one To a stirred solution of 2-chloro-4-(methylamino) pyrimidin-5-ol (500 mg, 3.14 mmol) in CH$_3$CN (10 mL) under an argon atmosphere were added 2-bromo-1-(2, 4-dichlorophenyl) ethan-1-one (927 mg, 3.45 mmol) and cesium carbonate (2 g, 6.28 mmol) at 0° C. The reaction mixture was stirred at 0° C. for 4 h. After consumption of the starting material (monitored by TLC), the reaction was diluted with water (20 mL) and extracted with EtOAc (2×20 mL). The combined organic extracts were dried over sodium sulfate, filtered and concentrated in vacuo. The crude material was purified by column chromatography using 15-20% EtOAc:hexanes to afford 2-((2-chloro-4-(methylamino) pyrimidin-5-yl) oxy)-1-(2, 4-dichlorophenyl) ethan-1-one (650 mg, 60%) as an off-white solid. $^1$H-NMR (DMSO-$d_6$, 500 MHz): δ 7.92-7.88 (m, 2H), 7.69 (s, 1H), 7.60 (d, 1H), 7.49 (s, 1H), 4.31-4.29 (m, 1H), 4.06-4.01 (m, 1H), 2.77 (s, 3H); LCMS: 347 (M+1); (column; X-Select CSH C-18 (50×3.0 mm, 3.5 μm); RT 4.50 min. 0.05% Aq TFA: ACN; 0.8 mL/min); TLC: 60% EtOAc:hexanes ($R_f$: 0.5).

Synthesis of 2-chloro-7-(2, 4-dichlorophenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(2, 4-dichlorophenyl) ethan-1-one (650 mg, 1.87 mmol) in 1, 2-dichloroethane (15 mL) under an argon atmosphere were added sodium triacetoxyborohydride (796 mg, 3.75 mmol) followed by trifluoroacetic acid (0.14 mL, 1.87 mmol) at room temperature. The reaction mixture was stirred at room temperature for 3 h. After consumption of the starting material (monitored by TLC), the reaction was diluted with a 1 N sodium hydroxide solution (20 mL) and extracted with $CH_2Cl_2$ (2×20 mL). The combined organic extracts were dried over sodium sulfate, filtered and concentrated in vacuo. The crude material was purified by column chromatography using 10-20% EtOAc: hexanes to afford 2-chloro-7-(2, 4-dichlorophenyl)-8-methyl-7, 8-dihydro-6H-pyrimido [5, 4-b] [1, 4] oxazine (350 mg, 56%) as an off-white solid.

$^1$H-NMR (CDCl$_3$, 400 MHz): δ 7.70 (s, 1H), 7.49 (s, 1H), 7.25 (s, 1H), 6.91 (d, 1H), 5.03-5.01 (m, 1H), 4.30 (d, 1H), 4.21 (d, 1H), 3.13 (s, 3H); LCMS: 332.1 (M+1); (column; X-Select CSH C-18 (50×3.0 mm, 3.5 μm); RT 4.78 min. 0.05% Aq TFA: ACN; 0.8 mL/min); TLC: 50% EtOAc: hexanes (R$_f$: 0.4).

Example 78

Synthesis of 2-chloro-7-(2-chloro-4-fluorophenyl)-8-methyl-7, 8-dihydro-6H-pyrimido [5, 4-b] [1, 4] oxazine

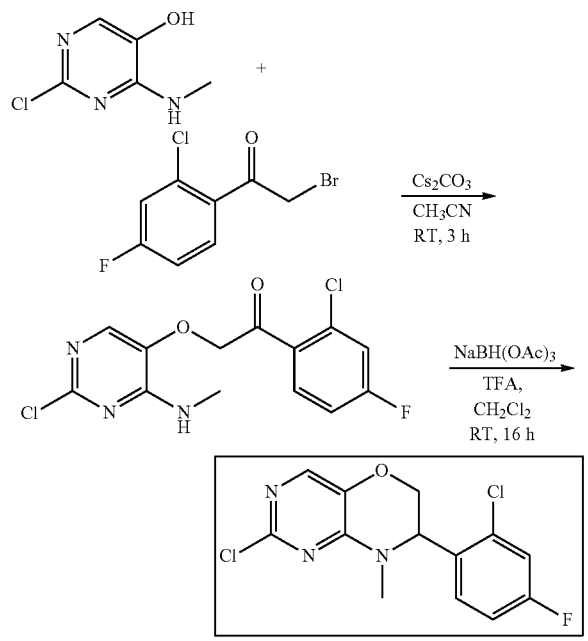

Synthesis of 2-((2-chloro-4-(methylamino) pyrimidin-5-yl) oxy)-1-(2-chloro-4-fluorophenyl) ethan-1-one To a stirred solution of 2-chloro-4-(methylamino) pyrimidin-5-ol (547 mg, 3.44 mmol) in CH$_3$CN (5 mL) under an argon atmosphere were added cesium carbonate (2.3 g, 6.88 mmol) and 2-bromo-1-(2-chloro-4-fluorophenyl) ethan-1-one (1 g, 3.78 mmol) at 0° C. The reaction mixture was stirred at room temperature for 3 h. After consumption of the starting material (monitored by TLC), the reaction was diluted with water (50 mL) and extracted with EtOAc (2×50 mL). The combined organic extracts were dried over sodium sulfate, filtered and concentrated in vacuo to afford 2-((2-chloro-4-(methylamino) pyrimidin-5-yl) oxy)-1-(2-chloro-4-fluorophenyl) ethan-1-one (1 g) as a brown solid. LCMS: 331.1 (M+1); (column; X-Select CSH C-18 (50×3.0 mm, 3.5 μm); RT 4.18 min. 0.05% Aq TFA: ACN; 0.8 mL/min); TLC: 30% EtOAc:hexanes (R$_f$: 0.6).

Synthesis of 2-chloro-7-(2-chloro-4-fluorophenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(2-chloro-4-fluorophenyl) ethan-1-one (1 g, 3.03 mmol) in 1, 2-dichloroethane (10 mL) under an argon atmosphere at room temperature were added sodium triacetoxyborohydride (1.2 g, 6.06 mmol) followed by trifluoroacetic acid (345 mg, 3.03 mmol). The reaction mixture was stirred at room temperature for 16 h. After consumption of the starting material (monitored by TLC), the reaction was quenched with a 1 N sodium hydroxide solution (50 mL) and extracted with CH$_2$Cl$_2$ (2×50 mL). The combined organic extracts were dried over sodium sulfate, filtered and concentrated in vacuo. The crude material was purified by column chromatography using 15% EtOAc: hexanes to afford 2-chloro-7-(2-chloro-4-fluorophenyl)-8-methyl-7, 8-dihydro-6H-pyrimido [5, 4-b] [1, 4] oxazine (300 mg, 32%) as a pale brown solid. $^1$H-NMR (CDCl$_3$, 500 MHz): δ 7.74 (s, 1H), 7.21 (d, 1H), 7.00-6.93 (m, 2H), 5.03 (s, 1H), 4.33-4.29 (m, 1H), 4.25-4.20 (m, 1H), 3.15 (s, 3H); LCMS: 314.1 (M+1); (column; X-Select CSH C-18 (50×3.0 mm, 3.5 μm); RT 4.38 min. 0.05% TFA in water: ACN; 0.8 mL/min); TLC: 30% EtOAc:hexanes (R$_f$: 0.6).

Example 79

Synthesis 2-chloro-8-methyl-7-(2, 4, 5-trifluorophenyl)-7, 8-dihydro-6H-pyrimido [5, 4-b] [1, 4] oxazine

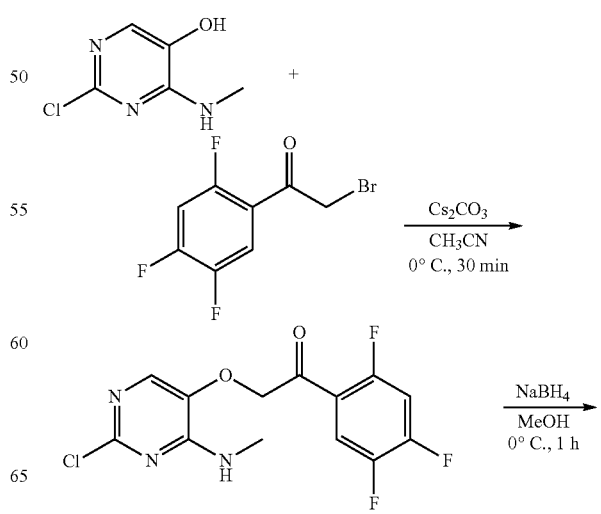

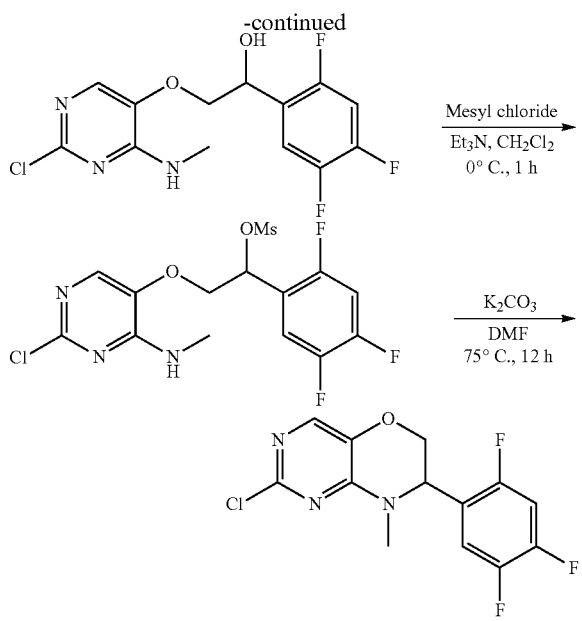

Synthesis of 2-((2-chloro-4-(methylamino) pyrimidin-5-yl) oxy)-1-(2, 4, 5-trifluorophenyl) ethan-1-one To a stirred solution of 2-chloro-4-(methylamino) pyrimidin-5-ol (500 mg, 3.14 mmol) in $CH_3CN$ (5 mL) under an argon atmosphere was added cesium carbonate (2.2 g, 6.91 mmol) at 0° C. After stirring 10 min, 2-bromo-1-(2, 4, 5-trifluorophenyl) ethan-1-one (800 mg, 3.45 mmol) was added to the reaction mixture and stirred for 30 min. After consumption of the starting material (monitored by TLC), the reaction was diluted with water (50 mL) and extracted with EtOAc (2×50 mL). The combined organic extracts were dried over sodium sulfate, filtered and concentrated in vacuo. The crude material was washed with EtOAc:hexane (1:1, 2×20 mL) to afford 2-((2-chloro-4-(methylamino) pyrimidin-5-yl) oxy)-1-(2, 4, 5-trifluorophenyl) ethan-1-one (550 mg, 55%) as a pale yellow solid used without further purification. $^1$H-NMR (DMSO-$d_6$, 500 MHz): δ 7.88 (s, 1H), 7.70-7.63 (m, 2H), 7.53 (s, 1H), 4.17-4.10 (m, 2H), 2.81 (s, 3H); LCMS: 332.2 (M+1); (column; X-Select CSH C-18 (50×3.0 mm, 3.5 μm); RT 4.07 min 0.05% Aq TFA: ACN; 0.80 mL/min); TLC: 30% EtOAc:hexanes ($R_f$: 0.7).

Synthesis of 2-((2-chloro-4-(methylamino) pyrimidin-5-yl) oxy)-1-(2, 4, 5-trifluorophenyl) ethan-1-ol To a stirred solution of 2-((2-chloro-4-(methylamino) pyrimidin-5-yl) oxy)-1-(2, 4, 5-trifluorophenyl) ethan-1-one (200 mg, 0.60 mmol) in MeOH (1 mL) under an argon atmosphere was added sodium borohydride (35 mg, 0.90 mmol) at 0° C. The reaction mixture was stirred at 0° C. for 1 h. After consumption of the starting material (monitored by TLC), the reaction was diluted with an ammonium chloride solution (20 mL) and extracted with EtOAc (2×20 mL). The combined organic extracts were dried over sodium sulfate, filtered and concentrated in vacuo to afford 2-((2-chloro-4-(methylamino) pyrimidin-5-yl) oxy)-1-(2, 4, 5-trifluorophenyl) ethan-1-ol (140 mg) as a pale yellow solid used without further purification. $^1$H-NMR (DMSO-$d_6$, 500 MHz): δ 7.69 (s, 1H), 7.68-7.53 (m, 2H), 7.41-7.39 (m, 1H), 6.00 (s, 1H), 5.20-5.18 (m, 1H), 4.20-4.17 (m, 1H), 3.99 (t, 1H), 2.83 (d, 3H); LCMS: 334.3 (M+1); (column; X-Select CSH C-18 (50×3.0 mm, 3.5 μm); RT 3.86 min 0.05% Aq TFA: ACN; 0.80 mL/min); TLC: 50% EtOAc:hexanes ($R_f$: 0.2).

Synthesis of 2-((2-chloro-4-(methylamino) pyrimidin-5-yl) oxy)-1-(2, 4, 5-trifluorophenyl) ethyl methanesulfonate To a stirred solution of 2-((2-chloro-4-(methylamino) pyrimidin-5-yl) oxy)-1-(2, 4, 5-trifluorophenyl) ethan-1-ol (140 mg, 0.42 mmol) in $CH_2Cl_2$ (2 mL) under an argon atmosphere were added triethylamine (0.12 mL, 0.84 mmol) followed by mesyl chloride (0.05 mL, 0.63 mmol) at 0° C. The reaction mixture was stirred at 0° C. for 1 h. After consumption of the starting material (monitored by TLC), the reaction was diluted with water (50 mL) and extracted with $CH_2Cl_2$ (2×50 mL). The combined organic extracts were dried over sodium sulfate, filtered and concentrated in vacuo to afford 2-((2-chloro-4-(methylamino) pyrimidin-5-yl) oxy)-1-(2, 4, 5-trifluorophenyl) ethyl methanesulfonate (200 mg) as a pale yellow solid used without further purification. $^1$H-NMR (CDCl$_3$, 500 MHz): δ 7.43 (s, 1H), 7.35-7.30 (m, 1H), 7.09-7.04 (m, 1H), 6.20-6.18 (m, 1H), 6.13 (br s, 1H), 4.25-4.20 (m, 2H), 3.13 (s, 3H), 3.06-3.03 (m, 3H); TLC: 50% EtOAc:hexanes ($R_f$: 0.5).

Synthesis of 2-chloro-8-methyl-7-(2, 4, 5-trifluorophenyl)-7, 8-dihydro-6H-pyrimido [5, 4-b] [1, 4] oxazine To a stirred solution of 2-((2-chloro-4-(methylamino) pyrimidin-5-yl) oxy)-1-(2, 4, 5-trifluorophenyl) ethyl methanesulfonate (200 mg, 0.48 mmol) in DMF (1 mL) under an argon atmosphere was added potassium carbonate (100 mg, 0.72 mmol) at room temperature. The reaction mixture was heated at 75° C. for 12 h. After consumption of the starting material (monitored by TLC), the reaction was diluted with water (20 mL) and extracted with EtOAc (2×20 mL). The combined organic extracts were dried over sodium sulfate, filtered and concentrated in vacuo. The crude material was purified by column chromatography using 10% EtOAc: hexane to afford 2-chloro-8-methyl-7-(2, 4, 5-trifluorophenyl)-7, 8-dihydro-6H-pyrimido [5, 4-b] [1, 4] oxazine (80 mg, 52%) as an off-white solid. $^1$H-NMR (CDCl$_3$, 500 MHz): δ 7.73 (s, 1H), 7.06-7.00 (m, 1H), 6.88-6.81 (m, 1H), 4.90 (s, 1H), 4.30-4.20 (m, 2H), 3.17 (s, 3H); LCMS: 316.3 (M+1); (column; X-Select CSH C-18 (50×3.0 mm, 3.5 μm); RT 4.34 min. 0.05% Aq TFA: ACN; 0.80 mL/min); TLC: 50% EtOAc:hexanes ($R_f$: 0.7).

Example 80

Synthesis of 2-chloro-7-(4-chloro-2-(trifluoromethyl) phenyl)-8-methyl-7, 8-dihydro-6H-pyrimido [5, 4-b] [1, 4] oxazine

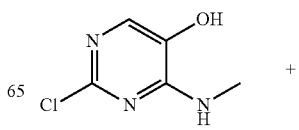

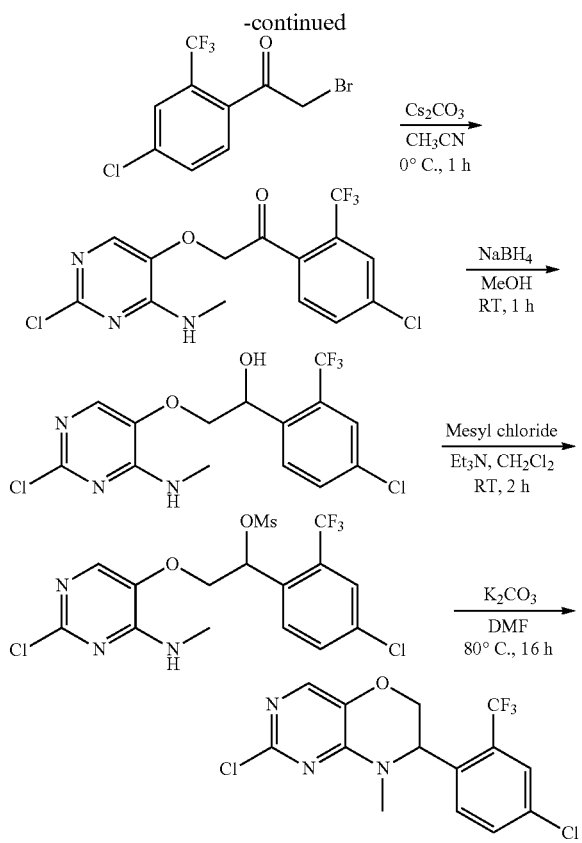

Synthesis of 1-(4-chloro-2-(trifluoromethyl) phenyl)-2-((2-chloro-4-(methylamino) pyrimidin-5-yl) oxy) ethan-1-one To a stirred solution of 2-chloro-4-(methylamino) pyrimidin-5-ol (250 mg, 1.57 mmol) in CH₃CN (10 mL) under an argon atmosphere was added cesium carbonate (1 g, 3.14 mmol) at 0° C. After stirring 10 min, 2-bromo-1-(4-chloro-2-(trifluoromethyl) phenyl) ethan-1-one (560 mg, 1.88 mmol) was added to the reaction mixture and stirred for 1 h. After consumption of the starting material (monitored by TLC), the reaction was diluted with water (20 mL) and extracted with EtOAc (2×20 mL). The combined organic extracts were dried over sodium sulfate, filtered and concentrated in vacuo. The crude material was purified by column chromatography using 5% EtOAc:hexane to afford 1-(4-chloro-2-(trifluoromethyl) phenyl)-2-((2-chloro-4-(methylamino) pyrimidin-5-yl) oxy) ethan-1-one (200 mg, 30%) as an off-white solid. ¹H-NMR (CDCl₃, 500 MHz): δ 7.78 (s, 1H), 7.66 (d, 1H), 7.50 (s, 1H), 7.43 (d, 1H), 5.70 (s, 1H), 5.00 (s, 2H), 3.02 (d, 3H); TLC: 40% EtOAc: hexanes (R$_f$: 0.6).

Synthesis of 1-(4-chloro-2-(trifluoromethyl) phenyl)-2-((2-chloro-4-(methylamino) pyrimidin-5-yl) oxy) ethan-1-ol To a stirred solution of 1-(4-chloro-2-(trifluoromethyl) phenyl)-2-((2-chloro-4-(methylamino) pyrimidin-5-yl) oxy) ethan-1-one (200 mg, 0.52 mmol) in MeOH (5 mL) under an argon atmosphere was added sodium borohydride (29 mg, 0.78 mmol) at 0° C. The reaction mixture was warmed to room temperature and stirred for 1 h. After consumption of the starting material (monitored by TLC), the volatile components were evaporated in vacuo, water (20 mL) was added and extracted with EtOAc (2×20 mL). The combined organic extracts were dried over sodium sulfate, filtered and concentrated in vacuo to afford 1-(4-chloro-2-(trifluoromethyl) phenyl)-2-((2-chloro-4-(methylamino) pyrimidin-5-yl) oxy) ethan-1-ol (150 mg, 75%) as a pale yellow solid used without further purification. ¹H-NMR (CDCl₃, 500 MHz): δ 7.80 (d, 1H), 7.67 (s, 1H), 7.61 (d, 1H), 7.50 (br s, 1H), 5.60 (br s, 1H), 5.55-5.49 (m, 1H), 4.10-4.07 (m, 1H), 4.01-3.97 (m, 1H), 3.05 (d, 3H), 2.67 (s, 1H); LCMS: 382.2 (M+1); (column; X-Select CSH C-18 (50×3.0 mm, 3.5 μm); RT 3.62 min. 5 mM Aq NH₄OAc: ACN; 0.80 mL/min); TLC: 40% EtOAc:hexanes (R$_f$: 0.5).

Synthesis of 1-(4-chloro-2-(trifluoromethyl) phenyl)-2-((2-chloro-4-(methylamino) pyrimidin-5-yl) oxy) ethyl methanesulfonate To a stirred solution of 1-(4-chloro-2-(trifluoromethyl) phenyl)-2-((2-chloro-4-(methylamino) pyrimidin-5-yl) oxy) ethan-1-ol (150 mg, 0.39 mmol) in CH₂Cl₂ (4 mL) under an argon atmosphere were added triethylamine (0.1 mL, 0.78 mmol) followed by mesyl chloride (0.05 mL, 0.58 mmol) at 0° C. The reaction mixture was warmed to room temperature for 2 h. After consumption of the starting material (monitored by TLC), the reaction was diluted with water (20 mL) and extracted with CH₂Cl₂ (2×20 mL). The combined organic extracts were dried over sodium sulfate, filtered and concentrated in vacuo to afford 1-(4-chloro-2-(trifluoromethyl) phenyl)-2-((2-chloro-4-(methylamino) pyrimidin-5-yl) oxy) ethyl methanesulfonate (180 mg) as pale yellow solid used without further purification. TLC: 40% EtOAc: hexanes (R$_f$: 0.6).

Synthesis of 2-chloro-7-(4-chloro-2-(trifluoromethyl) phenyl)-8-methyl-7, 8-dihydro-6H-pyrimido [5, 4-b] [1, 4] oxazine To a stirred solution of 1-(4-chloro-2-(trifluoromethyl) phenyl)-2-((2-chloro-4-(methylamino) pyrimidin-5-yl) oxy) ethyl methanesulfonate (180 mg, 0.39 mmol) in DMF (4 mL) under an argon atmosphere was added potassium carbonate (100 mg, 0.78 mmol) at room temperature. The reaction mixture was heated at 80° C. for 16 h. After consumption of the starting material (monitored by TLC), the reaction was diluted with water (2 mL) and extracted with EtOAc (2×20 mL). The combined organic extracts were dried over sodium sulfate, filtered and concentrated in vacuo. The crude material was purified by column chromatography using 5% EtOAc:hexane to afford 2-chloro-7-(4-chloro-2-(trifluoromethyl) phenyl)-8-methyl-7, 8-dihydro-6H-pyrimido [5, 4-b] [1, 4] oxazine (140 mg, 36%) as a pale yellow solid. ¹H-NMR (CDCl₃, 400 MHz): δ 7.75 (s, 1H), 7.74 (s, 1H), 7.51 (d, 1H), 7.11 (d, 1H), 5.09-5.07 (m, 1H), 4.28-4.26 (m, 1H), 4.13-4.11 (m, 1H), 3.01 (s, 3H); TLC: 40% EtOAc:hexanes (R$_f$: 0.7).

Example 81

Synthesis of 2-chloro-7-(2-chloro-4, 5-difluorophenyl)-7, 8-dihydro-6H-pyrimido [5, 4-b] [1, 4] oxazine

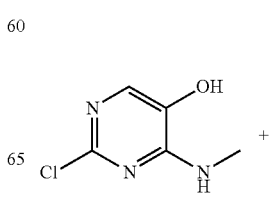

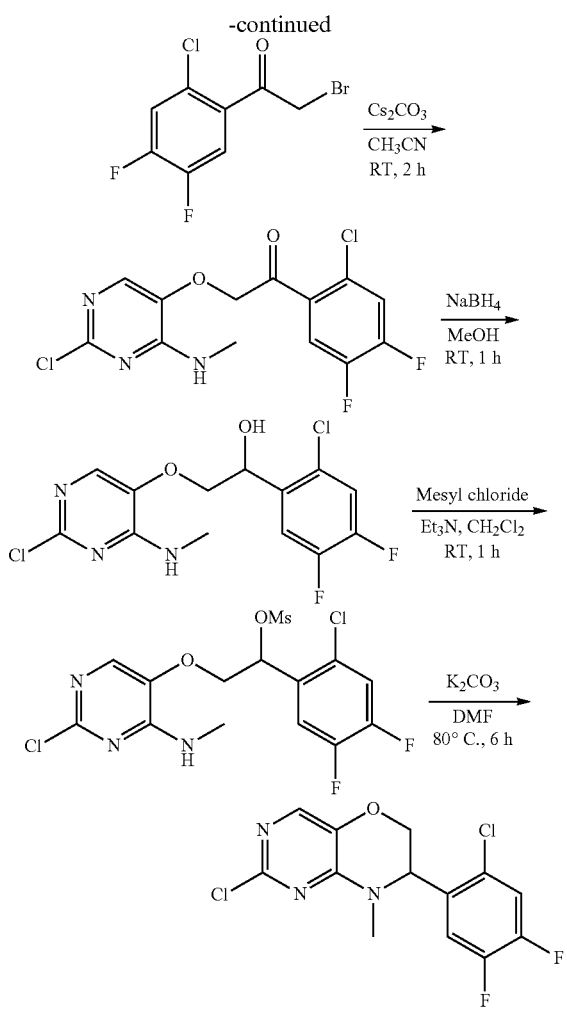

Synthesis of 1-(2-chloro-4, 5-difluorophenyl)-2-((2-chloro-4-(methylamino) pyrimidin-5-yl) oxy) ethan-1-one To a stirred solution of 2-chloro-4-(methylamino) pyrimidin-5-ol (1.47 g, 9.24 mmol) in CH$_3$CN (25 mL) under an argon atmosphere were added cesium carbonate (6 g, 18.49 mmol) and 2-bromo-1-(2-chloro-4, 5-difluorophenyl) ethan-1-one (2.5 g, 9.29 mmol) at room temperature. The reaction mixture was stirred at room temperature for 2 h. After consumption of the starting material (monitored by TLC), the reaction was diluted with water (50 mL) and extracted with EtOAc (2×50 mL). The combined organic extracts were dried over sodium sulfate, filtered and concentrated in vacuo to afford 1-(2-chloro-4, 5-difluorophenyl)-2-((2-chloro-4-(methylamino) pyrimidin-5-yl) oxy) ethan-1-one (2.5 g, 78%) as an off-white solid used without further purification. $^1$H-NMR (DMSO-d$_6$, 500 MHz): δ 7.92-7.80 (m, 3H), 7.60 (s, 1H), 4.28 (d, 1H), 4.08 (d, 1H), 2.76 (s, 3H); TLC: 30% EtOAc:hexanes (R$_f$: 0.5).

Synthesis of 1-(2-chloro-4, 5-difluorophenyl)-2-((2-chloro-4-(methylamino) pyrimidin-5-yl) oxy) ethan-1-ol To a stirred solution of 1-(2-chloro-4, 5-difluorophenyl)-2-((2-chloro-4-(methylamino) pyrimidin-5-yl) oxy) ethan-1-one (2.5 g, 7.18 mmol) in MeOH (25 mL) under an argon atmosphere was added sodium borohydride (531 mg, 14.36 mmol) at 0° C. The reaction mixture was warmed to room temperature and stirred for 1 h. After consumption of the starting material (monitored by TLC), the volatile components were evaporated in vacuo. The residue was diluted with water (50 mL) and extracted with CH$_2$Cl$_2$ (2×50 mL). The combined organic extracts were dried over sodium sulfate, filtered and concentrated in vacuo to afford 1-(2-chloro-4, 5-difluorophenyl)-2-((2-chloro-4-(methylamino) pyrimidin-5-yl) oxy) ethan-1-ol (2.2 g) as an off-white solid used without further purification. LCMS: 350 (M+); (column; X-Select CSH C-18 (50×3.0 mm, 3.5 μm); RT 3.39 min. 5 mM Aq NH$_4$OAc: ACN; 0.80 mL/min); TLC: 50% EtOAc:hexanes (R$_f$: 0.4).

Synthesis of 1-(2-chloro-4, 5-difluorophenyl)-2-((2-chloro-4-(methylamino) pyrimidin-5-yl) oxy) ethyl methanesulfonate To a stirred solution of 1-(2-chloro-4, 5-difluorophenyl)-2-((2-chloro-4-(methylamino) pyrimidin-5-yl) oxy) ethan-1-ol (2.2 g, 6.28 mmol) in CH$_2$Cl$_2$ (25 mL) under an argon atmosphere were added triethylamine (1.26 g, 12.57 mmol) and mesyl chloride (859 mg, 7.54 mmol) at room temperature. The reaction mixture was stirred at room temperature for 1 h. After consumption of the starting material (monitored by TLC), the reaction was diluted with water (50 mL) and extracted with CH$_2$Cl$_2$ (2×50 mL). The combined organic extracts were dried over sodium sulfate, filtered and concentrated in vacuo to afford 1-(2-chloro-4, 5-difluorophenyl)-2-((2-chloro-4-(methylamino) pyrimidin-5-yl) oxy) ethyl methanesulfonate (2.5 g) as an off-white solid used without further purification. LCMS: 428 (M+); (column; X-Select CSH C-18 (50×3.0 mm, 3.5 μm); RT 3.39 min. 5 mM Aq NH$_4$OAc: ACN; 0.80 mL/min); TLC: 50% EtOAc: hexanes (R$_f$: 0.6).

Synthesis of 2-chloro-7-(2-chloro-4, 5-difluorophenyl)-8-methyl-7, 8-dihydro-6H-pyrimido [5, 4-b] [1, 4] oxazine To a stirred solution of 1-(2-chloro-4, 5-difluorophenyl)-2-((2-chloro-4-(methylamino) pyrimidin-5-yl) oxy) ethyl methanesulfonate (2.5 g, 5.84 mmol) in DMF (25 mL) under an argon atmosphere was added potassium carbonate (1.61 g, 11.68 mmol) at room temperature. The reaction mixture was heated at 80° C. for 6 h. After consumption of the starting material (monitored by TLC), the reaction was diluted with water (200 mL) and extracted with EtOAc (2×50 mL). The combined organic extracts were washed with water (50 mL), dried over sodium sulfate, filtered and concentrated in vacuo. The crude material was purified by column chromatography using 5% EtOAc:hexane to afford 2-chloro-7-(2-chloro-4, 5-difluorophenyl)-8-methyl-7, 8-dihydro-6H-pyrimido [5, 4-b] [1, 4] oxazine (1.3 g, 68%) as an off-white solid. $^1$H-NMR (DMSO-d$_6$, 400 MHz): δ 7.90-7.87 (m, 1H), 7.79 (s, 1H), 7.18-7.10 (m, 1H), 5.19-5.17 (m, 1H), 4.30 (s, 2H), 3.01 (s, 3H); LCMS: 332.1 (M+2); (column; X-Select CSH C-18 (50×3.0 mm, 3.5 μm); RT 3.79 min. 5 mM Aq NH$_4$OAc: ACN; 0.80 mL/min); TLC: 30% EtOAc:hexanes (R$_f$: 0.7).

Example 82

Synthesis of 2-chloro-7-(5-fluoro-2-(trifluoromethyl) phenyl)-8-methyl-7, 8-dihydro-6H-pyrimido [5, 4-b] [1, 4] oxazine

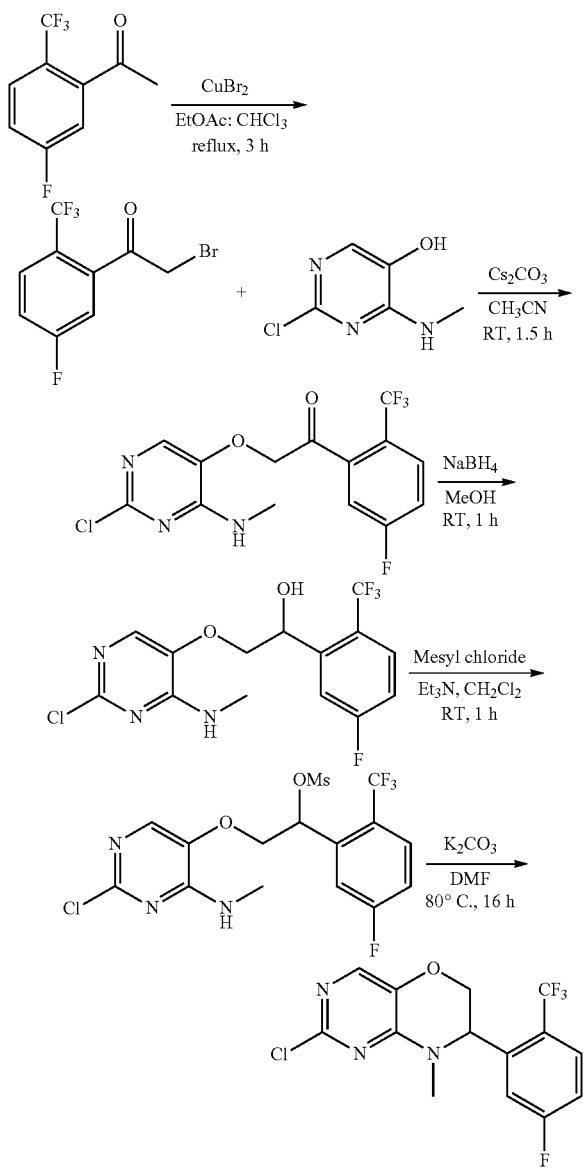

Synthesis of 2-bromo-1-(5-fluoro-2-(trifluoromethyl) phenyl) ethan-1-one

To a stirred solution of copper bromide (4.1 g, 18.40 mmol) in EtOAc (25 mL) under an argon atmosphere was added 1-(5-fluoro-2-(trifluoromethyl) phenyl) ethan-1-one (2 g, 9.70 mmol) in chloroform (10 mL) at 80° C. and stirred for 3 h. After consumption of the starting material (monitored by TLC), the reaction was filtered, washed with CHCl$_3$ and concentrated in vacuo to afford 2-bromo-1-(5-fluoro-2-(trifluoromethyl) phenyl) ethan-1-one (2 g) as a yellow liquid used without further purification. $^1$H-NMR (CDCl$_3$, 500 MHz): δ 7.79-7.72 (m, 1H); 7.31 (t, 1H); 7.20 (d, 1H); 4.32 (s, 2H); UPLC (column; Acquity UPLC BEH C-18, 2.1×50 mm, 1.7 μm); RT 2.45 min. ACN: 0.025% Aq TFA; 0.5 ml/min; TLC: 10% EtOAc:hexane (R$_f$: 0.4).

Synthesis of 2-((2-chloro-4-(methylamino) pyrimidin-5-yl) oxy)-1-(5-fluoro-2-(trifluoromethyl) phenyl) ethan-1-one To a stirred solution of 2-chloro-4-(methylamino) pyrimidin-5-ol (1.2 g, 7.50 mmol) in CH$_3$CN (40 mL) under an argon atmosphere were added cesium carbonate (4.9 g, 15.10 mmol) and 2-bromo-1-(5-fluoro-2-(trifluoromethyl) phenyl) ethan-1-one (2.1 g, 7.50 mmol) at room temperature. The reaction mixture was stirred at room temperature for 1.5 h. After consumption of the starting material (monitored by TLC), the reaction was diluted with water (50 mL) and extracted with EtOAc (2×50 mL). The combined organic extracts were dried over sodium sulfate, filtered and concentrated in vacuo. The crude material was purified by column chromatography using 20-30% EtOAc:hexanes to afford 2-((2-chloro-4-(methylamino) pyrimidin-5-yl) oxy)-1-(5-fluoro-2-(trifluoromethyl) phenyl) ethan-1-one (1.2 g, 47%) as an off-white solid. LCMS: 364.3 (M+1); (column; X-Select CSH C-18 (50×3.0 mm, 3.5 μm); RT 4.31 min 0.05% Aq TFA: ACN; 0.80 mL/min); TLC: 30% EtOAc: hexane (R$_f$: 0.6).

Synthesis of 2-((2-chloro-4-(methylamino) pyrimidin-5-yl) oxy)-1-(5-fluoro-2-(trifluoromethyl) phenyl) ethan-1-ol To a stirred solution of 2-((2-chloro-4-(methylamino) pyrimidin-5-yl) oxy)-1-(5-fluoro-2-(trifluoromethyl) phenyl) ethan-1-one (300 mg, 0.82 mmol) in MeOH (3 mL) under an argon atmosphere was added sodium borohydride (62 mg, 1.65 mmol) at 0° C. The reaction mixture was warmed to room temperature and stirred for 1 h. After consumption of the starting material (monitored by TLC), the volatile components were evaporated in vacuo. The residue was diluted with water (10 mL) and extracted with CH$_2$Cl$_2$ (2×10 mL). The combined organic extracts were dried over sodium sulfate, filtered and concentrated in vacuo to afford 2-((2-chloro-4-(methylamino) pyrimidin-5-yl) oxy)-1-(5-fluoro-2-(trifluoromethyl) phenyl) ethan-1-ol (300 mg) as an off-white solid used without further purification. LCMS: 366.3 (M+1); (column; X-Select CSH C-18 (50×3.0 mm, 3.5 μm); RT 4.03 min. 0.05% Aq TFA: ACN; 0.80 mL/min); TLC: 30% EtOAc:hexane (R$_f$: 0.6).

Synthesis of 2-((2-chloro-4-(methylamino) pyrimidin-5-yl) oxy)-1-(5-fluoro-2-(trifluoromethyl) phenyl) ethyl methanesulfonate To a stirred solution of 2-((2-chloro-4-(methylamino) pyrimidin-5-yl) oxy)-1-(5-fluoro-2-(trifluoromethyl) phenyl) ethan-1-ol (300 mg, 0.82 mmol) in CH$_2$Cl$_2$ (10 mL) under an argon atmosphere were added mesylchloride (140 mg, 1.23 mmol) and triethylamine (166 mg, 1.64 mmol) at 0° C. The reaction mixture was warmed to room temperature and stirred for 1 h. After consumption of the starting material (monitored by TLC), the reaction was diluted with water (10 mL) and extracted with CH$_2$Cl$_2$ (2×10 mL). The combined organic extracts were dried over sodium sulfate, filtered and concentrated in vacuo to afford 2-((2-chloro-4-(methylamino) pyrimidin-5-yl) oxy)-1-(5-fluoro-2-(trifluoromethyl) phenyl) ethyl methanesulfonate (405 mg) as an off-white solid used without further purification. LCMS: 444.3 (M+1);

(column; X-Select CSH C-18 (50×3.0 mm, 3.5 μm); RT 4.28 min. 0.05% Aq TFA: ACN; 0.80 mL/min); TLC: 30% EtOAc:hexane (R$_f$: 0.6).

Synthesis of 2-chloro-7-(5-fluoro-2-(trifluoromethyl) phenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(5-fluoro-2-(trifluoromethyl) phenyl) ethyl methanesulfonate (400 mg, 0.90 mmol) in DMF (4 mL) under an argon atmosphere was added potassium carbonate (248 mg, 1.80 mmol) at room temperature. The reaction mixture was stirred at 80° C. for 16 h. After consumption of the starting material (monitored by TLC), the reaction was diluted with water (20 mL) and extracted with EtOAc (2×20 mL). The combined organic extracts were dried over sodium sulfate, filtered and concentrated in vacuo. The crude material was purified by column chromatography using 10-20% EtOAc:hexanes to afford 2-chloro-7-(5-fluoro-2-(trifluoromethyl) phenyl)-8-methyl-7, 8-dihydro-6H-pyrimido [5, 4-b] [1, 4] oxazine (200 mg, 64%) as a pale yellow solid. $^1$H-NMR (DMSO-d$_6$, 400 MHz): δ 7.80 (s, 1H), 7.79-7.74 (m, 1H), 7.25 (t, 1H), 6.90-6.86 (m, 1H), 5.01-5.00 (m, 1H), 4.27-4.22 (m, 1H), 4.15-4.10 (m, 1H), 3.06 (s, 3H); UPLC (column; Acquity UPLC BEH C-18, 2.1×50 mm, 1.7 μm); RT 2.61 min. ACN: 0.025% Aq TFA; 0.5 ml/min; TLC: 30% EtOAc:hexane (R$_f$: 0.6).

Example 83

Synthesis of (S)-(2-chloro-8-methyl-7, 8-dihydro-6H-pyrimido [5, 4-b] [1, 4] oxazin-7-yl) methanol

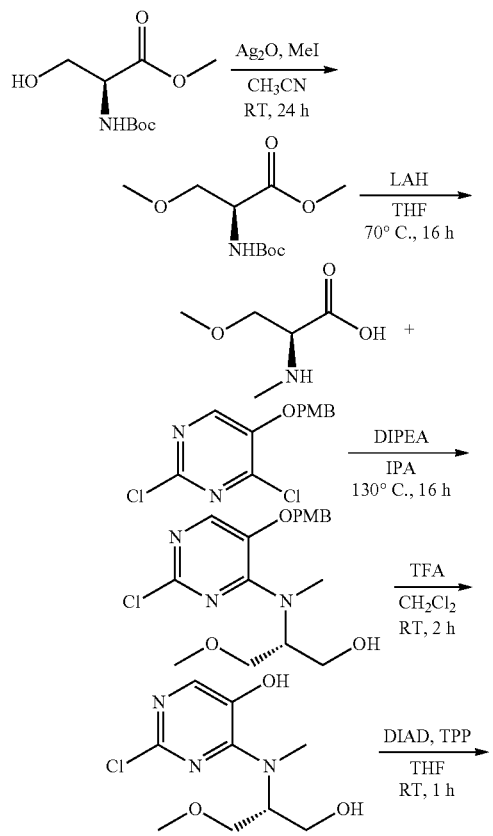

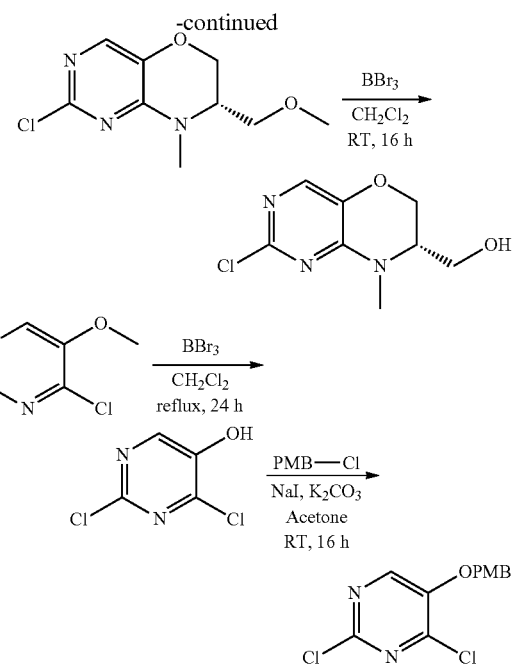

Synthesis of (S)-(2-chloro-8-methyl-7, 8-dihydro-6H-pyrimido [5, 4-b] [1, 4] oxazin-7-yl) methanol To a stirred solution of methyl (tert-butoxycarbonyl)-L-serinate (5 g, 22.80 mmol) in CH$_3$CN (200 mL) under an argon atmosphere were added silver oxide (26 g, 114.15 mmol) and methyl iodide (32 g, 228.10 mmol) at room temperature. The reaction mixture was stirred at room temperature for 24 h in the absence of light. After consumption of the starting material (monitored by TLC), the reaction was filtered and the filtrate concentrated in vacuo. The crude material was purified by column chromatography using 10% EtOAc:hexanes to afford (S)-(2-chloro-8-methyl-7, 8-dihydro-6H-pyrimido [5, 4-b] [1, 4] oxazin-7-yl) methanol (2.5 g, 47%) as a colorless liquid. $^1$H-NMR (CDCl$_3$, 400 MHz): δ 5.40-5.31 (m, 1H), 4.44-4.38 (m, 1H), 3.80-3.78 (m, 1H), 3.77 (s, 3H), 3.60-3.56 (m, 1H), 3.33 (s, 3H), 1.44 (s, 9H); TLC: 30% EtOAc:hexane (R$_f$: 0.5).

Synthesis of (R)-3-methoxy-2-(methylamino) propan-1-ol

To a stirred solution of (S)-(2-chloro-8-methyl-7, 8-dihydro-6H-pyrimido [5, 4-b] [1, 4] oxazin-7-yl) methanol (3.8 g, 16.30 mmol) in THF (100 mL) under an argon atmosphere was added lithium aluminum hydride (1.8 g, 48.92 mmol) portion wise at 0° C. The reaction mixture was stirred at 70° C. for 16 h. After consumption of the starting material (monitored by TLC), the reaction mixture was cooled to 0° C., quenched with water (2 mL), basified with a 15% sodium hydroxide solution (2 mL), water (3×2 mL) and stirred for 30 min. Then the reaction was filtered, the filtrate was dried over sodium sulfate, filtered and concentrated in vacuo to afford (R)-3-methoxy-2-(methylamino) propan-1-ol (1.7 g, 87%) as a colorless liquid. $^1$H-NMR (DMSO-d$_6$, 500 MHz): δ 3.46-3.32 (m, 2H), 3.30-3.26 (m, 3H), 3.25-3.21 (m, 4H), 2.52-2.48 (m, 1H), 2.30 (s, 3H); TLC: 50% EtOAc:hexane (R$_f$: 0.2).

Synthesis of 2, 4-dichloropyrimidin-5-ol

To a stirred solution of 2, 4-dichloro-5-methoxypyrimidine (20 g, 111.73 mmol) in $CH_2Cl_2$ (280 mL) under an argon atmosphere was added boron tribromide (54 mL, 558.65 mmol) drop-wise at 0° C. The reaction mixture was refluxed for 24 h. After consumption of the starting material (monitored by TLC), the reaction mixture was cooled to 0° C., basified with a 1N sodium hydroxide solution and stirred for 1 h. Then the reaction was acidified with acetic acid (pH 2-4) and the aqueous layer extracted with 5% MeOH:$CH_2Cl_2$ (2×250 mL). The combined organic extracts were dried over sodium sulfate, filtered and concentrated in vacuo to afford 2, 4-dichloropyrimidin-5-ol (12 g, 64%) as pale yellow solid. $^1$H-NMR (DMSO-$d_6$, 500 MHz): δ 8.33 (s, 1H), 4.00 (s, 1H); TLC: 30% EtOAc:hexane ($R_f$: 0.6).

Synthesis of 2, 4-dichloro-5-((4-methoxybenzyl)oxy) pyrimidine

To a stirred solution of 2, 4-dichloropyrimidin-5-ol (6 g, 36.50 mmol) in acetone (60 mL) under an argon atmosphere were added sodium iodide (600 mg, 3.65 mmol), potassium carbonate (13 g, 91.25 mmol) and p-methoxy benzylchloride (8.6 g, 54.87 mmol) drop-wise at room temperature. The reaction was stirred at room temperature for 16 h. After consumption of the starting material (monitored by TLC), the reaction was concentrated in vacuo. The crude material was purified by column chromatography using 10% EtOAc:hexanes (2% triethylamine) to afford 2, 4-dichloro-5-((4-methoxybenzyl) oxy) pyrimidine (5 g, 48%) as an off-white solid. $^1$H-NMR (DMSO-$d_6$, 400 MHz): δ 8.63 (s, 1H), 7.41 (d, 2H), 6.99 (d, 2H), 5.29 (s, 2H), 3.75 (s, 3H); TLC: 30% EtOAc:hexane ($R_f$: 0.6).

Synthesis of (R)-2-((2-chloro-5-((4-methoxybenzyl)oxy) pyrimidin-4-yl) (methyl) amino)-3-methoxy-propan-1-ol To a stirred solution of (R)-3-methoxy-2-(methylamino) propan-1-ol (1.1 g, 92.20 mmol) in isopropyl alcohol (11 mL) under an argon atmosphere were added diisopropylethylamine (11 mL, 101.42 mmol) and 2, 4-dichloro-5-((4-methoxybenzyl) oxy) pyrimidine (2.9 g, 101.42 mmol) at room temperature. The reaction mixture was stirred at 130° C. for 16 h. After consumption of the starting material (monitored by TLC), the volatile components were evaporated in vacuo. The crude material was purified by column chromatography using 20% EtOAc:hexanes to afford (R)-2-((2-chloro-5-((4-methoxybenzyl) oxy) pyrimidin-4-yl) (methyl) amino)-3-methoxypropan-1-ol (1.3 g, 38%) as a colorless liquid. $^1$H-NMR (CDCl$_3$, 400 MHz): δ 7.72 (s, 1H), 7.31 (d, 2H), 6.90 (d, 2H), 4.94 (s, 2H), 4.85-4.79 (m, 1H), 3.81 (s, 3H), 3.80-3.79 (m, 2H), 3.60-3.50 (m, 2H), 3.30 (s, 3H), 3.11 (s, 3H), 2.41-2.39 (m, 1H); LCMS: 368.5 (M+1); (column; X-Select CSH C-18 (50×3.0 mm, 3.5 μm); RT 3.77 min. 0.05% Aq TFA: ACN; 0.80 mL/min); TLC: 50% EtOAc:hexane ($R_f$: 0.4).

Synthesis of (R)-2-chloro-4-((1-hydroxy-3-methoxypropan-2-yl) (methyl) amino) pyrimidin-5-ol To a stirred solution of (R)-2-((2-chloro-5-((4-methoxybenzyl) oxy) pyrimidin-4-yl) (methyl) amino)-3-methoxypropan-1-ol (2.2 g, 5.99 mmol) in $CH_2Cl_2$ (34 mL) was added trifluoroacetic acid (6 mL) under an argon atmosphere at 0° C. The reaction mixture was warmed to room temperature and stirred for 2 h. After consumption of the starting material (monitored by TLC), the reaction was diluted with water (20 mL) and extracted with $CH_2Cl_2$ (2×20 mL). The aqueous layer was basified with a saturated sodium bicarbonate solution (50 mL) and extracted with $CH_2Cl_2$ (2×100 mL). The combined organic extracts were dried over sodium sulfate, filtered and concentrated in vacuo to afford (R)-2-chloro-4-((1-hydroxy-3-methoxypropan-2-yl) (methyl) amino) pyrimidin-5-ol (700 mg, 47%) as an off-white solid. $^1$H-NMR (CDCl$_3$, 500 MHz): δ 7.81 (s, 1H), 4.41-4.39 (m, 1H), 3.89-3.81 (m, 1H), 3.78-3.74 (m, 1H), 3.60-3.51 (m, 2H), 3.41 (s, 3H), 2.99 (s, 3H); LCMS: 247.8 (M+1); (column; X-Select CSH C-18 (50×3.0 mm, 3.5 μm); RT 1.88 min 0.05% Aq TFA: ACN; 0.80 mL/min); TLC: 70% EtOAc:hexane ($R_f$: 0.3).

Synthesis of (S)-2-chloro-7-(methoxymethyl)-8-methyl-7, 8-dihydro-6H-pyrimido [5, 4-b] [1, 4] oxazine To a stirred solution of (R)-2-chloro-4-((1-hydroxy-3-methoxypropan-2-yl) (methyl) amino) pyrimidin-5-ol (650 mg, 2.63 mmol) in THF (15 mL) under an argon atmosphere were added triphenylphosphine (1 g, 3.95 mmol) and DIAD (800 mg, 3.95 mmol) at 0° C. The reaction mixture was warmed to room temperature and stirred for 1 h. After consumption of the starting material (monitored by TLC), the volatile components were concentrated in vacuo. The crude material was purified by column chromatography using 20% EtOAc:hexanes to afford (S)-2-chloro-7-(methoxymethyl)-8-methyl-7, 8-dihydro-6H-pyrimido [5, 4-b] [1, 4] oxazine (450 mg, 75%) as a colorless liquid. $^1$H-NMR (CDCl$_3$, 400 MHz): δ 7.64 (s, 1H), 4.38-4.34 (m, 1H), 3.91-3.89 (m, 1H), 3.60-3.55 (m, 1H), 3.54-3.51 (m, 1H), 3.50-3.42 (m, 1H), 3.39 (s, 3H), 3.20 (s, 3H); LCMS: 229.8 (M+1); (column; X-Select CSH C-18 (50×3.0 mm, 3.5 μm); RT 2.56 min 0.05% Aq TFA: ACN; 0.80 mL/min); TLC: 50% EtOAc:hexane ($R_f$: 0.6).

Synthesis of (S)-(2-chloro-8-methyl-7, 8-dihydro-6H-pyrimido [5, 4-b] [1, 4] oxazin-7-yl) methanol To a stirred solution of (S)-2-chloro-7-(methoxymethyl)-8-methyl-7, 8-dihydro-6H-pyrimido [5, 4-b] [1, 4] oxazine (450 mg, 1.96 mmol) in $CH_2Cl_2$ (20 mL) was added boron tribromide (1.47 g, 5.89 mmol) under an argon atmosphere at 0° C. The reaction mixture was warmed to room temperature and stirred for 16 h. After consumption of the starting material (monitored by TLC), the reaction was cooled to 0° C., basified with a 2N sodium hydroxide solution, warmed to room temperature and stirred for 30 min. Then the reaction was acidified with acetic acid (pH 3-4) and the aqueous layer extracted with $CH_2Cl_2$ (3×40 mL). The combined organic extracts were dried over sodium sulfate, filtered and concentrated in vacuo to afford (S)-(2-chloro-8-methyl-7, 8-dihydro-6H-pyrimido [5, 4-b] [1, 4] oxazin-7-yl) methanol (300 mg, 71%) as a pale yellow solid. $^1$H-NMR (CDCl$_3$, 400 MHz): δ 7.63 (s, 1H), 4.45-4.40 (m, 1H), 3.94-3.90 (m, 1H), 3.89-3.83 (m, 1H), 3.80-3.73 (m, 1H), 3.57-3.51 (m, 1H), 3.23 (s, 3H); LCMS: 215.8 (M+1); (column; X-Select CSH C-18 (50×3.0 mm, 3.5 μm); RT 1.45 min. 0.05% Aq TFA: ACN; 0.80 mL/min); TLC: 50% EtOAc:hexane ($R_f$: 0.3).

Example 84

Synthesis of N-(3-fluoro-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine

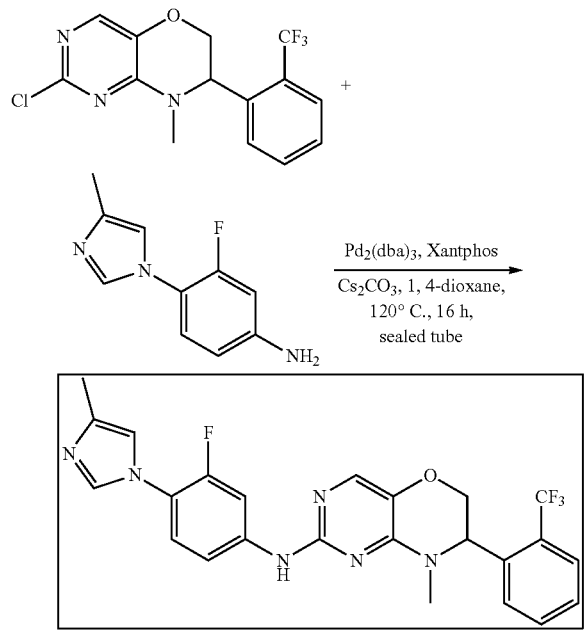

Synthesis of N-(3-fluoro-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine A dry vial charged with $Pd_2(dba)_3$ (35 mg, 0.04 mmol) and Xantphos (66 mg, 0.11 mmol) in 1, 4-dioxane (2.5 mL) at room temperature was degassed and the resultant reaction mixture was stirred at 120° C. for 3 min. A mixture of 2-chloro-8-methyl-7-(2-(trifluoromethyl) phenyl)-7, 8-dihydro-6H-pyrimido [5, 4-b] [1, 4] oxazine (250 mg, 0.75 mmol), 3-fluoro-4-(4-methyl-1H-imidazol-1-yl) aniline (290 mg, 1.51 mmol) and cesium carbonte (346 mg, 1.06 mmol) in 1, 4-dioxane (2.5 mL) was degassed and the catalyst premix was added. The resultant mixture was stirred at 120° C. for 16 h in a sealed tube. After consumption of the starting materials (monitored by TLC and LCMS), the reaction was diluted with water (20 mL) and extracted with EtOAc (2×20 mL). The combined organic extracts were dried over sodium sulfate, filtered and concentrated in vacuo. The crude material was purified by column chromatography using 3% MeOH: $CH_2Cl_2$ to afford Synthesis of N-(3-fluoro-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine (120 mg, 32%) as an off-white solid. $^1$H-NMR (CD$_3$OD, 500 MHz): δ 8.02 (d, 1H), 7.82 (d, 1H), 7.78 (s, 1H), 7.68 (s, 1H), 7.67-7.64 (m, 1H), 7.56 (t, 1H), 7.46-7.43 (m, 1H), 7.36 (t, 2H), 7.10 (s, 1H), 5.13-5.10 (m, 1H), 4.30 (d, 1H), 4.15 (d, 1H), 3.10 (s, 3H), 2.38 (s, 3H); LCMS: 485.4 (M+1); (column; X-Select CSH C-18 (50×3.0 mm, 3.5 μm); RT 3.05 min. 0.05% Aq TFA: ACN; 0.80 mL/min); HPLC (column; Eclipse-XDB-C18 150×4.6 mm, 5 μm); RT 11.79 min. ACN: 5 mM Aq NH$_4$OAc; 1.0 mL/min; TLC: 5% MeOH/CH$_2$Cl$_2$ (R$_f$: 0.3).

Racemic compound of Example 84 was separated using a Chiralpak IA (250×20 mm: 5 μm; (30 mg loading; 0.1% DEA in n-hexane: $CH_2Cl_2$:MeOH (50:50); (A:B: 85:15) as mobile phase) to provide the compound of Example 84A (Fraction I (+)) and the compound of Example 84B (Fraction II (−)).

Example 84A

Synthesis of (+)-N-(3-fluoro-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine

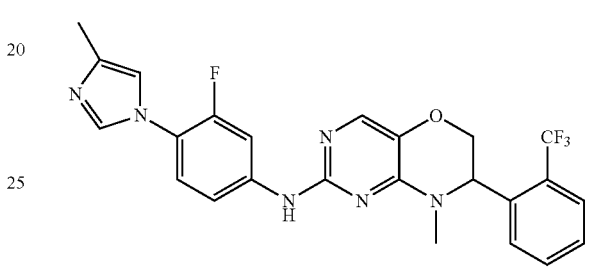

The compound of Example 84A was produced as described in Example 84. Analytical data for product Fraction I (+): $^1$H-NMR (CD$_3$OD, 400 MHz): δ 8.01 (d, 1H), 7.81 (d, 1H), 7.77 (s, 1H), 7.67 (s, 1H), 7.68-7.61 (m, 1H), 7.56 (t, 1H), 7.46-7.43 (m, 1H), 7.39-7.31 (m, 2H), 7.08 (s, 1H), 5.00-4.98 (m, 1H), 4.30 (d, 1H), 4.12 (d, 1H), 3.05 (s, 3H), 2.21 (s, 3H); Mass (ESI): 485.5 [M+1]; LCMS: 485.5 (M+1); (column; X-Select CSH C-18 (50×3.0 mm, 3.5 μm); RT 4.08 min. 5 mM Aq NH$_4$OAc: ACN; 0.80 mL/min); HPLC (column; Eclipse-XDB-C18 150×4.6 mm, 5 μm); RT 11.81 min. ACN: 5 mM Aq NH$_4$OAc; 1.0 mL/min; Chiral HPLC: 100% RT=18.37 min (CHIRALPAK-IA (250×4.6 mm, 5 μm; mobile phase (A) 0.1% DEA in n-hexane (B) $CH_2Cl_2$:MeOH (50:50) (A:B; 85:15); flow Rate: 1.0 mL/min); Optical rotation $[\alpha]_D^{22.99}$: +89.68 (c=0.25, DCM).

Example 84B

Synthesis of (−)-N-(3-fluoro-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine

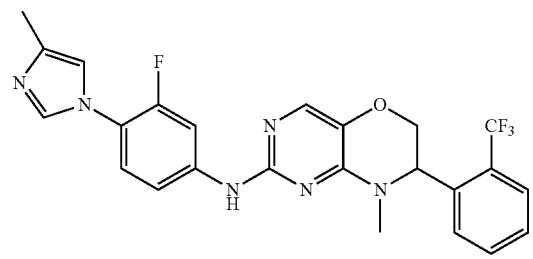

The compound of Example 84B was produced as described in Example 84. Analytical data for product Fraction II (−): $^1$H-NMR (CD$_3$OD, 400 MHz): δ 8.01 (d, 1H), 7.81 (d, 1H), 7.77 (s, 1H), 7.67 (s, 1H), 7.68-7.61 (m, 1H), 7.56 (t, 1H), 7.46-7.43 (m, 1H), 7.39-7.31 (m, 2H), 7.08 (s, 1H), 5.00-4.98 (m, 1H), 4.30 (d, 1H), 4.12 (d, 1H), 3.05 (s, 3H), 2.21 (s, 3H); Mass (ESI): 485.4 [M+1]; LCMS: 485.5 (M+1); (column; X-Select CSH C-18 (50×3.0 mm, 3.5 μm); RT 4.05 min. 5 mM Aq NH$_4$OAc: ACN; 0.80 mL/min); HPLC (column; Eclipse-XDB-C18 150×4.6 mm, 5 μm); RT 11.80 min. ACN: 5 mM Aq NH$_4$OAc; 1.0 mL/min; Chiral HPLC: 98.38% RT=26.04 min (CHIRALPAK-IA (250×4.6 mm, 5 μm; mobile phase (A) 0.1% DEA in n-hexane (B) CH$_2$Cl$_2$:MeOH (50:50) (A:B; 85:15); flow Rate: 1.0 mL/min); Optical rotation [α]$_D^{23.01}$: −82.32 (c=0.25, DCM).

Example 85

Synthesis of 2-(2-chlorophenyl)-N-(3-methoxy-4-(2-methylpyridin-4-yl) phenyl)-1-methyl-2, 3-dihydro-1H-pyrido [3, 4-b] [1, 4] oxazin-7-amine

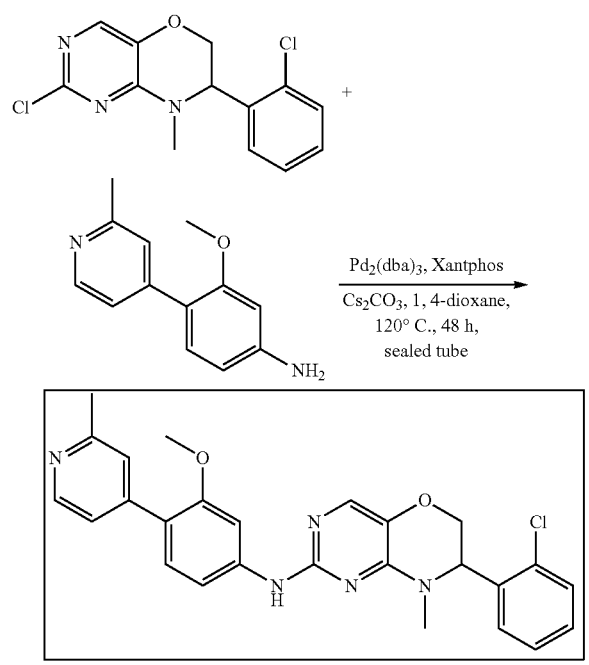

Synthesis of 2-(2-chlorophenyl)-N-(3-methoxy-4-(2-methylpyridin-4-yl) phenyl)-1-methyl-2, 3-dihydro-1H-pyrido [3, 4-b] [1, 4] oxazin-7-amine A dry vial charged with Pd$_2$(dba)$_3$ (36 mg, 0.04 mmol) and Xantphos (69 mg, 0.12 mmol) in 1, 4-dioxane (0.25 mL) at room temperature was degassed and the resultant reaction mixture was stirred at 120° C. for 3 min. A mixture of 2-chloro-7-(2-chlorophenyl)-8-methyl-7, 8-dihydro-6H-pyrimido [5, 4-b] [1, 4] oxazine (250 mg, 0.80 mmol), 3-methoxy-4-(2-methylpyridin-4-yl) aniline (189 mg, 0.88 mmol) and cesium carbonte (364 mg, 1.12 mmol) in 1, 4-dioxane (0.25 mL) was degassed and the catalyst premix was added. The resultant mixture was stirred at 120° C. for 48 h in a sealed tube. After consumption of the starting material (monitored by TLC and LCMS), the reaction was filtered through celite and the filtrate was concentrated in vacuo. The crude material was purified by column chromatography using 3% MeOH: CH$_2$Cl$_2$ to afford 2-(2-chlorophenyl)-N-(3-methoxy-4-(2-methylpyridin-4-yl) phenyl)-1-methyl-2, 3-dihydro-1H-pyrido [3, 4-b] [1, 4] oxazin-7-amine (150 mg, 39%) as an off-white solid. LCMS: 474.5 (M+1); (column; X-Select CSH C-18 (50×3.0 mm, 3.5 μm); RT 3.07 min. 0.05% Aq TFA: ACN; 0.80 mL/min); UPLC (column; Acquity UPLC-BEH-C18 2.1×50 mm, 1.7 μm); RT 1.70 min. ACN: 0.025% Aq TFA; 0.5 mL/min; TLC: 5% MeOH/CH$_2$Cl$_2$ (R$_f$: 0.3).

Racemic compound of Example 85 was separated using a Chiralpak IA (250×20 mm, 5 μm (20 mg loading; 0.1% DEA in n-hexane: DCM:MeOH (50:50); (85:15) as mobile phase) to provide the compound of Example 85A (Fraction I (−)) and the compound of Example 85B (Fraction II (+)).

Example 85A

Synthesis of (−)-2-(2-chlorophenyl)-N-(3-methoxy-4-(2-methylpyridin-4-yl) phenyl)-1-methyl-2, 3-dihydro-1H-pyrido [3, 4-b] [1, 4] oxazin-7-amine

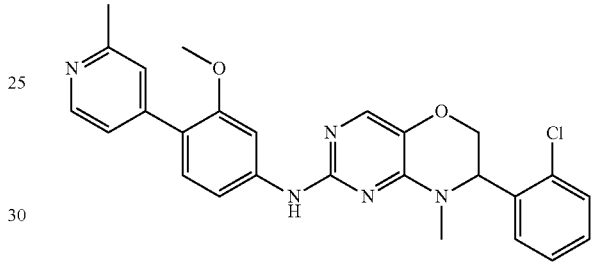

The compound of Example 85A was produced as described in Example 85. Analytical data for product Fraction I (−): $^1$H-NMR (CD$_3$OD, 400 MHz): δ 8.31 (d, 1H), 7.70 (s, 1H), 7.59 (s, 1H), 7.50-7.45 (m, 2H), 7.40 (d, 1H), 7.35-7.28 (m, 4H), 7.09 (d, 1H), 5.20-5.18 (m, 1H), 4.31-4.23 (m, 2H), 3.89 (s, 3H), 3.19 (s, 3H), 2.51 (s, 3H); Mass (ESI): 474.5 [M+1]; LCMS: 474.6 (M+1); (column; X-Select CSH C-18 (50×3.0 mm, 3.5 μm); RT 3.05 min. 0.05% Aq TFA: ACN; 0.80 mL/min); UPLC (column; Acquity UPLC-BEH-C18 2.1×50 mm, 1.7 μm); RT 1.71 min. ACN: 0.025% Aq TFA; 0.5 mL/min; Chiral HPLC: 99.7% RT=11.79 min (CHIRALPAK-IA (250×4.6 mm, 5 μm; mobile phase (A) 0.1% DEA in n-hexane (B) CH$_2$Cl$_2$:MeOH (50:50) (A:B; 80:20); flow Rate: 1.0 mL/min); Optical rotation [α]$_D^{20.00}$: −201.12 (c=0.25, DCM).

Example 85B

Synthesis of (+)-2-(2-chlorophenyl)-N-(3-methoxy-4-(2-methylpyridin-4-yl) phenyl)-1-methyl-2, 3-dihydro-1H-pyrido [3, 4-b] [1, 4] oxazin-7-amine

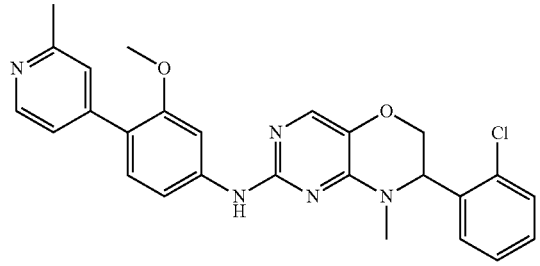

The compound of Example 85B was produced as described in Example 85. Analytical data for product Fraction II (+): $^1$H-NMR (CD$_3$OD, 400 MHz): δ 8.31 (d, 1H), 7.70 (s, 1H), 7.59 (s, 1H), 7.50-7.45 (m, 2H), 7.40 (d, 1H), 7.35-7.28 (m, 4H), 7.09 (d, 1H), 5.20-5.18 (m, 1H), 4.31-4.23 (m, 2H), 3.89 (s, 3H), 3.19 (s, 3H), 2.51 (s, 3H); Mass (ESI): 474.4 [M+1]; LCMS: 474.6 (M+1); (column; X-Select CSH C-18 (50×3.0 mm, 3.5 μm); RT 3.08 min. 0.05% Aq TFA: ACN; 0.80 mL/min); UPLC (column; Acquity UPLC-BEH-C18 2.1×50 mm, 1.7 μm); RT 1.70 min. ACN: 0.025% Aq TFA; 0.5 mL/min; Chiral HPLC: 96.7% RT=12.90 min (CHIRALPAK-IA (250×4.6 mm, 5 μm; mobile phase (A) 0.1% DEA in n-hexane (B) CH$_2$Cl$_2$: MeOH (50:50) (A:B; 80:20); flow Rate: 1.0 mL/min); Optical rotation [α]$_D^{20.00}$: +187.79 (c=0.25, DCM).

Example 86

Synthesis of 7-(2-chloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

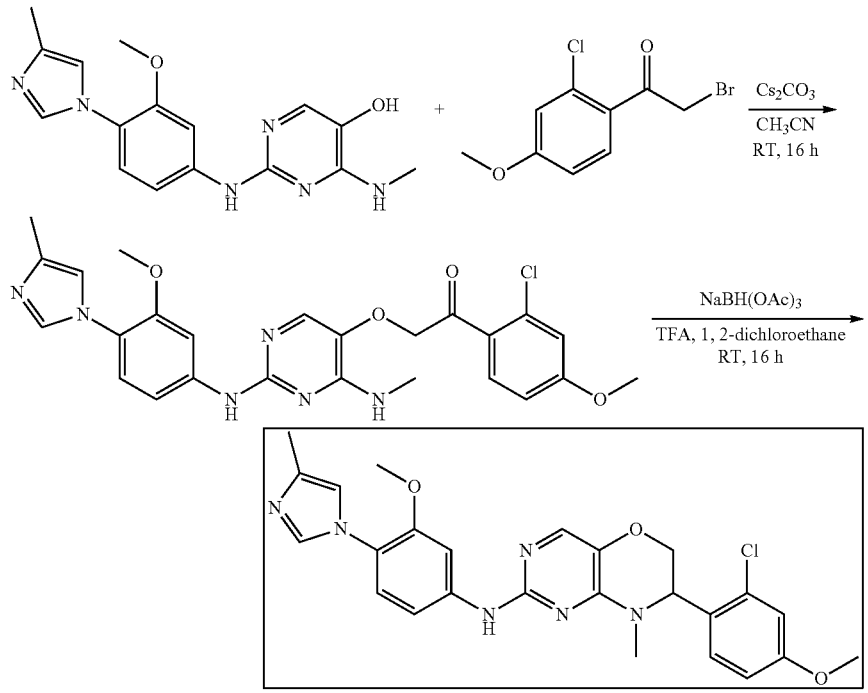

Synthesis of 1-(2-chloro-4-methoxyphenyl)-2-((2-((3-methoxy-4-(4-methyl-1H-imidazol-1-yl) phenyl) amino)-4-(methylamino) pyrimidin-5-yl) oxy) ethan-1-one To a stirred solution of 2-((3-methoxy-4-(4-methyl-1H-imidazol-1-yl) phenyl) amino)-4-(methylamino) pyrimidin-5-ol (100 mg, 0.30 mmol) in CH$_3$CN (1 mL) under an argon atmosphere were added cesium carbonate (200 mg, 0.61 mmol) followed by 2-bromo-1-(2-chloro-4-methoxyphenyl) ethan-1-one (122 mg, 0.33 mmol) at room temperature. The reaction mixture was stirred at room temperature for 16 h. After consumption of the starting material (monitored by TLC), the reaction was diluted with water (20 mL) and extracted with CH$_2$Cl$_2$ (2×20 mL). The combined organic extracts were dried over sodium sulfate, filtered and concentrated in vacuo to afford 1-(2-chloro-4-methoxyphenyl)-2-((2-((3-methoxy-4-(4-methyl-1H-imidazol-1-yl) phenyl) amino)-4-(methylamino) pyrimidin-5-yl) oxy) ethan-1-one (90 mg) as pale brown solid used without further purification. LCMS: 510.3 (M+1); (column; X-Select CSH C-18 (50×3.0 mm, 3.5 μm); RT 2.92 min. 0.05% Aq TFA: ACN; 0.8 mL/min); TLC: 5% MeOH/CH$_2$Cl$_2$ (R$_f$: 0.4).

Synthesis of 7-(2-chloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a stirred solution of 1-(2-chloro-4-methoxyphenyl)-2-((2-((3-methoxy-4-(4-methyl-1H-imidazol-1-yl) phenyl) amino)-4-(methylamino) pyrimidin-5-yl) oxy) ethan-1-one (160 mg, 0.31 mmol) in 1, 2-dichloroethane (1 mL) under an argon atmosphere were added trifluoroacetic acid (35.8 mg, 0.31 mmol) followed by sodium triacetoxyborohydride (140 mg, 0.66 mmol) at room temperature. The reaction mixture was stirred at room temperature for 16 h. After consumption of the starting material (monitored by TLC), the reaction was quenched with a 1 N sodium hydroxide solution (20 mL) and extracted with CH$_2$Cl$_2$ (2×20 mL). The combined organic extracts were dried over sodium sulfate, filtered and concentrated in vacuo. The crude material was purified by column chromatography using 2% MeOH: CH$_2$Cl$_2$ to afford 7-(2-chloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (20 mg, 13%) as a white solid. $^1$H-NMR (CD$_3$OD, 400 MHz): δ 7.76 (s, 1H), 7.67 (s, 1H), 7.58 (s, 1H), 7.27-7.23 (m, 1H), 7.20-7.18 (m, 1H), 7.06 (s, 1H), 7.01-6.97 (m, 2H), 6.89-6.86 (m, 1H), 5.00-4.98 (m, 1H), 4.22-4.20 (m, 2H), 3.83 (s, 3H), 3.80 (s, 3H), 3.13 (s, 3H), 2.21 (s, 3H); Mass (ESI): 493.1 [M+1];

LCMS: 493 (M+1); (column; X-Select CSH C-18 (50×3.0 mm, 3.5 μm); RT 2.50 min. 0.05% Aq TFA: ACN; 0.8 mL/min); UPLC (column; Acquity UPLC BEH C-18, 2.1× 50 mm, 1.7 μm); RT 1.73 min. ACN: 0.025% TFA (Aq); 0.50 mL/min; TLC: 5% MeOH/CH$_2$Cl$_2$ (R$_f$: 0.5).

Example 87

Synthesis of 7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

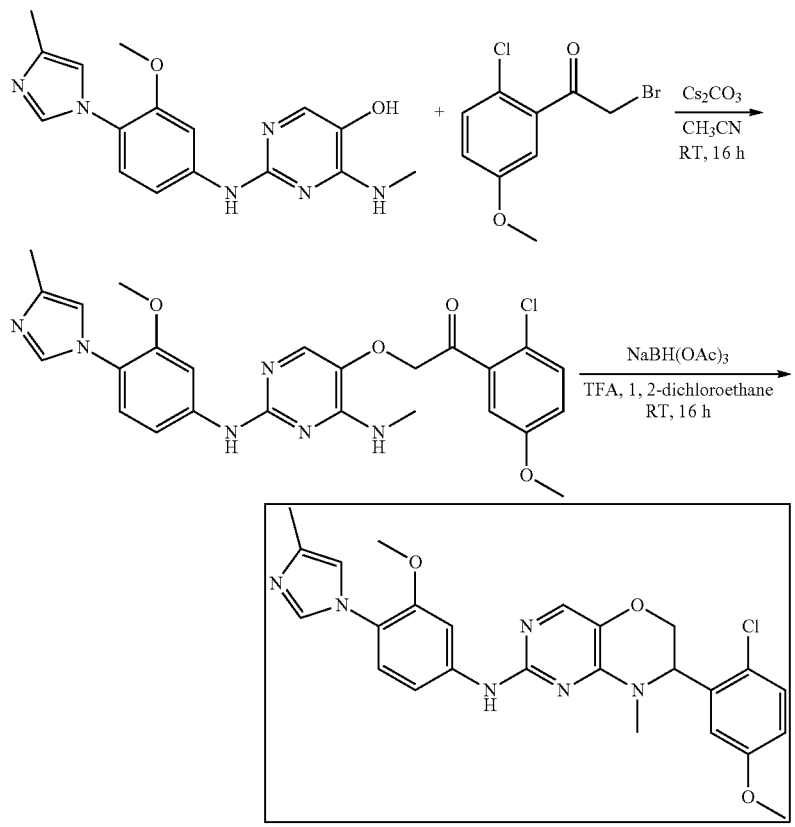

Synthesis of 1-(2-chloro-5-methoxyphenyl)-2-((2-((3-methoxy-4-(4-methyl-1H-imidazol-1-yl) phenyl) amino)-4-(methylamino) pyrimidin-5-yl) oxy) ethan-1-one To a stirred solution of 2-((3-methoxy-4-(4-methyl-1H-imidazol-1-yl) phenyl) amino)-4-(methylamino) pyrimidin-5-ol (50 mg, 0.15 mmol) in CH$_3$CN (0.5 mL) under an argon atmosphere were added cesium carbonate (100 mg, 0.30 mmol) followed by 2-bromo-1-(2-chloro-5-methoxyphenyl) ethan-1-one (61 mg, 0.16 mmol) at room temperature. The reaction mixture was stirred at room temperature for 16 h. After consumption of the starting material (monitored by TLC), the reaction was diluted with water (20 mL) and extracted with EtOAc (2×20 mL). The combined organic extracts were dried over sodium sulfate, filtered and concentrated in vacuo to afford 1-(2-chloro-5-methoxyphenyl)-2-((2-((3-methoxy-4-(4-methyl-1H-imidazol-1-yl) phenyl) amino)-4-(methylamino) pyrimidin-5-yl) oxy) ethan-1-one (60 mg) as a pale brown solid. LCMS: 509 (M+1); (column; X-Select CSH C-18 (50×3.0 mm, 3.5 μm); RT 2.42 min. 0.05% Aq TFA: ACN; 0.8 mL/min); TLC: 10% MeOH/ CH$_2$Cl$_2$ (R$_f$: 0.5).

Synthesis of 7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a stirred solution of 1-(2-chloro-5-methoxyphenyl)-2-((2-((3-methoxy-4-(4-methyl-1H-imidazol-1-yl) phenyl) amino)-4-(methylamino) pyrimidin-5-yl) oxy) ethan-1-one (150 mg, 0.29 mmol) in 1, 2-dichloroethane (1 mL) under an argon atmosphere were added trifluoroacetic acid (0.02 mL, 0.29 mmol) followed by sodium triacetoxyborohydride (131 mg, 0.61 mmol) at room temperature. The reaction mixture was stirred at room temperature for 16 h. After consumption of the starting material (monitored by TLC), the reaction was quenched with a 1 N sodium hydroxide solution (20 mL) and extracted with CH$_2$Cl$_2$ (2×20 mL). The combined organic extracts were dried over sodium sulfate, filtered and concentrated in vacuo. The crude material was purified by column chromatography using 3% MeOH: CH$_2$Cl$_2$ to afford 7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (25 mg, 16%) as an off-white solid. $^1$H-NMR (CD$_3$OD, 400 MHz): δ 7.87-7.82 (m, 2H), 7.59 (s, 1H), 7.39 (d, 1H), 7.27-7.21 (m, 1H), 7.19 (d, 1H), 7.00 (s, 1H), 6.90 (d, 1H), 6.58-6.56 (m, 1H), 5.11-5.08 (m, 1H), 4.30-4.20 (m, 2H), 3.83 (s, 3H), 3.67 (s, 3H), 3.14 (s, 3H), 2.21 (s, 3H); Mass (ESI): 493 [M+1];

LCMS: 493 (M+1); (column; X-Select CSH C-18 (50×3.0 mm, 3.5 μm); RT 2.45 min. 0.05% Aq TFA: ACN; 0.8 mL/min); UPLC (column; Acquity BEH C-18, 2.1×50 mm, 1.7 μm); RT 1.71 min. ACN: 0.025% TFA (Aq); 0.50 mL/min. TLC: 10% MeOH/CH$_2$Cl$_2$ (R$_f$: 0.5).

Example 88

Synthesis of 7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

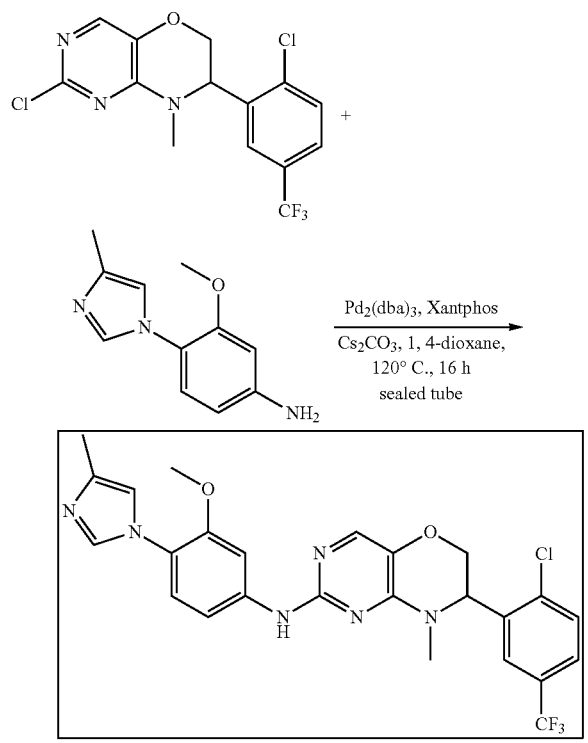

Synthesis of 7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine A dry vial charged with Pd$_2$(dba)$_3$ (25 mg, 0.02 mmol) and Xantphos (47 mg, 0.08 mmol) in 1, 4-dioxane (2 mL) at room temperature was degassed and the resultant reaction mixture was stirred at 120° C. for 3 min. A mixture of 2-chloro-7-(2-chloro-5-(trifluoromethyl) phenyl)-8-methyl-7, 8-dihydro-6H-pyrimido [5, 4-b] [1, 4] oxazine (200 mg, 0.54 mmol), 3-methoxy-4-(4-methyl-1H-imidazol-1-yl) aniline (223 mg, 1.09 mmol) and cesium carbonate (250 mg, 0.76 mmol) in 1, 4-dioxane (2 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (20 mL) and extracted with EtOAc (2×20 mL). The combined organic extracts were dried over sodium sulfate, filtered and concentrated in vacuo. The crude material was purified by column chromatography using 2% MeOH: CH$_2$Cl$_2$ to afford 7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (210 mg, 72%) as a white solid. $^1$H NMR (CD$_3$OD, 400 MHz) δ 7.78-7.72 (m, 2H), 7.70-7.64 (m, 3H), 7.32-7.25 (m, 2H), 7.20 (d, 1H), 6.98 (s, 1H), 5.29-5.27 (m, 1H), 4.36-4.26 (m, 2H), 3.86 (s, 3H), 3.19 (s, 3H), 2.21 (s, 3H); Mass (ESI): 531.1 [M+1]; LCMS: 530.9 (M+1); (column; X-Select CSH C-18 (50×3.0 mm, 3.5 μm); RT 2.60 min. 0.05% Aq TFA: ACN; 0.80 mL/min); HPLC (column; Acquity UPLC BEH C-18, 2.1×50 mm, 1.7 μm); RT 1.81 min. ACN: 0.025% Aq TFA; 0.5 ml/min; TLC: 5% MeOH/CH$_2$Cl$_2$ (R$_f$: 0.3).

Racemic compound of Example 88 was separated using a Chiralpak IA (250×4.6 mm: 5 μm; (30 mg loading; 0.1% DEA in n-hexane: CH$_2$Cl$_2$:MeOH (50:50); (A:B: 70:30) as mobile phase) to provide the compound of Example 88A (Fraction I (+)) and the compound of Example 88B (Fraction II (−)).

Example 88A

Synthesis of (+)-7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

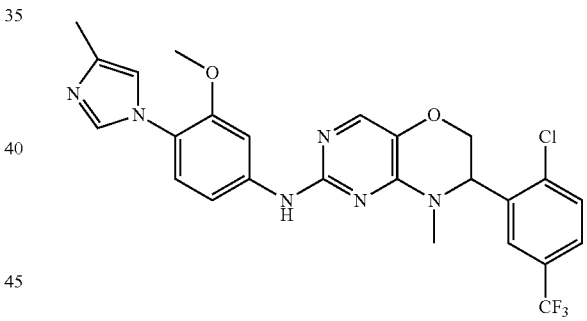

The compound of Example 88A was produced as described in Example 88. Analytical data for product Fraction I (+): $^1$H-NMR (CD$_3$OD, 400 MHz): δ 7.76 (d, 2H), 7.70-7.63 (m, 3H), 7.30-7.28 (m, 2H), 7.20 (d, 1H), 6.99 (s, 1H), 5.30-5.28 (m, 1H), 4.38-4.29 (m, 2H), 3.88 (s, 3H), 3.10 (s, 3H), 2.22 (s, 3H); Mass (ESI): 531.6 [M+1]; LCMS: 531.5 (M+1); (column; X-Select CSH C-18 (50×3.0 mm, 3.5 μm); RT 2.60 min. 0.05% Aq TFA: ACN; 0.80 mL/min); HPLC (column; Acquity UPLC BEH C-18, 2.1×50 mm, 1.7 μm); RT 1.82 min. ACN: 0.025% Aq TFA; 0.5 mL/min; Chiral HPLC: 99.0% RT=6.79 min (CHIRALPAK-IA (250× 4.6 mm, 5 μm; mobile phase (A) 0.1% DEA in n-hexane (B) CH$_2$Cl$_2$:MeOH (50:50) (A:B; 70:30); flow Rate: 1.0 mL/min); Optical rotation $[\alpha]_D^{20.01}$: +151.21 (c=0.25, CH$_2$Cl$_2$).

Example 88B

Synthesis of (−)-7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

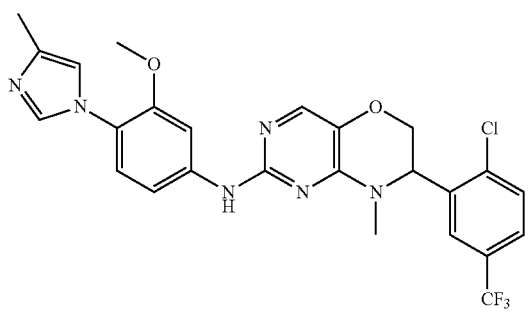

The compound of Example 88B was produced as described in Example 88. Analytical data for product Fraction II (−): $^1$H-NMR (CD$_3$OD, 400 MHz): δ 7.76 (d, 2H), 7.70-7.63 (m, 3H), 7.30-7.28 (m, 2H), 7.20 (d, 1H), 6.99 (s, 1H), 5.30-5.28 (m, 1H), 4.38-4.29 (m, 1H), 3.88 (s, 3H), 3.10 (s, 3H), 2.22 (s, 3H); Mass (ESI): 531.7 [M+1]; LCMS: 531.5 (M+1); (column; X-Select CSH C-18 (50×3.0 mm, 3.5 µm); RT 2.58 min. 0.05% Aq TFA: ACN; 0.80 mL/min); HPLC (column; Acquity UPLC BEH C-18, 2.1×50 mm, 1.7 µm); RT 1.83 min. ACN: 0.025% Aq TFA; 0.5 mL/min; Chiral HPLC: 99.1% RT=7.92 min (CHIRALPAK-IA (250× 4.6 mm, 5 µm; mobile phase (A) 0.1% DEA in n-hexane (B) CH$_2$Cl$_2$:MeOH (50:50) (A:B; 70:30); flow Rate: 1.0 mL/min); Optical rotation [α]$_D^{20.01}$: 147.52 (c=0.25, CH$_2$Cl$_2$).

Example 89

Synthesis of 7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

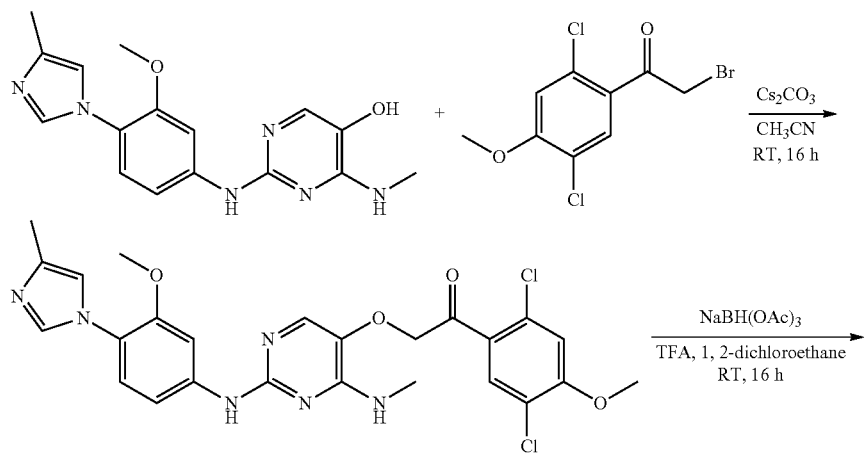

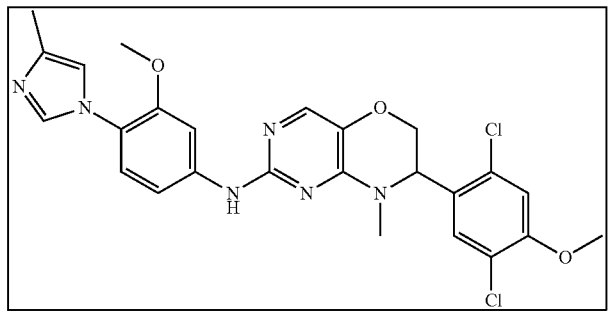

Synthesis of 1-(2, 5-dichloro-4-methoxyphenyl)-2-((2-((3-methoxy-4-(4-methyl-1H-imidazol-1-yl) phenyl) amino)-4-(methylamino) pyrimidin-5-yl) oxy) ethan-1-one To a stirred solution of 2-((3-methoxy-4-(4-methyl-1H-imidazol-1-yl) phenyl) amino)-4-(methylamino) pyrimidin- 5-ol (100 mg, 0.30 mmol) in CH₃CN (1 mL) under an argon atmosphere was added cesium carbonate (200 mg, 0.61 mmol) followed by 2-bromo-1-(2, 5-dichloro-4-methoxyphenyl) ethan-1-one (100 mg, 0.33 mmol) at room temperature. The reaction mixture was stirred at room temperature for 16 h. After consumption of the starting material (monitored by TLC), the reaction was diluted with water (20 mL) and extracted with EtOAc (2×20 mL). The combined organic extracts were dried over sodium sulfate, filtered and concentrated in vacuo to afford 1-(2, 5-dichloro-4-methoxyphenyl)-2-((2-((3-methoxy-4-(4-methyl-1H-imidazol-1-yl) phenyl) amino)-4-(methylamino) pyrimidin-5-yl) oxy) ethan-1-one (130 mg) as pale brown solid used without further purification. LCMS: 583.9 (M+ACN); (column; X-Select CSH C-18 (50×3.0 mm, 3.5 μm); RT 2.53 min. 0.05% Aq TFA: ACN; 0.8 mL/min); TLC: 10% MeOH/CH₂Cl₂ (R$_f$: 0.5).

Synthesis of 7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a stirred solution of 1-(2, 5-dichloro-4-methoxyphenyl)-2-((2-((3-methoxy-4-(4-methyl-1H-imidazol-1-yl) phenyl) amino)-4-(methylamino) pyrimidin-5-yl) oxy) ethan-1-one (120 mg, 0.22 mmol) in 1, 2-dichloroethane (2 mL) under an argon atmosphere was added trifluoroacetic acid (25 mg, 0.46 mmol) followed by sodium triacetoxyborohydride (98 mg, 0.46 mmol) at room temperature. The reaction mixture was stirred at room temperature for 16 h. After consumption of the starting material (monitored by TLC), the reaction was quenched with a 1 N sodium hydroxide solution (20 mL) and extracted with CH₂Cl₂ (2×20 mL). The combined organic extracts were dried over sodium sulfate, filtered and concentrated in vacuo. The crude material was purified by column chromatography using 2% MeOH: CH₂Cl₂ to afford 7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (20 mg, 17%) as a white solid. ¹H-NMR (CD₃OD, 400 MHz): δ 7.76 (s, 1H), 7.68 (s, 1H), 7.60 (s, 1H), 7.26-7.20 (m, 2H), 7.19 (d, 1H), 7.01 (s, 1H), 6.97-6.95 (m, 1H), 5.00-4.98 (m, 1H), 4.27-4.19 (m, 2H), 3.90 (s, 3H), 3.85 (s, 3H), 3.15 (s, 3H), 2.21 (s, 3H); Mass (ESI): 527 [M+1]; LCMS: 526.9 (M+); (column; X-Select CSH C-18 (50×3.0 mm, 3.5 μm); RT 2.47 min. 0.05% Aq TFA: ACN; 0.8 mL/min); UPLC (column; Acquity UPLC BEH C-18, 2.1×50 mm, 1.7 μm); RT 1.78 min. ACN: 0.025% TFA (Aq); 0.50 mL/min TLC: 10% MeOH/CH₂Cl₂ (R$_f$: 0.5).

Example 90

Synthesis of 7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

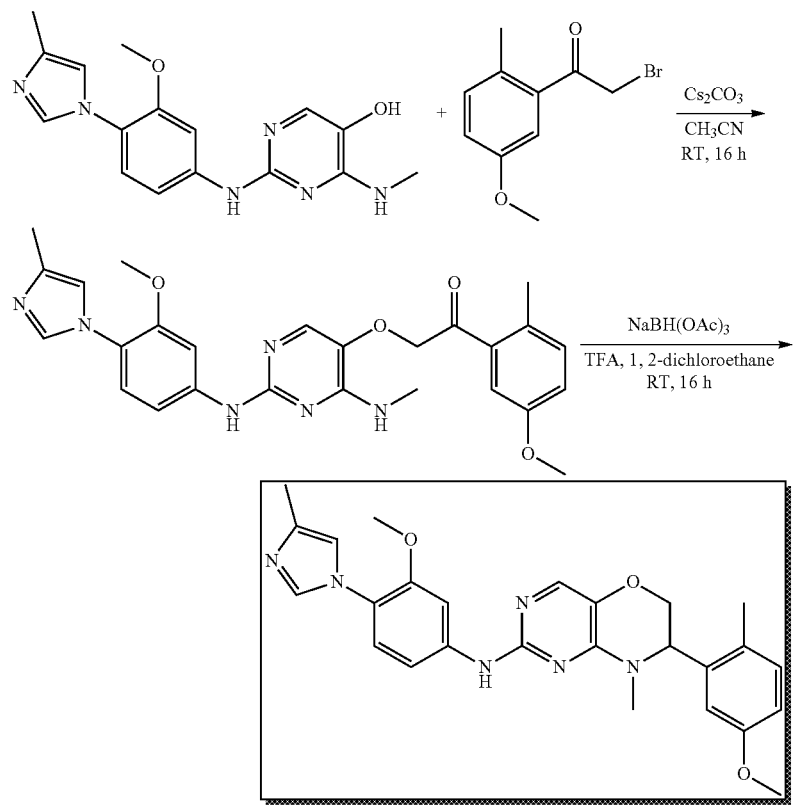

Synthesis of 1-(5-methoxy-2-methylphenyl)-2-((2-((3-methoxy-4-(4-methyl-1H-imidazol-1-yl) phenyl) amino)-4-(methylamino) pyrimidin-5-yl) oxy) ethan-1-one To a stirred solution of 2-((3-methoxy-4-(4-methyl-1H-imidazol-1-yl) phenyl) amino)-4-(methylamino) pyrimidin- 5-ol (100 mg, 0.30 mmol) in $CH_3CN$ (1 mL) under an argon atmosphere were added cesium carbonate (200 mg, 0.60 mmol) followed by 2-bromo-1-(5-methoxy-2-methylphenyl) ethan-1-one (82 mg, 0.33 mmol) at room temperature. The reaction mixture was stirred at room temperature for 16 h. After consumption of the starting material (monitored by TLC), the reaction was diluted with water (20 mL) and extracted with $CH_2Cl_2$ (2×20 mL). The combined organic extracts were dried over sodium sulfate, filtered and concentrated in vacuo to afford 1-(5-methoxy-2-methylphenyl)-2-((2-((3-methoxy-4-(4-methyl-1H-imidazol-1-yl) phenyl) amino)-4-(methylamino) pyrimidin-5-yl) oxy) ethan-1-one (130 mg) as a pale brown solid used without further purification. LCMS: 489.6 (M+1); (column; X-Select CSH C-18 (50×3.0 mm, 3.5 μm); RT 2.86 min. 0.05% Aq TFA: ACN; 0.8 mL/min); TLC: 5% $MeOH/CH_2Cl_2$ ($R_f$: 0.6).

Synthesis of 7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a stirred solution of 1-(5-methoxy-2-methylphenyl)-2-((2-((3-methoxy-4-(4-methyl-1H-imidazol-1-yl) phenyl) amino)-4-(methylamino) pyrimidin-5-yl) oxy) ethan-1-one (140 mg, 0.28 mmol) in 1, 2-dichloroethane (1.5 mL) under an argon atmosphere were added trifluoroacetic acid (0.02 mL, 0.28 mmol) followed by sodium triacetoxyborohydride (127 mg, 0.60 mmol) at room temperature. The reaction mixture was stirred at room temperature for 16 h. After consumption of the starting material (monitored by TLC), the reaction was quenched with a 1 N sodium hydroxide solution (20 mL) and extracted with $CH_2Cl_2$ (2×20 mL). The combined organic extracts were dried over sodium sulfate, filtered and concentrated in vacuo. The crude material was purified by column chromatography using 2% MeOH: $CH_2Cl_2$ to afford 7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (18 mg, 13%) as an off-white solid. $^1$H-NMR ($CD_3OD$, 400 MHz): δ 7.76 (s, 1H), 7.65 (s, 1H), 7.54 (s, 1H), 7.23-7.20 (m, 1H), 7.19-7.12 (m, 2H), 6.93 (s, 1H), 6.79 (d, 1H), 6.51 (s, 1H), 4.93-4.90 (m, 1H), 4.23-4.20 (m, 1H), 4.11-4.09 (m, 1H), 3.83 (s, 3H), 3.65 (s, 3H), 3.10 (s, 3H), 2.31 (s, 3H), 2.20 (s, 3H); Mass (ESI): 473 [M+1]; LCMS: 473.1 (M+1); (column; X-Select CSH C-18 (50×3.0 mm, 3.5 μm); RT 2.39 min. 0.05% Aq TFA: ACN; 0.8 mL/min); UPLC (column; Acquity UPLC BEH C-18, 2.1×50 mm, 1.7 μm); RT 1.67 min. ACN: 0.025% TFA (Aq); 0.50 ml/min TLC: 10% $MeOH/CH_2Cl_2$ ($R_f$: 0.5).

Example 91

Synthesis of 7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

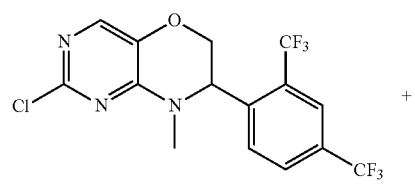

+

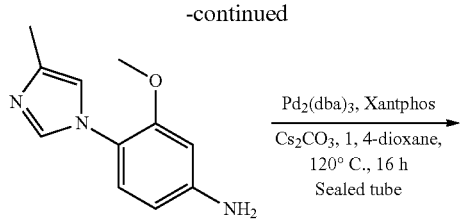

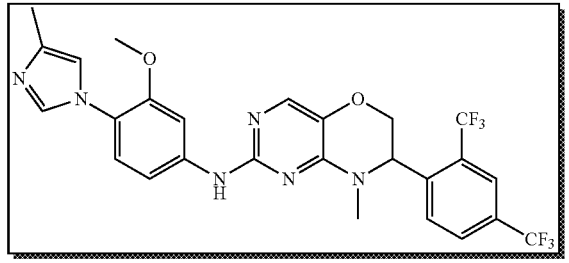

Synthesis of 7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine A dry vial charged with $Pd_2(dba)_3$ (23 mg, 0.02 mmol) and Xantphos (44 mg, 0.07 mmol) in 1, 4-dioxane (2 mL) at room temperature was degassed and the resultant reaction mixture was stirred at 120° C. for 3 min. A mixture of 7-(2, 4-bis (trifluoromethyl) phenyl)-2-chloro-8-methyl-7, 8-dihydro-6H-pyrimido [5, 4-b] [1, 4] oxazine (200 mg, 0.50 mmol), 3-methoxy-4-(4-methyl-1H-imidazol-1-yl) aniline (204 mg, 1.00 mmol) and cesium carbonate (229 mg, 0.70 mmol) in 1, 4-dioxane (2 mL) was degassed and the catalyst premix was added. The resultant mixture was stirred at 120° C. for 16 h in a sealed tube. After consumption of the starting material (monitored by TLC and LCMS), the reaction was diluted with a saturated sodium bicarbonate solution (20 mL) and extracted with EtOAc (2×20 mL). The combined organic extracts were dried over sodium sulfate, filtered and concentrated in vacuo. The crude material was purified by column chromatography using 4% MeOH: $CH_2Cl_2$ to afford 7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (130 mg, 45%) as an off-white solid. $^1$H-NMR ($CD_3OD$, 400 MHz): δ 8.07 (s, 1H), 7.99 (d, 1H), 7.72 (s, 1H), 7.68 (s, 2H), 7.55 (d, 1H), 7.25 (d, 1H), 7.18 (d, 1H), 6.96 (s, 1H), 5.20-5.18 (m, 1H), 4.33-4.30 (m, 1H), 4.17-4.15 (m, 1H), 3.84 (s, 3H), 3.11 (s, 3H), 2.21 (s, 3H); Mass (ESI): 565 [M+1]; LCMS: 565 (M+1); (column; X-Select CSH C-18 (50×3.0 mm, 3.5 μm); RT 2.65 min. 0.05% Aq TFA: ACN; 0.80 ml/min); HPLC (column; Acquity UPLC BEH C-18, 2.1×50 mm, 1.7 μm); RT 2.00 min. ACN: 0.025% Aq TFA; 0.5 mL/min; TLC: 5% $MeOH/CH_2Cl_2$ ($R_f$: 0.4).

Example 92

Synthesis of 7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

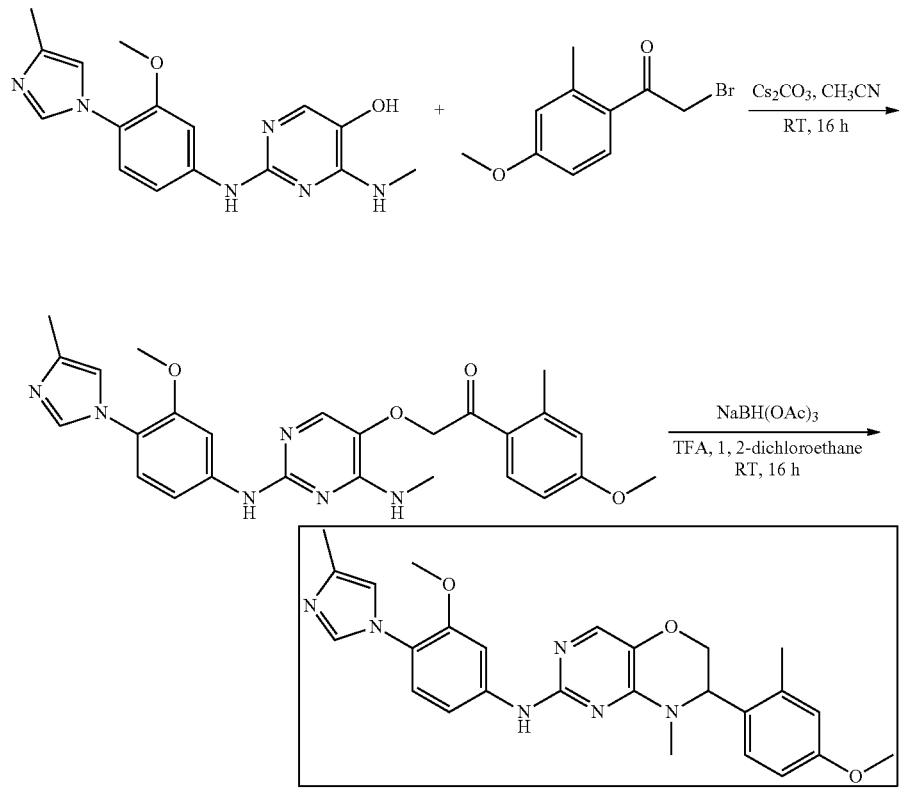

Synthesis of 1-(4-methoxy-2-methylphenyl)-2-((2-((3-methoxy-4-(4-methyl-1H-imidazol-1-yl) phenyl) amino)-4-(methylamino) pyrimidin-5-yl) oxy) ethan-1-one To a stirred solution of 2-((3-methoxy-4-(4-methyl-1H-imidazol-1-yl) phenyl) amino)-4-(methylamino) pyrimidin-5-ol (100 mg, 0.30 mmol) in CH₃CN (1 mL) under an argon atmosphere were added cesium carbonate (200 mg, 0.61 mmol) and 2-bromo-1-(4-methoxy-2-methylphenyl) ethan-1-one (90 mg, 0.33 mmol) at 0° C. The reaction mixture was stirred room temperature for 16 h. After consumption of the starting material (monitored by TLC), the reaction was diluted with water (20 mL) and extracted with CH₂Cl₂ (2×20 mL). The combined organic extracts were dried over sodium sulfate, filtered and concentrated in vacuo to afford 1-(4-methoxy-2-methylphenyl)-2-((2-((3-methoxy-4-(4-methyl-1H-imidazol-1-yl) phenyl) amino)-4-(methylamino) pyrimidin-5-yl) oxy) ethan-1-one (120 mg) as a pale yellow solid used without further purification. LCMS: 489.1 (M+1); (column; X-Select CSH C-18 (50×3.0 mm, 3.5 μm); RT 2.49 min. 0.05% Aq TFA: ACN; 0.80 mL/min); TLC: 5% MeOH/ CH₂Cl₂ (R$_f$: 0.4).

Synthesis of 7-(4-methoxy-2-methylphenyl)-N-(3-methoxy-4-(4-methyl-M-imidazol-1-yl)phenyl)-8-methyl-7,8-dihydro-6H-pyrimido[5,4-b][1,4]oxazin-2-amine To a stirred solution of 1-(4-methoxy-2-methylphenyl)-2-((2-((3-methoxy-4-(4-methyl-1H-imidazol-1-yl) phenyl) amino)-4-(methylamino) pyrimidin-5-yl) oxy) ethan-1-one (100 mg, 0.30 mmol) in 1, 2-dichloroethane (1 mL) under an argon atmosphere were added trifluoroacetic acid (30 mg, 0.26 mmol) and sodium triacetoxyborohydride (118 mg, 0.55 mmol) and stirred at room temperature for 16 h. After consumption of the starting material (monitored by TLC), the reaction was quenched with a 1 N sodium hydroxide solution (50 mL) and extracted with CH₂Cl₂ (2×50 mL). The combined organic extracts were dried over sodium sulfate, filtered and concentrated in vacuo. The crude material was purified by column chromatography using 3% MeOH: CH₂Cl₂ to afford 7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (13 mg, 10%) as an off-white solid. ¹H-NMR (CD₃OD, 400 MHz): δ 7.77 (s, 1H), 7.69 (s, 1H), 7.55 (s, 1H), 7.25-7.15 (m, 2H), 6.99 (s, 1H), 6.93 (d, 1H), 6.81 (s, 1H), 6.79-6.75 (m, 1H), 4.93-4.90 (m, 1H), 4.22-4.20 (m, 1H), 4.10-4.08 (m, 1H), 3.85 (s, 3H), 3.79 (s, 3H), 3.09 (s, 3H), 2.40 (s, 3H), 2.22 (s, 3H); Mass (ESI): 473 [M+1]; LCMS: 473 (M+1); (column; X-Select CSH C-18 (50×3.0 mm, 3.5 μm); RT 2.34 min. 0.05% Aq TFA: ACN; 0.80 mL/min); UPLC (column; Acquity UPLC BEH C-18, 2.1×50 mm, 1.7 μm); RT 1.66 min. ACN: 0.025% Aq TFA; 0.5 mL/min; TLC: 5% MeOH/ CH₂Cl₂ (R$_f$: 0.4).

Example 93

Synthesis of 7-(2-chloro-4-fluorophenyl)-N-(3-methoxy-4-(4-methyl-1H-imidazol-1-yl) phenyl)-8-methyl-7,8-dihydro-6H-pyrimido [5, 4-b] [1,4] oxazin-2-amine

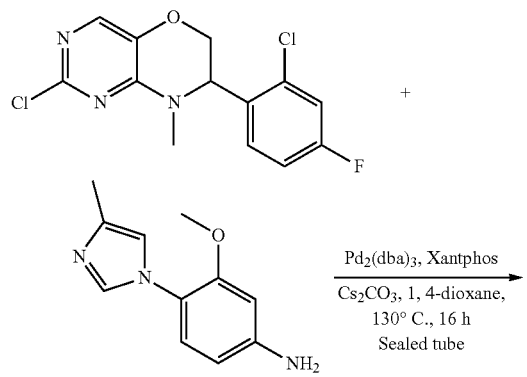

Synthesis of 7-(2-chloro-4-fluorophenyl)-N-(3-methoxy-4-(4-methyl-1H-imidazol-1-yl) phenyl)-8-methyl-7, 8-dihydro-6H-pyrimido [5, 4-b] [1,4] oxazin-2-amine A dry vial charged with Pd$_2$(dba)$_3$ (36 mg, 0.04 mmol) and Xantphos (69 mg, 0.11 mmol) in 1, 4-dioxane (1.25 mL) at room temperature was degassed and the resultant reaction mixture was stirred at 120° C. for 3 min. A mixture of 2-chloro-7-(2-chloro-4-fluorophenyl)-8-methyl-7, 8-dihydro-6H-pyrimido [5, 4-b] [1, 4] oxazine (250 mg, 0.79 mmol), 3-methoxy-4-(4-methyl-1H-imidazol-1-yl) aniline (324 mg, 1.59 mmol) and cesium carbonate (363 mg, 1.11 mmol) in 1, 4-dioxane (1.25 mL) was degassed and the catalyst premix was added. The resultant mixture was stirred at 130° C. for 16 h in a sealed tube. After consumption of the starting material (monitored by TLC and LCMS), the reaction was filtered, washed with EtOAc (2×20 mL) and the filtrate washed with water (20 mL). The combined organic extracts were dried over sodium sulfate, filtered and concentrated in vacuo. The crude material was purified by column chromatography using 100% EtOAc to afford 7-(2-chloro-4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (120 mg, 31%) as an off-white solid. LCMS: 481.3 (M+1); (column; X-Select CSH C-18 (50×3.0 mm, 3.5 µm); RT 3.03 min. 0.05% Aq TFA: ACN; 0.80 mL/min).

Racemic compound of Example 93 was separated using a Chiralpak ADH (250×4.6 mm: 5 µm; (20 mg loading; 0.1% DEA in n-hexane: EtOH:MeOH (50:50); (A:B: 75:25) as mobile phase) to provide the compound of Example 93A (Fraction I (−)) and the compound of Example 93B (Fraction II (+)).

Example 93A

Synthesis of (−)-7-(2-chloro-4-fluorophenyl)-N-(3-methoxy-4-(4-methyl-1H-imidazol-1-yl) phenyl)-8-methyl-7,8-dihydro-6H-pyrimido [5, 4-b] [1,4] oxazin-2-amine

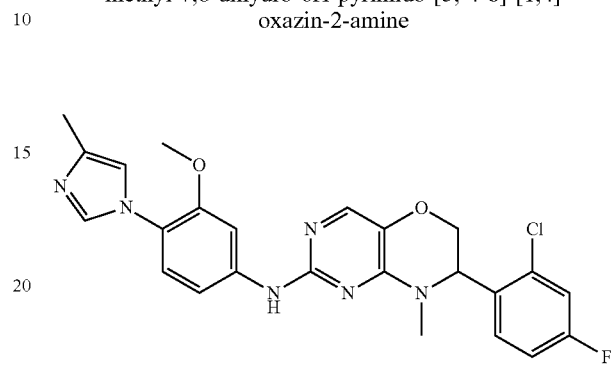

The compound of Example 93A was produced as described in Example 93. Analytical data for product Fraction I (−): $^1$H-NMR (CD$_3$OD, 400 MHz): δ 7.76 (s, 1H), 7.67 (s, 1H), 7.59 (s, 1H), 7.35 (d, 1H), 7.26 (d, 1H), 7.19 (d, 1H), 7.11-7.09 (m, 2H), 6.97 (s, 1H), 5.19-5.16 (m, 1H), 4.29-4.21 (m, 2H), 3.87 (s, 3H), 3.17 (s, 3H), 2.23 (s, 3H); Mass (ESI): 481.4 [M+1]; LCMS: 481.6 (M+1); (column; X-Select CSH C-18 (50×3.0 mm, 3.5 µm); RT 3.06 min. 0.05% Aq TFA: ACN; 0.80 mL/min); UPLC (column; Acquity UPLC BEH C-18, 2.1×50 mm, 1.7 µm); RT 1.70 min. ACN: 0.025% TFA (Aq); 0.50 mL/min; Chiral HPLC: 98.6% RT=18.86 min (CHIRALPAK-ADH (250×4.6 mm, 5 µm; mobile phase (A) 0.1% DEA in n-hexane (B) EtOH: MeOH (50:50) (A:B; 75:25); flow Rate: 1.0 mL/min); Optical rotation [α]$_D^{19.99}$: −148.54 (c=0.25, CH$_2$Cl$_2$).

Example 93B

Synthesis of (+)-7-(2-chloro-4-fluorophenyl)-N-(3-methoxy-4-(4-methyl-1H-imidazol-1-yl) phenyl)-8-methyl-7,8-dihydro-6H-pyrimido [5, 4-b] [1,4] oxazin-2-amine

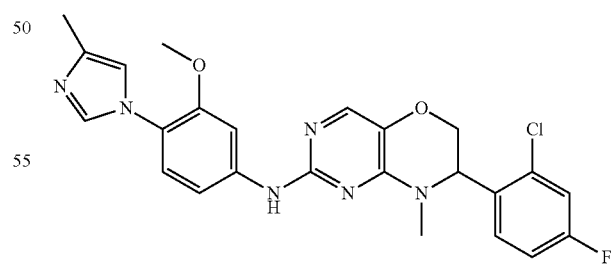

The compound of Example 93B was produced as described in Example 93. Analytical data for product Fraction II (+): $^1$H-NMR (CD$_3$OD, 400 MHz): δ 7.76 (s, 1H), 7.67 (s, 1H), 7.59 (s, 1H), 7.35 (d, 1H), 7.26 (d, 1H), 7.19 (d, 1H), 7.11-7.09 (m, 2H), 6.97 (s, 1H), 5.19-5.16 (m, 1H), 4.29-4.21 (m, 2H), 3.87 (s, 3H), 3.17 (s, 3H), 2.23 (s, 3H); Mass (ESI): 481.4 [M+1]; LCMS: 481.6 (M+1); (column;

X-Select CSH C-18 (50×3.0 mm, 3.5 μm); RT 3.05 min. 0.05% Aq TFA: ACN; 0.80 mL/min); UPLC (column; Acquity UPLC BEH C-18, 2.1×50 mm, 1.7 μm); RT 1.70 min. ACN: 0.025% TFA (Aq); 0.50 mL/min; Chiral HPLC: 98.4% RT=23.20 min (CHIRALPAK-ADH (250×4.6 mm, 5 μm; mobile phase (A) 0.1% DEA in n-hexane (B) EtOH: MeOH (50:50) (A:B; 75:25); flow Rate: 1.0 mL/min); Optical rotation $[\alpha]_D^{19.98}$: +155.15 (c=0.25, CH$_2$Cl$_2$).

Example 94

Synthesis of 7-(4-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

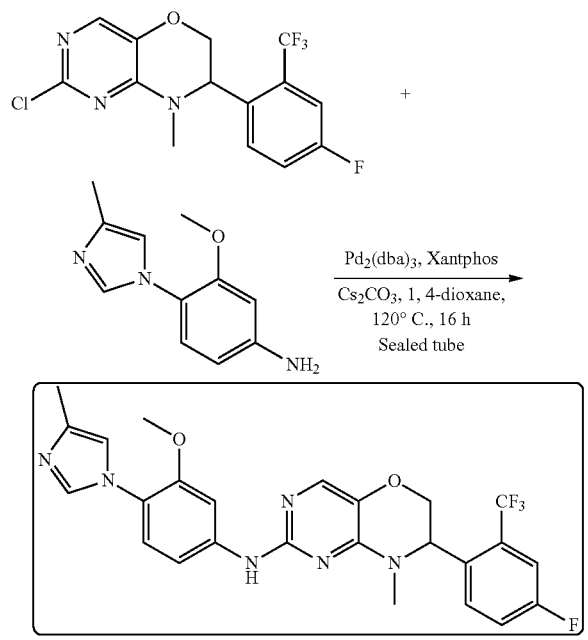

Synthesis of 7-(4-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine A dry vial charged with Pd$_2$(dba)$_3$ (26 mg, 0.03 mmol) and Xantphos (50 mg, 0.08 mmol) in 1, 4-dioxane (2 mL) at room temperature was degassed and the resultant reaction mixture was stirred at 120° C. for 3 min. A mixture of 2-chloro-7-(4-fluoro-2-(trifluoromethyl) phenyl)-8-methyl-7, 8-dihydro-6H-pyrimido [5, 4-b] [1, 4] oxazine (200 mg, 0.57 mmol), 3-methoxy-4-(4-methyl-1H-imidazol-1-yl) aniline (234 mg, 1.15 mmol) and cesium carbonate (262 mg, 0.80 mmol) in 1, 4-dioxane (2 mL) was degassed and the catalyst premix was added. The resultant mixture was stirred at 120° C. for 16 h in a sealed tube. After consumption of the starting material (monitored by TLC and LCMS), the reaction was diluted with water (20 mL) and extracted with EtOAc (2×20 mL). The combined organic extracts were dried over sodium sulfate, filtered and concentrated in vacuo. The crude material was purified by column chromatography using 3% MeOH/CH$_2$Cl$_2$ to afford 7-(4-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (200 mg, 67%) as an off-white solid. $^1$H-NMR (CD$_3$OD, 500 MHz): δ 7.77 (s, 1H), 7.68 (d, 2H), 7.60 (dd, 1H), 7.46-7.38 (m, 2H), 7.27 (dd, 1H), 7.20 (d, 1H), 6.90 (s, 1H), 5.19-5.17 (m, 1H), 4.30-4.28 (m, 1H), 4.18-4.10 (m, 1H), 3.85 (s, 3H), 3.10 (s, 3H), 2.25 (s, 3H); (column; Acquity UPLC BEH C-18 2.1×50 mm, 1.7 μm); RT 1.82 min. ACN: 0.025% Aq TFA; 0.5 mL/min; TLC: 5% MeOH/CH$_2$Cl$_2$ (R$_f$: 0.3).

Racemic compound of Example 94 was separated using a Chiralpak IA (250×4.6 mm: 5 μm; (30 mg loading; 0.1% DEA in n-hexane: CH$_2$Cl$_2$:MeOH (50:50); (A:B: 80:20) as mobile phase) to provide the compound of Example 94A (Fraction I (−)) and the compound of Example 94B (Fraction II (+)).

Example 94A

Synthesis of (−)-7-(4-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

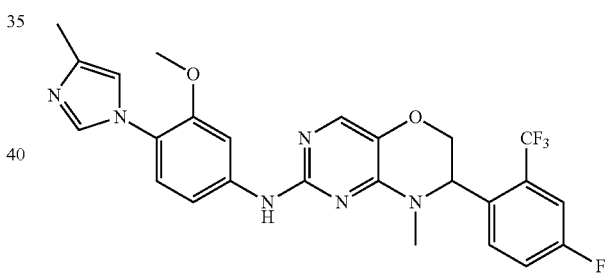

The compound of Example 94A was produced as described in Example 94. Analytical data for product Fraction I (−): $^1$H-NMR (CD$_3$OD, 400 MHz): δ 7.73 (s, 1H), 7.64 (s, 2H), 7.59 (d, 1H), 7.40-7.35 (m, 2H), 7.22 (d, 1H), 7.17 (d, 1H), 6.95 (s, 1H), 5.00-4.09 (m, 1H), 4.30-4.28 (m, 1H), 4.11-4.09 (m, 1H), 3.85 (s, 3H), 3.10 (s, 3H), 2.21 (s, 3H); Mass (ESI): 515.5 [M+1]; LCMS: 515.5 (M+1); (column; X-Select CSH C-18 (50×3.0 mm, 3.5 μm); RT 3.12 min. 0.05% Aq TFA: ACN; 0.80 mL/min); UPLC (column; Acquity UPLC BEH C-18, 2.1×50 mm, 1.7 μm); RT 1.84 min. ACN: 0.025% Aq TFA; 0.5 mL/min; Chiral HPLC: 99.2% RT=10.91 min (CHIRALPAK-IA (250×4.6 mm, 5 μm; mobile phase (A) 0.1% DEA in n-hexane (B) CH$_2$Cl$_2$: MeOH (50:50) (A:B; 80:20); flow Rate: 1.0 mL/min); Optical rotation $[\alpha]_D^{20.01}$: −107.92 (c=0.25, CH$_2$Cl$_2$).

Example 94B

Synthesis of (+)-7-(4-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

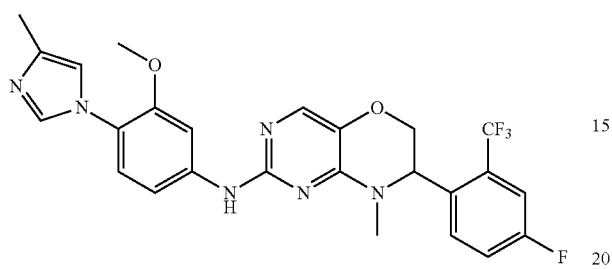

The compound of Example 94B was produced as described in Example 94. Analytical data for product Fraction II (+): $^1$H-NMR (CD$_3$OD, 400 MHz): δ 7.73 (s, 1H), 7.64 (s, 2H), 7.59 (d, 1H), 7.40-7.35 (m, 2H), 7.22 (d, 1H), 7.17 (d, 1H), 6.95 (s, 1H), 5.00-4.09 (m, 1H), 4.30-4.28 (m, 1H), 4.11-4.09 (m, 1H), 3.85 (s, 3H), 3.10 (s, 3H), 2.21 (s, 3H); Mass (ESI): 515.5 [M+1]; LCMS: 515.5 (M+1); (column; X-Select CSH C-18 (50×3.0 mm, 3.5 μm); RT 3.11 min. 0.05% Aq TFA: ACN; 0.80 mL/min); UPLC (column; Acquity UPLC BEH C-18, 2.1×50 mm, 1.7 μm); RT 1.84 min. ACN: 0.025% Aq TFA; 0.5 mL/min; Chiral HPLC: 98.2% RT=12.53 min (CHIRALPAK-IA (250×4.6 mm, 5 μm; mobile phase (A) 0.1% DEA in n-hexane (B) CH$_2$Cl$_2$: MeOH (50:50) (A:B; 80:20); flow Rate: 1.0 mL/min); Optical rotation $[α]_D^{19.99}$: +104.76 (c=0.25, CH$_2$Cl$_2$).

Example 95

Synthesis of 7-(2, 4-dichlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

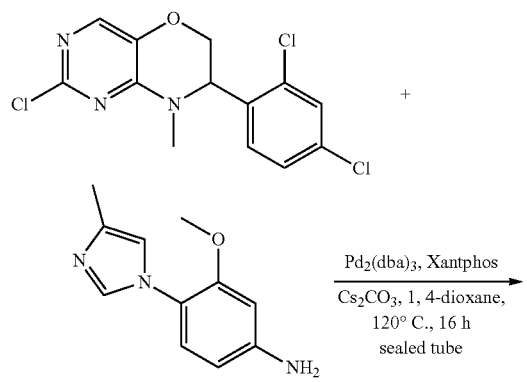

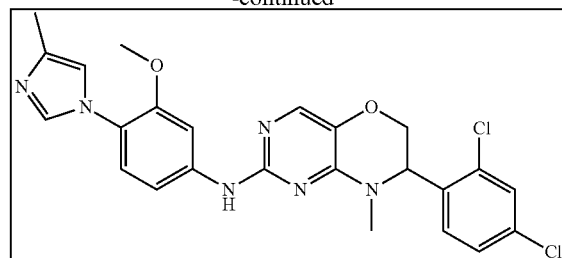

Synthesis of 7-(2, 4-dichlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine A dry vial charged with Pd$_2$(dba)$_3$ (28 mg, 0.03 mmol) and Xantphos (53 mg, 0.09 mmol) in 1, 4-dioxane (1 mL) at room temperature was degassed and the resultant reaction mixture was stirred at 120° C. for 3 min. A mixture of 2-chloro-7-(2, 4-dichlorophenyl)-8-methyl-7, 8-dihydro-6H-pyrimido [5, 4-b] [1, 4] oxazine 3-methoxy-4-(4-methyl-1H-imidazol-1-yl) aniline (246 mg, 1.21 mmol) and cesium carbonate (276 mg, 0.85 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction was diluted with water (20 mL) and extracted with EtOAc (2×20 mL). The combined organic extracts were dried over sodium sulfate, filtered and concentrated in vacuo. The crude material was purified by column chromatography using 0-5% MeOH/CH$_2$Cl$_2$ to afford 7-(2, 4-dichlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (140 mg, 35%) as a colorless liquid. LCMS: 497.7 (M+1); (column; X-Select CSH C-18 (50×3.0 mm, 3.5 μm); RT 3.11 min. 0.05% Aq TFA: ACN; 0.80 mL/min); UPLC (column; Acquity UPLC BEH C-18, 2.1×50 mm, 1.7 μm); RT 1.84 min. ACN: 0.025% Aq TFA; 0.5 ml/min; TLC: 5% MeOH/CH$_2$Cl$_2$ (R$_f$: 0.2).

Racemic compound of Example 95 was separated using a Chiralpak ADH (250×20 mm; 5 μm; (50 mg loading; 0.1% DEA in n-hexane: EtOH:MeOH (50:50); (A:B: 75:25) as mobile phase) to provide the compound of Example 95A (Fraction I (−)) and the compound of Example 95B (Fraction II (+)).

Example 95A

Synthesis of (−)-7-(2, 4-dichlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

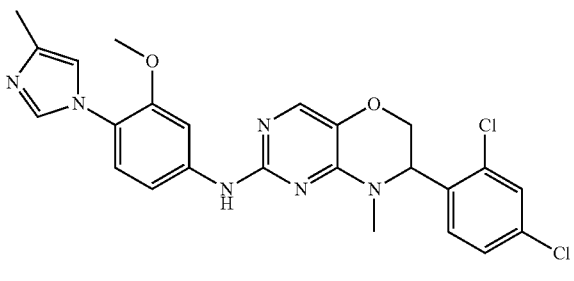 [SMILES: COc1cc(Nc2ncc3c(n2)N(C)C(c2ccc(Cl)cc2Cl)CO3)ccc1-n1cnc(C)c1]

The compound of Example 95A was produced as described in Example 95. Analytical data for product Fraction I (−): $^1$H-NMR (CD$_3$OD, 400 MHz): δ 7.76 (s, 1H), 7.67 (s, 1H), 7.59 (d, 2H), 7.33 (d, 1H), 7.26-7.23 (m, 1H), 7.20-7.18 (m, 1H), 7.09-7.06 (m, 1H), 6.98 (s, 1H), 5.19-5.17 (m, 1H), 4.30-4.20 (m, 2H), 3.84 (s, 3H), 3.16 (s, 3H), 2.21 (s, 3H); Mass (ESI): 497 [M+]; LCMS: 497 (M+); (column; X-Select CSH C-18 (50×3.0 mm, 3.5 μm); RT 2.65 min. 0.05% Aq TFA: ACN; 0.80 mL/min); UPLC (column; Acquity UPLC BEH C-18, 2.1×50 mm, 1.7 μm); RT 1.85 min. ACN: 0.025% Aq TFA; 0.5 mL/min; Chiral HPLC: 99.4% RT=16.48 min (CHIRALPAK-AD-H (250×4.6 mm, 5 μm; mobile phase (A) 0.1% DEA in n-hexane (B) EtOH: MeOH (50:50) (A:B; 75:25); flow Rate: 1.0 mL/min); Optical rotation [α]$_D^{20.00}$: −224.08 (c=0.25, CH$_2$Cl$_2$).

Example 95B

Synthesis of (+)-7-(2, 4-dichlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

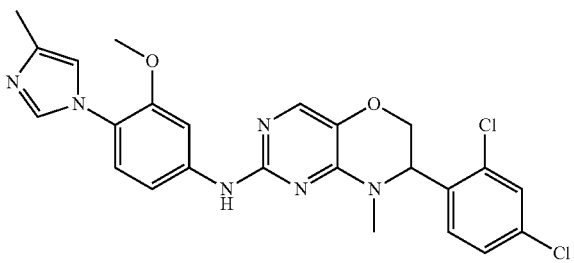 [SMILES: COc1cc(Nc2ncc3c(n2)N(C)C(c2ccc(Cl)cc2Cl)CO3)ccc1-n1cnc(C)c1]

The compound of Example 95B was produced as described in Example 95. Analytical data for product Fraction II (+): $^1$H-NMR (CD$_3$OD, 400 MHz): δ 7.76 (s, 1H), 7.67 (s, 1H), 7.59 (d, 2H), 7.33 (d, 1H), 7.26-7.23 (m, 1H), 7.20-7.18 (m, 1H), 7.09-7.06 (m, 1H), 6.98 (s, 1H), 5.19-5.17 (m, 1H), 4.30-4.20 (m, 2H), 3.84 (s, 3H), 3.16 (s, 3H), 2.21 (s, 3H); Mass (ESI): 497.1 [M+]; LCMS: 497 (M+); (column; X-Select CSH C-18 (50×3.0 mm, 3.5 μm); RT 2.65 min. 0.05% Aq TFA: ACN; 0.80 mL/min); UPLC (column; Acquity UPLC BEH C-18, 2.1×50 mm, 1.7 μm); RT 1.85 min. ACN: 0.025% Aq TFA; 0.5 mL/min; Chiral HPLC: 99.0% RT=25.87 min (CHIRALPAK-AD-H (250×4.6 mm, 5 μm; mobile phase (A) 0.1% DEA in n-hexane (B) EtOH: MeOH (50:50) (A:B; 80:20); flow Rate: 1.0 mL/min); Optical rotation [α]$_D^{19.99}$: +231.32 (c=0.25, CH$_2$Cl$_2$).

Example 96

Synthesis of 7-(2, 4-dichlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

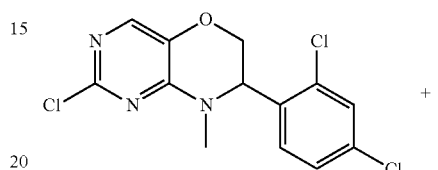

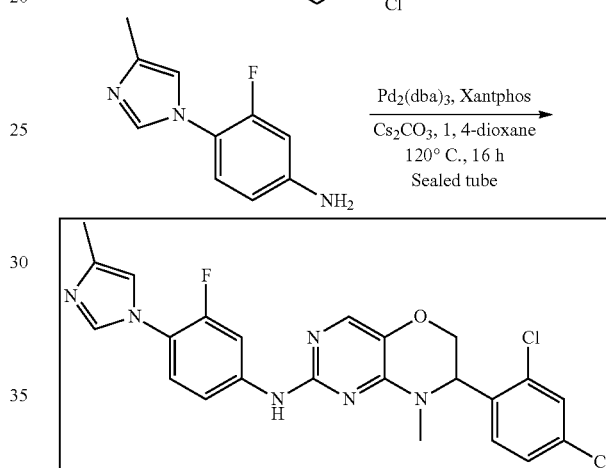

Synthesis of 7-(2, 4-dichlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine A dry vial charged with Pd$_2$(dba)$_3$ (27 mg, 0.03 mmol) and Xantphos (52 mg, 0.09 mmol) in 1, 4-dioxane (2 mL) at room temperature was degassed and the resultant reaction mixture was stirred at 120° C. for 3 min. A mixture of 2-chloro-7-(2, 4-dichlorophenyl)-8-methyl-7, 8-dihydro-6H-pyrimido [5, 4-b] [1, 4] oxazine (200 mg, 0.60 mmol), 3-fluoro-4-(4-methyl-1H-imidazol-1-yl) aniline (231 mg, 0.12 mmol) and cesium carbonate (275 mg, 0.84 mmol) in 1, 4-dioxane (2 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (50 mL) and extracted with 20% MeOH/CH$_2$Cl$_2$ (2×30 mL). The combined organic extracts were dried over sodium sulfate, filtered and concentrated in vacuo. The crude material was purified by column chromatography using 5% MeOH/CH$_2$Cl$_2$ to afford 7-(2, 4-dichlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine (100 mg, 34%) as a pale yellow solid. $^1$H-NMR (CDCl$_3$, 400 MHz): δ 7.95-7.90 (m, 1H), 7.69-7.63 (m, 1H), 7.47 (s, 1H), 7.27-7.20 (m, 3H), 7.12 (s, 1H), 7.00-6.98 (m, 1H), 6.90 (s, 1H), 5.02-5.00 (m, 1H), 4.70 (s, 1H), 4.30-4.20 (m, 2H), 3.14 (s, 3H), 2.30 (s, 3H); LCMS: 485.7 (M+1); (column; X-Select CSH C-18 (50×3.0 mm, 3.5 µm); RT 3.17 min. 0.05% Aq TFA: ACN; 0.80 mL/min); UPLC (column; Acquity UPLC BEH C-18, 2.1×50 mm, 1.7 µm); RT 1.87 min. ACN: 0.025% Aq TFA; 0.5 ml/min; TLC: 10% MeOH/CH$_2$Cl$_2$ (R$_f$: 0.5).

Racemic compound of Example 96 was separated using a Chiralpak IA (250×20 mm: 5 µm; (20 mg loading; 0.1% DEA in n-hexane: CH$_2$Cl$_2$:MeOH (50:50); (A:B; 75:25) as mobile phase) to provide the compound of Example 96A (Fraction I (+)) and the compound of Example 96B (Fraction II (−)).

Example 96A

Synthesis of (+)-7-(2, 4-dichlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

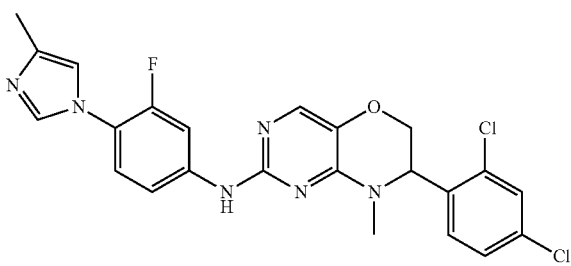 [SMILES: Cc1cn(-c2ccc(Nc3ncc4c(n3)N(C)C(c3ccc(Cl)cc3Cl)CO4)cc2F)cn1]

The compound of Example 96A was produced as described in Example 96. Analytical data for product Fraction I (+): $^1$H-NMR (CD$_3$OD, 400 MHz): δ 8.01-7.99 (m, 1H), 7.74 (s, 1H), 7.60 (s, 1H), 7.57 (s, 1H), 7.42-7.40 (m, 1H), 7.32 (t, 2H), 7.09 (s, 1H), 7.08 (s, 1H), 5.19-5.17 (m, 1H), 4.30-4.20 (m, 2H), 3.14 (s, 3H), 2.22 (s, 3H); Mass (ESI): 485.7 [M+1]; LCMS: 485.7 (M+1); (column; X-Select CSH C-18 (50×3.0 mm, 3.5 µm); RT 3.17 min. 0.05% Aq TFA: ACN; 0.80 mL/min); UPLC (column; Acquity UPLC BEH C-18, 2.1×50 mm, 1.7 µm); RT 1.87 min. ACN: 0.025% Aq TFA; 0.5 mL/min; Chiral HPLC: 99.1% RT=14.73 min (CHIRALPAK-IA (250×4.6 mm, 5 µm; mobile phase (A) 0.1% DEA in n-hexane (B) CH$_2$Cl$_2$:MeOH (50:50) (A:B; 75:25); flow Rate: 1.0 mL/min); Optical rotation [α]$_D^{20.01}$: +164.62 (c=0.25, DCM).

Example 96B

Synthesis of (−)-7-(2, 4-dichlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

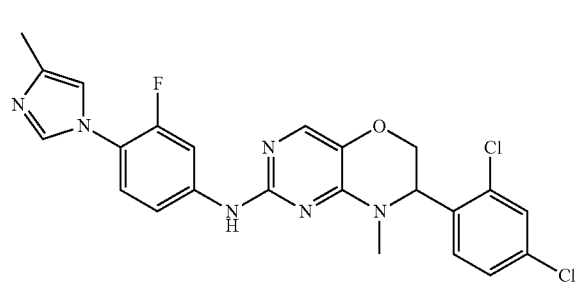 [SMILES: Cc1cn(-c2ccc(Nc3ncc4c(n3)N(C)C(c3ccc(Cl)cc3Cl)CO4)cc2F)cn1]

The compound of Example 96B was produced as described in Example 96. Analytical data for product Fraction II (−): $^1$H-NMR (CD$_3$OD, 400 MHz): δ 8.01-7.99 (m, 1H), 7.74 (s, 1H), 7.60 (s, 1H), 7.57 (s, 1H), 7.42-7.40 (m, 1H), 7.32 (t, 2H), 7.09 (s, 1H), 7.08 (s, 1H), 5.19-5.17 (m, 1H), 4.30-4.20 (m, 2H), 3.14 (s, 3H), 2.22 (s, 3H); Mass (ESI): 485.6 [M+1]; LCMS: 485.8 (M+1); (column; X-Select CSH C-18 (50×3.0 mm, 3.5 µm); RT 3.18 min. 0.05% Aq TFA: ACN; 0.80 mL/min); UPLC (column; Acquity UPLC BEH C-18, 2.1×50 mm, 1.7 µm); RT 1.87 min. ACN: 0.025% Aq TFA; 0.5 mL/min; Chiral HPLC: 98.1% RT=16.38 min (CHIRALPAK-IA (250×4.6 mm, 5 µm; mobile phase (A) 0.1% DEA in n-hexane (B) CH$_2$Cl$_2$:MeOH (50:50) (A:B; 75:25); flow Rate: 1.0 mL/min); Optical rotation [α]$_D^{20.01}$: −180.25 (c=0.25, DCM).

Example 97

Synthesis of N-(3-methoxy-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine

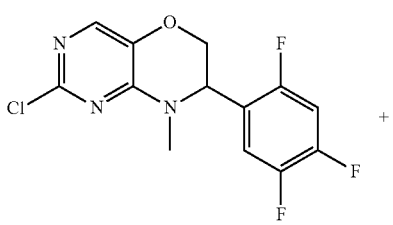

+

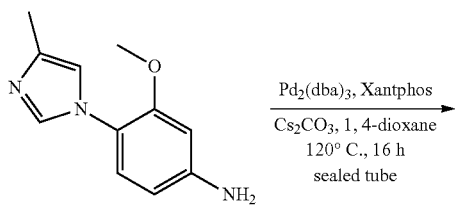

Pd$_2$(dba)$_3$, Xantphos
Cs$_2$CO$_3$, 1, 4-dioxane
120° C., 16 h
sealed tube

-continued

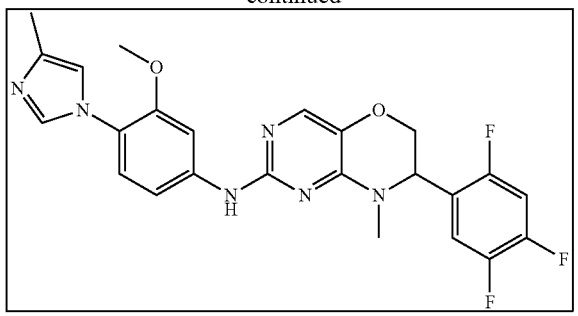

Synthesis of N-(3-methoxy-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine A dry vial charged with Pd$_2$(dba)$_3$ (36 mg, 0.04 mmol) and Xantphos (74 mg, 0.11 mmol) in 1, 4-dioxane (1.25 mL) at room temperature was degassed and the resultant reaction mixture was stirred at 120° C. for 3 min. A mixture of 2-chloro-8-methyl-7-(2, 4, 5-trifluorophenyl)-7, 8-dihydro-6H-pyrimido [5, 4-b] [1, 4] oxazine (250 mg, 0.79 mmol), 3-methoxy-4-(4-methyl-1H-imidazol-1-yl) aniline (321 mg, 1.58 mmol) and cesium carbonate (361 mg, 1.10 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (50 mL) and extracted with CH$_2$Cl$_2$ (2×50 mL). The combined organic extracts were dried over sodium sulfate, filtered and concentrated in vacuo. The crude material was purified by column chromatography using 3% MeOH/CH$_2$Cl$_2$ to afford N-(3-methoxy-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine (130 mg, 38%) as an off-white solid. $^1$H-NMR (DMSO-d$_6$, 400 MHz): δ 9.20 (s, 1H), 7.88 (s, 1H), 7.70-7.63 (m, 2H), 7.60 (s, 1H), 7.32-7.30 (m, 1H), 7.20-7.10 (m, 2H), 6.98 (s, 1H), 5.10-5.09 (m, 1H), 4.22-4.19 (m, 2H), 3.78 (s, 3H), 3.10 (s, 3H), 2.11 (s, 3H); LCMS: 483.4 (M+1); (column; X-Select CSH C-18 (50×3.0 mm, 3.5 μm); RT 2.87 min 0.05% Aq TFA: ACN; 0.80 mL/min); HPLC (column; Acquity UPLC BEH C-18 2.1×50 mm, 1.7 μm); RT 1.66 min. ACN: 0.025% Aq TFA; 0.5 mL/min; TLC: 5% MeOH/CH$_2$Cl$_2$ (R$_f$: 0.4).

Racemic compound of Example 97 was separated using a (Chiral pack-AD-H (250×4.6 mm, 5 μm (30 mg loading; 0.1% DEA in n-hexane: EtOH (A:B: 75:25) as mobile phase) to provide the compound of Example 97A (Fraction I (−)) and the compound of Example 97B (Fraction II (+)).

Example 97A

Synthesis of (−)-N-(3-methoxy-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine

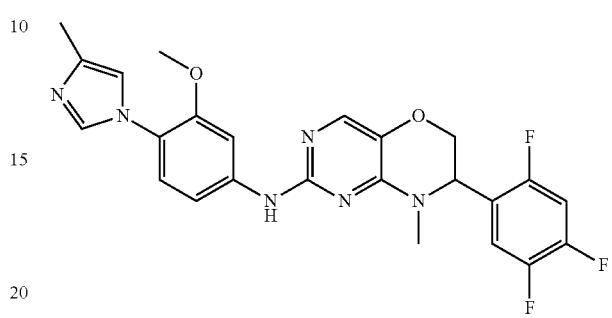

The compound of Example 97A was produced as described in Example 97. Analytical data for product Fraction I (−): $^1$H-NMR (DMSO-d$_6$, 400 MHz): δ 9.20 (s, 1H), 7.88 (s, 1H), 7.70-7.63 (m, 2H), 7.60 (s, 1H), 7.32-7.30 (m, 1H), 7.20-7.10 (m, 2H), 6.98 (s, 1H), 5.10-5.09 (m, 1H), 4.22-4.19 (m, 2H), 3.78 (s, 3H), 3.10 (s, 3H), 2.11 (s, 3H); Mass (ESI): 483.5 [M+1]; LCMS: 483.5 (M+1); (column; X-Select CSH C-18 (50×3.0 mm, 3.5 μm); RT 2.05 min. 0.05% Aq TFA: ACN; 0.80 mL/min); HPLC (column; Acquity UPLC BEH C-18, 2.1×50 mm, 1.7 μm); RT 1.67 min. ACN: 0.025% Aq TFA; 0.5 mL/min; Chiral HPLC: 100.0% RT=17.49 min (CHIRALPAK-AD-H (250×4.6 mm, 5 μm; mobile phase (A) 0.1% DEA in n-hexane (B) EtOH (A:B; 75:25); flow Rate: 1.0 mL/min); Optical rotation $[α]_D^{20.02}$: −149.29 (c=0.25, CH$_2$Cl$_2$).

Example 97B

Synthesis of (+)-N-(3-methoxy-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine

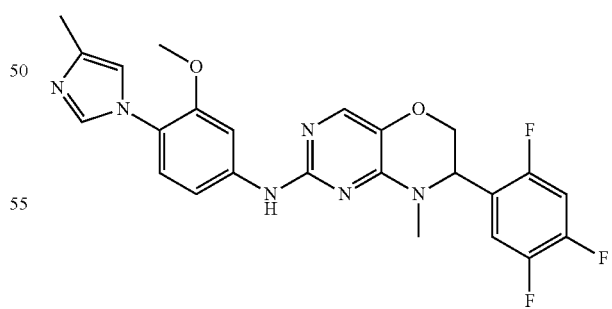

The compound of Example 97B was produced as described in Example 97. Analytical data for product Fraction II (+): $^1$H-NMR (DMSO-d$_6$, 400 MHz): δ 9.20 (s, 1H), 7.85 (s, 1H), 7.70-7.64 (m, 2H), 7.61 (s, 1H), 7.32-7.30 (m, 1H), 7.19-7.10 (m, 2H), 7.00 (s, 1H), 5.00-5.07 (m, 1H), 4.22-4.20 (m, 2H), 3.78 (s, 3H), 3.10 (s, 3H), 2.11 (s, 3H); Mass (ESI): 483.5 [M+1]; LCMS: 483.5 (M+1); (column;

X-Select CSH C-18 (50×3.0 mm, 3.5 μm); RT 2.05 min. 0.05% Aq TFA: ACN; 0.80 mL/min); HPLC (column; Acquity UPLC BEH C-18, 2.1×50 mm, 1.7 μm); RT 1.67 min. ACN: 0.025% Aq TFA; 0.5 mL/min; Chiral HPLC: 99.1% RT=27.82 min (CHIRALPAK-AD-H (250×4.6 mm, 5 μm; mobile phase (A) 0.1% DEA in n-hexane (B) EtOH (A:B; 75:25); flow Rate: 1.0 mL/min); Optical rotation $[\alpha]_D^{20.02}$: +152.65 (c=0.25, $CH_2Cl_2$).

Example 98

Synthesis of N-(3-fluoro-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine

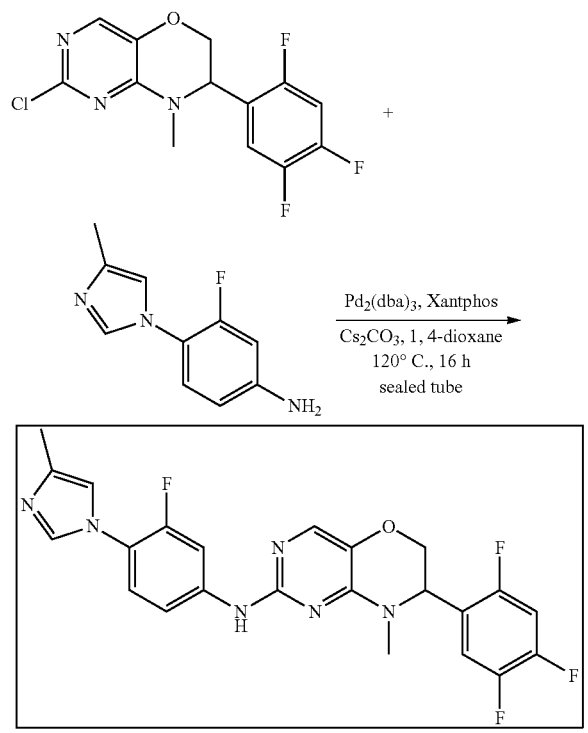

Synthesis of N-(3-fluoro-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine A dry vial charged with $Pd_2(dba)_3$ (36 mg, 0.04 mmol) and Xantphos (74 mg, 0.11 mmol) in 1, 4-dioxane (1.25 mL) at room temperature was degassed and the resultant reaction mixture was stirred at 120° C. for 3 min. A mixture of 2-chloro-8-methyl-7-(2, 4, 5-trifluorophenyl)-7, 8-dihydro-6H-pyrimido [5, 4-b] [1, 4] oxazine (250 mg, 0.79 mmol), 3-fluoro-4-(4-methyl-1H-imidazol-1-yl) aniline (302 mg, 1.58 mmol) and cesium carbonate (361 mg, 1.10 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the reaction was diluted with water (50 mL) and extracted with $CH_2Cl_2$ (2×50 mL). The combined organic extracts were dried over sodium sulfate, filtered and concentrated in vacuo. The crude material was purified by column chromatography using 3% $MeOH/CH_2Cl_2$ to afford N-(3-fluoro-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine (135 mg, 38%) as an off-white solid. $^1$H-NMR (DMSO-$d_6$, 400 MHz): δ 9.44 (s, 1H), 8.09-8.00 (m, 1H), 7.77 (s, 1H), 7.70-7.60 (m, 2H), 7.52 (d, 1H), 7.39 (t, 1H), 7.17-7.08 (m, 2H), 5.10-5.08 (m, 1H), 4.21 (s, 2H), 3.10 (s, 3H), 2.13 (s, 3H); LCMS: 471.4 (M+1); (column; X-Select CSH C-18 (50×3.0 mm, 3.5 μm); RT 2.91 min. 0.05% Aq TFA: ACN; 0.80 mL/min); HPLC (column; Acquity BEH C-18 50×2.1 mm, 1.7 μm); RT 1.65 min. ACN: 0.025% Aq TFA; 0.5 mL/min; TLC: 5% $MeOH/CH_2Cl_2$ ($R_f$: 0.4).

Racemic compound of Example 98 was separated using a Chiralcel ADH (250×20 mm: 5 μm; (20 mg loading; 0.1% DEA in n-hexane: EtOH (A:B: 65:35) as mobile phase) to provide the compound of Example 98A (Fraction I (+)) and the compound of Example 98B (Fraction II (−)).

Example 98A

Synthesis of (+)-N-(3-fluoro-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine

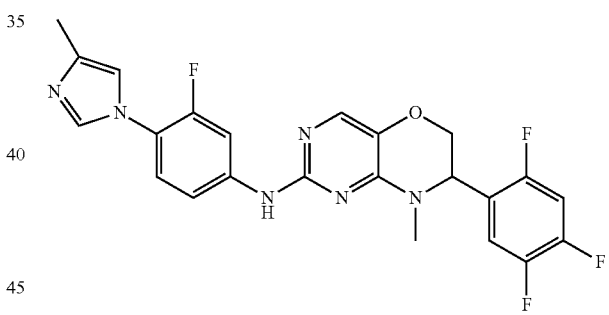

The compound of Example 98A was produced as described in Example 98. Analytical data for product Fraction I (+): $^1$H-NMR (DMSO-$d_6$, 400 MHz): δ 9.44 (s, 1H), 8.06-8.00 (m, 1H), 7.78 (s, 1H), 7.70-7.63 (m, 2H), 7.53 (d, 1H), 7.40 (t, 1H), 7.13-7.09 (m, 2H), 5.10-5.08 (m, 1H), 4.20 (s, 2H), 3.09 (s, 3H), 2.12 (s, 3H); Mass (ESI): 471.5 [M+1]; LCMS: 470.9 (M+1); (column; X-Select CSH C-18 (50×3.0 mm, 3.5 μm); RT 2.05 min 0.05% Aq TFA: ACN; 0.80 mL/min); HPLC (column; Acquity UPLC BEH C-18, 2.1× 50 mm, 1.7 μm); RT 1.66 min. ACN: 0.025% Aq TFA; 0.5 mL/min; Chiral HPLC: 99.8% RT=19.36 min (CHIRAL-PAK-AD-H (250×4.6 mm, 5 μm; mobile phase (A) 0.1% DEA in n-hexane (B) EtOH (A:B; 65:35); flow Rate: 1.0 mL/min); Optical rotation $[\alpha]_D^{20.00}$: +150.56 (c=0.25, $CH_2Cl_2$).

Example 98B

Synthesis of (−)-N-(3-fluoro-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine

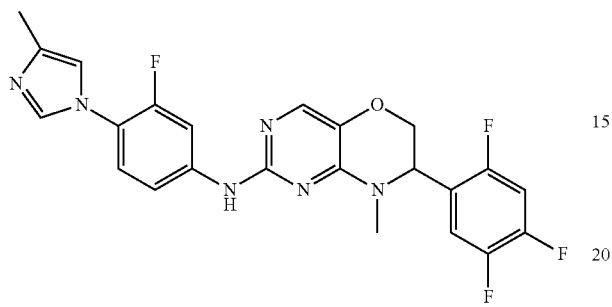

The compound of Example 98B was produced as described in Example 98. Analytical data for product Fraction II (−): $^1$H-NMR (DMSO-$d_6$, 400 MHz): δ 9.44 (s, 1H), 8.06-8.00 (m, 1H), 7.78 (s, 1H), 7.70-7.63 (m, 2H), 7.53 (d, 1H), 7.40 (t, 1H), 7.13-7.09 (m, 2H), 5.10-5.08 (m, 1H), 4.20 (s, 2H), 3.09 (s, 3H), 2.12 (s, 3H); Mass (ESI): 471.5 [M+1]; LCMS: 470.9 (M+1); (column; X-Select CSH C-18 (50×3.0 mm, 3.5 μm); RT 2.04 min 0.05% Aq TFA: ACN; 0.80 mL/min); HPLC (column; Acquity UPLC BEH C-18, 2.1× 50 mm, 1.7 μm); RT 1.66 min. ACN: 0.025% Aq TFA; 0.5 mL/min; Chiral HPLC: 97.8% RT=31.07 min (CHIRALPAK-AD-H (250×4.6 mm, 5 μm; mobile phase (A) 0.1% DEA in n-hexane (B) EtOH (A:B; 65:35); flow Rate: 1.0 mL/min); Optical rotation $[α]_D^{20.00}$: −113.98 (c=0.25, CH$_2$Cl$_2$).

Example 99

Synthesis of 7-(4-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

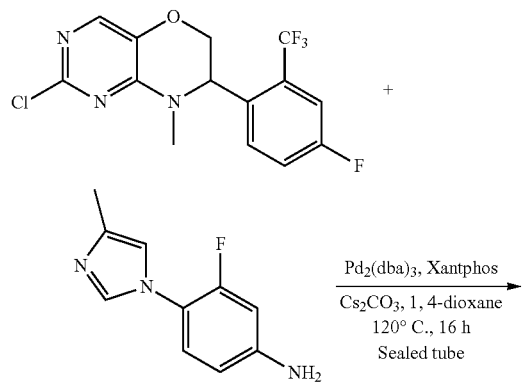

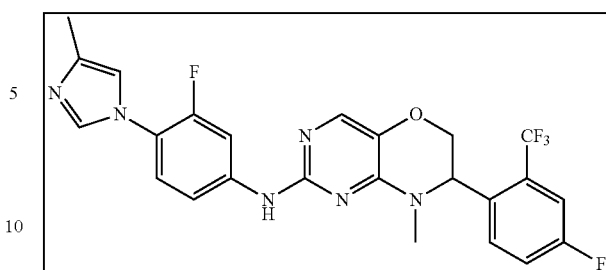

Synthesis of 7-(4-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine A dry vial charged with Pd$_2$(dba)$_3$ (33 mg, 0.03 mmol) and Xantphos (62 mg, 0.10 mmol) in 1, 4-dioxane (1 mL) at room temperature was degassed and the resultant reaction mixture was stirred at 120° C. for 3 min. A mixture of 2-chloro-7-(4-fluoro-2-(trifluoromethyl) phenyl)-8-methyl-7, 8-dihydro-6H-pyrimido [5, 4-b] [1, 4] oxazine (250 mg, 0.72 mmol), 3-fluoro-4-(4-methyl-1H-imidazol-1-yl) aniline (275 mg, 1.44 mmol) and cesium carbonate (328 mg, 1.00 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction was diluted with water (20 mL) and extracted with EtOAc (2×20 mL). The combined organic extracts were dried over sodium sulfate, filtered and concentrated in vacuo. The crude material was purified by column chromatography using 3% MeOH/CH$_2$Cl$_2$ to afford 7-(4-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine (200 mg, 55%) as an off-white solid. LCMS: 503 (M+1); (column; X-Select CSH C-18 (50×3.0 mm, 3.5 μm); RT 2.64 min 0.05% Aq TFA: ACN; 0.80 ml/min); HPLC (column; Eclipse XDB C-18 150×4.6 mm, 5.0 μm); RT 11.82 min. ACN: 5 mM Aq NH$_4$OAc; 1.0 mL/min; TLC: 5% MeOH/CH$_2$Cl$_2$ (R$_f$: 0.3).

Racemic compound of Example 99 was separated using a Chiralpak IA (250×4.6 mm: 5 μm; (30 mg loading; 0.1% DEA in n-hexane: CH$_2$Cl$_2$:MeOH (50:50); (A:B: 70:30) as mobile phase) to provide the compound of Example 99A (Fraction I (+)) and the compound of Example 99B (Fraction II (−)).

Example 99A

Synthesis of (+)-7-(4-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

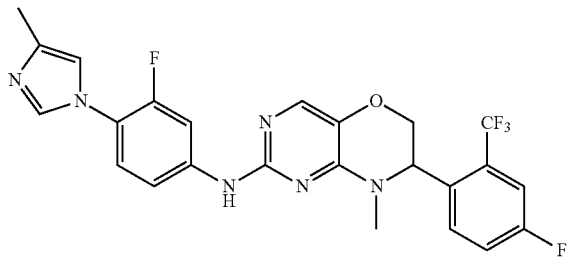

The compound of Example 99A was produced as described in Example 99. Analytical data for product Fraction I (+): $^1$H-NMR (CD$_3$OD, 400 MHz): δ 8.00-7.99 (m, 1H), 7.75 (s, 1H), 7.67 (s, 1H), 7.60-7.57 (m, 1H), 7.40-7.30 (m, 4H), 7.07-7.05 (m, 1H), 5.10-5.08 (m, 1H), 4.30-4.25 (m, 1H), 4.11-4.09 (m, 1H), 3.08 (s, 3H), 2.23 (s, 3H); Mass (ESI): 503.5 [M+1]; LCMS: 503.6 (M+1); (column; X-Select CSH C-18 (50×3.0 mm, 3.5 μm); RT 4.87 min. 5 mM Aq NH$_4$OAc: ACN; 0.80 mL/min); HPLC (column; Eclipse XDB C-18, 150×4.6 mm, 5.0μ); RT 11.78 min. ACN: 5 mM Aq NH$_4$OAc; 1.0 mL/min; Chiral HPLC: 98.2% RT=9.99 min (CHIRALPAK-IA (250×4.6 mm, 5 μm; mobile phase (A) 0.1% DEA in n-hexane (B) CH$_2$Cl$_2$:MeOH (50:50) (A:B; 70:30); flow Rate: 1.0 mL/min); Optical rotation $[α]_D^{20.00}$: +91.82 (c=0.25, CH$_2$Cl$_2$).

Example 99B

Synthesis of (−)-7-(4-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

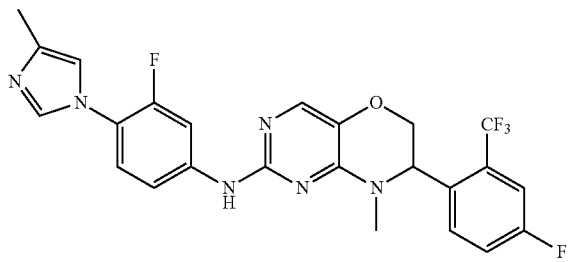

The compound of Example 99B was produced as described in Example 99. Analytical data for product Fraction II (−): $^1$H-NMR (CD$_3$OD, 400 MHz): δ 8.00-7.99 (m, 1H), 7.75 (s, 1H), 7.67 (s, 1H), 7.60-7.57 (m, 1H), 7.40-7.30 (m, 4H), 7.07-7.05 (m, 1H), 5.10-5.08 (m, 1H), 4.30-4.25 (m, 1H), 4.11-4.09 (m, 1H), 3.08 (s, 3H), 2.23 (s, 3H); Mass (ESI): 503.5 [M+1]; LCMS: 503.6 (M+1); (column; X-Select CSH C-18 (50×3.0 mm, 3.5 μm); RT 4.87 min. 5 mM Aq NH$_4$OAc: ACN; 0.80 mL/min); HPLC (column; Eclipse XDB C-18, 150×4.6 mm, 5.0μ); RT 11.79 min. ACN: 5 mM Aq NH$_4$OAc; 1.0 mL/min; Chiral HPLC: 99.0% RT=13.41 min (CHIRALPAK-IA (250×4.6 mm, 5 μm; mobile phase (A) 0.1% DEA in n-hexane (B) CH$_2$Cl$_2$:MeOH (50:50) (A:B; 70:30); flow Rate: 1.0 mL/min); Optical rotation $[α]_D^{20.00}$: −85.58 (c=0.25, CH$_2$Cl$_2$).

Example 100

Synthesis of 7-(5-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

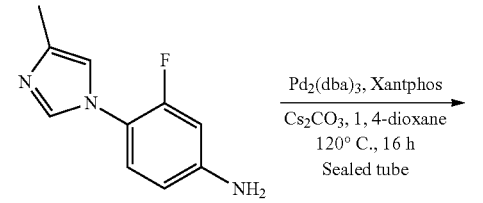

Synthesis of 7-(5-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine A dry vial charged with Pd$_2$(dba)$_3$ (25 mg, 0.02 mmol) and Xantphos (47 mg, 0.08 mmol) in 1, 4-dioxane (1 mL) at room temperature was degassed and the resultant reaction mixture was stirred at 120° C. for 3 min. A mixture of 2-chloro-7-(5-chloro-2-(trifluoromethyl) phenyl)-8-methyl-7, 8-dihydro-6H-pyrimido [5, 4-b] [1, 4] oxazine (200 mg, 0.55 mmol), 3-fluoro-4-(4-methyl-1H-imidazol-1-yl) aniline (114 mg, 0.60 mmol) and cesium carbonate (250 mg, 0.77 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction was diluted with water (20 mL) and extracted with EtOAc (2×20 mL). The combined organic extracts were dried over sodium sulfate, filtered and concentrated in vacuo. The crude material was purified by column chromatography using 3-5% MeOH: CH$_2$Cl$_2$ to afford 7-(5-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine (180 mg, 64%) as an off-white solid. LCMS: 518.9 (M+1); (column; X-Select CSH C-18 (50×3.0 mm, 3.5 µm); RT 2.66 min 0.05% Aq TFA: ACN; 0.80 mL/min); TLC: 5% MeOH/CH$_2$Cl$_2$ (R$_f$: 0.3).

Racemic compound of Example 100 was separated using a Chiralpak IC (250×4.6 mm: 5 µm; (30 mg loading; 0.1% DEA in n-hexane: CH$_2$Cl$_2$:MeOH (50:50); (A:B: 80:20) as mobile phase) to provide the compound of Example 100A (Fraction I (+)) and the compound of Example 100B (Fraction II (−)).

Example 100A

Synthesis of (+)-7-(5-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

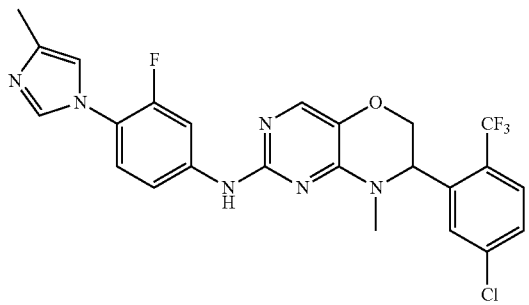 [SMILES: Cc1cn(-c2ccc(Nc3ncc4c(n3)N(C)C(c3cc(Cl)ccc3C(F)(F)F)CO4)cc2F)cn1]

The compound of Example 100A was produced as described in Example 100. Analytical data for product Fraction I (+): $^1$H-NMR (CD$_3$OD, 400 MHz): δ 8.00 (d, 1H), 7.80 (d, 1H), 7.78 (s, 1H), 7.70 (s, 1H), 7.60 (d, 1H), 7.41 (d, 1H), 7.37-7.31 (m, 1H), 7.28 (s, 1H), 7.08 (s, 1H), 5.10-5.08 (m, 1H), 4.30 (d, 1H), 4.11 (d, 1H), 3.11 (s, 3H), 2.23 (s, 3H); Mass (ESI): 519.1 [M+1]; LCMS: 519.1 (M+1); (column; X-Select CSH C-18 (50×3.0 mm, 3.5 µm); RT 2.84 min. 5 mM Aq NH$_4$OAc: ACN; 0.80 mL/min); UPLC (column; Acquity UPC BEH C-18, 2.1×50 mm, 1.7 µm); RT 1.88 min. ACN: 0.025% Aq TFA; 0.5 mL/min; Chiral HPLC: 99.61% RT=20.65 min (CHIRALPAK-IC (250×4.6 mm, 5 µm; mobile phase (A) 0.1% DEA in n-hexane (B) CH$_2$Cl$_2$:MeOH (50:50) (A:B; 85:15); flow Rate: 1.0 mL/min); Optical rotation [α]$_D^{20.00}$: +129.20 (c=0.25, CH$_2$Cl$_2$).

Example 100B

Synthesis of (−)-7-(5-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

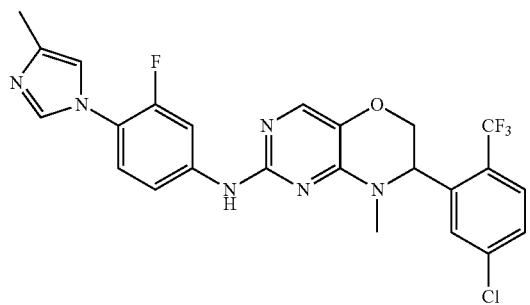 [SMILES: Cc1cn(-c2ccc(Nc3ncc4c(n3)N(C)C(c3cc(Cl)ccc3C(F)(F)F)CO4)cc2F)cn1]

The compound of Example 100B was produced as described in Example 100. Analytical data for product Fraction II (−): $^1$H-NMR (CD$_3$OD, 400 MHz): δ 8.00 (d, 1H), 7.80 (d, 1H), 7.78 (s, 1H), 7.70 (s, 1H), 7.60 (d, 1H), 7.41 (d, 1H), 7.37-7.31 (m, 1H), 7.28 (s, 1H), 7.08 (s, 1H), 5.10-5.08 (m, 1H), 4.30 (d, 1H), 4.11 (d, 1H), 3.11 (s, 3H), 2.23 (s, 3H); Mass (ESI): 519 [M+1]; LCMS: 519 (M+1); (column; X-Select CSH C-18 (50×3.0 mm, 3.5 µm); RT 2.86 min. 0.05% Aq TFA: ACN; 0.80 mL/min); UPLC (column; Acquity UPC BEH C-18, 2.1×50 mm, 1.7 µm); RT 1.88 min. ACN: 0.025% Aq TFA; 0.5 mL/min; Chiral HPLC: 95.4% RT=22.68 min (CHIRALPAK-IC (250×4.6 mm, 5 µm; mobile phase (A) 0.1% DEA in n-hexane (B) CH$_2$Cl$_2$: MeOH (50:50) (A:B; 85:15); flow Rate: 1.0 mL/min); Optical rotation [α]$_D^{20.00}$: −122.57 (c=0.25, CH$_2$Cl$_2$).

Example 101

Synthesis of 7-(2-chloro-4-fluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

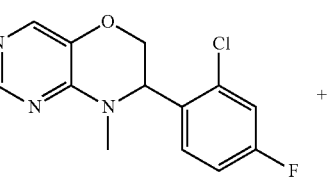

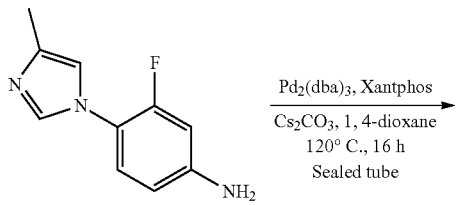

399

-continued

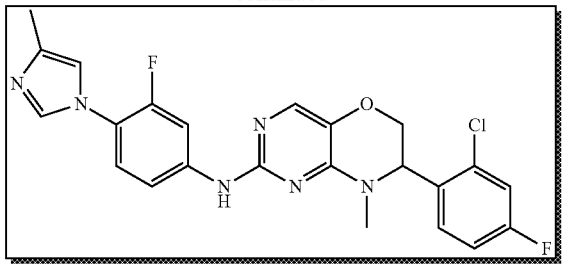

Synthesis of 7-(2-chloro-4-fluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine A dry vial charged with $Pd_2(dba)_3$ (37 mg, 0.04 mmol) and Xantphos (70 mg, 0.12 mmol) in 1, 4-dioxane (1.25 mL) at room temperature was degassed and the resultant reaction mixture was stirred at 120° C. for 3 min. A mixture of 2-chloro-7-(2-chloro-4-fluorophenyl)-8-methyl-7, 8-dihydro-6H-pyrimido [5, 4-b] [1, 4] oxazine (250 mg, 0.80 mmol), 3-fluoro-4-(4-methyl-1H-imidazol-1-yl) aniline (306 mg, 1.60 mmol) and cesium carbonate (366 mg, 1.12 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (50 mL) and extracted with $CH_2Cl_2$ (2×50 mL). The combined organic extracts were dried over sodium sulfate, filtered and concentrated in vacuo. The crude material was purified by column chromatography using 3% MeOH/$CH_2Cl_2$ to afford 7-(2-chloro-4-fluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine (100 mg, 26%) as an off-white solid. LCMS: 469.5 (M+1); (column; X-Select CSH C-18 (50×3.0 mm, 3.5 μm); RT 3.00 min. 0.05% Aq TFA: ACN; 0.80 mL/min); UPLC (column; Acquity UPLC BEH C-18 2.1×50 mm, 1.7 μm); RT 1.74 min. ACN: 0.025% Aq TFA; 0.5 mL/min; TLC: 5% MeOH/$CH_2Cl_2$ ($R_f$: 0.3).

Racemic compound of Example 101 was separated using a Chiralpak IA (250×20 mm: 5 μm; (40 mg loading; 0.1% DEA in n-hexane: $CH_2Cl_2$:MeOH (50:50); (A:B; 70:30) as mobile phase) to provide the compound of Example 101A (Fraction I (+)) and the compound of Example 101B (Fraction II (−)).

400

Example 101A

Synthesis of (+)-7-(2-chloro-4-fluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

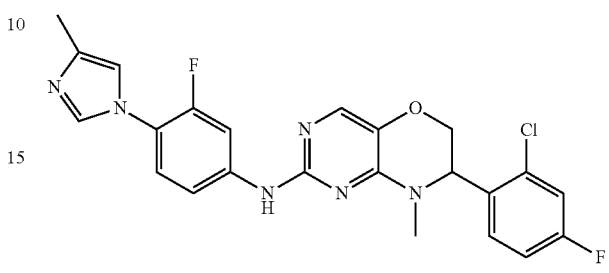

The compound of Example 101A was produced as described in Example 101. Analytical data for product Fraction I (+): $^1$H-NMR (CD$_3$OD, 400 MHz): δ 8.02-8.00 (m, 1H), 7.78 (s, 1H), 7.60 (s, 1H), 7.41-7.30 (m, 3H), 7.10-7.03 (m, 3H), 5.15-5.11 (m, 1H), 4.31-4.21 (m, 2H), 3.17 (s, 3H), 2.28 (s, 3H); Mass (ESI): 469 [M+1]; LCMS: 469 (M+1); (column; X-Select CSH C-18 (50×3.0 mm, 3.5 μm); RT 2.70 min. 0.05% Aq TFA: ACN; 0.80 mL/min); UPLC (column; Acquity UPLC BEH C-18, 2.1×50 mm, 1.7 μm); RT 1.75 min. ACN: 0.025% Aq TFA; 0.5 mL/min; Chiral HPLC: 100% RT=11.8 min (CHIRALPAK-IA (250× 4.6 mm, 5 μm; mobile phase (A) 0.1% DEA in n-hexane (B) $CH_2Cl_2$:MeOH (50:50) (A:B; 70:30); flow Rate: 1.0 mL/min); Optical rotation $[\alpha]_D^{20.02}$: +162.20 (c=0.25, $CH_2Cl_2$).

Example 101B

Synthesis of (−)-7-(2-chloro-4-fluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

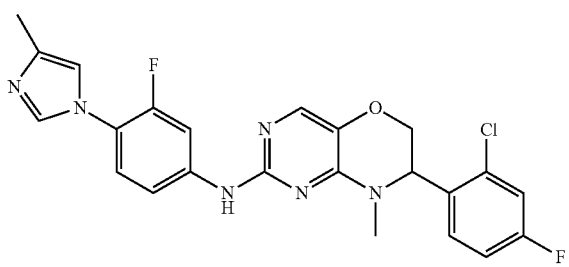

The compound of Example 101B was produced as described in Example 101. Analytical data for product Fraction II (−): $^1$H-NMR (CD$_3$OD, 400 MHz): δ 8.02-8.00 (m, 1H), 7.78 (s, 1H), 7.60 (s, 1H), 7.41-7.30 (m, 3H), 7.10-7.03 (m, 3H), 5.15-5.11 (m, 1H), 4.31-4.21 (m, 2H), 3.17 (s, 3H), 2.28 (s, 3H); Mass (ESI): 469.1 [M+1]; LCMS: 469 (M+1); (column; X-Select CSH C-18 (50×3.0 mm, 3.5 μm); RT 2.70 min. 0.05% Aq TFA: ACN; 0.80 mL/min); UPLC (column; Acquity UPLC BEH C-18, 2.1×50 mm, 1.7 μm); RT 1.75 min. ACN: 0.025% Aq TFA; 0.5 mL/min; Chiral HPLC: 99.1% RT=14.49 min (CHIRALPAK-IA (250×4.6 mm, 5 μm; mobile phase (A) 0.1% DEA in n-hexane (B) CH$_2$Cl$_2$:MeOH (50:50) (A:B; 70:30); flow Rate: 1.0 mL/min); Optical rotation [α]$_D^{20.00}$: −160.57 (c=0.25, CH$_2$Cl$_2$).

Example 102

Synthesis of 7-(2-chloro-4-fluorophenyl)-N-(3-fluoro-4-(2-methylpyridin-4-yl) phenyl)-8-methyl-7,8-dihydro-6H-pyrimido [5, 4-b] [1, 4] oxazin-2-amine

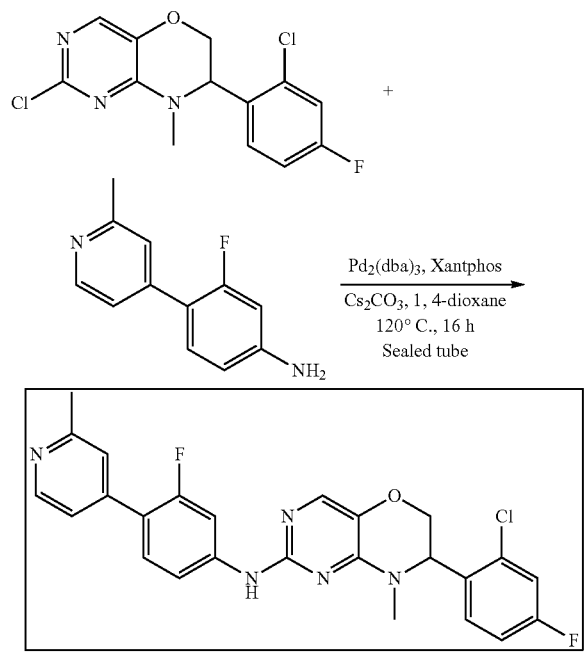

Synthesis of 7-(2-chloro-4-fluorophenyl)-N-(3-fluoro-4-(2-methylpyridin-4-yl) phenyl)-8-methyl-7,8-dihydro-6H-pyrimido [5, 4-b] [1, 4] oxazin-2-amine A dry vial charged with Pd$_2$(dba)$_3$ (29 mg, 0.03 mmol) and Xantphos (55 mg, 0.09 mmol) in 1, 4-dioxane (1 mL) at room temperature was degassed and the resultant reaction mixture was stirred at 120° C. for 3 min. A mixture of 2-chloro-7-(2-chloro-4-fluorophenyl)-8-methyl-7, 8-dihydro-6H-pyrimido [5, 4-b] [1, 4] oxazine (200 mg, 0.63 mmol), 3-fluoro-4-(2-methylpyridin-4-yl) aniline (260 mg, 0.12 mmol) and cesium carbonate (290 mg, 0.89 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction was diluted with water (20 mL) and extracted with CH$_2$Cl$_2$ (2×20 mL). The combined organic extracts were dried over sodium sulfate, filtered and concentrated in vacuo. The crude material was purified by column chromatography using 2% MeOH/CH$_2$Cl$_2$ to afford 7-(2-chloro-4-fluorophenyl)-N-(3-fluoro-4-(2-methylpyridin-4-yl) phenyl)-8-methyl-7, 8-dihydro-6H-pyrimido [5, 4-b] [1, 4] oxazin-2-amine (130 mg, 42%) as an off-white solid. HPLC (column; Acquity UPLC BEH C-18, 2.1×50 mm, 1.7 μm); RT 1.82 min. ACN: 0.025% Aq TFA; 0.5 ml/min; TLC: 5% MeOH/CH$_2$Cl$_2$ (R$_f$; 0.4).

Racemic compound of Example 102 was separated using a Chiralpak IA (250×20 mm: 5 μm; (20 mg loading; 0.1% DEA in n-hexane: CH$_2$Cl$_2$:MeOH (50:50); (A:B: 85:15) as mobile phase) to provide the compound of Example 102A (Fraction I (+)) and the compound of Example 102B (Fraction II (−)).

Example 102A

Synthesis of (+)-7-(2-chloro-4-fluorophenyl)-N-(3-fluoro-4-(2-methylpyridin-4-yl) phenyl)-8-methyl-7,8-dihydro-6H-pyrimido [5, 4-b] [1, 4] oxazin-2-amine

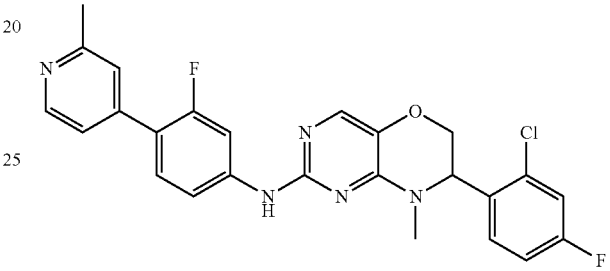

The compound of Example 102A was produced as described in Example 102. Analytical data for product Fraction I (+): $^1$H-NMR (CD$_3$OD, 400 MHz): δ 8.40 (d, 1H), 7.92-7.88 (m, 1H), 7.60 (s, 1H), 7.50-7.40 (m, 4H), 7.31 (d, 1H), 7.09 (d, 2H), 5.18 (s, 1H), 4.30-4.21 (m, 2H), 3.15 (s, 3H), 2.59 (s, 3H); Mass (ESI): 480 [M+1]; LCMS: 479.9 (M+1); (column; X-Select CSH C-18 (50×3.0 mm, 3.5 μm); RT 2.52 min. 0.05% Aq TFA: ACN; 0.80 mL/min); UPLC (column; Acquity UPLC BEH C-18, 2.1×50 mm, 1.7 μm); RT 1.81 min. ACN: 0.025% Aq TFA; 0.5 mL/min; Chiral HPLC: 100.0% RT=18.06 min (CHIRALPAK-IA (250×4.6 mm, 5 μm; mobile phase (A) 0.1% DEA in n-hexane (B) CH$_2$Cl$_2$:MeOH (50:50) (A:B; 85:15); flow Rate: 1.0 mL/min); Optical rotation [α]$_D^{20.02}$: +139.93 (c=0.25, DCM).

Example 102B

Synthesis of (−)-7-(2-chloro-4-fluorophenyl)-N-(3-fluoro-4-(2-methylpyridin-4-yl) phenyl)-8-methyl-7,8-dihydro-6H-pyrimido [5, 4-b] [1, 4] oxazin-2-amine

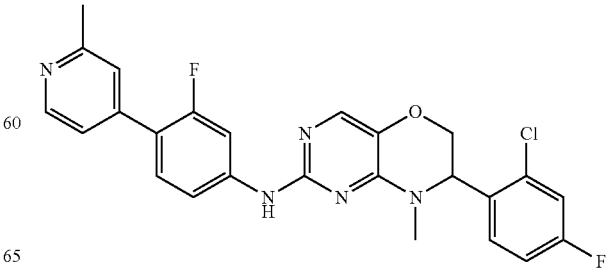

The compound of Example 102B was produced as described in Example 102. Analytical data for product Fraction II (−): $^1$H-NMR (CD$_3$OD, 400 MHz): δ 8.40 (d, 1H), 7.92-7.88 (m, 1H), 7.60 (s, 1H), 7.50-7.40 (m, 4H), 7.31 (d, 1H), 7.09 (d, 2H), 5.18 (s, 1H), 4.30-4.21 (m, 2H), 3.15 (s, 3H), 2.59 (s, 3H); Mass (ESI): 480.1 [M+1]; LCMS: 479.9 (M+1); (column; X-Select CSH C-18 (50×3.0 mm, 3.5 μm); RT 2.52 min. 0.05% Aq TFA: ACN; 0.80 mL/min); UPLC (column; Acquity UPLC BEH C-18, 2.1×50 mm, 1.7 μm); RT 1.82 min. ACN: 0.025% Aq TFA; 0.5 mL/min; Chiral HPLC: 97.7% RT=20.83 min (CHIRALPAK-IA (250×4.6 mm, 5 μm; mobile phase (A) 0.1% DEA in n-hexane (B) CH$_2$Cl$_2$:MeOH (50:50) (A:B; 85:15); flow Rate: 1.0 mL/min); Optical rotation $[α]_D^{20.01}$: −139.37 (c=0.25, DCM).

Example 103

Synthesis of 7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

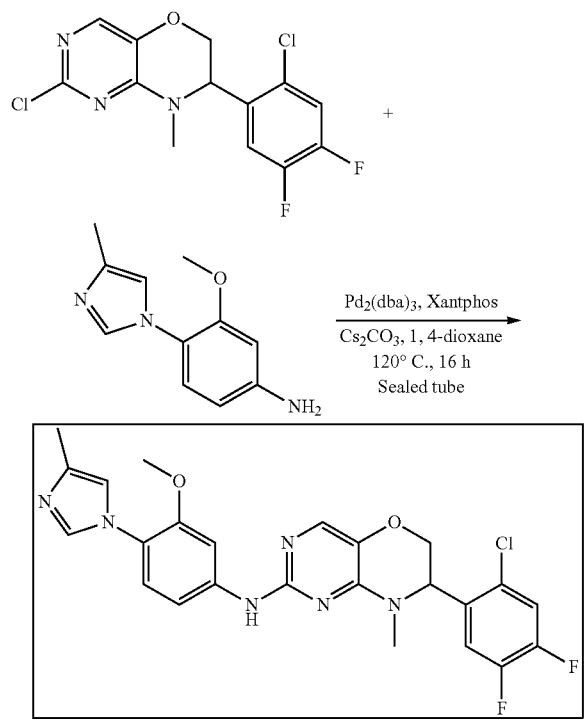

Synthesis of 7-(2-chloro-4, 5-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine A dry vial charged with Pd$_2$(dba)$_3$ (27 mg, 0.03 mmol) and Xantphos (52 mg, 0.90 mmol) in 1, 4-dioxane (1 mL) at room temperature was degassed and the resultant reaction mixture was stirred at 120° C. for 3 min. A mixture of 2-chloro-7-(2-chloro-4, 5-difluorophenyl)-8-methyl-7, 8-dihydro-6H-pyrimido [5, 4-b] [1, 4] oxazine (200 mg, 0.60 mmol), 3-methoxy-4-(4-methyl-1H-imidazol-1-yl) aniline (245 mg, 0.12 mmol) and cesium carbonate (274 mg, 0.84 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction was diluted with water (20 mL) and extracted with CH$_2$Cl$_2$ (2×20 mL). The combined organic extracts were dried over sodium sulfate, filtered and concentrated in vacuo. The crude material was washed with ether (2×20 mL) to afford 7-(2-chloro-4, 5-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (180 mg, 60%) as an off-white solid. $^1$H-NMR (CD$_3$OD, 400 MHz): δ 9.03 (s, 1H), 7.80 (s, 1H), 7.68 (s, 1H), 7.60-7.58 (m, 1H), 7.50 (s, 1H), 7.47 (d, 1H), 7.37 (d, 1H), 7.11-7.09 (m, 1H), 5.30-5.27 (m, 1H), 4.40-4.29 (m, 2H), 3.91 (s, 3H), 3.21 (s, 3H), 2.41 (s, 3H); UPLC (column; Acquity UPLC BEH C-18 2.1×50 mm, 1.7 μm); RT 1.75 min. ACN: 0.025% Aq TFA; 0.5 mL/min; TLC: 5% MeOH/CH$_2$Cl$_2$ (R$_f$: 0.4).

Racemic compound of Example 103 was separated using a Chiralpak IA (250×4.6 mm: 5 μm; (20 mg loading; 0.1% TFA in n-hexane: CH$_2$Cl$_2$:MeOH (50:50); (A:B: 80:20) as mobile phase) to provide the compound of Example 103A (Fraction I (+)) and the compound of Example 103B (Fraction II (−)).

Example 103A

Synthesis of (+)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

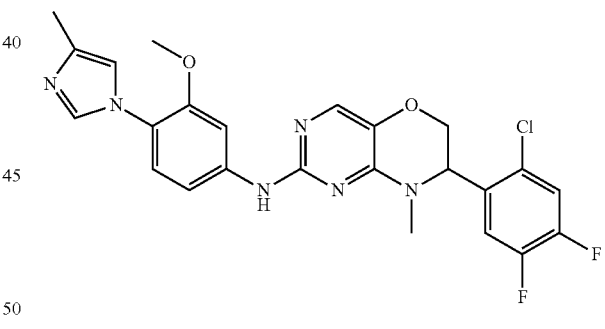

The compound of Example 103A was produced as described in Example 103. Analytical data for product Fraction I (+): $^1$H-NMR (CD$_3$OD, 400 MHz): δ 9.05 (s, 1H), 7.80 (s, 1H), 7.65 (s, 1H), 7.61-7.59 (m, 1H), 7.51 (s, 1H), 7.48 (d, 1H), 7.37 (d, 1H), 7.11-7.09 (m, 1H), 5.30-5.27 (m, 1H), 4.40-4.30 (m, 2H), 3.92 (s, 3H), 3.21 (s, 3H), 2.40 (s, 3H); Mass (ESI): 499 [M+1]; LCMS: 499 (M+1); (column; X-Select CSH C-18 (50×3.0 mm, 3.5 μm); RT 3.07 min. 0.05% Aq TFA: ACN; 0.80 mL/min); HPLC (column; Acquity UPLC BEH C-18, 2.1×50 mm, 1.7 μm); RT 1.75 min. ACN: 0.025% Aq TFA; 0.5 mL/min; Chiral HPLC: 99.9% RT=17.89 min (CHIRALPAK-IA (250×4.6 mm, 5 μm; mobile phase (A) 0.1% TFA in n-hexane (B) CH$_2$Cl$_2$:MeOH (50:50) (A:B: 80:20); flow Rate: 1.0 mL/min); Optical rotation $[α]_D^{20.00}$: +128.46 (c=0.25, CH$_2$Cl$_2$).

Example 103B

Synthesis of (−)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

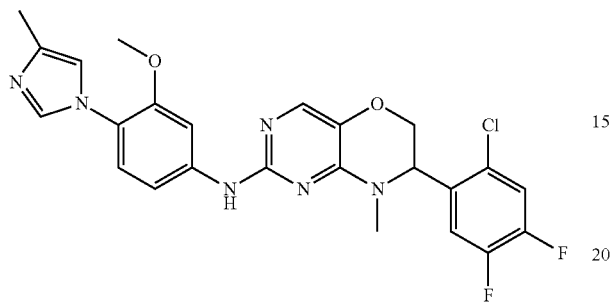

The compound of Example 103B was produced as described in Example 103. Analytical data for product Fraction II (−): $^1$H-NMR (CD$_3$OD, 400 MHz): δ 9.05 (s, 1H), 7.80 (s, 1H), 7.65 (s, 1H), 7.61-7.59 (m, 1H), 7.51 (s, 1H), 7.48 (d, 1H), 7.37 (d, 1H), 7.11-7.09 (m, 1H), 5.30-5.27 (m, 1H), 4.40-4.30 (m, 2H), 3.92 (s, 3H), 3.21 (s, 3H), 2.40 (s, 3H); Mass (ESI): 499 [M+1]; LCMS: 499 (M+1); (column; X-Select CSH C-18 (50×3.0 mm, 3.5 μm); RT 3.07 min. 0.05% Aq TFA: ACN; 0.80 mL/min); HPLC (column; Acquity UPLC BEH C-18, 2.1×50 mm, 1.7 μm); RT 1.74 min. ACN: 0.025% Aq TFA; 0.5 mL/min; Chiral HPLC: 99.3% RT=21.00 min (CHIRALPAK-IA (250×4.6 mm, 5 μm; mobile phase (A) 0.1% TFA in n-hexane (B) CH$_2$Cl$_2$: MeOH (50:50) (A:B; 80:20); flow Rate: 1.0 mL/min); Optical rotation $[\alpha]_D^{19.99}$: −121.56 (c=0.25, CH$_2$Cl$_2$).

Example 104

Synthesis of 7-(5-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

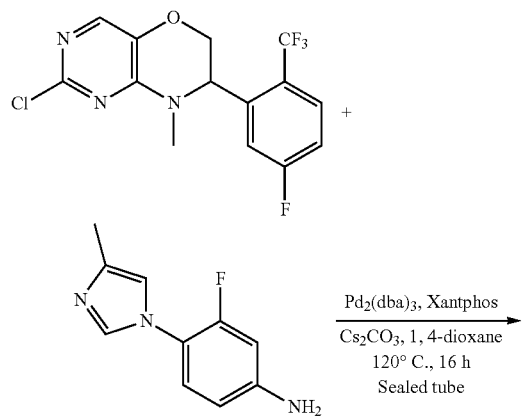

-continued

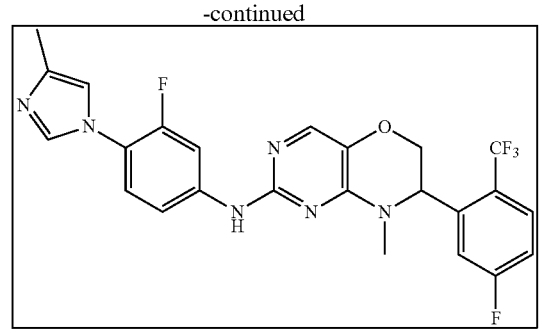

Synthesis of 7-(5-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine A dry vial charged with Pd$_2$(dba)$_3$ (33 mg, 0.03 mmol) and Xantphos (62 mg, 0.10 mmol) in 1, 4-dioxane (1.5 mL) at room temperature was degassed and the resultant reaction mixture was stirred at 120° C. for 3 min. A mixture of 2-chloro-7-(5-fluoro-2-(trifluoromethyl) phenyl)-8-methyl-7, 8-dihydro-6H-pyrimido [5, 4-b] [1, 4] oxazine (250 mg, 0.72 mmol), 3-fluoro-4-(4-methyl-1H-imidazol-1-yl) aniline (275 mg, 1.44 mmol) and cesium carbonate (327 mg, 1.00 mmol) in 1, 4-dioxane (1.5 mL) was degassed and the catalyst premix was added. The resultant mixture was stirred at 120° C. for 16 h in a sealed tube. After consumption of the starting material (monitored by TLC and LCMS), the reaction was diluted with water (20 mL) and extracted with CH$_2$Cl$_2$ (2×20 mL). The combined organic extracts were dried over sodium sulfate, filtered and concentrated in vacuo. The crude material was purified by column chromatography using 2% MeOH/CH$_2$Cl$_2$ to afford 7-(5-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine (180 mg, 50%) as an off-white solid. UPLC (column; Acquity UPLC BEH C-18 2.1×50 mm, 1.7 μm); RT 1.82 min. ACN: 0.025% Aq TFA; 0.5 mL/min; TLC: 5% MeOH/CH$_2$Cl$_2$ (R$_f$: 0.3).

Racemic compound of Example 104 was separated using a Chiralpak IA (250×4.6 mm: 5 μm; (30 mg loading; 0.1% DEA in n-hexane: THF:MeOH (85:15); (A:B: 80:20) as mobile phase) to provide the compound of Example 104A (Fraction I (−)) and the compound of Example 104B (Fraction II (+)).

Example 104A

Synthesis of (−)-7-(5-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

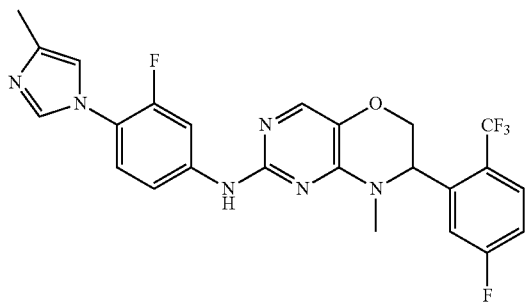 [SMILES: Cc1cn(-c2ccc(Nc3ncc4c(n3)N(C)C(c3cc(F)ccc3C(F)(F)F)CO4)cc2F)cn1]

The compound of Example 104A was produced as described in Example 104. Analytical data for product Fraction I (−): $^1$H-NMR (CD$_3$OD, 500 MHz): δ 8.02 (dd, 1H), 7.90-7.86 (m, 1H), 7.80-7.78 (m, 1H), 7.71 (s, 1H), 7.46-7.43 (m, 1H), 7.38-7.28 (m, 2H), 7.08 (s, 1H), 7.04 (d, 1H), 5.12-5.10 (m, 1H), 4.31 (d, 1H), 4.15 (d, 1H), 3.11 (s, 3H), 2.23 (s, 3H); Mass (ESI): 503 [M+1]; LCMS: 503 (M+1); (column; X-Select CSH C-18 (50×3.0 mm, 3.5 μm); RT 2.55 min. 0.05% Aq TFA: ACN; 0.80 mL/min); HPLC (column; Eclpise XDB C-18, 150×4.6 mm, 5.0μ); RT 11.65 min. ACN: 5 mM Aq NH$_4$OAc; 1.0 mL/min; Chiral HPLC: 94.1% RT=14.34 min (CHIRALPAK-IA (250×4.6 mm, 5 μm; mobile phase (A) 0.1% DEA in n-hexane (B) THF: MeOH (85:15) (A:B; 80:20); flow Rate: 1.0 mL/min); Optical rotation $[α]_D^{19.97}$: −64.56 (c=0.25, CH$_2$Cl$_2$).

Example 104B

Synthesis of (+)-7-(5-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

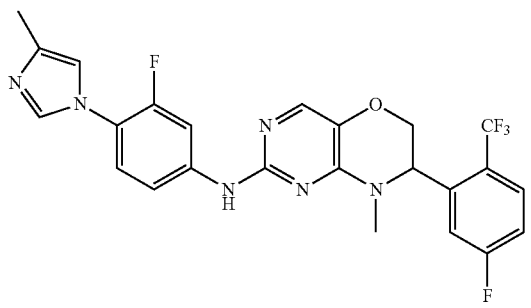 [SMILES: Cc1cn(-c2ccc(Nc3ncc4c(n3)N(C)C(c3cc(F)ccc3C(F)(F)F)CO4)cc2F)cn1]

The compound of Example 104B was produced as described in Example 104. Analytical data for product Fraction II (+): $^1$H-NMR (CD$_3$OD, 500 MHz): δ 8.02 (dd, 1H), 7.90-7.86 (m, 1H), 7.80-7.78 (m, 1H), 7.71 (s, 1H), 7.46-7.43 (m, 1H), 7.38-7.28 (m, 2H), 7.08 (s, 1H), 7.04 (d, 1H), 5.12-5.10 (m, 1H), 4.31 (d, 1H), 4.15 (d, 1H), 3.11 (s, 3H), 2.23 (s, 3H); Mass (ESI): 503 [M+1]; LCMS: 503 (M+1); (column; X-Select CSH C-18 (50×3.0 mm, 3.5 μm); RT 2.55 min. 0.05% Aq TFA: ACN; 0.80 mL/min); HPLC (column; Eclpise XDB C-18, 150×4.6 mm, 5.0μ); RT 11.66 min. ACN: 5 mM Aq NH$_4$OAc; 1.0 mL/min; Chiral HPLC: 98.5% RT=18.84 min (CHIRALPAK-IA (250×4.6 mm, 5 μm; mobile phase (A) 0.1% DEA in n-hexane (B) THF: MeOH (85:15) (A:B; 80:20); flow Rate: 1.0 mL/min); Optical rotation $[α]_D^{20.00}$: +67.23 (c=0.25, CH$_2$Cl$_2$).

Example 105

Synthesis of 7-(5-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

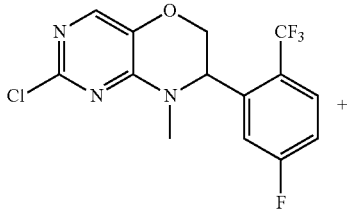

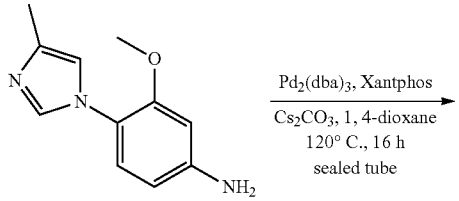

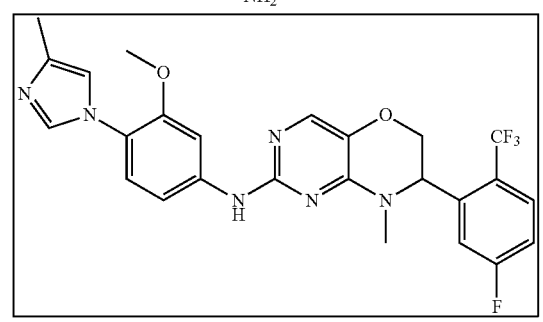

Synthesis of 7-(5-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine A dry vial charged with Pd$_2$(dba)$_3$ (33 mg, 0.03 mmol) and Xantphos (62 mg, 0.10 mmol) in 1, 4-dioxane (1.25 mL) at room temperature was degassed and the resultant reaction mixture was stirred at 120° C. for 3 min. A mixture of 2-chloro-7-(5-fluoro-2-(trifluoromethyl) phenyl)-8-methyl-7, 8-dihydro-6H-pyrimido [5, 4-b] [1, 4] oxazine (250 mg, 0.72 mmol), 3-methoxy-4-(4-methyl-1H-imidazol-1-yl) aniline (292 mg, 1.44 mmol) and cesium carbonate (327 mg, 1.00 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (50 mL) and extracted with EtOAc (2×50 mL). The combined organic extracts were dried over sodium sulfate, filtered and concentrated in vacuo. The crude material was purified by column chromatography using 8% MeOH/CH$_2$Cl$_2$ to afford 7-(5-fluoro-2-(trifluoromethyl)phenyl)-N-(3-methoxy-4-(4-methyl-1H-imidazol-1-yl)phenyl)-8-methyl-7, 8-dihydro-6H-pyrimido [5, 4-b] [1, 4] oxazin-2-amine (80 mg, 21%) as an off-white solid. $^1$H-NMR (CD$_3$OD, 500 MHz): δ 7.91-7.85 (m, 1H), 7.79-7.77 (m, 1H), 7.70-7.68 (m, 2H), 7.34-7.26 (m, 2H), 7.21-7.19 (m, 1H), 7.06-7.02 (m, 1H), 6.99 (s, 1H), 5.14-5.12 (m, 1H), 4.32-4.28 (m, 1H), 4.19-4.12 (m, 1H), 3.87 (s, 3H), 3.15 (s, 3H), 2.23 (s, 3H); LCMS: 514.9 (M+1); (column; X-Select CSH C-18 (50×3.0 mm, 3.5 μm); RT 2.54 min 0.05% Aq TFA: ACN; 0.80 mL/min); UPLC (column; Eclipse XDB-C-18 150×4.6 mm, 5.0 μm); RT 11.60 min. ACN: 5 mM Aq NH$_4$OAc; 1.0 mL/min; TLC: 10% MeOH/CH$_2$Cl$_2$ (R$_f$; 0.3).

Racemic compound of Example 105 was separated using a Chiralpak IA (250×20 mm; 5 μm; (150 mg loading; 0.1% DEA in n-hexane: CH$_2$Cl$_2$:MeOH (50:50) (A:B: 85:15) as mobile phase) to provide the compound of Example 105A (Fraction I (−)) and the compound of Example 105B (Fraction II (+)).

Example 105A

Synthesis of (−)-7-(5-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

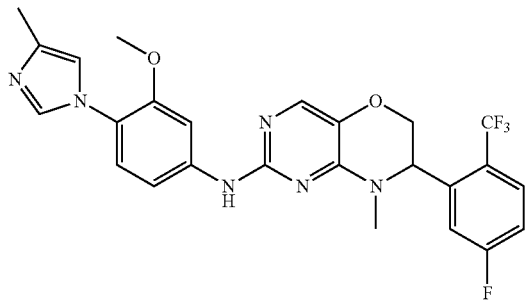

The compound of Example 105A was produced as described in Example 105. Analytical data for product Fraction I (−): $^1$H-NMR (CD$_3$OD, 400 MHz): δ 7.90-7.86 (m, 1H), 7.79-7.77 (m, 1H), 7.70-7.68 (m, 2H), 7.34-7.26 (m, 2H), 7.21-7.19 (m, 1H), 7.06-7.02 (m, 1H), 6.99 (s, 1H), 5.14-5.12 (m, 1H), 4.32-4.28 (m, 1H), 4.19-4.12 (m, 1H), 3.87 (s, 3H), 3.15 (s, 3H), 2.23 (s, 3H); Mass (ESI): 515.1 [M+1]; LCMS: 515 (M+1); (column; X-Select CSH C-18 (50×3.0 mm, 3.5 μm); RT 2.50 min. 0.05% Aq TFA: ACN; 0.80 mL/min); UPLC (column; Acquity UPLC BEH C-18, 2.1×50 mm, 1.7 μm); RT 1.80 min. ACN: 0.025% Aq TFA; 0.5 mL/min; Chiral HPLC: 99.7% RT=13.66 min (CHIRALPAK-IA (250×4.6 mm, 5 μm; mobile phase (A) 0.1% DEA in n-hexane (B) CH$_2$Cl$_2$:MeOH (50:50) (A:B; 85:15); flow Rate: 1.0 mL/min); Optical rotation [α]$_D^{20.01}$: −114.72 (c=0.25, CH$_2$Cl$_2$).

Example 105B

Synthesis of (+)-7-(5-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

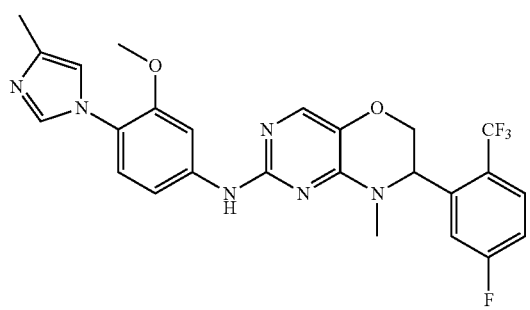 [SMILES: COc1cc(Nc2ncc3c(n2)N(C)C(c2cc(F)ccc2C(F)(F)F)CO3)ccc1-n1cnc(C)c1]

The compound of Example 105B was produced as described in Example 105. Analytical data for product Fraction II (+): $^1$H-NMR (CD$_3$OD, 400 MHz): δ 7.90-7.86 (m, 1H), 7.79-7.77 (m, 1H), 7.70-7.68 (m, 2H), 7.34-7.26 (m, 2H), 7.21-7.19 (m, 1H), 7.06-7.02 (m, 1H), 6.99 (s, 1H), 5.14-5.12 (m, 1H), 4.32-4.28 (m, 1H), 4.19-4.12 (m, 1H), 3.87 (s, 3H), 3.15 (s, 3H), 2.23 (s, 3H); Mass (ESI): 515 [M+1]; LCMS: 515 (M+1); (column; X-Select CSH C-18 (50×3.0 mm, 3.5 μm); RT 2.49 min. 0.05% Aq TFA: ACN; 0.80 mL/min); UPLC (column; Acquity UPLC BEH C-18, 2.1×50 mm, 1.7 μm); RT 1.79 min. ACN: 0.025% Aq TFA; 0.5 mL/min; Chiral HPLC: 98.3% RT=15.69 min (CHIRALPAK-IA (250×4.6 mm, 5 μm; mobile phase (A) 0.1% DEA in n-hexane (B) CH$_2$Cl$_2$:MeOH (50:50) (A:B; 85:15); flow Rate: 1.0 mL/min); Optical rotation [α]$_D^{19.99}$: +102.62 (c=0.25, CH$_2$Cl$_2$).

Example 106

Synthesis of 7-(4-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

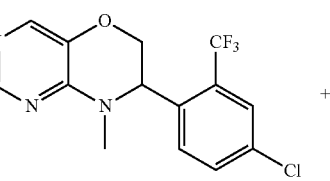

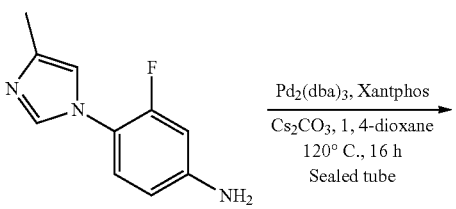

-continued

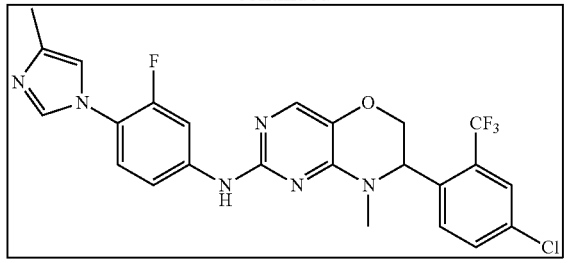

Synthesis of 7-(4-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine A dry vial charged with $Pd_2(dba)_3$ (31 mg, 0.03 mmol) and Xantphos (59 mg, 0.10 mmol) in 1, 4-dioxane (1.25 mL) at room temperature was degassed and the resultant reaction mixture was stirred at 120° C. for 3 min. A mixture of 2-chloro-7-(4-chloro-2-(trifluoromethyl) phenyl)-8-methyl-7, 8-dihydro-6H-pyrimido [5, 4-b] [1, 4] oxazine (250 mg, 0.68 mmol), 3-fluoro-4-(4-methyl-1H-imidazol-1-yl) aniline (157 mg, 0.82 mmol) and cesium carbonate (313 mg, 0.96 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the reaction was diluted with water (20 mL) and extracted with $CH_2Cl_2$ (2×20 mL). The combined organic extracts were dried over sodium sulfate, filtered and concentrated in vacuo. The crude material was purified by column chromatography using 10% MeOH/$CH_2Cl_2$ to afford 7-(4-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (80 mg, 22%) as an off-white solid. UPLC (column; Acquity UPLC BEH-C18 2.1×50 mm, 1.7 μm); RT 1.97 min. ACN: 0.025% Aq TFA; 0.5 mL/min; TLC: 10% MeOH/$CH_2Cl_2$ ($R_f$: 0.5).

Racemic compound of Example 106 was separated using a Chiralpak IA (250×4.6 mm: 5 μm; (30 mg loading; 0.1% DEA in n-hexane: $CH_2Cl_2$:MeOH (50:50); (A:B: 70:30) as mobile phase) to provide the compound of Example 106A (Fraction I (+)) and the compound of Example 106B (Fraction II (−)).

Example 106A

Synthesis of (+)-7-(4-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

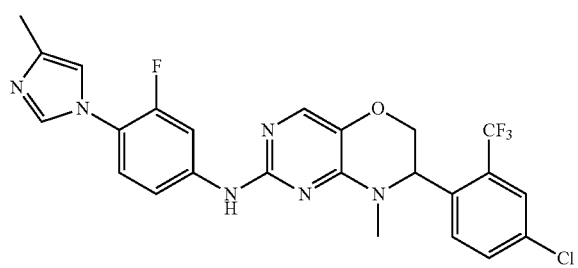

The compound of Example 106A was produced as described in Example 106. Analytical data for product Fraction I (+): $^1$H-NMR (CD$_3$OD, 500 MHz): δ 8.04-8.01 (m, 1H), 7.85-7.83 (m, 1H), 7.78 (s, 1H), 7.71-7.66 (m, 2H), 7.46-7.42 (m, 1H), 7.38-7.32 (m, 2H), 7.10 (s, 1H), 5.13-5.10 (m, 1H), 4.20 (d, 1H), 4.14 d, 1H), 3.09 (s, 3H), 2.25 (s, 3H); Mass (ESI): 519 [M+1]; LCMS: 519 (M+1); (column; X-Select CSH C-18 (50×3.0 mm, 3.5 μm); RT 2.74 min. 0.05% Aq TFA: ACN; 0.80 mL/min); UPLC (column; Acquity UPLC BEH C-18, 2.1×50 mm, 1.7 μm); RT 1.97 min. ACN: 0.025% Aq TFA; 0.5 mL/min; Chiral HPLC: 100.0% RT=15.68 min (CHIRALPAK-IA (250×4.6 mm, 5 μm; mobile phase (A) 0.1% DEA in n-hexane (B) $CH_2Cl_2$: MeOH (50:50) (A:B; 70:30); flow Rate: 1.0 mL/min); Optical rotation $[\alpha]_D^{20.00}$: +140.00 (c=0.25, MeOH).

Example 106B

Synthesis of (−)-7-(4-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

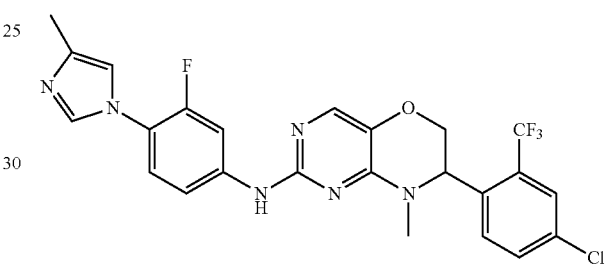

The compound of Example 106B was produced as described in Example 106. Analytical data for product Fraction II (−): $^1$H-NMR (CD$_3$OD, 500 MHz): δ 8.04-8.01 (m, 1H), 7.85-7.83 (m, 1H), 7.78 (s, 1H), 7.71-7.66 (m, 2H), 7.46-7.42 (m, 1H), 7.38-7.32 (m, 2H), 7.10 (s, 1H), 5.13-5.10 (m, 1H), 4.20 (d, 1H), 4.14 d, 1H), 3.09 (s, 3H), 2.25 (s, 3H); Mass (ESI): 519 [M+1]; LCMS: 519 (M+1); (column; X-Select CSH C-18 (50×3.0 mm, 3.5 μm); RT 2.74 min. 0.05% Aq TFA: ACN; 0.80 mL/min); UPLC (column; Acquity UPLC BEH C-18, 2.1×50 mm, 1.7 μm); RT 1.97 min. ACN: 0.025% Aq TFA; 0.5 mL/min; Chiral HPLC: 99.4% RT=21.36 min (CHIRALPAK-IA (250×4.6 mm, 5 μm; mobile phase (A) 0.1% DEA in n-hexane (B) $CH_2Cl_2$: MeOH (50:50) (A:B; 70:30); flow Rate: 1.0 mL/min); Optical rotation $[\alpha]_D^{19.99}$: −126.81 (c=0.25, MeOH).

Example 107

Synthesis of 7-(4-chloro-2-(trifluoromethyl) phenyl)-N-(3-methoxy-4-(2-methylpyridin-4-yl) phenyl)-8-methyl-7, 8-dihydro-6H-pyrimido [5, 4-b] [1, 4] oxazin-2-amine

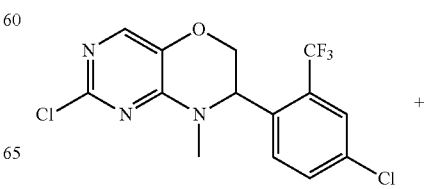

413
-continued

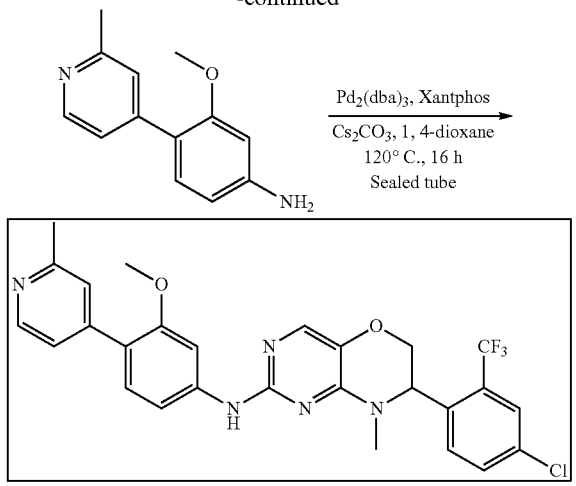

Synthesis of 7-(4-chloro-2-(trifluoromethyl) phenyl)-N-(3-methoxy-4-(2-methylpyridin-4-yl) phenyl)-8-methyl-7, 8-dihydro-6H-pyrimido [5, 4-b] [1, 4] oxazin-2-amine A dry vial charged with $Pd_2(dba)_3$ (31 mg, 0.03 mmol) and Xantphos (59 mg, 0.10 mmol) in 1, 4-dioxane (1.25 mL) at room temperature was degassed and the resultant reaction mixture was stirred at 120° C. for 3 min. A mixture of 2-chloro-7-(4-chloro-2-(trifluoromethyl) phenyl)-8-methyl-7, 8-dihydro-6H-pyrimido [5, 4-b] [1, 4] oxazine (250 mg, 0.68 mmol), 3-methoxy-4-(2-methylpyridin-4-yl) aniline (293 mg, 1.37 mmol) and cesium carbonate (312 mg, 0.96 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the reaction was diluted with water (50 mL) and extracted with $CH_2Cl_2$ (2×50 mL). The combined organic extracts were dried over sodium sulfate, filtered and concentrated in vacuo. The crude material was purified by column chromatography using 3% MeOH/$CH_2Cl_2$ to afford 7-(4-chloro-2-(trifluoromethyl) phenyl)-N-(3-methoxy-4-(2-methylpyridin-4-yl) phenyl)-8-methyl-7, 8-dihydro-6H-pyrimido [5, 4-b] [1, 4] oxazin-2-amine (90 mg, 24%) as an off-white solid. LCMS: 542.1 (M+1); (column; X-Select CSH C-18 (50×3.0 mm, 3.5 µm); RT 2.74 min. 0.05% Aq TFA: ACN; 0.80 mL/min); UPLC (column; Acquity UPLC BEH-C18 2.1×50 mm, 1.7 µm); RT 1.99 min. ACN: 0.025% Aq TFA; 0.5 mL/min; TLC: 5% MeOH/$CH_2Cl_2$ ($R_f$: 0.5).

Racemic compound of Example 107 was separated using a Chiralpak IA (250×4.6 mm: 5 µm; (30 mg loading; 0.1% DEA in n-hexane: $CH_2Cl_2$:MeOH (50:50); (A:B: 85:15) as mobile phase) to provide the compound of Example 107A (Fraction I (−)) and the compound of Example 107B (Fraction II (+)).

414

Example 107A

Synthesis of (−)-7-(4-chloro-2-(trifluoromethyl) phenyl)-N-(3-methoxy-4-(2-methylpyridin-4-yl) phenyl)-8-methyl-7, 8-dihydro-6H-pyrimido [5, 4-b] [1, 4] oxazin-2-amine

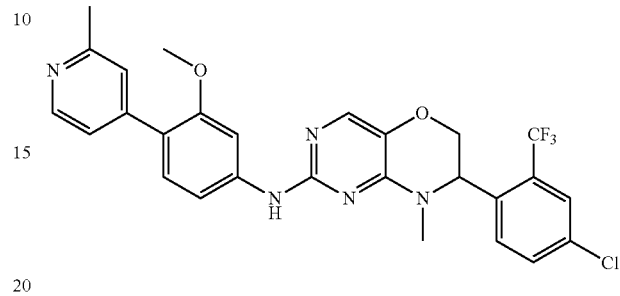

The compound of Example 107A was produced as described in Example 107. Analytical data for product Fraction I (−): $^1$H-NMR ($CD_3OD$, 400 MHz): δ 8.30 (d, 1H), 7.80 (s, 1H), 7.67 (d, 3H), 7.43 (s, 1H), 7.40 (d, 1H), 7.37-7.27 (m, 3H), 5.00-4.97 (m, 1H), 4.31-4.29 (m, 1H), 4.12-4.10 (m, 1H), 3.81 (s, 3H), 3.10 (s, 3H), 2.51 (s, 3H); Mass (ESI): 542 [M+1]; LCMS: 541.9 (M+1); (column; X-Select CSH C-18 (50×3.0 mm, 3.5 µm); RT 2.71 min. 0.05% Aq TFA: ACN; 0.80 mL/min); UPLC (column; Acquity UPLC BEH C-18, 2.1×50 mm, 1.7 µm); RT 1.98 min. ACN: 0.025% Aq TFA; 0.5 mL/min; Chiral HPLC: 99.7% RT=11.14 min (CHIRALPAK-IA (250×4.6 mm, 5 µm; mobile phase (A) 0.1% DEA in n-hexane (B) $CH_2Cl_2$: MeOH (50:50) (A:B; 85:15); flow Rate: 1.0 mL/min); Optical rotation $[\alpha]_D^{19.99}$: −139.98 (c=0.25, MeOH).

Example 107B

Synthesis of (+)-7-(4-chloro-2-(trifluoromethyl) phenyl)-N-(3-methoxy-4-(2-methylpyridin-4-yl) phenyl)-8-methyl-7, 8-dihydro-6H-pyrimido [5, 4-b] [1, 4] oxazin-2-amine

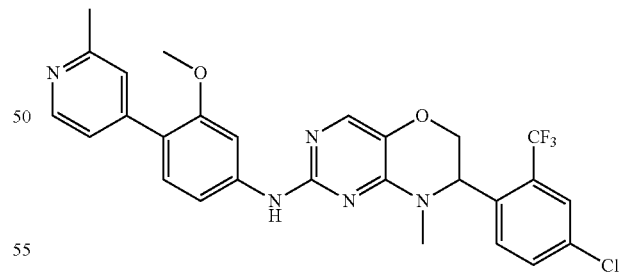

The compound of Example 107B was produced as described in Example 107. Analytical data for product Fraction II (+): $^1$H-NMR ($CD_3OD$, 400 MHz): δ 8.30 (d, 1H), 7.80 (s, 1H), 7.67 (d, 3H), 7.43 (s, 1H), 7.40 (d, 1H), 7.37-7.27 (m, 3H), 5.00-4.97 (m, 1H), 4.31-4.29 (m, 1H), 4.12-4.10 (m, 1H), 3.81 (s, 3H), 3.10 (s, 3H), 2.51 (s, 3H); Mass (ESI): 542 [M+1]; LCMS: 542 (M+1); (column; X-Select CSH C-18 (50×3.0 mm, 3.5 µm); RT 2.70 min. 0.05% Aq TFA: ACN; 0.80 mL/min); UPLC (column; Acquity UPLC BEH C-18, 2.1×50 mm, 1.7 µm); RT 1.99 min. ACN: 0.025% Aq TFA; 0.5 mL/min; Chiral HPLC: 98.9% RT=12.64 min (CHIRALPAK-IA (250×4.6 mm, 5 μm; mobile phase (A) 0.1% DEA in n-hexane (B) CH$_2$Cl$_2$: MeOH (50:50) (A:B; 85:15); flow Rate: 1.0 mL/min); Optical rotation $[\alpha]_D^{20.01}$: +148.44 (c=0.25, MeOH).

Example 108

Synthesis of N-(3-fluoro-4-(4-methyl-1H-imidazol-1-yl) phenyl)-7, 8-dimethyl-7, 8-dihydro-6H-pyrimido [5, 4-b] [1, 4] oxazin-2-amine

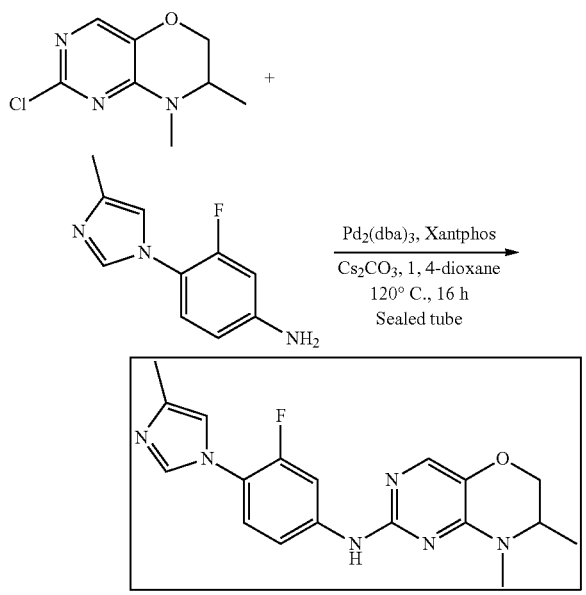

Synthesis of N-(3-fluoro-4-(4-methyl-1H-imidazol-1-yl) phenyl)-7, 8-dimethyl-7, 8-dihydro-6H-pyrimido [5, 4-b] [1, 4] oxazin-2-amine A dry vial charged with Pd$_2$(dba)$_3$ (53 mg, 0.05 mmol) and Xantphos (100 mg, 0.17 mmol) in 1, 4-dioxane (1.15 mL) at room temperature was degassed and the resultant reaction mixture was stirred at 120° C. for 3 min. A mixture of 2-chloro-7, 8-dimethyl-7, 8-dihydro-6H-pyrimido [5, 4-b] [1, 4] oxazine (230 mg, 1.15 mmol), 3-fluoro-4-(4-methyl-1H-imidazol-1-yl) aniline (441 mg, 2.31 mmol) and cesium carbonate (525 mg, 1.61 mmol) in 1, 4-dioxane (1.15 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (50 mL) and extracted with CH$_2$Cl$_2$ (2×50 mL). The combined organic extracts were dried over sodium sulfate, filtered and concentrated in vacuo. The crude material was washed with acetonitrile (2×20 mL) to afford N-(3-fluoro-4-(4-methyl-1H-imidazol-1-yl) phenyl)-7, 8-dimethyl-7, 8-dihydro-6H-pyrimido [5, 4-b] [1, 4] oxazin-2-amine (120 mg, 29%) as an off-white solid. LCMS: 354.9 (M+1); (column; X-Select CSH C-18 (50×3.0 mm, 3.5 μm); RT 1.86 min 0.05% Aq TFA: ACN; 0.80 mL/min); HPLC (column; Eclipse XDB-C18 150×4.6 mm, 5.0 μm); RT 9.72 min. 5 mM Aq NH$_4$OAc: ACN; 1.0 mL/min; TLC: 10% MeOH/CH$_2$Cl$_2$ (R$_f$: 0.5).

Racemic compound of Example 108 was separated using a Chiralpak IA (250×4.6 mm: 5 μm; (30 mg loading; 0.1% DEA in n-hexane: CH$_2$Cl$_2$:MeOH (50:50); (A:B: 65:35) as mobile phase) to provide the compound of Example 108A (Fraction I (−)) and the compound of Example 108B (Fraction II (+)).

Example 108A

Synthesis of (−)-N-(3-fluoro-4-(4-methyl-1H-imidazol-1-yl) phenyl)-7, 8-dimethyl-7, 8-dihydro-6H-pyrimido [5, 4-b] [1, 4] oxazin-2-amine

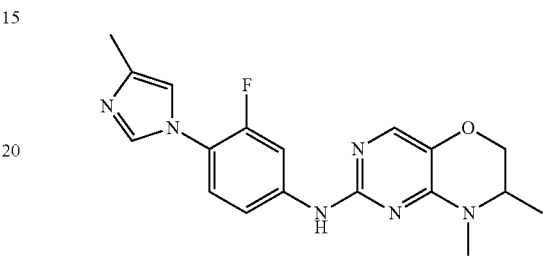

The compound of Example 108A was produced as described in Example 108. Analytical data for product Fraction I (−): $^1$H-NMR (CD$_3$OD, 400 MHz): δ 8.00-7.96 (m, 1H), 7.77 (s, 1H), 7.51 (s, 1H), 7.40-7.30 (m, 2H), 7.06-7.05 (m, 1H), 4.01-4.00 (m, 2H), 3.69-3.63 (m, 1H), 3.19 (s, 3H), 2.23 (s, 3H), 1.30 (d, 3H); Mass (ESI): 355.2 [M+1]; LCMS: 354.9 (M+1); (column; X-Select CSH C-18 (50×3.0 mm, 3.5 μm); RT 1.94 min. 0.05% Aq TFA: ACN; 0.80 mL/min); UPLC (column; Acquity UPLC BEH C-18, 2.1×50 mm, 1.7 μm); RT 1.28 min. ACN: 0.025% Aq TFA; 0.5 mL/min; Chiral HPLC: 100% RT=11.18 min (CHIRALPAK-IA (250×4.6 mm, 5 μm; mobile phase (A) 0.1% DEA in n-hexane (B) CH$_2$Cl$_2$:MeOH (50:50) (A:B; 65:35); flow Rate: 1.0 mL/min); Optical rotation $[\alpha]_D^{20.01}$: 19.08 (c=0.25, MeOH).

Example 108B

Synthesis of (+)-N-(3-fluoro-4-(4-methyl-1H-imidazol-1-yl) phenyl)-7, 8-dimethyl-7, 8-dihydro-6H-pyrimido [5, 4-b] [1, 4] oxazin-2-amine

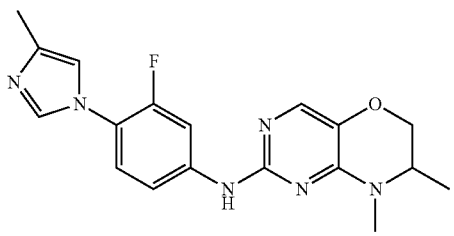 [SMILES: Cc1cn(-c2ccc(Nc3ncc4c(n3)N(C)C(C)CO4)cc2F)cn1]

The compound of Example 108B was produced as described in Example 108. Analytical data for product Fraction II (−): $^1$H-NMR (CD$_3$OD, 400 MHz): δ 8.00-7.96 (m, 1H), 7.76 (s, 1H), 7.51 (s, 1H), 7.40-7.30 (m, 2H), 7.08-7.06 (m, 1H), 4.01-4.00 (m, 2H), 3.69-3.63 (m, 1H), 3.19 (s, 3H), 2.23 (s, 3H), 1.30 (d, 3H); Mass (ESI): 355 [M+1]; LCMS: 354.9 (M+1); (column; X-Select CSH C-18 (50×3.0 mm, 3.5 μm); RT 1.97 min. 0.05% Aq TFA: ACN;

0.80 ml/min); UPLC (column; Acquity UPLC BEH C-18, 2.1×50 mm, 1.7 μm); RT 1.28 min. ACN: 0.025% Aq TFA; 0.5 mL/min; Chiral HPLC: 99.53% RT=16.23 min (CHIRALPAK-IA (250×4.6 mm, 5 μm; mobile phase (A) 0.1% DEA in n-hexane (B) CH$_2$Cl$_2$:MeOH (50:50) (A:B; 65:35); flow Rate: 1.0 mL/min); Optical rotation [α]$_D^{19.99}$: +26.72 (c=0.25, MeOH).

Example 109

Synthesis of N-(3-fluoro-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine

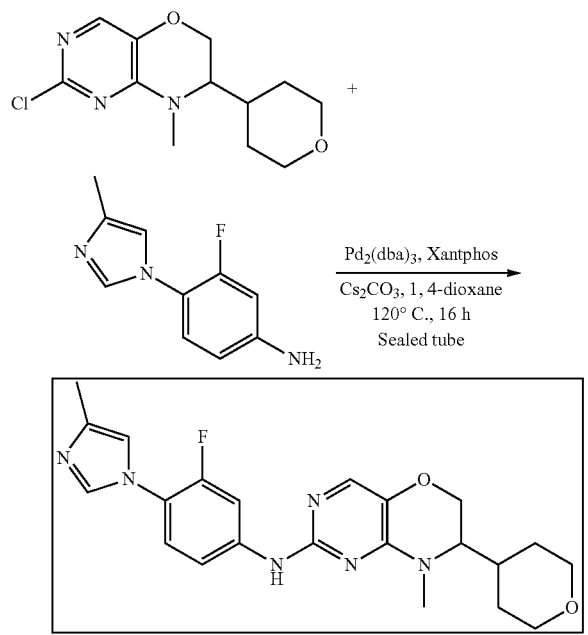

Synthesis of N-(3-fluoro-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine A dry vial charged with Pd$_2$(dba)$_3$ (50 mg, 0.05 mmol) and Xantphos (96 mg, 0.16 mmol) in 1, 4-dioxane (1.5 mL) at room temperature was degassed and the resultant reaction mixture was stirred at 120° C. for 3 min. A mixture of 2-chloro-8-methyl-7-(tetrahydro-2H-pyran-4-yl)-7, 8-dihydro-6H-pyrimido [5, 4-b] [1, 4] oxazine (300 mg, 1.11 mmol), 3-fluoro-4-(4-methyl-1H-imidazol-1-yl) aniline (424 mg, 2.22 mmol) and cesium carbonate (506 mg, 1.55 mmol) in 1, 4-dioxane (1.5 mL) was degassed and the catalyst premix was added. The resultant mixture was stirred at 120° C. for 16 h in a sealed tube. After consumption of the starting material (monitored by TLC and LCMS), the reaction was diluted with water (20 mL) and extracted with CH$_2$Cl$_2$ (2×20 mL). The combined organic extracts were dried over sodium sulfate, filtered and concentrated in vacuo. The crude material was purified by column chromatography using 2% MeOH/CH$_2$Cl$_2$ to afford N-(3-fluoro-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine (250 mg, 53%) as an off-white solid. $^1$H-NMR (CD$_3$OD, 400 MHz): δ 8.00 (d, 1H), 7.80 (s, 1H), 7.51 (s, 1H), 7.40-7.30 (m, 2H), 7.08 (s, 1H), 4.42 (d, 1H), 3.99 (t, 2H), 3.82 (d, 1H), 3.40-3.30 (m, 3H), 3.28 (s, 3H), 2.25 (s, 3H), 2.10-2.02 (m, 1H), 1.68-1.50 (m, 5H); LCMS: 425 (M+1); (column; X-Select CSH C-18 (50×3.0 mm, 3.5 μm); RT 1.98 min. 0.05% Aq TFA: ACN; 0.80 ml/min); UPLC (column; Acquity UPLC BEH C-18 2.1×50 mm, 1.7 μm); RT 1.26 min. ACN: 0.025% Aq TFA; 0.5 mL/min; TLC: 5% MeOH/CH$_2$Cl$_2$ (R$_f$; 0.4).

Racemic compound of Example 109 was separated using a Chiralpak IA (250×4.6 mm: 5 μm; (30 mg loading; 0.1% DEA in n-hexane: THF:MeOH (50:50); (A:B: 70:30) as mobile phase) to provide the compound of Example 109A (Fraction I (+)) and the compound of Example 109B (Fraction II (−)).

Example 109A

Synthesis of (+)-N-(3-fluoro-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine

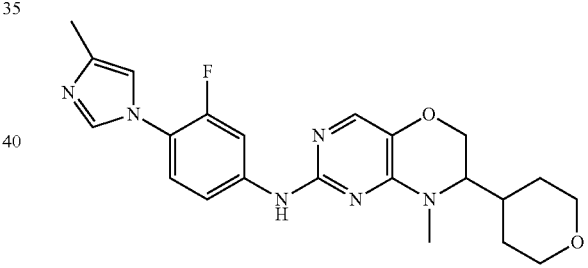

The compound of Example 109A was produced as described in Example 109. Analytical data for product Fraction I (+): $^1$H-NMR (CD$_3$OD, 500 MHz): δ 8.00 (d, 1H), 7.80 (s, 1H), 7.51 (s, 1H), 7.40-7.32 (m, 2H), 7.09 (s, 1H), 4.41 (d, 1H), 3.99 (t, 2H), 3.82 (d, 1H), 3.40-3.32 (m, 3H), 3.30 (s, 3H), 2.23 (s, 3H), 2.10-2.02 (m, 1H), 1.68-1.50 (m, 5H); Mass (ESI): 425 [M+1]; LCMS: 425 (M+1); (column; X-Select CSH C-18 (50×3.0 mm, 3.5 μm); RT 1.98 min. 0.05% Aq TFA: ACN; 0.80 mL/min); UPLC (column; Acquity UPLC BEH C-18, 2.1×50 mm, 1.7 μm); RT 1.28 min. ACN: 0.025% Aq TFA; 0.5 mL/min; Chiral HPLC: 99.5% RT=9.20 min (CHIRALPAK-IA (250×4.6 mm, 5 μm; mobile phase (A) 0.1% DEA in n-hexane (B) THF:MeOH (50:50) (A:B; 70:30); flow Rate: 1.0 mL/min); Optical rotation [α]$_D^{20.00}$: +64.08 (c=0.25, CH$_2$Cl$_2$).

Example 109B

Synthesis of (−)-N-(3-fluoro-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine

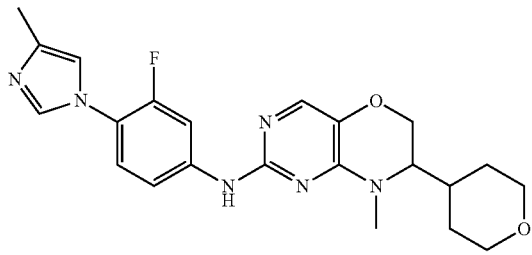 [SMILES: Cc1cn(-c2ccc(Nc3ncc4c(n3)N(C)C(C3CCOCC3)CO4)cc2F)cn1]

The compound of Example 109B was produced as described in Example 109. Analytical data for product Fraction II (−): $^1$H-NMR (CD$_3$OD, 500 MHz): δ 8.00 (d, 1H), 7.80 (s, 1H), 7.51 (s, 1H), 7.40-7.32 (m, 2H), 7.09 (s, 1H), 4.41 (d, 1H), 3.99 (t, 2H), 3.82 (d, 1H), 3.40-3.32 (m, 3H), 3.30 (s, 3H), 2.23 (s, 3H), 2.10-2.02 (m, 1H), 1.68-1.50 (m, 5H); Mass (ESI): 425 [M+1]; LCMS: 425 (M+1); (column; X-Select CSH C-18 (50×3.0 mm, 3.5 μm); RT 1.99 min. 0.05% Aq TFA: ACN; 0.80 mL/min); UPLC (column; Acquity UPLC BEH C-18, 2.1×50 mm, 1.7 μm); RT 1.28 min. ACN: 0.025% Aq TFA; 0.5 mL/min; Chiral HPLC: 99.3% RT=9.77 min (CHIRALPAK-IA (250×4.6 mm, 5 μm; mobile phase (A) 0.1% DEA in n-hexane (B) THF:MeOH (50:50) (A:B; 70:30); flow Rate: 1.0 mL/min); Optical rotation [α]$_D^{20.00}$: −39 (c=0.25, CH$_2$Cl$_2$).

Example 110

Synthesis of N-(3-methoxy-4-(2-methylpyridin-4-yl) phenyl)-7, 8-dimethyl-7, 8-dihydro-6H-pyrimido [5, 4-b] [1, 4] oxazin-2-amine

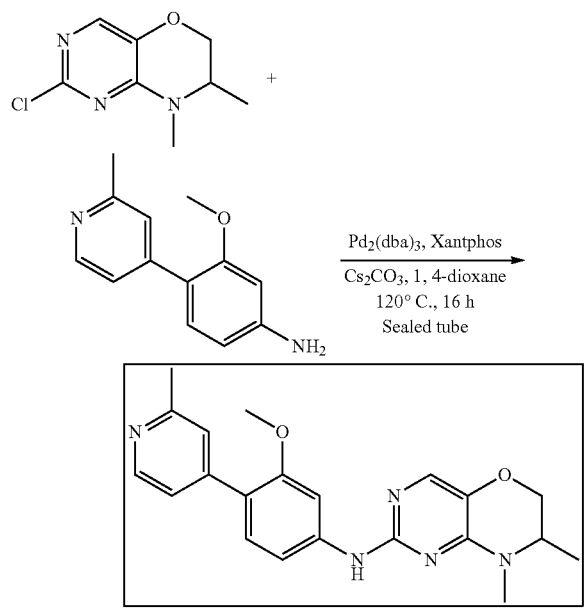

Synthesis of N-(3-methoxy-4-(2-methylpyridin-4-yl) phenyl)-7, 8-dimethyl-7, 8-dihydro-6H-pyrimido [5, 4-b] [1, 4] oxazin-2-amine A dry vial charged with Pd$_2$(dba)$_3$ (57 mg, 0.06 mmol) and Xantphos (109 mg, 0.18 mmol) in 1, 4-dioxane (1.25 mL) at room temperature was degassed and the resultant reaction mixture was stirred at 120° C. for 3 min. A mixture of 2-chloro-7, 8-dimethyl-7, 8-dihydro-6H-pyrimido [5, 4-b] [1, 4] oxazine (250 mg, 1.25 mmol), 3-methoxy-4-(2-methylpyridin-4-yl) aniline (537 mg, 2.50 mmol) and cesium carbonate (573 mg, 1.75 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (50 mL) and extracted with CH$_2$Cl$_2$ (2×50 mL). The combined organic extracts were dried over sodium sulfate, filtered and concentrated in vacuo. The crude was purified by column chromatography using 2% MeOH: CH$_2$Cl$_2$ to afford N-(3-methoxy-4-(2-methylpyridin-4-yl) phenyl)-7, 8-dimethyl-7, 8-dihydro-6H-pyrimido [5, 4-b] [1, 4] oxazin-2-amine (200 mg, 42%) as a pale yellow solid. LCMS: 378.1 (M+1); (column; X-Select CSH C-18 (50×3.0 mm, 3.5 μm); RT 2.02 min 0.05% Aq TFA: ACN; 0.80 mL/min); UPLC (column; Acquity UPLC BEH C-18 2.1×50 mm, 1.7 μm); RT 1.32 min. ACN: 0.025% Aq TFA; 0.5 mL/min; TLC: 5% MeOH/CH$_2$Cl$_2$ (R$_f$ 0.3).

Racemic compound of Example 110 was separated using a Chiralpak ADH (250×4.6 mm: 5 μm; (30 mg loading; 0.1% DEA in n-hexane: EtOH:MeOH (50:50); (A:B: 70:30) as mobile phase) to provide the compound of Example 110A (Fraction I (−)) and the compound of Example 110B (Fraction II (+)).

Example 110A

Synthesis of (−)-N-(3-methoxy-4-(2-methylpyridin-4-yl) phenyl)-7, 8-dimethyl-7, 8-dihydro-6H-pyrimido [5, 4-b] [1, 4] oxazin-2-amine

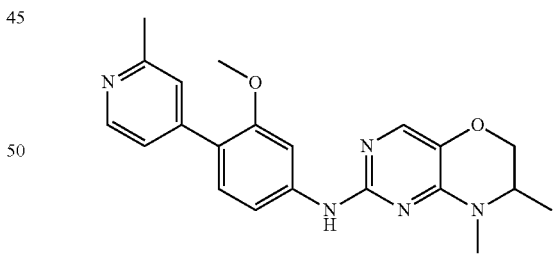

The compound of Example 110A was produced as described in Example 110. Analytical data for product Fraction I (−): $^1$H-NMR (CD$_3$OD, 400 MHz): δ 8.32-8.30 (m, 1H), 7.66 (s, 1H), 7.47 (s, 1H), 7.45 (s, 1H), 7.40 (d, 1H), 7.29-7.25 (m, 1H), 7.21 (d, 1H), 4.02-4.00 (m, 2H), 3.86 (s, 3H), 3.70-3.61 (m, 1H), 3.20 (s, 3H), 2.52 (s, 3H), 1.30 (d, 3H); Mass (ESI): 378.5 [M+1]; LCMS: 378.4 (M+1); (column; X-Select CSH C-18 (50×3.0 mm, 3.5 μm); RT 4.15 min. 5 mM Aq NH$_4$OAc: ACN; 0.80 mL/min); UPLC (column; Acquity UPLC BEH C-18, 2.1×50 mm, 1.7 μm); RT 1.34 min. ACN: 0.025% Aq TFA; 0.5 mL/min; Chiral HPLC: 99.3% RT=19.10 min (CHIRALPAK-IA (250×4.6 mm, 5 μm; mobile phase (A) 0.1% DEA in n-hexane (B) EtOH (85:15); flow Rate: 1.0 mL/min); Optical rotation $[\alpha]_D^{19.97}$: −6.89 (c=0.25, CH$_2$Cl$_2$).

Example 110B

Synthesis of (+)-N-(3-methoxy-4-(2-methylpyridin-4-yl) phenyl)-7, 8-dimethyl-7, 8-dihydro-6H-pyrimido [5, 4-b] [1, 4] oxazin-2-amine

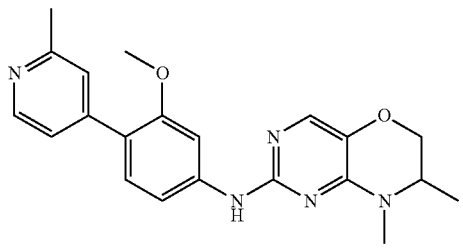 [SMILES: COc1cc(Nc2ncc3c(n2)N(C)C(C)CO3)ccc1-c1ccnc(C)c1]

The compound of Example 110B was produced as described in Example 110. Analytical data for product Fraction II (+): $^1$H-NMR (CD$_3$OD, 400 MHz): δ 8.32-8.30 (m, 1H), 7.66 (s, 1H), 7.47 (s, 1H), 7.45 (s, 1H), 7.40 (d, 1H), 7.29-7.25 (m, 1H), 7.21 (d, 1H), 4.02-4.00 (m, 2H), 3.86 (s, 3H), 3.70-3.61 (m, 1H), 3.20 (s, 3H), 2.52 (s, 3H), 1.30 (d, 3H); Mass (ESI): 378.5 [M+1]; LCMS: 378.5 (M+1); (column; X-Select CSH C-18 (50×3.0 mm, 3.5 μm); RT 4.16 min. 5 mM Aq NH$_4$OAc: ACN; 0.80 mL/min); HPLC (column; Acquity UPLC BEH C-18, 2.1×50 mm, 1.7 μm); RT 1.34 min. ACN: 0.025% Aq TFA; 0.5 mL/min; Chiral HPLC: 99.4% RT=22.07 min (CHIRALPAK-IA (250×4.6 mm, 5 μm; mobile phase (A) 0.1% DEA in n-hexane (B) EtOH (A:B; 85:15); flow Rate: 1.0 mL/min); Optical rotation $[\alpha]_D^{19.97}$: +7.63 (c=0.25, CH$_2$Cl$_2$).

Example 111

Synthesis of (S)—N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine

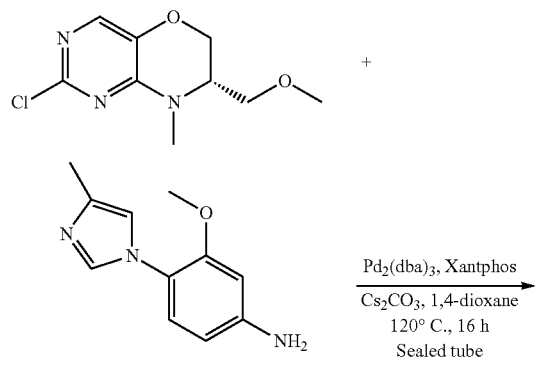

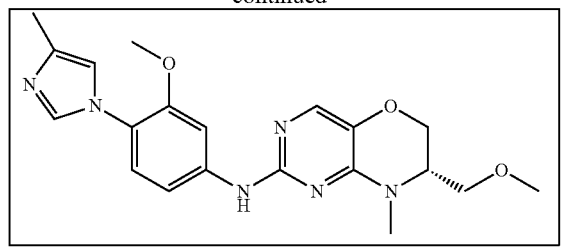

Synthesis of (S)—N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine A dry vial charged with Pd$_2$(dba)$_3$ (29 mg, 0.03 mmol) and Xantphos (56 mg, 0.98 mmol) in 1, 4-dioxane (0.75 mL) at room temperature was degassed and the resultant reaction mixture was stirred at 120° C. for 3 min. A mixture of (S)-2-chloro-7-(methoxymethyl)-8-methyl-7, 8-dihydro-6H-pyrimido [5, 4-b] [1, 4] oxazine (150 mg, 0.65 mmol), 3-methoxy-4-(4-methyl-1H-imidazol-1-yl) aniline (265 mg, 1.31 mmol) and cesium carbonate (298 mg, 0.91 mmol) in 1, 4-dioxane (0.75 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (20 mL) and extracted with 5% MeOH/CH$_2$Cl$_2$ (2×20 mL). The combined organic extracts were dried over sodium sulfate, filtered and concentrated in vacuo. The crude was purified by column chromatography using 4% MeOH: CH$_2$Cl$_2$ to afford (S)—N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine (55 mg, 21%) as an off-white solid. The product was further purified by Ascentic C-18 (250×4.6 mm: 5 μm; (50 mg loading; CH$_3$CN: 0.05% Aq TFA (0.01/95, 15/70, 25/10, 35/10) as mobile phase). $^1$H-NMR (DMSO-d$_6$, 500 MHz): δ 9.07 (s, 1H), 7.81 (s, 1H), 7.61 (s, 1H), 7.59 (s, 1H), 7.28 (d, 1H), 7.13 (d, 1H), 7.00 (s, 1H), 4.23 (d, 1H), 3.90-3.87 (m, 1H), 3.79 (s, 3H), 3.78-3.73 (m, 1H), 3.52-3.49 (m, 2H), 3.31 (s, 3H), 3.20 (s, 3H), 2.12 (s, 3H); LCMS: 397.5 (M+1); (column; X-Select CSH C-18 (50×3.0 mm, 3.5 μm); RT 3.39 min 5 mM Aq NH$_4$OAc: ACN; 0.80 mL/min); UPLC (column; Acquity UPLC BEH C-18 2.1×50 mm, 1.7 μm); RT 1.33 min. ACN: 0.025% Aq TFA; 0.5 mL/min; Chiral HPLC: 95.1% RT=9.15 min (CHIRALPAK-IA (250×4.6 mm, 5 μm; mobile phase (A) 0.1% DEA in n-hexane (B) CH$_2$Cl$_2$:MeOH (50:50) (A:B; 70:30); flow Rate: 1.0 mL/min); Optical rotation $[\alpha]_D^{20.01}$: +23.36 (c=0.25, CH$_2$Cl$_2$); TLC: 5% MeOH/CH$_2$Cl$_2$ (R$_f$: 0.3).

Example 112

Synthesis of 7-(4-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

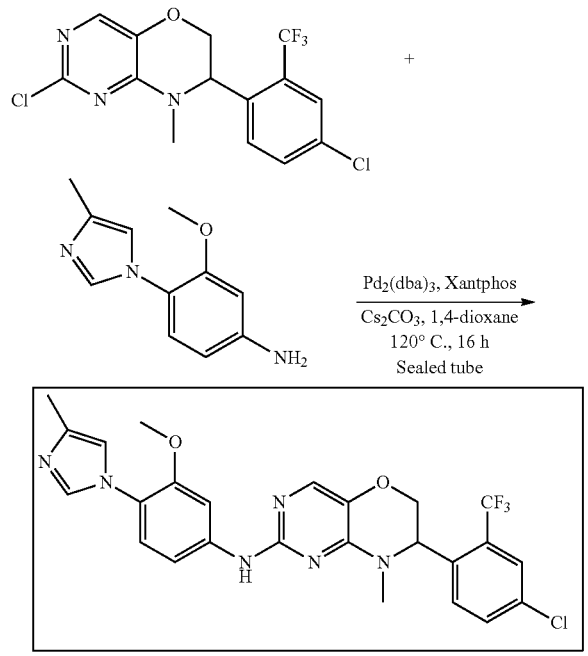

Synthesis of 7-(4-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine A dry vial charged with Pd$_2$(dba)$_3$ (31 mg, 0.03 mmol) and Xantphos (59 mg, 0.10 mmol) in 1, 4-dioxane (1.25 mL) at room temperature was degassed and the resultant reaction mixture was stirred at 120° C. for 3 min. A mixture of 2-chloro-7-(4-chloro-2-(trifluoromethyl) phenyl)-8-methyl-7, 8-dihydro-6H-pyrimido [5, 4-b] [1, 4] oxazine (250 mg, 0.68 mmol), 3-methoxy-4-(4-methyl-1H-imidazol-1-yl) aniline (278 mg, 1.37 mmol) and cesium carbonate (313 mg, 0.96 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (20 mL) and extracted with 5% MeOH/CH$_2$Cl$_2$ (2×20 mL). The combined organic extracts were dried over sodium sulfate, filtered and concentrated in vacuo. The crude was purified by column chromatography using 2% MeOH: CH$_2$Cl$_2$ to afford 7-(4-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (100 mg, 16%) as an off-white solid. LCMS: 531.1 (M+1); (column; X-Select CSH C-18 (50×3.0 mm, 3.5 μm); RT 2.70 min. 0.05% Aq TFA: ACN; 0.80 mL/min); UPLC (column; Acquity UPLC BEH C-18 2.1×50 mm, 1.7 μm); RT 1.95 min. ACN: 0.025% Aq TFA; 0.5 mL/min; TLC: 5% MeOH/CH$_2$Cl$_2$ (R$_f$: 0.3).

Racemic compound of Example 112 was separated using a Chiralpak IA (250×4.6 mm: 5 μm; (15 mg loading; 0.1% DEA in n-hexane: CH$_2$Cl$_2$:MeOH (50:50); (A:B: 80:20) as mobile phase) to provide the compound of Example 112A (Fraction I (−)) and the compound of Example 112B (Fraction II (+)).

Example 112A

Synthesis of (−)-7-(4-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

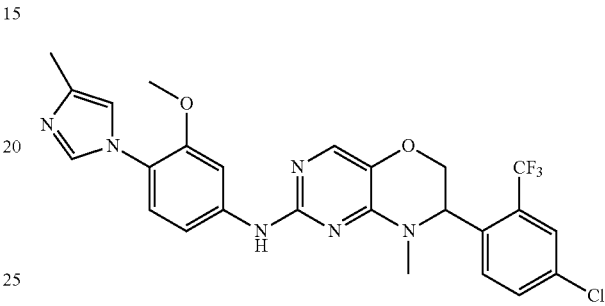

The compound of Example 112A was produced as described in Example 112. Analytical data for product Fraction I (−): $^1$H-NMR (CD$_3$OD, 400 MHz): δ 7.80 (s, 1H), 7.72 (s, 1H), 7.66-7.61 (m, 3H), 7.33 (d, 1H), 7.25 (d, 1H), 7.19 (d, 1H), 6.96 (s, 1H), 5.10-5.08 (m, 1H), 4.31 (d, 1H), 4.11 (d, 1H), 3.82 (s, 3H), 3.08 (s, 3H), 2.21 (s, 3H); Mass (ESI): 531.7 [M+1]; LCMS: 531.6 (M+1); (column; X-Select CSH C-18 (50×3.0 mm, 3.5 μm); RT 3.26 min. 0.05% Aq TFA: ACN; 0.80 mL/min); HPLC (column; Acquity UPLC BEH C-18, 2.1×50 mm, 1.7 μm); RT 1.96 min. ACN: 0.025% Aq TFA; 0.5 mL/min; Chiral HPLC: 100.0% RT=32.42 min (CHIRALPAK-IA (250×4.6 mm, 5 μm; mobile phase (A) 0.1% DEA in n-hexane (B) CH$_2$Cl$_2$: MeOH (50:50) (A:B; 90:10); flow Rate: 1.0 mL/min); Optical rotation [α]$_D^{19.99}$: −120.48 (c=0.25, CH$_2$Cl$_2$).

Example 112B

Synthesis of (+)-7-(4-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

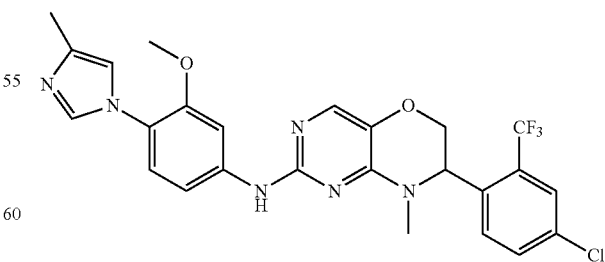

The compound of Example 112B was produced as described in Example 112. Analytical data for product Fraction II (+): $^1$H-NMR (CD$_3$OD, 400 MHz): δ 7.80 (s, 1H), 7.72 (s, 1H), 7.66-7.61 (m, 3H), 7.33 (d, 1H), 7.25 (d, 1H), 7.19 (d, 1H), 6.96 (s, 1H), 5.10-5.08 (m, 1H), 4.31 (d, 1H), 4.11 (d, 1H), 3.82 (s, 3H), 3.08 (s, 3H), 2.21 (s, 3H); Mass (ESI): 531.7 [M+1]; LCMS: 531.6 (M+1); (column; X-Select CSH C-18 (50×3.0 mm, 3.5 µm); RT 3.36 min. 0.05% Aq TFA: ACN; 0.80 mL/min); HPLC (column; Acquity UPLC BEH C-18, 2.1×50 mm, 1.7 µm); RT 1.94 min. ACN: 0.025% Aq TFA; 0.5 mL/min; Chiral HPLC: 95.1% RT=36.81 min (CHIRALPAK-IA (250×4.6 mm, 5 µm; mobile phase (A) 0.1% DEA in n-hexane (B) $CH_2Cl_2$:MeOH (50:50) (A:B; 90:10); flow Rate: 1.0 mL/min); Optical rotation $[α]_D^{19.98}$: +117.72 (c=0.25, $CH_2Cl_2$).

Example 113

Synthesis of (S)—N-(3-fluoro-4-(4-methyl-1H-imidazol-1-yl) phenyl)-7-(methoxymethyl)-8-methyl-7, 8-dihydro-6H-pyrimido [5, 4-b] [1, 4] oxazin-2-amine

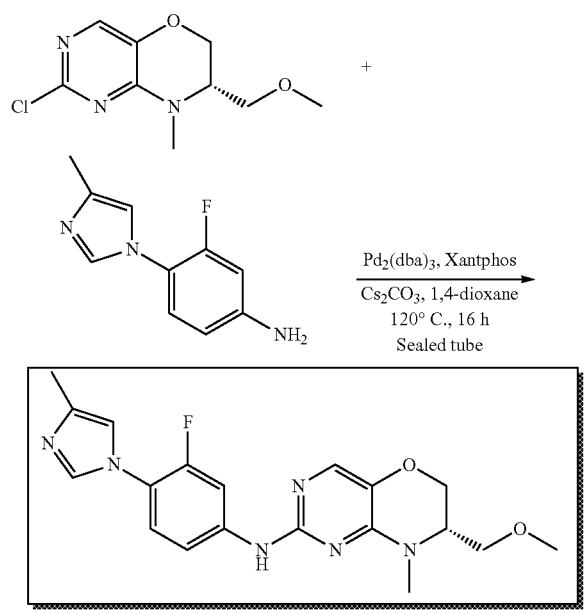

Synthesis of (S)—N-(3-fluoro-4-(4-methyl-1H-imidazol-1-yl) phenyl)-7-(methoxymethyl)-8-methyl-7, 8-dihydro-6H-pyrimido [5, 4-b] [1, 4] oxazin-2-amine A dry vial charged with $Pd_2(dba)_3$ (29 mg, 0.03 mmol) and Xantphos (56 mg, 0.10 mmol) in 1, 4-dioxane (0.75 mL) at room temperature was degassed and the resultant reaction mixture was stirred at 120° C. for 3 min. A mixture of (S)-2-chloro-7-(methoxymethyl)-8-methyl-7, 8-dihydro-6H-pyrimido [5, 4-b] [1, 4] oxazine (150 mg, 0.65 mmol), 3-fluoro-4-(4-methyl-1H-imidazol-1-yl) aniline (250 mg, 1.31 mmol) and cesium carbonate (298 mg, 0.91 mmol) in 1, 4-dioxane (0.75 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (20 mL) and extracted with 5% MeOH/$CH_2Cl_2$ (2×20 mL). The combined organic extracts were dried over sodium sulfate, filtered and concentrated in vacuo. The crude was purified by column chromatography using 3% MeOH: $CH_2Cl_2$ to afford (S)—N-(3-fluoro-4-(4-methyl-1H-imidazol-1-yl) phenyl)-7-(methoxymethyl)-8-methyl-7, 8-dihydro-6H-pyrimido [5, 4-b] [1, 4] oxazin-2-amine (36 mg, 14%) as an off-white solid. The product was further purified by Chiralpak IA (250×20 mm: 5 µm; (30 mg loading; 0.1% DEA in hexane: $CH_2Cl_2$:MeOH (50:50); (A:B: 70:30) as mobile phase). $^1$H-NMR (DMSO-$d_6$, 400 MHz): δ 9.31 (s, 1H), 8.04-8.00 (m, 1H), 7.75 (s, 1H), 7.60 (s, 1H), 7.51 (d, 1H), 7.38 (t, 1H), 7.12 (s, 1H), 4.21 (d, 1H), 3.89 (d, 1H), 3.75-3.71 (m, 1H), 3.54-3.50 (m, 1H), 3.48-3.43 (m, 1H), 3.30 (s, 3H), 3.18 (s, 3H), 2.15 (s, 3H); Mass (ESI): 385.4 [M+1]; LCMS: 385.4 (M+1); (column; X-Select CSH C-18 (50×3.0 mm, 3.5 µm); RT 2.24 min 0.05% Aq TFA: ACN; 0.80 mL/min); UPLC (column; Acquity UPLC BEH C-18 2.1×50 mm, 1.7 µm); RT 1.26 min. ACN: 0.025% Aq TFA; 0.5 mL/min; Chiral HPLC: 99.7% RT=10.07 min (CHIRALPAK-IA (250×4.6 mm, 5 µm; mobile phase (A) 0.1% DEA in n-hexane (B) $CH_2Cl_2$:MeOH (50:50) (A:B; 70:30); flow Rate: 1.0 mL/min); Optical rotation $[α]_D^{19.98}$: +20.36 (c=0.25, $CH_2Cl_2$); TLC: 5% MeOH/$CH_2Cl_2$ ($R_f$: 0.3).

Example 114

Synthesis of N-(3-methoxy-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine

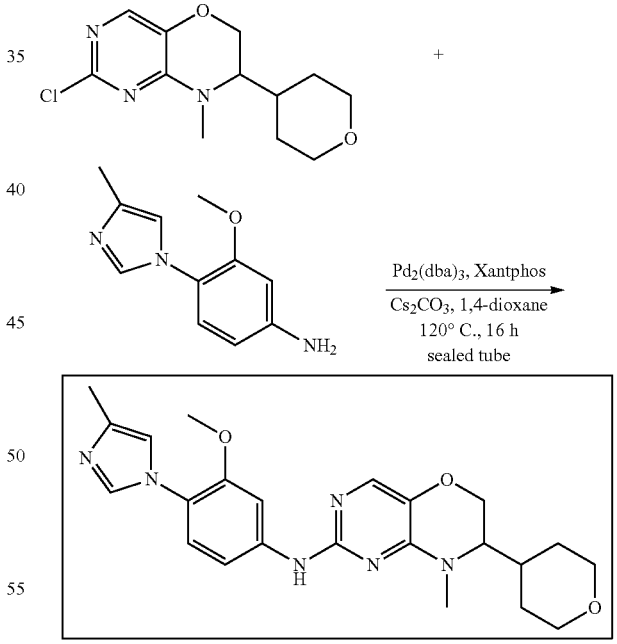

Synthesis of N-(3-methoxy-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine A dry vial charged with $Pd_2(dba)_3$ (34 mg, 0.03 mmol) and Xantphos (64 mg, 0.11 mmol) in 1, 4-dioxane (2 mL) at room temperature was degassed and the resultant reaction mixture was stirred at 120° C. for 3 min. A mixture of 2-chloro-8-methyl-7-(tetrahydro-2H-pyran-4-yl)-7, 8-dihydro-6H-pyrimido [5, 4-b] [1, 4] oxazine (200 mg, 0.74 mmol), 3-methoxy-4-(4-methyl-1H-imidazol-1-yl) aniline (301 mg, 1.48 mmol), cesium carbonate (338 mg, 1.00 mmol) in 1, 4-dioxane (2 mL) was degassed and the catalyst premix was added. The resultant mixture was stirred at 120° C. for 16 h in a sealed tube. After consumption of the starting material (monitored by TLC and LCMS), the reaction was diluted with water (10 mL) and extracted with EtOAc (2×10 mL). The combined organic extracts were dried over sodium sulfate, filtered and concentrated in vacuo. The crude was purified by column chromatography using 4% MeOH: $CH_2Cl_2$ to afford N-(3-methoxy-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine (70 mg, 21%) as a pale yellow solid. UPLC (column; Acquity BEH C-18, 2.1×50 mm, 1.7 µm); RT 1.29 min. ACN: 0.025% TFA (Aq); 0.50 mL/min; TLC: 5% MeOH/$CH_2Cl_2$ ($R_f$ 0.4).

Racemic compound of Example 114 was separated using a phenominex silica (250×20 mm: 5 µm; (50 mg loading; hexane: $CH_2Cl_2$:MeOH (50:50); (A:B: 75:25) as mobile phase) to provide the compound of Example 114A (Fraction I (–)) and the compound of Example 114B (Fraction II (+)).

Example 114A

Synthesis of (–)-N-(3-methoxy-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine

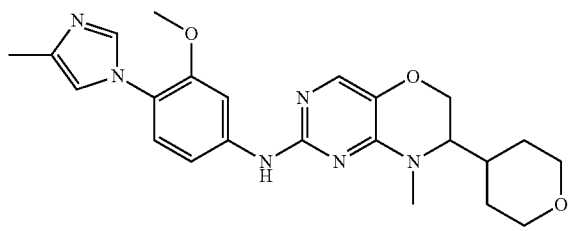 [SMILES: COc1cc(Nc2ncc3c(n2)N(C)C(C2CCOCC2)CO3)ccc1-n1cnc(C)c1]

The compound of Example 114A was produced as described in Example 114. Analytical data for product Fraction I (–): $^1$H NMR (CD$_3$OD, 400 MHz) δ7.74 (s, 1H), 7.65 (s, 1H), 7.49 (s, 1H), 7.21-7.14 (m, 2H), 6.95 (s, 1H), 4.40 (d, 1H), 3.96 (t, 2H), 3.84 (s, 3H), 3.82-3.80 (m, 1H), 3.40-3.30 (m, 3H), 3.29 (s, 3H), 2.23 (s, 3H), 2.10-2.00 (m, 1H), 1.66-1.44 (m, 4H); Mass (ESI): 437.4 [M+1]; LCMS: 437.5 (M+1); (column; X-Select CSH C-18 (50×3.0 mm, 3.5 µm); RT 3.92 min 5 mM Aq NH$_4$OAc: ACN; 0.80 mL/min); UPLC (column; Acquity UPLC BEH C-18, 2.1×50 mm, 1.7 µm); RT 1.29 min. ACN: 0.025% TFA (Aq); 0.50 mL/min; Chiral HPLC: 98.5% RT=11.56 min (CHIRALPAK-ADH (250×4.6 mm, 5 µm; mobile phase (A) 0.1% DEA in n-hexane (B) EtOH:MeOH (50:50) (A:B: 60:40); flow Rate: 1.0 mL/min; Optical rotation $[\alpha]_D^{19.99}$: –70.51 (c=0.25, $CH_2Cl_2$).

Example 114B

Synthesis of (+)-N-(3-methoxy-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine

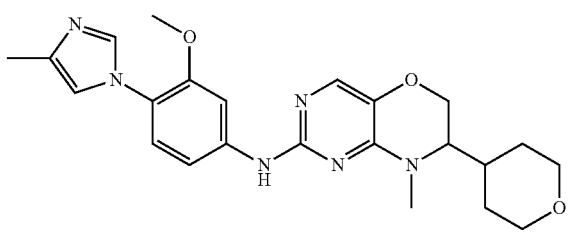 [SMILES: COc1cc(Nc2ncc3c(n2)N(C)C(C2CCOCC2)CO3)ccc1-n1cnc(C)c1]

The compound of Example 114B was produced as described in Example 114. Analytical data for product Fraction II (+): $^1$H NMR (CD$_3$OD, 400 MHz) δ 7.74 (s, 1H), 7.65 (s, 1H), 7.49 (s, 1H), 7.21-7.14 (m, 2H), 6.95 (s, 1H), 4.40 (d, 1H), 3.96 (t, 2H), 3.84 (s, 3H), 3.82-3.80 (m, 1H), 3.40-3.30 (m, 3H), 3.29 (s, 3H), 2.23 (s, 3H), 2.10-2.00 (m, 1H), 1.66-1.44 (m, 4H); Mass (ESI): 437.4 [M+1]; LCMS: 437.5 (M+1); (column; X-Select CSH C-18 (50×3.0 mm, 3.5 µm); RT 3.98 min 5 mM Aq NH$_4$OAc: ACN; 0.80 mL/min); UPLC (column; Acquity UPLC BEH C-18, 2.1×50 mm, 1.7 µm); RT 1.30 min. ACN: 0.025% TFA (Aq); 0.50 mL/min; Chiral HPLC: 98.2% RT=17.66 min (CHIRALPAK-ADH (250×4.6 mm, 5 µm; mobile phase (A) 0.1% DEA in n-hexane (B) EtOH:MeOH (50:50) (A:B: 60:40); flow Rate: 1.0 mL/min; Optical rotation $[\alpha]_D^{20.00}$: 71.82 (c=0.25, $CH_2Cl_2$).

Example 115

Synthesis of 8-methyl-N-(4-(4-methyl-1H-imidazol-1-yl) phenyl)-7-(3, 4, 5-trifluorophenyl)-7, 8-dihydro-6H-pyrimido [5, 4-b] [1, 4] oxazin-2-amine

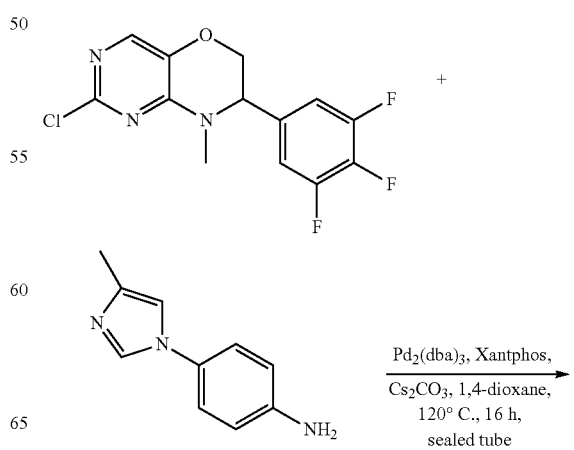

-continued

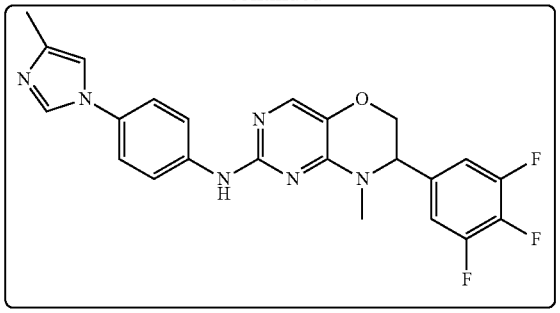

Synthesis of 8-methyl-N-(4-(4-methyl-1H-imidazol-1-yl) phenyl)-7-(3, 4, 5-trifluorophenyl)-7, 8-dihydro-6H-pyrimido [5, 4-b] [1, 4] oxazin-2-amine A dry vial charged with $Pd_2(dba)_3$ (36 mg, 0.04 mmol) and Xantphos (69 mg, 0.11 mmol) in 1, 4-dioxane (1.25 mL) at room temperature was degassed and the resultant reaction mixture was stirred at 120° C. for 3 min. A mixture of 2-chloro-8-methyl-7-(3, 4, 5-trifluorophenyl)-7, 8-dihydro-6H-pyrimido [5, 4-b] [1, 4] oxazine (250 mg, 0.79 mmol), 4-(4-methyl-1H-imidazol-1-yl) aniline (274 mg, 1.58 mmol) and cesium carbonate (361 mg, 1.10 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the reaction was diluted with water (5 mL) and extracted with EtOAc (2×5 mL). The combined organic extracts were dried over sodium sulfate, filtered and concentrated in vacuo. The crude was purified by column chromatography using 4% MeOH: $CH_2Cl_2$ to afford 8-methyl-N-(4-(4-methyl-1H-imidazol-1-yl) phenyl)-7-(3, 4, 5-trifluorophenyl)-7, 8-dihydro-6H-pyrimido [5, 4-b] [1, 4] oxazin-2-amine (90 mg, 25%) as an off-white solid. LCMS: 453.5 (M+1); (column; X-Select CSH C-18 (50×3.0 mm, 3.5 µm); RT 3.84 min 5 mM $NH_4OAc$: ACN; 0.80 mL/min); HPLC (column; Eclipse XDB C18, 150×4.6 mm, 5 µm); RT 10.81 min. ACN: 5 mM Aq $NH_4OAc$; 1 mL/min; TLC: 5% MeOH/DCM ($R_f$: 0.3).

Racemic compound of Example 115 was separated using a Chiralpak ADH (250×20 mm: 5 µm; (15 mg loading; 0.1% DEA in n-hexane: EtOH:MeOH (50:50); (A:B: 60:40) as mobile phase) to provide the compound of Example 115A (Fraction I (−)) and the compound of Example 115B (Fraction II (+)).

Example 115A

Synthesis of (−)-8-methyl-N-(4-(4-methyl-1H-imidazol-1-yl) phenyl)-7-(3, 4, 5-trifluorophenyl)-7, 8-dihydro-6H-pyrimido [5, 4-b] [1, 4] oxazin-2-amine

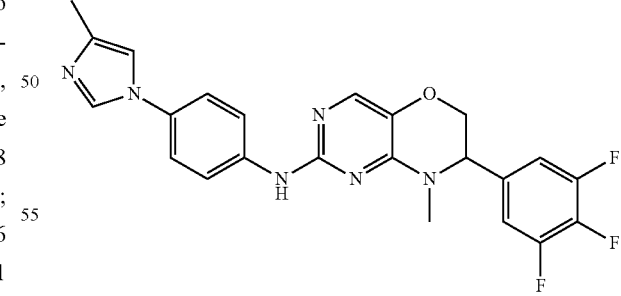

The compound of Example 115A was produced as described in Example 115. Analytical data for product Fraction I (−): $^1$H-NMR ($CD_3OD$, 400 MHz): δ 7.90 (s, 1H), 7.80 (d, 2H), 7.60 (s, 1H), 7.40 (d, 2H), 7.20 (s, 1H), 7.07-7.00 (m, 2H), 4.75-4.72 (m, 1H), 4.21 (d, 2H), 3.17 (s, 3H), 2.25 (s, 3H); Mass (ESI): 453.4 [M+1]; LCMS: 453.3 (M+1); (column; X-Select CSH C-18 (50×3.0 mm, 3.5 µm); RT 2.93 min. 0.05% Aq TFA: ACN; 0.80 mL/min); UPLC (column; Acquity UPLC BEH C18, 2.1×50 mm, 1.7 µm); RT 1.62 min. ACN: 0.025% Aq TFA; 0.5 mL/min; Chiral HPLC: 100.0% RT=18.48 min (CHIRALPAK-ADH (250× 4.6 mm, 5 µm; mobile phase (A) 0.1% DEA in n-hexane (B) EtOH:MeOH (50:50) (A:B: 60:40); flow Rate: 1.0 mL/min); Optical rotation $[\alpha]_D^{19.98}$: −134.76 (c=0.25, $CH_2Cl_2$).

Example 115B

Synthesis of (+)-8-methyl-N-(4-(4-methyl-1H-imidazol-1-yl) phenyl)-7-(3, 4, 5-trifluorophenyl)-7, 8-dihydro-6H-pyrimido [5, 4-b] [1, 4] oxazin-2-amine The compound of Example 115B was produced as described in Example 115. Analytical data for product Fraction II (+): $^1$H-NMR ($CD_3OD$, 400 MHz): δ 7.90 (s, 1H), 7.80 (d, 2H), 7.60 (s, 1H), 7.40 (d, 2H), 7.20 (s, 1H), 7.07-7.00 (m, 2H), 4.75-4.72 (m, 1H), 4.21 (s, 2H), 3.17 (s, 3H), 2.25 (s, 3H); Mass (ESI): 453.4 [M+1]; LCMS: 453.4 (M+1); (column; X-Select CSH C-18 (50×3.0 mm, 3.5 µm); RT 2.94 min 0.05% Aq TFA: ACN; 0.80 mL/min); UPLC (column; Acquity UPLC BEH C18, 2.1×50 mm, 1.7 µm); RT 1.61 min. ACN: 0.025% Aq TFA; 0.5 mL/min; Chiral HPLC: 98.5% RT=24.92 min (CHIRALPAK-ADH (250× 4.6 mm, 5 µm; mobile phase (A) 0.1% DEA in n-hexane (B) EtOH:MeOH (50:50) (A:B: 60:40); flow Rate: 1.0 mL/min); Optical rotation $[\alpha]_D^{20.00}$: +122.01 (c=0.25, CH$_2$Cl$_2$).

Example 116

Synthesis of N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine

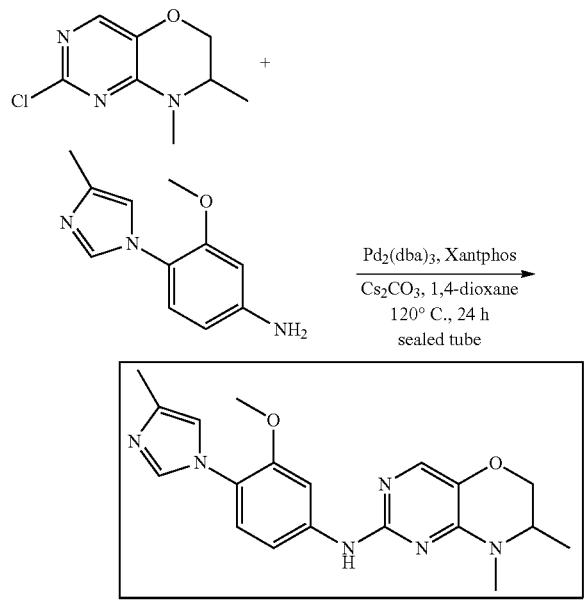

Synthesis of N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine A dry vial charged with Pd$_2$(dba)$_3$ (57 mg, 0.06 mmol) and Xantphos (108 mg, 0.18 mmol) in 1, 4-dioxane (1.25 mL) at room temperature was degassed and the resultant reaction mixture was stirred at 110° C. for 3 min. A mixture of 2-chloro-7, 8-dimethyl-7, 8-dihydro-6H-pyrimido [5, 4-b] [1, 4] oxazine (250 mg, 1.25 mmol), 3-methoxy-4-(4-methyl-1H-imidazol-1-yl) aniline (507 mg, 2.51 mmol), cesium carbonate (570 mg, 1.75 mmol) in 1, 4-dioxane (1.25 mL) was degassed and the catalyst premix was added. The resultant mixture was stirred at 120° C. for 24 h in a sealed tube. After consumption of the starting material (monitored by TLC and LCMS), the reaction was diluted with water (20 mL) and extracted with EtOAc (2×20 mL). The combined organic extracts were dried over sodium sulfate, filtered and concentrated in vacuo. The crude was purified by column chromatography using 0-5% MeOH: CH$_2$Cl$_2$ to afford N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine (130 mg, 28%) an off-white solid. LCMS: 367.4 (M+1); (column; X-Select CSH C-18 (50×3.0 mm, 3.5 µm); RT 3.84 min. 5 mM Aq NH$_4$OAc: ACN; 0.8 mL/min); TLC: 5% MeOH/CH$_2$Cl$_2$ (R$_f$: 0.2).

Racemic compound of Example 116 was separated using a Chiralpak ADH (250×20 mm: 5 µm; (20 mg loading; 0.1% DEA in n-hexane: CH$_2$Cl$_2$:MeOH (50:50); (A:B: 70:30) as mobile phase) to provide the compound of Example 116A (Fraction I (−)) and the compound of Example 116B (Fraction II (+)).

Example 116A

Synthesis of (−)-N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine

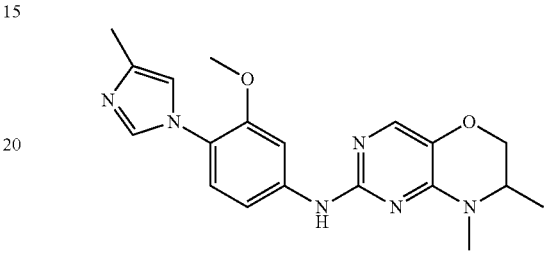

The compound of Example 116A was produced as described in Example 116. Analytical data for product Fraction I (−): $^1$H-NMR (CD$_3$OD, 400 MHz): δ 7.73 (d, 1H), 7.65 (s, 1H), 7.49 (s, 1H), 7.19 (d, 2H), 6.96 (s, 1H), 4.02-4.00 (m, 2H), 3.85 (s, 3H), 3.69-3.62 (m, 1H), 3.21 (s, 3H), 2.13 (s, 3H), 1.32 (d, 3H); Mass (ESI): 367.4 [M+1]; LCMS: 367.4 (M+1); (column; X-Select CSH C-18 (50×3.0 mm, 3.5 µm); RT 2.28 min. 0.05% Aq TFA: ACN; 0.80 mL/min); UPLC (column; Acquity UPLC HSS-T3, 100×2.1 mm, 1.8µ); RT 3.14 min. ACN: 0.025% TFA (Aq); 1.0 mL/min; Chiral HPLC: 98.1% RT=10.79 min (CHIRALPAK-ADH (250×4.6 mm, 5 µm; mobile phase (A) 0.1% DEA in n-hexane (B) EtOH:MeOH (50:50) (A:B; 70:30); flow Rate: 1.0 mL/min); Optical rotation $[\alpha]_D^{22.99}$: −2.91 (c=0.25, CH$_2$Cl$_2$).

Example 116B

Synthesis of (+)-N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine

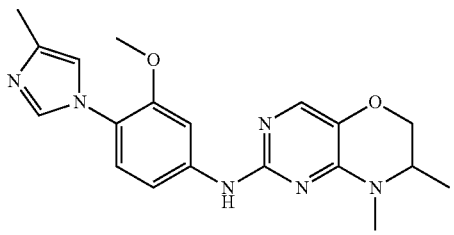

The compound of Example 116B was produced as described in Example 116. Analytical data for product Fraction II (+): $^1$H-NMR (CD$_3$OD, 400 MHz): δ 7.73 (d, 2H), 7.65 (s, 1H), 7.49 (s, 1H), 7.19 (d, 2H), 6.95 (s, 1H), 4.02-4.00 (m, 2H), 3.85 (s, 3H), 3.69-3.62 (m, 1H), 3.21 (s, 3H), 2.13 (s, 3H), 1.32 (d, 3H); Mass (ESI): 367.4 [M+1]; LCMS: 367.4 (M+1); (column; X-Select CSH C-18 (50×3.0 mm, 3.5 µm); RT 2.28 min. 0.05% Aq TFA: ACN; 0.80 mL/min); UPLC (column; Acquity UPLC HSS-T3, 100×2.1 mm, 1.8μ); RT 3.14 min. ACN: 0.025% TFA (Aq); 1.0 mL/min; Chiral HPLC: 98.1% RT=13.70 min (CHIRAL-PAK-AD-H (250×4.6 mm, 5 μm; mobile phase (A) 0.1% DEA in n-hexane (B) EtOH:MeOH (50:50) (A:B; 70:30); flow Rate: 1.0 mL/min); Optical rotation $[\alpha]_D^{23.02}$: +2.43 (c=0.25, CH$_2$Cl$_2$).

Example 117

Synthesis of 7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

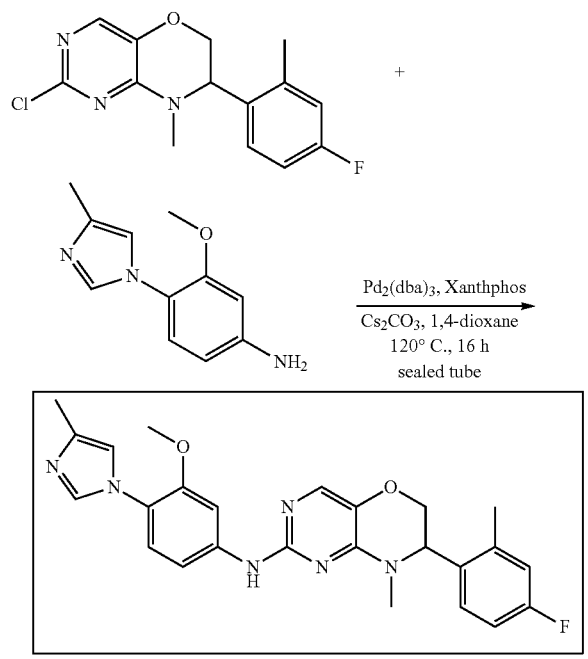

Synthesis of 7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine A dry vial charged with Pd$_2$(dba)$_3$ (15 mg, 0.01 mmol) and Xantphos (29 mg, 0.05 mmol) in 1, 4-dioxane (1 mL) at room temperature was degassed and the resultant reaction mixture was stirred at 120° C. for 3 min. A mixture of 2-chloro-7-(4-fluoro-2-methylphenyl)-8-methyl-7, 8-dihydro-6H-pyrimido [5, 4-b] [1, 4] oxazine (100 mg, 0.34 mmol), 3-methoxy-4-(4-methyl-1H-imidazol-1-yl) aniline (138 mg, 0.68 mmol), cesium carbonate (155 mg, 0.47 mmol) in 1, 4-dioxane (0.5 mL) was degassed and the catalyst premix was added. The resultant mixture was stirred at 120° C. for 16 h in a sealed tube. After consumption of the starting material (monitored by TLC and LCMS), the reaction was diluted with water (20 mL) and extracted with EtOAc (2×20 mL). The combined organic extracts were dried over sodium sulfate, filtered and concentrated in vacuo. The crude was purified by column chromatography using 8% MeOH: CH$_2$Cl$_2$ to afford 7-(4-fluoro-2-methylphenyl)-N-(3-methoxy-4-(4-methyl-1H-imidazol-1-yl) phe- nyl)-8-methyl-7, 8-dihydro-6H-pyrimido [5, 4-b] [1, 4] oxazin-2-amine (40 mg, 25%) as an off-white solid. LCMS: 461.6 (M+1); (column; X-Select CSH C-18 (50×3.0 mm, 3.5 μm); RT 4.50 min. 5 mM NH$_4$OAc: ACN; 0.80 mL/min); HPLC (column; Eclipse XDB C-18, 150×4.6 mm, 5 μm); RT 10.97 min. ACN: 5 mM Aq NH$_4$OAc; 1.0 ml/min; TLC: 10% MeOH/CH$_2$Cl$_2$ (R$_f$: 0.3).

Racemic compound of Example 117 was separated using a Chiralpak IA (250×20 mm: 5 μm; (20 mg loading; 0.1% DEA in n-hexane: THF:MeOH (50:50); (A:B: 80:20) as mobile phase) to provide the compound of Example 117A (Fraction I (−)) and the compound of Example 117B (Fraction II (+)).

Example 117A

Synthesis of (−)-7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

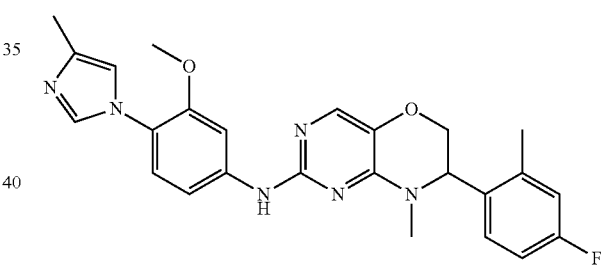

The compound of Example 117A was produced as described in Example 117. Analytical data for product Fraction I (−): $^1$H NMR (CD$_3$OD, 400 MHz) δ 7.76 (s, 1H), 7.67 (s, 1H), 7.58 (s, 1H), 7.24 (d, 1H), 7.21 (d, 1H), 7.04-6.88 (m, 3H), 6.86-6.80 (m, 1H), 4.99-4.97 (m, 1H), 4.24-4.18 (m, 1H), 4.14-4.08 (m, 1H), 3.85 (s, 3H), 3.10 (s, 3H), 2.43 (s, 3H), 2.23 (m, 3H); Mass (ESI): 461.6 [M+1]; LCMS: 461.6 (M+1); (column; X-Select CSH C-18 (50×3.0 mm, 3.5 μm); RT 4.46 min 5 mM Aq NH$_4$OAc: ACN; 0.80 mL/min); HPLC (column; Eclipse XDB C18, 150×4.6 mm, 5 μm); RT 10.97 min. ACN: 5 mM Aq NH$_4$OAc; 1.0 mL/min; Chiral HPLC: 99.5% RT=17.00 min (CHIRAL-PAK-IA (250×4.6 mm, 5 μm; mobile phase (A) 0.1% DEA in n-hexane (B) THF:MeOH (50:50) (A:B: 80:20); flow Rate: 1.0 mL/min); Optical rotation $[\alpha]_D^{20.00}$: −154.32 (c=0.25, CH$_2$Cl$_2$).

Example 117B

Synthesis of (+)-7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

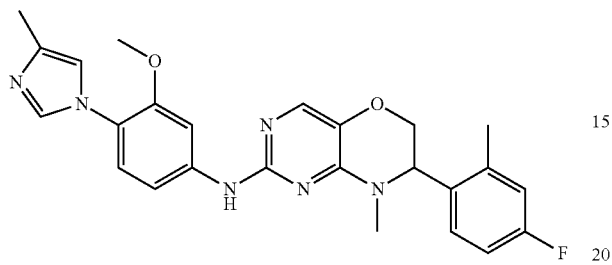

The compound of Example 117B was produced as described in Example 117. Analytical data for product Fraction II (+): $^1$H NMR (CD$_3$OD, 400 MHz) δ 7.76 (s, 1H), 7.67 (s, 1H), 7.58 (s, 1H), 7.24 (d, 1H), 7.21 (d, 1H), 7.04-6.88 (m, 3H), 6.86-6.80 (m, 1H), 4.99-4.97 (m, 1H), 4.24-4.18 (m, 1H), 4.14-4.08 (m, 1H), 3.85 (s, 3H), 3.10 (s, 3H), 2.43 (s, 3H), 2.23 (m, 3H); Mass (ESI): 461.6 [M+1]; LCMS: 461.6 (M+1); (column; X-Select CSH C-18 (50×3.0 mm, 3.5 μm); RT 4.46 min 5 mM Aq NH$_4$OAc: ACN; 0.80 mL/min); HPLC (column; Eclipse XDB C18, 150×4.6 mm, 5 μm); RT 10.97 min. ACN: 5 mM Aq NH$_4$OAc; 1.0 mL/min; Chiral HPLC: 99.2% RT=19.06 min (CHIRALPAK-IA (250×4.6 mm, 5 μm; mobile phase (A) 0.1% DEA in n-hexane (B) THF:MeOH (50:50) (A:B: 80:20); flow Rate: 1.0 mL/min); Optical rotation $[α]_D^{20.01}$: +143.12 (c=0.25, CH$_2$Cl$_2$).

Example 118

Synthesis of N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine

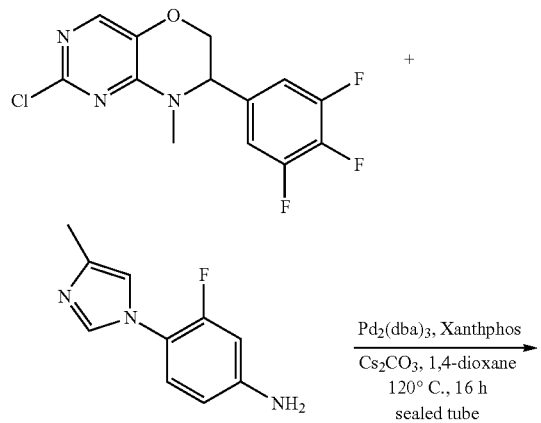

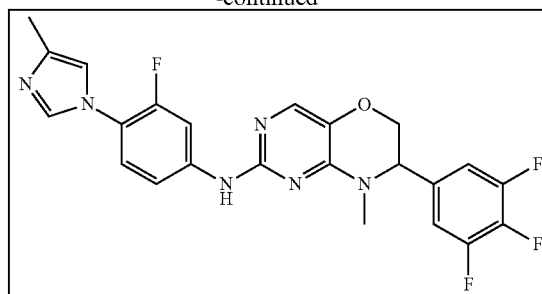

Synthesis of N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine A dry vial charged with Pd$_2$(dba)$_3$ (34 mg, 0.03 mmol) and Xantphos (65 mg, 0.11 mmol) in 1, 4-dioxane (1.25 mL) at room temperature was degassed and the resultant reaction mixture was stirred at 120° C. for 3 min. A mixture of 2-chloro-8-methyl-7-(3, 4, 5-trifluorophenyl)-7, 8-dihydro-6H-pyrimido [5, 4-b] [1, 4] oxazine (250 mg, 0.75 mmol), 3-fluoro-4-(4-methyl-1H-imidazol-1-yl) aniline (290 mg, 1.51 mmol), cesium carbonate (343 mg, 1.05 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the reaction was diluted with water (20 mL) and extracted with EtOAc (2×20 mL). The combined organic extracts were dried over sodium sulfate, filtered and concentrated in vacuo. The crude was purified by column chromatography using 4% MeOH: CH$_2$Cl$_2$ to afford N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine (100 mg, 26%) as an off-white solid. LCMS: 471.4 (M+1); (column; Zorbax SB C-18 (150×4.6 mm, 5.0 μm); RT 11.64 min 5 mM Aq NH$_4$OAc: ACN; 1.0 mL/min); TLC: 5% MeOH/CH$_2$Cl$_2$ (R$_f$: 0.3).

Racemic compound of Example 118 was separated using a Chiralpak ADH (250×20 mm: 5 μm; (15 mg loading; 0.1% DEA in n-hexane: EtOH:MeOH (50:50); (A:B: 55:45) as mobile phase) to provide the compound of Example 118A (Fraction I (+)) and the compound of Example 118B (Fraction II (−)).

Example 118A

Synthesis of (+)-N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine

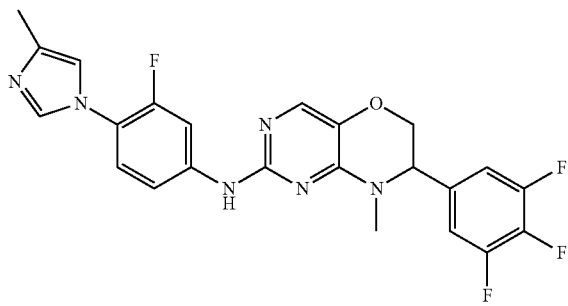 [SMILES: Cc1cn(-c2ccc(Nc3ncc4c(n3)N(C)C(c3cc(F)c(F)c(F)c3)CO4)cc2F)cn1]

The compound of Example 118A was produced as described in Example 118. Analytical data for product Fraction I (+): $^1$H-NMR (CD$_3$OD, 400 MHz): δ 8.00-7.98 (m, 1H), 7.75 (s, 1H), 7.61 (s, 1H), 7.42-7.40 (m, 1H), 7.35-7.30 (m, 1H), 7.06-7.00 (m, 3H), 4.74-4.71 (m, 1H), 4.20 (s, 2H), 3.15 (s, 3H), 2.22 (s, 3H); Mass (ESI): 471.4 [M+1]; LCMS: 471.4 (M+1); (column; X-Select CSH C-18 (50×3.0 mm, 3.5 μm); RT 2.99 min 0.05% Aq TFA: ACN; 0.80 mL/min); UPLC (column; Acquity UPLC BEH C18, 2.1×50 mm, 1.7 μm); RT 1.72 min. ACN: 0.025% Aq TFA; 0.5 mL/min; Chiral HPLC: 100% RT=13.95 min (CHIRAL-PAK-ADH (250×4.6 mm, 5 μm; mobile phase (A) 0.1% DEA in n-hexane (B) EtOH:MeOH (50:50) (A:B: 55:45); flow Rate: 1.0 mL/min); Optical rotation [α]$_D^{20.01}$: +103.31 (c=0.25, CH$_2$Cl$_2$).

Example 118B

Synthesis of (−)-N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine

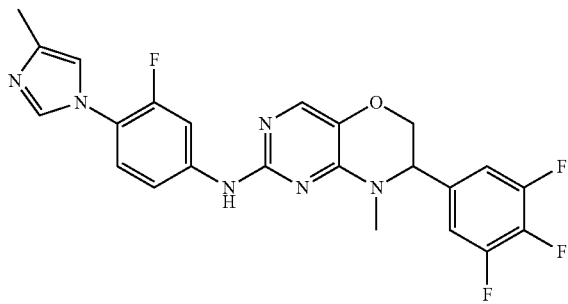 [SMILES: Cc1cn(-c2ccc(Nc3ncc4c(n3)N(C)C(c3cc(F)c(F)c(F)c3)CO4)cc2F)cn1]

The compound of Example 118B was produced as described in Example 118. Analytical data for product Fraction II (−): $^1$H-NMR (CD$_3$OD, 400 MHz): δ 8.00-7.98 (m, 1H), 7.75 (s, 1H), 7.61 (s, 1H), 7.42-7.40 (m, 1H), 7.35-7.30 (m, 1H), 7.06-7.00 (m, 3H), 4.74-4.71 (m, 1H), 4.20 (s, 2H), 3.15 (s, 3H), 2.22 (s, 3H); Mass (ESI): 471.4 [M+1]; LCMS: 471.4 (M+1); (column; X-Select CSH C-18 (50×3.0 mm, 3.5 μm); RT 2.98 min 0.05% Aq TFA: ACN; 0.80 mL/min); UPLC (column; Acquity UPLC BEH C18, 2.1×50 mm, 1.7 μm); RT 1.71 min. ACN: 0.025% Aq TFA; 0.5 mL/min; Chiral HPLC: 100%=25.41 min (CHIRAL-PAK-ADH (250×4.6 mm, 5 μm; mobile phase (A) 0.1% DEA in n-hexane (B) EtOH:MeOH (50:50) (A:B: 55:45); flow Rate: 1.0 mL/min); Optical rotation [α]$_D^{20.00}$: −93.40 (c=0.25, CH$_2$Cl$_2$).

Example 119

Synthesis of 5-methoxy-6-(4-methyl-1H-imidazol-1-yl) pyridin-3-amine

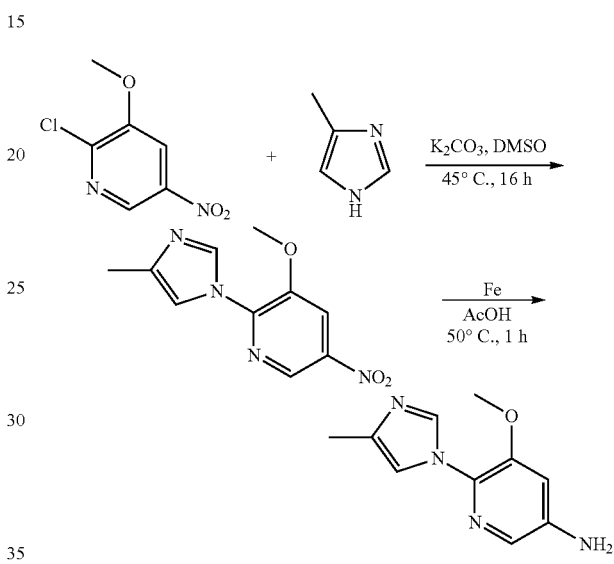

Synthesis of 3-methoxy-2-(4-methyl-1H-imidazol-1-yl)-5-nitropyridine

To a stirred solution of 2-chloro-3-methoxy-5-nitropyridine (2 g, 10.60 mmol) in DMSO (40 mL) under an argon atmosphere were added potassium carbonate (3.65 g, 26.51 mmol) and 4-methyl-1H-imidazole (1 g, 12.72 mmol) at room temperature. The reaction mixture was stirred at 45° C. for 16 h. After consumption of the starting material (monitored by TLC), the reaction mixture was diluted with water (40 mL) to obtain solid which was filtered and dried in vacuo to afford 3-methoxy-2-(4-methyl-1H-imidazol-1-yl)-5-nitropyridine (1.8 g, 72%) as a yellow solid. $^1$H-NMR (DMSO-d$_6$, 400 MHz): δ 8.92-8.90 (m, 1H), 8.45 (s, 1H), 8.36-8.32 (m, 1H), 7.68 (s, 1H), 4.10 (s, 3H), 2.20 (s, 3H); LC-MS: 235 (M+1); (column; X-Bridge C-18 (50×3.0 mm, 3.5 μm); RT 2.09 min. 0.05% aq TFA: ACN; 0.80 mL/min); TLC: 5% MeOH/CH$_2$Cl$_2$ (R$_f$: 0.4).

Synthesis of 5-methoxy-6-(4-methyl-1H-imidazol-1-yl) pyridin-3-amine

To a stirred solution of 3-methoxy-2-(4-methyl-1H-imidazol-1-yl)-5-nitropyridine (1.8 g, 7.69 mmol) in acetic acid (18 mL) under an argon atmosphere was added iron powder (4.3 g, 7.69 mmol) at room temperature. The reaction mixture was stirred at 50° C. for 1 h. After consumption of the starting material (monitored by TLC), the reaction mixture was diluted with a saturated sodium bicarbonate solution (50 mL) and extracted with 10% MeOH: CH$_2$Cl$_2$ (2×50 mL). The combined organic extracts were dried over sodium sulfate, filtered and concentrated in vacuo to obtain 5-methoxy-6-(4-methyl-1H-imidazol-1-yl) pyridin-3-amine (1.3 g, 83%) as a brown solid. $^1$H-NMR (DMSO-$d_6$, 500 MHz): δ 7.83 (s, 1H), 7.37 (s, 1H), 7.20 (s, 1H), 6.78 (s, 1H), 5.57-5.53 (m, 2H), 3.79 (s, 3H), 2.16 (s, 3H); LC-MS: 205 (M+1); (column; Eclipse XDB C-18 (150×4.6 mm, 5 μm); RT 5.69 min. 0.05% aq TFA: ACN; 1.0 mL/min); UPLC (column; Acquity UPLC HSS T3 2.1×100 mm, 1.8μ); RT 2.93 min. ACN: 0.025% TFA (Aq); 0.30 mL/min; TLC: 5% MeOH/CH$_2$Cl$_2$ ($R_f$: 0.1).

Example 120

Synthesis of 6-methoxy-5-(4-methyl-1H-imidazol-1-yl) pyridin-2-amine

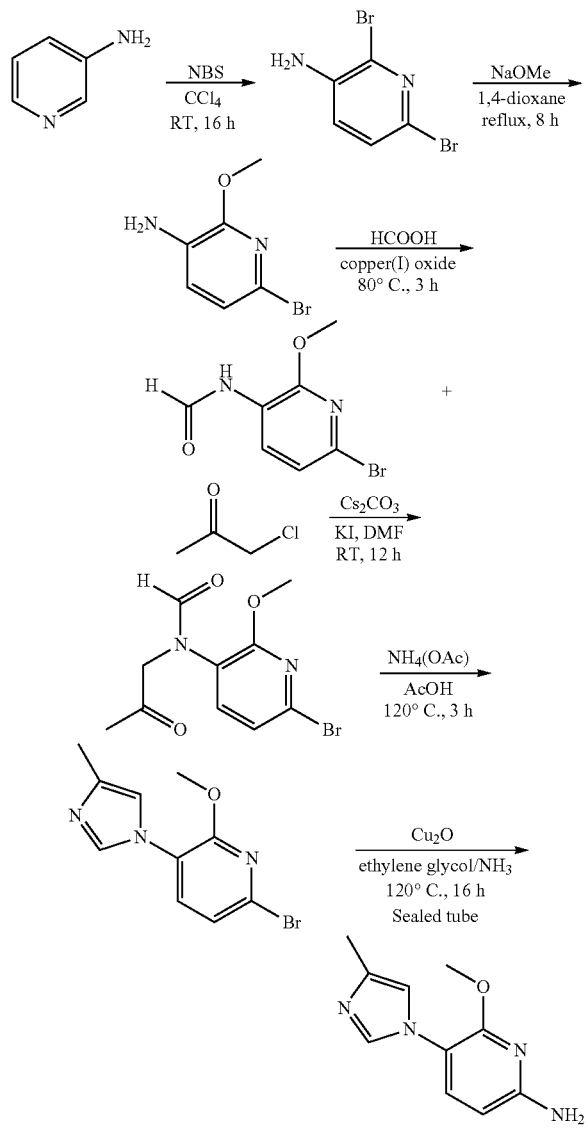

Synthesis of 2, 6-dibromopyridin-3-amine

To a stirred solution of pyridin-3-amine (20.0 g, 0.21 mol) in CCl$_4$ (200 mL) under an argon atmosphere was added N-bromosuccinimide (82.87 g, 0.42 mol) portion wise at 0° C. for 20 min. The reaction mixture was warmed to room temperature and stirred for 16 h. After consumption of the starting material (monitored by TLC), the volatile components were evaporated in vacuo. The crude material was purified by silica gel column chromatography using 5-8% EtOAc:hexanes to afford 2, 6-dibromopyridin-3-amine (18 g, 34%) as a brown solid. $^1$H-NMR (CDCl$_3$, 400 MHz): δ 7.24 (d, 1H), 6.92 (d, 1H), 4.15 (br s, 2H); TLC: 30% EtOAc:hexane ($R_f$: 0.35).

Synthesis of 6-bromo-2-methoxypyridin-3-amine

To a stirred solution of 2, 6-dibromopyridin-3-amine (38 g, 0.188 mol) in 1, 4-dioxane (400 mL) under an argon atmosphere was added sodium methoxide (70.55 g, 1.30 mol) at room temperature. The reaction mixture was stirred at reflux for 8 h. After consumption of the starting material (monitored by TLC), the reaction mixture was quenched with ice cold water (200 mL) and extracted with EtOAc (3×200 mL). The combined organic extracts were washed with cold water (2×100 mL), dried over sodium sulfate and concentrated in vacuo. The crude material was purified by column chromatography using 10% EtOAc:hexanes to afford 6-bromo-2-methoxypyridin-3-amine (13 g, 42%) as a brown solid. $^1$H-NMR (CDCl$_3$, 400 MHz): δ 6.87 (d, 1H), 6.76 (d, 1H), 4.01 (s, 3H), 3.75 (br s, 2H); TLC: 20% EtOAc:hexane ($R_f$: 0.5).

Synthesis of N-(6-bromo-2-methoxypyridin-3-yl) formamide

To a stirred solution of 6-bromo-2-methoxypyridin-3-amine (13.0 g, 64.03 mmol) in formic acid (39 mL) under an argon atmosphere was added copper oxide (2.6 g, 32.60 mmol) at room temperature. The reaction mixture was stirred at 80° C. for 3 h. After consumption of the starting material (monitored by TLC), the reaction mixture was quenched with ice cold water (100 mL) and extracted with EtOAc (3×200 mL). The combined organic extracts were washed with cold water (100 mL) and dried over sodium sulfate, filtered and concentrated in vacuo to obtain N-(6-bromo-2-methoxypyridin-3-yl) formamide (10.8 g, 73%) as a brown solid used in the next step without further purification. $^1$H-NMR (CDCl$_3$, 400 MHz): δ 8.49-8.48 (m, 2H), 8.16 (s, 1H), 7.09 (d, 1H), 4.06 (s, 3H); TLC: 30% EtOAc:hexane ($R_f$: 0.5).

Synthesis of N-(6-bromo-2-methoxypyridin-3-yl)-N-(2-oxopropyl) formamide

To a stirred solution of N-(6-bromo-2-methoxypyridin-3-yl) formamide (10.0 g, 43.36 mmol) in DMF (100 mL) under an argon atmosphere were added cesium carbonate (27.56 g, 84.53 mmol) and potassium iodide (0.88 g, 5.20 mmol) at 0° C. After 20 min, a solution of chloroacetone (8.02 g, 86.73 mmol) in DMF (20 mL) was added to the reaction mixture at room temperature. The reaction mixture was stirred at room temperature for 12 h. After consumption of the starting material (monitored by TLC), the reaction mixture was poured into cold water (100 mL) and extracted with EtOAc (3×100 mL). The combined organic extracts were washed with cold water (100 mL), dried over sodium sulfate, filtered and concentrated in vacuo to obtain N-(6-bromo-2-methoxypyridin-3-yl)-N-(2-oxopropyl) forma-

Synthesis of 6-bromo-2-methoxy-3-(4-methyl-M-imidazol-1-yl) pyridine

To a stirred solution of N-(6-bromo-2-methoxypyridin-3-yl)-N-(2-oxopropyl) formamide (18 g, 62.69 mmol) in AcOH (60 mL) under an argon atmosphere was added ammonium acetate (24 g, 3.11 mmol) at room temperature and then stirred at 120° C. for 3 h. After consumption of the starting material (monitored by TLC), the reaction mixture was quenched with cold water (100 mL) and extracted with EtOAc (3×100 mL). The combined organic extracts were dried over sodium sulfate, filtered and concentrated in vacuo. The crude material was purified by column chromatography using 20% EtOAc:hexane to afford 6-bromo-2-methoxy-3-(4-methyl-1H-imidazol-1-yl) pyridine (10 g, 60%) as a white solid.

$^1$H-NMR (DMSO d$_6$, 400 MHz): δ7.90 (s, 1H), 7.81 (d, 1H), 7.38 (d, 1H), 7.21 (s, 1H), 3.94 (s, 3H), 2.14 (s, 3H); TLC: 60% EtOAc:hexane (R$_f$: 0.4).

Synthesis of 6-methoxy-5-(4-methyl-1H-imidazol-1-yl) pyridin-2-amine

To a stirred solution of 6-bromo-2-methoxy-3-(4-methyl-1H-imidazol-1-yl) pyridine (10 g, 37.29 mmol) in ethylene glycol/NH$_3$ (50 mL) under an argon atmosphere was added copper (I) oxide (106 mg, 0.74 mmol) at room temperature. The reaction mixture was stirred at 120° C. for 16 h in a sealed tube. After consumption of the starting material (monitored by TLC), the reaction mixture was diluted with water (100 mL) and extracted with EtOAc (3×150 mL). The combined organic extracts were washed with cold water (2×100 mL), dried over sodium sulfate and concentrated in vacuo. The crude material was purified by column chromatography using 60-80% EtOAc:hexanes to afford 6-methoxy-5-(4-methyl-1H-imidazol-1-yl) pyridin-2-amine (5.0 g, 66%) as a white solid. $^1$H-NMR (DMSO d$_6$, 400 MHz): δ 7.54 (s, 1H), 7.37 (d, 1H), 6.92 (s, 1H), 6.18 (br s, 2H), 6.05 (d, 1H), 3.78 (s, 3H), 2.12 (s, 3H); TLC: 10% MeOH/CH$_2$Cl$_2$ (R$_f$: 0.4).

Example 121

Synthesis of 6-methoxy-5-(2-methylpyrimidin-4-yl) pyridin-2-amine

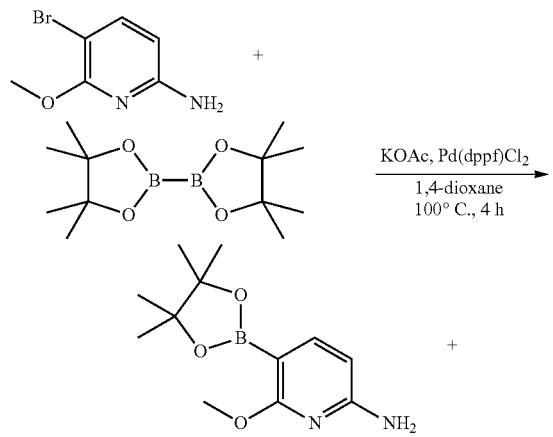

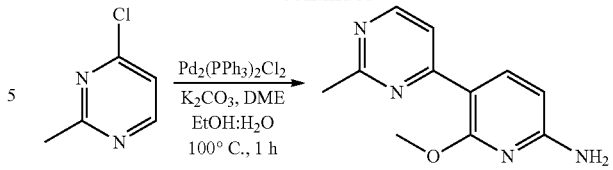

Synthesis of 6-methoxy-5-(4, 4, 5, 5-tetramethyl-1, 3, 2-dioxaborolan-2-yl) pyridin-2-amine To a stirred solution of 5-bromo-6-methoxypyridin-2-amine (3.5 g, 17.24 mmol) in 1, 4-dioxane (250 mL) under an argon atmosphere were added Bis (pinacolato) diboron (8.7 g, 34.48 mmol) and potassium acetate (5.08 g, 57.72 mmol) at room temperature and purged under an argon atmosphere for 30 min. Then Pd(dppf)Cl$_2$ (3.8 g, 5.17 mmol) was added to the reaction mixture and stirred at 100° C. for 4 h. The reaction mixture was brought to room temperature and stirred for 1 h. After consumption of the starting material (monitored by TLC), the reaction was diluted with EtOAc (100 mL), filtered and the filtrate was concentrated in vacuo. The crude material was purified by column chromatography using 20% EtOAc:hexanes (neutralized with triethylamine) to afford 6-methoxy-5-(4,4,5,5-tetramethyl-1,3,2-dioxaborolan-2-yl)pyridin-2-amine (1.3 g, 30%) as a pale yellow solid. $^1$H-NMR (CDCl$_3$, 400 MHz): δ 7.75 (d, 1H), 6.01 (d, 1H), 4.44 (br s, 2H), 3.88 (s, 3H), 1.31 (s, 12H); TLC: 30% EtOAc:hexanes (R$_f$: 0.3).

Synthesis of 6-methoxy-5-(2-methylpyrimidin-4-yl) pyridin-2-amine

To a stirred solution of 4-chloro-2-methylpyrimidine (500 mg, 3.88 mmol) in DME:EtOH:H$_2$O (6:2:1) (135 mL) under an argon atmosphere were added 6-methoxy-5-(4,4,5,5-tetramethyl-1,3,2-dioxaborolan-2-yl)pyridin-2-amine (1.4 g, 5.83 mmol) and potassium carbonate (1.6 g, 11.64 mmol) at room temperature and purged under an argon atmosphere for 30 min. Then Pd(PPh$_3$)$_2$Cl$_2$ (272 mg, 0.38 mmol) was added to the reaction mixture at room temperature. The reaction mixture was stirred at 100° C. for 1 h. After consumption of the starting material (monitored by TLC), the reaction was diluted with EtOAc (100 mL), filtered and the filtrate was concentrated in vacuo. The crude material was purified by column chromatography using 30% EtOAc:hexanes to afford 6-methoxy-5-(2-methylpyrimidin-4-yl)pyridin-2-amine (540 mg, 64%) as a pale yellow solid. $^1$H-NMR (CDCl$_3$, 400 MHz): δ 8.51 (d, 1H), 8.41 (d, 1H), 7.81 (d, 1H), 6.20 (d, 1H), 4.60 (br s, 2H), 3.99 (s, 3H), 2.71 (s, 3H); LCMS: 217.1 (M+1); (column; X-Select CSH C-18 (50×3.0 mm, 3.5 μm); RT 1.69 min 0.05% Aq TFA: ACN; 0.80 mL/min); TLC: 50% EtOAc:hexanes (R$_f$: 0.3).

Example 122

Synthesis of 5-chloro-6-(4-methyl-1H-imidazol-1-yl) pyridin-3-amine

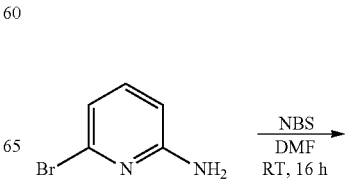

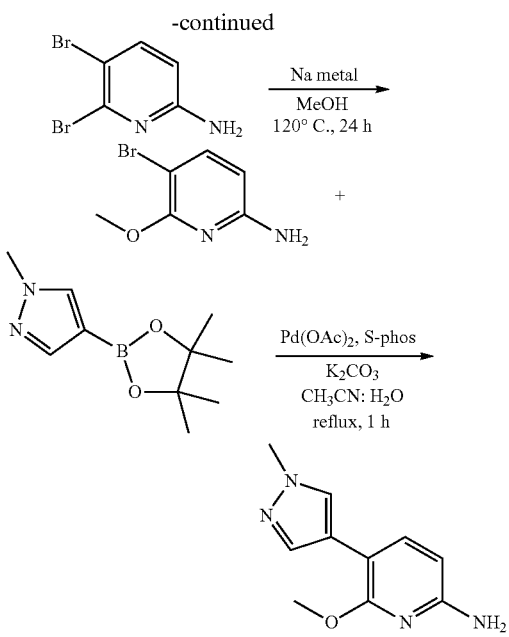

Synthesis of 5,6-dibromopyridin-2-amine

To a stirred solution of 6-bromopyridin-2-amine (5 g, 28.90 mmol) in DMF (75 mL) under an argon atmosphere was added N-bromosuccinimide (35 mg, 1.04 mmol) at 0° C. The reaction mixture was warmed to room temperature and stirred for 16 h. After consumption of the starting material (monitored by TLC), the reaction was quenched with ice cold water (50 mL) and extracted with EtOAc (2×50 mL). The combined organic extracts were dried over sodium sulfate, filtered and concentrated in vacuo. The crude material was purified by column chromatography using 30% EtOAc:hexanes to afford 5,6-dibromopyridin-2-amine (6.1 g, 85%) as an off-white solid. $^{1}$H-NMR (CDCl$_3$, 400 MHz): δ 7.51 (d, 1H), 6.32 (d, 1H), 4.60 (br s, 2H); LCMS: 252.6 (M+1); (column; X-Select CSH C-18 (50×3.0 mm, 3.5 μm); RT 3.04 min 0.05% Aq TFA: ACN; 0.80 mL/min).

Synthesis of 5-bromo-6-methoxypyridin-2-amine

A mixture of sodium metal (1.1 g, 47.80 mmol) in MeOH (45 mL) under an argon atmosphere was stirred at −20° C. to 0° C. for 4 h. The reaction mixture was stirred at 120° C. for 24 h. After consumption of the starting material (monitored by TLC), the volatile components were evaporated in vacuo. The residue was diluted with water (100 mL), neutralized with a 2 M HCl solution (20 mL) and extracted with EtOAc (2×200 mL). The combined organic extracts were dried were sodium sulfate, filtered and concentrated in vacuo. The crude material was purified by column chromatography using 10% EtOAc:hexanes to afford 5-bromo-6-methoxypyridin-2-amine (3.5 g, 72%) as an off-white solid. $^{1}$H-NMR (CD$_3$OD, 400 MHz): δ 7.48 (d, 1H), 5.98 (d, 1H), 4.30 (s, 2H), 3.90 (s, 3H); LCMS: 205.2 (M+2); (column; X-Select CSH C-18 (50×3.0 mm, 3.5 μm); RT 3.52 min 0.05% Aq TFA: ACN; 0.80 mL/min); TLC: 30% EtOAc: hexanes (R$_f$: 0.5).

Synthesis of 6-methoxy-5-(1-methyl-1H-pyrazol-4-yl) pyridin-2-amine

To a stirred solution of 5-bromo-6-methoxypyridin-2-amine (2 g, 9.85 mmol) in CH$_3$CN: water (2:1, 30 mL) under an argon atmosphere were added potassium carbonate (2.7 g, 19.70 mmol), S-phos (404 mg, 0.98 mmol), Pd(OAc)$_2$ (332 mg, 0.49 mmol) and degassed for 30 min at room temperature. Then (1-methyl-4-(4, 4, 5, 5-tetramethyl-1, 3, 2-dioxaborolan-2-yl)-1H-pyrazole (6 g, 23.90 mmol) was added to the reaction mixture at room temperature. The reaction mixture was stirred at reflux for 1 h. After consumption of the starting material (monitored by TLC), the reaction mixture was diluted with water (100 mL) and extracted with EtOAc (2×200 mL). The combined organic extracts were dried over sodium sulfate, filtered and concentrated in vacuo. The crude material was recrystallized with CH$_2$Cl$_2$ (2×30 mL) to obtain 6-methoxy-5-(1-methyl-1H-pyrazol-4-yl) pyridin-2-amine (1.2 g, 60%) as a pale yellow solid. $^{1}$H-NMR (DMSO-d$_6$, 400 MHz): δ 7.82 (s, 1H), 7.69 (s, 1H), 7.55 (d, 1H), 6.03 (d, 1H), 5.80 (s, 2H), 3.82 (s, 3H), 3.80 (s, 3H); LCMS: 205 (M+1); (column; X-Select CSH C-18 (50×3.0 mm, 3.5 μm); RT 2.19 min 0.05% Aq TFA: ACN; 0.80 mL/min); TLC: 50% EtOAc: hexanes (R$_f$: 0.2).

Example 123

Synthesis of 6-(4-methyl-1H-imidazol-1-yl) pyridin-3-amine

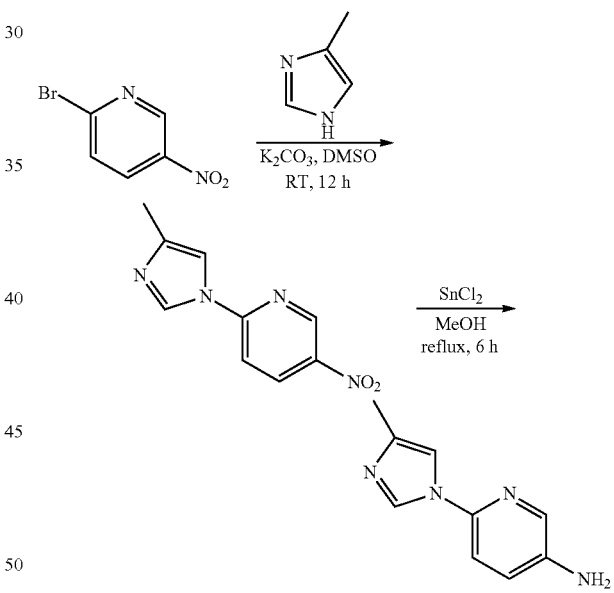

Synthesis of 2-(4-methyl-1H-imidazol-1-yl)-5-nitropyridine

To a stirred solution of 2-bromo-5-nitropyridine (10 g, 0.05 mol) in DMSO (100 mL) under an argon atmosphere were added 4-methyl imidazole (16.3 g, 0.2 mol) and potassium carbonate (20.5 g, 0.15 mol) at room temperature. The reaction mixture was stirred for 12 h at room temperature. After consumption of the starting material (monitored by TLC), the reaction was diluted with water (100 mL) and the solid was filtered. The filtrate was extracted with EtOAc (2×200 mL), the combined organic extracts were dried over sodium sulfate, filtered and concentrated in vacuo to obtain 2-(4-methyl-1H-imidazol-1-yl)-5-nitropyridine (8 g) as a yellow solid used in the next step without further purification. TLC: 30% EtOAc:hexane ($R_f$: 0.45).

Synthesis of 6-(4-methyl-M-imidazol-1-yl) pyridin-3-amine

To a stirred solution of 2-(4-methyl-1H-imidazol-1-yl)-5-nitropyridine (8 g, 0.039 mol) in MeOH (80 mL) under an argon atmosphere was added $SnCl_2$ (29.6 g, 0.156 mol) at room temperature. The reaction mixture was refluxed for 6 h. After consumption of the starting material (monitored by TLC), the volatile components were concentrated in vacuo. The crude material was washed with ether to afford 6-(4-methyl-1H-imidazol-1-yl) pyridin-3-amine (3 g, 44%) as a brown solid. TLC: 30% EtOAc:hexane ($R_f$: 0.1).

Example 124

Synthesis of 5-amino-2-(4-methyl-1H-imidazol-1-yl) benzonitrile

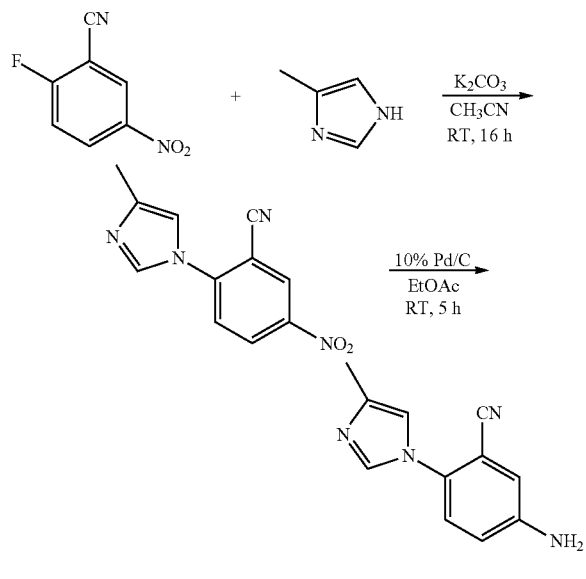

Synthesis of 2-(4-methyl-1H-imidazol-1-yl)-5-nitrobenzonitrile

To a stirred solution of 2-fluoro-5-nitrobenzonitrile (2 g, 12.04 mmol) in $CH_3CN$ (20 mL) under an argon atmosphere were added potassium carbonate (3.32 g, 24.02 mmol) and 4-methyl-1H-imidazole (1.97 g, 24.02 mmol) at room temperature. The reaction mixture was stirred for 16 h at room temperature. After consumption of the starting material (monitored by TLC), the volatile components were evaporated in vacuo. The residue was diluted with a 1N sodium hydroxide solution (100 mL) and extracted with EtOAc (2×100 mL). The combined organic extracts were washed with brine (50 mL), dried over sodium sulfate, filtered and concentrated in vacuo. The crude material was washed with ethanol: water (1:1, 20 mL) to afford 2-(4-methyl-1H-imidazol-1-yl)-5-nitrobenzonitrile (1.6 g, 58%) as a pale yellow solid. $^1$H-NMR (DMSO-$d_6$, 400 MHz): δ 8.92 (s, 1H), 8.61 (d, 1H), 8.15 (s, 1H), 7.91 (d, 1H), 7.49 (s, 1H), 2.20 (s, 3H); LCMS: 228.9 (M+1); (column; X-Select CSH C-18 (50×3.0 mm, 3.5 μm); RT 1.03 min 0.05% Aq TFA: ACN; 0.80 mL/min); UPLC (column; Acquity BEH C-18 2.1×50 mm, 1.7 μm); RT 1.04 min. ACN: 0.025% Aq TFA; 0.5 mL/min; TLC: 5% MeOH/$CH_2Cl_2$ ($R_f$: 0.4).

Synthesis of 5-amino-2-(4-methyl-1H-imidazol-1-yl) benzonitrile

To a stirred solution of 3-methoxy-2-(1-methyl-1H-pyrazol-4-yl)-5-nitropyridine (2.5 g, 10.68 mmol) in EtOAc (50 mL) under an argon atmosphere was added 10% Pd/C (1.2 g) at room temperature. The reaction mixture was stirred for 5 h at room temperature. After consumption of the starting material (monitored by TLC), the reaction mixture was filtered, washed with EtOAc (50 mL) and 5% MeOH:$CH_2Cl_2$ (50 mL). The filtrate was concentrated in vacuo. The crude material was washed with n-pentane (2×20 mL) to afford 5-amino-2-(4-methyl-1H-imidazol-1-yl) benzonitrile (2 g, 92%) as a brown solid. $^1$H-NMR (DMSO-$d_6$, 400 MHz): δ 7.71 (s, 1H), 7.22 (d, 1H), 7.10 (s, 1H), 6.95 (s, 1H), 6.93-6.89 (m, 1H), 5.85 (s, 2H), 2.13 (s, 3H); LCMS: 199.2 (M+1); (column; X-Select CSH C-18 (50×3.0 mm, 3.5 μm); RT 2.61 min 5 mM Aq $NH_4OAc$: ACN; 0.80 mL/min); HPLC (column; Acquity UPLC HSS T3 (100×2.1 mm, 1.8μ); RT 2.97 min. ACN: 0.025% Aq TFA; 0.5 mL/min; TLC: 5% MeOH/$CH_2Cl_2$ ($R_f$: 0.3).

Example 125

Synthesis of 5-(4-methyl-1H-imidazol-1-yl) pyridin-2-amine

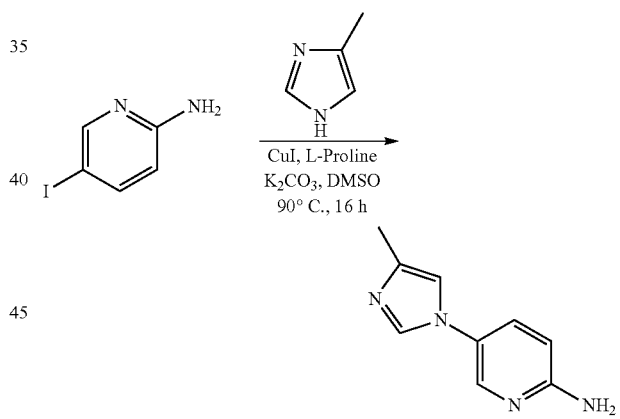

Synthesis of 5-(4-methyl-M-imidazol-1-yl) pyridin-2-amine

To a stirred solution of 5-iodopyridin-2-amine (1 g, 4.54 mmol) in DMSO (9 mL) under an argon atmosphere were added 4-methyl-1H-imidazole (521 mg, 6.36 mmol), copper iodide (172 mg, 0.90 mmol), L-proline (209 mg, 0.18 mmol) and potassium carbonate (1.2 g, 9.09 mmol) at room temperature. The reaction mixture was stirred at 90° C. for 16 h. After consumption of the starting material (monitored by TLC), the reaction mixture was diluted with water (30 mL) and extracted with EtOAc (2×30 mL). The combined organic extracts were dried over sodium sulfate, filtered and concentrated in vacuo. The crude material was purified by column chromatography using 3% MeOH: $CH_2Cl_2$ to afford 5-(4-methyl-1H-imidazol-1-yl) pyridin-2-amine (500 mg, 63%) as a brown solid. ¹H-NMR (DMSO-d₆, 500 MHz): δ 8.09 (s, 1H), 7.84 (s, 1H), 7.57-7.54 (m, 1H), 7.20 (s, 1H), 6.53-6.51 (m, 1H), 6.12 (s, 2H), 2.13 (s, 3H); LCMS: 175.1 (M+1); (column; X-Bridge C-18 (50×3.0 mm, 3.5 μm); RT 3.67 min. 5 mM NH₄OAc: ACN; 0.80 mL/min); TLC: 10% MeOH/CH₂Cl₂ (R$_f$: 0.5).

Example 126

Synthesis of 5-methoxy-6-(4-(trifluoromethyl)-1H-imidazol-1-yl) pyridin-3-amine

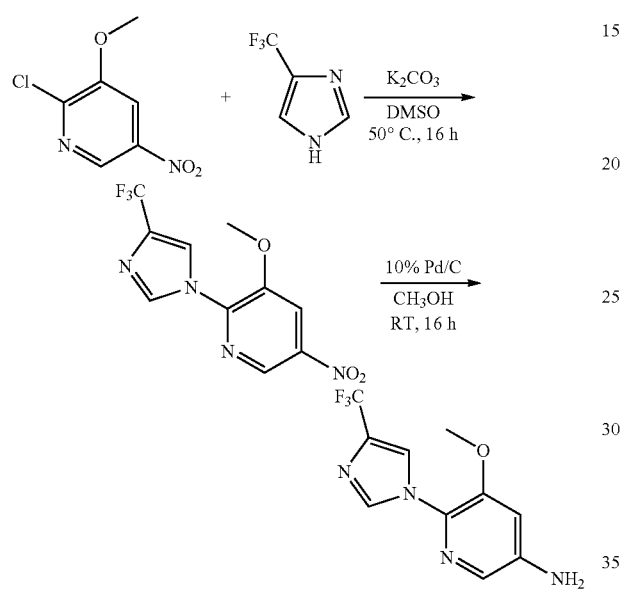

Synthesis of 3-methoxy-5-nitro-2-(4-(trifluoromethyl)-1H-imidazol-1-yl) pyridine To a stirred solution of 2-chloro-3-methoxy-5-nitropyridine (2 g, 10.60 mmol) in DMSO (30 mL) under an argon atmosphere were added potassium carbonate (6.70 g, 48.61 mmol) and 4-(trifluoromethyl)-1H-imidazole (1.7 g, 12.76 mmol) at room temperature. The reaction mixture was stirred at 50° C. for 16 h. After consumption of the starting material (monitored by TLC), the reaction mixture was diluted with water (20 mL). The obtained solid was filtered and dried in vacuo to afford 3-methoxy-5-nitro-2-(4-(trifluoromethyl)-1H-imidazol-1-yl) pyridine (1.4 g, 46%) as a yellow solid. ¹H-NMR (DMSO-d₆, 400 MHz): δ 8.97 (s, 1H), 8.65 (s, 1H), 8.45 (s, 1H), 8.44 (s, 1H), 4.11 (s, 3H); LCMS: 288.8 (M+1); (column; X-Select CSH C-18 (50×3.0 mm, 3.5 μm); RT 3.46 min. 0.05% aq TFA: ACN; 0.80 mL/min); TLC: 5% MeOH/CH₂Cl₂ (R$_f$: 0.4).

Synthesis of 5-methoxy-6-(4-(trifluoromethyl)-1H-imidazol-1-yl) pyridin-3-amine

To a stirred solution of 3-methoxy-5-nitro-2-(4-(trifluoromethyl)-1H-imidazol-1-yl) pyridine (1.4 g, 4.86 mmol) in MeOH (20 mL) under an argon atmosphere was added 10% Pd/C (300 mg) at room temperature. The suspension was stirred under a H₂ atmosphere (balloon pressure) for 16 h. After consumption of the starting material (monitored by TLC), the reaction was filtered through celite. The filtrate was concentrated in vacuo. The residue was washed with ether (2×30 mL) and dried in vacuo to obtain 5-methoxy-6-(4-(trifluoromethyl)-1H-imidazol-1-yl) pyridin-3-amine (1.1 g, 88%) as an off white solid used in the next step without further purification. ¹H-NMR (DMSO-d₆, 400 MHz): δ 8.13 (s, 1H), 8.07 (s, 1H), 7.41 (s, 1H), 6.81 (s, 1H), 5.70 (s, 2H), 3.80 (s, 3H); LCMS: 258.9 (M+1); (column; X-Bridge C-18 (50×3.0 mm, 3.5 μm); RT 2.76 min. 0.05% Aq TFA: ACN; 0.80 mL/min) TLC: 5% MeOH/CH₂Cl₂ (R$_f$: 0.4).

Example 127

Synthesis of 1-(5-amino-3-methoxypyridin-2-yl)-1H-imidazole-4-carbonitrile

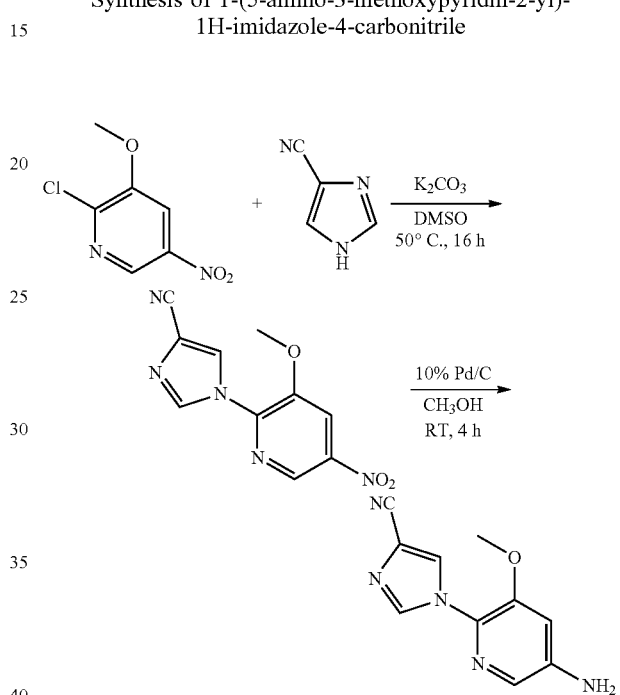

Synthesis of 1-(3-methoxy-5-nitropyridin-2-yl)-1H-imidazole-4-carbonitrile

To a stirred solution of 2-chloro-3-methoxy-5-nitropyridine (1.5 g, 79.78 mmol) in DMSO (15 mL) under an argon atmosphere were added potassium carbonate (4.4 g, 31.91 mmol) and 1H-imidazole-4-carbonitrile (890 mg, 9.57 mmol) at room temperature. The reaction mixture was stirred at 50° C. for 16 h. After consumption of the starting material (monitored by TLC), the reaction mixture was diluted with water (20 mL). The obtained solid was filtered and dried in vacuo to obtain 1-(3-methoxy-5-nitropyridin-2-yl)-1H-imidazole-4-carbonitrile (1.1 g, 56%) as a yellow solid. ¹H-NMR (DMSO-d₆, 400 MHz): δ 8.97 (s, 1H), 8.86 (s, 1H), 8.67 (s, 1H), 8.47 (s, 1H), 4.11 (s, 3H); LCMS: 245.8 (M+1); (column; X-Select CSH C-18 (50×3.0 mm, 3.5 μm); RT 2.96 min. 0.05% aq TFA: ACN; 0.80 mL/min); TLC: 40% EtOAc:hexane (R$_f$: 0.4).

Synthesis of 1-(5-amino-3-methoxypyridin-2-yl)-1H-imidazole-4-carbonitrile

To a stirred solution of 1-(3-methoxy-5-nitropyridin-2-yl)-1H-imidazole-4-carbonitrile (1.1 g, 4.48 mmol) in MeOH (12 mL) under an argon atmosphere was added 10%

Pd/C (300 mg) at room temperature. The suspension was stirred under a $H_2$ atmosphere (balloon pressure) for 4 h. After consumption of the starting material (monitored by TLC), the reaction was filtered through celite. The filtrate was concentrated in vacuo. The crude material was purified by column chromatography using 3% MeOH: $CH_2Cl_2$ to afford 1-(5-amino-3-methoxypyridin-2-yl)-1H-imidazole-4-carbonitrile (700 mg, 72%) as a pale yellow solid. $^1$H-NMR (DMSO-$d_6$, 400 MHz): δ 8.44 (s, 1H), 8.21 (s, 1H), 7.43 (s, 1H), 6.83 (s, 1H), 5.75 (s, 2H), 3.81 (s, 3H); UPLC (column; Acquity BEH C18 50×2.1 mm, 1.7 µm); RT 1.39 min. ACN: 0.025% TFA (Aq); 0.50 mL/min; TLC: 5% MeOH/$CH_2Cl_2$ ($R_f$: 0.4).

Example 128

Synthesis of 4-(4-methyl-1H-imidazol-1-yl)-3-(trifluoromethoxy) aniline

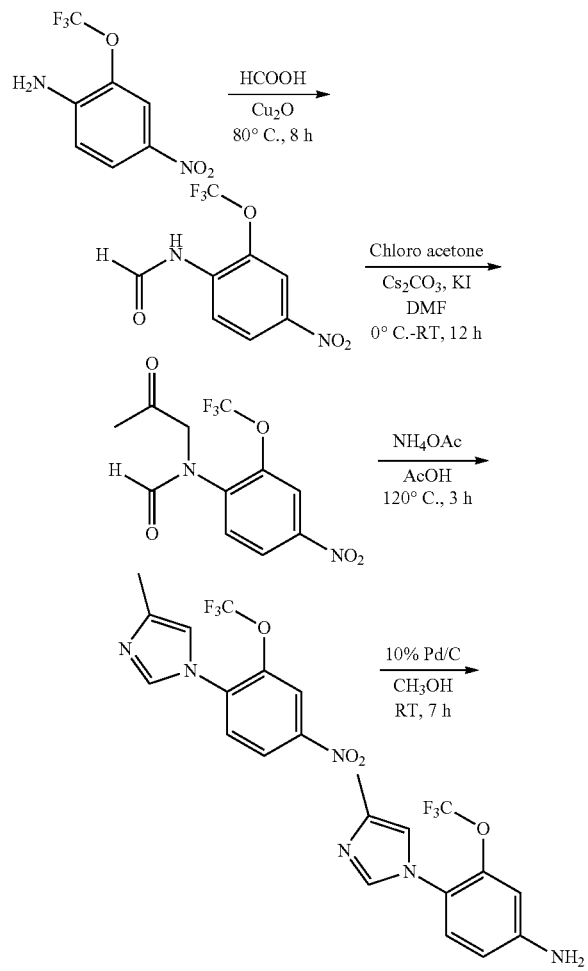

Synthesis of N-(4-nitro-2-(trifluoromethoxy) phenyl) formamide

To a stirred solution of 4-nitro-2-(trifluoromethoxy) aniline (5 g, 22.52 mmol) in formic acid (25 mL) under an argon atmosphere was added copper oxide (1.61 g, 11.26 mmol) at room temperature. The reaction mixture was stirred at 80° C. for 8 h. After consumption of the starting material (monitored by TLC), the reaction mixture was diluted with water (20 mL), neutralized with a sodium bicarbonate solution (20 mL) and extracted with EtOAc (2×20 mL). The combined organic extracts were dried over sodium sulfate, filtered and concentrated in vacuo to obtain N-(4-nitro-2-(trifluoromethoxy) phenyl) formamide (5 g, 89%) as a yellow solid used in the next step without further purification. $^1$H-NMR (DMSO-$d_6$, 400 MHz): δ 10.60 (s, 1H), 9.20 (s, 1H), 8.44 (s, 1H), 8.05 (d, 1H), 7.71 (d, 1H); TLC: 30% EtOAc:hexane ($R_f$: 0.5).

Synthesis of N-(4-nitro-2-(trifluoromethoxy) phenyl)-N-(2-oxopropyl) formamide

To a stirred solution of N-(4-nitro-2-(trifluoromethoxy) phenyl) formamide (5 g, 20.00 mmol) in DMF (30 mL) under an argon atmosphere was added cesium carbonate (12.71 g, 39.00 mmol) and potassium iodide (398 mg, 2.40 mmol) at 0° C. The reaction mixture was stirred for 20 min at 0° C. and chloroacetone (3.7 g, 40.00 mmol) was added to the reaction mixture at 0° C. The reaction mixture was stirred for 12 h at room temperature. After consumption of the starting material (monitored by TLC), the reaction mixture was diluted with water (100 mL) and extracted with EtOAc (2×200 mL). The combined organic extracts were dried over sodium sulfate, filtered and concentrated in vacuo. The crude material was purified by column chromatography using 20% EtOAc:hexane to afford N-(4-nitro-2-(trifluoromethoxy) phenyl)-N-(2-oxopropyl) formamide (4 g, 65%) as a pale yellow solid. LCMS: 307.2 (M+1); (column; X-Select CSH C-18 (50×3.0 mm, 3.5 µm); RT 3.66 min. 0.05% aq TFA: ACN; 0.80 mL/min); TLC: 30% EtOAc:hexane ($R_f$: 0.5).

Synthesis of 4-methyl-1-(4-nitro-2-(trifluoromethoxy) phenyl)-1H-imidazole

To a stirred solution of N-(4-nitro-2-(trifluoromethoxy) phenyl)-N-(2-oxopropyl) formamide (4 g, 13.07 mmol) in acetic acid (30 mL) under an argon atmosphere was added ammonium acetate (5 g, 65.35 mmol) at room temperature. The reaction mixture was stirred at 120° C. for 3 h. After consumption of the starting material (monitored by TLC), the reaction mixture was diluted with a sodium bicarbonate solution (100 mL) and extracted with EtOAc (2×200 mL). The combined organic extracts were dried over sodium sulfate, filtered and concentrated in vacuo. The crude material was purified by column chromatography using 30% EtOAc:hexane to afford 4-methyl-1-(4-nitro-2-(trifluoromethoxy) phenyl)-1H-imidazole (1.8 g, 49%) as a pale yellow solid. $^1$H-NMR (DMSO-$d_6$, 400 MHz): δ 8.45 (s, 1H), 8.38 (d, 1H), 7.96 (s, 1H), 7.90 (d, 1H), 7.30 (s, 1H), 2.19 (s, 3H); LCMS: 288.1 (M+1); (column; X-Select CSH C-18 (50×3.0 mm, 3.5 µm); RT 3.81 min. 5 mM Aq $NH_4OAc$: ACN; 0.80 mL/min); TLC: 40% EtOAc:hexane ($R_f$: 0.2).

Synthesis of 4-(4-methyl-1H-imidazol-1-yl)-3-(trifluoromethoxy) aniline

To a stirred solution of 4-methyl-1-(4-nitro-2-(trifluoromethoxy) phenyl)-1H-imidazole (1.8 g, 6.27 mmol) in MeOH (30 mL) under an argon atmosphere was added 10% Pd/C (450 mg) at room temperature. The suspension was stirred under a $H_2$ atmosphere (balloon pressure) for 7 h. After consumption of the starting material (monitored by TLC), the reaction was filtered through celite. The filtrate was concentrated in vacuo. The crude material was washed with 20% ether: pentane to afford 4-(4-methyl-1H-imidazol-1-yl)-3-(trifluoromethoxy) aniline (1.1 g, 71%) as a pale yellow solid. $^1$H-NMR (CD$_3$OD, 500 MHz): δ 7.78 (s, 1H), 7.19 (d, 1H), 7.03 (s, 1H), 6.73-6.70 (m, 2H), 2.15 (s, 3H); LCMS: 258 (M+1); (column; X-Select CSH C-18 (50×3.0 mm, 3.5 μm); RT 2.45 min. 0.05% aq TFA: ACN; 0.80 mL/min); UPLC (column; Acquity BEH C18 50×2.1 mm, 1.7 μm); RT 1.46 min. ACN: 0.025% TFA (Aq); 0.50 mL/min; TLC: 5% MeOH/CH$_2$Cl$_2$ (R$_f$: 0.2).

Example 129

Synthesis of 4-methoxy-5-(4-methyl-1H-imidazol-1-yl) pyridin-2-amine

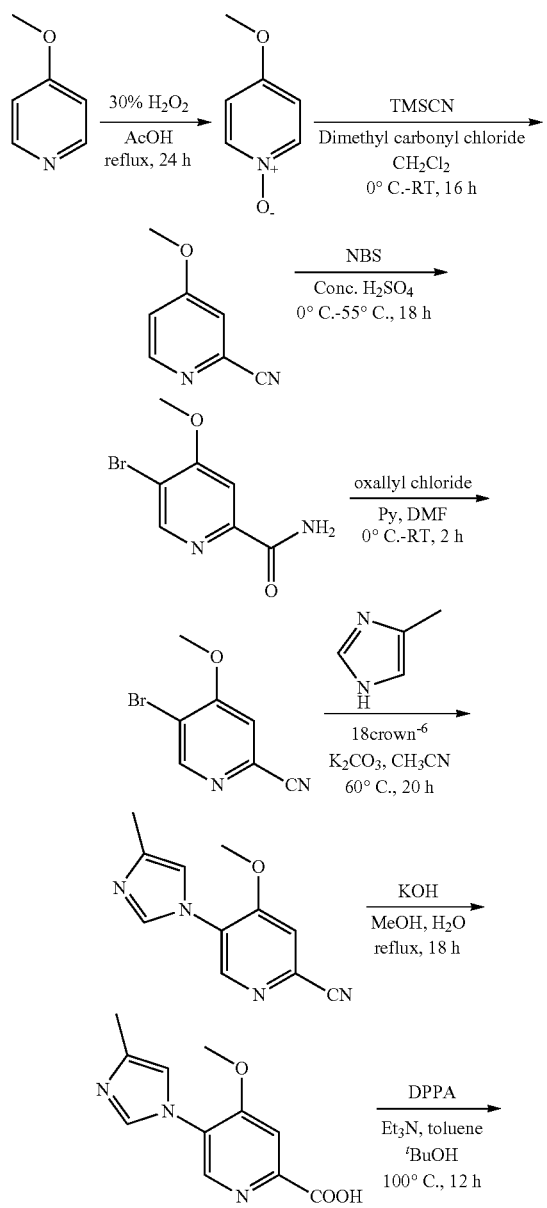

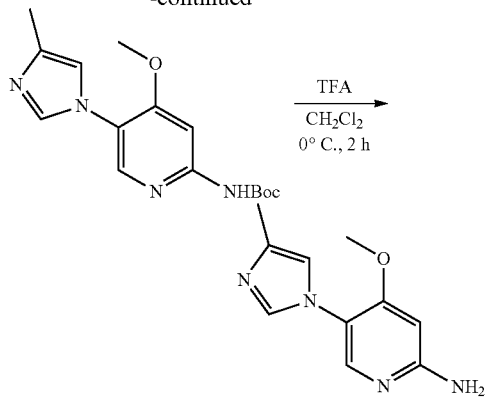

Synthesis of 4-methoxypyridine 1-oxide

To a stirred solution of 4-methoxypyridine (5 g, 45.87 mmol) in acetic acid (25 mL) under an argon atmosphere was added a 30% hydrogen peroxide solution (4.2 mL) at room temperature. The reaction mixture was stirred at reflux for 24 h. After consumption of the starting material (monitored by TLC), the volatile components were evaporated in vacuo to afford 4-methoxypyridine 1-oxide (5 g, 88%) as a yellow liquid. LCMS: 125.9 (M+1); (column; Eclipse XDB C-18 (150×4.6 mm, 5.0 μm); RT 5.02 min. 0.05% Aq TFA: ACN; 1.0 mL/min); TLC: 5% MeOH: CH$_2$Cl$_2$ (R$_f$: 0.1).

Synthesis of 4-methoxypicolinonitrile

To a stirred solution of 4-methoxypyridine 1-oxide (5 g, 40.00 mmol) in CH$_2$Cl$_2$ (75 mL) were added TMSCN (6.66 mL) and dimethyl carbonyl chloride (3.75 mL) at 0° C. under an argon atmosphere. The reaction mixture was warmed to room temperature and stirred for 16 h. After consumption of the starting material (monitored by TLC), the reaction mixture was diluted with a 10% potassium carbonate solution (200 mL) and extracted with CH$_2$Cl$_2$ (3×100 mL). The combined organic extracts were dried over sodium sulfate, filtered and concentrated in vacuo. The crude material was purified by column chromatography using 25% EtOAc:hexanes to afford 4-methoxypicolinonitrile (4 g, 75%) as a white solid. $^1$H-NMR (CDCl$_3$, 500 MHz): δ 8.50 (d, 1H), 7.20 (s, 1H), 7.00-6.99 (m, 1H), 3.89 (s, 3H); LCMS: 135 (M+1); (column; X-bridge C-18 (50× 3.0 mm, 3.5 μm); RT 2.19 min. 0.05% Aq TFA: ACN; 0.8 mL/min); TLC: 50% EtOAc:hexanes (R$_f$: 0.6).

Synthesis of 5-bromo-4-methoxypicolinamide

To a stirred solution of 4-methoxypicolinonitrile (4 g, 30.00 mmol) in concentrated sulfuric acid (15 mL) under an argon atmosphere was added N-bromosuccinimide (6.95 g, 39.00 mmol) at 0° C. The reaction mixture was stirred at 55° C. for 18 h. After consumption of the starting material (monitored by TLC), the reaction mixture was basified with a 8 N sodium hydroxide solution to pH 8 at 0° C. The obtained solid was filtered and dried in vacuo to afford 5-bromo-4-methoxypicolinamide (3 g, 43%) as a white solid. $^1$H-NMR (DMSO-d$_6$, 500 MHz): δ 8.62 (s, 1H), 8.13-8.10 (m, 2H), 7.70 (s, 1H), 4.01 (s, 3H); LCMS: 232.9 (M+2); (column; X-Bridge C-18 (50×3.0 mm, 3.5 μm); RT 2.60 min 0.05% Aq TFA: ACN; 0.8 mL/min); TLC: 80% EtOAc:hexanes (R$_f$: 0.6).

Synthesis of 5-bromo-4-methoxypicolinonitrile

To a stirred solution of oxalyl chloride (3.3 mL) in DMF (40 mL) under an argon atmosphere was added pyridine (5.3 mL) drop wise at 0° C. After stirring for 10 min, 5-bromo-4-methoxypicolinamide (3 g, 12.98 mmol) was added at 0° C. The reaction mixture was warmed to room temperature and stirred for 2 h. After consumption of the starting material (monitored by TLC), the reaction mixture was diluted with water (50 mL) and extracted with EtOAc (2×50 mL). The combined organic extracts were dried over sodium sulfate, filtered and concentrated in vacuo. The crude material was purified by column chromatography using 10% EtOAc: hexanes to afford 5-bromo-4-methoxypicolinonitrile (2 g, 72%) as an off-white solid. $^1$H-NMR (CDCl$_3$, 400 MHz): δ 8.61 (s, 1H), 7.19 (s, 1H), 4.00 (s, 3H); LCMS: 212.8 (M+1); (column; X-Bridge C-18 (50×3.0 mm, 3.5 μm); RT 3.07 min. 0.05% Aq TFA: ACN; 0.8 mL/min); TLC: 80% EtOAc: hexanes (R$_f$: 0.7).

Synthesis of 4-methoxy-5-(4-methyl-1H-imidazol-1-yl) picolinonitrile

To a stirred solution of 4-methyl-1H-imidazole (580 mg, 7.04 mmol) in acetonitrile (24 mL) under an argon atmosphere were added potassium carbonate (1.3 g, 9.38 mmol) and 18-crown-6 (2.47 g, 9.38 mmol) at room temperature. The reaction mixture was stirred at 60° C. for 2 h. Then 5-bromo-4-methoxypicolinonitrile (1 g, 4.69 mmol) was added to the reaction mixture at room temperature. The reaction mixture was stirred at reflux for 18 h. After consumption of the starting material (monitored by TLC), the reaction mixture was diluted with water (20 mL) and extracted with EtOAc (2×30 mL). The combined organic extracts were dried over sodium sulfate, filtered and concentrated in vacuo. The crude material was purified by column chromatography using 90% EtOAc:hexanes to afford 4-methoxy-5-(4-methyl-1H-imidazol-1-yl) picolinonitrile (250 mg, 25%) as a yellow solid. $^1$H-NMR (CDCl$_3$, 500 MHz): δ 8.58 (s, 1H), 7.82 (s, 1H), 7.39 (s, 1H), 6.99 (s, 1H), 401 (s, 3H), 2.23 (s, 3H); LCMS: 215 (M+1); (column; X-Bridge C-18 (50×3.0 mm, 3.5 μm); RT 2.45 min. 0.05% Aq TFA: ACN; 0.8 mL/min); TLC: EtOAc (R$_f$: 0.2).

Synthesis of 4-methoxy-5-(4-methyl-1H-imidazol-1-yl) picolinic acid

To a stirred solution of 4-methoxy-5-(4-methyl-1H-imidazol-1-yl) picolinonitrile (2 g, 9.34 mmol) in MeOH: CH$_3$CN (1:1, 40 mL) under an argon atmosphere was added potassium hydroxide (1.05 g, 18.69 mmol) at room temperature. The reaction mixture was stirred under reflux conditions for 18 h. After consumption of the starting material (monitored by TLC), the volatile components were evaporated in vacuo. The residue was acidified with concentrated hydrochloric acid (20 mL) to pH 5-6. The obtained solid was filtered and dried in vacuo to afford 4-methoxy-5-(4-methyl-1H-imidazol-1-yl) picolinic acid (1 g, 50%) as an off-white solid. $^1$H-NMR (DMSO-d$_6$, 500 MHz): δ 8.73-8.70 (m, 2H), 7.83 (s, 1H), 2.58 (s, 1H), 4.00 (s, 3H), 2.25 (s, 3H); LCMS: 234 (M+1); (column; Eclipse XDB C-18 (150×4.6 mm, 5.0μ); RT 3.84 min. 0.05% Aq TFA: ACN; 1.0 mL/min); TLC: 5% MeOH: CH$_2$Cl$_2$ (R$_f$: 0.1).

Synthesis of tert-butyl (4-methoxy-5-(4-methyl-M-imidazol-1-yl) pyridin-2-yl) carbamate To a stirred solution of 4-methoxy-5-(4-methyl-1H-imidazol-1-yl) picolinic acid (1 g, 4.29 mmol) in toluene: $^t$BuOH (1:1, 13 mL) under an argon atmosphere were added triethylamine (1.5 mL, 10.72 mmol) and diphenylphosphorylazide (1.85 mL, 8.58 mmol) at 0° C. The reaction mixture was stirred for 15 min, then stirred at 65° C. for 2 h. The temperature was raised to 100° C. for 12 h. After consumption of the starting material (monitored by TLC), the volatile components were evaporated in vacuo. The residue was diluted with water (60 mL) and extracted with EtOAc (2×50 mL). The combined organic extracts were dried over sodium sulfate, filtered and concentrated in vacuo. The crude was purified by column chromatography using 3% MeOH: CH$_2$Cl$_2$ to afford tert-butyl (4-methoxy-5-(4-methyl-1H-imidazol-1-yl) pyridin-2-yl) carbamate (350 mg, 27%) as an off white-solid. $^1$H-NMR (CDCl$_3$, 400 MHz): δ 8.07 (s, 1H), 7.94-7.90 (m, 1H), 7.78 (s, 1H), 7.57 (s, 1H), 6.83 (s, 1H), 4.96 (s, 3H), 2.30 (s, 3H), 1.52 (s, 9H); LCMS: 305.1 (M+1); (column; Eclipse XDB C-18 (150×4.6 mm, 5.0 μm); RT 6.72 min. 0.05% Aq TFA: ACN; 1.0 mL/min); TLC: 5% MeOH: CH$_2$Cl$_2$ (R$_f$: 0.5).

Synthesis of 4-methoxy-5-(4-methyl-1H-imidazol-1-yl) pyridin-2-amine

To a stirred solution of tert-butyl (4-methoxy-5-(4-methyl-1H-imidazol-1-yl) pyridin-2-yl) carbamate (350 mg, 1.15 mmol) in CH$_2$Cl$_2$ (5 mL) under an argon atmosphere was added trifluoroacetic acid (0.3 mL) at 0° C. The reaction mixture was stirred for 2 h at 0° C. After consumption of the starting material (monitored by TLC), the reaction mixture was basified with a sodium bicarbonate solution (30 mL) and extracted with MeOH: CH$_2$Cl$_2$ (2×100 mL). The combined organic extracts were dried over sodium sulfate, filtered and concentrated in vacuo. The crude material was washed with hexane (2×10 mL) to afford 4-methoxy-5-(4-methyl-1H-imidazol-1-yl) pyridin-2-amine (200 mg, 85%) as an off white-solid. $^1$H-NMR (DMSO-d$_6$, 400 MHz): δ 7.72 (s, 1H), 7.50 (s, 1H), 7.89 (s, 1H), 6.10 (d, 3H), 3.73 (s, 3H), 2.10 (s, 3H); LCMS: 205.1 (M+1); (column; X-Bridge C-18 (50×3.0 mm, 3.5 μm); RT 1.99 min. 5 mM NH$_4$OAc: ACN; 0.8 mL/min); TLC: 5% MeOH: CH$_2$Cl$_2$ (R$_f$: 0.5).

Example 130

Synthesis of 5-chloro-6-(4-methyl-1H-imidazol-1-yl) pyridin-3-amine

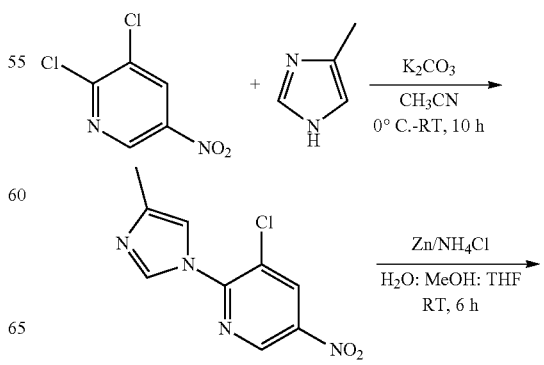

Synthesis of 3-chloro-2-(4-methyl-1H-imidazol-1-yl)-5-nitropyridine

To a stirred solution of 2,3-dichloro-5-nitropyridine (2 g, 10.36 mmol) in CH₃CN (30 mL) under an argon atmosphere was added potassium carbonate (2.86 g, 20.72 mmol) and 4-methyl imidazole (1.7 g, 20.72 mmol) at room temperature. The reaction mixture was stirred at room temperature for 10 h. After consumption of the starting material (monitored by TLC), the reaction was quenched with cold water (500 mL) and extracted with EtOAc (2×300 mL). The combined organic extracts were dried over sodium sulfate, filtered and concentrated in vacuo. The crude material was purified by column chromatography using 30% EtOAc: hexanes to afford 3-chloro-2-(4-methyl-1H-imidazol-1-yl)-5-nitropyridine (1.8 g, 73%) as an off-white solid. ¹H-NMR (CDCl₃, 400 MHz): δ 9.20 (s, 1H), 8.69 (s, 1H), 8.39 (s, 1H), 7.51 (s, 1H), 2.30 (s, 3H); LCMS: 238.8 (M+1); (column; X-Select CSH C-18 (50×3.0 mm, 3.5 μm); RT 1.03 min 0.05% Aq TFA: ACN; 0.80 mL/min).

Synthesis of 5-chloro-6-(4-methyl-1H-imidazol-1-yl) pyridin-3-amine

To a stirred solution of 3-chloro-2-(4-methyl-1H-imidazol-1-yl)-5-nitropyridine (1.8 g, 7.56 mmol) in THF (29 mL) under an argon atmosphere were added ammonium chloride (820 mg, 15.12 mmol) in water:MeOH (1:1, 72 mL) and zinc powder (1 g, 15.12 mmol) at room temperature. The reaction mixture was stirred for 6 h at room temperature. After consumption of the starting material (monitored by TLC), the reaction was filtered. The filtrate was concentrated in vacuo and the obtained solid filtered and dried in vacuo to afford 5-chloro-6-(4-methyl-1H-imidazol-1-yl) pyridin-3-amine (1.25 g, 80%) as an off-white solid.

¹H-NMR (DMSO-d₆, 400 MHz): δ 7.99 (s, 1H), 7.79 (s, 1H), 7.30 (s, 1H), 7.18 (s, 1H), 5.99 (s, 2H), 2.20 (s, 3H); LCMS: 209.1 (M+1); (column; X-Select CSH C-18 (50×3.0 mm, 3.5 μm); RT 2.75 min 5 mM NH₄OAc in water: ACN; 0.80 mL/min); TLC: 5% MeOH/CH₂Cl₂ (R_f: 0.4).

Example 131

Synthesis of 5-methoxy-6-(1-methyl-1H-pyrazol-4-yl) pyridin-3-amine

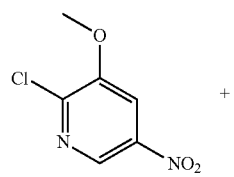 +

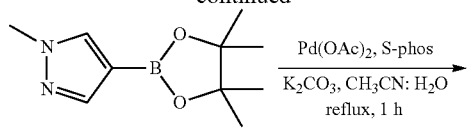

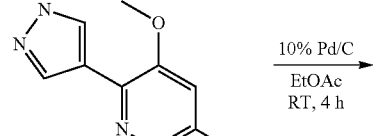

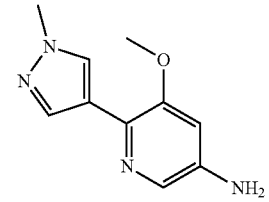

Synthesis of 3-methoxy-2-(1-methyl-1H-pyrazol-4-yl)-5-nitropyridine

A stirred solution of Pd(OAc)₂ (89 mg, 0.13 mmol) and S-phos (273 mg, 0.66 mmol) in CH₃CN: H₂O (2:1, 60 mL) was purged under an argon atmosphere for 15 min. Then 2-chloro-3-methoxy-5-nitropyridine (2.5 g, 13.29 mmol), 1-methyl-4-(4,4,5,5-tetramethyl-1,3,2-dioxaborolan-2-yl)-1H-pyrazole (3.6 g, 17.30 mmol) and potassium carbonate (3.67 g, 26.59 mmol) was added at room temperature. The reaction mixture and stirred at reflux for 1 h. After consumption of the starting material (monitored by TLC), the reaction mixture was diluted with water (100 mL) and extracted with EtOAc (2×100 mL). The combined organic extracts were washed with brine (50 mL), dried over sodium sulfate, filtered and concentrated in vacuo. The crude material was purified by column chromatography using 30-80% EtOAc:hexanes to afford 3-methoxy-2-(1-methyl-1H-pyrazol-4-yl)-5-nitropyridine (2.6 g, 84%) as a yellow solid. ¹H-NMR (DMSO-d₆, 400 MHz): δ 8.95 (d, 1H), 8.50 (s, 1H), 8.16 (s, 1H), 8.10 (s, 1H), 4.10 (s, 3H), 3.93 (s, 3H); LCMS: 234.9 (M+1); (column; X-Select CSH C-18 (50×3.0 mm, 3.5 μm); RT 2.94 min 0.05% Aq TFA: ACN; 0.80 mL/min); UPLC (column; Acquity BEH C-18 2.1×50 mm, 1.7 μm); RT 1.87 min. ACN: 0.025% Aq TFA; 0.5 mL/min; TLC: 50% EtOAc:hexane (R_f: 0.3).

Synthesis of 5-methoxy-6-(1-methyl-1H-pyrazol-4-yl)pyridin-3-amine

To a stirred solution of 3-methoxy-2-(1-methyl-1H-pyrazol-4-yl)-5-nitropyridine (2.5 g, 10.68 mmol) in EtOAc (50 mL) under an argon atmosphere was added 10% Pd/C (1.2 g) at room temperature. The suspension placed under an H₂ atmosphere (balloon pressure) and stirred for 4 h at room temperature. After consumption of the starting material (monitored by TLC), the reaction mixture was filtered and washed with EtOAc (50 mL) and 5% MeOH: CH₂Cl₂ (50 mL). The filtrate was concentrated in vacuo and the crude material was washed with n-pentane (2×20 mL) to afford 5-methoxy-6-(1-methyl-1H-pyrazol-4-yl) pyridin-3-amine (2 g, 92%) as a brown solid. ¹H-NMR (DMSO-d₆, 400 MHz): δ 7.96 (s, 1H), 7.80 (s, 1H), 7.51 (s, 1H), 6.62 (s, 1H), 5.27 (s, 2H), 3.81 (s, 3H), 3.80 (s, 3H); LC-MS: 205 (M+1);

(column; X-Select CSH C-18 (50×3.0 mm, 3.5 µm); RT 1.01 min 0.05% Aq TFA: ACN; 0.80 mL/min); HPLC (column; Acquity UPLC HSS T3 (100×2.1 mm, 1.8µ); RT 2.95 min. ACN: 0.025% Aq TFA; 0.5 mL/min; TLC: 5% MeOH/ $CH_2Cl_2$ ($R_f$: 0.3).

Example 132

Synthesis of
3-methoxy-4-(1-methyl-1H-pyrazol-4-yl) aniline

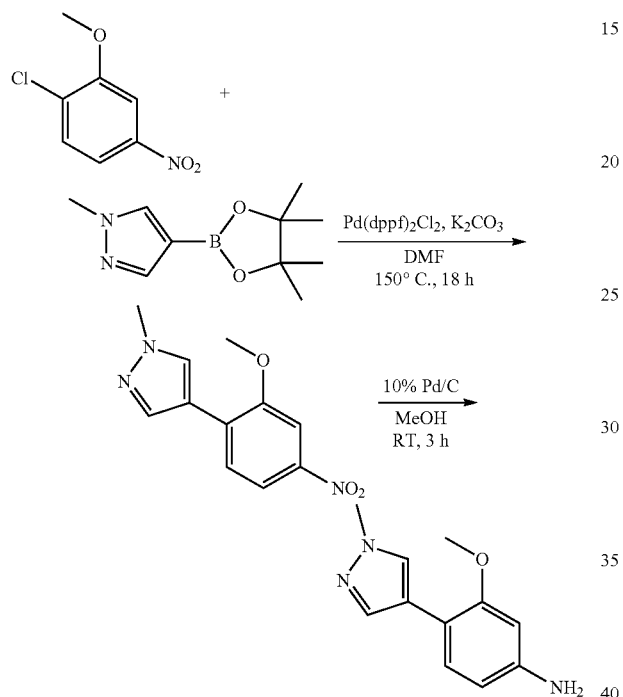

Synthesis of
4-(2-methoxy-4-nitrophenyl)-1-methyl-1H-pyrazole

To a stirred solution of 1-chloro-2-methoxy-4-nitrobenzene (2.4 g, 13.27 mmol) in DMF (24 mL) under an argon atmosphere were added 1-methyl-4-(4, 4, 5, 5-tetramethyl-1, 3, 2-dioxaborolan-2-yl)-1H-pyrazole (3.6 g, 17.25 mmol) and potassium carbonate (2.56 g, 18.57 mmol) at room temperature. The suspension was purged with argon for 30 min. Then $Pd(dppf)_2Cl_2$ (970 mg, 1.32 mmol) was added to the reaction mixture and stirred at 150° C. for 18 h. After consumption of the starting material (monitored by TLC), the reaction mixture was diluted with water (100 mL) and extracted with EtOAc (2×100 mL). The combined organic extracts were dried over sodium sulfate, filtered and concentrated in vacuo. The crude material was purified by column chromatography using 20% EtOAc:hexanes to afford 4-(2-methoxy-4-nitrophenyl)-1-methyl-1H-pyrazole (1.8 g, 58%) as a brown solid. $^1$H-NMR (DMSO-$d_6$, 400 MHz): δ 8.34 (s, 1H), 8.08 (s, 1H), 7.89-7.82 (m, 3H), 4.02 (s, 3H), 3.90 (s, 3H); LC-MS: 233.8 (M+1); (column; X-Select CSH C-18 (50×3.0 mm, 3.5 µm); RT 3.24 min 0.05% Aq TFA: ACN; 0.80 mL/min); TLC: 20% EtOAc: hexane ($R_f$: 0.3).

Synthesis of
3-methoxy-4-(1-methyl-1H-pyrazol-4-yl) aniline

To a stirred solution of 4-(2-methoxy-4-nitrophenyl)-1-methyl-1H-pyrazole (1.7 g, 7.28 mmol) in methanol (20 mL) under an argon atmosphere was added 10% Pd/C (200 mg) at room temperature. The suspension was stirred under a $H_2$ atmosphere (balloon pressure) for 3 h. After consumption of the starting material (monitored by TLC), the volatile components were concentrated in vacuo. The crude material was purified by column chromatography using 20% EtOAc: hexanes to afford 3-methoxy-4-(1-methyl-1H-pyrazol-4-yl) aniline (1.1 g, 70%) as a brown solid. $^1$H-NMR (DMSO-$d_6$, 500 MHz): δ 7.81 (s, 1H), 7.63 (s, 1H), 7.18 (d, 1H), 6.25 (s, 1H), 6.15 (d, 1H), 5.02 (s, 2H), 3.80 (s, 3H), 3.78 (s, 3H); LC-MS: 203.8 (M+1); (column; X-Select CSH C-18 (50× 3.0 mm, 3.5 µm); RT 1.00 min 0.05% Aq TFA: ACN; 0.80 mL/min); TLC: 30% EtOAc:hexane ($R_f$: 0.2).

Example 133

Synthesis of 3-methoxy-4-(3-methyl-1H-1, 2, 4-triazol-1-yl) aniline

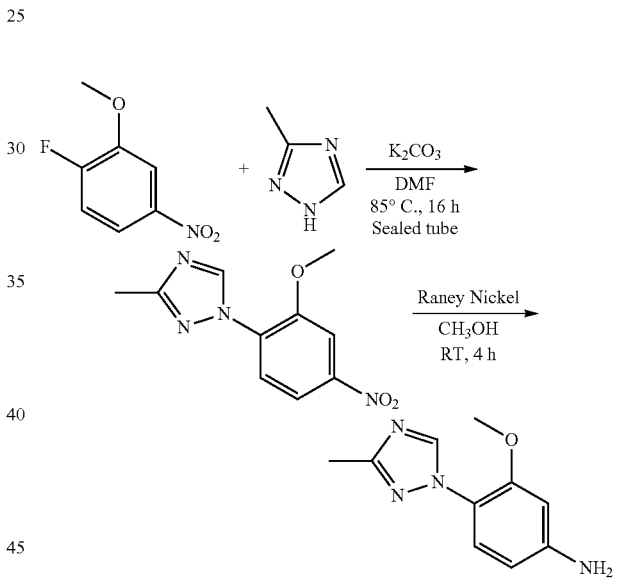

Synthesis of 1-fluoro-2-methoxy-4-nitrobenzene

To a stirred solution of 1-fluoro-2-methoxy-4-nitrobenzene (2.5 g, 14.60 mmol) in DMF (25 mL) under an argon atmosphere were added potassium carbonate (4 g, 29.20 mmol) and 3-methyl-1H-1, 2, 4-triazole (1.2 g, 14.60 mmol) at room temperature. The reaction mixture was stirred at 85° C. for 16 h in a sealed tube. After consumption of the starting material (monitored by TLC), the reaction mixture was diluted with water (100 mL) and extracted with EtOAc (2×50 mL). The combined organic extracts were dried over sodium sulfate, filtered and concentrated in vacuo. The crude material was purified by column chromatography using 15-25% EtOAc:hexane to afford 1-fluoro-2-methoxy-4-nitrobenzene (1.2 g, 35%) as an off-white solid. $^1$H-NMR (CDCl$_3$, 400 MHz): δ 8.87 (s, 1H), 8.10 (d, 1H), 8.00-7.97 (m, 2H), 4.10 (s, 3H), 2.50 (s, 3H); LCMS: 234.9 (M+1); (column; Ascentis Express C-18 (50×3.0 mm, 2.7 µm); RT 2.02 min. 0.025% Aq TFA+5% ACN: ACN+5% 0.025% Aq TFA; 1.2 mL/min); TLC: 30% EtOAc:hexane ($R_f$: 0.2).

Synthesis of 3-methoxy-4-(3-methyl-1H-1, 2, 4-triazol-1-yl) aniline

To a stirred solution of 1-fluoro-2-methoxy-4-nitrobenzene (100 mg, 0.42 mmol) in MeOH (3 mL) under an argon atmosphere was added Raney nickel (50 mg) at room temperature. The suspension was stirred under an $H_2$ atmosphere (balloon pressure) for 4 h. After consumption of the starting material (monitored by TLC), the reaction was filtered through celite. The filtrate was concentrated in vacuo to afford 3-methoxy-4-(3-methyl-1H-1, 2, 4-triazol-1-yl) aniline (70 mg, 55%) as an off white solid. $^1$H-NMR (DMSO-$d_6$, 400 MHz): δ 8.43 (s, 1H), 7.10 (d, 1H), 6.35 (s, 1H), 6.20 (dd, 1H), 5.44 (s, 2H), 3.70 (s, 3H), 2.25 (s, 3H); LCMS: 204.9 (M+1); (column; Ascentis Express C-18 (50× 3.0 mm, 2.7 μm); RT 0.62 min. 0.025% Aq TFA+5% ACN: ACN+5% 0.025% Aq TFA; 1.2 mL/min); TLC: 50% EtOAc:hexane ($R_f$: 0.1).

Example 134

Synthesis of 3-fluoro-6-methoxy-5-(1-methyl-1H-pyrazol-4-yl) pyridin-2-amine

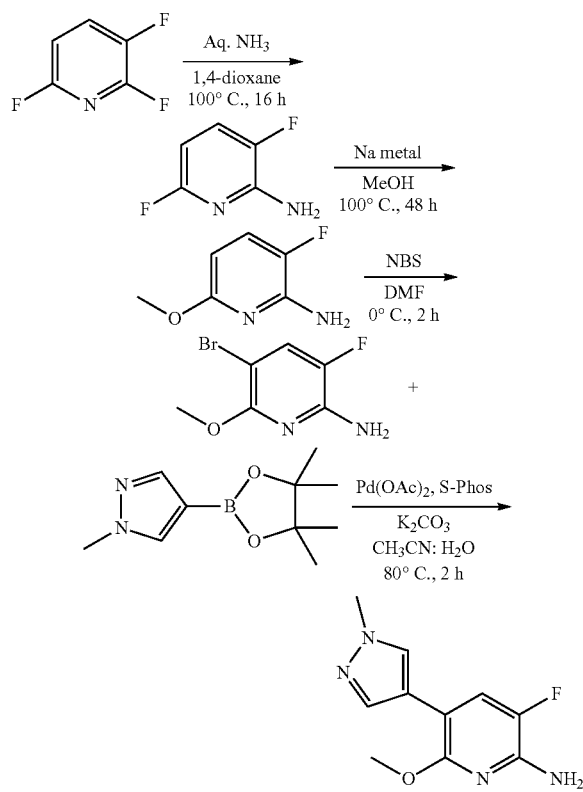

Synthesis of 3, 6-difluoropyridin-2-amine

To a stirred solution of 2,3,6-trifluoropyridine (5 g, 37.59 mmol) in 1, 4-dioxane (20 mL) under an argon atmosphere was added aq ammonia (20 mL) at room temperature. The reaction mixture was stirred at 100° C. for 16 h. After consumption of the starting material (monitored by TLC), the reaction was quenched with cold water (500 mL) and extracted with $CH_2Cl_2$ (2×500 mL). The combined organic extracts were dried over sodium sulfate, filtered and concentrated in vacuo to obtain 3,6-difluoropyridin-2-amine (3 g, 62%) as an off-white solid used in the next step without further purification. TLC: 10% EtOAc:hexanes ($R_f$: 0.5).

Synthesis of 3-fluoro-6-methoxypyridin-2-amine

To a stirred solution of sodium metal (1.06 g, 46.15 mmol) in MeOH (60 mL) under an argon atmosphere was added 3, 6-difluoropyridin-2-amine (3 g, 23.07 mmol) at 0° C. The reaction mixture was stirred at 100° C. for 48 h sealed tube. After consumption of the starting material (monitored by TLC), the volatile components were evaporated in vacuo. The residue was diluted with water (100 mL) and extracted with $CH_2Cl_2$ (2×200 mL). The combined organic extracts were dried over sodium sulfate, filtered and concentrated in vacuo to obtain 3-fluoro-6-methoxypyridin-2-amine (2.5 g, 78%) as a colorless liquid. $^1$H-NMR (CDCl$_3$, 400 MHz): δ7.14 (t, 1H), 8.00 (d, 1H), 4.40 (br s, 2H), 3.80 (s, 3H); TLC: 10% EtOAc:hexanes ($R_f$: 0.5).

Synthesis of 5-bromo-3-fluoro-6-methoxypyridin-2-amine

To a stirred solution of 3-fluoro-6-methoxypyridin-2-amine (3 g, 21.12 mmol) in DMF (45 mL) under an argon atmosphere was added N-bromosuccinimide (3.78 g, 21.12 mmol) at 0° C. The reaction mixture was stirred at 0° C. for 2 h. After consumption of the starting material (monitored by TLC), the reaction was quenched with cold water (50 mL) and extracted with EtOAc (2×50 mL). The combined organic extracts were dried over sodium sulfate, filtered and concentrated in vacuo. The crude material was purified by column chromatography using 10% EtOAc:hexanes to afford 5-bromo-3-fluoro-6-methoxypyridin-2-amine (3.5 g, 76%) as an off-white solid. $^1$H-NMR (CDCl$_3$, 500 MHz): δ 7.41 (d, 1H), 4.44 (br s, 2H), 3.90 (s, 3H); TLC: 20% EtOAc:hexanes ($R_f$: 0.5).

Synthesis of 3-fluoro-6-methoxy-5-(1-methyl-M-pyrazol-4-yl) pyridin-2-amine

To a stirred solution of 5-bromo-3-fluoro-6-methoxypyridin-2-amine (3.5 g, 15.83 mmol) in CH$_3$CN: water (2:1, 52 mL) under an argon atmosphere were added potassium carbonate (4.37 g, 31.67 mmol), S-phos (973 mg, 23.70 mmol) and Pd(OAc)$_2$ (532 mg, 0.79 mmol). The mixture was degassed with argon for 30 min, then heated to 80° C. for 2 h. After consumption of the starting material (monitored by TLC), the reaction mixture was diluted with water (100 mL) and extracted with EtOAc (2×200 mL). The combined organic extracts were dried over sodium sulfate, filtered and concentrated in vacuo. The crude material was purified by column chromatography using 30% EtOAc: hexanes to afford 3-fluoro-6-methoxy-5-(1-methyl-1H-pyrazol-4-yl) pyridin-2-amine (2 g, 57%) as an off-white solid. $^1$H-NMR (DMSO-$d_6$, 400 MHz): δ 7.90 (s, 1H), 7.33 (s, 1H), 7.63 (d, 1H), 6.00 (s, 2H), 3.83 (s, 3H), 3.80 (s, 3H); TLC: 50% EtOAc:hexanes ($R_f$: 0.5).

Example 135

Synthesis of 6-amino-3-(4-methyl-1H-imidazol-1-yl) picolinonitrile

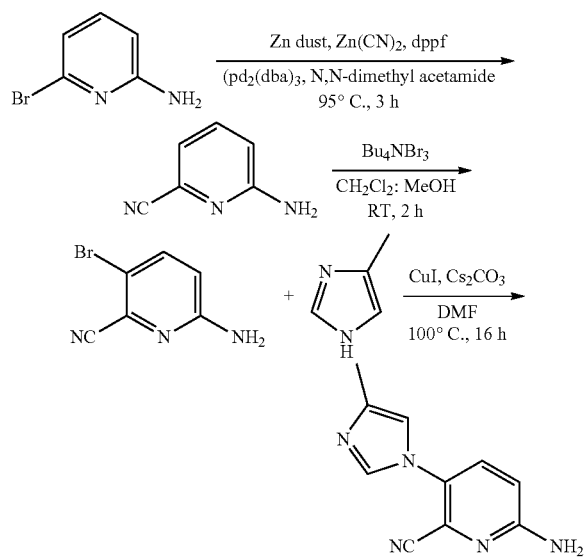

Synthesis 6-aminopicolinonitrile

To a stirred solution of 6-bromopyridin-2-amine (1 g, 5.78 mmol) in N, N-dimethyl acetamide (10 mL) were added zinc cyanide (441 mg, 3.75 mmol), zinc dust (94 mg, 1.44 mmol), dppf (128 mg, 0.23 mmol), and $Pd_2(dba)_3$ (105 mg, 0.11 mmol). The mixture was purged with argon for 15 min, then stirred at 95° C. for 3 h. After consumption of the starting material (monitored by TLC), the reaction was diluted with water (100 mL) and extracted with EtOAc (2×50 mL). The combined organic extracts were dried over sodium sulfate, filtered and concentrated in vacuo. The crude material was purified by column chromatography using 20% EtOAc: hexanes to afford 6-aminopicolinonitrile (580 mg, 84%) as an off-white solid. $^1$H-NMR (DMSO-$d_6$, 400 MHz): δ 7.52 (t, 1H), 7.02 (d, 1H), 6.71 (d, 1H), 6.55 (br s, 2H); TLC: 30% EtOAc:hexanes ($R_f$: 0.3).

Synthesis of 6-amino-3-bromopicolinonitrile

To a stirred solution of 6-aminopicolinonitrile (3.5 g, 29.41 mmol) in $CH_2Cl_2$:MeOH (1:1, 70 mL) under an argon atmosphere was added tetrabutylammonium tribromide (17 g, 35.29 mmol) at room temperature. The reaction mixture was stirred at room temperature for 2 h. After consumption of the starting material (monitored by TLC), the volatile components were concentrated in vacuo. The crude material was recrystallized with $CH_2Cl_2$ (2×20 mL) to obtain 6-amino-3-bromopicolinonitrile (1.8 g, 31%) as an off-white solid used in the next step without further purification. $^1$H-NMR (DMSO-$d_6$, 400 MHz): δ 7.74 (d, 1H), 6.70 (d, 1H), 6.60 (br s, 2H); LCMS: 199.8 (M+2); (column; X-Select CSH C-18 (50×3.0 mm, 3.5 μm); RT 2.69 min 0.05% Aq TFA: ACN; 0.80 mL/min); TLC: 5% MeOH/$CH_2Cl_2$ ($R_f$: 0.5).

Synthesis of 6-amino-3-(4-methyl-1H-imidazol-1-yl) picolinonitrile

To a stirred solution of 6-amino-5-bromopicolinonitrile (1.3 g, 6.59 mmol) in DMF (13 mL) under an argon atmosphere were added copper iodide (502 mg, 2.63 mmol), cesium carbonate (6.4 g, 19.79 mmol) and 4-methyl imidazole (1.6 g, 19.79 mmol) at room temperature. The reaction mixture was stirred at 120° C. for 16 h. After consumption of the starting material (monitored by TLC), the reaction mixture was diluted with water (50 mL) and extracted with EtOAc (2×50 mL). The combined organic extracts were dried over sodium sulfate, filtered and concentrated in vacuo. The crude material was purified by column chromatography using 3% MeOH: $CH_2Cl_2$ to afford 6-amino-3-(4-methyl-1H-imidazol-1-yl)picolinonitrile (410 mg, 31%) as a pale yellow solid. $^1$H-NMR (DMSO-$d_6$, 500 MHz): δ 7.80 (s, 1H), 7.60 (d, 1H), 7.13 (s, 1H), 6.89 (s, 2H), 6.80 (d, 1H), 2.15 (s, 3H); LCMS: 199.9 (M+1); (column; X-Select CSH C-18 (50×3.0 mm, 3.5 μm); RT 2.18 min 5mAqNH$_4$OAc: ACN; 0.80 mL/min); TLC: 5% MeOH/$CH_2Cl_2$ ($R_f$: 0.3).

Example 136

Synthesis of 3-(difluoromethyl)-4-(4-methyl-1H-imidazol-1-yl) aniline

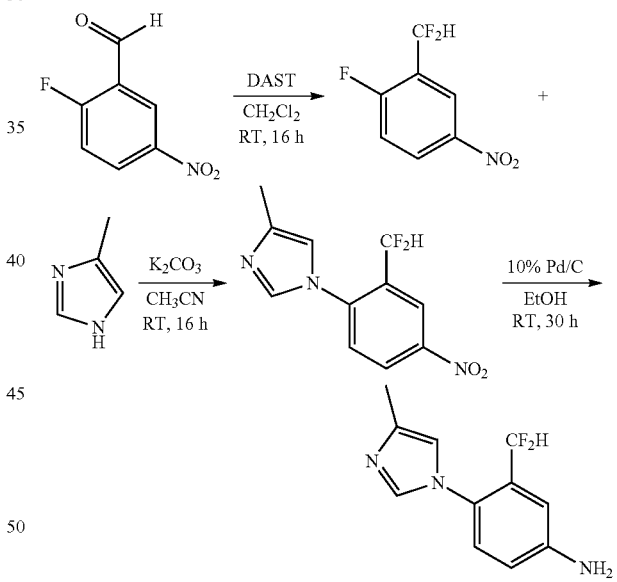

Synthesis of 2-(difluoromethyl)-1-fluoro-4-nitrobenzene

To a stirred solution of 2-fluoro-5-nitrobenzaldehyde (3 g, 17.75 mmol) in $CH_2Cl_2$ (30 mL) under an argon atmosphere was added DAST (2.8 mL, 21.30 mmol) at room temperature. The reaction mixture was stirred at room temperature for 16 h. After consumption of the starting material (monitored by TLC), the reaction was quenched with cold water (500 mL) and extracted with $CH_2Cl_2$ (2×500 mL). The combined organic extracts were dried over sodium sulfate, filtered and concentrated in vacuo to obtain 2-(difluoromethyl)-1-fluoro-4-nitrobenzene (2.8 g, 82%) as pale brown oil. $^1$H-NMR (CD$_3$OD, 400 MHz): δ 8.55-8.50 (m, 2H), 7.75 (t, 1H), 7.35 (t, 1H); TLC: 20% EtOAc:hexanes (R$_f$: 0.5).

Synthesis of 1-(2-(difluoromethyl)-4-nitrophenyl)-4-methyl-1H-imidazole

To a stirred solution of 2-(difluoromethyl)-1-fluoro-4-nitrobenzene (2.8 g, 14.65 mmol) in acetonitrile (50 mL) under an argon atmosphere were added potassium carbonate (2.4 g, 29.31 mmol) and 4-methyl-1H-imidazole (2.4 g, 29.31 mmol) at room temperature. The reaction mixture was stirred at room temperature for 16 h. After consumption of the starting material (monitored by TLC), the reaction mixture was diluted with water (40 mL). The obtained solid was filtered and dried in vacuo to afford 1-(2-(difluoromethyl)-4-nitrophenyl)-4-methyl-1H-imidazole (1.8 g, 72%) as a yellow solid. LC-MS: 253.9 (M+1); (column; X-Select CSH C-18 (50×3.0 mm, 3.5 μm); RT 1.88 min. 0.05% aq TFA: ACN; 0.80 mL/min); TLC: 5% MeOH/CH$_2$Cl$_2$ (R$_f$: 0.4).

Synthesis of 3-(difluoromethyl)-4-(4-methyl-1H-imidazol-1-yl) aniline

To a stirred solution of 1-(2-(difluoromethyl)-4-nitrophenyl)-4-methyl-1H-imidazole (500 mg, 10.68 mmol) in EtOH (15 mL) under an argon atmosphere was added 10% Pd/C (50 mg) at room temperature. The suspension was stirred under a H$_2$ atmosphere (balloon pressure) for 30 h. After consumption of the starting material (monitored by TLC), the reaction mixture was filtered, washed with EtOAc (50 mL) and 5% MeOH: CH$_2$Cl$_2$ (50 mL). The filtrate was concentrated in vacuo. The crude material was washed with n-pentane (2×20 mL) to afford 3-(difluoromethyl)-4-(4-methyl-1H-imidazol-1-yl) aniline (400 mg, 90%) as a brown solid. $^1$H-NMR (CD$_3$OD, 400 MHz): δ 7.51 (s, 1H), 7.02 (d, 1H), 6.93 (s, 1H), 6.88 (s, 1H), 6.73 (d, 1H), 6.53 (t, 1H), 5.69 (br s, 2H), 2.13 (s, 3H); TLC: 5% MeOH/CH$_2$Cl$_2$ (R$_f$: 0.5).

Example 137

Synthesis of (S)-(2-chloro-8-methyl-7, 8-dihydro-6H-pyrimido [5, 4-b] [1, 4] oxazin-7-yl) methanol

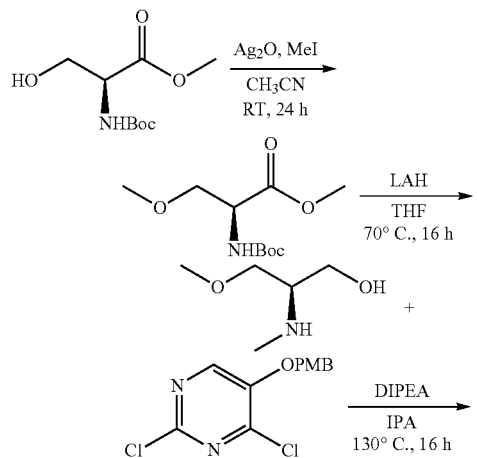

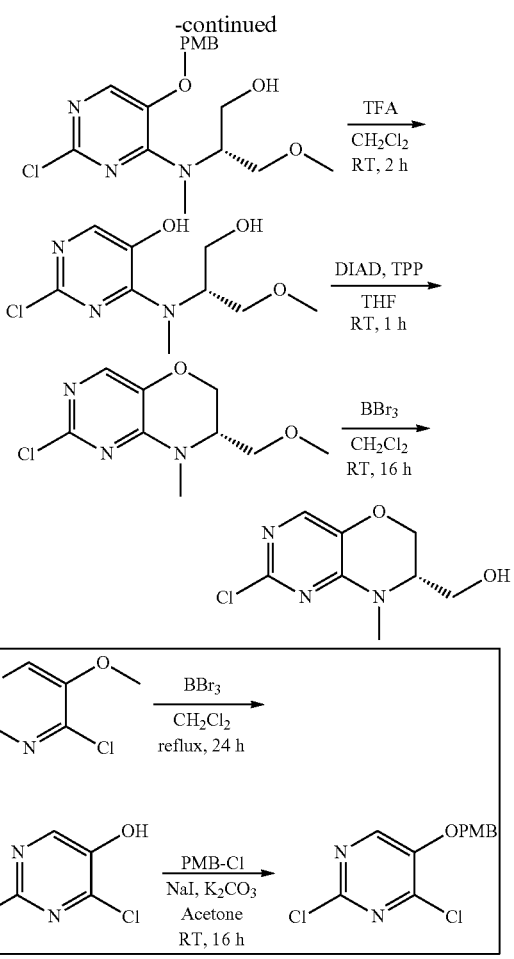

Synthesis of (S)-methyl 2-((tert-butoxycarbonyl) amino)-3-methoxypropanoate

To a stirred solution of methyl (tert-butoxycarbonyl)-L-serinate (5 g, 22.80 mmol) in CH$_3$CN (200 mL) under an argon atmosphere were added silver oxide (26 g, 114.15 mmol) and methyl iodide (32 g, 228.10 mmol) at room temperature. The reaction mixture was stirred at room temperature for 24 h in the absence of light. After consumption of the starting material (monitored by TLC), the reaction mixture was filtered and the filtrate concentrated in vacuo. The crude material was purified by column chromatography using 10% EtOAc:hexanes to afford (S)-methyl 2-((tert-butoxycarbonyl)amino)-3-methoxypropanoate (2.5 g, 47%) as a colorless liquid. $^1$H-NMR (CDCl$_3$, 400 MHz): δ 5.40-5.31 (m, 1H), 4.44-4.38 (m, 1H), 3.80-3.78 (m, 1H), 3.77 (s, 3H), 3.60-3.56 (m, 1H), 3.33 (s, 3H), 1.44 (s, 9H); TLC: 30% EtOAc:hexane (R$_f$: 0.5).

Synthesis of (R)-3-methoxy-2-(methylamino) propan-1-ol

To a stirred solution of (S)-methyl 2-((tert-butoxycarbonyl)amino)-3-methoxypropanoate (3.8 g, 16.30 mmol) in THF (100 mL) under an argon atmosphere was added lithium aluminum hydride (1.8 g, 48.92 mmol) portion wise at 0° C. The reaction mixture was stirred at 70° C. for 16 h. After consumption of the starting material (monitored by TLC), the reaction mixture was cooled to 0° C., quenched with water (2 mL), basified with a 15% sodium hydroxide solution (2 mL) and stirred for 30 min and filtered. The filtrate was dried over sodium sulfate, filtered and concentrated in vacuo to obtain (R)-3-methoxy-2-(methylamino) propan-1-ol (1.7 g, 87%) as a colorless liquid. $^1$H-NMR (DMSO-d$_6$, 500 MHz): δ 3.46-3.32 (m, 2H), 3.30-3.26 (m, 3H), 3.25-3.21 (m, 4H), 2.52-2.48 (m, 1H), 2.30 (s, 3H); TLC: 50% EtOAc:hexane (R$_f$: 0.2).

Synthesis of 2, 4-dichloropyrimidin-5-ol

To a stirred solution of 2, 4-dichloro-5-methoxypyrimidine (20 g, 111.73 mmol) in CH$_2$Cl$_2$ (280 mL) under an argon atmosphere was added borontribromide (54 mL, 558.65 mmol) drop wise at 0° C. The reaction mixture was refluxed for 24 h. After consumption of the starting material (monitored by TLC), the reaction mixture was cooled to 0° C., basified with a 1N sodium hydroxide solution and stirred for 1 h. Then the reaction mixture was acidified with acetic acid (pH 2-4) and the aqueous layer was extracted with 5% MeOH: CH$_2$Cl$_2$ (2×250 mL). The combined organic extracts were dried over sodium sulfate, filtered and concentrated in vacuo to obtain 2, 4-dichloropyrimidin-5-ol (12 g, 64%) as pale yellow solid. $^1$H-NMR (DMSO-d$_6$, 500 MHz): δ 8.33 (s, 1H), 4.00 (s, 1H); TLC: 30% EtOAc:hexane (R$_f$: 0.6).

Synthesis of 2, 4-dichloro-5-((4-methoxybenzyl) oxy) pyrimidine

To a stirred solution of 2, 4-dichloropyrimidin-5-ol (6 g, 36.50 mmol) in acetone (60 mL) under an argon atmosphere were added sodium iodide (600 mg, 3.65 mmol), potassium carbonate (13 g, 91.25 mmol) and p-methoxy benzyl chloride (8.6 g, 54.87 mmol) drop wise at room temperature. The reaction was stirred at room temperature for 16 h. After consumption of the starting material (monitored by TLC), the reaction mixture was concentrated in vacuo. The crude material was purified by column chromatography using 10% EtOAc:hexanes (2% triethylamine) to afford 2, 4-dichloro-5-((4-methoxybenzyl) oxy) pyrimidine (5 g, 48%) as an off-white solid. $^1$H-NMR (DMSO-d$_6$, 400 MHz): δ 8.63 (s, 1H), 7.41 (d, 2H), 6.99 (d, 2H), 5.29 (s, 2H), 3.75 (s, 3H); TLC: 30% EtOAc:hexane (R$_f$: 0.6).

Synthesis of (R)-2-((2-chloro-5-((4-methoxybenzyl) oxy) pyrimidin-4-yl) (methyl) amino)-3-methoxypropan-1-ol To a stirred solution of (R)-3-methoxy-2-(methylamino) propan-1-ol (1.1 g, 92.20 mmol) in isopropyl alcohol (11 mL) under an argon atmosphere were added diisopropylethylamine (11 mL, 101.42 mmol) and 2,4-dichloro-5-((4-methoxybenzyl)oxy)pyrimidine (2.9 g, 101.42 mmol) at room temperature. The reaction mixture was stirred at 130° C. for 16 h. After consumption of the starting material (monitored by TLC), the volatile components were evaporated in vacuo. The crude material was purified by column chromatography using 20% EtOAc:hexanes to afford (R)-2-((2-chloro-5-((4-methoxybenzyl) oxy) pyrimidin-4-yl) (methyl) amino)-3-methoxypropan-1-ol (1.3 g, 38%) as a colorless liquid. $^1$H-NMR (CDCl$_3$, 400 MHz): δ 7.72 (s, 1H), 7.31 (d, 2H), 6.90 (d, 2H), 4.94 (s, 2H), 4.85-4.79 (m, 1H), 3.81 (s, 3H), 3.80-3.79 (m, 2H), 3.60-3.50 (m, 2H), 3.30 (s, 3H), 3.11 (s, 3H), 2.41-2.39 (m, 1H); LCMS: 368.5 (M+1); (column; X-Select CSH C-18 (50×3.0 mm, 3.5 μm); RT 3.77 min. 0.05% Aq TFA: ACN; 0.80 mL/min); TLC: 50% EtOAc:hexane (R$_f$: 0.4).

Synthesis of (R)-2-chloro-4-((1-hydroxy-3-methoxypropan-2-yl) (methyl) amino) pyrimidin-5-ol To a stirred solution of (R)-2-((2-chloro-5-((4-methoxybenzyl) oxy) pyrimidin-4-yl) (methyl) amino)-3-methoxypropan-1-ol (2.2 g, 5.99 mmol) in CH$_2$Cl$_2$ (34 mL) was added trifluoroacetic acid (6 mL) under an argon atmosphere at 0° C. The reaction mixture was warmed to room temperature and stirred for 2 h. After consumption of the starting material (monitored by TLC), the reaction mixture was diluted with water (20 mL) and extracted with CH$_2$Cl$_2$ (2×20 mL). The aqueous layer was basified with a saturated sodium bicarbonate solution (50 mL) and extracted with CH$_2$Cl$_2$ (2×100 mL). The combined organic extracts were dried over sodium sulfate, filtered and concentrated in vacuo to obtain (R)-2-chloro-4-((1-hydroxy-3-methoxypropan-2-yl) (methyl) amino) pyrimidin-5-ol (700 mg, 47%) as an off-white solid. $^1$H-NMR (CDCl$_3$, 500 MHz): δ 7.81 (s, 1H), 4.41-4.39 (m, 1H), 3.89-3.81 (m, 1H), 3.78-3.74 (m, 1H), 3.60-3.51 (m, 2H), 3.41 (s, 3H), 2.99 (s, 3H); LCMS: 247.8 (M+1); (column; X-Select CSH C-18 (50×3.0 mm, 3.5 μm); RT 1.88 min 0.05% Aq TFA: ACN; 0.80 mL/min); TLC: 70% EtOAc:hexane (R$_f$: 0.3).

Synthesis of (S)-2-chloro-7-(methoxymethyl)-8-methyl-7, 8-dihydro-6H-pyrimido [5, 4-b] [1, 4] oxazine To a stirred solution of (R)-2-chloro-4-((1-hydroxy-3-methoxypropan-2-yl) (methyl) amino) pyrimidin-5-ol (650 mg, 2.63 mmol) in THF (15 mL) under an argon atmosphere were added triphenylphosphine (1 g, 3.95 mmol) and diisopropylazodicarboxylate (800 mg, 3.95 mmol) at 0° C. The reaction mixture was warmed to room temperature and stirred for 1 h. After consumption of the starting material (monitored by TLC), the volatile components were concentrated in vacuo. The crude material was purified by column chromatography using 20% EtOAc:hexanes to afford (S)-2-chloro-7-(methoxymethyl)-8-methyl-7, 8-dihydro-6H-pyrimido [5, 4-b] [1, 4] oxazine (450 mg, 75%) as a colorless liquid. $^1$H-NMR (CDCl$_3$, 400 MHz): δ 7.64 (s, 1H), 4.38-4.34 (m, 1H), 3.91-3.89 (m, 1H), 3.60-3.55 (m, 1H), 3.54-3.51 (m, 1H), 3.50-3.42 (m, 1H), 3.39 (s, 3H), 3.20 (s, 3H); LCMS: 229.8 (M+1); (column; X-Select CSH C-18 (50×3.0 mm, 3.5 μm); RT 2.56 min 0.05% Aq TFA: ACN; 0.80 mL/min); TLC: 50% EtOAc:hexane (R$_f$: 0.6).

Synthesis of (S)-(2-chloro-8-methyl-7, 8-dihydro-6H-pyrimido [5, 4-b] [1, 4] oxazin-7-yl) methanol To a stirred solution of (S)-2-chloro-7-(methoxymethyl)-8-methyl-7, 8-dihydro-6H-pyrimido [5, 4-b] [1, 4] oxazine (450 mg, 1.96 mmol) in CH$_2$Cl$_2$ (20 mL) was added borontribromide (1.47 g, 5.89 mmol) at 0° C. under an argon atmosphere. The reaction mixture was warmed to room temperature and stirred for 16 h. After consumption of the starting material (monitored by TLC), the reaction mixture was cooled to 0° C., basified with a 2N sodium hydroxide solution, warmed to room temperature and stirred for 30 min. Then the reaction mixture was acidified with acetic acid (pH 3-4), aqueous layer was extracted with CH$_2$Cl$_2$ (3×40 mL). The combined organic extracts were dried over sodium sulfate, filtered and concentrated in vacuo to obtain (S)-(2- chloro-8-methyl-7, 8-dihydro-6H-pyrimido [5, 4-b] [1, 4] oxazin-7-yl) methanol (300 mg, 71%) as a pale yellow solid. $^1$H-NMR (CDCl$_3$, 400 MHz): δ 7.63 (s, 1H), 4.45-4.40 (m, 1H), 3.94-3.90 (m, 1H), 3.89-3.83 (m, 1H), 3.80-3.73 (m, 1H), 3.57-3.51 (m, 1H), 3.23 (s, 3H); LCMS: 215.8 (M+1); (column; X-Select CSH C-18 (50×3.0 mm, 3.5 µm); RT 1.45 min 0.05% Aq TFA: ACN; 0.80 mL/min); TLC: 50% EtOAc:hexane (R$_f$: 0.3).

Example 138

Synthesis of 2-chloro-7-(5-chloro-2-(trifluoromethyl) phenyl)-8-methyl-7, 8-dihydro-6H-pyrimido [5, 4-b] [1, 4] oxazine

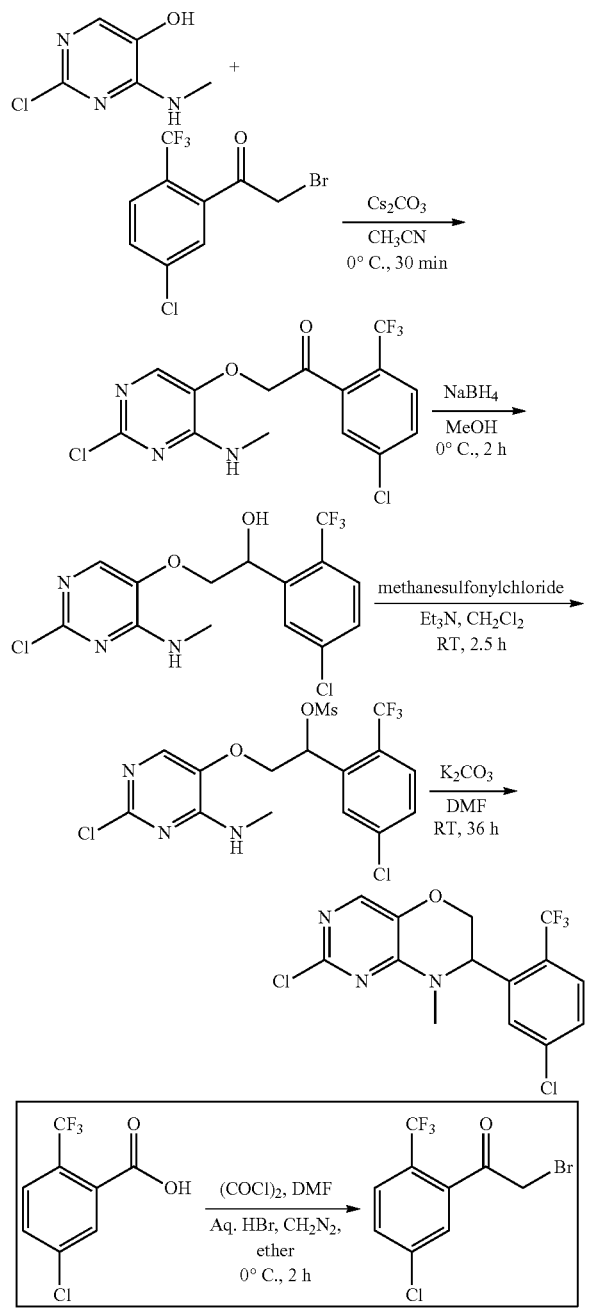

Synthesis of 2-bromo-1-(5-chloro-2-(trifluoromethyl) phenyl) ethan-1-one

To a stirred solution of 5-chloro-2-(trifluoromethyl) benzoic acid (4 g, 17.85 mmol) in CH$_2$Cl$_2$ (100 mL) under an argon atmosphere was added oxalyl chloride (2 mL, 19.64 mmol) and DMF (0.2 mL) at 0° C. The reaction mixture was stirred at 0° C. for 2 h. After consumption of acid (monitored by TLC), the volatile components were evaporated in vacuo. To a stirred solution of the residue in ether a CH$_2$N$_2$ in ether solution was added at 0° C. The reaction mixture was stirred at 0° C. for 2 h and aq. HBr (40 mL) was added to the reaction mixture at 0° C. The reaction mixture was stirred for 2 h. After consumption of the starting material (monitored by TLC), the reaction mixture was quenched with water (800 mL) and extracted with CH$_2$Cl$_2$ (2×100 mL). The combined organic extracts were washed with a sodium bicarbonate solution (50 mL), water (50 mL), dried over sodium sulfate, filtered and concentrated in vacuo to obtain 2-bromo-1-(5-chloro-2-(trifluoromethyl) phenyl) ethan-1-one (5 g, 93%) as a pale yellow liquid. $^1$H-NMR (CDCl$_3$, 400 MHz): δ 7.79 (d, 1H), 7.59 (d, 1H), 7.49 (s, 1H), 4.33 (s, 2H); LCMS: 301 (M-2); (column; X-Select CSH C-18 (50×3.0 mm, 3.5 µm); RT 3.86 min. 5 mM Aq NH$_4$OAc: ACN; 0.8 mL/min); TLC: 20% EtOAc:hexanes (R$_f$: 0.7).

Synthesis of 1-(5-chloro-2-(trifluoromethyl) phenyl)-2-((2-chloro-4-(methylamino) pyrimidin-5-yl) oxy) ethan-1-one To a stirred solution of 2-chloro-4-(methylamino) pyrimidin-5-ol (2.7 g, 16.98 mmol) in CH$_3$CN (110 mL) under an argon atmosphere was added cesium carbonate (16 g, 33.96 mmol) at 0° C. After stirring for 5 min, 2-bromo-1-(5-chloro-2-(trifluoromethyl) phenyl) ethan-1-one (6.4 g, 21.22 mmol) was added and stirred for 30 min. After consumption of the starting material (monitored by TLC), the reaction mixture was diluted with water (20 mL) and extracted with EtOAc (2×20 mL). The combined organic extracts were dried over sodium sulfate, filtered and concentrated in vacuo. The crude material was washed with hexane (2×, 10 mL) to afford 1-(5-chloro-2-(trifluoromethyl) phenyl)-2-((2-chloro-4-(methylamino) pyrimidin-5-yl) oxy) ethan-1-one (5.5 g, 86%) as a pale yellow solid. LCMS: 380.4 (M+1); (column; X-Select CSH C-18 (50×3.0 mm, 3.5 µm); RT 4.29 min 0.05% Aq TFA: ACN; 0.8 mL/min); TLC: 30% EtOAc: hexanes (R$_f$: 0.5).

Synthesis of 1-(5-chloro-2-(trifluoromethyl)phenyl)-2-((2-chloro-4-(methylamino)pyrimidin-5-yl)oxy) ethan-1-ol)

To a stirred solution of 1-(5-chloro-2-(trifluoromethyl) phenyl)-2-((2-chloro-4-(methylamino) pyrimidin-5-yl) oxy) ethan-1-one (5.5 g, 14.43 mmol) in MeOH (110 mL) under an argon atmosphere was added sodium borohydride (1.1 g, 28.86 mmol) at 0° C. The reaction mixture was stirred at 0° C. for 2 h. After consumption of the starting material (monitored by TLC), the reaction mixture was quenched with cold water. The volatile components were evaporated in vacuo, saturated ammonium chloride solution (100 mL) was added and extracted with EtOAc (2×100 mL). The combined organic extracts were dried over sodium sulfate, filtered and concentrated in vacuo to obtain 1-(5-chloro-2-(trifluoromethyl)phenyl)-2-((2-chloro-4-(methylamino)pyrimidin-5-yl) oxy) ethan-1-ol) (5.5 g, crude) as an off-white solid. $^1$H-NMR (DMSO-d$_6$, 500 MHz): δ 7.93 (s, 1H), 7.77 (d, 1H), 7.70-7.60 (m, 2H), 7.50-7.43 (m, 1H), 6.13 (d, 1H), 5.27-5.20 (m, 1H), 4.11-4.10 (m, 2H), 2.88 (d, 3H); LCMS: 383.1 (M+1); (column; X-Select CSH C-18 (50×3.0 mm, 3.5 µm); RT 4.23 min. 0.05% Aq TFA: ACN; 0.8 mL/min); TLC: 30% EtOAc:hexanes ($R_f$: 0.4).

Synthesis of 1-(5-chloro-2-(trifluoromethyl) phenyl)-2-((2-chloro-4-(methylamino) pyrimidin-5-yl) oxy) ethyl methanesulfonate To a stirred solution of 1-(5-chloro-2-(trifluoromethyl) phenyl)-2-((2-chloro-4-(methylamino)pyrimidin-5-yl)oxy) ethan-1-ol) (5.3 g, 14.00 mmol) in $CH_2Cl_2$ (100 mL) under an argon atmosphere was added triethylamine (6.82 mL, 49.00 mmol) followed by methanesulfonyl chloride (2.2 mL, 28.00 mmol) at 0° C. The reaction mixture was warmed to room temperature and stirred for 2.5 h. After consumption of the starting material (monitored by TLC), the reaction mixture was neutralized with a 5% sodium bicarbonate solution (100 mL) and extracted with $CH_2Cl_2$ (2×100 mL). The combined organic extracts were dried over sodium sulfate, filtered and concentrated in vacuo to obtain 1-(5-chloro-2-(trifluoromethyl)phenyl)-2-((2-chloro-4-(methylamino)pyrimidin-5-yl)oxy)ethyl methanesulfonate (5 g, 78%) as an off-white solid. $^1$H-NMR (DMSO-$d_6$, 400 MHz): δ 7.99 (s, 1H), 7.83 (d, 1H), 7.75-7.71 (m, 2H), 7.43-7.40 (m, 1H), 6.10 (d, 1H), 4.62-4.58 (m, 1H), 4.23-4.20 (m, 1H), 3.30 (s, 3H), 2.87 (d, 3H); LCMS: 461.2 (M+1); (column; X-Select CSH C-18 (50×3.0 mm, 3.5 µm); RT 4.44 min. 0.05% Aq TFA: ACN; 0.8 mL/min); UPLC (column; Acquity UPLC-BEH-C18 2.1×50 mm, 1.7 µm); RT 2.49 min. ACN: 0.025% Aq TFA; 0.5 mL/min; TLC: 30% EtOAc:hexanes ($R_f$: 0.5).

Synthesis of 2-chloro-7-(5-chloro-2-(trifluoromethyl) phenyl)-8-methyl-7, 8-dihydro-6H-pyrimido [5, 4-b] [1, 4] oxazine To a stirred solution of 1-(5-chloro-2-(trifluoromethyl) phenyl)-2-((2-chloro-4-(methylamino) pyrimidin-5-yl) oxy) ethyl methanesulfonate (900 mg, 1.95 mmol) in DMF (30 mL) under an argon atmosphere was added potassium carbonate (808 mg, 5.85 mmol) at room temperature. The reaction mixture was stirred at 120° C. for 36 h. After consumption of the starting material (monitored by TLC), the reaction mixture was quenched with water (50 mL) and extracted with EtOAc (2×50 mL). The combined organic extracts were dried over sodium sulfate, filtered and concentrated in vacuo. The crude material was purified by column chromatography using 15% EtOAc:hexanes to afford 2-chloro-7-(5-chloro-2-(trifluoromethyl) phenyl)-8-methyl-7, 8-dihydro-6H-pyrimido [5, 4-b] [1, 4] oxazine (300 mg, 42%) as a pale yellow solid. $^1$H-NMR (DMSO-$d_6$, 400 MHz): δ 7.90-7.84 (m, 2H), 7.80 (d, 1H), 7.30 (s, 1H), 5.01-4.99 (m, 1H), 4.33-4.30 (m, 1H), 4.21-4.18 (m, 1H), 2.95 (s, 3H); LCMS: 365.1 (M+1); (column; X-Select CSH C-18 (50×3.0 mm, 3.5 µm); RT 4.75 min 0.05% Aq TFA: ACN; 0.8 mL/min); UPLC (column; Acquity UPLC-BEH-C18 2.1×50 mm, 1.7 µm); RT 2.73 min. ACN: 0.025% Aq TFA; 0.5 mL/min; TLC: 30% EtOAc:hexanes ($R_f$: 0.7).

Example 139

Synthesis of 7-(2, 4-bis (trifluoromethyl) phenyl)-2-chloro-8-methyl-7, 8-dihydro-6H-pyrimido [5, 4-b] [1, 4] oxazine

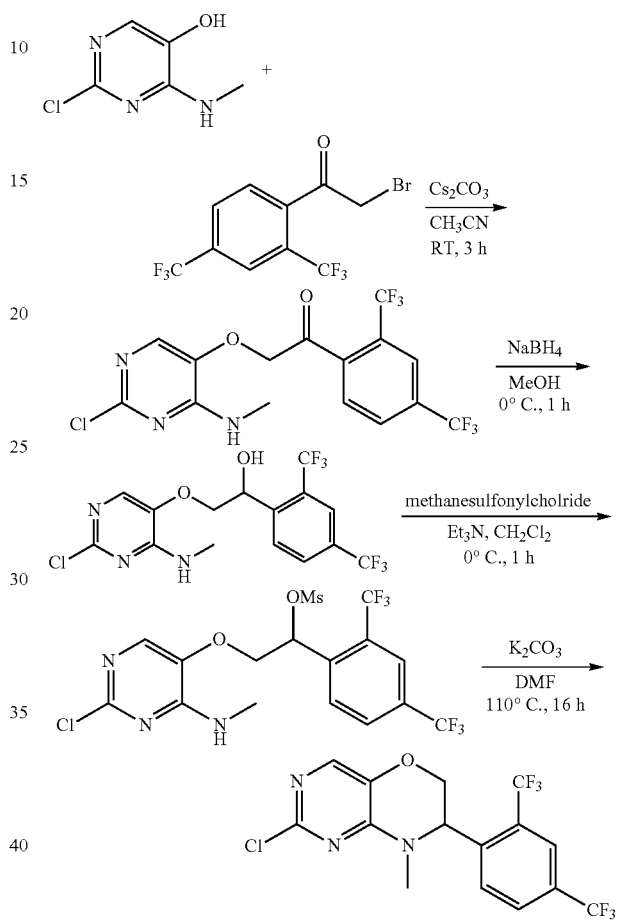

Synthesis of 1-(2, 4-bis (trifluoromethyl) phenyl)-2-((2-chloro-4-(methylamino) pyrimidin-5-yl) oxy) ethan-1-one To a stirred solution of 2-chloro-4-(methylamino) pyrimidin-5-ol (600 mg, 3.77 mmol) in $CH_3CN$ (6 mL) under an argon atmosphere were added cesium carbonate (2.4 g, 7.54 mmol) and 1-(2, 4-bis (trifluoromethyl) phenyl)-2-bromoethan-1-one (1.4 g, 4.15 mmol) at room temperature. The reaction mixture was stirred at room temperature for 3 h. After consumption of the starting material (monitored by TLC), the reaction mixture was diluted with water (50 mL) and extracted with EtOAc (2×50 mL). The combined organic extracts were dried over sodium sulfate, filtered and concentrated in vacuo. The crude material was purified by column chromatography using 20% EtOAc:hexane to afford 1-(2, 4-bis (trifluoromethyl) phenyl)-2-((2-chloro-4-(methylamino) pyrimidin-5-yl) oxy) ethan-1-one (500 mg, 33%) as an off-white solid. $^1$H-NMR (DMSO-$d_6$, 500 MHz): δ 8.30 (s, 2H), 8.27 (s, 1H), 7.71 (s, 1H), 7.46-7.42 (m, 1H), 5.59 (s, 2H), 2.85 (d, 3H); LCMS: 413.8 (M+1); (column;

X-Select CSH C-18 (50×3.0 mm, 3.5 μm); RT 3.83 min. 0.05% Aq TFA: ACN; 0.80 mL/min); TLC: 50% EtOAc:hexanes ($R_f$: 0.6).

Synthesis of 1-(2, 4-bis (trifluoromethyl) phenyl)-2-((2-chloro-4-(methylamino) pyrimidin-5-yl) oxy) ethan-1-ol To a stirred solution of 1-(2, 4-bis (trifluoromethyl) phenyl)-2-((2-chloro-4-(methylamino) pyrimidin-5-yl) oxy) ethan-1-one (1.5 g, 3.63 mmol) in MeOH (15 mL) under an argon atmosphere was added sodium borohydride (201 mg, 5.44 mmol) at 0° C. The reaction mixture was stirred at 0° C. for 1 h. After consumption of the starting material (monitored by TLC), the volatile components were evaporated in vacuo, water (50 mL) was added and extracted with EtOAc (2×50 mL). The combined organic extracts were dried over sodium sulfate, filtered and concentrated in vacuo. The crude material was purified by column chromatography using 20% EtOAc:hexane to afford 1-(2, 4-bis-(trifluoromethyl) phenyl)-2-((2-chloro-4-(methylamino) pyrimidin-5-yl) oxy) ethan-1-ol (1.1 g, 73%) as an off-white solid. $^1$H-NMR (CDCl$_3$, 500 MHz): δ 8.02 (d, 1H), 7.96 (s, 1H), 7.92 (d, 1H), 7.51 (s, 1H), 5.62-5.59 (m, 2H), 4.15-4.12 (m, 1H), 4.03 (t, 1H), 3.03 (d, 3H); LCMS: 415.8 (M+1); (column; X-Select CSH C-18 (50×3.0 mm, 3.5 μm); RT 3.74 min 0.05% Aq TFA: ACN; 0.80 mL/min); TLC: 30% EtOAc:hexanes ($R_f$: 0.4).

Synthesis of 1-(2, 4-bis (trifluoromethyl) phenyl)-2-((2-chloro-4-(methylamino) pyrimidin-5-yl) oxy) ethyl methanesulfonate To a stirred solution of 1-(2, 4-bis-(trifluoromethyl) phenyl)-2-((2-chloro-4-(methylamino) pyrimidin-5-yl) oxy) ethan-1-ol (1.2 g, 2.89 mmol) in CH$_2$Cl$_2$ (12 mL) were added triethylamine (0.5 mL, 3.46 mmol) followed by methanesulfonyl chloride (329 mg, 2.89 mmol) at 0° C. under an argon atmosphere. The reaction mixture was stirred at 0° C. for 1 h. After consumption of the starting material (monitored by TLC), the reaction mixture was neutralized with water (50 mL) and extracted with CH$_2$Cl$_2$ (2×50 mL). The combined organic extracts were dried over sodium sulfate, filtered and concentrated in vacuo. The crude material was purified by column chromatography using 30% EtOAc:hexane to afford 1-(2, 4-bis (trifluoromethyl) phenyl)-2-((2-chloro-4-(methylamino) pyrimidin-5-yl) oxy) ethyl methanesulfonate (1 g, 71%) as an off-white solid. $^1$H-NMR (CDCl$_3$, 400 MHz): δ 8.02 (d, 1H), 8.00-7.98 (m, 1H), 7.91 (d, 1H), 7.40 (s, 1H), 6.10-6.08 (m, 1H), 4.22-4.10 (m, 2H), 3.68 (s, 1H), 3.07 (d, 3H), 3.00 (s, 3H); LCMS: 493.9 (M+1); (column; X-Select CSH C-18 (50×3.0 mm, 3.5 μm); RT 3.89 min 0.05% Aq TFA: ACN; 0.80 mL/min); TLC: 40% EtOAc:hexanes ($R_f$: 0.4).

Synthesis of 7-(2, 4-bis (trifluoromethyl) phenyl)-2-chloro-8-methyl-7, 8-dihydro-6H-pyrimido [5, 4-b] [1, 4] oxazine To a stirred solution of 1-(2, 4-bis-(trifluoromethyl) phenyl)-2-((2-chloro-4-(methylamino) pyrimidin-5-yl) oxy) ethyl methanesulfonate (1 g, 2.02 mmol) in DMF (10 mL) under an argon atmosphere was added potassium carbonate (419 mg, 3.04 mmol) at room temperature. The reaction mixture was stirred at 110° C. for 16 h. After consumption of the starting material (monitored by TLC), the volatile components were evaporated in vacuo. The reaction mixture was diluted with cold water (50 mL) and extracted with ether (2×50 mL). The combined organic extracts were washed with water (50 mL), dried over sodium sulfate, filtered and concentrated in vacuo. The crude material was purified by column chromatography using 5% EtOAc:hexane to afford 7-(2, 4-bis (trifluoromethyl) phenyl)-2-chloro-8-methyl-7, 8-dihydro-6H-pyrimido [5, 4-b] [1, 4] oxazine (200 mg, 25%) as an off-white solid. $^1$H-NMR (CDCl$_3$, 500 MHz): δ 8.00 (s, 1H), 7.81 (d, 1H), 7.80 (s, 1H), 7.34 (d, 1H), 5.10-5.08 (m, 1H), 4.31-4.29 (m, 1H), 4.20-4.16 (m, 1H), 3.08 (s, 3H); LCMS: 397.8 (M+1); (column; X-Select CSH C-18 (50×3.0 mm, 3.5 μm); RT 4.20 min 0.05% Aq TFA: ACN; 0.80 mL/min); TLC: 30% EtOAc:hexanes ($R_f$: 0.6).

Example 140

Synthesis of 2-chloro-7-(2-chloro-4, 5-difluorophenyl)-7, 8-dihydro-6H-pyrimido [5, 4-b] [1, 4] oxazine

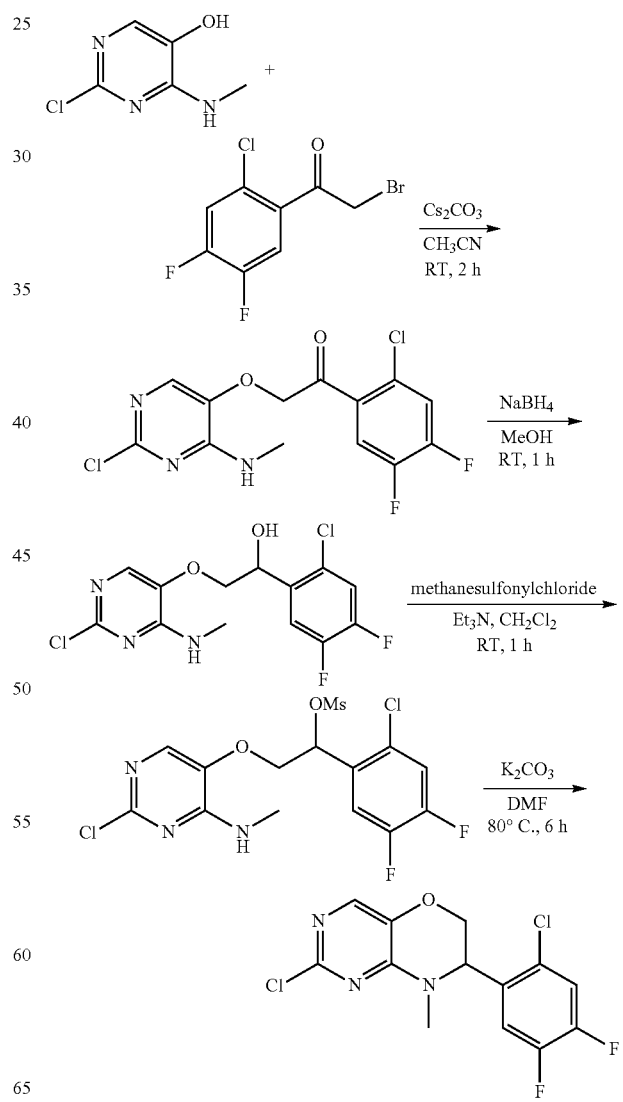

Synthesis of 1-(2-chloro-4, 5-difluorophenyl)-2-((2-chloro-4-(methylamino) pyrimidin-5-yl) oxy) ethan-1-one To a stirred solution of 2-chloro-4-(methylamino) pyrimidin-5-ol (1.47 g, 9.24 mmol) in $CH_3CN$ (25 mL) under an argon atmosphere were added cesium carbonate (6 g, 18.49 mmol) and 2-bromo-1-(2-chloro-4, 5-difluorophenyl) ethan-1-one (2.5 g, 9.29 mmol) at room temperature. The reaction mixture was stirred at room temperature for 2 h. After consumption of the starting material (monitored by TLC), the reaction mixture was diluted with water (50 mL) and extracted with EtOAc (2×50 mL). The combined organic extracts were dried over sodium sulfate, filtered and concentrated in vacuo to obtain 1-(2-chloro-4, 5-difluorophenyl)-2-((2-chloro-4-(methylamino) pyrimidin-5-yl) oxy) ethan-1-one (2.5 g, 78%) as an off-white solid used in the next step without further purification. $^1$H-NMR (DMSO-$d_6$, 500 MHz): δ 7.92-7.80 (m, 3H), 7.60 (s, 1H), 4.28 (d, 1H), 4.08 (d, 1H), 2.76 (s, 3H); TLC: 30% EtOAc:hexanes ($R_f$: 0.5).

Synthesis of 1-(2-chloro-4, 5-difluorophenyl)-2-((2-chloro-4-(methylamino) pyrimidin-5-yl) oxy) ethan-1-ol To a stirred solution of 1-(2-chloro-4, 5-difluorophenyl)-2-((2-chloro-4-(methylamino) pyrimidin-5-yl) oxy) ethan-1-one (2.5 g, 7.18 mmol) in MeOH (25 mL) under an argon atmosphere was added sodium borohydride (531 mg, 14.36 mmol) at 0° C. The reaction mixture was warmed to room temperature and stirred for 1 h. After consumption of the starting material (monitored by TLC), the volatile components were evaporated in vacuo. The residue was diluted with water (50 mL) and extracted with $CH_2Cl_2$ (2×50 mL). The combined organic extracts were dried over sodium sulfate, filtered and concentrated in vacuo to obtain 1-(2-chloro-4, 5-difluorophenyl)-2-((2-chloro-4-(methylamino) pyrimidin-5-yl) oxy) ethan-1-ol (2.2 g, crude) as an off-white solid used in the next step without further purification. LCMS: 350 (M+); (column; X-Select CSH C-18 (50×3.0 mm, 3.5 μm); RT 3.39 min 5 mM Aq $NH_4OAc$: ACN; 0.80 mL/min); TLC: 50% EtOAc:hexanes ($R_f$: 0.4).

Synthesis of 1-(2-chloro-4, 5-difluorophenyl)-2-((2-chloro-4-(methylamino) pyrimidin-5-yl) oxy) ethyl methanesulfonate To a stirred solution of 1-(2-chloro-4, 5-difluorophenyl)-2-((2-chloro-4-(methylamino) pyrimidin-5-yl) oxy) ethan-1-ol (2.2 g, 6.28 mmol) in $CH_2Cl_2$ (25 mL) under an argon atmosphere were added triethylamine (1.26 g, 12.57 mmol) and methanesulfonyl chloride (859 mg, 7.54 mmol) at room temperature. The reaction mixture was stirred at room temperature for 1 h. After consumption of the starting material (monitored by TLC), the reaction mixture was diluted with water (50 mL) and extracted with $CH_2Cl_2$ (2×50 mL). The combined organic extracts were dried over sodium sulfate, filtered and concentrated in vacuo to obtain 1-(2-chloro-4, 5-difluorophenyl)-2-((2-chloro-4-(methylamino) pyrimidin-5-yl) oxy) ethyl methanesulfonate (2.5 g, crude) as an off-white solid used in the next step without further purification. LCMS: 428 (M+); (column; X-Select CSH C-18 (50×3.0 mm, 3.5 μm); RT 3.39 min 5 mM Aq $NH_4OAc$: ACN; 0.80 mL/min); TLC: 50% EtOAc:hexanes ($R_f$: 0.6).

Synthesis of 2-chloro-7-(2-chloro-4, 5-difluorophenyl)-8-methyl-7, 8-dihydro-6H-pyrimido [5, 4-b] [1, 4] oxazine To a stirred solution of 1-(2-chloro-4, 5-difluorophenyl)-2-((2-chloro-4-(methylamino) pyrimidin-5-yl) oxy) ethyl methanesulfonate (2.5 g, 5.84 mmol) in DMF (25 mL) under an argon atmosphere was added potassium carbonate (1.61 g, 11.68 mmol) at room temperature. The reaction mixture was stirred at 80° C. for 6 h. After consumption of the starting material (monitored by TLC), the reaction mixture was diluted with water (200 mL) and extracted with EtOAc (2×50 mL). The combined organic extracts were washed with water (50 mL), dried over sodium sulfate, filtered and concentrated in vacuo. The crude material was purified by column chromatography using 5% EtOAc:hexane to afford 2-chloro-7-(2-chloro-4, 5-difluorophenyl)-8-methyl-7, 8-dihydro-6H-pyrimido [5, 4-b] [1, 4] oxazine (1.3 g, 68%) as an off-white solid. $^1$H-NMR (DMSO-$d_6$, 400 MHz): δ 7.90-7.87 (m, 1H), 7.79 (s, 1H), 7.18-7.10 (m, 1H), 5.19-5.17 (m, 1H), 4.30 (s, 2H), 3.01 (s, 3H); LCMS: 332.1 (M+2); (column; X-Select CSH C-18 (50×3.0 mm, 3.5 μm); RT 3.79 min 5 mM Aq $NH_4OAc$: ACN; 0.80 mL/min); TLC: 30% EtOAc:hexanes ($R_f$: 0.7).

Example 141

Synthesis of 2-chloro-7-(2-chloro-5-(trifluoromethyl) phenyl)-8-methyl-7, 8-dihydro-6H-pyrimido [5, 4-b] [1, 4] oxazine

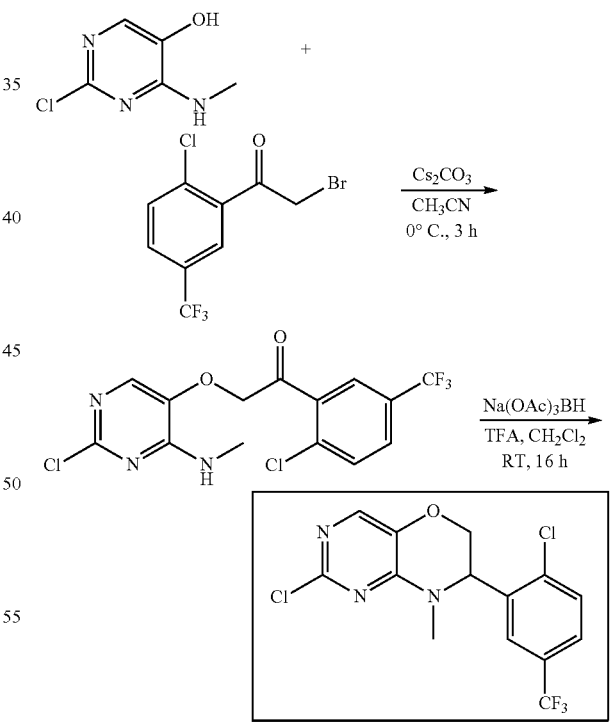

Synthesis of 2-((2-chloro-4-(methylamino) pyrimidin-5-yl) oxy)-1-(2-chloro-5-(trifluoromethyl) phenyl) ethan-1-one To a stirred solution of 2-chloro-4-(methylamino) pyrimidin-5-ol (1 g, 6.28 mmol) in $CH_3CN$ (10 mL) under an argon atmosphere were added 2-bromo-1-(2-chloro-5-(trifluoromethyl) phenyl) ethan-1-one (2 g, 6.91 mmol) and cesium carbonate (4 g, 12.57 mmol) at 0° C. The reaction mixture was stirred at 0° C. for 3 h. After consumption of the starting material (monitored by TLC), the reaction mixture was diluted with water (20 mL) and extracted with EtOAc (2×20 mL). The combined organic extracts were dried over sodium sulfate, filtered and concentrated in vacuo. The crude material was recrystallized from $CH_2Cl_2$: pentane (1:1, 2×10 mL) to afford 2-((2-chloro-4-(methylamino) pyrimidin-5-yl) oxy)-1-(2-chloro-5-(trifluoromethyl) phenyl) ethan-1-one (1.45 g, 63%) as an off-white solid. $^1$H-NMR (DMSO-$d_6$, 500 MHz): δ 8.24-8.22 (m, 1H), 7.95 (s, 1H), 7.89-7.86 (m, 1H), 7.80 (d, 1H), 7.68 (br s, 1H), 4.33-4.29 (m, 1H), 4.14-4.11 (m, 1H), 2.73 (s, 3H); LCMS: 379.8 (M+1); (column; X-Select CSH C-18 (50×3.0 mm, 3.5 μm); RT 3.76 min. 0.05% Aq TFA: ACN; 0.8 mL/min); TLC: 40% EtOAc: hexanes ($R_f$: 0.6).

Synthesis of 2-chloro-7-(2-chloro-5-(trifluoromethyl) phenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(2-chloro-5-(trifluoromethyl) phenyl) ethan-1-one (1.4 g, 3.68 mmol) in 1, 2-dichloroethane (10 mL) under an argon atmosphere was added sodium triacetoxyborohydride (1.6 g, 7.73 mmol) followed by trifluoroacetic acid (281 mL, 3.68 mmol) at room temperature. The reaction mixture was stirred at room temperature for 16 h. After consumption of the starting material (monitored by TLC), the reaction mixture was quenched with a 1 N sodium hydroxide solution (20 mL) and extracted with $CH_2Cl_2$ (2×20 mL). The combined organic extracts were dried over sodium sulfate, filtered and concentrated in vacuo. The crude material was purified by column chromatography using 10% EtOAc:hexanes to afford 2-chloro-7-(2-chloro-5-(trifluoromethyl) phenyl)-8-methyl-7, 8-dihydro-6H-pyrimido [5, 4-b] [1, 4] oxazine (800 mg, 58%) as an off-white solid. $^1$H-NMR (DMSO-$d_6$, 500 MHz): δ 7.88-7.80 (m, 1H), 7.23 (s, 1H), 5.31-5.29 (m, 1H), 4.39-4.30 (m, 2H), 3.01 (s, 3H); LCMS: 365.6 (M+1); (column; X-Select CSH C-18 (50×3.0 mm, 3.5 μm); RT 3.84 min. 0.05% Aq TFA: ACN; 0.8 mL/min); TLC: 25% EtOAc:hexanes ($R_f$: 0.5).

Example 142

Synthesis of (R)-(2-chloro-8-methyl-7, 8-dihydro-6H-pyrimido [5, 4-b] [1, 4] oxazin-7-yl) methanol

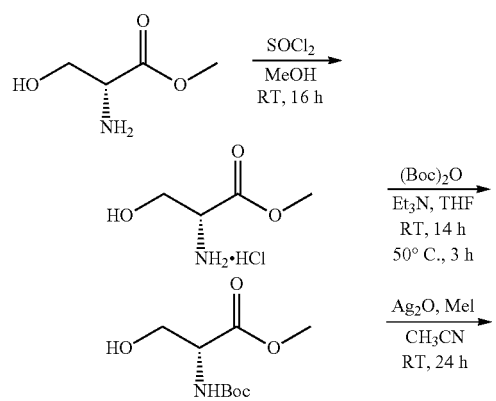

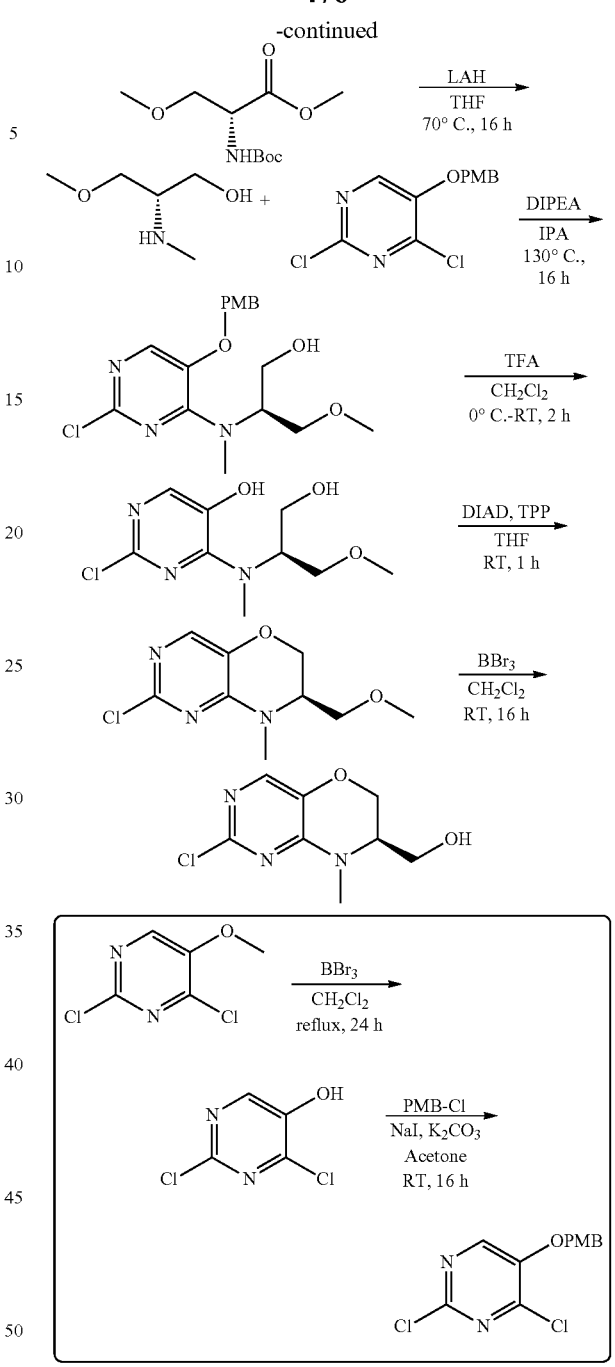

Synthesis of methyl D-serinate hydrochloride

To a stirred solution of D-serine (10 g, 95.23 mmol) in MeOH (100 mL) under an argon atmosphere was added thionylchloride (56.65 g, 476.19 mmol) at 0° C. The reaction mixture was warmed to room temperature and stirred for 16 h. After consumption of the starting material (monitored by TLC), the volatile components were concentrated in vacuo. The crude material was washed with ether (2×100 mL) and dried in vacuo to obtain the methyl D-serinate hydrochloride (10 g, 67.75%) as an off-white solid. $^1$H-NMR (DMSO-$d_6$, 500 MHz): δ 8.60-8.55 (m, 3H), 5.61-5.59 (m, 1H), 4.10-4.08 (m, 1H), 3.83-3.79 (m, 2H), 3.74 (s, 3H); TLC: 10% MeOH/$CH_2Cl_2$ ($R_f$: 0.3).

Synthesis of methyl (tert-butoxycarbonyl)-D-serinate

To a stirred solution of methyl D-serinate (10 g, 67.51 mmol) in THF (160 mL) under an argon atmosphere were added triethylamine (19.4 mL, 138.70 mmol) and Boc anhydride (15 mL, 64.51 mmol) in THF (76 mL) for 30 min at 0° C. The reaction mixture was warmed to room temperature and stirred for 14 h. Then the reaction mixture was again stirred at 50° C. for 3 h. After consumption of the starting material (monitored by TLC), the volatile components were concentrated in vacuo. The residue was diluted with a saturated sodium bicarbonate solution (20 mL) and extracted with ether (3×200 mL). The combined organic extracts were dried over sodium sulfate, filtered and concentrated in vacuo. The crude material was purified by column chromatography using 20% EtOAc:hexanes to afford methyl (tert-butoxycarbonyl)-D-serinate (8 g, 57%) as a colorless liquid. $^1$H-NMR (CDCl$_3$, 500 MHz): δ 5.50-5.47 (m, 1H), 4.41-4.39 (m, 1H), 4.00-3.87 (m, 2H), 3.80 (s, 3H), 2.39-2.31 (m, 1H), 1.44 (s, 9H); TLC: 50% EtOAc:hexanes (R$_f$: 0.5).

Synthesis of methyl N-(tert-butoxycarbonyl)-O-methyl-D-serinate

To a stirred solution of methyl (tert-butoxycarbonyl)-L-serinate (6 g, 27.35 mmol) in CH$_3$CN (240 mL) under an argon atmosphere were added silver oxide (32 g, 136.79 mmol) and methyl iodide (38 g, 273.50 mmol) at room temperature. The reaction mixture was stirred for 24 h at room temperature. After consumption of the starting material (monitored by TLC), the reaction mixture was filtered and washed with EtOAc (200 mL). The filtrate was concentrated in vacuo and the crude material was purified by column chromatography using 15% EtOAc:hexanes to afford methyl N-(tert-butoxycarbonyl)-O-methyl-D-serinate (3.3 g, 52%) as a colorless liquid. $^1$H-NMR (CDCl$_3$, 500 MHz): δ 5.40-5.38 (m, 1H), 4.43-4.40 (m, 1H), 3.80-3.77 (m, 1H), 3.76 (s, 3H), 3.60-3.58 (m, 1H), 3.35 (s, 3H), 1.46 (s, 9H); TLC: 30% EtOAc:hexane (R$_f$: 0.6).

Synthesis of (S)-3-methoxy-2-(methylamino) propan-1-ol

To a stirred solution of methyl N-(tert-butoxycarbonyl)-O-methyl-D-serinate (3.3 g, 14.16 mmol) in THF (85 mL) under an argon atmosphere was added lithium aluminum hydride (1.6 g, 42.48 mmol) portion wise at 0° C. The reaction mixture was stirred at 70° C. for 16 h. After consumption of the starting material (monitored by TLC), the reaction mixture was cooled to 0° C., quenched with water (4 mL), and 15% sodium hydroxide solution (4 mL) and water (3×4 mL) was added. After stirring for 30 min, the reaction mixture was filtered and washed with EtOAc (20 mL). The filtrate was dried over sodium sulfate, filtered and concentrated in vacuo to obtain (S)-3-methoxy-2-(methylamino) propan-1-ol (1.4 g, 87%) as a colorless liquid. $^1$H-NMR (DMSO-d$_6$, 500 MHz): δ 3.39-3.31 (m, 2H), 3.30-3.21 (m, 3H), 2.51-2.49 (m, 2H), 2.28 (s, 3H); TLC: 50% EtOAc:hexane (R$_f$: 0.2).

Synthesis of 2, 4-dichloropyrimidin-5-ol

To a stirred solution of 2, 4-dichloro-5-methoxypyrimidine (20 g, 111.73 mmol) in CH$_2$Cl$_2$ (280 mL) under an argon atmosphere was added borontribromide (54 mL, 558.65 mmol) drop wise at 0° C. The reaction mixture was refluxed for 24 h. After consumption of the starting material (monitored by TLC), the reaction mixture was cooled to 0° C., quenched with a 1N sodium hydroxide solution and stirred for 1 h. Then the reaction mixture was acidified with acetic acid (pH'2-4) and the aqueous layer was extracted with 5% MeOH: CH$_2$Cl$_2$ (2×250 mL). The combined organic extracts were dried over sodium sulfate, filtered and concentrated in vacuo to obtain 2, 4-dichloropyrimidin-5-ol (12 g, 64%) as a pale yellow solid. $^1$H-NMR (DMSO-d$_6$, 500 MHz): δ 8.33 (s, 1H), 4.00 (s, 1H); TLC: 30% EtOAc:hexane (R$_f$: 0.6).

Synthesis of 2, 4-dichloro-5-((4-methoxybenzyl) oxy) pyrimidine

To a stirred solution of 2, 4-dichloropyrimidin-5-ol (6 g, 36.50 mmol) in acetone (60 mL) under an argon atmosphere were added sodium iodide (600 mg, 3.65 mmol), potassium carbonate (13 g, 91.25 mmol) and p-methoxy benzyl chloride (8.6 g, 54.87 mmol) drop wise at room temperature. The reaction mixture was stirred for 16 h. After consumption of the starting material (monitored by TLC), the reaction mixture was concentrated in vacuo. The crude material was purified by column chromatography (basic condition) using 10% EtOAc:hexanes to afford 2, 4-dichloro-5-((4-methoxybenzyl) oxy) pyrimidine (5 g, 48%) as an off-white solid. $^1$H-NMR (DMSO-d$_6$, 400 MHz): δ 8.63 (s, 1H), 7.41 (d, 2H), 6.99 (d, 2H), 5.29 (s, 2H), 3.75 (s, 3H); TLC: 30% EtOAc:hexane (R$_f$: 0.6).

Synthesis of (S)-2-((2-chloro-5-((4-methoxybenzyl) oxy) pyrimidin-4-yl) (methyl) amino)-3-methoxy-propan-1-ol To a stirred solution of (S)-3-methoxy-2-(methylamino) propan-1-ol (1.4 g, 11.73 mmol) in isopropyl alcohol (14 mL) under an argon atmosphere were added diisopropylethylamine (14 mL) and 2,4-dichloro-5-((4-methoxybenzyl) oxy)pyrimidine (3.6 g, 12.90 mmol) at room temperature. The reaction mixture was stirred at 130° C. for 16 h. After consumption of the starting material (monitored by TLC), the volatile components were evaporated in vacuo. The crude material was purified by column chromatography using 20% EtOAc:hexanes to afford (S)-2-((2-chloro-5-((4-methoxybenzyl) oxy) pyrimidin-4-yl) (methyl) amino)-3-methoxypropan-1-ol (1.7 g, 39%) as a pale yellow oil. $^1$H-NMR (CDCl$_3$, 400 MHz): δ 7.72 (s, 1H), 7.31 (d, 2H), 6.90 (d, 2H), 4.94 (s, 2H), 4.85-4.79 (m, 1H), 3.81 (s, 3H), 3.80-3.79 (m, 2H), 3.60-3.50 (m, 2H), 3.30 (s, 3H), 3.11 (s, 3H), 2.41-2.39 (m, 1H); LCMS: 368.5 (M+1); (column; X-Select CSH C-18 (50×3.0 mm, 3.5 μm); RT 3.77 min 0.05% Aq TFA: ACN; 0.80 mL/min); TLC: 50% EtOAc:hexane (R$_f$: 0.4).

Synthesis of (S)-2-((2-chloro-5-((4-methoxybenzyl) oxy)pyrimidin-4-yl)(methyl)amino)-3-methoxypropan-1-ol To a stirred solution of (S)-2-((2-chloro-5-((4-methoxybenzyl) oxy) pyrimidin-4-yl) (methyl) amino)-3-methoxypropan-1-ol (1.7 g, 4.63 mmol) in CH$_2$Cl$_2$ (26 mL) under an argon atmosphere was added trifluoroacetic acid (4.6 mL) at 0° C. The reaction mixture was warmed to room temperature and stirred for 2 h. After consumption of the starting material (monitored by TLC), the reaction mixture was diluted with water (20 mL) and extracted with CH$_2$Cl$_2$ (2×20 mL). The aqueous layer was basified with a saturated sodium bicarbonate solution (50 mL) and extracted with CH$_2$Cl$_2$ (2×20 mL). The combined organic extracts were dried over sodium sulfate, filtered and concentrated in vacuo to obtain (S)-2-((2-chloro-5-((4-methoxybenzyl) oxy) pyrimidin-4-yl) (methyl) amino)-3-methoxypropan-1-ol (500 mg, 45%) as an off-white solid. $^1$H-NMR (DMSO-d$_6$, 500 MHz): δ 9.99 (br s, 1H), 7.59 (s, 1H), 5.00-4.99 (m, 1H), 4.80 (br s, 1H), 3.61-3.50 (m, 3H), 3.49-3.43 (m, 1H), 3.21 (s, 3H), 2.99 (s, 3H); TLC: 80% EtOAc:hexane (R$_f$: 0.3).

Synthesis of (R)-2-chloro-4-((1-hydroxy-3-methoxypropan-2-yl)(methyl)amino)pyrimidin-5-ol To a stirred solution of (S)-2-((2-chloro-5-((4-methoxybenzyl) oxy) pyrimidin-4-yl) (methyl) amino)-3-methoxypropan-1-ol (600 mg, 2.43 mmol) in THF (20 mL) under an argon atmosphere were added triphenylphosphine (954 mg, 3.64 mmol) and diisopropylazodicarboxylate (736 mg, 3.64 mmol) at 0° C. The reaction mixture was warmed to room temperature and stirred for 1 h. After consumption of the starting material (monitored by TLC), the volatile components were concentrated in vacuo. The crude material was purified by column chromatography using 20% EtOAc:hexanes to afford (R)-2-chloro-4-((1-hydroxy-3-methoxypropan-2-yl) (methyl) amino) pyrimidin-5-ol (450 mg, 81%) as a colorless liquid. $^1$H-NMR (CDCl$_3$, 400 MHz): δ 7.63 (s, 1H), 4.39-4.35 (m, 1H), 3.91-3.88 (m, 1H), 3.60-3.50 (m, 2H), 3.49-3.42 (m, 1H), 3.39 (s, 3H), 3.21 (s, 3H); LCMS: 229.9 (M+1); (column; X-Select CSH C-18 (50×3.0 mm, 3.5 μm); RT 2.55 min 0.05% Aq TFA: ACN; 0.80 mL/min); TLC: 50% EtOAc:hexane (R$_f$: 0.5).

Synthesis of (R)-(2-chloro-8-methyl-7, 8-dihydro-6H-pyrimido [5, 4-b] [1, 4] oxazin-7-yl) methanol To a stirred solution of (R)-2-chloro-4-((1-hydroxy-3-methoxypropan-2-yl) (methyl) amino) pyrimidin-5-ol (300 mg, 1.31 mmol) in CH$_2$Cl$_2$ (10 mL) was added borontribromide (0.37 mL, 3.93 mmol) at 0° C. under an argon atmosphere. The reaction mixture was warmed to room temperature and stirred for 16 h. After consumption of the starting material (monitored by TLC), the reaction mixture was cooled to 0° C., quenched with a 2N sodium hydroxide solution, warmed to room temperature and stirred for 30 min. Then the reaction mixture was acidified with acetic acid (pH'3-4) and extracted with CH$_2$Cl$_2$ (2×30 mL). The combined organic extracts were dried over sodium sulfate, filtered and concentrated in vacuo to obtain (R)-(2-chloro-8-methyl-7, 8-dihydro-6H-pyrimido [5, 4-b] [1, 4] oxazin-7-yl) methanol (180 mg, 64%) as a pale yellow solid. $^1$H-NMR (CDCl$_3$, 400 MHz): δ 7.63 (s, 1H), 4.45-4.40 (m, 1H), 3.94-3.90 (m, 1H), 3.89-3.83 (m, 1H), 3.80-3.73 (m, 1H), 3.57-3.51 (m, 1H), 3.23 (s, 3H); LCMS: 215.9 (M+1); (column; X-Select CSH C-18 (50×3.0 mm, 3.5 μm); RT 1.65 min. 0.05% Aq TFA: ACN; 0.80 mL/min); TLC: 50% EtOAc:hexane (R$_f$: 0.3).

Example 143

Synthesis of 2-chloro-7-(4, 5-difluoro-2-(trifluoromethyl) phenyl)-8-methyl-7, 8-dihydro-6H-pyrimido [5, 4-b] [1, 4] oxazine

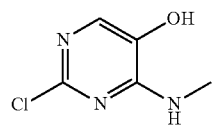

+

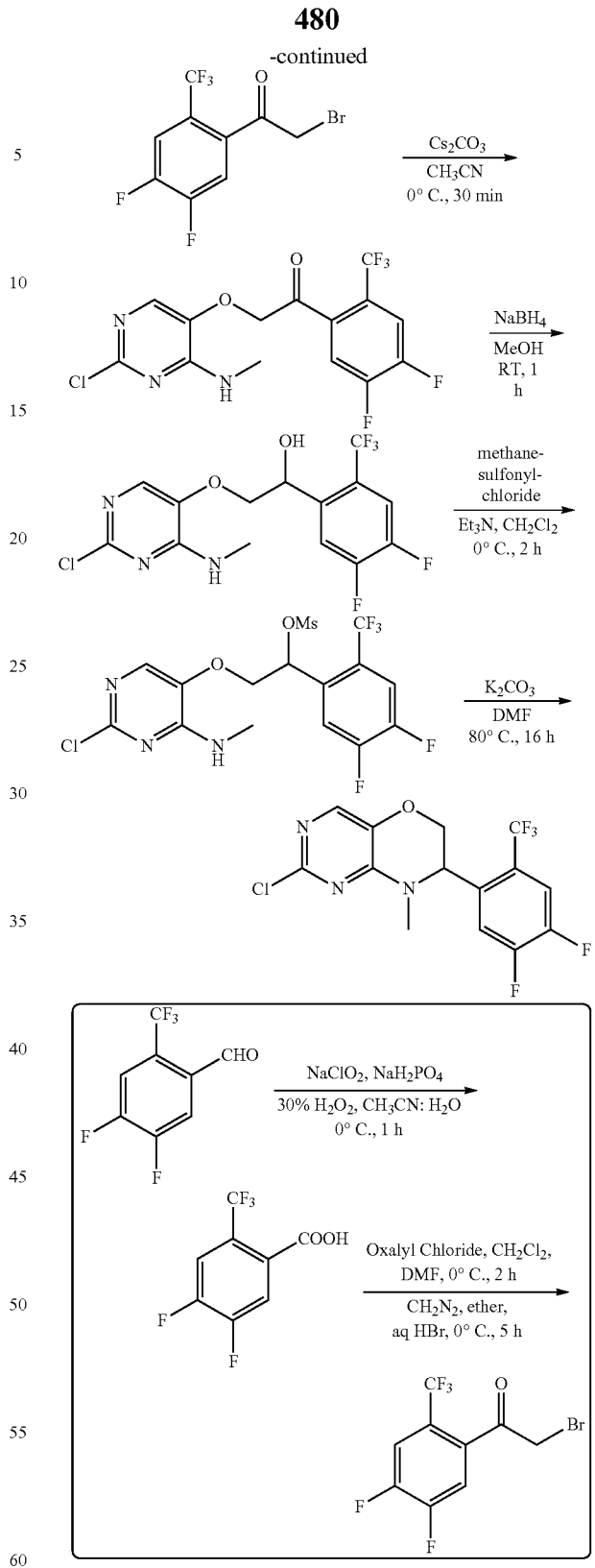

Synthesis of 4, 5-difluoro-2-(trifluoromethyl) benzoic acid

To a stirred solution of 4, 5-difluoro-2-(trifluoromethyl) benzaldehyde (500 mg, 2.38 mmol) in CH$_3$CN: water (1:1, 20 mL) under an argon atmosphere were added sodium dihydrogen phosphate (171 mg, 1.42 mmol), sodium chlorite (535 mg, 5.94 mmol) and 30% hydrogen peroxide (0.3 mL) at 0° C. The reaction mixture was stirred for 1 h at 0° C. After consumption of the starting material (monitored by TLC), the volatile components were evaporated in vacuo. The residue was acidified with a 2 N HCl solution (20 mL) and extracted with EtOAc (2×100 mL). The combined organic extracts were dried over sodium sulfate, filtered and concentrated in vacuo to obtain 4, 5-difluoro-2-(trifluoromethyl) benzoic acid (450 mg, 83%) as a white solid used in the next step without further purification. $^{1}$H-NMR (DMSO-$d_6$, 500 MHz): δ 13.95 (br s, 1H), 8.02-8.00 (m, 1H), 7.99-7.97 (m, 1H); UPLC (column; Acquity UPLC BEH C-18, 2.1×50 mm, 1.7 µm); RT 2.08 min. ACN: 0.025% Aq TFA; 0.5 mL/min; TLC: 5% EtOAc:hexanes ($R_f$: 0.1).

Synthesis of 2-bromo-1-(4, 5-difluoro-2-(trifluoromethyl) phenyl) ethan-1-one

To a stirred solution of 4, 5-difluoro-2-(trifluoromethyl) benzoic acid (500 mg, 1.99 mmol) in $CH_2Cl_2$ (50 mL) were added oxalyl chloride (0.2 mL, 1.99 mmol) and DMF (5 drops) at 0° C. under an argon atmosphere. The reaction mixture was stirred for 2 h at 0° C. After consumption of the starting material (monitored by TLC), the volatile components were concentrated in vacuo. To a stirred solution of the residue in ether (10 mL) was added a diazomethane solution in ether (5 mL) at 0° C. The reaction mixture was stirred for 2 h and aq. HBr (2.5 mL) was added to the reaction mixture at 0° C. The reaction mixture was stirred for 3 h at 0° C. After consumption of the starting material (monitored by TLC), the reaction mixture was quenched with a saturated sodium bicarbonate solution (20 mL) and extracted with EtOAc (2×20 mL). The combined organic extracts were dried over sodium sulfate, filtered and concentrated in vacuo. The crude material was purified by column chromatography using 5% EtOAc:hexane to afford 2-bromo-1-(4, 5-difluoro-2-(trifluoromethyl) phenyl) ethan-1-one (350 mg, 52%) as a pale yellow liquid. $^{1}$H-NMR (CD$_3$OD, 500 MHz): δ 7.90-7.87 (m, 2H), 4.63 (s, 2H); LCMS: 303.1 (M+1); (column; X-Select CSH C-18 (50×3.0 mm, 3.5 µm); RT 3.80 min 5 mM Aq NH$_4$OAc: ACN; 0.80 mL/min); HPLC (column; Eclipse XDB C-18, 150×4.6 mm, 5.0 µm); RT 11.03 min. ACN: 5 mM Aq NH$_4$OAc; 1.0 mL/min; TLC: 10% EtOAc:hexanes ($R_f$: 0.6).

Synthesis of 2-((2-chloro-4-(methylamino) pyrimidin-5-yl) oxy)-1-(4, 5-difluoro-2-(trifluoromethyl) phenyl) ethan-1-one)

To a stirred solution of 2-bromo-1-(4, 5-difluoro-2-(trifluoromethyl) phenyl) ethan-1-one (450 mg, 2.83 mmol) in $CH_3CN$ (25 mL) were added cesium carbonate (950 mg, 3.12 mmol) and 2-bromo-1-(4, 5-difluoro-2-(trifluoromethyl) phenyl) ethan-1-one (2 g, 6.22 mmol) at 0° C. under an argon atmosphere. The reaction mixture was stirred for 30 min at 0° C. After consumption of the starting material (monitored by TLC), the reaction mixture was diluted with water (50 mL) and extracted with EtOAc (2×50 mL). The combined organic extracts were dried over sodium sulfate, filtered and concentrated in vacuo. The crude material was washed with n-pentane (2×5 mL) to afford 2-((2-chloro-4-(methylamino) pyrimidin-5-yl) oxy)-1-(4, 5-difluoro-2-(trifluoromethyl) phenyl) ethan-1-one (800 mg, 75%) as an off-white solid used in the next step without further purification. TLC: 30% EtOAc:hexanes ($R_f$: 0.4).

Synthesis of 2-((2-chloro-4-(methylamino) pyrimidin-5-yl) oxy)-1-(4, 5-difluoro-2-(trifluoromethyl) phenyl) ethan-1-ol To a stirred solution of 2-((2-chloro-4-(methylamino) pyrimidin-5-yl) oxy)-1-(4, 5-difluoro-2-(trifluoromethyl) phenyl) ethan-1-one (800 mg, 2.10 mmol) in MeOH (20 mL) under an argon atmosphere was added sodium borohydride (160 mg, 4.20 mmol) at 0° C. The reaction mixture was warmed to room temperature and stirred for 1 h. After consumption of the starting material (monitored by TLC), the volatile components were evaporated in vacuo. The residue was diluted with water (50 mL) and extracted with EtOAc (2×50 mL). The combined organic extracts were washed with water (20 mL), brine (20 mL), dried over sodium sulfate, filtered and concentrated in vacuo to obtain 2-((2-chloro-4-(methylamino) pyrimidin-5-yl) oxy)-1-(4, 5-difluoro-2-(trifluoromethyl) phenyl) ethan-1-ol (700 mg, 87%) as an off-white solid used in the next step without further purification. $^{1}$H-NMR (DMSO-$d_6$, 500 MHz): δ 8.00-7.90 (m, 2H), 7.64 (s, 1H), 7.47-7.43 (m, 1H), 6.15-6.13 (m, 1H), 5.21-5.19 (m, 1H), 4.08-4.00 (m, 2H), 2.88 (d, 3H); LCMS: 384.3 (M+1); (column; X-Select CSH C-18 (50×3.0 mm, 3.5 µm); RT 3.44 min. 0.05% Aq TFA: ACN; 0.80 mL/min); UPLC (column; Acquity UPLC BEH C-18, 2.1×50 mm, 1.7 µm); RT 2.30 min. ACN: 0.025% Aq TFA; 0.5 mL/min; TLC: 30% EtOAc:hexanes ($R_f$: 0.2).

Synthesis of 2-((2-chloro-4-(methylamino) pyrimidin-5-yl) oxy)-1-(4, 5-difluoro-2-(trifluoromethyl) phenyl) ethyl methanesulfonate To a stirred solution of 2-((2-chloro-4-(methylamino) pyrimidin-5-yl) oxy)-1-(4, 5-difluoro-2-(trifluoromethyl) phenyl) ethan-1-ol (700 mg, 1.82 mmol) in $CH_2Cl_2$ (20 mL) was added triethylamine (370 mg, 3.66 mmol) at 0° C. under an argon atmosphere. The reaction mixture was stirred for 10 min, then methanesulfonyl chloride (250 mg, 2.19 mmol) was added. The reaction mixture was stirred for 2 h at 0° C. After consumption of the starting material (monitored by TLC), the reaction mixture was diluted with water (50 mL) and extracted with $CH_2Cl_2$ (2×50 mL). The combined organic extracts were dried over sodium sulfate, filtered and concentrated in vacuo to obtain 2-((2-chloro-4-(methylamino) pyrimidin-5-yl) oxy)-1-(4, 5-difluoro-2-(trifluoromethyl) phenyl) ethyl methanesulfonate (700 mg, 83%) as an off-white solid used in the next step without further purification. $^{1}$H-NMR (DMSO-$d_6$, 400 MHz): δ 8.10-8.01 (m, 1H), 7.70 (s, 1H), 7.40-7.33 (m, 1H), 6.09-6.06 (m, 1H), 4.59-4.51 (m, 1H), 4.26-4.21 (m, 1H), 3.33 (s, 1H), 3.27 (s, 3H), 2.85 (d, 3H); LCMS: 462.4 (M+1); (column; X-Select CSH C-18 (50×3.0 mm, 3.5 µm); RT 3.65 min. 0.05% Aq TFA: ACN; 0.80 mL/min); UPLC (column; Acquity UPLC BEH C-18, 2.1×50 mm, 1.7 µm); RT 2.46 min. ACN: 0.025% Aq TFA; 0.5 mL/min; TLC: 30% EtOAc:hexanes ($R_f$: 0.3).

Synthesis of 2-chloro-7-(4, 5-difluoro-2-(trifluoromethyl) phenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(4, 5-difluoro-2-(trifluoromethyl) phenyl) ethyl methanesulfonate (700 mg, 1.52 mmol) in DMF (20 mL) under an argon atmosphere was added potassium carbonate (419 mg, 3.03 mmol) at room temperature. The reaction mixture was stirred at 80° C. for 16 h. After consumption of the starting material (monitored by TLC), the reaction mixture was diluted with water (50 mL) and extracted with EtOAc (2×50 mL). The combined organic extracts were washed with water (20 mL), brine (20 mL), dried over sodium sulfate, filtered and concentrated in vacuo. The crude material was purified by column chromatography using 5-15% EtOAc:hexane to afford 2-chloro-7-(4, 5-difluoro-2-(trifluoromethyl) phenyl)-8-methyl-7, 8-dihydro-6H-pyrimido [5, 4-b] [1, 4] oxazine (450 mg, 82%) as a pale yellow solid. $^1$H-NMR (DMSO-$d_6$, 400 MHz): δ 8.10-8.01 (m, 1H), 7.82 (s, 1H), 7.41-7.39 (m, 1H), 5.08-5.05 (m, 1H), 4.30 (d, 1H), 4.15 (d, 1H), 2.91 (s, 3H); LCMS: 366.3 (M+1); (column; X-Select CSH C-18 (50×3.0 mm, 3.5 μm); RT 4.52 min. 0.05% Aq TFA: ACN; 0.80 mL/min); UPLC (column; Acquity UPLC BEH C-18, 2.1× 50 mm, 1.7 μm); RT 2.67 min. ACN: 0.025% Aq TFA; 0.5 mL/min; TLC: 20% EtOAc:hexanes ($R_f$: 0.5).

Example 144

Synthesis of 2-chloro-8-methyl-7-(2, 4, 5-trifluorophenyl)-7, 8-dihydro-6H-pyrimido [5, 4-b] [1, 4] oxazine

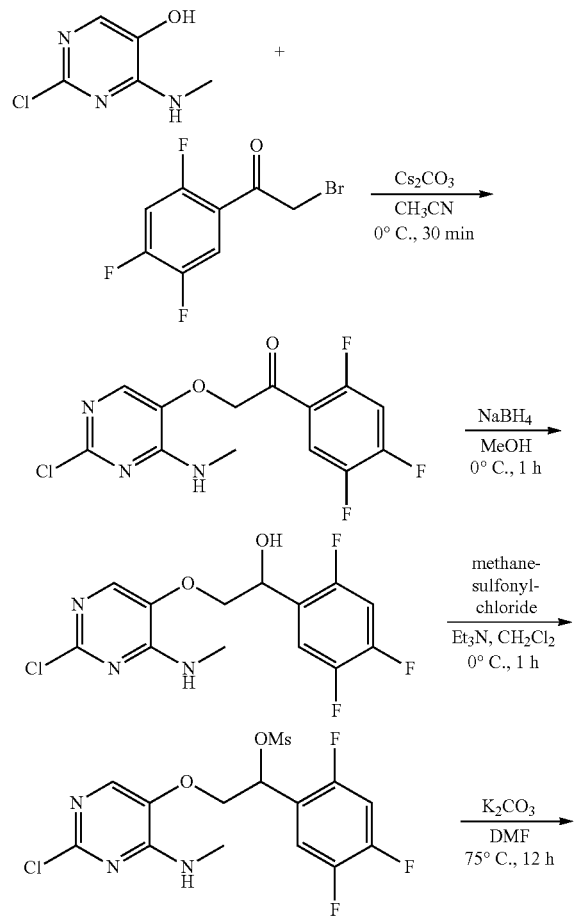

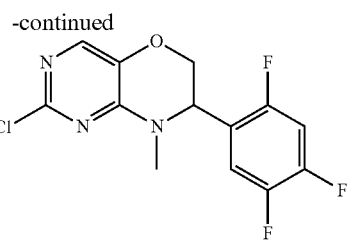

Synthesis of 2-((2-chloro-4-(methylamino) pyrimidin-5-yl) oxy)-1-(2, 4, 5-trifluorophenyl) ethan-1-one To a stirred solution of 2-chloro-4-(methylamino) pyrimidin-5-ol (500 mg, 3.14 mmol) in $CH_3CN$ (5 mL) under an argon atmosphere was added cesium carbonate (2.2 g, 6.91 mmol) at 0° C. After stirring for 10 min, 2-bromo-1-(2, 4, 5-trifluorophenyl) ethan-1-one (800 mg, 3.45 mmol) was added to the reaction mixture at 0° C. The reaction mixture was stirred for 30 min. After consumption of the starting material (monitored by TLC), the reaction mixture was diluted with water (50 mL) and extracted with EtOAc (2×50 mL). The combined organic extracts were dried over sodium sulfate, filtered and concentrated in vacuo. The crude material was washed with EtOAc:hexane (1:1, 2×20 mL) to obtain 2-((2-chloro-4-(methylamino) pyrimidin-5-yl) oxy)-1-(2, 4, 5-trifluorophenyl) ethan-1-one (550 mg, 55%) as a pale yellow solid used in the next step without further purification. $^1$H-NMR (DMSO-$d_6$, 500 MHz): δ 7.88 (s, 1H), 7.70-7.63 (m, 2H), 7.53 (s, 1H), 4.17-4.10 (m, 2H), 2.81 (s, 3H); LCMS: 332.2 (M+1); (column; X-Select CSH C-18 (50×3.0 mm, 3.5 μm); RT 4.07 min 0.05% Aq TFA: ACN; 0.80 mL/min); TLC: 30% EtOAc:hexanes ($R_f$: 0.7).

Synthesis of 2-((2-chloro-4-(methylamino) pyrimidin-5-yl) oxy)-1-(2, 4, 5-trifluorophenyl) ethan-1-ol To a stirred solution of 2-((2-chloro-4-(methylamino) pyrimidin-5-yl) oxy)-1-(2, 4, 5-trifluorophenyl) ethan-1-one (200 mg, 0.60 mmol) in MeOH (1 mL) under an argon atmosphere was added sodium borohydride (35 mg, 0.90 mmol) at 0° C. The reaction mixture was stirred at 0° C. for 1 h. After consumption of the starting material (monitored by TLC), the reaction mixture was diluted with an ammonium chloride solution (20 mL) and extracted with EtOAc (2×20 mL). The combined organic extracts were dried over sodium sulfate, filtered and concentrated in vacuo to obtain 2-((2-chloro-4-(methylamino) pyrimidin-5-yl) oxy)-1-(2, 4, 5-trifluorophenyl) ethan-1-ol (140 mg, crude) as a pale yellow solid used in the next step without further purification. $^1$H-NMR (DMSO-$d_6$, 500 MHz): δ 7.69 (s, 1H), 7.68-7.53 (m, 2H), 7.41-7.39 (m, 1H), 6.00 (s, 1H), 5.20-5.18 (m, 1H), 4.20-4.17 (m, 1H), 3.99 (t, 1H), 2.83 (d, 3H); LCMS: 334.3 (M+1); (column; X-Select CSH C-18 (50×3.0 mm, 3.5 μm); RT 3.86 min. 0.05% Aq TFA: ACN; 0.80 mL/min); TLC: 50% EtOAc:hexanes ($R_f$: 0.2).

Synthesis of 2-((2-chloro-4-(methylamino) pyrimidin-5-yl) oxy)-1-(2, 4, 5-trifluorophenyl) ethyl methanesulfonate To a stirred solution of 2-((2-chloro-4-(methylamino) pyrimidin-5-yl) oxy)-1-(2, 4, 5-trifluorophenyl) ethan-1-ol (140 mg, 0.42 mmol) in $CH_2Cl_2$ (2 mL) under an argon atmosphere were added triethylamine (0.12 mL, 0.84 mmol) followed by methanesulfonyl chloride (0.05 mL, 0.63 mmol) at 0° C. The reaction mixture was stirred at 0° C. for 1 h. After consumption of the starting material (monitored by TLC), the reaction mixture was basified with water (50 mL) and extracted with CH$_2$Cl$_2$ (2×50 mL). The combined organic extracts were dried over sodium sulfate, filtered and concentrated in vacuo to obtain 2-((2-chloro-4-(methylamino) pyrimidin-5-yl) oxy)-1-(2, 4, 5-trifluorophenyl) ethyl methanesulfonate (200 mg, crude) as a pale yellow solid used in the next step without further purification. $^1$H-NMR (CDCl$_3$, 500 MHz): δ 7.43 (s, 1H), 7.35-7.30 (m, 1H), 7.09-7.04 (m, 1H), 6.20-6.18 (m, 1H), 6.13 (br s, 1H), 4.25-4.20 (m, 2H), 3.13 (s, 3H), 3.06-3.03 (m, 3H); TLC: 50% EtOAc:hexanes (R$_f$: 0.5).

Synthesis of 2-chloro-8-methyl-7-(2, 4, 5-trifluorophenyl)-7, 8-dihydro-6H-pyrimido [5, 4-b] [1, 4] oxazine To a stirred solution of 2-((2-chloro-4-(methylamino) pyrimidin-5-yl) oxy)-1-(2, 4, 5-trifluorophenyl) ethyl methanesulfonate (200 mg, 0.48 mmol) in DMF (1 mL) under an argon atmosphere was added potassium carbonate (100 mg, 0.72 mmol) at room temperature. The reaction mixture was heated at 75° C. for 12 h. After consumption of the starting material (monitored by TLC), the reaction mixture was diluted with water (20 mL) and extracted with EtOAc (2×20 mL). The combined organic extracts were dried over sodium sulfate, filtered and concentrated in vacuo. The crude material was purified by column chromatography using 10% EtOAc:hexane to afford 2-chloro-8-methyl-7-(2, 4, 5-trifluorophenyl)-7, 8-dihydro-6H-pyrimido [5, 4-b] [1, 4] oxazine (80 mg, 52%) as an off-white solid. $^1$H-NMR (CDCl$_3$, 500 MHz): δ 7.73 (s, 1H), 7.06-7.00 (m, 1H), 6.88-6.81 (m, 1H), 4.90 (s, 1H), 4.30-4.20 (m, 2H), 3.17 (s, 3H); LCMS: 316.3 (M+1); (column; X-Select CSH C-18 (50×3.0 mm, 3.5 μm); RT 4.34 min 0.05% Aq TFA: ACN; 0.80 mL/min); TLC: 50% EtOAc:hexanes (R$_f$: 0.7).

Example 145

Synthesis of 2-chloro-7-(2, 4-difluorophenyl)-8-methyl-7, 8-dihydro-6H-pyrimido [5, 4-b] [1, 4] oxazine

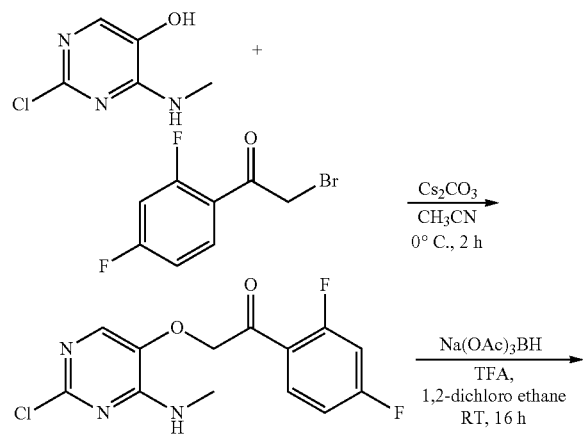

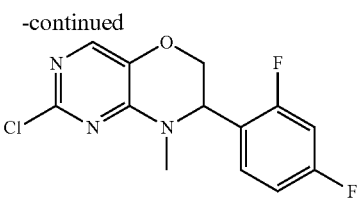

Synthesis of 2-((2-chloro-4-(methylamino) pyrimidin-5-yl) oxy)-1-(2, 4-difluorophenyl) ethan-1-one To a stirred solution of 2-chloro-4-(methylamino) pyrimidin-5-ol (500 mg, 3.14 mmol) in CH$_3$CN (10 mL) under an argon atmosphere were added cesium carbonate (2 g, 6.28 mmol). After stirring for 5 min, 2-bromo-1-(2, 4-difluorophenyl) ethan-1-one (812 mg, 3.46 mmol) was added at 0° C. The reaction mixture was stirred for 2 h at 0° C. After consumption of the starting material (monitored by TLC), the reaction mixture was diluted with a saturated sodium bicarbonate solution (20 mL) and extracted with EtOAc (2×20 mL). The combined organic extracts were dried over sodium sulfate, filtered and concentrated in vacuo. The crude material was purified by column chromatography using 15-20% EtOAc:hexanes to afford 2-((2-chloro-4-(methylamino) pyrimidin-5-yl) oxy)-1-(2, 4-difluorophenyl) ethan-1-one (620 mg, 63%) an off-white solid. $^1$H-NMR (DMSO-d$_6$, 400 MHz): δ 7.85 (s, 1H), 7.70-7.67 (m, 1H), 7.39 (s, 1H), 7.30 (t, 1H), 7.19 (t, 1H), 4.15 (d AB q, 1H), 4.08 (d AB q, 1H), 2.80 (s, 3H); LCMS: 313.8 (M+1); (column; X-Select CSH C-18 (50×3.0 mm, 3.5 μm); RT 3.43 min. 0.05% Aq TFA: ACN; 0.8 mL/min); TLC: 50% EtOAc: hexanes (R$_f$: 0.3).

Synthesis of 2-chloro-7-(2, 4-difluorophenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(2, 4-difluorophenyl) ethan-1-one (600 mg, 1.91 mmol) in 1, 2-dichloroethane (12 mL) under an argon atmosphere were added sodium triacetoxyborohydride (812 mg, 3.83 mmol) and trifluoroacetic acid (147 mL, 1.91 mmol) at room temperature. The reaction mixture was stirred for 16 h at room temperature. After consumption of the starting material (monitored by TLC), the reaction mixture was diluted with a 1N sodium hydroxide solution (20 mL) and extracted with CH$_2$Cl$_2$ (2×20 mL). The combined organic extracts were dried over sodium sulfate, filtered and concentrated in vacuo. The crude material was purified by column chromatography using 10-15% EtOAc: hexanes to afford 2-chloro-7-(2,4-difluorophenyl)-8-methyl-7,8-dihydro-6H-pyrimido [5, 4-b] [1, 4] oxazine (500 mg, 87%) as a pale yellow solid. $^1$H-NMR (CDCl$_3$, 400 MHz): δ 7.70 (s, 1H), 6.99-6.81 (m, 3H), 4.92-4.90 (m, 1H), 4.24-4.20 (m, 2H), 3.10 (s, 3H); LCMS: 298.1 (M+1); (column; X-Select CSH C-18 (50×3.0 mm, 3.5 μm); RT 4.20 min. 0.05% Aq TFA: ACN; 0.8 mL/min); TLC: 50% EtOAc: hexanes (R$_f$: 0.6).

Example 146

Synthesis of 2-chloro-8-methyl-7-(trifluoromethyl)-7, 8-dihydro-6H-pyrimido [5, 4-b] [1, 4] oxazine

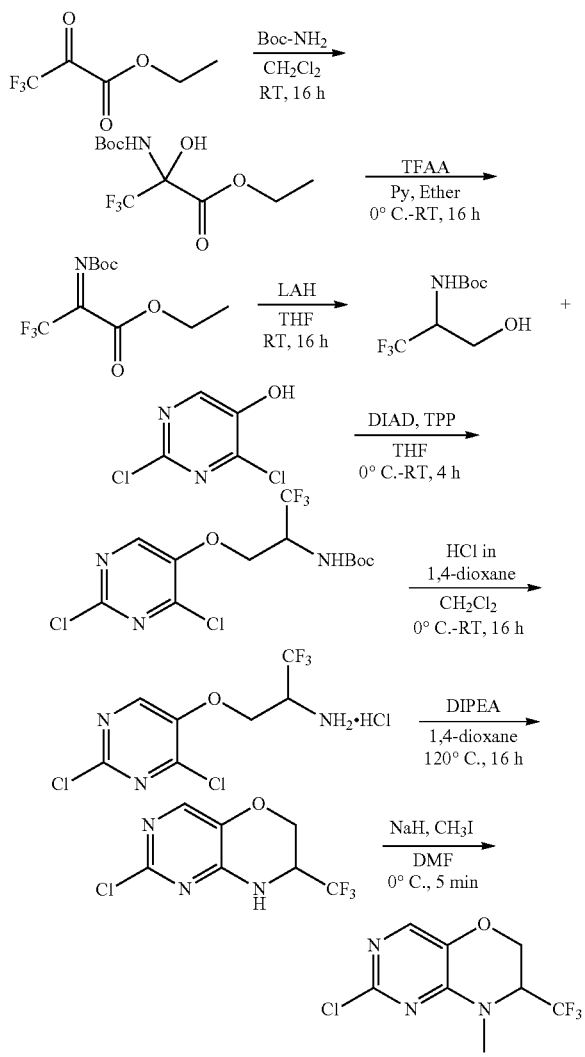

Synthesis of ethyl 2-((tert-butoxycarbonyl) amino)-3, 3, 3-trifluoro-2-hydroxypropanoate To a stirred solution of ethyl 3, 3, 3-trifluoro-2-oxopropanoate (25 g, 147.05 mmol) in $CH_2Cl_2$ (250 mL) under an argon atmosphere was added Boc-amine (19 g, 161.76 mmol) at room temperature. The reaction mixture was stirred for 16 h at room temperature. After consumption of the starting material (monitored by TLC), the volatile components were evaporated in vacuo to obtain ethyl 2-((tert-butoxycarbonyl) amino)-3, 3, 3-trifluoro-2-hydroxypropanoate (40 g, 95%) as pale yellow oil used in the next step without further purification. TLC: 20% EtOAc:hexane ($R_f$: 0.5).

Synthesis of ethyl 2-((tert-butoxycarbonyl)imino)-3, 3,3-trifluoropropanoate To a stirred solution of ethyl 2-((tert-butoxycarbonyl) amino)-3, 3, 3-trifluoro-2-hydroxypropanoate (20 g, 69.56 mmol) in ether (300 mL) under an argon atmosphere were added trifluoroacetic anhydride (14.6 g, 69.56 mmol) and pyridine (11.2 mL, 139.12 mmol) at 0° C. The reaction mixture was warmed to room temperature and stirred for 16 h. After consumption of the starting material (monitored by TLC), the reaction mixture was filtered. The filtrate was washed with water (100 mL), dried over sodium sulfate, filtered and concentrated in vacuo to obtain ethyl 2-((tert-butoxycarbonyl)imino)-3,3,3-trifluoropropanoate (11 g, 59%) as an off-white solid used without further purification. $^1$H-NMR (DMSO-$d_6$, 400 MHz): δ 4.26-4.11 (m, 2H), 1.38 (s, 9H), 1.19 (t, 3H); TLC: 20% EtOAc:hexane ($R_f$: 0.5).

Synthesis of tert-butyl (1,1,1-trifluoro-3-hydroxypropan-2-yl)carbamate

To a stirred solution of ethyl 2-((tert-butoxycarbonyl) imino)-3,3,3-trifluoropropanoate (11 g, 40.81 mmol) in THF (2.75 mL) under an argon atmosphere was added lithium aluminum hydride (4.65 g, 122.44 mmol) portion wise at 0° C. The reaction mixture was warmed to room temperature and stirred for 16 h. After consumption of the starting material (monitored by TLC), the reaction mixture was diluted with water (5 mL) and basified with a 15% sodium hydroxide solution (5 mL) at 0° C. The reaction mixture was warmed to room temperature and stirred for 1 h. The reaction mixture was filtered and washed with EtOAc (2×20 mL). The combined organic extracts were dried over sodium sulfate, filtered and concentrated in vacuo to obtain tert-butyl (1,1,1-trifluoro-3-hydroxypropan-2-yl)carbamate (6 g, 64%) as an off-white solid. $^1$H-NMR (DMSO-$d_6$, 400 MHz): δ 6.11 (br s, 1H), 5.04 (br s, 1H), 4.21-4.07 (m, 1H), 3.69-3.45 (m, 2H), 1.37 (d, 9H); TLC: 30% EtOAc:hexane ($R_f$: 0.3).

Synthesis of tert-butyl (3-((2,4-dichloropyrimidin-5-yl)oxy)-1,1,1-trifluoropropan-2-yl)carbamate To a stirred solution of tert-butyl (1,1,1-trifluoro-3-hydroxypropan-2-yl)carbamate (65 g, 26.20 mmol) in THF (180 mL) under an argon atmosphere were added diisopropylazodicarboxylate (7.9 g, 39.30 mmol), triphenylphosphine (10 g, 39.30 mmol) and 2, 4-dichloropyrimidin-5-ol (4.3 g, 26.20 mmol) at 0° C. The reaction mixture was warmed to room temperature and stirred for 4 h. After consumption of the starting material (monitored by TLC), the volatile components were concentrated in vacuo. The crude material was purified by column chromatography using 20-30% EtOAc:hexane to afford tert-butyl (3-((2,4-dichloropyrimidin-5-yl)oxy)-1,1,1-trifluoropropan-2-yl)carbamate (3.5 g, 36%) as an off-white solid. $^1$H-NMR (CDCl$_3$, 400 MHz): δ 8.21 (s, 1H), 5.21-5.18 (m, 1H), 4.74 (br s, 1H), 4.43-4.18 (m, 2H), 1.48 (s, 9H); TLC: 50% EtOAc:hexane ($R_f$: 0.5).

Synthesis of 3-((2, 4-dichloropyrimidin-5-yl) oxy)-1, 1, 1-trifluoropropan-2-amine hydrochloride To a stirred solution of tert-butyl (3-((2,4-dichloropyrimidin-5-yl)oxy)-1,1,1-trifluoropropan-2-yl)carbamate (3.5 g, 9.30 mmol) in $CH_2Cl_2$ (30 mL) under an argon atmosphere was added 4N HCl in 1, 4-dioxane (10 mL) at 0° C. The reaction mixture was warmed to room temperature and stirred for 16 h. After consumption of the starting material (monitored by TLC), the volatile components were concentrated in vacuo. The crude material was washed with n-pentane (2×10 mL) to obtain 3-((2,4-dichloropyrimidin-5-yl)

oxy)-1,1,1-trifluoropropan-2-amine hydrochloride (2.2 g) as an off-white solid. LCMS: 316.8 (M+CH₃CN); (column; Ascentis Express C-18 (50×3.0 mm, 2.7 μm); RT 1.82 min. 0.025% Aq TFA+5% ACN: ACN+5% 0.025% Aq TFA; 1.2 mL/min); TLC: 30% EtOAc:hexane ($R_f$: 0.3).

Synthesis of 2-chloro-7-(trifluoromethyl)-7, 8-dihydro-6H-pyrimido [5, 4-b] [1, 4] oxazine To a stirred solution of 3-((2,4-dichloropyrimidin-5-yl) oxy)-1,1,1-trifluoropropan-2-amine hydrochloride (2.2 g, 7.97 mmol) in 1, 4-dioxane (5.5 mL) under an argon atmosphere was added diisopropylethylamine (5.5 mL, 31.88 mmol) at room temperature. The reaction mixture was stirred at 120° C. for 16 h. After consumption of the starting material (monitored by TLC), the reaction mixture was diluted with water (50 mL) and extracted with EtOAc (2×50 mL). The combined organic extracts were dried over sodium sulfate, filtered and concentrated in vacuo to obtain 2-chloro-7-(trifluoromethyl)-7, 8-dihydro-6H-pyrimido [5, 4-b] [1, 4] oxazine (1.6 g, 84%) as a pale yellow solid. ¹H-NMR (CDCl₃, 400 MHz): δ 7.90 (s, 1H), 7.43 (br s, 1H), 5.01-4.97 (m, 1H), 4.4.61-4.58 (m, 1H), 4.17-4.09 (m, 1H); LCMS: 239.8 (M+1); (column; Ascentis Express C-18 (50× 3.0 mm, 2.7 μm); RT 1.82 min. 0.025% Aq TFA+5% ACN: ACN+5% 0.025% Aq TFA; 1.2 mL/min); TLC: 30% EtOAc:hexane ($R_f$: 0.4).

Synthesis of 2-chloro-8-methyl-7-(trifluoromethyl)-7, 8-dihydro-6H-pyrimido [5, 4-b] [1, 4] oxazine To a stirred solution of 2-chloro-7-(trifluoromethyl)-7, 8-dihydro-6H-pyrimido [5, 4-b] [1, 4] oxazine (1.6 g, 6.69 mmol) in DMF (20 mL) under an argon atmosphere was added sodium hydride (193 mg, 8.03 mmol) at 0° C. The reaction mixture was stirred for 5 min at 0° C., then methyliodide (1.14 g, 8.03 mmol) was added to the reaction mixture at 0° C. The reaction mixture was stirred for 5 min at 0° C. After consumption of the starting material (monitored by TLC), the reaction mixture was diluted with water (50 mL) and extracted with EtOAc (2×50 mL). The combined organic extracts were dried over sodium sulfate, filtered and concentrated in vacuo. The crude material was purified by column chromatography using 20% EtOAc:hexane to afford 2-chloro-8-methyl-7-(trifluoromethyl)-7, 8-dihydro-6H-pyrimido [5, 4-b] [1, 4] oxazine (1.2 g, 71%) as a pale yellow oil. ¹H-NMR (400 MHz, CDCl₃): δ 7.82 (s, 1H), 4.62 (d, 1H), 4.03-4.00 (m, 1H), 3.99-3.95 (m, 1H), 3.31 (s, 3H); LCMS: 253.8 (M+1); (column; Ascentis Express C-18 (50×3.0 mm, 2.7 μm); RT 2.18 min. 0.025% Aq TFA+5% ACN: ACN+5% 0.025% Aq TFA; 1.2 mL/min); TLC: 30% EtOAc:hexane ($R_f$: 0.3).

Example 147

Synthesis of (S)-2-chloro-8-methyl-7-(phenoxymethyl)-7, 8-dihydro-6H-pyrimido [5, 4-b] [1, 4] oxazine

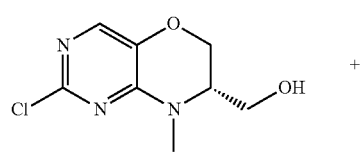
+

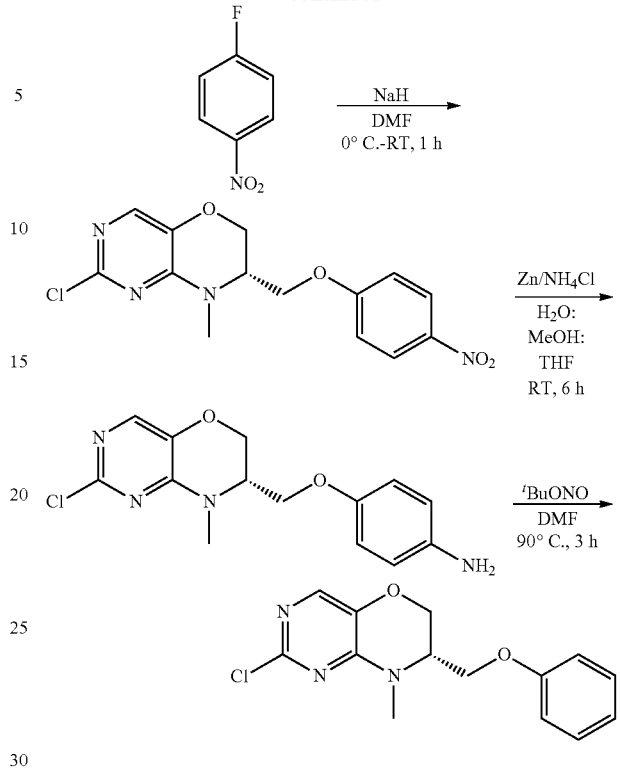

Synthesis of (S)-(2-chloro-8-methyl-7, 8-dihydro-6H-pyrimido [5, 4-b] [1, 4] oxazin-7-yl) methanol To a stirred solution of (S)-(2-chloro-8-methyl-7, 8-dihydro-6H-pyrimido [5, 4-b] [1, 4] oxazin-7-yl) methanol (150 mg, 0.69 mmol) in DMF (1 mL) under an argon atmosphere was added sodium hydride (35 mg, 1.04 mmol) at 0° C. The reaction mixture was stirred for 5 min, then 1-fluoro-4-nitrobenzene (118 mg, 0.83 mmol) was added to the reaction mixture at 0° C. The reaction mixture was warmed to room temperature and stirred for 1 h. After consumption of the starting material (monitored by TLC), the reaction was quenched with ice cold water (50 mL) and extracted with EtOAc (2×50 mL). The combined organic extracts were dried over sodium sulfate, filtered and concentrated in vacuo. The crude material was purified by column chromatography using 30% EtOAc:hexanes to afford (S)-2-chloro-8-methyl-7-((4-nitrophenoxy) methyl)-7, 8-dihydro-6H-pyrimido [5, 4-b] [1, 4] oxazine (100 mg, 47%) as an off-white solid. ¹H-NMR (CDCl₃, 400 MHz): δ 8.25 (d, 2H), 7.73 (s, 1H), 7.00 (d, 2H), 4.52 (d, 1H), 4.21 (d, 2H), 4.10-4.05 (m, 1H), 3.99-3.93 (m, 1H), 3.35 (s, 3H); LCMS: 336.9 (M+1); (column; X-Select CSH C-18 (50×3.0 mm, 3.5 μm); RT 3.54 min 0.05% Aq TFA: ACN; 0.80 mL/min).

Synthesis of (S)-4-((2-chloro-8-methyl-7, 8-dihydro-6H-pyrimido [5, 4-b] [1, 4] oxazin-7-yl) methoxy) aniline To a stirred solution of (S)-2-chloro-8-methyl-7-((4-nitrophenoxy) methyl)-7, 8-dihydro-6H-pyrimido [5, 4-b] [1, 4] oxazine (150 mg, 0.52 mmol) in THF (2.5 mL) under an argon atmosphere were added ammonium chloride (56 mg, 1.04 mmol) in water:MeOH (1:1, 2 mL) and zinc powder (69 mg, 1.04 mmol) at room temperature. The reaction mixture was stirred for 6 h at room temperature. After consumption of the starting material (monitored by TLC), the reaction was filtered and the filtrate was diluted with water (50 mL) and extracted with EtOAc (2×50 mL). The combined organic extracts were dried over sodium sulfate, filtered and concentrated in vacuo to obtain (S)-4-((2-chloro-8-methyl-7, 8-dihydro-6H-pyrimido [5, 4-b] [1, 4] oxazin-7-yl) methoxy) aniline (130 mg, 89%) as a pale yellow solid. $^1$H-NMR (CDCl$_3$, 400 MHz): δ 7.69 (s, 1H), 6.71 (d, 2H), 6.63 (d, 2H), 4.50 (d, 1H), 4.05-3.95 (m, 3H), 3.83-3.77 (m, 1H), 3.29 (s, 3H); LCMS: 306.9 (M+1); (column; X-Select CSH C-18 (50×3.0 mm, 3.5 μm); RT 2.03 min 0.05% Aq TFA: ACN; 0.80 mL/min).

Synthesis of (S)-2-chloro-8-methyl-7-(phenoxymethyl)-7, 8-dihydro-6H-pyrimido [5, 4-b] [1, 4] oxazine To a stirred solution of (S)-4-((2-chloro-8-methyl-7, 8-dihydro-6H-pyrimido [5, 4-b] [1, 4] oxazin-7-yl) methoxy) aniline (130 mg, 0.42 mmol) in DMF (3 mL) under an argon atmosphere was added tert-butyl nitrite (87 mg, 0.84 mmol) drop wise at 0° C. The reaction mixture was stirred at 90° C. for 3 h. After consumption of the starting material (monitored by TLC), the reaction was acidified with acetic acid solution and concentrated in vacuo. The crude material was purified by column chromatography using 10% EtOAc: hexanes to afford (S)-2-chloro-8-methyl-7-(phenoxymethyl)-7, 8-dihydro-6H-pyrimido [5, 4-b] [1, 4] oxazine (110 mg, 89%) as an off-white solid. $^1$H-NMR (CDCl$_3$, 400 MHz): δ 7.70 (s, 1H), 7.31-7.25 (m, 2H), 7.00 (t, 1H), 6.89 (d, 2H), 4.50 (d, 1H), 4.10-4.02 (m, 2H), 4.00 (d, 1H), 3.89-3.83 (m, 1H), 3.30 (s, 3H); LCMS: 291.9 (M+1); (column; X-Select CSH C-18 (50×3.0 mm, 3.5 μm); RT 3.45 min 0.05% Aq TFA: ACN; 0.80 mL/min).

Example 148

Synthesis of (R)-2-chloro-8-methyl-7-(phenoxymethyl)-7, 8-dihydro-6H-pyrimido [5, 4-b] [1, 4] oxazine

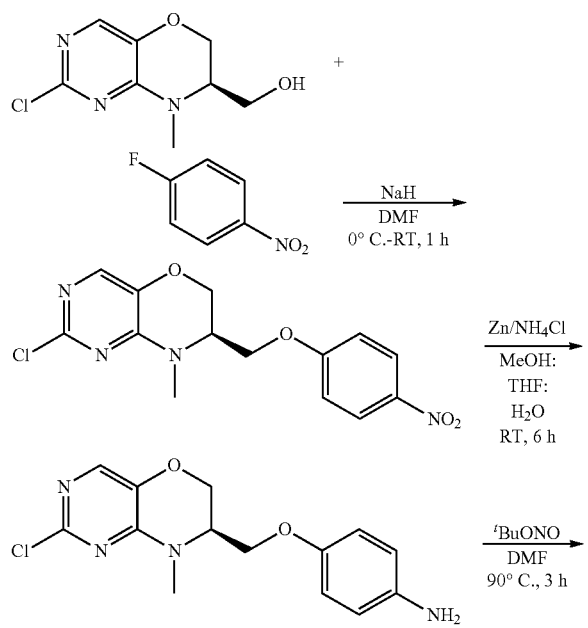

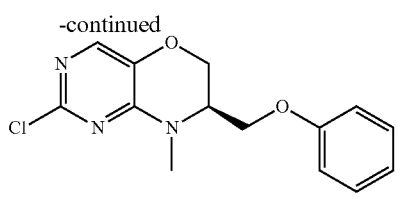

Synthesis of (R)-2-chloro-8-methyl-7-((4-nitrophenoxy) methyl)-7, 8-dihydro-6H-pyrimido [5, 4-b] [1, 4] oxazine To a stirred solution of (R)-(2-chloro-8-methyl-7, 8-dihydro-6H-pyrimido [5, 4-b] [1, 4] oxazin-7-yl) methanol (300 mg, 1.39 mmol) in DMF (5 mL) under an argon atmosphere was added sodium hydride (100 mg, 2.04 mmol) at 0° C. After stirring the reaction mixture for 5 min, 1-fluoro-4-nitrobenzene (230 mg, 1.67 mmol) was added at 0° C. The reaction mixture was warmed to room temperature and stirred for 1 h. After consumption of the starting material (monitored by TLC), the reaction mixture was diluted with ice cold water (50 mL) and extracted with EtOAc (2×50 mL). The combined organic extracts were dried over sodium sulfate, filtered and concentrated in vacuo to obtain (R)-2-chloro-8-methyl-7-((4-nitrophenoxy) methyl)-7, 8-dihydro-6H-pyrimido [5, 4-b] [1, 4] oxazine (200 mg, 42%) as a brown solid. LC-MS: 336.8 (M+1); (column; X-Select CSH C-18 (50×3.0 mm, 3.5 μm); RT 3.53 min 0.05% Aq TFA: ACN; 0.80 mL/min); TLC: 50% EtOAc:hexane (R$_f$: 0.6).

Synthesis of (R)-4-((2-chloro-8-methyl-7, 8-dihydro-6H-pyrimido [5, 4-b] [1, 4] oxazin-7-yl) methoxy) aniline To a stirred solution of (R)-2-chloro-8-methyl-7-((4-nitrophenoxy) methyl)-7, 8-dihydro-6H-pyrimido [5, 4-b] [1, 4] oxazine (200 mg, 0.59 mmol) in THF (10 mL) under an argon atmosphere were added ammonium chloride (64 mg, 1.19 mmol) in MeOH: H$_2$O (1:1, 20 mL) and zinc powder (78 mg, 1.19 mmol) portion wise at room temperature. The reaction mixture was stirred for 6 h at room temperature. After consumption of the starting material (monitored by TLC), the reaction was filtered and the filtrate was concentrated in vacuo. The residue was diluted with water (50 mL) and extracted with EtOAc (2×50 mL). The combined organic extract was dried over sodium sulfate, filtered and concentrated in vacuo to obtain (R)-4-((2-chloro-8-methyl-7, 8-dihydro-6H-pyrimido [5, 4-b] [1, 4] oxazin-7-yl) methoxy) aniline (160 mg, 88%) as a white solid. LC-MS: 306.8 (M+1); (column; X-Select CSH C-18 (50×3.0 mm, 3.5 μm); RT 2.05 min 0.05% Aq TFA: ACN; 0.80 mL/min); TLC: 50% EtOAc:hexane (R$_f$: 0.3).

Synthesis of (R)-2-chloro-8-methyl-7-(phenoxymethyl)-7, 8-dihydro-6H-pyrimido [5, 4-b] [1, 4] oxazine To a stirred solution of (R)-4-((2-chloro-8-methyl-7, 8-dihydro-6H-pyrimido [5, 4-b] [1, 4] oxazin-7-yl) methoxy) aniline (160 mg, 0.52 mmol) in DMF (4 mL) under an argon atmosphere was added tert-butyl nitrite (107 mg, 1.04 mmol) at 0° C. The reaction mixture was stirred at 90° C. for 3 h. After consumption of the starting material (monitored by TLC), the reaction mixture was acidified with acetic acid (2 mL) and concentrated in vacuo. The crude material was purified by column chromatography using 40% EtOAc: hexanes to afford (R)-2-chloro-8-methyl-7-(phenoxymethyl)-7, 8-dihydro-6H-pyrimido [5, 4-b] [1, 4] oxazine (100 mg, 66%) as an off-white solid. $^1$H-NMR (CDCl$_3$, 400 MHz): δ 7.70 (s, 1H), 7.30-7.25 (m, 2H), 7.00 (t, 1H), 6.90 (d, 2H), 4.50 (d, 1H), 4.11-4.01 (m, 3H), 3.90-3.80 (m, 1H), 3.30 (s, 3H); LC-MS: 291.8 (M+1); (column; X-Select CSH C-18 (50×3.0 mm, 3.5 μm); RT 3.57 min 0.05% Aq TFA: ACN; 0.80 mL/min); TLC: 50% EtOAc:hexane (R$_f$: 0.7).

Example 149

Synthesis of 2-chloro-7-(5-methoxy-2-methylphenyl)-8-methyl-7, 8-dihydro-6H-pyrimido [5, 4-b] [1, 4] oxazine

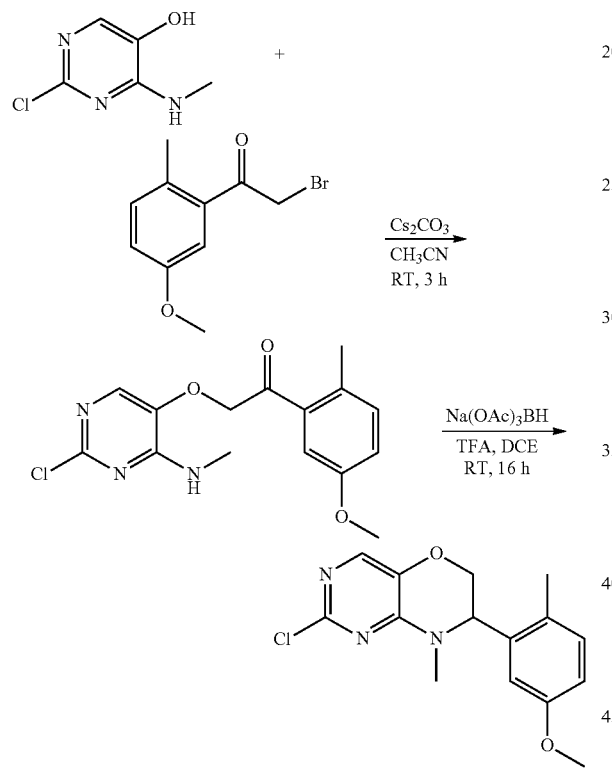

Synthesis of 2-((2-chloro-4-(methylamino) pyrimidin-5-yl) oxy)-1-(5-methoxy-2-methylphenyl) ethan-1-one To a stirred solution of 2-chloro-4-(methylamino) pyrimidin-5-ol (2 g, 12.57 mmol) in CH$_3$CN (20 mL) under an argon atmosphere were added cesium carbonate (8.1 g, 25.14 mmol) and 2-bromo-1-(5-methoxy-2-methylphenyl) ethan-1-one (3.3 g, 13.83 mmol) at room temperature. The reaction mixture was stirred for 3 h at room temperature. After consumption of the starting material (monitored by TLC), the reaction mixture was diluted with water (50 mL) and extracted with EtOAc (2×50 mL). The combined organic extracts were dried over sodium sulfate, filtered and concentrated in vacuo. The crude material was purified by column chromatography using 5% EtOAc:hexane to afford 2-((2-chloro-4-(methylamino) pyrimidin-5-yl) oxy)-1-(5-methoxy-2-methylphenyl) ethan-1-one (2 g, 50%) as an off-white solid. $^1$H-NMR (CDCl$_3$, 500 MHz): δ 7.81 (s, 1H), 7.43 (s, 1H), 7.10 (d, 1H), 6.84 (d, 1H), 4.15-4.13 (m, 1H), 4.08-4.05 (m, 1H), 3.81 (s, 1H), 3.26 (s, 3H), 2.92 (s, 3H), 2.20 (s, 3H); LCMS: 321.7 (M+1); (column; X-Select CSH C-18 (50×3.0 mm, 3.5 μm); RT 3.31 min 0.05% Aq TFA: ACN; 0.80 mL/min); TLC: 30% EtOAc:hexanes (R$_f$: 0.5).

Synthesis of 2-chloro-7-(5-methoxy-2-methylphenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(5-methoxy-2-methylphenyl) ethan-1-one (2 g, 6.23 mmol) in dichloroethane (20 mL) under an argon atmosphere were added trifluoroacetic acid (0.49 mL, 6.23 mmol) and sodium triacetoxyborohydride (2.8 g, 13.08 mmol) at room temperature. The reaction mixture was stirred for 16 h at room temperature. After consumption of the starting material (monitored by TLC), the reaction mixture was quenched with a 1 N sodium hydroxide solution (100 mL) and extracted with CH$_2$Cl$_2$ (2×100 mL). The combined organic extracts were dried over sodium sulfate, filtered and concentrated in vacuo. The crude material was purified by column chromatography using 15% EtOAc: hexane to afford 2-chloro-7-(5-methoxy-2-methylphenyl)-8-methyl-7, 8-dihydro-6H-pyrimido [5, 4-b] [1, 4] oxazine (750 mg, 39%) as an off-white solid. $^1$H-NMR (CDCl$_3$, 400 MHz): δ 7.70 (s, 1H), 7.14 (d, 1H), 6.79 (d, 1H), 6.50 (s, 1H), 4.80 (t, 1H), 4.21 (d, 1H), 4.10 (d, 1H), 3.71 (s, 3H), 3.05 (s, 3H), 2.30 (s, 3H); LCMS: 306.3 (M+1); (column; X-Select CSH C-18 (50×3.0 mm, 3.5 μm); RT 4.26 min 0.05% Aq TFA: ACN; 0.80 mL/min); TLC: 30% EtOAc: hexanes (R$_f$: 0.5).

Example 150

Synthesis of 2-chloro-7-(2-chloro-5-methoxyphenyl)-8-methyl-7, 8-dihydro-6H-pyrimido [5, 4-b] [1, 4] oxazine

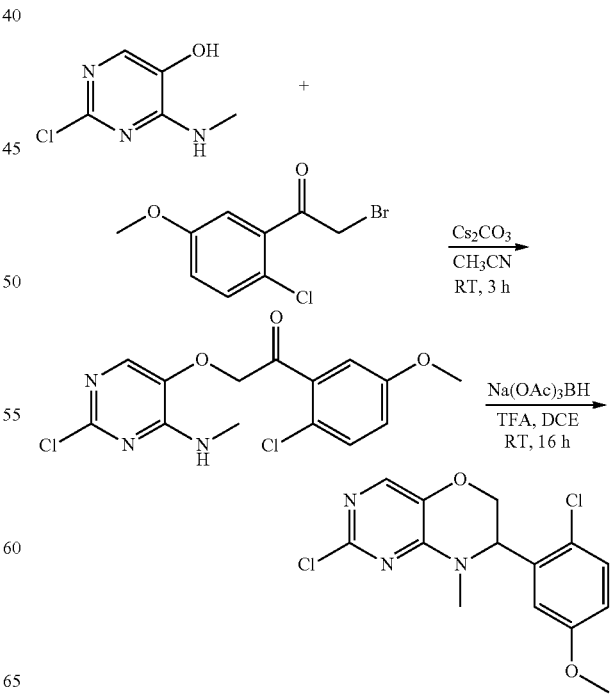

Synthesis of 2-((2-chloro-4-(methylamino) pyrimidin-5-yl) oxy)-1-(2-chloro-5-methoxyphenyl) ethan-1-one To a stirred solution of 2-chloro-4-(methylamino) pyrimidin-5-ol (2 g, 12.57 mmol) in CH$_3$CN (20 mL) under an argon atmosphere were added cesium carbonate (8 g, 25.09 mmol) and 2-bromo-1-(2-chloro-5-methoxyphenyl) ethan-1-one (3.6 g, 13.83 mmol) at room temperature. The reaction mixture was stirred for 3 h at room temperature. After consumption of the starting material (monitored by TLC), the reaction mixture was diluted with water (50 mL) and extracted with EtOAc (2×50 mL). The combined organic extracts were dried over sodium sulfate, filtered and concentrated in vacuo. The crude material was purified by column chromatography using 10% EtOAc:hexane to afford 2-((2-chloro-4-(methylamino) pyrimidin-5-yl) oxy)-1-(2-chloro-5-methoxyphenyl) ethan-1-one (2.2 g, 51%) as an off-white solid. $^1$H-NMR (DMSO-d$_6$, 500 MHz): δ 7.89 (s, 1H), 7.47-7.40 (m, 2H), 7.37 (s, 1H), 7.03 (d, 1H), 4.29-4.27 (m, 1H), 4.07-4.03 (m, 1H), 3.80 (s, 3H), 2.73 (s, 3H); TLC: 30% EtOAc:hexane (R$_f$: 0.6).

Synthesis of 2-chloro-7-(2-chloro-5-methoxyphenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(2-chloro-5-methoxyphenyl) ethan-1-one (2.2 g, 6.43 mmol) in dichloroethane (20 mL) under an argon atmosphere were added trifluoroacetic acid (0.49 mL, 6.43 mmol) and sodium triacetoxyborohydride (2.86 g, 13.50 mmol) at room temperature. The reaction mixture was stirred for 16 h at room temperature. After consumption of the starting material (monitored by TLC), the reaction mixture was quenched with a 1N sodium hydroxide solution (50 mL) and extracted with CH$_2$Cl$_2$ (2×50 mL). The combined organic extracts were dried over sodium sulfate, filtered and concentrated in vacuo. The crude material was purified by column chromatography using 15% EtOAc:hexane to afford 2-chloro-7-(2-chloro-5-methoxyphenyl)-8-methyl-7, 8-dihydro-6H-pyrimido [5, 4-b] [1, 4] oxazine (1 g, 47%) as an off-white solid. $^1$H-NMR (CDCl$_3$, 400 MHz): δ 7.70 (s, 1H), 7.33 (d, 1H), 6.80 (d, 1H), 6.50 (s, 1H), 5.01-5.00 (m, 1H), 4.34-4.30 (m, 1H), 4.22-4.20 (m, 1H), 3.70 (s, 3H), 3.11 (s, 3H); LCMS: 326.2 (M+1); (column; X-Select CSH C-18 (50×3.0 mm, 3.5 μm); RT 4.40 min 0.05% Aq TFA: ACN; 0.80 mL/min); TLC: 30% EtOAc:hexanes (R$_f$: 0.5).

Example 151

Synthesis of 2-chloro-7-(2-chloro-4-methoxyphenyl)-8-methyl-7, 8-dihydro-6H-pyrimido [5, 4-b] [1, 4] oxazine

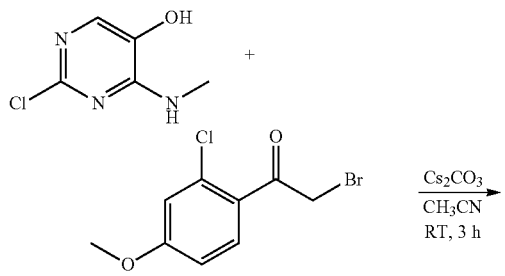

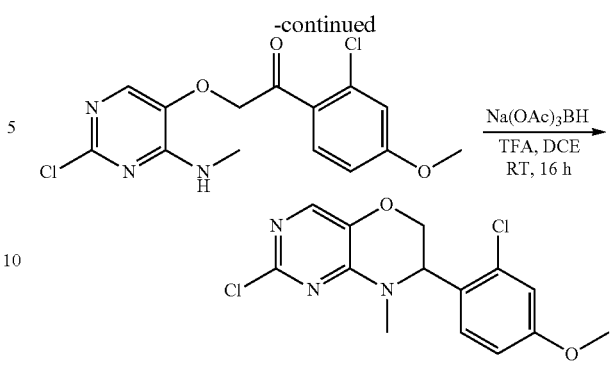

Synthesis of 2-((2-chloro-4-(methylamino) pyrimidin-5-yl) oxy)-1-(2-chloro-4-methoxyphenyl) ethan-1-one To a stirred solution of 2-chloro-4-(methylamino) pyrimidin-5-ol (500 mg, 3.14 mmol) in CH$_3$CN (5 mL) under an argon atmosphere were added cesium carbonate (2.0 g, 6.28 mmol) and 2-bromo-1-(2-chloro-4-methoxyphenyl) ethan-1-one (1.2 g, 3.45 mmol) at room temperature. The reaction mixture was stirred for 3 h at room temperature. After consumption of the starting material (monitored by TLC), the reaction mixture was diluted with water (50 mL) and extracted with EtOAc (2×50 mL). The combined organic extracts were dried over sodium sulfate, filtered and concentrated in vacuo. The crude material was purified by column chromatography using 5% EtOAc:hexane to afford 2-((2-chloro-4-(methylamino) pyrimidin-5-yl) oxy)-1-(2-chloro-4-methoxyphenyl) ethan-1-one (600 mg, 56%) as an off-white solid. $^1$H-NMR (CDCl$_3$, 500 MHz): δ 7.91 (d, 1H), 7.79 (s, 1H), 6.99 (s, 1H), 6.93 (d, 1H), 4.48-4.46 (m, 1H), 4.01-3.99 (m, 1H), 3.83 (s, 3H), 2.92 (s, 3H); LCMS: 341.9 (M+); (column; X-Select CSH C-18 (50×3.0 mm, 3.5 μm); RT 3.58 min 0.05% Aq TFA: ACN; 0.80 mL/min); TLC: 30% EtOAc:hexanes (R$_f$: 0.6).

Synthesis of 2-chloro-7-(2-chloro-4-methoxyphenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(2-chloro-4-methoxyphenyl) ethan-1-one (600 mg, 1.75 mmol) in dichloroethane (6 mL) under an argon atmosphere were added trifluoroacetic acid (200 mg, 5.44 mmol) and sodium triacetoxyborohydride (781 mg, 3.68 mmol) at room temperature. The reaction mixture was stirred for 16 h at room temperature. After consumption of the starting material (monitored by TLC), the reaction mixture was quenched with a 1 N sodium hydroxide solution (50 mL) and extracted with CH$_2$Cl$_2$ (2×50 mL). The combined organic extracts were dried over sodium sulfate, filtered and concentrated in vacuo. The crude material was purified by column chromatography using 15% EtOAc:hexane to afford 2-chloro-7-(2-chloro-4-methoxyphenyl)-8-methyl-7, 8-dihydro-6H-pyrimido [5, 4-b] [1, 4] oxazine (350 mg, 61%) as an off-white solid. $^1$H-NMR (CD$_3$OD, 500 MHz): δ 7.63 (s, 1H), 7.08 (s, 1H), 6.95-6.89 (m, 2H), 5.20-5.18 (m, 1H), 4.34-4.29 (m, 2H), 3.80 (s, 3H), 3.10 (s, 3H); LCMS: 327.7 (M+1); (column; X-Select CSH C-18 (50×3.0 mm, 3.5 μm); RT 3.84 min 0.05% Aq TFA: ACN; 0.80 mL/min); TLC: 30% EtOAc:hexanes (R$_f$: 0.4).

Example 152

Synthesis of 2-chloro-7-(3, 3-difluorocyclobutyl)-8-methyl-7, 8-dihydro-6H-pyrimido [5, 4-b] [1, 4] oxazine

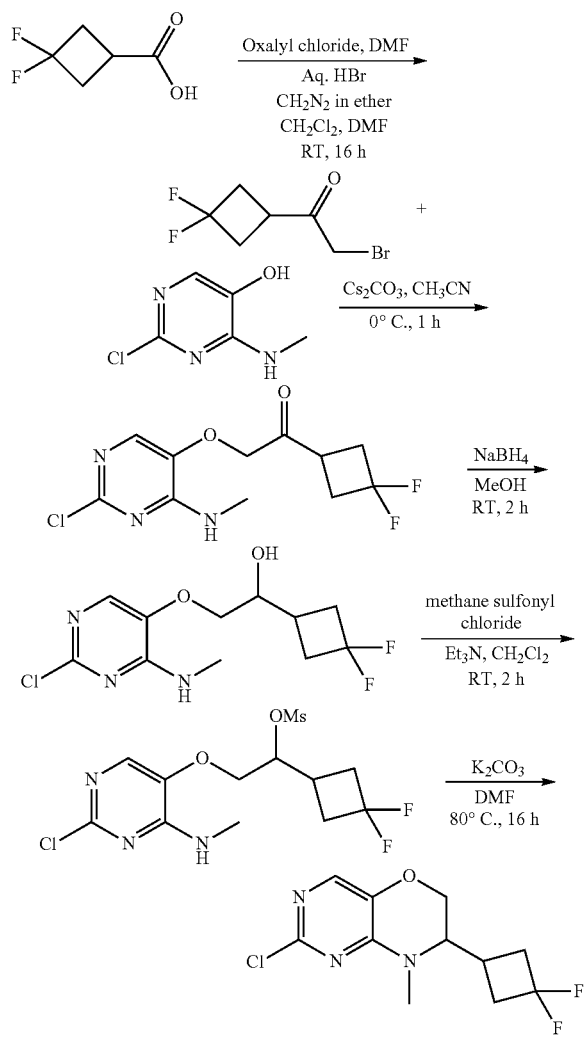

Synthesis of 2-bromo-1-(3, 3-difluorocyclobutyl) ethan-1-one

To a stirred solution of 3, 3-difluorocyclobutane-1-carboxylic acid (4 g, 29.19 mmol) in CH$_2$Cl$_2$ (60 mL) were added oxalyl chloride (3.7 g, 1.99 mmol) and DMF (0.5 drops) at 0° C. under an argon atmosphere. The reaction mixture was stirred for 2 h at 0° C. After consumption of the starting material (monitored by TLC), the volatile components were concentrated in vacuo. To a stirred solution of the residue in ether (5 mL) was added a diazomethane solution (12 mL) at 0° C. The reaction mixture was stirred for 2 h. Then aq. HBr (20 mL) was added to the reaction mixture at 0° C. The reaction mixture was stirred for 16 h at 0° C. After consumption of the starting material (monitored by TLC), the reaction mixture was quenched with a saturated sodium bicarbonate solution (20 mL) and extracted with EtOAc (2×20 mL). The combined organic extracts were dried over sodium sulfate, filtered and concentrated in vacuo. The crude material was purified by column chromatography using 5% EtOAc:hexane to afford 2-bromo-1-(4, 5-difluoro-2-(trifluoromethyl) phenyl) ethan-1-one (350 mg, 52%) as a pale yellow liquid. $^1$H-NMR (CDCl$_3$, 400 MHz): 3.90 (s, 2H), 3.46-3.39 (m, 1H), 2.90-2.70 (m, 4H); TLC: 30% EtOAc:hexanes (R$_f$; 0.7).

Synthesis of 2-((2-chloro-4-(methylamino) pyrimidin-5-yl) oxy)-1-(3, 3-difluorocyclobutyl) ethan-1-one To a stirred solution of 2-chloro-4-(methylamino) pyrimidin-5-ol (2.3 g, 14.46 mmol) in CH$_3$CN (40 mL) under an argon atmosphere was added cesium carbonate (10.4 g, 31.81 mmol) and stirred for 5 min. Then 2-bromo-1-(3, 3-difluorocyclobutyl) ethan-1-one (3.4 g, 15.90 mmol) was added to the reaction mixture at 0° C. The reaction mixture was stirred for 1 h at 0° C. After consumption of the starting material (monitored by TLC), the reaction mixture was diluted with water (100 mL) and extracted with EtOAc (2×100 mL). The combined organic extracts were dried over sodium sulfate, filtered and concentrated in vacuo. The crude material was purified by column chromatography using 20% EtOAc:hexane to afford 2-((2-chloro-4-(methylamino) pyrimidin-5-yl) oxy)-1-(3, 3-difluorocyclobutyl) ethan-1-one (2.6 g, 62%) as an off-white solid. $^1$H-NMR (CDCl$_3$, 400 MHz): δ 7.70 (s, 1H), 3.92 (s, 2H), 3.45 (br s, 1H), 3.12-3.11 (m, 1H), 3.10 (s, 3H), 2.70-2.56 (m, 3H), 2.50-2.40 (m, 1H); LCMS: 291.8 (M+1); (column; X-Select CSH C-18 (50×3.0 mm, 3.5 μm); RT 3.16 min 0.05% Aq TFA: ACN; 0.80 mL/min); TLC: 30% EtOAc:hexanes (R$_f$; 0.3).

Synthesis of 2-((2-chloro-4-(methylamino) pyrimidin-5-yl) oxy)-1-(3, 3-difluorocyclobutyl) ethan-1-ol To a stirred solution of 2-((2-chloro-4-(methylamino) pyrimidin-5-yl) oxy)-1-(3, 3-difluorocyclobutyl) ethan-1-one (2.6 g, 8.93 mmol) in MeOH (40 mL) under an argon atmosphere was added sodium borohydride (680 mg, 17.86 mmol) at 0° C. The reaction mixture was stirred for 2 h at room temperature. After consumption of the starting material (monitored by TLC), the volatile components were evaporated in vacuo. The residue was diluted with water (50 mL) and extracted with EtOAc (2×50 mL). The combined organic extracts were dried over sodium sulfate, filtered and concentrated in vacuo to obtain 2-((2-chloro-4-(methylamino) pyrimidin-5-yl) oxy)-1-(3, 3-difluorocyclobutyl) ethan-1-ol (2.3 g, 88%) as an off-white solid used in the next step without further purification. LCMS: 293.8 (M+1); (column; X-Select CSH C-18 (50×3.0 mm, 3.5 μm); RT 2.68 min 0.05% Aq TFA: ACN; 0.80 mL/min); TLC: 50% EtOAc:hexanes (R$_f$; 0.4).

Synthesis of 2-((2-chloro-4-(methylamino) pyrimidin-5-yl) oxy)-1-(3, 3-difluorocyclobutyl) ethyl methanesulfonate To a stirred solution of 2-((2-chloro-4-(methylamino) pyrimidin-5-yl) oxy)-1-(3, 3-difluorocyclobutyl) ethan-1-ol (2.3 g, 7.84 mmol) in CH$_2$Cl$_2$ (30 mL) under an argon atmosphere was added triethylamine (1.6 g, 15.68 mmol) at 0° C. The reaction mixture was stirred at room temperature for 10 min, then methanesulfonyl chloride (1.3 g, 11.80 mmol) was added drop wise at 0° C. The reaction mixture was stirred for 2 h at room temperature. After consumption of the starting material (monitored by TLC), the reaction mixture was diluted with water (100 mL) and extracted with CH$_2$Cl$_2$ (2×80 mL). The combined organic extracts were washed with water (50 mL), brine (50 mL), dried over sodium sulfate, filtered and concentrated in vacuo to obtain 2-((2-chloro-4-(methylamino) pyrimidin-5-yl) oxy)-1-(3,3-difluorocyclobutyl) ethyl methanesulfonate (2.6 g, 89%) as an off-white solid. LCMS: 371.9 (M+1); (column; X-Select CSH C-18 (50×3.0 mm, 3.5 μm); RT 3.20 min 0.05% Aq TFA: ACN; 0.80 mL/min); TLC: 50% EtOAc:hexanes (R$_f$: 0.5).

Synthesis of 2-chloro-7-(3, 3-difluorocyclobutyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(3, 3-difluorocyclobutyl) ethyl methanesulfonate (2.6 g, 7.00 mmol) in DMF (30 mL) under an argon atmosphere was added potassium carbonate (1.9 g, 14.00 mmol) at room temperature. The reaction mixture was stirred at 80° C. for 16 h. After consumption of the starting material (monitored by TLC), the reaction mixture was diluted with ice cold water (50 mL) and extracted with EtOAc (2×50 mL). The combined organic extracts were washed with water (50 mL), dried over sodium sulfate, filtered and concentrated in vacuo. The crude material was purified by column chromatography using 10% EtOAc:hexane to afford 2-chloro-7-(3, 3-difluorocyclobutyl)-8-methyl-7, 8-dihydro-6H-pyrimido [5, 4-b] [1, 4] oxazine (1.5 g, 78%) as an off-white solid. $^1$H-NMR (CDCl$_3$, 400 MHz): δ 7.69 (s, 1H), 4.12 (d, 1H), 3.91 (d, 1H), 3.43 (d, 1H), 3.21 (s, 3H), 2.80-2.70 (m, 2H), 2.60-2.30 (m, 3H); LCMS: 275.9 (M+1); (column; X-Select CSH C-18 (50×3.0 mm, 3.5 μm); RT 3.25 min 0.05% Aq TFA: ACN; 0.80 mL/min); TLC: 50% EtOAc:hexanes (R$_f$: 0.6).

Example 153

Synthesis of 2-chloro-7-(4-methoxy-2-methylphenyl)-7, 8-dihydro-6H-pyrimido [5, 4-b] [1, 4] oxazine

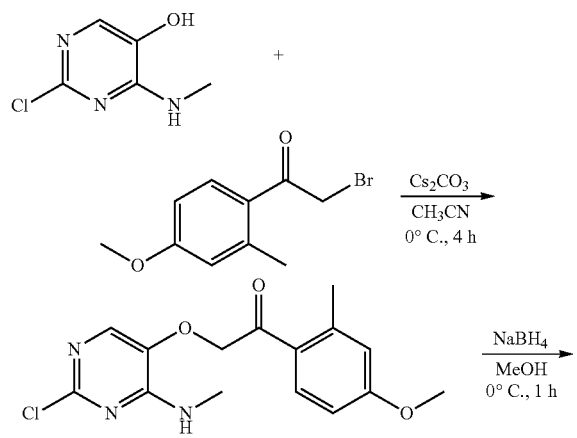

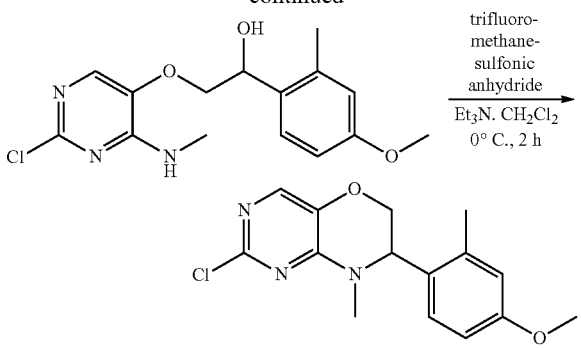

Synthesis of 2-((2-chloro-4-(methylamino)pyrimidin-5-yl)oxy)-1-(4-methoxy-2-methylphenyl)ethanone To a stirred solution of 2-chloro-4-(methylamino) pyrimidin-5-ol (1 g, 6.28 mmol) in CH$_3$CN (20 mL) under an argon atmosphere was added cesium carbonate (1.68 g, 6.92 mmol) at 0° C. After stirring for 5 min, 2-bromo-1-(4-methoxy-2-methylphenyl) ethan-1-one (1.7 g, 6.92 mmol) was added to the reaction mixture and stirred for 4 h at 0° C. After consumption of the starting material (monitored by TLC), the reaction mixture was diluted with water (100 mL) and extracted with EtOAc (2×50 mL). The combined organic extracts were dried over sodium sulfate, filtered and concentrated in vacuo. The crude material was purified by column chromatography using 15-20% EtOAc:hexane to afford 2-((2-chloro-4-(methylamino)pyrimidin-5-yl)oxy)-1-(4-methoxy-2-methylphenyl)ethanone (1.3 g, 65%) as an off-white solid. $^1$H-NMR (DMSO-d$_6$, 400 MHz): δ 7.92 (d, 1H), 7.58 (s, 1H), 7.49-7.43 (m, 1H), 6.90 (s, 1H), 6.89-6.87 (m, 1H), 5.50 (s, 2H), 3.83 (s, 3H), 2.86 (d, 3H), 2.45 (s, 3H); LCMS: 322.4 (M+1); (column; X-Select CSH C-18 (50×3.0 mm, 3.5 μm); RT 3.92 min 0.05% Aq TFA: ACN; 0.80 mL/min); TLC: 50% EtOAc:hexanes (R$_f$: 0.5).

Synthesis of 2-((2-chloro-4-(methylamino) pyrimidin-5-yl) oxy)-1-(4-methoxy-2-methylphenyl) ethan-1-ol To a stirred solution of 2-((2-chloro-4-(methylamino) pyrimidin-5-yl)oxy)-1-(4-methoxy-2-methylphenyl)ethanone (1.1 g, 3.40 mmol) in MeOH (20 mL) under an argon atmosphere was added sodium borohydride (194 mg, 5.14 mmol) at 0° C. The reaction mixture was stirred for 1 h at 0° C. After consumption of the starting material (monitored by TLC), the volatile components were evaporated, water (50 mL) was added and extracted with EtOAc (2×50 mL). The combined organic extracts were dried over sodium sulfate, filtered and concentrated in vacuo to obtain 2-((2-chloro-4-(methylamino) pyrimidin-5-yl) oxy)-1-(4-methoxy-2-methylphenyl) ethan-1-ol (800 mg, 73%) as an off-white solid. TLC: 40% EtOAc:hexanes (R$_f$: 0.2).

Synthesis of 2-chloro-7-(4-methoxy-2-methylphenyl)-7, 8-dihydro-6H-pyrimido [5, 4-b] [1, 4] oxazine To a stirred solution of 2-((2-chloro-4-(methylamino) pyrimidin-5-yl) oxy)-1-(4-methoxy-2-methylphenyl) ethan-1-ol (50 mg, 0.15 mmol) in CH$_2$Cl$_2$ (3 mL) under an argon atmosphere were added triethylamine (0.04 mL, 0.31 mmol) and trifluoromethanesulfonic anhydride (55 mg, 0.19 mmol) at 0° C. The reaction mixture was stirred for 2 h at 0° C. After consumption of the starting material (monitored by TLC), the reaction mixture was basified with a saturated sodium bicarbonate solution (50 mL) and extracted with CH₂Cl₂ (2×50 mL). The combined organic extracts were dried over sodium sulfate, filtered and concentrated in vacuo. The crude material was purified by column chromatography using 20-30% EtOAc:hexane to afford 2-chloro-7-(4-methoxy-2-methylphenyl)-7, 8-dihydro-6H-pyrimido [5, 4-b] [1, 4] oxazine (14 mg, 30%) as a white solid. ¹H-NMR (CDCl₃, 400 MHz): δ 7.70 (s, 1H), 6.90 (d, 1H), 6.79-6.73 (m, 2H), 4.80 (t, 1H), 4.20 (d, 1H), 4.09 (d, 1H), 3.80 (s, 3H), 3.01 (s, 3H), 2.35 (s, 3H); LCMS: 306.3 (M+1); (column; X-Select CSH C-18 (50×3.0 mm, 3.5 µm); RT 4.78 min 0.05% Aq TFA: ACN; 0.80 mL/min); TLC: 50% EtOAc:hexanes (R$_f$: 0.5).

Example 154

Synthesis of 2-chloro-7-(4, 4-difluorocyclohexyl)-8-methyl-7, 8-dihydro-6H-pyrimido [5, 4-b] [1, 4] oxazine

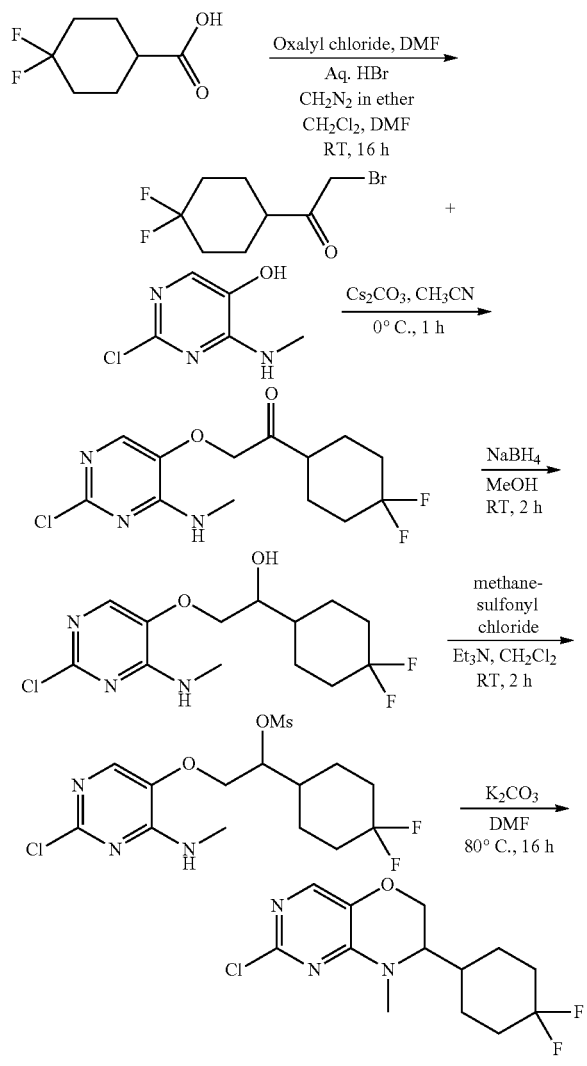

Synthesis of 2-bromo-1-(4,4-difluorocyclohexyl)ethan-1-one

To a stirred solution of 4, 4-difluorocyclohexane-1-carboxylic acid (4 g, 24.39 mmol) in CH₂Cl₂ (60 mL) under an argon atmosphere were added oxalyl chloride (3.1 g, 24.39 mmol) and DMF (0.5 mL) at 0° C. The reaction mixture was stirred for 2 h at room temperature. After consumption of the starting material (monitored by TLC), the volatile components were concentrated in vacuo. To a stirred solution of the residue in ether (5 mL) was added a diazomethane solution (12 mL) at 0° C. The reaction mixture was stirred for 2 h. Then aq. HBr (20 mL) was added to the reaction mixture at 0° C. The reaction mixture was warmed to room temperature and stirred for 16 h. After consumption of the starting material (monitored by TLC), the reaction mixture was quenched with water (800 mL) and extracted with EtOAc (2×500 mL). The combined organic extracts were dried over sodium sulfate, filtered and concentrated in vacuo to obtain 2-bromo-1-(4, 4-difluorocyclohexyl) ethan-1-one (4 g, 68%) as a colorless liquid used in the next step without further purification. ¹H-NMR (CDCl₃, 400 MHz): δ 3.92 (s, 2H), 2.87-2.80 (m, 1H), 2.20-2.10 (m, 2H), 2.00-1.90 (m, 2H), 1.86-1.73 (m, 4H); TLC: 30% EtOAc:hexanes (R$_f$: 0.7).

Synthesis of 2-((2-chloro-4-(methylamino) pyrimidin-5-yl) oxy)-1-(4, 4-difluorocyclohexyl) ethan-1-one To a stirred solution of 2-chloro-4-(methylamino) pyrimidin-5-ol (2.4 g, 15.09 mmol) in CH₃CN (50 mL) under an argon atmosphere was added cesium carbonate (10.8 g, 33.20 mmol) and stirred for 5 min. Then 2-bromo-1-(4, 4-difluorocyclohexyl) ethan-1-one (4 g, 16.60 mmol) was added to the reaction mixture at 0° C. The reaction mixture was stirred for 1 h at 0° C. After consumption of the starting material (monitored by TLC), the reaction mixture was diluted with water (100 mL) and extracted with EtOAc (2×100 mL). The combined organic extracts were dried over sodium sulfate, filtered and concentrated in vacuo. The crude material was purified by column chromatography using 20% EtOAc:hexane to afford 2-((2-chloro-4-(methylamino) pyrimidin-5-yl) oxy)-1-(4, 4-difluorocyclohexyl) ethan-1-one (2.6 g, 55%) as an off-white solid. ¹H-NMR (CDCl₃, 400 MHz): δ 7.69 (s, 1H), 4.20 (d, 1H), 3.90 (d, 1H), 3.13 (s, 3H), 2.20-2.00 (m, 5H), 1.80-1.40 (m, 4H); TLC: 30% EtOAc:hexanes (R$_f$: 0.3).

Synthesis of 2-((2-chloro-4-(methylamino) pyrimidin-5-yl) oxy)-1-(4, 4-difluorocyclohexyl) ethan-1-ol To a stirred solution of 2-((2-chloro-4-(methylamino) pyrimidin-5-yl) oxy)-1-(4, 4-difluorocyclohexyl) ethan-1-one (2.6 g, 8.15 mmol) in MeOH (30 mL) under an argon atmosphere was added sodium borohydride (620 mg, 16.30 mmol) at 0° C. The reaction mixture was stirred at room temperature for 2 h. After consumption of the starting material (monitored by TLC), the volatile components were evaporated in vacuo. The residue was diluted with water (50 mL) and extracted with EtOAc (2×50 mL). The combined organic extracts were dried over sodium sulfate, filtered and concentrated in vacuo to obtain 2-((2-chloro-4-(methylamino) pyrimidin-5-yl) oxy)-1-(4, 4-difluorocyclohexyl) ethan-1-ol (2.4 g, 92%) as an off-white solid used in the next step without further purification. LCMS: 321.9 (M+1); (column; X-Select CSH C-18 (50×3.0 mm, 3.5 μm); RT 2.95 min 0.05% Aq TFA: ACN; 0.80 mL/min); TLC: 50% EtOAc:hexanes ($R_f$: 0.3).

Synthesis of 2-((2-chloro-4-(methylamino) pyrimidin-5-yl) oxy)-1-(4, 4-difluorocyclohexyl) ethyl methanesulfonate To a stirred solution of 2-((2-chloro-4-(methylamino) pyrimidin-5-yl) oxy)-1-(4, 4-difluorocyclohexyl) ethan-1-ol (2.4 g, 7.47 mmol) in $CH_2Cl_2$ (30 mL) was added triethylamine (1.52 g, 14.94 mmol) at 0° C. under an argon atmosphere. The reaction mixture was stirred at room temperature for 10 min. Then methanesulfonyl chloride (1.28 g, 11.14 mmol) was added drop wise at 0° C. The reaction mixture was warmed to room temperature and stirred for 2 h. After consumption of the starting material (monitored by TLC), the reaction mixture was diluted with water (100 mL) and extracted with $CH_2Cl_2$ (2×80 mL). The combined organic extracts were washed with water (50 mL), brine (50 mL), dried over sodium sulfate, filtered and concentrated in vacuo to obtain 2-((2-chloro-4-(methylamino) pyrimidin-5-yl) oxy)-1-(4, 4-difluorocyclohexyl) ethyl methanesulfonate (2.6 g, 89%) as an off-white solid. LCMS: 400 (M+1); (column; X-Select CSH C-18 (50×3.0 mm, 3.5 μm); RT 3.41 min 0.05% Aq TFA: ACN; 0.80 mL/min); TLC: 50% EtOAc:hexanes ($R_f$: 0.5).

Synthesis of 2-chloro-7-(4, 4-difluorocyclohexyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(4, 4-difluorocyclohexyl) ethyl methanesulfonate (2.6 g, 6.51 mmol) in DMF (30 mL) under an argon atmosphere was added potassium carbonate (1.8 g, 13.03 mmol) at room temperature. The reaction mixture was stirred at 80° C. for 16 h. After consumption of the starting material (monitored by TLC), the reaction mixture was diluted with ice cold water (50 mL) and extracted with EtOAc (2×50 mL). The combined organic extracts were washed with water (50 mL), dried over sodium sulfate, filtered and concentrated in vacuo. The crude material was purified by column chromatography using 10% EtOAc: hexane to afford 2-chloro-7-(4, 4-difluorocyclohexyl)-8-methyl-7, 8-dihydro-6H-pyrimido [5, 4-b] [1, 4] oxazine (1.8 g, 91%) as an off-white solid. $^1$H-NMR ($CDCl_3$, 400 MHz): δ 7.67 (s, 1H), 4.38 (d, 1H), 3.89 (d, 1H), 3.30-3.28 (m, 1H), 3.27 (s, 3H), 1.90-1.70 (m, 4H), 1.65 (s, 1H), 1.60-1.50 (m, 4H); LCMS: 303.9 (M+1); (column; X-Select CSH C-18 (50×3.0 mm, 3.5 μm); RT 3.44 min 0.05% Aq TFA: ACN; 0.80 mL/min); TLC: 50% EtOAc:hexanes ($R_f$: 0.6).

Example 155

Synthesis of (S)-2-chloro-7-cyclopropyl-8-methyl-7, 8-dihydro-6H-pyrimido [5, 4-b] [1, 4] oxazine

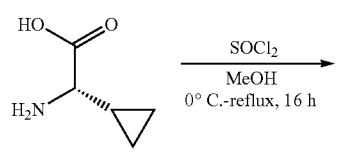

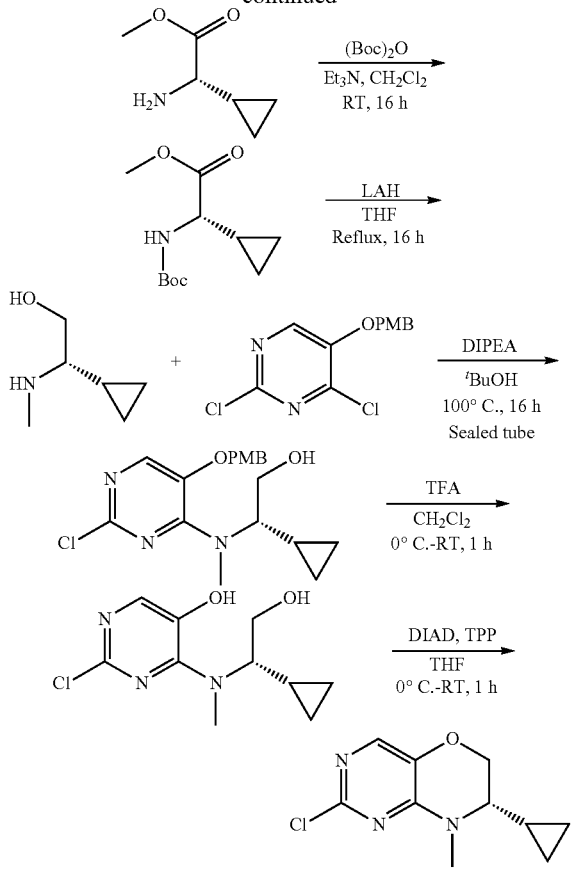

Synthesis of methyl (S)-2-amino-2-cyclopropylacetate

To a stirred solution of (S)-2-amino-2-cyclopropylacetic acid (4 g, 34.78 mmol) in MeOH (40 mL) under an argon atmosphere was added thionylchloride (12.5 mL, 173.91 mmol) at 0° C. The reaction mixture was refluxed for 16 h. After consumption of the starting material (monitored by TLC), the volatile components were evaporated in vacuo to obtain methyl (S)-2-amino-2-cyclopropylacetate (4.2 g, crude) as a pale yellow solid used without further purification. $^1$H-NMR (DMSO-$d_6$, 500 MHz): δ 8.62 (br s, 2H), 3.79-3.72 (m, 4H), 1.13-1.05 (m, 1H), 0.67-0.50 (m, 4H); TLC: 10% MeOH/$CH_2Cl_2$ ($R_f$: 0.7).

Synthesis of methyl (S)-2-((tert-butoxycarbonyl) amino)-2-cyclopropylacetate To a stirred solution of methyl (S)-2-amino-2-cyclopropylacetate (4.2 g, 32.50 mmol) in $CH_2Cl_2$ (100 mL) under an argon atmosphere were added triethylamine (22.6 mL, 162.50 mmol) and Boc anhydride (8.5 g, 39.06 mmol) at 0° C. The reaction mixture was warmed to room temperature and stirred for 16 h. After consumption of the starting material (monitored by TLC), the reaction mixture was diluted with water (100 mL) and extracted with $CH_2Cl_2$ (2×100 mL). The combined organic extracts were dried over sodium sulfate, filtered and concentrated in vacuo to obtain methyl (S)-2-((tert-butoxycarbonyl) amino)-2-cyclopropylacetate (7 g, 94%) as a brown oil used without further purification. $^1$H-NMR (DMSO-$d_6$, 400 MHz): δ 7.37 (d, 1H), 3.63 (s, 3H), 3.38-3.34 (m, 1H), 1.38 (s, 9H), 1.07-1.00 (m, 1H), 0.50-0.25 (m, 4H); TLC: 30% EtOAc:hexane ($R_f$: 0.7).

Synthesis of (S)-2-cyclopropyl-2-(methylamino) ethan-1-ol

To a stirred solution of methyl (S)-2-((tert-butoxycarbonyl) amino)-2-cyclopropylacetate (7 g, 30.70 mmol) in THF (200 mL) under an argon atmosphere was added lithiumaluminiumhydride (5.8 g, 153.50 mmol) at 0° C. The reaction mixture was warmed to room temperature and stirred for 16 h. After consumption of the starting material (monitored by TLC), the reaction mixture was quenched with a saturated sodium sulfate solution (50 mL) at 0° C. The reaction mixture was warmed to room temperature and stirred for 2 h. The volatile components were evaporated in vacuo. The residue was dissolved in methanol (50 mL), stirred at room temperature for 30 min and filtered. The filtrate was concentrated in vacuo to obtain (S)-2-cyclopropyl-2-(methylamino) ethan-1-ol (3 g, crude) as an off-white solid used without further purification. $^1$H-NMR (CDCl$_3$, 400 MHz): δ 3.70-3.68 (m, 1H), 3.46 (s, 3H), 3.45-3.43 (m, 1H), 1.72-1.68 (m, 1H), 0.78-0.70 (m, 1H), 0.60-0.51 (m, 1H), 0.48-0.42 (m, 1H), 0.27-0.21 (m, 1H), 0.15-0.10 (m, 1H); TLC: 10% MeOH/CH$_2$Cl$_2$ ($R_f$ 0.1).

Synthesis of (S)-2-((2-chloro-5-((4-methoxybenzyl) oxy) pyrimidin-4-yl) (methyl) amino)-2-cyclopropylethan-1-ol To a stirred solution of (S)-2-cyclopropyl-2-(methylamino) ethan-1-ol (500 mg, 1.76 mmol) in tert-butanol (10 mL) under an argon atmosphere was added diisopropylethylamine (1.4 mL, 8.80 mmol) and 2, 4-dichloro-5-((4-methoxybenzyl) oxy) pyrimidine (242 mg, 2.11 mmol) at room temperature. The reaction mixture was stirred at 100° C. for 16 h in a sealed tube. After consumption of the starting material (monitored by TLC), the volatile components were evaporated in vacuo. The crude material was purified by column chromatography using 40-50% EtOAc:hexane to afford (S)-2-((2-chloro-5-((4-methoxybenzyl) oxy) pyrimidin-4-yl) (methyl) amino)-2-cyclopropylethan-1-ol (250 mg, 39%) as a colorless thick oil. $^1$H-NMR (DMSO-d$_6$, 400 MHz): δ 7.85 (s, 1H), 7.37 (d, 2H), 6.96 (d, 2H), 4.99 (s, 2H), 4.67 (t, 1H), 4.10-4.07 (m, 1H), 3.75 (s, 3H), 3.65-3.53 (m, 1H), 3.50-3.44 (m, 1H), 3.03 (s, 3H), 1.00-0.90 (m, 1H), 0.47-0.40 (m, 1H), 0.35-0.28 (m, 1H), 0.17-0.10 (m, 1H), 0.05-0.01 (m, 1H); TLC: 50% EtOAc:hexane ($R_f$: 0.5).

Synthesis of (S)-2-chloro-4-((1-cyclopropyl-2-hydroxyethyl) (methyl) amino) pyrimidin-5-ol To a stirred solution (S)-2-((2-chloro-5-((4-methoxybenzyl) oxy) pyrimidin-4-yl) (methyl) amino)-2-cyclopropylethan-1-ol (50 mg, 0.13 mmol) in CH$_2$Cl$_2$ (2 mL) under an argon atmosphere was added trifluoroacetic acid (0.05 mL) at 0° C. The reaction mixture was warmed to room temperature and stirred for 1 h. After consumption of the starting material (monitored by TLC), the volatile components were evaporated in vacuo. The crude material was purified by column chromatography using 50% EtOAc:hexane to afford (S)-2-chloro-4-((1-cyclopropyl-2-hydroxyethyl) (methyl) amino) pyrimidin-5-ol (20 mg, 60%) as a white solid. $^1$H-NMR (DMSO-d$_6$, 400 MHz): δ 9.88 (s, 1H), 7.50 (s, 1H), 4.78-4.70 (m, 1H), 4.15-4.10 (m, 1H), 3.70-3.60 (m, 1H), 3.59-3.50 (m, 1H), 3.01 (s, 3H), 1.04-1.00 (m, 1H), 0.60-0.53 (m, 1H), 0.41-0.37 (m, 1H), 0.31-0.25 (m, 2H); TLC: 50% EtOAc:hexane ($R_f$: 0.3).

Synthesis of (S)-2-chloro-7-cyclopropyl-8-methyl-7, 8-dihydro-6H-pyrimido [5, 4-b] [1, 4] oxazine To a stirred solution of (S)-2-chloro-4-((1-cyclopropyl-2-hydroxyethyl) (methyl) amino) pyrimidin-5-ol (100 mg, 0.41 mmol) in THF (2 mL) under an argon atmosphere were added triphenylphosphine (161 mg, 0.61) and diisopropylazodicarboxylate (124 mg, 0.61 mmol) at 0° C. The reaction mixture was warmed to room temperature and stirred for 1 h. After consumption of the starting material (monitored by TLC), the volatile components were evaporated in vacuo. The crude material was purified by column chromatography using 20-30% EtOAc:hexane to afford (S)-2-chloro-7-cyclopropyl-8-methyl-7, 8-dihydro-6H-pyrimido [5, 4-b] [1, 4] oxazine (80 mg, 87%) as a white solid. $^1$H-NMR (DMSO-d$_6$, 400 MHz): δ 7.67 (s, 1H), 4.22-4.19 (m, 1H), 4.07-4.04 (m, 1H), 3.12 (s, 3H), 2.93-2.90 (m, 1H), 0.93-0.87 (m, 1H), 0.70-0.58 (m, 2H), 0.50-0.43 (m, 1H), 0.28-0.22 (m, 1H); TLC: 50% EtOAc:hexane ($R_f$: 0.6).

Example 156

Synthesis of (S)-2-chloro-7-(cyclopropylmethyl)-8-methyl-7, 8-dihydro-6H-pyrimido [5, 4-b] [1, 4] oxazine

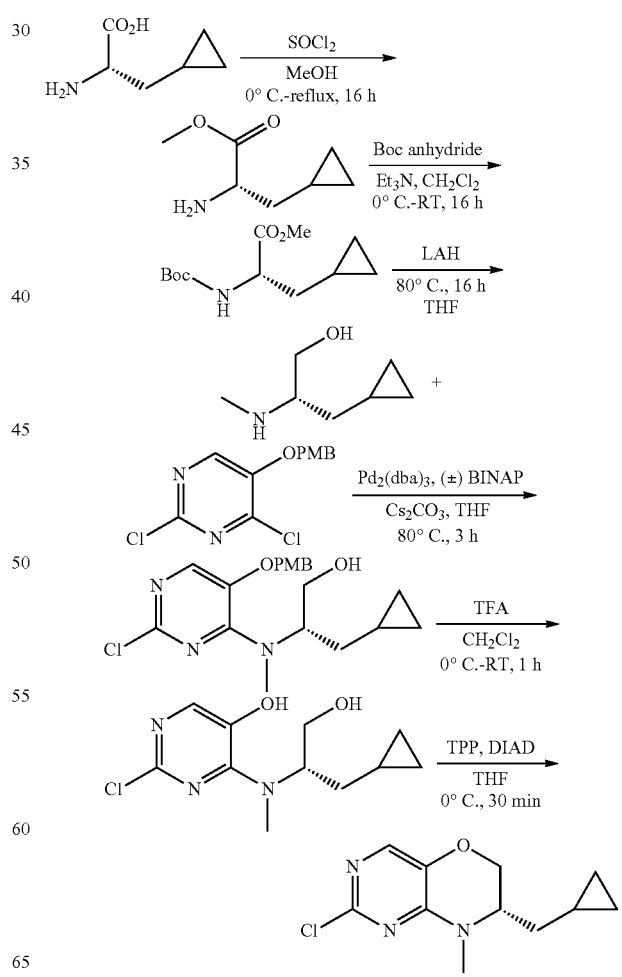

Synthesis of methyl (S)-2-amino-3-cyclopropylpropanoate

To a stirred solution of (S)-2-amino-3-cyclopropylpropanoic acid (2 g, 15.50 mmol) in MeOH (20 mL) under an argon atmosphere was added thionyl chloride (3.3 mL, 46.51 mmol) at 0° C. The reaction mixture was refluxed for 16 h. After consumption of the starting material (monitored by TLC), the volatile components were evaporated in vacuo to obtain methyl (S)-2-amino-3-cyclopropylpropanoate (2.2 g, crude) as a pale yellow solid used in the next step without further purification. LCMS: 144.7 (M+1); (column; Eclipse XDB C-18 (150×4.6 mm, 5 μm); RT 1.62 min. 0.05% Aq TFA; ACN 0.8 mL/min); TLC: 5% MeOH/$CH_2Cl_2$ ($R_f$: 0.3).

Synthesis of methyl (S)-2-((tert-butoxycarbonyl) amino)-3-cyclopropylpropanoate To a stirred solution of methyl (S)-2-amino-3-cyclopropylpropanoate (2.2 g, 15.38 mmol) in $CH_2Cl_2$ (20 mL) under an argon atmosphere were added triethylamine (10.7 mL, 76.92 mmol) and Boc anhydride (4.1 mL, 18.46 mmol) at 0° C. The reaction mixture was warmed to room temperature and stirred for 16 h. After consumption of the starting material (monitored by TLC), the reaction mixture was diluted with water (50 mL) and extracted with $CH_2Cl_2$ (2×50 mL). The combined organic extracts were dried over sodium sulfate, filtered and concentrated in vacuo. The crude material was purified by column chromatography using 5% EtOAc:hexanes to afford methyl (S)-2-((tert-butoxycarbonyl) amino)-3-cyclopropylpropanoate (2.5 g, 67%) as an off-white solid.
$^1$H-NMR (CDCl$_3$, 500 MHz): δ 5.20-5.17 (m, 1H), 4.40-4.37 (m, 1H), 3.75 (s, 3H), 1.70-1.67 (m, 2H), 1.44 (s, 9H), 0.75-0.65 (m, 1H), 0.52-0.47 (m, 2H), 0.14-0.03 (m, 2H); TLC: 20% EtOAc:hexane ($R_f$: 0.7).

Synthesis of (S)-3-cyclopropyl-2-(methylamino) propan-1-ol

To a stirred solution of methyl (S)-2-((tert-butoxycarbonyl) amino)-3-cyclopropylpropanoate (500 mg, 2.05 mmol) in dry THF (10 mL) under an argon atmosphere was added lithium aluminum hydride (156 mg, 4.11 mmol) at 0° C. The reaction mixture was stirred at 80° C. for 16 h. After consumption of the starting material (monitored by TLC), the reaction mixture was quenched with a saturated sodium sulfate solution (50 mL). The filtrate was concentrated in vacuo to obtain (S)-3-cyclopropyl-2-(methylamino) propan-1-ol (200 mg, crude) as an off-white solid used in the next step without further purification. TLC: 20% EtOAc:hexane ($R_f$: 0.2).

Synthesis of (S)-2-((2-chloro-5-((4-methoxybenzyl) oxy) pyrimidin-4-yl) (methyl) amino)-3-cyclopropylpropan-1-ol To a stirred solution of 2, 4-dichloro-5-((4-methoxybenzyl) oxy) pyrimidine (200 mg, 0.70 mmol) in THF (2 mL) under an argon atmosphere were added methyl (S)-2-((tert-butoxycarbonyl) amino)-3-cyclopropylpropanoate (181 mg, 1.40 mmol), (±) BINAP (65 mg, 0.10 mmol) and cesium carbonate (319 mg, 0.98 mmol). The suspension was purged with argon for 30 min. Pd$_2$(dba)$_3$ (32 mg, 0.03 mmol) was added to the reaction mixture at room temperature. The reaction mixture was stirred at 80° C. for 3 h. After consumption of the starting material (monitored by TLC), the reaction mixture was diluted with water (10 mL) and extracted with EtOAc (2×10 mL). The combined organic extracts were dried over sodium sulfate, filtered and concentrated in vacuo to obtain (S)-2-((2-chloro-5-((4-methoxybenzyl) oxy) pyrimidin-4-yl) (methyl) amino)-3-cyclopropylpropan-1-ol (80 mg, 30%) as an off-white solid.
$^1$H-NMR (CDCl$_3$, 500 MHz): δ 7.75 (s, 1H), 7.27 (d, 2H), 6.90 (d, 2H), 4.97 (s, 2H), 4.83-4.78 (m, 1H), 3.82 (s, 3H), 3.62-3.56 (m, 1H), 3.03 (s, 3H), 2.04-2.00 (m, 1H), 1.24-1.20 (m, 1H), 0.58-0.53 (m, 1H), 0.47-0.39 (m, 2H), 0.05-0.01 (m, 2H); TLC: 20% EtOAc:hexane ($R_f$: 0.5).

Synthesis of (S)-2-chloro-4-((1-cyclopropyl-3-hydroxypropan-2-yl) (methyl) amino) pyrimidin-5-ol To a stirred solution of (S)-2-((2-chloro-5-((4-methoxybenzyl) oxy) pyrimidin-4-yl) (methyl) amino)-3-cyclopropylpropan-1-ol (80 mg, 0.21 mmol) in $CH_2Cl_2$ (1 mL) under an argon atmosphere was added trifluoroacetic acid (0.1 mL, 0.21 mmol) at 0° C. The reaction mixture was warmed to room temperature and stirred for 1 h. After consumption of the starting material (monitored by TLC), the reaction mixture was basified with a saturated sodium bicarbonate solution (20 mL) and extracted with $CH_2Cl_2$ (2×20 mL). The combined organic extracts were dried over sodium sulfate, filtered and concentrated in vacuo to obtain (S)-2-chloro-4-((1-cyclopropyl-3-hydroxypropan-2-yl) (methyl) amino) pyrimidin-5-ol (30 mg, 55%) as an off-white solid. LCMS: 257.8 (M+1); (column; X-select CSH C-18 (50×3.0 mm, 3.5 μm); RT 2.64 min. 0.05% Aq TFA; ACN 0.8 mL/min); TLC: 50% EtOAc:hexane ($R_f$: 0.4).

Synthesis of (S)-2-chloro-7-(cyclopropylmethyl)-8-methyl-7, 8-dihydro-6H-pyrimido [5, 4-b] [1, 4] oxazine To a stirred solution of (S)-2-chloro-4-((1-cyclopropyl-3-hydroxypropan-2-yl) (methyl) amino) pyrimidin-5-ol (25 mg, 0.09 mmol) in THF (0.5 mL) under an argon atmosphere were added triphenylphosphine (38 mg, 0.14) and diisopropylazodicarboxylate (29 mg, 0.14 mmol) at 0° C. The reaction mixture was stirred for 30 min at 0° C. After consumption of the starting material (monitored by TLC), the reaction mixture was diluted with a saturated ammonium chloride solution (10 mL) and extracted with $CH_2Cl_2$ (2×10 mL). The combined organic extracts were dried over sodium sulfate, filtered and concentrated in vacuo. The crude material was purified by column chromatography using 10% EtOAc:hexane to afford (S)-2-chloro-7-(cyclopropylmethyl)-8-methyl-7, 8-dihydro-6H-pyrimido [5, 4-b] [1, 4] oxazine (10 mg, 43%) as an off-white solid. $^1$H-NMR (CDCl$_3$, 500 MHz): δ 7.60 (s, 1H), 4.20 (d, 1H), 3.99 (d, 1H), 3.50-3.47 (m, 1H), 3.20 (s, 3H), 2.67-2.62 (m, 2H), 0.71-0.66 (m, 1H), 0.58-0.45 (m, 2H), 0.20-0.18 (m, 1H), 0.10-0.02 (m, 1H); TLC: 40% EtOAc:hexane ($R_f$: 0.6).

Example 157

Synthesis of (S)-2-chloro-7-(cyclopropylmethyl)-8-methyl-7, 8-dihydro-6H-pyrimido [5, 4-b] [1, 4] oxazine

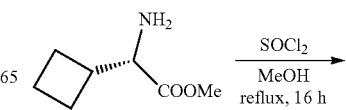

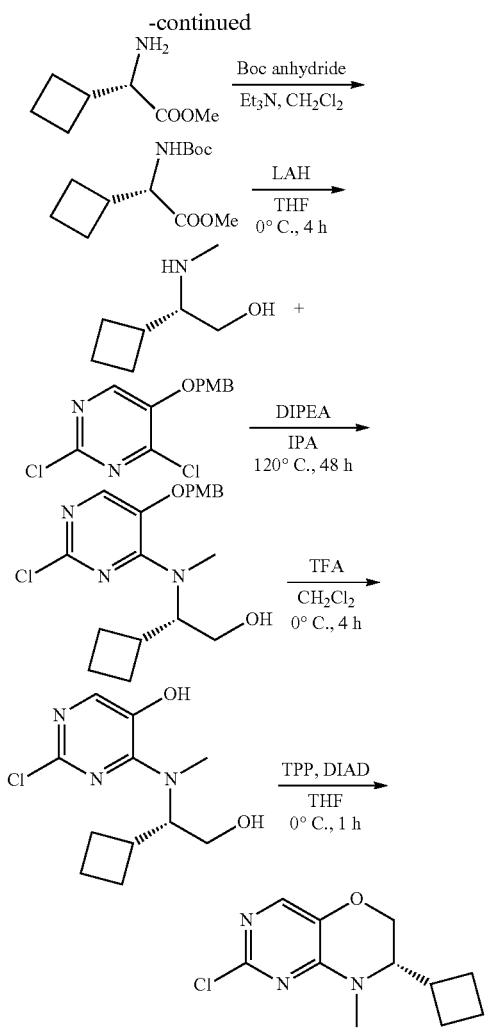

Synthesis of methyl (S)-2-amino-2-cyclobutylacetate

To a stirred solution of (S)-2-amino-2-cyclobutylacetic acid (1 g, 7.81 mmol) in MeOH (10 mL) under an argon atmosphere was added thionyl chloride (1.1 g, 9.36 mmol) at 0° C. The reaction mixture was stirred at reflux for 16 h. After consumption of the starting material (monitored by TLC), the volatile components were evaporated in vacuo. The residue was diluted with water (20 mL) and extracted with EtOAc (2×50 mL). The combined organic extracts were dried over sodium sulfate, filtered and concentrated in vacuo to obtain methyl (S)-2-amino-2-cyclobutylacetate (1 g, crude) as a white solid used for the next step without further purification. $^1$H-NMR (CD$_3$OD, 500 MHz): δ 3.97 (d, 1H), 3.81 (s, 3H), 2.79-2.70 (m, 1H), 2.17-2.00 (m, 5H), 1.90-1.80 (m, 1H); TLC: 10% MeOH/CH$_2$Cl$_2$ (R$_f$: 0.5).

Synthesis of methyl (S)-2-((tert-butoxycarbonyl)amino)-2-cyclobutylacetate

To a stirred solution of methyl (S)-2-amino-2-cyclobutylacetate (200 mg, 1.40 mmol) in CH$_2$Cl$_2$ (5 mL) under an argon atmosphere were added triethylamine (0.24 mL, 1.69 mmol) and Boc anhydride (368 mg, 1.69 mmol) at 0° C. The reaction mixture was warmed to room temperature and stirred for 16 h. After consumption of the starting material (monitored by TLC), the reaction mixture was diluted with a 10% citric acid solution (20 mL) and extracted with CH$_2$Cl$_2$ (2×20 mL). The combined organic extracts were washed with water (20 mL), brine (20 mL), dried over sodium sulfate, filtered and concentrated in vacuo to afford methyl (S)-2-((tert-butoxycarbonyl) amino)-2-cyclobutylacetate (300 mg, 88%) as a white solid used in the next step without further purification. TLC: EtOAc (R$_f$: 0.6).

Synthesis of (S)-2-cyclobutyl-2-(methylamino)ethan-1-ol

To a stirred solution of methyl (S)-2-amino-2-cyclobutylacetate (300 mg, 1.24 mmol) in dry THF (5 mL) under argon atmosphere was added lithium aluminum hydride (188 mg, 4.96 mmol) at 0° C. The reaction mixture was stirred at 0° C. for 4 h. After consumption of the starting material (monitored by TLC), the reaction mixture was quenched with a 1N sodium hydroxide solution (50 mL) and filtered. The filtrate was concentrated in vacuo to obtain (S)-2-cyclobutyl-2-(methylamino) ethan-1-ol (160 mg, 81%) as an off-white solid. TLC: 10% MeOH/CH$_2$Cl$_2$ (R$_f$: 0.5).

Synthesis of (S)-2-((2-chloro-5-((4-methoxybenzyl)oxy) pyrimidin-4-yl)(methyl)amino)-2-cyclobutylethan-1-ol To a stirred solution of (S)-2-cyclobutyl-2-(methylamino) ethan-1-ol (300 mg, 1.05 mmol) in isopropanol (3 mL) under an argon atmosphere were added diisopropylethylamine (272 mg, 2.11 mmol) and 2, 4-dichloro-5-((4-methoxybenzyl) oxy) pyrimidine (136 mg, 1.05 mmol) at room temperature. The reaction mixture was stirred at 120° C. for 48 h. After consumption of the starting material (monitored by TLC), the volatile components were concentrated in vacuo. The crude material was purified by column chromatography using 30% EtOAc:hexanes to afford (S)-2-((2-chloro-5-((4-methoxybenzyl) oxy) pyrimidin-4-yl) (methyl) amino)-2-cyclobutylethan-1-ol (120 mg, 30%) as a pale yellow liquid. $^1$H-NMR (DMSO-d$_6$, 500 MHz): δ 7.88 (s, 1H), 7.43-7.40 (m, 2H), 6.99-6.94 (m, 2H), 5.08-5.00 (m, 2H), 4.93-4.90 (m, 1H), 4.60-4.58 (m, 1H), 3.75 (s, 3H), 2.70 (br s, 3H), 1.90-1.80 (m, 1H), 1.73-1.60 (m, 4H), 1.50-1.30 (m, 2H); TLC: 30% EtOAc:hexane (R$_f$: 0.2).

Synthesis of (S)-2-chloro-4-((1-cyclobutyl-2-hydroxyethyl) (methyl) amino) pyrimidin-5-ol To a stirred solution of (S)-2-((2-chloro-5-((4-methoxybenzyl) oxy) pyrimidin-4-yl) (methyl) amino)-2-cyclobutylethan-1-ol (120 mg, 0.38 mmol) in THF (0.5 mL) under an argon atmosphere was added trifluoroacetic acid (0.5 mL) at 0° C. The reaction mixture was stirred for 4 h at room temperature. After consumption of the starting material (monitored by TLC), the reaction mixture was basified with a saturated sodium bicarbonate solution (20 mL) and extracted with CH$_2$Cl$_2$ (2×20 mL). The combined organic extracts were dried over sodium sulfate, filtered and concentrated in vacuo to afford (S)-2-chloro-4-((1-cyclobutyl-2-hydroxyethyl) (methyl) amino) pyrimidin-5-ol (280 mg, 90%) as a white solid used in the next step without further purification. TLC: 50% EtOAc:hexane (R$_f$: 0.1).

Synthesis of (S)-2-chloro-7-cyclobutyl-8-methyl-7,8-dihydro-6H-pyrimido [5, 4-b] [1, 4] oxazine To a stirred solution of (S)-2-chloro-4-((1-cyclobutyl-2-hydroxyethyl) (methyl) amino) pyrimidin-5-ol (48 mg, 0.18 mmol) in THF (0.5 mL) under an argon atmosphere were added triphenylphosphine (45 mg, 0.22) and diisopropylazodicarboxylate (58 mg, 0.22 mmol) at 0° C. The reaction mixture was stirred for 1 h at 0° C. After consumption of the starting material (monitored by TLC), the volatile components were concentrated in vacuo. The crude material was purified by column chromatography using 10% EtOAc:hexane to afford (S)-2-chloro-7-cyclobutyl-8-methyl-7,8-dihydro-6H-pyrimido [5, 4-b] [1, 4] oxazine (20 mg, 45%) as a white solid. $^1$H-NMR (CDCl$_3$, 500 MHz): δ 7.62 (s, 1H), 4.10 (d, 1H), 3.87 (d, 1H), 3.35 (d, 1H), 3.22 (s, 3H), 2.63-2.59 (m, 1H), 2.20-1.90 (m, 4H), 1.87-1.80 (m, 2H); TLC: 20% EtOAc:hexane (R$_f$: 0.5).

Example 158

Synthesis of 4-(2-chloro-8-methyl-7, 8-dihydro-6H-pyrimido [5, 4-b] [1, 4] oxazin-7-yl) tetrahydro-2H-thiopyran 1, 1-dioxide

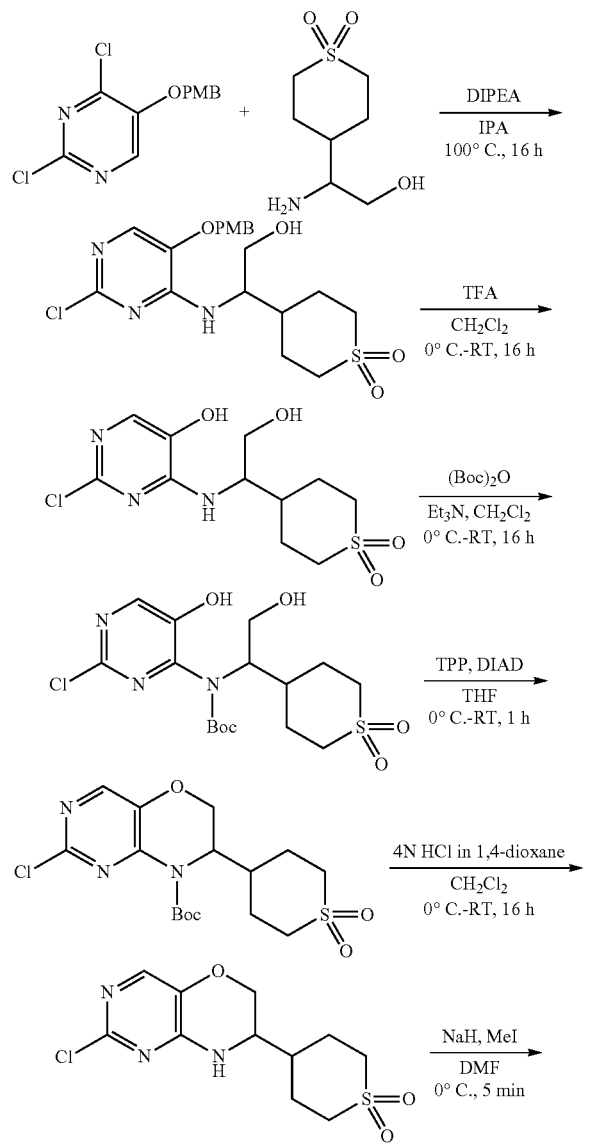

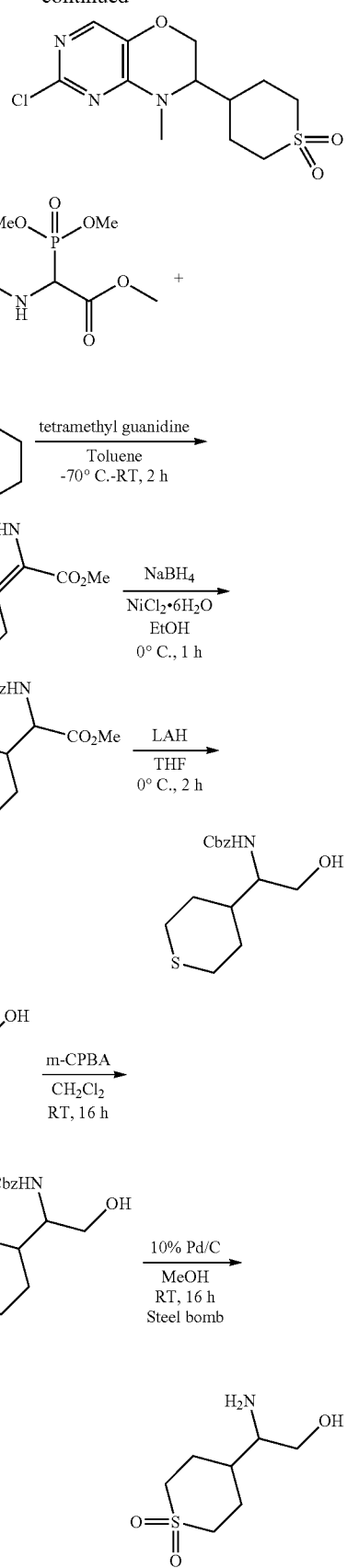

Synthesis of methyl 2-(((benzyloxy) carbonyl) amino)-2-(tetrahydro-4H-thiopyran-4-ylidene) acetate To a stirred solution of methyl 2-(((benzyloxy) carbonyl) amino)-2-(dimethoxyphosphoryl) acetate (15 g, 45.31 mmol) in toluene (150 mL) under an argon atmosphere was added tetramethylguanidine (5.5 mL, 43.50 mmol) at −70° C. and stirred for 1 h. Then tetrahydro-4H-thiopyran-4-one (5 g, 0.96 mmol) was added to the reaction mixture at −70° C. The reaction mixture was warmed to room temperature and stirred for 1 h. After consumption of the starting material (monitored by TLC), the reaction mixture was diluted with a 1% citric acid solution (100 mL) and extracted with EtOAc (2×100 mL). The combined organic extracts were washed with brine (100 mL), dried over sodium sulfate, filtered and concentrated in vacuo. The crude material was washed with n-hexane (2×50 mL) to afford methyl 2-(((benzyloxy) carbonyl) amino)-2-(tetrahydro-4H-thiopyran-4-ylidene) acetate (8.5 g, 58%) as a white solid. LCMS: 321.9 (M+1); (column; X-Select CSH C-18 (50×3.0 mm, 3.5 μm); RT 3.53 min 0.05% Aq TFA: ACN; 0.80 mL/min); TLC: 20% EtOAc:hexane ($R_f$: 0.6).

Synthesis of methyl 2-(((benzyloxy) carbonyl) amino)-2-(tetrahydro-2H-thiopyran-4-yl) acetate To a stirred solution of methyl 2-(((benzyloxy) carbonyl) amino)-2-(tetrahydro-4H-thiopyran-4-ylidene) acetate (8 g, 24.92 mmol) in ethanol (80 mL) under an argon atmosphere were added sodium borohydride (4.73 g, 124.61 mmol) and $NiCl_2 \cdot 6H_2O$ (2.96 g, 12.46 mmol) at 0° C. The reaction mixture was stirred for 1 h at 0° C. After consumption of the starting material (monitored by TLC), the reaction mixture was filtered and the filtrate was concentrated in vacuo. The residue was dissolved in EtOAc (100 mL) and washed with water (100 mL). The organic extract was dried over sodium sulfate, filtered and concentrated in vacuo. The crude material was purified by column chromatography using 10% EtOAc:hexane to afford methyl 2-(((benzyloxy) carbonyl) amino)-2-(tetrahydro-2H-thiopyran-4-yl) acetate (4 g, 50%) as a white solid. $^1$H-NMR ($CDCl_3$, 400 MHz): δ 7.40-7.29 (m, 5H), 5.15-5.06 (m, 2H), 4.36-4.30 (m, 1H), 3.75 (s, 3H), 2.73-2.56 (m, 4H), 2.01 (d, 1H), 1.86 (d, 2H), 1.46-1.42 (m, 2H); LCMS: 324.6 (M+1); (column; X-Select CSH C-18 (50×3.0 mm, 3.5 μm); RT 4.32 min 5 mM Aq $NH_4OAc$: ACN; 0.80 mL/min); TLC: 30% EtOAc:hexane ($R_f$: 0.5).

Synthesis of benzyl (2-hydroxy-1-(tetrahydro-2H-thiopyran-4-yl) ethyl) carbamate To a stirred solution of methyl 2-(((benzyloxy) carbonyl) amino)-2-(tetrahydro-2H-thiopyran-4-yl) acetate (4 g, 12.38 mmol) in THF (40 mL) under an argon atmosphere was added lithium aluminium hydride (1.88 g, 49.53 mmol) at 0° C. The reaction mixture was stirred for 2 h at 0° C. After consumption of the starting material (monitored by TLC), the reaction mixture was quenched with a 1N sodium hydroxide solution (100 mL), filtered and the filtrate was concentrated in vacuo. The crude material was purified by column chromatography using 30% EtOAc:hexane to afford benzyl (2-hydroxy-1-(tetrahydro-2H-thiopyran-4-yl) ethyl) carbamate (1.7 g, 47%) as a white solid. $^1$H-NMR (DMSO-$d_6$, 500 MHz): δ 7.40-7.30 (m, 4H), 7.00-6.98 (m, 1H), 5.01 (s, 2H), 4.60-4.55 (m, 1H), 3.42-3.36 (m, 3H), 2.60-2.50 (m, 4H), 1.93-1.88 (m, 2H), 1.59-1.50 (m, 1H), 1.39-1.30 (m, 2H); LCMS: 296.4 (M+1); (column; X-Select CSH C-18 (50×3.0 mm, 3.5 μm); RT 3.82 min 5 mM Aq $NH_4OAc$: ACN; 0.80 mL/min); TLC: 50% EtOAc:hexane ($R_f$: 0.3).

Synthesis of benzyl (1-(1, 1-dioxidotetrahydro-2H-thiopyran-4-yl)-2-hydroxyethyl) carbamate To a stirred solution of benzyl (2-hydroxy-1-(tetrahydro-2H-thiopyran-4-yl) ethyl) carbamate (1.7 g, 5.76 mmol) in $CH_2Cl_2$ (17 mL) under an argon atmosphere was added m-chloroperoxy benzoic acid (4.97 g, 28.81 mmol) at 0° C. The reaction mixture was warmed to room temperature and stirred for 16 h. After consumption of the starting material (monitored by TLC), the reaction mixture was quenched with a sodium sulfate solution (50 mL) and extracted with $CH_2Cl_2$ (2×50 mL). The combined organic extracts were washed with a saturated sodium bicarbonate solution (50 mL), brine (50 mL), dried over sodium sulfate, filtered and concentrated in vacuo. The crude material was purified by column chromatography using 30% EtOAc:hexane to afford benzyl (1-(1, 1-dioxidotetrahydro-2H-thiopyran-4-yl)-2-hydroxyethyl) carbamate (1.5 g, 83%) as a white solid. $^1$H-NMR (DMSO-$d_6$, 400 MHz): δ 7.40-7.30 (m, 5H), 7.11 (d, 1H), 5.01 (s, 2H), 4.70-4.65 (m, 1H), 3.52-3.49 (m, 1H), 3.40-3.35 (m, 2H), 3.15-3.10 (m, 1H), 3.05-3.00 (m, 3H), 1.98-1.90 (m, 3H), 1.79-1.65 (m, 2H); LCMS: 296.4 (M+1); (column; X-Select CSH C-18 (50×3.0 mm, 3.5 μm); RT 3.82 min 5 mM Aq $NH_4OAc$: ACN; 0.80 mL/min); TLC: 60% EtOAc:hexane ($R_f$: 0.4).

Synthesis of 4-(1-amino-2-hydroxyethyl) tetrahydro-2H-thiopyran 1, 1-dioxide To a stirred solution of benzyl (1-(1, 1-dioxidotetrahydro-2H-thiopyran-4-yl)-2-hydroxyethyl) carbamate (250 mg, 0.76 mmol) in MeOH (2.5 mL) under an argon atmosphere was added 10% Pd/C (catalytic amount) at room temperature. The reaction mixture was stirred for 16 h under a $H_2$ atmosphere of 40 psi at room temperature in steel bomb. After consumption of the starting material (monitored by TLC), the reaction mixture was filtered and the filtrate was concentrated in vacuo to obtain 4-(1-amino-2-hydroxyethyl) tetrahydro-2H-thiopyran 1, 1-dioxide (105 mg, 71%) as a white solid. LCMS: 194 (M+1); (column; Eclipse XDB C-18 (50×4.6 mm, 5 μm); RT 1.81 min 5 mM Aq $NH_4OAc$: ACN; 1.0 mL/min); TLC: 60% EtOAc:hexane ($R_f$: 0.4).

Synthesis of 4-(1-(2-chloro-5-((4-methoxybenzyl) oxy) pyrimidin-4-yl) amino)-2-hydroxyethyl) tetrahydro-2H-thiopyran 1, 1-dioxide To a stirred solution of 2,4-dichloro-5-((4-methoxybenzyl)oxy)pyrimidine (650 mg, 2.28 mmol) in isopropyl alcohol (6.5 mL) under an argon atmosphere were added diisopropylethylamine (8.4 mL, 4.56 mmol) and 4-(1-amino-2-hydroxyethyl) tetrahydro-2H-thiopyran 1, 1-dioxide (440 mg, 2.28 mmol) at room temperature. The reaction mixture was stirred at 100° C. for 16 h. After consumption of the starting material (monitored by TLC), the volatile components were concentrated in vacuo. The crude material was purified by column chromatography using 50% EtOAc: hexanes to afford 4-(1-((2-chloro-5-((4-methoxybenzyl) oxy) pyrimidin-4-yl) amino)-2-hydroxyethyl) tetrahydro-2H-thiopyran 1, 1-dioxide (425 mg, 42%) as a white solid. $^1$H-NMR ($CDCl_3$, 400 MHz): δ 7.67 (s, 1H), 7.31 (d, 2H), 6.93 (d, 2H), 5.73 (d, 1H), 5.01 (s, 2H), 4.18-4.15 (m, 2H), 3.86-3.84 (m, 1H), 3.83 (s, 3H), 3.79-3.73 (m, 1H), 3.13-3.03 (m, 2H), 3.02-2.90 (m, 2H), 2.06-1.94 (m, 3H); LCMS:

417.5 (M+1); (column; X-Select CSH C-18 (50×3.0 mm, 3.5 µm); RT 2.80 min. 0.05% Aq TFA: ACN; 0.80 mL/min); TLC: 80% EtOAc:hexane ($R_f$: 0.3).

Synthesis of 4-(1-((2-chloro-5-hydroxypyrimidin-4-yl) amino)-2-hydroxyethyl) tetrahydro-2H-thiopyran 1, 1-dioxide To a stirred solution of 4-(1-((2-chloro-5-((4-methoxybenzyl) oxy) pyrimidin-4-yl) amino)-2-hydroxyethyl) tetrahydro-2H-thiopyran 1, 1-dioxide (425 mg, 0.96 mmol) in $CH_2Cl_2$ (5 mL) under an argon atmosphere was added trifluoroacetic acid (2 mL) at 0° C. The reaction mixture was stirred for 16 h at room temperature. After consumption of the starting material (monitored by TLC), the reaction mixture was basified with a saturated sodium bicarbonate solution (20 mL) and extracted with 5% MeOH/$CH_2Cl_2$ (2×20 mL). The combined organic extracts were dried over sodium sulfate, filtered and concentrated in vacuo. The crude material was washed with n-hexane (2×20 mL) to afford 4-(1-((2-chloro-5-hydroxypyrimidin-4-yl) amino)-2-hydroxyethyl) tetrahydro-2H-thiopyran 1, 1-dioxide (280 mg, 90%) as a white solid. $^1$H-NMR (DMSO-$d_6$, 500 MHz): δ 10.41 (br s, 1H), 7.48 (s, 1H), 6.86 (d, 1H), 3.61-3.45 (m, 2H), 3.13-2.95 (m, 4H), 2.06 (d, 1H), 2.02-1.90 (m, 2H), 1.75-1.62 (m, 2H); LCMS: 322.5 (M+1); (column; Eclipse XDB C-18 (150×4.6 mm, 5 µm); RT 6.34 min 5 mM Aq $NH_4OAc$: ACN; 1.0 mL/min); TLC: 10% MeOH/$CH_2Cl_2$ ($R_f$: 0.2).

Synthesis of tert-butyl (2-chloro-5-hydroxypyrimidin-4-yl)(1-(1, 1-dioxidotetrahydro-2H-thiopyran-4-yl)-2-hydroxyethyl) carbamate To a stirred solution of 4-(1-((2-chloro-5-hydroxypyrimidin-4-yl) amino)-2-hydroxyethyl) tetrahydro-2H-thiopyran 1, 1-dioxide (300 mg, 3.11 mmol) in $CH_2Cl_2$ (10 mL) under an argon atmosphere were added triethylamine (0.53 mL, 3.73 mmol) and Boc anhydride (800 mg, 3.73 mmol) at 0° C. The reaction mixture was warmed to room temperature and stirred for 16 h. After consumption of the starting material (monitored by TLC), the reaction mixture was diluted with a sodium bicarbonate solution (20 mL) and extracted with $CH_2Cl_2$ (2×20 mL). The combined organic extracts were washed with water (20 mL), brine (20 mL), dried over sodium sulfate, filtered and concentrated in vacuo. The crude material was purified by column chromatography using 2-3% MeOH: $CH_2Cl_2$ to afford tert-butyl (2-chloro-5-hydroxypyrimidin-4-yl)(1-(1, 1-dioxidotetrahydro-2H-thiopyran-4-yl)-2-hydroxyethyl) carbamate (250 mg, 64%) as a white solid. $^1$H-NMR (CDCl$_3$, 500 MHz): δ 8.42 (s, 1H), 4.13-3.96 (m, 3H), 3.06-3.04 (m, 2H), 3.01-2.93 (m, 1H), 2.93-2.82 (m, 1H), 2.21 (br s, 2H), 2.00-1.88 (m, 2H), 1.49 (s, 9H), 1.29 (s, 3H): LCMS: 321.9 (M-Boc); (column; X-Select CSH C-18 (50×3.0 mm, 3.5 µm); RT 2.85 min 0.05% Aq TFA: ACN; 0.80 mL/min); TLC: 5% MeOH/$CH_2Cl_2$ ($R_f$: 0.2).

Synthesis of tert-butyl 2-chloro-7-(1, 1-dioxidotetrahydro-2H-thiopyran-4-yl)-6, 7-dihydro-8H-pyrimido [5, 4-b] [1, 4] oxazine-8-carboxylate To a stirred solution of tert-butyl (2-chloro-5-hydroxypyrimidin-4-yl)(1-(1, 1-dioxidotetrahydro-2H-thiopyran-4-yl)-2-hydroxyethyl) carbamate (100 mg, 0.23 mmol) in THF (1 mL) under argon atmosphere were added triphenylphosphine (57 mg, 0.22 mmol) and diisopropylazodicarboxylate (75 mg, 0.28 mmol) at 0° C. The reaction mixture was warmed to room temperature and stirred for 1 h. After consumption of the starting material (monitored by TLC), the reaction mixture was diluted with a sodium bicarbonate solution (20 mL) and extracted with $CH_2Cl_2$ (2×20 mL). The combined organic extracts were washed with water (20 mL), brine (20 mL), dried over sodium sulfate, filtered and concentrated in vacuo. The crude material was purified by column chromatography using 2-3% MeOH: $CH_2Cl_2$ to afford tert-butyl 2-chloro-7-(1, 1-dioxidotetrahydro-2H-thiopyran-4-yl)-6, 7-dihydro-8H-pyrimido [5, 4-b] [1, 4] oxazine-8-carboxylate (250 mg, 64%) as a white solid. LCMS: 303.8 (M-Boc); (column; X-Select CSH C-18 (50×3.0 mm, 3.5 µm); RT 3.22 min 0.05% Aq TFA: ACN; 0.80 mL/min); TLC: 5% MeOH/$CH_2Cl_2$ ($R_f$: 0.2).

Synthesis of 4-(2-chloro-7, 8-dihydro-6H-pyrimido [5, 4-b] [1, 4] oxazin-7-yl) tetrahydro-2H-thiopyran 1, 1-dioxide To a stirred solution of tert-butyl 2-chloro-7-(1, 1-dioxidotetrahydro-2H-thiopyran-4-yl)-6, 7-dihydro-8H-pyrimido [5, 4-b] [1, 4] oxazine-8-carboxylate (100 mg, 0.24 mmol) in $CH_2Cl_2$ (1 mL) under an argon atmosphere was added 4N HCl in 1, 4-dioxane (10 mL) at 0° C. The reaction mixture was stirred at room temperature for 16 h. After consumption of the starting material (monitored by TLC), the volatile components were evaporated in vacuo. The residue was basified with a saturated sodium bicarbonate solution (10 mL) and extracted with EtOAc (2×10 mL). The combined organic extracts were dried over sodium sulfate, filtered and concentrated in vacuo. The crude material was purified by column chromatography using 5% MeOH: $CH_2Cl_2$ to afford 4-(2-chloro-7, 8-dihydro-6H-pyrimido [5, 4-b] [1, 4] oxazin-7-yl) tetrahydro-2H-thiopyran 1, 1-dioxide (45 mg, 60%) as a white solid. $^1$H-NMR (DMSO-$d_6$, 400 MHz): δ 8.66-8.64 (m, 1H), 7.69-7.67 (m, 1H), 4.25 (dd, 1H), 3.96 (dd, 1H), 3.53-3.51 (m, 1H), 3.20-2.96 (m, 4H), 2.11 (d, 1H), 2.02-2.00 (m, 1H), 1.87-1.78 (m, 2H), 1.77-1.66 (m, 1H); LCMS: 304.2 (M+1); (column; X-select CSH C-18 (50×30 mm, 3.5 µm); RT 3.21 min. 5 mM $NH_4Oac$ in water: ACN; 0.8 mL/min); TLC: 10% MeOH/$CH_2Cl_2$ ($R_f$: 0.2).

Synthesis of 4-(2-chloro-8-methyl-7, 8-dihydro-6H-pyrimido [5, 4-b] [1, 4] oxazin-7-yl) tetrahydro-2H-thiopyran 1, 1-dioxide To a stirred solution of 4-(2-chloro-7, 8-dihydro-6H-pyrimido [5, 4-b] [1, 4] oxazin-7-yl) tetrahydro-2H-thiopyran 1, 1-dioxide (45 mg, 0.15 mmol) in DMF (0.1 mL) under an argon atmosphere were added sodium hydride (5.4 mg, 0.22 mmol) and methyl iodine (25 mg, 0.18 mmol) at 0° C. The reaction mixture was stirred for 5 min at 0° C. After consumption of the starting material (monitored by TLC), the reaction mixture was basified with an ammonium chloride solution (10 mL) and extracted with 10% MeOH/$CH_2Cl_2$ (2×10 mL). The combined organic extracts were dried over sodium sulfate, filtered and concentrated in vacuo. The crude material was purified by column chromatography using 2% MeOH: $CH_2Cl_2$ to afford 4-(2-chloro-8-methyl-7, 8-dihydro-6H-pyrimido [5, 4-b] [1, 4] oxazin-7-yl) tetrahydro-2H-thiopyran 1, 1-dioxide (20 mg, 42%) as a white solid. $^1$H-NMR (CDCl$_3$, 400 MHz): δ 7.26 (s, 1H), 4.37 (dd, 1H), 3.89 (dd, 1H), 3.36-3.32 (m, 1H), 3.24 (s, 3H), 3.12-2.88 (m, 4H), 2.13-2.03 (m, 5H); LCMS: 317.9 (M+1);

(column; X-select CSH C-18 (50×30 mm, 3.5 μm); RT 2.24 min. 0.05% Aq TFA: ACN; 0.8 mL/min).

Example 159

Synthesis of (S)-7-(tert-butyl)-2-chloro-8-methyl-7, 8-dihydro-6H-pyrimido [5, 4-b] [1, 4]oxazine

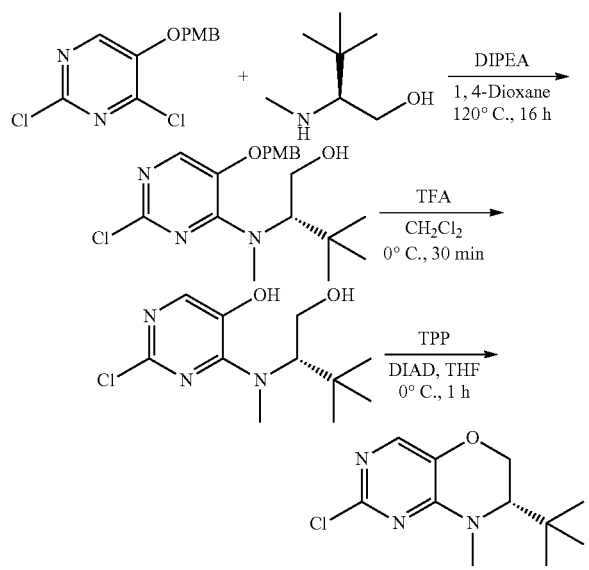

Synthesis of 2-((2-chloro-5-((4-methoxybenzyl) oxy) pyrimidin-4-yl) (methyl) amino)-3, 3-dimethylbutan-1-ol To a stirred solution of 2, 4-dichloro-5-((4-methoxybenzyl) oxy) pyrimidine (3.2 g, 11.45 mmol) in 1, 4-dioxane (60 mL) under an argon atmosphere were added diisopropylethylamine (1.5 g, 11.45 mmol) and (S)-3, 3-dimethyl-2-(methylamino) butan-1-ol (1.5 g, 11.45 mmol) at room temperature. The reaction mixture was stirred at 120° C. for 16 h. After consumption of the starting material (monitored by TLC), the volatile components were evaporated in vacuo. The crude material was purified by column chromatography using 30% EtOAc:hexane to afford (S)-2-((2-chloro-5-((4-methoxybenzyl) oxy) pyrimidin-4-yl) (methyl) amino)-3, 3-dimethylbutan-1-ol (2 g, 49%) as a pale yellow liquid. LCMS: 380.0 (M+); (column; Ascentis Express C-18 (50× 3.0 mm, 2.7 μm); RT 2.64 min. 0.025% Aq TFA+5% ACN: ACN+5% 0.025% Aq TFA; 1.2 mL/min); TLC: 50% EtOAc:hexane ($R_f$ 0.4).

Synthesis of (S)-2-chloro-4-((1-hydroxy-3, 3-dimethylbutan-2-yl) (methyl) amino) pyrimidin-5-ol To a stirred solution of (S)-2-((2-chloro-5-((4-methoxybenzyl) oxy) pyrimidin-4-yl) (methyl) amino)-3, 3-dimethylbutan-1-ol (2 g, 8.27 mmol) in CH$_2$Cl$_2$ (20 mL) under an argon atmosphere was added trifluoroacetic acid (5 mL) at 0° C. The reaction mixture was stirred for 30 min at 0° C. After consumption of the starting material (monitored by TLC), the reaction mixture was quenched with a saturated sodium bicarbonate solution (50 mL) and extracted with EtOAc (2×50 mL). The combined organic extracts were dried over sodium sulfate, filtered and concentrated in vacuo. The crude material was purified by column chromatography using 10% EtOAc:hexane to afford (S)-2-chloro-4-((1-hydroxy-3, 3-dimethylbutan-2-yl) (methyl) amino) pyrimidin-5-ol (1.1 g, 80%) as a white solid. $^1$H-NMR (DMSO-d$_6$, 400 MHz): δ 9.92 (br s, 1H), 7.53 (s, 1H), 4.99-4.92 (m, 1H), 4.60-4.58 (m, 1H), 3.75-3.66 (m, 1H), 3.65-3.53 (m, 1H), 3.99 (s, 3H), 0.91 (s, 9H); LCMS: 259.9 (M+1); (column; Ascentis Express C-18 (50×3.0 mm, 2.7 μm); RT 1.94 min. 0.025% Aq TFA+5% ACN: ACN+5% 0.025% Aq TFA; 1.2 mL/min); TLC: 50% EtOAc:hexane ($R_f$ 0.4).

Synthesis of (S)-7-(tert-butyl)-2-chloro-8-methyl-7, 8-dihydro-6H-pyrimido [5, 4-b] [1, 4] oxazine To a stirred solution of (S)-2-chloro-4-((1-hydroxy-3, 3-dimethylbutan-2-yl) (methyl) amino) pyrimidin-5-ol (1.1 g, 4.24 mmol) in THF (20 mL) under an argon atmosphere were added triphenylphosphine (1.3 g, 5.09 mmol) and diisopropylazodicarboxylate (1.36 g, 5.09 mmol) at 0° C. The reaction mixture was stirred for 1 h at 0° C. After consumption of the starting material (monitored by TLC), the volatile components were concentrated in vacuo. The crude material was purified by column chromatography using 20% EtOAc:hexane to afford (S)-7-(tert-butyl)-2-chloro-8-methyl-7, 8-dihydro-6H-pyrimido [5, 4-b] [1, 4] oxazine (360 mg, 36%) as a white solid. $^1$H-NMR (CDCl$_3$, 400 MHz): δ 7.62 (s, 1H), 4.51 (d, 1H), 3.74 (dd, 1H), 3.29 (s, 3H), 3.11-3.08 (m, 1H), 1.00 (s, 9H); LCMS: 242.0 (M+); (column; Ascentis Express C-18 (50×3.0 mm, 2.7 μm); RT 2.39 min. 0.025% Aq TFA+5% ACN: ACN+5% 0.025% Aq TFA; 1.2 mL/min); TLC: 20% EtOAc:hexane ($R_f$ 0.5).

Example 160

Synthesis of 2-chloro-8-methyl-7-(oxetan-3-yl)-7, 8-dihydro-6H-pyrimido [5, 4-b] [1, 4] oxazine

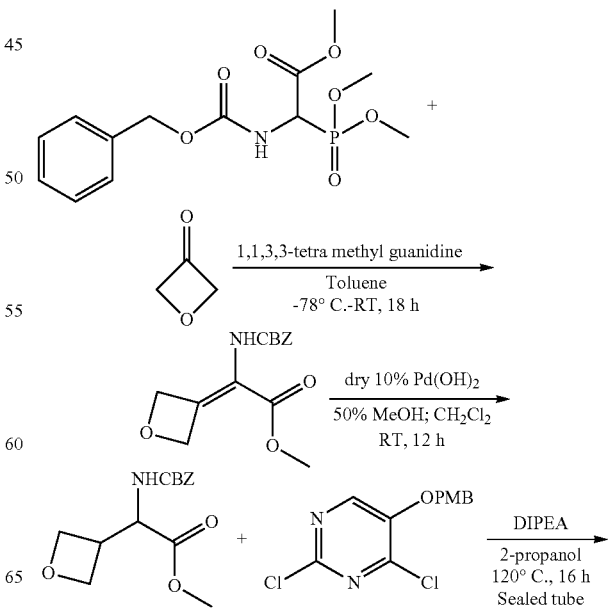

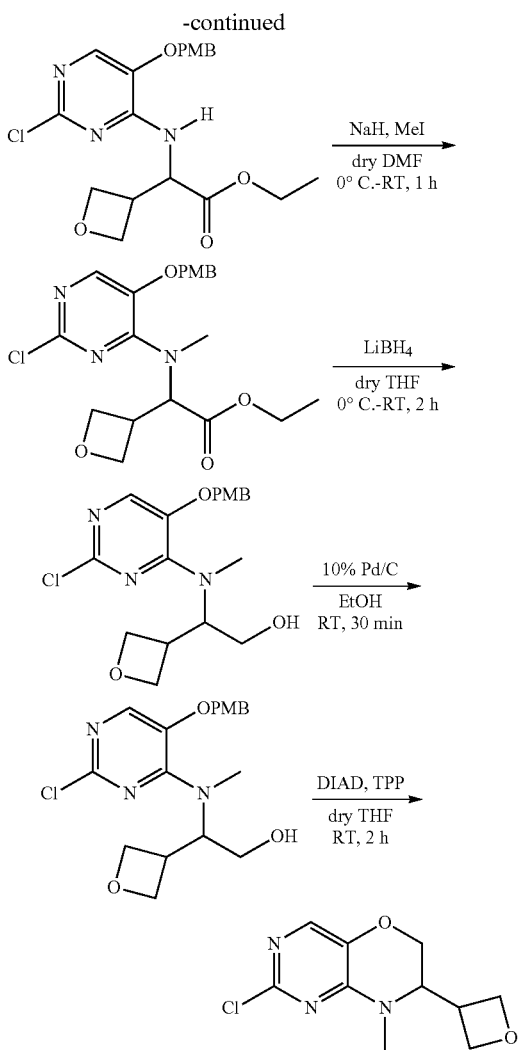

Synthesis of methyl 2-((2-(benzyloxy)-2-oxoethyl) amino)-2-(oxetan-3-ylidene) acetate To a stirred solution of methyl 2-(((benzyloxy) carbonyl) amino)-2-(dimethoxyphosphoryl) acetate (20 g, 60.42 mmol) in toluene (200 mL) under an argon atmosphere was added 1, 1, 3, 3-tetramethyl guanidine (7 g, 60.42 mmol) at −78° C. and stirred for 30 min. Then a solution of oxetan-3-one (4.2 g, 60.42 mmol) in toluene (20 mL) was added to the reaction mixture at −78° C. The reaction mixture was warmed to room temperature and stirred for 18 h. After consumption of the starting material (monitored by TLC), the reaction mixture was diluted with water (500 mL) and extracted with EtOAc (2×250 mL) and 20% MeOH: CH$_2$Cl$_2$ (2×250 mL). The combined organic extracts were dried over sodium sulfate, filtered and concentrated in vacuo. The crude material was purified by column chromatography using 5-10% MeOH: CH$_2$Cl$_2$ to afford methyl 2-((2-(benzyloxy)-2-oxoethyl) amino)-2-(oxetan-3-ylidene) acetate (13 g, 78%) as a white solid. $^1$H-NMR (DMSO-d$_6$, 500 MHz): δ 8.76 (br s, 1H), 7.40-7.30 (m, 5H), 5.30-5.27 (m., 2H), 5.17-5.14 (m, 2H), 5.04 (s, 2H), 3.70-3.65 (m, 1H), 3.64 (s, 2H); LCMS: 277.9 (M+1); (column; X-Select CSH C-18 (50×3.0 mm, 3.5 μm); RT 3.12 min 0.05% Aq TFA: ACN; 0.80 mL/min); TLC: 30% EtOAc:hexane (R$_f$; 0.7).

Synthesis of methyl 2-amino-2-(oxetan-3-yl) acetate

To a stirred solution of methyl 2-((2-(benzyloxy)-2-oxoethyl) amino)-2-(oxetan-3-ylidene) acetate (13 g, 46.93 mmol) in 50% MeOH: CH$_2$Cl$_2$ (700 mL) under an argon atmosphere was added dry 10% Pd(OH)$_2$ (2 g) at room temperature. The reaction mixture was stirred at room temperature for 12 h under a hydrogen atmosphere. After consumption of the starting material (monitored by TLC), the reaction mixture was filtered, washed with 50% MeOH: CH$_2$Cl$_2$ (2×100 mL) and the filtrate was concentrated in vacuo to afford methyl 2-amino-2-(oxetan-3-yl) acetate (5 g, crude) as a brown liquid. $^1$H-NMR (DMSO-d$_6$, 500 MHz): δ 4.55-4.50 (m, 2H), 4.49-4.40 (m, 2H), 3.84 (d, 1H), 3.70-3.65 (m, 1H), 3.62 (s, 3H), 3.17 (s, 2H); TLC: 5% MeOH/CH$_2$Cl$_2$ (R$_f$; 0.2).

Synthesis of methyl 2-((2-chloro-5-((4-methoxybenzyl) oxy) pyrimidin-4-yl) amino)-2-(oxetan-3-yl) acetate To a stirred solution of methyl 2-amino-2-(oxetan-3-yl) acetate (2 g, 13.79 mmol) in 2-propanol (12 mL) under an argon atmosphere were added diisopropylethylamine (9 g, 68.96 mmol) and 2, 4-dichloro-5-((4-methoxybenzyl) oxy) pyrimidine) (3.9 g, 13.79 mmol) at room temperature. The reaction mixture was stirred at 120° C. for 16 h. After consumption of the starting material (monitored by TLC), the reaction mixture was diluted with water (100 mL) and extracted with EtOAc (2×100 mL). The combined organic extracts were dried over sodium sulfate, filtered and concentrated in vacuo. The crude material was purified by column chromatography using 50% EtOAc:hexane to afford methyl 2-((2-chloro-5-((4-methoxybenzyl) oxy) pyrimidin-4-yl) amino)-2-(oxetan-3-yl) acetate (1.8 g, 33%) as an off-white solid. $^1$H-NMR (DMSO-d$_6$, 400 MHz): δ 7.85 (s, 1H), 7.82 (d, 1H), 7.40 (d, 2H), 6.95 (d, 2H), 5.13 (s, 2H), 4.97 (dd, 2H), 4.66 (dd, 1H), 4.54 (dd, 2H), 4.49 (t, 1H), 4.30 (t, 1H), 3.75 (s, 3H), 3.60 (s, 3H), 3.59-3.57 (m, 1H); LCMS: 394.2 (M+1); (column; X-Select CSH C-18 (50×3.0 mm, 3.5 μm); RT 3.81 min 5 mM Aq NH$_4$OAc: ACN; 0.80 mL/min); TLC: 5% MeOH/CH$_2$Cl$_2$ (R$_f$; 0.6).

Synthesis of methyl 2-((2-chloro-5-((4-methoxybenzyl) oxy) pyrimidin-4-yl) (methyl) amino)-2-(oxetan-3-yl) acetate To a stirred solution of methyl 2-((2-chloro-5-((4-methoxybenzyl) oxy) pyrimidin-4-yl) amino)-2-(oxetan-3-yl) acetate (3.6 g, 9.14 mmol) in dry DMF (50 mL) under an argon atmosphere was added sodium hydride (732 mg, 27.44 mmol) at 0° C. and stirred for 10 min. Then a solution of methyl iodide (2.16 g, 13.71 mmol) in DMF (10 mL) was added to the reaction mixture at 0° C. The reaction mixture was warmed to room temperature and stirred for 1 h. After consumption of the starting material (monitored by TLC), the reaction mixture was diluted with a saturated ammonium chloride solution (100 mL) and extracted with EtOAc (2×100 mL). The combined organic extracts were dried over sodium sulfate, filtered and concentrated in vacuo to obtain methyl 2-((2-chloro-5-((4-methoxybenzyl) oxy) pyrimidin-4-yl) (methyl) amino)-2-(oxetan-3-yl) acetate (3.5 g, crude) as an off-white solid in the next step without further purification. LCMS: 408 (M+1); (column; Ascentis Express C-18 (50×3.0 mm, 2.7 μm); RT 2.42 min. 0.025% Aq

Synthesis of 2-((2-chloro-5-((4-methoxybenzyl) oxy) pyrimidin-4-yl) (methyl) amino)-2-(oxetan-3-yl) ethan-1-ol To a stirred solution of methyl 2-((2-chloro-5-((4-methoxybenzyl) oxy) pyrimidin-4-yl) (methyl) amino)-2-(oxetan-3-yl) acetate (3.5 g, crude) in dry DMF (35 mL) under an argon atmosphere was added 2M lithium borohydride in THF (567 mg, 25.70 mmol) at 0° C. The reaction mixture was warmed to room temperature and stirred for 2 h. After consumption of the starting material (monitored by TLC), the reaction mixture was diluted with a saturated ammonium chloride solution (100 mL) and extracted with EtOAc (2×100 mL). The combined organic extracts were dried over sodium sulfate, filtered and concentrated in vacuo. The crude material was purified by column chromatography using 2% MeOH: $CH_2Cl_2$ to afford 2-((2-chloro-5-((4-methoxybenzyl) oxy) pyrimidin-4-yl) (methyl) amino)-2-(oxetan-3-yl) ethan-1-ol (2.4 g, 74%) as an off-white solid. $^1$H-NMR (DMSO-$d_6$, 400 MHz): δ 7.95 (s, 1H), 7.43 (d, 2H), 6.95 (d, 2H), 5.27-5.20 (m, 1H), 5.08 (s, 2H), 4.74 (t, 1H), 4.55 (dd, 1H), 4.48 (dd, 2H), 4.30-4.21 (m, 2H), 3.76 (s, 3H), 3.58-3.40 (m, 1H), 3.39-3.33 (m, 1H), 2.85 (s, 3H); LCMS: 380.3 (M+1); (column; X-Select CSH C-18 (50×3.0 mm, 3.5 µm); RT 3.53 min 5 mM Aq NH$_4$OAc: ACN: 0.8 mL/min); TLC: 70% EtOAc:hexane ($R_f$: 0.3).

Synthesis of 2-chloro-8-methyl-7-(oxetan-3-yl)-7,8-dihydro-6H-pyrimido [5, 4-b] [1, 4] oxazine To a stirred solution of 2-((2-chloro-5-((4-methoxybenzyl) oxy) pyrimidin-4-yl) (methyl) amino)-2-(oxetan-3-yl) ethan-1-ol (750 mg, 2.90 mmol) in dry DMF (20 mL) under an argon atmosphere were added triphenylphosphine (1.5 g, 5.78 mmol) and diisopropylazodicarboxylate (1.1 g, 5.78 mmol) at 0° C. The reaction mixture was warmed to room temperature and stirred for 2 h. After consumption of the starting material (monitored by TLC), the reaction mixture was diluted with water (30 mL) and extracted with EtOAc (2×30 mL). The combined organic extracts were dried over sodium sulfate, filtered and concentrated in vacuo. The crude material was purified by column chromatography using 2% MeOH: $CH_2Cl_2$ to afford 2-chloro-8-methyl-7-(oxetan-3-yl)-7,8-dihydro-6H-pyrimido [5, 4-b] [1, 4] oxazine (550 mg, 78%) as an off-white solid. $^1$H-NMR (DMSO-$d_6$, 500 MHz): δ 7.68 (s, 1H), 4.69-4.61 (m, 2H), 4.59-4.51 (m, 2H), 4.13 (dd, 1H), 4.09 (d, 1H), 3.94 (dd, 1H), 3.30-3.26 (m, 1H), 3.10 (s, 3H); LCMS: 242 (M+1); (column; X-Select CSH C-18 (50×3.0 mm, 3.5 µm); RT 1.36 min 2.5 mM NH$_4$OAc in water: 5% ACN; ACN: 5% 2.5 mM NH$_4$OAc in water: 1.0 mL/min); TLC: 5% MeOH/CH$_2$Cl$_2$ ($R_f$: 0.6).

Example 161

Synthesis of 2-chloro-8-methyl-7-(1-(trifluoromethyl) cyclopropyl)-7,8-dihydro-6H-pyrimido [5, 4-b] [1, 4] oxazine

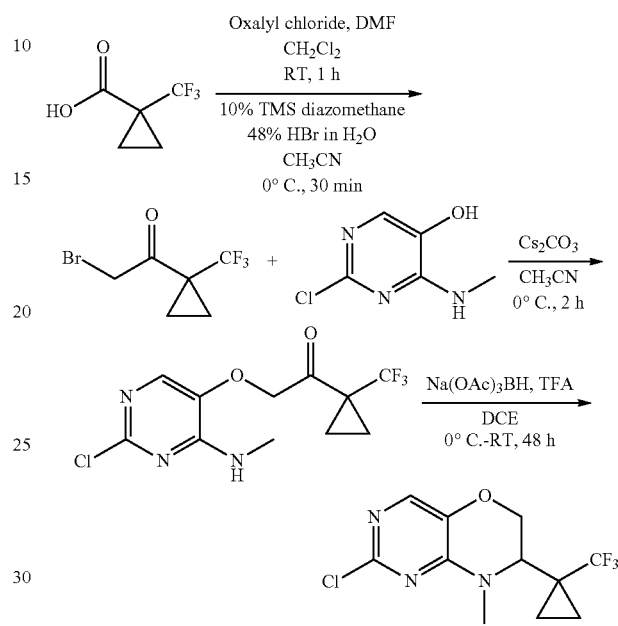

Synthesis of 2-bromo-1-(1-(trifluoromethyl) cyclopropyl) ethan-1-one

To a stirred solution of 1-(trifluoromethyl) cyclopropane-1-carboxylic acid (1 g, 6.49 mmol) in $CH_2Cl_2$ (10 mL) under an argon atmosphere were added oxalyl chloride (0.6 mL, 7.14 mmol) and DMF (5 drops) at 0° C. The reaction mixture was stirred for 1 h at 0° C. After consumption of the starting material (monitored by TLC), the volatile components were evaporated in vacuo. To the stirred solution of the above residue in acetonitrile (7 mL) was added 10% TMS diazomethane in hexane solution (14.7 mL) at 0° C. The reaction mixture was stirred for 2 h at 0° C. Then 48% HBr in water (1.2 mL) was added to the reaction mixture at 0° C. The reaction mixture was stirred for 30 min at 0° C. After consumption of the starting material (monitored by TLC), the reaction mixture was diluted with a saturated sodium bicarbonate solution (50 mL) and extracted with EtOAc (2×50 mL). The combined organic extracts were dried over sodium sulfate, filtered and concentrated in vacuo to obtain 2-bromo-1-(1-(trifluoromethyl) cyclopropyl) ethan-1-one (1.2 g, crude) as a brown oil.

Synthesis of 2-((2-chloro-4-(methylamino) pyrimidin-5-yl) oxy)-1-(1-(trifluoromethyl) cyclopropyl) ethan-1-one To a stirred solution of 2-chloro-4-(methylamino) pyrimidin-5-ol (750 mg, 4.68 mmol) in acetonitrile (10 mL) under an argon atmosphere were added cesium carbonate (3 g, 9.36 mmol) and 2-bromo-1-(1-(trifluoromethyl) cyclopropyl) ethan-1-one (1.2 g, 5.15 mmol) at 0° C. The reaction mixture was stirred for 2 h at 0° C. After consumption of the starting material (monitored by TLC), the reaction mixture was diluted with ice cold water (20 mL) and extracted with EtOAc (2×20 mL). The combined organic extracts were dried over sodium sulfate, filtered and concentrated in vacuo to obtain 2-((2-chloro-4-(methylamino) pyrimidin-5-yl) oxy)-1-(1-(trifluoromethyl) cyclopropyl) ethan-1-one (1.1 g, crude) as a colorless oil. LCMS: 309.8 (M+1); (column; Ascentis Express C-18 (50×3.0 mm, 2.7μ); RT 2.39 min. 0.025% Aq TFA+5% ACN; ACN+5% 0.025% Aq TFA 1.2 mL/min); TLC: 20% EtOAc:hexane ($R_f$: 0.6).

Synthesis of 2-chloro-8-methyl-7-(1-(trifluoromethyl) cyclopropyl)-7, 8-dihydro-6H-pyrimido [5, 4-b] [1, 4] oxazine To a stirred solution of 2-((2-chloro-4-(methylamino) pyrimidin-5-yl) oxy)-1-(1-(trifluoromethyl) cyclopropyl) ethan-1-one (2 g, 6.47 mmol) in dichloroethane (4 mL) under an argon atmosphere were added trifluoroacetic acid (catalytic amount) and sodium triacetoxyborohydride (2.7 g, 12.94 mmol) at 0° C. The reaction mixture was warmed to room temperature and stirred for 48 h. After consumption of the starting material (monitored by TLC), the reaction mixture was quenched with a 1N sodium hydroxide solution (20 mL) and extracted with EtOAc (2×20 mL). The combined organic extracts were dried over sodium sulfate, filtered and concentrated in vacuo. The crude material was purified by column chromatography using 15% EtOAc:hexanes to afford 2-chloro-8-methyl-7-(1-(trifluoromethyl) cyclopropyl)-7, 8-dihydro-6H-pyrimido [5, 4-b] [1, 4] oxazine (300 mg, 51%) as a white solid. $^1$H-NMR (CDCl$_3$, 400 MHz): δ 7.68 (s, 1H), 4.50 (d, 1H), 4.01 (dd, 1H), 3.89-3.87 (m, 1H), 3.20 (s, 3H), 1.13-1.01 (m, 3H), 0.59-0.55 (m, 1H); LCMS: 293.8 (M+1); (column; Ascentis Express C-18 (50×3.0 mm, 2.7μ); RT 2.41 min. 0.025% Aq TFA+5% ACN; ACN+5% 0.025% Aq TFA 1.2 mL/min); TLC: 20% EtOAc:hexane ($R_f$: 0.3).

Example 162

Synthesis of 2-chloro-7-(2, 5-dichloro-4-methoxyphenyl)-8-methyl-7, 8-dihydro-6H-pyrimido [5, 4-b] [1, 4] oxazine

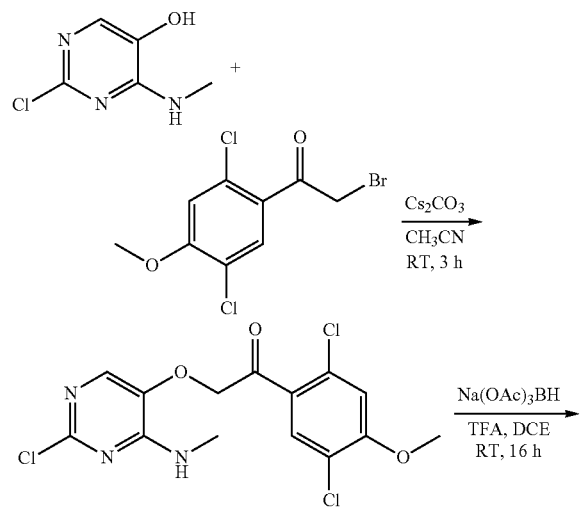

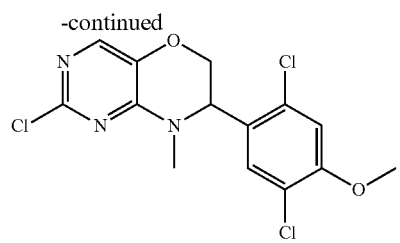

Synthesis of 2-((2-chloro-4-(methylamino) pyrimidin-5-yl) oxy)-1-(2, 5-dichloro-4-methoxyphenyl) ethan-1-one To a stirred solution of 2-chloro-4-(methylamino) pyrimidin-5-ol (500 mg, 3.14 mmol) in CH$_3$CN (5 mL) under an argon atmosphere were added cesium carbonate (2.0 g, 6.28 mmol) and 2-bromo-1-(2, 5-dichloro-4-methoxyphenyl) ethan-1-one (1 g, 3.45 mmol) at room temperature. The reaction mixture was stirred for 3 h. After consumption of the starting material (monitored by TLC), the reaction mixture was diluted with water (50 mL) and extracted with EtOAc (2×50 mL). The combined organic extracts were dried over sodium sulfite, filtered and concentrated in vacuo. The crude material was purified by column chromatography using 5% EtOAc:hexane to afford 2-((2-chloro-4-(methylamino) pyrimidin-5-yl) oxy)-1-(2, 5-dichloro-4-methoxyphenyl) ethan-1-one (600 mg, 56%) as an off-white solid. $^1$H-NMR (DMSO-d$_6$, 500 MHz): δ 7.90-7.88 (m, 2H), 7.42 (s, 1H), 7.34 (s, 1H), 4.25 (d, 1H), 4.05 (d, 1H), 3.93 (s, 3H), 2.73 (s, 3H); LCMS: 376.4 (M+); (column; X-Select CSH C-18 (50×3.0 mm, 3.5 μm); RT 4.39 min 0.05% Aq TFA: ACN; 0.80 mL/min); TLC: 30% EtOAc:hexanes ($R_f$: 0.5).

Synthesis of 2-chloro-7-(2, 5-dichloro-4-methoxyphenyl)-8-methyl-7, 8-dihydro-6H-pyrimido [5, 4-b] [1, 4] oxazine To a stirred solution of 2-((2-chloro-4-(methylamino) pyrimidin-5-yl) oxy)-1-(2, 5-dichloro-4-methoxyphenyl) ethan-1-one (600 mg, 1.59 mmol) in dichloroethane (6 mL) under an argon atmosphere were added trifluoroacetic acid (0.12 mL, 1.59 mmol) and sodium triacetoxyborohydride (710 mg, 3.35 mmol) at room temperature. The reaction mixture was stirred for 16 h. After consumption of the starting material (monitored by TLC), the reaction mixture was quenched with a 1 N sodium hydroxide solution (50 mL) and extracted with CH$_2$Cl$_2$ (2×50 mL). The combined organic extracts were dried over sodium sulfite, filtered and concentrated in vacuo. The crude material was purified by column chromatography using 15% EtOAc:hexane to afford 2-chloro-7-(2, 5-dichloro-4-methoxyphenyl)-8-methyl-7, 8-dihydro-6H-pyrimido [5, 4-b] [1, 4] oxazine (300 mg, 52%) as an off-white solid. $^1$H-NMR (CDCl$_3$, 500 MHz): δ 7.74 (s, 1H), 7.00 (s, 1H), 6.98 (s, 1H), 5.00 (t, 1H), 4.26 (d, 1H), 4.20 (d, 1H), 3.90 (s, 3H), 3.13 (s, 3H); LCMS: 361.8 (M+1); (column; X-Select CSH C-18 (50×3.0 mm, 3.5 μm); RT 3.88 min 0.05% Aq TFA: ACN; 0.80 mL/min); TLC: 30% EtOAc:hexanes ($R_f$: 0.5).

Example 163

Synthesis of N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine

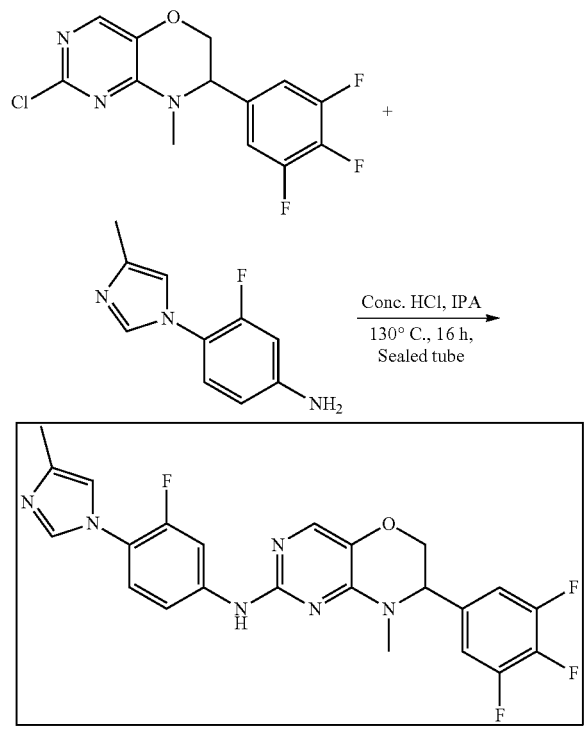

Synthesis of N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine To a stirred solution of 2-chloro-8-methyl-7-(3, 4, 5-trifluorophenyl)-7, 8-dihydro-6H-pyrimido [5, 4-b] [1, 4] oxazine (80 mg, 0.29 mmol) in isopropanol (0.8 mL) under an argon atmosphere were added concentrated hydrochloric acid (catalytic amount) and 3-fluoro-4-(4-methyl-1H-imidazol-1-yl) aniline (97 mg, 0.50 mmol) at room temperature. The reaction mixture was stirred at 130° C. for 16 h in a sealed tube. After consumption of the starting material (monitored by TLC), the reaction mixture was diluted with a saturated sodium carbonate solution (20 mL) and extracted with EtOAc (2×20 mL). The combined organic extracts were dried over sodium sulfate, filtered and concentrated in vacuo. The crude material was purified by column chromatography using 3% MeOH: $CH_2Cl_2$ to afford N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine (12 mg, 10%) as an off-white solid. $^1$H-NMR ($CD_3OD$, 400 MHz): δ 8.00-7.99 (m, 1H), 7.73 (s, 1H), 7.60 (s, 1H), 7.40-7.39 (m, 1H), 7.30 (t, 1H), 7.07-7.00 (m, 3H), 4.71 (s, 1H), 4.21 (s, 2H), 3.13 (s, 3H), 2.23 (s, 3H); Mass (ESI): 471.4 [M+1]; LCMS: 471.6 (M+1); (column; X-Selected CSH C-18 (50×3.0 mm, 3.5 μm); RT 2.99 min 0.05% Aq TFA: ACN; 0.80 mL/min); UPLC (column; Acquity BEH C-18 50×2.1 mm, 1.7 μm); RT 1.75 min. ACN: 0.025% TFA (Aq); 0.50 mL/min; TLC: 5% MeOH/ $CH_2Cl_2$ ($R_f$: 0.2).

Example 164

Synthesis of (S)—N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine

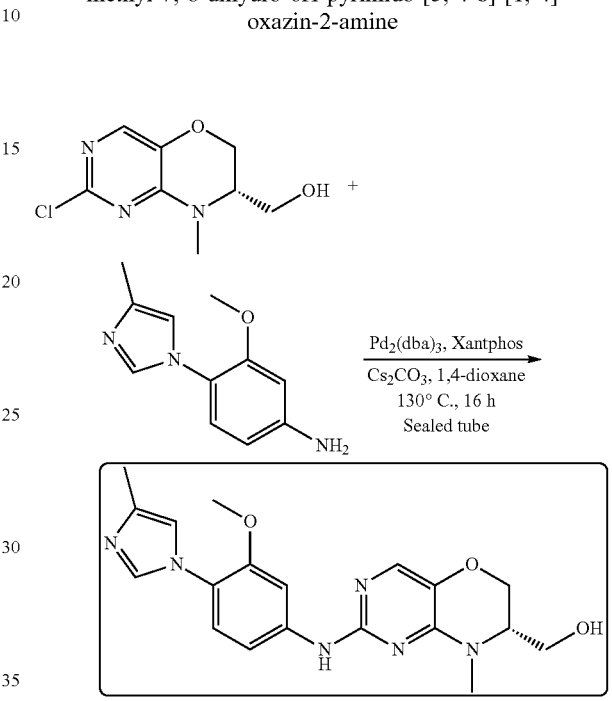

Synthesis of (S)—N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine To a dry vial was added a suspension of $Pd_2(dba)_3$ (26 mg, 0.03 mmol) and Xantphos (49 mg, 0.08 mmol) in 1, 4-dioxane (0.6 mL) at room temperature. The suspension was degassed with argon, heated to 120° C., and stirred for 3 min. A mixture of (S)-(2-chloro-8-methyl-7, 8-dihydro-6H-pyrimido [5, 4-b] [1, 4] oxazin-7-yl) methanol (120 mg, 0.56 mmol), 3-methoxy-4-(4-methyl-1H-imidazol-1-yl) aniline (227 mg, 1.12 mmol) and cesium carbonate (256 mg, 0.78 mmol) in 1, 4-dioxane (0.6 mL) was degassed and the catalyst premix was added. The resultant mixture was stirred at 130° C. for 16 h in a sealed tube. After consumption of the starting material (monitored by TLC and LCMS), the volatile components were evaporated in vacuo. The residue was diluted with water (50 mL) and extracted with $CH_2Cl_2$ (2×50 mL). The combined organic extracts were dried over sodium sulfate, filtered and concentrated in vacuo. The crude material was purified by column chromatography using 3% MeOH: EtOAc to afford (S)—N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine (42 mg, 19%) as a yellow solid. $^1$H-NMR (DMSO-$d_6$, 400 MHz): δ 9.03 (s, 1H), 7.85-7.82 (m, 1H), 7.60-7.58 (m, 1H), 7.56 (s, 1H), 7.29 (d, 1H), 7.12 (d, 1H), 6.99 (s, 1H), 5.09 (t, 1H), 4.30-4.25 (m, 1H), 3.88-3.80 (m, 1H), 3.77 (s, 3H), 3.62-3.59 (m, 1H), 3.52-3.42 (m, 2H), 3.20 (s, 3H), 2.13 (s, 3H); Mass (ESI): 383.4 [M+1]; LCMS: 383.4 (M+1); (column; X-Select CSH C-18 (50×3.0 mm, 3.5 µm); RT 2.95 min 5 mM Aq NH$_4$OAc in water: ACN; 0.8 mL/min); UPLC (column; Acquity UPLC BEH-C-18 2.1×50 mm, 1.7 µm); RT 1.12 min. ACN: 0.025% Aq TFA; 0.5 mL/min; Chiral HPLC: 96.2% RT=11.93 min (CHIRALPAK-IA (250×4.6 mm, 5 µm; mobile phase (A) 0.1% DEA in n-hexane (B) EtOH (A:B: 70:30); flow Rate: 1.0 mL/min); Optical rotation $[\alpha]_D^{20.00}$: 15.31 (c=0.25, CH$_2$Cl$_2$); TLC: 5% MeOH/CH$_2$Cl$_2$ (R$_f$: 0.3).

Example 165

Synthesis of 7-(5-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

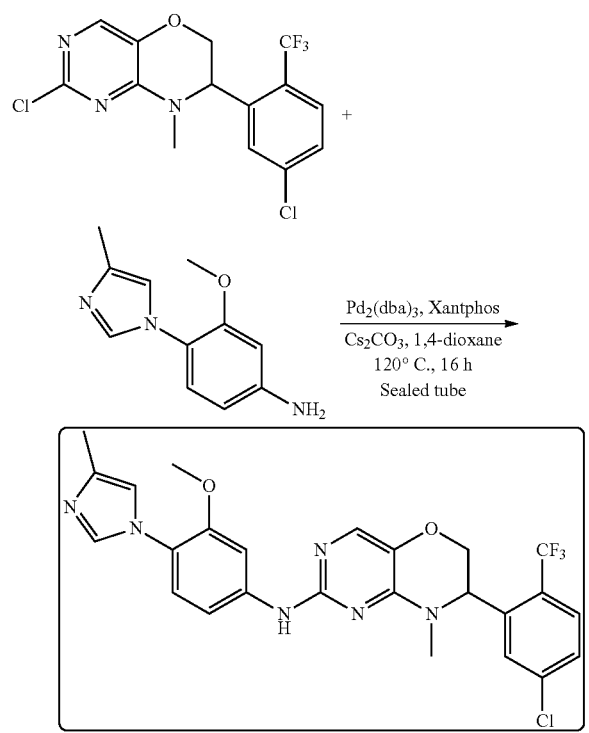

Synthesis of 7-(5-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a dry vial was added a suspension of Pd$_2$(dba)$_3$ (27 mg, 0.03 mmol) and Xantphos (52 mg, 0.07 mmol) in 1, 4-dioxane (0.25 mL) at room temperature. The suspension was degassed with argon, heated to 120° C., and stirred for 3 min. A mixture of 2-chloro-7-(5-chloro-2-(trifluoromethyl) phenyl)-8-methyl-7, 8-dihydro-6H-pyrimido [5, 4-b] [1, 4] oxazine (220 mg, 0.60 mmol), 3-methoxy-4-(4-methyl-1H-imidazol-1-yl) aniline (240 mg, 1.20 mmol) and cesium carbonate (275 mg, 0.84 mmol) in 1, 4-dioxane (0.25 mL) was degassed and the catalyst premix was added. The resultant mixture was stirred at 120° C. for 16 h in a sealed tube. After consumption of the starting material (monitored by TLC and LCMS), the volatile components were evaporated in vacuo. The crude material was purified by column chromatography using 3% MeOH: CH$_2$Cl$_2$ to afford 7-(5-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (25 mg, 8%) as an off-white solid. LCMS: 530.9 (M+1); (column; X-Select CSH C-18 (50×3.0 mm, 3.5 µm); RT 2.63 min 0.05% Aq TFA: ACN; 0.80 mL/min); UPLC (column; Acquity UPLC BEH C-18, 2.1×50 mm, 1.7 µm); RT 1.85 min. ACN: 0.025% Aq TFA; 0.5 mL/min; TLC: 5% MeOH/CH$_2$Cl$_2$ (R$_f$: 0.4).

Racemic compound of Example 165 was separated using a Chiralpak IB column (250×4.6 mm: 5 µm; (20 mg loading; 0.1% DEA in n-hexane: CH$_2$Cl$_2$:MeOH (50:50); (A:B: 95:05) as mobile phase) to provide the compound of Example 165A (Fraction I (+)) and pure Example 165B (Fraction II (−)).

Example 165A

Synthesis of (+)-7-(5-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

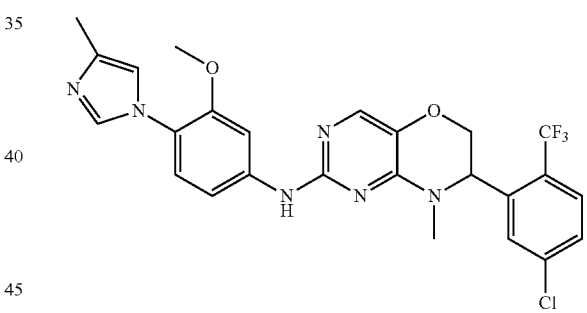

The compound of Example 165A was produced as described in Example 165. Analytical data for product Fraction I (+): $^1$H-NMR (CD$_3$OD, 400 MHz): δ 7.81 (d, 1H), 7.77 (s, 1H), 7.70 (s, 2H), 7.60-7.58 (m, 1H), 7.30-7.23 (m, 2H), 7.10 (d, 1H), 6.98 (s, 1H), 5.11-5.10 (m, 1H), 4.30-4.25 (m, 1H), 4.14-4.10 (m, 1H), 3.88 (s, 3H), 3.10 (s, 3H), 2.21 (s, 3H); Mass (ESI): 531.1 [M+1]; LCMS: 531.1 (M+1); (column; X-Select CSH C-18 (50×3.0 mm, 3.5 µm); RT 2.98 min. 0.05% Aq TFA: ACN; 0.80 mL/min); UPLC (column; Acquity UPLC BEH C-18, 2.1×50 mm, 1.7 µm); RT 1.87 min. ACN: 0.025% Aq TFA; 0.5 mL/min; Chiral HPLC: 99.3% RT=13.21 min (CHIRALPAK-IB (250×4.6 mm, 5 µm; mobile phase (A) 0.1% DEA in n-hexane (B) CH$_2$Cl$_2$: MeOH (50:50) (A:B: 90:10); flow Rate: 1.0 mL/min); Optical rotation $[\alpha]_D^{19.97}$: +57.16 (c=0.25, CH$_2$Cl$_2$).

Example 165B

Synthesis of (−)-7-(5-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

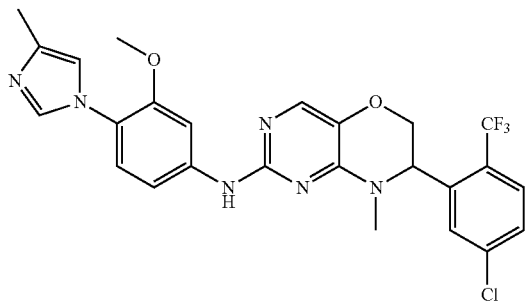 [SMILES: COc1cc(Nc2ncc3c(n2)N(C)C(c2cc(Cl)ccc2C(F)(F)F)CO3)ccc1-n1cnc(C)c1]

The compound of Example 165B was produced as described in Example 165. Analytical data for product Fraction II (−): $^1$H-NMR (CD$_3$OD, 400 MHz): δ 7.81 (d, 1H), 7.77 (s, 1H), 7.70 (s, 2H), 7.60-7.58 (m, 1H), 7.30-7.23 (m, 2H), 7.10 (d, 1H), 6.98 (s, 1H), 5.11-5.10 (m, 1H), 4.30-4.25 (m, 1H), 4.16-4.10 (m, 1H), 3.88 (s, 3H), 3.11 (s, 3H), 2.21 (s, 3H); Mass (ESI): 531.1 [M+1]; LCMS: 531.1 (M+1); (column; X-Select CSH C-18 (50×3.0 mm, 3.5 μm); RT 2.97 min. 0.05% Aq TFA: ACN; 0.80 mL/min); UPLC (column; Acquity UPLC BEH C-18, 2.1×50 mm, 1.7 μm); RT 1.87 min. ACN: 0.025% Aq TFA; 0.5 mL/min; Chiral HPLC: 95.8% RT=14.46 min (CHIRALPAK-IB (250×4.6 mm, 5 μm; mobile phase (A) 0.1% DEA in n-hexane (B) CH$_2$Cl$_2$:MeOH (50:50) (A:B: 90:10); flow Rate: 1.0 mL/min); Optical rotation $[\alpha]_D^{20.00}$: −52.46 (c=0.25, CH$_2$Cl$_2$).

Example 166

Synthesis of 7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

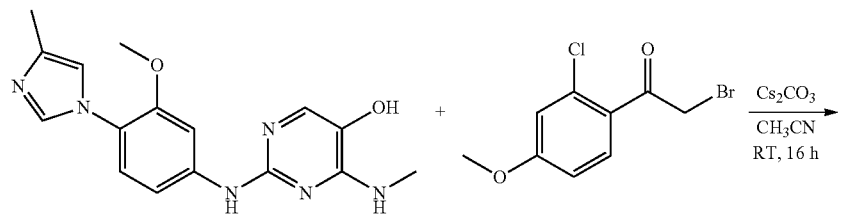

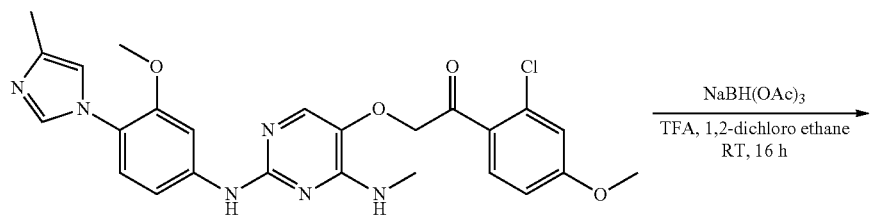

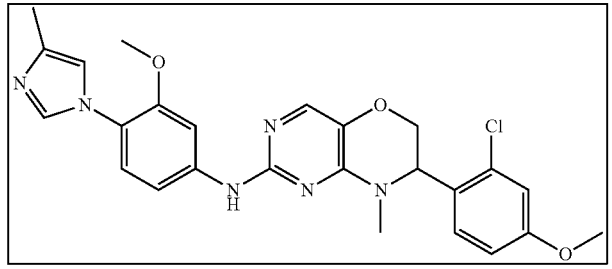

Synthesis of 1-(2-chloro-4-methoxyphenyl)-2-((2-((3-methoxy-4-(4-methyl-1H-imidazol-1-yl) phenyl) amino)-4-(methylamino) pyrimidin-5-yl) oxy) ethan-1-one To a stirred solution of 2-((3-methoxy-4-(4-methyl-1H-imidazol-1-yl) phenyl) amino)-4-(methylamino) pyrimidin-5-ol (100 mg, 0.30 mmol) in CH₃CN (1 mL) under an argon atmosphere were added cesium carbonate (200 mg, 0.61 mmol) followed by 2-bromo-1-(2-chloro-4-methoxyphenyl) ethan-1-one (122 mg, 0.33 mmol) at room temperature. The reaction mixture was stirred at room temperature for 16 h. After consumption of the starting material (monitored by TLC), the reaction mixture was diluted with water (20 mL) and extracted with CH₂Cl₂ (2×20 mL). The combined organic extracts were dried over sodium sulfate, filtered and concentrated in vacuo to obtain 1-(2-chloro-4-methoxyphenyl)-2-((2-((3-methoxy-4-(4-methyl-1H-imidazol-1-yl) phenyl) amino)-4-(methylamino) pyrimidin-5-yl) oxy) ethan-1-one (90 mg, crude) as a pale brown solid. LCMS: 510.3 (M+1); (column; X-Select CSH C-18 (50×3.0 mm, 3.5 μm); RT 2.92 min. 0.05% Aq TFA: ACN; 0.8 mL/min); TLC: 5% MeOH/CH₂Cl₂(R$_f$: 0.4).

Synthesis of 7-(2-chloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a stirred solution of 1-(2-chloro-4-methoxyphenyl)-2-((2-((3-methoxy-4-(4-methyl-1H-imidazol-1-yl) phenyl) amino)-4-(methylamino) pyrimidin-5-yl) oxy) ethan-1-one (160 mg, 0.31 mmol) in 1, 2-dichloroethane (1 mL) under an argon atmosphere were added trifluoroacetic acid (35.8 mg, 0.31 mmol) followed by sodium triacetoxyborohydride (140 mg, 0.66 mmol) at room temperature. The reaction mixture was stirred at room temperature for 16 h. After consumption of the starting material (monitored by TLC), the reaction mixture was quenched with a 1 N sodium hydroxide solution (20 mL) and extracted with CH₂Cl₂ (2×20 mL). The combined organic extracts were dried over sodium sulfate, filtered and concentrated in vacuo. The crude material was purified by column chromatography using 2% MeOH: CH₂Cl₂ to afford 7-(2-chloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (20 mg, 13%) as a white solid. $^1$H-NMR (CD₃OD, 400 MHz): δ 7.76 (s, 1H), 7.67 (s, 1H), 7.58 (s, 1H), 7.27-7.23 (m, 1H), 7.20-7.18 (m, 1H), 7.06 (s, 1H), 7.01-6.97 (m, 2H), 6.89-6.86 (m, 1H), 5.00-4.98 (m, 1H), 4.22-4.20 (m, 2H), 3.83 (s, 3H), 3.80 (s, 3H), 3.13 (s, 3H), 2.21 (s, 3H); Mass (ESI): 493.1 [M+1]; LCMS: 493 (M+1); (column; X-Select CSH C-18 (50×3.0 mm, 3.5 μm); RT 2.50 min. 0.05% Aq TFA: ACN; 0.8 mL/min); UPLC (column; Acquity UPLC BEH C-18, 2.1×50 mm, 1.7 μm); RT 1.73 min. ACN: 0.025% TFA (Aq); 0.50 mL/min; TLC: 5% MeOH/CH₂Cl₂ (R$_f$: 0.5).

Racemic compound of Example 166 was separated using a Chiralpak IC column (250×4.6 mm: 5 μm; (20 mg loading; 0.1% DEA in n-hexane: EtOH (A:B: 80:20) as mobile phase) to provide the compound of Example 166A (Fraction I (+)) and the compound of Example 166B (Fraction II (−)).

Example 166A

Synthesis of (+)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

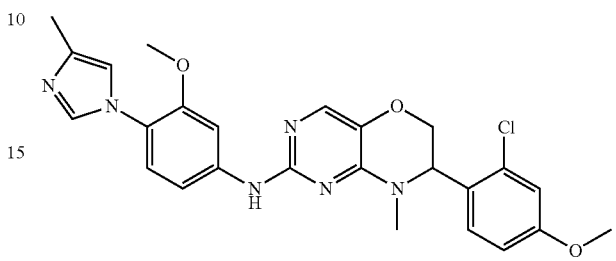

The compound of Example 166A was produced as described in Example 166. Analytical data for product Fraction I (+): $^1$H-NMR (CD₃OD, 400 MHz): δ 7.77 (s, 1H), 7.69 (br s, 1H), 7.57 (s, 1H), 7.25-7.23 (m, 1H), 7.20-7.19 (m, 1H), 7.06 (s, 1H), 7.00-6.97 (m, 2H), 6.90-6.88 (m, 1H), 5.11-5.09 (m, 1H), 4.23-4.21 (m, 2H), 3.84 (s, 3H), 3.80 (s, 3H), 3.13 (s, 3H), 2.21 (s, 3H); Mass (ESI): 493.7 [M+1]; LCMS: 493.1 (M+1); (column; X-Select CSH C-18 (50×3.0 mm, 3.5 μm); RT 2.47 min. 0.05% Aq TFA: ACN; 0.80 ml/min); UPLC (column; Acquity UPLC BEH C-18, 2.1×50 mm, 1.7 μm); RT 1.74 min. ACN: 0.025% Aq TFA; 0.5 ml/min; Chiral HPLC: 100% RT=30.08 min (Chiralpak-IC (250×4.6 mm, 5 μm; mobile phase (A) 0.1% DEA in n-hexane (B) EtOH (A:B; 80:20); flow Rate: 1.0 mL/min); Optical rotation $[\alpha]_D^{20.00}$: +196.81 (c=0.25, CH₂Cl₂).

Example 166B

Synthesis of (−)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

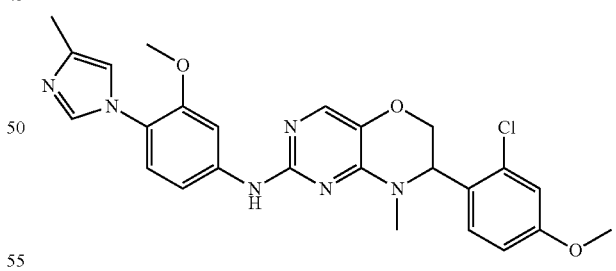

The compound of Example 166B was produced as described in Example 166. Analytical data for product Fraction II (−): $^1$H-NMR (CD₃OD, 400 MHz): δ 7.77 (s, 1H), 7.69 (br s, 1H), 7.57 (s, 1H), 7.25-7.23 (m, 1H), 7.20-7.19 (m, 1H), 7.06 (s, 1H), 7.00-6.97 (m, 2H), 6.90-6.88 (m, 1H), 5.11-5.09 (m, 1H), 4.23-4.21 (m, 2H), 3.84 (s, 3H), 3.80 (s, 3H), 3.13 (s, 3H), 2.21 (s, 3H); Mass (ESI): 493.6 [M+1]; LCMS: 493.1 (M+1); (column; X-Select CSH C-18 (50×3.0 mm, 3.5 μm); RT 2.48 min. 0.05% Aq TFA: ACN; 0.80 ml/min); UPLC (column; Acquity UPLC BEH C-18, 2.1×50 mm, 1.7 μm); RT 1.75 min. ACN: 0.025% Aq TFA; 0.5 ml/min; Chiral HPLC: 99.3% RT=34.23 min (Chiralpak-IC (250×4.6 mm, 5 μm; mobile phase (A) 0.1% DEA in n-hexane (B) EtOH (A:B; 80:20); flow Rate: 1.0 mL/min); Optical rotation $[\alpha]_D^{20.01}$: −192.68 (c=0.25, $CH_2Cl_2$).

Example 167

Synthesis of 7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

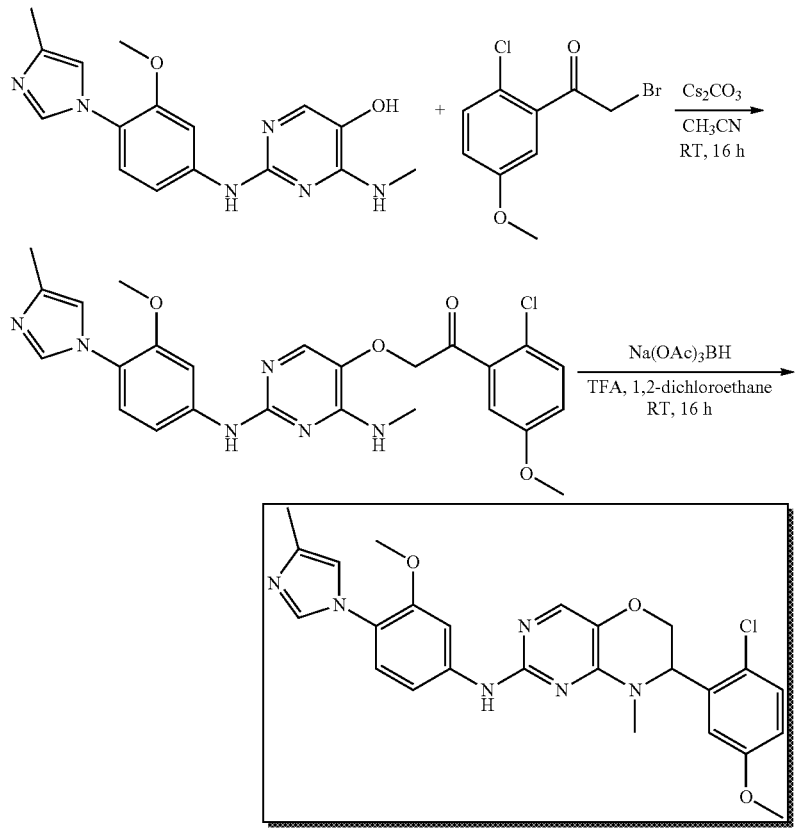

Synthesis of 1-(2-chloro-5-methoxyphenyl)-2-((2-((3-methoxy-4-(4-methyl-1H-imidazol-1-yl) phenyl) amino)-4-(methylamino) pyrimidin-5-yl) oxy) ethan-1-one To a stirred solution of 2-((3-methoxy-4-(4-methyl-1H-imidazol-1-yl) phenyl) amino)-4-(methylamino) pyrimidin-5-ol (50 mg, 0.15 mmol) in $CH_3CN$ (0.5 mL) under an argon atmosphere were added cesium carbonate (100 mg, 0.30 mmol) followed by 2-bromo-1-(2-chloro-5-methoxyphenyl) ethan-1-one (61 mg, 0.16 mmol) at room temperature. The reaction mixture was stirred at room temperature for 16 h. After consumption of the starting material (monitored by TLC), the reaction mixture was diluted with water (20 mL) and extracted with EtOAc (2×20 mL). The combined organic extracts were dried over sodium sulfate, filtered and concentrated in vacuo to obtain 1-(2-chloro-5-methoxyphenyl)-2-((2-((3-methoxy-4-(4-methyl-1H-imidazol-1-yl) phenyl) amino)-4-(methylamino) pyrimidin-5-yl) oxy) ethan-1-one (60 mg, crude) as a pale brown solid. LCMS: 509 (M+1); (column; X-Select CSH C-18 (50×3.0 mm, 3.5 μm); RT 2.42 min. 0.05% Aq TFA: ACN; 0.8 mL/min); TLC: 10% MeOH/$CH_2Cl_2$ ($R_f$: 0.5).

Synthesis of 7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a stirred solution of 1-(2-chloro-5-methoxyphenyl)-2-((2-((3-methoxy-4-(4-methyl-1H-imidazol-1-yl) phenyl) amino)-4-(methylamino) pyrimidin-5-yl) oxy) ethan-1-one (150 mg, 0.29 mmol) in 1, 2-dichloroethane (1 mL) under an argon atmosphere were added trifluoroacetic acid (0.02 mL, 0.29 mmol) followed by sodium triacetoxyborohydride (131 mg, 0.61 mmol) at room temperature. The reaction mixture was stirred at room temperature for 16 h. After consumption of the starting material (monitored by TLC), the reaction mixture was quenched with a 1 N sodium hydroxide solution (20 mL) and extracted with $CH_2Cl_2$ (2×20 mL). The combined organic extracts were dried over sodium sulfate, filtered and concentrated in vacuo. The crude material was purified by column chromatography using 3% MeOH: $CH_2Cl_2$ to afford 7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (25 mg, 16%) as an off-white solid. $^1$H-NMR ($CD_3OD$, 400 MHz): δ 7.87-7.82 (m, 2H), 7.59 (s, 1H), 7.39 (d, 1H), 7.27-7.21 (m, 1H), 7.19 (d, 1H), 7.00 (s, 1H), 6.90 (d, 1H), 6.58-6.56 (m, 1H), 5.11-5.08 (m, 1H), 4.30-4.20 (m, 2H), 3.83 (s, 3H), 3.67 (s, 3H), 3.14 (s, 3H), 2.21 (s, 3H); Mass (ESI): 493 [M+1]; LCMS: 493 (M+1); (column; X-Select CSH C-18 (50×3.0 mm, 3.5 μm); RT 2.45 min. 0.05% Aq TFA: ACN; 0.8 mL/min); UPLC (column; Acquity BEH C-18, 2.1×50 mm, 1.7 μm); RT 1.71 min. ACN: 0.025% TFA (Aq); 0.50 mL/min TLC: 10% MeOH/CH$_2$Cl$_2$ (R$_f$; 0.5).

Racemic compound of Example 167 was separated using a Chiralpak IC column (250×4.6 mm: 5 μm; (40 mg loading; 0.1% DEA in n-hexane: CH$_2$Cl$_2$:MeOH (50:50); (A:B: 80:20) as mobile phase) to provide the compound of Example 167A (Fraction I (+)) and the compound of Example 167B (Fraction II (−)).

Example 167A

Synthesis of (+)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

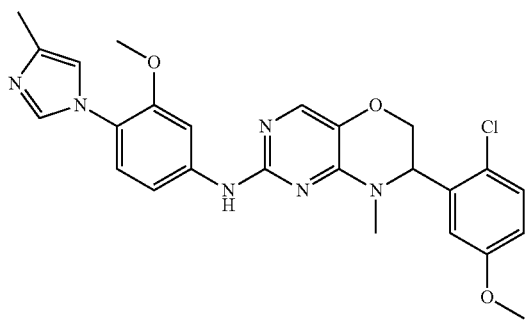 [SMILES: COc1ccc(Cl)c(C2COc3cnc(Nc4ccc(-n5cnc(C)c5)c(OC)c4)nc3N2C)c1]

The compound of Example 167A was produced as described in Example 167. Analytical data for product Fraction I (+): $^1$H-NMR (CD$_3$OD, 400 MHz): δ 7.75 (s, 1H), 7.69 (s, 1H), 7.60 (s, 1H), 7.39 (d, 1H), 7.26-7.24 (m, 1H), 7.19 (d, 1H), 6.97 (s, 1H), 6.91 (d, 1H), 6.58-6.56 (m, 1H), 5.11-5.10 (m, 1H), 4.30-4.20 (m, 2H), 3.86 (s, 3H), 3.70 (s, 3H), 3.17 (s, 3H), 2.21 (s, 3H); Mass (ESI): 493.7 [M+1]; LCMS: 493.1 (M+1); (column; X-Select CSH C-18 (50×3.0 mm, 3.5 μm); RT 2.46 min. 0.05% Aq TFA: ACN; 0.80 ml/min); UPLC (column; Acquity UPLC BEH C-18, 2.1×50 mm, 1.7 μm); RT 1.75 min. ACN: 0.025% Aq TFA; 0.5 ml/min; Chiral HPLC: 100% RT=21.27 min (Chiralpak-IC (250×4.6 mm, 5 μm; mobile phase (A) 0.1% DEA in n-hexane (B) CH$_2$Cl$_2$:MeOH (50:50) (A:B; 80:20); flow Rate: 1.0 mL/min); Optical rotation [α]$_D^{19.97}$: +195.20 (c=0.25, CH$_2$Cl$_2$).

Example 167B

Synthesis of (−)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

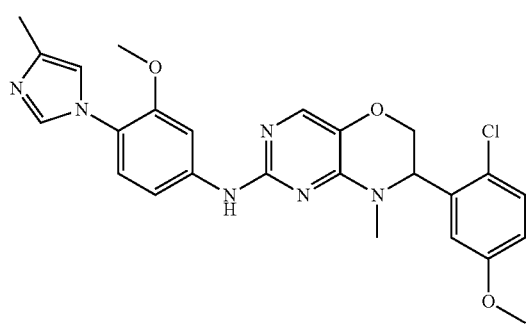

The compound of Example 167B was produced as described in Example 167. Analytical data for product Fraction II (−): $^1$H-NMR (CD$_3$OD, 400 MHz): δ 7.75 (s, 1H), 7.69 (s, 1H), 7.60 (s, 1H), 7.39 (d, 1H), 7.26-7.24 (m, 1H), 7.19 (d, 1H), 6.97 (s, 1H), 6.91 (d, 1H), 6.58-6.56 (m, 1H), 5.11-5.10 (m, 1H), 4.30-4.20 (m, 2H), 3.86 (s, 3H), 3.70 (s, 3H), 3.17 (s, 3H), 2.21 (s, 3H); Mass (ESI): 493.6 [M+1]; LCMS: 493.1 (M+1); (column; X-Select CSH C-18 (50×3.0 mm, 3.5 μm); RT 2.46 min. 0.05% Aq TFA: ACN; 0.80 ml/min); UPLC (column; Acquity UPLC BEH C-18, 2.1×50 mm, 1.7 μm); RT 1.75 min. ACN: 0.025% Aq TFA; 0.5 ml/min; Chiral HPLC: 100% RT=25.76 min (Chiralpak-IC (250×4.6 mm, 5 μm; mobile phase (A) 0.1% DEA in n-hexane (B) CH$_2$Cl$_2$:MeOH (50:50) (A:B; 80:20); flow Rate: 1.0 mL/min); Optical rotation [α]$_D^{20.01}$: −188.43 (c=0.25, CH$_2$Cl$_2$).

Example 168

Synthesis of 7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

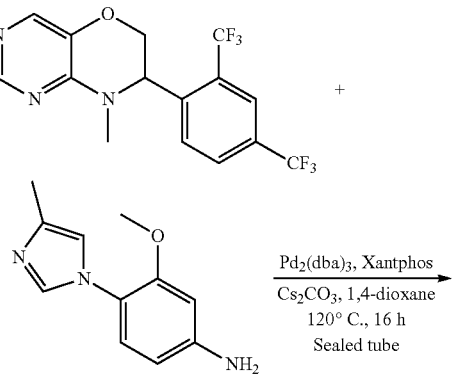

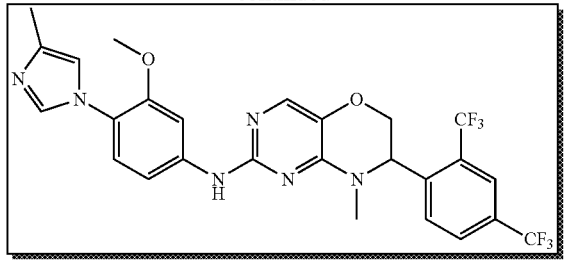

Synthesis of 7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a dry vial was added a suspension of Pd$_2$(dba)$_3$ (23 mg, 0.02 mmol) and Xantphos (44 mg, 0.07 mmol) in 1, 4-dioxane (2 mL) at room temperature. The suspension was degassed with argon, heated to 120° C., and stirred for 3 min. A mixture of 7-(2, 4-bis (trifluoromethyl) phenyl)-2-chloro-8-methyl-7, 8-dihydro-6H-pyrimido [5, 4-b] [1, 4] oxazine (200 mg, 0.50 mmol), 3-methoxy-4-(4-methyl-1H-imidazol-1-yl) aniline (204 mg, 1.00 mmol) and cesium carbonate (229 mg, 0.70 mmol) in 1, 4-dioxane (2 mL) was degassed and the catalyst premix was added. The resultant mixture was stirred at 120° C. for 16 h in a sealed tube. After consumption of the starting material (monitored by TLC and LCMS), the reaction mixture was diluted with a saturated sodium bicarbonate solution (20 mL) and extracted with EtOAc (2×20 mL). The combined organic extracts were dried over sodium sulfate, filtered and concentrated in vacuo. The crude material was purified by column chromatography using 4% MeOH: CH$_2$Cl$_2$ to afford 7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (130 mg, 45%) as an off-white solid. $^1$H-NMR (CD$_3$OD, 400 MHz): δ 8.07 (s, 1H), 7.99 (d, 1H), 7.72 (s, 1H), 7.68 (s, 2H), 7.55 (d, 1H), 7.25 (d, 1H), 7.18 (d, 1H), 6.96 (s, 1H), 5.20-5.18 (m, 1H), 4.33-4.30 (m, 1H), 4.17-4.15 (m, 1H), 3.84 (s, 3H), 3.11 (s, 3H), 2.21 (s, 3H); Mass (ESI): 565 [M+1]; LCMS: 565 (M+1); (column; X-Select CSH C-18 (50×3.0 mm, 3.5 μm); RT 2.65 min. 0.05% Aq TFA: ACN; 0.80 mL/min); UPLC (column; Acquity UPLC BEH C-18, 2.1×50 mm, 1.7 μm); RT 2.00 min. ACN: 0.025% Aq TFA; 0.5 mL/min; TLC: 5% MeOH/CH$_2$Cl$_2$ (R$_f$; 0.4).

Racemic compound of Example 168 was separated using a Chiralpak IA column (250×4.6 mm: 5 μm; (20 mg loading; 0.1% DEA in n-hexane: EtOH (A:B: 75:25) as mobile phase) to provide the compound of Example 168A (Fraction I (−)) and the compound of Example 168B (Fraction II (+)).

Example 168A

Synthesis of (−)-7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

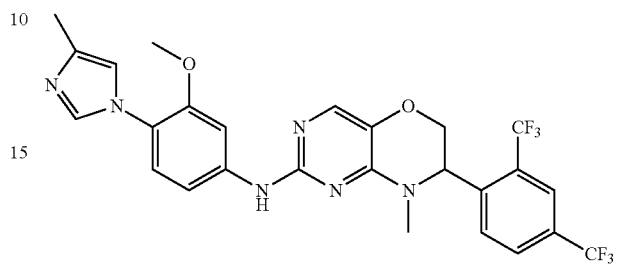

The compound of Example 168A was produced as described in Example 168. Analytical data for product Fraction I (−): $^1$H-NMR (CD$_3$OD, 400 MHz): δ 8.09 (s, 1H), 7.99 (d, 1H), 7.75 (s, 1H), 7.68 (s, 2H), 7.58 (d, 1H), 7.24 (d, 1H), 7.19 (d, 1H), 6.98 (s, 1H), 5.20-5.18 (m, 1H), 4.33-4.30 (m, 1H), 4.17-4.15 (m, 1H), 3.82 (s, 3H), 3.10 (s, 3H), 2.21 (s, 3H); Mass (ESI): 565.1 [M+1]; LCMS: 565.1 (M+1); (column; X-Select CSH C-18 (50×3.0 mm, 3.5 μm); RT 3.13 min. 0.05% Aq TFA: ACN; 0.80 ml/min); UPLC (column; Acquity UPLC BEH C-18, 2.1×50 mm, 1.7 μm); RT 2.01 min. ACN: 0.025% Aq TFA; 0.5 ml/min; Chiral HPLC: 99.37% RT=8.96 min (Chiralpak-IA (250×4.6 mm, 5 μm; mobile phase (A) 0.1% DFA in n-hexane (B) EtOH (A:B; 75:25); flow Rate: 1.0 mL/min); Optical rotation [α]$_D^{19.97}$: −98.16 (c=0.25, CH$_2$Cl$_2$).

Example 168B

Synthesis of (+)-7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

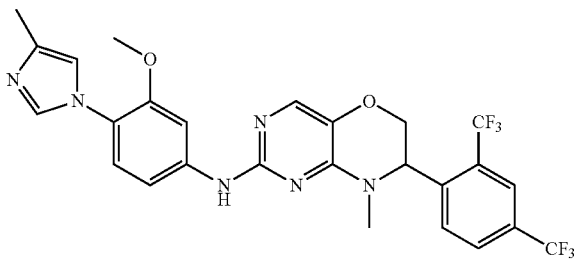 [SMILES: COc1cc(Nc2ncc3c(n2)N(C)C(c2ccc(C(F)(F)F)cc2C(F)(F)F)CO3)ccc1-n1cnc(C)c1]

The compound of Example 168B was produced as described in Example 168. Analytical data for product Fraction II (+): $^1$H-NMR (CD$_3$OD, 400 MHz): δ 8.09 (s, 1H), 7.99 (d, 1H), 7.75 (s, 1H), 7.66 (s, 2H), 7.58 (d, 1H), 7.24 (d, 1H), 7.19 (d, 1H), 6.98 (s, 1H), 5.20-5.18 (m, 1H), 4.33-4.30 (m, 1H), 4.17-4.15 (m, 1H), 3.82 (s, 3H), 3.10 (s, 3H), 2.21 (s, 3H); Mass (ESI): 565.1 [M+1]; LCMS: 565.1 (M+1); (column; X-Select CSH C-18 (50×3.0 mm, 3.5 μm); RT 3.14 min. 0.05% Aq TFA: ACN; 0.80 ml/min); UPLC (column; Acquity UPLC BEH C-18, 2.1×50 mm, 1.7 μm);

RT 2.00 min. ACN: 0.025% Aq TFA; 0.5 ml/min; Chiral HPLC: 97.1% RT=10.47 min (Chiralpak-IA (250×4.6 mm, 5 μm; mobile phase (A) 0.1% DEA in n-hexane (B) EtOH (A:B; 75:25); flow Rate: 1.0 mL/min); Optical rotation $[\alpha]_D^{19.98}$: +97.00 (c=0.25, CH$_2$Cl$_2$).

Example 169

Synthesis of 7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

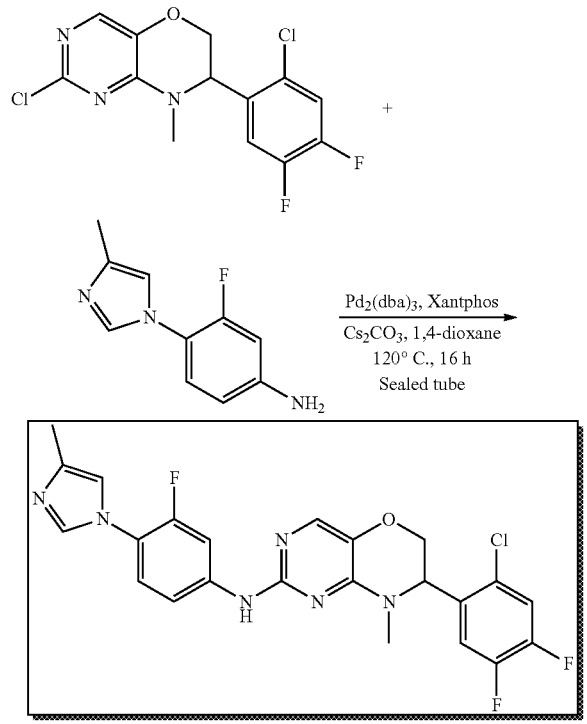

Synthesis of 7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine To a dry vial was added a suspension of Pd$_2$(dba)$_3$ (27 mg, 0.03 mmol) and Xantphos (52 mg, 0.09 mmol) in 1, 4-dioxane (1 mL) at room temperature. The suspension was degassed with argon, heated to 120° C., and stirred for 3 min. A mixture of 2-chloro-7-(2-chloro-4, 5-difluorophenyl)-8-methyl-7, 8-dihydro-6H-pyrimido [5, 4-b] [1, 4] oxazine (200 mg, 0.60 mmol), 3-fluoro-4-(4-methyl-1H-imidazol-1-yl) aniline (230 mg, 0.12 mmol) and cesium carbonate (274 mg, 0.84 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with CH$_2$Cl$_2$ (2×20 mL). The combined organic extracts were dried over sodium sulfate, filtered and concentrated in vacuo. The crude material was washed with ether (2×10 mL) to afford 7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine (200 mg, 68%) as an off-white solid. $^1$H-NMR (CD$_3$OD, 400 MHz): δ 8.01-7.99 (m, 1H), 7.77 (s, 1H), 7.64 (s, 1H), 7.56-7.54 (m, 1H), 7.44-7.40 (m, 1H), 7.37-7.34 (m, 1H), 7.10-7.08 (m, 1H), 6.98-6.96 (m, 1H), 5.15-5.13 (m, 1H), 4.30-4.20 (m, 2H), 3.17 (s, 3H), 2.22 (s, 3H); UPLC (column; Acquity UPLC BEH C-18 2.1×50 mm, 1.7 μm); RT 1.78 min. ACN: 0.025% Aq TFA; 0.5 mL/min; TLC: 5% MeOH/CH$_2$Cl$_2$ (R$_f$: 0.4).

Racemic compound of Example 169 was separated using a Chiralpak ADH column (250×4.6 mm: 5 μm; (10 mg loading; 0.1% DEA in n-hexane: EtOH:MeOH (40:60); (A:B: 55:45) as mobile phase) to provide the compound of Example 169A (Fraction I (+)) and the compound of Example 169B (Fraction II (−)).

Example 169A

Synthesis of (+)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

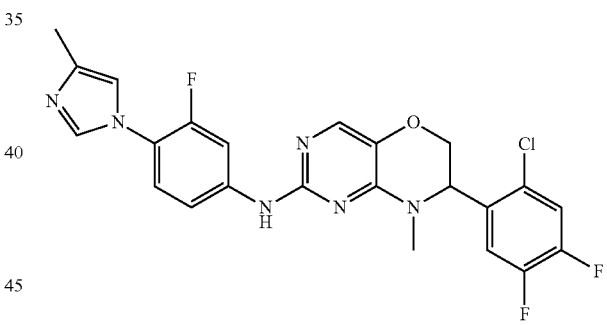

The compound of Example 169A was produced as described in Example 169. Analytical data for product Fraction I (+): $^1$H-NMR (CD$_3$OD, 400 MHz): δ 8.01-7.99 (m, 1H), 7.76 (s, 1H), 7.65 (s, 1H), 7.54-7.52 (m, 1H), 7.42-7.40 (m, 1H), 7.36-7.34 (m, 1H), 7.10-7.08 (m, 1H), 6.95 (t, 1H), 5.15-5.14 (m, 1H), 4.30-4.20 (m, 2H), 3.19 (s, 3H), 2.24 (s, 3H); Mass (ESI): 487.6 [M+1]; LCMS: 487 (M+1); (column; X-Select CSH C-18 (50×3.0 mm, 3.5 μm); RT 2.49 min. 0.05% Aq TFA: ACN; 0.80 mL/min); UPLC (column; Acquity BEH C-18, 50×2.1 mm, 1.7 μm); RT 1.96 min. ACN: 0.025% Aq TFA; 0.5 mL/min; Chiral HPLC: 99.8% RT=11.43 min (CHIRALPAK-AD-H (250×4.6 mm, 5 μm; mobile phase (A) 0.1% DEA in n-hexane (B) EtOH: MeOH (50:50) (A:B; 55:45); flow Rate: 1.0 mL/min); Optical rotation $[\alpha]_D^{20.01}$: +157.90 (c=0.25, CH$_2$Cl$_2$).

Example 169B

Synthesis of (−)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

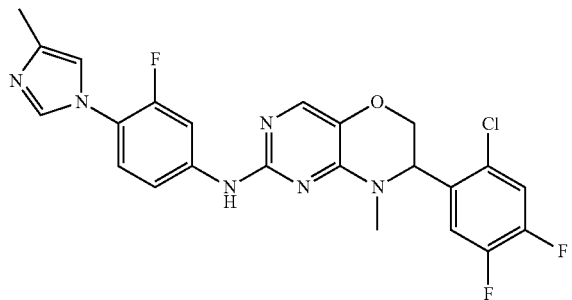

The compound of Example 169B was produced as described in Example 169. Analytical data for product Fraction II (−): $^1$H-NMR (CD$_3$OD, 400 MHz): δ 8.01-7.99 (m, 1H), 7.76 (s, 1H), 7.65 (s, 1H), 7.3 (t, 1H), 7.42-7.40 (m, 1H), 7.35 (t, 1H), 7.10-7.08 (m, 1H), 6.95 (t, 1H), 5.15-5.14 (m, 1H), 4.30-4.20 (m, 2H), 3.19 (s, 3H), 2.24 (s, 3H); Mass (ESI): 487.6 [M+1]; LCMS: 487 (M+1); (column; X-Select CSH C-18 (50×3.0 mm, 3.5 µm); RT 2.48 min. 0.05% Aq TFA: ACN; 0.80 mL/min); UPLC (column; Acquity BEH C-18, 50×2.1 mm, 1.7 µm); RT 1.95 min. ACN: 0.025% Aq TFA; 0.5 mL/min; Chiral HPLC: 99.5% RT=16.83 min (CHIRALPAK-AD-H (250×4.6 mm, 5 µm; mobile phase (A) 0.1% DEA in n-hexane (B) EtOH:MeOH (50:50) (A:B; 55:45); flow Rate: 1.0 mL/min); Optical rotation $[α]_D^{20.00}$: −146.04 (c=0.25, CH$_2$Cl$_2$).

Example 170

Synthesis of (S)-(2-((3-fluoro-4-(4-methyl-1H-imidazol-1-yl) phenyl) amino)-8-methyl-7, 8-dihydro-6H-pyrimido [5, 4-b] [1, 4] oxazin-7-yl) methanol

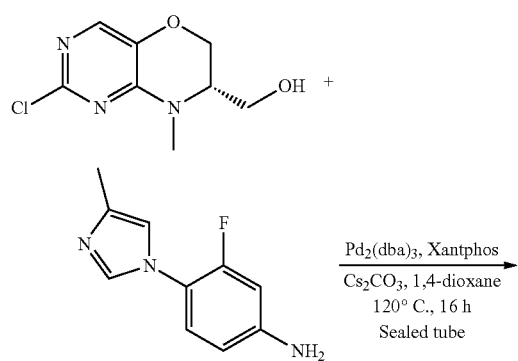

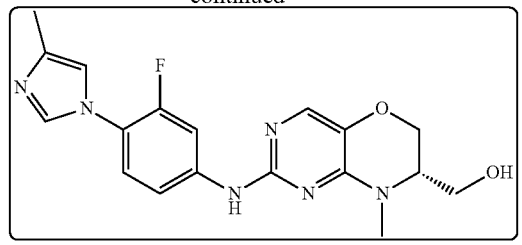

Synthesis of (S)-(2-((3-fluoro-4-(4-methyl-1H-imidazol-1-yl) phenyl) amino)-8-methyl-7, 8-dihydro-6H-pyrimido [5, 4-b] [1, 4] oxazin-7-yl) methanol To a dry vial was added a suspension of Pd$_2$(dba)$_3$ (26 mg, 0.03 mmol) and Xantphos (49 mg, 0.08 mmol) in 1, 4-dioxane (0.6 mL) at room temperature. The suspension was degassed with argon, heated to 120° C., and stirred for 3 min. A mixture of (S)-(2-chloro-8-methyl-7, 8-dihydro-6H-pyrimido [5, 4-b] [1, 4] oxazin-7-yl) methanol (120 mg, 0.56 mmol), 3-fluoro-4-(4-methyl-1H-imidazol-1-yl) aniline (214 mg, 1.12 mmol) and cesium carbonate (256 mg, 0.78 mmol) in 1, 4-dioxane (0.6 mL) was degassed and the catalyst premix was added. The resultant mixture was stirred at 120° C. for 16 h in a sealed tube. After consumption of the reaction (monitored by TLC and LCMS), the volatile components were evaporated in vacuo. The residue was diluted with water (50 mL) and extracted with CH$_2$Cl$_2$ (2×50 mL). The combined organic extracts were dried over sodium sulfate, filtered and concentrated in vacuo. The crude material was purified by column chromatography using 3% MeOH: EtOAc to afford (S)-(2-((3-fluoro-4-(4-methyl-1H-imidazol-1-yl) phenyl) amino)-8-methyl-7, 8-dihydro-6H-pyrimido [5, 4-b] [1, 4] oxazin-7-yl) methanol (40 mg, 19%) as a yellow solid. $^1$H-NMR (DMSO-d$_6$, 400 MHz): δ 9.30 (s, 1H), 8.04-7.99 (m, 1H), 7.74 (s, 1H), 7.58 (s, 1H), 7.51-7.48 (m, 1H), 7.38 (t, 1H), 7.12 (s, 1H), 5.08 (t, 1H), 4.30-4.28 (m, 1H), 3.88-3.83 (m, 1H), 3.65-3.60 (m, 1H), 3.58-3.41 (m, 2H), 3.20 (s, 3H), 2.13 (s, 3H); Mass (ESI): 371.4 [M+1]; LCMS: 371.4 (M+1); (column; X-Select CSH C-18 (50×3.0 mm, 3.5 µm); RT 2.79 min 5 mM Aq NH$_4$OAc: ACN; 0.80 mL/min); UPLC (column; Acquity UPLC HSS T-3 100×2.1 mm, 1.8µ); RT 2.89 min. ACN: 0.025% Aq TFA; 1.0 mL/min; Chiral HPLC: 97.8% RT=13.67 min (CHIRALPAK-IA (250×4.6 mm, 5 µm; mobile phase (A) 0.1% DEA in n-hexane (B) EtOH (A:B: 70:30); flow Rate: 1.0 mL/min); Optical rotation $[α]_D^{19.98}$: +13.44 (c=0.25, CH$_2$Cl$_2$); TLC: 5% MeOH/CH$_2$Cl$_2$ (R$_f$: 0.3).

Example 171

Synthesis of N-(5-methoxy-6-(4-methyl-1H-imidazol-1-yl) pyridin-3-yl)-8-methyl-7-(o-tolyl)-7, 8-dihydro-6H-pyrimido [5, 4-b] [1, 4] oxazin-2-amine

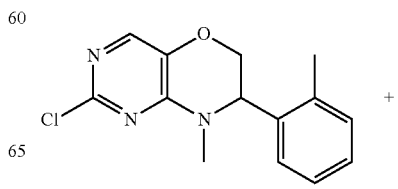

543
-continued

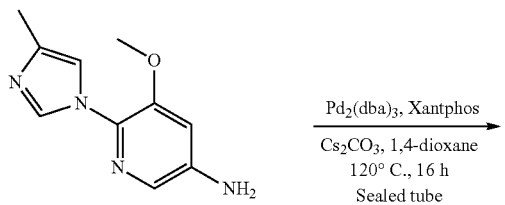

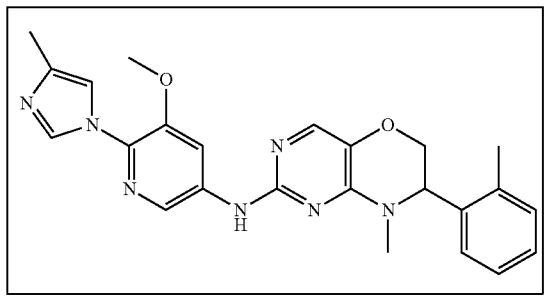

Synthesis of N-(5-methoxy-6-(4-methyl-1H-imidazol-1-yl) pyridin-3-yl)-8-methyl-7-(o-tolyl)-7, 8-dihydro-6H-pyrimido [5, 4-b] [1, 4] oxazin-2-amine To a dry vial was added a suspension of Pd$_2$(dba)$_3$ (33 mg, 0.03 mmol) and Xantphos (63 mg, 0.10 mmol) in 1, 4-dioxane (1 mL) at room temperature. The suspension was degassed with argon, heated to 120° C., and stirred for 3 min. A mixture of 2-chloro-8-methyl-7-(o-tolyl)-7, 8-dihydro-6H-pyrimido [5, 4-b] [1, 4] oxazine (200 mg, 0.72 mmol), 5-methoxy-6-(4-methyl-1H-imidazol-1-yl) pyridin-3-amine (297 mg, 1.45 mmol) and cesium carbonate (331 mg, 1.01 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (20 mL) and extracted with EtOAc (2×20 mL). The combined organic extracts were dried over sodium sulfate, filtered and concentrated in vacuo. The crude material was washed with MeOH:ether (1:1, 2×10 mL) to afford N-(5-methoxy-6-(4-methyl-1H-imidazol-1-yl) pyridin-3-yl)-8-methyl-7-(o-tolyl)-7, 8-dihydro-6H-pyrimido [5, 4-b] [1, 4] oxazin-2-amine (220 mg, 68%) as an off-white solid. LCMS: 444.1 (M+1); (column; X-Select CSH C-18 (50×3.0 mm, 3.5 μm); RT 2.33 min. 0.05% Aq TFA: ACN; 0.80 mL/min); UPLC (column; Acquity UPLC BEH C-18 2.1×50 mm, 1.7 μm); RT 1.65 min. ACN: 0.025% Aq TFA; 0.5 mL/min; TLC: 10% MeOH/CH$_2$Cl$_2$ (R$_f$: 0.4).

Racemic compound of Example 171 was separated using a Chiralpak IA column (250×4.6 mm: 5 μm; (15 mg loading; 0.1% DEA in n-hexane: CH$_2$Cl$_2$:MeOH (50:50); (A:B: 85:15) as mobile phase) to provide the compound of Example 171A (Fraction I (+)) and the compound of Example 171B (Fraction II (−)).

544

Example 171A

Synthesis of (+)-N-(5-methoxy-6-(4-methyl-1H-imidazol-1-yl) pyridin-3-yl)-8-methyl-7-(o-tolyl)-7, 8-dihydro-6H-pyrimido [5, 4-b] [1, 4] oxazin-2-amine

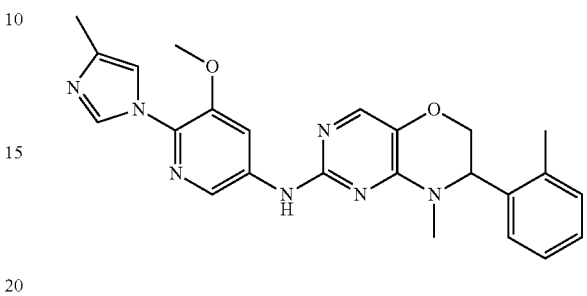

The compound of Example 171A was produced as described in Example 171. Analytical data for product Fraction I (+): $^1$H-NMR (CD$_3$OD, 400 MHz): δ 8.32-8.30 (m, 2H), 8.13 (s, 1H), 7.60 (s, 1H), 7.40-7.38 (m, 1H), 7.27-7.14 (m, 3H), 7.00 (d, 1H), 5.02-5.00 (m, 1H), 4.28-4.24 (m, 1H), 4.16-4.00 (m, 1H), 4.00 (s, 3H), 3.11 (s, 3H), 2.42 (s, 3H), 2.27 (s, 3H); Mass (ESI): 444.5 [M+1]; LCMS: 444.1 (M+1); (column; X-Select CSH C-18 (50×3.0 mm, 3.5 μm); RT 2.39 min. 0.05% Aq TFA: ACN; 0.80 mL/min); UPLC (column; Acquity UPLC BEH C-18, 2.1×50 mm, 1.7 μm); RT 1.63 min. ACN: 0.025% Aq TFA; 0.5 mL/min; Chiral HPLC: 99.7% RT=22.44 min (CHIRALPAK-IA (250×4.6 mm, 5 μm; mobile phase (A) 0.1% DEA in n-hexane (B) CH$_2$Cl$_2$:MeOH (50:50) (A:B; 85:15); flow Rate: 1.0 mL/min); Optical rotation [α]$_D^{20.00}$: +136.12 (c=0.25, CH$_2$Cl$_2$).

Example 171B

Synthesis of (−)-N-(5-methoxy-6-(4-methyl-1H-imidazol-1-yl) pyridin-3-yl)-8-methyl-7-(o-tolyl)-7, 8-dihydro-6H-pyrimido [5, 4-b] [1, 4] oxazin-2-amine

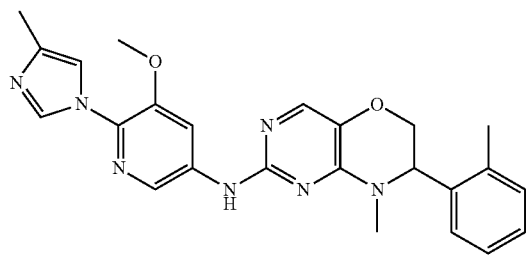

The compound of Example 171B was produced as described in Example 171. Analytical data for product Fraction II (−): $^1$H-NMR (CD$_3$OD, 400 MHz): δ 8.32-8.30 (m, 2H), 8.13 (s, 1H), 7.60 (s, 1H), 7.40-7.38 (m, 1H), 7.27-7.14 (m, 3H), 7.00 (d, 1H), 5.02-5.00 (m, 1H), 4.28-4.24 (m, 1H), 4.16-4.00 (m, 1H), 4.00 (s, 3H), 3.11 (s, 3H), 2.42 (s, 3H), 2.27 (s, 3H); Mass (ESI): 444.5 [M+1]; LCMS: 444.1 (M+1); (column; X-Select CSH C-18 (50×3.0 mm, 3.5 μm); RT 2.41 min. 0.05% Aq TFA: ACN; 0.80 mL/min); UPLC (column; Acquity UPLC BEH C-18, 2.1×50 mm, 1.7

μm); RT 1.63 min. ACN: 0.025% Aq TFA; 0.5 mL/min; Chiral HPLC: 96.1% RT=25.32 min (CHIRALPAK-IA (250×4.6 mm, 5 μm; mobile phase (A) 0.1% DEA in n-hexane (B) CH$_2$Cl$_2$:MeOH (50:50) (A:B; 85:15); flow Rate: 1.0 mL/min); Optical rotation [α]$_D^{19.99}$: −143.72 (c=0.25, CH$_2$Cl$_2$).

Example 172

Synthesis of N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine

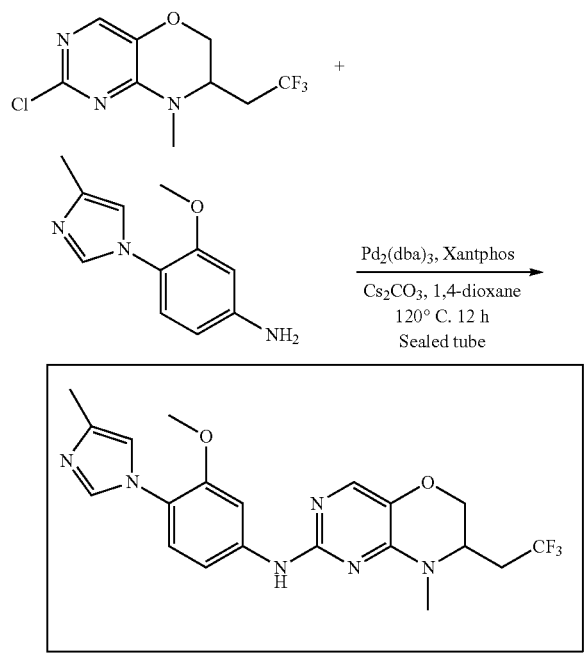

Synthesis of N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine To a dry vial was added a suspension of Pd$_2$(dba)$_3$ (10 mg, 0.01 mmol) and Xantphos (19 mg, 0.03 mmol) in 1, 4-dioxane (0.3 mL) at room temperature. The suspension was degassed with argon, heated to 120° C., and stirred for 3 min. A mixture of 2-chloro-8-methyl-7-(2, 2, 2-trifluoroethyl)-7, 8-dihydro-6H-pyrimido [5, 4-b] [1, 4] oxazine (60 mg, 0.22 mmol), 3-methoxy-4-(4-methyl-1H-imidazol-1-yl) aniline (91 mg, 0.44 mmol) and cesium carbonate (100 mg, 0.31 mmol) in 1, 4-dioxane (1 mL) was degassed and the catalyst premix was added. The resultant mixture was stirred at 120° C. for 12 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 5% MeOH: CH$_2$Cl$_2$ to afford N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine (80 mg, 84%) as an off-white solid. $^1$H-NMR (CD$_3$OD, 400 MHz): δ 7.72 (s, 2H), 7.59 (s, 1H), 7.22-7.19 (m, 2H), 6.99 (br s, 1H), 4.29-4.26 (m, 1H), 3.99-3.91 (m, 2H), 3.82 (s, 3H), 3.21 (s, 3H), 2.66-2.57 (m, 2H), 2.21 (s, 3H); TLC: 5% MeOH/CH$_2$Cl$_2$ (R$_f$; 0.3).

Racemic compound of Example 172 was separated using a Chiralpak IA column (250×4.6 mm: 5 μm; (15 mg loading; 0.1% DEA in n-hexane (B) EtOH (A:B; 75:25) as mobile phase) to provide the compound of Example 172A (Fraction I (−)) and the compound of Example 172B (Fraction II (+)).

Example 172A

Synthesis of (−)-N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine

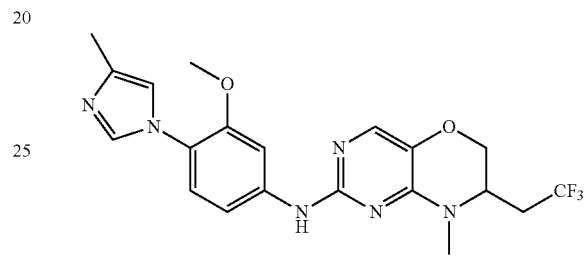

The compound of Example 172A was produced as described in Example 172. Analytical data for product Fraction I (−): $^1$H-NMR (CD$_3$OD, 400 MHz): δ 7.72 (s, 2H), 7.59 (s, 1H), 7.22-7.19 (m, 2H), 6.99 (br s, 1H), 4.29-4.26 (m, 1H), 3.99-3.91 (m, 2H), 3.82 (s, 3H), 3.21 (s, 3H), 2.66-2.57 (m, 2H), 2.21 (s, 3H); Mass (ESI): 435.4 [M+1]; LCMS: 435.4 (M+1); (column; X-Select CSH C-18 (50×3.0 mm, 3.5 μm); RT 2.56 min. 0.05% Aq TFA: ACN; 0.8 mL/min); UPLC (column; Acquity UPLC BEH C-18, 2.1× 50 mm, 1.7 μm); RT 1.50 min. ACN: 0.025% Aq TFA; 0.5 mL/min; Chiral HPLC: 99.4% RT=11.53 min (CHIRALPAK-IC (250×4.6 mm, 5 μm; mobile phase (A) 0.1% DEA in n-hexane (B) EtOH (A:B; 75:25); flow Rate: 1.0 mL/min); Optical rotation [α]$_D^{20.01}$: −4.09 (c=0.25, CH$_2$Cl$_2$).

Example 172B

Synthesis of (+)-N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine

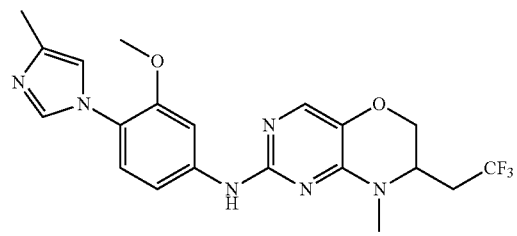

The compound of Example 172B was produced as described in Example 172. Analytical data for product Fraction II (+): $^1$H-NMR (CD$_3$OD, 400 MHz): δ 7.72 (s, 2H), 7.59 (s, 1H), 7.22-7.19 (m, 2H), 6.99 (br s, 1H), 4.29-4.26 (m, 1H), 3.99-3.91 (m, 2H), 3.82 (s, 3H), 3.21 (s, 3H), 2.66-2.57 (m, 2H), 2.21 (s, 3H); Mass (ESI): 435.5 [M+1]; LCMS: 435.4 (M+1); (column; X-Select CSH C-18 (50×3.0 mm, 3.5 μm); RT 2.55 min. 0.05% Aq TFA: ACN; 0.8 mL/min); UPLC (column; Acquity UPLC BEH C-18, 2.1×50 mm, 1.7 μm); RT 1.50 min. ACN: 0.025% Aq TFA; 0.5 mL/min; Chiral HPLC: 98.1% RT=13.35 min (CHIRALPAK-IA (250×4.6 mm, 5 μm; mobile phase (A) 0.1% DEA in n-hexane (B) EtOH (A:B; 75:25); flow Rate: 1.0 mL/min); Optical rotation $[α]_D^{20.01}$: +5.50 (c=0.25, CH$_2$Cl$_2$).

Example 173

Synthesis of 7-(2-chloro-5-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

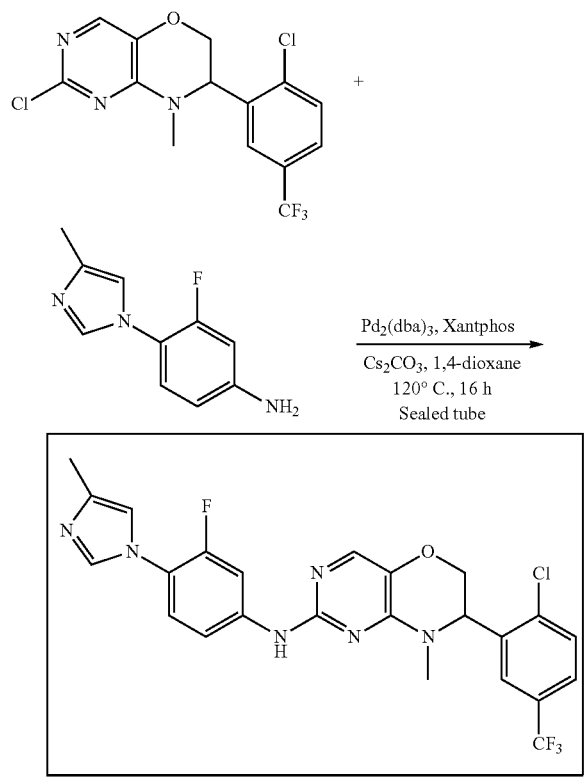

Synthesis of 7-(2-chloro-5-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine To a dry vial was added a suspension of Pd$_2$(dba)$_3$ (25 mg, 0.02 mmol) and Xantphos (47 mg, 0.08 mmol) in 1, 4-dioxane (2 mL) at room temperature. The suspension was degassed with argon, heated to 120° C., and stirred for 3 min. A mixture of 2-chloro-7-(2-chloro-5-(trifluoromethyl) phenyl)-8-methyl-7, 8-dihydro-6H-pyrimido [5, 4-b] [1, 4] oxazine (200 mg, 0.54 mmol), 3-fluoro-4-(4-methyl-1H-imidazol-1-yl) aniline (209 mg, 1.09 mmol) and cesium carbonate (250 mg, 0.76 mmol) in 1, 4-dioxane (2 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (20 mL) and extracted with EtOAc (2×20 mL). The combined organic extracts were dried over sodium sulfate, filtered and concentrated in vacuo. The crude material was purified by preparative HPLC (Ascentis C-18 (250×21.2 mm, 5 μm (60 mg loading; CH$_3$CN: 5 mM NH$_4$OAc (0.1/80, 2/80, 8/30, 15/20, 20/10, 35/10)) to afford 7-(2-chloro-5-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine (110 mg, 38%) as an off-white solid. LCMS: 519.1 (M+1); (column; X-Select CSH C-18 (50×3.0 mm, 3.5 μm); RT 2.60 min. 0.05% Aq TFA: ACN; 0.80 mL/min); HPLC (column; Eclipse XDB C-18 150×4.6 mm, 5.0 μm); RT 11.73 min. ACN: 5 mM Aq NH$_4$OAc; 1.0 mL/min; TLC: 10% MeOH/ CH$_2$Cl$_2$ (R$_f$: 0.4).

Racemic compound of Example 173 was separated using a Chiralpak IA column (250×4.6 mm: 5 μm; (15 mg loading; 0.1% DEA in n-hexane: CH$_2$Cl$_2$:MeOH (50:50); (A:B; 85:15) as mobile phase) to provide the compound of Example 173A (Fraction I (+)) and the compound of Example 173B (Fraction II (−)).

Example 173A

Synthesis of (+)-7-(2-chloro-5-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

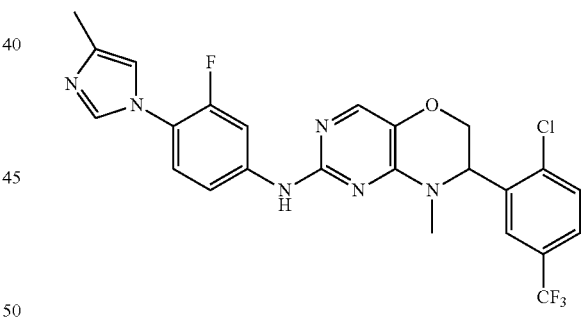

The compound of Example 173A was produced as described in Example 173. Analytical data for product Fraction I (+): $^1$H-NMR (CD$_3$OD, 400 MHz): δ 8.01-7.99 (m, 1H), 7.77-7.71 (m, 2H), 7.69-7.67 (m, 1H), 7.66 (s, 1H), 7.45-7.41 (m, 1H), 7.36-7.34 (m, 1H), 7.29-7.27 (m, 1H), 7.09 (s, 1H), 5.30-5.28 (m, 1H), 4.36-4.23 (m, 2H), 3.19 (s, 3H), 2.26 (s, 3H); Mass (ESI): 519.1 [M+1]; LCMS: 519.1 (M+1); (column; X-Select CSH C-18 (50×3.0 mm, 3.5 μm); RT 2.60 min. 0.05% Aq TFA: ACN; 0.80 mL/min); UPLC (column; Acquity UPLC BEH C-18, 2.1×50 mm, 1.7 μm); RT 1.83 min. ACN: 0.025% Aq TFA; 0.5 mL/min; Chiral HPLC: 99.6% RT=13.38 min (CHIRALPAK-IA (250×4.6 mm, 5 μm; mobile phase (A) 0.1% DEA in n-hexane (B) CH$_2$Cl$_2$:MeOH (50:50) (A:B; 80:20); flow Rate: 1.0 mL/min); Optical rotation $[α]_D^{19.99}$: +115.79 (c=0.25, CH$_2$Cl$_2$).

Example 173B

Synthesis of (−)-7-(2-chloro-5-(trifluoromethyl)phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine

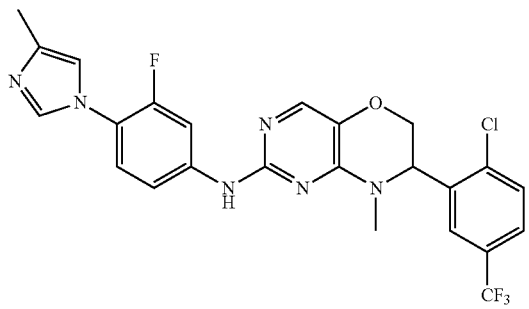 [SMILES: Cc1cn(-c2ccc(Nc3ncc4c(n3)N(C)C(c3cc(C(F)(F)F)ccc3Cl)CO4)cc2F)cn1]

The compound of Example 173B was produced as described in Example 173. Analytical data for product Fraction II (−): ¹H-NMR (CD₃OD, 400 MHz): δ 8.01-7.99 (m, 1H), 7.77-7.71 (m, 2H), 7.69-7.67 (m, 1H), 7.66 (s, 1H), 7.45-7.41 (m, 1H), 7.36-7.34 (m, 1H), 7.29-7.27 (m, 1H), 7.09 (s, 1H), 5.30-5.28 (m, 1H), 4.36-4.23 (m, 2H), 3.19 (s, 3H), 2.26 (s, 3H); Mass (ESI): 519.1 [M+1]; LCMS: 519 (M+1); (column; X-Select CSH C-18 (50×3.0 mm, 3.5 μm); RT 2.60 min. 0.05% Aq TFA: ACN; 0.80 mL/min); UPLC (column; Acquity UPLC BEH C-18, 2.1×50 mm, 1.7 μm); RT 1.83 min. ACN: 0.025% Aq TFA; 0.5 mL/min; Chiral HPLC: 99.1% RT=14.47 min (CHIRALPAK-IC (250×4.6 mm, 5 μm; mobile phase (A) 0.1% DEA in n-hexane (B) CH₂Cl₂:MeOH (50:50) (A:B; 80:20); flow Rate: 1.0 mL/min); Optical rotation $[\alpha]_D^{20.01}$: −126.38 (c=0.25, CH₂Cl₂).

Example 174

Synthesis of 7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

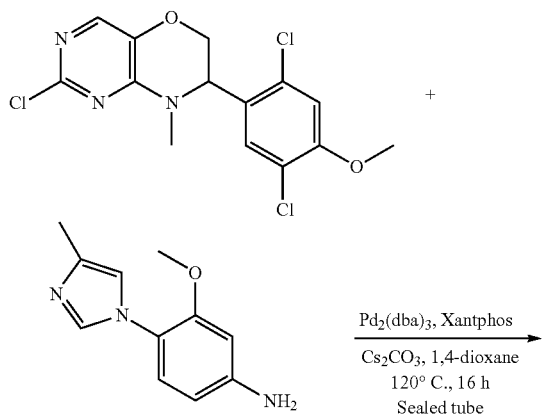

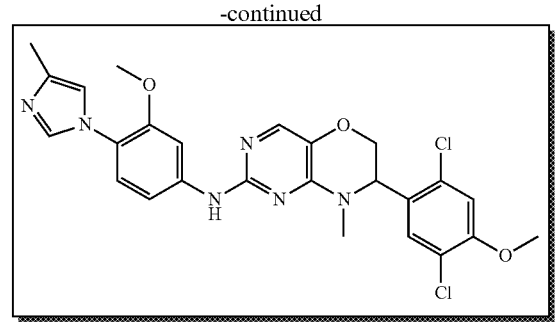

Synthesis of 7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a dry vial was added a suspension of Pd₂(dba)₃ (13 mg, 0.01 mmol) and Xantphos (24 mg, 0.04 mmol) in 1, 4-dioxane (0.3 mL) at room temperature. The suspension was degassed with argon, heated to 120° C., and stirred for 3 min. A mixture of 2-chloro-7-(2, 5-dichloro-4-methoxyphenyl)-8-methyl-7, 8-dihydro-6H-pyrimido [5, 4-b] [1, 4] oxazine (100 mg, 0.27 mmol), 3-methoxy-4-(4-methyl-1H-imidazol-1-yl) aniline (112 mg, 0.55 mmol) and cesium carbonate (126 mg, 0.38 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 5% MeOH: CH₂Cl₂ to afford N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine (80 mg, 54%) as an off-white solid. ¹H-NMR (CD₃OD, 400 MHz): δ 7.76 (s, 1H), 7.68 (s, 1H), 7.60 (s, 1H), 7.26-7.20 (m, 2H), 7.19 (d, 1H), 7.01 (s, 1H), 6.97-6.95 (m, 1H), 5.00-4.98 (m, 1H), 4.27-4.19 (m, 2H), 3.90 (s, 3H), 3.85 (s, 3H), 3.15 (s, 3H), 2.21 (s, 3H); TLC: 10% MeOH/CH₂Cl₂ ($R_f$: 0.5).

Racemic compound of Example 174 was separated using a Chiralpak AD-H column (250×20 mm: 5 μm; (15 mg loading; 0.1% DEA in n-hexane (B) EtOH:MeOH (50:50) (A:B; 70:30) as mobile phase) to provide the compound of Example 174A (Fraction I (−)) and the compound of Example 174B (Fraction II (+)).

Example 174A

Synthesis of (−)-7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

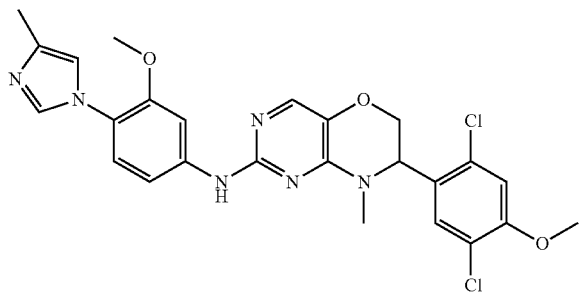 [SMILES: COc1cc(Cl)c(C2COc3cnc(Nc4ccc(-n5cnc(C)c5)c(OC)c4)nc3N2C)cc1Cl]

The compound of Example 174A was produced as described in Example 174. Analytical data for product Fraction I (−): $^1$H-NMR (CD$_3$OD, 400 MHz): δ 7.76 (s, 1H), 7.68 (s, 1H), 7.60 (s, 1H), 7.26-7.20 (m, 2H), 7.19 (d, 1H), 7.01 (s, 1H), 6.97-6.95 (m, 1H), 5.00-4.98 (m, 1H), 4.27-4.19 (m, 2H), 3.90 (s, 3H), 3.85 (s, 3H), 3.15 (s, 3H), 2.21 (s, 3H); Mass (ESI): 527.1 [M+1]; LCMS: 527.1 (M+1); (column; X-Select CSH C-18 (50×3.0 mm, 3.5 μm); RT 2.51 min. 0.05% Aq TFA: ACN; 0.8 mL/min); UPLC (column; Acquity UPLC BEH C-18, 2.1×50 mm, 1.7 μm); RT 1.77 min. ACN: 0.025% TFA (Aq); 0.50 mL/min; Chiral HPLC: 100.0% RT=13.35 min (CHIRALPAK-AD-H (250×20 mm, 5 μm; mobile phase (A) 0.1% DEA in n-hexane (B) EtOH: MeOH (50:50) (A:B; 70:30); flow Rate: 1.0 mL/min); Optical rotation [α]$_D^{20.01}$: −201.40 (c=0.25, CH$_2$Cl$_2$).

Example 174B

Synthesis of (+)-7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

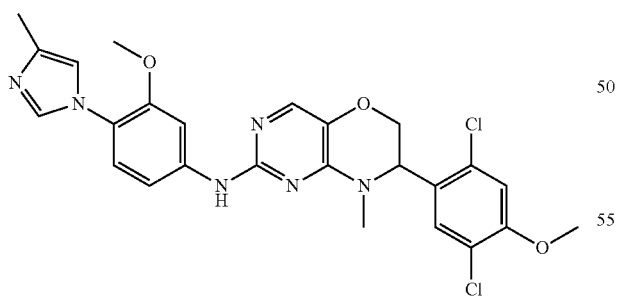

The compound of Example 174B was produced as described in Example 174. Analytical data for product Fraction II (+): $^1$H-NMR (CD$_3$OD, 400 MHz): δ 7.76 (s, 1H), 7.68 (s, 1H), 7.60 (s, 1H), 7.26-7.20 (m, 2H), 7.19 (d, 1H), 7.01 (s, 1H), 6.97-6.95 (m, 1H), 5.00-4.98 (m, 1H), 4.27-4.19 (m, 2H), 3.90 (s, 3H), 3.85 (s, 3H), 3.15 (s, 3H), 2.21 (s, 3H); Mass (ESI): 527.1 [M+1]; LCMS: 527.1 (M+1); (column; X-Select CSH C-18 (50×3.0 mm, 3.5 μm); RT 2.52 min. 0.05% Aq TFA: ACN; 0.8 mL/min); UPLC (column; Acquity UPLC BEH C-18, 2.1×50 mm, 1.7 μm); RT 1.76 min. ACN: 0.025% TFA (Aq); 0.50 mL/min; Chiral HPLC: 98.0% RT=16.51 min (CHIRALPAK-AD-H (250×20 mm, 5 μm; mobile phase (A) 0.1% DEA in n-hexane (B) EtOH:MeOH (50:50) (A:B; 70:30); flow Rate: 1.0 mL/min); Optical rotation [α]$_D^{20.01}$: +119.71 (c=0.25, CH$_2$Cl$_2$).

Example 175

Synthesis of 7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

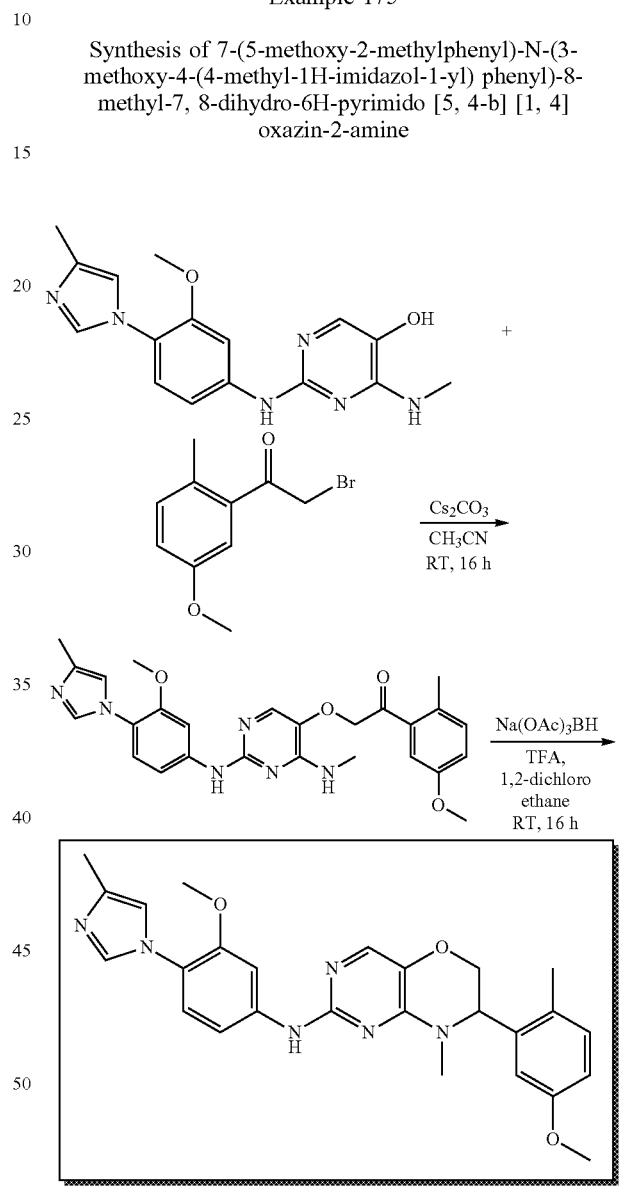

Synthesis of 1-(5-methoxy-2-methylphenyl)-2-((2-((3-methoxy-4-(4-methyl-1H-imidazol-1-yl) phenyl) amino)-4-(methylamino) pyrimidin-5-yl) oxy) ethan-1-one To a stirred solution of 2-((3-methoxy-4-(4-methyl-1H-imidazol-1-yl) phenyl) amino)-4-(methylamino) pyrimidin-5-ol (100 mg, 0.30 mmol) in CH$_3$CN (1 mL) under an argon atmosphere were added cesium carbonate (200 mg, 0.60 mmol) followed by 2-bromo-1-(5-methoxy-2-methylphenyl) ethan-1-one (82 mg, 0.33 mmol) at room temperature.

The reaction mixture was stirred at room temperature for 16 h. After consumption of the starting material (monitored by TLC), the reaction mixture was diluted with water (20 mL) and extracted with $CH_2Cl_2$ (2×20 mL). The combined organic extracts were dried over sodium sulfate, filtered and concentrated in vacuo to obtain 1-(5-methoxy-2-methylphenyl)-2-((2-((3-methoxy-4-(4-methyl-1H-imidazol-1-yl) phenyl) amino)-4-(methylamino) pyrimidin-5-yl) oxy) ethan-1-one (130 mg, crude) as a pale brown solid. LCMS: 489.6 (M+1); (column; X-Select CSH C-18 (50×3.0 mm, 3.5 µm); RT 2.86 min. 0.05% Aq TFA: ACN; 0.8 mL/min); TLC: 5% MeOH/$CH_2Cl_2$ ($R_f$: 0.6).

Synthesis of 7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a stirred solution of 1-(5-methoxy-2-methylphenyl)-2-((2-((3-methoxy-4-(4-methyl-1H-imidazol-1-yl) phenyl) amino)-4-(methylamino) pyrimidin-5-yl) oxy) ethan-1-one (140 mg, 0.28 mmol) in 1, 2-dichloroethane (1.5 mL) under an argon atmosphere were added trifluoroacetic acid (0.02 mL, 0.28 mmol) followed by sodium triacetoxyborohydride (127 mg, 0.60 mmol) at room temperature. The reaction mixture was stirred at room temperature for 16 h. After consumption of the starting material (monitored by TLC), the reaction mixture was quenched with a 1 N sodium hydroxide solution (20 mL) and extracted with $CH_2Cl_2$ (2×20 mL). The combined organic extracts were dried over sodium sulfate, filtered and concentrated in vacuo. The crude material was purified by column chromatography using 2% MeOH: $CH_2Cl_2$ to afford 7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (18 mg, 13%) as an off-white solid. $^1$H-NMR ($CD_3OD$, 400 MHz): δ 7.76 (s, 1H), 7.65 (s, 1H), 7.54 (s, 1H), 7.23-7.20 (m, 1H), 7.19-7.12 (m, 2H), 6.93 (s, 1H), 6.79 (d, 1H), 6.51 (s, 1H), 4.93-4.90 (m, 1H), 4.23-4.20 (m, 1H), 4.11-4.09 (m, 1H), 3.83 (s, 3H), 3.65 (s, 3H), 3.10 (s, 3H), 2.31 (s, 3H), 2.20 (s, 3H); Mass (ESI): 473 [M+1]; LCMS: 473.1 (M+1); (column; X-Select CSH C-18 (50×3.0 mm, 3.5 µm); RT 2.39 min. 0.05% Aq TFA: ACN; 0.8 mL/min); UPLC (column; Acquity UPLC BEH C-18, 2.1× 50 mm, 1.7 µm); RT 1.67 min. ACN: 0.025% TFA (Aq); 0.50 mL/min TLC: 10% MeOH/$CH_2Cl_2$ ($R_f$: 0.5).

Racemic compound of Example 175 was separated using a Chiralpak-IC column (250×20 mm, 5 µm) (25 mg loading; 0.1% DEA in n-hexane; EtOH:MeOH (50:50) (A:B; 70:30); 0.1% DEA in n-hexane: $CH_2Cl_2$:MeOH (50:50) (A:B: 75:25) as mobile phase) to provide the compound of Example 175A (Fraction I (+)) and the compound of Example 175B (Fraction II (−)).

Example 175A

Synthesis of (+)-7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

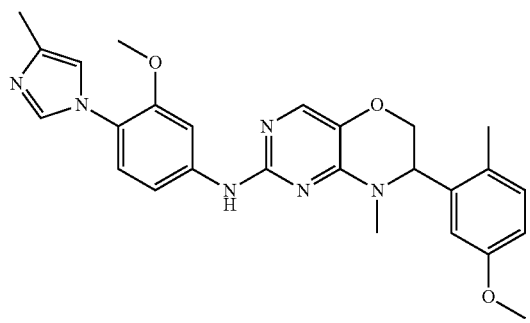 [SMILES: COc1ccc(C)c(C2COc3cnc(Nc4ccc(-n5cnc(C)c5)c(OC)c4)nc3N2C)c1]

The compound of Example 175A was produced as described in Example 175. Analytical data for product Fraction I (+): $^1$H-NMR ($CD_3OD$, 400 MHz): δ 7.77 (s, 1H), 7.64 (s, 1H), 7.59 (s, 1H), 7.26-7.21 (m, 1H), 7.20-7.14 (m, 2H), 6.97-6.95 (m, 1H), 6.81-6.79 (m, 1H), 6.51 (d, 1H), 4.95 (t, 1H), 4.23-4.21 (m, 1H), 4.12-4.10 (m, 1H), 3.84 (s, 3H), 3.69 (s, 3H), 3.10 (s, 3H), 2.31 (s, 3H), 2.21 (s, 3H); Mass (ESI): 473.1 [M+1]; LCMS: 473.1 (M+1); (column; X-Select CSH C-18 (50×3.0 mm, 3.5 µm); RT 2.41 min. 0.05% Aq TFA: ACN; 0.80 ml/min); UPLC (column; Acquity UPLC BEH C-18, 2.1×50 mm, 1.7 µm); RT 1.68 min. ACN: 0.025% Aq TFA; 0.5 ml/min; Chiral HPLC: 100% RT=17.08 min (Chiralpak-IC (250×4.6 mm, 5 µm; mobile phase (A) 0.1% DEA in n-hexane (B) $CH_2Cl_2$: MeOH (50:50) (A:B; 75:25); flow Rate: 1.0 mL/min); Optical rotation $[α]_D^{20.00}$:199.98 (c=0.25, $CH_2Cl_2$).

Example 175B

Synthesis of (−)-7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

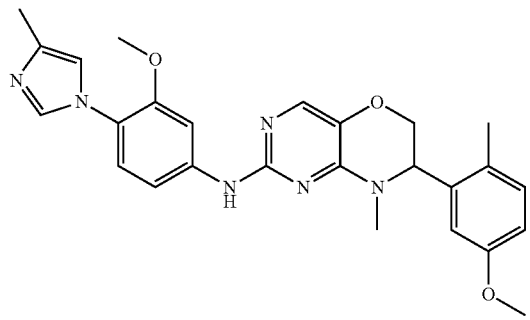 [SMILES: COc1ccc(C)c(C2COc3cnc(Nc4ccc(-n5cnc(C)c5)c(OC)c4)nc3N2C)c1]

The compound of Example 175B was produced as described in Example 175. Analytical data for product Fraction II (−): $^1$H-NMR ($CD_3OD$, 400 MHz): δ 7.77 (s, 1H), 7.64 (s, 1H), 7.59 (s, 1H), 7.26-7.21 (m, 1H), 7.20-7.14 (m, 2H), 6.97-6.95 (m, 1H), 6.81-6.79 (m, 1H), 6.51 (d, 1H), 4.95 (t, 1H), 4.23-4.21 (m, 1H), 4.12-4.10 (m, 1H), 3.84 (s, 3H), 3.69 (s, 3H), 3.10 (s, 3H), 2.31 (s, 3H), 2.21 (s, 3H); Mass (ESI): 473.2 [M+1]; LCMS: 473.1 (M+1); (column; X-Select CSH C-18 (50×3.0 mm, 3.5 μm); RT 2.41 min. 0.05% Aq TFA: ACN; 0.80 ml/min); UPLC (column; Acquity UPLC BEH C-18, 2.1×50 mm, 1.7 μm); RT 1.68 min. ACN: 0.025% Aq TFA; 0.5 ml/min; Chiral HPLC: 99.8% RT=21.72 min (Chiralpak-IC (250×4.6 mm, 5 μm; mobile phase (A) 0.1% DEA in n-hexane (B) $CH_2Cl_2$: MeOH (50:50) (A:B; 75:25); flow Rate: 1.0 mL/min); Optical rotation $[\alpha]_D^{19.97}$: −203.36 (c=0.25, $CH_2Cl_2$).

Example 176

Synthesis of (R)—N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine

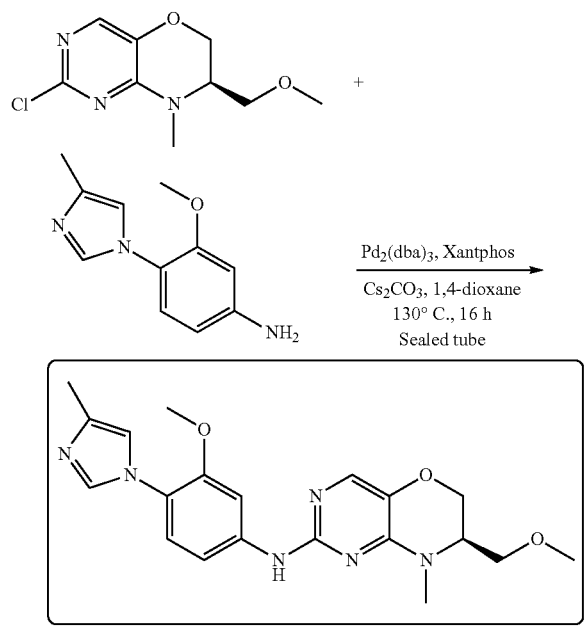

Synthesis of (R)—N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine To a dry vial was added a suspension of $Pd_2(dba)_3$ (24 mg, 0.02 mmol) and Xantphos (46 mg, 0.07 mmol) in 1, 4-dioxane (0.6 mL) at room temperature. The suspension was degassed with argon, heated to 120° C., and stirred for 3 min. A mixture of (R)-2-chloro-7-(methoxymethyl)-8-methyl-7, 8-dihydro-6H-pyrimido [5, 4-b] [1, 4] oxazine (120 mg, 0.52 mmol), 3-methoxy-4-(4-methyl-1H-imidazol-1-yl) aniline (213 mg, 1.04 mmol) and cesium carbonate (240 mg, 0.73 mmol) in 1, 4-dioxane (0.6 mL) was degassed and the catalyst premix was added. The resultant mixture was stirred at 130° C. for 16 h in a sealed tube. After consumption of the staring material (monitored by TLC and LCMS), the volatile components were evaporated in vacuo. The residue was diluted with water (50 mL) and extracted with $CH_2Cl_2$ (2×50 mL). The combined organic extracts were dried over sodium sulfate, filtered and concentrated in vacuo. The crude material was purified by column chromatography using 4% MeOH: EtOAc to afford (R)—N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine (60 mg, 29%) as a yellow solid. $^1$H-NMR (CD$_3$OD, 400 MHz): δ 7.75-7.73 (m, 1H), 7.69 (s, 1H), 7.50 (s, 1H), 7.20-7.15 (m, 2H), 6.97 (s, 1H), 4.30-4.28 (m, 1H), 3.90-3.84 (m, 1H), 3.83 (s, 3H), 3.70-3.67 (m, 1H), 3.60-3.50 (m, 2H), 3.40 (s, 3H), 3.30 (s, 3H), 2.21 (s, 3H); Mass (ESI): 397.1 [M+1]; LCMS: 397.1 (M+1); (column; X-Select CSH C-18 (50×3.0 mm, 3.5 μm); RT 1.97 min 0.05% Aq TFA: ACN; 0.80 mL/min); UPLC (column; Acquity BEH C-18 50×2.1 mm, 1.7 μm); RT 1.35 min. ACN: 0.025% Aq TFA; 0.5 mL/min; Chiral HPLC: 97.1% RT=14.38 min (CHIRALPAK-IA (250×4.6 mm, 5μ; mobile phase (A) 0.1% DEA in n-hexane (B) $CH_2Cl_2$:MeOH (50:50) (A:B; 80:20); flow Rate: 1.0 mL/min); Optical rotation $[\alpha]_D^{20.00}$: −17.56 (c=0.25, $CH_2Cl_2$); TLC: 5% MeOH/EtOAc ($R_f$: 0.3).

Example 177

Synthesis of (R)-(2-((3-methoxy-4-(4-methyl-1H-imidazol-1-yl) phenyl) amino)-8-methyl-7, 8-dihydro-6H-pyrimido [5, 4-b] [1, 4] oxazin-7-yl) methanol

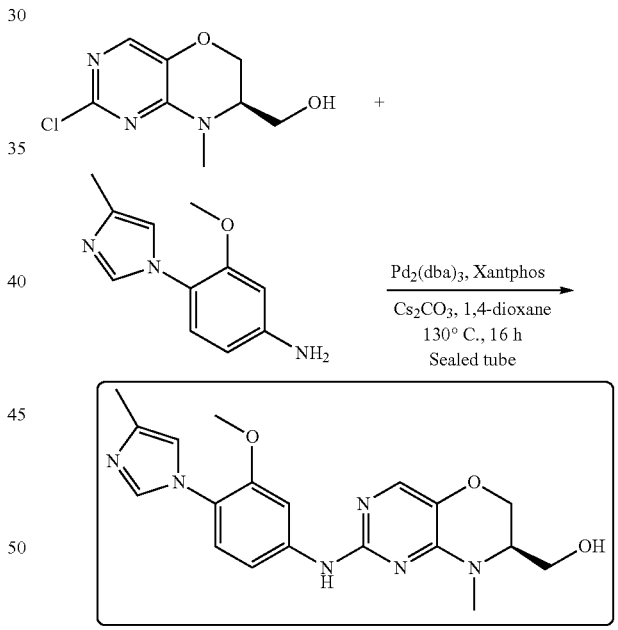

Synthesis of (R)-(2-((3-methoxy-4-(4-methyl-1H-imidazol-1-yl) phenyl) amino)-8-methyl-7, 8-dihydro-6H-pyrimido [5, 4-b] [1, 4] oxazin-7-yl) methanol To a dry vial was added a suspension of $Pd_2(dba)_3$ (25 mg, 0.02 mmol) and Xantphos (48 mg, 0.08 mmol) in 1, 4-dioxane (0.6 mL) at room temperature. The suspension was degassed with argon, heated to 120° C., and stirred for 3 min. A mixture of (R)-(2-chloro-8-methyl-7, 8-dihydro-6H-pyrimido [5, 4-b] [1, 4] oxazin-7-yl) methanol (120 mg, 0.55 mmol), 3-methoxy-4-(4-methyl-1H-imidazol-1-yl) aniline (227 mg, 1.11 mmol) and cesium carbonate (254 mg, 0.78 mmol) in 1, 4-dioxane (0.6 mL) was degassed and the catalyst premix was added. The resultant mixture was stirred at 130° C. for 16 h in a sealed tube. After consumption of the reaction (monitored by TLC and LCMS), the volatile components were evaporated in vacuo. The residue was diluted with water (50 mL) and extracted with $CH_2Cl_2$ (2×50 mL). The combined organic extracts were dried over sodium sulfate, filtered and concentrated in vacuo. The crude material was purified by column chromatography using 3% MeOH: EtOAc to afford (R)-(2-((3-methoxy-4-(4-methyl-1H-imidazol-1-yl) phenyl) amino)-8-methyl-7, 8-dihydro-6H-pyrimido [5, 4-b] [1, 4] oxazin-7-yl) methanol (62 mg, 29%) as a pale yellow solid. $^1$H-NMR (DMSO-$d_6$, 400 MHz): δ 9.05 (s, 1H), 7.85 (s, 1H), 7.60 (s, 1H), 7.57 (s, 1H), 7.29 (d, 1H), 7.13 (d, 1H), 6.99 (s, 1H), 5.08 (t, 1H), 4.30-4.27 (m, 1H), 3.85-3.80 (m, 1H), 3.77 (s, 3H), 3.62-3.59 (m, 1H), 3.51-3.42 (m, 2H), 3.19 (s, 3H), 2.11 (s, 3H); Mass (ESI): 383.4 [M+1]; LCMS: 383.4 (M+1); (column; X-Select CSH C-18 (50×3.0 mm, 3.5 μm); RT 3.07 min 5 mM Aq $NH_4OAc$: ACN; 0.8 mL/min); UPLC (column; Acquity BEH C-18 50×2.1 mm, 1.7 μm); RT 1.18 min. ACN: 0.025% Aq TFA; 0.5 mL/min; Chiral HPLC: 99.8% RT=19.61 min (CHIRALPAK-IA (250×4.6 mm, 5μ; mobile phase (A) 0.1% DEA in n-hexane (B) $CH_2Cl_2$:MeOH (50: 50) (A:B: 80:20); flow Rate: 1.0 mL/min); Optical rotation $[α]_D^{20.00}$: −7.15 (c=0.25, $CH_2Cl_2$); TLC: 5% MeOH/EtOAc ($R_f$: 0.3).

Example 178

Synthesis of 7-(4, 5-difluoro-2-(trifluoromethyl) phenyl)-N-(1-(2-methoxypyridin-4-yl) piperidin-4-yl)-8-methyl-7, 8-dihydro-6H-pyrimido [5, 4-b] [1, 4] oxazin-7-amine

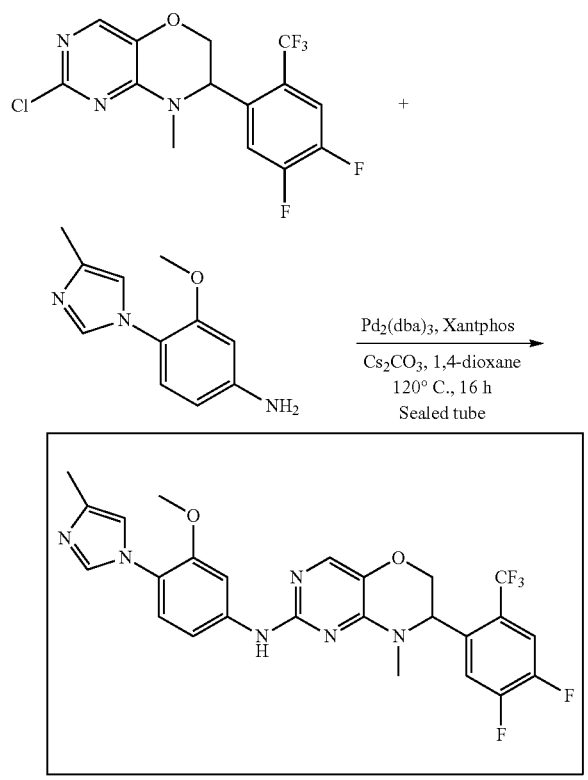

Synthesis of 7-(4, 5-difluoro-2-(trifluoromethyl) phenyl)-N-(1-(2-methoxypyridin-4-yl) piperidin-4-yl)-8-methyl-7, 8-dihydro-6H-pyrimido [5, 4-b] [1, 4] oxazin-2-amine To a dry vial was added a suspension of $Pd_2(dba)_3$ (22 mg, 0.02 mmol) and Xantphos (42 mg, 0.07 mmol) in 1, 4-dioxane (1 mL) at room temperature. The suspension was degassed with argon, heated to 120° C., and stirred for 3 min. A mixture of 2-chloro-7-(4, 5-difluoro-2-(trifluoromethyl) phenyl)-8-methyl-7, 8-dihydro-6H-pyrimido [5, 4-b] [1, 4] oxazine (180 mg, 0.49 mmol), 1-(2-methoxypyridin-4-yl) piperidin-4-amine hydrochloride (200 mg, 0.98 mmol) and cesium carbonate (225 mg, 0.69 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction mixture was diluted with water (50 mL) and extracted with $CH_2Cl_2$ (2×50 mL). The combined organic extracts were dried over sodium sulfate, filtered and concentrated in vacuo. The crude material was purified by column chromatography using 50% EtOAc: $CH_2Cl_2$ to afford 7-(4, 5-difluoro-2-(trifluoromethyl) phenyl)-N-(1-(2-methoxypyridin-4-yl) piperidin-4-yl)-8-methyl-7, 8-dihydro-6H-pyrimido [5, 4-b] [1, 4] oxazin-2-amine (170 mg, 58%) as an off-white solid. $^1$H-NMR ($CD_3OD$, 500 MHz): δ 7.82-7.80 (m, 1H), 7.78 (s, 1H), 7.70 (d, 2H), 7.28-7.17 (m, 3H), 6.99 (s, 1H), 5.10-5.08 (m, 1H), 4.28 (d, 1H), 4.13 (d, 1H), 3.85 (s, 3H), 3.12 (s, 3H), 2.22 (s, 3H); LCMS: 533.1 (M+1); (column; X-Select CSH C-18 (50×3.0 mm, 3.5 μm); RT 2.58 min 0.05% Aq TFA: ACN; 0.80 mL/min); UPLC (column; Acquity BEH C-18 (50×2.1 mm, 1.7 μm); RT 1.92 min. ACN: 0.025% Aq TFA; 0.50 mL/min; TLC: 5% MeOH/$CH_2Cl_2$ ($R_f$: 0.3).

Racemic compound of Example 178 was separated using a Chiralpak ODH column (250×4.6 mm: 5 μm; (25 mg loading; 0.1% DEA in n-hexane: $CH_2Cl_2$:MeOH (50:50); (A:B: 90:10) as mobile phase) to provide the compound of Example 178A (Fraction I (+)) and the compound of Example 178B (Fraction II (−)).

Example 178A

Synthesis of (+)-7-(4, 5-difluoro-2-(trifluoromethyl) phenyl)-N-(1-(2-methoxypyridin-4-yl) piperidin-4-yl)-8-methyl-7, 8-dihydro-6H-pyrimido [5, 4-b] [1, 4] oxazin-2-amine

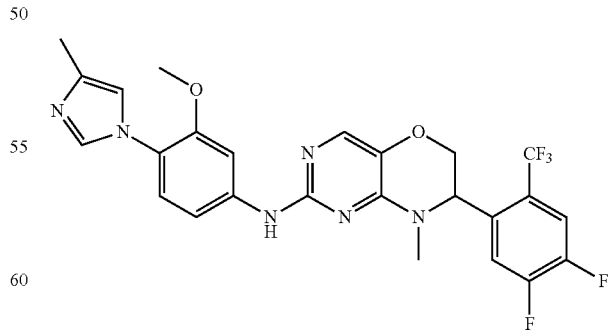

The compound of Example 178A was produced as described in Example 178. Analytical data for product Fraction I (+): $^1$H-NMR ($CD_3OD$, 400 MHz): δ 7.83-7.80 (m, 1H), 7.76 (s, 1H), 7.68 (d, 2H), 7.26-7.15 (m, 3H), 6.95

(s, 1H), 5.09-5.07 (m, 1H), 4.28 (d, 1H), 4.10 (d, 1H), 3.85 (s, 3H), 3.10 (s, 3H), 2.21 (s, 3H); Mass (ESI): 533.5 [M+1]; LCMS: 533.3 (M+1); (column; X-Select CSH C-18 (50×3.0 mm, 3.5 μm); RT 3.33 min. 0.05% Aq TFA: ACN; 0.80 mL/min); UPLC (column; Acquity UPLC BEH C-18, 2.1× 50 mm, 1.7 μm); RT 1.83 min. ACN: 0.025% Aq TFA; 0.5 mL/min; Chiral HPLC: 100% RT=12.84 min (CHIRALPAK-ODH (250×4.6 mm, 5 μm; mobile phase (A) 0.1% DEA in n-hexane (B) EtOH:MeOH (50:50) (A:B; 90:10); flow Rate: 1.0 mL/min); Optical rotation $[\alpha]_D^{19.99}$: +78.56 (c=0.25, CH$_2$Cl$_2$).

Example 178B

Synthesis of (−)-7-(4, 5-difluoro-2-(trifluoromethyl) phenyl)-N-(1-(2-methoxypyridin-4-yl) piperidin-4-yl)-8-methyl-7, 8-dihydro-6H-pyrimido [5, 4-b] [1, 4] oxazin-2-amine

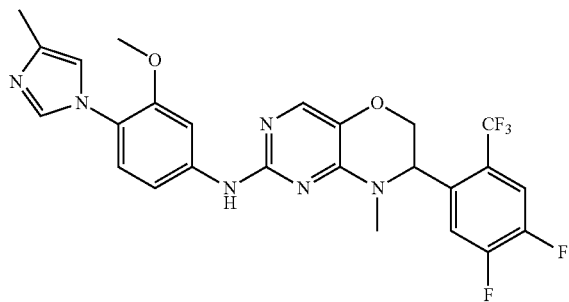

The compound of Example 178B was produced as described in Example 178. Analytical data for Fraction II (−): $^1$H-NMR (CD$_3$OD, 400 MHz): δ 7.83-7.80 (m, 1H), 7.76 (s, 1H), 7.68 (d, 2H), 7.26-7.15 (m, 3H), 6.95 (s, 1H), 5.09-5.07 (m, 1H), 4.28 (d, 1H), 4.10 (d, 1H), 3.85 (s, 3H), 3.10 (s, 3H), 2.21 (s, 3H); Mass (ESI): 533.5 [M+1]; LCMS: 533.3 (M+1); (column; X-Select CSH C-18 (50×3.0 mm, 3.5 μm); RT 3.33 min. 0.05% Aq TFA: ACN; 0.80 mL/min); UPLC (column; Acquity UPLC BEH C-18, 2.1×50 mm, 1.7 μm); RT 1.84 min. ACN: 0.025% Aq TFA; 0.5 mL/min; Chiral HPLC: 98.6% RT=15.97 min (CHIRALPAK-ODH (250×4.6 mm, 5 μm; mobile phase (A) 0.1% DEA in n-hexane (B) EtOH:MeOH (50:50) (A:B; 90:10); flow Rate: 1.0 mL/min); Optical rotation $[\alpha]_D^{20.02}$: −85.68 (c=0.25, CH$_2$Cl$_2$).

Example 179

Synthesis of 7-(3, 5-difluorophenyl)-N-(6-methoxy-5-(4-methyl-1H-imidazol-1-yl) pyridin-2-yl)-8-methyl-7, 8-dihydro-6H-pyrimido [5, 4-b] [1, 4] oxazin-2-amine

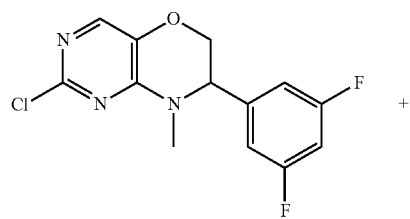

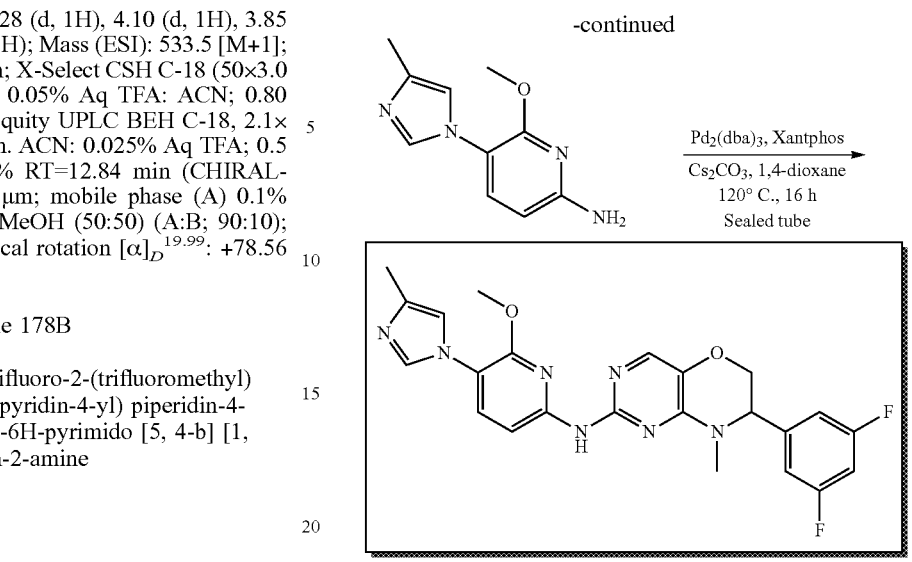

Synthesis of 7-(3, 5-difluorophenyl)-N-(6-methoxy-5-(4-methyl-1H-imidazol-1-yl) pyridin-2-yl)-8-methyl-7, 8-dihydro-6H-pyrimido [5, 4-b] [1, 4] oxazin-2-amine To a dry vial was added a suspension of Pd$_2$(dba)$_3$ (38 mg, 0.04 mmol) and Xantphos (73 mg, 0.12 mmol) in 1, 4-dioxane (2.5 mL) at room temperature. The suspension was degassed with argon, heated to 120° C., and stirred for 3 min. A mixture of 2-chloro-7-(3, 5-difluorophenyl)-8-methyl-7, 8-dihydro-6H-pyrimido [5, 4-b] [1, 4] oxazine (250 mg, 0.84 mmol), 6-methoxy-5-(4-methyl-1H-imidazol-1-yl) pyridin-2-amine (343 mg, 1.68 mmol) and cesium carbonate (384 mg, 1.17 mmol) in 1, 4-dioxane (2.5 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 5% MeOH: CH$_2$Cl$_2$ to afford 7-(3, 5-difluorophenyl)-N-(6-methoxy-5-(4-methyl-1H-imidazol-1-yl) pyridin-2-yl)-8-methyl-7, 8-dihydro-6H-pyrimido [5, 4-b] [1, 4] oxazin-2-amine (180 mg, 46%) as an off-white solid. LCMS: 466.1 (M+1); (column; X-Select CSH C-18 (50×3.0 mm, 3.5 μm); RT 2.32 min. 0.05% Aq TFA: ACN; 0.80 mL/min); TLC: 10% MeOH/CH$_2$Cl$_2$ (R$_f$: 0.5).

Racemic compound of Example 179 was separated using a Chiralpak IA column (250×4.6 mm: 5 μm; (30 mg loading; 0.1% DEA in n-hexane: CH$_2$Cl$_2$:MeOH (80:20); (A:B: 75:25) as mobile phase) to provide the compound of Example 179A (Fraction I (−)) and the compound of Example 179B (Fraction II (+)).

Example 179A

Synthesis of (−)-7-(3, 5-difluorophenyl)-N-(6-methoxy-5-(4-methyl-1H-imidazol-1-yl) pyridin-2-yl)-8-methyl-7, 8-dihydro-6H-pyrimido [5, 4-b] [1, 4] oxazin-2-amine

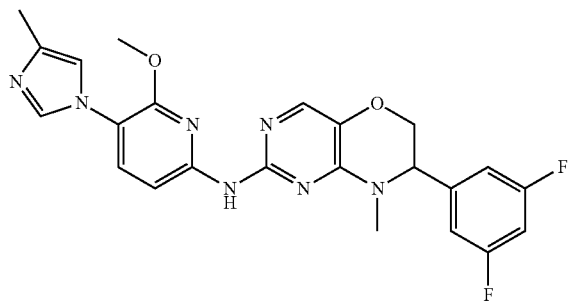 [SMILES: COc1nc(Nc2ncc3c(n2)N(C)C(c2cc(F)cc(F)c2)CO3)ccc1-n1cnc(C)c1]

The compound of Example 179A was produced as described in Example 179. Analytical data for product Fraction I (−): $^1$H-NMR (CD$_3$OD, 400 MHz): δ 8.00-7.97 (m, 1H), 7.74 (s, 1H), 7.66 (s, 1H), 7.64 (s, 1H), 7.01 (br s, 1H), 6.95-6.81 (m, 3H), 4.80-4.78 (m, 1H), 4.25-4.22 (m, 2H), 3.96 (s, 3H), 3.19 (s, 3H), 2.22 (s, 3H); Mass (ESI): 466.4 [M+1]; LCMS: 466 (M+1); (column; X-Select CSH C-18 (50×3.0 mm, 3.5 μm); RT 2.27 min. 0.05% Aq TFA: ACN; 0.80 mL/min); UPLC (column; Acquity BEH C-18, 50×2.1 mm, 1.7 μm); RT 1.64 min. ACN: 0.025% Aq TFA; 0.5 mL/min; Chiral HPLC: 98.0% RT=8.35 min (CHIRAL-PAK-IA (250×4.6 mm, 5 μm; mobile phase (A) 0.1% DEA in n-hexane (B) CH$_2$Cl$_2$:MeOH (80:20) (A:B; 75:25); flow Rate: 1.0 mL/min); Optical rotation $[α]_D^{20.00}$: −131.95 (c=0.25, CH$_2$Cl$_2$).

Example 179B

Synthesis of (+)-7-(3, 5-difluorophenyl)-N-(6-methoxy-5-(4-methyl-1H-imidazol-1-yl) pyridin-2-yl)-8-methyl-7, 8-dihydro-6H-pyrimido [5, 4-b] [1, 4] oxazin-2-amine

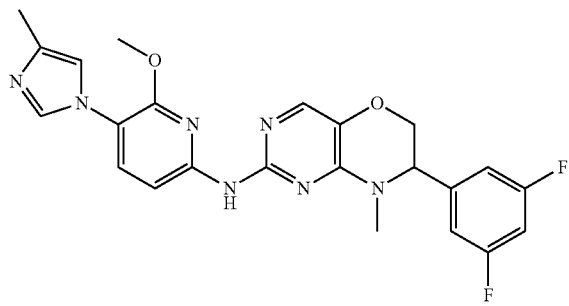

The compound of Example 179B was produced as described in Example 179. Analytical data for product Fraction II (+): $^1$H-NMR (CD$_3$OD, 400 MHz): δ 8.00-7.97 (m, 1H), 7.74 (s, 1H), 7.66 (s, 1H), 7.64 (s, 1H), 7.01 (br s, 1H), 6.95-6.81 (m, 3H), 4.80-4.78 (m, 1H), 4.25-4.22 (m, 2H), 3.96 (s, 3H), 3.19 (s, 3H), 2.22 (s, 3H); Mass (ESI): 466.4 [M+1]; LCMS: 466.1 (M+1); (column; X-Select CSH C-18 (50×3.0 mm, 3.5 μm); RT 2.28 min 0.05% Aq TFA: ACN; 0.80 mL/min); UPLC (column; Acquity BEH C-18, 50×2.1 mm, 1.7 μm); RT 1.63 min. ACN: 0.025% Aq TFA; 0.5 mL/min; Chiral HPLC: 97.7% RT=9.65 min (CHIRAL-PAK-IA (250×4.6 mm, 5 μm; mobile phase (A) 0.1% DEA in n-hexane (B) CH$_2$Cl$_2$:MeOH (80:20) (A:B; 75:25); flow Rate: 1.0 mL/min); Optical rotation $[α]_D^{19.99}$: +124.14 (c=0.25, CH$_2$Cl$_2$).

Example 180

Synthesis of N-(6-methoxy-5-(4-methyl-1H-imidazol-1-yl) pyridin-2-yl)-8-methyl-7-(o-tolyl)-7, 8-dihydro-6H-pyrimido [5, 4-b] [1, 4] oxazin-2-amine

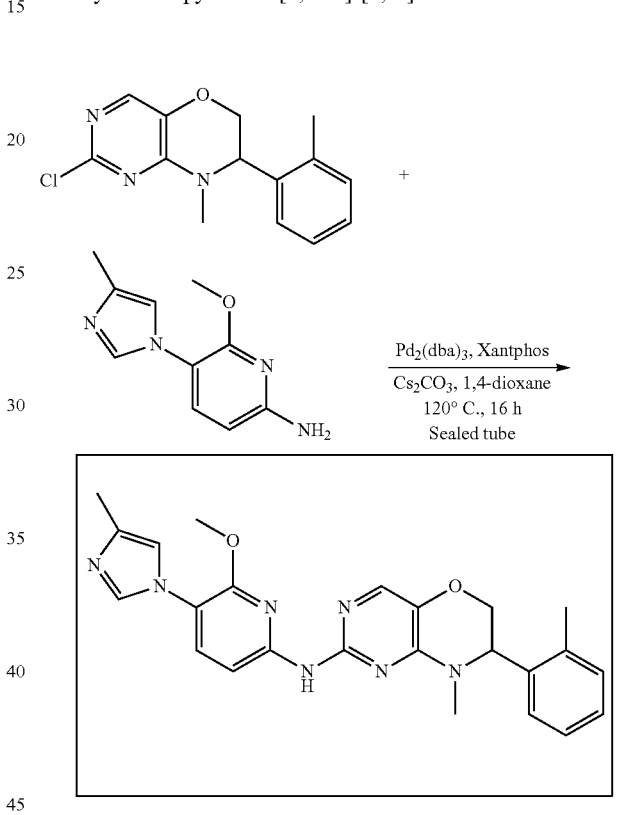

Synthesis of N-(6-methoxy-5-(4-methyl-1H-imidazol-1-yl) pyridin-2-yl)-8-methyl-7-(o-tolyl)-7, 8-dihydro-6H-pyrimido [5, 4-b] [1, 4] oxazin-2-amine To a dry vial was added a suspension of Pd$_2$(dba)$_3$ (33 mg, 0.03 mmol) and Xantphos (63 mg, 0.11 mmol) in 1, 4-dioxane (1 mL) at room temperature. The suspension was degassed with argon, heated to 120° C., and stirred for 3 min. A mixture of 2-chloro-8-methyl-7-(o-tolyl)-7, 8-dihydro-6H-pyrimido [5, 4-b] [1, 4] oxazine (200 mg, 0.72 mmol), 6-methoxy-5-(4-methyl-1H-imidazol-1-yl) pyridin-2-amine (297 mg, 1.45 mmol) and cesium carbonate (331 mg, 1.01 mmol) in 1, 4-dioxane (2 mL) was degassed and the catalyst premix was added. The resultant mixture was stirred at 120° C. for 16 h in a sealed tube. After consumption of the reaction (monitored by TLC and LCMS), the volatile components were evaporated in vacuo. The residue was diluted with water (20 mL) and extracted with EtOAc (2×20 mL). The combined organic extracts were dried over sodium sulfate, filtered and concentrated in vacuo. The crude material was washed with MeOH: ether (1:1, 2×10 mL) to afford N-(6-methoxy-5-(4-methyl-1H-imidazol-1-yl) pyridin-2-yl)-8-methyl-7-(o-tolyl)-7, 8-dihydro-6H-pyrimido [5, 4-b] [1, 4] oxazin-2-amine (280 mg, 87%) as an off-white solid. LCMS: 444 (M+1); (column; X-Select CSH C-18 (50×3.0 mm, 3.5 µm); RT 2.31 min 0.05% Aq TFA: ACN; 0.80 mL/min); TLC: 10% MeOH/CH$_2$Cl$_2$ (R$_f$: 0.3).

Racemic compound of Example 180 was separated using a Chiralpak IA column (250×4.6 mm: 5 µm; (25 mg loading; 0.1% DEA in n-hexane: CH$_2$Cl$_2$:MeOH (50:50); (A:B: 75:25) as mobile phase) to provide the compound of Example 180A (Fraction I (−)) and the compound of Example 180B (Fraction II (+)).

Example 180A

Synthesis of (−)-N-(6-methoxy-5-(4-methyl-1H-imidazol-1-yl) pyridin-2-yl)-8-methyl-7-(o-tolyl)-7, 8-dihydro-6H-pyrimido [5, 4-b] [1, 4] oxazin-2-amine

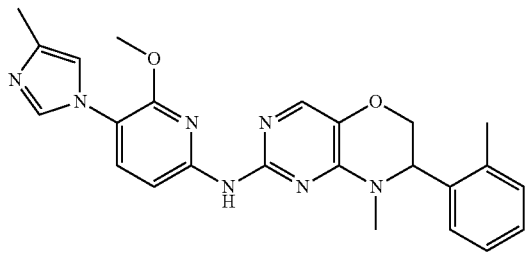 [SMILES: COc1nc(Nc2ncc3c(n2)N(C)C(c2ccccc2C)CO3)ccc1-n1cnc(C)c1]

The compound of Example 180A was produced as described in Example 180. Analytical data for product for Fraction I (−): $^1$H-NMR (CD$_3$OD, 400 MHz): δ 8.00-7.99 (m, 1H), 7.72 (s, 1H), 7.65-7.60 (m, 2H), 7.28-7.12 (m, 3H), 7.08-6.97 (m, 2H), 5.04-5.01 (m, 1H), 4.26-4.21 (m, 1H), 4.17-4.11 (m, 1H), 3.96 (s, 3H), 3.10 (s, 3H), 2.41 (s, 3H), 2.22 (s, 3H); Mass (ESI): 444.5 [M+1]; LCMS: 444.1 (M+1); (column; X-Select CSH C-18 (50×3.0 mm, 3.5 µm); RT 2.30 min. 0.05% Aq TFA: ACN; 0.80 mL/min); UPLC (column; Acquity BEH C-18, 50×2.1 mm, 1.7 µm); RT 1.64 min. ACN: 0.025% Aq TFA; 0.5 mL/min; Chiral HPLC: 98.5% RT=7.38 min (CHIRALPAK-IA (250×4.6 mm, 5 µm; mobile phase (A) 0.1 DEA in n-hexane (B) CH$_2$Cl$_2$:MeOH (50:50) (A:B; 75:25); flow Rate: 1.0 mL/min); Optical rotation [α]$_D^{20.00}$: −155.36 (c=0.25, CH$_2$Cl$_2$).

Example 180B

Synthesis of (+)-N-(6-methoxy-5-(4-methyl-1H-imidazol-1-yl) pyridin-2-yl)-8-methyl-7-(o-tolyl)-7, 8-dihydro-6H-pyrimido [5, 4-b] [1, 4] oxazin-2-amine

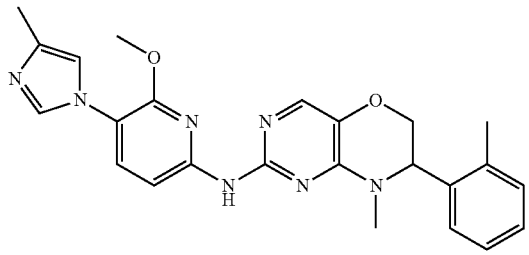 [SMILES: COc1nc(Nc2ncc3c(n2)N(C)C(c2ccccc2C)CO3)ccc1-n1cnc(C)c1]

The compound of Example 180B was produced as described in Example 180. Analytical data for product for Fraction II (+): $^1$H-NMR (CD$_3$OD, 400 MHz): δ 8.00-7.99 (m, 1H), 7.72 (s, 1H), 7.65-7.60 (m, 2H), 7.28-7.12 (m, 3H), 7.08-6.97 (m, 2H), 5.04-5.01 (m, 1H), 4.26-4.21 (m, 1H), 4.17-4.11 (m, 1H), 3.96 (s, 3H), 3.10 (s, 3H), 2.41 (s, 3H), 2.22 (s, 3H); Mass (ESI): 444.4 [M+1]; LCMS: 444 (M+1); (column; X-Select CSH C-18 (50×3.0 mm, 3.5 µm); RT 2.30 min. 0.05% Aq TFA: ACN; 0.80 mL/min); UPLC (column; Acquity BEH C-18, 50×2.1 mm, 1.7 µm); RT 1.63 min. ACN: 0.025% Aq TFA; 0.5 mL/min; Chiral HPLC: 95.7% RT=10.13 min (CHIRALPAK-IA (250×4.6 mm, 5 µm; mobile phase (A) 0.1% DEA in n-hexane (B) CH$_2$Cl$_2$: MeOH (50:50) (A:B; 75:25); flow Rate: 1.0 mL/min); Optical rotation [α]$_D^{20.01}$: +143.77 (c=0.25, CH$_2$Cl$_2$).

Example 181

Synthesis of N-(5-methoxy-6-(4-methyl-1H-imidazol-1-yl) pyridin-3-yl)-8-methyl-7-(2, 4, 5-trifluorophenyl)-7, 8-dihydro-6H-pyrimido [5, 4-b] [1, 4] oxazin-2-amine

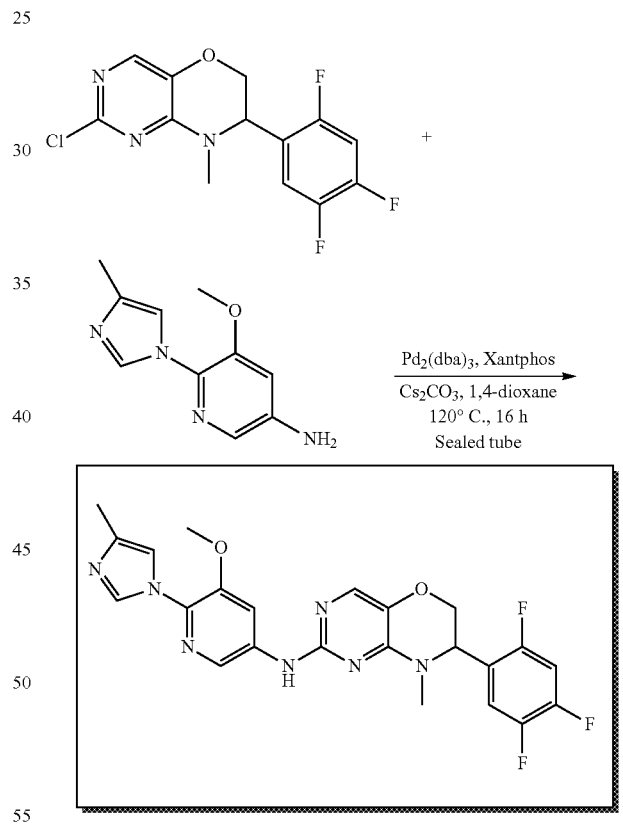

Synthesis of N-(5-methoxy-6-(4-methyl-1H-imidazol-1-yl) pyridin-3-yl)-8-methyl-7-(2, 4, 5-trifluorophenyl)-7, 8-dihydro-6H-pyrimido [5, 4-b] [1, 4] oxazin-2-amine To a dry vial was added a suspension of Pd$_2$(dba)$_3$ (36 mg, 0.04 mmol) and Xantphos (69 mg, 0.11 mmol) in 1, 4-dioxane (1.25 mL) at room temperature. The suspension was degassed with argon, heated to 120° C., and stirred for 3 min. A mixture of 2-chloro-8-methyl-7-(2, 4, 5-trifluorophenyl)-7, 8-dihydro-6H-pyrimido [5, 4-b] [1, 4] oxazine (250 mg, 0.79 mmol), 5-methoxy-6-(4-methyl-1H-imidazol-1-yl) pyridin-3-amine (194 mg, 0.95 mmol) and cesium carbonate (360 mg, 1.11 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (20 mL) and extracted with 5% MeOH/CH$_2$Cl$_2$ (2×20 mL). The combined organic extracts were dried over sodium sulfate, filtered and concentrated in vacuo. The crude material was purified by column chromatography using 2-5% MeOH: CH$_2$Cl$_2$ to afford N-(5-methoxy-6-(4-methyl-1H-imidazol-1-yl) pyridin-3-yl)-8-methyl-7-(2, 4, 5-trifluorophenyl)-7, 8-dihydro-6H-pyrimido [5, 4-b] [1, 4] oxazin-2-amine (100 mg, 26%) as an off-white solid. LCMS 484 (M+1); (column; X-select CSH C-18 50×3.0 mm, 3.5 µm); RT 2.38 min. ACN: 0.025% Aq TFA; 0.8 mL/min; TLC: 5% MeOH/CH$_2$Cl$_2$ (R$_f$: 0.3).

Racemic compound of Example 181 was separated using a Chiralpak ADH (250×4.6 mm: 5 µm; (20 mg loading; 0.1% DEA in n-hexane: CH$_2$Cl$_2$:MeOH (50:50); (A:B: 75:25) as mobile phase) to provide the compound of Example 181A (Fraction I (−)) and the compound of Example 181B (Fraction II (+)).

Example 181A

Synthesis of (−)-N-(5-methoxy-6-(4-methyl-1H-imidazol-1-yl) pyridin-3-yl)-8-methyl-7-(2, 4, 5-trifluorophenyl)-7, 8-dihydro-6H-pyrimido [5, 4-b] [1, 4] oxazin-2-amine

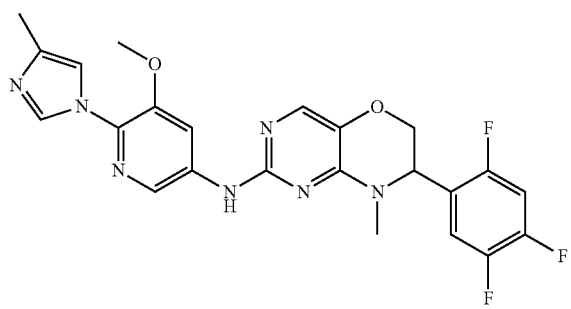 [SMILES: COc1cc(Nc2ncc3c(n2)N(C)C(c2cc(F)c(F)cc2F)CO3)cnc1-n1cnc(C)c1]

The compound of Example 181A was produced as described in Example 181. Analytical data for product for Fraction I (−): $^1$H-NMR (CD$_3$OD, 400 MHz): δ 8.30 (d, 2H), 8.11 (s, 1H), 7.64 (s, 1H), 7.40 (s, 1H), 7.30-7.25 (m, 1H), 7.05-7.00 (m, 1H), 5.06-5.03 (m, 1H), 4.25-4.21 (m, 2H), 3.98 (s, 3H), 3.20 (s, 3H), 2.22 (s, 3H); Mass (ESI): 484.3 [M+1]; LCMS: 484.2 (M+1); (column; X-Select CSH C-18 (50×3.0 mm, 3.5 µm); RT 3.11 min 0.05% Aq TFA: ACN; 0.80 mL/min); UPLC (column; Acquity BEH C-18, 50×2.1 mm, 1.7 µm); RT 1.69 min. ACN: 0.025% Aq TFA; 0.5 mL/min; Chiral HPLC: 99.7% RT=12.89 min (CHIRALPAK-ADH (250×4.6 mm, 5 µm; mobile phase (A) 0.1% DEA in n-hexane (B) EtOH:MeOH (50:50) (A:B; 75:25); flow Rate: 1.0 mL/min); Optical rotation [α]$_D^{20.02}$: −154.99 (c=0.25, CH$_2$Cl$_2$).

Example 181B

Synthesis of (+)-N-(5-methoxy-6-(4-methyl-1H-imidazol-1-yl) pyridin-3-yl)-8-methyl-7-(2, 4, 5-trifluorophenyl)-7, 8-dihydro-6H-pyrimido [5, 4-b] [1, 4] oxazin-2-amine

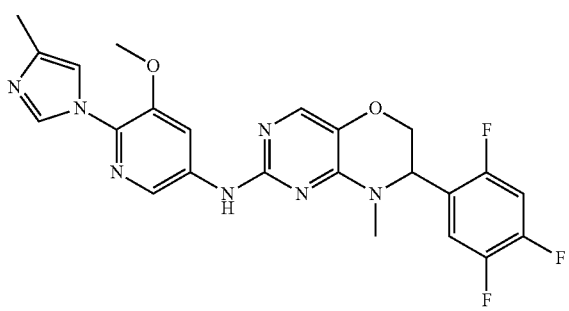

The compound of Example 181B was produced as described in Example 181. Analytical data for product for Fraction II (+): $^1$H-NMR (CD$_3$OD, 400 MHz): δ 8.30 (d, 2H), 8.11 (s, 1H), 7.64 (s, 1H), 7.40 (s, 1H), 7.30-7.25 (m, 1H), 7.05-7.00 (m, 1H), 5.06-5.03 (m, 1H), 4.25-4.21 (m, 2H), 3.98 (s, 3H), 3.20 (s, 3H), 2.22 (s, 3H); Mass (ESI): 484.4 [M+1]; LCMS: 484.2 (M+1); (column; X-Select CSH C-18 (50×3.0 mm, 3.5 µm); RT 3.10 min 0.05% Aq TFA: ACN; 0.80 mL/min); UPLC (column; Acquity BEH C-18, 50×2.1 mm, 1.7 µm); RT 1.69 min. ACN: 0.025% Aq TFA; 0.5 mL/min; Chiral HPLC: 97.0% RT=15.44 min (CHIRALPAK-ADH (250×4.6 mm, 5 µm; mobile phase (A) 0.1% DEA in n-hexane (B) CH$_2$Cl$_2$:MeOH (50:50) (A:B; 75:25); flow Rate: 1.0 mL/min); Optical rotation [α]$_D^{20.01}$: +141.95 (c=0.25, CH$_2$Cl$_2$).

Example 182

Synthesis of N-(5-methoxy-6-(4-methyl-1H-imidazol-1-yl) pyridin-3-yl)-8-methyl-7-(3, 4, 5-trifluorophenyl)-7, 8-dihydro-6H-pyrimido [5, 4-b] [1, 4] oxazin-2-amine

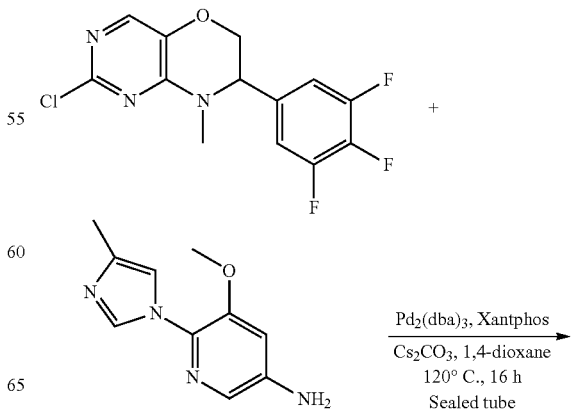

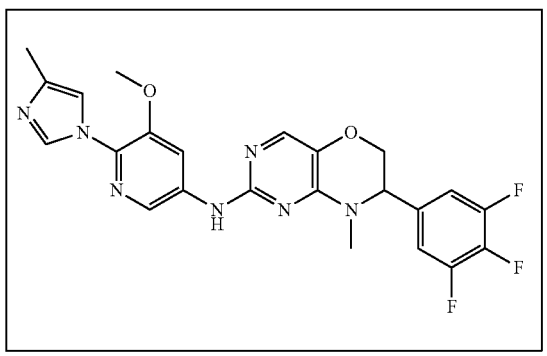

Synthesis of N-(5-methoxy-6-(4-methyl-1H-imidazol-1-yl) pyridin-3-yl)-8-methyl-7-(3, 4, 5-trifluorophenyl)-7, 8-dihydro-6H-pyrimido [5, 4-b] [1, 4] oxazin-2-amine To a dry vial was added a suspension of Pd$_2$(dba)$_3$ (29 mg, 0.03 mmol) and Xantphos (55 mg, 0.09 mmol) in 1, 4-dioxane (1 mL) at room temperature. The suspension was degassed with argon, heated to 120° C., and stirred for 3 min. A mixture of 2-chloro-8-methyl-7-(3, 4, 5-trifluorophenyl)-7, 8-dihydro-6H-pyrimido [5, 4-b] [1, 4] oxazine (200 mg, 0.63 mmol), 5-methoxy-6-(4-methyl-1H-imidazol-1-yl) pyridin-3-amine (259 mg, 1.26 mmol) and cesium carbonate (289 mg, 0.88 mmol) in 1, 4-dioxane (1 mL) was degassed and the catalyst premix was added. The resultant mixture was stirred at 120° C. for 16 h in sealed tube. After consumption of the starting material (monitored by TLC and LCMS), the volatile components were evaporated in vacuo. The residue was diluted with water (20 mL) and extracted with EtOAc (2×20 mL). The combined organic extracts were dried over sodium sulfate, filtered and concentrated in vacuo. The crude material was washed with CH$_3$CN: MeOH (1:1, 2×10 mL) to afford N-(5-methoxy-6-(4-methyl-1H-imidazol-1-yl) pyridin-3-yl)-8-methyl-7-(3, 4, 5-trifluorophenyl)-7, 8-dihydro-6H-pyrimido [5, 4-b] [1, 4] oxazin-2-amine (110 mg, 35%) as an off-white solid. LCMS: 484 (M+1); (column; X-Select CSH C-18 (50×3.0 mm, 3.5 µm); RT 2.44 min. 0.05% Aq TFA: ACN; 0.80 mL/min); TLC: 10% MeOH/CH$_2$Cl$_2$ (R$_f$: 0.3).

Racemic compound of Example 182 was separated using a Chiralpak IA column (250×4.6 mm: 5 µm; (15 mg loading; 0.1% DEA in n-hexane: CH$_2$Cl$_2$:MeOH (50:50); (A:B: 80:20) as mobile phase) to provide the compound of Example 182A (Fraction I (+)) and the compound of Example 182B (Fraction II (−)).

Example 182A

Synthesis of (+)-N-(5-methoxy-6-(4-methyl-1H-imidazol-1-yl) pyridin-3-yl)-8-methyl-7-(3, 4, 5-trifluorophenyl)-7, 8-dihydro-6H-pyrimido [5, 4-b] [1, 4] oxazin-2-amine

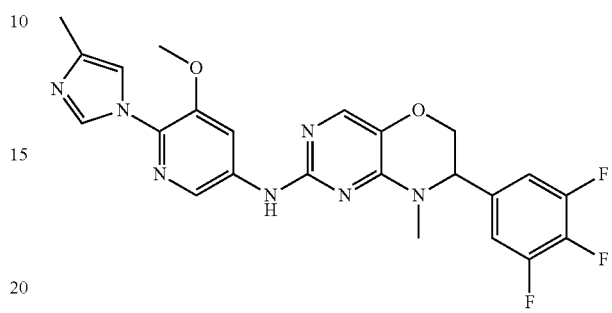

The compound of Example 182A was produced as described in Example 182. Analytical data for product for Fraction I (+): $^1$H-NMR (CD$_3$OD, 400 MHz): δ 8.30-8.29 (m, 2H), 8.10 (s, 1H), 7.62 (s, 1H), 7.39 (s, 1H), 7.03 (t, 2H), 4.75-4.73 (m, 1H), 4.21-4.19 (m, 2H), 3.97 (s, 3H), 3.18 (s, 3H), 2.21 (s, 3H); Mass (ESI): 484.1 [M+1]; LCMS: 484.0 (M+1); (column; X-Select CSH C-18 (50×3.0 mm, 3.5 µm); RT 2.46 min. 0.05% Aq TFA: ACN; 0.80 mL/min); UPLC (column; Acquity BEH C-18, 50×2.1 mm, 1.7 µm); RT 1.74 min. ACN: 0.025% Aq TFA; 0.5 mL/min; Chiral HPLC: 99.2% RT=15.03 min (CHIRALPAK-IA (250×4.6 mm, 5 µm; mobile phase (A) 0.1% DEA in n-hexane (B) CH$_2$Cl$_2$: MeOH (50:50) (A:B; 80:20); flow Rate: 1.0 mL/min); Optical rotation [α]$_D^{20.00}$: +126.12 (c=0.25, CH$_2$Cl$_2$).

Example 182B

Synthesis of (−)-N-(5-methoxy-6-(4-methyl-1H-imidazol-1-yl) pyridin-3-yl)-8-methyl-7-(3, 4, 5-trifluorophenyl)-7, 8-dihydro-6H-pyrimido [5, 4-b] [1, 4] oxazin-2-amine

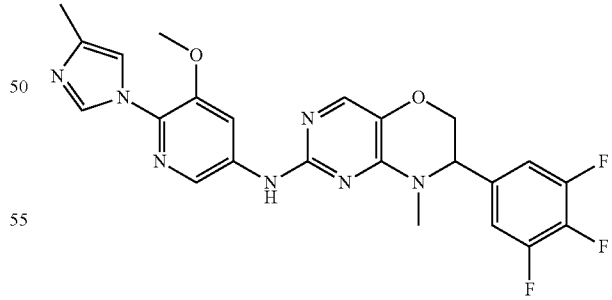

The compound of Example 182B was produced as described in Example 182. Analytical data for product Fraction II (−): $^1$H-NMR (CD$_3$OD, 400 MHz): δ 8.30-8.29 (m, 2H), 8.10 (s, 1H), 7.62 (s, 1H), 7.39 (s, 1H), 7.03 (t, 2H), 4.75-4.73 (m, 1H), 4.21-4.19 (m, 2H), 3.97 (s, 3H), 3.18 (s, 3H), 2.21 (s, 3H); Mass (ESI): 484 [M+1]; LCMS: 484.1 (M+1); (column; X-Select CSH C-18 (50×3.0 mm, 3.5 µm); RT 2.46 min. 0.05% Aq TFA: ACN; 0.80 mL/min); UPLC (column; Acquity BEH C-18, 50×2.1 mm, 1.7 μm); RT 1.74 min. ACN: 0.025% Aq TFA; 0.5 mL/min; Chiral HPLC: 95.2% RT=16.78 min (CHIRALPAK-IA (250×4.6 mm, 5 μm; mobile phase (A) 0.1% DEA in n-hexane (B) $CH_2Cl_2$: MeOH (50:50) (A:B; 80:20); flow Rate: 1.0 mL/min); Optical rotation $[\alpha]_D^{20.00}$: −131.61 (c=0.25, $CH_2Cl_2$).

Example 183

Synthesis of 7-(3, 5-difluorophenyl)-N-(6-methoxy-5-(2-methylpyrimidin-4-yl) pyridin-2-yl)-8-methyl-7, 8-dihydro-6H-pyrimido [5, 4-b] [1, 4] oxazin-2-amine

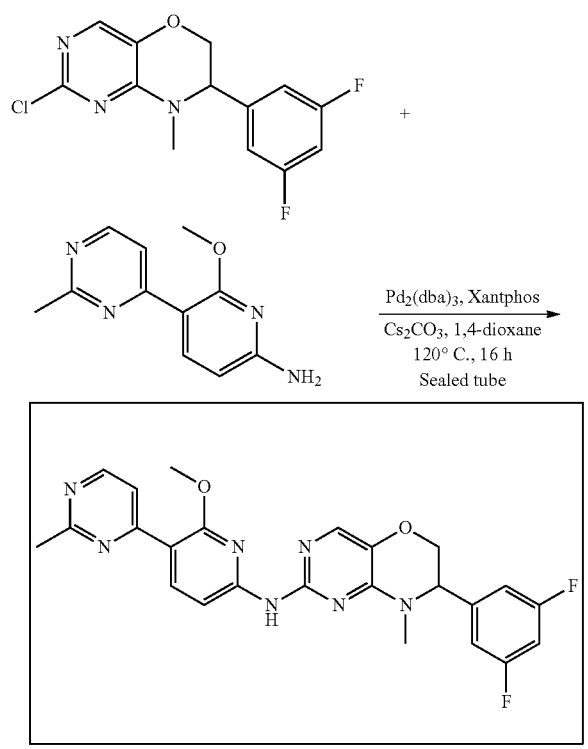

Synthesis of 7-(3, 5-difluorophenyl)-N-(6-methoxy-5-(2-methylpyrimidin-4-yl) pyridin-2-yl)-8-methyl-7, 8-dihydro-6H-pyrimido [5, 4-b] [1, 4] oxazin-2-amine To a dry vial was added a suspension of $Pd_2(dba)_3$ (35 mg, 0.04 mmol) and Xantphos (67 mg, 0.11 mmol) in 1, 4-dioxane (1.15 mL) at room temperature. The suspension was degassed with argon, heated to 120° C., and stirred for 3 min. A mixture of 2-chloro-7-(3, 5-difluorophenyl)-8-methyl-7, 8-dihydro-6H-pyrimido [5, 4-b] [1, 4] oxazine (230 mg, 0.77 mmol), 6-methoxy-5-(2-methylpyrimidin-4-yl) pyridin-2-amine (334 mg, 1.54 mmol) and cesium carbonate (352 mg, 1.08 mmol) in 1, 4-dioxane (1.15 mL) was degassed and the catalyst premix was added. The resultant mixture was stirred at 120° C. for 16 h in a sealed tube. After consumption of the starting material (monitored by TLC and LCMS), the reaction mixture was diluted with water (50 mL) and extracted with $CH_2Cl_2$ (2×50 mL). The combined organic extracts were dried over sodium sulfate, filtered and concentrated in vacuo. The crude material was purified by column chromatography using 3% MeOH: $CH_2Cl_2$ to afford 7-(3, 5-difluorophenyl)-N-(6-methoxy-5-(2-methylpyrimidin-4-yl) pyridin-2-yl)-8-methyl-7, 8-dihydro-6H-pyrimido [5, 4-b] [1, 4] oxazin-2-amine (100 mg, 27%) as an off-white solid. LCMS: 478.1 (M+1); (column; X-Select CSH C-18 (50×3.0 mm, 3.5 μm); RT 2.64 min 0.05% Aq TFA: ACN; 0.80 mL/min); UPLC (column; Acquity BEH C-18 50×2.1 mm, 1.7 μm); RT 1.94 min. ACN: 0.025% Aq TFA; 0.5 mL/min; TLC: 5% MeOH/$CH_2Cl_2$ ($R_f$: 0.4).

Racemic compound of Example 183 was separated using a Chiralpak IC column (250×4.6 mm: 5 μm; (20 mg loading; 0.1% DEA in n-hexane: $CH_2Cl_2$:MeOH (50:50); (A:B: 85:15) as mobile phase) to provide the compound of Example 183A (Fraction I (+)) and the compound of Example 183B (Fraction II (−)).

Example 183A

Synthesis of (+)-7-(3, 5-difluorophenyl)-N-(6-methoxy-5-(2-methylpyrimidin-4-yl) pyridin-2-yl)-8-methyl-7, 8-dihydro-6H-pyrimido [5, 4-b] [1, 4] oxazin-2-amine

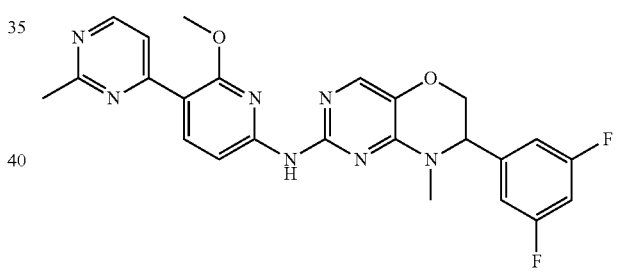

The compound of Example 183A was produced as described in Example 183. Analytical data for product for Fraction I (+): $^1$H-NMR (DMSO-$d_6$, 400 MHz): δ 9.29 (s, 1H), 8.63 (d, 1H), 8.51 (d, 1H), 8.02 (d, 1H), 7.90 (d, 1H), 7.72 (s, 1H), 7.24 (t, 1H), 7.00-6.93 (m, 2H), 4.92-4.90 (m, 1H), 4.30-4.20 (m, 2H), 4.00 (s, 3H), 3.11 (s, 3H), 2.61 (s, 3H); Mass (ESI): 478.1 [M+1]; LCMS: 478.1 (M+1); (column; X-Select CSH C-18 (50×3.0 mm, 3.5 μm); RT 2.65 min. 0.05% Aq TFA: ACN; 0.80 mL/min); UPLC (column; Acquity BEH C-18, 50×2.1 mm, 1.7 μm); RT 1.95 min. ACN: 0.025% Aq TFA; 0.5 mL/min; Chiral HPLC: 98.7% RT=17.76 min (CHIRALPAK-IC (250×4.6 mm, 5 μm; mobile phase (A) 0.1% DEA in n-hexane (B) $CH_2Cl_2$: MeOH (50:50) (A:B; 85:15); flow Rate: 1.0 mL/min); Optical rotation $[\alpha]_D^{20.00}$: +0.25 (c=0.25, $CH_2Cl_2$).

Example 183B

Synthesis of (−)-7-(3, 5-difluorophenyl)-N-(6-methoxy-5-(2-methylpyrimidin-4-yl) pyridin-2-yl)-8-methyl-7, 8-dihydro-6H-pyrimido [5, 4-b] [1, 4] oxazin-2-amine

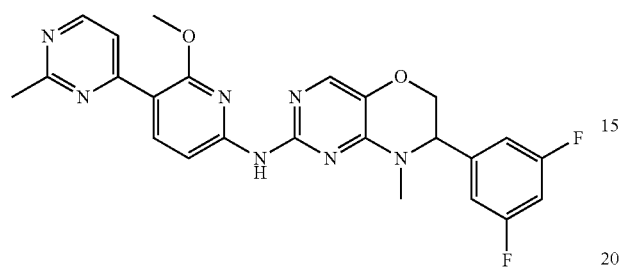

The compound of Example 183B was produced as described in Example 183. Analytical data for product Fraction II (−): $^1$H-NMR (DMSO-d$_6$, 400 MHz): δ 9.29 (s, 1H), 8.63 (d, 1H), 8.51 (d, 1H), 8.02 (d, 1H), 7.90 (d, 1H), 7.72 (s, 1H), 7.24 (t, 1H), 7.00-6.93 (m, 2H), 4.92-4.90 (m, 1H), 4.30-4.20 (m, 2H), 4.00 (s, 3H), 3.11 (s, 3H), 2.61 (s, 3H); Mass (ESI): 478.1 [M+1]; LCMS: 478.1 (M+1); (column; X-Select CSH C-18 (50×3.0 mm, 3.5 nm); RT 2.64 min. 0.05% Aq TFA: ACN; 0.80 mL/min); UPLC (column; Acquity BEH C-18, 50×2.1 mm, 1.7 μm); RT 1.95 min. ACN: 0.025% Aq TFA; 0.5 mL/min; Chiral HPLC: 99.4% RT=20.77 min (CHIRALPAK-IC (250×4.6 mm, 5 μm; mobile phase (A) 0.1% DEA in n-hexane (B) CH$_2$Cl$_2$: MeOH (50:50) (A:B; 85:15); flow Rate: 1.0 mL/min); Optical rotation [α]$_D^{20.00}$: −0.25 (c=0.25, CH$_2$Cl$_2$).

Example 184

Synthesis of 7-(3, 5-difluorophenyl)-N-(6-methoxy-5-(1-methyl-1H-pyrazol-4-yl) pyridin-2-yl)-8-methyl-7, 8-dihydro-6H-pyrimido [5, 4-b] [1, 4] oxazin-2-amine

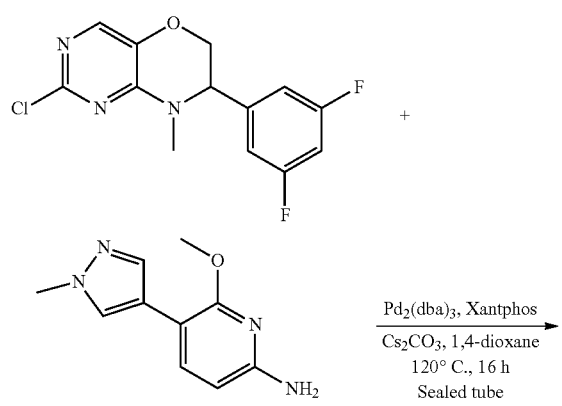

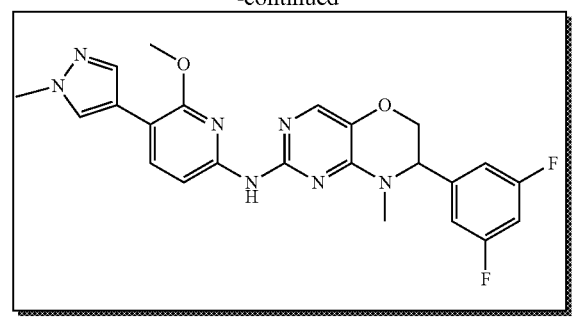

Synthesis of 7-(3, 5-difluorophenyl)-N-(6-methoxy-5-(1-methyl-1H-pyrazol-4-yl) pyridin-2-yl)-8-methyl-7, 8-dihydro-6H-pyrimido [5, 4-b] [1, 4] oxazin-2-amine To a dry vial was added a suspension of Pd$_2$(dba)$_3$ (35 mg, 0.04 mmol) and Xantphos (67 mg, 0.11 mmol) in 1, 4-dioxane (1.15 mL) at room temperature. The suspension was degassed with argon, heated to 120° C., and stirred for 3 min. A mixture of 2-chloro-7-(3, 5-difluorophenyl)-8-methyl-7, 8-dihydro-6H-pyrimido [5, 4-b] [1, 4] oxazine (230 mg, 0.77 mmol), 6-methoxy-5-(2-methylpyrimidin-4-yl) pyridin-2-amine (316 mg, 1.54 mmol) and cesium carbonate (352 mg, 1.08 mmol) in 1, 4-dioxane (1.15 mL) was degassed and the catalyst premix was added. The resultant mixture was stirred at 120° C. for 16 h in a sealed tube. After consumption of the starting material (monitored by TLC and LCMS), the reaction mixture was diluted with water (50 mL) and extracted with EtOAc (2×50 mL). The combined organic extracts were dried over sodium sulfate, filtered and concentrated in vacuo. The crude material was purified by column chromatography using 3% MeOH: CH$_2$Cl$_2$ to afford 7-(3, 5-difluorophenyl)-N-(6-methoxy-5-(1-methyl-1H-pyrazol-4-yl) pyridin-2-yl)-8-methyl-7, 8-dihydro-6H-pyrimido [5, 4-b] [1, 4] oxazin-2-amine (120 mg, 33%) as an off-white solid. LCMS: 466.1 (M+1); (column; X-Select CSH C-18 (50×3.0 mm, 3.5 μm); RT 2.83 min 0.05% Aq TFA: ACN; 0.80 mL/min); UPLC (column; Acquity BEH C-18 50×2.1 mm, 1.7 μm); RT 2.06 min. ACN: 0.025% Aq TFA; 0.5 mL/min; TLC: 5% MeOH/CH$_2$Cl$_2$ (R$_f$: 0.5).

Racemic compound of Example 184 was separated using a Chiralpak IA column (250×4.6 mm: 5 μm; (20 mg loading; 0.1% DEA in n-hexane: CH$_2$Cl$_2$:MeOH (50:50); (A:B: 80:20) as mobile phase) to provide the compound of Example 184A (Fraction I (−)) and the compound of Example 184B (Fraction II (+)).

Example 184A

Synthesis of (−)-7-(3, 5-difluorophenyl)-N-(6-methoxy-5-(1-methyl-1H-pyrazol-4-yl) pyridin-2-yl)-8-methyl-7, 8-dihydro-6H-pyrimido [5, 4-b] [1, 4] oxazin-2-amine

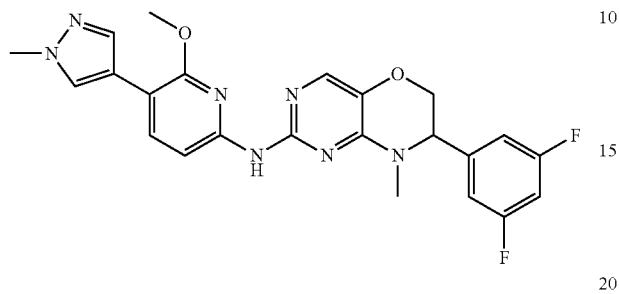

The compound of Example 184A was produced as described in Example 184. Analytical data for product Fraction I (−): $^1$H-NMR (DMSO-$d_6$, 400 MHz): δ 8.70 (s, 1H), 8.00 (s, 1H), 7.90-7.84 (m, 2H), 7.83 (s, 1H), 7.70 (s, 1H), 7.25 (t, 1H), 7.00-6.94 (m, 2H), 4.90-4.88 (m, 1H), 4.30-4.17 (m, 2H), 3.95 (s, 3H), 3.83 (s, 3H), 3.10 (s, 3H); Mass (ESI): 466.1 [M+1]; LCMS: 466.1 (M+1); (column; X-Select CSH C-18 (50×3.0 mm, 3.5 μm); RT 2.81 min. 0.05% Aq TFA: ACN; 0.80 mL/min); UPLC (column; Acquity BEH C-18, 50×2.1 mm, 1.7 μm); RT 2.04 min. ACN: 0.025% Aq TFA; 0.5 mL/min; Chiral HPLC: 100% RT=11.54 min (CHIRALPAK-IA (250×4.6 mm, 5 μm; mobile phase (A) 0.1% DEA in n-hexane (B) $CH_2Cl_2$: MeOH (50:50) (A:B; 80:20); flow Rate: 1.0 mL/min); Optical rotation $[\alpha]_D^{20.00}$: −146.43 (c=0.25, $CH_2Cl_2$).

Example 184B

Synthesis of (+)-7-(3, 5-difluorophenyl)-N-(6-methoxy-5-(1-methyl-1H-pyrazol-4-yl) pyridin-2-yl)-8-methyl-7, 8-dihydro-6H-pyrimido [5, 4-b] [1, 4] oxazin-2-amine

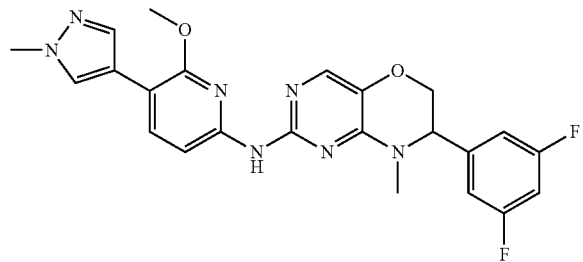 [SMILES: COc1nc(Nc2ncc3c(n2)N(C)C(c2cc(F)cc(F)c2)CO3)ccc1-c1cnn(C)c1]

The compound of Example 184B was produced as described in Example 184. Analytical data for product Fraction II (+): $^1$H-NMR (DMSO-$d_6$, 400 MHz): δ 8.70 (s, 1H), 8.00 (s, 1H), 7.90-7.84 (m, 2H), 7.83 (s, 1H), 7.70 (s, 1H), 7.25 (t, 1H), 7.00-6.94 (m, 2H), 4.90-4.88 (m, 1H), 4.30-4.17 (m, 2H), 3.95 (s, 3H), 3.83 (s, 3H), 3.10 (s, 3H); Mass (ESI): 466.1 [M+1]; LCMS: 466.1 (M+1); (column; X-Select CSH C-18 (50×3.0 mm, 3.5 μm); RT 2.83 min. 0.05% Aq TFA: ACN; 0.80 mL/min); UPLC (column; Acquity BEH C-18, 50×2.1 mm, 1.7 μm); RT 2.04 min. ACN: 0.025% Aq TFA; 0.5 mL/min; Chiral HPLC: 99.4% RT=15.02 min (CHIRALPAK-IA (250×4.6 mm, 5 μm; mobile phase (A) 0.1% DEA in n-hexane (B) $CH_2Cl_2$: MeOH (50:50) (A:B; 80:20); flow Rate: 1.0 mL/min); Optical rotation $[\alpha]_D^{20.01}$: +153.26 (c=0.25, $CH_2Cl_2$).

Example 185

Synthesis of N-(5-methoxy-6-(4-methyl-1H-imidazol-1-yl) pyridin-3-yl)-7, 8-dimethyl-7, 8-dihydro-6H-pyrimido [5, 4-b] [1, 4] oxazin-2-amine

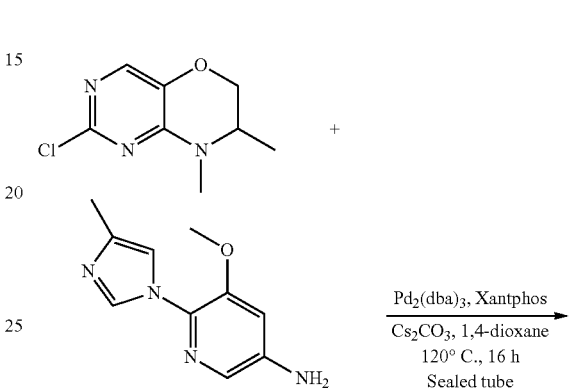

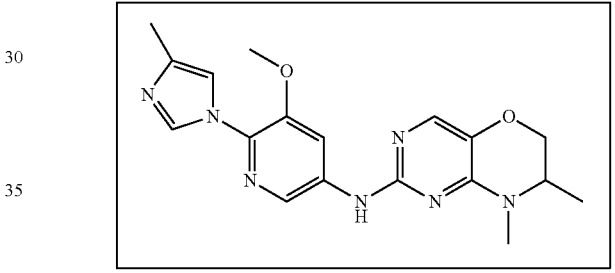

Synthesis of N-(5-methoxy-6-(4-methyl-1H-imidazol-1-yl) pyridin-3-yl)-7, 8-dimethyl-7, 8-dihydro-6H-pyrimido [5, 4-b] [1, 4] oxazin-2-amine To a dry vial was added a suspension of $Pd_2(dba)_3$ (57 mg, 0.06 mmol) and Xantphos (108 mg, 0.01 mmol) in 1, 4-dioxane (1.25 mL) at room temperature. The suspension was degassed with argon, heated to 120° C., and stirred for 3 min. A mixture of 2-chloro-7, 8-dimethyl-7,8-dihydro-6H-pyrimido [5, 4-b] [1, 4] oxazine (250 mg, 0.12 mmol), 5-methoxy-6-(4-methyl-1H-imidazol-1-yl) pyridin-3-amine (512 mg, 0.25 mmol) and cesium carbonate (571 mg, 1.75 mmol) in 1, 4-dioxane (1.25 mL) was degassed and the catalyst premix was added. The resultant mixture was stirred at 120° C. for 16 h in a sealed tube. After consumption of the staring material (monitored by TLC and LCMS), the reaction mixture was diluted with water (20 mL) and extracted with $CH_2Cl_2$ (2×20 mL). The combined organic extracts were dried over sodium sulfate, filtered and concentrated in vacuo. The crude material was purified by column chromatography using 3% MeOH: $CH_2Cl_2$ to afford N-(5-methoxy-6-(4-methyl-1H-imidazol-1-yl) pyridin-3-yl)-7, 8-dimethyl-7, 8-dihydro-6H-pyrimido [5, 4-b] [1, 4] oxazin-2-amine (250 mg, 54%) as an off-white solid. $^1$H-NMR ($CD_3OD$, 400 MHz): δ 8.11-8.10 (m, 2H), 8.00 (s, 1H), 7.52 (s, 1H), 7.37-7.30 (m, 4H), 7.21 (d, 2H), 6.21 (s, 1H), 4.58-4.56 (m, 1H), 4.29-4.15 (m, 2H), 3.95 (s, 3H), 2.90 (s, 3H), 2.25 (s, 3H); UPLC (column; Acquity BEH C-18 50×2.1 mm, 1.7 µm); RT 1.28 min. ACN: 0.025% Aq TFA; 0.5 mL/min; TLC: 5% MeOH/CH$_2$Cl$_2$ (R$_f$: 0.3).

Racemic compound of Example 185 was separated using a Chiralpak IA column (250×4.6 mm: 5 µm; (15 mg loading; 0.1% DEA in n-hexane: EtOH:MeOH (40:60); (A:B: 80:20) as mobile phase) to provide the compound of Example 185A (Fraction I (+)) and the compound of Example 185B (Fraction II (−)).

Example 185A

Synthesis of (+)-N-(5-methoxy-6-(4-methyl-1H-imidazol-1-yl) pyridin-3-yl)-7, 8-dimethyl-7, 8-dihydro-6H-pyrimido [5, 4-b] [1, 4] oxazin-2-amine

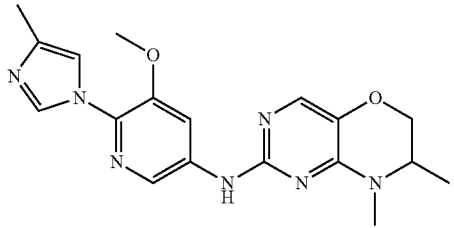 [SMILES: COc1cc(Nc2ncc3c(n2)N(C)C(C)CO3)cnc1-n1cnc(C)c1]

The compound of Example 185B was produced as described in Example 185. Analytical data for product Fraction I (+): $^1$H-NMR (CD$_3$OD, 400 MHz): δ 8.29-8.24 (m, 2H), 8.11 (s, 1H), 7.51 (s, 1H), 7.39 (s, 1H), 4.01-4.00 (m, 2H), 3.97 (s, 3H), 3.68-3.64 (m, 1H), 3.20 (s, 3H), 2.32 (s, 3H), 1.31 (d, 3H); Mass (ESI): 368.3 [M+1]; LCMS: 368.2 (M+1); (column; X-Select CSH C-18 (50×3.0 mm, 3.5 µm); RT 1.94 min. 0.05% Aq TFA: ACN; 0.80 mL/min); UPLC (column; Acquity BEH C-18, 50×2.1 mm, 1.7 µm); RT 1.28 min. ACN: 0.025% Aq TFA; 0.5 mL/min; Chiral HPLC: 99.1% RT=13.95 min (CHIRALPAK-AD-H (250×4.6 mm, 5 µm; mobile phase (A) 0.1% DEA in n-hexane (B) EtOH:MeOH (60:40) (A:B; 80:20); flow Rate: 1.0 mL/min); Optical rotation $[α]_D^{20.00}$: +22.25 (c=0.25, CH$_2$Cl$_2$).

Example 185B

Synthesis of (−)-N-(5-methoxy-6-(4-methyl-1H-imidazol-1-yl) pyridin-3-yl)-7, 8-dimethyl-7, 8-dihydro-6H-pyrimido [5, 4-b] [1, 4] oxazin-2-amine

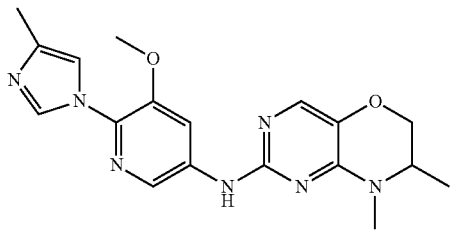 [SMILES: COc1cc(Nc2ncc3c(n2)N(C)C(C)CO3)cnc1-n1cnc(C)c1]

The compound of Example 185B was produced as described in Example 185. Analytical data for product Fraction II (−): $^1$H-NMR (CD$_3$OD, 400 MHz): δ 8.29-8.24 (m, 2H), 8.11 (s, 1H), 7.51 (s, 1H), 7.39 (s, 1H), 4.01-4.00 (m, 2H), 3.97 (s, 3H), 3.68-3.64 (m, 1H), 3.20 (s, 3H), 2.32 (s, 3H), 1.31 (d, 3H); Mass (ESI): 368.3 [M+1]; LCMS: 368 (M+1); (column; X-Select CSH C-18 (50×3.0 mm, 3.5 µm); RT 1.95 min. 0.05% Aq TFA: ACN; 0.80 mL/min); UPLC (column; Acquity BEH C-18, 50×2.1 mm, 1.7 µm); RT 1.29 min. ACN: 0.025% Aq TFA; 0.5 mL/min; Chiral HPLC: 99.4% RT=16.03 min (CHIRALPAK-AD-H (250×4.6 mm, 5 µm; mobile phase (A) 0.1% DEA in n-hexane (B) EtOH:MeOH (60:40) (A:B; 80:20); flow Rate: 1.0 mL/min); Optical rotation $[α]_D^{20.00}$: −11.90 (c=0.25, CH$_2$Cl$_2$).

Example 186

Synthesis of 7-(2, 4-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

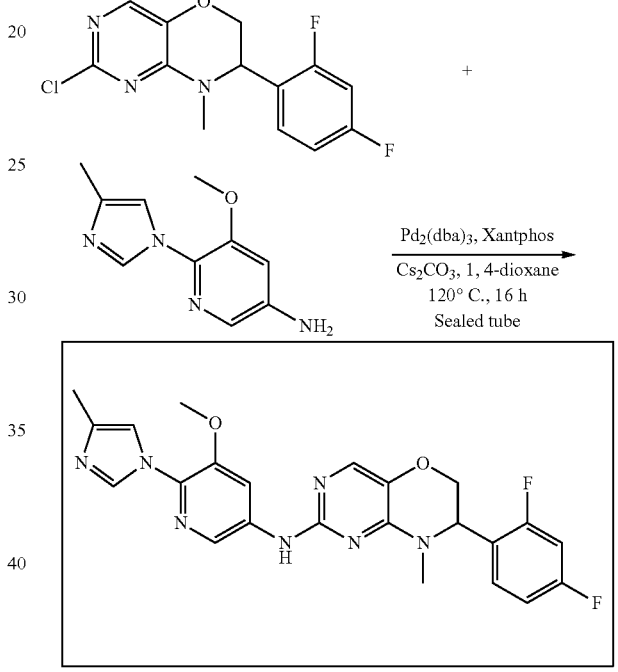

Synthesis of 7-(2, 4-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine To a dry vial was added a suspension of Pd$_2$(dba)$_3$ (38 mg, 0.04 mmol) and Xantphos (73 mg, 0.12 mmol) in 1, 4-dioxane (1.5 mL) at room temperature. The suspension was degassed with argon, heated to 120° C., and stirred for 3 min. A mixture of 2-chloro-7-(2, 4-difluorophenyl)-8-methyl-7, 8-dihydro-6H-pyrimido [5, 4-b] [1, 4] oxazine (250 mg, 0.84 mmol), 5-methoxy-6-(4-methyl-1H-imidazol-1-yl) pyridin-3-amine (206 mg, 1.01 mmol) and cesium carbonate (382 mg, 1.17 mmol) in 1, 4-dioxane (1.5 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (20 mL) and extracted with 5% MeOH/CH$_2$Cl$_2$ (2×20 mL). The combined organic extracts were dried over sodium sulfate, filtered and concentrated in vacuo. The crude material was purified by column chromatography using 2-5% MeOH:CH₂Cl₂ to obtain 100 and further purified by preparative HPLC which was further purified by preparative HPLC to afford (Ascentis C-18 (250×21.2 mm, 5 µm (50 mg loading; CH₃CN: 0.05% TFA (0.1/90, 2/80, 15/30, 25/10, 30/10, 35/10)) which was further purified by chiral preparative HPLC to afford 7-(2, 4-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine (60 mg, 15%) as an off-white solid. UPLC (column; Acquity BEH C-18 50×2.1 mm, 1.7 µm); RT 1.67 min. ACN: 0.025% Aq TFA; 0.5 mL/min; TLC: 10% MeOH/CH₂Cl₂ ($R_f$: 0.3).

Racemic compound of Example 186 was separated using a Chiralpak IA column (250×20 mm: 5 µm; (40 mg loading; 0.1% DEA in n-hexane: CH₂Cl₂:MeOH (50:50); (A:B: 80:20) as mobile phase) to provide the compound of Example 186A (Fraction I (+)) and the compound of Example 186B (Fraction II (−)).

Example 186A

Synthesis of (+)-7-(2, 4-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

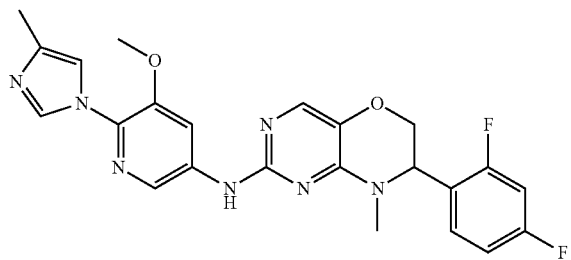

The compound of Example 186A was produced as described in Example 186. Analytical data for product Fraction I (+): ¹H-NMR (CD₃OD, 400 MHz): δ 8.31-8.30 (m, 2H), 8.11 (s, 1H), 7.61 (s, 1H), 7.40 (s, 1H), 7.15-7.10 (m, 1H), 7.09-7.04 (m, 1H), 6.99-6.94 (m, 1H), 5.06-5.04 (m, 1H), 4.27-4.25 (m, 2H), 3.95 (s, 3H), 3.19 (s, 3H), 2.22 (s, 3H); Mass (ESI): 466.4 [M+1]; LCMS: 466 (M+1); (column; X-Select CSH C-18 (50×3.0 mm, 3.5 µm); RT 2.33 min 0.05% Aq TFA: ACN; 0.80 mL/min); UPLC (column; Acquity BEH C-18, 2.1×50 mm, 1.7 µm); RT 1.68 min. ACN: 0.025% Aq TFA; 0.5 mL/min; Chiral HPLC: 96.4% RT=17.96 min (CHIRALPAK-IA (250×4.6 mm, 5 µm; mobile phase (A) 0.1% DEA in n-hexane (B) CH₂Cl₂:MeOH (50:50) (A:B; 80:20); flow Rate: 1.0 mL/min); Optical rotation $[\alpha]_D^{19.97}$: +149.47 (c=0.25, CH₂Cl₂).

Example 186B

Synthesis of (−)-7-(2, 4-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

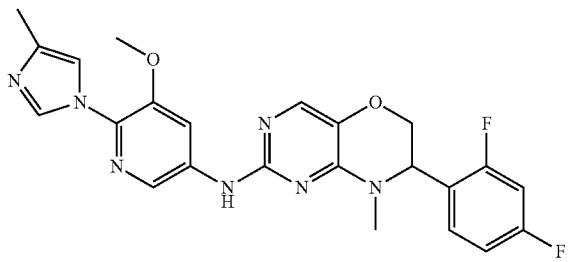

The compound of Example 186B was produced as described in Example 186. Analytical data for product Fraction II (−): ¹H-NMR (CD₃OD, 400 MHz): δ 8.31-8.30 (m, 2H), 8.11 (s, 1H), 7.61 (s, 1H), 7.40 (s, 1H), 7.15-7.10 (m, 1H), 7.09-7.04 (m, 1H), 6.99-6.94 (m, 1H), 5.06-5.04 (m, 1H), 4.27-4.25 (m, 2H), 3.95 (s, 3H), 3.19 (s, 3H), 2.22 (s, 3H); Mass (ESI): 466.4 [M+1]; LCMS: 466.1 (M+1); (column; X-Select CSH C-18 (50×3.0 mm, 3.5 µm); RT 2.36 min. 0.05% Aq TFA: ACN; 0.80 mL/min); UPLC (column; Acquity BEH C-18, 50×2.1 mm, 1.7 µm); RT 1.67 min. ACN: 0.025% Aq TFA; 0.5 mL/min; Chiral HPLC: 98.1% RT=20.26 min (CHIRALPAK-IA (250×4.6 mm, 5 µm; mobile phase (A) 0.1% DEA in n-hexane (B) CH₂Cl₂:MeOH (50:50) (A:B; 80:20); flow Rate: 1.0 mL/min); Optical rotation $[\alpha]_D^{20.00}$: −146.12 (c=0.25, CH₂Cl₂).

Example 187

Synthesis of N-(3-methoxy-4-(4-methyl-1H-imidazol-1-yl) phenyl)-8-methyl-7-(trifluoromethyl)-7, 8-dihydro-6H-pyrimido [5, 4-b] [1, 4] oxazin-2-amine

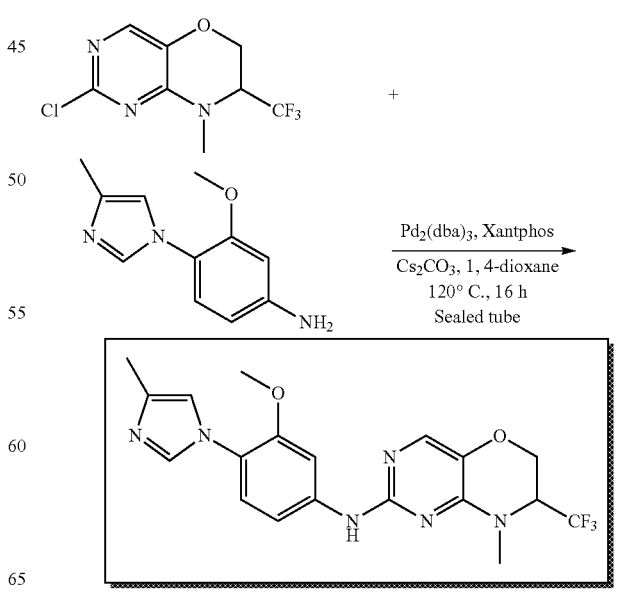

Synthesis of N-(3-methoxy-4-(4-methyl-1H-imidazol-1-yl) phenyl)-8-methyl-7-(trifluoromethyl)-7, 8-dihydro-6H-pyrimido [5, 4-b] [1, 4] oxazin-2-amine To a dry vial was added a suspension of Pd$_2$(dba)$_3$ (43 mg, 0.04 mmol) and Xantphos (82 mg, 0.14 mmol) in 1, 4-dioxane (2.5 mL) at room temperature. The suspension was degassed with argon, heated to 120° C., and stirred for 3 min. A mixture of 2-chloro-8-methyl-7-(4-(trifluoromethyl) phenyl)-7, 8-dihydro-6H-pyrimido [5, 4-b] [1, 4] oxazine (240 mg, 0.94 mmol), 3-methoxy-4-(4-methyl-1H-imidazol-1-yl) aniline (212 mg, 1.04 mmol) and cesium carbonate (431 mg, 1.31 mmol) in 1, 4-dioxane (2.5 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (20 mL) and extracted with 5% MeOH/CH$_2$Cl$_2$ (2×20 mL). The combined organic extracts were dried over sodium sulfate, filtered and concentrated in vacuo. The crude material was purified by column chromatography using 4% MeOH: CH$_2$Cl$_2$ to obtain 300 and further purified by preparative HPLC to afford (Ascentis C-18 (250×21.2 mm, 5 μm (60 mg loading; CH$_3$CN: 0.05% TFA (0.1/90, 2/80, 15/70, 25/20, 30/10, 35/10)) as mobile phase) to afford N-(3-methoxy-4-(4-methyl-1H-imidazol-1-yl) phenyl)-8-methyl-7-(trifluoromethyl)-7, 8-dihydro-6H-pyrimido [5, 4-b] [1, 4] oxazin-2-amine (98 mg, 26%) as an off-white solid. UPLC (column; Acquity BEH C-18 50×2.1 mm, 1.7 μm); RT 2.15 min. ACN: 0.05% Aq TFA; 0.5 mL/min; TLC: 5% MeOH/ CH$_2$Cl$_2$ (R$_f$; 0.5).

Racemic compound of Example 187 was separated using a Chiralpak ADH column (250×20 mm: 5 μm; (30 mg loading; 0.1% DEA in n-hexane; EtOH:MeOH (50:50) (A:B; 70:30) as mobile phase) to provide the compound of Example 187A (Fraction I (+)) and the compound of Example 187B (Fraction II (−)).

Example 187A

Synthesis of (+)-N-(3-methoxy-4-(4-methyl-1H-imidazol-1-yl) phenyl)-8-methyl-7-(trifluoromethyl)-7, 8-dihydro-6H-pyrimido [5, 4-b] [1, 4] oxazin-2-amine

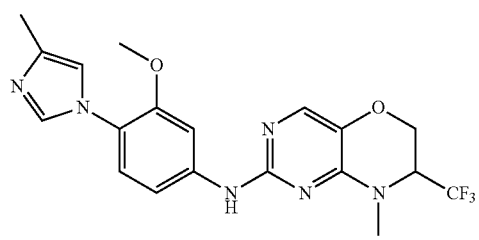 [SMILES: COc1cc(Nc2ncc3c(n2)N(C)C(C(F)(F)F)CO3)ccc1-n1cnc(C)c1]

The compound of Example 187A was produced as described in Example 187. Analytical data for Fraction I (+): $^1$H-NMR (CD$_3$OD, 400 MHz): δ 7.71 (s, 1H), 7.65-7.61 (m, 2H), 7.22 (d, 1H), 7.19 (d, 1H), 6.99 (s, 1H), 4.58-4.51 (m, 1H), 4.39-4.31 (m, 1H), 4.07-4.00 (m, 1H), 3.88 (s, 3H), 3.37 (s, 3H), 2.20 (s, 3H); Mass (ESI): 421.4 [M+1]; LCMS: 421.1 (M+1); (column; X-Select CSH C-18 (50×3.0 mm, 3.5 μm); RT 2.15 min. 0.05% Aq TFA: ACN; 0.80 mL/min); UPLC (column; Acquity BEH C-18, 2.1×50 mm, 1.7 μm); RT 1.50 min. ACN: 0.025% Aq TFA; 0.5 mL/min; Chiral HPLC: 99.1% RT=7.26 min (CHIRALPAK-ADH (250×4.6 mm, 5 μm; mobile phase (A) 0.1% DEA in n-hexane (B) EtOH:MeOH (50:50) (A:B; 70:30); flow Rate: 1.0 mL/min); Optical rotation [α]$_D^{20.00}$: +73.64 (c=0.25, CH$_2$Cl$_2$).

Example 187B

Synthesis of (−)-N-(3-methoxy-4-(4-methyl-1H-imidazol-1-yl) phenyl)-8-methyl-7-(trifluoromethyl)-7, 8-dihydro-6H-pyrimido [5, 4-b] [1, 4] oxazin-2-amine

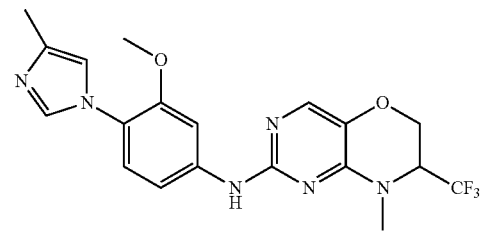 [SMILES: COc1cc(Nc2ncc3c(n2)N(C)C(C(F)(F)F)CO3)ccc1-n1cnc(C)c1]

The compound of Example 187B was produced as described in Example 187. Analytical data for Fraction II (−): $^1$H-NMR (CD$_3$OD, 400 MHz): δ 7.71 (s, 1H), 7.65-7.61 (m, 2H), 7.22 (d, 1H), 7.19 (d, 1H), 6.99 (s, 1H), 4.58-4.51 (m, 1H), 4.39-4.31 (m, 1H), 4.07-4.00 (m, 1H), 3.88 (s, 3H), 3.37 (s, 3H), 2.20 (s, 3H); Mass (ESI): 421.4 [M+1]; LCMS: 421 (M+1); (column; X-Select CSH C-18 (50×3.0 mm, 3.5 μm); RT 2.15 min. 0.05% Aq TFA: ACN; 0.80 mL/min); UPLC (column; Acquity BEH C-18, 2.1×50 mm, 1.7 μm); RT 1.50 min. ACN: 0.025% Aq TFA; 0.5 mL/min; Chiral HPLC: 99.3% RT=12.65 min (CHIRALPAK-ADH (250× 4.6 mm, 5 μm; mobile phase (A) 0.1% DEA in n-hexane (B) EtOH:MeOH (50:50) (A:B; 70:30); flow Rate: 1.0 mL/min); Optical rotation [α]$^{19.99}$: −77.87 (c=0.25, CH$_2$Cl$_2$).

Example 188

Synthesis of N-(6-methoxy-5-(4-methyl-1H-imidazol-1-yl) pyridin-2-yl)-8-methyl-7-(3, 4, 5-trifluorophenyl)-7, 8-dihydro-6H-pyrimido [5, 4-b] [1, 4] oxazin-2-amine

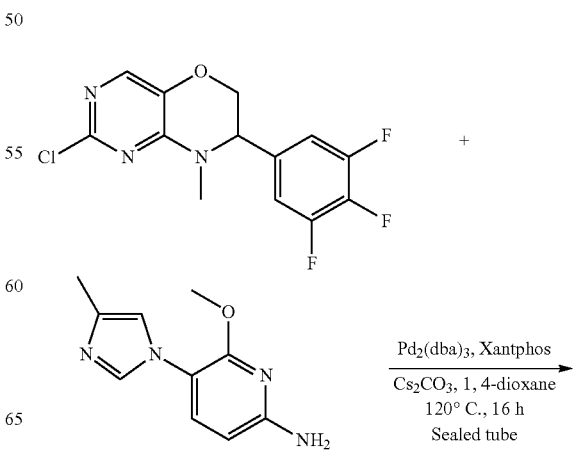

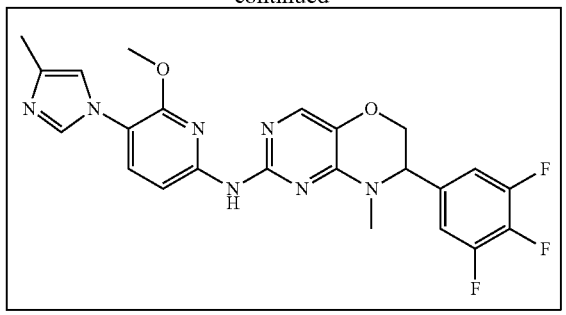

Synthesis of N-(6-methoxy-5-(4-methyl-1H-imidazol-1-yl) pyridin-2-yl)-8-methyl-7-(3, 4, 5-trifluorophenyl)-7, 8-dihydro-6H-pyrimido [5, 4-b] [1, 4] oxazin-2-amine To a dry vial was added a suspension of $Pd_2(dba)_3$ (36 mg, 0.04 mmol) and Xantphos (68 mg, 0.11 mmol) in 1, 4-dioxane (1.5 mL) at room temperature. The suspension was degassed with argon, heated to 120° C., and stirred for 3 min. A mixture of 2-chloro-8-methyl-7-(3, 4, 5-trifluorophenyl)-7, 8-dihydro-6H-pyrimido [5, 4-b] [1, 4] oxazine (250 mg, 0.79 mmol), 6-methoxy-5-(4-methyl-1H-imidazol-1-yl) pyridin-2-amine (178 mg, 0.87 mmol) and cesium carbonate (835 mg, 1.11 mmol) in 1, 4-dioxane (1.5 mL) was degassed and the catalyst premix was added. The resultant mixture was stirred at 120° C. for 16 h in a sealed tube. After consumption of the starting material (monitored by TLC and LCMS), the volatile components were concentrated in vacuo. The crude material was purified by column chromatography using 4% MeOH: $CH_2Cl_2$ to obtain 280 and further purified by preparative HPLC to afford (Ascentis C-18 (250×21.2 mm, 5 μm (50 mg loading; $CH_3CN$: 5 mM $NH_4OAc$ (0.1/80, 2/70, 8/50, 16/20, 24/10, 35/10)) to afford N-(6-methoxy-5-(4-methyl-1H-imidazol-1-yl) pyridin-2-yl)-8-methyl-7-(3, 4, 5-trifluorophenyl)-7, 8-dihydro-6H-pyrimido [5, 4-b] [1, 4] oxazin-2-amine (210 mg, 55%) as a pale yellow solid. LCMS: 484.1 (M+); (column; X-Select CSH C-18 (50×3.0 mm, 3.5 μm); RT 2.37 min. 0.05% Aq TFA: ACN; 0.80 mL/min); TLC: 5% MeOH/$CH_2Cl_2$ ($R_f$: 0.3).

Racemic compound of Example 188 was separated using a Chiralpak IA column (250×20 mm: 5 μm; (18 mg loading; 0.1% DEA in n-hexane: $CH_2Cl_2$:MeOH (50:50); (A:B: 80:20) as mobile phase) to provide the compound of Example 188A (Fraction I (−)) and the compound of Example 188B (Fraction II (+)).

Example 188A

Synthesis of (−)-N-(6-methoxy-5-(4-methyl-1H-imidazol-1-yl) pyridin-2-yl)-8-methyl-7-(3, 4, 5-trifluorophenyl)-7, 8-dihydro-6H-pyrimido [5, 4-b] [1, 4] oxazin-2-amine

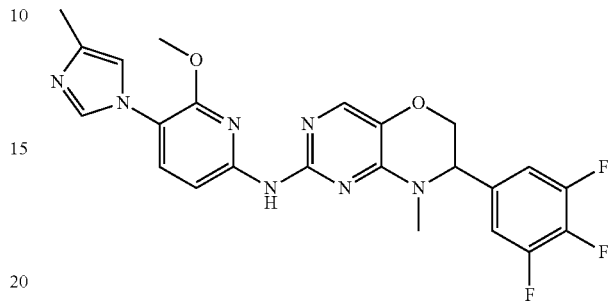

The compound of Example 188A was produced as described in Example 188. Analytical data for product Fraction I (−): $^1$H-NMR ($CD_3OD$, 400 MHz): δ 7.99-7.97 (m, 1H), 7.71 (s, 1H), 7.64-7.60 (m, 2H), 7.03-7.00 (m, 3H), 4.75-4.73 (m, 1H), 4.20 (s, 2H), 3.93 (s, 3H), 3.13 (s, 3H), 2.20 (s, 3H); Mass (ESI): 484.4 [M+1]; LCMS: 484.1 (M+1); (column; X-Select CSH C-18 (50×3.0 mm, 3.5 μm); RT 2.36 min. 0.05% Aq TFA: ACN; 0.80 mL/min); UPLC (column; Acquity UPLC BEH C-18, 2.1×50 mm, 1.7 μm); RT 1.68 min. ACN: 0.025% Aq TFA; 0.5 mL/min; Chiral HPLC: 97.9% RT=13.12 min (CHIRALPAK-IA (250×4.6 mm, 5 μm; mobile phase (A) 0.1% DEA in n-hexane (B) $CH_2Cl_2$:MeOH (50:50) (A:B: 80:20); flow Rate: 1.0 mL/min); Optical rotation $[\alpha]_D^{19.99}$: −106.08 (c=0.25, $CH_2Cl_2$).

Example 188B

Synthesis of (+)-N-(6-methoxy-5-(4-methyl-1H-imidazol-1-yl) pyridin-2-yl)-8-methyl-7-(3, 4, 5-trifluorophenyl)-7, 8-dihydro-6H-pyrimido [5, 4-b] [1, 4] oxazin-2-amine

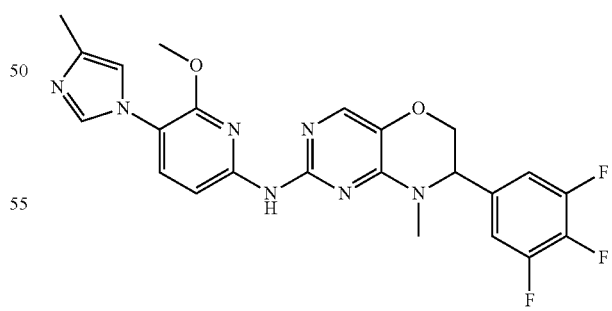

The compound of Example 188B was produced as described in Example 188. Analytical data for product Fraction II (+): $^1$H-NMR ($CD_3OD$, 400 MHz): δ 7.99-7.97 (m, 1H), 7.71 (s, 1H), 7.64-7.60 (m, 2H), 7.03-7.00 (m, 3H), 4.75-4.73 (m, 1H), 4.20 (s, 2H), 3.93 (s, 3H), 3.13 (s, 3H), 2.20 (s, 3H); Mass (ESI): 484.4 [M+1]; LCMS: 484.1 (M+1); (column; X-Select CSH C-18 (50×3.0 mm, 3.5 μm);

RT 2.35 min. 0.05% Aq TFA: ACN; 0.80 mL/min); UPLC (column; Acquity BEH C-18, 2.1×50 mm, 1.7 μm); RT 1.68 min. ACN: 0.025% Aq TFA; 0.5 mL/min; Chiral HPLC: 97.2% RT=14.77 min (CHIRALPAK-IA (250×4.6 mm, 5 μm; mobile phase (A) 0.1% DEA in n-hexane (B) $CH_2Cl_2$: MeOH (50:50) (A:B: 80:20); flow Rate: 1.0 mL/min); Optical rotation $[\alpha]_D^{19.99}$: +103.07 (c=0.25, $CH_2Cl_2$).

Example 189

Synthesis of 7-(3, 5-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

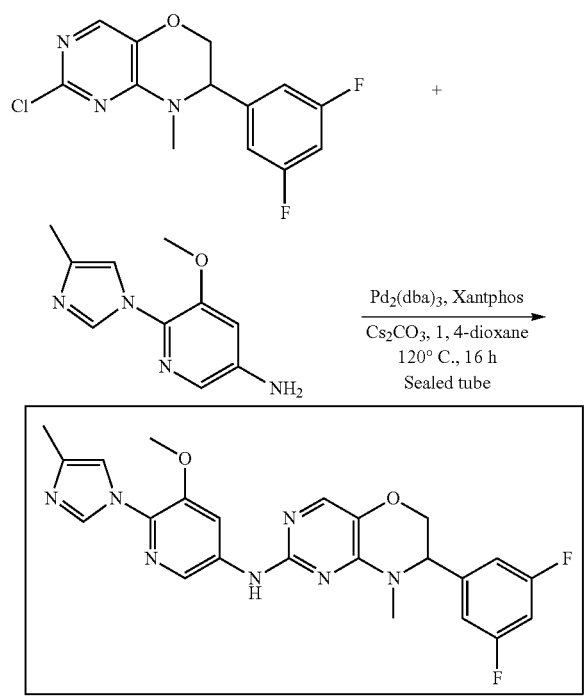

Synthesis of 7-(3, 5-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine To a dry vial was added a suspension of $Pd_2(dba)_3$ (31 mg, 0.03 mmol) and Xantphos (58 mg, 0.10 mmol) in 1, 4-dioxane (1 mL) at room temperature. The suspension was degassed with argon, heated to 120° C., and stirred for 3 min. A mixture of 2-chloro-7-(3, 5-difluorophenyl)-8-methyl-7, 8-dihydro-6H-pyrimido [5, 4-b] [1, 4] oxazine (200 mg, 0.67 mmol), 5-methoxy-6-(4-methyl-1H-imidazol-1-yl) pyridin-3-amine (274 mg, 1.34 mmol) and cesium carbonate (307 mg, 0.94 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (20 mL) and extracted with EtOAc (2×20 mL). The combined organic extracts were dried over sodium sulfate, filtered and concentrated in vacuo. The crude material was washed with $CH_2Cl_2$ (2 mL), n-pentane (2 mL) to afford 7-(3, 5-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine (90 mg, 29%) as an off-white solid. LCMS: 466.1 (M+1); (column; X-Select CSH C-18 (50×3.0 mm, 3.5 μm); RT 2.74 min. 0.05% Aq TFA: ACN; 0.80 mL/min); UPLC (column; Acquity BEH C-18, 2.1×50 mm, 1.7 μm); RT 1.63 min. ACN: 0.025% Aq TFA; 0.5 mL/min; TLC: 10% MeOH/$CH_2Cl_2$ ($R_f$: 0.4).

Racemic compound of Example 189 was separated using a Chiralpak IC column (250×4.6 mm: 5 μm; (15 mg loading; 0.1% DEA in n-hexane: $CH_2Cl_2$:MeOH (80:20); (A:B: 60:40) as mobile phase) to provide the compound of Example 189A (Fraction I (+)) and the compound of Example 189B (Fraction II (−)).

Example 189A

Synthesis of (+)-7-(3, 5-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

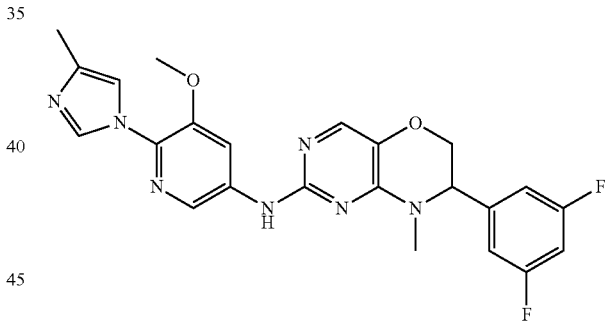

The compound of Example 189A was produced as described in Example 189. Analytical data for Fraction I (+): $^1$H-NMR (CD$_3$OD, 400 MHz): δ 8.30 (d, 2H), 8.10 (s, 1H), 7.61 (s, 1H), 7.35 (s, 1H), 6.92-6.81 (m, 3H), 4.80-4.78 (m, 1H), 4.22-4.20 (m, 2H), 3.97 (s, 3H), 3.18 (s, 3H), 2.22 (s, 3H); Mass (ESI): 466.4 [M+1]; LCMS: 466.3 (M+1); (column; X-Select CSH C-18 (50×3.0 mm, 3.5 μm); RT 3.29 min. 0.05% Aq TFA: ACN; 0.80 mL/min); HPLC (column; Eclipse XDB C-18, 150×4.6 mm, 5.0 μm); RT 10.40 min. ACN: 5 mM Aq NH$_4$OAc; 1.0 mL/min; Chiral HPLC: 98.7% RT=16.53 min (CHIRALPAK-IC (250×4.6 mm, 5 μm; mobile phase (A) 0.1% DEA in n-hexane (B) $CH_2Cl_2$: MeOH (80:20) (A;B; 60:40); flow Rate: 1.0 mL/min); Optical rotation $[\alpha]_D^{20.00}$: +115.39 (c=0.25, $CH_2Cl_2$).

Example 189B

Synthesis of (−)-7-(3, 5-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

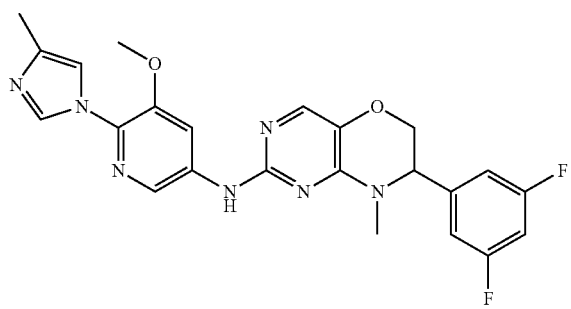 [SMILES: COc1cc(Nc2ncc3c(n2)N(C)C(c2cc(F)cc(F)c2)CO3)cnc1-n1cnc(C)c1]

The compound of Example 189B was produced as described in Example 189. Analytical data for Fraction II (−): $^1$H-NMR (CD$_3$OD, 400 MHz): δ 8.30-8.29 (m, 2H), 8.10 (s, 1H), 7.62 (s, 1H), 7.39 (s, 1H), 7.03 (t, 2H), 4.75-4.73 (m, 1H), 4.21-4.19 (m, 2H), 3.97 (s, 3H), 3.18 (s, 3H), 2.21 (s, 3H); Mass (ESI): 466.5 [M+1]; LCMS: 466.3 (M+1); (column; X-Select CSH C-18 (50×3.0 mm, 3.5 μm); RT 3.26 min. 0.05% Aq TFA: ACN; 0.80 mL/min); HPLC (column; Eclipse XDB C-18 150×4.6 mm, 5.0 μm); RT 10.36 min. ACN: 5 mM Aq NH$_4$OAc; 1.0 mL/min; Chiral HPLC: 97.6% RT=18.45 min (CHIRALPAK-IC (250×4.6 mm, 5 μm; mobile phase (A) 0.1% DEA in n-hexane (B) CH$_2$Cl$_2$:MeOH (80:20) (A:B; 60:40); flow Rate: 1.0 mL/min); Optical rotation [α]D$^{20.00}$: −113.07 (c=0.25, CH$_2$Cl$_2$).

Example 190

Synthesis of N-(6-methoxy-5-(4-methyl-1H-imidazol-1-yl) pyridin-2-yl)-7, 8-dimethyl-7, 8-dihydro-6H-pyrimido [5, 4-b] [1, 4] oxazin-2-amine

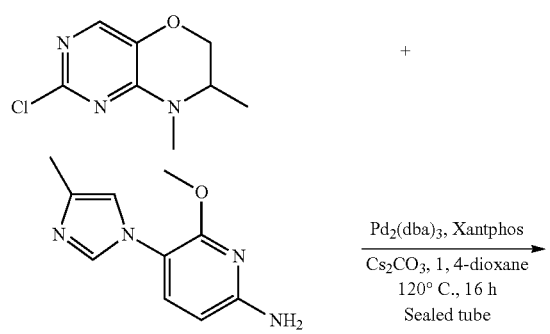

Pd$_2$(dba)$_3$, Xantphos
Cs$_2$CO$_3$, 1, 4-dioxane
120° C., 16 h
Sealed tube

-continued

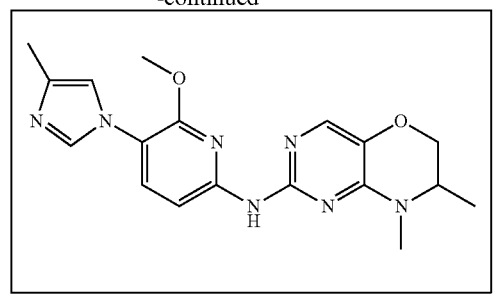

Synthesis of N-(6-methoxy-5-(4-methyl-1H-imidazol-1-yl) pyridin-2-yl)-7, 8-dimethyl-7, 8-dihydro-6H-pyrimido [5, 4-b] [1, 4] oxazin-2-amine To a dry vial was added a suspension of Pd$_2$(dba)$_3$ (57 mg, 0.06 mmol) and Xantphos (109 mg, 0.18 mmol) in 1, 4-dioxane (1 mL) at room temperature. The suspension was degassed with argon, heated to 120° C., and stirred for 3 min. A mixture of 2-chloro-7, 8-dimethyl-7, 8-dihydro-6H-pyrimido [5, 4-b] [1, 4] oxazine (250 mg, 1.25 mmol), 6-methoxy-5-(4-methyl-1H-imidazol-1-yl) pyridin-2-amine (512 mg, 2.51 mmol) and cesium carbonate (571 mg, 1.75 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction mixture was diluted with saturated sodium carbonate solution (20 mL) and extracted with EtOAc (2×20 mL). The combined organic extracts were dried over sodium sulfate, filtered and concentrated in vacuo. The crude material was purified by column chromatography using 3% MeOH:CH$_2$Cl$_2$ to afford N-(6-methoxy-5-(4-methyl-1H-imidazol-1-yl) pyridin-2-yl)-7, 8-dimethyl-7, 8-dihydro-6H-pyrimido [5, 4-b] [1, 4] oxazin-2-amine (200 mg, 43%) as an off-white solid. $^1$H-NMR (CD$_3$OD, 400 MHz): δ 7.93 (d, 1H), 7.72 (s, 1H), 7.60 (d, 1H), 7.53 (br s, 1H), 7.00 (s, 1H), 4.06-3.97 (m, 2H), 3.93 (s, 3H), 3.69-3.64 (m, 1H), 3.32-3.30 (m, 1H), 3.19 (s, 3H), 2.22 (s, 3H), 1.30 (d, 3H); Mass (ESI): 368.4 [M+1]; LCMS: 368 (M+1); (column; X-Select CSH C-18 (50×3.0 mm, 3.5 μm); RT 2.06 min. 0.05% Aq TFA: ACN; 0.80 mL/min); UPLC (column; Acquity BEH C-18, 50×2.1 mm, 1.7 μm); RT 1.29 min. ACN: 0.025% Aq TFA; 0.5 mL/min; TLC: 5% MeOH/CH$_2$Cl$_2$ (R$_f$: 0.3).

Example 191

Synthesis of N-(6-methoxy-5-(4-methyl-1H-imidazol-1-yl) pyridin-2-yl)-8-methyl-7-(2, 4, 5-trifluorophenyl)-7, 8-dihydro-6H-pyrimido [5, 4-b] [1, 4] oxazin-2-amine

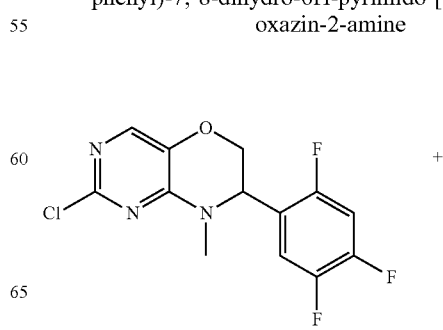

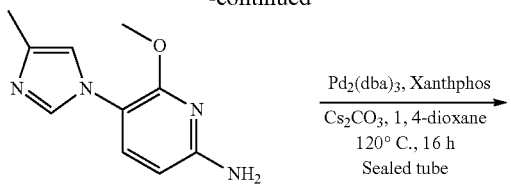

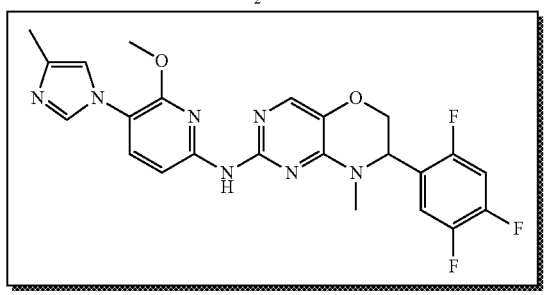

Synthesis of N-(6-methoxy-5-(4-methyl-1H-imidazol-1-yl) pyridin-2-yl)-8-methyl-7-(2, 4, 5-trifluorophenyl)-7, 8-dihydro-6H-pyrimido [5, 4-b] [1, 4] oxazin-2-amine To a dry vial was added a suspension of $Pd_2(dba)_3$ (36 mg, 0.04 mmol) and Xantphos (68 mg, 0.11 mmol) in 1, 4-dioxane (1.25 mL) at room temperature. The suspension was degassed with argon, heated to 120° C., and stirred for 3 min. A mixture of 2-chloro-8-methyl-7-(2, 4, 5-trifluorophenyl)-7, 8-dihydro-6H-pyrimido [5, 4-b] [1, 4] oxazine (250 mg, 0.79 mmol), 6-methoxy-5-(4-methyl-1H-imidazol-1-yl) pyridin-2-amine (323 mg, 1.58 mmol), cesium carbonate (361 mg, 1.11 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (50 mL) and extracted with $CH_2Cl_2$ (2×50 mL). The combined organic extracts were dried over sodium sulfate, filtered and concentrated in vacuo. The crude material was purified by column chromatography using 2-5% MeOH: $CH_2Cl_2$ to afford N-(6-methoxy-5-(4-methyl-1H-imidazol-1-yl) pyridin-2-yl)-8-methyl-7-(2, 4, 5-trifluorophenyl)-7, 8-dihydro-6H-pyrimido [5, 4-b] [1, 4] oxazin-2-amine (120 mg, 31%) as an off-white solid. $^1$H-NMR (CD$_3$OD, 400 MHz): δ 7.99 (d, 1H), 7.73 (s, 1H), 7.68-7.60 (m, 2H), 7.33-7.25 (m, 1H), 7.03-6.98 (m, 2H), 5.08-5.05 (m, 1H), 4.28-4.23 (m, 2H), 3.97 (s, 3H), 3.19 (s, 3H), 2.21 (s, 3H); Mass (ESI): 484.4 [M+1]; LCMS: 484.1 (M+1); (column; X-Select CSH C-18 (50×3.0 mm, 3.5 μm); RT 2.50 min 0.05% Aq TFA: ACN; 0.80 mL/min); UPLC (column; Acquity BEH C18, 50×2.1 mm, 1.7 μm); RT 1.65 min. ACN: 0.025% Aq TFA; 0.5 mL/min; TLC: 5% MeOH/CH$_2$Cl$_2$ (R$_f$: 0.4).

Example 192

Synthesis of 6-((7-(3, 5-difluorophenyl)-8-methyl-7, 8-dihydro-6H-pyrimido [5, 4-b] [1, 4] oxazin-2-yl) amino)-3-(4-methyl-1H-imidazol-1-yl) picolinonitrile

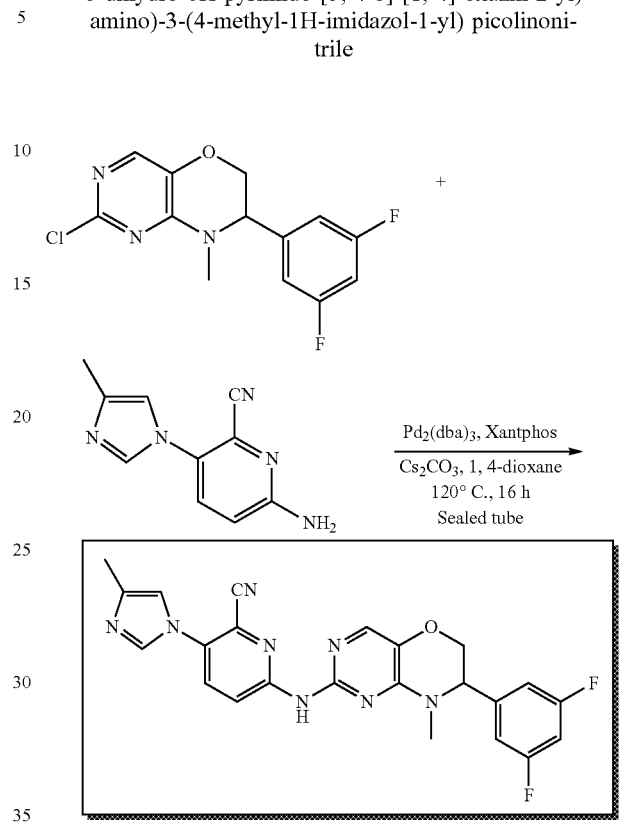

Synthesis of 6-((7-(3, 5-difluorophenyl)-8-methyl-7, 8-dihydro-6H-pyrimido [5, 4-b] [1, 4] oxazin-2-yl) amino)-3-(4-methyl-1H-imidazol-1-yl) picolinonitrile To a dry vial was added a suspension of $Pd_2(dba)_3$ (38 mg, 0.04 mmol) and Xantphos (73 mg, 0.12 mmol) in 1, 4-dioxane (2 mL) at room temperature. The suspension was degassed with argon, heated to 120° C., and stirred for 3 min. A mixture of 2-chloro-7-(3, 5-difluorophenyl)-8-methyl-7, 8-dihydro-6H-pyrimido [5, 4-b] [1, 4] oxazine (250 mg, 0.84 mmol), 6-amino-3-(4-methyl-1H-imidazol-1-yl) picolinonitrile (185 mg, 0.93 mmol) and cesium carbonate (384 mg, 1.18 mmol) in 1, 4-dioxane (2 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (20 mL) and extracted with $CH_2Cl_2$ (2×20 mL). The combined organic extracts were dried over sodium sulfate, filtered and concentrated in vacuo. The crude material was purified by column chromatography using 2-5% MeOH/$CH_2Cl_2$ to afford 6-((7-(3, 5-difluorophenyl)-8-methyl-7, 8-dihydro-6H-pyrimido [5, 4-b] [1, 4] oxazin-2-yl) amino)-3-(4-methyl-1H-imidazol-1-yl) picolinonitrile (130 mg, 33%) as an off-white solid. LCMS (purity): 484 (M+1); (column; X-select CSH C-18 50×3.0 mm, 3.5 μm); RT 2.38 min. ACN: 0.025% Aq TFA; 0.8 mL/min; TLC: 5% MeOH/CH$_2$Cl$_2$ (R$_f$: 0.3).

Racemic compound of Example 192 was separated using a Chiralpak ADH column (250×4.6 mm: 5 μm; (20 mg loading; 0.1% DEA in n-hexane: EtOH:MeOH (50:50); (A:B: 75:25) as mobile phase) to provide the compound of Example 192A (Fraction I (−)) and the compound of Example 192B (Fraction II (+)).

Example 192A

Synthesis of (−)-6-((7-(3, 5-difluorophenyl)-8-methyl-7, 8-dihydro-6H-pyrimido [5, 4-b] [1, 4] oxazin-2-yl) amino)-3-(4-methyl-1H-imidazol-1-yl) picolinonitrile

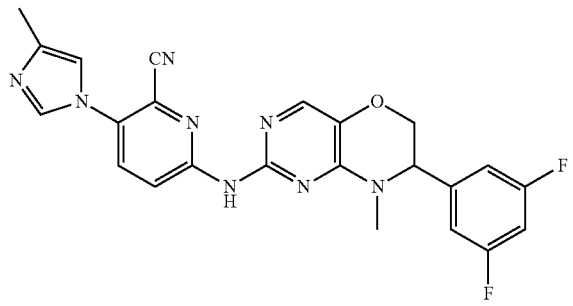 [SMILES: Cc1cn(-c2ccc(Nc3ncc4c(n3)N(C)C(c3cc(F)cc(F)c3)CO4)nc2C#N)cn1]

The compound of Example 192A was produced as described in Example 192. Analytical data for Fraction I (−): $^1$H-NMR (DMSO-$d_6$, 400 MHz): δ 10.09 (s, 1H), 8.65 (d, 1H), 8.00 (d, 1H), 7.97 (s, 1H), 7.70 (s, 1H), 7.30 (s, 1H), 7.22 (t, 1H), 7.00-6.97 (m, 2H), 4.90 (s, 1H), 4.30-4.27 (m, 1H), 4.21-4.18 (m, 1H), 3.08 (s, 3H), 2.15 (s, 3H); Mass (ESI): 461.6 [M+1]; LCMS: 461 (M+1); (column; X-Select CSH C-18 (50×3.0 mm, 3.5 μm); RT 2.32 min. 0.05% Aq TFA: ACN; 0.80 mL/min); HPLC (column; Eclipse XDB C-18, 150×4.6 mm, 5.0 μm); RT 10.38 min. ACN: 5 mM Aq NH$_4$OAc; 0.5 mL/min; Chiral HPLC: 98.6% RT=9.71 min (CHIRALPAK-IB (250×4.6 mm, 5 μm; mobile phase (A) 0.1% DEA in n-hexane (B) CH$_2$Cl$_2$:MeOH (80:20) (A:B; 70 30); flow Rate: 1.0 mL/min); Optical rotation $[α]_D^{20.02}$: −82.80 (c=0.25, CH$_2$Cl$_2$).

Example 192B

Synthesis of (+)-6-((7-(3, 5-difluorophenyl)-8-methyl-7, 8-dihydro-6H-pyrimido [5, 4-b] [1, 4] oxazin-2-yl) amino)-3-(4-methyl-1H-imidazol-1-yl) picolinonitrile

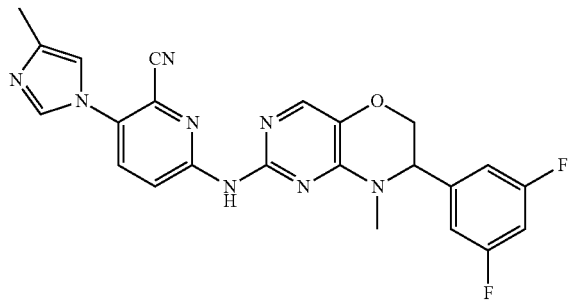 [SMILES: Cc1cn(-c2ccc(Nc3ncc4c(n3)N(C)C(c3cc(F)cc(F)c3)CO4)nc2C#N)cn1]

The compound of Example 192B was produced as described in Example 192. Analytical data for Fraction II (+): $^1$H-NMR (DMSO-$d_6$, 400 MHz): δ 10.09 (s, 1H), 8.65 (d, 1H), 8.00 (d, 1H), 7.97 (s, 1H), 7.70 (s, 1H), 7.30 (s, 1H), 7.22 (t, 1H), 7.00-6.97 (m, 2H), 4.90 (s, 1H), 4.30-4.27 (m, 1H), 4.21-4.18 (m, 1H), 3.08 (s, 3H), 2.15 (s, 3H); Mass (ESI): 461.5 [M+1]; LCMS: 461 (M+1); (column; X-Select CSH C-18 (50×3.0 mm, 3.5 μm); RT 2.32 min. 0.05% Aq TFA: ACN; 0.80 mL/min); HPLC (column; Eclipse XDB C-18, 150×4.6 mm, 5.0 μm); RT 10.39 min. ACN: 5 mM Aq NH$_4$OAc; 0.5 mL/min; Chiral HPLC: 99.4% RT=15.08 min (CHIRALPAK-IB (250×4.6 mm, 5 μm; mobile phase (A) 0.1% DEA in n-hexane (B) CH$_2$Cl$_2$:MeOH (80:20) (A:B; 70 30); flow Rate: 1.0 mL/min); Optical rotation $[α]_D^{20.00}$: +87.53 (c=0.25, CH$_2$Cl$_2$).

Example 193

Synthesis of N-(5-methoxy-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine

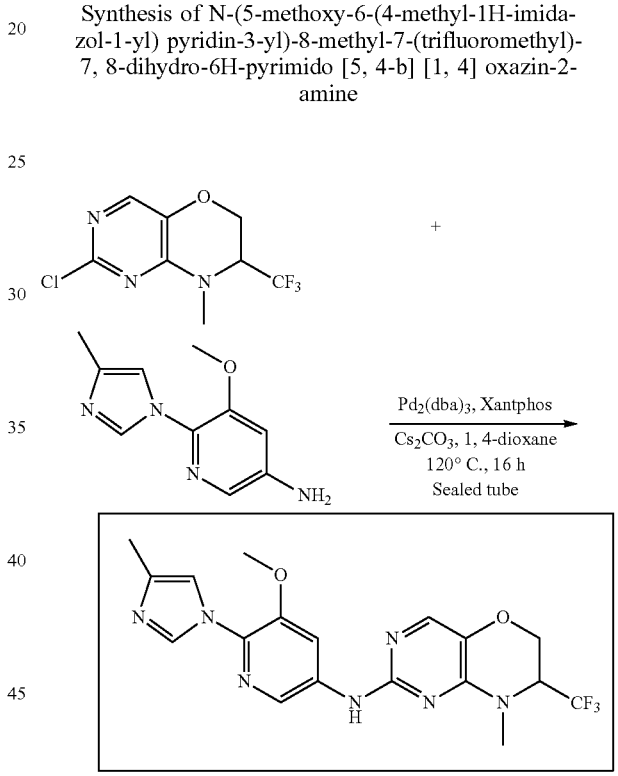

Synthesis of N-(5-methoxy-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine To a dry vial was added a suspension of Pd$_2$(dba)$_3$ (25 mg, 0.02 mmol) and Xantphos (47 mg, 0.08 mmol) in 1, 4-dioxane (3 mL) at room temperature. The suspension was degassed with argon, heated to 120° C., and stirred for 3 min. A mixture of 2-chloro-8-methyl-7-(trifluoromethyl)-7, 8-dihydro-6H-pyrimido [5, 4-b] [1, 4] oxazine (210 mg, 0.83 mmol), 5-methoxy-6-(4-methyl-1H-imidazol-1-yl) pyridin-3-amine (187 mg, 0.91 mmol) and cesium carbonate (378 mg, 1.16 mmol) in 1, 4-dioxane (3 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (20 mL) and extracted with EtOAc (2×20 mL). The combined organic extracts were dried over sodium sulfate, filtered and concentrated in vacuo. The crude material was purified by preparative HPLC (column (Ascentis C-18 (250×21.2 mm, 5 µm (75 mg loading; $CH_3CN$: 0.05% TFA (0.1/90, 15/70, 25/20, 30/10, 35/10)) to afford N-(5-methoxy-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine (120 mg, 34%) as an off-white solid. $^1$H-NMR ($CD_3OD$, 400 MHz): δ 8.29-8.27 (m, 2H), 8.14 (s, 1H), 7.70 (s, 1H), 7.40 (s, 1H), 4.60-4.57 (m, 1H), 4.40-4.34 (m, 1H), 4.03-4.00 (m, 1H), 3.99 (s, 3H), 3.37 (s, 3H), 2.21 (s, 3H); LCMS: 422 (M+1); (column; X-Select CSH C-18 (50×3.0 mm, 3.5 µm); RT 2.36 min. 0.05% Aq TFA: ACN; 0.80 mL/min); UPLC (column; Acquity BEH C-18, 50×2.1 mm, 1.7 µm); RT 1.53 min. ACN: 0.025% Aq TFA; 0.5 mL/min; TLC: 10% MeOH/ $CH_2Cl_2$ ($R_f$: 0.5).

Racemic compound of Example 193 was separated using a Chiralpak AD-H column (250×20 mm: 5 µm; (40 mg loading; 0.1% DEA in n-hexane (B) EtOH (A:B; 75:25 as mobile phase) to provide the compound of Example 193A (Fraction I (+)) and the compound of Example 193B (Fraction II (−)).

Example 193A

Synthesis of (+)-N-(5-methoxy-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine

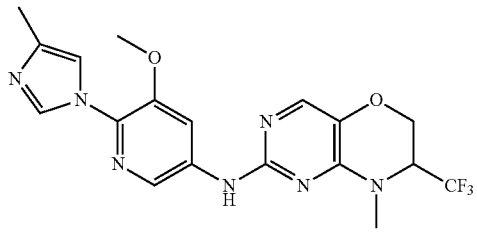 [SMILES: COc1cc(Nc2ncc3c(n2)N(C)C(C(F)(F)F)CO3)cnc1-n1cnc(C)c1]

The compound of Example 193A was produced as described in Example 193. Analytical data for Fraction I (+): $^1$H-NMR ($CD_3OD$, 400 MHz): δ 8.29-8.27 (m, 2H), 8.12 (s, 1H), 7.67 (s, 1H), 7.40 (s, 1H), 4.59-4.51 (m, 1H), 4.40-4.33 (m, 1H), 4.05-4.00 (m, 1H), 3.98 (s, 3H), 3.38 (s, 3H), 2.23 (s, 3H); Mass (ESI): 422.3 [M+1]; LCMS: 422 (M+1); (column; X-Select CSH C-18 (50×3.0 mm, 3.5 µm); RT 2.22 min. 0.05% Aq TFA: ACN; 0.80 mL/min); UPLC (column; Acquity BEH C-18, 50×2.1 mm, 1.7 µm); RT 1.55 min. ACN: 0.025% Aq TFA; 0.5 mL/min; Chiral HPLC: 100% RT=10.97 min (CHIRALPAK-AD-H (250×4.6 mm, 5 µm; mobile phase (A) 0.1% DEA in n-hexane (B) EtOH (A:B; 75:25); flow Rate: 1.0 mL/min); Optical rotation $[\alpha]_D^{20.02}$: +67.31 (c=0.25, $CH_2Cl_2$).

Example 193B

Synthesis of (−)-N-(5-methoxy-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine

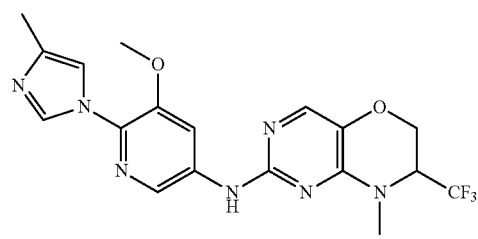 [SMILES: COc1cc(Nc2ncc3c(n2)N(C)C(C(F)(F)F)CO3)cnc1-n1cnc(C)c1]

The compound of Example 193B was produced as described in Example 193. Analytical data for Fraction II (−): $^1$H-NMR ($CD_3OD$, 400 MHz): δ 8.29-8.27 (m, 2H), 8.12 (s, 1H), 7.67 (s, 1H), 7.40-7.39 (m, 1H), 4.59-4.51 (m, 1H), 4.40-4.33 (m, 1H), 4.05-4.00 (m, 1H), 3.98 (s, 3H), 3.38 (s, 3H), 2.23 (s, 3H); Mass (ESI): 422.4 [M+1]; LCMS: 422 (M+1); (column; X-Select CSH C-18 (50×3.0 mm, 3.5 µm); RT 2.21 min. 0.05% Aq TFA: ACN; 0.80 mL/min); UPLC (column; Acquity BEH C-18, 50×2.1 mm, 1.7 µm); RT 1.55 min. ACN: 0.025% Aq TFA; 0.5 mL/min; Chiral HPLC: 99.7% RT=17.61 min (CHIRALPAK-AD-H (250×4.6 mm, 5 µm; mobile phase (A) 0.1% DEA in n-hexane (B) EtOH (A:B; 75:25); flow Rate: 1.0 mL/min); Optical rotation $[\alpha]_D^{20.00}$: −61.31 (c=0.25, $CH_2Cl_2$).

Example 194

Synthesis of 7, 8-dimethyl-N-(6-(4-methyl-1H-imidazol-1-yl) pyridin-3-yl)-7, 8-dihydro-6H-pyrimido [5, 4-b] [1, 4] oxazin-2-amine

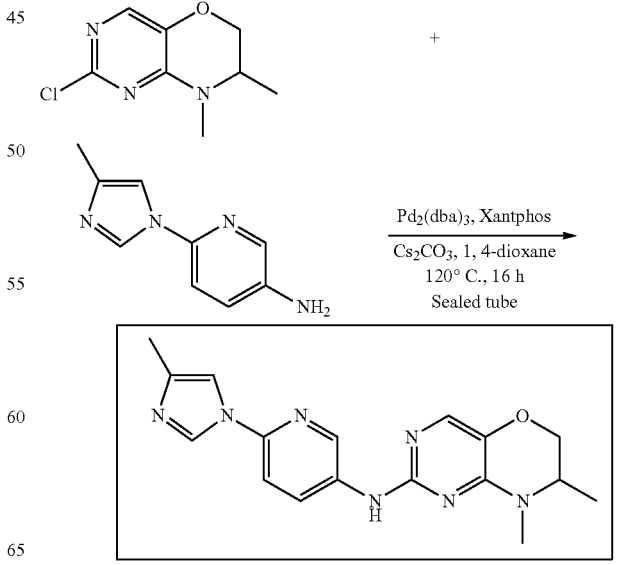

Synthesis of 7, 8-dimethyl-N-(6-(4-methyl-1H-imidazol-1-yl) pyridin-3-yl)-7, 8-dihydro-6H-pyrimido [5, 4-b] [1, 4] oxazin-2-amine To a dry vial was added a suspension of Pd$_2$(dba)$_3$ (58 mg, 0.05 mmol) and Xantphos (98 mg, 0.16 mmol) in 1, 4-dioxane (1 mL) at room temperature. The suspension was degassed with argon, heated to 120° C., and stirred for 3 min. A mixture of 2-chloro-7, 8-dimethyl-7, 8-dihydro-6H-pyrimido [5, 4-b] [1, 4] oxazine (225 mg, 1.13 mmol), 6-(4-methyl-1H-imidazol-1-yl) pyridin-3-amine (514 mg, 1.58 mmol) and cesium carbonate (515 mg, 1.58 mmol) in 1, 4-dioxane (1 mL) was degassed and the catalyst premix was added. The resultant mixture was stirred at 120° C. for 16 h in a sealed tube, After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 40% EtOAc:hexane to afford 7, 8-dimethyl-N-(6-(4-methyl-1H-imidazol-1-yl) pyridin-3-yl)-7, 8-dihydro-6H-pyrimido [5, 4-b] [1, 4] oxazin-2-amine (300 mg, 79%) as an off-white solid. LCMS: 337.9 (M+1); (column; X-Select CSH C-18 (50×3.0 mm, 3.5 μm); RT 1.79 min 0.05% Aq TFA: ACN; 0.80 mL/min); HPLC (column; Eclipse XDB C-18 150×4.6 mm, 5.0 μm); RT 8.77 min. ACN: 5 mM Aq NH$_4$OAc; 1.0 mL/min; TLC: 50% EtOAc: hexanes (R$_f$: 0.2).

Racemic compound of Example 194 was separated using a Chiralpak IA column (250×4.6 mm: 5 μm; (25 mg loading; 0.1% DEA in n-hexane: CH$_2$Cl$_2$:MeOH (80:20); (A:B: 60:40) as mobile phase) to provide the compound of Example 194A (Fraction I (+)) and the compound of Example 194B (Fraction II (−)).

Example 194A

Synthesis of (+)-7, 8-dimethyl-N-(6-(4-methyl-1H-imidazol-1-yl) pyridin-3-yl)-7, 8-dihydro-6H-pyrimido [5, 4-b] [1, 4] oxazin-2-amine

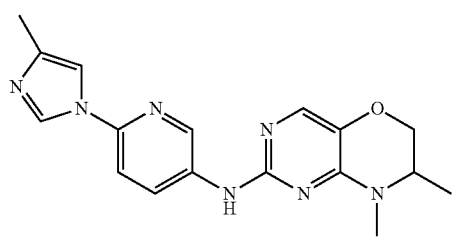 [SMILES: Cc1cn(-c2ccc(Nc3ncc4c(n3)N(C)C(C)CO4)cn2)cn1]

The compound of Example 194A was produced as described in Example 194. Analytical data for Fraction I (+): $^1$H-NMR (CD$_3$OD, 400 MHz): δ 8.71 (s, 1H), 8.30 (s, 1H), 8.28 (d, 1H), 7.50-7.47 (m, 3H), 4.01-4.00 (m, 2H), 3.69-3.66 (m, 1H), 3.19 (s, 3H), 2.25 (s, 3H), 1.30 (d, 3H); Mass (ESI): 337.9 [M+1]; LCMS: 337.9 (M+1); (column; X-Select CSH C-18 (50×3.0 mm, 3.5 μm); RT 1.86 min. 0.05% Aq TFA: ACN; 0.80 mL/min); HPLC (column; Eclipse XDB C-18, 150×4.6 mm, 5.0 μm); RT 8.81 min. ACN: 5 mM Aq NH$_4$OAc; 1.0 mL/min; Chiral HPLC: 98.0% RT=9.18 min (CHIRALPAK-IA (250×4.6 mm, 5 μm; mobile phase (A) 0.1% DEA in n-hexane (B) CH$_2$Cl$_2$: MeOH (80:20) (A:B; 60:40); flow Rate: 1.0 mL/min); Optical rotation [α]$_D^{20.01}$: +5.55 (c=0.25, CH$_2$Cl$_2$).

Example 194B

Synthesis of (−)-7, 8-dimethyl-N-(6-(4-methyl-1H-imidazol-1-yl) pyridin-3-yl)-7, 8-dihydro-6H-pyrimido [5, 4-b] [1, 4] oxazin-2-amine

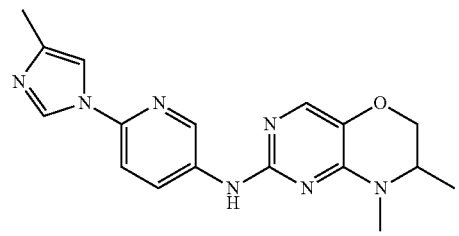 [SMILES: Cc1cn(-c2ccc(Nc3ncc4c(n3)N(C)C(C)CO4)cn2)cn1]

The compound of Example 194B was produced as described in Example 194. Analytical data for Fraction II (−): $^1$H-NMR (CD$_3$OD, 400 MHz): δ 8.71 (s, 1H), 8.30 (s, 1H), 8.28 (d, 1H), 7.50-7.47 (m, 3H), 4.01-4.00 (m, 2H), 3.69-3.66 (m, 1H), 3.19 (s, 3H), 2.25 (s, 3H), 1.30 (d, 3H); Mass (ESI): 337.9 [M+1]; LCMS: 337.9 (M+1); (column; X-Select CSH C-18 (50×3.0 mm, 3.5 μm); RT 1.88 min. 0.05% Aq TFA: ACN; 0.80 mL/min); HPLC (column; Eclipse XDB C-18, 150×4.6 mm, 5.0 μm); RT 8.80 min. ACN: 5 mM Aq NH$_4$OAc; 1.0 mL/min; Chiral HPLC: 97.7% RT=10.81 min (CHIRALPAK-IA (250×4.6 mm, 5 μm; mobile phase (A) 0.1% DEA in n-hexane (B) CH$_2$Cl$_2$: MeOH (80:20) (A:B; 60:40); flow Rate: 1.0 mL/min); Optical rotation [α]$_D^{19.99}$: −1.68 (c=0.25, CH$_2$Cl$_2$).

Example 195

Synthesis of N-(6-methoxy-5-(1-methyl-1H-pyrazol-4-yl) pyridin-2-yl)-7, 8-dimethyl-7, 8-dihydro-6H-pyrimido [5, 4-b] [1, 4] oxazin-2-amine

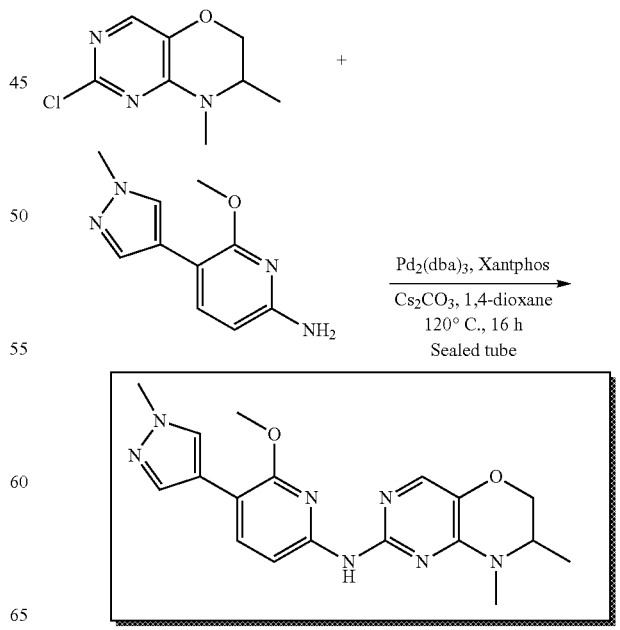

Synthesis of N-(6-methoxy-5-(1-methyl-1H-pyrazol-4-yl) pyridin-2-yl)-7, 8-dimethyl-7, 8-dihydro-6H-pyrimido [5, 4-b] [1, 4] oxazin-2-amine To a dry vial was added a suspension of Pd$_2$(dba)$_3$ (46 mg, 0.05 mmol) and Xantphos (87 mg, 0.15 mmol) in 1, 4-dioxane (1 mL) at room temperature. The suspension was degassed with argon, heated to 120° C., and stirred for 3 min. A mixture of 2-chloro-7, 8-dimethyl-7, 8-dihydro-6H-pyrimido [5, 4-b] [1, 4] oxazine (200 mg, 1.00 mmol), 6-methoxy-5-(1-methyl-1H-pyrazol-4-yl) pyridin-2-amine (410 mg, 2.01 mmol) and cesium carbonate (458 mg, 1.40 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (50 mL) and extracted with EtOAc (2×50 mL). The combined organic extracts were dried over sodium sulfate, filtered and concentrated in vacuo. The crude material was purified by column chromatography using 1% MeOH/CH$_2$Cl$_2$ to afford N-(6-methoxy-5-(1-methyl-1H-pyrazol-4-yl) pyridin-2-yl)-7, 8-dimethyl-7, 8-dihydro-6H-pyrimido [5, 4-b] [1, 4] oxazin-2-amine (130 mg, 35%) as an off-white solid. $^1$H-NMR (CD$_3$OD, 400 MHz): δ 7.95 (s, 1H), 7.84 (s, 3H), 7.50 (s, 1H), 4.05-4.01 (m, 2H), 4.00 (s, 3H), 3.91 (s, 3H), 3.72-3.67 (m, 1H), 3.22 (s, 3H), 1.32 (d, 3H); Mass (ESI): 368.4 [M+1]; LCMS: 368 (M+1); (column; X-Select CSH C-18 (50×3.0 mm, 3.5 μm); RT 2.43 min. 0.05% Aq TFA: ACN; 0.80 mL/min); UPLC (column; Acquity BEH C-18, 50×2.1 mm, 1.7 μm); RT 1.69 min. ACN: 0.025% Aq TFA; 1.0 mL/min; TLC: 10% MeOH/CH$_2$Cl$_2$ (R$_f$: 0.4).

Example 196

Synthesis of N-(3-fluoro-6-methoxy-5-(1-methyl-1H-pyrazol-4-yl) pyridin-2-yl)-8-methyl-7-(3, 4, 5-trifluorophenyl)-7, 8-dihydro-6H-pyrimido [5, 4-b] [1, 4] oxazin-2-amine

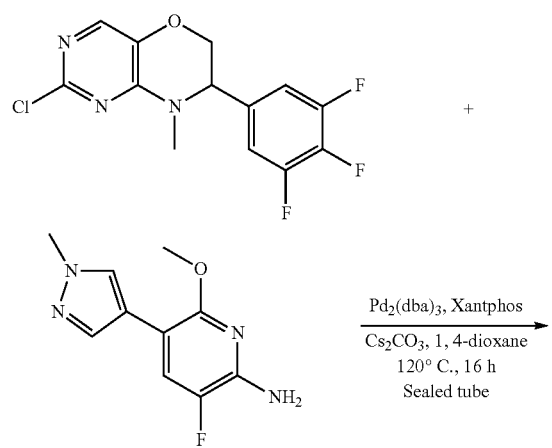

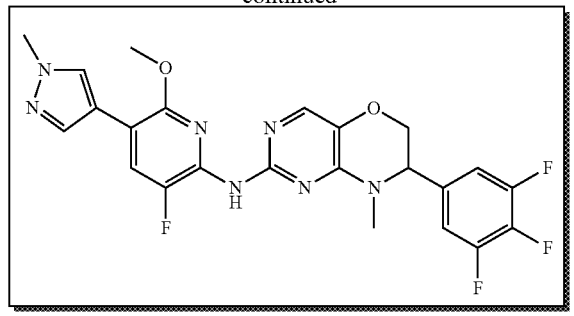

Synthesis of N-(3-fluoro-6-methoxy-5-(1-methyl-1H-pyrazol-4-yl) pyridin-2-yl)-8-methyl-7-(3, 4, 5-trifluorophenyl)-7, 8-dihydro-6H-pyrimido [5, 4-b] [1, 4] oxazin-2-amine To a dry vial was added a suspension of Pd$_2$(dba)$_3$ (29 mg, 0.03 mmol) and Xantphos (55 mg, 0.09 mmol) in 1, 4-dioxane (1 mL) at room temperature. The suspension was degassed with argon, heated to 120° C., and stirred for 3 min. A mixture of 2-chloro-8-methyl-7-(3, 4, 5-trifluorophenyl)-7, 8-dihydro-6H-pyrimido [5, 4-b] [1, 4] oxazine (200 mg, 0.63 mmol), 3-fluoro-6-methoxy-5-(1-methyl-1H-pyrazol-4-yl) pyridin-2-amine (281 mg, 1.26 mmol) and cesium carbonate (290 mg, 0.88 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (50 mL) and extracted with EtOAc (2×50 mL). The combined organic extracts were dried over sodium sulfate, filtered and concentrated in vacuo. The crude material was purified by column chromatography using 1% MeOH/CH$_2$Cl$_2$ to afford N-(3-fluoro-6-methoxy-5-(1-methyl-1H-pyrazol-4-yl) pyridin-2-yl)-8-methyl-7-(3, 4, 5-trifluorophenyl)-7, 8-dihydro-6H-pyrimido [5, 4-b] [1, 4] oxazin-2-amine (180 mg, 56%) as a yellow solid. $^1$H-NMR (CD$_3$OD, 400 MHz): δ 8.06 (s, 1H), 7.92 (s, 1H), 7.79 (d, 1H), 7.56 (s, 1H), 7.02 (t, 2H), 4.73-4.70 (m, 1H), 4.21 (s, 2H), 4.01 (s, 3H), 3.93 (s, 3H), 3.07 (s, 3H); Mass (ESI): 502.1 [M+1]; LCMS: 502.1 (M+1); (column; X-Select CSH C-18 (50×3.0 mm, 3.5 μm); RT 2.88 min. 0.05% Aq TFA: ACN; 0.80 mL/min); UPLC (column; Acquity BEH C-18, 50×2.1 mm, 1.7μ); RT 2.11 min. ACN: 0.025% Aq TFA; 0.5 mL/min; TLC: 10% MeOH/CH$_2$Cl$_2$ (R$_f$: 0.4).

Example 197

Synthesis of 7-(3, 5-difluorophenyl)-N-(3-fluoro-6-methoxy-5-(1-methyl-1H-pyrazol-4-yl) pyridin-2-yl)-8-methyl-7, 8-dihydro-6H-pyrimido [5, 4-b] [1, 4] oxazin-2-amine

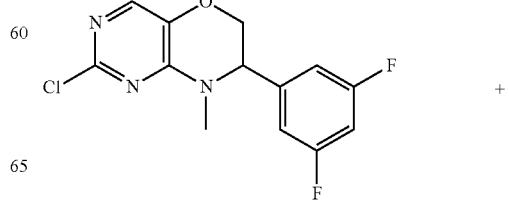

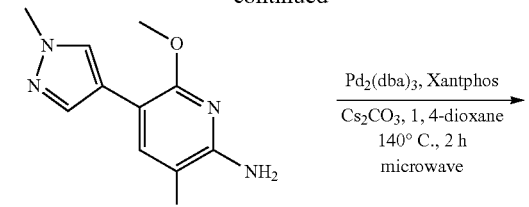

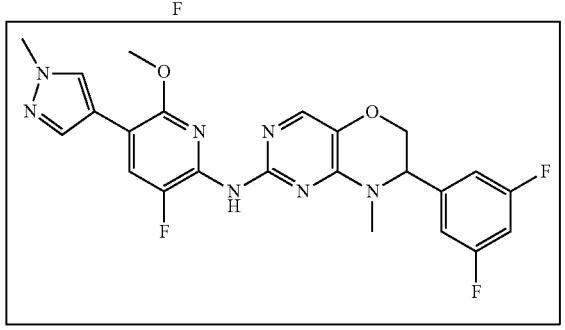

Synthesis of 7-(3, 5-difluorophenyl)-N-(3-fluoro-6-methoxy-5-(1-methyl-1H-pyrazol-4-yl) pyridin-2-yl)-8-methyl-7, 8-dihydro-6H-pyrimido [5, 4-b] [1, 4] oxazin-2-amine To a dry vial was added a suspension of Pd$_2$(dba)$_3$ (15 mg, 0.01 mmol) and Xantphos (29 mg, 0.05 mmol) in 1, 4-dioxane (1 mL) at room temperature. The suspension was degassed with argon, heated to 120° C., and stirred for 3 min. Then 2-chloro-7-(3, 5-difluorophenyl)-8-methyl-7, 8-dihydro-6H-pyrimido [5, 4-b] [1, 4] oxazine (100 mg, 0.33 mmol), 3-fluoro-6-methoxy-5-(1-methyl-1H-pyrazol-4-yl) pyridin-2-amine (149 mg, 0.67 mmol) and cesium carbonate (153 mg, 0.47 mmol) were added to the reaction mixture at room temperature. The reaction mixture was stirred at 140° C. for 2 h in a microwave. After consumption of the starting material (monitored by TLC), the reaction was diluted with water (20 mL) and extracted with EtOAc (2×20 mL). The combined organic extracts were dried over sodium sulfate, filtered and concentrated in vacuo. The crude material was purified by column chromatography using 5% MeOH: CH$_2$Cl$_2$ to afford 7-(3, 5-difluorophenyl)-N-(3-fluoro-6-methoxy-5-(1-methyl-1H-pyrazol-4-yl) pyridin-2-yl)-8-methyl-7, 8-dihydro-6H-pyrimido [5, 4-b] [1, 4] oxazin-2-amine (20 mg, 12%) as an off-white solid. $^1$H-NMR (CD$_3$OD, 400 MHz): δ 8.06 (s, 1H), 7.92 (s, 1H), 7.78 (d, 1H), 7.55 (s, 1H), 6.95-6.89 (m, 1H), 6.85 (dd, 2H), 4.74 (t, 1H), 4.23 (d, 2H), 4.01 (s, 3H), 3.92 (s, 3H), 3.07 (s, 3H); Mass (ESI): 484 [M+]; LCMS: 484 (M+1); (column; X-Select CSH C-18 (50×3.0 mm, 3.5 µm); RT 2.81 min. 0.05% Aq TFA: ACN; 0.80 mL/min); UPLC (column; Acquity BEH C-18, 50×2.1 mm, 1.7 µm); RT 2.01 min. ACN: 0.025% Aq TFA; 0.5 mL/min; TLC: 10% MeOH/CH$_2$Cl$_2$ (R$_f$: 0.3).

Example 198

Synthesis of N-(5-methoxy-6-(4-methyl-1H-imidazol-1-yl) pyridin-3-yl)-7, 7, 8-trimethyl-7, 8-dihydro-6H-pyrimido [5, 4-b] [1, 4] oxazin-2-amine

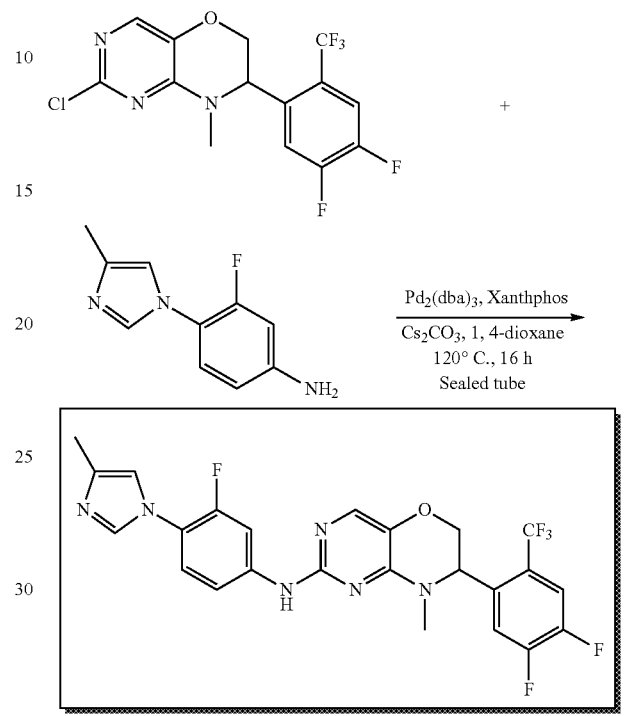

Synthesis of 7-(4, 5-difluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine To a dry vial was added a suspension of Pd$_2$(dba)$_3$ (22 mg, 0.02 mmol) and Xantphos (43 mg, 0.07 mmol) in 1, 4-dioxane (0.9 mL) at room temperature. The suspension was degassed with argon, heated to 120° C., and stirred for 3 min. A mixture of 2-chloro-7-(4, 5-difluoro-2-(trifluoromethyl) phenyl)-8-methyl-7, 8-dihydro-6H-pyrimido [5, 4-b] [1, 4] oxazine (180 mg, 0.49 mmol), 3-fluoro-4-(4-methyl-1H-imidazol-1-yl) aniline (188 mg, 0.98 mmol), cesium carbonate (225 mg, 0.69 mmol) in 1, 4-dioxane (0.9 mL) was degassed and the catalyst premix was added. The resultant mixture was stirred at 120° C. for 16 h in a sealed tube. After consumption of the starting material (monitored by TLC and LCMS), the reaction mixture was diluted with water (50 mL) and extracted with CH$_2$Cl$_2$ (2×30 mL). The combined organic extracts were dried over sodium sulfate, filtered and concentrated in vacuo. The crude material was purified by column chromatography using 5% MeOH: CH$_2$Cl$_2$ to afford 7-(4, 5-difluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine (110 mg, 43%) as an off-white solid. LCMS: 521.0 (M+1); (column; X-Select CSH C-18 (50×3.0 mm, 3.5 µm); RT 2.63 min 0.05% Aq TFA: ACN; 0.80 mL/min); UPLC (column; Acquity BEH C18 (50×2.1 mm, 1.7 µm); RT 1.93 min. ACN: 0.025% Aq TFA; 0.5 mL/min; TLC: 5% MeOH/CH$_2$Cl$_2$ (R$_f$: 0.3).

Racemic compound of Example 198 was separated using a Chiralpak IC column (250×4.6 mm: 5 μm; (50 mg loading; 0.1% DEA in n-hexane: CH₂Cl₂:MeOH (50:50); (A:B: 80:20) as mobile phase) to provide the compound of Example 198A (Fraction I (−)) and the compound of Example 198B (Fraction II (+)).

Example 198A

Synthesis of (−)-N-(5-methoxy-6-(4-methyl-1H-imidazol-1-yl) pyridin-3-yl)-7, 7, 8-trimethyl-7, 8-dihydro-6H-pyrimido [5, 4-b] [1, 4] oxazin-2-amine

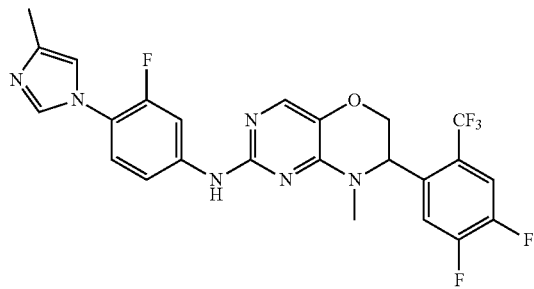 [SMILES: Cc1cn(-c2ccc(Nc3ncc4c(n3)N(C)C(c3cc(F)c(F)cc3C(F)(F)F)CO4)cc2F)cn1]

The compound of Example 198A was produced as described in Example 198. Analytical data for product Fraction I (−): $^1$H-NMR (DMSO-$d_6$, 400 MHz): δ 9.50 (s, 1H), 8.10-8.00 (m, 2H), 7.78-7.75 (m, 2H), 7.55-7.50 (m, 1H), 7.40 (t, 1H), 7.38-7.28 (m, 1H), 7.14 (s, 1H), 5.03-5.00 (m, 1H), 4.29-4.23 (m, 1H), 4.12-4.08 (m, 1H), 3.00 (s, 3H), 2.15 (s, 3H); Mass (ESI): 521.4 [M+1]; LCMS: 521.3 (M+1); (column; X-Select CSH C-18 (50×3.0 mm, 3.5 μm); RT 3.16 min. 0.05% Aq TFA: ACN; 0.80 mL/min); UPLC (column; Acquity BEH C-18, 50×2.1 mm, 1.7μ); RT 1.91 min. ACN: 0.025% Aq TFA; 0.5 mL/min; Chiral HPLC: 100% RT=11.57 min (CHIRALPAK-OJ-H (250×4.6 mm, 5 μm; mobile phase (A) 0.1% DEA in n-hexane (B) EtOH: MeOH (50:50) (A:B; 80:20); flow Rate: 1.0 mL/min); Optical rotation $[α]_D^{20.01}$: −67.44 (c=0.25, CH₂Cl₂).

Example 198B

Synthesis of (+)-N-(5-methoxy-6-(4-methyl-1H-imidazol-1-yl) pyridin-3-yl)-7, 7, 8-trimethyl-7, 8-dihydro-6H-pyrimido [5, 4-b] [1, 4] oxazin-2-amine

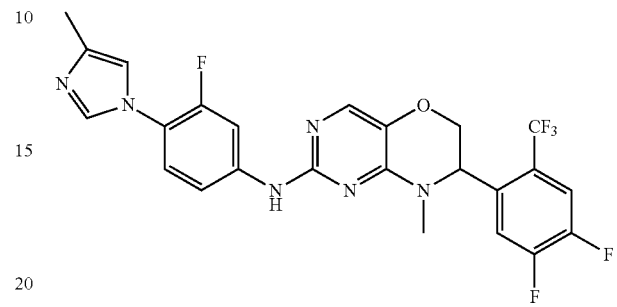

The compound of Example 198B was produced as described in Example 198. Analytical data for product Fraction II (+): $^1$H-NMR (DMSO-$d_6$, 400 MHz): δ 9.50 (s, 1H), 8.10-8.00 (m, 2H), 7.77-7.75 (m, 2H), 7.55-7.50 (m, 1H), 7.40 (t, 1H), 7.38-7.28 (m, 1H), 7.14 (s, 1H), 5.03-5.00 (m, 1H), 4.29-4.23 (m, 1H), 4.12-4.08 (m, 1H), 3.00 (s, 3H), 2.15 (s, 3H); Mass (ESI): 521.4 [M+1]; LCMS: 521.3 (M+1); (column; X-Select CSH C-18 (50×3.0 mm, 3.5 μm); RT 3.16 min. 0.05% Aq TFA: ACN; 0.80 mL/min); UPLC (column; Acquity BEH C-18, 50×2.1 mm, 1.7μ); RT 1.91 min. ACN: 0.025% Aq TFA; 0.5 mL/min; Chiral HPLC: 99.8% RT=17.65 min (CHIRALCEL-OJ-H (250×4.6 mm, 5 μm; mobile phase (A) 0.1% DEA in n-hexane (B) EtOH: MeOH (50:50) (A:B; 80:20); flow Rate: 1.0 mL/min); Optical rotation $[α]_D^{20.02}$: +73.88 (c=0.25, CH₂Cl₂).

Example 199

Synthesis of 7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

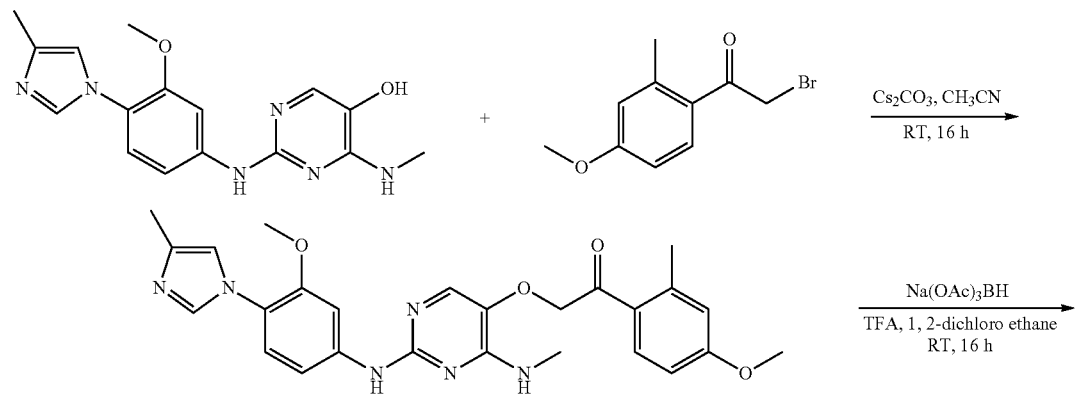

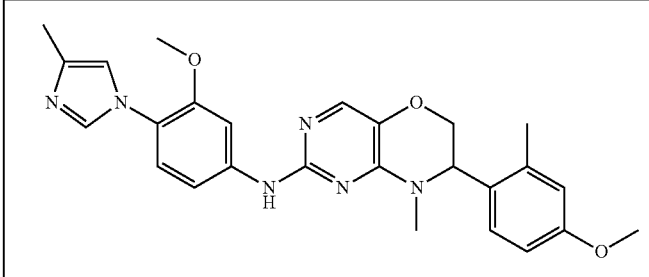

Synthesis of 1-(4-methoxy-2-methylphenyl)-2-((2-((3-methoxy-4-(4-methyl-1H-imidazol-1-yl) phenyl) amino)-4-(methylamino) pyrimidin-5-yl) oxy) ethan-1-one To a stirred solution of 2-((3-methoxy-4-(4-methyl-1H-imidazol-1-yl) phenyl) amino)-4-(methylamino) pyrimidin-5-ol (100 mg, 0.30 mmol) in CH$_3$CN (1 mL) under an argon atmosphere were added cesium carbonate (200 mg, 0.61 mmol) and 2-bromo-1-(4-methoxy-2-methylphenyl) ethan-1-one (90 mg, 0.33 mmol) at 0° C. The reaction mixture was stirred room temperature for 16 h. After consumption of the starting material (monitored by TLC), the reaction mixture was diluted with water (20 mL) and extracted with CH$_2$Cl$_2$ (2×20 mL). The combined organic extracts were dried over sodium sulfate, filtered and concentrated in vacuo to obtain 1-(4-methoxy-2-methylphenyl)-2-((2-((3-methoxy-4-(4-methyl-1H-imidazol-1-yl) phenyl) amino)-4-(methylamino) pyrimidin-5-yl) oxy) ethan-1-one (120 mg, crude) as a pale yellow solid. LCMS: 489.1 (M+1); (column; X-Select CSH C-18 (50×3.0 mm, 3.5 μm); RT 2.49 min. 0.05% Aq TFA: ACN; 0.80 mL/min); TLC: 5% MeOH/CH$_2$Cl$_2$ (R$_f$: 0.4).

Synthesis of 7-(4-methoxy-2-methylphenyl)-N-(3-methoxy-4-(4-methyl-1H-imidazol-1-yl)phenyl)-8-methyl-7,8-dihydro-6 h-pyrimido[5,4-b][1,4]oxazin-2-amine To a stirred solution of 1-(4-methoxy-2-methylphenyl)-2-((2-((3-methoxy-4-(4-methyl-1H-imidazol-1-yl) phenyl) amino)-4-(methylamino) pyrimidin-5-yl) oxy) ethan-1-one (100 mg, 0.30 mmol) in 1, 2-dichloroethane (1 mL) under an argon atmosphere were added trifluoroacetic acid (30 mg, 0.26 mmol) and sodium triacetoxyborohydride (118 mg, 0.55 mmol) and stirred at room temperature for 16 h. After consumption of the starting material (monitored by TLC), the reaction mixture was quenched with a 1 N sodium hydroxide solution (50 mL) and extracted with CH$_2$Cl$_2$ (2×50 mL). The combined organic extracts were dried over sodium sulfate, filtered and concentrated in vacuo. The crude material was purified by column chromatography using 3% MeOH: CH$_2$Cl$_2$ to afford 7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (13 mg, 10%) as an off-white solid. $^1$H-NMR (CD$_3$OD, 400 MHz): δ 7.77 (s, 1H), 7.69 (s, 1H), 7.55 (s, 1H), 7.25-7.15 (m, 2H), 6.99 (s, 1H), 6.93 (d, 1H), 6.81 (s, 1H), 6.79-6.75 (m, 1H), 4.93-4.90 (m, 1H), 4.22-4.20 (m, 1H), 4.10-4.08 (m, 1H), 3.85 (s, 3H), 3.79 (s, 3H), 3.09 (s, 3H), 2.40 (s, 3H), 2.22 (s, 3H); Mass (ESI): 473 [M+1]; LCMS: 473 (M+1); (column; X-Select CSH C-18 (50×3.0 mm, 3.5 μm); RT 2.34 min. 0.05% Aq TFA: ACN; 0.80 mL/min); UPLC (column; Acquity UPLC BEH C-18, 2.1×50 mm, 1.7 μm); RT 1.66 min. ACN: 0.025% Aq TFA; 0.5 mL/min; TLC: 5% MeOH/CH$_2$Cl$_2$ (R$_f$: 0.4).

Racemic compound of Example 199 was separated using a Chiralpak-IC column (250×20 mm, 5 μm) (20 mg loading; 0.1% DEA in n-hexane; EtOH:MeOH (50:50) (A:B; 70:30); 0.1% DEA in n-hexane: CH$_2$Cl$_2$:MeOH (50:50) (A:B: 75:25) as mobile phase) to provide the compound of Example 199A (Fraction I (+)) and the compound of Example 199B (Fraction II (−)).

Example 199A

Synthesis of (+)-7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

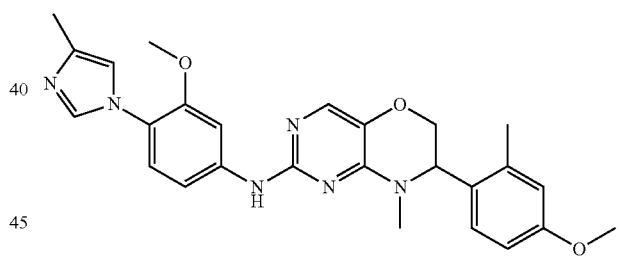

The compound of Example 199A was produced as described in Example 199. Analytical data for product Fraction I (+): $^1$H-NMR (CD$_3$OD, 400 MHz): δ 7.77 (s, 1H), 7.69 (s, 1H), 7.56 (s, 1H), 7.23-7.21 (m, 1H), 7.19-7.16 (m, 1H), 6.99 (s, 1H), 6.93 (d, 1H), 6.81 (s, 1H), 6.79-6.75 (m, 1H), 4.93-4.90 (m, 1H), 4.22-4.20 (m, 1H), 4.10-4.08 (m, 1H), 3.87 (s, 3H), 3.79 (s, 3H), 3.09 (s, 3H), 2.40 (s, 3H), 2.22 (s, 3H); Mass (ESI): 473.6 [M+1]; LCMS: 473.1 (M+1); (column; X-Select CSH C-18 (50×3.0 mm, 3.5 μm); RT 2.39 min. 0.05% Aq TFA: ACN; 0.80 ml/min); UPLC (column; Acquity BEH C-18, 2.1×50 mm, 1.7 μm); RT 1.70 min. ACN: 0.025% Aq TFA; 0.5 ml/min; Chiral HPLC: 97.2% RT=15.65 min (Chiralpak-IC (250×4.6 mm, 5 μm; mobile phase (A) 0.1% DEA in n-hexane (B) CH$_2$Cl$_2$: MeOH (50:50) (A:B; 75:25); flow Rate: 1.0 mL/min); Optical rotation $[α]_D^{20.00}$: +177.95 (c=0.25, CH$_2$Cl$_2$).

Example 199B

Synthesis of (−)-7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

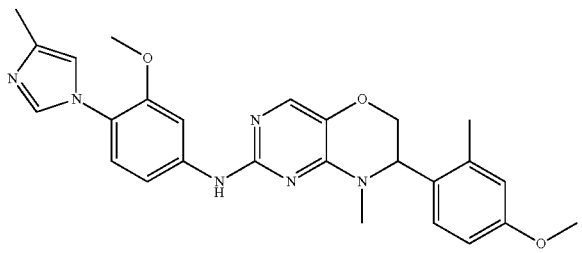

The compound of Example 199B was produced as described in Example 199. Analytical data for product Fraction II (−): $^1$H-NMR (CD$_3$OD, 400 MHz): δ 7.77 (s, 1H), 7.69 (s, 1H), 7.56 (s, 1H), 7.23-7.21 (m, 1H), 7.19-7.16 (m, 1H), 6.99 (s, 1H), 6.93 (d, 1H), 6.81 (s, 1H), 6.79-6.75 (m, 1H), 4.93-4.90 (m, 1H), 4.22-4.20 (m, 1H), 4.10-4.08 (m, 1H), 3.87 (s, 3H), 3.79 (s, 3H), 3.09 (s, 3H), 2.40 (s, 3H), 2.22 (s, 3H); Mass (ESI): 473.6 [M+1]; LCMS: 473.1 (M+1); (column; X-Select CSH C-18 (50×3.0 mm, 3.5 μm); RT 2.39 min. 0.05% Aq TFA: ACN; 0.80 ml/min); UPLC (column; Acquity BEH C-18, 2.1×50 mm, 1.7 μm); RT 1.70 min. ACN: 0.025% Aq TFA; 0.5 ml/min; Chiral HPLC: 99.0% RT=17.20 min (Chiralpak-IC (250×4.6 mm, 5 μm; mobile phase (A) 0.1% DEA in n-hexane (B) CH$_2$Cl$_2$: MeOH (50:50) (A:B; 75:25); flow Rate: 1.0 mL/min); Optical rotation [α]$_D^{19.99}$: −161.82 (c=0.25, CH$_2$Cl$_2$).

Example 200

Synthesis of (S)—N-(3-methoxy-4-(4-methyl-1H-imidazol-1-yl) phenyl)-8-methyl-7-(phenoxymethyl)-7, 8-dihydro-6H-pyrimido [5, 4-b] [1, 4] oxazin-2-amine

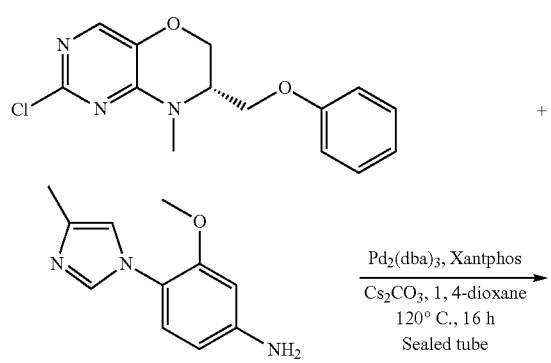

-continued

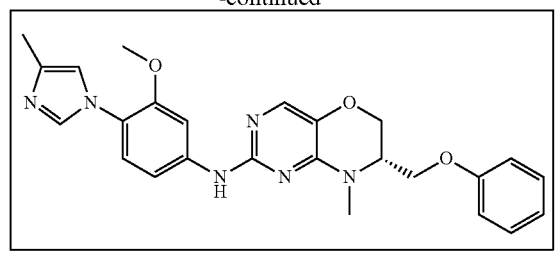

Synthesis of (S)—N-(3-methoxy-4-(4-methyl-1H-imidazol-1-yl) phenyl)-8-methyl-7-(phenoxymethyl)-7, 8-dihydro-6H-pyrimido [5, 4-b] [1, 4] oxazin-2-amine To a dry vial was added a suspension of Pd$_2$(dba)$_3$ (16 mg, 0.01 mmol) and Xantphos (30 mg, 0.05 mmol) in 1, 4-dioxane (1.25 mL) at room temperature. The suspension was degassed with argon, heated to 120° C., and stirred for 3 min. A mixture of (S)-2-chloro-8-methyl-7-(phenoxymethyl)-7, 8-dihydro-6H-pyrimido [5, 4-b] [1, 4] oxazine (100 mg, 0.34 mmol), 3-methoxy-4-(4-methyl-1H-imidazol-1-yl) aniline (140 mg, 0.68 mmol), cesium carbonate (335 mg, 1.02 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the reaction mixture was diluted with water (50 mL) and extracted with CH$_2$Cl$_2$ (2×50 mL). The combined organic extracts were dried over sodium sulfate, filtered and concentrated in vacuo. The crude material was purified by column chromatography using 0-5% MeOH: CH$_2$Cl$_2$ to afford (S)—N-(3-methoxy-4-(4-methyl-1H-imidazol-1-yl) phenyl)-8-methyl-7-(phenoxymethyl)-7, 8-dihydro-6H-pyrimido [5, 4-b] [1, 4] oxazin-2-amine (50 mg, 32%) as an off-white solid. $^1$H-NMR (DMSO-d$_6$, 400 MHz): δ 9.11 (s, 1H), 7.82 (s, 1H), 7.60 (s, 2H), 7.30-7.27 (m, 3H), 7.15-7.11 (m, 1H), 7.00-6.90 (m, 4H), 4.39 (d, 1H), 4.20-4.16 (m, 1H), 4.13-4.09 (m, 1H), 4.00-3.95 (m, 2H), 3.78 (s, 3H), 3.28 (s, 3H), 2.11 (s, 3H); Mass (ESI): 459.5 [M+1]; LCMS: 459 (M+1); (column; X-Select CSH C-18 (50×3.0 mm, 3.5 μm); RT 2.41 min. 0.05% Aq TFA: ACN; 0.80 mL/min); UPLC (column; Acquity BEH C18, 50×2.1 mm, 1.7 μm); RT 1.70 min. ACN: 0.025% Aq TFA; 0.5 mL/min; Chiral HPLC: 100% RT=14.41 min (CHIRALPAK-IA (250×4.6 mm, 5 μm; mobile phase (A) 0.1% DEA in n-hexane (B) EtOH (A:B: 70:30); flow Rate: 1.0 mL/min); Optical rotation [α]$_D^{20.01}$: +129.40 (c=0.25, CH$_2$Cl$_2$); TLC: 5% MeOH/CH$_2$Cl$_2$ (R$_f$: 0.4).

Example 201

Synthesis of (R)—N-(3-methoxy-4-(4-methyl-1H-imidazol-1-yl) phenyl)-8-methyl-7-(phenoxymethyl)-7, 8-dihydro-6H-pyrimido [5, 4-b] [1, 4] oxazin-2-amine

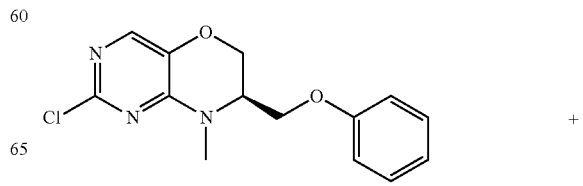

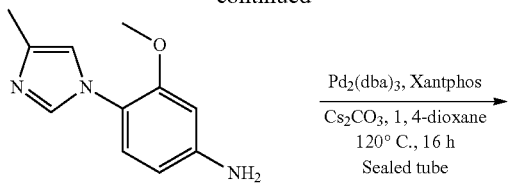

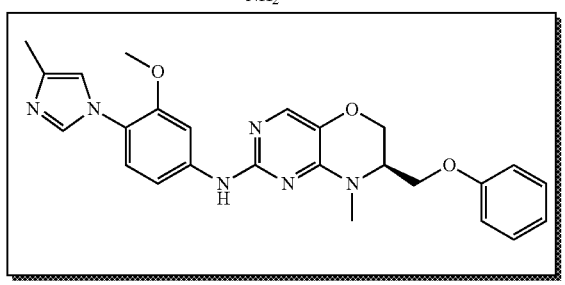

Synthesis of (R)—N-(3-methoxy-4-(4-methyl-1H-imidazol-1-yl) phenyl)-8-methyl-7-(phenoxymethyl)-7, 8-dihydro-6H-pyrimido [5, 4-b] [1, 4] oxazin-2-amine To a dry vial was added a suspension of $Pd_2(dba)_3$ (12 mg, 0.01 mmol) and Xantphos (23 mg, 0.04 mmol) in 1, 4-dioxane (0.4 mL) at room temperature. The suspension was degassed with argon, heated to 120° C., and stirred for 3 min. A mixture of (R)-2-chloro-8-methyl-7-(phenoxymethyl)-7, 8-dihydro-6H-pyrimido [5, 4-b] [1, 4] oxazine (80 mg, 0.27 mmol), 3-methoxy-4-(4-methyl-1H-imidazol-1-yl) aniline (44 mg, 0.21 mmol) and cesium carbonate (125 mg, 0.38 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the volatile components were concentrated in vacuo. The crude material was purified by column chromatography using 3% MeOH: $CH_2Cl_2$ to afford (R)—N-(3-methoxy-4-(4-methyl-1H-imidazol-1-yl) phenyl)-8-methyl-7-(phenoxymethyl)-7, 8-dihydro-6H-pyrimido [5, 4-b] [1, 4] oxazin-2-amine (43 mg, 27%) as an off-white solid. $^1$H-NMR (DMSO-$d_6$, 400 MHz): δ 9.10 (s, 1H), 7.85 (s, 1H), 7.61 (s, 2H), 7.31-7.29 (m, 3H), 7.16-7.14 (m, 1H), 7.00-6.95 (m, 4H), 4.40 (d, 1H), 4.20-4.15 (m, 1H), 4.13-4.10 (m, 1H), 4.00-3.95 (m, 2H), 3.78 (s, 3H), 3.30 (s, 3H), 2.13 (s, 3H); Mass (ESI): 459.5 [M+1]; LCMS: 459 (M+1); (column; X-Select CSH C-18 (50×3.0 mm, 3.5 μm); RT 2.42 min 0.05% Aq TFA: ACN; 0.80 mL/min); UPLC (column; Acquity BEH C-18 50×2.1 mm, 1.7 μm); RT 1.70 min. ACN: 0.025% Aq TFA; 0.5 mL/min; Chiral HPLC: 98.8% RT=13.10 min (CHIRALPAK-IA (250×4.6 mm, 5 μm; mobile phase (A) 0.1% DEA in n-hexane (B) EtOH (A:B; 70:30); flow Rate: 1.0 mL/min); Optical rotation $[α]_D^{20.01}$: −111.64 (c=0.25, $CH_2Cl_2$); TLC: 5% MeOH/$CH_2Cl_2$ ($R_f$: 0.3).

Example 202

Synthesis of N-(4-(4-chloro-1H-imidazol-1-yl)-3-methoxyphenyl)-7, 8-dimethyl-7, 8-dihydro-6H-pyrimido [5, 4-b] [1, 4] oxazin-2-amine

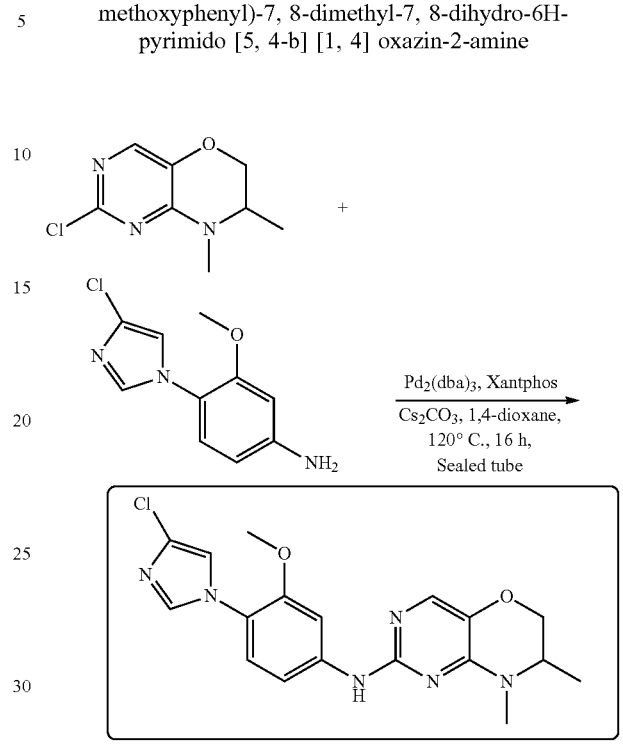

Synthesis of N-(4-(4-chloro-1H-imidazol-1-yl)-3-methoxyphenyl)-7, 8-dimethyl-7, 8-dihydro-6H-pyrimido [5, 4-b] [1, 4] oxazin-2-amine To a dry vial was added a suspension of $Pd_2(dba)_3$ (34 mg, 0.04 mmol) and Xantphos (43 mg, 0.07 mmol) in 1, 4-dioxane (0.75 mL) at room temperature. The suspension was degassed with argon, heated to 120° C., and stirred for 3 min. A mixture of 4-(4-chloro-1H-imidazol-1-yl)-3-methoxyaniline (150 mg, 0.75 mmol), 3-methoxy-4-(4-methyl-1H-imidazol-1-yl) aniline (336 mg, 0.15 mmol) and cesium carbonate (342 mg, 1.05 mmol) in 1, 4-dioxane (0.75 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 3% MeOH: $CH_2Cl_2$ to afford N-(4-(4-chloro-1H-imidazol-1-yl)-3-methoxyphenyl)-7, 8-dimethyl-7, 8-dihydro-6H-pyrimido [5, 4-b] [1, 4] oxazin-2-amine (130 mg, 45%) as an off-white solid. LCMS: 387 (M+1); (column; X-Select CSH C-18 (50×3.0 mm, 3.5 μm); RT 2.57 min 0.05% Aq TFA: ACN; 0.80 mL/min); TLC: 50% EtOAc:hexanes ($R_f$: 0.2).

Racemic compound of Example 202 was separated using a Chiralpak IA column (250×20 mm: 5 μm; (25 mg loading; 0.1% DEA in n-hexane: IPA (A:B: 75:25) as mobile phase) to provide the compound of Example 202A (Fraction I (−)) and the compound of Example 202B (Fraction II (+)).

Example 202A

Synthesis of (−)-N-(4-(4-chloro-1H-imidazol-1-yl)-3-methoxyphenyl)-7, 8-dimethyl-7, 8-dihydro-6H-pyrimido [5, 4-b] [1, 4] oxazin-2-amine

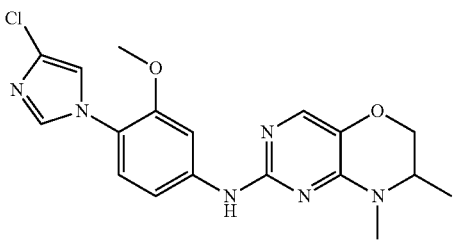 [SMILES: COc1cc(Nc2ncc3c(n2)N(C)C(C)CO3)ccc1-n1cnc(Cl)c1]

The compound of Example 202A was produced as described in Example 202. Analytical data for product Fraction I (−): $^1$H-NMR (CD$_3$OD, 400 MHz): δ 7.78 (s, 1H), 7.70 (s, 1H), 7.50 (s, 1H), 7.23 (s, 1H), 7.20 (s, 2H), 4.01-3.99 (m, 2H), 3.86 (s, 3H), 3.69-3.62 (m, 1H), 3.20 (s, 3H), 1.31 (d, 3H); Mass (ESI): 387.7 [M+1]; LCMS: 386.9 (M+1); (column; X-Select CSH C-18 (50×3.0 mm, 3.5 μm); RT 2.57 min. 0.05% Aq TFA: ACN; 0.80 mL/min); UPLC (column; Acquity BEH C-18, 50×2.1 mm, 1.7μ); RT 1.74 min. ACN: 0.025% Aq TFA; 0.5 mL/min; Chiral HPLC: 100% RT=15.50 min (CHIRALPAK-IA (250×4.6 mm, 5 μm; mobile phase (A) 0.1% DEA in n-hexane (B) IPA (A:B; 75:25); flow Rate: 1.0 mL/min); Optical rotation $[α]_D^{19.98}$: −1.56 (c=0.25, CH$_2$Cl$_2$).

Example 202B

Synthesis of (+)-N-(4-(4-chloro-1H-imidazol-1-yl)-3-methoxyphenyl)-7, 8-dimethyl-7, 8-dihydro-6H-pyrimido [5, 4-b] [1, 4] oxazin-2-amine

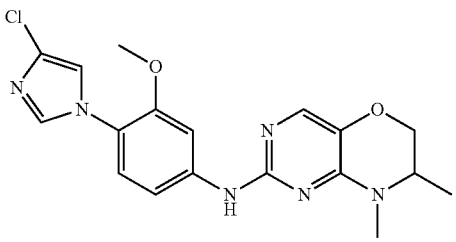 [SMILES: COc1cc(Nc2ncc3c(n2)N(C)C(C)CO3)ccc1-n1cnc(Cl)c1]

The compound of Example 202B was produced as described in Example 202. Analytical data for product Fraction II (+): $^1$H-NMR (CD$_3$OD, 400 MHz): δ 7.78 (s, 1H), 7.70 (s, 1H), 7.50 (s, 1H), 7.23 (s, 1H), 7.20 (s, 2H), 4.01-3.99 (m, 2H), 3.86 (s, 3H), 3.69-3.62 (m, 1H), 3.20 (s, 3H), 1.31 (d, 3H); Mass (ESI): 387.7 [M+1]; LCMS: 387 (M+1); (column; X-Select CSH C-18 (50×3.0 mm, 3.5 μm); RT 2.57 min. 0.05% Aq TFA: ACN; 0.80 mL/min); UPLC (column; Acquity BEH C-18, 50×2.1 mm, 1.7μ); RT 1.74 min. ACN: 0.025% Aq TFA; 0.5 mL/min; Chiral HPLC: 99.3% RT=19.89 min (CHIRALPAK-IA (250×4.6 mm, 5 μm; mobile phase (A) 0.1% DEA in n-hexane (B) IPA (A:B; 75:25); flow Rate: 1.0 mL/min); Optical rotation $[α]_D^{19.96}$: +3.69 (c=0.25, CH$_2$Cl$_2$).

Example 203

Synthesis of 5-((7-(3, 5-difluorophenyl)-8-methyl-7, 8-dihydro-6H-pyrimido [5, 4-b] [1, 4] oxazin-2-yl) amino)-2-(4-methyl-1H-imidazol-1-yl) benzonitrile

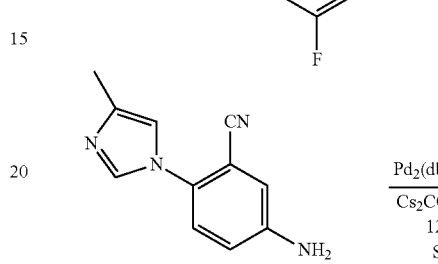

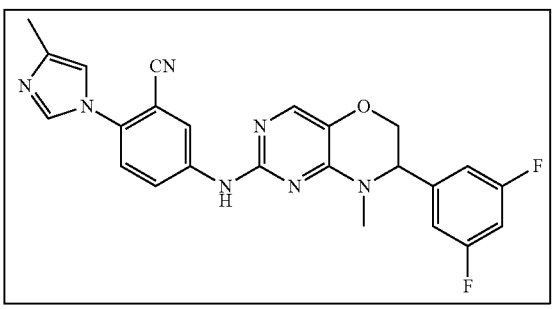

Synthesis of 5-((7-(3, 5-difluorophenyl)-8-methyl-7, 8-dihydro-6H-pyrimido [5, 4-b] [1, 4] oxazin-2-yl) amino)-2-(4-methyl-1H-imidazol-1-yl) benzonitrile To a dry vial was added a suspension of Pd$_2$(dba)$_3$ (35 mg, 0.04 mmol) and Xantphos (67 mg, 0.11 mmol) in 1, 4-dioxane (1.25 mL) at room temperature. The suspension was degassed with argon, heated to 120° C., and stirred for 3 min. A mixture of 2-chloro-7-(3, 5-difluorophenyl)-8-methyl-7, 8-dihydro-6H-pyrimido [5, 4-b] [1, 4] oxazine (230 mg, 0.77 mmol), 5-amino-2-(4-methyl-1H-imidazol-1-yl) benzonitrile (306 mg, 1.54 mmol), cesium carbonate (353 mg, 1.08 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the reaction mixture was diluted with water (50 mL) and extracted with CH$_2$Cl$_2$ (2×50 mL). The combined organic extracts were dried over sodium sulfate, filtered and concentrated in vacuo. The crude material was purified by preparative HPLC (Ascentis C-18 (250×21.2 mm, 5 μm (60 mg loading; CH$_3$CN: 0.05% TFA (0.1/90, 2/80, 15/70, 25/20, 30/10, 35/10)) to afford 5-((7-(3, 5-difluorophenyl)-8-methyl-7, 8-dihydro-6H-pyrimido [5, 4-b] [1, 4] oxazin-2-yl) amino)-2-(4-methyl-1H-imidazol-1-yl) benzonitrile (110 mg, 31%) as an off-white solid. LCMS: 460 (M+1); (column; X-Select CSH C-18 (50×3.0 mm, 3.5 μm); RT 2.40 min 0.05% Aq TFA: ACN; 0.80 mL/min); UPLC (column; Acquity BEH C18, 50×2.1 mm, 1.7 μm); RT 1.70 min. ACN: 0.025% Aq TFA; 0.5 mL/min; TLC: 5% MeOH/CH$_2$Cl$_2$ (R$_f$: 0.3).

Racemic compound of Example 203 was separated using a Chiralpak IA column (250×20 mm: 5 μm; (10 mg loading; 0.1% DEA in n-hexane: CH₂Cl₂:MeOH (50:50); (A:B: 70:30) as mobile phase) to provide the compound of Example-203A (Fraction I (+)) and the compound of Example 203B (Fraction II (−)).

Example 203A

Synthesis of (+)-5-((7-(3, 5-difluorophenyl)-8-methyl-7, 8-dihydro-6H-pyrimido [5, 4-b] [1, 4] oxazin-2-yl) amino)-2-(4-methyl-1H-imidazol-1-yl) benzonitrile

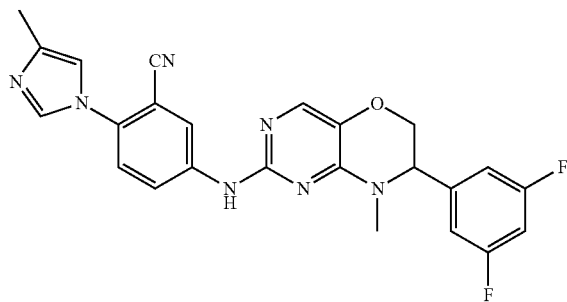 [SMILES: Cc1cn(-c2ccc(Nc3ncc4c(n3)N(C)C(c3cc(F)cc(F)c3)CO4)cc2C#N)cn1]

The compound of Example 203A was produced as described in Example 203. Analytical data for product Fraction I (+): $^1$H-NMR (CD₃OD, 400 MHz): δ 8.43 (s, 1H), 7.98 (d, 1H), 7.87 (s, 1H), 7.67 (s, 1H), 7.46 (d, 1H), 7.14 (s, 1H), 6.92-6.90 (m, 1H), 6.89-6.85 (m, 2H), 4.79-.477 (m, 1H), 4.23 (d, 2H), 3.17 (s, 3H), 2.26 (d, 3H); Mass (ESI): 460.5 [M+1]; LCMS: 460.4 (M+1); (column; X-Select CSH C-18 (50×3.0 mm, 3.5 μm); RT 2.91 min 0.05% Aq TFA: ACN; 0.80 mL/min); UPLC (column; Acquity BEH C18, 50×2.1 mm, 1.7 μm); RT 1.70 min. ACN: 0.025% Aq TFA; 0.5 mL/min; Chiral HPLC: 98.1% RT=13.01 min (CHIRALPAK-IA (250×4.6 mm, 5 μm; mobile phase (A) 0.1% DEA in n-hexane (B) CH₂Cl₂:MeOH (80:20) (A:B: 70:30); flow Rate: 1.0 mL/min); Optical rotation $[\alpha]_D^{19.99}$: +103.32 (c=0.25, CH₂Cl₂).

Example 203B

Synthesis of (−)-5-((7-(3, 5-difluorophenyl)-8-methyl-7, 8-dihydro-6H-pyrimido [5, 4-b] [1, 4] oxazin-2-yl) amino)-2-(4-methyl-1H-imidazol-1-yl) benzonitrile

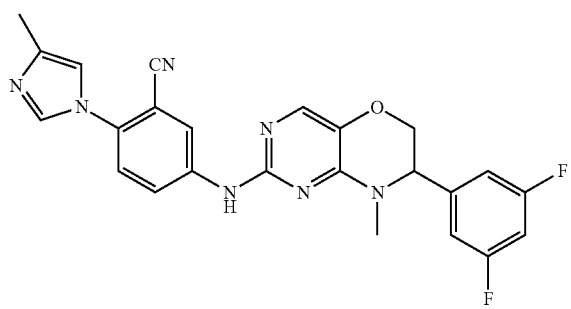 [SMILES: Cc1cn(-c2ccc(Nc3ncc4c(n3)N(C)C(c3cc(F)cc(F)c3)CO4)cc2C#N)cn1]

The compound of Example 203B was produced as described in Example 203. Analytical data for product Fraction II (−): $^1$H-NMR (CD₃OD, 400 MHz): δ 8.43 (s, 1H), 7.98 (d, 1H), 7.87 (s, 1H), 7.67 (s, 1H), 7.46 (d, 1H), 7.14 (s, 1H), 6.92-6.90 (m, 1H), 6.89-6.85 (m, 2H), 4.79-.477 (m, 1H), 4.23 (d, 2H), 3.17 (s, 3H), 2.26 (d, 3H); Mass (ESI): 460.5 [M+1]; LCMS: 460.4 (M+1); (column; X-Select CSH C-18 (50×3.0 mm, 3.5 μm); RT 2.91 min 0.05% Aq TFA: ACN; 0.80 mL/min); UPLC (column; Acquity BEH C18, 50×2.1 mm, 1.7 μm); RT 1.70 min. ACN: 0.025% Aq TFA; 0.5 mL/min; Chiral HPLC: 97.1% RT=14.14 min (CHIRALPAK-IA (250×4.6 mm, 5 μm; mobile phase (A) 0.1% DEA in n-hexane (B) CH₂Cl₂:MeOH (80:20) (A:B: 70:30); flow Rate: 1.0 mL/min); Optical rotation $[\alpha]_D^{20.00}$: −111.16 (c=0.25, CH₂Cl₂).

Example 204

Synthesis of N-(4-(4-chloro-1H-imidazol-1-yl)-3-methoxyphenyl)-7-(3, 5-difluorophenyl)-8-methyl-7, 8-dihydro-6H-pyrimido [5, 4-b] [1, 4] oxazin-2-amine

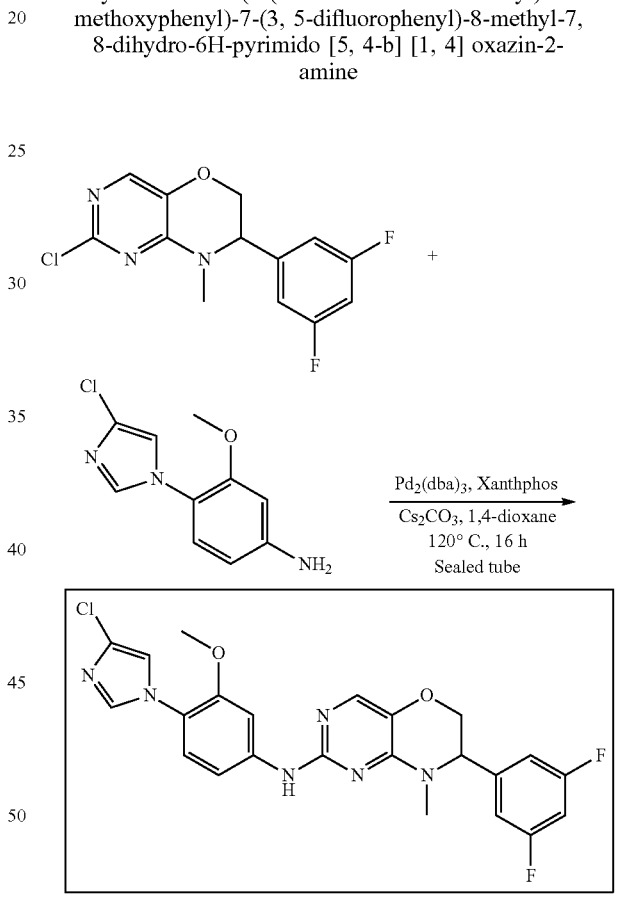

Synthesis of N-(4-(4-chloro-1H-imidazol-1-yl)-3-methoxyphenyl)-7-(3, 5-difluorophenyl)-8-methyl-7, 8-dihydro-6H-pyrimido [5, 4-b] [1, 4] oxazin-2-amine To a dry vial was added a suspension of Pd₂(dba)₃ (38 mg, 0.04 mmol) and Xantphos (73 mg, 0.12 mmol) in 1, 4-dioxane (1 mL) at room temperature. The suspension was degassed with argon, heated to 120° C., and stirred for 3 min. A mixture of 2-chloro-7-(3, 5-difluorophenyl)-8-methyl-7, 8-dihydro-6H-pyrimido [5, 4-b] [1, 4] oxazine (250 mg, 0.84 mmol), 4-(4-chloro-1H-imidazol-1-yl)-3- methoxyaniline (375 mg, 1.68 mmol), cesium carbonate (383 mg, 1.17 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction mixture was diluted with water (50 mL) and extracted with EtOAc (2×50 mL). The combined organic extracts were dried over sodium sulfate, filtered and concentrated in vacuo. The crude material was purified by column chromatography using 5-10% MeOH: $CH_2Cl_2$ to afford N-(4-(4-chloro-1H-imidazol-1-yl)-3-methoxyphenyl)-7-(3, 5-difluorophenyl)-8-methyl-7, 8-dihydro-6H-pyrimido [5, 4-b] [1, 4] oxazin-2-amine (170 mg, 41%) as an off-white solid. LCMS: 485 (M+1); (column; X-Select CSH C-18 (50×3.0 mm, 3.5 μm); RT 2.96 min 0.05% Aq TFA: ACN; 0.80 mL/min); TLC: 10% $MeOH/CH_2Cl_2$ ($R_f$: 0.3).

Racemic compound of Example 204 was separated using a Chiralpak ADH column (250×20 mm: 5 μm; (20 mg loading; 0.1% DEA in n-hexane: EtOH:MeOH (50:50); (A:B: 70:30) as mobile phase) to provide the compound of Example 204A (Fraction I (−)) and the compound of Example 204B (Fraction II (+)).

Example 204A

Synthesis of (−)-N-(4-(4-chloro-1H-imidazol-1-yl)-3-methoxyphenyl)-7-(3, 5-difluorophenyl)-8-methyl-7, 8-dihydro-6H-pyrimido [5, 4-b] [1, 4] oxazin-2-amine

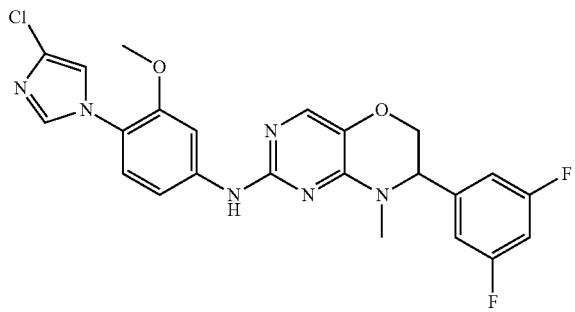 [SMILES: COc1cc(Nc2ncc3c(n2)N(C)C(c2cc(F)cc(F)c2)CO3)ccc1-n1cnc(Cl)c1]

The compound of Example 204A was produced as described in Example 204. Analytical data for product Fraction I (−): $^1$H-NMR ($CD_3OD$, 400 MHz): δ 7.79-7.77 (m, 1H), 7.69 (s, 1H), 7.61 (s, 1H), 7.27-7.20 (m, 3H), 6.95-6.83 (m, 3H), 4.75 (t, 1H), 4.22 (d, 2H), 3.89 (s, 3H), 3.19 (s, 3H); Mass (ESI): 485.8 [M+1]; LCMS: 485 (M+1); (column; X-Select CSH C-18 (50×3.0 mm, 3.5 μm); RT 3.01 min. 0.05% Aq TFA: ACN; 0.80 mL/min); UPLC (column; Acquity BEH C-18, 50×2.1 mm, 1.7 μm); RT 2.08 min. ACN: 0.025% Aq TFA; 0.5 mL/min; Chiral HPLC: 100% RT=20.27 min (CHIRALPAK-AD-H (250×4.6 mm, 5 μm; mobile phase (A) 0.1% DEA in n-hexane (B) EtOH:MeOH (50:50) (A:B; 70:30); flow Rate: 1.0 mL/min); Optical rotation $[α]_D^{20.01}$: −107.66 (c=0.25, $CH_2Cl_2$).

Example 204B

Synthesis of (+)-N-(4-(4-chloro-1H-imidazol-1-yl)-3-methoxyphenyl)-7-(3, 5-difluorophenyl)-8-methyl-7, 8-dihydro-6H-pyrimido [5, 4-b] [1, 4] oxazin-2-amine

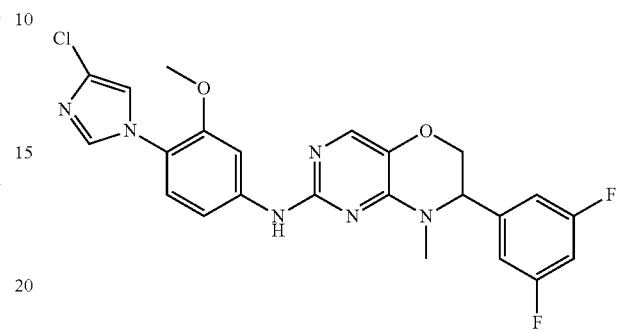

The compound of Example 204B was produced as described in Example 204. Analytical data for product Fraction II (+): $^1$H-NMR ($CD_3OD$, 400 MHz): δ 7.79-7.77 (m, 1H), 7.69 (s, 1H), 7.61 (s, 1H), 7.27-7.20 (m, 3H), 6.95-6.83 (m, 3H), 4.75 (t, 1H), 4.22 (d, 2H), 3.89 (s, 3H), 3.19 (s, 3H); Mass (ESI): 485.6 [M+1]; LCMS: 485 (M+1); (column; X-Select CSH C-18 (50×3.0 mm, 3.5 μm); RT 3.00 min 0.05% Aq TFA: ACN; 0.80 mL/min); UPLC (column; Acquity BEH C-18, 50×2.1 mm, 1.7 μm); RT 2.08 min. ACN: 0.025% Aq TFA; 0.5 mL/min; Chiral HPLC: 99.6% RT=28.28 min (CHIRALPAK-AD-H (250×4.6 mm, 5 μm; mobile phase (A) 0.1% DEA in n-hexane (B) EtOH:MeOH (50:50) (A:B; 70:30); flow Rate: 1.0 mL/min); Optical rotation $[α]_D^{20.00}$: +110.81 (c=0.25, $CH_2Cl_2$).

Example 205

Synthesis of 5-((7, 8-dimethyl-7, 8-dihydro-6H-pyrimido [5, 4-b] [1, 4] oxazin-2-yl) amino)-2-(4-methyl-1H-imidazol-1-yl) benzonitrile

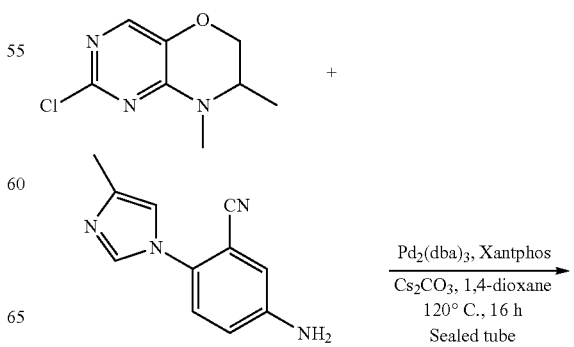

-continued

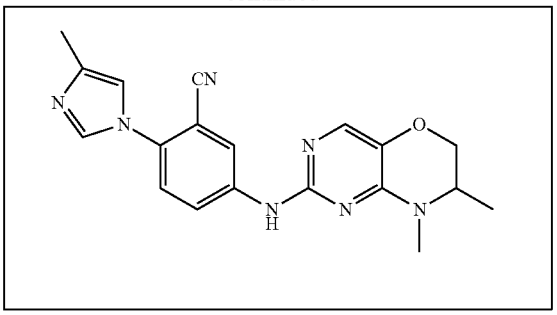

Synthesis of 5-((7, 8-dimethyl-7, 8-dihydro-6H-pyrimido [5, 4-b] [1, 4] oxazin-2-yl) amino)-2-(4-methyl-1H-imidazol-1-yl) benzonitrile To a dry vial was added a suspension of Pd$_2$(dba)$_3$ (57 mg, 0.06 mmol) and Xantphos (108 mg, 0.18 mmol) in 1, 4-dioxane (1.25 mL) at room temperature. The suspension was degassed with argon, heated to 120° C., and stirred for 3 min. A mixture of 2-chloro-7, 8-dimethyl-7, 8-dihydro-6H-pyrimido [5, 4-b] [1, 4] oxazine (250 mg, 1.25 mmol), 5-amino-2-(4-methyl-1H-imidazol-1-yl) benzonitrile (173 mg, 0.87 mmol) and cesium carbonate (571 mg, 1.75 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 3% MeOH: CH$_2$Cl$_2$ to afford 5-((7, 8-dimethyl-7, 8-dihydro-6H-pyrimido [5, 4-b] [1, 4] oxazin-2-yl) amino)-2-(4-methyl-1H-imidazol-1-yl) benzonitrile (140 mg, 31%) as an off-white solid. LCMS: 362 (M+1); (column; X-Select CSH C-18 (50×3.0 mm, 3.5 µm); RT 1.91 min 0.05% Aq TFA: ACN; 0.80 mL/min); UPLC (column; Acquity BEH C-18, 50×2.1 mm, 1.7 µm); RT 1.28 min. ACN: 0.025% Aq TFA; 0.5 mL/min.

Racemic compound of Example 205 was separated using a Chiralpak OJ-H column (250×20 mm: 5 µm; (10 mg loading; 0.1% DEA in n-hexane: EtOH:MeOH (50:50); (A:B; 75:25) as mobile phase) to provide the compound of Example 205A (Fraction I (+)) and the compound of Example 205B (Fraction II (−)).

Example 205A

Synthesis of (+)-5-((7, 8-dimethyl-7, 8-dihydro-6H-pyrimido [5, 4-b] [1, 4] oxazin-2-yl) amino)-2-(4-methyl-1H-imidazol-1-yl) benzonitrile

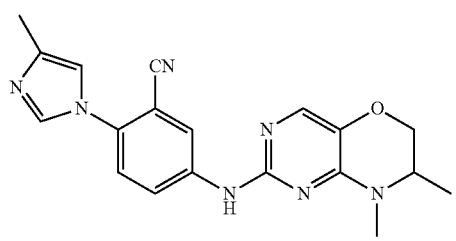 [SMILES: Cc1cn(-c2ccc(Nc3ncc4c(n3)N(C)C(C)CO4)cc2C#N)cn1]

The compound of Example 205A was produced as described in Example 205. Analytical data for product Fraction I (+): $^1$H-NMR (DMSO-d$_6$, 400 MHz): δ 9.45 (s, 1H), 8.40 (s, 1H), 7.99 (d, 1H), 7.81 (s, 1H), 7.60 (s, 1H), 7.45 (d, 1H), 7.19 (s, 1H), 4.00-3.92 (m, 2H), 3.70-3.65 (m, 1H), 3.10 (s, 3H), 2.14 (s, 3H), 1.20 (d, 3H); Mass (ESI): 362.4 [M+1]; LCMS: 362 (M+1); (column; X-Select CSH C-18 (50×3.0 mm, 3.5 µm); RT 1.89 min 0.05% Aq TFA: ACN; 0.80 mL/min); UPLC (column; Acquity BEH C-18, 50×2.1 mm, 1.7 µm); RT 1.28 min. ACN: 0.025% Aq TFA; 0.5 mL/min; Chiral HPLC: 99.0% RT=15.57 min (CHIRALPAK-IA (250×4.6 mm, 5 µm; mobile phase (A) 0.1% DEA in n-hexane (B) EtOH:MeOH (25:75) (A:B; 75:25); flow Rate: 1.0 mL/min); Optical rotation $[\alpha]_D^{20.01}$: +19.02 (c=0.25, CH$_2$Cl$_2$); TLC: 5% MeOH/CH$_2$Cl$_2$ (R$_f$; 0.3).

Example 205B

Synthesis of (−)-5-((7, 8-dimethyl-7, 8-dihydro-6H-pyrimido [5, 4-b] [1, 4] oxazin-2-yl) amino)-2-(4-methyl-1H-imidazol-1-yl) benzonitrile

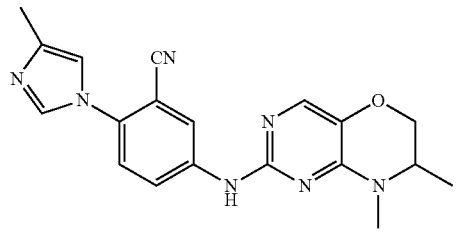 [SMILES: Cc1cn(-c2ccc(Nc3ncc4c(n3)N(C)C(C)CO4)cc2C#N)cn1]

The compound of Example 205B was produced as described in Example 205. Analytical data for product Fraction II (−): $^1$H-NMR (DMSO-d$_6$, 400 MHz): δ 9.45 (s, 1H), 8.40 (s, 1H), 7.99 (d, 1H), 7.81 (s, 1H), 7.60 (s, 1H), 7.45 (d, 1H), 7.19 (s, 1H), 4.00-3.92 (m, 2H), 3.70-3.65 (m, 1H), 3.10 (s, 3H), 2.14 (s, 3H), 1.20 (d, 3H); Mass (ESI): 362.5 [M+1]; LCMS: 362 (M+1); (column; X-Select CSH C-18 (50×3.0 mm, 3.5 µm); RT 1.88 min 0.05% Aq TFA: ACN; 0.80 mL/min); UPLC (column; Acquity BEH C-18, 50×2.1 mm, 1.7 µm); RT 1.28 min. ACN: 0.025% Aq TFA; 0.5 mL/min; Chiral HPLC: 100% RT=18.38 min (CHIRALPAK-IA (250×4.6 mm, 5 µm; mobile phase (A) 0.1% DEA in n-hexane (B) EtOH:MeOH (25:75) (A:B; 75:25); flow Rate: 1.0 mL/min); Optical rotation $[\alpha]_D^{20.00}$: −21.79 (c=0.25, CH$_2$Cl$_2$).

Example 206

Synthesis of 7-(3, 5-difluorophenyl)-N-(5-methoxy-6-(4-(trifluoromethyl)-1H-imidazol-1-yl) pyridin-3-yl)-8-methyl-7, 8-dihydro-6H-pyrimido [5, 4-b] [1, 4] oxazin-2-amine

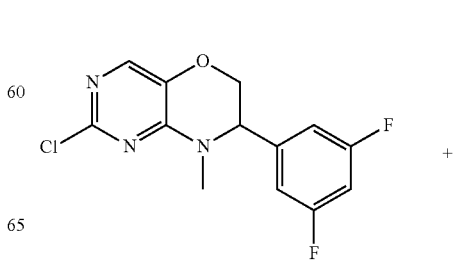 +

615

-continued

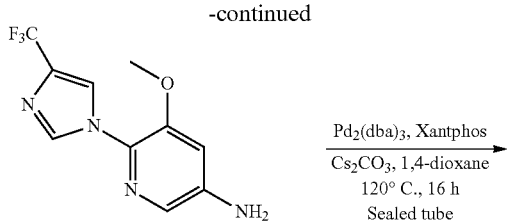

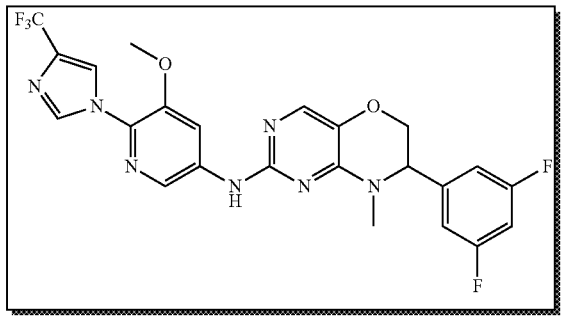

Synthesis of 7-(3, 5-difluorophenyl)-N-(5-methoxy-6-(4-(trifluoromethyl)-1H-imidazol-1-yl) pyridin-3-yl)-8-methyl-7, 8-dihydro-6H-pyrimido [5, 4-b] [1, 4] oxazin-2-amine To a dry vial was added a suspension of Pd$_2$(dba)$_3$ (38 mg, 0.04 mmol) and Xantphos (72 mg, 0.12 mmol) in 1, 4-dioxane (1.25 mL) at room temperature. The suspension was degassed with argon, heated to 120° C., and stirred for 3 min. A mixture of 2-chloro-7-(3, 5-difluorophenyl)-8-methyl-7, 8-dihydro-6H-pyrimido [5, 4-b] [1, 4] oxazine (250 mg, 0.83 mmol), 5-methoxy-6-(4-(trifluoromethyl)-1H-imidazol-1-yl) pyridin-3-amine (151 mg, 0.58 mmol) and cesium carbonate (382 mg, 1.17 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 3% MeOH: CH$_2$Cl$_2$ to afford 7-(3, 5-difluorophenyl)-N-(5-methoxy-6-(4-(trifluoromethyl)-1H-imidazol-1-yl) pyridin-3-yl)-8-methyl-7, 8-dihydro-6H-pyrimido [5, 4-b] [1, 4] oxazin-2-amine (78 mg, 18%) as an off-white solid. UPLC (column; Acquity BEH C-18 50×2.1 mm, 1.7 μm); RT 2.21 min. ACN: 0.025% Aq TFA; 0.5 mL/min; TLC: 5% MeOH/ CH$_2$Cl$_2$ (R$_f$; 0.3).

Racemic compound of Example 206 was separated using a Chiralpak IA column (250×20 mm: 5 μm; (15 mg loading; 0.1% DEA in n-hexane: CH$_2$Cl$_2$:MeOH (80:20); (A:B: 75:25) as mobile phase) to provide the compound of Example 206A (Fraction I (+)) and the compound of Example 206B (Fraction II (−)).

616

Example 206A

Synthesis of (+)-7-(3, 5-difluorophenyl)-N-(5-methoxy-6-(4-(trifluoromethyl)-1H-imidazol-1-yl) pyridin-3-yl)-8-methyl-7, 8-dihydro-6H-pyrimido [5, 4-b] [1, 4] oxazin-2-amine

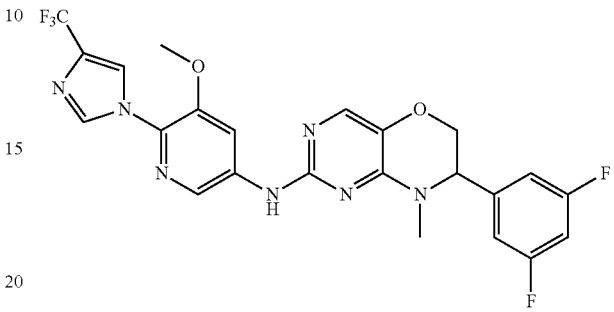

The compound of Example 206A was produced as described in Example 206. Analytical data for product Fraction I (+): $^1$H-NMR (DMSO-d$_6$, 400 MHz): δ 8.40 (s, 1H), 8.32 (s, 1H), 8.31 (s, 1H), 8.11 (s, 1H), 7.65 (s, 1H), 6.94-6.83 (m, 3H), 4.80 (s, 1H), 4.24 (s, 2H), 4.00 (s, 3H), 3.19 (s, 3H); Mass (ESI): 520.4 [M+1]; LCMS: 520 (M+1); (column; X-Select CSH C-18 (50×3.0 mm, 3.5 μm); RT 3.12 min. 0.05% Aq TFA: ACN; 0.80 mL/min); UPLC (column; Acquity BEH C-18, 50×2.1 mm, 1.7 μm); RT 2.21 min. ACN: 0.025% Aq TFA; 0.5 mL/min; Chiral HPLC: 99.7% RT=16.29 min (CHIRALPAK-IA (250×4.6 mm, 5 μm; mobile phase (A) 0.1% DEA in n-hexane (B) CH$_2$Cl$_2$: MeOH (80:20) (A:B; 75:25); flow Rate: 1.0 mL/min); Optical rotation [α]$_D^{19.99}$: +99.40 (c=0.25, CH$_2$Cl$_2$).

Example 206B

Synthesis of (−)-7-(3, 5-difluorophenyl)-N-(5-methoxy-6-(4-(trifluoromethyl)-1H-imidazol-1-yl) pyridin-3-yl)-8-methyl-7, 8-dihydro-6H-pyrimido [5, 4-b] [1, 4] oxazin-2-amine

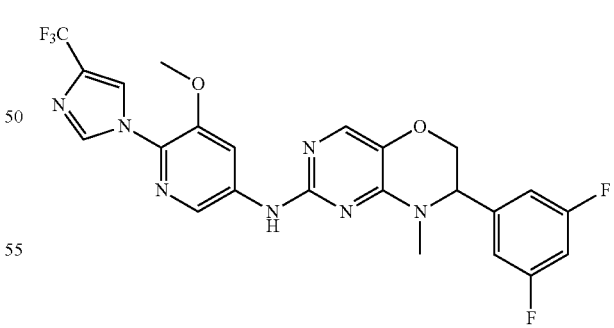

The compound of Example 206B was produced as described in Example 206. Analytical data for product Fraction II (−): $^1$H-NMR (DMSO-d$_6$, 400 MHz): δ 8.40 (s, 1H), 8.32 (s, 1H), 8.31 (s, 1H), 8.11 (s, 1H), 7.65 (s, 1H), 6.94-6.83 (m, 3H), 4.80 (s, 1H), 4.24 (s, 2H), 4.00 (s, 3H), 3.19 (s, 3H); Mass (ESI): 520.4 [M+1]; LCMS: 520 (M+1); (column; X-Select CSH C-18 (50×3.0 mm, 3.5 μm); RT 3.12 min. 0.05% Aq TFA: ACN; 0.80 mL/min); UPLC (column;

Acquity BEH C-18, 50×2.1 mm, 1.7 μm); RT 2.21 min. ACN: 0.025% Aq TFA; 0.5 mL/min; Chiral HPLC: 96.4% RT=17.56 min (CHIRALPAK-IA (250×4.6 mm, 5 μm; mobile phase (A) 0.1% DEA in n-hexane (B) $CH_2Cl_2$: MeOH (80:20) (A:B; 75:25); flow Rate: 1.0 mL/min); Optical rotation $[α]_D^{20.00}$: −93.37 (c=0.25, $CH_2Cl_2$).

Example 207

Synthesis of 7-(5-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

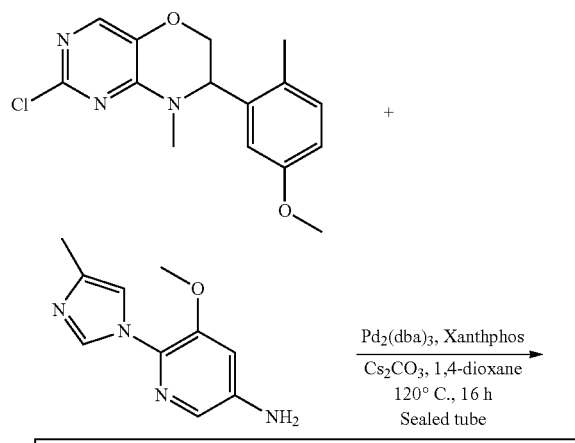

Synthesis of 7-(5-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine To a dry vial was added a suspension of $Pd_2(dba)_3$ (37 mg, 0.04 mmol) and Xantphos (71 mg, 0.12 mmol) in 1, 4-dioxane (1.25 mL) at room temperature. The suspension was degassed with argon, heated to 120° C., and stirred for 3 min. A mixture of 2-chloro-7-(5-methoxy-2-methylphenyl)-8-methyl-7, 8-dihydro-6H-pyrimido [5, 4-b] [1, 4] oxazine (250 mg, 0.82 mmol), 5-methoxy-6-(4-methyl-1H-imidazol-1-yl) pyridin-3-amine (184 mg, 0.90 mmol), cesium carbonate (399 mg, 1.22 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with $CH_2Cl_2$ (2×20 mL). The combined organic extracts were dried over sodium sulfate, filtered and concentrated in vacuo. The crude material was purified by column chromatography using 3% MeOH: $CH_2Cl_2$ to afford 7-(5-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine (230 mg, 59%) as an off-white solid. LCMS: 474 (M+1); (column; X-Select CSH C-18 (50×3.0 mm, 3.5 μm); RT 2.40 min 0.05% Aq TFA: ACN; 0.80 mL/min); TLC: 5% MeOH/$CH_2Cl_2$ ($R_f$: 0.3).

Racemic compound of Example 207 was separated using a Chiralpak IA column (250×20 mm: 5 μm; (10 mg loading; 0.1% DEA in n-hexane: EtOH:MeOH (80:20); (A:B: 75:25) as mobile phase) to provide the compound of Example 207A (Fraction I (+)) and the compound of Example 207B (Fraction II (−)).

Example 207A

Synthesis of (+)-7-(5-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

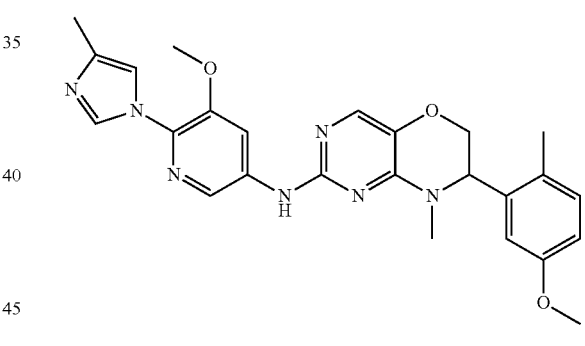

The compound of Example 207A was produced as described in Example 207. Analytical data for product Fraction I (+): $^1$H-NMR ($CD_3OD$, 400 MHz): δ 8.31 (d, 2H), 8.13 (s, 1H), 7.61 (s, 1H), 7.39 (s, 1H), 7.17 (d, 1H), 6.81 (dd, 1H), 6.54-6.51 (m, 1H), 4.95 (t, 1H), 4.24 (dd, 1H), 4.13 (dd, 1H), 3.97 (s, 3H), 3.68 (s, 3H), 3.11 (s, 3H), 2.34 (s, 3H), 2.24 (s, 3H); Mass (ESI): 474.5 [M+1]; LCMS: 474 (M+1); (column; X-Select CSH C-18 (50×3.0 mm, 3.5 μm); RT 2.40 min. 0.05% Aq TFA: ACN; 0.80 mL/min); UPLC (column; Acquity BEH C18, 2.1×50 mm, 1.7 μm); RT 1.69 min. ACN: 0.025% Aq TFA; 0.5 mL/min; Chiral HPLC: 99.0% RT=13.19 min (CHIRALPAK-IA (250×4.6 mm, 5 μm; mobile phase (A) 0.1% DEA in n-hexane (B) $CH_2Cl_2$: MeOH (80:20) (A:B: 75:25); flow Rate: 1.0 mL/min); Optical rotation $[α]_D^{19.97}$: +167.04 (c=0.25, $CH_2Cl_2$).

Example 207B

Synthesis of (−)-7-(5-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

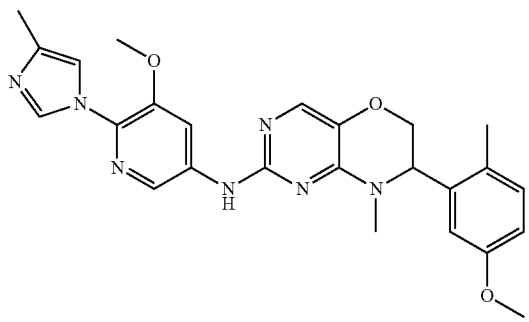 [SMILES: COc1ccc(C)c(C2COc3cnc(Nc4cnc(-n5cnc(C)c5)c(OC)c4)nc3N2C)c1]

The compound of Example 207B was produced as described in Example 207. Analytical data for product Fraction II (−): $^1$H-NMR (CD$_3$OD, 400 MHz): δ 8.31 (d, 2H), 8.13 (s, 1H), 7.61 (s, 1H), 7.39 (s, 1H), 7.17 (d, 1H), 6.81 (dd, 1H), 6.54-6.51 (m, 1H), 4.95 (t, 1H), 4.24 (dd, 1H), 4.13 (dd, 1H), 3.97 (s, 3H), 3.68 (s, 3H), 3.11 (s, 3H), 2.34 (s, 3H), 2.24 (s, 3H); Mass (ESI): 474.5 [M+1]; LCMS: 474 (M+1); (column; X-Select CSH C-18 (50×3.0 mm, 3.5 μm); RT 2.40 min. 0.05% Aq TFA: ACN; 0.80 mL/min); UPLC (column; Acquity BEH C18, 2.1×50 mm, 1.7 μm); RT 1.69 min. ACN: 0.025% Aq TFA; 0.5 mL/min; Chiral HPLC: 97.3% RT=14.78 min (CHIRALPAK-IA (250×4.6 mm, 5 μm; mobile phase (A) 0.1% DEA in n-hexane (B) CH$_2$Cl$_2$: MeOH (80:20) (A:B: 75:25); flow Rate: 1.0 mL/min); Optical rotation $[\alpha]_D^{20.01}$: −179.53 (c=0.25, CH$_2$Cl$_2$).

Example 208

Synthesis of 7-(2-chloro-5-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

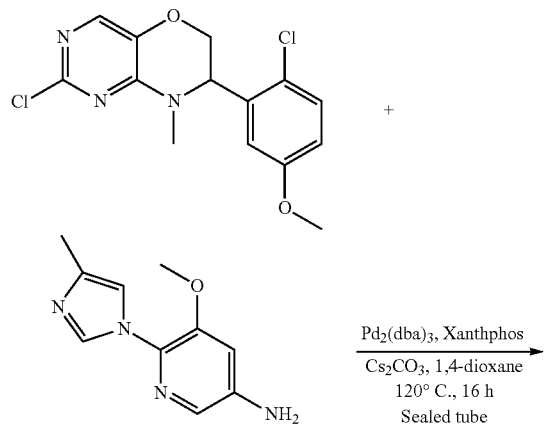

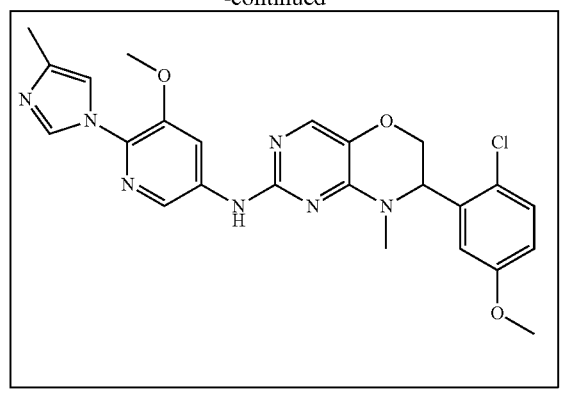

Synthesis of 7-(2-chloro-5-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine To a dry vial was added a suspension of Pd$_2$(dba) (35 mg, 0.04 mmol) and Xantphos (66 mg, 0.11 mmol) in 1, 4-dioxane (1.25 mL) at room temperature. The suspension was degassed with argon, heated to 120° C., and stirred for 3 min. A mixture of 2-chloro-7-(2-chloro-5-methoxyphenyl)-8-methyl-7, 8-dihydro-6H-pyrimido [5, 4-b] [1, 4] oxazine (250 mg, 0.76 mmol), 5-methoxy-6-(4-methyl-1H-imidazol-1-yl) pyridin-3-amine (311 mg, 1.53 mmol), cesium carbonate (300 mg, 0.91 mmol) in 1, 4-dioxane (1.25 mL) was degassed and the catalyst premix was added. The resultant mixture was stirred at 130° C. for 16 h in a sealed tube. After consumption of the starting material (monitored by TLC and LCMS), the reaction mixture was diluted with water (50 mL) and extracted with CH$_2$Cl$_2$ (2×50 mL). The combined organic extracts were dried over sodium sulfate, filtered and concentrated in vacuo. The crude material was purified by preparative HPLC (Ascentis C-18 (250×21.2 mm, 5 μm (60 mg loading; CH$_3$CN: 0.05% TFA (0.1/90, 2/80, 15/70, 25/20, 30/10, 35/10)) to afford 7-(2-chloro-5-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine (150 mg, 39%) as a yellow solid. UPLC (column; Acquity BEH C18, 50×2.1 mm, 1.7 μm); RT 1.76 min. ACN: 0.025% Aq TFA; 0.5 mL/min; TLC: 5% MeOH/CH$_2$Cl$_2$ (R$_f$: 0.4).

Racemic compound of Example 208 was separated using a Chiralpak IC column (250×20 mm: 5 μm; (40 mg loading; 0.1% DEA in n-hexane: CH$_2$Cl$_2$:MeOH (50:50); (A:B: 70:30) as mobile phase) to provide the compound of Example 208A (Fraction I (+)) and the compound of Example 208B (Fraction II (−)).

Example 208A

Synthesis of (+)-7-(2-chloro-5-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

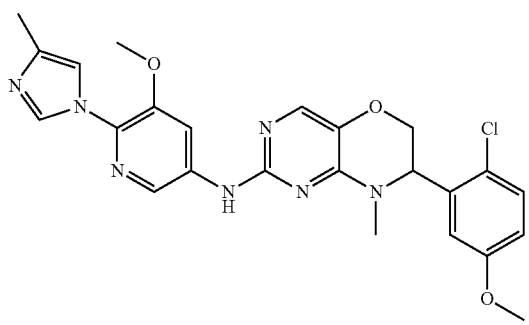 [SMILES: COc1ccc(Cl)c(C2COc3cnc(Nc4cnc(-n5cnc(C)c5)c(OC)c4)nc3N2C)c1]

The compound of Example 208A was produced as described in Example 208. Analytical data for product Fraction I (+): $^1$H-NMR (DMSO-$d_6$, 400 MHz): δ 9.40 (s, 1H), 8.36 (s, 1H), 8.31 (s, 1H), 8.03 (s, 1H), 7.69 (s, 1H), 7.48 (d, 1H), 7.38 (s, 1H), 6.99 (d, 1H), 6.50 (s, 1H), 5.10-5.08 (m, 1H), 4.24 (s, 2H), 3.89 (s, 3H), 3.69 (s, 3H), 3.11 (s, 3H), 2.15 (s, 3H); Mass (ESI): 494.6 [M+1]; LCMS: 494.1 (M+1); (column; X-Select CSH C-18 (50×3.0 mm, 3.5 μm); RT 2.51 min 0.05% Aq TFA: ACN; 0.80 mL/min); UPLC (column; Acquity BEH C18, 2.1×50 mm, 1.7 μm); RT 1.76 min. ACN: 0.025% Aq TFA; 0.5 mL/min; Chiral HPLC: 100% RT=20.27 min (CHIRALPAK-IC (250×4.6 mm, 5 μm; mobile phase (A) 0.1% DEA in n-hexane (B) $CH_2Cl_2$:MeOH (50:50) (A:B: 70:30); flow Rate: 1.0 mL/min); Optical rotation $[\alpha]_D^{20.01}$: +157.47 (c=0.25, $CH_2Cl_2$).

Example 208B

Synthesis of (−)-7-(2-chloro-5-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

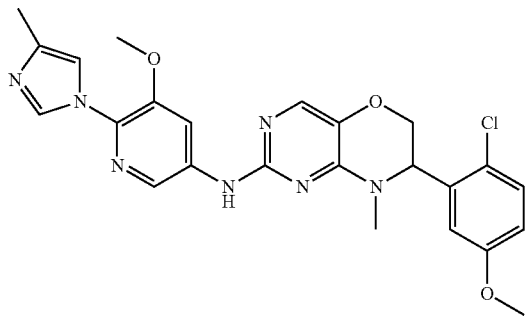 [SMILES: COc1ccc(Cl)c(C2COc3cnc(Nc4cnc(-n5cnc(C)c5)c(OC)c4)nc3N2C)c1]

The compound of Example 208B was produced as described in Example 208. Analytical data for product Fraction II (−): $^1$H-NMR (DMSO-$d_6$, 400 MHz): δ 9.40 (s, 1H), 8.36 (s, 1H), 8.31 (s, 1H), 8.03 (s, 1H), 7.69 (s, 1H), 7.48 (d, 1H), 7.38 (s, 1H), 6.99 (d, 1H), 6.50 (s, 1H), 5.10-5.08 (m, 1H), 4.24 (s, 2H), 3.89 (s, 3H), 3.69 (s, 3H), 3.11 (s, 3H), 2.15 (s, 3H); Mass (ESI): 494.7 [M+1]; LCMS: 494.1 (M+1); (column; X-Select CSH C-18 (50×3.0 mm, 3.5 μm); RT 2.52 min 0.05% Aq TFA: ACN; 0.80 mL/min); UPLC (column; Acquity BEH C18, 2.1×50 mm, 1.7 μm); RT 1.77 min. ACN: 0.025% Aq TFA; 0.5 mL/min; Chiral HPLC: 98.7% RT=25.20 min (CHIRALPAK-IC (250×4.6 mm, 5 μm; mobile phase (A) 0.1 DEA in n-hexane (B) $CH_2Cl_2$:MeOH (50:50) (A:B: 70:30); flow Rate: 1.0 mL/min); Optical rotation $[\alpha]_D^{19.99}$: −160.22 (c=0.25, $CH_2Cl_2$).

Example 209

Synthesis of 7-(2-chloro-4-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

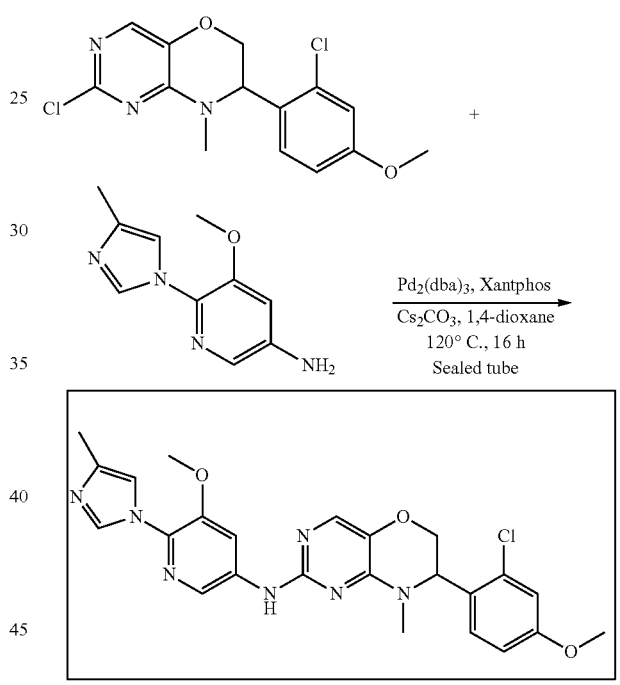

Synthesis of 7-(2-chloro-4-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine To a dry vial was added a suspension of $Pd_2(dba)_3$ (35 mg, 0.04 mmol) and Xantphos (66 mg, 0.11 mmol) in 1, 4-dioxane (1.25 mL) at room temperature. The suspension was degassed with argon, heated to 120° C., and stirred for 3 min. A mixture of 2-chloro-7-(2-chloro-4-methoxyphenyl)-8-methyl-7, 8-dihydro-6H-pyrimido [5, 4-b] [1, 4] oxazine (250 mg, 0.76 mmol), 5-methoxy-6-(4-methyl-1H-imidazol-1-yl) pyridin-3-amine (172 mg, 0.84 mmol) and cesium carbonate (37 mg, 1.15 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the reaction mixture was diluted with water (50 mL) and extracted with CH₂Cl₂ (2×50 mL). The combined organic extracts were dried over sodium sulfate, filtered and concentrated in vacuo. The crude material was purified by column chromatography using 3% MeOH: CH₂Cl₂ to afford 7-(2-chloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (110 mg, 29%) as an off-white solid. LCMS: 494 (M+1); (column; X-Select CSH C-18 (50×3.0 mm, 3.5 μm); RT 2.52 min 0.05% Aq TFA: ACN; 0.80 mL/min); UPLC (column; Acquity BEH C-18 50×2.1 mm, 1.7 μm); RT 1.77 min. ACN: 0.025% Aq TFA; 0.5 mL/min; TLC: 5% MeOH/ CH₂Cl₂ (R$_f$; 0.3).

Racemic compound of Example 209 was separated using a Chiralpak IC column (250×20 mm: 5 μm; (15 mg loading; 0.1% DEA in n-hexane: CH₂Cl₂:MeOH (50:50); (A:B: 70:30) as mobile phase) to provide the compound of Example 209A (Fraction I (+)) and the compound of Example 209B (Fraction II (−)).

Example 209A

Synthesis of (+)-7-(2-chloro-4-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

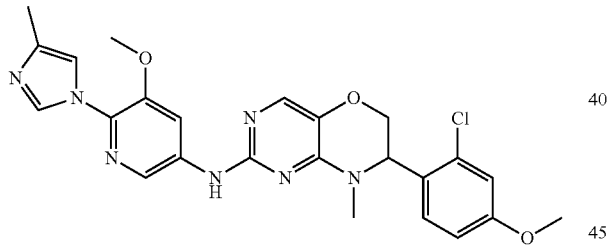

The compound of Example 209A was produced as described in Example 209. Analytical data for product Fraction I (+): ¹H-NMR (CD₃OD, 400 MHz): δ 8.31-8.28 (m, 2H), 8.11 (s, 1H), 7.60 (s, 1H), 7.40 (s, 1H), 7.10 (s, 1H), 7.00 (d, 1H), 6.99 (d, 1H), 5.52-5.50 (m, 1H), 4.25-4.23 (m, 2H), 3.95 (s, 3H), 3.80 (s, 3H), 3.12 (s, 3H), 2.22 (s, 3H); Mass (ESI): 494.5 [M+1]; LCMS: 494 (M+1); (column; X-Select CSH C-18 (50×3.0 mm, 3.5 μm); RT 2.52 min. 0.05% Aq TFA: ACN; 0.80 mL/min); UPLC (column; Acquity BEH C-18, 50×2.1 mm, 1.7 μm); RT 1.77 min. ACN: 0.025% Aq TFA; 0.5 mL/min; Chiral HPLC: 99.8% RT=21.64 min (CHIRALPAK-IC (250×4.6 mm, 5 μm; mobile phase (A) 0.1% DEA in n-hexane (B) CH₂Cl₂: MeOH (50:50) (A:B; 70:30); flow Rate: 1.0 mL/min); Optical rotation [α]$_D^{20.00}$: +205.77 (c=0.25, CH₂Cl₂).

Example 209B

Synthesis of (−)-7-(2-chloro-4-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

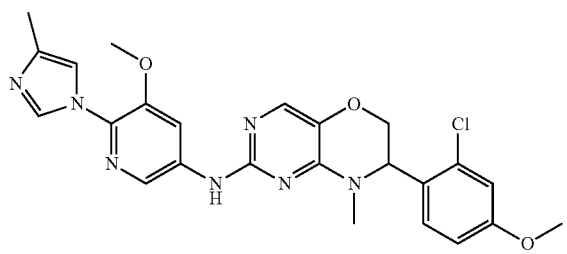 [SMILES: COc1ccc(C2COc3cnc(Nc4cnc(-n5cnc(C)c5)c(OC)c4)nc3N2C)c(Cl)c1]

The compound of Example 209B was produced as described in Example 209. Analytical data for product Fraction II (−): ¹H-NMR (CD₃OD, 400 MHz): δ 8.31-8.28 (m, 2H), 8.11 (s, 1H), 7.60 (s, 1H), 7.40 (s, 1H), 7.10 (s, 1H), 7.00 (d, 1H), 6.99 (d, 1H), 5.52-5.50 (m, 1H), 4.25-4.23 (m, 2H), 3.95 (s, 3H), 3.80 (s, 3H), 3.12 (s, 3H), 2.22 (s, 3H); Mass (ESI): 494.7 [M+1]; LCMS: 494 (M+1); (column; X-Select CSH C-18 (50×3.0 mm, 3.5 μm); RT 2.52 min. 0.05% Aq TFA: ACN; 0.80 mL/min); UPLC (column; Acquity BEH C-18, 50×2.1 mm, 1.7 μm); RT 1.77 min. ACN: 0.025% Aq TFA; 0.5 mL/min; Chiral HPLC: 99.5% RT=24.67 min (CHIRALPAK-IC (250×4.6 mm, 5 μm; mobile phase (A) 0.1% DEA in n-hexane (B) CH₂Cl₂: MeOH (50:50) (A:B; 70:30); flow Rate: 1.0 mL/min); Optical rotation [α]$_D^{20.01}$: −195.71 (c=0.25, CH₂Cl₂).

Example 210

Synthesis of N-(5-chloro-6-(4-methyl-1H-imidazol-1-yl) pyridin-3-yl)-7-(3, 5-difluorophenyl)-8-methyl-7, 8-dihydro-6H-pyrimido [5, 4-b] [1, 4] oxazin-2-amine

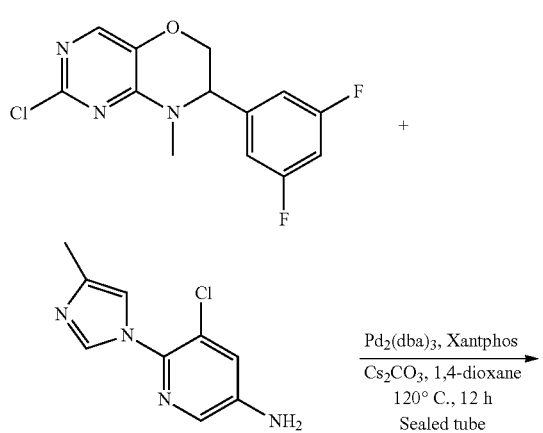

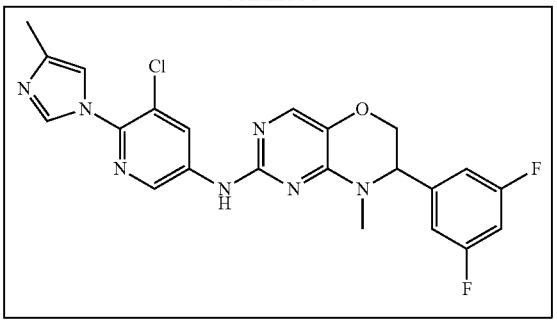

Synthesis of N-(5-chloro-6-(4-methyl-1H-imidazol-1-yl) pyridin-3-yl)-7-(3, 5-difluorophenyl)-8-methyl-7, 8-dihydro-6H-pyrimido [5, 4-b] [1, 4] oxazin-2-amine To a dry vial was added a suspension of $Pd_2(dba)_3$ (38 mg, 0.04 mmol) and Xantphos (73 mg, 0.12 mmol) in 1, 4-dioxane (1 mL) at room temperature. The suspension was degassed with argon, heated to 120° C., and stirred for 3 min. A mixture of 2-chloro-7-(3, 5-difluorophenyl)-8-methyl-7, 8-dihydro-6H-pyrimido [5, 4-b] [1, 4] oxazine (250 mg, 0.84 mmol), 5-chloro-6-(4-methyl-1H-imidazol-1-yl) pyridin-3-amine (157 mg, 0.75 mmol) and cesium carbonate (383 mg, 1.17 mmol) in 1, 4-dioxane (1 mL) was degassed and the catalyst premix was added. The resultant mixture was stirred at 120° C. for 12 h in a sealed tube. After consumption of the starting material (monitored by TLC and LCMS), the reaction mixture was filtered and the filtrate was concentrated in vacuo. The crude material was purified by column chromatography using 3% MeOH: $CH_2Cl_2$ to afford N-(5-chloro-6-(4-methyl-1H-imidazol-1-yl) pyridin-3-yl)-7-(3, 5-difluorophenyl)-8-methyl-7, 8-dihydro-6H-pyrimido [5, 4-b] [1, 4] oxazin-2-amine (130 mg, 33%) as an off-white solid. LCMS: 470 (M+1); (column; X-select CSH C-18 (50×3.0 mm, 3.5 μm); RT 2.43 min. 0.05% Aq TFA: ACN; 0.8 mL/min); TLC: 5% MeOH/$CH_2Cl_2$ ($R_f$: 0.2).

Racemic compound of Example 210 was separated using a Chiralpak IA column (250×20 mm: 5 μm; (40 mg loading; 0.1% DEA in n-hexane: $CH_2Cl_2$:MeOH (50:50); (A:B: 70:30) as mobile phase) to provide the compound of Example 210A (Fraction I (+)) and the compound of Example 210B (Fraction II (−)).

Example 210A

Synthesis of (+)-N-(5-chloro-6-(4-methyl-1H-imidazol-1-yl) pyridin-3-yl)-7-(3, 5-difluorophenyl)-8-methyl-7, 8-dihydro-6H-pyrimido [5, 4-b] [1, 4] oxazin-2-amine

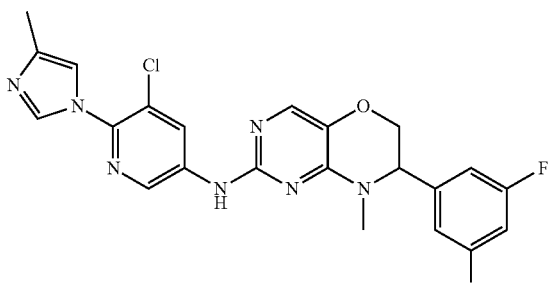

The compound of Example 210A was produced as described in Example 210. Analytical data for product Fraction I (+): $^1$H-NMR (CD$_3$OD, 400 MHz): δ 8.73-8.71 (s, 1H), 8.65-8.63 (s, 1H), 7.96 (s, 1H), 7.66 (s, 1H), 7.26-7.24 (m, 1H), 6.96-6.83 (m, 3H), 4.79 (s, 1H), 4.24 (d, 2H), 3.17 (s, 3H), 2.26 (s, 3H); Mass (ESI): 470.5 [M+1]; LCMS: 470 (M+1); (column; X-Select CSH C-18 (50×3.0 mm, 3.5 μm); RT 2.47 min. 0.05% Aq TFA: ACN; 0.80 mL/min); UPLC (column; Acquity BEH C-18, 50×2.1 mm, 1.7 μm); RT 1.75 min. ACN: 0.025% Aq TFA; 0.5 mL/min; Chiral HPLC: 99.2% RT=15.47 min (CHIRALPAK-IC (250×4.6 mm, 5 μm; mobile phase (A) 0.1% DEA in n-hexane (B) $CH_2Cl_2$:MeOH (80:20) (A:B; 60:40); flow Rate: 1.0 mL/min); Optical rotation $[\alpha]_D^{20.01}$: +128.09 (c=0.25, $CH_2Cl_2$).

Example 110B

Synthesis of (−)-N-(5-chloro-6-(4-methyl-1H-imidazol-1-yl) pyridin-3-yl)-7-(3, 5-difluorophenyl)-8-methyl-7, 8-dihydro-6H-pyrimido [5, 4-b] [1, 4] oxazin-2-amine

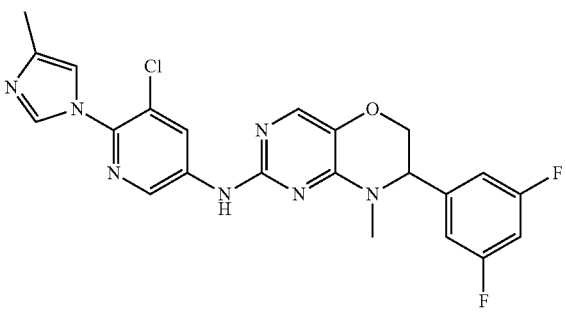

The compound of Example 210B was produced as described in Example 210. Analytical data for product Fraction II (−): $^1$H-NMR (CD$_3$OD, 400 MHz): δ 8.73-8.71 (s, 1H), 8.65-8.63 (s, 1H), 7.96 (s, 1H), 7.66 (s, 1H), 7.26-7.24 (m, 1H), 6.96-6.83 (m, 3H), 4.79 (s, 1H), 4.24 (d, 2H), 3.17 (s, 3H), 2.26 (s, 3H); Mass (ESI): 470.5 [M+1]; LCMS: 470.2 (M+1); (column; X-Select CSH C-18 (50×3.0 mm, 3.5 μm); RT 2.47 min. 0.05% Aq TFA: ACN; 0.80 mL/min); UPLC (column; Acquity BEH C-18, 50×2.1 mm, 1.7 µm); RT 1.74 min. ACN: 0.025% Aq TFA; 0.5 mL/min; Chiral HPLC: 98.8% RT=17.30 min (CHIRALPAK-IC (250×4.6 mm, 5 µm; mobile phase (A) 0.1% DEA in n-hexane (B) CH$_2$Cl$_2$:MeOH (80:20) (A:B; 60:40); flow Rate: 1.0 mL/min); Optical rotation $[\alpha]_D^{19.99}$: −121.64 (c=0.25, CH$_2$Cl$_2$).

Example 211

Synthesis of 1-(5-((7-(3, 5-difluorophenyl)-8-methyl-7, 8-dihydro-6H-pyrimido [5, 4-b] [1, 4] oxazin-2-yl) amino)-3-methoxypyridin-2-yl)-1H-imidazole-4-carbonitrile

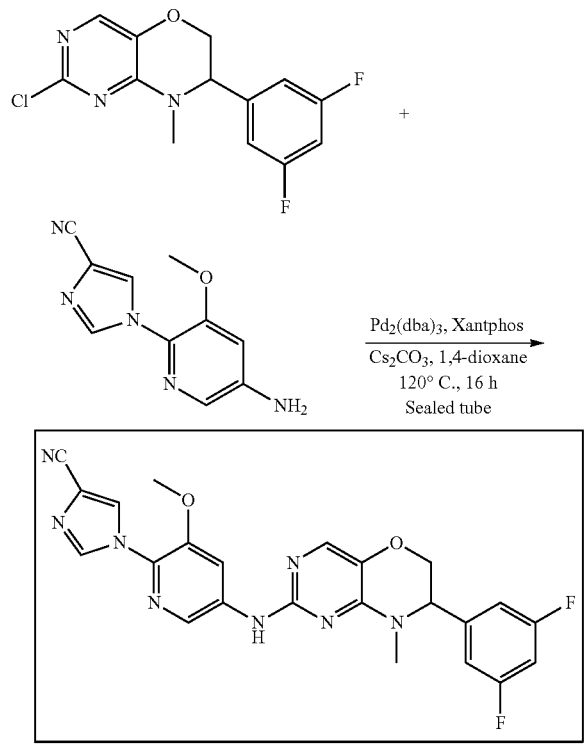

Synthesis of 1-(5-((7-(3, 5-difluorophenyl)-8-methyl-7, 8-dihydro-6H-pyrimido [5, 4-b] [1, 4] oxazin-2-yl) amino)-3-methoxypyridin-2-yl)-1H-imidazole-4-carbonitrile To a dry vial was added a suspension of Pd$_2$(dba)$_3$ (21 mg, 0.02 mmol) and Xantphos (40 mg, 0.07 mmol) in 1, 4-dioxane (1 mL) at room temperature. The suspension was degassed with argon, heated to 120° C., and stirred for 3 min. A mixture of 2-chloro-7-(3, 5-difluorophenyl)-8-methyl-7, 8-dihydro-6H-pyrimido [5, 4-b] [1, 4] oxazine (138 mg, 0.46 mmol), 1-(5-amino-3-methoxypyridin-2-yl)-1H-imidazole-4-carbonitrile (200 mg, 0.92 mmol) and cesium carbonate (211 mg, 0.65 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction mixture was diluted with water (50 mL) and extracted with CH$_2$Cl$_2$ (2×50 mL). The combined organic extracts were dried over sodium sulfate, filtered, concentrated in vacuo, and purified by column chromatography using 3% MeOH: CH$_2$Cl$_2$ to afford 1-(5-(((7-(3, 5-difluorophenyl)-8-methyl-7, 8-dihydro-6H-pyrimido [5, 4-b] [1, 4] oxazin-2-yl) amino)-3-methoxypyridin-2-yl)-1H-imidazole-4-carbonitrile (180 mg, 81%) as an off-white solid. LCMS: 477 (M+1); (column; X-Select CSH C-18 (50×3.0 mm, 3.5 µm); RT 2.93 min 0.05% Aq TFA: ACN; 0.80 mL/min); TLC: 5% MeOH/CH$_2$Cl$_2$ (R$_f$: 0.3).

Racemic compound of Example 211 was separated using a Chiralpak IA column (250×20 mm: 5 µm; (15 mg loading; 0.1% DEA in n-hexane: CH$_2$Cl$_2$:MeOH (90:10); (A:B: 65:35) as mobile phase) to provide the compound of Example 211A (Fraction I (+)) and the compound of Example 211B (Fraction II (−)).

Example 211A

Synthesis of (+)-1-(5-((7-(3, 5-difluorophenyl)-8-methyl-7, 8-dihydro-6H-pyrimido [5, 4-b] [1, 4] oxazin-2-yl) amino)-3-methoxypyridin-2-yl)-1H-imidazole-4-carbonitrile

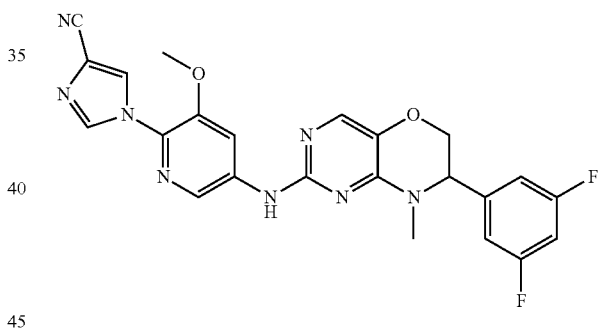

The compound of Example 211A was produced as described in Example 211. Analytical data for product Fraction I (+): $^1$H-NMR (CD$_3$OD, 400 MHz): δ 8.43 (s, 1H), 8.41 (d, 1H), 8.38 (s, 1H), 8.32 (s, 1H), 7.66 (s, 1H), 6.93-6.83 (m, 3H), 4.79-4.77 (m, 1H), 4.24 (d, 2H), 4.00 (s, 3H), 3.19 (s, 3H); Mass (ESI): 477.6 [M+1]; LCMS: 477.1 (M+1); (column;

X-Select CSH C-18 (50×3.0 mm, 3.5 µm); RT 2.93 min 0.05% Aq TFA: ACN; 0.80 mL/min); UPLC (column; Acquity BEH C18, 50×2.1 mm, 1.7 µm); RT 2.01 min. ACN: 0.025% Aq TFA; 0.5 mL/min; Chiral HPLC: 99.4% RT=11.02 min (CHIRALPAK-IA (250×4.6 mm, 5 µm; mobile phase (A) 0.1% DEA in n-hexane (B) CH$_2$Cl$_2$: MeOH (90:10) (A:B: 65:35); flow Rate: 1.0 mL/min); Optical rotation $[\alpha]_D^{19.99}$: +135.82 (c=0.25, CH$_2$Cl$_2$).

Example 211B

Synthesis of (−)-1-(5-((7-(3, 5-difluorophenyl)-8-methyl-7, 8-dihydro-6H-pyrimido [5, 4-b] [1, 4] oxazin-2-yl) amino)-3-methoxypyridin-2-yl)-1H-imidazole-4-carbonitrile

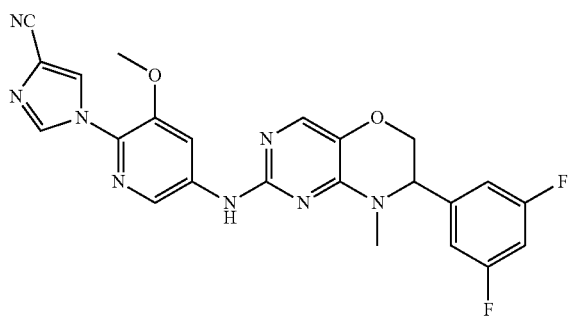 [SMILES: COc1cc(Nc2ncc3c(n2)N(C)C(c2cc(F)cc(F)c2)CO3)cnc1-n1cnc(C#N)c1]

The compound of Example 211B was produced as described in Example 211. Analytical data for product Fraction II (−): $^1$H-NMR (CD$_3$OD, 400 MHz): δ 8.43 (s, 1H), 8.41 (d, 1H), 8.38 (s, 1H), 8.32 (s, 1H), 7.66 (s, 1H), 6.93-6.83 (m, 3H), 4.79-4.77 (m, 1H), 4.24 (d, 2H), 4.00 (s, 3H), 3.19 (s, 3H); Mass (ESI): 477.5 [M+1]; LCMS: 477.1 (M+1); (column; X-Select CSH C-18 (50×3.0 mm, 3.5 μm); RT 2.92 min 0.05% Aq TFA: ACN; 0.80 mL/min); UPLC (column; Acquity BEH C18, 50×2.1 mm, 1.7 μm); RT 2.01 min. ACN: 0.025% Aq TFA; 0.5 mL/min; Chiral HPLC: 99.3% RT=12.59 min (CHIRALPAK-IA (250×4.6 mm, 5 μm; mobile phase (A) 0.1% DEA in n-hexane (B) CH$_2$Cl$_2$: MeOH (90:10) (A:B: 65:35); flow Rate: 1.0 mL/min); Optical rotation $[α]_D^{20.00}$: −133.28 (c=0.25, CH$_2$Cl$_2$).

Example 212

Synthesis of 7-(3, 3-difluorocyclobutyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

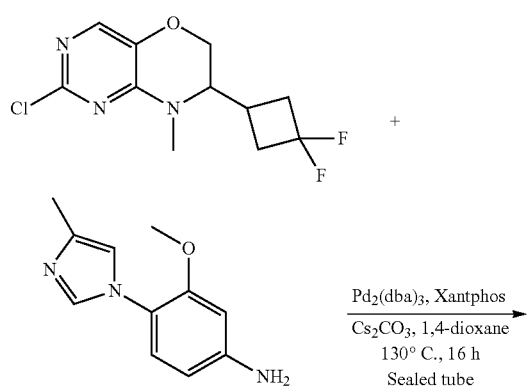

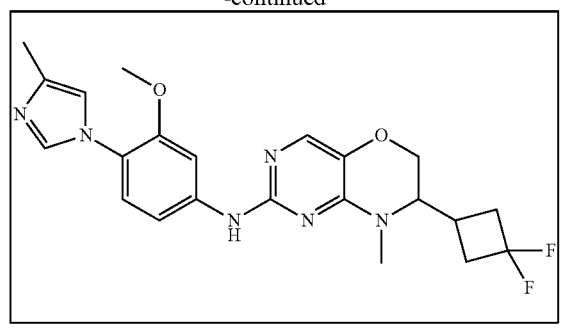

Synthesis of 7-(3, 3-difluorocyclobutyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a dry vial was added a suspension of Pd$_2$(dba)$_3$ (42 mg, 0.04 mmol) and Xantphos (79 mg, 0.13 mmol) in 1, 4-dioxane (1.25 mL) at room temperature. The suspension was degassed with argon, heated to 120° C., and stirred for 3 min. A mixture of 2-chloro-7-(3, 3-difluorocyclobutyl)-8-methyl-7, 8-dihydro-6H-pyrimido [5, 4-b] [1, 4] oxazine (250 mg, 0.90 mmol), 3-methoxy-4-(4-methyl-1H-imidazol-1-yl) aniline (369 mg, 1.81 mmol), cesium carbonate (890 mg, 2.72 mmol) in 1, 4-dioxane (1.25 mL) was degassed and the catalyst premix was added. The resultant mixture was stirred at 130° C. for 16 h in a sealed tube. After consumption of the starting material (monitored by TLC and LCMS), the volatile components were evaporated in vacuo. The residue was diluted with water (50 mL) and extracted with CH$_2$Cl$_2$ (2×50 mL). The combined organic extracts were dried over sodium sulfate, filtered and concentrated in vacuo. The crude material was purified by column chromatography using 3% MeOH: CH$_2$Cl$_2$ to afford 7-(3, 3-difluorocyclobutyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (160 mg, 37%) as a pale yellow solid. LCMS: 443.1 (M+1); (column; X-Select CSH C-18 (50×3.0 mm, 3.5 μm); RT 2.29 min 0.05% Aq TFA: ACN; 0.80 mL/min); UPLC (column; Acquity BEH C18, 50×2.1 mm, 1.7 μm); RT 1.56 min. ACN: 0.025% Aq TFA; 0.5 mL/min; TLC: 5% EtOAc:hexane (R$_f$: 0.3).

Racemic compound of Example 212 was separated using a Chiralpak IA column (250×20 mm: 5 μm; (40 mg loading; 0.1% DEA in n-hexane: CH$_2$Cl$_2$:MeOH (50:50); (A:B: 75:25) as mobile phase) to provide the compound of Example 212A (Fraction I (−)) and the compound of Example 212B (Fraction II (+)).

Example 212A

Synthesis of (−)-7-(3, 3-difluorocyclobutyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

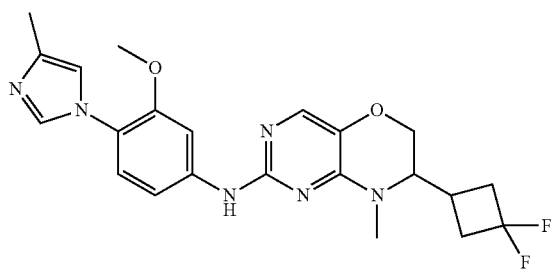 [SMILES: COc1cc(Nc2ncc3c(n2)N(C)C(C2CC(F)(F)C2)CO3)ccc1-n1cnc(C)c1]

The compound of Example 212A was produced as described in Example 212. Analytical data for product Fraction I (−): $^1$H-NMR (CD$_3$OD, 400 MHz): δ 7.72 (s, 1H), 7.63 (s, 1H), 7.51 (s, 1H), 7.20-7.12 (m, 2H), 6.94 (s, 1H), 4.17 (d, 1H), 3.90-3.86 (m, 1H), 3.84 (s, 3H), 3.60-3.58 (m, 1H), 3.30 (s, 3H), 2.70-2.60 (m, 3H), 2.50-2.40 (m, 2H), 2.21 (s, 3H); Mass (ESI): 443.1 [M+1]; LCMS: 443.1 (M+1); (column; X-Select CSH C-18 (50×3.0 mm, 3.5 µm); RT 2.25 min 0.05% Aq TFA: ACN; 0.80 mL/min); UPLC (column; Acquity BEH C18, 50×2.1 mm, 1.7 µm); RT 1.56 min. ACN: 0.025% Aq TFA; 0.5 mL/min; Chiral HPLC: 99.3% RT=10.07 min (CHIRALPAK-ADH (250×4.6 mm, 5 µm; mobile phase (A) 0.1% DEA in n-hexane (B) EtOH:MeOH (50:50) (A:B: 65:35); flow Rate: 1.0 mL/min); Optical rotation $[α]_D^{19.98}$: −17.13 (c=0.25, CH$_2$Cl$_2$).

Example 212B

Synthesis of (+)-7-(3, 3-difluorocyclobutyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

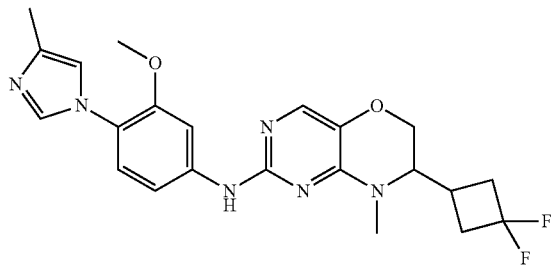 [SMILES: COc1cc(Nc2ncc3c(n2)N(C)C(C2CC(F)(F)C2)CO3)ccc1-n1cnc(C)c1]

The compound of Example 212B was produced as described in Example 212. Analytical data for product Fraction II (+): $^1$H-NMR (CD$_3$OD, 400 MHz): δ 7.72 (s, 1H), 7.63 (s, 1H), 7.51 (s, 1H), 7.20-7.12 (m, 2H), 6.94 (s, 1H), 4.17 (d, 1H), 3.90-3.86 (m, 1H), 3.84 (s, 3H), 3.60-3.58 (m, 1H), 3.30 (s, 3H), 2.70-2.60 (m, 3H), 2.50-2.40 (m, 2H), 2.21 (s, 3H); Mass (ESI): 443.1 [M+1]; LCMS: 443 (M+1); (column; X-Select CSH C-18 (50×3.0 mm, 3.5 µm); RT 2.25 min 0.05% Aq TFA: ACN; 0.80 mL/min); UPLC (column; Acquity BEH C18, 50×2.1 mm, 1.7 µm); RT 1.56 min. ACN: 0.025% Aq TFA; 0.5 mL/min; Chiral HPLC: 98.8% RT=16.89 min (CHIRALPAK-ADH (250×4.6 mm, 5 µm; mobile phase (A) 0.1% DEA in n-hexane (B) EtOH:MeOH (50:50) (A:B: 65:35); flow Rate: 1.0 mL/min); Optical rotation $[α]_D^{20.00}$: +16.20 (c=0.25, CH$_2$Cl$_2$).

Example 213

Synthesis of 7, 8-dimethyl-N-(4-(4-methyl-1H-imidazol-1-yl)-3-(trifluoromethoxy) phenyl)-7, 8-dihydro-6H-pyrimido [5, 4-b] [1, 4] oxazin-2-amine

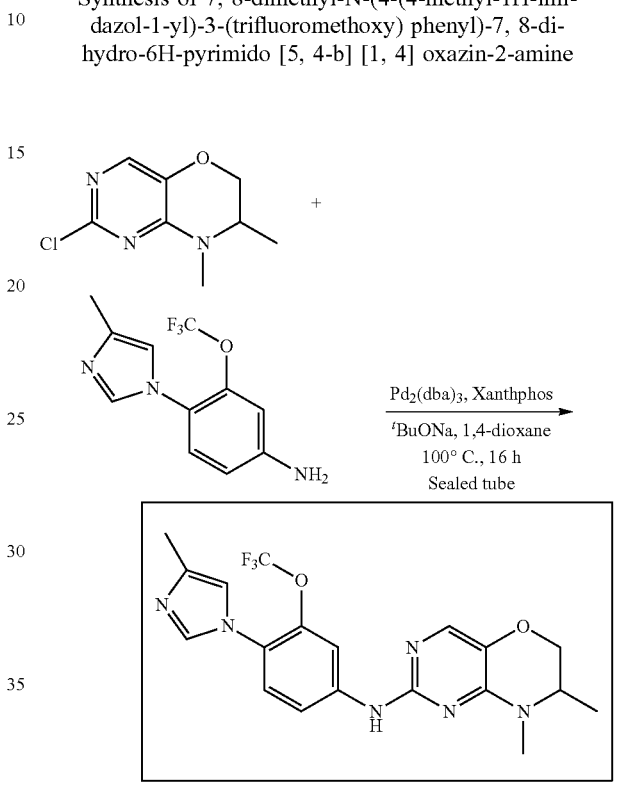

Synthesis of 7, 8-dimethyl-N-(4-(4-methyl-1H-imidazol-1-yl)-3-(trifluoromethoxy) phenyl)-7, 8-dihydro-6H-pyrimido [5, 4-b] [1, 4] oxazin-2-amine To a dry vial was added a suspension of Pd$_2$(dba)$_3$ (53 mg, 0.06 mmol) and Xantphos (100 mg, 0.17 mmol) in 1, 4-dioxane (1.15 mL) at room temperature. The suspension was degassed with argon, heated to 120° C., and stirred for 3 min. A mixture of 2-chloro-7, 8-dimethyl-7, 8-dihydro-6H-pyrimido [5, 4-b] [1, 4] oxazine (230 mg, 1.15 mmol), 4-(4-methyl-1H-imidazol-1-yl)-3-(trifluoromethoxy) aniline (594 mg, 2.31 mmol), sodium tert-butoxide (155 mg, 1.61 mmol) in 1, 4-dioxane (1.15 mL) was degassed and the catalyst premix was added. The resultant mixture was stirred at 100° C. for 16 h in a sealed tube. After consumption of the starting material (monitored by TLC and LCMS), the reaction mixture was diluted with water (50 mL) and extracted with CH$_2$Cl$_2$ (2×50 mL). The combined organic extracts were dried over sodium sulfate, filtered and concentrated in vacuo. The crude material was purified by preparative HPLC (Ascentis C-18 (250×21.2 mm, 5 µm (60 mg loading; CH$_3$CN: 5 mM NH$_4$OAc (0.1/80, 2/80, 10/50, 20/20, 25/10, 35/10)) which was further purified by chiral preparative HPLC to afford 7, 8-dimethyl-N-(4-(4-methyl-1H-imidazol-1-yl)-3-(trifluoromethoxy) phenyl)-7, 8-dihydro-6H-pyrimido [5, 4-b] [1, 4] oxazin-2-amine (200 mg, 38%) as an off-white solid. LCMS: 421 (M+1); (column; X-Select CSH C-18 (50×3.0 mm, 3.5 μm); RT 2.23 min 0.05% Aq TFA: ACN; 0.80 mL/min); UPLC (column; Acquity BEH C18, 50×2.1 mm, 1.7 μm); RT 1.52 min. ACN: 0.025% Aq TFA; 0.5 mL/min; TLC: 5% MeOH/CH$_2$Cl$_2$ (R$_f$: 0.3).

Racemic compound of Example 213 was separated using a Chiralpak IA column (250×20 mm: 5 μm; (30 mg loading; 0.1% DEA in n-hexane: CH$_2$Cl$_2$:MeOH (50:50); (A:B: 90:10) as mobile phase) to provide the compound of Example 213A (Fraction I (−)) and the compound of Example 213B (Fraction II (+)).

Example 213A

Synthesis of (−)-7, 8-dimethyl-N-(4-(4-methyl-1H-imidazol-1-yl)-3-(trifluoromethoxy) phenyl)-7, 8-dihydro-6H-pyrimido [5, 4-b] [1, 4] oxazin-2-amine

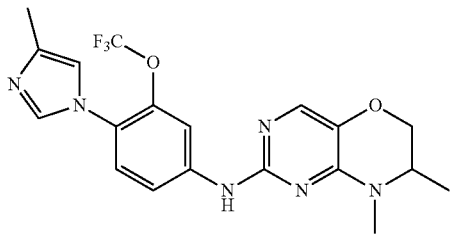 [SMILES: Cc1cn(-c2ccc(Nc3ncc4c(n3)N(C)C(C)CO4)cc2OC(F)(F)F)cn1]

The compound of Example 213A was produced as described in Example 213. Analytical data for product Fraction I (−): $^1$H-NMR (CD$_3$OD, 400 MHz): δ 8.10 (s, 1H), 7.75 (s, 1H), 7.60 (d, 1H), 7.50 (s, 1H), 7.34 (d, 1H), 7.07 (s, 1H), 4.01-.99 (m, 2H), 3.67-3.61 (m, 1H), 3.12 (s, 3H), 2.25 (s, 3H), 1.30 (d, 3H); LCMS: 421.4 (M+1); (column; X-Select CSH C-18 (50×3.0 mm, 3.5 μm); RT 4.20 min 5 mM Aq NH$_4$OAc: ACN; 0.80 mL/min); UPLC (column; Acquity UPLC BEH C18, 50×2.1 mm, 1.7 μm); RT 1.52 min. ACN: 0.025% Aq TFA; 0.5 mL/min; Chiral HPLC: 99.7% RT=20.61 min (CHIRALPAK-IA (250×4.6 mm, 5 μm; mobile phase (A) 0.1% DEA in n-hexane (B) CH$_2$Cl$_2$:MeOH (50:50) (A:B: 90:10); flow Rate: 1.0 mL/min); Optical rotation [α]$_D^{19.99}$: −7.50 (c=0.25, CH$_2$Cl$_2$).

Example 213B

Synthesis of (+)-7, 8-dimethyl-N-(4-(4-methyl-1H-imidazol-1-yl)-3-(trifluoromethoxy) phenyl)-7, 8-dihydro-6H-pyrimido [5, 4-b] [1, 4] oxazin-2-amine

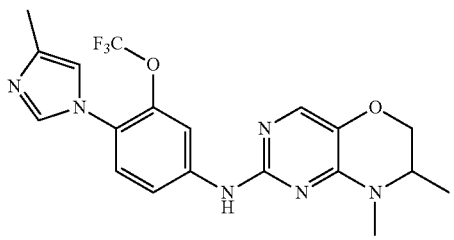 [SMILES: Cc1cn(-c2ccc(Nc3ncc4c(n3)N(C)C(C)CO4)cc2OC(F)(F)F)cn1]

The compound of Example 213B was produced as described in Example 213. Analytical data for product Fraction II (+): $^1$H-NMR (CD$_3$OD, 400 MHz): δ 8.10 (s, 1H), 7.75 (s, 1H), 7.60 (d, 1H), 7.50 (s, 1H), 7.34 (d, 1H), 7.07 (s, 1H), 4.01-.99 (m, 2H), 3.67-3.61 (m, 1H), 3.12 (s, 3H), 2.25 (s, 3H), 1.30 (d, 3H); LCMS: 421.4 (M+1); (column; X-Select CSH C-18 (50×3.0 mm, 3.5 μm); RT 4.19 min 5 mM Aq NH$_4$OAc: ACN; 0.80 mL/min); UPLC (column; Acquity UPLC BEH C18, 50×2.1 mm, 1.7 μm); RT 1.52 min. ACN: 0.025% Aq TFA; 0.5 mL/min; Chiral HPLC: 99.4% RT=24.33 min (CHIRALPAK-IA (250×4.6 mm, 5 μm; mobile phase (A) 0.1% DEA in n-hexane (B) CH$_2$Cl$_2$:MeOH (50:50) (A:B: 90:10); flow Rate: 1.0 mL/min); Optical rotation [α]$_D^{20.00}$: +7.82 (c=0.25, CH$_2$Cl$_2$).

Example 214

Synthesis of N-(3-(difluoromethyl)-4-(4-methyl-1H-imidazol-1-yl) phenyl)-7, 8-dimethyl-7, 8-dihydro-6H-pyrimido [5, 4-b] [1, 4] oxazin-2-amine

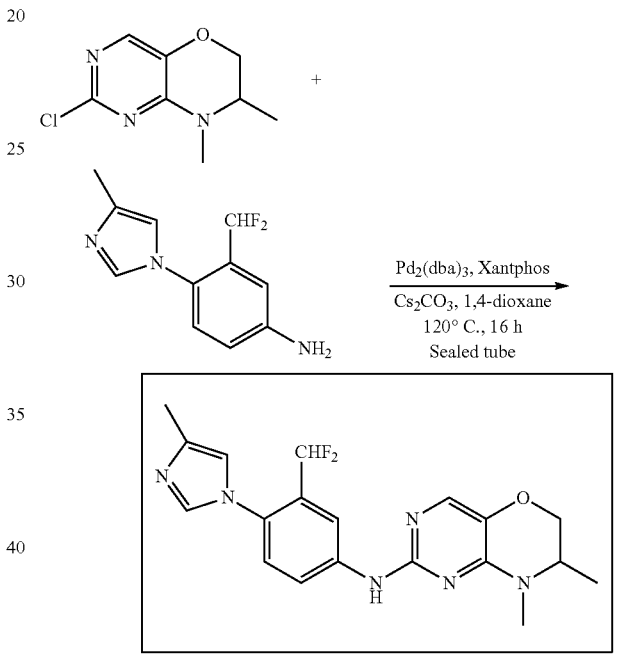

Synthesis of N-(3-(difluoromethyl)-4-(4-methyl-1H-imidazol-1-yl) phenyl)-7, 8-dimethyl-7, 8-dihydro-6H-pyrimido [5, 4-b] [1, 4] oxazin-2-amine To a dry vial was added a suspension of Pd$_2$(dba)$_3$ (57 mg, 0.06 mmol) and Xantphos (108 mg, 0.18 mmol) in 1, 4-dioxane (1.25 mL) at room temperature. The suspension was degassed with argon, heated to 120° C., and stirred for 3 min. A mixture of 2-chloro-7, 8-dimethyl-7, 8-dihydro-6H-pyrimido [5, 4-b] [1, 4] oxazine (250 mg, 1.25 mmol), 3-(difluoromethyl)-4-(4-methyl-1H-imidazol-1-yl) aniline (308 mg, 1.38 mmol) and cesium carbonate (612 mg, 1.88 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the reaction mixture was diluted with water (50 mL) and extracted with CH$_2$Cl$_2$ (2×50 mL). The combined organic extracts were dried over sodium sulfate, filtered and concentrated in vacuo. The crude material was purified by column chromatography using 5% MeOH: CH$_2$Cl$_2$ and further purified by preparative HPLC (Ascentis C-18 (250×21.2 mm, 5 μm (50 mg loading; CH₃CN: 5 mM NH₄OAc (0.1/90, 15/70, 25/20, 30/10, 35/10)) to afford N-(3-(difluoromethyl)-4-(4-methyl-1H-imidazol-1-yl) phenyl)-7, 8-dimethyl-7, 8-dihydro-6H-pyrimido [5, 4-b] [1, 4] oxazin-2-amine (110 mg, 23%) as an off-white solid. LCMS: 387 (M+1); (column; X-Select CSH C-18 (50×3.0 mm, 3.5 μm); RT 2.04 min 0.05% Aq TFA: ACN; 0.80 mL/min); UPLC (column; Acquity BEH C-18 50×2.1 mm, 1.7 μm); RT 1.35 min. ACN: 0.025% Aq TFA; 0.5 mL/min); TLC: 10% MeOH/CH₂Cl₂ (R$_f$; 0.5).

Racemic compound of Example 214 was separated using a Chiralpak ADH column (250×20 mm: 5 μm; (15 mg loading; 0.1% DEA in n-hexane: EtOH:MeOH (25:75); (A:B: 75:25) as mobile phase) to provide the compound of Example 214A (Fraction I (+)) and the compound of Example 214B (Fraction II (−)).

Example 214A

Synthesis of (+)-N-(3-(difluoromethyl)-4-(4-methyl-1H-imidazol-1-yl) phenyl)-7, 8-dimethyl-7, 8-dihydro-6H-pyrimido [5, 4-b] [1, 4] oxazin-2-amine

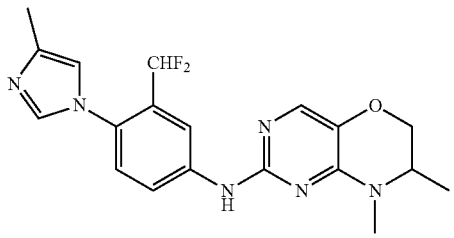 [SMILES: Cc1cn(-c2ccc(Nc3ncc4c(n3)N(C)C(C)CO4)cc2C(F)F)cn1]

The compound of Example 214A was produced as described in Example 214. Analytical data for product Fraction I (+): ¹H-NMR (CD₃OD, 400 MHz): δ 8.39-8.37 (m, 1H), 7.72 (d, 1H), 7.61 (s, 1H), 7.50 (s, 1H), 7.27 (d, 1H), 6.99 (s, 1H), 6.50 (t, 1H), 4.02-4.00 (m, 2H), 3.70-3.64 (m, 1H), 3.20 (s, 3H), 2.24 (s, 3H), 1.31 (s, 3H); Mass (ESI): 387.3 [M+1]; LCMS: 387 (M+1); (column; X-Select CSH C-18 (50×3.0 mm, 3.5 μm); RT 2.45 min. 0.05% Aq TFA: ACN; 0.80 mL/min); UPLC (column; Acquity BEH C-18, 50×2.1 mm, 1.7 μm); RT 1.35 min. ACN: 0.025% Aq TFA; 0.5 mL/min; Chiral HPLC: 99.8% RT=16.05 min (CHIRALPAK-OJ-H (250×4.6 mm, 5 μm; mobile phase (A) 0.1% DEA in n-hexane (B) EtOH:MeOH (25:75) (A:B; 75:25); flow Rate: 1.0 mL/min); Optical rotation $[\alpha]_D^{19.98}$: +4.08 (c=0.25, CH₂Cl₂).

Example 214B

Synthesis of (−)-N-(3-(difluoromethyl)-4-(4-methyl-1H-imidazol-1-yl) phenyl)-7, 8-dimethyl-7, 8-dihydro-6H-pyrimido [5, 4-b] [1, 4] oxazin-2-amine

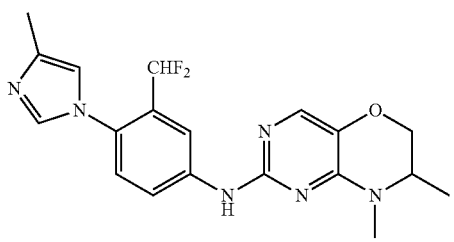 [SMILES: Cc1cn(-c2ccc(Nc3ncc4c(n3)N(C)C(C)CO4)cc2C(F)F)cn1]

The compound of Example 214B was produced as described in Example 214. Analytical data for product Fraction II (−): ¹H-NMR (CD₃OD, 400 MHz): δ 8.39-8.37 (m, 1H), 7.72 (d, 1H), 7.61 (s, 1H), 7.50 (s, 1H), 7.27 (d, 1H), 6.99 (s, 1H), 6.50 (t, 1H), 4.02-4.00 (m, 2H), 3.70-3.64 (m, 1H), 3.20 (s, 3H), 2.24 (s, 3H), 1.31 (s, 3H); Mass (ESI): 387.4 [M+1]; LCMS: 387 (M+1); (column; X-Select CSH C-18 (50×3.0 mm, 3.5 μm); RT 2.06 min. 0.05% Aq TFA: ACN; 0.80 mL/min); UPLC (column; Acquity BEH C-18, 50×2.1 mm, 1.7 μm); RT 1.35 min. ACN: 0.025% Aq TFA; 0.5 mL/min; Chiral HPLC: 98.6% RT=13.68 min (CHIRALPAK-OJ-H (250×4.6 mm, 5 μm; mobile phase (A) 0.1% DEA in n-hexane (B) EtOH:MeOH (25:75) (A:B; 75:25); flow Rate: 1.0 mL/min); Optical rotation $[\alpha]_D^{20.01}$: −4.11 (c=0.25, CH₂Cl₂).

Example 215

Synthesis of 7-(4-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

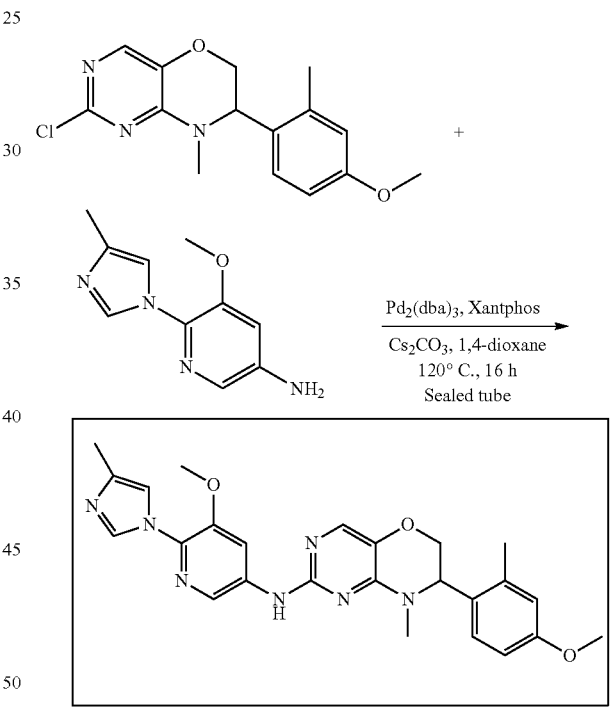

Synthesis of 7-(4-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine To a dry vial was added a suspension of Pd₂(dba)₃ (30 mg, 0.03 mmol) and Xantphos (56 mg, 0.09 mmol) in 1, 4-dioxane (1 mL) at room temperature. The suspension was degassed with argon, heated to 120° C., and stirred for 3 min. A mixture of 2-chloro-7-(4-methoxy-2-methylphenyl)-8-methyl-7, 8-dihydro-6H-pyrimido [5, 4-b] [1, 4] oxazine (200 mg, 0.65 mmol), 5-methoxy-6-(4-methyl-1H-imidazol-1-yl) pyridin-3-amine (267 mg, 1.30 mmol) and cesium carbonate (297 mg, 0.91 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 3% MeOH: CH₂Cl₂ to afford 7-(4-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine (140 mg, 46%) as an off-white solid. LCMS: 474 (M+1); (column; X-select CSH C-18 (50×3.0 mm, 3.5 μm); RT 2.39 min. 0.05% Aq TFA: ACN; 0.8 mL/min); TLC: 5% MeOH/CH₂Cl₂ ($R_f$: 0.3).

Racemic compound of Example 215 was separated using a Chiralpak IC column (250×20 mm: 5 μm; (15 mg loading; 0.1% DEA in n-hexane: CH₂Cl₂:MeOH (50:50); (A:B: 60:40) as mobile phase) to provide the compound of Example 215A (Fraction I (+)) and the compound of Example 215B (Fraction II (−)).

Example 215A

Synthesis of (+)-7-(4-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

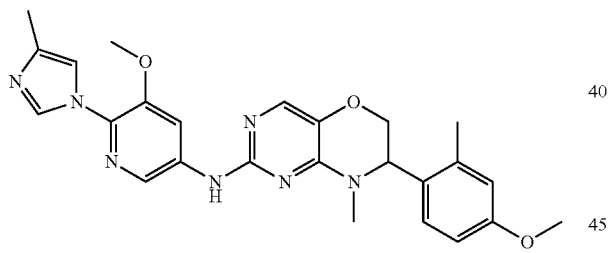

The compound of Example 215A was produced as described in Example 215. Analytical data for product Fraction I (+): ¹H-NMR (CD₃OD, 400 MHz): δ 8.30-8.27 (s, 2H), 8.10 (s, 1H), 7.59 (s, 1H), 7.39 (s, 1H), 6.92 (d, 1H), 6.82-6.80 (m, 1H), 6.73-6.70 (m, 1H), 4.91 (t, 1H), 4.22-4.19 (m, 1H), 4.10-4.07 (m, 1H), 3.96 (s, 3H), 3.78 (s, 3H), 3.08 (s, 3H), 2.39 (s, 3H), 2.22 (s, 3H); Mass (ESI): 474.5 [M+1]; LCMS: 474.1 (M+1); (column; X-Select CSH C-18 (50×3.0 mm, 3.5 μm); RT 2.40 min. 0.05% Aq TFA: ACN; 0.80 mL/min); UPLC (column; Acquity BEH C-18, 50×2.1 mm, 1.7 μm); RT 1.68 min. ACN: 0.025% Aq TFA; 0.5 mL/min; Chiral HPLC: 99.3% RT=13.23 min (CHIRAL-PAK-IC (250×4.6 mm, 5 μm; mobile phase (A) 0.1% DEA in n-hexane (B) CH₂Cl₂:MeOH (50:50) (A:B; 60:40); flow Rate: 1.0 mL/min); Optical rotation $[\alpha]_D^{20.01}$: +196.28 (c=0.25, CH₂Cl₂).

Example 215B

Synthesis of (−)-7-(4-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

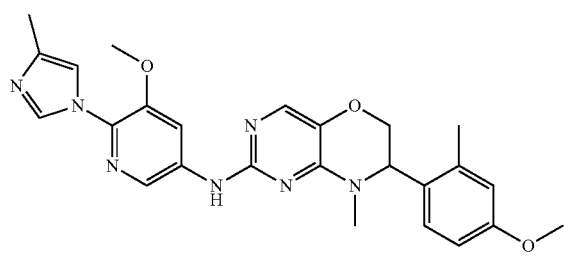

The compound of Example 215B was produced as described in Example 215. Analytical data for product Fraction II (−): ¹H-NMR (CD₃OD, 400 MHz): δ 8.30-8.27 (s, 2H), 8.10 (s, 1H), 7.59 (s, 1H), 7.39 (s, 1H), 6.92 (d, 1H), 6.82-6.80 (m, 1H), 6.73-6.70 (m, 1H), 4.91 (t, 1H), 4.22-4.19 (m, 1H), 4.10-4.07 (m, 1H), 3.96 (s, 3H), 3.78 (s, 3H), 3.08 (s, 3H), 2.39 (s, 3H), 2.22 (s, 3H); Mass (ESI): 474.5 [M+1]; LCMS: 474.1 (M+1); (column; X-Select CSH C-18 (50×3.0 mm, 3.5 μm); RT 2.39 min. 0.05% Aq TFA: ACN; 0.80 mL/min); UPLC (column; Acquity BEH C-18, 50×2.1 mm, 1.7 μm); RT 1.68 min. ACN: 0.025% Aq TFA; 0.5 mL/min; Chiral HPLC: 98.7% RT=14.99 min (CHIRAL-PAK-IC (250×4.6 mm, 5 μm; mobile phase (A) 0.1% DEA in n-hexane (B) CH₂Cl₂:MeOH (50:50) (A:B; 60:40); flow Rate: 1.0 mL/min); Optical rotation $[\alpha]_D^{20.01}$: −188.68 (c=0.25, CH₂Cl₂).

Example 216

Synthesis of 7-(4, 4-difluorocyclohexyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

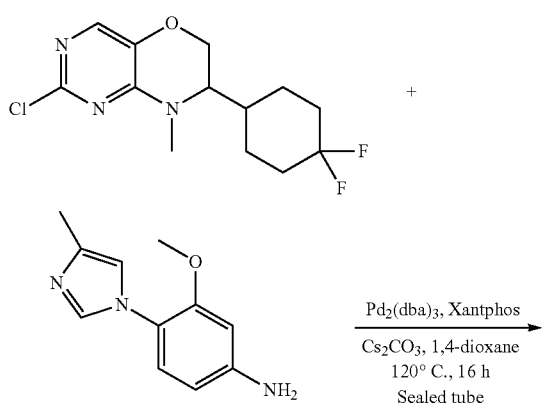

-continued

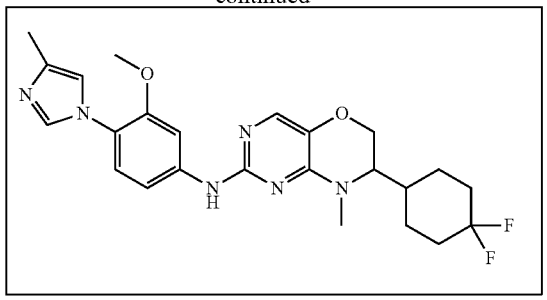

Synthesis of 7-(4, 4-difluorocyclohexyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a dry vial was added a suspension of $Pd_2(dba)_3$ (38 mg, 0.04 mmol) and Xantphos (76 mg, 0.12 mmol) in 1, 4-dioxane (3.5 mL) at room temperature. The suspension was degassed with argon, heated to 120° C., and stirred for 3 min. A mixture of 2-chloro-7-(4, 4-difluorocyclohexyl)-8-methyl-7, 8-dihydro-6H-pyrimido [5, 4-b] [1, 4] oxazine (250 mg, 0.82 mmol), 3-methoxy-4-(4-methyl-1H-imidazol-1-yl) aniline (167 mg, 0.82 mmol) and cesium carbonate (807 mg, 2.47 mmol) in 1, 4-dioxane (3.5 mL) was degassed and the catalyst premix was added. The resultant mixture was stirred at 120° C. for 16 h in a sealed tube. After consumption of the starting material (monitored by TLC and LCMS), the reaction mixture was diluted with water (50 mL) and extracted with $CH_2Cl_2$ (2×50 mL). The combined organic extracts were dried over sodium sulfate, filtered and concentrated in vacuo. The crude material was purified by column chromatography using 1-3% MeOH: $CH_2Cl_2$ and further purified by preparative HPLC (Ascentis C-18 (250× 21.2 mm, 5 μm (50 mg loading; $CH_3CN$: 0.05% TFA water (0.1/95, 15/70, 25/30, 35/10)) to afford 7-(4, 4-difluorocyclohexyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (220 mg, 57%) as an off-white solid. LCMS: 471.1 (M+1); (column; X-Select CSH C-18 (50×3.0 mm, 3.5 μm); RT 2.41 min 0.05% Aq TFA: ACN; 0.80 mL/min); TLC: 5% MeOH/$CH_2Cl_2$ ($R_f$: 0.2).

Racemic compound of Example 216 was separated using a Chiralpak ADH column (250×20 mm: 5 μm; (25 mg loading; 0.1% DEA in n-hexane: EtOH:MeOH (50:50); (A:B: 70:30) as mobile phase) to provide the compound of Example 216A (Fraction I (−)) and the compound of Example 216B (Fraction II (+)).

Example 216A

Synthesis of (−)-7-(4, 4-difluorocyclohexyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

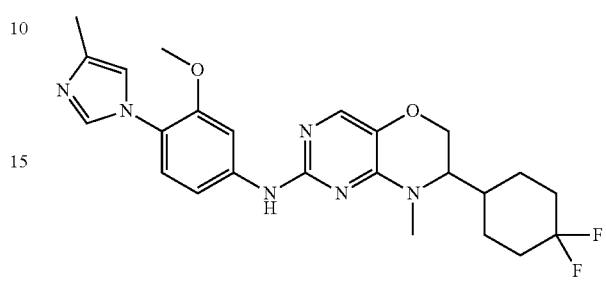

The compound of Example 216A was produced as described in Example 216. Analytical data for product Fraction I (−): $^1$H-NMR (DMSO-$d_6$, 400 MHz): δ 9.01 (s, 1H), 7.83-7.81 (m, 1H), 7.60 (s, 1H), 7.58 (s, 1H), 7.30 (d, 1H), 7.15 (d, 1H), 7.00 (s, 1H), 4.33 (d, 1H), 3.80-3.78 (m, 1H), 3.77 (s, 3H), 3.48-3.45 (m, 1H), 3.20 (s, 3H), 2.11 (s, 3H), 2.10-2.00 (m, 2H), 1.90-1.70 (m, 5H), 1.50-1.33 (m 2H); Mass (ESI): 471.8 [M+1]; LCMS: 471.1 (M+1); (column; X-Select CSH C-18 (50×3.0 mm, 3.5 μm); RT 2.36 min. 0.05% Aq TFA: ACN; 0.80 mL/min); UPLC (column; Acquity BEH C-18, 50×2.1 mm, 1.7 μm); RT 1.65 min. ACN: 0.025% Aq TFA; 0.5 mL/min; Chiral HPLC: 100% RT=13.72 min (CHIRALPAK-ADH (250×4.6 mm, 5 μm; mobile phase (A) 0.1% DEA in n-hexane (B) EtOH:MeOH (50:50) (A:B; 70:30); flow Rate: 1.0 mL/min); Optical rotation $[α]_D^{20.00}$: −74.28 (c=0.25, $CH_2Cl_2$).

Example 216B

Synthesis of (+)-7-(4, 4-difluorocyclohexyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

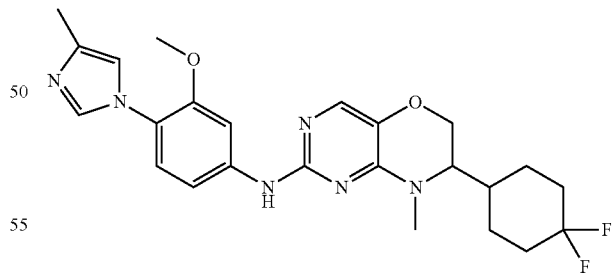

The compound of Example 216B was produced as described in Example 216. Analytical data for product Fraction II (+): $^1$H-NMR (DMSO-$d_6$, 400 MHz): δ 9.01 (s, 1H), 7.83-7.81 (m, 1H), 7.60 (s, 1H), 7.58 (s, 1H), 7.30 (d, 1H), 7.15 (d, 1H), 7.00 (s, 1H), 4.33 (d, 1H), 3.80-3.78 (m, 1H), 3.77 (s, 3H), 3.48-3.45 (m, 1H), 3.20 (s, 3H), 2.11 (s, 3H), 2.10-2.00 (m, 2H), 1.90-1.70 (m, 5H), 1.50-1.33 (m 2H); Mass (ESI): 471.8 [M+1]; LCMS: 471.1 (M+1); (column; X-Select CSH C-18 (50×3.0 mm, 3.5 μm); RT 2.37 min. 0.05% Aq TFA: ACN; 0.80 mL/min); UPLC (column; Acquity BEH C-18, 50×2.1 mm, 1.7 µm); RT 1.66 min. ACN: 0.025% Aq TFA; 0.5 mL/min; Chiral HPLC: 99.1% RT=19.61 min (CHIRALPAK-ADH (250×4.6 mm, 5 µm; mobile phase (A) 0.1% DEA in n-hexane (B) $CH_2Cl_2$: MeOH (50:50) (A:B; 70:30); flow Rate: 1.0 mL/min); Optical rotation $[\alpha]_D^{20.02}$: +77.07 (c=0.25, $CH_2Cl_2$).

Example 217

Synthesis of (S)-7-(cyclopropylmethyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

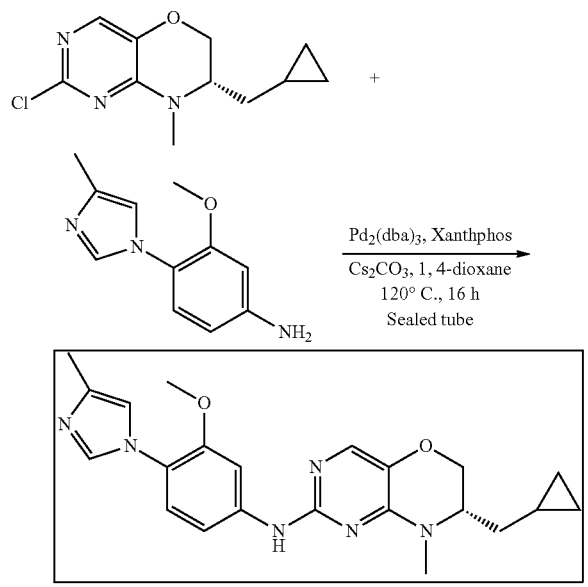

Synthesis of (S)-7-(cyclopropylmethyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a dry vial was added a suspension of $Pd_2(dba)_3$ (48 mg, 0.05 mmol) and Xantphos (91 mg, 0.15 mmol) in 1, 4-dioxane (1 mL) at room temperature. The suspension was degassed with argon, heated to 120° C., and stirred for 3 min. A mixture of (S)-2-chloro-7-(cyclopropylmethyl)-8-methyl-7, 8-dihydro-6H-pyrimido [5, 4-b] [1, 4] oxazine (250 mg, 1.04 mmol), 3-methoxy-4-(4-methyl-1H-imidazol-1-yl) aniline (424 mg, 2.09 mmol), cesium carbonate (477 mg, 1.46 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction mixture was diluted with water (50 mL) and extracted with EtOAc (2×50 mL). The combined organic extracts were dried over sodium sulfate, filtered and concentrated in vacuo. The crude material was purified by column chromatography using 2% MeOH: $CH_2Cl_2$ to afford (S)-7-(cyclopropylmethyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (95 mg, 22%) as an off-white solid.

$^1$H-NMR ($CD_3OD$, 400 MHz): δ 7.74 (s, 1H), 7.68 (s, 1H), 7.48 (s, 1H), 7.19-7.17 (m, 1H), 7.15 (s, 1H), 6.97 (s, 1H), 4.38 (dd, 1H), 3.95 (dd, 1H), 3.85 (s, 3H), 3.59 (t, 1H), 3.24 (s, 3H), 2.23 (s, 3H), 1.73-1.65 (m, 1H), 1.57-1.48 (m, 1H), 0.80-0.73 (m, 1H), 0.55-0.40 (m, 2H), 0.20-0.08 (m, 2H); Mass (ESI): 407.4 [M+1]; LCMS: 407.4 (M+1); (column; X-Select CSH C-18 (50×3.0 mm, 3.5 µm); RT 4.31 min 5 mM Aq $NH_4OAc$: ACN; 0.80 mL/min); HPLC (column; Eclipse XDB C-18, 150×4.6 mm, 5.0 µm); RT 10.84 min. ACN: 5 mM Aq $NH_4OAc$; 1.0 mL/min; Chiral HPLC: 96.5% RT=10.37 min (CHIRALPAK-IA (250×4.6 mm, 5µ; mobile phase (A) 0.1% DEA in n-hexane (B) $CH_2Cl_2$:MeOH (50:50) (A:B; 70:30); flow Rate: 1.0 mL/min); Optical rotation $[\alpha]_D^{20.02}$: +53.28 (c=0.25, $CH_2Cl_2$); TLC: 5% MeOH/$CH_2Cl_2$ ($R_f$: 0.3).

Example 218

Synthesis of (S)-7-(cyclopropylmethyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

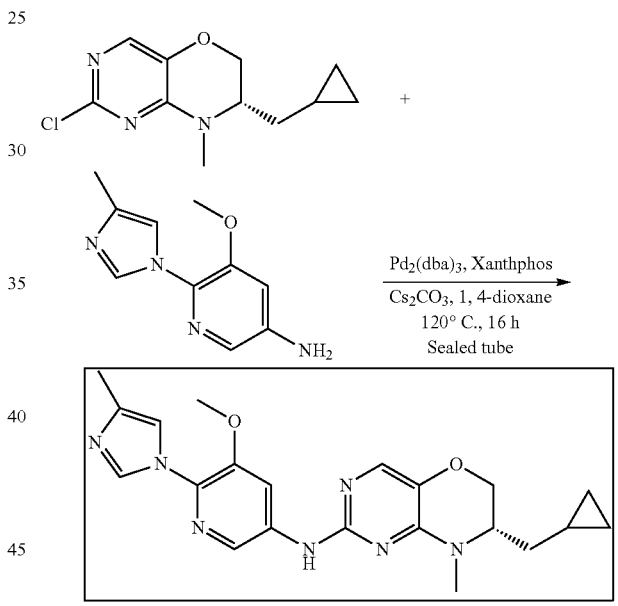

Synthesis of (S)-7-(cyclopropylmethyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine)

To a dry vial was added a suspension of $Pd_2(dba)_3$ (29 mg, 0.03 mmol) and Xantphos (54 mg, 0.09 mmol) in 1, 4-dioxane (1 mL) at room temperature. The suspension was degassed with argon, heated to 120° C., and stirred for 3 min. A mixture of (S)-2-chloro-7-(cyclopropylmethyl)-8-methyl-7, 8-dihydro-6H-pyrimido [5, 4-b] [1, 4] oxazine (150 mg, 0.62 mmol), 5-methoxy-6-(4-methyl-1H-imidazol-1-yl) pyridin-3-amine (256 mg, 1.25 mmol), cesium carbonate (286 mg, 0.87 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 5% MeOH: CH$_2$Cl$_2$ to afford (S)-7-(cyclopropylmethyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine (60 mg, 23%) as an off-white solid. $^1$H-NMR (CD$_3$OD, 400 MHz): δ 8.27 (d, 2H), 8.12 (s, 1H), 7.51 (s, 1H), 7.38 (s, 1H), 4.39 (dd, 1H), 3.96 (s, 3H), 3.95-3.93 (m, 1H), 3.62-3.56 (m, 1H), 3.21 (s, 3H), 2.21 (s, 3H), 1.70-1.66 (m, 1H), 1.52-1.47 (m, 1H), 0.80-0.73 (m, 1H), 0.52-0.47 (m, 2H), 0.20-0.08 (m, 2H); Mass (ESI): 408.6 [M+1]; LCMS: 408.1 (M+1); (column; X-Select CSH C-18 (50×3.0 mm, 3.5 μm); RT 2.23 min 0.05% Aq TFA: ACN; 0.80 mL/min); UPLC (column; Acquity BEH C-18, 50×2.1 mm, 1.7 μm); RT 2.21 min. ACN: 0.025% Aq TFA; 0.5 mL/min; Chiral HPLC: 98.7% RT=7.83 min (CHIRALPAK-IA (250×4.6 mm, 5μ; mobile phase (A) 0.1% DEA in n-hexane (B) CH$_2$Cl$_2$:MeOH (50: 50) (A:B; 70:30); flow Rate: 1.0 mL/min); Optical rotation $[α]_D^{20.00}$: +61.34 (c=0.25, CH$_2$Cl$_2$); TLC: 5% MeOH/CH$_2$Cl$_2$ (R$_f$; 0.3).

Example 219

Synthesis of 7-(3, 3-difluorocyclobutyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

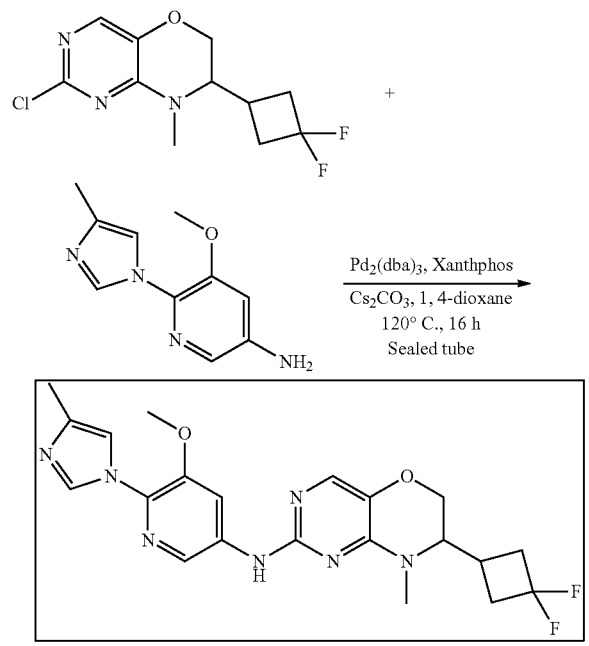

Synthesis of 7-(3, 3-difluorocyclobutyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine To a dry vial was added a suspension of Pd$_2$(dba)$_3$ (42 mg, 0.04 mmol) and Xantphos (79 mg, 0.13 mmol) in 1, 4-dioxane (1.25 mL) at room temperature. The suspension was degassed with argon, heated to 120° C., and stirred for 3 min. A mixture of 2-chloro-7-(3, 3-difluorocyclobutyl)-8-methyl-7, 8-dihydro-6H-pyrimido [5, 4-b] [1, 4] oxazine (250 mg, 0.90 mmol), 5-methoxy-6-(4-methyl-1H-imidazol-1-yl) pyridin-3-amine (370 mg, 1.81 mmol), cesium carbonate (890 mg, 2.72 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the volatile components were evaporated in vacuo. The residue was diluted with water (20 mL) and extracted with CH$_2$Cl$_2$ (2×20 mL). The combined organic extracts were dried over sodium sulfate, filtered and concentrated in vacuo. The crude material was purified by column chromatography using 3% EtOAc:hexane to afford 7-(3, 3-difluorocyclobutyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine (150 mg, 37%) as an off-white solid. LCMS: 444.1 (M+1); (column; X-Select CSH C-18 (50×3.0 mm, 3.5 μm); RT 2.20 min 0.05% Aq TFA: ACN; 0.80 mL/min); TLC: 5% EtOAc:hexane (R$_f$; 0.3).

Racemic compound of Example 219 was separated using a Chiralpak IA column (250×20 mm: 5 μm; (10 mg loading; 0.1% DEA in n-hexane: CH$_2$Cl$_2$:MeOH (50:50); (A:B: 75:25) as mobile phase) to provide the compound of Example 219A (Fraction I (+)) and the compound of Example 219B (Fraction II (−)).

Example 219A

Synthesis of (+)-7-(3, 3-difluorocyclobutyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

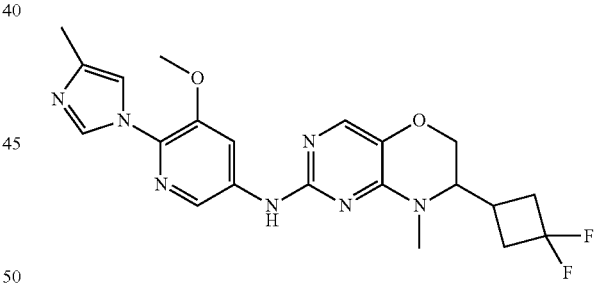

The compound of Example 219A was produced as described in Example 219. Analytical data for product Fraction I (+): $^1$H-NMR (CD$_3$OD, 400 MHz): δ 8.30-8.25 (m, 2H), 8.12 (s, 1H), 7.57 (s, 1H), 7.39 (s, 1H), 4.19 (dd, 1H), 3.97 (s, 3H), 3.90 (dd, 1H), 3.61 (d, 1H), 3.29 (s, 3H), 2.79-2.60 (m, 3H), 2.57-2.40 (m, 2H), 2.25 (s, 3H); Mass (ESI): 444.5 [M+1]; LCMS: 444.1 (M+1); (column; X-Select CSH C-18 (50×3.0 mm, 3.5 μm); RT 2.22 min 0.05% Aq TFA: ACN; 0.80 mL/min); UPLC (column; Acquity BEH C-18, 50×2.1 mm, 1.7 μm); RT 1.48 min. ACN: 0.025% Aq TFA; 0.5 mL/min; Chiral HPLC: 99.5% RT=12.33 min (CHIRALPAK-IA (250×4.6 mm, 5μ; mobile phase (A) 0.1% DEA in n-hexane (B) CH$_2$Cl$_2$:MeOH (50:50) (A:B; 75:25); flow Rate: 1.0 mL/min); Optical rotation $[α]_D^{19.98}$: +20.11 (c=0.25, CH$_2$Cl$_2$).

Example 219B

Synthesis of (−)-7-(3, 3-difluorocyclobutyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

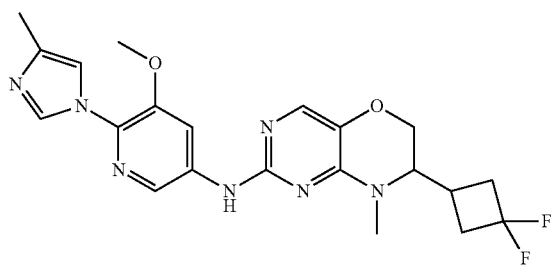

The compound of Example 219B was produced as described in Example 219. Analytical data for product Fraction II (−): $^1$H-NMR (CD$_3$OD, 400 MHz): δ 8.30-8.25 (m, 2H), 8.12 (s, 1H), 7.57 (s, 1H), 7.39 (s, 1H), 4.19 (dd, 1H), 3.97 (s, 3H), 3.90 (dd, 1H), 3.61 (d, 1H), 3.29 (s, 3H), 2.79-2.60 (m, 3H), 2.57-2.40 (m, 2H), 2.25 (s, 3H); Mass (ESI): 444.5 [M+1]; LCMS: 444 (M+1); (column; X-Select CSH C-18 (50×3.0 mm, 3.5 μm); RT 2.21 min 0.05% Aq TFA: ACN; 0.80 mL/min); UPLC (column; Acquity BEH C-18, 50×2.1 mm, 1.7 μm); RT 1.47 min. ACN: 0.025% Aq TFA; 0.5 mL/min; Chiral HPLC: 97.6% RT=13.34 min (CHIRALPAK-IA (250×4.6 mm, 5μ; mobile phase (A) 0.1% DEA in n-hexane (B) CH$_2$Cl$_2$:MeOH (50:50) (A:B; 75:25); flow Rate: 1.0 mL/min); Optical rotation $[α]_D^{20.01}$: −14.78 (c=0.25, CH$_2$Cl$_2$).

Example 220

Synthesis of 7-(3, 5-difluorophenyl)-N-(4-methoxy-5-(4-methyl-1H-imidazol-1-yl) pyridin-2-yl)-8-methyl-7, 8-dihydro-6H-pyrimido [5, 4-b] [1, 4] oxazin-2-amine

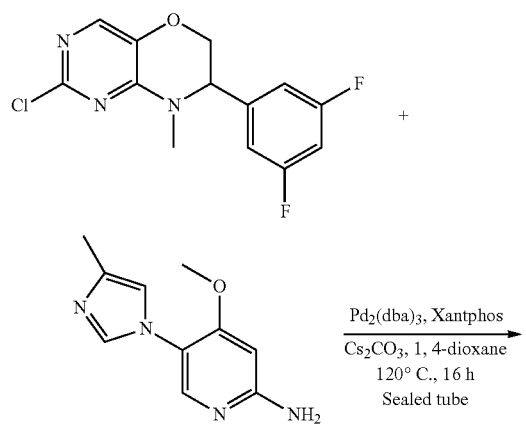

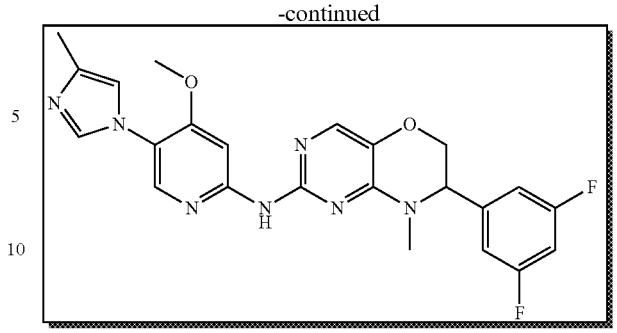

Synthesis of 7-(3, 5-difluorophenyl)-N-(4-methoxy-5-(4-methyl-1H-imidazol-1-yl) pyridin-2-yl)-8-methyl-7, 8-dihydro-6H-pyrimido [5, 4-b] [1, 4] oxazin-2-amine To a dry vial was added a suspension of Pd$_2$(dba)$_3$ (38 mg, 0.04 mmol) and Xantphos (72 mg, 0.12 mmol) in 1, 4-dioxane (1.25 mL) at room temperature. The suspension was degassed with argon, heated to 120° C., and stirred for 3 min. A mixture of 2-chloro-7-(3, 5-difluorophenyl)-8-methyl-7, 8-dihydro-6H-pyrimido [5, 4-b] [1, 4] oxazine (250 mg, 0.84 mmol), 4-methoxy-5-(4-methyl-1H-imidazol-1-yl) pyridin-2-amine (343 mg, 1.68 mmol) and cesium carbonate (383 mg, 1.17 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the volatile components were concentrated in vacuo. The crude material was purified by column chromatography using 3% MeOH: CH$_2$Cl$_2$ to afford 7-(3, 5-difluorophenyl)-N-(4-methoxy-5-(4-methyl-1H-imidazol-1-yl) pyridin-2-yl)-8-methyl-7, 8-dihydro-6H-pyrimido [5, 4-b] [1, 4] oxazin-2-amine (180 mg, 46%) as an off-white solid. LCMS: 466 (M+1); (column; X-Select CSH C-18 (50×3.0 mm, 3.5 μm); RT 2.26 min 0.05% Aq TFA: ACN; 0.80 mL/min); HPLC (column; Eclipse XDB-C-18 150×4.6 mm, 5.0 μm); RT 10.40 min. ACN: 5 mM Aq NH$_4$OAc; 1.0 mL/min; TLC: 5% MeOH/CH$_2$Cl$_2$ (R$_f$: 0.3).

Racemic compound of Example 220 was separated using a Chiralpak IA column (250×20 mm: 5 μm; (40 mg loading; 0.1% DEA in n-hexane: CH$_2$Cl$_2$:MeOH (50:50); (A:B: 70:30) as mobile phase) to provide the compound of Example 220A (Fraction I (−)) and the compound of Example 220B (Fraction II (+)).

Example 220A

Synthesis of (−)-7-(3, 5-difluorophenyl)-N-(4-methoxy-5-(4-methyl-1H-imidazol-1-yl) pyridin-2-yl)-8-methyl-7, 8-dihydro-6H-pyrimido [5, 4-b] [1, 4] oxazin-2-amine

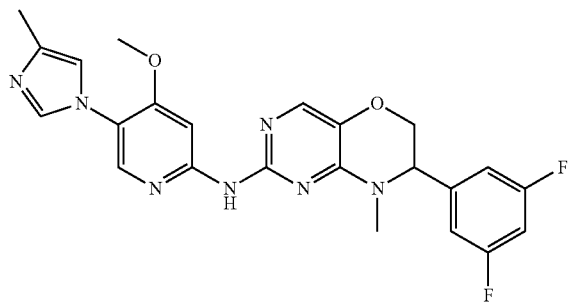 [SMILES: COc1cc(Nc2ncc3c(n2)N(C)C(c2cc(F)cc(F)c2)CO3)ncc1-n1cnc(C)c1]

The compound of Example 220A was produced as described in Example 220. Analytical data for product Fraction I (−): ¹H-NMR (DMSO-d$_6$, 400 MHz): δ 9.30 (s, 1H), 8.25 (s, 1H), 8.00 (s, 1H), 7.70 (s, 1H), 7.68 (s, 1H), 7.25-7.20 (m, 1H), 7.04 (s, 1H), 6.99 (d, 2H), 4.92-4.90 (m, 1H), 4.32-4.30 (m, 1H), 4.22-4.19 (m, 1H), 3.88 (s, 3H), 3.13 (s, 3H), 2.12 (s, 3H); Mass (ESI): 466.5 [M+1]; LCMS: 466 (M+1); (column; X-Select CSH C-18 (50×3.0 mm, 3.5 μm); RT 2.27 min. 0.05% Aq TFA: ACN; 0.80 mL/min); UPLC (column; Acquity BEH C-18, 50×2.1 mm, 1.7 μm); RT 1.58 min. ACN: 0.025% Aq TFA; 0.5 mL/min; Chiral HPLC: 98.7% RT=12.32 min (CHIRALPAK-IA (250×4.6 mm, 5 μm; mobile phase (A) 0.1% DEA in n-hexane (B) CH$_2$Cl$_2$:MeOH (80:20) (A:B; 70:30); flow Rate: 1.0 mL/min); Optical rotation [α]$_D^{19.98}$: −104.01 (c=0.25, CH$_2$Cl$_2$).

Example 220B

Synthesis of (+)-7-(3, 5-difluorophenyl)-N-(4-methoxy-5-(4-methyl-1H-imidazol-1-yl) pyridin-2-yl)-8-methyl-7, 8-dihydro-6H-pyrimido [5, 4-b] [1, 4] oxazin-2-amine

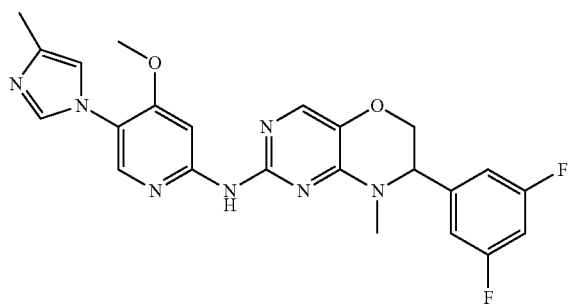 [SMILES: COc1cc(Nc2ncc3c(n2)N(C)C(c2cc(F)cc(F)c2)CO3)ncc1-n1cnc(C)c1]

The compound of Example 220B was produced as described in Example 220. Analytical data for product Fraction II (+): ¹H-NMR (DMSO-d$_6$, 400 MHz): δ 9.30 (s, 1H), 8.25 (s, 1H), 8.00 (s, 1H), 7.70 (s, 1H), 7.68 (s, 1H), 7.25-7.20 (m, 1H), 7.04 (s, 1H), 6.99 (d, 2H), 4.92-4.90 (m, 1H), 4.32-4.30 (m, 1H), 4.22-4.19 (m, 1H), 3.88 (s, 3H), 3.13 (s, 3H), 2.12 (s, 3H); Mass (ESI): 466.6 [M+1]; LCMS: 466 (M+1); (column; X-Select CSH C-18 (50×3.0 mm, 3.5 μm); RT 2.26 min. 0.05% Aq TFA: ACN; 0.80 mL/min); UPLC (column; Acquity BEH C-18, 50×2.1 mm, 1.7 μm); RT 1.58 min. ACN: 0.025% Aq TFA; 0.5 mL/min; Chiral HPLC: 98.5% RT=16.22 min (CHIRALPAK-IA (250×4.6 mm, 5 μm; mobile phase (A) 0.1% DEA in n-hexane (B) CH$_2$Cl$_2$:MeOH (50:50) (A:B; 70:30); flow Rate: 1.0 mL/min); Optical rotation [α]$_D^{19.99}$: +88.78 (c=0.25, CH$_2$Cl$_2$).

Example 221

Synthesis of 7-(4, 4-difluorocyclohexyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

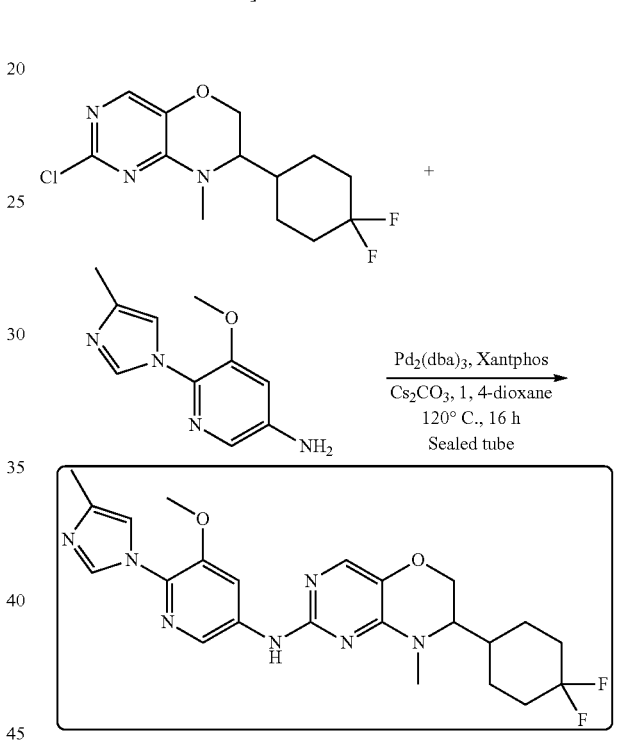

Synthesis of 7-(4, 4-difluorocyclohexyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine To a dry vial was added a suspension of Pd$_2$(dba)$_3$ (37 mg, 0.04 mmol) and Xantphos (71 mg, 0.12 mmol) in 1, 4-dioxane (1.25 mL) at room temperature. The suspension was degassed with argon, heated to 120° C., and stirred for 3 min. A mixture of 2-chloro-7-(4, 4-difluorocyclohexyl)-8-methyl-7, 8-dihydro-6H-pyrimido [5, 4-b] [1, 4] oxazine (250 mg, 0.82 mmol), 5-methoxy-6-(4-methyl-1H-imidazol-1-yl) pyridin-3-amine (336 mg, 1.65 mmol) and cesium carbonate (376 mg, 1.15 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the volatile components were concentrated in vacuo. The crude material was purified by column chromatography using 5% MeOH: EtOAc to afford 7-(4, 4-difluorocyclohexyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine (32 mg, 12%) as an off-white solid. LCMS: 472.1 (M+1); (column; X-Select CSH C-18 (50×3.0 mm, 3.5 μm); RT 2.33 min 0.05% Aq TFA: ACN; 0.80 mL/min); UPLC (column; Acquity BEH C-18 50×2.1 mm, 1.7 μm); RT 1.58 min. ACN: 0.025% Aq TFA; 0.5 mL/min; TLC: 5% MeOH/CH$_2$Cl$_2$ (R$_f$: 0.3).

Racemic compound of Example 221 was separated using a Chiralpak IC column (250×20 mm: 5 μm; (100 mg loading; 0.1% DEA in n-hexane: CH$_2$Cl$_2$:MeOH (80:20); (A:B: 60:40) as mobile phase) to provide the compound of Example 221A (Fraction I (+)) and the compound of Example 221B (Fraction II (−)).

Example 221A

Synthesis of (+)-7-(4, 4-difluorocyclohexyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

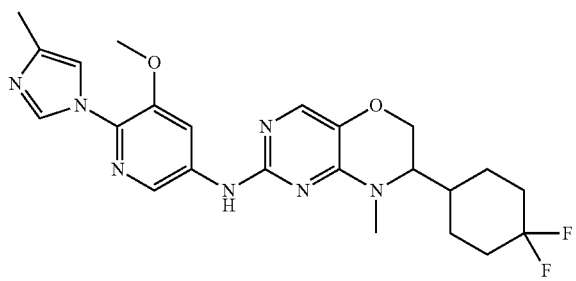

The compound of Example 221A was produced as described in Example 221. Analytical data for product Fraction I (+): $^1$H-NMR (DMSO-d$_6$, 400 MHz): δ 9.30 (s, 1H), 8.32-8.30 (m, 2H), 8.01 (s, 1H), 7.60 (s, 1H), 7.35 (s, 1H), 4.39-4.33 (m, 1H), 3.88 (s, 3H), 3.78 (d, 1H), 3.50-3.47 (m, 1H), 3.20 (s, 3H), 2.12 (s, 3H), 2.07-1.93 (m, 2H), 1.90-1.70 (m, 5H), 1.50-1.30 (m, 2H); Mass (ESI): 472.5 [M+1]; LCMS: 472.1 (M+1); (column; X-Select CSH C-18 (50×3.0 mm, 3.5 μm); RT 2.32 min. 0.05% Aq TFA: ACN; 0.80 mL/min); UPLC (column; Acquity BEH C-18, 50×2.1 mm, 1.7 μm); RT 1.59 min. ACN: 0.025% Aq TFA; 0.5 mL/min; Chiral HPLC: 100% RT=16.56 min (CHIRALPAK-IC (250×4.6 mm, 5 μm; mobile phase (A) 0.1% DEA in n-hexane (B) CH$_2$Cl$_2$:MeOH (80:20) (A:B; 60:40); flow Rate: 1.0 mL/min); Optical rotation [α]$_D^{19.99}$: +64.86 (c=0.25, CH$_2$Cl$_2$).

Example 221B

Synthesis of (−)-7-(4, 4-difluorocyclohexyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

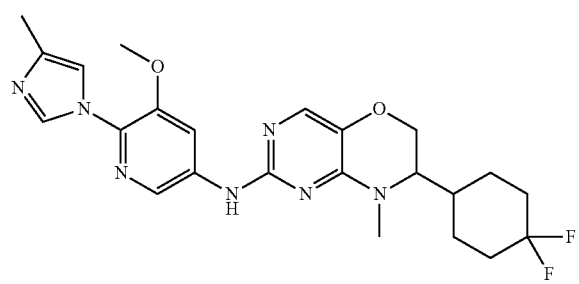

The compound of Example 221B was produced as described in Example 221. Analytical data for product Fraction II (−): $^1$H-NMR (DMSO-d$_6$, 400 MHz): δ 9.30 (s, 1H), 8.32-8.30 (m, 2H), 8.01 (s, 1H), 7.60 (s, 1H), 7.35 (s, 1H), 4.39-4.33 (m, 1H), 3.88 (s, 3H), 3.78 (d, 1H), 3.50-3.47 (m, 1H), 3.20 (s, 3H), 2.12 (s, 3H), 2.07-1.93 (m, 2H), 1.90-1.70 (m, 5H), 1.50-1.30 (m, 2H); Mass (ESI): 472.5 [M+1]; LCMS: 472.1 (M+1); (column; X-Select CSH C-18 (50×3.0 mm, 3.5 μm); RT 2.32 min. 0.05% Aq TFA: ACN; 0.80 mL/min); UPLC (column; Acquity BEH C-18, 50×2.1 mm, 1.7 μm); RT 1.59 min. ACN: 0.025% Aq TFA; 0.5 mL/min; Chiral HPLC: 97.8% RT=19.22 min (CHIRALPAK-IC (250×4.6 mm, 5 μm; mobile phase (A) 0.1% DEA in n-hexane (B) CH$_2$Cl$_2$:MeOH (80:20) (A:B; 60:40); flow Rate: 1.0 mL/min); Optical rotation [α]$_D^{20.00}$: −59.63 (c=0.25, CH$_2$Cl$_2$).

Example 222

Synthesis of N-(3-(difluoromethyl)-4-(4-methyl-1H-imidazol-1-yl) phenyl)-7-(3, 5-difluorophenyl)-8-methyl-7, 8-dihydro-6H-pyrimido [5, 4-b] [1, 4] oxazin-2-amine

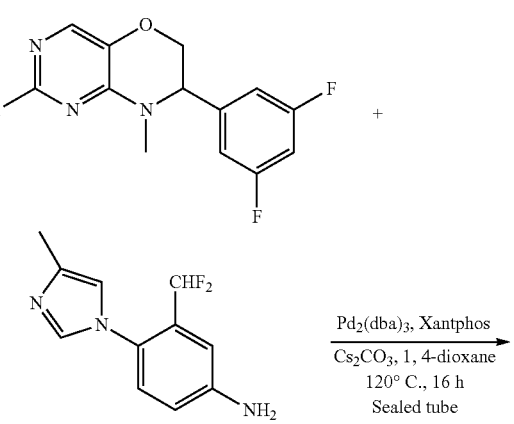

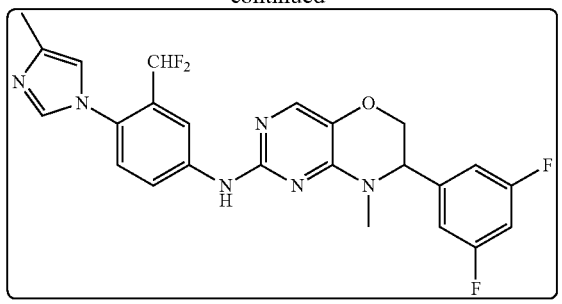

Synthesis of N-(3-(difluoromethyl)-4-(4-methyl-1H-imidazol-1-yl) phenyl)-7-(3, 5-difluorophenyl)-8-methyl-7, 8-dihydro-6H-pyrimido [5, 4-b] [1, 4] oxazin-2-amine To a dry vial was added a suspension of Pd$_2$(dba)$_3$ (30 mg, 0.03 mmol) and Xantphos (60 mg, 0.10 mmol) in 1, 4-dioxane (1.5 mL) at room temperature. The suspension was degassed with argon, heated to 120° C., and stirred for 3 min. A mixture of 2-chloro-7-(3, 5-difluorophenyl)-8-methyl-7, 8-dihydro-6H-pyrimido [5, 4-b] [1, 4] oxazine (200 mg, 0.67 mmol), 3-(difluoromethyl)-4-(4-methyl-1H-imidazol-1-yl) aniline (300 mg, 1.30 mmol) and cesium carbonate (311 mg, 0.90 mmol) in 1, 4-dioxane (1.5 mL) was degassed and the catalyst premix was added. The resultant mixture was stirred at 120° C. for 16 h in a sealed tube. After consumption of the starting material (monitored by TLC and LCMS), the volatile components were concentrated in vacuo. The crude material was purified by preparative HPLC (Ascentis C-18 (250×21.2 mm, 5 μm (60 mg loading; CH$_3$CN: 5 mM NH$_4$OAc (0.1/90, 2/85, 15/70, 25/20, 30/10, 35/10)) to afford N-(3-(difluoromethyl)-4-(4-methyl-1H-imidazol-1-yl) phenyl)-7-(3, 5-difluorophenyl)-8-methyl-7, 8-dihydro-6H-pyrimido [5, 4-b] [1, 4] oxazin-2-amine (150 mg, 46%) as an off-white solid. LCMS: 485.1 (M+1); (column; X-Select CSH C-18 (50×3.0 mm, 3.5 μm); RT 2.44 min 0.05% Aq TFA: ACN; 0.80 mL/min); TLC: 5% MeOH/CH$_2$Cl$_2$ (R$_f$: 0.2).

Racemic compound of Example 222 was separated using a Chiralpak ADH column (250×20 mm: 5 μm; (40 mg loading; 0.1% DEA in n-hexane; EtOH (A:B; 60:40) as mobile phase) to provide the compound of Example 222A (Fraction I (+)) and the compound of Example 222B (Fraction II (−)).

Example 222A

Synthesis of (+)-N-(3-(difluoromethyl)-4-(4-methyl-1H-imidazol-1-yl) phenyl)-7-(3, 5-difluorophenyl)-8-methyl-7, 8-dihydro-6H-pyrimido [5, 4-b] [1, 4] oxazin-2-amine

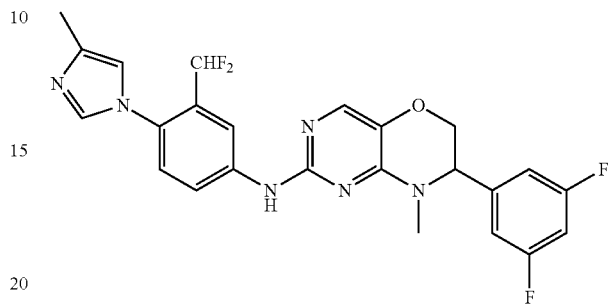

The compound of Example 222A was produced as described in Example 222. Analytical data for product Fraction I (+): $^1$H-NMR (CD$_3$OD, 500 MHz): δ 8.38 (s, 1H), 7.83 (d, 1H), 7.66 (d, 2H), 7.31 (d, 1H), 7.01 (s, 1H), 6.94 (t, 1H), 6.88 (d, 2H), 652 (t, 1H), 4.75 (br s, 1H), 4.25 (s, 2H), 3.18 (s, 3H), 2.27 (s, 3H); Mass (ESI): 485.5 [M+1]; LCMS: 485 (M+1); (column; X-Select CSH C-18 (50×3.0 mm, 3.5 μm); RT 2.46 min. 0.05% Aq TFA: ACN; 0.80 mL/min); UPLC (column; Acquity BEH C-18, 50×2.1 mm, 1.7 μm); RT 1.71 min. ACN: 0.025% Aq TFA; 0.5 mL/min; Chiral HPLC: 100% RT=13.08 min (CHIRALPAK-ADH (250×4.6 mm, 5 μm; mobile phase (A) 0.1% DEA in n-hexane (B) EtOH (A:B; 60:40); flow Rate: 1.0 mL/min); Optical rotation [α]$_D^{20.02}$: +118.80 (c=0.25, CH$_2$Cl$_2$).

Example 222B

Synthesis of (−)-N-(3-(difluoromethyl)-4-(4-methyl-1H-imidazol-1-yl) phenyl)-7-(3, 5-difluorophenyl)-8-methyl-7, 8-dihydro-6H-pyrimido [5, 4-b] [1, 4] oxazin-2-amine

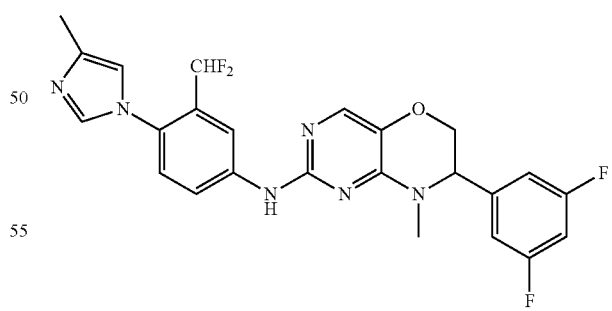

The compound of Example 222B was produced as described in Example 222. Analytical data for product Fraction II (−): $^1$H-NMR (CD$_3$OD, 500 MHz): δ 8.38 (s, 1H), 7.83 (d, 1H), 7.66 (d, 2H), 7.31 (d, 1H), 7.01 (s, 1H), 6.94 (t, 1H), 6.88 (d, 2H), 652 (t, 1H), 4.75 (br s, 1H), 4.25 (s, 2H), 3.18 (s, 3H), 2.27 (s, 3H); Mass (ESI): 485.4 [M+1]; LCMS: 485 (M+1); (column; X-Select CSH C-18 (50×3.0 mm, 3.5 μm); RT 2.46 min. 0.05% Aq TFA: ACN; 0.80 mL/min); UPLC (column; Acquity BEH C-18, 50×2.1 mm, 1.7 µm); RT 1.73 min. ACN: 0.025% Aq TFA; 0.5 mL/min; Chiral HPLC: 100% RT=29.06 min (CHIRALPAK-ADH (250×4.6 mm, 5 µm; mobile phase (A) 0.1% DEA in n-hexane (B) EtOH (A:B; 60:40); flow Rate: 1.0 mL/min); Optical rotation $[\alpha]_D^{20.00}$: –121.32 (c=0.25, CH$_2$Cl$_2$).

Example 223

Synthesis of 7-(3, 5-difluorophenyl)-8-methyl-N-(4-(4-methyl-1H-imidazol-1-yl)-3-(trifluoromethoxy) phenyl)-7, 8-dihydro-6H-pyrimido [5, 4-b] [1, 4] oxazin-2-amine

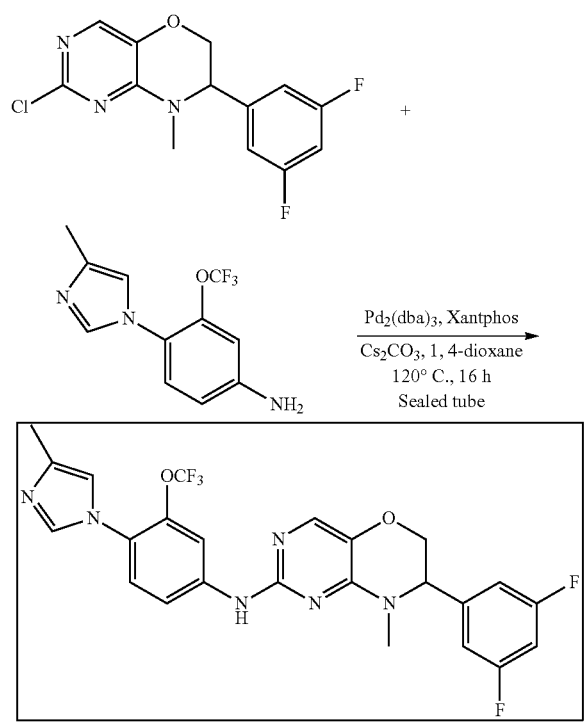

Synthesis of 7-(3, 5-difluorophenyl)-8-methyl-N-(4-(4-methyl-1H-imidazol-1-yl)-3-(trifluoromethoxy) phenyl)-7, 8-dihydro-6H-pyrimido [5, 4-b] [1, 4] oxazin-2-amine To a dry vial was added a suspension of Pd$_2$(dba)$_3$ (30 mg, 0.03 mmol) and Xantphos (60 mg, 0.10 mmol) in 1, 4-dioxane (1 mL) at room temperature. The suspension was degassed with argon, heated to 120° C., and stirred for 3 min. A mixture of 2-chloro-7-(3, 5-difluorophenyl)-8-methyl-7, 8-dihydro-6H-pyrimido [5, 4-b] [1, 4] oxazine (200 mg, 0.67 mmol), 4-(4-methyl-1H-imidazol-1-yl)-3-(trifluoromethoxy) aniline (350 mg, 1.30 mmol) and cesium carbonate (310 mg, 0.90 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by preparative HPLC (Ascentis C-18 (250×21.2 mm, 5 µm (70 mg loading; CH$_3$CN: TFA (0.01/90, 15/70, 25/30, 30/10)) to afford 7-(3, 5-difluorophenyl)-8-methyl-N-(4-(4-methyl-1H-imidazol-1-yl)-3-(trifluoromethoxy) phenyl)-7, 8-dihydro-6H-pyrimido [5, 4-b] [1, 4] oxazin-2-amine (150 mg, 43%) as an off-white solid. LCMS: 519.1 (M+1); (column; X-select CSH C-18 (50×3.0 mm, 3.5 µm); RT 2.58 min 0.05% Aq TFA: ACN; 0.8 mL/min); TLC: 5% MeOH/ CH$_2$Cl$_2$ (R$_f$: 0.2).

Racemic compound of Example 223 was separated using a Chiralpak AD-H column (250×20 mm: 5 µm; (50 mg loading; 0.1% DEA in n-hexane: EtOH:MeOH (50:50); (A:B: 60:40) as mobile phase) to provide the compound of Example 223A (Fraction I (–)) and the compound of Example 223B (Fraction II (+)).

Example 223A

Synthesis of (–)-7-(3, 5-difluorophenyl)-8-methyl-N-(4-(4-methyl-1H-imidazol-1-yl)-3-(trifluoromethoxy) phenyl)-7, 8-dihydro-6H-pyrimido [5, 4-b] [1, 4] oxazin-2-amine

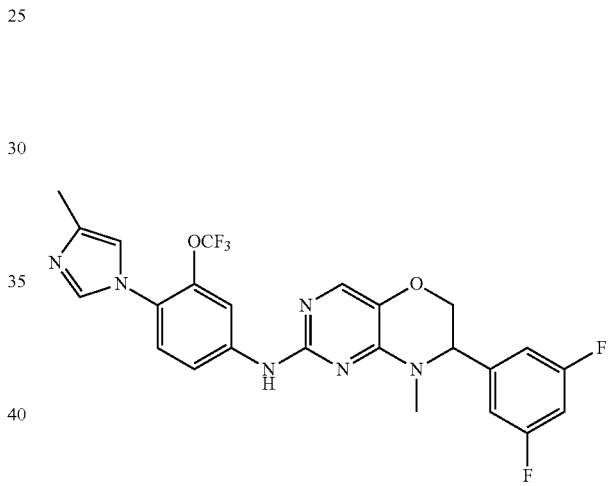

The compound of Example 223A was produced as described in Example 223. Analytical data for product Fraction I (–): $^1$H-NMR (CD$_3$OD, 400 MHz): δ 8.14-8.12 (m, 1H), 7.79 (s, 1H), 7.67 (dd, 1H), 7.62 (s, 1H), 7.38 (dd, 1H), 7.10 (t, 1H), 6.96-6.90 (m, 1H), 6.86 (dd, 2H), 4.76 (t, 1H), 4.22 (d, 2H), 3.13 (s, 3H), 2.25 (d, 3H); Mass (ESI): 519.5 [M+1]; LCMS: 519.1 (M+1); (column; X-Select CSH C-18 (50×3.0 mm, 3.5 µm); RT 2.62 min 0.05% Aq TFA: ACN; 0.80 mL/min); UPLC (column; Acquity BEH C-18, 50×2.1 mm, 1.7 µm); RT 1.84 min. ACN: 0.025% Aq TFA; 0.5 mL/min; Chiral HPLC: 100% RT=8.92 min (CHIRAL-PAK-ADH (250×4.6 mm, 5 µm; mobile phase (A) 0.1% DEA in n-hexane (B) EtOH:MeOH (50:50) (A:B; 65:35); flow Rate: 1.0 mL/min; Optical rotation $[\alpha]_D^{20.00}$: –105.68 (c=0.25, CH$_2$Cl$_2$).

Example 223B

Synthesis of (+)-7-(3, 5-difluorophenyl)-8-methyl-N-(4-(4-methyl-1H-imidazol-1-yl)-3-(trifluoromethoxy) phenyl)-7, 8-dihydro-6H-pyrimido [5, 4-b] [1, 4] oxazin-2-amine

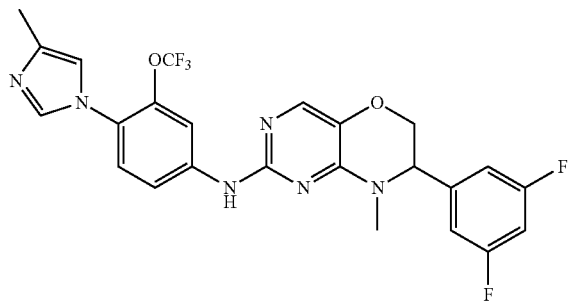 [SMILES: Cc1cn(-c2ccc(Nc3ncc4c(n3)N(C)C(c3cc(F)cc(F)c3)CO4)cc2OC(F)(F)F)cn1]

The compound of Example 223B was produced as described in Example 223. Analytical data for product Fraction II (+): $^1$H-NMR (CD$_3$OD, 400 MHz): δ 8.14-8.12 (m, 1H), 7.79 (s, 1H), 7.67 (dd, 1H), 7.62 (s, 1H), 7.38 (dd, 1H), 7.10 (t, 1H), 6.96-6.90 (m, 1H), 6.86 (dd, 2H), 4.76 (t, 1H), 4.22 (d, 2H), 3.13 (s, 3H), 2.25 (d, 3H); Mass (ESI): 519.5 [M+1]; LCMS: 519.0 (M+1); (column; X-Select CSH C-18 (50×3.0 mm, 3.5 μm); RT 2.61 min 0.05% Aq TFA: ACN; 0.80 mL/min); UPLC (column; Acquity BEH C-18, 50×2.1 mm, 1.7 μm); RT 1.83 min. ACN: 0.025% Aq TFA; 0.5 mL/min; Chiral HPLC: 99.5% RT=32.18 min (CHIRALPAK-ADH (250×4.6 mm, 5 μm; mobile phase (A) 0.1% DEA in n-hexane (B) EtOH:MeOH (50:50) (A:B; 65:35); flow Rate: 1.0 mL/min); Optical rotation $[\alpha]_D^{19.99}$: +108.24 (c=0.25, CH$_2$Cl$_2$).

Example 224

Synthesis of (S)-7-cyclopropyl-N-(3-methoxy-4-(4-methyl-1H-imidazol-1-yl) phenyl)-8-methyl-7, 8-dihydro-6H-pyrimido [5, 4-b] [1, 4] oxazin-2-amine

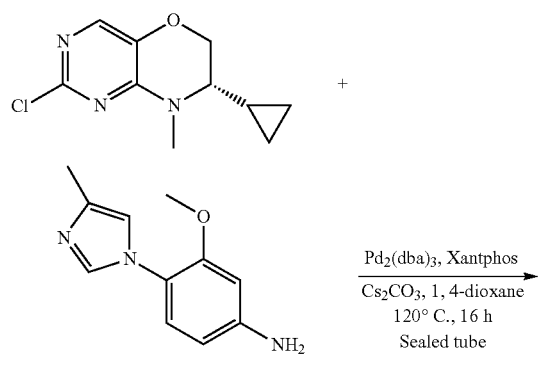

Pd$_2$(dba)$_3$, Xantphos
Cs$_2$CO$_3$, 1, 4-dioxane
120° C., 16 h
Sealed tube

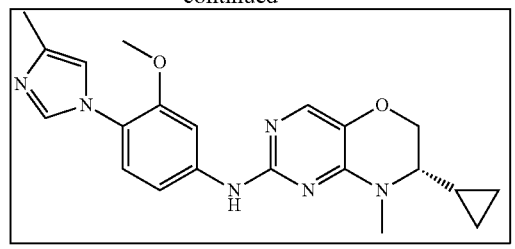

Synthesis of (S)-7-cyclopropyl-N-(3-methoxy-4-(4-methyl-1H-imidazol-1-yl) phenyl)-8-methyl-7, 8-dihydro-6H-pyrimido [5, 4-b] [1, 4] oxazin-2-amine To a dry vial was added a suspension of Pd$_2$(dba)$_3$ (30 mg, 0.03 mmol) and Xantphos (57 mg, 0.09 mmol) in 1, 4-dioxane (0.75 mL) at room temperature. The suspension was degassed with argon, heated to 120° C., and stirred for 3 min. A mixture of (S)-2-chloro-7-cyclopropyl-8-methyl-7, 8-dihydro-6H-pyrimido [5, 4-b] [1, 4] oxazine (150 mg, 0.66 mmol), 3-methoxy-4-(4-methyl-1H-imidazol-1-yl) aniline (270 mg, 1.33 mmol) and cesium carbonate (303 mg, 0.93 mmol) in 1, 4-dioxane (0.75 mL) was degassed and the catalyst premix was added. The resultant mixture was stirred at 120° C. for 16 h in a sealed tube. After consumption of the starting material (monitored by TLC and LCMS), the volatile components were concentrated in vacuo. The crude material was purified by preparative HPLC (Ascentis C-18 (250×21.2 mm, 5 μm (50 mg loading; CH$_3$CN: 0.05% TFA (0.1/90, 2/85, 8/30, 15/70, 25/20, 30/10, 45/10)) to afford (S)-7-cyclopropyl-N-(3-methoxy-4-(4-methyl-1H-imidazol-1-yl) phenyl)-8-methyl-7, 8-dihydro-6H-pyrimido [5, 4-b] [1, 4] oxazin-2-amine (32 mg, 12%) as an off-white solid. $^1$H-NMR (CDCl$_3$, 400 MHz): δ 7.68 (s, 1H), 7.61 (s, 1H), 7.59 (s, 1H), 7.13 (d, 1H), 6.98 (d, 1H), 6.90 (s, 1H), 6.84 (s, 1H), 4.20-4.15 (m, 1H), 4.07-4.01 (m, 1H), 3.83 (s, 3H), 3.29 (s, 3H), 2.63 (d, 1H), 2.30 (s, 3H), 1.05-1.00 (m, 1H), 0.84-0.80 (m, 1H), 0.60-0.50 (m, 2H), 0.23-0.19 (m, 1H); Mass (ESI): 393.5 [M+1]; LCMS: 393 (M+1); (column; X-Select CSH C-18 (50×3.0 mm, 3.5 μm); RT 2.16 min 0.05% Aq TFA: ACN; 0.80 mL/min); UPLC (column; Acquity BEH C-18 50×2.1 mm, 1.7 μm); RT 1.47 min. ACN: 0.025% Aq TFA; 0.5 mL/min; Chiral HPLC: 98.6% RT=9.10 min (CHIRALPAK-IA (250×4.6 mm, 5 μm; mobile phase (A) 0.1% DEA in n-hexane (B) CH$_2$Cl$_2$: MeOH (50:50) (A:B; 70:30); flow Rate: 1.0 mL/min); Optical rotation $[\alpha]_D^{19.99}$: -9.00 (c=0.25, CH$_2$Cl$_2$); TLC: 5% MeOH/CH$_2$Cl$_2$ (R$_f$: 0.3).

Example 225

Synthesis of (S)-7-cyclopropyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

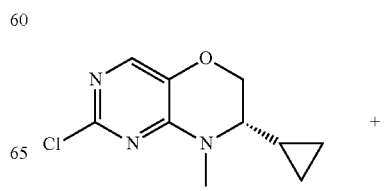

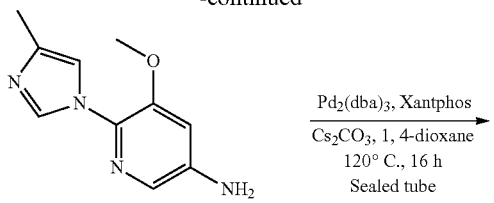

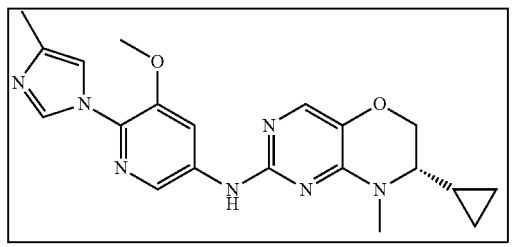

Synthesis of (S)-7-cyclopropyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine To a dry vial was added a suspension of $Pd_2(dba)_3$ (20 mg, 0.02 mmol) and Xantphos (38 mg, 0.06 mmol) in 1, 4-dioxane (0.5 mL) at room temperature. The suspension was degassed with argon, heated to 120° C., and stirred for 3 min. A mixture of (S)-2-chloro-7-cyclopropyl-8-methyl-7, 8-dihydro-6H-pyrimido [5, 4-b] [1, 4] oxazine (100 mg, 0.44 mmol), 5-methoxy-6-(4-methyl-1H-imidazol-1-yl) pyridin-3-amine (108 mg, 0.53 mmol), cesium carbonate (200 mg, 0.61 mmol) in 1, 4-dioxane (0.5 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with $CH_2Cl_2$ (2×20 mL). The combined organic extracts were dried over sodium sulfate, filtered and concentrated in vacuo. The crude material was purified by column chromatography using 5% MeOH: $CH_2Cl_2$ to afford (S)-7-cyclopropyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine (20 mg, 11%) as an off-white solid. $^1$H-NMR (CDCl$_3$, 400 MHz): δ 8.25-8.23 (m, 1H), 8.17 (s, 1H), 8.04-8.02 (m, 1H), 7.63 (s, 1H), 7.38 (s, 1H), 6.96 (s, 1H), 4.18 (dd, 1H), 4.07 (dd, 1H), 3.95 (s, 3H), 3.28 (s, 3H), 2.64 (d, 1H), 2.29 (s, 3H), 1.07-0.98 (m, 1H), 0.85-0.78 (m, 1H), 0.65-0.51 (m, 2H), 0.25-0.20 (m, 1H); Mass (ESI): 394.4 [M+1]; LCMS: 394 (M+1); (column; X-Select CSH C-18 (50×3.0 mm, 3.5 μm); RT 2.14 min 0.05% Aq TFA: ACN; 0.80 mL/min); UPLC (column; Acquity BEH C-18, 50×2.1 mm, 1.7 μm); RT 1.42 min. ACN: 0.025% Aq TFA; 0.5 mL/min; Chiral HPLC: 99.1% RT=8.62 min (CHIRALPAK-IA (250×4.6 mm, 5μ; mobile phase (A) 0.1% DEA in n-hexane (B) $CH_2Cl_2$:MeOH (50:50) (A:B; 70:30); flow Rate: 1.0 mL/min); Optical rotation $[α]_D^{20.01}$: -6.38 (c=0.25, $CH_2Cl_2$); TLC: 20% EtOAc:hexane ($R_f$: 0.1).

Example 226

Synthesis of 4-((8-methyl-7-(trifluoromethyl)-7, 8-dihydro-6H-pyrimido [5, 4-b] [1, 4] oxazin-2-yl) amino) benzonitrile

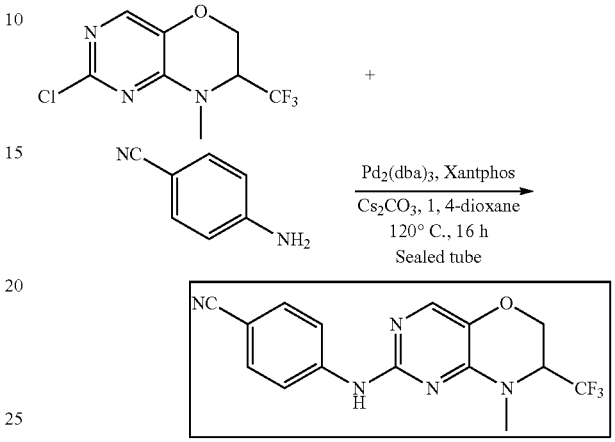

Synthesis of 4-((8-methyl-7-(trifluoromethyl)-7, 8-dihydro-6H-pyrimido [5, 4-b] [1, 4] oxazin-2-yl) amino) benzonitrile To a dry vial was added a suspension of $Pd_2(dba)_3$ (18 mg, 0.02 mmol) and Xantphos (34 mg, 0.06 mmol) in 1, 4-dioxane (0.5 mL) at room temperature. The suspension was degassed with argon, heated to 120° C., and stirred for 3 min. A mixture of 2-chloro-8-methyl-7-(trifluoromethyl)-7, 8-dihydro-6H-pyrimido [5, 4-b] [1, 4] oxazine (100 mg, 0.40 mmol), 4-aminobenzonitrile (93 mg, 0.80 mmol), cesium carbonate (180 mg, 0.55 mmol) in 1, 4-dioxane (0.5 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with $CH_2Cl_2$ (2×20 mL). The combined organic extracts were dried over sodium sulfate, filtered and concentrated in vacuo. The crude material was purified by column chromatography using 20-30% EtOAc: hexane to afford 4-((8-methyl-7-(trifluoromethyl)-7, 8-dihydro-6H-pyrimido [5, 4-b] [1, 4] oxazin-2-yl) amino) benzonitrile (100 mg, 75%) as an off-white solid. LCMS: 335.9 (M+1); (column; X-Select CSH C-18 (50×3.0 mm, 3.5 μm); RT 3.53 min 0.05% Aq TFA: ACN; 0.80 mL/min); TLC: 30% EtOAc:hexane ($R_f$: 0.2).

Racemic compound of Example 226 was separated using a Chiralpak IA column (250×20 mm: 5 μm; (25 mg loading; 0.1% DEA in n-hexane: $CH_2Cl_2$:MeOH (50:50); (A:B: 75:25) as mobile phase) to provide the compound of Example 226A (Fraction I (+)) and the compound of Example 226B (Fraction II (-)).

Example 226A

Synthesis of (+)-4-((8-methyl-7-(trifluoromethyl)-7, 8-dihydro-6H-pyrimido [5, 4-b] [1, 4] oxazin-2-yl) amino) benzonitrile

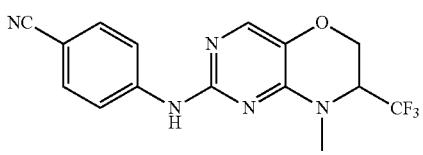 [SMILES: CN1c2nc(Nc3ccc(C#N)cc3)ncc2OCC1C(F)(F)F]

The compound of Example 226A was produced as described in Example 226. Analytical data for product Fraction I (+): $^1$H-NMR (CD$_3$OD, 400 MHz): δ 7.85 (d, 2H), 7.68 (s, 1H), 7.56 (d, 2H), 4.57 (dd, 1H), 4.40-4.37 (m, 1H), 4.05-3.99 (m, 1H), 3.34 (s, 3H); Mass (ESI): 336.4 [M+1]; LCMS: 335.9 (M+1); (column; X-select CSH C-18 (50×3.0 mm, 3.5 μm); RT 2.75 min. 0.05% Aq TFA: ACN; 0.8 mL/min); UPLC (column; Acquity BEH C-18, 50×2.1 mm, 1.7 μm); RT 1.87 min. ACN: 0.025% Aq TFA; 0.5 mL/min; Chiral HPLC: 98.3% RT=6.78 min (CHIRALPAK-IA (250× 4.6 mm, 5 μm; mobile phase (A) 0.1% DEA in n-hexane (B) CH$_2$Cl$_2$:MeOH (50:50) (A:B; 70:30); flow Rate: 1.0 mL/min); Optical rotation $[α]_D^{19.99}$: +75.10 (c=0.25, CH$_2$Cl$_2$).

Example 226B

Synthesis of (−)-4-((8-methyl-7-(trifluoromethyl)-7, 8-dihydro-6H-pyrimido [5, 4-b] [1, 4] oxazin-2-yl) amino) benzonitrile

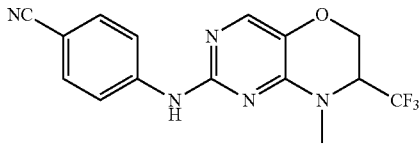 [SMILES: CN1c2nc(Nc3ccc(C#N)cc3)ncc2OCC1C(F)(F)F]

The compound of Example 226B was produced as described in Example 226. Analytical data for product Fraction II (−): $^1$H-NMR (CD$_3$OD, 400 MHz): δ 7.85 (d, 2H), 7.68 (s, 1H), 7.56 (d, 2H), 4.57 (dd, 1H), 4.40-4.37 (m, 1H), 4.05-3.99 (m, 1H), 3.34 (s, 3H); Mass (ESI): 336.4 [M+1]; LCMS: 335.9 (M+1); (column; X-select CSH C-18 (50×3.0 mm, 3.5 μm); RT 2.74 min. 0.05% Aq TFA: ACN; 0.8 mL/min); UPLC (column; Acquity BEH C-18, 50×2.1 mm, 1.7 μm); RT 1.87 min. ACN: 0.025% Aq TFA; 0.5 mL/min; Chiral HPLC: 99.3% RT=7.99 min (CHIRALPAK-IA (250×4.6 mm, 5 μm; mobile phase (A) 0.1% DEA in n-hexane (B) CH$_2$Cl$_2$:MeOH (50:50) (A:B; 70:30); flow Rate: 1.0 mL/min); Optical rotation $[α]_D^{19.99}$: −80.60 (c=0.25, CH$_2$Cl$_2$).

Example 227

Synthesis of (S)-7-cyclobutyl-N-(3-methoxy-4-(4-methyl-1H-imidazol-1-yl) phenyl)-8-methyl-7, 8-dihydro-6H-pyrimido [5, 4-b] [1, 4] oxazin-2-amine

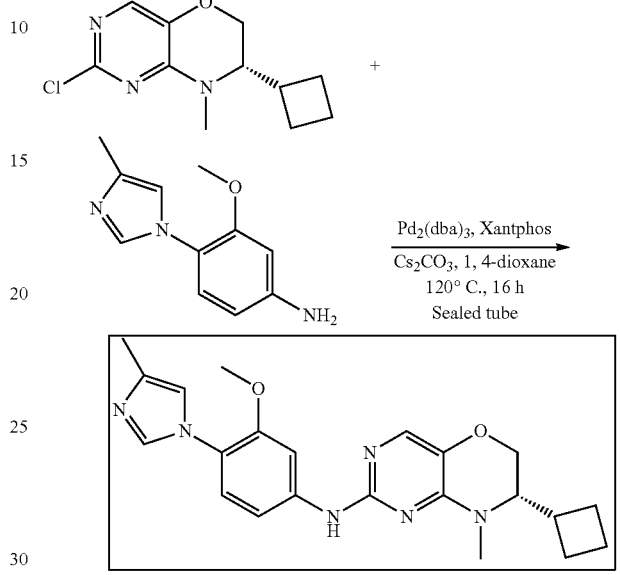

Synthesis of (S)-7-cyclobutyl-N-(3-methoxy-4-(4-methyl-1H-imidazol-1-yl) phenyl)-8-methyl-7, 8-dihydro-6H-pyrimido [5, 4-b] [1, 4] oxazin-2-amine)

To a dry vial was added a suspension of Pd$_2$(dba)$_3$ (19 mg, 0.02 mmol) and Xantphos (36 mg, 0.06 mmol) in 1, 4-dioxane (0.5 mL) at room temperature. The suspension was degassed with argon, heated to 120° C., and stirred for 3 min. A mixture of (S)-2-chloro-7-cyclobutyl-8-methyl-7, 8-dihydro-6H-pyrimido [5, 4-b] [1, 4] oxazine (100 mg, 0.41 mmol), 3-methoxy-4-(4-methyl-1H-imidazol-1-yl) aniline (170 mg, 0.83 mmol), cesium carbonate (191 mg, 0.58 mmol) in 1, 4-dioxane (0.5 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with CH$_2$Cl$_2$ (2×20 mL). The combined organic extracts were dried over sodium sulfate, filtered and concentrated in vacuo. The crude material was purified by preparative HPLC (Ascentis C-18 (250×21.2 mm, 5 μm (50 mg loading; CH$_3$CN: 0.05% TFA (0.1/90, 2/80, 15/70, 25/20, 30/10, 35/10)) to afford (S)-7-cyclobutyl-N-(3-methoxy-4-(4-methyl-1H-imidazol-1-yl) phenyl)-8-methyl-7, 8-dihydro-6H-pyrimido [5, 4-b] [1, 4] oxazin-2-amine (1.8 g, 58%) as a brown solid. $^1$H-NMR (CD$_3$OD, 400 MHz): δ 7.72 (d, 2H), 7.47 (s, 1H), 7.20 (d, 2H), 7.00 (s, 1H), 4.12-4.10 (m, 1H), 3.82 (s, 3H), 3.81-3.79 (m, 1H), 3.45-3.42 (m, 1H), 3.25 (s, 3H), 2.70-2.61 (m, 1H), 2.24 (s, 3H), 2.14-2.10 (m, 2H), 2.08-2.00 (m, 1H), 1.96-1.90 (m, 2H), 1.87-1.80 (m, 1H); Mass (ESI): 407.5 [M+1]; LCMS: 407.1 (M+1); (column; X-Select CSH C-18 (50×3.0 mm, 3.5 μm); RT 2.28 min 0.05% Aq TFA: ACN; 0.80 mL/min); UPLC (column;

Acquity BEH C18, 50×2.1 mm, 1.7 μm); RT 1.59 min. ACN: 0.025% Aq TFA; 0.5 mL/min; TLC: 5% MeOH/CH$_2$Cl$_2$ (R$_f$: 0.3).

Example 228

Synthesis of N-(4-(4-chloro-1H-imidazol-1-yl)-3-methoxyphenyl)-8-methyl-7-(trifluoromethyl)-7,8-dihydro-6H-pyrimido [5, 4-b] [1, 4] oxazin-2-amine

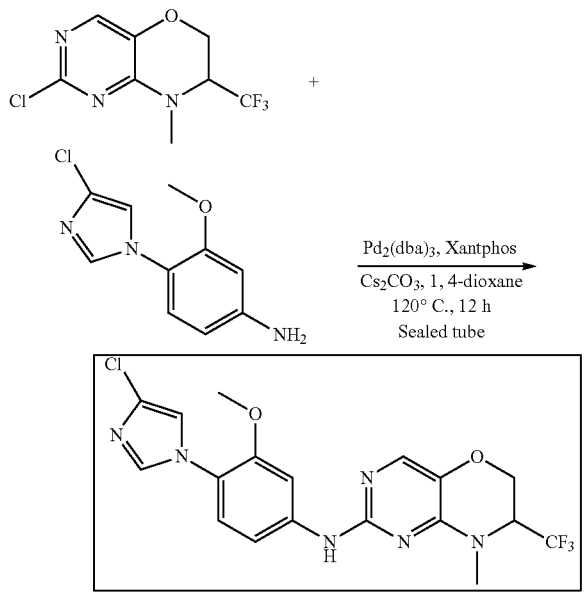

Synthesis of N-(4-(4-chloro-1H-imidazol-1-yl)-3-methoxyphenyl)-8-methyl-7-(trifluoromethyl)-7,8-dihydro-6H-pyrimido [5, 4-b] [1, 4] oxazin-2-amine To a dry vial was added a suspension of Pd$_2$(dba)$_3$ (41 mg, 0.04 mmol) and Xantphos (78 mg, 0.13 mmol) in 1, 4-dioxane (5 mL) at room temperature. The suspension was degassed with argon, heated to 120° C., and stirred for 3 min. A mixture of 2-chloro-8-methyl-7-(trifluoromethyl)-7,8-dihydro-6H-pyrimido [5, 4-b] [1, 4] oxazine (230 mg, 0.90 mmol), 4-(4-chloro-1H-imidazol-1-yl)-3-methoxyaniline (240 mg, 1.08 mmol) and cesium carbonate (410 mg, 1.26 mmol) in 1, 4-dioxane (5 mL) was degassed and the catalyst premix was added. The resultant mixture was stirred at 120° C. for 12 h in a sealed tube. After consumption of the starting material (monitored by TLC and LCMS), the reaction mixture was filtered and the filtrate was concentrated in vacuo. The crude material was purified by column chromatography using 5% MeOH: CH$_2$Cl$_2$ to afford N-(4-(4-chloro-1H-imidazol-1-yl)-3-methoxyphenyl)-8-methyl-7-(trifluoromethyl)-7, 8-dihydro-6H-pyrimido [5, 4-b] [1, 4] oxazin-2-amine (85 mg, 21%) as a brown solid. LCMS: 440.9 (M+1); (column; X-Select CSH C-18 (50×3.0 mm, 3.5 μm); RT 2.78 min 0.05% Aq TFA: ACN; 0.80 mL/min); TLC: 5% MeOH/ CH$_2$Cl$_2$ (R$_f$: 0.4).

Racemic compound of Example 228 was separated using a Chiralpak IA column (250×20 mm: 5 μm; (30 mg loading; 0.1% DEA in n-hexane: EtOH (A:B: 80:20) as mobile phase) to provide the compound of Example 228A (Fraction I (+)) and the compound of Example 228B (Fraction II (−)).

Example 228A

Synthesis of (+)-N-(4-(4-chloro-1H-imidazol-1-yl)-3-methoxyphenyl)-8-methyl-7-(trifluoromethyl)-7,8-dihydro-6H-pyrimido [5, 4-b] [1, 4] oxazin-2-amine

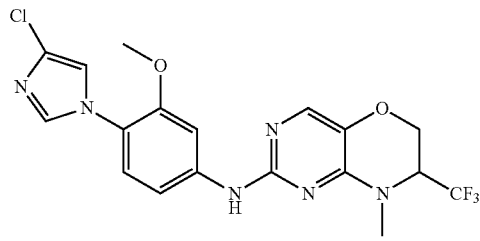 [SMILES: COc1cc(Nc2ncc3c(n2)N(C)C(C(F)(F)F)CO3)ccc1-n1cnc(Cl)c1]

The compound of Example 228A was produced as described in Example 228. Analytical data for product Fraction I (+): $^1$H-NMR (DMSO-d$_6$, 400 MHz): δ 9.31 (s, 1H), 7.85-7.83 (m, 1H), 7.75 (s, 1H), 7.74 (s, 1H), 7.44 (s, 1H), 7.32 (d, 1H), 7.24 (d, 1H), 4.71-4.66 (m, 1H), 4.54 (d, 1H), 4.09-4.01 (m, 1H), 3.80 (s, 3H), 3.30 (s, 3H); Mass (ESI): 441.7 [M+1]; LCMS: 441 (M+1); (column; X-Select CSH C-18 (50×3.0 mm, 3.5 μm); RT 2.78 min 0.05% Aq TFA: ACN; 0.80 mL/min); UPLC (column; Acquity UPLC HSS-T3, 100×2.1 mm, 1.8μ); RT 1.86 min. ACN: 0.025% Aq TFA; 0.5 mL/min; Chiral HPLC: 100% RT=14.35 min (CHIRALPAK-IA (250×4.6 mm, 5 μm; mobile phase (A) 0.1% DEA in n-hexane (B) EtOH (A:B; 80:20); flow Rate: 1.0 mL/min); Optical rotation [α]$_D^{20.01}$: +62.65 (c=0.25, CH$_2$Cl$_2$).

Example 228B

Synthesis of (−)-N-(4-(4-chloro-1H-imidazol-1-yl)-3-methoxyphenyl)-8-methyl-7-(trifluoromethyl)-7,8-dihydro-6H-pyrimido [5, 4-b] [1, 4] oxazin-2-amine

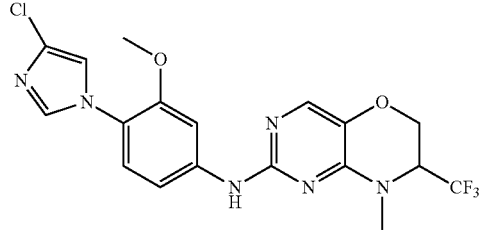 [SMILES: COc1cc(Nc2ncc3c(n2)N(C)C(C(F)(F)F)CO3)ccc1-n1cnc(Cl)c1]

The compound of Example 228B was produced as described in Example 228. Analytical data for product Fraction II (−): $^1$H-NMR (DMSO-d$_6$, 400 MHz): δ 9.31 (s, 1H), 7.85-7.83 (m, 1H), 7.75 (s, 1H), 7.74 (s, 1H), 7.44 (s, 1H), 7.32 (d, 1H), 7.24 (d, 1H), 4.71-4.66 (m, 1H), 4.54 (d, 1H), 4.09-4.01 (m, 1H), 3.80 (s, 3H), 3.30 (s, 3H); Mass (ESI): 441.7 [M+1]; LCMS: 441 (M+1); (column; X-Select CSH C-18 (50×3.0 mm, 3.5 μm); RT 2.79 min 0.05% Aq TFA: ACN; 0.80 mL/min); UPLC (column; Acquity BEH C-18, 50×2.1 mm, 1.8μ); RT 1.87 min. ACN: 0.025% Aq TFA; 0.5 mL/min; Chiral HPLC: 99.6% RT=16.94 min (CHIRALPAK-IA (250×4.6 mm, 5 μm; mobile phase (A) 0.1% DEA in n-hexane (B) EtOH (A:B; 80:20); flow Rate: 1.0 mL/min); Optical rotation $[\alpha]_D^{19.99}$: −60.33 (c=0.25, CH$_2$Cl$_2$).

Example 229

Synthesis of N-(5-chloro-6-(4-methyl-1H-imidazol-1-yl) pyridin-3-yl)-8-methyl-7-(trifluoromethyl)-7,8-dihydro-6H-pyrimido [5, 4-b] [1, 4] oxazin-2-amine

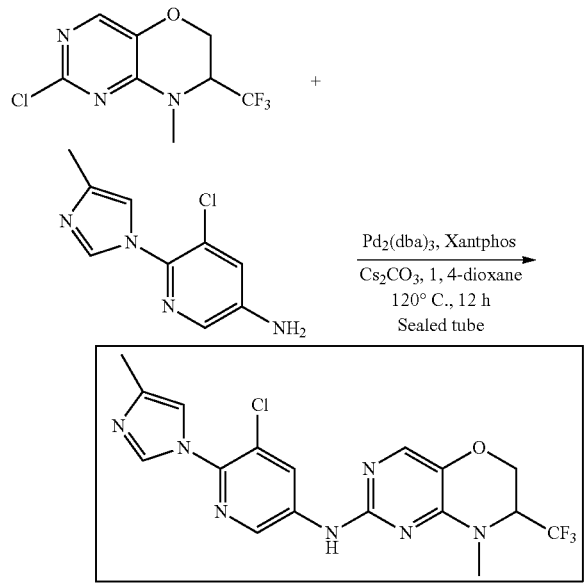

Synthesis of N-(5-chloro-6-(4-methyl-1H-imidazol-1-yl) pyridin-3-yl)-8-methyl-7-(trifluoromethyl)-7,8-dihydro-6H-pyrimido [5, 4-b] [1, 4] oxazin-2-amine To a dry vial was added a suspension of Pd$_2$(dba)$_3$ (41 mg, 0.04 mmol) and Xantphos (78 mg, 0.13 mmol) in 1, 4-dioxane (5 mL) at room temperature. The suspension was degassed with argon, heated to 120° C., and stirred for 3 min. A mixture of 2-chloro-8-methyl-7-(trifluoromethyl)-7,8-dihydro-6H-pyrimido [5, 4-b] [1, 4] oxazine (230 mg, 0.90 mmol), 5-chloro-6-(4-methyl-1H-imidazol-1-yl) pyridin-3-amine (240 mg, 1.08 mmol) and cesium carbonate (410 mg, 1.26 mmol) in 1, 4-dioxane (5 mL) was degassed and the catalyst premix was added. The resultant mixture was stirred at 120° C. for 12 h in a sealed tube. After consumption of the starting material (monitored by TLC and LCMS), the reaction mixture was filtered and the filtrate was concentrated in vacuo. The crude material was purified by column chromatography using 0-3% MeOH: CH$_2$Cl$_2$ to afford N-(5-chloro-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine (180 mg, 46%) as an off-white solid. LCMS: 425.9 (M+1); (column; X-Select CSH C-18 (50×3.0 mm, 3.5 μm); RT 2.28 min 0.05% Aq TFA: ACN; 0.80 mL/min); TLC: 5% MeOH/CH$_2$Cl$_2$ (R$_f$: 0.3).

Racemic compound of Example 229 was separated using a Chiralpak IB column (250×20 mm: 5 μm; (15 mg loading; 0.1% DEA in n-hexane: EtOH (A:B: 80:20) as mobile phase) to provide the compound of Example 229A (Fraction I (−)) and the compound of Example 229B (Fraction II (+)).

Example 229A

Synthesis of (−)-N-(5-chloro-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine

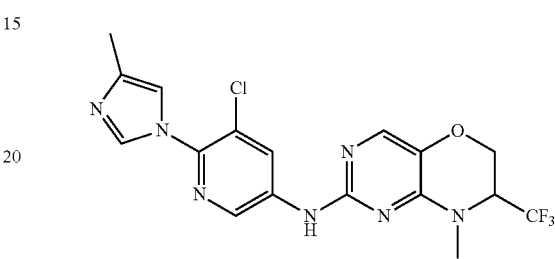

The compound of Example 229A was produced as described in Example 229. Analytical data for product Fraction I (−): $^1$H-NMR (CD$_3$OD, 400 MHz): δ 8.72 (s, 1H), 8.62 (s, 1H), 7.97 (s, 1H), 7.71 (s, 1H), 7.25 (s, 1H), 4.58 (dd, 1H), 4.42-4.35 (m, 1H), 4.12-4.08 (m, 1H), 3.35 (s, 3H), 2.26 (s, 3H); Mass (ESI): 425.9 [M+1]; LCMS: 425.9 (M+1); (column; X-Select CSH C-18 (50×3.0 mm, 3.5 μm); RT 2.31 min 0.05% Aq TFA: ACN; 0.80 mL/min); UPLC (column; Acquity BEH C-18, 50×2.1 mm, 1.8μ); RT 1.62 min. ACN: 0.025% Aq TFA; 0.5 mL/min; Chiral HPLC: 98.0% RT=7.27 min (CHIRALPAK-IB (150×4.6 mm, 5 μm; mobile phase (A) 0.1% DEA in n-hexane (B) EtOH (A:B; 80:20); flow Rate: 1.0 mL/min); Optical rotation $[\alpha]_D^{20.00}$: −38.91 (c=0.25, CH$_2$Cl$_2$).

Example 229B

Synthesis of (+)-N-(5-chloro-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine

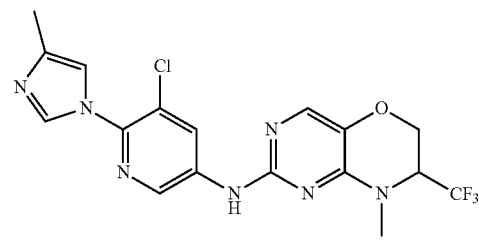 [SMILES: Cc1cn(-c2ncc(Nc3ncc4c(n3)N(C)C(C(F)(F)F)CO4)cc2Cl)cn1]

The compound of Example 229B was produced as described in Example 229. Analytical data for product Fraction II (+): $^1$H-NMR (CD$_3$OD, 400 MHz): δ 8.72 (s, 1H), 8.62 (s, 1H), 7.97 (s, 1H), 7.71 (s, 1H), 7.25 (s, 1H), 4.58 (dd, 1H), 4.42-4.35 (m, 1H), 4.12-4.08 (m, 1H), 3.35 (s, 3H), 2.26 (s, 3H); Mass (ESI): 425.9 [M+1]; LCMS: 425.9 (M+1); (column; X-Select CSH C-18 (50×3.0 mm, 3.5 μm); RT 2.31 min 0.05% Aq TFA: ACN; 0.80 mL/min); UPLC (column; Acquity BEH C-18, 50×2.1 mm, 1.8µ); RT 1.61 min. ACN: 0.025% Aq TFA; 0.5 mL/min; Chiral HPLC: 98.0% RT=7.86 min (CHIRALPAK-IB (150×4.6 mm, 5 µm; mobile phase (A) 0.1% DEA in n-hexane (B) EtOH (A:B; 80:20); flow Rate: 1.0 mL/min); Optical rotation $[\alpha]_D^{20.00}$: +44.68 (c=0.25, CH$_2$Cl$_2$).

Example 230

Synthesis of 2-methoxy-4-((8-methyl-7-(trifluoromethyl)-7, 8-dihydro-6H-pyrimido [5, 4-b] [1, 4] oxazin-2-yl) amino) benzonitrile

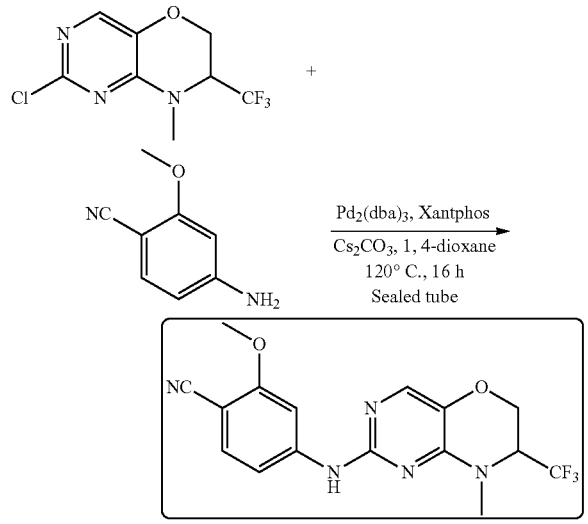

Synthesis of 2-methoxy-4-((8-methyl-7-(trifluoromethyl)-7, 8-dihydro-6H-pyrimido [5, 4-b] [1, 4] oxazin-2-yl) amino) benzonitrile To a dry vial was added a suspension of Pd$_2$(dba)$_3$ (18 mg, 0.02 mmol) and Xantphos (34 mg, 0.06 mmol) in 1, 4-dioxane (1 mL) at room temperature. The suspension was degassed with argon, heated to 120° C., and stirred for 3 min. A mixture of 2-chloro-8-methyl-7-(trifluoromethyl)-7, 8-dihydro-6H-pyrimido [5, 4-b] [1, 4] oxazine (100 mg, 0.40 mmol), 4-amino-2-methoxybenzonitrile (59 mg, 0.40 mmol) and cesium carbonate (180 mg, 0.55 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with CH$_2$Cl$_2$ (2×20 mL). The combined organic extracts were dried over sodium sulfate, filtered and concentrated in vacuo. The crude material was purified by column chromatography using 30% EtOAc: hexane to afford 2-methoxy-4-((8-methyl-7-(trifluoromethyl)-7, 8-dihydro-6H-pyrimido [5, 4-b] [1, 4] oxazin-2-yl) amino) benzonitrile (80 mg, 55%) as a brown solid. LCMS: 365.9 (M+1); (column; X-Select CSH C-18 (50×3.0 mm, 3.5 µm); RT 2.86 min 0.05% Aq TFA: ACN; 0.80 mL/min); TLC: 40% EtOAc:hexane (R$_f$: 0.4).

Racemic compound of Example 230 was separated using a CHIRALPAK-ADH column (250×20 mm; 5 µm; (30 mg loading; 0.1% DEA in n-hexane (B) EtOH:MeOH (50:50) (A:B; 60:40); flow Rate: 1.0 mL/min) as mobile phase) to provide the compound of Example 230A (Fraction I (+)) and the compound of Example 230B (Fraction II (−)).

Example 230A

Synthesis of (+)-2-methoxy-4-((8-methyl-7-(trifluoromethyl)-7, 8-dihydro-6H-pyrimido [5, 4-b] [1, 4] oxazin-2-yl) amino) benzonitrile

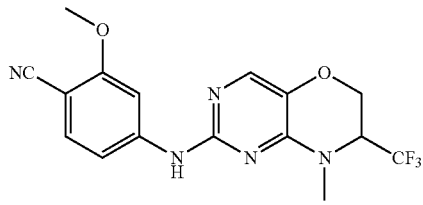 [SMILES: COc1cc(Nc2ncc3c(n2)N(C)C(C(F)(F)F)CO3)ccc1C#N]

The compound of Example 230A was produced as described in Example 230. Analytical data for product Fraction I (+): $^1$H-NMR (CD$_3$OD, 500 MHz): δ 7.79 (s, 1H), 7.68 (s, 1H), 7.41 (d, 1H), 7.22 (dd, 1H), 4.56 (d, 1H), 4.40-4.37 (m, 1H), 4.03 (d, 1H), 3.93 (s, 3H), 3.35 (s, 3H); Mass (ESI): 366.5 [M+1]; LCMS: 366 (M+1); (column; X-Select CSH C-18 (50×3.0 mm, 3.5 µm); RT 3.33 min 0.05% Aq TFA: ACN; 0.80 mL/min); UPLC (column; Acquity BEH C-18, 50×2.1 mm, 1.8µ); RT 1.93 min. ACN: 0.025% Aq TFA; 0.5 mL/min; Chiral HPLC: 100% RT=6.13 min (CHIRALPAK-ADH (250×4.6 mm, 5 µm; mobile phase (A) 0.1% DEA in n-hexane (B) EtOH:MeOH (50:50) (A:B; 60:40); flow Rate: 1.0 mL/min); Optical rotation $[\alpha]_D^{20.00}$: +57.04 (c=0.25, CH$_2$Cl$_2$).

Example 230B

Synthesis of (−)-2-methoxy-4-((8-methyl-7-(trifluoromethyl)-7, 8-dihydro-6H-pyrimido [5, 4-b] [1, 4] oxazin-2-yl) amino) benzonitrile

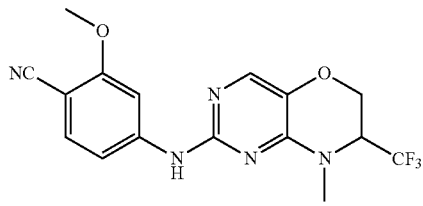 [SMILES: COc1cc(Nc2ncc3c(n2)N(C)C(C(F)(F)F)CO3)ccc1C#N]

The compound of Example 230B was produced as described in Example 230. Analytical data for product Fraction II (−): $^1$H-NMR (CD$_3$OD, 500 MHz): δ 7.79 (s, 1H), 7.68 (s, 1H), 7.41 (d, 1H), 7.22 (dd, 1H), 4.56 (d, 1H), 4.40-4.37 (m, 1H), 4.03 (d, 1H), 3.93 (s, 3H), 3.35 (s, 3H); Mass (ESI): 366.5 [M+1]; LCMS: 366 (M+1); (column; X-Select CSH C-18 (50×3.0 mm, 3.5 µm); RT 3.33 min 0.05% Aq TFA: ACN; 0.80 mL/min); UPLC (column; Acquity BEH C-18, 50×2.1 mm, 1.8µ); RT 1.93 min. ACN: 0.025% Aq TFA; 0.5 mL/min; Chiral HPLC: 98.3% RT=15.16 min (CHIRALPAK-ADH (250×4.6 mm, 5 µm; mobile phase (A) 0.1% DEA in n-hexane (B) EtOH:MeOH (50:50) (A:B; 60:40); flow Rate: 1.0 mL/min); Optical rotation $[\alpha]_D^{20.00}$: −64.73 (c=0.25, CH$_2$Cl$_2$).

Example 231

Synthesis of 7-(4, 4-difluorocyclohexyl)-N-(5-methoxy-6-(1-methyl-1H-pyrazol-4-yl) pyridin-3-yl)-8-methyl-7, 8-dihydro-6H-pyrimido [5, 4-b] [1, 4] oxazin-2-amine

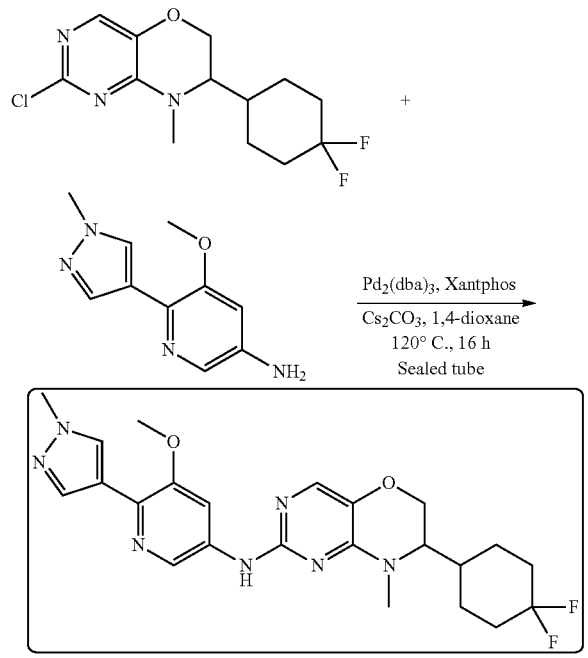

Synthesis of 7-(4, 4-difluorocyclohexyl)-N-(5-methoxy-6-(1-methyl-1H-pyrazol-4-yl) pyridin-3-yl)-8-methyl-7, 8-dihydro-6H-pyrimido [5, 4-b] [1, 4] oxazin-2-amine To a dry vial was added a suspension of Pd$_2$(dba)$_3$ (37 mg, 0.04 mmol) and Xantphos (71 mg, 0.12 mmol) in 1, 4-dioxane (1.25 mL) at room temperature. The suspension was degassed with argon, heated to 120° C., and stirred for 3 min. A mixture of 2-chloro-7-(4, 4-difluorocyclohexyl)-8-methyl-7, 8-dihydro-6H-pyrimido [5, 4-b] [1, 4] oxazine (250 mg, 0.82 mmol), 5-methoxy-6-(1-methyl-1H-pyrazol-4-yl) pyridin-3-amine (336 mg, 1.65 mmol) and cesium carbonate (376 mg, 1.15 mmol) in 1, 4-dioxane (1.25 mL) was degassed and the catalyst premix was added. The resultant mixture was stirred at 120° C. for 16 h in a sealed tube. After consumption of the starting material (monitored by TLC and LCMS), the volatile components were concentrated in vacuo. The crude material was purified by preparative HPLC (Kromasil-C-18 250×21.2 mm, 5 u (50 mg loading; CH$_3$CN: 0.05% TFA (0.1/90, 2/80, 15/70, 25/30, 30/10, 35/10)) 5 μm to afford 7-(4, 4-difluorocyclohexyl)-N-(5-methoxy-6-(1-methyl-1H-pyrazol-4-yl) pyridin-3-yl)-8-methyl-7, 8-dihydro-6H-pyrimido [5, 4-b] [1, 4] oxazin-2-amine (120 mg, 31%) as a brown solid. LCMS: 472.1 (M+1); (column; X-Select CSH C-18 (50×3.0 mm, 3.5 μm); RT 2.65 min 0.05% Aq TFA: ACN; 0.80 mL/min); UPLC (column; Acquity BEH C-18 50×2.1 mm, 1.7 μm); RT 1.72 min. ACN: 0.025% Aq TFA; 0.5 mL/min; TLC: 5% MeOH/CH$_2$Cl$_2$ (R$_f$: 0.3).

Racemic compound of Example 231 was separated using a Chiralpak IA column (250×20 mm: 5 μm; (20 mg loading; 0.1% DEA in n-hexane: CH$_2$Cl$_2$:MeOH (50:50); (A:B: 75:25) as mobile phase) to provide the compound of Example 231A (Fraction I (+)) and the compound of Example 231B (Fraction II (−)).

Example 231A

Synthesis of (+)-7-(4, 4-difluorocyclohexyl)-N-(5-methoxy-6-(1-methyl-1H-pyrazol-4-yl) pyridin-3-yl)-8-methyl-7, 8-dihydro-6H-pyrimido [5, 4-b] [1, 4] oxazin-2-amine

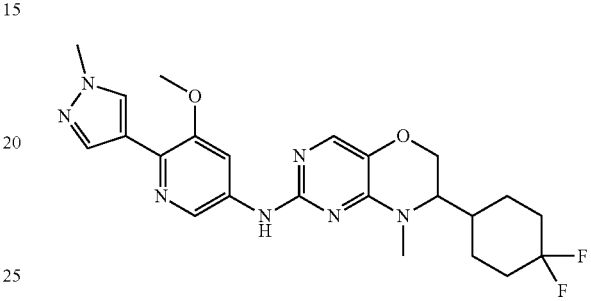

The compound of Example 231A was produced as described in Example 231. Analytical data for product Fraction I (+): $^1$H-NMR (DMSO-d$_6$, 400 MHz): δ 9.10 (s, 1H), 8.38 (s, 1H), 8.15 (s, 1H), 8.11 (s, 1H), 7.92 (s, 1H), 7.57 (s, 1H), 4.36 (d, 1H), 3.90 (s, 3H), 3.87 (s, 3H), 3.79 (dd, 1H), 3.49-3.46 (m, 1H), 3.23 (s, 3H), 2.09-2.00 (m, 2H), 1.92-1.67 (m, 5H), 1.50-1.31 (m, 2H); Mass (ESI): 472.6 [M+1]; LCMS: 472.1 (M+1); (column; X-Select CSH C-18 (50×3.0 mm, 3.5 μm); RT 2.46 min 0.05% Aq TFA: ACN; 0.80 mL/min); UPLC (column; Acquity BEH C-18, 50×2.1 mm, 1.7 μm); RT 1.77 min. ACN: 0.025% Aq TFA; 0.5 mL/min; Chiral HPLC: 99.4% RT=15.14 min (CHIRAL-PAK-IA (250×4.6 mm, 5 μm; mobile phase (A) 0.1% DEA in n-hexane (B) CH$_2$Cl$_2$:MeOH (50:50) (A:B; 75:25); flow Rate: 1.0 mL/min); Optical rotation [α]$_D^{20.00}$: +94.08 (c=0.25, CH$_2$Cl$_2$).

Example 231B

Synthesis of (−)-7-(4, 4-difluorocyclohexyl)-N-(5-methoxy-6-(1-methyl-1H-pyrazol-4-yl) pyridin-3-yl)-8-methyl-7, 8-dihydro-6H-pyrimido [5, 4-b] [1, 4] oxazin-2-amine

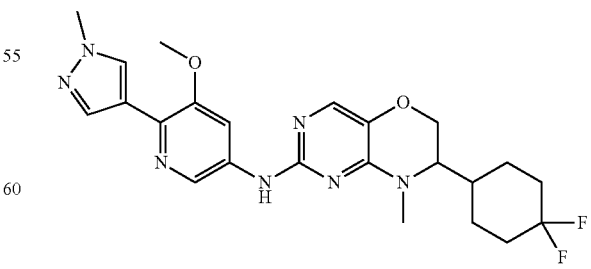

The compound of Example 231B was produced as described in Example 231. Analytical data for product Fraction II (−): $^1$H-NMR (DMSO-d$_6$, 400 MHz): δ 9.10 (s, 1H), 8.38 (s, 1H), 8.15 (s, 1H), 8.11 (s, 1H), 7.92 (s, 1H), 7.57 (s, 1H), 4.36 (d, 1H), 3.90 (s, 3H), 3.87 (s, 3H), 3.79 (dd, 1H), 3.49-3.46 (m, 1H), 3.23 (s, 3H), 2.09-2.00 (m, 2H), 1.92-1.67 (m, 5H), 1.50-1.31 (m, 2H); Mass (ESI): 472.6 [M+1]; LCMS: 472.1 (M+1); (column; X-Select CSH C-18 (50×3.0 mm, 3.5 μm); RT 2.46 min 0.05% Aq TFA: ACN; 0.80 mL/min); UPLC (column; Acquity BEH C-18, 50×2.1 mm, 1.7 μm); RT 1.77 min. ACN: 0.025% Aq TFA; 0.5 mL/min; Chiral HPLC: 98.2% RT=17.80 min (CHIRAL-PAK-IA (250×4.6 mm, 5 μm; mobile phase (A) 0.1% DEA in n-hexane (B) CH2Cl2:MeOH (50:50) (A:B; 75:25); flow Rate: 1.0 mL/min); Optical rotation $[\alpha]_D^{20.01}$: −93.72 (c=0.25, CH$_2$Cl$_2$).

Example 232

Synthesis of 2-(4-methyl-1H-imidazol-1-yl)-5-((8-methyl-7-(trifluoromethyl)-7, 8-dihydro-6H-pyrimido [5, 4-b] [1, 4] oxazin-2-yl) amino) benzonitrile

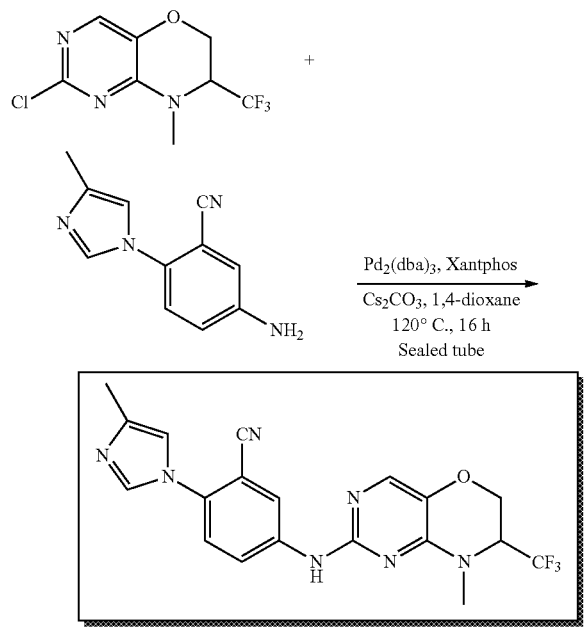

Synthesis of 2-(4-methyl-1H-imidazol-1-yl)-5-((8-methyl-7-(trifluoromethyl)-7, 8-dihydro-6H-pyrimido [5, 4-b] [1, 4] oxazin-2-yl) amino) benzonitrile To a dry vial was added a suspension of Pd$_2$(dba)$_3$ (41 mg, 0.04 mmol) and Xantphos (78 mg, 0.13 mmol) in 1, 4-dioxane (1 mL) at room temperature. The suspension was degassed with argon, heated to 120° C., and stirred for 3 min. A mixture of 2-chloro-8-methyl-7-(trifluoromethyl)-7, 8-dihydro-6H-pyrimido [5, 4-b] [1, 4] oxazine (230 mg, 0.90 mmol), 5-amino-2-(4-methyl-1H-imidazol-1-yl) benzonitrile (360 mg, 1.81 mmol) and cesium carbonate (413 mg, 1.27 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction mixture was filtered and the filtrate was concentrated in vacuo. The crude material was purified by preparative HPLC (Kromasil-C-18 250×21.2 mm, 5 u (50 mg loading; CH$_3$CN: 0.05% TFA (0.1/90, 2/90, 15/70, 25/30, 30/10, 35/10)) to afford 2-(4-methyl-1H-imidazol-1-yl)-5-((8-methyl-7-(trifluoromethyl)-7, 8-dihydro-6H-pyrimido [5, 4-b] [1, 4] oxazin-2-yl) amino) benzonitrile (95 mg, 25%) as a white solid. LCMS: 416 (M+1); (column; X-Select CSH C-18 (50×3.0 mm, 3.5 μm); RT 2.18 min 0.05% Aq TFA: ACN; 0.80 mL/min); TLC: 5% MeOH/CH$_2$Cl$_2$ (R$_f$: 0.3).

Racemic compound of Example 232 was separated using a Chiralpak ADH column (250×20 mm: 5 μm; (30 mg loading; 0.1% DEA in n-hexane: EtOH (A:B: 75:25) as mobile phase) to provide the compound of Example 232A (Fraction I (+)) and the compound of Example 232B (Fraction II (−)).

Example 232A

Synthesis of (+)-2-(4-methyl-1H-imidazol-1-yl)-5-((8-methyl-7-(trifluoromethyl))-7, 8-dihydro-6H-pyrimido [5, 4-b] [1, 4] oxazin-2-yl) amino) benzonitrile

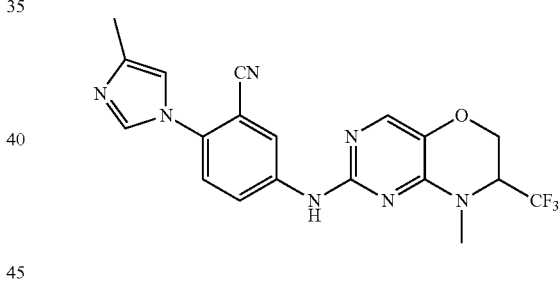

The compound of Example 232A was produced as described in Example 232. Analytical data for product Fraction I (+): $^1$H-NMR (DMSO-d$_6$, 400 MHz): δ 9.66 (s, 1H), 8.42 (s, 1H), 8.03 (dd, 1H), 7.86 (s, 1H), 7.79 (s, 1H), 7.50 (d, 1H), 7.23 (s, 1H), 4.76-4.67 (m, 1H), 4.56 (d, 1H), 4.07 (d, 1H), 3.27 (s, 3H), 2.18 (s, 3H); Mass (ESI): 416.5 [M+1]; LCMS: 416 (M+1); (column; X-Select CSH C-18 (50×3.0 mm, 3.5 μm); RT 2.16 min 0.05% Aq TFA: ACN; 0.80 mL/min); UPLC (column; Acquity BEH C-18, 50×2.1 mm, 1.7 μm); RT 1.55 min. ACN: 0.025% Aq TFA; 0.5 mL/min; Chiral HPLC: 100% RT=12.19 min (CHIRAL-PAK-ADH (250×4.6 mm, 5 μm; mobile phase (A) 0.1% DEA in n-hexane (B) EtOH (A:B; 75:25); flow Rate: 1.0 mL/min); Optical rotation $[\alpha]_D^{20.01}$: +59.90 (c=0.25, CH$_2$Cl$_2$);

Example 232B

Synthesis of (−)-2-(4-methyl-1H-imidazol-1-yl)-5-((8-methyl-7-(trifluoromethyl)-7, 8-dihydro-6H-pyrimido [5, 4-b] [1, 4] oxazin-2-yl) amino) benzonitrile

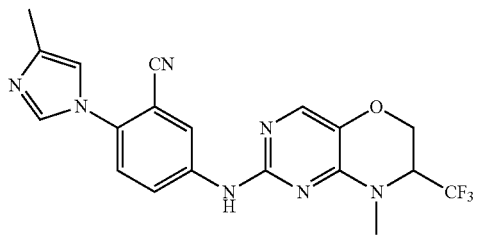 [SMILES: Cc1cn(-c2ccc(Nc3ncc4c(n3)N(C)C(C(F)(F)F)CO4)cc2C#N)cn1]

The compound of Example 232B was produced as described in Example 232. Analytical data for product Fraction II (−): $^1$H-NMR (DMSO-$d_6$, 400 MHz): δ 9.66 (s, 1H), 8.42 (s, 1H), 8.03 (dd, 1H), 7.86 (s, 1H), 7.79 (s, 1H), 7.50 (d, 1H), 7.23 (s, 1H), 4.76-4.67 (m, 1H), 4.56 (d, 1H), 4.07 (d, 1H), 3.27 (s, 3H), 2.18 (s, 3H); Mass (ESI): 416.5 [M+1]; LCMS: 416 (M+1); (column; X-Select CSH C-18 (50×3.0 mm, 3.5 μm); RT 2.17 min 0.05% Aq TFA: ACN; 0.80 mL/min); UPLC (column; Acquity BEH C-18, 50×2.1 mm, 1.7 μm); RT 1.54 min. ACN: 0.025% Aq TFA; 0.5 mL/min; Chiral HPLC: 98.8% RT=18.19 min (CHIRAL-PAK-ADH (250×4.6 mm, 5 μm; mobile phase (A) 0.1% DEA in n-hexane (B) EtOH (A:B; 75:25); flow Rate: 1.0 mL/min); Optical rotation $[α]_D^{20.01}$: −46.64 (c=0.25, $CH_2Cl_2$).

Example 233

Synthesis of 4-((7-(3, 5-difluorophenyl)-8-methyl-7, 8-dihydro-6H-pyrimido [5, 4-b] [1, 4] oxazin-2-yl) amino) benzonitrile

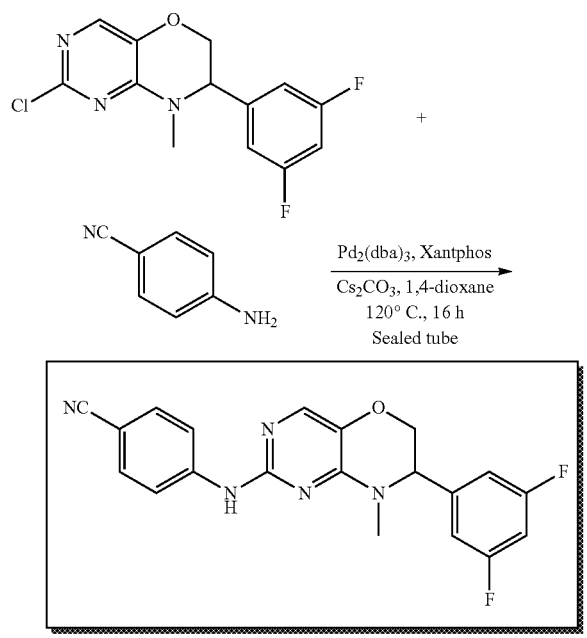

Synthesis of 4-((7-(3, 5-difluorophenyl)-8-methyl-7, 8-dihydro-6H-pyrimido [5, 4-b] [1, 4] oxazin-2-yl) amino) benzonitrile To a dry vial was added a suspension of $Pd_2(dba)_3$ (23 mg, 0.02 mmol) and Xantphos (43 mg, 0.07 mmol) in 1, 4-dioxane (0.75 mL) at room temperature. The suspension was degassed with argon, heated to 120° C., and stirred for 3 min. A mixture of 2-chloro-7-(3, 5-difluorophenyl)-8-methyl-7, 8-dihydro-6H-pyrimido [5, 4-b] [1, 4] oxazine (150 mg, 0.50 mmol), 4-aminobenzonitrile (119 mg, 1.01 mmol) and cesium carbonate (230 mg, 0.70 mmol) in 1, 4-dioxane (0.75 mL) was degassed and the catalyst premix was added. The resultant mixture was stirred at 120° C. for 16 h in sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 0-5% MeOH: $CH_2Cl_2$ to afford 4-((7-(3, 5-difluorophenyl)-8-methyl-7, 8-dihydro-6H-pyrimido [5, 4-b] [1, 4] oxazin-2-yl) amino) benzonitrile (90 mg, 47%) as a brown solid. LCMS: 381.1 (M+1); (column; X-Select CSH C-18 (50×3.0 mm, 3.5 μm); RT 2.92 min 0.05% Aq TFA: ACN; 0.80 mL/min); TLC: 10% MeOH/$CH_2Cl_2$ ($R_f$; 0.4).

Racemic compound of Example 233 was separated using a Chiralpak IA column (250×20 mm: 5 μm; (20 mg loading; 0.1% DEA in n-hexane (B) IPA:$CH_2Cl_2$ (A:B; 75:20:5); as mobile phase) to provide the compound of Example 233A (Fraction I (+)) and the compound of Example 233B (Fraction II (−)).

Example 233A

Synthesis of (+)-4-((7-(3, 5-difluorophenyl)-8-methyl-7, 8-dihydro-6H-pyrimido [5, 4-b] [1, 4] oxazin-2-yl) amino) benzonitrile

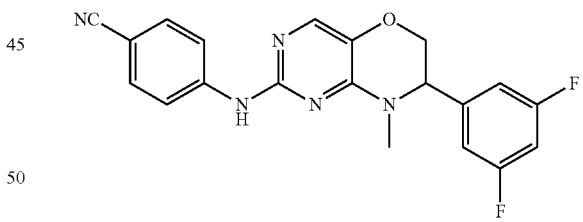

The compound of Example 233A was produced as described in Example 233. Analytical data for product Fraction I (+): $^1$H-NMR ($CD_3OD$, 400 MHz): δ 7.90 (d, 2H), 7.67 (s, 1H), 7.61 (d, 2H), 6.99-6.90 (m, 1H), 6.89-6.83 (m, 2H), 4.80 (t, 1H), 4.24-4.22 (m, 2H), 3.18 (s, 3H); Mass (ESI): 380.5 [M+1]; LCMS: 380 (M+1); (column; X-Select CSH C-18 (50×3.0 mm, 3.5 μm); RT 3.02 min 0.05% Aq TFA: ACN; 0.80 mL/min); UPLC (column; Acquity BEH C-18, 50×2.1 mm, 1.7 μm); RT 2.06 min. ACN: 0.025% Aq TFA; 0.5 mL/min; Chiral HPLC: 100% RT=16.12 min (CHIRALPAK-IA (250×4.6 mm, 5 μm; mobile phase (A) 0.1% DEA in n-hexane (B) IPA:$CH_2Cl_2$ (A:B; 75:20:5); flow Rate: 1.0 mL/min); Optical rotation $[α]_D^{20.02}$: +183.44 (c=0.25, $CH_2Cl_2$).

Example 233B

Synthesis of (−)-4-((7-(3, 5-difluorophenyl)-8-methyl-7, 8-dihydro-6H-pyrimido [5, 4-b] [1, 4] oxazin-2-yl) amino) benzonitrile

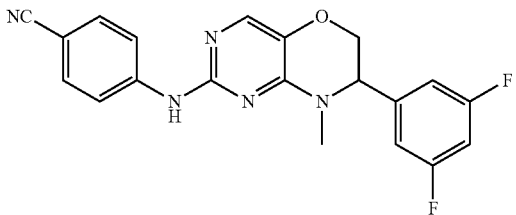 [SMILES: CN1c2nc(Nc3ccc(C#N)cc3)ncc2OCC1c1cc(F)cc(F)c1]

The compound of Example 233B was produced as described in Example 233. Analytical data for product Fraction II (−): $^1$H-NMR (CD$_3$OD, 400 MHz): δ 7.90 (d, 2H), 7.67 (s, 1H), 7.61 (d, 2H), 6.99-6.90 (m, 1H), 6.89-6.83 (m, 2H), 4.80 (t, 1H), 4.24-4.22 (m, 2H), 3.18 (s, 3H); Mass (ESI): 380.5 [M+1]; LCMS: 380 (M+1); (column; X-Select CSH C-18 (50×3.0 mm, 3.5 μm); RT 3.00 min 0.05% Aq TFA: ACN; 0.80 mL/min); UPLC (column; Acquity BEH C-18, 50×2.1 mm, 1.7 μm); RT 2.06 min. ACN: 0.025% Aq TFA; 0.5 mL/min; Chiral HPLC: 98.4% RT=18.18 min (CHIRALPAK-IA (250×4.6 mm, 5 μm; mobile phase (A) 0.1% DEA in n-hexane (B) IPA:CH$_2$Cl$_2$ (A:B; 75:20:5); flow Rate: 1.0 mL/min); Optical rotation [α]$_D^{20.01}$: −175.90 (c=0.25, CH$_2$Cl$_2$).

Example 234

Synthesis of N-(4-methoxy-5-(4-methyl-1H-imidazol-1-yl) pyridin-2-yl)-7, 8-dimethyl-7, 8-dihydro-6H-pyrimido [5, 4-b] [1, 4] oxazin-2-amine

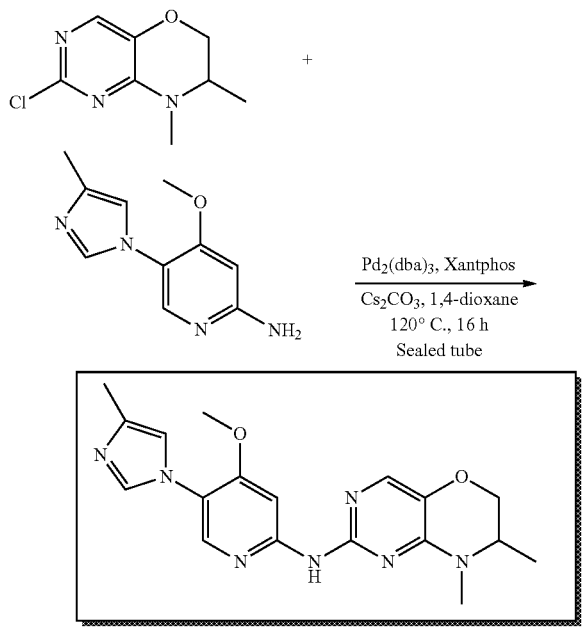

Synthesis of N-(4-methoxy-5-(4-methyl-1H-imidazol-1-yl) pyridin-2-yl)-7, 8-dimethyl-7, 8-dihydro-6H-pyrimido [5, 4-b] [1, 4] oxazin-2-amine To a dry vial was added a suspension of Pd$_2$(dba)$_3$ (34 mg, 0.04 mmol) and Xantphos (65 mg, 0.11 mmol) in 1, 4-dioxane (1 mL) at room temperature. The suspension was degassed with argon, heated to 120° C., and stirred for 3 min. A mixture of 2-chloro-7, 8-dimethyl-7, 8-dihydro-6H-pyrimido [5, 4-b] [1, 4] oxazine (150 mg, 0.75 mmol), 4-methoxy-5-(4-methyl-1H-imidazol-1-yl) pyridin-2-amine (307 mg, 0.15 mmol) and cesium carbonate (368 mg, 0.11 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with 10% MeOH: CH$_2$Cl$_2$ (2×25 mL). The combined organic extracts were dried over sodium sulfate, filtered and concentrated in vacuo. The crude material was purified by column chromatography using 0-4% MeOH: CH$_2$Cl$_2$ to afford N-(4-methoxy-5-(4-methyl-1H-imidazol-1-yl) pyridin-2-yl)-7, 8-dimethyl-7, 8-dihydro-6H-pyrimido [5, 4-b] [1, 4] oxazin-2-amine (220 mg, 80%) as a yellow solid. $^1$H-NMR (DMSO-d$_6$, 400 MHz): δ 9.14 (s, 1H), 8.23 (s, 1H), 8.07 (s, 1H), 7.67 (s, 1H), 7.63 (s, 1H), 7.05 (s, 1H), 4.11-3.93 (m, 2H), 3.89 (s, 3H), 3.75-3.65 (m, 1H), 3.16 (s, 3H), 2.15-2.12 (m, 3H), 1.23 (d, 3H); Mass (ESI): 368 [M+1]; LCMS: 368 (M+1); (column; X-Select CSH C-18 (50×3.0 mm, 3.5 μm); RT 1.97 min 0.05% Aq TFA: ACN; 0.80 mL/min); UPLC (column; Acquity BEH C-18, 50×2.1 mm, 1.7 μm); RT 1.26 min. ACN: 0.025% Aq TFA; 0.5 mL/min; TLC: 5% MeOH/CH$_2$Cl$_2$ (R$_f$: 0.5).

Example 235

Synthesis of (S)-7-cyclobutyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

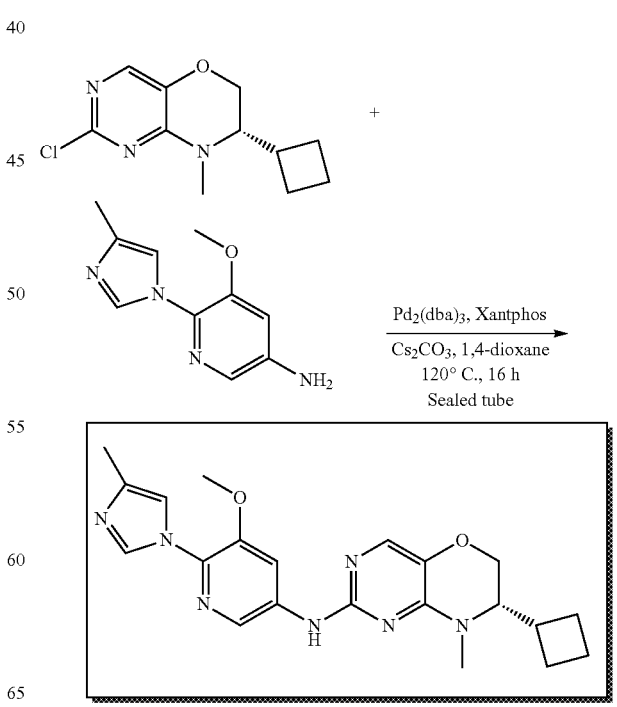

Synthesis of (S)-7-cyclobutyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine To a dry vial was added a suspension of $Pd_2(dba)_3$ (19 mg, 0.02 mmol) and Xantphos (36 mg, 0.06 mmol) in 1, 4-dioxane (0.5 mL) at room temperature. The suspension was degassed with argon, heated to 120° C., and stirred for 3 min. A mixture of (S)-2-chloro-7-cyclobutyl-8-methyl-7, 8-dihydro-6H-pyrimido [5, 4-b] [1, 4] oxazine (100 mg, 0.42 mmol), 5-methoxy-6-(4-methyl-1H-imidazol-1-yl) pyridin-3-amine (170 mg, 0.83 mmol) and cesium carbonate (191 mg, 0.58 mmol) in 1, 4-dioxane (0.5 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with $CH_2Cl_2$ (2×20 mL). The combined organic extracts were dried over sodium sulfate, filtered and concentrated in vacuo. The crude material was purified column chromatography using 50% EtOAc:hexane to afford (S)-7-cyclobutyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine (40 mg, 24%) as an off-white solid. $^1$H-NMR (CD$_3$OD, 400 MHz): δ 8.27 (d, 2H), 8.13 (s, 1H), 7.51 (s, 1H), 7.39 (s, 1H), 4.12 (dd, 1H), 3.97 (s, 3H), 3.84 (dd, 1H), 3.46-3.40 (m, 1H), 3.27 (s, 3H), 2.70-2.61 (m, 1H), 2.25 (s, 3H), 2.18-2.0 (m, 2H), 2.07-2.00 (m, 1H), 1.99-1.90 (m, 2H), 1.88-1.80 (m, 1H); Mass (ESI): 408.5 [M+1]; LCMS: 408.1 (M+1); (column; X-Select CSH C-18 (50×3.0 mm, 3.5 μm); RT 2.24 min 0.05% Aq TFA: ACN; 0.80 mL/min); UPLC (column; Acquity BEH C-18, 50×2.1 mm, 1.7 μm); RT 1.52 min. ACN: 0.025% Aq TFA; 0.5 mL/min; Chiral HPLC: 97.4% RT=10.01 min (CHIRALPAK-IA (250×4.6 mm, 5 μm; mobile phase (A) 0.1% DEA in n-hexane (B) $CH_2Cl_2$:MeOH (50:50) (A:B; 75:25); flow Rate: 1.0 mL/min); Optical rotation $[α]_D^{19.99}$: +25.71 (c=0.25, $CH_2Cl_2$); TLC: 5% MeOH/$CH_2Cl_2$ ($R_f$: 0.3).

Example 236

Synthesis of N-(4-methoxy-5-(4-methyl-1H-imidazol-1-yl) pyridin-2-yl)-8-methyl-7-(trifluoromethyl)-7, 8-dihydro-6H-pyrimido [5, 4-b] [1, 4] oxazin-2-amine

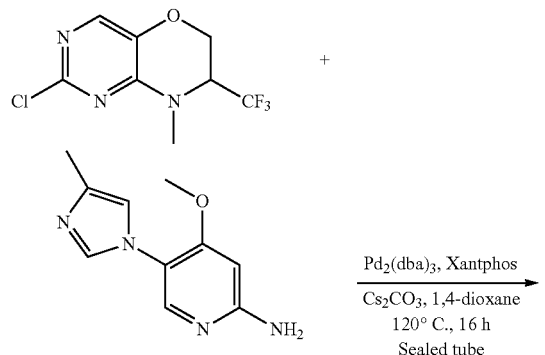

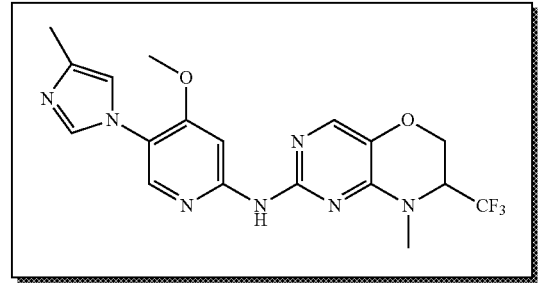

Synthesis of N-(4-methoxy-5-(4-methyl-1H-imidazol-1-yl) pyridin-2-yl)-8-methyl-7-(trifluoromethyl)-7, 8-dihydro-6H-pyrimido [5, 4-b] [1, 4] oxazin-2-amine To a dry vial was added a suspension of $Pd_2(dba)_3$ (41 mg, 0.04 mmol) and Xantphos (78 mg, 0.13 mmol) in 1, 4-dioxane (1.15 mL) at room temperature. The suspension was degassed with argon, heated to 120° C., and stirred for 3 min. A mixture of 2-chloro-8-methyl-7-(trifluoromethyl)-7, 8-dihydro-6H-pyrimido [5, 4-b] [1, 4] oxazine (230 mg, 0.90 mmol), 4-methoxy-5-(4-methyl-1H-imidazol-1-yl) pyridin-2-amine (203 mg, 0.99 mmol) and cesium carbonate (413 mg, 1.27 mmol) in 1, 4-dioxane (1.15 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with $CH_2Cl_2$ (2×20 mL). The combined organic extracts were dried over sodium sulfate, filtered and concentrated in vacuo. The crude material was purified by column chromatography using 40% EtOAc:hexane to afford N-(4-methoxy-5-(4-methyl-1H-imidazol-1-yl) pyridin-2-yl)-8-methyl-7-(trifluoromethyl)-7, 8-dihydro-6H-pyrimido [5, 4-b] [1, 4] oxazin-2-amine (120 mg, 31%) as an off-white solid. LCMS: 422 (M+1); (column; X-select CSH C-18 (50×3.0 mm, 3.5 μm); RT 2.01 min. 0.05% Aq TFA: ACN; 0.8 mL/min); TLC: 50% EtOAc:hexane ($R_f$: 0.2).

Racemic compound of Example 236 was separated using a Chiralpak IA column (250×20 mm: 5 μm; (40 mg loading; 0.1% DEA in n-hexane: IPA:$CH_2Cl_2$ (2:1); (A:B: 70:30) as mobile phase) to provide the compound of Example 236A (Fraction I (+)) and the compound of Example 236B (Fraction II (−)).

Example 236A

Synthesis of (+)-N-(4-methoxy-5-(4-methyl-1H-imidazol-1-yl) pyridin-2-yl)-8-methyl-7-(trifluoromethyl)-7, 8-dihydro-6H-pyrimido [5, 4-b] [1, 4] oxazin-2-amine

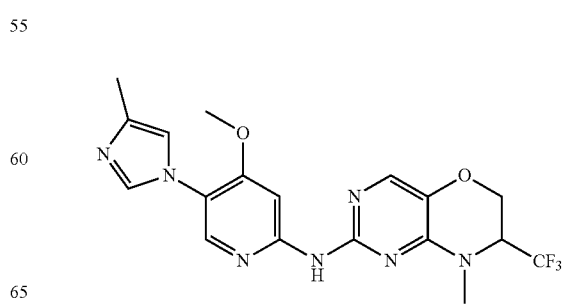

The compound of Example 236A was produced as described in Example 236. Analytical data for product Fraction I (+): $^1$H-NMR (DMSO-d$_6$, 400 MHz): δ 9.39 (s, 1H), 8.20 (s, 1H), 8.09 (s, 1H), 7.79 (s, 1H), 7.68 (s, 1H), 7.09-7.03 (m, 1H), 4.78-4.70 (m, 1H), 4.57 (d, 1H), 4.07 (d, 1H), 3.91 (s, 3H), 3.30 (s, 3H), 2.12 (s, 3H); Mass (ESI): 422.3 [M+1]; LCMS: 422 (M+1); (column; X-Select CSH C-18 (50×3.0 mm, 3.5 μm); RT 2.11 min 0.05% Aq TFA: ACN; 0.80 mL/min); UPLC (column; Acquity BEH C-18, 50×2.1 mm, 1.7 μm); RT 1.39 min. ACN: 0.025% Aq TFA; 0.5 mL/min; Chiral HPLC: 97.9% RT=10.43 min (CHIRALPAK-IA (250×4.6 mm, 5 μm; mobile phase (A) 0.1% DEA in n-hexane (B) IPA:CH$_2$Cl$_2$ (A:B; 70:20:10); flow Rate: 1.0 mL/min); Optical rotation [α]$_D^{20.00}$: +57.12 (c=0.25, CH$_2$Cl$_2$).

Example 236B

Synthesis of (−)-N-(4-methoxy-5-(4-methyl-1H-imidazol-1-yl) pyridin-2-yl)-8-methyl-7-(trifluoromethyl)-7, 8-dihydro-6H-pyrimido [5, 4-b] [1, 4] oxazin-2-amine

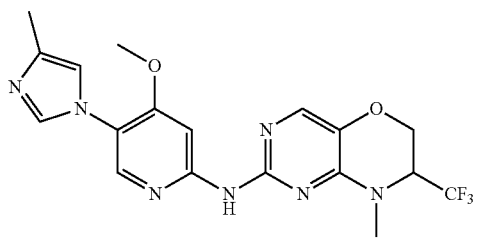 [SMILES: COc1cc(Nc2ncc3c(n2)N(C)C(C(F)(F)F)CO3)ncc1-n1cnc(C)c1]

The compound of Example 236B was produced as described in Example 236. Analytical data for product Fraction II (−): $^1$H-NMR (DMSO-d$_6$, 400 MHz): δ 9.39 (s, 1H), 8.20 (s, 1H), 8.09 (s, 1H), 7.79 (s, 1H), 7.68 (s, 1H), 7.09-7.03 (m, 1H), 4.78-4.70 (m, 1H), 4.57 (d, 1H), 4.07 (d, 1H), 3.91 (s, 3H), 3.30 (s, 3H), 2.12 (s, 3H); Mass (ESI): 380.5 [M+1]; LCMS: 422 (M+1); (column; X-Select CSH C-18 (50×3.0 mm, 3.5 μm); RT 2.00 min 0.05% Aq TFA: ACN; 0.80 mL/min); UPLC (column; Acquity BEH C-18, 50×2.1 mm, 1.7 μm); RT 1.36 min. ACN: 0.025% Aq TFA; 0.5 mL/min; Chiral HPLC: 97.7% RT=18.43 min (CHIRALPAK-IA (250×4.6 mm, 5 μm; mobile phase (A) 0.1% DEA in n-hexane (B) IPA:CH$_2$Cl$_2$ (A:B; 70:20:10); flow Rate: 1.0 mL/min); Optical rotation [α]$_D^{19.99}$: −56.35 (c=0.25, CH$_2$Cl$_2$).

Example 237

Synthesis of 4-((7-(3, 5-difluorophenyl)-8-methyl-7, 8-dihydro-6H-pyrimido [5, 4-b] [1, 4] oxazin-2-yl) amino)-2-methoxybenzonitrile

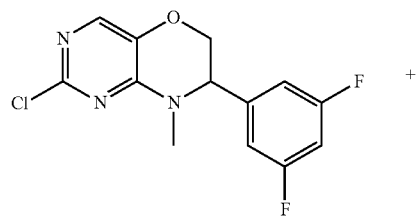 +

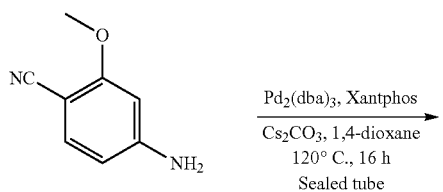

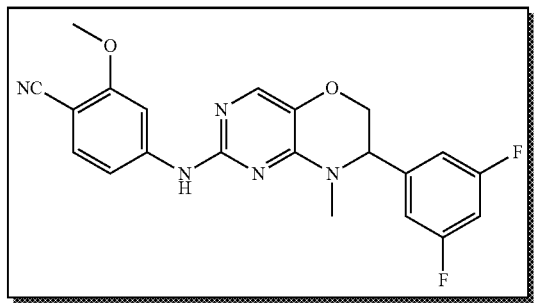

Synthesis of 4-((7-(3, 5-difluorophenyl)-8-methyl-7, 8-dihydro-6H-pyrimido [5, 4-b] [1, 4] oxazin-2-yl) amino)-2-methoxybenzonitrile To a dry vial was added a suspension of Pd$_2$(dba)$_3$ (15 mg, 0.01 mmol) and Xantphos (29 mg, 0.05 mmol) in 1, 4-dioxane (0.5 mL) at room temperature. The suspension was degassed with argon, heated to 120° C., and stirred for 3 min. A mixture of 2-chloro-7-(3, 5-difluorophenyl)-8-methyl-7, 8-dihydro-6H-pyrimido [5, 4-b] [1, 4] oxazine (100 mg, 0.33 mmol), 4-amino-2-methoxybenzonitrile (99 mg, 0.67 mmol) and cesium carbonate (153 mg, 0.47 mmol) in 1, 4-dioxane (0.5 mL) was degassed and the catalyst premix was added. The resultant mixture was stirred at 120° C. for 16 h in sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by preparative HPLC (column; X-select CSH C-18 (250×190 mm, 2.7 μm); (50 mg loading; CH$_3$CN: 0.05% TFA (0.1/90, 2/80, 15/50, 25/30, 30/10, 40/10)) to afford 4-((7-(3, 5-difluorophenyl)-8-methyl-7, 8-dihydro-6H-pyrimido [5, 4-b] [1, 4] oxazin-2-yl) amino)-2-methoxybenzonitrile (60 mg, 43%) as an off-white solid. LCMS: 410 (M+1); (column; X-select CSH C-18 (50×3.0 mm, 3.5 μm); RT 3.04 min. 0.05% Aq TFA: ACN; 0.8 mL/min); TLC: 50% EtOAc:hexane (R$_f$: 0.2).

Racemic compound of Example 237 was separated using a Chiralpak ADH column (250×20 mm: 5 μm; (25 mg loading; 0.1% DEA in n-hexane: EtOH:MeOH (50:50); (A:B: 60:40) as mobile phase) to provide the compound of Example 237A (Fraction I (−)) and the compound of Example 237B (Fraction II (+)).

Example 237A

Synthesis of (−)-4-((7-(3, 5-difluorophenyl)-8-methyl-7, 8-dihydro-6H-pyrimido [5, 4-b] [1, 4] oxazin-2-yl) amino)-2-methoxybenzonitrile

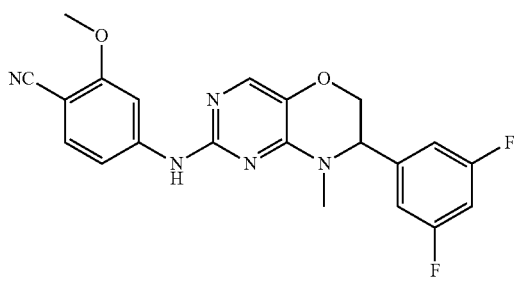 [SMILES: COc1cc(Nc2ncc3c(n2)N(C)C(c2cc(F)cc(F)c2)CO3)ccc1C#N]

The compound of Example 237A was produced as described in Example 237. Analytical data for product Fraction I (−): $^1$H-NMR (CD$_3$OD, 400 MHz): δ 7.83 (s, 1H), 7.65 (s, 1H), 7.41 (d, 1H), 7.23 (dd, 1H), 6.97-6.89 (m, 1H), 6.88-6.81 (m, 2H), 4.79-4.76 (m, 1H), 4.24 (s, 2H), 3.93 (s, 3H), 3.18 (s, 3H); Mass (ESI): 410.6 [M+1]; LCMS: 410 (M+1); (column; X-Select CSH C-18 (50×3.0 mm, 3.5 μm); RT 3.04 min 0.05% Aq TFA: ACN; 0.80 mL/min); UPLC (column; Acquity BEH C-18, 50×2.1 mm, 1.7 μm); RT 2.05 min. ACN: 0.025% Aq TFA; 0.5 mL/min; Chiral HPLC: 100% RT=10.21 min (CHIRALPAK-ADH (250×4.6 mm, 5 μm; mobile phase (A) 0.1% DEA in n-hexane (B) EtOH: MeOH (50:50) (A:B; 60:40); flow Rate: 1.0 mL/min); Optical rotation [α]$_D$$^{19.99}$: −108.83 (c=0.25, CH$_2$Cl$_2$).

Example 237B

Synthesis of (+)-4-((7-(3, 5-difluorophenyl)-8-methyl-7, 8-dihydro-6H-pyrimido [5, 4-b] [1, 4] oxazin-2-yl) amino)-2-methoxybenzonitrile

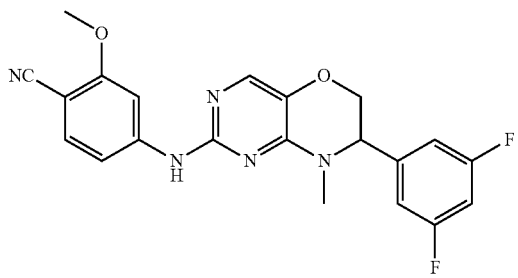 [SMILES: COc1cc(Nc2ncc3c(n2)N(C)C(c2cc(F)cc(F)c2)CO3)ccc1C#N]

The compound of Example 237B was produced as described in Example 237. Analytical data for product Fraction II (+): $^1$H-NMR (CD$_3$OD, 400 MHz): δ 7.83 (s, 1H), 7.65 (s, 1H), 7.41 (d, 1H), 7.23 (dd, 1H), 6.97-6.89 (m, 1H), 6.88-6.81 (m, 2H), 4.79-4.76 (m, 1H), 4.24 (s, 2H), 3.93 (s, 3H), 3.18 (s, 3H); Mass (ESI): 410.5 [M+1]; LCMS: 410 (M+1); (column; X-Select CSH C-18 (50×3.0 mm, 3.5 μm); RT 3.04 min 0.05% Aq TFA: ACN; 0.80 mL/min); UPLC (column; Acquity BEH C-18, 50×2.1 mm, 1.7 μm); RT 2.04 min. ACN: 0.025% Aq TFA; 0.5 mL/min; Chiral HPLC: 99.9% RT=16.37 min (CHIRALPAK-ADH (250×4.6 mm, 5 μm; mobile phase (A) 0.1% DEA in n-hexane (B) EtOH:MeOH (50:50) (A:B; 60:40); flow Rate: 1.0 mL/min); Optical rotation [α]$_D$$^{20.04}$: +107.45 (c=0.25, CH$_2$Cl$_2$).

Example 238

Synthesis of N-(5-methoxy-6-(4-methyl-1H-imidazol-1-yl) pyridin-3-yl)-8-methyl-7-(2, 2, 2-trifluoroethyl)-7, 8-dihydro-6H-pyrimido [5, 4-b] [1, 4] oxazin-2-amine

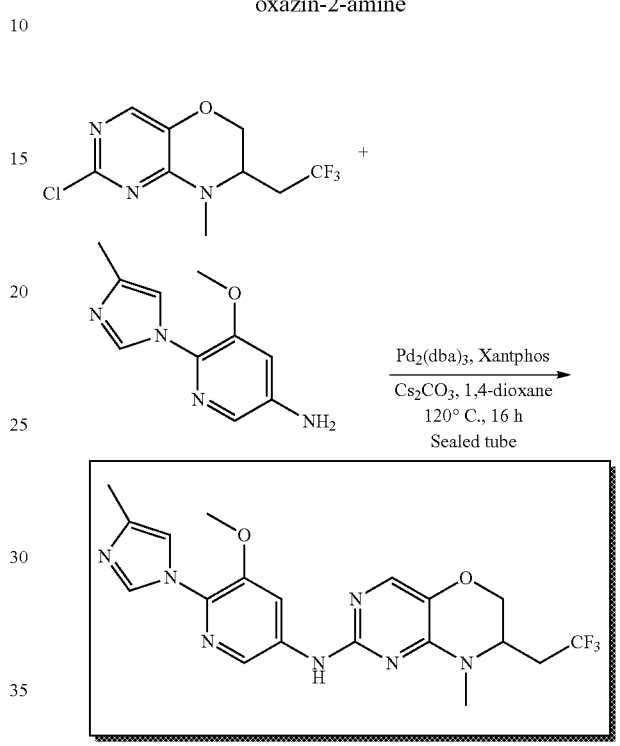

Synthesis of N-(5-methoxy-6-(4-methyl-1H-imidazol-1-yl) pyridin-3-yl)-8-methyl-7-(2, 2, 2-trifluoroethyl)-7, 8-dihydro-6H-pyrimido [5, 4-b] [1, 4] oxazin-2-amine To a dry vial was added a suspension of Pd$_2$(dba)$_3$ (26 mg, 0.03 mmol) and Xantphos (49 mg, 0.08 mmol) in 1, 4-dioxane (0.75 mL) at room temperature. The suspension was degassed with argon, heated to 120° C., and stirred for 3 min. A mixture of 2-chloro-8-methyl-7-(2, 2, 2-trifluoroethyl)-7, 8-dihydro-6H-pyrimido [5, 4-b] [1, 4] oxazine (150 mg, 0.56 mmol), 5-methoxy-6-(4-methyl-1H-imidazol-1-yl) pyridin-3-amine (230 mg, 1.12 mmol) and cesium carbonate (255 mg, 0.78 mmol) in 1, 4-dioxane (0.75 mL) was degassed and the catalyst premix was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by preparative HPLC (column; X-select CSH C-18 (250×190 mm, 2.7 μm); (70 mg loading; CH$_3$CN: 0.05% TFA (0.1/90, 2/80, 15/50, 25/20, 30/10, 40/10)) to afford N-(5-methoxy-6-(4-methyl-1H-imidazol-1-yl) pyridin-3-yl)-8-methyl-7-(2, 2, 2-trifluoroethyl)-7, 8-dihydro-6H-pyrimido [5, 4-b] [1, 4] oxazin-2-amine (100 mg, 41%) as an off-white solid. LCMS: 436 (M+1); (column; X-select CSH C-18 (50×3.0 mm, 3.5 μm); RT 2.23 min. 0.05% Aq TFA: ACN; 0.8 mL/min); TLC: 5% MeOH/CH$_2$Cl$_2$ (R$_f$: 0.2).

Racemic compound of Example 238 was separated using a Chiralpak AD-H column (250×20 mm: 5 μm; (50 mg loading; 0.1% DEA in n-hexane (B) EtOH:MeOH (50:50) (A:B; 75:25); as mobile phase) to provide the compound of Example 238A (Fraction I (−)) and the compound of Example 238B (Fraction II (+)).

Example 238A

Synthesis of (−)-N-(5-methoxy-6-(4-methyl-1H-imidazol-1-yl) pyridin-3-yl)-8-methyl-7-(2, 2, 2-trifluoroethyl)-7, 8-dihydro-6H-pyrimido [5, 4-b] [1, 4] oxazin-2-amine

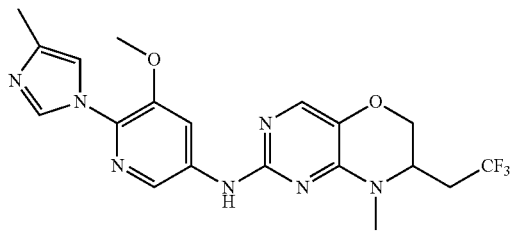 [SMILES: COc1cc(Nc2ncc3c(n2)N(C)C(CC(F)(F)F)CO3)cnc1-n1cnc(C)c1]

The compound of Example 238A was produced as described in Example 238. Analytical data for product Fraction I (−): $^1$H-NMR (CD$_3$OD, 400 MHz): δ 8.30-8.26 (m, 2H), 8.12 (s, 1H), 7.63 (s, 1H), 7.39 (s, 1H), 4.28 (dd, 1H), 4.00 (d, 2H), 3.97 (s, 3H), 3.25 (s, 3H), 2.68-2.57 (m, 2H), 2.26 (s, 3H); Mass (ESI): 436.7 [M+1]; LCMS: 436 (M+1); (column; X-Select CSH C-18 (50×3.0 mm, 3.5 μm); RT 2.15 min 0.05% Aq TFA: ACN; 0.80 mL/min); UPLC (column; Acquity BEH C-18, 50×2.1 mm, 1.7 μm); RT 1.46 min. ACN: 0.025% Aq TFA; 0.5 mL/min; Chiral HPLC: 98.4% RT=11.60 min (CHIRALPAK-ADH (250×4.6 mm, 5 μm; mobile phase (A) 0.1% DEA in n-hexane (B) EtOH: MeOH (50:50) (A:B; 75:25); flow Rate: 1.0 mL/min); Optical rotation $[\alpha]_D^{20.00}$: −3.58 (c=0.25, CH$_2$Cl$_2$).

Example 238B

Synthesis of (+)-N-(5-methoxy-6-(4-methyl-1H-imidazol-1-yl) pyridin-3-yl)-8-methyl-7-(2, 2, 2-trifluoroethyl)-7, 8-dihydro-6H-pyrimido [5, 4-b] [1, 4] oxazin-2-amine

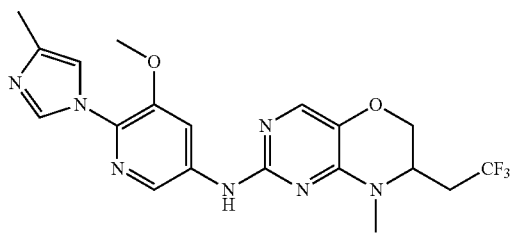 [SMILES: COc1cc(Nc2ncc3c(n2)N(C)C(CC(F)(F)F)CO3)cnc1-n1cnc(C)c1]

The compound of Example 238B was produced as described in Example 238. Analytical data for product Fraction II (+): $^1$H-NMR (CD$_3$OD, 400 MHz): δ 8.30-8.26 (m, 2H), 8.12 (s, 1H), 7.63 (s, 1H), 7.39 (s, 1H), 4.28 (dd, 1H), 4.00 (d, 2H), 3.97 (s, 3H), 3.25 (s, 3H), 2.68-2.57 (m, 2H), 2.26 (s, 3H); Mass (ESI): 436.6 [M+1]; LCMS: 436 (M+1); (column; X-Select CSH C-18 (50×3.0 mm, 3.5 μm); RT 2.16 min 0.05% Aq TFA: ACN; 0.80 mL/min); UPLC (column; Acquity BEH C-18, 50×2.1 mm, 1.7 μm); RT 1.48 min. ACN: 0.025% Aq TFA; 0.5 mL/min; Chiral HPLC: 99.7% RT=17.40 min (CHIRALPAK-ADH (250×4.6 mm, 5 μm; mobile phase (A) 0.1% DEA in n-hexane (B) EtOH: MeOH (50:50) (A:B; 75:25); flow Rate: 1.0 mL/min); Optical rotation $[\alpha]_D^{20.01}$: +7.42 (c=0.25, CH$_2$Cl$_2$).

Example 239

Synthesis of 4-(2-((3-methoxy-4-(4-methyl-1H-imidazol-1-yl) phenyl) amino)-8-methyl-7, 8-dihydro-6H-pyrimido [5, 4-b] [1, 4] oxazin-7-yl) tetrahydro-2H-thiopyran 1, 1-dioxide

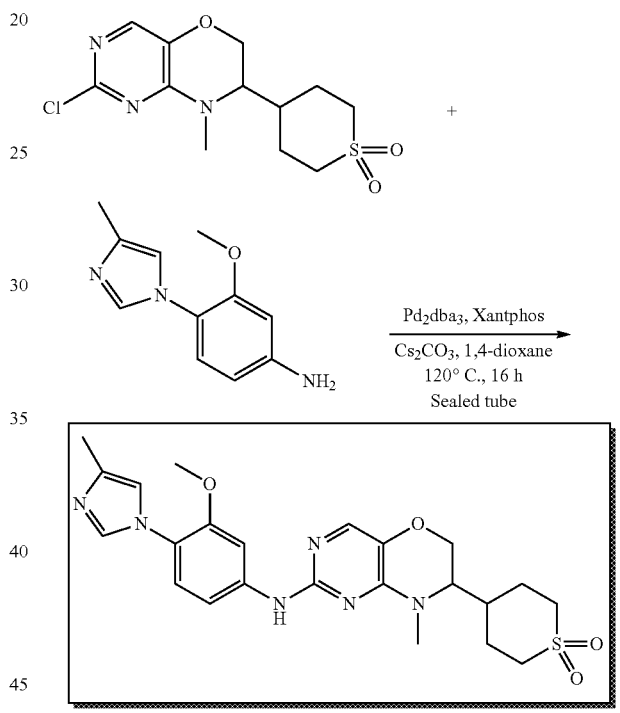

Synthesis of 4-(2-((3-methoxy-4-(4-methyl-1H-imidazol-1-yl) phenyl) amino)-8-methyl-7, 8-dihydro-6H-pyrimido [5, 4-b] [1, 4] oxazin-7-yl) tetrahydro-2H-thiopyran 1, 1-dioxide To a dry vial was added a suspension of Pd$_2$(dba)$_3$ (21 mg, 0.02 mmol) and Xantphos (41 mg, 0.07 mmol) in 1, 4-dioxane (0.5 mL) at room temperature. The suspension was degassed with argon, heated to 120° C., and stirred for 3 min. A mixture of 4-(2-chloro-8-methyl-7, 8-dihydro-6H-pyrimido [5, 4-b] [1, 4] oxazin-7-yl) tetrahydro-2H-thiopyran 1, 1-dioxide (150 mg, 0.47 mmol), 3-methoxy-4-(4-methyl-1H-imidazol-1-yl) aniline (192 mg, 0.94 mmol), cesium carbonate (2.5 mg, 0.66 mmol) in 1, 4-dioxane (0.5 mL) was degassed and the catalyst premix was added. The resultant mixture was stirred at 120° C. for 16 h in a sealed tube. After consumption of the starting material (monitored by TLC and LCMS), the reaction mixture was filtered and the filtrate was concentrated in vacuo. The crude material was purified by column chromatography using 2% MeOH: CH₂Cl₂ to afford 4-(2-((3-methoxy-4-(4-methyl-1H-imidazol-1-yl) phenyl) amino)-8-methyl-7, 8-dihydro-6H-pyrimido [5, 4-b] [1, 4] oxazin-7-yl) tetrahydro-2H-thiopyran 1, 1-dioxide (170 mg, 85%) as an off-white solid. UPLC (column; Acquity BEH C18, 50×2.1 mm, 1.7 μm); RT 1.20 min. ACN: 0.025% Aq TFA; 0.5 mL/min; TLC: 10% MeOH/CH₂Cl₂ (R_f: 0.2).

Racemic compound of Example 239 was separated using a Chiralpak IA column (250×20 mm: 5 μm; (30 mg loading; 0.1% DEA in n-hexane: CH₂Cl₂:MeOH (50:50); (A:B: 60:40) as mobile phase) to provide the compound of Example 239A (Fraction I (−)) and the compound of Example 239B (Fraction II (+)).

Example 239A

Synthesis of (−)-4-(2-((3-methoxy-4-(4-methyl-1H-imidazol-1-yl) phenyl) amino)-8-methyl-7, 8-dihydro-6H-pyrimido [5, 4-b] [1, 4] oxazin-7-yl) tetrahydro-2H-thiopyran 1, 1-dioxide

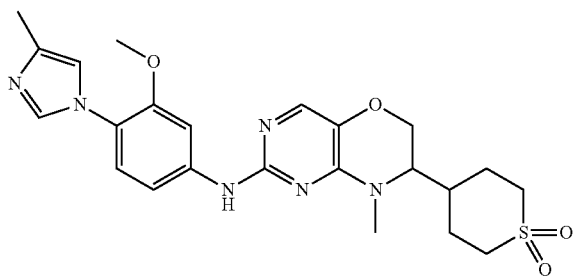 [SMILES: COc1cc(Nc2ncc3c(n2)N(C)C(C2CCS(=O)(=O)CC2)CO3)ccc1-n1cnc(C)c1]

The compound of Example 239A was produced as described in Example 239. Analytical data for product Fraction I (−): ¹H-NMR (CD₃OD, 400 MHz): δ 7.75-7.73 (m, 1H), 7.65-7.63 (m, 1H), 7.53 (s, 1H), 7.24-7.16 (m, 2H), 6.96 (s, 1H), 4.41 (d, 1H), 3.89-3.87 (m, 1H), 3.86 (s, 3H), 3.52-3.48 (m, 1H), 3.30 (s, 3H), 3.20-2.99 (m, 4H), 2.23 (s, 4H), 2.14-2.00 (m, 4H); Mass (ESI): 485.5 [M+1]; LCMS: 485 (M+1); (column; Ascentis Express C-18 (50×3.0 mm, 2.7 μm); RT 1.38 min. 0.025% Aq TFA+5% ACN: ACN+ 0.025% Aq TFA; 1.2 mL/min); UPLC (column; Acquity BEH C-18, 50×2.1 mm, 1.7 μm); RT 1.22 min. ACN: 0.025% Aq TFA; 0.5 mL/min; Chiral HPLC: 99.0% RT=11.04 min (CHIRALPAK-IA (250×4.6 mm, 5 μm; mobile phase (A) 0.1% DEA in n-hexane (B) CH₂Cl₂: MeOH (50:50) (A:B; 60:40); flow Rate: 1.0 mL/min); Optical rotation $[\alpha]_D^{20.00}$: −97.64 (c=0.25, CH₂Cl₂).

Example 239B

Synthesis of (+)-4-(2-((3-methoxy-4-(4-methyl-1H-imidazol-1-yl) phenyl) amino)-8-methyl-7, 8-dihydro-6H-pyrimido [5, 4-b] [1, 4] oxazin-7-yl) tetrahydro-2H-thiopyran 1, 1-dioxide

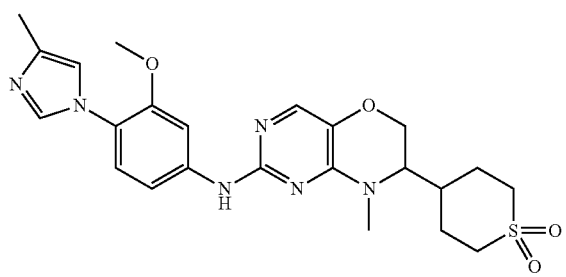 [SMILES: COc1cc(Nc2ncc3c(n2)N(C)C(C2CCS(=O)(=O)CC2)CO3)ccc1-n1cnc(C)c1]

The compound of Example 239B was produced as described in Example 239. Analytical data for product Fraction II (+): ¹H-NMR (CD₃OD, 400 MHz): δ 7.75-7.73 (m, 1H), 7.65-7.63 (m, 1H), 7.53 (s, 1H), 7.24-7.16 (m, 2H), 6.96 (s, 1H), 4.41 (d, 1H), 3.89-3.87 (m, 1H), 3.86 (s, 3H), 3.52-3.48 (m, 1H), 3.30 (s, 3H), 3.20-2.99 (m, 4H), 2.23 (s, 4H), 2.14-2.00 (m, 4H); Mass (ESI): 485.5 [M+1]; LCMS: 485 (M+1); (column; Ascentis Express C-18 (50×3.0 mm, 2.7 μm); RT 1.38 min. 0.025% Aq TFA+5% ACN: ACN+ 0.025% Aq TFA; 1.2 mL/min); UPLC (column; Acquity BEH C-18, 50×2.1 mm, 1.7 μm); RT 1.22 min. ACN: 0.025% Aq TFA; 0.5 mL/min; Chiral HPLC: 99.1% RT=12.95 min (CHIRALPAK-IA (250×4.6 mm, 5 μm; mobile phase (A) 0.1% DEA in n-hexane (B) CH₂Cl₂: MeOH (50:50) (A:B; 60:40); flow Rate: 1.0 mL/min); Optical rotation $[\alpha]_D^{19.99}$: +101.45 (c=0.25, CH₂Cl₂).

Example 240

Synthesis of (S)-7-(tert-butyl)-N-(3-methoxy-4-(4-methyl-1H-imidazol-1-yl) phenyl)-8-methyl-7, 8-dihydro-6H-pyrimido [5, 4-b] [1, 4] oxazin-2-amine

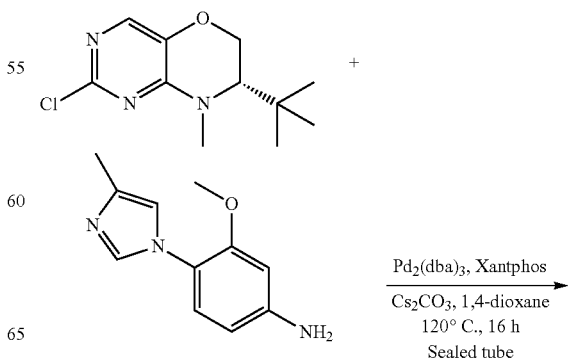

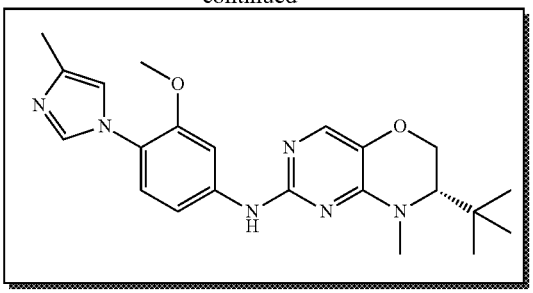

Synthesis of (S)-7-(tert-butyl)-N-(3-methoxy-4-(4-methyl-1H-imidazol-1-yl) phenyl)-8-methyl-7, 8-dihydro-6H-pyrimido [5, 4-b] [1, 4] oxazin-2-amine To a dry vial was added a suspension of $Pd_2(dba)_3$ (38 mg, 0.04 mmol) and Xantphos (76 mg, 0.12 mmol) in 1, 4-dioxane (0.25 mL) at room temperature. The suspension was degassed with argon, heated to 120° C., and stirred for 3 min. A mixture of (S)-7-(tert-butyl)-2-chloro-8-methyl-7, 8-dihydro-6H-pyrimido [5, 4-b] [1, 4] oxazine (200 mg, 0.83 mmol), 3-methoxy-4-(4-methyl-1H-imidazol-1-yl) aniline (338 mg, 1.65 mmol) and cesium carbonate (377 mg, 1.16 mmol) in 1, 4-dioxane (0.25 mL) was degassed and the catalyst premix was added. The resultant mixture was stirred at 120° C. for 16 h in sealed tube. After consumption of the starting material (monitored by TLC and LCMS), the reaction mixture was filtered and the filtrate was concentrated in vacuo. The crude material was purified by preparative HPLC (Ascentis C-18 (250×21.2 mm, 5 µm (10 mg loading; $CH_3CN$: 0.05% TFA (0.1/90, 2/80, 15/30, 25/10, 30/10, 35/10)) to afford (S)-7-(tert-butyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (40 mg, 12%) as a white solid. $^1$H-NMR ($CD_3OD$, 400 MHz): δ 7.77 (s, 1H), 7.66 (s, 1H), 7.49 (s, 1H), 7.32-7.20 (m, 1H), 7.20-7.08 (m, 1H), 6.97 (s, 1H), 4.54 (d, 1H), 3.86 (s, 3H), 3.76 (dd, 1H), 3.32 (s, 3H), 3.27-3.25 (m, 1H), 2.23 (s, 3H), 1.09 (s, 9H); Mass (ESI): 409.5 [M+1]; LCMS: 409 (M+1); (column; Ascentis Express C-18 (50×3.0 mm, 2.7 µm); RT 1.63 min. 0.025% Aq TFA+5% ACN: 5% ACN+0.025% Aq TFA; 1.2 mL/min); HPLC (column; Eclipse XDB C-18, 150×4.6 mm, 5 µm); RT 6.67 min. ACN: 0.05% Aq TFA; 1.0 mL/min; Chiral HPLC: 95.6% RT=19.05 min (CHIRALPAK-IC (250×4.6 mm, 5 µm; mobile phase (A) 0.1% DEA in n-hexane (B) $CH_2Cl_2$:MeOH (50:50) (A:B; 80:20); flow Rate: 1.0 mL/min); Optical rotation $[α]_D^{19.99}$: +25.60 (c=0.25, $CH_2Cl_2$); TLC: 5% MeOH/$CH_2Cl_2$ ($R_f$: 0.4).

Example 241

Synthesis of N-(3-methoxy-4-(4-methyl-1H-imidazol-1-yl) phenyl)-8-methyl-7-(oxetan-3-yl)-7, 8-dihydro-6H-pyrimido [5, 4-b] [1, 4] oxazin-2-amine

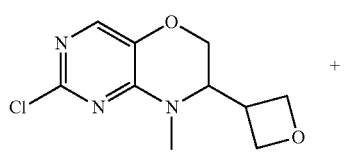

+

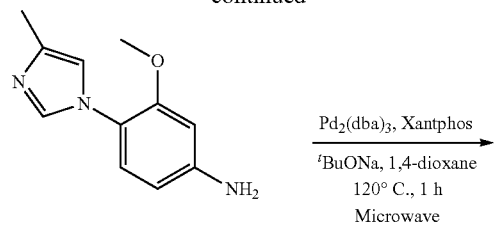

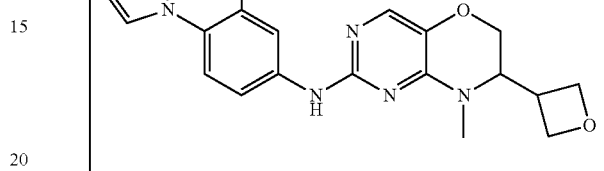

Synthesis of N-(3-methoxy-4-(4-methyl-1H-imidazol-1-yl) phenyl)-8-methyl-7-(oxetan-3-yl)-7, 8-dihydro-6H-pyrimido [5, 4-b] [1, 4] oxazin-2-amine To a dry vial was added a suspension of $Pd_2(dba)_3$ (47 mg, 0.05 mmol) and Xantphos (90 mg, 0.15 mmol) in 1, 4-dioxane (2.5 mL) at room temperature. The suspension was degassed with argon, heated to 120° C., and stirred for 3 min. A mixture of 2-chloro-8-methyl-7-(oxetan-3-yl)-7, 8-dihydro-6H-pyrimido [5, 4-b] [1, 4] oxazine (250 mg, 1.03 mmol), 3-methoxy-4-(4-methyl-1H-imidazol-1-yl) aniline (420 mg, 2.07 mmol) and sodium tert-butoxide (298 mg, 3.10 mmol) in 1, 4-dioxane (2.5 mL) was degassed and the catalyst premix was added. The resultant mixture was stirred at 120° C. for 1 h in a microwave. After consumption of the starting material (monitored by TLC and LCMS), the reaction mixture was filtered, washed with 10% MeOH: $CH_2Cl_2$ and the filtrate was concentrated in vacuo. The crude material was purified by preparative HPLC (Column YMC Actus Triart C18 (250×20 mm: 5µ; (100 mg loading; $CH_3CN$: 5 mM $NH_4OAc$ (0.1/90, 2/90, 15/70, 25/30, 30/10, 35/10) to afford N-(3-methoxy-4-(4-methyl-1H-imidazol-1-yl) phenyl)-8-methyl-7-(oxetan-3-yl)-7, 8-dihydro-6H-pyrimido [5, 4-b] [1, 4] oxazin-2-amine (180 mg, 42%) as an off-white solid. $^1$H-NMR (DMSO-$d_6$, 500 MHz): δ 9.09 (s, 1H), 7.83 (s, 1H), 7.60 (s, 1H), 7.58 (s, 1H), 7.27 (dd, 1H), 7.13 (d, 1H), 6.98 (s, 1H), 4.70-4.64 (m, 2H), 4.61-4.53 (m, 2H), 4.06-3.96 (m, 2H), 3.86 (dd, 1H), 3.75 (s, 3H), 3.32-3.30 (m, 1H), 3.16 (s, 3H), 2.12 (s, 3H); LCMS: 409.4 (M+1); (column; X-select CSH C-18 (50×3.0 mm, 3.5 µm); RT 3.39 min. 5 mM Aq $NH_4OAc$: ACN; 0.8 mL/min); HPLC (column; Eclipse XDB C-18, 150×4.6 mm, 5.0 µm); RT 8.50 min. ACN: 5 mM Aq $NH_4OAc$; 1.0 mL/min; TLC: 5% MeOH/$CH_2Cl_2$ ($R_f$: 0.5).

Racemic compound of Example 241 was separated using a Chiralpak IA column (250×20 mm: 5 µm; (40 mg loading; 0.1% DEA in n-hexane: EtOH:MeOH (50:50); (A:B: 50:50) as mobile phase) to provide the compound of Example 241A (Fraction I (−)) and the compound of Example 241B (Fraction II (+)).

Example 241A

Synthesis of (−)-N-(3-methoxy-4-(4-methyl-1H-imidazol-1-yl) phenyl)-8-methyl-7-(oxetan-3-yl)-7, 8-dihydro-6H-pyrimido [5, 4-b] [1, 4] oxazin-2-amine

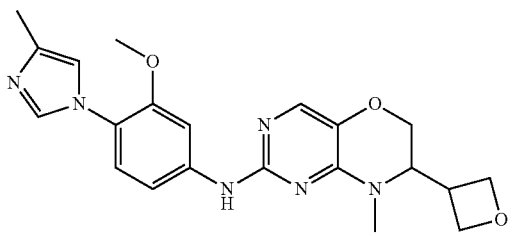

The compound of Example 241A was produced as described in Example 241. Analytical data for product Fraction I (−): $^1$H-NMR (DMSO-$d_6$, 500 MHz): δ 9.09 (s, 1H), 7.83 (s, 1H), 7.60 (s, 1H), 7.58 (s, 1H), 7.27 (dd, 1H), 7.13 (d, 1H), 6.98 (s, 1H), 4.70-4.64 (m, 2H), 4.61-4.53 (m, 2H), 4.06-3.96 (m, 2H), 3.86 (dd, 1H), 3.75 (s, 3H), 3.32-3.30 (m, 1H), 3.16 (s, 3H), 2.12 (s, 3H); Mass (ESI): 409.5 [M+1]; LCMS: 409.5 (M+1); (column; X-Select CSH C-18 (50×3.0 mm, 3.5 μm); RT 3.39 min. 5 mM Aq NH$_4$OAc: ACN; 0.80 mL/min); HPLC (column; Eclipse XDB C-18, 150×4.6 mm, 5.0 μm); RT 8.57 min. ACN: 5 mM Aq NH$_4$OAc; 1.0 mL/min; Chiral HPLC: 99.1% RT=15.03 min (CHIRALPAK-ADH (250×4.6 mm, 5 μm; mobile phase (A) 0.1% DEA in n-hexane (B) EtOH:MeOH (50:50) (A:B; 50:50); flow Rate: 1.0 mL/min); Optical rotation $[α]_D^{20.01}$: −14.94 (c=0.25, CH$_2$Cl$_2$).

Example 241B

Synthesis of (+)-N-(3-methoxy-4-(4-methyl-1H-imidazol-1-yl) phenyl)-8-methyl-7-(oxetan-3-yl)-7, 8-dihydro-6H-pyrimido [5, 4-b] [1, 4] oxazin-2-amine

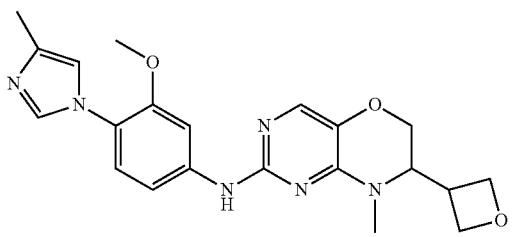

The compound of Example 241B was produced as described in Example 241. Analytical data for product Fraction II (+): $^1$H-NMR (DMSO-$d_6$, 500 MHz): δ 9.09 (s, 1H), 7.83 (s, 1H), 7.60 (s, 1H), 7.58 (s, 1H), 7.27 (dd, 1H), 7.13 (d, 1H), 6.98 (s, 1H), 4.70-4.64 (m, 2H), 4.61-4.53 (m, 2H), 4.06-3.96 (m, 2H), 3.86 (dd, 1H), 3.75 (s, 3H), 3.32-3.30 (m, 1H), 3.16 (s, 3H), 2.12 (s, 3H); Mass (ESI): 409.5 [M+1]; LCMS: 409.5 (M+1); (column; X-Select CSH C-18 (50×3.0 mm, 3.5 μm); RT 3.39 min. 5 mM Aq NH$_4$OAc: ACN; 0.80 mL/min); HPLC (column; Eclipse XDB C-18, 150×4.6 mm, 5.0 μm); RT 8.57 min. ACN: 5 mM Aq NH$_4$OAc; 1.0 mL/min; Chiral HPLC: 98.0% RT=19.91 min (CHIRALPAK-ADH (250×4.6 mm, 5 μm; mobile phase (A) 0.1% DEA in n-hexane (B) EtOH:MeOH (50:50) (A:B; 50:50); flow Rate: 1.0 mL/min); Optical rotation $[α]_D^{19.99}$: +22.06 (c=0.25, CH$_2$Cl$_2$).

Example 242

Synthesis of N-(3-methoxy-4-(3-methyl-1H-1, 2, 4-triazol-1-yl) phenyl)-8-methyl-7-(trifluoromethyl)-7, 8-dihydro-6H-pyrimido [5, 4-b] [1, 4] oxazin-2-amine

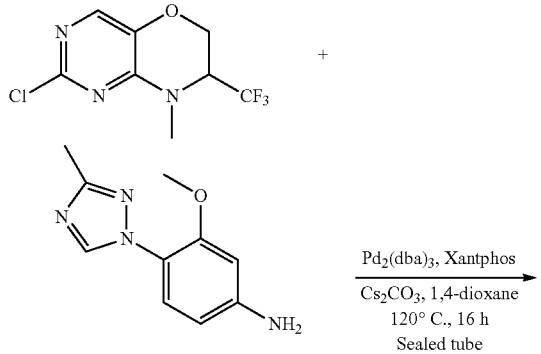

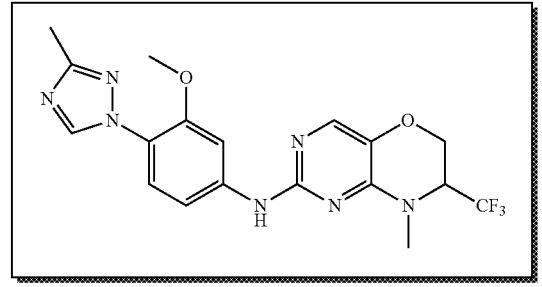

Synthesis of N-(3-methoxy-4-(3-methyl-1H-1, 2, 4-triazol-1-yl) phenyl)-8-methyl-7-(trifluoromethyl)-7, 8-dihydro-6H-pyrimido [5, 4-b] [1, 4] oxazin-2-amine To a dry vial was added a suspension of Pd$_2$(dba)$_3$ (46 mg, 0.05 mmol) and Xantphos (85 mg, 0.14 mmol) in 1, 4-dioxane (0.25 mL) at room temperature. The suspension was degassed with argon, heated to 120° C., and stirred for 3 min. A mixture of 2-chloro-8-methyl-7-(trifluoromethyl)-7, 8-dihydro-6H-pyrimido [5, 4-b] [1, 4] oxazine (200 mg, 0.98 mmol), 3-methoxy-4-(3-methyl-1H-1, 2, 4-triazol-1-yl) aniline (248 mg, 0.98 mmol) and cesium carbonate (446 mg, 1.37 mmol) in 1, 4-dioxane (0.25 mL) was degassed and the catalyst premix was added. The resultant mixture was stirred at 120° C. for 16 h in a sealed tube. After consumption of the starting material (monitored by TLC and LCMS), the reaction mixture was filtered and the filtrate was concentrated in vacuo. The crude material was purified by column chromatography using 3% MeOH/CH$_2$Cl$_2$ to afford N-(3-methoxy-4-(3-methyl-1H-1, 2, 4-triazol-1-yl) phenyl)-8-methyl-7-(trifluoromethyl)-7, 8-dihydro-6H-pyrimido [5, 4-b] [1, 4] oxazin-2-amine (180 mg, 54%) as an off-white solid. LCMS: 422 (M+1); (column; Ascentis Express C-18 (50×3.0 mm, 2.7 μm); RT 1.75 min. 0.025% Aq TFA+5% ACN: ACN+5% 0.025% Aq TFA; 1.2 mL/min); TLC: 10% MeOH/CH$_2$Cl$_2$ (R$_f$: 0.3).

Racemic compound of Example 242 was separated using a Chiralpak IA column (250×20 mm: 5 μm; (35 mg loading; 0.1% DEA in n-hexane: CH₂Cl₂:MeOH (50:50); (A:B: 80:20) as mobile phase) to provide the compound of Example 242A (Fraction I (−)) and the compound of Example 242B (Fraction II (+)).

Example 242A

Synthesis of (−)-N-(3-methoxy-4-(3-methyl-1H-1,2,4-triazol-1-yl) phenyl)-8-methyl-7-(trifluoromethyl)-7,8-dihydro-6H-pyrimido [5, 4-b] [1, 4] oxazin-2-amine

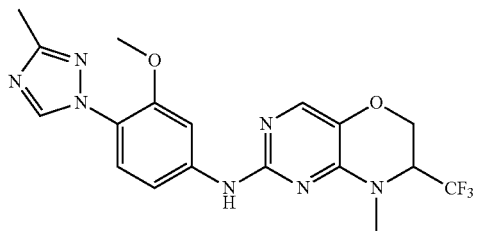 [SMILES: COc1cc(Nc2ncc3c(n2)N(C)C(C(F)(F)F)CO3)ccc1-n1cnc(C)n1]

The compound of Example 242A was produced as described in Example 242. Analytical data for product Fraction I (−): ¹H-NMR (CD₃OD, 400 MHz): δ 8.61 (s, 1H), 7.83-7.81 (m, 1H), 7.66 (s, 1H), 7.45 (d, 1H), 7.28 (dd, 1H), 4.57 (dd, 1H), 4.36 (dd, 1H), 4.03 (dt, 1H), 3.93 (s, 3H), 3.38 (s, 3H), 2.42 (s, 3H); Mass (ESI): 422.4 [M+1]; LCMS: 422 (M+1); (column; Ascentis Express C-18 (50×3.0 mm, 2.7 μm); RT 1.76 min. 0.025% Aq TFA+5% ACN: ACN+5% 0.025% Aq TFA; 1.2 mL/min); HPLC (column; Eclipse XDB-C-18, 150×4.6 mm, 5.0 μm); RT 6.89 min. ACN: 0.05% Aq TFA; 1.0 mL/min; Chiral HPLC: 100% RT=12.84 min (CHIRALPAK-IA (250×4.6 mm, 5 μm; mobile phase (A) 0.1% DEA in n-hexane (B) CH₂Cl₂:MeOH (50:50) (A:B; 80:20); flow Rate: 1.0 mL/min); Optical rotation $[\alpha]_D^{19.99}$: −62.81 (c=0.25, CH₂Cl₂).

Example 242B

Synthesis of (+)-N-(3-methoxy-4-(3-methyl-1H-1,2,4-triazol-1-yl) phenyl)-8-methyl-7-(trifluoromethyl)-7,8-dihydro-6H-pyrimido [5, 4-b] [1, 4] oxazin-2-amine

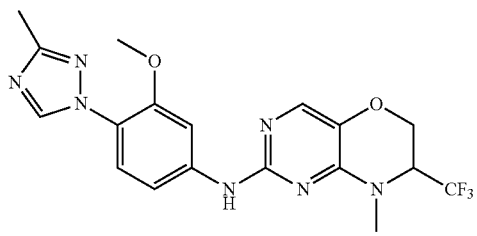 [SMILES: COc1cc(Nc2ncc3c(n2)N(C)C(C(F)(F)F)CO3)ccc1-n1cnc(C)n1]

The compound of Example 242B was produced as described in Example 242. Analytical data for product Fraction II (+): ¹H-NMR (CD₃OD, 400 MHz): δ 8.61 (s, 1H), 7.83-7.81 (m, 1H), 7.66 (s, 1H), 7.45 (d, 1H), 7.28 (dd, 1H), 4.57 (dd, 1H), 4.36 (dd, 1H), 4.03 (dt, 1H), 3.93 (s, 3H), 3.38 (s, 3H), 2.42 (s, 3H); Mass (ESI): 422.5 [M+1]; LCMS: 422 (M+1); (column; Ascentis Express C-18 (50×3.0 mm, 2.7 μm); RT 1.76 min. 0.025% Aq TFA+5% ACN: ACN+5% 0.025% Aq TFA; 1.2 mL/min); HPLC (column; Eclipse XDB-C-18, 150×4.6 mm, 5.0 μm); RT 6.89 min. ACN: 0.05% Aq TFA; 1.0 mL/min; Chiral HPLC: 100% RT=14.68 min (CHIRALPAK-IA (250×4.6 mm, 5 μm; mobile phase (A) 0.1% DEA in n-hexane (B) CH₂Cl₂:MeOH (50:50) (A:B; 80:20); flow Rate: 1.0 mL/min); Optical rotation $[\alpha]_D^{19.99}$: +65.52 (c=0.25, CH₂Cl₂).

Example 243

Synthesis of N-(5-methoxy-6-(4-methyl-1H-imidazol-1-yl) pyridin-3-yl)-8-methyl-7-(oxetan-3-yl)-7,8-dihydro-6H-pyrimido [5, 4-b] [1, 4] oxazin-2-amine

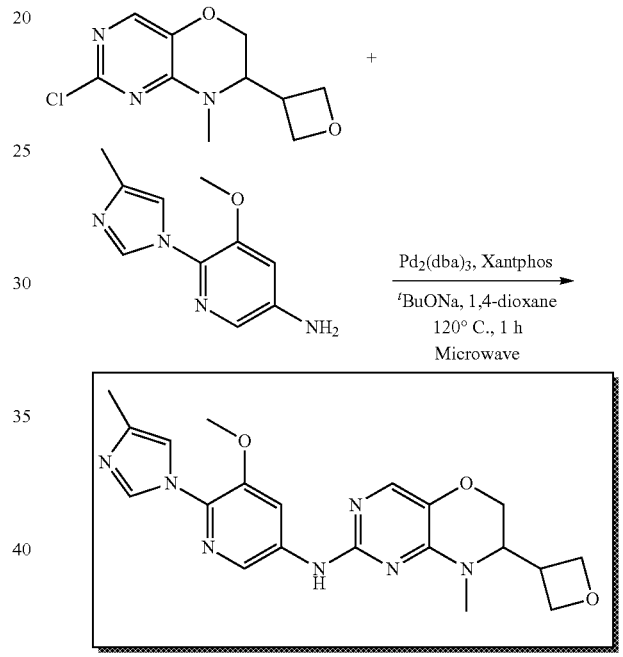

Synthesis of N-(5-methoxy-6-(4-methyl-1H-imidazol-1-yl) pyridin-3-yl)-8-methyl-7-(oxetan-3-yl)-7,8-dihydro-6H-pyrimido [5, 4-b] [1, 4] oxazin-2-amine To a dry vial was added a suspension of Pd₂(dba)₃ (47 mg, 0.05 mmol) and Xantphos (90 mg, 0.15 mmol) in 1,4-dioxane (2.5 mL) at room temperature. The suspension was degassed with argon, heated to 120° C., and stirred for 3 min. A mixture of 2-chloro-8-methyl-7-(oxetan-3-yl)-7,8-dihydro-6H-pyrimido [5, 4-b] [1, 4] oxazine (250 mg, 1.03 mmol), 5-methoxy-6-(4-methyl-1H-imidazol-1-yl) pyridin-3-amine (420 mg, 2.07 mmol) and sodium tert-butoxide (298 mg, 3.10 mmol) in 1,4-dioxane (2.5 mL) was degassed and the catalyst premix was added. The resultant mixture was stirred at 120° C. for 1 h in a microwave. After consumption of the starting material (monitored by TLC and LCMS), the reaction mixture was filtered, washed with 10% MeOH/CH₂Cl₂ and concentrated in vacuo. The crude material was purified by preparative HPLC (Kromasil-C-18 250×21.2 mm, 5 u (50 mg loading; CH₃CN: 0.05% TFA (0.1/90, 2/80, 15/70, 25/30, 30/10, 35/10) to afford N-(5-methoxy-6-(4-methyl-1H-imidazol-1-yl) pyridin-3-yl)-8-methyl-7-(oxetan-3-yl)-7, 8-dihydro-6H-pyrimido [5, 4-b] [1, 4] oxazin-2-amine (150 mg, 35%) as an off-white solid. LCMS: 410.4 (M+1); (column; X-select CSH C-18 (50×3.0 mm, 3.5 μm); RT 3.29 min. 5 mM Aq NH$_4$OAc: ACN; 0.8 mL/min); TLC: 10% MeOH/CH$_2$Cl$_2$ (R$_f$: 0.2).

Racemic compound of Example 243 was separated using a Chiralpak IA column (250×4.6 mm: 5 μm; (15 mg loading; 0.1% DEA in n-hexane: EtOH: THF (A:B: C: 70:25:5) as mobile phase) to provide the compound of Example 243A (Fraction I (+)) and the compound of Example 243B (Fraction II (−)).

Example 243A

Synthesis of (+)-N-(5-methoxy-6-(4-methyl-1H-imidazol-1-yl) pyridin-3-yl)-8-methyl-7-(oxetan-3-yl)-7, 8-dihydro-6H-pyrimido [5, 4-b] [1, 4] oxazin-2-amine

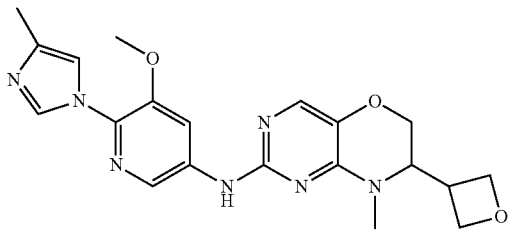

The compound of Example 243A was produced as described in Example 243. Analytical data for product Fraction I (+): $^1$H-NMR (400 MHz, DMSO-d$_6$): δ 9.32 (s, 1H), 8.32-8.30 (m, 2H), 8.05 (s, 1H), 7.61 (s, 1H), 7.37 (s, 1H), 4.72-4.69 (m, 2H), 4.67-4.58 (m, 2H), 4.10-4.01 (m, 2H), 3.89 (s, 3H), 3.88-3.86 (m, 1H), 3.32-3.30 (m, 1H), 3.20 (s, 3H), 2.18 (s, 3H); Mass (ESI): 410.4 [M+1]; LCMS: 410.4 (M+1); (column; X-Select CSH C-18 (50×3.0 mm, 3.5 μm); RT 3.34 min 0.05% Aq TFA: ACN; 0.80 mL/min); HPLC (column; Eclipse XDB-C-18, 150×4.6 mm, 5.0 μm); RT 9.55 min. ACN: 5 mM Aq NH$_4$OAc; 1.0 mL/min; Chiral HPLC: 99.7% RT=17.52 min (CHIRALPAK-IA (250×4.6 mm, 5 μm; mobile phase (A) 0.1% DEA in n-hexane (B) EtOH: THF (A:B; 70:25:5); flow Rate: 1.0 mL/min); Optical rotation [α]$_D^{19.99}$: +29.88 (c=0.25, CH$_2$Cl$_2$).

Example 243B

Synthesis of (−)-N-(5-methoxy-6-(4-methyl-1H-imidazol-1-yl) pyridin-3-yl)-8-methyl-7-(oxetan-3-yl)-7, 8-dihydro-6H-pyrimido [5, 4-b] [1, 4] oxazin-2-amine

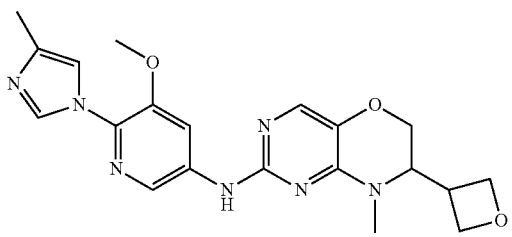

The compound of Example 243B was produced as described in Example 243. Analytical data for product Fraction II (−): $^1$H-NMR (400 MHz, DMSO-d$_6$): δ 9.32 (s, 1H), 8.32-8.30 (m, 2H), 8.05 (s, 1H), 7.61 (s, 1H), 7.37 (s, 1H), 4.72-4.69 (m, 2H), 4.67-4.58 (m, 2H), 4.10-4.01 (m, 2H), 3.89 (s, 3H), 3.88-3.86 (m, 1H), 3.32-3.30 (m, 1H), 3.20 (s, 3H), 2.18 (s, 3H); Mass (ESI): 410.4 [M+1]; LCMS: 410.4 (M+1); (column; X-Select CSH C-18 (50×3.0 mm, 3.5 μm); RT 3.32 min 5 mM Aq NH$_4$OAc: ACN; 0.80 mL/min); HPLC (column; Eclipse XDB-C-18, 150×4.6 mm, 5.0 μm); RT 9.56 min. ACN: 5 mM Aq NH$_4$OAc; 1.0 mL/min; Chiral HPLC: 96.0% RT=18.91 min (CHIRALPAK-IA (250×4.6 mm, 5 μm; mobile phase (A) 0.1% DEA in n-hexane (B) EtOH: THF (A:B; 70:25:5); flow Rate: 1.0 mL/min); Optical rotation [α]$_D^{19.99}$: −22.27 (c=0.25, CH$_2$Cl$_2$).

Example 244

Synthesis of 7-(3, 5-difluorophenyl)-N-(3-methoxy-4-(3-methyl-1H-1, 2, 4-triazol-1-yl) phenyl)-8-methyl-7, 8-dihydro-6H-pyrimido [5, 4-b] [1, 4] oxazin-2-amine

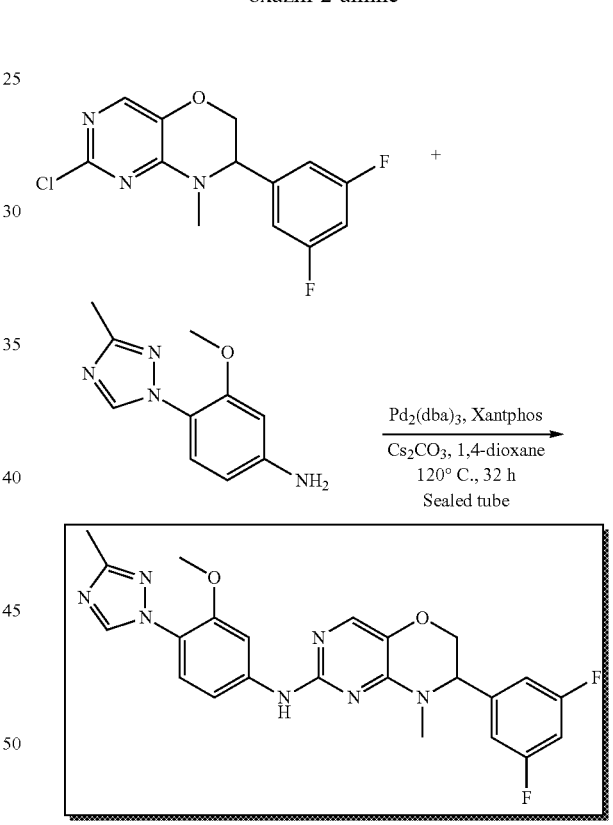

Synthesis of 7-(3, 5-difluorophenyl)-N-(3-methoxy-4-(3-methyl-1H-1, 2, 4-triazol-1-yl) phenyl)-8-methyl-7, 8-dihydro-6H-pyrimido [5, 4-b] [1, 4] oxazin-2-amine To a dry vial was added a suspension of Pd$_2$(dba)$_3$ (38 mg, 0.04 mmol) and Xantphos (73 mg, 0.12 mmol) in 1, 4-dioxane (1.25 mL) at room temperature. The suspension was degassed with argon, heated to 120° C., and stirred for 3 min. A mixture of 2-chloro-7-(3, 5-difluorophenyl)-8-methyl-7, 8-dihydro-6H-pyrimido [5, 4-b] [1, 4] oxazine (250 mg, 0.84 mmol), 3-methoxy-4-(3-methyl-1H-1, 2, 4-triazol-1-yl) aniline (343 mg, 1.68 mmol) and cesium carbonate (383 mg, 1.17 mmol) in 1,4-dioxane (1.25 mL) was degassed and the catalyst premix was added. The resultant mixture was stirred at 120° C. for 32 h in a sealed tube. After consumption of the starting material (monitored by TLC and LCMS), the reaction mixture was diluted with water (50 mL) and extracted with EtOAc (2×50 mL). The combined organic extracts were dried over sodium sulfate, filtered and concentrated in vacuo. The crude material was purified by column chromatography using 1-5% MeOH/CH$_2$Cl$_2$ to afford 7-(3, 5-difluorophenyl)-N-(3-methoxy-4-(3-methyl-1H-1, 2, 4-triazol-1-yl) phenyl)-8-methyl-7, 8-dihydro-6H-pyrimido [5, 4-b] [1, 4] oxazin-2-amine (200 mg, 51%) as an off-white solid. LCMS: 466 (M+1); (column; Ascentis Express C-18 (50×3.0 mm, 2.7 μm); RT 1.91 min. 0.025% Aq TFA+5% ACN: ACN+5% 0.025% Aq TFA; 1.2 mL/min); TLC: 5% MeOH/CH$_2$Cl$_2$ (R$_f$: 0.3).

Racemic compound of Example 244 was separated using a Chiralpak IA column (250×20 mm: 5 μm; (25 mg loading; 0.1% DEA in n-hexane: CH$_2$Cl$_2$:MeOH (50:50); (A:B; 80:20) as mobile phase) to provide the compound of Example 244A (Fraction I (+)) and the compound of Example 244B (Fraction II (−)).

Example 244A

Synthesis of (+)-7-(3, 5-difluorophenyl)-N-(3-methoxy-4-(3-methyl-1H-1, 2, 4-triazol-1-yl) phenyl)-8-methyl-7, 8-dihydro-6H-pyrimido [5, 4-b] [1, 4] oxazin-2-amine

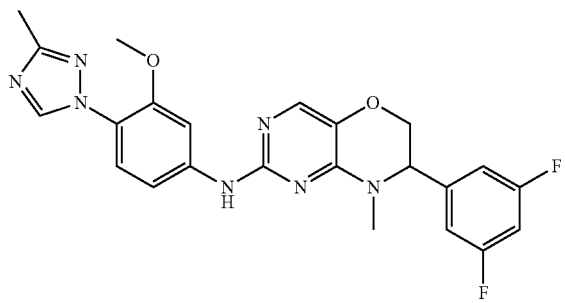 [SMILES: COc1cc(Nc2ncc3c(n2)N(C)C(c2cc(F)cc(F)c2)CO3)ccc1-n1cnc(C)n1]

The compound of Example 244A was produced as described in Example 244. Analytical data for product Fraction I (+): $^1$H-NMR (CD$_3$OD, 400 MHz): δ 8.61 (s, 1H), 7.85-7.83 (m, 1H), 7.62 (s, 1H), 7.45 (d, 1H), 7.28 (dd, 1H), 6.97-6.82 (m, 3H), 4.77-4.74 (m, 1H), 4.24-4.22 (m, 2H), 3.91 (s, 3H), 3.18 (s, 3H), 2.42 (s, 3H); Mass (ESI): 466.4 [M+1]; LCMS: 466 (M+1); (column; Ascentis Express C-18 (50×3.0 mm, 2.7 μm); RT 1.94 min 0.025% Aq TFA+5% ACN: ACN+5% 0.025% Aq TFA; 1.2 mL/min); HPLC (column; Eclipse XDB-C-18, 150×4.6 mm, 5.0 μm); RT 7.36 min. ACN: 0.05% Aq TFA; 1.0 mL/min; Chiral HPLC: 99.2% RT=13.75 min (CHIRALPAK-IA (250×4.6 mm, 5 μm; mobile phase (A) 0.1% DEA in n-hexane (B) CH$_2$Cl$_2$: MeOH (50:50) (A:B; 80:20); flow Rate: 1.0 mL/min); Optical rotation [α]$_D^{20.00}$: +158.97 (c=0.25, CH$_2$Cl$_2$).

Example 244B

Synthesis of (−)-7-(3, 5-difluorophenyl)-N-(3-methoxy-4-(3-methyl-1H-1, 2, 4-triazol-1-yl) phenyl)-8-methyl-7, 8-dihydro-6H-pyrimido [5, 4-b] [1, 4] oxazin-2-amine

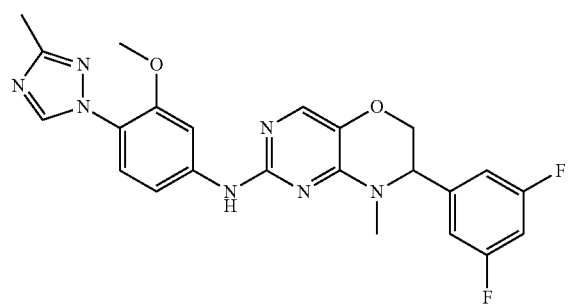 [SMILES: COc1cc(Nc2ncc3c(n2)N(C)C(c2cc(F)cc(F)c2)CO3)ccc1-n1cnc(C)n1]

The compound of Example 244B was produced as described in Example 244. Analytical data for product Fraction II (−): $^1$H-NMR (CD$_3$OD, 400 MHz): δ 8.61 (s, 1H), 7.85-7.83 (m, 1H), 7.62 (s, 1H), 7.45 (d, 1H), 7.28 (dd, 1H), 6.97-6.82 (m, 3H), 4.77-4.74 (m, 1H), 4.24-4.22 (m, 2H), 3.91 (s, 3H), 3.18 (s, 3H), 2.42 (s, 3H); Mass (ESI): 466.4 [M+1]; LCMS: 466 (M+1); (column; Ascentis Express C-18 (50×3.0 mm, 2.7 μm); RT 1.95 min 0.025% Aq TFA+5% ACN: ACN+5% 0.025% Aq TFA; 1.2 mL/min); HPLC (column; Eclipse XDB-C-18, 150×4.6 mm, 5.0 μm); RT 7.37 min. ACN: 0.05% Aq TFA; 1.0 mL/min; Chiral HPLC: 99.4% RT=17.25 min (CHIRALPAK-IA (250×4.6 mm, 5 μm; mobile phase (A) 0.1% DEA in n-hexane (B) CH$_2$Cl$_2$:MeOH (50:50) (A:B; 80:20); flow Rate: 1.0 mL/min); Optical rotation [α]$_D^{19.98}$: −151.52 (c=0.25, CH$_2$Cl$_2$).

Example 245

Synthesis of N-(3-methoxy-4-(4-methyl-1H-imidazol-1-yl) phenyl)-8-methyl-7-(1-(trifluoromethyl) cyclopropyl)-7, 8-dihydro-6H-pyrimido [5, 4-b] [1, 4] oxazin-2-amine

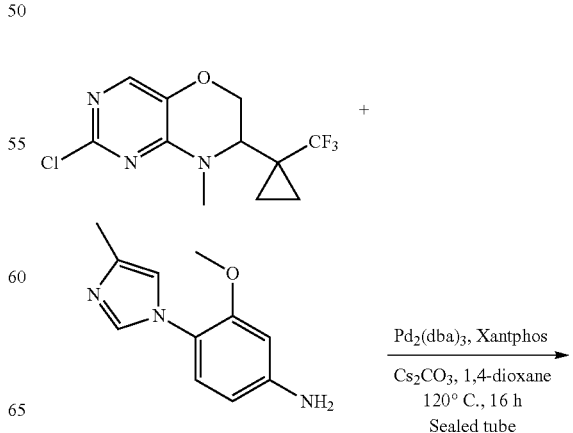

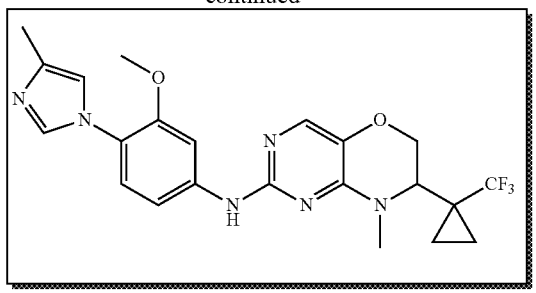

Synthesis of N-(3-methoxy-4-(4-methyl-1H-imidazol-1-yl) phenyl)-8-methyl-7-(1-(trifluoromethyl) cyclopropyl)-7, 8-dihydro-6H-pyrimido [5, 4-b] [1, 4] oxazin-2-amine To a dry vial was added a suspension of $Pd_2(dba)_3$ (31 mg, 0.03 mmol) and Xantphos (59 mg, 0.10 mmol) in 1, 4-dioxane (1 mL) at room temperature. The suspension was degassed with argon, heated to 120° C., and stirred for 3 min. A mixture of 2-chloro-8-methyl-7-(1-(trifluoromethyl) cyclopropyl)-7, 8-dihydro-6H-pyrimido [5, 4-b] [1, 4] oxazine (200 mg, 0.68 mmol), 3-methoxy-4-(4-methyl-1H-imidazol-1-yl) aniline (278 mg, 1.36 mmol) and cesium carbonate (620 mg, 1.91 mmol) in 1, 4-dioxane (1 mL) was degassed and the catalyst premix was added. The resultant mixture was stirred at 120° C. for 16 h in a sealed tube. After consumption of the starting material (monitored by TLC and LCMS), the reaction mixture was filtered and the filtrate was concentrated in vacuo. The crude material was purified by column chromatography using 4% $MeOH/CH_2Cl_2$ and further purified by preparative HPLC (Column YMC Actus Triart C18 (250×20 mm: 5μ; (50 mg loading; $CH_3CN$: 0-05% aq TFA (0.1/90, 2/90, 15/70, 25/30, 30/10, 35/10) to afford N-(3-methoxy-4-(4-methyl-1H-imidazol-1-yl) phenyl)-8-methyl-7-(1-(trifluoromethyl) cyclopropyl)-7, 8-dihydro-6H-pyrimido [5, 4-b] [1, 4] oxazin-2-amine (180 mg, 57%) as an off-white solid. LCMS: 461 (M+1); (column; Ascentis Express C-18 (50×3.0 mm, 2.7 μm); RT 1.68 min 0.025% Aq TFA+5% ACN: ACN+5% 0.025% Aq TFA; 1.2 mL/min); TLC: 5% $MeOH/CH_2Cl_2$ ($R_f$: 0.3).

Racemic compound of Example 245 was separated using a Chiralpak-IA column (250×4.6 mm, 5 μm) (20 mg loading; 0.1% DEA in n-hexane: $CH_2Cl_2$:MeOH (50:50) (A:B: 80:20) as mobile phase) to provide the compound of Example 245A (Fraction I (−)) and the compound of Example 245B (Fraction II (+)).

Example 245A

Synthesis of (−)-N-(3-methoxy-4-(4-methyl-1H-imidazol-1-yl) phenyl)-8-methyl-7-(1-(trifluoromethyl) cyclopropyl)-7, 8-dihydro-6H-pyrimido [5, 4-b] [1, 4] oxazin-2-amine

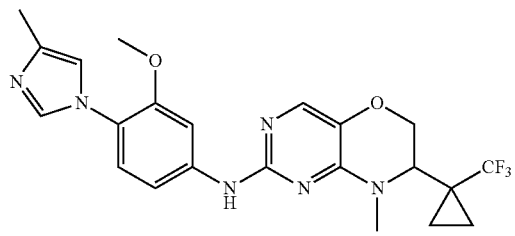

The compound of Example 245A was produced as described in Example 245. Analytical data for product Fraction I (−): $^1$H-NMR ($CD_3OD$, 400 MHz): δ 7.72 (s, 1H), 7.66 (s, 1H), 7.55 (s, 1H), 7.24-7.14 (m, 2H), 6.97 (s, 1H), 4.45 (d, 1H), 4.05 (dd, 1H), 3.91-3.88 (m, 1H), 3.86 (s, 3H), 3.27 (s, 3H), 2.23 (s, 3H), 1.38-1.20 (m, 1H), 1.18-1.12 (m, 1H), 1.09-1.02 (m, 1H), 0.75-0.65 (m, 1H); Mass (ESI): 461.5 [M+1]; LCMS: 461.1 (M+1); (column; Ascentis Express C-18 (50×3.0 mm, 2.7 μm); RT 1.50 min. 0.025% Aq TFA+5% ACN: ACN+5% 0.025% Aq TFA; 1.2 mL/min); HPLC (column; Eclipse XDB-C-18, 150×4.6 mm, 5.0 μm); RT 6.84 min. ACN: 0.05% Aq TFA; 1.0 mL/min; Chiral HPLC: 100% RT=11.23 min (CHIRALPAK-IA (250×4.6 mm, 5 μm; mobile phase (A) 0.1% DEA in n-hexane (B) $CH_2Cl_2$:MeOH (50:50) (A:B; 80:20); flow Rate: 1.0 mL/min); Optical rotation $[α]_D^{19.99}$: −10.25 (c=0.25, $CH_2Cl_2$).

Example 245B

Synthesis of (+)-N-(3-methoxy-4-(4-methyl-1H-imidazol-1-yl) phenyl)-8-methyl-7-(1-(trifluoromethyl) cyclopropyl)-7, 8-dihydro-6H-pyrimido [5, 4-b] [1, 4] oxazin-2-amine

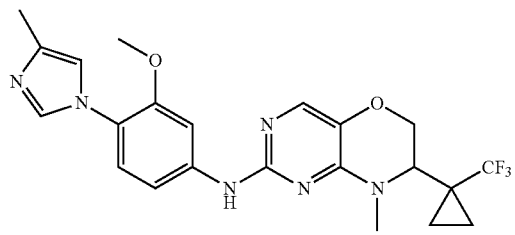

The compound of Example 245B was produced as described in Example 245. Analytical data for product Fraction II (+): $^1$H-NMR ($CD_3OD$, 400 MHz): δ 7.72 (s, 1H), 7.66 (s, 1H), 7.55 (s, 1H), 7.24-7.14 (m, 2H), 6.97 (s, 1H), 4.45 (d, 1H), 4.05 (dd, 1H), 3.91-3.88 (m, 1H), 3.86 (s, 3H), 3.27 (s, 3H), 2.23 (s, 3H), 1.38-1.20 (m, 1H), 1.18-1.12 (m, 1H), 1.09-1.02 (m, 1H), 0.75-0.65 (m, 1H); Mass (ESI): 461.5 [M+1]; LCMS: 461 (M+1); (column; Ascentis Express C-18 (50×3.0 mm, 2.7 μm); RT 1.49 min. 0.025% Aq TFA+5% ACN: ACN+5% 0.025% Aq TFA; 1.2 mL/min); HPLC (column; Eclipse XDB-C-18, 150×4.6 mm, 5.0 µm); RT 6.83 min. ACN: 0.05% Aq TFA; 1.0 mL/min; Chiral HPLC: 99.4% RT=13.12 min (CHIRALPAK-IA (250×4.6 mm, 5 µm; mobile phase (A) 0.1% DEA in n-hexane (B) CH$_2$Cl$_2$:MeOH (50:50) (A:B; 80:20); flow Rate: 1.0 mL/min); Optical rotation [α]$_D^{19.98}$: +17.29 (c=0.25, CH$_2$Cl$_2$).

Example 246

Synthesis of (S)-7-(tert-butyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine

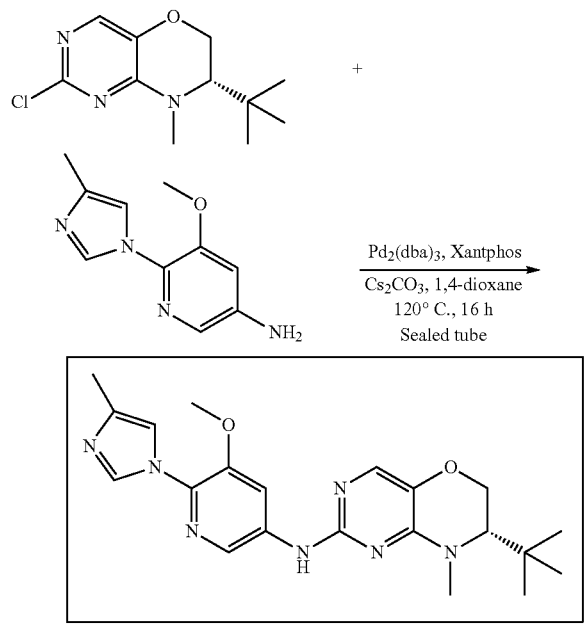

Synthesis of (S)-7-(tert-butyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine To a dry vial was added a suspension of Pd$_2$(dba)$_3$ (19 mg, 0.02 mmol) and Xantphos (36 mg, 0.06 mmol) in 1, 4-dioxane (0.5 mL) at room temperature. The suspension was degassed with argon, heated to 120° C., and stirred for 3 min. A mixture of (S)-7-(tert-butyl)-2-chloro-8-methyl-7, 8-dihydro-6H-pyrimido [5, 4-b] [1, 4] oxazine (100 mg, 0.41 mmol), 5-methoxy-6-(4-methyl-1H-imidazol-1-yl) pyridin-3-amine (170 mg, 0.83 mmol) and cesium carbonate (189 mg, 0.58 mmol) in 1, 4-dioxane (0.5 mL) was degassed and the catalyst premix was added. The resultant mixture was stirred at 120° C. for 16 h in a sealed tube. After consumption of the starting material (monitored by TLC and LCMS), the reaction mixture was diluted with water (50 mL) and extracted with EtOAc (2×50 mL). The combined organic extracts were dried over sodium sulfate, filtered and concentrated in vacuo. The crude material was purified by column chromatography using 1-5% MeOH/CH$_2$Cl$_2$ to afford (S)-7-(tert-butyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine (20 mg, 12%) as pale yellow solid. $^1$H-NMR (CD$_3$OD, 400 MHz): δ 8.32 (s, 1H), 8.29 (s, 1H), 8.13 (s, 1H), 7.52 (s, 1H), 7.39 (s, 1H), 4.56 (d, 1H), 3.98 (s, 3H), 3.77 (dd, 1H), 3.36 (s, 3H), 3.26-3.24 (m, 1H), 2.25 (s, 3H), 1.06 (s, 9H) Mass (ESI): 410.1 [M+1]; LCMS: 410.1 (M+1); (column; Ascentis Express C-18 (50× 3.0 mm, 2.7 µm); RT 1.60 min. 0.025% Aq TFA+5% ACN: ACN+5% 0.025% Aq TFA; 1.2 mL/min); UPLC (column; Acquity UPLC BEH C-18, 50×2.1 mm, 1.7 µm); RT 1.51 min. ACN: 0.025% Aq TFA; 0.5 mL/min); Chiral HPLC: 95.1% RT=17.59 min (CHIRALPAK-IC (250×4.6 mm, 5 µm; mobile phase (A) 0.1% DEA in n-hexane (B) CH$_2$Cl$_2$: MeOH (50:50) (A:B; 75:25); flow Rate: 1.0 mL/min); Optical rotation [α]$_D^{20.02}$: +47.31 (c=0.25, CH$_2$Cl$_2$).

Example 247

Synthesis of N-(5-methoxy-6-(4-methyl-1H-imidazol-1-yl) pyridin-3-yl)-8-methyl-7-(1-(trifluoromethyl) cyclopropyl)-7, 8-dihydro-6H-pyrimido [5, 4-b] [1, 4] oxazin-2-amine

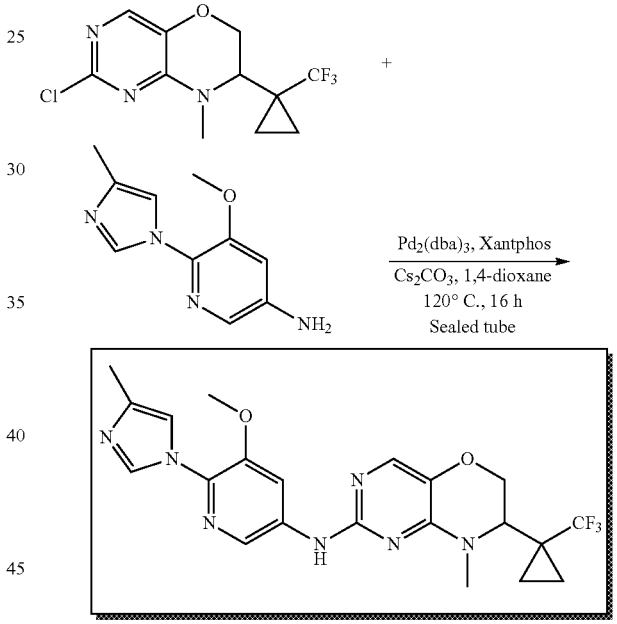

Synthesis of N-(5-methoxy-6-(4-methyl-1H-imidazol-1-yl) pyridin-3-yl)-8-methyl-7-(1-(trifluoromethyl) cyclopropyl)-7, 8-dihydro-6H-pyrimido [5, 4-b] [1, 4] oxazin-2-amine To a dry vial was added a suspension of Pd$_2$(dba)$_3$ (23.4 mg, 0.02 mmol) and Xantphos (44 mg, 0.07 mmol) in 1, 4-dioxane (0.25 mL) at room temperature. The suspension was degassed with argon, heated to 120° C., and stirred for 3 min. A mixture of 2-chloro-8-methyl-7-(1-(trifluoromethyl) cyclopropyl)-7, 8-dihydro-6H-pyrimido [5, 4-b] [1, 4] oxazine (150 mg, 0.51 mmol), 5-methoxy-6-(4-methyl-1H-imidazol-1-yl) pyridin-3-amine (205 mg, 1.02 mmol) and cesium carbonate (234 mg, 0.72 mmol) in 1, 4-dioxane (0.25 mL) was degassed and the catalyst premix was added. The resultant mixture was stirred at 120° C. for 16 h in a sealed tube. After consumption of the starting material (monitored by TLC and LCMS), the reaction mixture was filtered and the filtrate was concentrated in vacuo. The crude material was purified by column chromatography using 6-8% MeOH/CH$_2$Cl$_2$ to afford N-(5-methoxy-6-(4-methyl-1H-imidazol-1-yl) pyridin-3-yl)-8-methyl-7-(1-(trifluoromethyl) cyclopropyl)-7, 8-dihydro-6H-pyrimido [5, 4-b] [1, 4] oxazin-2-amine (180 mg, 57%) as a pale yellow solid. LCMS: 462 (M+1); (column; Ascentis Express C-18 (50×3.0 mm, 2.7 µm); RT 1.69 min. 0.025% Aq TFA+5% ACN: ACN+5% 0.025% Aq TFA; 1.2 mL/min); TLC: 10% MeOH/CH$_2$Cl$_2$ (R$_f$: 0.4).

Racemic compound of Example 247 was separated using a Chiralpak-AD-H column (250×20 mm, 5 µm) (20 mg loading; 0.1% DEA in n-hexane; EtOH:MeOH (50:50) (A:B; 70:30); 0.1% DEA in n-hexane: CH$_2$Cl$_2$:MeOH (50:50) (A:B: 70:30) as mobile phase) to provide the compound of Example 247A (Fraction I (−)) and the compound of Example 247B (Fraction II (+)).

Example 247A

Synthesis of (−)-N-(5-methoxy-6-(4-methyl-1H-imidazol-1-yl) pyridin-3-yl)-8-methyl-7-(1-(trifluoromethyl) cyclopropyl)-7, 8-dihydro-6H-pyrimido [5, 4-b] [1, 4] oxazin-2-amine

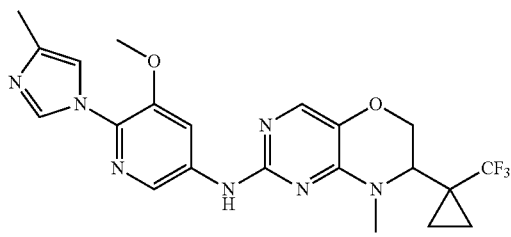

The compound of Example 247A was produced as described in Example 247. Analytical data for product Fraction I (−): $^1$H-NMR (CD$_3$OD, 400 MHz): δ 8.28-8.26 (m, 2H), 8.13 (s, 1H), 7.58 (s, 1H), 7.40 (s, 1H), 4.45 (d, 1H), 4.06 (dd, 1H), 3.97 (s, 3H), 3.89-3.86 (m, 1H), 3.28 (s, 3H), 2.25 (s, 3H), 1.25-1.20 (m, 1H), 1.19-1.16 (m, 1H), 1.10-1.02 (m, 1H), 0.73-0.69 (m, 1H); Mass (ESI): 462.4 [M+1]; LCMS: 462 (M+1); (column; Ascentis Express C-18 (50× 3.0 mm, 2.7 µm); RT 1.67 min. 0.025% Aq TFA+5% ACN: ACN+5% 0.025% Aq TFA; 1.2 mL/min); UPLC (column; Acquity UPLC BEH C-18, 50×2.1 mm, 1.7 µm); RT 1.56 min. ACN: 0.025% Aq TFA; 0.5 mL/min); Chiral HPLC: 95.0% RT=6.02 min (CHIRALPAK-ADH (250×4.6 mm, 5 µm; mobile phase (A) 0.1% DEA in n-hexane (B) EtOH: MeOH (50:50) (A:B; 70:30); flow Rate: 1.0 mL/min); Optical rotation [α]$_D^{20.01}$: −11.12 (c=0.25, CH$_2$Cl$_2$).

Example 247B

Synthesis of (+)-N-(5-methoxy-6-(4-methyl-1H-imidazol-1-yl) pyridin-3-yl)-8-methyl-7-(1-(trifluoromethyl) cyclopropyl)-7, 8-dihydro-6H-pyrimido [5, 4-b] [1, 4] oxazin-2-amine

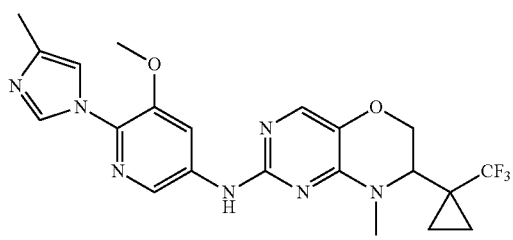

The compound of Example 247B was produced as described in Example 247. Analytical data for product Fraction II (+): $^1$H-NMR (CD$_3$OD, 400 MHz): δ 8.28-8.26 (m, 2H), 8.13 (s, 1H), 7.58 (s, 1H), 7.40 (s, 1H), 4.45 (d, 1H), 4.06 (dd, 1H), 3.97 (s, 3H), 3.89-3.86 (m, 1H), 3.28 (s, 3H), 2.25 (s, 3H), 1.25-1.20 (m, 1H), 1.19-1.16 (m, 1H), 1.10-1.02 (m, 1H), 0.73-0.69 (m, 1H); Mass (ESI): 462.4 [M+1]; LCMS: 462 (M+1); (column; Ascentis Express C-18 (50× 3.0 mm, 2.7 µm); RT 1.67 min. 0.025% Aq TFA+5% ACN: ACN+5% 0.025% Aq TFA; 1.2 mL/min); UPLC (column; Acquity UPLC BEH C-18, 50×2.1 mm, 1.7 µm); RT 1.56 min. ACN: 0.025% Aq TFA; 0.5 mL/min); Chiral HPLC: 97.6% RT=10.38 min (CHIRALPAK-ADH (250×4.6 mm, 5 µm; mobile phase (A) 0.1% DEA in n-hexane (B) EtOH: MeOH (50:50) (A:B; 70:30); flow Rate: 1.0 mL/min); Optical rotation [α]$_D^{19.96}$: +9.68 (c=0.25, CH$_2$Cl$_2$).

Example 248

Synthesis of 2-chloro-7, 7-dimethyl-8-phenyl-7, 8-dihydro-6H-pyrimido [5, 4-b] [1, 4] oxazine

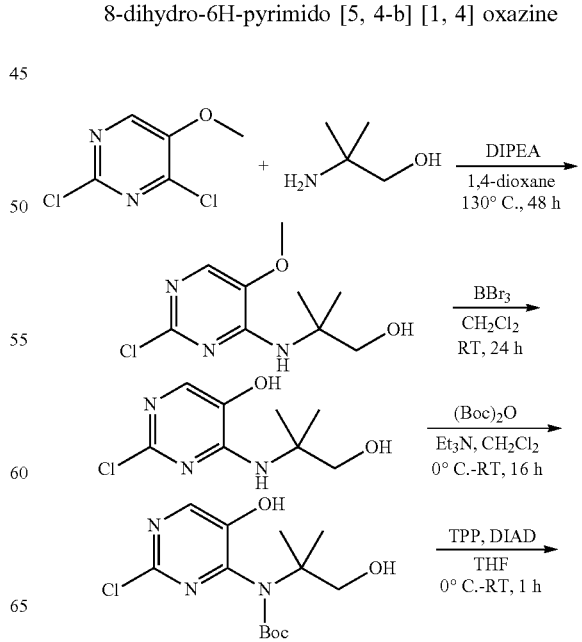

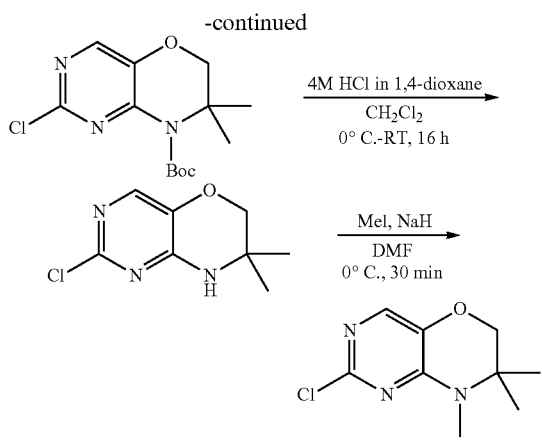

Synthesis of 2-((2-chloro-5-methoxypyrimidin-4-yl) amino)-2-methylpropan-1-ol To a stirred solution of 2, 4-dichloro-5-methoxypyrimidine (5 g, 27.93 mmol) in 1, 4-dioxane (50 mL) under an argon atmosphere were added diisopropylethylamine (7.2 g, 55.86 mmol) and 2-amino-2-methylpropan-1-ol (2.4 g, 27.93 mmol) at room temperature. The reaction mixture was stirred at 130° C. for 48 h. After consumption of the starting materials (monitored by TLC), the volatile components were removed in vacuo. The residue was diluted with a saturated sodium bicarbonate solution (50 mL) and extracted with EtOAc (2×50 mL). The combined organic extracts were dried over sodium sulfate, filtered and concentrated in vacuo. The crude material was purified by column chromatography using 10% EtOAc:hexanes to afford 2-((2-chloro-5-methoxypyrimidin-4-yl) amino)-2-methylpropan-1-ol (5.5 g, 84%) as a white solid. $^1$H-NMR (DMSO-$d_6$, 500 MHz): δ 7.69 (s, 1H), 6.19 (s, 1H), 6.11 (t, 1H), 3.82 (s, 3H), 3.45 (d, 2H), 1.33 (s, 6H); TLC: 50% EtOAc:hexanes ($R_f$: 0.3).

Synthesis of 2-chloro-4-((1-hydroxy-2-methylpropan-2-yl) amino) pyrimidin-5-ol To a stirred solution of 2-((2-chloro-5-methoxypyrimidin-4-yl) amino)-2-methylpropan-1-ol (5.5 g, 23.80 mmol) in CH$_2$Cl$_2$ (100 mL) was added boron tribromide (34 mL, 357.14 mmol) at 0° C. under an argon atmosphere. The reaction mixture was warmed to room temperature and stirred for 24 h. After consumption of the starting materials (monitored by TLC), the reaction mixture was quenched with methanol (50 mL) at 0° C. and concentrated in vacuo. The residue was dissolved in EtOAc (2×100 mL) and washed with a sodium bicarbonate solution (2×100 mL). The combined organic extracts were dried over sodium sulfate, filtered and concentrated in vacuo to obtain the 2-chloro-4-((1-hydroxy-2-methylpropan-2-yl) amino) pyrimidin-5-ol (4 g, 81%) as a white solid used in the next step without further purification. $^1$H-NMR (DMSO-$d_6$, 500 MHz): δ 10.38 (br s, 1H), 7.48 (s, 1H), 6.03 (s, 1H), 5.11 (br s, 1H), 3.45 (s, 2H), 1.37 (s, 6H); TLC: 80% EtOAc:hexanes ($R_f$: 0.3).

Synthesis of tert-butyl (2-chloro-5-hydroxypyrimidin-4-yl) (1-hydroxy-2-methylpropan-2-yl) carbamate To a stirred solution of 2-chloro-4-((1-hydroxy-2-methylpropan-2-yl) amino) pyrimidin-5-ol (4.3 g, 19.90 mmol) in CH$_2$Cl$_2$ (50 mL) under an argon atmosphere were added triethylamine (4.3 mL, 29.80 mmol) and Boc anhydride (4.3 g, 19.90 mmol) at 0° C. The reaction mixture was warmed to room temperature and stirred for 16 h. After consumption of the starting materials (monitored by TLC), the volatile components were evaporated in vacuo. The crude material was purified by column chromatography using 40% EtOAc:hexanes to afford tert-butyl (2-chloro-5-hydroxypyrimidin-4-yl) (1-hydroxy-2-methylpropan-2-yl) carbamate (3 g, 48%) as a white solid. $^1$H-NMR (DMSO-$d_6$, 500 MHz): δ 8.00 (s, 1H), 6.61 (s, 1H), 5.07 (t, 1H), 3.49 (d, 2H), 1.50 (s, 9H), 1.37 (s, 6H); TLC: 50% EtOAc:hexanes ($R_f$: 0.5).

Synthesis of tert-butyl 2-chloro-7, 7-dimethyl-6, 7-dihydro-8H-pyrimido [5, 4-b] [1, 4] oxazine-8-carboxylate To a stirred solution of tert-butyl (2-chloro-5-hydroxypyrimidin-4-yl) (1-hydroxy-2-methylpropan-2-yl)carbamate (3 g, 9.46 mmol) in THF (30 mL) were added triphenylphosphine (2.9 g, 11.36 mmol) and diisopropylazodicarboxylate (2.3 g, 11.35 mmol) at 0° C. under an argon atmosphere. The reaction mixture was stirred for 1 h at 0° C. After consumption of the starting materials (monitored by TLC), the volatile components were evaporated in vacuo. The crude material was purified by column chromatography using 20% EtOAc:hexanes to afford tert-butyl 2-chloro-7, 7-dimethyl-6, 7-dihydro-8H-pyrimido [5, 4-b] [1, 4] oxazine-8-carboxylate (1.5 g, 53%) as a white solid. $^1$H-NMR (DMSO-$d_6$, 400 MHz): δ 8.11 (s, 1H), 4.01 (s, 2H), 1.52 (s, 9H), 1.38 (s, 6H); LCMS: 300.3 (M+1); (column; X-Select CSH C-18 (50×3.0 mm, 3.5 μm); RT 4.69 min. 5 mM Aq NH$_4$OAc: ACN; 0.80 mL/min); TLC: 30% EtOAc:hexanes ($R_f$: 0.3).

Synthesis of 2-chloro-7, 7-dimethyl-7, 8-dihydro-6H-pyrimido [5, 4-b] [1, 4] oxazine To a stirred solution of tert-butyl 2-chloro-7, 7-dimethyl-6, 7-dihydro-8H-pyrimido [5, 4-b] [1, 4] oxazine-8-carboxylate (500 mg, 1.67 mmol) in CH$_2$Cl$_2$ (5 mL) under an argon atmosphere was added 4M HCl in 1, 4-dioxane (5 mL) at 0° C. The reaction mixture was stirred for 16 h at room temperature. After consumption of the starting materials (monitored by TLC), the volatile components were evaporated in vacuo. The residue was diluted with a saturated sodium bicarbonate solution (50 mL) and extracted with EtOAc (2×50 mL). The combined organic extracts were dried over sodium sulfate, filtered and concentrated in vacuo to obtain the 2-chloro-7, 7-dimethyl-7, 8-dihydro-6H-pyrimido [5, 4-b] [1, 4] oxazine (260 mg, 78%) as a white solid. $^1$H-NMR (DMSO-$d_6$, 400 MHz): δ 8.50 (s, 1H), 7.71 (s, 2H), 1.20 (s, 6H); TLC: 50% EtOAc:hexanes ($R_f$: 0.3).

Synthesis of 2-chloro-7, 7, 8-trimethyl-7, 8-dihydro-6H-pyrimido [5, 4-b] [1, 4] oxazine To a stirred solution of 2-chloro-7, 7-dimethyl-7, 8-dihydro-6H-pyrimido [5, 4-b] [1, 4] oxazine (50 mg, 0.25 mmol) in DMF (0.5 mL) under an argon atmosphere were added sodium hydride (8.8 mg, 0.37 mmol) and methyl iodide (35.5 mg, 0.25 mmol) at 0° C. The reaction mixture was stirred for 30 min at 0° C. After consumption of the starting materials (monitored by TLC), the volatile components were evaporated in vacuo. The reaction mixture was diluted with ice cold water (20 mL) and extracted with EtOAc (2×20 mL). The combined organic extracts were dried over sodium sulfate, filtered and concentrated in vacuo. The crude material was purified by column chromatography using 20% EtOAc:hexanes to afford 2-chloro-7, 7, 8-trimethyl-7, 8-dihydro-6H-pyrimido [5, 4-b] [1, 4] oxazine (30 mg, 56%) as a white solid. $^1$H NMR (DMSO-d$_6$, 400 MHz): δ 7.68 (s, 1H), 3.93 (s, 2H), 3.00 (s, 3H), 1.24 (s, 6H); TLC: 50% EtOAc:hexanes (R$_f$: 0.4).

Example 249

Synthesis of 2'-chloro-6'H, 8'H-spiro [cyclopentane-1, 7'-pyrimido [5, 4-b] [1, 4] oxazine]

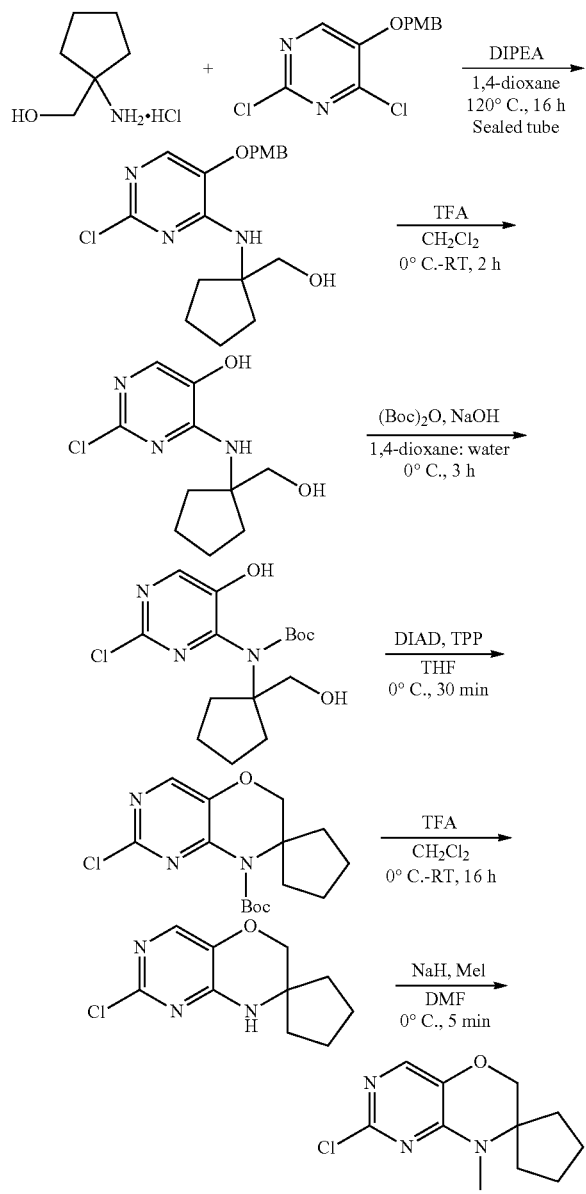

Synthesis of (1-((2-chloro-5-(4-methoxybenzyl) oxy) pyrimidin-4-yl) amino) cyclopentyl) methanol To a stirred solution of 2, 4-dichloro-5-((4-methoxybenzyl) oxy) pyrimidine (1.5 g, 5.26 mmol) in 1, 4-dioxane (4 mL) under an argon atmosphere were added diisopropylethylamine (1.3 g, 21.05 mmol) and (1-aminocyclopentyl) methanol hydrochloride (1 g, 6.84 mmol) at room temperature. The reaction mixture was stirred at 120° C. for 16 h in a sealed tube. After consumption of starting material (monitored by TLC), the volatile components were evaporated in vacuo to obtain (1-((2-chloro-5-((4-methoxybenzyl) oxy) pyrimidin-4-yl) amino) cyclopentyl) methanol (700 mg, 37%) as a brown liquid. LCMS: 364.4 (M+1); (column; X-Select CSH C-18 (50×3.0 mm, 3.5 μm); RT 4.29 min 0.05% Aq TFA: ACN; 0.80 mL/min); TLC: 20% EtOAc: hexane (R$_f$: 0.4).

Synthesis of 2-chloro-4-((1-(hydroxymethyl) cyclopentyl) amino) pyrimidin-5-ol

To a stirred solution of (1-((2-chloro-5-((4-methoxybenzyl) oxy) pyrimidin-4-yl) amino) cyclopentyl) methanol (120 mg, 0.33 mmol) in CH$_2$Cl$_2$ (1.2 mL) under an argon atmosphere was added trifluoroacetic acid (150 mg, 1.32 mmol) at 0° C. The reaction mixture was warmed to room temperature and stirred for 2 h. After consumption of starting material (monitored by TLC), the reaction mixture was quenched with a saturated sodium bicarbonate solution (10 mL) and extracted with CH$_2$Cl$_2$ (2×10 mL). The aqueous layer was acidified with citric acid up to pH=5 and extracted with EtOAc (2×10 mL). The combined organic extracts were dried over sodium sulfate, filtered and concentrated in vacuo to obtain the 2-chloro-4-((1-(hydroxymethyl) cyclopentyl) amino) pyrimidin-5-ol (80 mg, 99%) as an off-white solid used in the next step without further purification. $^1$H-NMR (DMSO-d$_6$, 400 MHz): δ 10.30 (br s, 1H), 8.13-8.11 (m, 1H), 7.46 (s, 1H), 6.13 (s, 1H), 3.70 (s, 2H), 2.00-1.93 (m, 2H), 1.90-1.88 (m, 2H), 1.80-1.61 (m, 4H); TLC: 50% EtOAc:hexane (R$_f$: 0.1).

Synthesis of tert-butyl (2-chloro-5-hydroxypyrimidin-4-yl) (1-(hydroxymethyl) cyclopentyl) carbamate To a stirred solution of 2-chloro-4-((1-(hydroxymethyl) cyclopentyl) amino) pyrimidin-5-ol (500 mg, 2.05 mmol) in 1, 4-dioxane: water (1:1, 10 mL) under an argon atmosphere were added sodium hydroxide (98 mg, 2.46 mmol) and Boc anhydride (538 mg, 2.46 mmol) at 0° C. The reaction mixture was stirred for 3 h at 0° C. After consumption of starting material (monitored by TLC), the reaction mixture was diluted with water (10 mL) and extracted with EtOAc (2×10 mL). The aqueous layer was acidified with citric acid up to pH=5 and extracted with EtOAc (2×10 mL). The combined organic extracts were dried over sodium sulfate, filtered and concentrated in vacuo to obtain the tert-butyl (2-chloro-5-hydroxypyrimidin-4-yl) (1-(hydroxymethyl) cyclopentyl) carbamate (700 mg, 99%) as a brown liquid. LCMS: 344.1 (M+1); (column; X-Select CSH C-18 (50×3.0 mm, 3.5 μm); RT 3.70 min 0.05% Aq TFA: ACN; 0.80 mL/min); TLC: 50% EtOAc:hexane (R$_f$: 0.6).

Synthesis of tert-butyl 2'-chloro-6'H, 8'H-spiro [cyclopentane-1, 7'-pyrimido [5, 4-b][1,4]oxazine]-8'-carboxylate To a stirred solution of tert-butyl (2-chloro-5-hydroxypyrimidin-4-yl) (1-(hydroxymethyl) cyclopentyl) carbamate (150 mg, 0.43 mmol) in THF (2 mL) under an argon atmosphere were added diisopropylazodicarboxylate (132 g, 0.65 mmol) and triphenylphosphine (171 mg, 0.65 mmol) at 0° C. The reaction mixture was stirred for 30 min at 0° C. After consumption of starting material (monitored by TLC), the reaction mixture was diluted with water (20 mL) and extracted with EtOAc (2×20 mL). The combined organic extracts were dried over sodium sulfate, filtered and concentrated in vacuo. The crude material was purified by column chromatography using 10% EtOAc:hexanes to afford tert-butyl 2'-chloro-6'H, 8'H-spiro [cyclopentane-1, 7'-pyrimido [5, 4-b] [1, 4] oxazine]-8'-carboxylate (60 mg, 42%) as a colorless liquid. $^1$H-NMR (CD$_3$OD, 400 MHz): δ 7.93 (s, 1H), 3.99 (s, 2H), 2.08-1.94 (m, 4H), 1.80-1.65 (m, 4H), 1.95 (s, 9H); TLC: 20% EtOAc:hexane ($R_f$: 0.7).

Synthesis of 2'-chloro-6'H, 8'H-spiro [cyclopentane-1, 7'-pyrimido [5, 4-b] [1, 4] oxazine]

To a stirred solution of tert-butyl 2'-chloro-6'H, 8'H-spiro [cyclopentane-1, 7'-pyrimido [5, 4-b] [1, 4] oxazine]-8'-carboxylate (400 mg, 1.23 mmol) in CH$_2$Cl$_2$ (4 mL) under an argon atmosphere was added trifluoroacetic acid (561 mg, 4.92 mmol) at 0° C. The reaction mixture was warmed to room temperature and stirred for 16 h at room temperature. After consumption of starting material (monitored by TLC), the reaction mixture was quenched with a saturated sodium bicarbonate solution (20 mL) and extracted with CH$_2$Cl$_2$ (2×20 mL). The combined organic extracts were dried over sodium sulfate, filtered and concentrated in vacuo to obtain the 2'-chloro-6'H, 8'H-spiro [cyclopentane-1, 7'-pyrimido [5, 4-b] [1, 4] oxazine] (270 mg, 97%) as a brown solid. $^1$H-NMR (CDCl$_3$, 400 MHz): δ 7.75 (s, 1H), 5.50-5.43 (m, 1H), 3.90 (s, 2H), 1.89-1.80 (m, 4H), 1.79-1.70 (m, 4H); TLC: 20% EtOAc:hexane ($R_f$: 0.3).

Synthesis of 2'-chloro-6'H, 8'H-spiro [cyclopentane-1, 7'-pyrimido [5, 4-b] [1, 4] oxazine]

To a stirred solution of 2'-chloro-6'H, 8'H-spiro [cyclopentane-1, 7'-pyrimido [5, 4-b] [1, 4] oxazine] (100 mg, 0.44 mmol) in DMF (1 mL) under an argon atmosphere was added sodium hydride (26 mg, 0.66 mmol) and methyl iodide (94 mg, 0.66 mmol) at 0° C. The reaction mixture was stirred for 5 min. After consumption of starting material (monitored by TLC), the reaction mixture was quenched with ice water (10 mL) and extracted with EtOAc (2×10 mL). The combined organic extracts were washed with water, dried over sodium sulfate, filtered and concentrated in vacuo to obtain the 2'-chloro-6'H, 8'H-spiro [cyclopentane-1, 7'-pyrimido [5, 4-b] [1, 4] oxazine] (100 mg, 95%) as a brown liquid. 1H-NMR (CDCl3, 400 MHz): δ 7.61 (s, 1H), 3.82 (s, 2H), 3.09 (s, 3H), 1.87-1.80 (m, 4H), 1.73-1.67 (m, 4H); LCMS: 240.1 (M+1); (column; X-Select CSH C-18 (50×3.0 mm, 3.5 μm); RT 3.32 min 0.05% Aq TFA: ACN; 0.80 mL/min); TLC: 20% EtOAc:hexane (Rf: 0.3).

Example 250

Synthesis of 2'-chloro-8'-methyl-6'H, 8'H-spiro [cyclopropane-1, 7'-pyrimido [5, 4-b] [1, 4] oxazine]

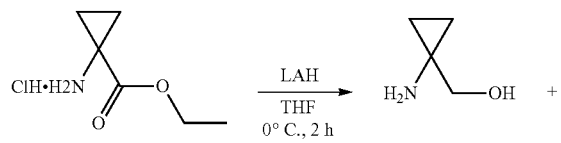

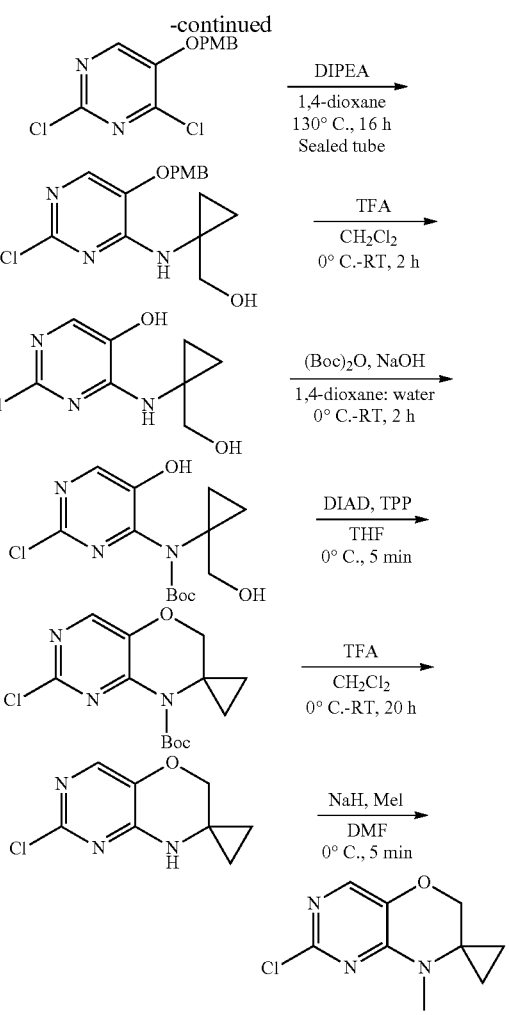

Synthesis of (1-aminocyclopropyl) methanol

To a stirred solution of lithium aluminum hydride (1.3 g, 36.23 mmol) in THF (30 mL) under an argon atmosphere was added ethyl 1-aminocyclopropane-1-carboxylate hydrochloride (3 g, 18.11 mmol) at 0° C. and stirred for 2 h. After consumption of starting material (monitored by TLC), the reaction mixture was quenched with a saturated sodium sulfate solution (100 mL) and stirred for 1 h. The reaction mixture was filtered and washed with 20% MeOH: CH$_2$Cl$_2$. The filtrate was concentrated in vacuo to obtain (1-aminocyclopropyl) methanol (1.5 g, 95%) as a colorless liquid used in the next step without further purification. TLC: EtOAc ($R_f$: 0.1).

Synthesis of (1-((2-chloro-5-(4-methoxybenzyl) oxy) pyrimidin-4-yl) amino) cyclopropyl) methanol To a stirred solution of (1-aminocyclopropyl) methanol (1.5 g, 17.54 mmol) in 1, 4-dioxane (6.4 mL) under an argon atmosphere were added diisopropylethylamine (6.4 mL, 35.08 mmol) and 2, 4-dichloro-5-((4-methoxybenzyl) oxy) pyrimidine (5 g, 17.54 mmol) at room temperature. The reaction mixture was stirred at 130° C. for 16 h in a sealed tube. After consumption of starting material (monitored by TLC), the volatile components were evaporated in vacuo.

The crude material was purified by column chromatography using 50% EtOAc:hexanes to afford (1-((2-chloro-5-((4-methoxybenzyl) oxy) pyrimidin-4-yl) amino) cyclopropyl) methanol (1 g, 17%) as a brown liquid. $^1$H-NMR (CDCl$_3$, 500 MHz): δ 7.62 (s, 1H), 7.30 (d, 1H), 7.28 (s, 1H), 6.93 (d, 2H), 5.87 (s, 1H), 4.97 (s, 2H), 4.10-4.07 (m, 1H), 3.80 (s, 3H), 3.65 (s, 2H), 1.01-0.99 (m, 2H), 0.85-0.83 (m, 2H); TLC: 30% EtOAc:hexane (R$_f$: 0.2).

Synthesis of 2-chloro-4-((1-(hydroxymethyl) cyclopropyl) amino) pyrimidin-5-ol

To a stirred solution of (1-((2-chloro-5-((4-methoxybenzyl) oxy) pyrimidin-4-yl) amino) cyclopropyl) methanol (200 mg, 0.59 mmol) in CH$_2$Cl$_2$ (2 mL) under an argon atmosphere was added trifluoroacetic acid (136 mg) at 0° C. The reaction mixture was warmed to room temperature and stirred for 2 h. After consumption of starting material (monitored by TLC), the reaction mixture was quenched with a saturated sodium bicarbonate solution (20 mL) and extracted with CH$_2$Cl$_2$ (2×20 mL). The aqueous layer was acidified with citric acid up to pH=5 and extracted with EtOAc (2×20 mL). The combined organic extracts were dried over sodium sulfate, filtered and concentrated in vacuo to obtain the 2-chloro-4-((1-(hydroxymethyl) cyclopropyl) amino) pyrimidin-5-ol (50 mg, 39%) as an off-white solid used in the next step without further purification. $^1$H-NMR (CD$_3$OD, 400 MHz): δ 7.40 (s, 1H), 3.69 (s, 2H), 0.99-0.90 (m, 2H), 0.89-0.82 (m, 2H); TLC: 50% EtOAc:hexane (R$_f$: 0.2).

Synthesis of tert-butyl (2-chloro-5-hydroxypyrimidin-4-yl) (1-(hydroxymethyl) cyclopropyl) carbamate To a stirred solution of 2-chloro-4-((1-(hydroxymethyl) cyclopropyl) amino) pyrimidin-5-ol (50 mg, 0.23 mmol) in 1, 4-dioxane: water (1:1, 1 mL) under an argon atmosphere were added sodium hydroxide (18 g, 0.46 mmol) and Boc anhydride (76 mg, 0.34 mmol) at 0° C. The reaction mixture was warmed to room temperature and stirred for 2 h. After consumption of starting material (monitored by TLC), the reaction mixture was diluted with water (10 mL) and extracted with EtOAc (2×10 mL). The aqueous layer was acidified with citric acid up to pH=5 and extracted with EtOAc (2×10 mL). The combined organic extracts were washed with water, dried over sodium sulfate, filtered and concentrated in vacuo. The crude material was purified by column chromatography using 80% EtOAc:hexanes to afford tert-butyl (2-chloro-5-hydroxypyrimidin-4-yl) (1-(hydroxymethyl) cyclopropyl) carbamate (20 mg, 27%) as an off-white solid. $^1$H-NMR (CD$_3$OD, 400 MHz): δ 8.22 (s, 1H), 3.80 (s, 2H), 1.42 (s, 9H), 1.00-0.91 (m, 2H), 0.85-0.80 (m, 2H); TLC: 50% EtOAc:hexane (R$_f$: 0.3).

Synthesis of tert-butyl 2'-chloro-6'H, 8'H-spiro [cyclopropane-1, 7'-pyrimido [5, 4-b] [1, 4] oxazine]-8'-carboxylate To a stirred solution of tert-butyl (2-chloro-5-hydroxypyrimidin-4-yl) (1-(hydroxymethyl) cyclopropyl) carbamate (200 mg, 0.63 mmol) in THF (2 mL) under an argon atmosphere were added diisopropylazodicarboxylate (192 g, 0.95 mmol) and triphenylphosphine (249 mg, 0.95 mmol) at 0° C. The reaction mixture was stirred for 5 min. After consumption of starting material (monitored by TLC), the reaction mixture was diluted with water (20 mL) and extracted with EtOAc (2×20 mL). The combined organic extracts were dried over sodium sulfate, filtered and concentrated in vacuo. The crude material was purified by column chromatography using 20% EtOAc:hexanes to afford tert-butyl 2'-chloro-6'H, 8'H-spiro [cyclopropane-1, 7'-pyrimido [5, 4-b] [1, 4] oxazine]-8'-carboxylate (32 mg, 17%) as an off-white solid. $^1$H-NMR (CDCl$_3$, 400 MHz): δ 8.20 (s, 1H), 4.11 (s, 2H), 1.50 (s, 9H), 1.39-1.33 (m, 2H), 1.01-0.98 (m, 2H); TLC: 30% EtOAc:hexane (R$_f$: 0.4).

Synthesis of 2'-chloro-6'H, 8'H-spiro [cyclopropane-1, 7'-pyrimido [5, 4-b] [1, 4] oxazine]

To a stirred solution of tert-butyl 2'-chloro-6'H, 8'H-spiro [cyclopropane-1, 7'-pyrimido [5, 4-b] [1, 4] oxazine]-8'-carboxylate (30 mg, 0.10 mmol) in CH$_2$Cl$_2$ (0.3 mL) under an argon atmosphere was added trifluoroacetic acid (23 mg, 0.20 mmol) at 0° C. The reaction mixture was warmed to room temperature and stirred for 20 h. After consumption of starting material (monitored by TLC), the reaction mixture was quenched with a saturated sodium bicarbonate solution (10 mL) and extracted with CH$_2$Cl$_2$ (2×10 mL). The combined organic extracts were dried over sodium sulfate, filtered and concentrated in vacuo to obtain the 2'-chloro-6'H, 8'H-spiro [cyclopropane-1, 7'-pyrimido [5, 4-b] [1, 4] oxazine] (19 mg, 96%) as an off-white solid. $^1$H-NMR (CDCl$_3$, 400 MHz): δ 7.80 (s, 1H), 5.33 (br s, 1H), 3.95 (s, 2H), 0.96-0.94 (m, 4H); TLC: 50% EtOAc:hexane (R$_f$: 0.5).

Synthesis of 2'-chloro-8'-methyl-6'H, 8'H-spiro [cyclopropane-1, 7'-pyrimido [5, 4-b] [1, 4] oxazine]

To a stirred solution of 2'-chloro-6'H, 8'H-spiro [cyclopropane-1, 7'-pyrimido [5, 4-b] [1, 4] oxazine] (300 mg, 1.52 mmol) in DMF (3 mL) under an argon atmosphere were added sodium hydride (91 mg, 2.28 mmol) and methyl iodide (324 mg, 2.28 mmol) at 0° C. The reaction mixture was stirred for 5 min. After consumption of starting material (monitored by TLC), the reaction mixture was quenched with ice water (10 mL) and extracted with EtOAc (2×10 mL). The combined organic extracts were washed with water, dried over sodium sulfate, filtered and concentrated in vacuo to obtain the 2'-chloro-8'-methyl-6'H, 8'H-spiro [cyclopropane-1, 7'-pyrimido [5, 4-b] [1, 4] oxazine] (230 mg, 72%) as a brown liquid. 1H-NMR (CDCl3, 400 MHz): δ 7.69 (s, 1H), 3.91 (s, 2H), 2.91 (s, 3H), 1.20 (t, 2H), 0.81 (t, 2H); TLC: 40% EtOAc:hexane (Rf: 0.5).

Example 251

Synthesis of 2'-chloro-8'-methyl-6'H, 8'H-spiro [oxetane-3, 7'-pyrimido [5, 4-b] [1, 4] oxazine]

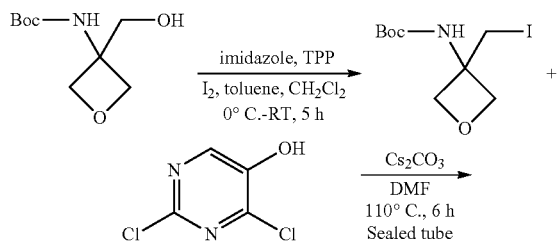

-continued

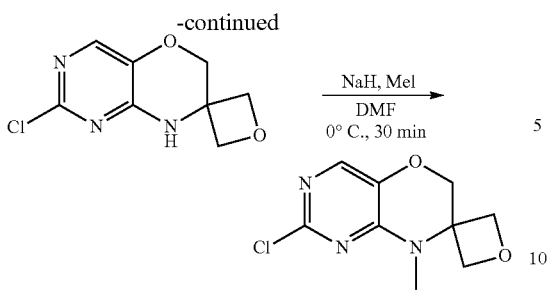

Synthesis of tert-butyl (3-(iodomethyl) oxetan-3-yl) carbamate

To a stirred solution of tert-butyl (3-(hydroxymethyl) oxetan-3-yl) carbamate (2 g, 9.85 mmol) in $CH_2Cl_2$: toluene (2:1.60 mL) under an argon atmosphere were added imidazole (2.7 g, 39.40 mmol), triphenylphosphine (5 g, 19.70 mmol) and iodine (5 g, 19.70 mmol) at 0° C. The reaction mixture was warmed to room temperature and stirred for 5 h. After consumption of starting material (monitored by TLC), the reaction mixture was diluted with water (20 mL) and extracted with $CH_2Cl_2$ (2×20 mL). The combined organic extracts were dried over sodium sulfate, filtered and concentrated in vacuo. The crude material was purified by column chromatography using 10-15% MeOH: $CH_2Cl_2$ to afford tert-butyl (3-(iodomethyl) oxetan-3-yl) carbamate (2.6 g, 84%) as a white solid. $^1$H-NMR (DMSO-$d_6$, 500 MHz): δ 7.79 (br s, 1H), 4.43 (d, 2H), 4.32-4.29 (m, 2H), 3.80 (s, 2H), 1.40 (s, 9H); LCMS: 314.1 (M+1); (column; X-Select CSH C-18 (50×3.0 mm, 3.5 μm); RT 3.73 min 5 mM Aq $NH_4OAc$: ACN; 0.80 mL/min); TLC: 30% EtOAc: hexane ($R_f$: 0.7).

Synthesis of 2'-chloro-6'H, 8'H-spiro [oxetane-3, 7'-pyrimido [5, 4-b] [1, 4] oxazine]

To a stirred solution of tert-butyl (3-(iodomethyl) oxetan-3-yl) carbamate (1.6 g, 5.11 mmol) in DMF (16 mL) under an argon atmosphere were added cesium carbonate (4.1 g, 15.33 mmol) and 2, 4-dichloropyrimidin-5-ol (700 mg, 5.11 mmol) at room temperature. The reaction mixture was stirred at 110° C. for 6 h in a sealed tube. After consumption of starting material (monitored by TLC), the reaction mixture was diluted with water (50 mL) and extracted with EtOAc (2×50 mL). The combined organic extracts were dried over sodium sulfate, filtered and concentrated in vacuo. The crude material was purified by column chromatography using 40-60% EtOAc:hexane to afford 2'-chloro-6'H, 8'H-spiro [oxetane-3, 7'-pyrimido [5, 4-b] [1, 4] oxazine] (800 mg, 44%) as a white solid. $^1$H NMR (DMSO-$d_6$, 500 MHz): δ 9.25 (s, 1H), 7.77 (s, 1H), 4.63 (d, 2H), 4.46 (d, 2H), 4.34 (s, 2H); LCMS: 214.1 (M+1); (column; Eclipse XDB C-18 (150×4.6 mm, 5.0 μm); RT 6.42 min 5 mM Aq $NH_4OAc$: ACN; 1.0 mL/min); TLC: EtOAc ($R_f$: 0.3).

Synthesis of 2'-chloro-8'-methyl-6'H, 8'H-spiro [oxetane-3, 7'-pyrimido [5, 4-b] [1, 4] oxazine]

To a stirred solution of 2'-chloro-6'H, 8'H-spiro [oxetane-3, 7'-pyrimido [5, 4-b] [1, 4] oxazine] (800 mg, 3.75 mmol) in DMF (20 mL) under an argon atmosphere were added sodium hydride (225 mg, 5.63 mmol) portion wise at 0° C. Then methyl iodide (640 mg, 4.50 mmol) was added dropwise to the reaction mixture at 0° C. and stirred for 30 min. After consumption of starting material (monitored by TLC), the reaction mixture was diluted with water (50 mL) and extracted with EtOAc (2×50 mL). The combined organic extracts were dried over sodium sulfate, filtered and concentrated in vacuo. The crude material was purified by column chromatography using 50% EtOAc:hexane to afford 2'-chloro-8'-methyl-6'H, 8'H-spiro [oxetane-3, 7'-pyrimido [5, 4-b] [1, 4] oxazine] (750 mg, 88%) as an off-white solid. $^1$H NMR (CDCl$_3$, 400 MHz): δ 7.71 (s, 1H), 4.99 (d, 2H), 4.52 (d, 2H), 4.39 (s, 2H), 3.41 (s, 3H); LCMS: 228.1 (M+1); (column; X-Select CSH C-18 (50×3.0 mm, 3.5 μm); RT 2.90 min 5 mM $NH_4OAc$ in water: ACN; 0.80 mL/min); TLC: 30% EtOAc:hexane ($R_f$: 0.7).

Example 252

Synthesis of 2'-chloro-8'-methyl-2, 3, 5, 6-tetrahydro-6'H, 8'H-spiro[pyran-4,7'-pyrimido [5, 4-b] [1,4] oxazine]

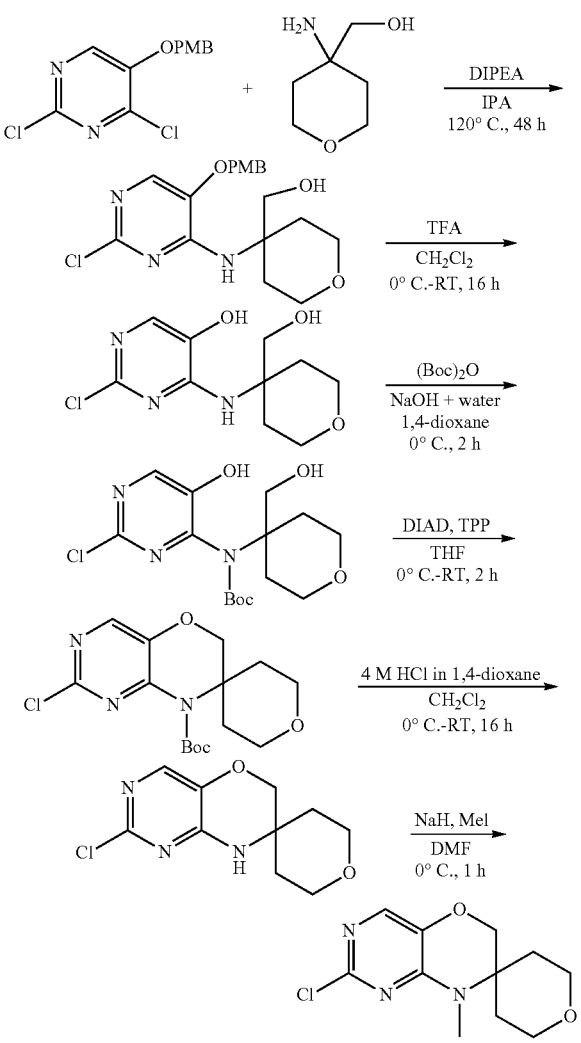

Synthesis of (4-((2-chloro-5-((4-methoxybenzyl) oxy) pyrimidin-4-yl) amino) tetrahydro-2H-pyran-4-yl) methanol To a stirred solution of 2, 4-dichloro-5-((4-methoxybenzyl) oxy) pyrimidine (2 g, 7.04 mmol) in isopropyl alcohol (30 mL) under an argon atmosphere were added diisopropylethylamine (2.4 mL, 14.08 mmol) and (4-aminotetrahydro-2H-pyran-4-yl) methanol (900 mg, 7.04 mmol) at room temperature. The reaction mixture was stirred at 120° C. for 48 h. After consumption of starting material (monitored by TLC), the volatile components were evaporated in vacuo. The crude material was purified by column chromatography using 20-30% EtOAc:hexanes to afford (4-((2-chloro-5-((4-methoxybenzyl) oxy) pyrimidin-4-yl) amino) tetrahydro-2H-pyran-4-yl) methanol (1 g, 38%) as a white solid.
$^1$H NMR (CDCl$_3$, 400 MHz): δ 7.66 (s, 1H), 7.30 (d, 2H), 6.94 (d, 2H), 5.47 (s, 1H), 5.03 (s, 2H), 4.60 (t, 1H), 3.87-3.83 (m, 5H), 3.80-3.73 (m, 2H), 3.68-3.60 (m, 2H), 1.97-1.87 (m, 4H); LCMS: 379.9 (M+1); (column; X-select CSH C-18 (50×3.0 mm, 3.5 μm); RT 3.07 min. 0.05% Aq TFA: CH$_3$CN; 0.8 mL/min); TLC: 50% EtOAc:hexane (R$_f$: 0.3).

Synthesis of 2-chloro-4-((4-(hydroxymethyl) tetrahydro-2H-pyran-4-yl) amino) pyrimidin-5-ol To a stirred solution of (4-((2-chloro-5-((4-methoxybenzyl) oxy) pyrimidin-4-yl) amino) tetrahydro-2H-pyran-4-yl) methanol (200 g, 0.52 mmol) in CH$_2$Cl$_2$ (2 mL) under an argon atmosphere was added trifluoroacetic acid (1 mL) at 0° C. The reaction mixture was warmed to room temperature and stirred for 16 h. After consumption of starting material (monitored by TLC), the reaction mixture was diluted with a saturated sodium bicarbonate solution (10 mL) and extracted with EtOAc (2×10 mL). The combined organic extracts were dried over sodium sulfate, filtered and concentrated in vacuo. The crude material was purified by column chromatography using 2% MeOH: CH$_2$Cl$_2$ to afford 2-chloro-4-((4-(hydroxymethyl) tetrahydro-2H-pyran-4-yl) amino) pyrimidin-5-ol (50 mg, 45%) as a white solid. $^1$H NMR (DMSO-d$_6$, 500 MHz): δ 10.40 (s, 1H), 7.50 (s, 1H), 5.94 (s, 1H), 4.83 (br s, 1H), 3.71-3.60 (m, 4H), 3.50 (t, 2H), 2.26 (d, 2H), 1.72-1.58 (m, 2H); LCMS: 259.9 (M+1); (column; X-select CSH C-18 (50×3.0 mm, 3.5 μm); RT 1.90 min. 0.05% Aq TFA: CH$_3$CN; 0.8 mL/min); TLC: 5% MeOH/CH$_2$Cl$_2$ (R$_f$: 0.3).

Synthesis of tert-butyl (2-chloro-5-hydroxypyrimidin-4-yl) (4-(hydroxymethyl) tetrahydro-2H-pyran-4-yl) carbamate To a stirred solution of 2-chloro-4-((4-(hydroxymethyl) tetrahydro-2H-pyran-4-yl) amino) pyrimidin-5-ol (120 g, 0.46 mmol) in 1, 4-dioxane: water (1:1, 5 mL) under an argon atmosphere were added sodium hydroxide (22 mg, 0.55) and Boc anhydride (150 mg, 0.69 mmol) at 0° C. The reaction mixture was stirred for 2 h. After consumption of starting material (monitored by TLC), the reaction mixture was diluted with water (10 mL) and extracted with EtOAc (2×10 mL). The combined organic extracts were dried over sodium sulfate, filtered and concentrated in vacuo to obtain tert-butyl (2-chloro-5-hydroxypyrimidin-4-yl) (4-(hydroxymethyl) tetrahydro-2H-pyran-4-yl) carbamate (100 mg, 60%) as a colorless liquid. LCMS: 360.0 (M+1); (column; X-select CSH C-18 (50×3.0 mm, 3.5 μm); RT 3.27 min. 0.05% Aq TFA: CH$_3$CN; 0.8 mL/min); TLC: 50% EtOAc:hexane (R$_f$: 0.3).

Synthesis of tert-butyl 2'-chloro-2, 3, 5, 6-tetrahydro-6'H, 8'H-spiro [pyran-4, 7'-pyrimido [5, 4-b] [1, 4] oxazine]-8'-carboxylate To a stirred solution of tert-butyl (2-chloro-5-hydroxypyrimidin-4-yl) (4-(hydroxymethyl) tetrahydro-2H-pyran-4-yl) carbamate (100 mg, 0.28 mmol) in THF (2 mL) under an argon atmosphere were added triphenylphosphine (66 mg, 0.33) and diisopropylazodicarboxylate (86 mg, 0.33 mmol) at 0° C. The reaction mixture was warmed to room temperature and stirred for 2 h. After consumption of starting material (monitored by TLC), the volatile components were concentrated in vacuo. The crude material was purified by column chromatography using 10% EtOAc:hexane to afford tert-butyl 2'-chloro-2, 3, 5, 6-tetrahydro-6'H, 8'H-spiro [pyran-4, 7'-pyrimido [5, 4-b] [1, 4] oxazine]-8'-carboxylate (38 mg, 40%) as a white solid. $^1$H NMR (CDCl$_3$, 500 MHz) δ 7.95 (s, 1H), 4.29 (s, 2H), 4.02-3.99 (m, 2H), 3.60-3.57 (m, 2H), 1.61-1.57 (m, 4H), 1.29 (s, 9H); TLC: 50% EtOAc: hexane (R$_f$: 0.6).

Synthesis of 2'-chloro-2, 3, 5, 6-tetrahydro-6'H, 8'H-spiro [pyran-4, 7'-pyrimido [5, 4-b] [1, 4] oxazine To a stirred solution of tert-butyl 2'-chloro-2, 3, 5, 6-tetrahydro-6'H, 8'H-spiro [pyran-4, 7'-pyrimido [5, 4-b] [1, 4] oxazine]-8'-carboxylate (120 mg, 0.35 mmol) in CH$_2$Cl$_2$ (2 mL) under an argon atmosphere was added 4 M HCl in 1, 4-dioxane (2 mL) at 0° C. The reaction mixture was warmed to room temperature and stirred for 16 h. After consumption of starting material (monitored by TLC), the volatile components were concentrated in vacuo. The crude material was purified by column chromatography using 50% EtOAc: hexane to afford 2'-chloro-2, 3, 5, 6-tetrahydro-6'H, 8'H-spiro [pyran-4, 7'-pyrimido [5, 4-b] [1, 4] oxazine] (60 mg, 71%) as a white solid. $^1$H NMR (CDCl$_3$, 500 MHz): δ 7.79 (s, 1H), 5.87 (br s, 1H), 3.95 (s, 2H), 3.89-3.77 (m, 2H), 3.76-3.68 (m, 2H), 1.82-1.78 (m, 2H), 1.70-1.67 (m, 2H); LCMS: 241.9 (M+1); (column; X-select CSH C-18 (50×3.0 mm, 3.5 μm); RT 2.15 min. 0.05% Aq TFA: CH$_3$CN; 0.8 mL/min); TLC: 50% EtOAc:hexane (R$_f$: 0.7).

Synthesis of 2'-chloro-8'-methyl-2, 3, 5, 6-tetrahydro-6'H, 8'H-spiro[pyran-4,7'-pyrimido [5, 4-b] [1,4] oxazine]

To a stirred solution of 2'-chloro-2, 3, 5, 6-tetrahydro-6'H, 8'H-spiro [pyran-4, 7'-pyrimido [5, 4-b] [1, 4] oxazine] (50 mg, 0.20 mmol) in DMF (0.5 mL) under an argon atmosphere was added sodium hydride (7.4 mg, 0.31 mmol) portion wise at 0° C. Then methyl iodide (29 mg, 0.20 mmol) was added drop wise to the reaction mixture at 0° C. and stirred for 1 h. After consumption of starting material (monitored by TLC), the reaction mixture was diluted with water (50 mL) and extracted with EtOAc (2×50 mL). The combined organic extracts were dried over sodium sulfate, filtered and concentrated in vacuo. The crude material was purified by column chromatography using 50% EtOAc: hexane to afford 2'-chloro-8'-methyl-2, 3, 5, 6-tetrahydro-6'H, 8'H-spiro[pyran-4,7'-pyrimido [5, 4-b] [1,4] oxazine] (30 mg, 57%) as a colorless liquid. $^1$H NMR (CDCl$_3$, 400 MHz): δ 7.65 (s, 1H), 4.19 (s, 2H), 4.00-3.97 (m, 2H), 3.57 (t, 2H), 3.15 (s, 3H), 2.23-2.13 (m, 2H), 1.60-1.57 (m, 2H); LCMS: 255.9 (M+1); (column; X-Select CSH C-18 (50×3.0 mm, 3.5 μm); RT 2.63 min 0.05% Aq TFA: ACN; 0.80 mL/min); TLC: 50% EtOAc:hexane (R$_f$: 0.5).

Example 253

Synthesis of 2'-chloro-3, 3-difluoro-8'-methyl-6'H, 8'H-spiro [cyclobutane-1, 7'-pyrimido [5, 4-b] [1, 4] oxazine]

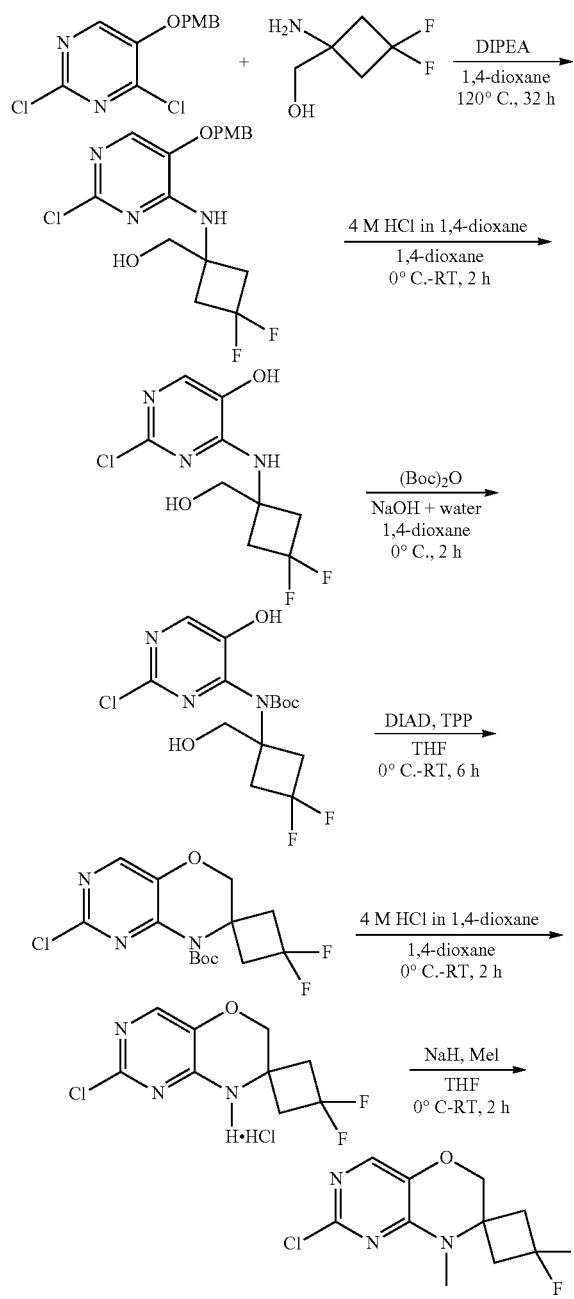

Synthesis of (1-((2-chloro-5-(4-methoxybenzyl) oxy) pyrimidin-4-yl) amino)-3, 3-difluorocyclobutyl) methanol To a stirred solution of 2, 4-dichloro-5-((4-methoxybenzyl) oxy) pyrimidine (350 mg, 1.22 mmol) in 1, 4-dioxane (1 mL) under an argon atmosphere were added diisopropylethylamine (0.42 mL, 2.45 mmol) and (1-amino-3, 3-difluorocyclobutyl) methanol (213 mg, 1.22 mmol) at room temperature. The reaction mixture was stirred at 120° C. for 32 h. After consumption of starting material (monitored by TLC), the volatile components were evaporated in vacuo. The crude material was purified by column chromatography using 40% EtOAc:hexane to afford (1-((2-chloro-5-((4-methoxybenzyl) oxy) pyrimidin-4-yl) amino)-3, 3-difluorocyclobutyl) methanol (240 mg, 51%) as a brown solid. $^1$H NMR (DMSO-$d_6$, 500 MHz): δ 7.77 (s, 1H), 7.47 (s, 1H), 7.40 (d, 2H), 6.93 (d, 2H), 5.14 (t, 1H), 5.10 (s, 2H), 3.75 (s, 3H), 3.61 (d, 2H), 2.96-2.76 (m, 4H); LCMS: 385.9 (M+1); (column; X-Select CSH C-18 (50×3.0 mm, 3.5 µm); RT 3.52 min 0.05% Aq TFA: ACN; 0.80 mL/min); TLC: 50% EtOAc:hexane ($R_f$: 0.3).

Synthesis of 2-chloro-4-((3, 3-difluoro-1-(hydroxymethyl) cyclobutyl) amino) pyrimidin-5-ol To a stirred solution of (1-((2-chloro-5-((4-methoxybenzyl) oxy) pyrimidin-4-yl) amino)-3, 3-difluorocyclobutyl) methanol (400 mg, 1.03 mmol) in 1, 4-dioxane (3 mL) under an argon atmosphere was added 4M HCl in 1, 4-dioxane (3 mL) at 0° C. The reaction mixture was warmed to room temperature and stirred for 2 h. After consumption of starting material (monitored by TLC), the volatile components were evaporated in vacuo to obtain 2-chloro-4-((3, 3-difluoro-1-(hydroxymethyl) cyclobutyl) amino) pyrimidin-5-ol (225 mg, 82%) as an off-white solid. LCMS: 265.9 (M+1); (column; X-Select CSH C-18 (50×3.0 mm, 3.5 µm); RT 2.64 min 0.05% Aq TFA: ACN; 0.80 mL/min); TLC: 50% EtOAc:hexane ($R_f$: 0.1).

Synthesis of tert-butyl (2-chloro-5-hydroxypyrimidin-4-yl) (3, 3-difluoro-1-(hydroxymethyl) cyclobutyl) carbamate To a stirred solution of 2-chloro-4-((3, 3-difluoro-1-(hydroxymethyl) cyclobutyl) amino) pyrimidin-5-ol (250 mg, 0.94 mmol) in 1, 4-dioxane (5 mL) under an argon atmosphere was added sodium hydroxide (75 mg, 1.88 mmol) in water (2 mL) at 0° C. and stirred for 10 min. Then Boc anhydride (246 mg, 1.12 mmol) was added to the reaction mixture at 0° C. and stirred for 2 h. After consumption of starting material (monitored by TLC), the volatile components were evaporated in vacuo. The crude material was washed with ether (2×10 mL) to afford tert-butyl (2-chloro-5-hydroxypyrimidin-4-yl) (3, 3-difluoro-1-(hydroxymethyl) cyclobutyl) carbamate (220 mg, crude) as a brown solid used in the next step without further purification. LCMS: 366.9 (M+1); (column; X-Select CSH C-18 (50×3.0 mm, 3.5 µm); RT 4.44 min 5 mM NH$_4$OAc in water: ACN; 0.80 mL/min); TLC: 80% EtOAc:hexane ($R_f$: 0.6).

Synthesis of tert-butyl 2'-chloro-3, 3-difluoro-6'H, 8'H-spiro [cyclobutane-1, 7'-pyrimido [5, 4-b] [1, 4] oxazine]-8'-carboxylate To a stirred solution of tert-butyl (2-chloro-5-hydroxypyrimidin-4-yl) (3, 3-difluoro-1-(hydroxymethyl) cyclobutyl) carbamate (220 mg, 0.60 mmol) in THF (30 mL) under an argon atmosphere was added triphenylphosphine (236 mg, 0.90 mmol) at 0° C. The reaction mixture was stirred for 5 min, then diisopropylazodicarboxylate (182 mg, 0.90 mmol) was added at 0° C. The reaction mixture was warmed to room temperature and stirred for 6 h. After consumption of starting material (monitored by TLC), the reaction mixture was diluted with water (20 mL) and extracted with EtOAc (2×20 mL). The combined organic extracts were dried over sodium sulfate, filtered and concentrated in vacuo. The crude material was purified by column chromatography using 5% EtOAc:hexane to afford tert-butyl 2'-chloro-3, 3-difluoro-6'H, 8'H-spiro [cyclobutane-1, 7'-pyrimido [5, 4-b] [1, 4] oxazine]-8'-carboxylate (100 mg, 48%) as a brown solid. $^1$H-NMR (DMSO-$d_6$, 500 MHz): δ 8.27 (s, 1H), 4.30 (s, 2H), 3.30 (s, 2H), 2.81-2.79 (m, 2H), 1.53 (s, 9H); LCMS: 347.9 (M+1); (column; X-Select CSH C-18 (50×3.0 mm, 3.5 μm); RT 4.13 min 0.05% Aq TFA: ACN; 0.80 mL/min); TLC: 20% EtOAc:hexane ($R_f$: 0.6).

Synthesis of 2'-chloro-3, 3-difluoro-6'H, 8'H-spiro [cyclobutane-1, 7'-pyrimido [5, 4-b] [1, 4] oxazine] hydrochloride To a stirred solution of tert-butyl 2'-chloro-3, 3-difluoro-6'H, 8'H-spiro [cyclobutane-1, 7'-pyrimido [5, 4-b] [1, 4] oxazine]-8'-carboxylate (100 mg, 0.28 mmol) in 1, 4-dioxane (5 mL) under an argon atmosphere was added 4M HCl in 1, 4-dioxane (5 mL) at 0° C. The reaction mixture was warmed to room temperature and stirred for 2 h. After consumption of starting material (monitored by TLC), the volatile components were evaporated in vacuo to obtain 2'-chloro-3, 3-difluoro-6'H, 8'H-spiro [cyclobutane-1, 7'-pyrimido [5, 4-b] [1, 4] oxazine] hydrochloride (80 mg, 99%) as an off-white solid. LCMS: 247.8 (M+1); (column; X-Select CSH C-18 (50×3.0 mm, 3.5 μm); RT 2.76 min 0.05% Aq TFA: ACN; 0.80 mL/min); TLC: 20% EtOAc:hexane ($R_f$: 0.1).

Synthesis of 2'-chloro-3, 3-difluoro-8'-methyl-6'H, 8'H-spiro [cyclobutane-1, 7'-pyrimido [5, 4-b] [1, 4] oxazine]

To a stirred solution of 2'-chloro-3, 3-difluoro-6'H, 8'H-spiro [cyclobutane-1, 7'-pyrimido [5, 4-b] [1, 4] oxazine] hydrochloride (80 mg, 0.32 mmol) in THF (20 mL) under an argon atmosphere was added sodium hydride (23 mg, 0.97 mmol) at 0° C. The reaction mixture was stirred for 15 min, then methyl iodide (91 mg, 0.64 mmol) was added at 0° C. The reaction mixture was stirred for 2 h. After consumption of starting material (monitored by TLC), the reaction mixture was diluted with water (20 mL) and extracted with EtOAc (2×20 mL). The combined organic extracts were dried over sodium sulfate, filtered and concentrated in vacuo. The crude material was purified by column chromatography using 5% EtOAc:hexanes to afford 2'-chloro-3, 3-difluoro-8'-methyl-6'H, 8'H-spiro [cyclobutane-1, 7'-pyrimido [5, 4-b] [1, 4] oxazine] (70 mg, 83%) as a brown solid. $^1$H NMR (CDCl$_3$, 400 MHz): δ 7.73 (s, 1H), 4.15 (s, 2H), 3.23 (s, 3H), 3.13-3.01 (m, 2H), 2.77-2.66 (m, 2H); LCMS: 261.8 (M+1); (column; Ascentis Express C-18 (50× 3.0 mm, 2.7 μm); RT 2.23 min. 0.025% Aq TFA+5% ACN: 5% ACN+0.025% Aq TFA; 1.2 mL/min); TLC: 20% EtOAc: hexane ($R_f$: 0.5).

Example 254

Synthesis of N-(3-methoxy-4-(4-methyl-1H-imidazol-1-yl) phenyl)-7, 7, 8-trimethyl-7, 8-dihydro-6H-pyrimido [5, 4-b] [1, 4] oxazin-2-amine

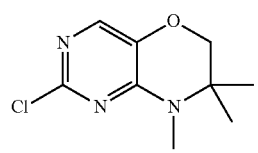

+

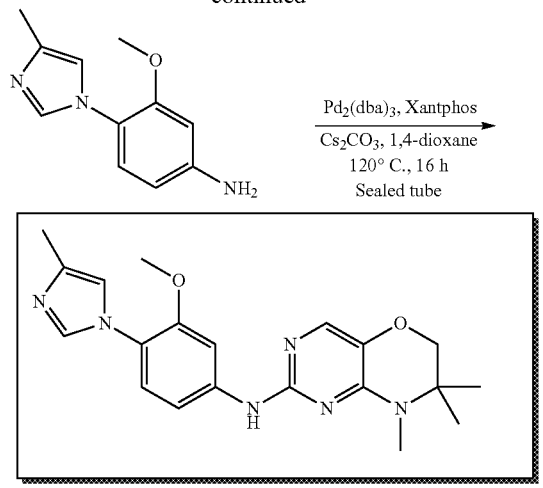

Synthesis of N-(3-methoxy-4-(4-methyl-1H-imidazol-1-yl) phenyl)-7, 7, 8-trimethyl-7, 8-dihydro-6H-pyrimido [5, 4-b] [1, 4] oxazin-2-amine To a dry vial was added a suspension of Pd$_2$(dba)$_3$ (32 mg, 0.03 mmol) and Xantphos (61 mg, 0.01 mmol) in 1, 4-dioxane (0.75 mL) at room temperature. The suspension was degassed with argon, heated to 120° C., and stirred for 3 min. A mixture of 2-chloro-7, 7-dimethyl-8-phenyl-7, 8-dihydro-6H-pyrimido [5, 4-b] [1, 4] oxazine (150 mg, 0.70 mmol), 3-methoxy-4-(4-methyl-1H-imidazol-1-yl) aniline (285 mg, 1.40 mmol) and cesium carbonate (320 mg, 0.98 mmol) in 1, 4-dioxane (0.75 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with CH$_2$Cl$_2$ (2×20 mL). The combined organic extracts were dried over sodium sulfate, filtered and concentrated in vacuo. The crude material was purified by column chromatography using 3-4% MeOH: CH$_2$Cl$_2$ to afford N-(3-methoxy-4-(4-methyl-1H-imidazol-1-yl) phenyl)-7, 7, 8-trimethyl-7, 8-dihydro-6H-pyrimido [5, 4-b] [1, 4] oxazin-2-amine (60 mg, 22%) as an off-white solid. $^1$H-NMR (CD$_3$OD, 400 MHz): δ 7.71 (s, 1H), 7.68 (s, 1H), 7.51 (s, 1H), 7.17-7.12 (m, 2H), 6.93 (s, 1H), 3.84 (s, 5H), 3.14 (s, 3H), 2.21 (s, 3H), 1.31 (s, 6H); Mass (ESI): 381.0 [M+1]; LCMS: 381.1 (M+1); (column; X-Select CSH C-18 (50×3.0 mm, 3.5 μm); RT 2.28 min 0.05% Aq TFA: ACN; 0.80 mL/min); UPLC (column; Acquity UPLC BEH C-18, 2.1×50 mm, 1.7 μm); RT 1.37 min. ACN: 0.025% Aq TFA; 0.5 mL/min; TLC: 5% MeOH/CH$_2$Cl$_2$ ($R_f$: 0.5).

Example 255

Synthesis of N-(3-fluoro-4-(4-methyl-1H-imidazol-1-yl) phenyl)-7, 7, 8-trimethyl-7, 8-dihydro-6H-pyrimido [5, 4-b] [1, 4] oxazin-2-amine

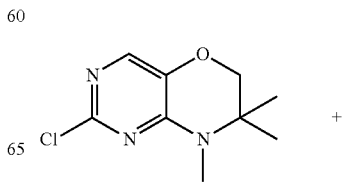

+

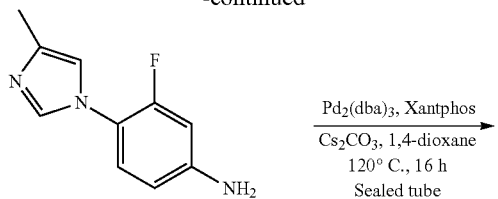

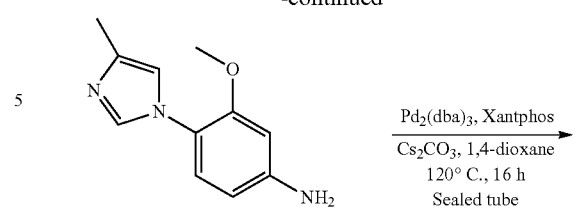

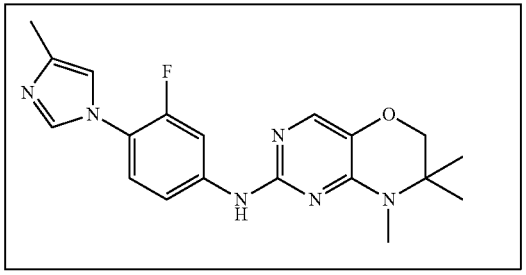

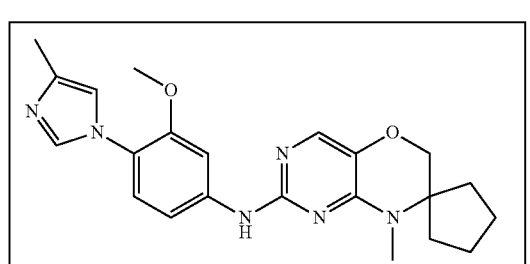

Synthesis of N-(3-fluoro-4-(4-methyl-1H-imidazol-1-yl) phenyl)-7, 7, 8-trimethyl-7, 8-dihydro-6H-pyrimido [5, 4-b] [1, 4] oxazin-2-amine To a dry vial was added a suspension of Pd$_2$(dba)$_3$ (32 mg, 0.03 mmol) and Xantphos (61 mg, 0.01 mmol) in 1, 4-dioxane (0.75 mL) at room temperature. The suspension was degassed with argon, heated to 120° C., and stirred for 3 min. A mixture of 2-chloro-7, 7-dimethyl-8-phenyl-7, 8-dihydro-6H-pyrimido [5, 4-b] [1, 4] oxazine (150 mg, 0.70 mmol), 3-fluoro-4-(4-methyl-1H-imidazol-1-yl)aniline (268 mg, 1.40 mmol) and cesium carbonate (320 mg, 0.98 mmol) in 1, 4-dioxane (0.75 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with CH$_2$Cl$_2$ (2×20 mL). The combined organic extracts were dried over sodium sulfate, filtered and concentrated in vacuo. The crude material was purified by column chromatography using 3-4% MeOH: CH$_2$Cl$_2$ to afford N-(3-fluoro-4-(4-methyl-1H-imidazol-1-yl) phenyl)-7,7,8-trimethyl-7,8-dihydro-6H-pyrimido [5, 4-b] [1, 4] oxazin-2-amine (60 mg, 23%) as an off-white solid. $^1$H-NMR (CD$_3$OD, 400 MHz): δ 7.95 (d, 1H), 7.75 (s, 1H), 7.53 (s, 1H), 7.40-7.30 (m, 2H), 7.05 (s, 1H), 3.84 (s, 2H), 3.12 (s, 3H), 2.25 (s, 3H), 1.31 (s, 6H); Mass (ESI): 369.1 [M+1]; LCMS: 369 (M+1); (column; X-Select CSH C-18 (50×3.0 mm, 3.5 μm); RT 2.03 min 0.05% Aq TFA: ACN; 0.80 mL/min); HPLC (column; Eclipse XDB-C-18, 150×4.6 mm, 5.0 μm); RT 10.27 min. ACN: 5 mM Aq NH$_4$OAc; 1.0 mL/min; TLC: 5% MeOH/CH$_2$Cl$_2$ (R$_f$: 0.5).

Example 256

Synthesis of N-(3-fluoro-4-(4-methyl-1H-imidazol-1-yl) phenyl)-7, 7, 8-trimethyl-7, 8-dihydro-6H-pyrimido [5, 4-b] [1, 4] oxazin-2-amine

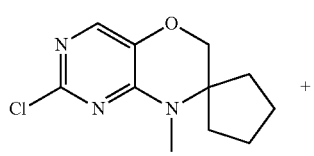

+

Synthesis of N-(3-methoxy-4-(4-methyl-1H-imidazol-1-yl) phenyl)-8'-methyl-6'H, 8'H-spiro [cyclopentane-1, 7'-pyrimido [5, 4-b] [1, 4] oxazin]-2'-amine To a dry vial was added a suspension of Pd$_2$(dba)$_3$ (23 mg, 0.02 mmol) and Xantphos (36 mg, 0.06 mmol) in 1, 4-dioxane (0.5 mL) at room temperature. The suspension was degassed with argon, heated to 120° C., and stirred for 3 min. A mixture of 2'-chloro-8'-methyl-6'H, 8'H-spiro [cyclopentane-1, 7'-pyrimido [5, 4-b] [1, 4] oxazine] (100 mg, 0.41 mmol), 3-methoxy-4-(4-methyl-1H-imidazol-1-yl) aniline (169 mg, 0.83 mmol) and cesium carbonate (190 mg, 0.58 mmol) in 1, 4-dioxane (0.5 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with CH$_2$Cl$_2$ (2×20 mL). The combined organic extracts were dried over sodium sulfate, filtered and concentrated in vacuo. The crude material was purified by column chromatography using 3-4% MeOH: CH$_2$Cl$_2$ to afford N-(3-methoxy-4-(4-methyl-1H-imidazol-1-yl) phenyl)-8'-methyl-6'H, 8'H-spiro [cyclopentane-1, 7'-pyrimido [5, 4-b] [1, 4] oxazin]-2'-amine (60 mg, 35%) as an off-white solid. $^1$H-NMR (CD$_3$OD, 400 MHz): δ 7.73 (s, 1H), 7.68 (s, 1H), 7.50 (s, 1H), 7.15 (s, 2H), 6.97 (s, 1H), 3.84 (s, 5H), 3.12 (s, 3H), 2.20 (s, 3H), 1.95-1.80 (m, 4H), 1.79-1.69 (m, 4H); Mass (ESI): 407 [M+1]; LCMS: 407 (M+1); (column; X-Select CSH C-18 (50×3.0 mm, 3.5 nm); RT 2.24 min 0.05% Aq TFA: ACN; 0.80 mL/min); UPLC (column; Acquity UPLC BEH C-18, 2.1×50 mm, 1.7 μm); RT 1.51 min. ACN: 0.025% Aq TFA; 0.5 mL/min; TLC: 5% MeOH/CH$_2$Cl$_2$ (R$_f$: 0.4).

Example 257

Synthesis of N-(3-methoxy-4-(4-methyl-1H-imidazol-1-yl) phenyl)-8'-methyl-6'H, 8'H-spiro [cyclopropane-1, 7'-pyrimido [5, 4-b] [1, 4] oxazin]-2'-amine

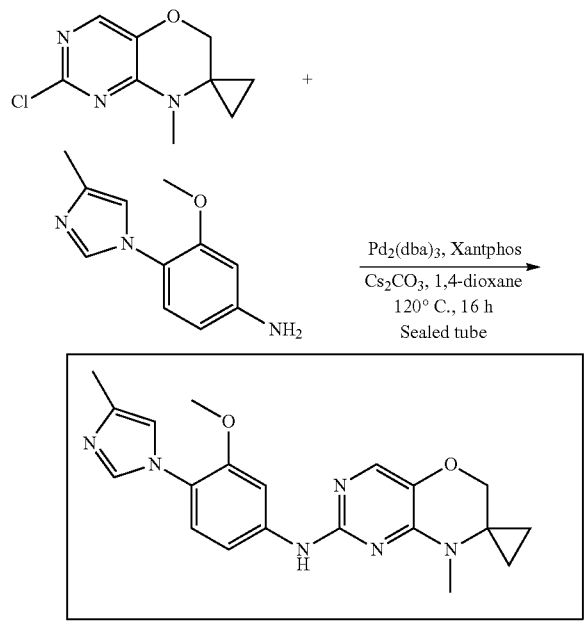

Synthesis of N-(3-methoxy-4-(4-methyl-1H-imidazol-1-yl) phenyl)-8'-methyl-6'H, 8'H-spiro [cyclopropane-1, 7'-pyrimido [5, 4-b] [1, 4] oxazin]-2'-amine To a dry vial was added a suspension of $Pd_2(dba)_3$ (17 mg, 0.02 mmol) and Xantphos (33 mg, 0.05 mmol) in 1, 4-dioxane (0.4 mL) at room temperature. The suspension was degassed with argon, heated to 120° C., and stirred for 3 min. A mixture of 2'-chloro-8'-methyl-6'H, 8'H-spiro [cyclopropane-1, 7'-pyrimido [5, 4-b] [1, 4] oxazine] (80 mg, 0.37 mmol), 3-methoxy-4-(4-methyl-1H-imidazol-1-yl) aniline (154 mg, 0.75 mmol) and cesium carbonate (175 mg, 0.53 mmol) in 1, 4-dioxane (0.4 mL) was degassed and the catalyst premixture was added. The resultant mixture was stirred at 120° C. for 16 h in a sealed tube. After consumption of the starting material (monitored by TLC and LCMS), the volatile components were evaporated in vacuo. The residue was diluted with water (20 mL) and extracted with $CH_2Cl_2$ (2×20 mL). The combined organic extracts were dried over sodium sulfate, filtered and concentrated in vacuo. The crude material was purified by preparative HPLC (Ascentis C-18 (250×21.2 mm, 5 μm (60 mg loading; $CH_3CN$: 0.05% TFA (0.1/90, 15/70, 25/20, 30/10, 35/10)) to afford N-(3-methoxy-4-(4-methyl-1H-imidazol-1-yl) phenyl)-8'-methyl-6'H, 8'H-spiro [cyclopropane-1, 7'-pyrimido [5, 4-b] [1, 4] oxazin]-2'-amine (100 mg, 56%) as an off-white solid. $^1$H-NMR (DMSO-$d_6$, 500 MHz): δ 9.09 (s, 1H), 7.80 (s, 1H), 7.61 (d, 2H), 7.29 (d, 1H), 7.14 (d, 1H), 6.99 (s, 1H), 3.93 (s, 2H), 3.79 (s, 3H), 2.90 (s, 3H), 2.14 (s, 3H), 1.23-1.20 (m, 2H), 0.80-0.78 (m, 2H); Mass (ESI): 379.4 [M+1]; LCMS: 379.4 (M+1); (column; X-Select CSH C-18 (50×3.0 mm, 3.5 μm); RT 2.39 min. 0.05% Aq TFA: ACN; 0.80 mL/min); UPLC (column; Acquity UPLC BEH C-18, 2.1×50 mm, 1.7 μm); RT 1.36 min. ACN: 0.025% Aq TFA; 0.5 mL/min; TLC: 5% MeOH/$CH_2Cl_2$ ($R_f$: 0.3).

Example 258

Synthesis of N-(3-fluoro-4-(4-methyl-1H-imidazol-1-yl) phenyl)-8'-methyl-6'H, 8'H-spiro [cyclopropane-1, 7'-pyrimido [5, 4-b] [1, 4] oxazin]-2'-amine

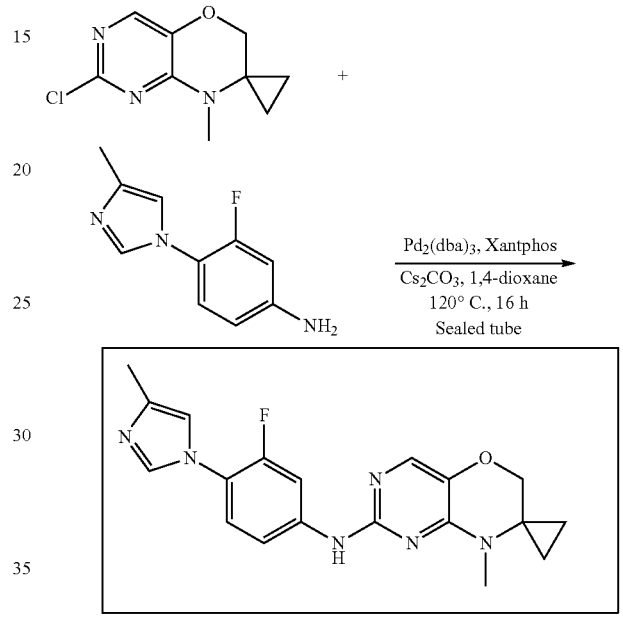

Synthesis of N-(3-fluoro-4-(4-methyl-1H-imidazol-1-yl) phenyl)-8'-methyl-6'H, 8'H-spiro [cyclopropane-1, 7'-pyrimido [5, 4-b] [1, 4] oxazin]-2'-amine To a dry vial was added a suspension of $Pd_2(dba)_3$ (21 mg, 0.02 mmol) and Xantphos (41 mg, 0.07 mmol) in 1, 4-dioxane (0.5 mL) at room temperature. The suspension was degassed with argon, heated to 120° C., and stirred for 3 min. A mixture of 2'-chloro-8'-methyl-6'H, 8'H-spiro [cyclopropane-1, 7'-pyrimido [5, 4-b] [1, 4] oxazine] (100 mg, 0.47 mmol), 3-fluoro-4-(4-methyl-1H-imidazol-1-yl) aniline (181 mg, 0.94 mmol) and cesium carbonate (215 mg, 0.66 mmol) in 1, 4-dioxane (0.5 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with $CH_2Cl_2$ (2×20 mL). The combined organic extracts were dried over sodium sulfate, filtered and concentrated in vacuo. The crude material was purified by column chromatography using 4% MeOH: $CH_2Cl_2$ to obtain 130 mg of compound which was further purified by preparative HPLC (phenominex silica (250×21.2 mm, 10 μm (30 mg loading; n-hexane: $CH_2Cl_2$:MeOH (50:50) to afford N-(3-fluoro-4-(4-methyl-1H-imidazol-1-yl) phenyl)-8'-methyl-6'H, 8'H-spiro [cyclopropane-1, 7'-pyrimido [5, 4-b] [1, 4] oxazin]-2'-amine (90 mg, 52%) as an off-white solid. $^1$H-NMR (DMSO-$d_6$, 400 MHz): δ 9.31 (s, 1H), 7.00-7.97

(m, 1H), 7.74 (s, 1H), 7.65 (s, 1H), 7.50-7.48 (m, 1H), 7.37 (t, 1H), 7.11-7.10 (m, 1H), 3.91 (s, 2H), 2.89 (s, 3H), 2.13 (s, 3H), 1.22-1.20 (m, 2H), 0.78-0.75 (m, 2H); Mass (ESI): 367.3 [M+1]; LCMS: 367.4 (M+1); (column; X-Select CSH C-18 (50×3.0 mm, 3.5 μm); RT 4.01 min. 5 mM Aq NH$_4$OAc: ACN; 0.80 mL/min); UPLC (column; Acquity UPLC BEH C-18, 2.1×50 mm, 1.7 μm); RT 1.32 min. ACN: 0.025% Aq TFA; 0.5 mL/min; TLC: 5% MeOH/CH$_2$Cl$_2$ (R$_f$: 0.3).

Example 259

Synthesis of N-(5-methoxy-6-(4-methyl-1H-imidazol-1-yl) pyridin-3-yl)-8'-methyl-6'H, 8'H-spiro [cyclopentane-1, 7'-pyrimido [5, 4-b] [1, 4] oxazin]-2'-amine

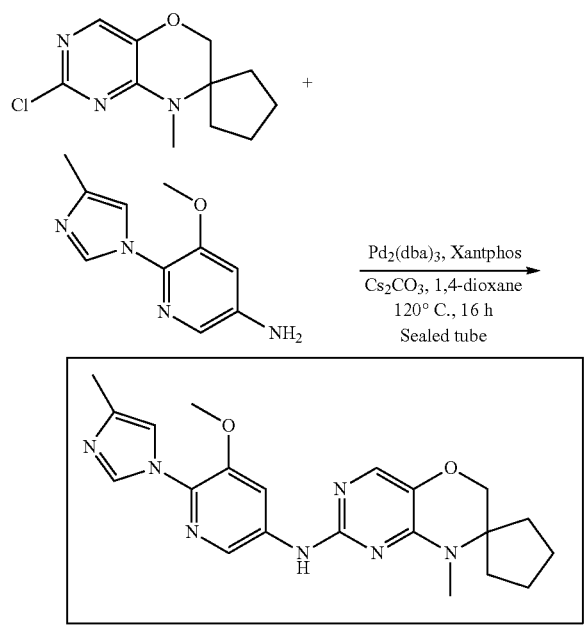

Synthesis of N-(5-methoxy-6-(4-methyl-1H-imidazol-1-yl) pyridin-3-yl)-8'-methyl-6'H, 8'H-spiro [cyclopentane-1, 7'-pyrimido [5, 4-b] [1, 4] oxazin]-2'-amine To a dry vial was added a suspension of Pd$_2$(dba)$_3$ (23 mg, 0.02 mmol) and Xantphos (43 mg, 0.07 mmol) in 1, 4-dioxane (1 mL) at room temperature. The suspension was degassed with argon, heated to 120° C., and stirred for 3 min. A mixture of 2'-chloro-8'-methyl-6'H, 8'H-spiro [cyclopentane-1, 7'-pyrimido [5, 4-b] [1, 4] oxazine] (120 mg, 0.50 mmol), 5-methoxy-6-(4-methyl-1H-imidazol-1-yl) pyridin-3-amine (113 mg, 0.55 mmol) and cesium carbonate (228 mg, 0.70 mmol) in 1, 4-dioxane (1 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with CH$_2$Cl$_2$ (2×20 mL). The combined organic extracts were dried over sodium sulfate, filtered and concentrated in vacuo. The crude material was purified by column chromatography using 4% MeOH: CH$_2$Cl$_2$ to afford N-(5-methoxy-6-(4-methyl-1H-imidazol-1-yl) pyridin-3-yl)-8'-methyl-6'H,8'H-spiro [cyclopentane-1, 7'-pyrimido [5, 4-b] [1, 4] oxazin]-2'-amine (70 mg, 34%) as an off-white solid. $^1$H-NMR (CD$_3$OD, 500 MHz): δ 8.30 (s, 1H), 8.29 (s, 1H), 8.11 (s, 1H), 7.51 (s, 1H), 7.40 (s, 1H), 3.98 (s, 3H), 3.88 (s, 2H), 3.18 (s, 3H), 2.22 (s, 3H), 1.96-1.81 (m, 4H), 1.80-1.67 (m, 4H); Mass (ESI): 408.4 [M+1]; LCMS: 408.1 (M+1); (column; X-Select CSH C-18 (50×3.0 mm, 3.5 μm); RT 2.22 min. 0.05% Aq TFA: ACN; 0.80 mL/min); UPLC (column; Acquity BEH C-18, 50×2.1 mm, 1.7 μm); RT 1.51 min. ACN: 0.025% Aq TFA; 0.5 mL/min; TLC: 5% MeOH/ CH$_2$Cl$_2$ (R$_f$: 0.2).

Example 260

Synthesis of N-(5-methoxy-6-(4-methyl-1H-imidazol-1-yl) pyridin-3-yl)-8'-methyl-6'H, 8'H-spiro [cyclopropane-1, 7'-pyrimido [5, 4-b] [1, 4] oxazin]-2'-amine

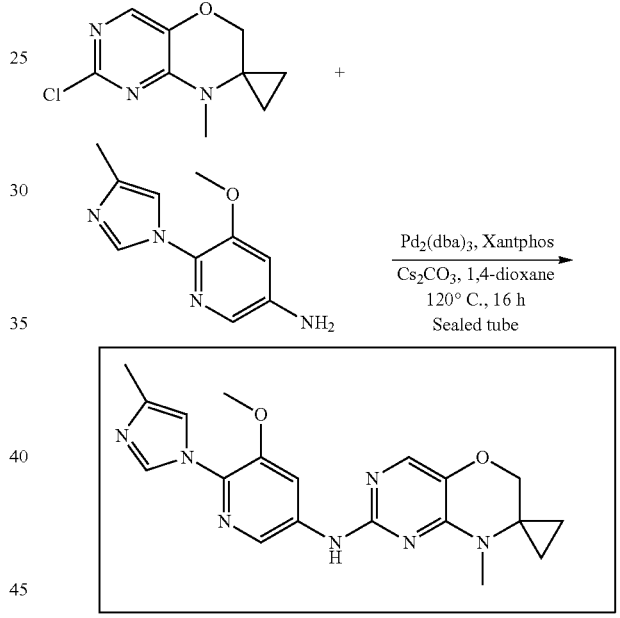

Synthesis of N-(5-methoxy-6-(4-methyl-1H-imidazol-1-yl) pyridin-3-yl)-8'-methyl-6'H, 8'H-spiro [cyclopropane-1, 7'-pyrimido [5, 4-b] [1, 4] oxazin]-2'-amine To a dry vial was added a suspension of Pd$_2$(dba)$_3$ (30 mg, 0.03 mmol) and Xantphos (57 mg, 0.09 mmol) in 1, 4-dioxane (1 mL) at room temperature. The suspension was degassed with argon, heated to 120° C., and stirred for 3 min. A mixture of 2'-chloro-8'-methyl-6'H, 8'H-spiro [cyclopropane-1, 7'-pyrimido [5, 4-b] [1, 4] oxazine] (140 mg, 0.66 mmol), 5-methoxy-6-(4-methyl-1H-imidazol-1-yl) pyridin-3-amine (149 mg, 0.72 mmol) and cesium carbonate (300 mg, 0.92 mmol) in 1, 4-dioxane (1 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with CH$_2$Cl$_2$ (2×20 mL). The combined organic extracts were dried over sodium sulfate, filtered and concentrated in vacuo. The crude material was purified by column chromatography using 4% MeOH: $CH_2Cl_2$ to obtain 95 mg of compound which was washed with acetonitrile (2 mL), ether (2 mL) and n-pentane (2 mL) to afford N-(5-methoxy-6-(4-methyl-1H-imidazol-1-yl) pyridin-3-yl)-8'-methyl-6'H, 8'H-spiro [cyclopropane-1, 7'-pyrimido [5, 4-b] [1, 4] oxazin]-2'-amine (70 mg, 28%) as an off-white solid. $^1$H-NMR (CD$_3$OD, 500 MHz): δ 8.23 (s, 2H), 7.11 (s, 1H), 7.59 (s, 1H), 7.39 (s, 1H), 3.99 (s, 3H), 3.98 (s, 2H), 2.99 (s, 3H), 2.22 (s, 3H), 1.28-1.25 (m, 2H), 0.83-0.80 (m, 2H); Mass (ESI): 380.3 [M+1]; LCMS: 380.1 (M+1); (column; X-Select CSH C-18 (50×3.0 mm, 3.5 μm); RT 1.99 min. 0.05% Aq TFA: ACN; 0.80 mL/min); UPLC (column; Acquity BEH C-18, 2.1×50 mm, 1.7 μm); RT 1.34 min. ACN: 0.025% Aq TFA; 0.5 mL/min; TLC: 5% MeOH/$CH_2Cl_2$ ($R_f$: 0.2).

Example 261

Synthesis of N-(5-methoxy-6-(4-methyl-1H-imidazol-1-yl) pyridin-3-yl)-7, 7, 8-trimethyl-7, 8-dihydro-6H-pyrimido [5, 4-b] [1, 4] oxazin-2-amine

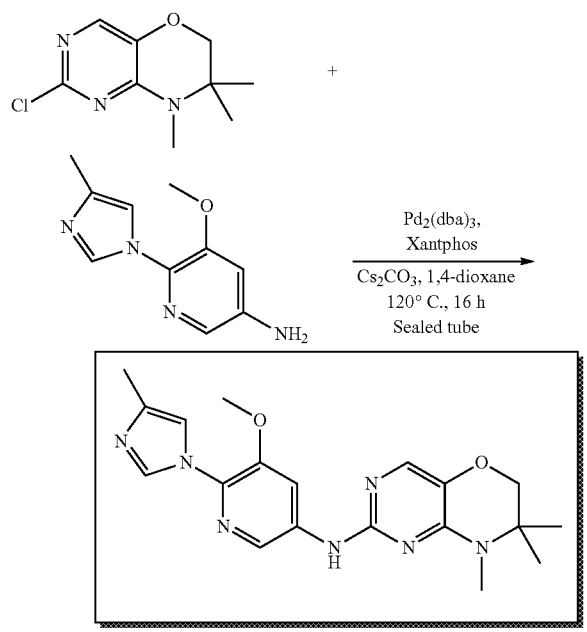

Synthesis of N-(5-methoxy-6-(4-methyl-1H-imidazol-1-yl) pyridin-3-yl)-7, 7, 8-trimethyl-7, 8-dihydro-6H-pyrimido [5, 4-b] [1, 4] oxazin-2-amine To a dry vial was added a suspension of $Pd_2(dba)_3$ (26 mg, 0.03 mmol) and Xantphos (49 mg, 0.08 mmol) in 1, 4-dioxane (0.6 mL) at room temperature. The suspension was degassed with argon, heated to 120° C., and stirred for 3 min. A mixture of (2-chloro-7, 8-dimethyl-7, 8-dihydro-6H-pyrimido [5, 4-b] [1, 4] oxazin-7-yl) methylium (120 mg, 0.56 mmol), 5-methoxy-6-(4-methyl-1H-imidazol-1-yl) pyridin-3-amine (230 mg, 1.12 mmol), cesium carbonate (256 mg, 0.78 mmol) in 1, 4-dioxane (0.6 mL) was degassed and the catalyst premixture was added. The resultant mixture was stirred at 120° C. for 16 h in a sealed tube. After consumption of the starting material (monitored by TLC and LCMS), the reaction mixture was diluted with water (50 mL) and extracted with $CH_2Cl_2$ (2×50 mL). The combined organic extracts were dried over sodium sulfate, filtered and concentrated in vacuo. The crude material was purified by column chromatography using 50% EtOAc:hexanes to afford N-(5-methoxy-6-(4-methyl-1H-imidazol-1-yl) pyridin-3-yl)-7, 7, 8-trimethyl-7, 8-dihydro-6H-pyrimido [5, 4-b] [1, 4] oxazin-2-amine (80 mg, 37%) as an off-white solid. $^1$H-NMR (CD$_3$OD, 400 MHz): δ 8.29-8.27 (m, 2H), 8.10 (s, 1H), 7.52 (s, 1H), 7.38 (s, 1H), 3.94 (s, 3H), 3.86 (s, 2H), 3.15 (s, 3H), 2.21 (s, 3H), 1.31 (s, 6H); Mass (ESI): 382.4 [M+1]; LCMS: 382.4 (M+1); (column; X-Select CSH C-18 (50×3.0 mm, 3.5 μm); RT 2.45 min 0.05% Aq TFA: ACN; 0.80 mL/min); HPLC (column; Eclipse XDB C18, 150×4.6 mm, 5.0 μm); RT 9.61 min. ACN: 5 mM Aq NH$_4$OAc; 1.0 mL/min; TLC: 5% MeOH/$CH_2Cl_2$ ($R_f$: 0.3).

Example 262

Synthesis of 7, 7, 8-trimethyl-N-(5-(4-methyl-1H-imidazol-1-yl) pyridin-2-yl)-7, 8-dihydro-6H-pyrimido [5, 4-b] [1, 4] oxazin-2-amine

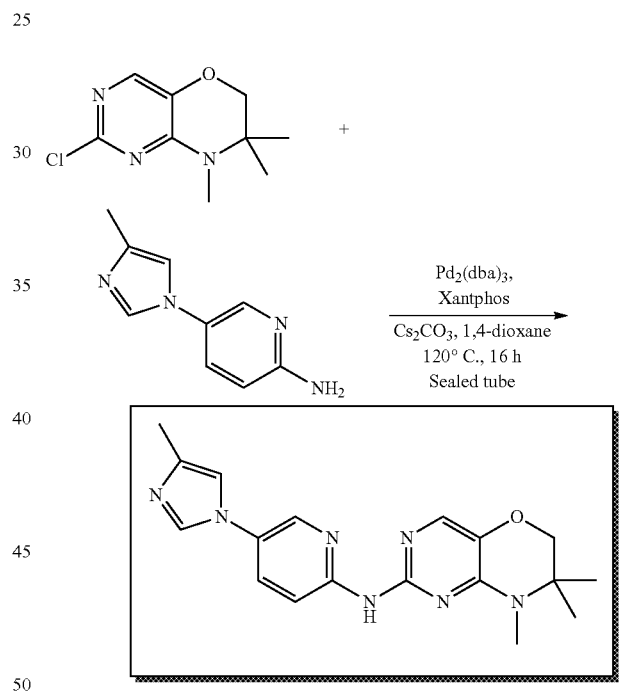

Synthesis of 7, 7, 8-trimethyl-N-(5-(4-methyl-1H-imidazol-1-yl) pyridin-2-yl)-7, 8-dihydro-6H-pyrimido [5, 4-b] [1, 4] oxazin-2-amine To a dry vial was added a suspension of $Pd_2(dba)_3$ (26 mg, 0.03 mmol) and Xantphos (49 mg, 0.08 mmol) in 1, 4-dioxane (0.6 mL) at room temperature. The suspension was degassed with argon, heated to 120° C., and stirred for 3 min. A mixture of 2-chloro-7, 7, 8-trimethyl-7, 8-dihydro-6H-pyrimido [5, 4-b] [1, 4] oxazine (120 mg, 0.56 mmol), 5-(4-methyl-1H-imidazol-1-yl) pyridin-2-amine (196 mg, 1.12 mmol), cesium carbonate (256 mg, 0.78 mmol) in 1, 4-dioxane (0.6 mL) was degassed and the catalyst premixture was added. The resultant mixture was stirred at 120° C. for 16 h in a sealed tube. After consumption of the starting material (monitored by TLC and LCMS), the reaction mixture was diluted with water (50 mL) and extracted with $CH_2Cl_2$ (2×50 mL). The combined organic extracts were dried over sodium sulfate, filtered and concentrated in vacuo. The crude material was purified by column chromatography using 50% EtOAc:hexanes to afford 7, 7, 8-trimethyl-N-(5-(4-methyl-1H-imidazol-1-yl) pyridin-2-yl)-7, 8-dihydro-6H-pyrimido [5, 4-b] [1, 4] oxazin-2-amine (70 mg, 35%) as an off-white solid. $^1$H-NMR ($CD_3OD$, 400 MHz): δ 8.40-8.35 (m, 2H), 7.92 (s, 1H), 7.85 (d, 1H), 7.56 (s, 1H), 7.23-7.21 (m, 1H), 3.88 (s, 2H), 3.14 (s, 3H), 2.24 (s, 3H), 1.33 (s, 6H); Mass (ESI): 352.4 [M+1]; LCMS: 352.4 (M+1); (column; X-Select CSH C-18 (50×3.0 mm, 3.5 μm); RT 3.68 min 5 mM Aq $NH_4OAc$: ACN; 0.80 mL/min); UPLC (column; Acquity BEH C18, 50×2.1 mm, 1.7 μm); RT 1.27 min. ACN: 0.025% Aq TFA; 0.5 mL/min; TLC: 5% MeOH/$CH_2Cl_2$ ($R_f$; 0.3).

Example 263

Synthesis of 8'-methyl-N-(5-(4-methyl-1H-imidazol-1-yl) pyridin-2-yl)-6'H, 8'H-spiro [cyclopentane-1, 7'-pyrimido [5, 4-b] [1, 4] oxazin]-2'-amine

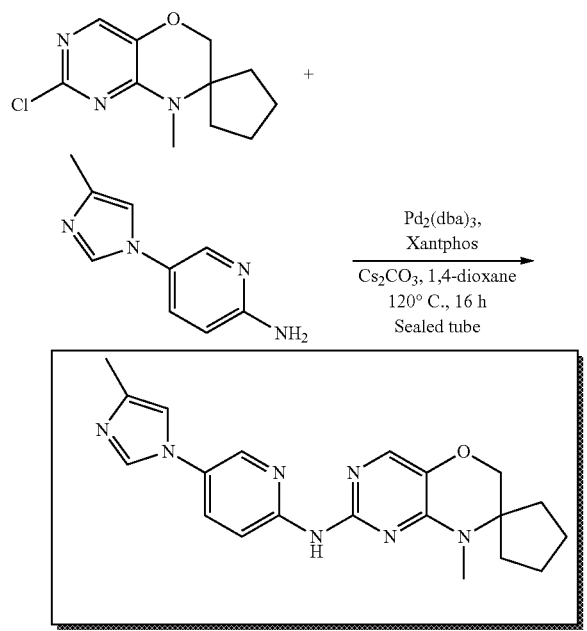

Synthesis of 8'-methyl-N-(5-(4-methyl-1H-imidazol-1-yl) pyridin-2-yl)-6'H, 8'H-spiro [cyclopentane-1, 7'-pyrimido [5, 4-b] [1, 4] oxazin]-2'-amine To a dry vial was added a suspension of $Pd_2(dba)_3$ (19 mg, 0.02 mmol) and Xantphos (36 mg, 0.63 mmol) in 1, 4-dioxane (0.5 mL) at room temperature. The suspension was degassed with argon, heated to 120° C., and stirred for 3 min. A mixture of 2'-chloro-8'-methyl-6'H, 8'H-spiro [cyclopentane-1, 7'-pyrimido [5, 4-b] [1, 4] oxazine] (100 mg, 0.42 mmol), 5-(4-methyl-1H-imidazol-1-yl) pyridin-2-amine (146 mg, 0.84 mmol) and cesium carbonate (191 mg, 0.58 mmol) in 1, 4-dioxane (0.5 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with $CH_2Cl_2$ (2×20 mL). The combined organic extracts were dried over sodium sulfate, filtered and concentrated in vacuo. The crude material was purified by column chromatography using 3% MeOH: $CH_2Cl_2$ to afford 8'-methyl-N-(5-(4-methyl-1H-imidazol-1-yl) pyridin-2-yl)-6'H, 8'H-spiro [cyclopentane-1, 7'-pyrimido [5, 4-b] [1, 4] oxazin]-2'-amine (80 mg, 51%) as an off-white solid.[1195] $^1$H NMR ($CD_3OD$, 400 MHz): δ 8.41 (d, 1H), 8.38-8.36 (m, 1H), 7.94 (s, 1H), 7.86 (dd, 1H), 7.55 (s, 1H), 7.23 (s, 1H), 3.87 (s, 2H), 3.15 (s, 3H), 2.26 (s, 3H), 1.93-1.85 (m, 4H), 1.79-1.72 (m, 4H); Mass (ESI): 378.4 [M+1]; LCMS: 378 (M+1); (column; X-Select CSH C-18 (50×3.0 mm, 3.5 μm); RT 2.10 min. 0.05% Aq TFA: ACN; 0.80 mL/min); UPLC (column; Acquity BEH C-18, 50×2.1 mm, 1.7 μm); RT 1.46 min. ACN: 0.025% Aq TFA; 0.5 mL/min; TLC: 5% MeOH/$CH_2Cl_2$ ($R_f$; 0.5).

Example 264

Synthesis of N-(3-methoxy-4-(1-methyl-1H-pyrazol-4-yl) phenyl)-8'-methyl-6'H, 8'H-spiro [cyclopentane-1, 7'-pyrimido [5, 4-b] [1, 4] oxazin]-2'-amine

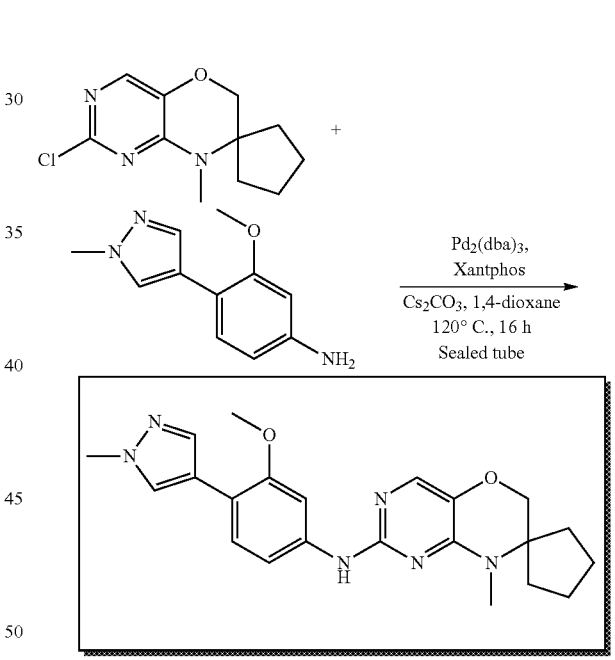

Synthesis of N-(3-methoxy-4-(1-methyl-1H-pyrazol-4-yl) phenyl)-8'-methyl-6'H, 8'H-spiro [cyclopentane-1, 7'-pyrimido [5, 4-b] [1, 4] oxazin]-2'-amine To a dry vial was added a suspension of $Pd_2(dba)_3$ (19 mg, 0.02 mmol) and Xantphos (36 mg, 0.63 mmol) in 1, 4-dioxane (0.5 mL) at room temperature. The suspension was degassed with argon, heated to 120° C., and stirred for 3 min. A mixture of 2'-chloro-8'-methyl-6'H, 8'H-spiro [cyclopentane-1, 7'-pyrimido [5, 4-b] [1, 4] oxazine] (100 mg, 0.42 mmol), 3-methoxy-4-(1-methyl-1H-pyrazol-4-yl) aniline (170 mg, 0.84 mmol) and cesium carbonate (191 mg, 0.58 mmol) in 1, 4-dioxane (0.5 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with CH₂Cl₂ (2×20 mL). The combined organic extracts were dried over sodium sulfate, filtered and concentrated in vacuo. The crude material was purified by column chromatography using 3% MeOH: CH₂Cl₂ to afford N-(3-methoxy-4-(1-methyl-1H-pyrazol-4-yl) phenyl)-8'-methyl-6'H, 8'H-spiro [cyclopentane-1, 7'-pyrimido [5, 4-b] [1, 4] oxazin]-2'-amine (80 mg, 47%) as an off-white solid. ¹H NMR (CD₃OD, 400 MHz): δ 7.91 (s, 1H), 7.80 (s, 1H), 7.56-7.54 (m, 1H), 7.45 (s, 1H), 7.39 (d, 1H), 7.08 (d, 1H), 3.90 (s, 3H), 3.89 (s, 3H), 3.83 (s, 2H), 3.14 (s, 3H), 1.91-1.80 (m, 4H), 1.74-1.70 (m, 4H); Mass (ESI): 407.5 [M+1]; LCMS: 407.1 (M+1); (column; X-Select CSH C-18 (50×3.0 mm, 3.5 μm); RT 2.79 min. 0.05% Aq TFA: ACN; 0.80 mL/min); UPLC (column; Acquity BEH C-18, 50×2.1 mm, 1.7 μm); RT 1.89 min. ACN: 0.025% Aq TFA; 0.5 mL/min; TLC: 5% MeOH/CH₂Cl₂ (R$_f$: 0.5).

mmol) in 1, 4-dioxane (0.5 mL) was degassed and the catalyst premixture was added. The resultant mixture was stirred at 130° C. for 16 h in a sealed tube. After consumption of the starting material (monitored by TLC and LCMS), the reaction mixture was diluted with water (50 mL) and extracted with CH₂Cl₂ (2×50 mL). The combined organic extracts were dried over sodium sulfate, filtered and concentrated in vacuo. The crude material was washed with methanol (2×5 mL) to afford 8'-methyl-N-(5-(4-methyl-1H-imidazol-1-yl) pyridin-2-yl)-6'H, 8'H-spiro [cyclopropane-1, 7'-pyrimido [5, 4-b] [1, 4] oxazin]-2'-amine (50 mg, 30%) as an off-white solid. ¹H-NMR (CD₃OD, 500 MHz): δ 8.40-8.38 (m, 2H), 7.98 (s, 1H), 7.90-7.87 (m, 1H), 7.60 (s, 1H), 7.22 (s, 1H), 3.97 (s, 2H), 2.99 (s, 3H), 2.28 (s, 3H), 1.30-1.28 (m, 2H), 0.85-0.80 (m, 2H); Mass (ESI): 350.3 [M+1]; LCMS: 349.9 (M+1); (column; X-Select CSH C-18 (50×3.0 mm, 3.5 μm); RT 1.87 min 0.05% Aq TFA: ACN; 0.80 mL/min); UPLC (column; Acquity BEH C-18, 50×2.1 mm, 1.7 μm); RT 1.22 min. ACN: 0.025% Aq TFA; 0.5 mL/min; TLC: 50% EtOAc:hexane (R$_f$: 0.3).

Example 265

Synthesis of 8'-methyl-N-(5-(4-methyl-1H-imidazol-1-yl) pyridin-2-yl)-6'H, 8'H-spiro [cyclopropane-1, 7'-pyrimido [5, 4-b] [1, 4] oxazin]-2'-amine Example 266

Synthesis of N-(5-methoxy-6-(1-methyl-1H-pyrazol-4-yl) pyridin-3-yl)-8'-methyl-6'H, 8'H-spiro [cyclopentane-1, 7'-pyrimido [5, 4-b] [1, 4] oxazin]-2'-amine

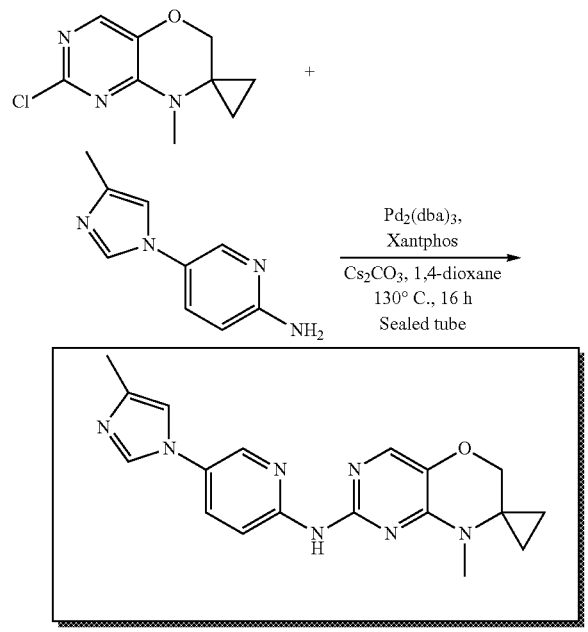

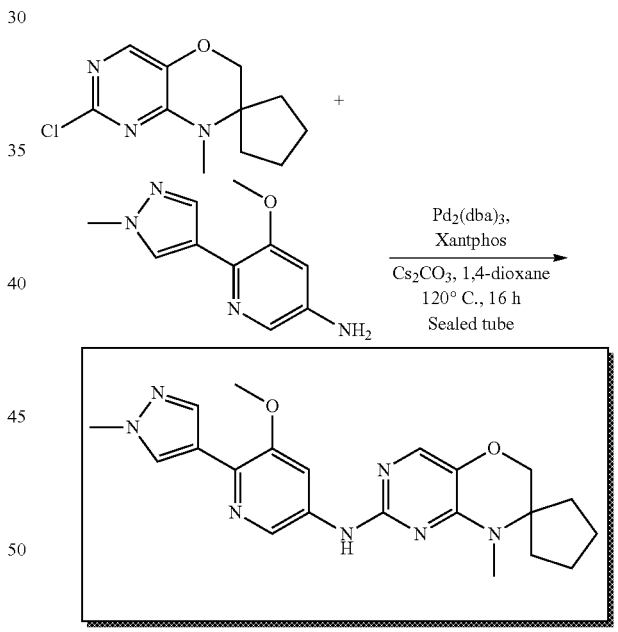

Synthesis of 8'-methyl-N-(5-(4-methyl-1H-imidazol-1-yl) pyridin-2-yl)-6'H, 8'H-spiro [cyclopropane-1, 7'-pyrimido [5, 4-b] [1, 4] oxazin]-2'-amine To a dry vial was added a suspension of Pd₂(dba)₃ (22 mg, 0.02 mmol) and Xantphos (41 mg, 0.07 mmol) in 1, 4-dioxane (0.5 mL) at room temperature. The suspension was degassed with argon, heated to 120° C., and stirred for 3 min. A mixture of 2'-chloro-8'-methyl-6'H,8'H-spiro [cyclopropane-1,7'-pyrimido [5, 4-b] [1, 4] oxazine] (100 mg, 0.47 mmol), 5-(4-methyl-1H-imidazol-1-yl) pyridin-2-amine (164 mg, 0.94 mmol) and cesium carbonate (215 mg, 0.66

Synthesis of N-(5-methoxy-6-(1-methyl-1H-pyrazol-4-yl) pyridin-3-yl)-8'-methyl-6'H, 8'H-spiro [cyclopentane-1, 7'-pyrimido [5, 4-b] [1, 4] oxazin]-2'-amine To a dry vial was added a suspension of Pd₂(dba)₃ (19 mg, 0.02 mmol) and Xantphos (36 mg, 0.06 mmol) in 1, 4-dioxane (0.5 mL) at room temperature. The suspension was degassed with argon, heated to 120° C., and stirred for 3 min. A mixture of 2'-chloro-8'-methyl-6'H, 8'H-spiro [cyclopentane-1, 7'-pyrimido [5, 4-b] [1, 4] oxazine] (100 mg, 0.42 mmol), 5-methoxy-6-(1-methyl-1H-pyrazol-4-yl) pyridin-3- amine (171 mg, 0.84 mmol) and cesium carbonate (191 mg, 0.58 mmol) in 1, 4-dioxane (0.5 mL) was degassed and the catalyst premixture was added. The resultant mixture was stirred at 120° C. for 16 h in a sealed tube. After consumption of the starting material (monitored by TLC and LCMS), the reaction mixture was diluted with water (50 mL) and extracted with 10% MeOH: $CH_2Cl_2$ (2×50 mL). The combined organic extracts were dried over sodium sulfate, filtered and concentrated in vacuo. The crude material was washed with methanol (2×5 mL) to afford N-(5-methoxy-6-(1-methyl-1H-pyrazol-4-yl) pyridin-3-yl)-8'-methyl-6'H, 8'H-spiro [cyclopentane-1, 7'-pyrimido [5, 4-b] [1, 4] oxazin]-2'-amine (20 mg, 12%) as an off-white solid. $^1$H NMR (CD$_3$OD, 400 MHz): δ 8.35-8.33 (m, 1H), 8.10 (s, 1H), 8.07-8.05 (m, 1H), 8.04 (s, 1H), 7.51 (s, 1H), 3.98 (s, 3H), 3.93 (s, 3H), 3.85 (s, 2H), 3.16 (s, 3H), 1.91-1.80 (m, 4H), 1.79-1.70 (m, 4H); Mass (ESI): 408.4 [M+1]; LCMS: 408.1 (M+1); (column; X-Select CSH C-18 (50×3.0 mm, 3.5 μm); RT 2.40 min. 0.05% Aq TFA: ACN; 0.80 mL/min); UPLC (column; Acquity BEH C-18, 50×2.1 mm, 1.7 μm); RT 1.66 min. ACN: 0.025% Aq TFA; 0.5 mL/min; TLC: 10% MeOH/CH$_2$Cl$_2$ (R$_f$: 0.3).

Example 267

Synthesis of N-(3-methoxy-4-(1-methyl-1H-pyrazol-4-yl phenyl)-7, 7, 8-trimethyl-7, 8-dihydro-6H-pyrimido [5, 4-b] [1, 4] oxazin-2-amine

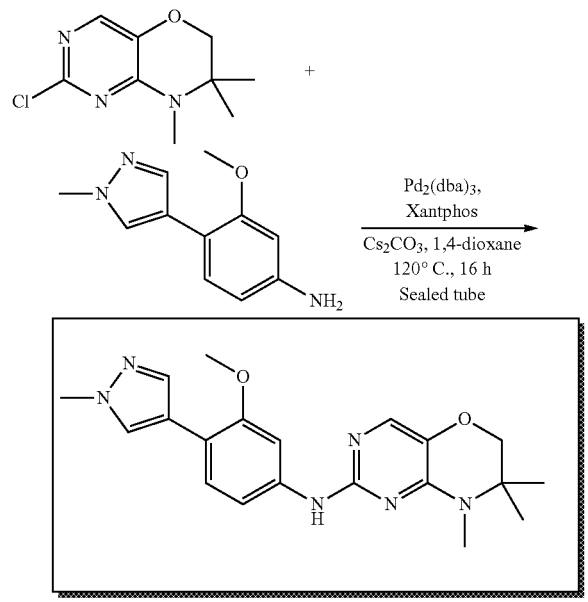

Synthesis of N-(3-methoxy-4-(1-methyl-1H-pyrazol-4-yl phenyl)-7, 7, 8-trimethyl-7, 8-dihydro-6H-pyrimido [5, 4-b] [1, 4] oxazin-2-amine To a dry vial was added a suspension of Pd$_2$(dba)$_3$ (25 mg, 0.28 mmol) and Xantphos (48 mg, 0.39 mmol) in 1, 4-dioxane (0.6 mL) at room temperature. The suspension was degassed with argon, heated to 120° C., and stirred for 3 min. A mixture of 2-chloro-7, 7, 8-trimethyl-7, 8-dihydro-6H-pyrimido [5, 4-b] [1, 4] oxazine (120 mg, 0.56 mmol), 3-methoxy-4-(1-methyl-1H-pyrazol-4-yl) aniline (80 mg, 0.39 mmol) and cesium carbonate (256 mg, 0.78 mmol) in 1, 4-dioxane (1.25 mL) was degassed and the catalyst premixture was added. The resultant mixture was stirred at 120° C. for 16 h in a sealed tube. After consumption of the starting material (monitored by TLC and LCMS), the volatile components were concentrated in vacuo. The crude material was purified by column chromatography using 3% MeOH: CH$_2$Cl$_2$ to afford N-(3-methoxy-4-(1-methyl-1H-pyrazol-4-yl phenyl)-7, 7, 8-trimethyl-7, 8-dihydro-6H-pyrimido [5, 4-b] [1, 4] oxazin-2-amine (180 mg, 46%) as an off-white solid. $^1$H-NMR (DMSO-d$_6$, 500 MHz): δ 8.86 (s, 1H), 7.96 (s, 1H), 7.77 (s, 1H), 7.68 (s, 1H), 7.57 (s, 1H), 7.38 (d, 1H), 7.21 (d, 1H), 3.83 (s, 8H), 3.10 (s, 3H), 1.22 (s, 6H); Mass (ESI): 381.5 [M+1]; LCMS: 381 (M+1); (column; X-Select CSH C-18 (50×3.0 mm, 3.5 μm); RT 2.57 min 0.05% Aq TFA: ACN; 0.80 mL/min); UPLC (column; Acquity BEH C-18 50×2.1 mm, 1.7 μm); RT 1.73 min. ACN: 0.025% Aq TFA; 0.5 mL/min; TLC: 5% MeOH/ CH$_2$Cl$_2$ (R$_f$: 0.3).

Example 268

Synthesis of N-(5-methoxy-6-(1-methyl-1H-pyrazol-4-yl) pyridin-3-yl)-8'-methyl-6'H, 8'H-spiro [cyclopropane-1, 7'-pyrimido [5, 4-b] [1, 4] oxazin]-2'-amine

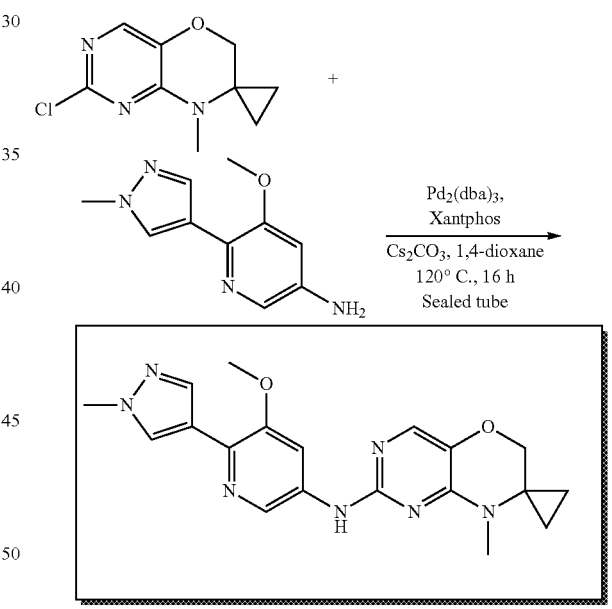

Synthesis of N-(5-methoxy-6-(1-methyl-1H-pyrazol-4-yl) pyridin-3-yl)-8'-methyl-6'H, 8'H-spiro [cyclopropane-1, 7'-pyrimido [5, 4-b] [1, 4] oxazin]-2'-amine To a dry vial was added a suspension of Pd$_2$(dba)$_3$ (22 mg, 0.02 mmol) and Xantphos (41 mg, 0.07 mmol) in 1, 4-dioxane (0.5 mL) at room temperature. The suspension was degassed with argon, heated to 120° C., and stirred for 3 min. A mixture of 2'-chloro-8'-methyl-6'H, 8'H-spiro [cyclopropane-1, 7'-pyrimido [5, 4-b] [1, 4] oxazine] (100 mg, 0.47 mmol), 5-methoxy-6-(1-methyl-1H-pyrazol-4-yl) pyridin-3-amine (193 mg, 0.94 mmol) and cesium carbonate (216 mg, 0.66 mmol) in 1, 4-dioxane (0.5 mL) was degassed and the catalyst premixture was added. The resultant mixture was stirred at 120° C. for 16 h in a sealed tube. After consumption of the starting material (monitored by TLC and LCMS), the volatile components were evaporated in vacuo. The residue was diluted with water (20 mL) and extracted with EtOAc (2×20 mL). The combined organic extracts were dried over sodium sulfate, filtered and concentrated in vacuo. The crude material was purified by preparative HPLC (Ascentis C18 (250×21.2 mm: 5μ; (50 mg loading; $CH_3CN$: 0.05% TFA (0.1/90, 2/85, 15/70, 25/20, 30/10, 35/10) to afford N-(5-methoxy-6-(1-methyl-1H-pyrazol-4-yl) pyridin-3-yl)-8'-methyl-6'H, 8'H-spiro [cyclopropane-1, 7'-pyrimido [5, 4-b] [1, 4] oxazin]-2'-amine (55 mg, 31%) as an off-white solid. $^1$H-NMR ($CD_3OD$, 400 MHz): δ 8.31 (s, 1H), 8.10 (s, 1H), 8.01 (s, 2H), 7.51 (s, 1H), 3.99 (s, 3H), 3.92 (s, 5H), 3.00 (s, 3H), 1.27-1.21 (m, 2H), 0.82-0.79 (m, 2H); Mass (ESI): 380.4 [M+1]; LCMS: 380.1 (M+1); (column; X-Select CSH C-18 (50×3.0 mm, 3.5 μm); RT 2.13 min 0.05% Aq TFA: ACN; 0.80 mL/min); UPLC (column; Acquity BEH C-18 50×2.1 mm, 1.7 μm); RT 1.46 min. ACN: 0.025% Aq TFA; 0.5 mL/min; TLC: 5% $MeOH/CH_2Cl_2$ ($R_f$: 0.3).

Example 269

Synthesis of N-(3-methoxy-4-(1-methyl-1H-pyrazol-4-yl) phenyl)-8'-methyl-6'H, 8'H-spiro [cyclopropane-1, 7'-pyrimido [5, 4-b] [1, 4] oxazin]-2'-amine

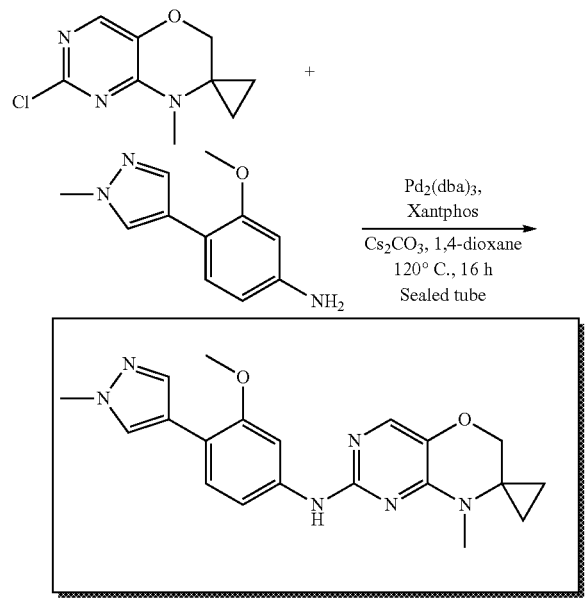

Synthesis of N-(3-methoxy-4-(1-methyl-1H-pyrazol-4-yl) phenyl)-8'-methyl-6'H, 8'H-spiro [cyclopropane-1, 7'-pyrimido [5, 4-b] [1, 4] oxazin]-2'-amine To a dry vial was added a suspension of $Pd_2(dba)_3$ (21 mg, 0.02 mmol) and Xantphos (41 mg, 0.07 mmol) in 1, 4-dioxane (0.5 mL) at room temperature. The suspension was degassed with argon, heated to 120° C., and stirred for 3 min. A mixture of 2'-chloro-8'-methyl-6'H, 8'H-spiro [cyclopropane-1, 7'-pyrimido [5, 4-b] [1, 4] oxazine] (100 mg, 0.47 mmol), 3-methoxy-4-(1-methyl-1H-pyrazol-4-yl) aniline (192 mg, 0.94 mmol), cesium carbonate (215 mg, 0.66 mmol) in 1, 4-dioxane (0.5 mL) was degassed and the catalyst premixture was added. The resultant mixture was stirred at 120° C. for 16 h in a sealed tube. After consumption of the starting material (monitored by TLC and LCMS), the reaction mixture was filtered, filtrate was concentrated in vacuo. The crude material was purified by column chromatography using 2% $MeOH$: $CH_2Cl_2$ to afford N-(3-methoxy-4-(1-methyl-1H-pyrazol-4-yl) phenyl)-8'-methyl-6'H, 8'H-spiro [cyclopropane-1, 7'-pyrimido [5, 4-b] [1, 4] oxazin]-2'-amine (40 mg, 24%) as an off-white solid. $^1$H NMR ($CD_3OD$, 400 MHz): δ 7.92 (s, 1H), 7.81 (s, 1H), 7.52 (s, 2H), 7.40 (d, 1H), 7.10 (dd, 1H), 3.93-3.88 (m, 8H), 2.99 (s, 3H), 1.28-1.19 (m, 2H), 0.84-0.75 (m, 2H); Mass (ESI): 379.4 [M+1]; LCMS: 379 (M+1); (column; X-Select CSH C-18 (50×3.0 mm, 3.5 μm); RT 2.55 min 0.05% Aq TFA: ACN; 0.80 mL/min); UPLC (column; Acquity BEH C18, 50×2.1 mm, 1.7 μm); RT 1.69 min. ACN: 0.025% Aq TFA; 0.5 mL/min; TLC: 5% $MeOH/CH_2Cl_2$ ($R_f$: 0.3).

Example 270

Synthesis of N-(5-methoxy-6-(1-methyl-1H-pyrazol-4-yl) pyridin-3-yl)-7, 7, 8-trimethyl-7, 8-dihydro-6H-pyrimido [5, 4-b] [1, 4] oxazin-2-amine

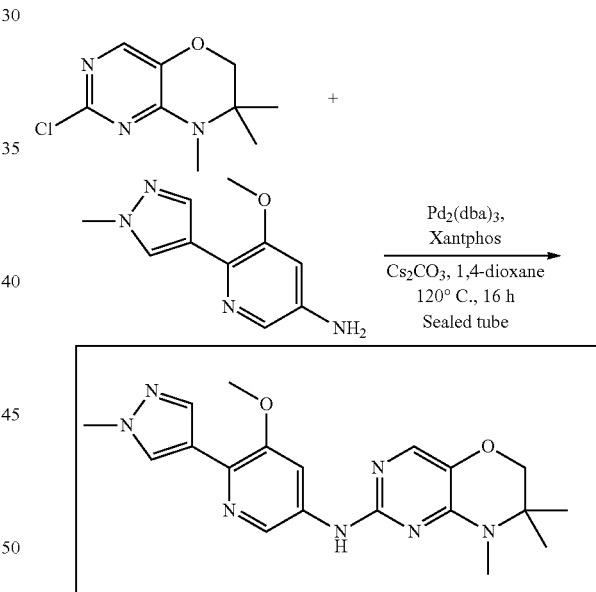

Synthesis of N-(5-methoxy-6-(1-methyl-1H-pyrazol-4-yl) pyridin-3-yl)-7, 7, 8-trimethyl-7, 8-dihydro-6H-pyrimido [5, 4-b] [1, 4] oxazin-2-amine To a dry vial was added a suspension of $Pd_2(dba)_3$ (26 mg, 0.03 mmol) and Xantphos (49 mg, 0.08 mmol) in 1, 4-dioxane (0.6 mL) at room temperature. The suspension was degassed with argon, heated to 120° C., and stirred for 3 min. A mixture of (2-chloro-7, 8-dimethyl-7, 8-dihydro-6H-pyrimido [5, 4-b] [1, 4] oxazin-7-yl) methylium (120 mg, 0.56 mmol), 5-methoxy-6-(1-methyl-1H-pyrazol-4-yl) pyridin-3-amine (230 mg, 1.12 mmol), cesium carbonate (256 mg, 0.78 mmol) in 1, 4-dioxane (0.6 mL) was degassed and the catalyst premixture was added. The resultant mixture was stirred at 120° C. for 16 h in a sealed tube. After consumption of the starting material (monitored by TLC and LCMS), the reaction mixture was diluted with water (50 mL) and extracted with $CH_2Cl_2$ (2×50 mL). The combined organic extracts were dried over sodium sulfate, filtered and concentrated in vacuo. The crude material was purified by column chromatography using 50% EtOAc:hexanes-3% MEOH/$CH_2Cl_2$ to afford N-(5-methoxy-6-(1-methyl-1H-pyrazol-4-yl) pyridin-3-yl)-7, 7, 8-trimethyl-7, 8-dihydro-6H-pyrimido [5, 4-b] [1, 4] oxazin-2-amine (80 mg, 37%) as an off-white solid. $^1$H-NMR (CD$_3$OD, 400 MHz): δ 8.34 (s, 1H), 8.10 (s, 1H), 8.05 (d, 2H), 7.51 (s, 1H), 3.98 (s, 3H), 3.94 (s, 3H), 3.87 (s, 2H), 3.18 (s, 3H), 1.32 (s, 6H); Mass (ESI): 382.4 [M+1]; LCMS: 382.3 (M+1); (column; X-Select CSH C-18 (50×3.0 mm, 3.5 μm); RT 2.63 min 0.05% Aq TFA: ACN; 0.80 mL/min); UPLC (column; Acquity BEH C18, 50×2.1 mm, 1.7 μm); RT 1.48 min. ACN: 0.025% Aq TFA; 0.5 mL/min; TLC: 5% MeOH/$CH_2Cl_2$ ($R_f$: 0.3).

Example 271

Synthesis of N-(3-methoxy-4-(4-methyl-1H-imidazol-1-yl) phenyl)-8'-methyl-6'H, 8'H-spiro [oxetane-3, 7'-pyrimido [5, 4-b] [1, 4] oxazin]-2'-amine

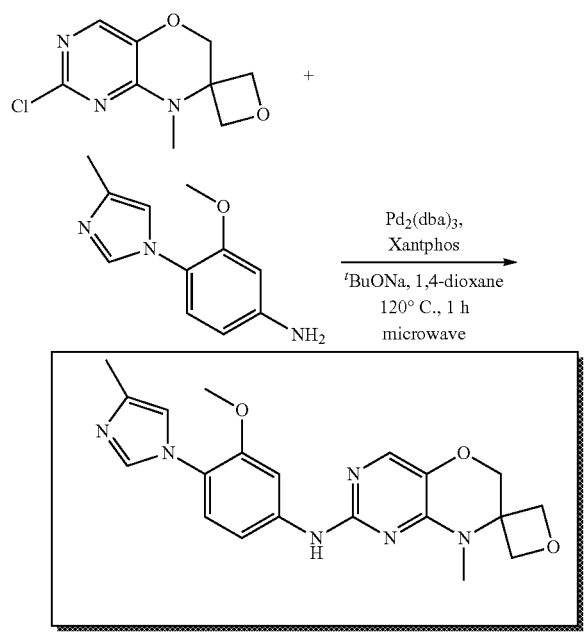

Synthesis of N-(3-methoxy-4-(4-methyl-1H-imidazol-1-yl) phenyl)-8'-methyl-6'H, 8'H-spiro [oxetane-3, 7'-pyrimido [5, 4-b] [1, 4] oxazin]-2'-amine To a dry vial was added a suspension of Pd$_2$(dba)$_3$ (20 mg, 0.02 mmol) and Xantphos (40 mg, 0.06 mmol) in 1, 4-dioxane (1.5 mL) at room temperature. The suspension was degassed with argon, heated to 120° C., and stirred for 3 min. A mixture of 2'-chloro-8'-methyl-6'H, 8'H-spiro [oxetane-3, 7'-pyrimido [5, 4-b] [1, 4] oxazine] (100 mg, 0.44 mmol), 3-methoxy-4-(4-methyl-1H-imidazol-1-yl) aniline (90 mg, 0.44 mmol) and sodium tert-butoxide (130 mg, 1.32 mmol) in 1, 4-dioxane (1.5 mL) was degassed and the catalyst premixture was added. The resultant mixture was stirred at 120° C. for 1 h in a microwave. After consumption of the starting material (monitored by TLC and LCMS), the reaction mixture was diluted with water (25 mL) and extracted with EtOAc (2×25 mL). The combined organic extracts were dried over sodium sulfate, filtered and concentrated in vacuo. The crude material was purified by column chromatography using 2% MeOH: $CH_2Cl_2$ to afford N-(3-methoxy-4-(4-methyl-1H-imidazol-1-yl) phenyl)-8'-methyl-6'H, 8'H-spiro [oxetane-3, 7'-pyrimido [5, 4-b] [1, 4] oxazin]-2'-amine (60 mg, 35%) as an off-white solid.

$^1$H NMR (DMSO-d$_6$, 500 MHz): δ 9.18 (s, 1H), 7.81 (s, 1H), 7.66 (s, 1H), 7.62 (s, 1H), 7.30 (dd, 1H), 7.16 (d, 1H), 7.00 (s, 1H), 4.95 (d, 2H), 4.45 (d, 2H), 4.37 (s, 2H), 3.78 (s, 3H), 3.40 (s, 3H), 2.13 (s, 3H); Mass (ESI): 395.6 [M+1]; LCMS: 395.4 (M+1); (column; X-Select CSH C-18 (50×3.0 mm, 3.5 μm); RT 3.05 min 5 mM Aq NH$_4$OAc: ACN; 0.80 mL/min); UPLC (column; Eclipse XDB C-18 150×4.6 mm, 5.0 μm); RT 8.73 min. ACN: 5 mM Aq NH$_4$OAc; 0.5 mL/min; TLC: 5% MeOH/$CH_2Cl_2$ ($R_f$: 0.2).

Example 272

Synthesis of N-(5-methoxy-6-(4-methyl-1H-imidazol-1-yl) pyridin-3-yl)-8'-methyl-6'H, 8'H-spiro [oxetane-3,7'-pyrimido [5, 4-b] [1,4] oxazin]-2'-amine

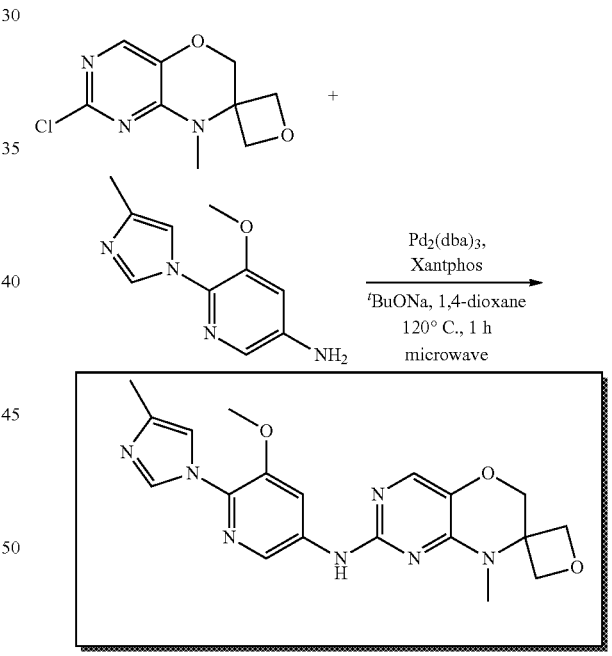

Synthesis of N-(5-methoxy-6-(4-methyl-1H-imidazol-1-yl) pyridin-3-yl)-8'-methyl-6'H, 8'H-spiro [oxetane-3, 7'-pyrimido [5, 4-b] [1, 4] oxazin]-2'-amine To a dry vial was added a suspension of Pd$_2$(dba)$_3$ (24 mg, 0.02 mmol) and Xantphos (48 mg, 0.08 mmol) in 1, 4-dioxane (1.5 mL) at room temperature. The suspension was degassed with argon, heated to 120° C., and stirred for 3 min. A mixture of 2'-chloro-8'-methyl-6'H,8'H-spiro [oxetane-3, 7'-pyrimido [5, 4-b] [1, 4] oxazine] (120 mg, 0.52 mmol), 5-methoxy-6-(4-methyl-1H-imidazol-1-yl) pyridin- 3-amine (108 mg, 0.52 mmol) and sodium tert-butoxide (152 mg, 1.58 mmol) in 1, 4-dioxane (1.5 mL) was degassed and the catalyst premixture was added. The resultant mixture was stirred at 120° C. for 2 h in a microwave. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 2% MeOH: $CH_2Cl_2$ to afford N-(5-methoxy-6-(4-methyl-1H-imidazol-1-yl) pyridin-3-yl)-8'-methyl-6'H, 8'H-spiro [oxetane-3,7'-pyrimido [5, 4-b] [1,4] oxazin]-2'-amine (60 mg, 29%) as an off-white solid. $^1$H NMR (DMSO-$d_6$, 400 MHz): δ 9.40 (s, 1H), 8.33 (s, 1H), 8.27 (s, 1H), 8.09 (br s, 1H), 7.68 (s, 1H), 7.39 (br s, 1H), 4.94 (d, 2H), 4.46 (d, 2H), 4.38 (s, 2H), 3.90 (s, 3H), 3.41 (s, 3H), 2.16 (s, 3H); Mass (ESI): 396.5 [M+1]; LCMS: 396.4 (M+1); (column; X-Select CSH C-18 (50×3.0 mm, 3.5 μm); RT 3.17 min 5 mM Aq $NH_4OAc$: ACN; 0.80 mL/min); HPLC (column; Eclipse XDB C-18 150×4.6 mm, 5.0 μm); RT 8.28 min. ACN: 5 mM Aq $NH_4OAc$; 1.0 mL/min; TLC: 5% MeOH/$CH_2Cl_2$ ($R_f$: 0.2).

Example 273

Synthesis of N-(3-methoxy-4-(4-methyl-1H-imidazol-1-yl) phenyl)-8'-methyl-2, 3, 5, 6-tetrahydro-6'H, 8'H-spiro [pyran-4, 7'-pyrimido [5, 4-b] [1, 4] oxazin]-2'-amine

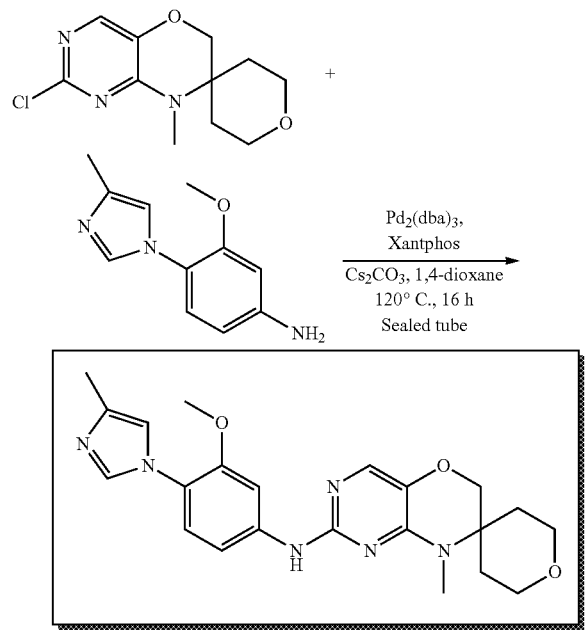

Synthesis of N-(3-methoxy-4-(4-methyl-1H-imidazol-1-yl) phenyl)-8'-methyl-2, 3, 5, 6-tetrahydro-6'H, 8'H-spiro [pyran-4, 7'-pyrimido [5, 4-b] [1,4] oxazin]-2'-amine To a dry vial was added a suspension of $Pd_2(dba)_3$ (7 mg, 0.007 mmol) and Xantphos (13 mg, 0.02 mmol) in 1, 4-dioxane (0.25 mL) at room temperature. The suspension was degassed with argon, heated to 120° C., and stirred for 3 min. A mixture of 2'-chloro-8'-methyl-2, 3, 5, 6-tetrahydro-6'H, 8'H-spiro[pyran-4,7'-pyrimido [5, 4-b] [1,4] oxazine] (40 mg, 0.15 mmol), 3-methoxy-4-(4-methyl-1H-imidazol-1-yl) aniline (63 mg, 0.31 mmol), cesium carbonate (72 mg, 0.21 mmol) in 1, 4-dioxane (0.25 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with $CH_2Cl_2$ (2×20 mL). The combined organic extracts were dried over sodium sulfate, filtered and concentrated in vacuo. The crude material was washed with MeOH (2×5 mL) and n-pentane (2×5 mL) to afford N-(3-methoxy-4-(4-methyl-1H-imidazol-1-yl) phenyl)-8'-methyl-2, 3, 5, 6-tetrahydro-6'H, 8'H-spiro [pyran-4, 7'-pyrimido [5, 4-b] [1, 4] oxazin]-2'-amine (30 mg, 45%) as an off-white solid. $^1$H-NMR (CD$_3$OD, 400 MHz): δ 7.70 (s, 1H), 7.66-7.64 (m, 1H), 7.53 (s, 1H), 7.16-7.14 (m, 2H), 6.95 (s, 1H), 4.23 (s, 2H), 3.93-3.89 (m, 2H), 3.83 (s, 3H), 3.63 (t, 2H), 3.20 (s, 3H), 2.22-2.18 (m, 5H), 1.64-1.60 (m, 2H); Mass (ESI): 423.5 [M+1]; LCMS: 423 (M+1); (column; X-Select CSH C-18 (50×3.0 mm, 3.5 μm); RT 1.95 min 0.05% Aq TFA: ACN; 0.80 mL/min); UPLC (column; Acquity BEH C18, 50×2.1 mm, 1.7 μm); RT 1.30 min. ACN: 0.025% Aq TFA; 0.5 mL/min; TLC: 5% MeOH/$CH_2Cl_2$ ($R_f$: 0.3).

Example 274

Synthesis of N-(5-methoxy-6-(4-methyl-1H-imidazol-1-yl) pyridin-3-yl)-8'-methyl-2, 3, 5, 6-tetrahydro-6'H, 8'H-spiro [pyran-4, 7'-pyrimido [5, 4-b] [1, 4] oxazin]-2'-amine

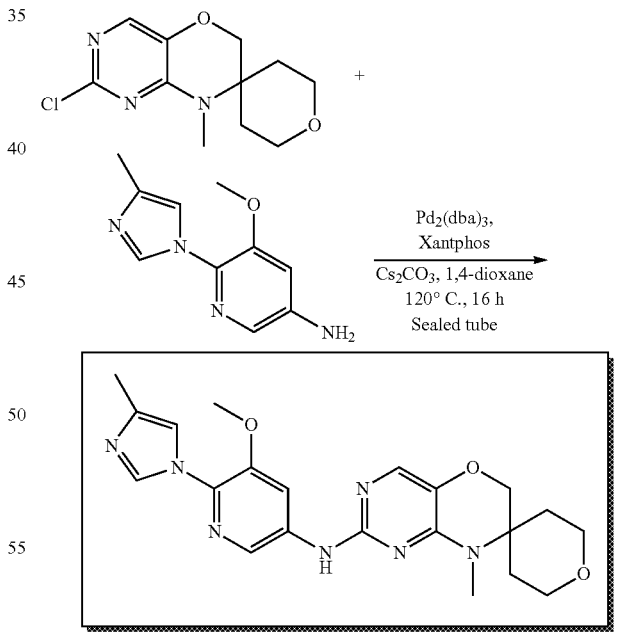

Synthesis of N-(5-methoxy-6-(4-methyl-1H-imidazol-1-yl) pyridin-3-yl)-8'-methyl-2, 3, 5, 6-tetrahydro-6'H, 8'H-spiro [pyran-4, 7'-pyrimido [5, 4-b] [1, 4] oxazin]-2'-amine To a dry vial was added a suspension of $Pd_2(dba)_3$ (12 mg, 0.01 mmol) and Xantphos (23 mg, 0.04 mmol) in 1, 4-dioxane (0.25 mL) at room temperature. The suspension was degassed with argon, heated to 120° C., and stirred for 3 min. A mixture of 2'-chloro-8'-methyl-2, 3, 5, 6-tetrahydro-6'H, 8'H-spiro [pyran-4, 7'-pyrimido [5, 4-b] [1, 4] oxazine] (70 mg, 0.27 mmol), 5-methoxy-6-(4-methyl-1H-imidazol-1-yl) pyridin-3-amine (110 mg, 0.54 mmol), cesium carbonate (122 mg, 0.37 mmol) in 1, 4-dioxane (0.25 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with 5% MeOH: $CH_2Cl_2$ (2×20 mL). The combined organic extracts were dried over sodium sulfate, filtered and concentrated in vacuo. The crude material was washed with MeOH: $CH_3CN$ (1:1, 2×5 mL) to afford N-(5-methoxy-6-(4-methyl-1H-imidazol-1-yl) pyridin-3-yl)-8'-methyl-2, 3, 5, 6-tetrahydro-6'H, 8'H-spiro [pyran-4, 7'-pyrimido [5, 4-b] [1, 4] oxazin]-2'-amine (21 mg, 18%) as an off-white solid. $^1$H NMR (400 MHz, $CD_3OD$): δ 8.27 (s, 2H), 8.15 (s, 1H), 7.57 (s, 1H), 7.41 (s, 1H), 4.26 (s, 2H), 3.97 (s, 3H), 3.96-3.88 (m, 2H), 3.70-3.61 (m, 2H), 3.22 (s, 3H), 2.27 (s, 3H), 2.26-2.21 (m, 2H), 1.64 (d, 2H); Mass (ESI): 424.9 [M+1]; LCMS: 424 (M+1); (column; X-Select CSH C-18 (50×3.0 mm, 3.5 μm); RT 1.92 min 0.05% Aq TFA: ACN; 0.80 mL/min; HPLC (column; Eclipse XDB C-18, 150×4.6 mm, 5.0 μm); RT 8.73 min. ACN: 5 mM Aq $NH_4OAc$; 1.0 mL/min; TLC: 5% MeOH/ $CH_2Cl_2$ ($R_f$: 0.3).

Example 275

Synthesis of N-(3-methoxy-4-(4-methyl-1H-imidazol-1-yl) phenyl)-8'-(2, 2, 2-trifluoroethyl)-2, 3, 5, 6-tetrahydro-6'H, 8'H-spiro [pyran-4, 7'-pyrimido [5, 4-b] [1, 4] oxazin]-2'-amine

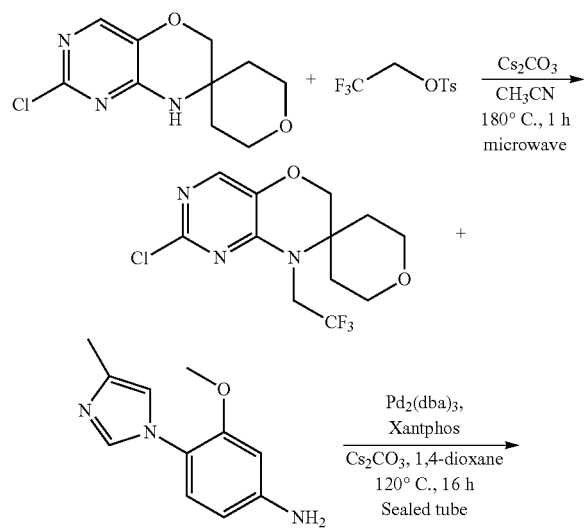

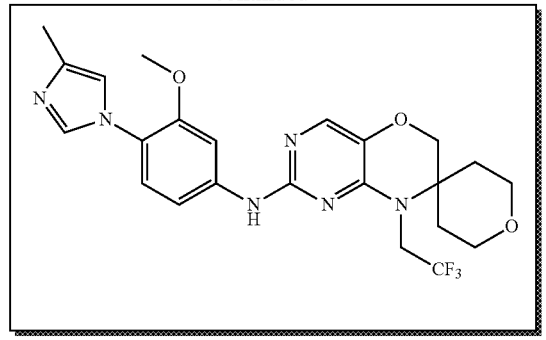

Synthesis of 2'-chloro-8'-(2, 2, 2-trifluoroethyl)-2, 3, 5, 6-tetrahydro-6'H, 8'H-spiro [pyran-4, 7'-pyrimido [5, 4-b] [1, 4] oxazine]

To a stirred solution of 2'-chloro-2, 3, 5, 6-tetrahydro-6'H, 8'H-spiro [pyran-4, 7'-pyrimido [5, 4-b] [1, 4] oxazine] (50 mg, 0.20 mmol) in $CH_3CN$ (0.5 mL) under an argon atmosphere were added cesium carbonate (134 mg, 0.41 mmol) and 2, 2, 2-trifluoroethyl 4-methylbenzenesulfonate (210 mg, 0.82 mmol) at room temperature. The reaction mixture was stirred at 180° C. for 1 h in a microwave. The reaction was filtered and the filtrate was concentrated in vacuo to obtain 2'-chloro-8'-(2, 2, 2-trifluoroethyl)-2, 3, 5, 6-tetrahydro-6'H, 8'H-spiro [pyran-4, 7'-pyrimido [5, 4-b] [1, 4] oxazine] (15 mg, 22%) as a colorless liquid. LCMS: 323.9 (M+1); (column; X-Select CSH C-18 (50×3.0 mm, 3.5 μm); RT 3.30 min 0.05% Aq TFA: ACN; 0.80 mL/min); TLC: 50% EtOAc:hexane ($R_f$: 0.5).

Synthesis of N-(3-methoxy-4-(4-methyl-1H-imidazol-1-yl) phenyl)-8'-(2, 2, 2-trifluoroethyl)-2, 3, 5, 6-tetrahydro-6'H, 8'H-spiro [pyran-4, 7'-pyrimido [5, 4-b] [1, 4] oxazin]-2'-amine To a dry vial was added a suspension of $Pd_2(dba)_3$ (4 mg, 0.004 mmol) and Xantphos (8 mg, 0.01 mmol) in 1, 4-dioxane (0.25 mL) at room temperature. The suspension was degassed with argon, heated to 120° C., and stirred for 3 min. A mixture of 2'-chloro-8'-(2, 2, 2-trifluoroethyl)-2, 3, 5, 6-tetrahydro-6'H, 8'H-spiro [pyran-4, 7'-pyrimido [5, 4-b] [1, 4] oxazine] (30 mg, 0.09 mmol), 3-methoxy-4-(4-methyl-1H-imidazol-1-yl) aniline (37 mg, 0.18 mmol), cesium carbonate (42 mg, 0.12 mmol) in 1, 4-dioxane (0.25 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with EtOAc (2×20 mL). The combined organic extracts were dried over sodium sulfate, filtered and concentrated in vacuo. The crude material was purified by column chromatography using 2% MeOH: $CH_2Cl_2$ to afford N-(3-methoxy-4-(4-methyl-1H-imidazol-1-yl) phenyl)-8'-(2, 2, 2-trifluoroethyl)-2, 3, 5, 6-tetrahydro-6'H, 8'H-spiro [pyran-4, 7'-pyrimido [5, 4-b] [1, 4] oxazin]-2'-amine (5 mg, 10%) as a brown thick oil. $^1$H-NMR ($CD_3OD$, 400 MHz): δ 7.99 (br s, 1H), 7.74 (s, 1H), 7.51-7.48 (m, 1H), 7.42 (d, 1H), 7.21 (d, 1H), 7.10 (br s, 1H), 4.57 (br s, 2H), 4.35 (br s, 2H), 3.98-3.89 (m, 2H), 3.86 (s, 3H), 3.67 (t, 2H), 2.28 (s, 3H), 2.09 (br s, 2H), 1.70 (d, 2H); Mass (ESI): 491.7 [M+1]; LCMS: 491.5 (M+1);

(column; X-Select CSH C-18 (50×3.0 mm, 3.5 RT 3.89 min 5.0 mM NH₄OAc in water: ACN; 0.80 mL/min); HPLC (column; Eclipse XDB C18, 150×4.6 mm, 5.0 μm); RT 1.59 min. ACN: 5 mM Aq NH₄OAc; 1.0 mL/min; TLC: 50% EtOAc:hexane ($R_f$: 0.5).

Example 276

Synthesis of 3, 3-difluoro-N-(3-methoxy-4-(4-methyl-1H-imidazol-1-yl) phenyl)-8'-methyl-6'H, 8'H-spiro [cyclobutane-1, 7'-pyrimido [5, 4-b] [1, 4] oxazin]-2'-amine

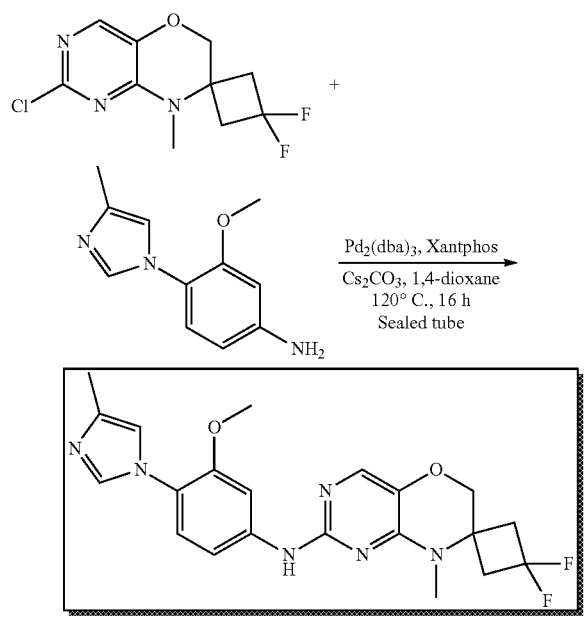

Synthesis of 3, 3-difluoro-N-(3-methoxy-4-(4-methyl-1H-imidazol-1-yl) phenyl)-8'-methyl-6'H, 8'H-spiro [cyclobutane-1, 7'-pyrimido [5, 4-b] [1, 4] oxazin]-2'-amine To a dry vial was added a suspension of Pd₂(dba)₃ (12 mg, 0.01 mmol) and Xantphos (23 mg, 0.04 mmol) in 1, 4-dioxane (0.75 mL) at room temperature. The suspension was degassed with argon, heated to 120° C., and stirred for 3 min. A mixture of 2'-chloro-3, 3-difluoro-8'-methyl-6'H, 8'H-spiro [cyclobutane-1, 7'-pyrimido [5, 4-b] [1, 4] oxazine] (70 mg, 0.26 mmol), 3-methoxy-4-(4-methyl-1H-imidazol-1-yl) aniline (37 mg, 0.18 mmol) and cesium carbonate (121 mg, 0.37 mmol) in 1, 4-dioxane (0.75 mL) was degassed and the catalyst premixture was added. The resultant mixture was stirred at 120° C. for 16 h in a sealed tube. After consumption of the starting material (monitored by TLC and LCMS), the volatile components were concentrated in vacuo. The crude material was purified by preparative HPLC (Column X-select CSH C18 (250×19 mm: 5μ; (50 mg loading; CH₃CN: 0.05% TFA (0.1/90, 2/90, 15/70, 25/30, 30/10, 35/10) to afford 3, 3-difluoro-N-(3-methoxy-4-(4-methyl-1H-imidazol-1-yl) phenyl)-8'-methyl-6'H, 8'H-spiro [cyclobutane-1, 7'-pyrimido [5, 4-b] [1, 4] oxazin]-2'-amine (33 mg, 29%) as a brown solid. ¹H NMR (DMSO-d₆, 400 MHz): δ 9.18 (s, 1H), 7.79 (s, 1H), 7.68 (s, 1H), 7.61 (s, 1H), 7.29 (dd, 1H), 7.16 (d, 1H), 7.00 (s, 1H), 4.12 (s, 2H), 3.79 (s, 3H), 3.30-3.28 (m, 2H), 3.22 (s, 3H), 2.80-2.71 (m, 2H), 2.12 (s, 3H); Mass (ESI): 429.4 [M+1]; LCMS: 429 (M+1); (column; Ascentis Express C-18 (50×3.0 mm, 2.7 μm); RT 1.69 min. 0.025% Aq TFA+5% ACN: ACN+5% 0.025% Aq TFA; 1.2 mL/min); UPLC (column; Acquity UPLC BEH C-18, 50×2.1 mm, 1.7 μm); RT 1.48 min. ACN: 0.025% Aq TFA; 0.5 mL/min.

Example 277

Synthesis of N-(4-(4-chloro-1H-imidazol-1-yl)-3-methoxyphenyl)-3, 3-difluoro-8'-methyl-6'H, 8'H-spiro [cyclobutane-1, 7'-pyrimido [5, 4-b] [1, 4] oxazin]-2'-amine

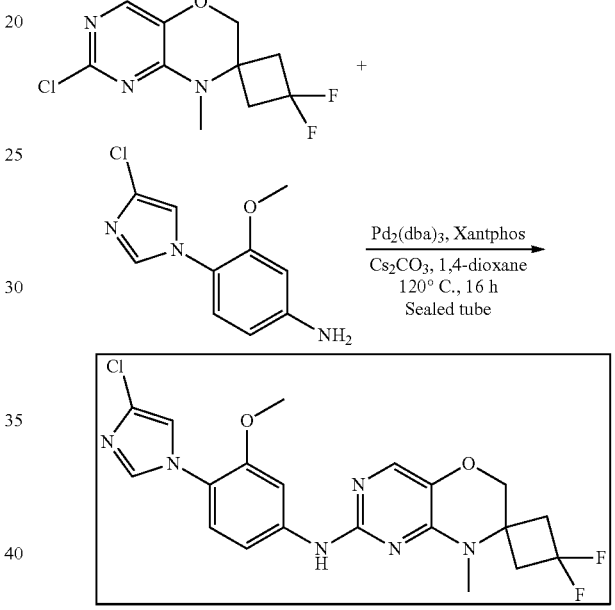

Synthesis of N-(4-(4-chloro-1H-imidazol-1-yl)-3-methoxyphenyl)-3, 3-difluoro-8'-methyl-6'H, 8'H-spiro [cyclobutane-1, 7'-pyrimido [5, 4-b] [1, 4] oxazin]-2'-amine To a dry vial was added a suspension of Pd₂(dba)₃ (15 mg, 0.02 mmol) and Xantphos (29 mg, 0.05 mmol) in 1, 4-dioxane (0.9 mL) at room temperature. The suspension was degassed with argon, heated to 120° C., and stirred for 3 min. A mixture of 2'-chloro-3, 3-difluoro-8'-methyl-6'H, 8'H-spiro [cyclobutane-1, 7'-pyrimido [5, 4-b] [1, 4] oxazine] (90 mg, 0.34 mmol), 4-(4-chloro-1H-imidazol-1-yl)-3-methoxyaniline (53 mg, 0.24 mmol) and cesium carbonate (156 mg, 0.48 mmol) in 1, 4-dioxane (0.9 mL) was degassed and the catalyst premixture was added. The resultant mixture was stirred at 120° C. for 16 h in a sealed tube. After consumption of the starting material (monitored by TLC and LCMS), the volatile components were concentrated in vacuo. The crude material was purified by preparative HPLC (Column YMC Actus Triart C18 (250×20 mm: 5μ; (60 mg loading; CH₃CN: 0.05% TFA (0.1/90, 2/90, 15/70, 25/30, 30/10, 35/10) to afford N-(4-(4-chloro-1H-imidazol-1-yl)-3-methoxyphenyl)-3, 3-difluoro-8'-methyl- 6'H, 8'H-spiro [cyclobutane-1, 7'-pyrimido [5, 4-b] [1, 4] oxazin]-2'-amine (35 mg, 23%) as an off-white solid. $^1$H NMR (DMSO-d$_6$, 400 MHz): δ 9.25 (s, 1H), 7.83 (s, 1H), 7.76 (s, 1H), 7.69 (s, 1H), 7.45 (s, 1H), 7.31 (d, 1H), 7.23 (d, 1H), 4.12 (s, 2H), 3.79 (s, 3H), 3.29-3.24 (m, 2H), 3.22 (s, 3H), 2.80-2.72 (m, 2H); Mass (ESI): 449.9 [M+1]; LCMS: 449 (M+1); (column; Ascentis Express C-18 (50×3.0 mm, 2.7 μm); RT 2.00 min. 0.025% Aq TFA+5% ACN: ACN+5% 0.025% Aq TFA; 1.2 mL/min); HPLC (column; Eclipse XDB C-18, 150×4.6 mm, 5 μm); RT 7.69 min. ACN: 0.05% Aq TFA; 1.0 mL/min; TLC: 5% MeOH/CH$_2$Cl$_2$ (R$_f$: 0.2).

Example 278

Synthesis of 3, 3-difluoro-N-(5-methoxy-6-(4-methyl-1H-imidazol-1-yl) pyridin-3-yl)-8'-methyl-6'H, 8'H-spiro [cyclobutane-1, 7'-pyrimido [5, 4-b] [1, 4] oxazin]-2'-amine

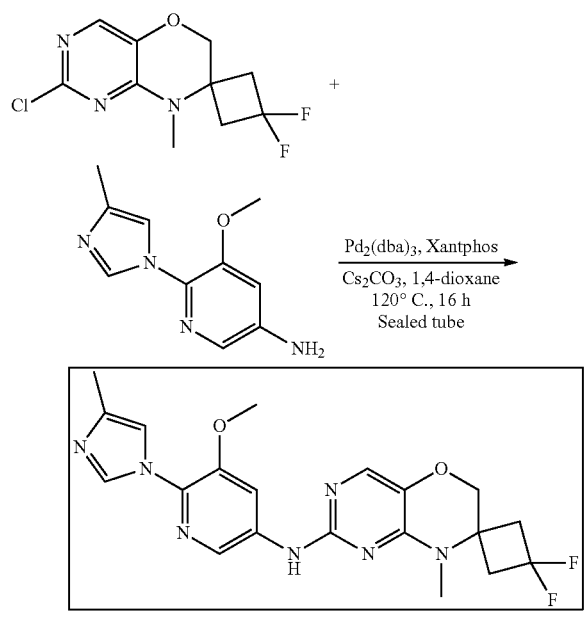

Synthesis of 3, 3-difluoro-N-(5-methoxy-6-(4-methyl-1H-imidazol-1-yl) pyridin-3-yl)-8'-methyl-6'H, 8'H-spiro [cyclobutane-1, 7'-pyrimido [5, 4-b] [1, 4] oxazin]-2'-amine To a dry vial was added a suspension of Pd$_2$(dba)$_3$ (15 mg, 0.02 mmol) and Xantphos (29 mg, 0.05 mmol) in 1, 4-dioxane (0.9 mL) at room temperature. The suspension was degassed with argon, heated to 120° C., and stirred for 3 min. A mixture of 2'-chloro-3, 3-difluoro-8'-methyl-6'H, 8'H-spiro [cyclobutane-1, 7'-pyrimido [5, 4-b] [1, 4] oxazine] (90 mg, 0.34 mmol), 5-methoxy-6-(4-methyl-1H-imidazol-1-yl) pyridin-3-amine (49 mg, 0.24 mmol) and cesium carbonate (156 mg, 0.48 mmol) in 1, 4-dioxane (0.9 mL) was degassed and the catalyst premixture was added. The resultant mixture was stirred at 120° C. for 16 h in a sealed tube. After consumption of the starting material (monitored by TLC and LCMS), the volatile components were concentrated in vacuo. The crude material was purified by preparative HPLC (Column YMC Actus Triart C18 (250×20 mm; 5μ; (70 mg loading; CH$_3$CN: 0.05% TFA (0.1/95, 2/95, 15/70, 25/30, 40/10) to afford 3, 3-difluoro-N-(5-methoxy-6-(4-methyl-1H-imidazol-1-yl) pyridin-3-yl)-8'-methyl-6'H, 8'H-spiro [cyclobutane-1, 7'-pyrimido [5, 4-b] [1, 4] oxazin]-2'-amine (30 mg, 20%) as an off-white solid. $^1$H NMR (DMSO-d$_6$, 400 MHz): δ 9.39 (s, 1H), 8.32 (s, 1H), 8.25 (s, 1H), 8.05 (s, 1H), 7.71 (s, 1H), 7.38 (s, 1H), 4.13 (s, 2H), 3.90 (s, 3H), 3.29-3.27 (m, 1H), 3.26-3.24 (m, 1H), 3.23 (s, 3H), 2.82-2.71 (m, 2H), 2.15 (s, 3H); Mass (ESI): 430.4 [M+1]; LCMS: 430 (M+1); (column; Ascentis Express C-18 (50×3.0 mm, 2.7 μm); RT 1.58 min. 0.025% Aq TFA+5% ACN: ACN+5% 0.025% Aq TFA; 1.2 mL/min); HPLC (column; Eclipse XDB C-18, 150×4.6 mm, 5 μm); RT 6.43 min. ACN: 0.05% Aq TFA; 1.0 mL/min; TLC: 5% MeOH/CH$_2$Cl$_2$ (R$_f$: 0.2).

Example 279

Synthesis of N-(3-fluoro-4-(4-methyl-1H-imidazol-1-yl) phenyl)-8'-methyl-6'H, 8'H-spiro [cyclopentane-1, 7'-pyrimido [5, 4-b] [1, 4] oxazin]-2'-amine

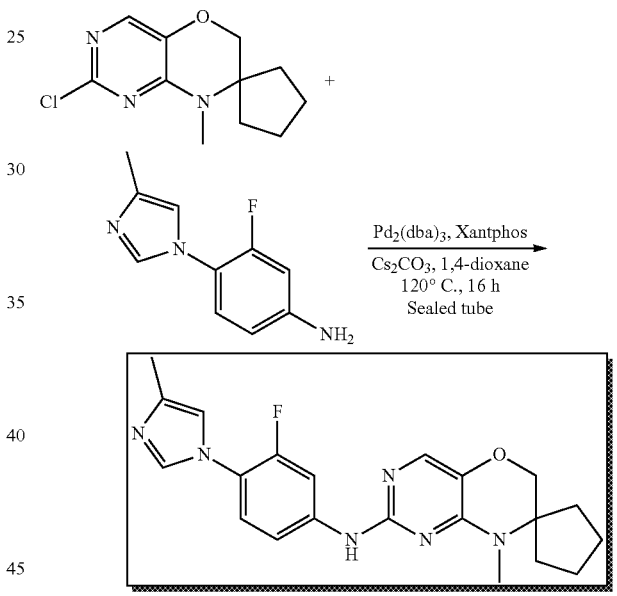

Synthesis of N-(3-fluoro-4-(4-methyl-1H-imidazol-1-yl) phenyl)-8'-methyl-6'H, 8'H-spiro [cyclopentane-1, 7'-pyrimido [5, 4-b] [1, 4] oxazin]-2'-amine To a dry vial was added a suspension of Pd$_2$(dba)$_3$ (29 mg, 0.03 mmol) and Xantphos (54 mg, 0.09 mmol) in 1, 4-dioxane (0.75 mL) at room temperature. The suspension was degassed with argon, heated to 120° C., and stirred for 3 min. A mixture of 2'-chloro-8'-methyl-6'H, 8'H-spiro [cyclopentane-1, 7'-pyrimido [5, 4-b] [1, 4] oxazine] (150 mg, 0.62 mmol), 3-fluoro-4-(4-methyl-1H-imidazol-1-yl) aniline (131 mg, 0.69 mmol) and cesium carbonate (285 mg, 0.87 mmol) in 1, 4-dioxane (0.75 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with CH$_2$Cl$_2$ (2×20 mL). The combined organic extracts were dried over sodium sulfate, filtered and concentrated in vacuo. The crude material was purified by preparative HPLC (Ascentis C-18 (250×21.2 mm, 5 μm (70 mg loading; CH$_3$CN: 0.05% TFA (0.1/80, 2/80, 15/70, 25/20, 30/10, 35/10)) to afford N-(3-fluoro-4-(4-methyl-1H-imidazol-1-yl) phenyl)-8'-methyl-6'H, 8'H-spiro [cyclopentane-1, 7'-pyrimido [5, 4-b] [1, 4] oxazin]-2'-amine (50 mg, 20%) as an off-white solid. $^1$H-NMR (CD$_3$OD, 400 MHz): δ 7.96-7.90 (m, 1H), 7.75-7.71 (m, 1H), 7.50 (s, 1H), 7.39-7.29 (m, 2H), 7.05-7.03 (m, 1H), 3.83 (s, 2H), 3.11 (s, 3H), 2.23 (s, 3H), 1.90-1.80 (m, 4H), 1.79-1.70 (m, 4H); Mass (ESI): 395.5 [M+1]; LCMS: 395.1 (M+1); (column; X-Select CSH C-18 (50×3.0 mm, 3.5 μm); RT 2.18 min. 0.05% Aq TFA: ACN; 0.80 mL/min); HPLC (column; Eclipse XDB-C18 (150×4.6 mm, 5.0 μm); RT 11.16 min. ACN: 5 mM Aq NH$_4$OAc; 1.0 mL/min; TLC: 5% MeOH/ CH$_2$Cl$_2$ (R$_f$: 0.3).

Example 280

Synthesis of 2-chloro-6a, 7, 8, 9-tetrahydro-6H-pyrimido [5, 4-b] pyrrolo [1, 2-d] [1, 4] oxazine

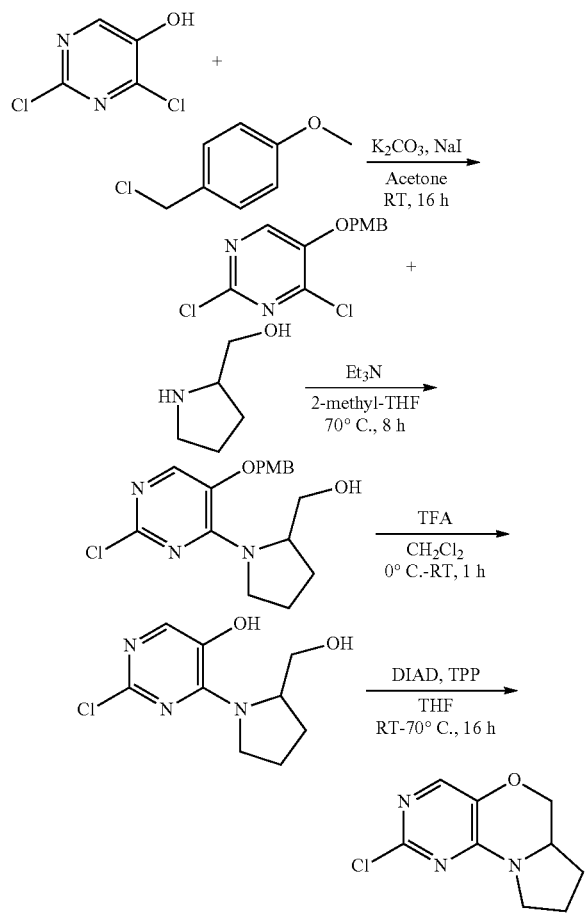

Synthesis of 2, 4-dichloro-5-((4-methoxybenzyl) oxy) pyrimidine

To a stirred solution of 2, 4-dichloropyrimidin-5-ol (7 g, 42.68 mmol) in acetone (100 mL) under an argon atmosphere were added 1-(chloromethyl)-4-methoxybenzene (10 g, 64.02 mmol), potassium carbonate (14.7 g, 106.70 mmol) and sodium iodide (600 mg, 4.26 mmol) at room temperature. The reaction mixture was stirred for 16 h. After consumption of starting material (monitored by TLC), the reaction mixture was diluted with water (50 mL) and extracted with EtOAc (2×100 mL). The combined organic extracts were dried over sodium sulfate, filtered and concentrated in vacuo. The crude material was purified by column chromatography using 10% EtOAc:hexanes to afford 2, 4-dichloro-5-((4-methoxybenzyl) oxy) pyrimidine (6.2 g, 51%) as a pale yellow solid. $^1$H-NMR (CDCl$_3$, 500 MHz): δ 8.19 (s, 1H), 7.34 (d, 2H), 6.93 (d, 2H), 5.19 (s, 2H), 3.80 (s, 3H); TLC: 30% EtOAc:hexane (R$_f$: 0.6).

Synthesis of (1-(2-chloro-5-((4-methoxybenzyl) oxy) pyrimidin-4-yl) pyrrolidin-2-yl) methanol To a stirred solution of 2, 4-dichloro-5-((4-methoxybenzyl) oxy) pyrimidine (100 mg, 0.35 mmol) in 2-methyl THF (1 mL) under an argon atmosphere were added pyrrolidin-2-ylmethanol (40 mg, 0.39 mmol) and triethylamine (0.12 mL, 0.87 mmol) at room temperature. The reaction mixture was stirred at 70° C. for 8 h. After consumption of starting material (monitored by TLC), the reaction mixture was diluted with water (50 mL) and extracted with EtOAc (2×50 mL). The combined organic extracts were dried over sodium sulfate, filtered and concentrated in vacuo. The crude was purified by column chromatography using 50% EtOAc: hexanes to afford (1-(2-chloro-5-((4-methoxybenzyl) oxy) pyrimidin-4-yl) pyrrolidin-2-yl) methanol (120 mg, 98%) as a colorless oil. $^1$H-NMR (CDCl$_3$, 500 MHz): δ 7.67 (s, 1H), 7.41 (d, 2H), 6.91 (d, 2H), 4.90 (s, 2H), 4.48-4.41 (m, 1H), 3.88-3.78 (m, 5H), 3.69-3.60 (m, 2H), 3.21 (br s, 1H), 2.00-1.80 (m, 4H); LCMS: 350.2 (M+1); (column; X-Select CSH C-18 (50×3.0 mm, 3.5 μm); RT 3.91 min 0.05% Aq TFA: ACN; 0.80 mL/min); TLC: 50% EtOAc:hexane (R$_f$: 0.3).

Synthesis of 2-chloro-4-(2-(hydroxymethyl) pyrrolidin-1-yl) pyrimidin-5-ol

To a stirred solution of (1-(2-chloro-5-((4-methoxybenzyl) oxy) pyrimidin-4-yl) pyrrolidin-2-yl) methanol (120 mg, 0.34 mmol) in CH$_2$Cl$_2$ (2 mL) under an argon atmosphere was added trifluoroacetic acid (1 mL) at 0° C. The reaction mixture was warmed to room temperature and stirred for 1 h. After consumption of starting material (monitored by TLC), the reaction mixture was diluted with a saturated sodium bicarbonate solution (20 mL) and extracted with 5% MeOH/CH$_2$Cl$_2$ (2×10 mL). The combined organic extracts were dried over sodium sulfate, filtered and concentrated in vacuo to obtain 2-chloro-4-(2-(hydroxymethyl) pyrrolidin-1-yl) pyrimidin-5-ol (50 mg 64%) as a white solid. $^1$H-NMR (DMSO-d$_6$, 400 MHz): δ 9.80 (s, 1H), 7.50 (s, 1H), 4.79 (br s, 1H), 4.50-4.40 (m, 1H), 3.75-3.69 (m, 1H), 3.67-3.60 (m, 1H), 3.59-3.50 (m, 1H), 2.00-1.71 (m, 4H); LCMS: 230.2 (M+1); (column; X-Select CSH C-18 (50×3.0 mm, 3.5 μm); RT 2.06 min 0.05% Aq TFA: ACN; 0.80 mL/min); TLC: 50% EtOAc:hexane (R$_f$: 0.3).

Synthesis of 2-chloro-6a, 7, 8, 9-tetrahydro-6H-pyrimido [5, 4-b] pyrrolo [1, 2-d] [1, 4] oxazine To a stirred solution of 2-chloro-4-(2-(hydroxymethyl) pyrrolidin-1-yl) pyrimidin-5-ol (1.8 g, 0.56 mmol) in THF (20 mL) under an argon atmosphere were added triphenylphosphine (2.2 g, 0.85 mmol) and diisopropylazodicarboxylate (1.7 mL, 0.85 mmol) at room temperature. The reaction mixture was stirred at 70° C. for 16 h. After consumption of starting material (monitored by TLC), the reaction mixture was diluted with water (50 mL) and extracted with EtOAc (2×50 mL). The combined organic extracts were dried over sodium sulfate, filtered and concentrated in vacuo. The crude material was purified by column chromatography using 30% EtOAc:hexanes to afford 2-chloro-6a, 7, 8, 9-tetrahydro-6H-pyrimido [5, 4-b] pyrrolo [1, 2-d] [1, 4] oxazine (800 mg, 66%) as an off-white solid. $^1$H-NMR (CDCl$_3$, 500 MHz): δ 7.68 (d, 1H), 4.52 (d, 1H), 3.78-3.70 (m, 2H), 3.60-3.56 (m, 1H), 3.39 (t, 1H), 2.20-2.10 (m, 2H), 2.08-1.99 (m, 1H), 1.53-1.40 (m, 1H); LCMS: 212.2 (M+1); (column; X-Select CSH C-18 (50×3.0 mm, 3.5 μm); RT 2.73 min 0.05% Aq TFA: ACN; 0.80 mL/min); TLC: 50% EtOAc:hexanes (R$_f$: 0.5).

Example 281

Synthesis of (S)-2-chloro-6a-methyl-6a, 7, 8, 9-tetrahydro-6H-pyrimido [5, 4-b] pyrrolo [1, 2-d] [1, 4] oxazine

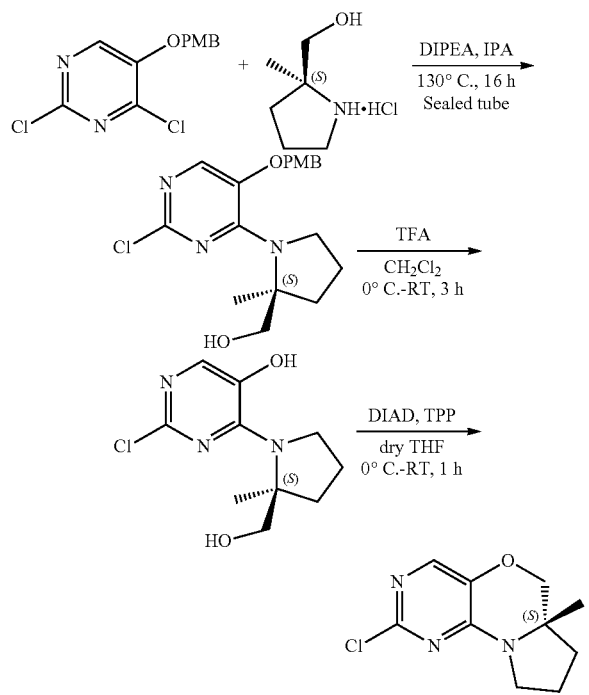

Synthesis of (S)-(1-(2-chloro-5-((4-methoxybenzyl) oxy) pyrimidin-4-yl)-2-methylpyrrolidin-2-yl) methanol To a stirred solution of 2, 4-dichloro-5-((4-methoxybenzyl) oxy) pyrimidine (1.5 g, 5.26 mmol) in isopropyl alcohol (10 mL) under an argon atmosphere were added diisopropylethylamine (9.5 mL, 52.63 mmol) and (S)-(2-methylpyrrolidin-2-yl) methanol hydrochloride (957 mg, 6.31 mmol) at room temperature. The reaction mixture was stirred at 130° C. for 16 h in a sealed tube. After consumption of starting material (monitored by TLC), the volatile components were evaporated in vacuo. The crude material was purified by column chromatography using 30-50% EtOAc: hexanes to afford (S)-(1-(2-chloro-5-((4-methoxybenzyl) oxy) pyrimidin-4-yl)-2-methylpyrrolidin-2-yl) methanol (1.1 g, 57%) as an off-white solid. $^1$H-NMR (DMSO-d$_6$, 400 MHz): δ 7.79 (s, 1H), 7.35 (d, 2H), 6.94 (d, 2H), 4.93 (s, 2H), 4.70 (t, 1H), 4.00-3.84 (m, 1H), 3.77 (s, 3H), 3.75-3.70 (m, 1H), 3.60-3.53 (m, 1H), 2.11-2.03 (m, 1H), 1.80-1.70 (m, 2H), 1.57-1.50 (m, 1H), 1.39 (s, 3H); LCMS: 364.4 (M+1); (column; X-Select CSH C-18 (50×3.0 mm, 3.5 μm); RT 4.10 min 0.05% Aq TFA: ACN; 0.80 mL/min); TLC: 30% EtOAc:hexane (R$_f$: 0.2).

Synthesis of (S)-2-chloro-4-(2-(hydroxymethyl)-2-methylpyrrolidin-1-yl) pyrimidin-5-ol To a stirred solution of (S)-(1-(2-chloro-5-((4-methoxybenzyl) oxy) pyrimidin-4-yl)-2-methylpyrrolidin-2-yl) methanol (1.1 g, 3.02 mmol) in CH$_2$Cl$_2$ (80 mL) under an argon atmosphere was added trifluoroacetic acid (8 mL) at 0° C. The reaction mixture was warmed to room temperature and stirred for 3 h. After consumption of starting material (monitored by TLC), the reaction mixture was quenched with a saturated sodium bicarbonate solution (30 mL) and extracted with 20% MeOH: CH$_2$Cl$_2$ (2×30 mL). The combined organic extracts were dried over sodium sulfate, filtered and concentrated in vacuo. The crude material was purified by column chromatography using 70% EtOAc: hexanes-EtOAc to afford (S)-2-chloro-4-(2-(hydroxymethyl)-2-methylpyrrolidin-1-yl) pyrimidin-5-ol (485 mg, 65%) as an off-white solid. $^1$H-NMR (DMSO-d$_6$, 400 MHz): δ 9.60 (s, 1H), 7.49 (s, 1H), 4.72 (t, 1H), 4.05-3.99 (m, 1H), 3.98-3.92 (m, 1H), 3.87-3.80 (m, 1H), 3.63-3.58 (m, 1H), 2.15-2.08 (m, 1H), 1.80-1.71 (m, 2H), 1.58-1.50 (m, 1H), 1.40 (s, 3H); LCMS: 244 (M+); (column; X-Select CSH C-18 (50×3.0 mm, 3.5 μm); RT 2.27 min 0.05% Aq TFA: ACN; 0.80 mL/min); TLC: 50% EtOAc:hexane (R$_f$: 0.2).

Synthesis of (S)-2-chloro-6a-methyl-6a, 7, 8, 9-tetrahydro-6H-pyrimido [5, 4-b] pyrrolo [1, 2-d] [1, 4] oxazine To a stirred solution of (S)-2-chloro-4-(2-(hydroxymethyl)-2-methylpyrrolidin-1-yl) pyrimidin-5-ol (950 mg, 3.89 mmol) in dry THF (50 mL) under an argon atmosphere were added triphenylphosphine (1.2 g, 4.67 mmol) and diisopropylazodicarboxylate (944 mg, 4.67 mmol) at 0° C. The reaction mixture was warmed to room temperature and stirred for 1 h. After consumption of starting material (monitored by TLC), the reaction mixture was quenched with water (50 mL) and extracted with EtOAc (2×50 mL). The combined organic extracts were dried over sodium sulfate, filtered and concentrated in vacuo. The crude material was purified by column chromatography using 30% EtOAc:hexanes-EtOAc to afford (S)-2-chloro-6a-methyl-6a, 7, 8, 9-tetrahydro-6H-pyrimido [5, 4-b] pyrrolo [1, 2-d] [1, 4] oxazine (750 mg, 85%) as an off-white solid. $^1$H-NMR (CDCl$_3$, 400 MHz): δ 7.70 (s, 1H), 4.30-4.27 (m, 1H), 3.78-3.70 (m, 1H), 3.68-3.60 (m, 1H), 3.35-3.30 (m, 1H), 2.20-2.10 (m, 2H), 1.98-1.90 (m, 1H), 1.70-1.60 (m, 1H), 1.27 (s, 3H); LCMS: 226 (M+); (column; X-Select CSH C-18 (50×3.0 mm, 3.5 μm); RT 3.23 min 0.05% Aq TFA: ACN; 0.80 mL/min); UPLC (column; Acquity UPLC BEH C-18, 2.1×50 mm, 1.7 μm); RT 1.77 min. ACN: 0.025% Aq TFA; 0.5 mL/min; Chiral HPLC: 100% RT=5.28 min (Chiralpak-IA (250×4.6 mm, 5 μm; mobile phase (A) 0.1% DEA in n-hexane (B) CH$_2$Cl$_2$:MeOH (50:50) (A:B: 75:25); flow Rate: 1.0 mL/min); Optical rotation $[\alpha]_D^{20.01}$: +58.30 (c=0.25, CH$_2$Cl$_2$); TLC: EtOAc (R$_f$: 0.7).

Example 282

Synthesis of (R)-2-chloro-6a-methyl-6a, 7, 8, 9-tetrahydro-6H-pyrimido [5, 4-b] pyrrolo [1, 2-d] [1, 4] oxazine

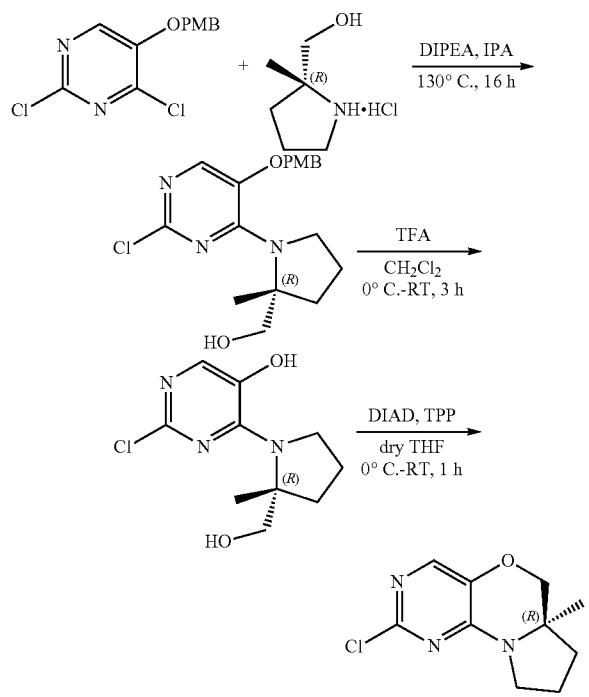

Synthesis of (R)-(1-(2-chloro-5-((4-methoxybenzyl) oxy) pyrimidin-4-yl)-2-methylpyrrolidin-2-yl) methanol To a stirred solution of 2, 4-dichloro-5-((4-methoxybenzyl) oxy) pyrimidine (1.5 g, 5.26 mmol) in isopropyl alcohol (10 mL) under an argon atmosphere were added (R)-(2-methylpyrrolidin-2-yl) methanol hydrochloride (957 mg, 0.95 mmol) and diisopropylethylamine (9.5 mL, 52.63 mmol) at room temperature. The reaction mixture was stirred at 130° C. for 16 h. After consumption of starting material (monitored by TLC), the volatile components were evaporated in vacuo. The crude material was purified by column chromatography using 30-50% EtOAc:hexanes to afford (R)-(1-(2-chloro-5-((4-methoxybenzyl) oxy) pyrimidin-4-yl)-2-methylpyrrolidin-2-yl) methanol (1.1 g, 57%) as an off-white solid. $^1$H-NMR (DMSO-d$_6$, 400 MHz): δ 7.79 (s, 1H), 7.35 (d, 2H), 6.93 (d, 2H), 4.92 (s, 2H), 4.70 (t, 1H), 4.00-3.95 (m, 1H), 3.94-3.88 (m, 1H), 3.75 (s, 3H), 3.75-3.70 (m, 1H), 3.60-3.53 (m, 1H), 2.13-2.08 (m, 1H), 1.80-1.70 (m, 2H), 1.54-1.49 (m, 1H), 1.37 (s, 3H); LCMS: 364.3 (M+1); (column; X-Select CSH C-18 (50×3.0 mm, 3.5 µm); RT 4.07 min 0.05% Aq TFA: ACN; 0.80 mL/min); TLC: 30% EtOAc:hexane (R$_f$: 0.2).

Synthesis of (R)-2-chloro-4-(2-(hydroxymethyl)-2-methylpyrrolidin-1-yl) pyrimidin-5-ol To a stirred solution of (R)-(1-(2-chloro-5-((4-methoxybenzyl) oxy) pyrimidin-4-yl)-2-methylpyrrolidin-2-yl) methanol (1.1 g, 3.02 mmol) in CH$_2$Cl$_2$ (80 mL) under an argon atmosphere was added trifluoroacetic acid (7.8 mL) at 0° C. The reaction mixture was warmed to room temperature and stirred for 3 h. After consumption of starting material (monitored by TLC), the reaction mixture was quenched with a saturated sodium bicarbonate solution (30 mL) and extracted with CH$_2$Cl$_2$ (2×30 mL). The combined organic extracts were dried over sodium sulfate, filtered and concentrated in vacuo. The crude material was purified by column chromatography using 70% EtOAc:hexanes-EtOAc to afford (R)-2-chloro-4-(2-(hydroxymethyl)-2-methylpyrrolidin-1-yl) pyrimidin-5-ol (480 mg, 65%) as an off-white solid. $^1$H-NMR (DMSO-d$_6$, 400 MHz): δ 9.60 (s, 1H), 7.49 (s, 1H), 4.71 (t, 1H), 4.02-3.99 (m, 1H), 3.98-3.90 (m, 1H), 3.87-3.80 (m, 1H), 3.62-3.58 (m, 1H), 2.11-2.05 (m, 1H), 1.80-1.70 (m, 2H), 1.55-1.50 (m, 1H), 1.35 (s, 3H); LCMS: 244 (M+); (column; X-Select CSH C-18 (50×3.0 mm, 3.5 µm); RT 2.28 min 0.05% Aq TFA: ACN; 0.80 mL/min); TLC: 50% EtOAc:hexane (R$_f$: 0.2).

Synthesis of (R)-2-chloro-6a-methyl-6a, 7, 8, 9-tetrahydro-6H-pyrimido [5, 4-b] pyrrolo [1, 2-d] [1, 4] oxazine To a stirred solution of (R)-2-chloro-4-(2-(hydroxymethyl)-2-methylpyrrolidin-1-yl) pyrimidin-5-ol (950 mg, 3.89 mmol) in dry THF (50 mL) under an argon atmosphere were added triphenylphosphine (1.2 g, 4.67 mmol) and diisopropylazodicarboxylate (944 mg, 4.67 mmol) at 0° C. The reaction mixture was warmed to room temperature and stirred for 1 h. After consumption of starting material (monitored by TLC), the reaction mixture was quenched with cold water (30 mL) and extracted with EtOAc (2×30 mL). The combined organic extracts were dried over sodium sulfate, filtered and concentrated in vacuo. The crude material was purified by column chromatography using 30% EtOAc:hexanes-EtOAc to afford (R)-2-chloro-6a-methyl-6a, 7, 8, 9-tetrahydro-6H-pyrimido [5, 4-b] pyrrolo [1, 2-d] [1, 4] oxazine (770 mg, 87%) as an off-white solid. $^1$H-NMR (CDCl$_3$, 400 MHz): δ 7.70 (s, 1H), 4.30-4.28 (m, 1H), 3.78-3.70 (m, 1H), 3.67-3.60 (m, 1H), 3.35-3.30 (m, 1H), 2.21-2.10 (m, 2H), 1.96-1.90 (m, 1H), 1.69-1.60 (m, 1H), 1.28 (s, 3H); LCMS: 226 (M+); (column; X-Select CSH C-18 (50×3.0 mm, 3.5 µm); RT 3.19 min 0.05% Aq TFA: ACN; 0.80 mL/min); UPLC (column; Acquity UPLC BEH C-18, 2.1×50 mm, 1.7 µm); RT 1.78 min. ACN: 0.025% Aq TFA; 0.5 mL/min; Chiral HPLC: 97.4% RT=5.90 min (Chiralpak-IA (250×4.6 mm, 5 µm; mobile phase (A) 0.1% DEA in n-hexane (B) CH$_2$Cl$_2$:MeOH (50:50) (A:B: 75:25); flow Rate: 1.0 mL/min); Optical rotation $[\alpha]_D^{20.00}$: −50.16 (c=0.25, CH$_2$Cl$_2$); TLC: EtOAc (R$_f$: 0.7).

Example 283

Synthesis of (S)-2-chloro-6a, 7, 9, 10-tetrahydro-6H-[1, 4] oxazino [4, 3-d] pyrimido [5, 4-b] [1, 4] oxazine

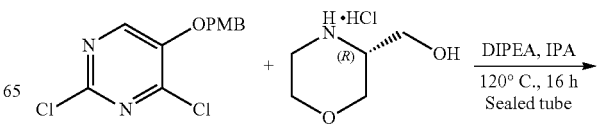

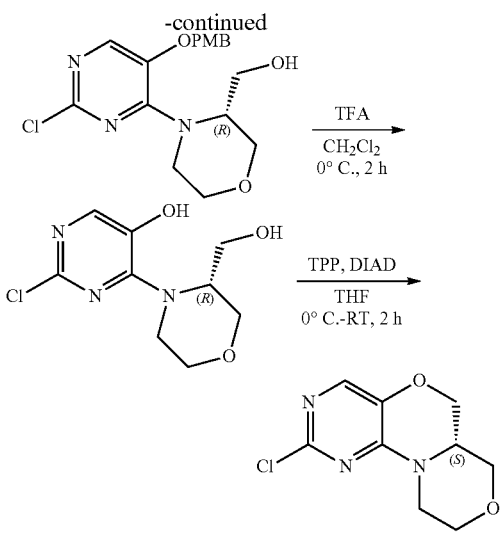

Synthesis of (R)-(4-(2-chloro-5-((4-methoxybenzyl)oxy) pyrimidin-4-yl) morpholin-3-yl) methanol To a stirred solution of 2, 4-dichloro-5-((4-methoxybenzyl) oxy) pyrimidine (500 mg, 1.75 mmol) in isopropyl alcohol (5 mL) under an argon atmosphere were added diisopropylethylamine (5 mL) and (R)-morpholin-3-yl-methanol hydrochloride (295 mg, 1.92 mmol) at room temperature. The reaction mixture was stirred at 120° C. for 16 h in a sealed tube. After consumption of starting material (monitored by TLC), the reaction mixture was diluted with a sodium bicarbonate solution (20 mL) and extracted with EtOAc (2×20 mL). The combined organic extracts were dried over sodium sulfate, filtered and concentrated in vacuo. The crude material was purified by column chromatography using 30-40% EtOAc:hexanes to afford (R)-(4-(2-chloro-5-((4-methoxybenzyl) oxy) pyrimidin-4-yl) morpholin-3-yl) methanol (400 mg, 62%) as a colorless liquid. $^1$H-NMR (DMSO-$d_6$, 500 MHz): δ 7.96 (s, 1H), 7.39 (d, 2H), 6.95 (d, 2H), 5.04 (s, 2H), 4.83 (t, 1H), 4.70-4.64 (m, 1H), 4.09-4.01 (m, 1H), 3.86-3.81 (m, 2H), 3.76 (s, 3H), 3.69-3.60 (m, 2H), 3.54-3.42 (m, 2H), 3.26-3.20 (m, 1H); LCMS: 366.3 (M+1); (column; X-Select CSH C-18 (50×3.0 mm, 3.5 μm); RT 3.75 min 5 mM Aq NH$_4$OAc: ACN; 0.8 mL/min); TLC: 50% EtOAc:hexane (R$_f$: 0.3).

Synthesis of (R)-2-chloro-4-(3-(hydroxymethyl) morpholino) pyrimidin-5-ol

To a stirred solution of (R)-(4-(2-chloro-5-((4-methoxybenzyl) oxy) pyrimidin-4-yl) morpholin-3-yl) methanol (400 mg, 1.09 mmol) in CH$_2$Cl$_2$ (5 mL) under an argon atmosphere was added trifluoroacetic acid (2 mL) at 0° C. The reaction mixture was stirred for 2 h. After consumption of starting material (monitored by TLC), the reaction mixture was quenched with a sodium bicarbonate solution (20 mL) and extracted with EtOAc (2×20 mL). The combined organic extracts were dried over sodium sulfate, filtered and concentrated in vacuo. The crude material was purified by column chromatography using 2-3% MeOH: CH$_2$Cl$_2$ to afford (R)-2-chloro-4-(3-(hydroxymethyl) morpholino) pyrimidin-5-ol (200 mg, 75%) as a colorless liquid. $^1$H-NMR (DMSO-$d_6$, 500 MHz): δ 10.25 (br s, 1H), 7.62 (s, 1H), 4.86 (br s, 1H), 4.70-4.65 (m, 1H), 4.15-4.10 (m, 1H), 3.90-3.82 (m, 2H), 3.70-3.63 (m, 1H), 3.43 (t, 3H), 3.21-3.18 (m, 1H); TLC: 5% MeOH/CH$_2$Cl$_2$ (R$_f$: 0.4).

Synthesis of (S)-2-chloro-6a, 7, 9, 10-tetrahydro-6H-[1, 4] oxazino [4, 3-d] pyrimido [5, 4-b] [1, 4] oxazine To a stirred solution of (R)-2-chloro-4-(3-(hydroxymethyl) morpholino) pyrimidin-5-ol (120 mg, 0.48 mmol) in THF (2 mL) under an argon atmosphere were added triphenylphosphine (154 mg, 0.97 mmol) and diisopropylazodicarboxylate (118 mg, 0.97 mmol) at 0° C. The reaction mixture was warmed to room temperature and stirred for 2 h. After consumption of starting material (monitored by TLC), the volatile components were concentrated in vacuo. The crude material was purified by column chromatography using 30% EtOAc:hexanes to afford (S)-2-chloro-6a, 7, 9, 10-tetrahydro-6H-[1, 4] oxazino [4, 3-d] pyrimido [5, 4-b] [1, 4] oxazine (80 mg, 72%) as an off-white solid. $^1$H-NMR (DMSO-$d_6$, 500 MHz): δ 7.75 (s, 1H), 4.80-4.77 (m, 1H), 4.38-4.30 (m, 1H), 3.99-3.81 (m, 3H), 3.70-3.65 (m, 1H), 3.50-3.45 (m, 1H), 3.15 (t, 1H), 3.00 (t, 1H); LCMS: 228.1 (M+1); (column; X-Select CSH C-18 (50×3.0 mm, 3.5 μm); RT 2.85 min 0.05% Aq TFA: ACN; 0.8 mL/min); TLC: 50% EtOAc:hexane (R$_f$: 0.5).

Example 284

Synthesis of (R)-2-chloro-6a, 7, 9, 10-tetrahydro-6H-[1, 4] oxazino [4, 3-d] pyrimido [5, 4-b] [1, 4] oxazine

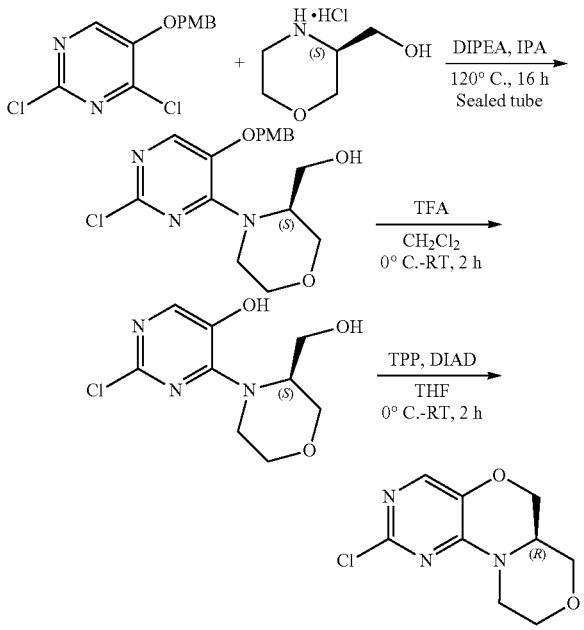

Synthesis of (S)-(4-(2-chloro-5-((4-methoxybenzyl) oxy) pyrimidin-4-yl) morpholin-3-yl) methanol To a stirred solution of 2, 4-dichloro-5-((4-methoxybenzyl) oxy) pyrimidine (500 mg, 1.75 mmol) in isopropyl alcohol (5 mL) under an argon atmosphere were added diisopropylethylamine (5 mL) and (S)-morpholin-3-ylmethanol hydrochloride (295 mg, 1.92 mmol) at room temperature. The reaction mixture was stirred at 120° C. for 16 h in a sealed tube. After consumption of starting material (monitored by TLC), the reaction mixture was diluted with a sodium bicarbonate solution (20 mL) and extracted with EtOAc (2×20 mL). The combined organic extracts were dried over sodium sulfate, filtered and concentrated in vacuo. The crude material was purified by column chromatography using 30-40% EtOAc:hexane to afford (S)-(4-(2-chloro-5-((4-methoxybenzyl) oxy) pyrimidin-4-yl) morpholin-3-yl) methanol (430 mg, 67%) as a colorless liquid. $^1$H-NMR (DMSO-d$_6$, 500 MHz): δ 7.96 (s, 1H), 7.39 (d, 2H), 6.95 (d, 2H), 5.04 (s, 2H), 4.83 (t, 1H), 4.70-4.64 (m, 1H), 4.09-4.01 (m, 1H), 3.86-3.81 (m, 2H), 3.76 (s, 3H), 3.69-3.60 (m, 2H), 3.54-3.42 (m, 2H), 3.26-3.20 (m, 1H); LCMS: 366.3 (M+1); (column; X-Select CSH C-18 (50×3.0 mm, 3.5 μm); RT 3.75 min 5 mM Aq NH$_4$OAc: ACN; 0.8 mL/min); TLC: 50% EtOAc:hexane (R$_f$: 0.3).

Synthesis of (S)-2-chloro-4-(3-(hydroxymethyl) morpholino) pyrimidin-5-ol

To a stirred solution of (S)-(4-(2-chloro-5-((4-methoxybenzyl) oxy) pyrimidin-4-yl) morpholin-3-yl) methanol (430 mg, 1.17 mmol) in CH$_2$Cl$_2$ (5 mL) under an argon atmosphere was added trifluoroacetic acid (2 mL) at 0° C. The reaction mixture was warmed to room temperature stirred for 2 h. After consumption of starting material (monitored by TLC), the reaction mixture was quenched with a saturated sodium bicarbonate solution (20 mL) and extracted with EtOAc (2×20 mL). The combined organic extracts were dried over sodium sulfate, filtered and concentrated in vacuo. The crude material was purified by column chromatography using 2-3% MeOH: CH$_2$Cl$_2$ to afford (S)-2-chloro-4-(3-(hydroxymethyl) morpholino) pyrimidin-5-ol (230 mg, 79%) as an off-white solid. $^1$H-NMR (DMSO-d$_6$, 500 MHz): δ 10.20 (br s, 1H), δ 7.62 (s, 1H), 4.86 (br s, 1H), 4.70-4.65 (m, 1H), 4.15-4.10 (m, 1H), 3.90-3.82 (m, 2H), 3.70-3.63 (m, 1H), 3.43 (t, 3H), 3.21-3.18 (m, 1H); TLC: 5% MeOH/CH$_2$Cl$_2$ (R$_f$: 0.4).

Synthesis of (R)-2-chloro-6a, 7, 9, 10-tetrahydro-6H-[1, 4] oxazino [4, 3-d] pyrimido [5, 4-b] [1, 4] oxazine To a stirred solution of (S)-2-chloro-4-(3-(hydroxymethyl) morpholino) pyrimidin-5-ol (200 mg, 0.81 mmol) in THF (2 mL) under an argon atmosphere were added triphenylphosphine (255 mg, 0.97 mmol) and diisopropylazodicarboxylate (207 mg, 0.97 mmol) at 0° C. The reaction mixture was warmed to room temperature and stirred for 2 h. After consumption of starting material (monitored by TLC), the volatile components were concentrated in vacuo. The crude material was purified by column chromatography using 30% EtOAc:hexane to afford (R)-2-chloro-6a, 7, 9, 10-tetrahydro-6H-[1, 4] oxazino [4, 3-d] pyrimido [5, 4-b] [1, 4] oxazine (100 mg, 55%) as an off-white solid. $^1$H-NMR (DMSO-d$_6$, 500 MHz): δ 7.75 (s, 1H), 4.80-4.77 (m, 1H), 4.38-4.30 (m, 1H), 3.99-3.81 (m, 3H), 3.70-3.65 (m, 1H), 3.50-3.45 (m, 1H), 3.15 (t, 1H), 3.00 (t, 1H); LCMS: 228.1 (M+1); (column; X-Select CSH C-18 (50×3.0 mm, 3.5 μm); RT 2.85 min 0.05% Aq TFA: ACN; 0.8 mL/min); TLC: 50% EtOAc:hexane (R$_f$: 0.5).

Example 285

Synthesis of N-(3-methoxy-4-(2-methylpyridin-4-yl) phenyl)-7, 8-dimethyl-7, 8-dihydro-6H-pyrimido [5, 4-b] [1, 4] oxazin-2-amine

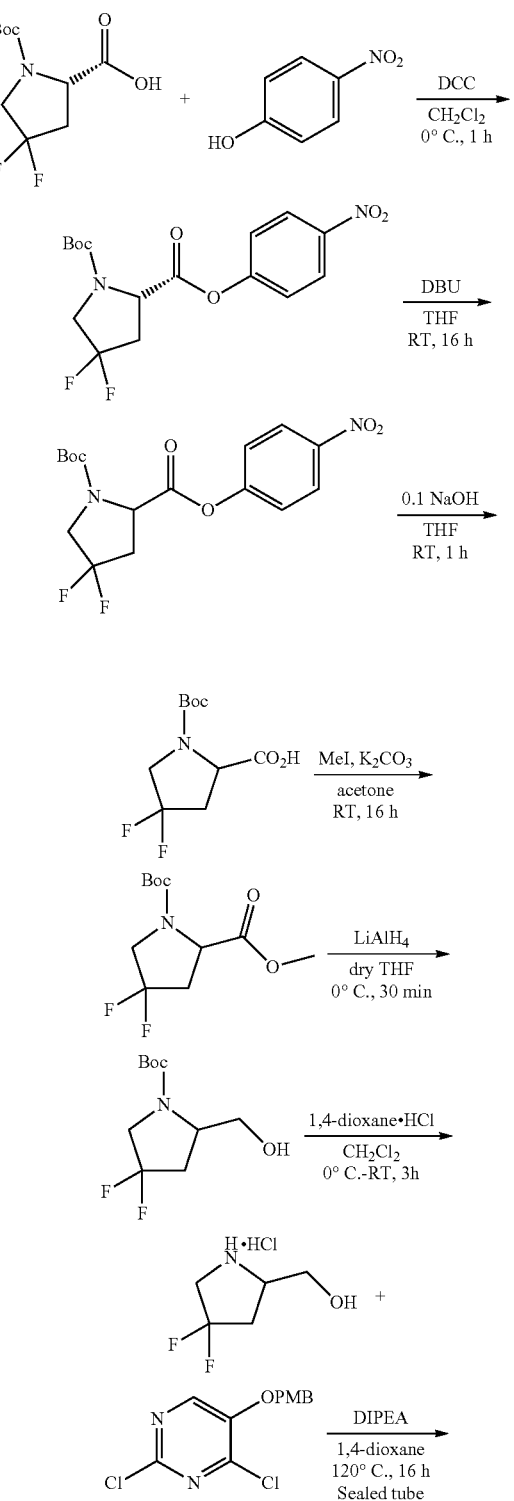

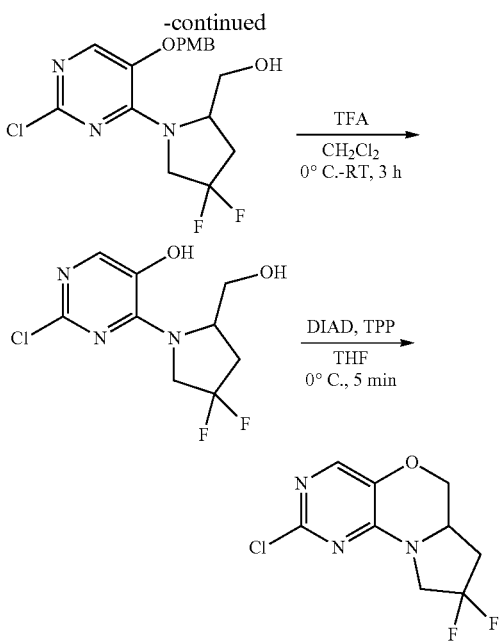

Synthesis of 1-(tert-butyl) 2-(4-nitrophenyl) (S)-4, 4-difluoropyrrolidine-1, 2-dicarboxylate To a stirred solution of (S)-1-(tert-butoxycarbonyl)-4,4-difluoropyrrolidine-2-carboxylic acid (2.05 g, 8.16 mmol) in CH$_2$Cl$_2$ (20 mL) under an argon atmosphere were added DCC (2.01 g, 9.80 mmol) and 4-nitrophenol (1.13 g, 8.16 mmol) at 0° C. The reaction mixture was stirred for 1 h. After consumption of starting material (monitored by TLC), the reaction mixture was filtered. The filtrate was washed with a saturated sodium bicarbonate solution (2×100 mL), ammonium chloride solution (50 mL), and water (50 mL). The combined organic extracts were dried over sodium sulfate, filtered and concentrated in vacuo to obtain 1-(tert-butyl) 2-(4-nitrophenyl) (S)-4, 4-difluoropyrrolidine-1, 2-dicarboxylate (3 g, 99%) as an off-white solid used in the next step without further purification. $^1$H-NMR (400 MHz, CDCl$_3$): δ 8.32-8.27 (m, 2H), 7.30-7.28 (m, 2H), 4.80-4.70 (m, 1H), 3.95-3.80 (m, 2H), 2.90-2.80 (m, 1H), 2.70-2.60 (m, 1H), 1.50 (s, 9H): TLC: 20% EtOAc:hexanes (R$_f$: 0.7).

Synthesis of 1-(tert-butyl) 2-(4-nitrophenyl) 4, 4-difluoropyrrolidine-1, 2-dicarboxylate To a stirred solution of 1-(tert-butyl) 2-(4-nitrophenyl) (S)-4, 4-difluoropyrrolidine-1, 2-dicarboxylate (3 g, 8.06 mmol) in THF (30 mL) under an argon atmosphere was added DBU (1.8 g, 12.09 mmol) at room temperature. The reaction mixture was stirred for 16 h. After consumption of starting material (monitored by TLC), the reaction mixture was diluted with water (100 mL) and extracted with EtOAc (2×100 mL). The combined organic extracts were dried over sodium sulfate, filtered and concentrated in vacuo to obtain 1-(tert-butyl) 2-(4-nitrophenyl) 4, 4-difluoropyrrolidine-1, 2-dicarboxylate (3 g, 99%) as an off-white solid used in the next step without further purification. TLC: 20% EtOAc:hexanes (R$_f$: 0.7).

Synthesis of 1-(tert-butoxycarbonyl)-4, 4-difluoropyrrolidine-2-carboxylic acid To a stirred solution of 1-(tert-butyl) 2-(4-nitrophenyl) 4, 4-difluoropyrrolidine-1, 2-dicarboxylate (3 g, 8.06 mmol) in THF (161 mL) under an argon atmosphere was added a 0.1 N sodium hydroxide solution (161.29 mL, 161.2 mmol) at room temperature. The reaction mixture was stirred for 1 h. After consumption of starting material (monitored by TLC), the reaction mixture was acidified with citric acid solution up to pH=4 and extracted with EtOAc (2×100 mL). The combined organic extracts were dried over sodium sulfate, filtered and concentrated in vacuo to obtain 1-(tert-butoxycarbonyl)-4, 4-difluoropyrrolidine-2-carboxylic acid (3 g, crude) as an off-white solid used in the next step without further purification. $^1$H NMR (500 MHz, CDCl$_3$): δ 4.50-4.43 (m, 1H), 3.80-3.73 (m, 2H), 2.88-2.78 (m, 1H), 2.50-2.348 (m, 1H), 1.42 (s, 9H): TLC: 50% EtOAc:hexanes (R$_f$: 0.2).

Synthesis of 1-(tert-butyl) 2-methyl 4, 4-difluoropyrrolidine-1, 2-dicarboxylate To a stirred solution of 1-(tert-butoxycarbonyl)-4, 4-difluoropyrrolidine-2-carboxylic acid (3 g, 11.95 mmol) in acetone (30 mL) under an argon atmosphere were added potassium carbonate (1.64 g, 11.95 mmol) and methyl iodide (1.86 g, 13.10 mmol) at room temperature. The reaction mixture was stirred for 16 h. After consumption of starting material (monitored by TLC), the reaction mixture was filtered and washed with EtOAc (100 mL). The filtrate was concentrated in vacuo to obtain 1-(tert-butyl) 2-methyl 4, 4-difluoropyrrolidine-1, 2-dicarboxylate (1.2 g, 38%) as a yellow liquid used in the next step without further purification. $^1$H NMR (500 MHz, CDCl$_3$): δ 4.50-4.46 (m, 1H), 3.88-3.82 (m, 2H), 3.78 (s, 3H), 2.75-2.68 (m, 1H), 2.51-2.44 (m, 1H), 1.49 (s, 9H): TLC: 20% EtOAc:hexanes (R$_f$: 0.5).

Synthesis of tert-butyl 4, 4-difluoro-2-(hydroxymethyl) pyrrolidine-1-carboxylate To a stirred solution of 1-(tert-butyl) 2-methyl 4, 4-difluoropyrrolidine-1, 2-dicarboxylate (1.2 g, 4.52 mmol) in dry THF (12 mL) under an argon atmosphere was added lithium aluminum hydride (172 mg, 4.52 mmol) at 0° C. The reaction mixture was stirred for 30 min. After consumption of starting material (monitored by TLC), the reaction mixture was filtered and washed with EtOAc (100 mL). The filtrate was concentrated in vacuo to obtain tert-butyl 4, 4-difluoro-2-(hydroxymethyl) pyrrolidine-1-carboxylate (1 g, 93%) as a colorless oil used in the next step without further purification. $^1$H-NMR (CDCl$_3$ 500 MHz): δ 4.20-4.13 (m, 1H), 3.82-3.65 (m, 2H), 2.53-2.49 (m, 1H), 2.16-2.12 (m, 1H), 1.63-1.61 (m, 2H), 1.45 (s, 9H), 1.29-1.26 (m, 1H); TLC: 20% EtOAc:hexanes (R$_f$: 0.3).

Synthesis of (4, 4-difluoropyrrolidin-2-yl) methanol hydrochloride

To a stirred solution of tert-butyl 4, 4-difluoro-2-(hydroxymethyl) pyrrolidine-1-carboxylate (1 g, 4.21 mmol) in CH$_2$Cl$_2$ (5 mL) under an argon atmosphere was added HCl in 1, 4-dioxane (5 mL) at 0° C. The reaction mixture was warmed to room temperature and stirred for 3 h. After consumption of starting material (monitored by TLC), the volatile components were evaporated in vacuo. The crude material was washed with n-heptane (2×25 mL) to afford (4, 4-difluoropyrrolidin-2-yl) methanol hydrochloride (560 mg, 97%) as an off-white solid used in the next step without further purification. $^1$H-NMR (DMSO-d$_6$, 500 MHz): δ 9.87

(br s, 1H), 5.55 (br s, 1H), 3.89-3.87 (m, 1H), 3.75-3.61 (m, 3H), 2.63-2.60 (m, 1H), 2.37-2.33 (m, 1H); TLC: 30% EtOAc:hexanes ($R_f$: 0.1).

Synthesis of (1-(2-chloro-5-((4-methoxybenzyl) oxy) pyrimidin-4-yl)-4, 4-difluoropyrrolidin-2-yl) methanol To a stirred solution of 2, 4-dichloro-5-((4-methoxybenzyl) oxy) pyrimidine (560 mg, 4.08 mmol) in 1, 4-dioxane (3 mL) under an argon atmosphere were added diisopropylethylamine (3 mL, 16.35 mmol) and (4, 4-difluoropyrrolidin-2-yl) methanol hydrochloride (1.16 g, 4.08 mmol) at room temperature. The reaction mixture was stirred at 120° C. for 16 h in a sealed tube. After consumption of starting material (monitored by TLC), the volatile components were evaporated in vacuo. The crude material was purified by column chromatography using 40% EtOAc:hexanes to afford (1-(2-chloro-5-((4-methoxybenzyl) oxy) pyrimidin-4-yl)-4, 4-difluoropyrrolidin-2-yl) methanol (1.1 g, 70%) as an off-white solid. $^1$H NMR (500 MHz, $CDCl_3$): δ 7.78 (s, 1H), 7.30 (d, 2H), 6.94 (d, 2H), 4.95 (s, 2H), 4.72-4.70 (m, 1H), 4.24-4.22 (m, 1H), 4.06-4.03 (m, 1H), 3.84 (s, 3H), 3.81-3.75 (m, 2H), 2.51-2.37 (m, 2H); TLC: 50% EtOAc:hexanes ($R_f$: 0.4).

Synthesis of 2-chloro-4-(4, 4-difluoro-2-(hydroxymethyl) pyrrolidin-1-yl) pyrimidin-5-ol To a stirred solution of (1-(2-chloro-5-((4-methoxybenzyl) oxy) pyrimidin-4-yl)-4, 4-difluoropyrrolidin-2-yl) methanol (1.1 g, 2.84 mmol) in $CH_2Cl_2$ (15 mL) under an argon atmosphere was added trifluoroacetic acid (1.3 g, 11.39 mmol) at 0° C. The reaction mixture was warmed to room temperature and stirred for 3 h. After consumption of starting material (monitored by TLC), the reaction mixture was quenched with a saturated sodium bicarbonate solution (100 mL) and extracted with $CH_2Cl_2$ (2×100 mL). The aqueous layer was acidified with citric acid solution (100 mL) and extracted with EtOAc (2×100 mL). The combined organic extracts were dried over sodium sulfate, filtered and concentrated in vacuo to obtain the 2-chloro-4-(4, 4-difluoro-2-(hydroxymethyl) pyrrolidin-1-yl) pyrimidin-5-ol (1.1 g, crude) as an off-white solid used in the next step without further purification. LCMS: 265.9 (M+1); (column; X-Select CSH C-18 (50×3.0 mm, 3.5 μm); RT 2.58 min 0.05% Aq TFA: ACN; 0.80 mL/min); TLC: 60% EtOAc: hexanes ($R_f$: 0.3).

Synthesis of 2-chloro-8, 8-difluoro-6a, 7, 8, 9-tetrahydro-6H-pyrimido [5, 4-b] pyrrolo [1, 2-d] [1, 4] oxazine To a stirred solution of 2-chloro-4-(4, 4-difluoro-2-(hydroxymethyl) pyrrolidin-1-yl) pyrimidin-5-ol (800 mg, 3.01 mmol) in THF (10 mL) under an argon atmosphere were added triphenylphosphine (1.18 g, 4.52 mmol) and diisopropylazodicarboxylate (914 mg, 4.52 mmol) at 0° C. The reaction mixture was stirred for 5 min. After consumption of starting material (monitored by TLC), the volatile components were concentrated in vacuo. The crude material was purified by column chromatography using 30% EtOAc: hexane to afford 2-chloro-8, 8-difluoro-6a, 7, 8, 9-tetrahydro-6H-pyrimido [5, 4-b] pyrrolo [1, 2-d] [1, 4] oxazine (1.2 g, 99%) as an off-white solid. $^1$H NMR (400 MHz, $CDCl_3$): δ 7.78 (s, 1H), 5.00-4.92 (m, 1H), 4.57-4.54 (m, 1H), 4.20-4.10 (m, 2H), 3.99-3.90 (m, 1H), 3.59-3.53 (m, 1H), 2.68-2.60 (m, 1H); LCMS: 247.8 (M+1); (column; X-Select CSH C-18 (50×3.0 mm, 3.5 μm); RT 2.91 min 0.05% Aq TFA: ACN; 0.80 mL/min); TLC: 50% EtOAc: hexane ($R_f$: 0.7).

Example 286

Synthesis of 2-chloro-6, 6a, 7, 8-tetrahydro-9H-pyrimido [5, 4-b] pyrrolo [1, 2-d] [1, 4] oxazin-9-one

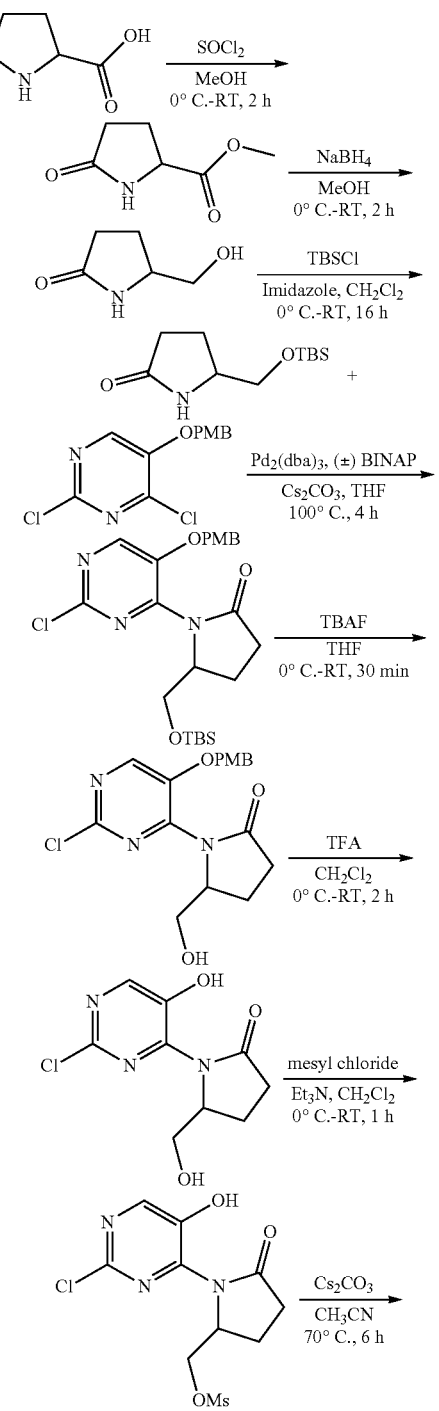

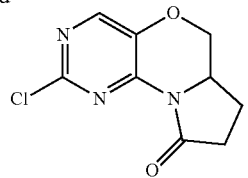

Synthesis of methyl 5-oxopyrrolidine-2-carboxylate

To a stirred solution of 5-oxopyrrolidine-2-carboxylic acid (10 g, 77.51 mmol) in MeOH (80 mL) under an argon atmosphere was added thionyl chloride (8.3 mL, 116.0 mmol) at 0° C. The reaction mixture was warmed to room temperature and stirred for 2 h. After consumption of starting material (monitored by TLC), the volatile components were concentrated in vacuo. The residue was diluted with a saturated sodium bicarbonate solution (200 mL) and extracted with 5% MeOH: $CH_2Cl_2$ (2×200 mL). The combined organic extracts were dried over sodium sulfate, filtered and concentrated in vacuo to obtain methyl 5-oxopyrrolidine-2-carboxylate (9 g, 82%) as a colorless oil. TLC: 10% MeOH/$CH_2Cl_2$ ($R_f$: 0.4).

Synthesis of 5-(hydroxymethyl) pyrrolidin-2-one

To a stirred solution of methyl 5-oxopyrrolidine-2-carboxylate (9 g, 62.93 mmol) in MeOH (150 mL) under an argon atmosphere was added sodium borohydride (3.6 g, 95.2 mmol) at 0° C. The reaction mixture was warmed to room temperature and stirred for 2 h. After consumption of starting material (monitored by TLC), the reaction mixture was quenched with concentrated HCl at 0° C., filtered, and washed with MeOH (2×50 mL). The filtrate was concentrated in vacuo. The crude material was purified by column chromatography using 10% MeOH: $CH_2Cl_2$ to afford 5-(hydroxymethyl) pyrrolidin-2-one (6 g, 83%) as a colorless oil. LCMS: 116 (M+1); (column; X-Select CSH C-18 (50×3.0 mm, 3.5 μm); RT 0.44 min 5 mM $NH_4OAc$ in water: ACN; 0.80 mL/min); TLC: 10% MeOH/$CH_2Cl_2$ ($R_f$: 0.3).

Synthesis of 5-(((tert-butyldimethylsilyl) oxy) methyl) pyrrolidin-2-one

To a stirred solution of 5-(hydroxymethyl) pyrrolidin-2-one (6 g, 52.17 mmol) in $CH_2Cl_2$ (100 mL) under an argon atmosphere were added imidazole (5.3 g, 78.26 mmol) and TBSCl (10.2 g, 67.82 mmol) at 0° C. The reaction mixture was warmed to room temperature and stirred for 16 h. After consumption of starting material (monitored by TLC), the reaction mixture was diluted with water (100 mL) and extracted with $CH_2Cl_2$ (2×100 mL). The combined organic extracts were dried over sodium sulfate, filtered and concentrated in vacuo. The crude material was purified by column chromatography using 5% MeOH: $CH_2Cl_2$ to afford 5-(((tert-butyldimethylsilyl) oxy) methyl) pyrrolidin-2-one (9 g, 76%) as a colorless liquid. $^1$H-NMR ($CDCl_3$, 500 MHz): δ 5.90 (br s, 1H), 3.90-3.80 (m, 1H), 3.62 (dd, 1H), 3.43 (dt, 1H), 2.38-2.31 (m, 2H), 2.20-2.15 (m, 1H), 1.79-1.80 (m, 1H), 1.87 (s, 9H), 0.04 (s, 6H); LCMS: 230 (M+1); (column; X-Select CSH C-18 (50×3.0 mm, 3.5 μm); RT 3.48 min 0.05% Aq TFA: ACN; 0.80 mL/min); TLC: 10% MeOH/$CH_2Cl_2$ ($R_f$: 0.5).

Synthesis of 5-(((tert-butyldimethylsilyl) oxy) methyl)-1-(2-chloro-5-((4-methoxybenzyl) oxy) pyrimidin-4-yl) pyrrolidin-2-one To a stirred solution of 5-(((tert-butyldimethylsilyl) oxy) methyl) pyrrolidin-2-one (2 g, 8.73 mmol) in THF (15 mL) under an argon atmosphere were added 2, 4-dichloro-5-((4-methoxybenzyl) oxy) pyrimidine (2.5 g, 8.73 mmol), (±) BINAP (814 mg, 1.31 mmol) and cesium carbonate (3.9 g, 12.22 mmol) and purged with argon for 15 min. Then $Pd_2(dba)_3$ (399 mg, 0.43 mmol) was added to the reaction mixture at room temperature. The reaction mixture was stirred at 100° C. for 4 h. After consumption of starting material (monitored by TLC), the reaction mixture was filtered and washed with EtOAc (2×50 mL). The filtrate was concentrated in vacuo. The crude material was purified by column chromatography using 30% EtOAc:hexanes to afford 5-(((tert-butyldimethylsilyl) oxy) methyl)-1-(2-chloro-5-((4-methoxybenzyl) oxy) pyrimidin-4-yl) pyrrolidin-2-one (1.5 g, 24%) as a pale yellow oil. $^1$H-NMR ($CDCl_3$, 500 MHz): δ 8.22 (s, 1H), 7.39 (d, 2H), 6.90 (d, 2H), 5.10 (s, 2H), 4.57-4.55 (m, 1H), 3.80 (s, 3H), 3.79-3.77 (m, 1H), 3.63 (dd, 1H), 2.70-2.63 (m, 1H), 2.50-2.42 (m, 1H), 2.33-2.25 (m, 1H), 2.10-2.00 (m, 1H), 0.76 (s, 9H), 0.08 (s, 6H); LCMS: 478 (M+1); (column; X-Select CSH C-18 (50×3.0 mm, 3.5 μm); RT 4.64 min 0.05% Aq TFA: ACN; 0.80 mL/min); TLC: 10% MeOH/$CH_2Cl_2$ ($R_f$: 0.5).

Synthesis of 1-(2-chloro-5-((4-methoxybenzyl) oxy) pyrimidin-4-yl)-5-(hydroxymethyl) pyrrolidin-2-one To a stirred solution of 5-(((tert-butyldimethylsilyl) oxy) methyl)-1-(2-chloro-5-((4-methoxybenzyl) oxy) pyrimidin-4-yl) pyrrolidin-2-one (1.5 g, 3.14 mmol) in THF (20 mL) under an argon atmosphere was added tert-butyl ammonium fluoride (3.7 mL, 3.77 mmol) at 0° C. The reaction mixture was warmed to room temperature and stirred for 30 min. After consumption of starting material (monitored by TLC), the reaction mixture was diluted with water (50 mL) and extracted with EtOAc (2×50 mL). The combined organic extracts were dried over sodium sulfate, filtered and concentrated in vacuo. The crude material was purified by column chromatography using 3% MeOH: $CH_2Cl_2$ to afford 1-(2-chloro-5-((4-methoxybenzyl) oxy) pyrimidin-4-yl)-5-(hydroxymethyl) pyrrolidin-2-one (1 g, 88%) as a yellow solid. $^1$H-NMR (DMSO-$d_6$, 400 MHz): δ 8.20 (s, 1H), 7.71 (s, 1H), 7.31 (d, 2H), 6.90 (d, 2H), 5.10 (s, 2H), 4.30-4.20 (m, 2H), 3.90-3.86 (m, 1H), 3.70 (s, 3H), 2.25-2.00 (m, 3H), 1.86-1.80 (m, 1H); LCMS: 363.9 (M+1); (column; X-Select CSH C-18 (50×3.0 mm, 3.5 μm); RT 3.08 min 0.05% Aq TFA: ACN; 0.80 mL/min); TLC: 5% MeOH/$CH_2Cl_2$ ($R_f$: 0.5).

Synthesis of 1-(2-chloro-5-hydroxypyrimidin-4-yl)-5-(hydroxymethyl) pyrrolidin-2-one To a stirred solution of 1-(2-chloro-5-((4-methoxybenzyl) oxy) pyrimidin-4-yl)-5-(hydroxymethyl) pyrrolidin-2-one (1 g, 2.75 mmol) in $CH_2Cl_2$ (20 mL) under an argon atmosphere was added trifluoroacetic acid (1 mL) at 0° C. The reaction mixture was warmed at room temperature and stirred for 2 h. After consumption of starting material (monitored by TLC), the volatile components were concentrated in vacuo. The crude material was purified by column chromatography using 4% MeOH: $CH_2Cl_2$ to afford 1-(2-chloro-5-hydroxypyrimidin-4-yl)-5-(hydroxymethyl) pyrrolidin-2-one (200 mg, 30%) as a pale yellow solid. LCMS:

243.9 (M+1); (column; X-Select CSH C-18 (50×3.0 mm, 3.5 µm); RT 2.12 min 0.05% Aq TFA: ACN; 0.80 mL/min); TLC: 5% MeOH/CH$_2$Cl$_2$ (R$_f$: 0.5).

Synthesis of (1-(2-chloro-5-hydroxypyrimidin-4-yl)-5-oxopyrrolidin-2-yl) methyl methanesulfonate To a stirred solution of 1-(2-chloro-5-hydroxypyrimidin-4-yl)-5-(hydroxymethyl) pyrrolidin-2-one (200 mg, 0.82 mmol) in CH$_2$Cl$_2$ (10 mL) under an argon atmosphere were added triethylamine (0.16 mL, 1.64 mmol) and methanesulfonyl chloride (0.09 mL, 1.23 mmol) at 0° C. The reaction mixture was warmed to room temperature and stirred for 1 h. After consumption of starting material (monitored by TLC), the reaction mixture was diluted with water (20 mL) and extracted with CH$_2$Cl$_2$ (2×20 mL). The combined organic extracts were dried over sodium sulfate, filtered and concentrated in vacuo to obtain (1-(2-chloro-5-hydroxypyrimidin-4-yl)-5-oxopyrrolidin-2-yl) methyl methanesulfonate (220 mg, crude) as a yellow solid used in the next step without further purification. TLC: 10% MeOH/CH$_2$Cl$_2$ (R$_f$: 0.6).

Synthesis of 2-chloro-6, 6a, 7, 8-tetrahydro-9H-pyrimido [5, 4-b] pyrrolo [1, 2-d] [1, 4] oxazin-9-one To a stirred solution of (1-(2-chloro-5-hydroxypyrimidin-4-yl)-5-oxopyrrolidin-2-yl) methyl methanesulfonate (220 mg, 0.68 mmol) in CH$_3$CN (10 mL) under an argon atmosphere was added cesium carbonate (666 mg, 2.04 mmol) at room temperature. The reaction mixture was stirred at 70° C. for 6 h. After consumption of starting material (monitored by TLC), the reaction mixture was diluted with water (20 mL) and extracted with EtOAc (2×20 mL). The combined organic extracts were dried over sodium sulfate, filtered and concentrated in vacuo. The crude material was purified by column chromatography using 2% MeOH: CH$_2$Cl$_2$ to afford 2-chloro-6, 6a, 7, 8-tetrahydro-9H-pyrimido [5, 4-b] pyrrolo [1, 2-d] [1, 4] oxazin-9-one (70 mg, 45%) as a pale yellow solid. $^1$H-NMR (CDCl$_3$, 500 MHz): δ 8.20 (s, 1H), 4.29 (dd, 1H), 4.16-4.06 (m, 1H), 3.83 (t, 1H), 2.73-2.60 (m, 2H), 2.41-2.37 (m, 1H), 1.80-1.72 (m, 1H); LCMS: 225.8 (M+1); (column; X-Select CSH C-18 (50×3.0 mm, 3.5 µm); RT 1.58 min 0.05% Aq TFA: ACN; 0.80 mL/min); UPLC (column; Acquity BEH C-18, 50×2.1 mm, 1.7 µm); RT 1.58 min. ACN: 0.025% Aq TFA; 0.5 mL/min; TLC: 10% MeOH/CH$_2$Cl$_2$ (R$_f$: 0.6).

Example 287

Synthesis of (S)-2-chloro-8, 8-difluoro-6a, 7, 8, 9-tetrahydro-6H-pyrimido [5, 4-b] pyrrolo [1, 2-d] [1, 4] oxazine

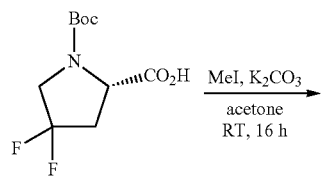

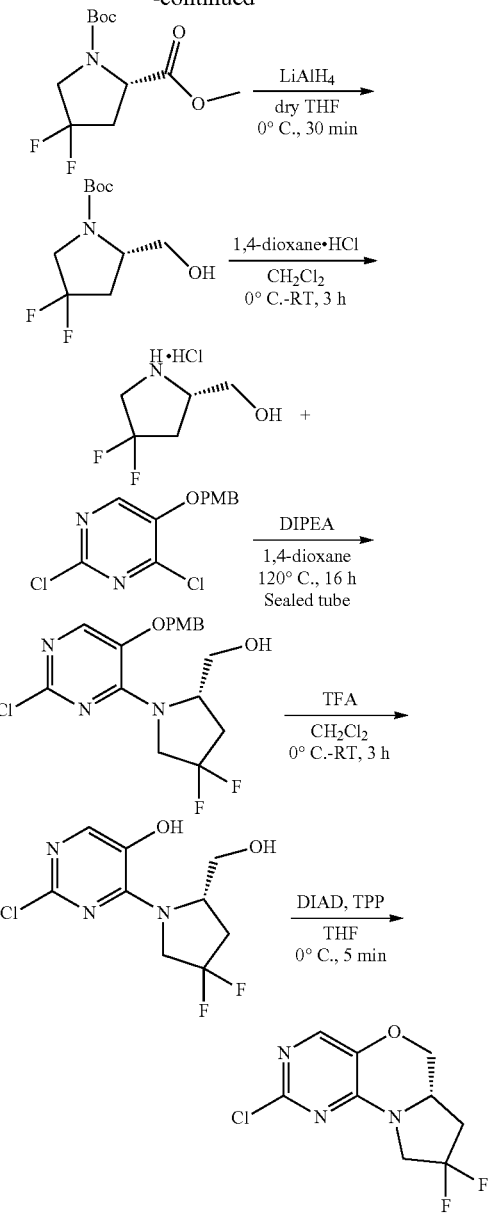

Synthesis of 1-(tert-butyl) 2-methyl (S)-4, 4-difluoropyrrolidine-1, 2-dicarboxylate To a stirred solution of (S)-1-(tert-butoxycarbonyl)-4, 4-difluoropyrrolidine-2-carboxylic acid (1 g, 3.98 mmol) in acetone (10 mL) under an argon atmosphere were added potassium carbonate (824 mg, 5.97 mmol) and methyl iodide (848 mg, 5.97 mmol) at room temperature. The reaction mixture was stirred for 16 h. After consumption of starting material (monitored by TLC), the reaction mixture was filtered and washed with EtOAc (100 mL). The filtrate was concentrated in vacuo to obtain 1-(tert-butyl) 2-methyl (S)-4, 4-difluoropyrrolidine-1, 2-dicarboxylate (1 g, 95%) as a yellow liquid used in the next step without further purification. $^1$H NMR (500 MHz, CDCl$_3$): δ 4.50-4.46 (m, 1H), 3.88-3.82 (m, 2H), 3.78 (s, 3H), 2.75-2.68 (m, 1H), 2.51-2.44 (m, 1H), 1.49 (s, 9H): TLC: 20% EtOAc:hexanes (R$_f$: 0.5).

Synthesis of tert-butyl (S)-4, 4-difluoro-2-(hydroxymethyl) pyrrolidine-1-carboxylate To a stirred solution of 1-(tert-butyl) 2-methyl (S)-4, 4-difluoropyrrolidine-1, 2-dicarboxylate (2 g, 7.54 mmol) in dry THF (20 mL) under an argon atmosphere was added lithium aluminum hydride (286 mg, 7.54 mmol) at 0° C. The reaction mixture was stirred for 30 min. After consumption of starting material (monitored by TLC), the reaction mixture was filtered, washed with EtOAc (100 mL) and the filtrate was concentrated in vacuo to obtain tert-butyl (S)-4, 4-difluoro-2-(hydroxymethyl) pyrrolidine-1-carboxylate (1.7 g, 95%) as a colorless oil used in the next step without further purification. $^1$H-NMR (CDCl$_3$ 500 MHz): δ 4.20-4.13 (m, 1H), 3.82-3.65 (m, 2H), 2.53-2.49 (m, 1H), 2.16-2.12 (m, 1H), 1.63-1.61 (m, 2H), 1.45 (s, 9H), 1.29-1.26 (m, 1H); TLC: 20% EtOAc:hexanes ($R_f$: 0.3).

Synthesis of (S)-(4, 4-difluoropyrrolidin-2-yl) methanol hydrochloride

To a stirred solution of tert-butyl (S)-4, 4-difluoro-2-(hydroxymethyl) pyrrolidine-1-carboxylate (1.7 g, 7.17 mmol) in CH$_2$Cl$_2$ (10 mL) under an argon atmosphere was added 4N HCl in 1, 4-dioxane (10 mL) at 0° C. The reaction mixture was warmed to room temperature and stirred for 3 h. After consumption of starting material (monitored by TLC), the volatile components were evaporated in vacuo. The crude material was washed with n-heptane (2×25 mL) to afford (S)-(4, 4-difluoropyrrolidin-2-yl) methanol hydrochloride (1.2 g, 97%) as an off-white solid used in the next step without further purification. $^1$H-NMR (DMSO-d$_6$, 500 MHz): δ 9.87 (br s, 1H), 5.55 (br s, 1H), 3.89-3.87 (m, 1H), 3.75-3.61 (m, 3H), 2.63-2.60 (m, 1H), 2.37-2.33 (m, 1H); TLC: 30% EtOAc:hexanes ($R_f$: 0.1).

Synthesis of (S)-(1-(2-chloro-5-((4-methoxybenzyl) oxy) pyrimidin-4-yl)-4, 4-difluoropyrrolidin-2-yl) methanol To a stirred solution of 2, 4-dichloro-5-((4-methoxybenzyl) oxy) pyrimidine (1.5 g, 5.26 mmol) in 1, 4-dioxane (4 mL) under an argon atmosphere were added diisopropylethylamine (3.8 mL, 21.01 mmol) and (S)-(4, 4-difluoropyrrolidin-2-yl) methanol hydrochloride (910 mg, 5.26 mmol) at room temperature. The reaction mixture was stirred at 120° C. for 16 h in a sealed tube. After consumption of starting material (monitored by TLC), the volatile components were evaporated in vacuo. The crude material was purified by column chromatography using 40% EtOAc:hexanes to afford (S)-(1-(2-chloro-5-((4-methoxybenzyl) oxy) pyrimidin-4-yl)-4, 4-difluoropyrrolidin-2-yl) methanol (1.2 g, 59%) as an off-white solid. $^1$H NMR (500 MHz, CDCl$_3$): δ 7.78 (s, 1H), 7.30 (d, 2H), 6.94 (d, 2H), 4.95 (s, 2H), 4.72-4.70 (m, 1H), 4.24-4.22 (m, 1H), 4.06-4.03 (m, 1H), 3.84 (s, 3H), 3.81-3.75 (m, 2H), 2.51-2.37 (m, 2H); TLC: 50% EtOAc:hexanes ($R_f$: 0.4).

Synthesis of (S)-2-chloro-4-(4, 4-difluoro-2-(hydroxymethyl) pyrrolidin-1-yl) pyrimidin-5-ol To a stirred solution of (S)-(1-(2-chloro-5-((4-methoxybenzyl) oxy) pyrimidin-4-yl)-4, 4-difluoropyrrolidin-2-yl) methanol (1.2 g, 3.10 mmol) in CH$_2$Cl$_2$ (15 mL) under an argon atmosphere was added trifluoroacetic acid (1.4 g, 12.43 mmol) at 0° C. The reaction mixture was warmed to room temperature and stirred for 3 h. After consumption of starting material (monitored by TLC), the reaction mixture was quenched with a saturated sodium bicarbonate solution (100 mL) and extracted with CH$_2$Cl$_2$ (2×100 mL). The aqueous layer was acidified with a citric acid solution (100 mL) and extracted with EtOAc (2×100 mL). The combined organic extracts were dried over sodium sulfate, filtered and concentrated in vacuo to obtain the (S)-2-chloro-4-(4, 4-difluoro-2-(hydroxymethyl) pyrrolidin-1-yl) pyrimidin-5-ol (800 mg, 97%) as an off-white solid used in the next step without further purification. LCMS: 265.9 (M+1); (column; X-Select CSH C-18 (50×3.0 mm, 3.5 μm); RT 2.58 min 0.05% Aq TFA: ACN; 0.80 mL/min); TLC: 60% EtOAc: hexanes ($R_f$: 0.3).

Synthesis of (S)-2-chloro-8, 8-difluoro-6a, 7, 8, 9-tetrahydro-6H-pyrimido [5, 4-b] pyrrolo [1, 2-d] [1, 4] oxazine To a stirred solution of (S)-2-chloro-4-(4, 4-difluoro-2-(hydroxymethyl) pyrrolidin-1-yl) pyrimidin-5-ol (800 mg, 3.01 mmol) in THF (10 mL) under an argon atmosphere were added triphenylphosphine (1.18 g, 4.52 mmol) and diisopropylazodicarboxylate (914 mg, 4.52 mmol) at 0° C. The reaction mixture was stirred for 5 min. After consumption of starting material (monitored by TLC), the reaction mixture was diluted with water (50 mL) and extracted with EtOAc (2×50 mL). The combined organic extracts were dried over sodium sulfate, filtered and concentrated in vacuo. The crude material was purified by column chromatography using 5% MeOH: CH$_2$Cl$_2$ to afford (S)-2-chloro-8, 8-difluoro-6a, 7, 8, 9-tetrahydro-6H-pyrimido [5, 4-b] pyrrolo [1, 2-d] [1, 4] oxazine (740 mg, 99%) as an off-white solid. $^1$H NMR (400 MHz, CDCl$_3$): δ 7.78 (s, 1H), 5.00-4.92 (m, 1H), 4.57-4.54 (m, 1H), 4.20-4.10 (m, 2H), 3.99-3.90 (m, 1H), 3.59-3.53 (m, 1H), 2.68-2.60 (m, 1H); LCMS: 247.8 (M+1); (column; X-Select CSH C-18 (50×3.0 mm, 3.5 μm); RT 2.91 min 0.05% Aq TFA: ACN; 0.80 mL/min); TLC: 2% MeOH/CH$_2$Cl$_2$ ($R_f$: 0.3).

Example 288

Synthesis of 2-chloro-7, 7-difluoro-6a, 7, 8, 9-tetrahydro-6H-pyrimido [5, 4-b] pyrrolo [1, 2-d] [1, 4]oxazine

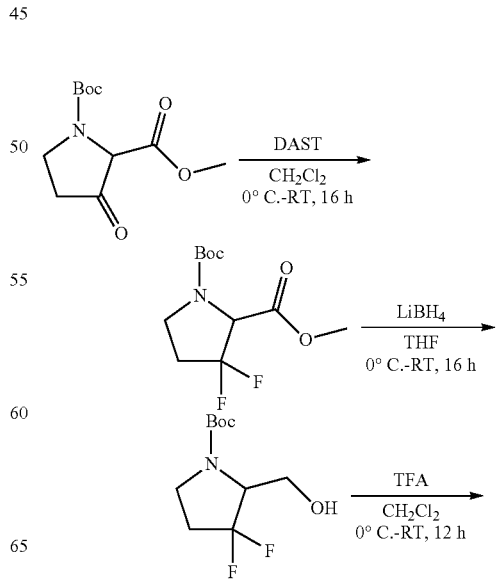

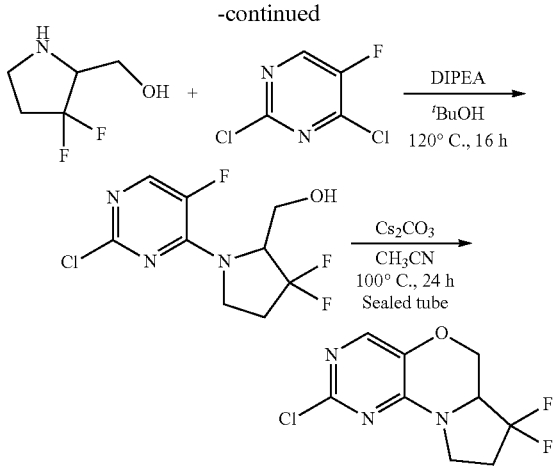

Synthesis of tert-butyl 2, 2-difluoro-3-oxopyrrolidine-1-carboxylate

To a stirred solution of 1-(tert-butyl) 2-methyl 3-oxopyrrolidine-1, 2-dicarboxylate (2 g, 7.78 mmol) in $CH_2Cl_2$ (40 mL) under an argon atmosphere was added DAST (3.75 g, 23.34 mmol) at 0° C. The reaction mixture was warmed to room temperature and stirred for 16 h. After consumption of starting material (monitored by TLC), the reaction mixture was quenched with a saturated sodium bicarbonate solution (100 mL) and extracted with $CH_2Cl_2$ (2×100 mL). The combined organic extracts were dried over sodium sulfate, filtered and concentrated in vacuo. The crude material was purified by column chromatography using 5% EtOAc: hexanes to afford tert-butyl 2, 2-difluoro-3-oxopyrrolidine-1-carboxylate (1.4 g, 65%) as a pale yellow liquid. $^1$H-NMR (DMSO-$d_6$, 500 MHz, $CDCl_3$): δ 4.50-4.45 (m, 1H), 4.21-4.13 (m, 2H), 3.60-3.47 (m, 1H), 2.41-2.32 (m, 1H), 1.40 (s, 9H), 1.21-1.17 (m, 3H): TLC: 20% EtOAc:hexanes ($R_f$: 0.7).

Synthesis of 1-(tert-butyl) 2-methyl 3, 3-difluoropyrrolidine-1, 2-dicarboxylate To a stirred solution of tert-butyl 2, 2-difluoro-3-oxopyrrolidine-1-carboxylate (1.5 g, 5.37 mmol) in THF (30 mL) under an argon atmosphere was added lithium borohydride (225 mg, 10.75 mmol) at 0° C. The reaction mixture was warmed to room temperature and stirred for 16 h. After consumption of starting material (monitored by TLC), the reaction mixture was quenched with a saturated sodium bicarbonate solution (50 mL) and extracted with $CH_2Cl_2$ (2×50 mL). The combined organic extracts were dried over sodium sulfate, filtered and concentrated in vacuo. The crude material was purified by column chromatography using 15% EtOAc:hexanes to afford 1-(tert-butyl) 2-methyl 3, 3-difluoropyrrolidine-1, 2-dicarboxylate (1.1 g, 67%) as a pale yellow liquid. $^1$H-NMR (DMSO-$d_6$, 400 MHz): δ 5.00-4.94 (m, 1H), 3.80-3.71 (m, 1H), 3.70-3.62 (m, 1H), 3.57-3.50 (m, 1H), 3.49-3.40 (m, 1H), 3.34-3.30 (m, 1H) 2.37-2.27 (m, 2H), 1.40 (s, 9H); TLC: 20% EtOAc:hexanes ($R_f$: 0.2).

Synthesis of tert-butyl 3, 3-difluoro-2-(hydroxymethyl) pyrrolidine-1-carboxylate To a stirred solution of 1-(tert-butyl) 2-methyl 3, 3-difluoropyrrolidine-1, 2-dicarboxylate (1.1 g, 4.64 mmol) in $CH_2Cl_2$ (20 mL) under an argon atmosphere was added trifluoroacetic acid (2.6 g, 23.20 mmol) at 0° C. The reaction mixture was warmed to room temperature and stirred for 12 h. After consumption of starting material (monitored by TLC), the reaction mixture was quenched with a saturated sodium bicarbonate solution (50 mL) and extracted with $CH_2Cl_2$ (2×50 mL). The combined organic extracts were dried over sodium sulfate, filtered and concentrated in vacuo to afford tert-butyl 3, 3-difluoro-2-(hydroxymethyl) pyrrolidine-1-carboxylate (730 mg, crude) as a colorless thick oil used in the next step without further purification. TLC: 10% MeOH/$CH_2Cl_2$ ($R_f$: 0.2).

Synthesis of (3, 3-difluoropyrrolidin-2-yl) methanol

To a stirred solution of tert-butyl 3, 3-difluoro-2-(hydroxymethyl) pyrrolidine-1-carboxylate (600 mg, 3.59 mmol) in tert-butanol (8 mL) under an argon atmosphere were added diisopropylethylamine (1.2 mL, 10.77 mmol) and 2, 4-dichloro-5-fluoropyrimidine (639 mg, 4.67 mmol) at room temperature. The reaction mixture was stirred at 120° C. for 16 h. After consumption of starting material (monitored by TLC), the reaction mixture was diluted with water (20 mL) and extracted with EtOAc (2×20 mL). The combined organic extracts were dried over sodium sulfate, filtered and concentrated in vacuo. The crude material was purified by column chromatography using 25% EtOAc: hexanes to afford (3, 3-difluoropyrrolidin-2-yl) methanol (300 mg, 31%) as an off-white solid. $^1$H NMR (DMSO-$d_6$, 400 MHz): δ 8.21 (d, 1H), 5.10 (t, 1H), 4.35 (d, 1H), 3.95-3.90 (m, 1H), 3.85-3.71 (m, 2H), 3.69-3.63 (m, 1H), 2.67-2.60 (m, 1H), 2.50-2.43 (m, 1H); LCMS: 267.9 (M+1); (column; Ascentis Express C-18 (50×3.0 mm, 2.7 μm); RT 1.97 min. 0.025% Aq TFA+5% ACN: 5% ACN+0.025% Aq TFA; 1.2 mL/min); TLC: 30% EtOAc:hexanes ($R_f$: 0.3).

Synthesis of 2-chloro-7, 7-difluoro-6a, 7, 8, 9-tetrahydro-6H-pyrimido [5, 4-b] pyrrolo [1, 2-d] [1, 4] oxazine To a stirred solution of (3, 3-difluoropyrrolidin-2-yl) methanol (450 mg, 1.68 mmol) in acetonitrile (15 mL) under an argon atmosphere was added cesium carbonate (1.36 g, 4.21 mmol) at room temperature. The reaction mixture was stirred at 100° C. for 24 h in a sealed tube. After consumption of starting material (monitored by TLC), the reaction mixture was diluted with water (20 mL) and extracted with EtOAc (2×20 mL). The combined organic extracts were dried over sodium sulfate, filtered and concentrated in vacuo. The crude material was purified by column chromatography using 20% EtOAc:hexanes to afford 2-chloro-7, 7-difluoro-6a, 7, 8, 9-tetrahydro-6H-pyrimido [5, 4-b] pyrrolo [1, 2-d] [1, 4] oxazine (205 mg, 49%) as an off-white solid. $^1$H-NMR ($CDCl_3$ 500 MHz): δ 7.79 (s, 1H), 4.61 (dd, 1H), 4.09-4.00 (m, 2H), 3.92-3.87 (m, 3H), 3.74-3.70 (m, 1H); LCMS: 247.9 (M+1); (column; Ascentis Express C-18 (50×3.0 mm, 2.7 μm); RT 2.00 min. 0.025% Aq TFA+5% ACN: 5% ACN+0.025% Aq TFA; 1.2 mL/min); TLC: 30% EtOAc:hexanes ($R_f$: 0.6).

Example 289

Synthesis of N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine

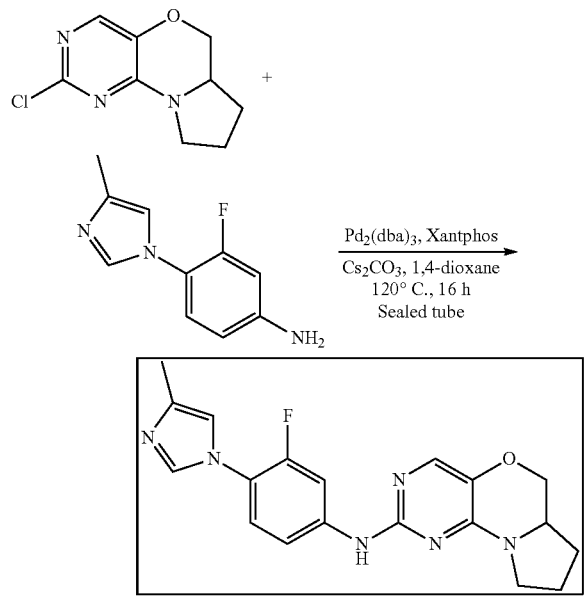

Synthesis of N-(3-fluoro-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine To a dry vial was added a suspension of Pd$_2$(dba)$_3$ (55 mg, 0.05 mmol) and Xantphos (100 mg, 0.19 mmol) in 1, 4-dioxane (2.5 mL) at room temperature. The suspension was degassed with argon, heated to 120° C., and stirred for 3 min. A mixture of 2-chloro-6a, 7, 8, 9-tetrahydro-6H-pyrimido [5, 4-b] pyrrolo [1, 2-d] [1, 4] oxazine (250 mg, 0.12 mmol), 3-fluoro-4-(4-methyl-1H-imidazol-1-yl) aniline (248 mg, 0.13 mmol) and cesium carbonate (700 mg, 2.36 mmol) in 1, 4-dioxane (2.5 mL) was degassed and the catalyst premixture was added. The resultant mixture was stirred at 120° C. for 16 h in a sealed tube. After consumption of the starting material (monitored by TLC and LCMS), the reaction mixture was filtered and the filtrate was concentrated in vacuo. The crude material was purified by column chromatography using 5% MeOH: CH$_2$Cl$_2$ to afford N-(3-fluoro-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine (140 mg, 32%) as an off-white solid. LCMS: 367.3 (M+1); (column; X-Select CSH C-18 (50×3.0 mm, 3.5 µm); RT 1.98 min 0.05% Aq TFA: ACN; 0.80 mL/min); UPLC (column; Acquity BEH C-18 2.1×50 mm, 1.7 µm); RT 1.29 min. ACN: 0.025% Aq TFA; 0.5 mL/min; TLC: 10% MeOH/CH$_2$Cl$_2$ (R$_f$; 0.2).

Racemic compound of Example 289 separated using a Chiralpak-IA column (250×4.6 mm, 5 µm (15 mg loading; 0.1% DEA in n-hexane: CH$_2$Cl$_2$:MeOH (50:50) (A:B: 70:30) as mobile phase) to provide the compound of Example 289A (Fraction I (+)) the compound of Example 289B (Fraction II (−)).

Example 289A

Synthesis of (+)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine

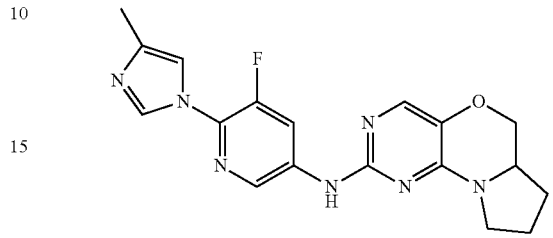

The compound of Example 289A was produced as described in Example 289. Analytical data for Fraction I (+): $^1$H-NMR (CD$_3$OD, 400 MHz): δ 7.72-7.69 (m, 1H), 7.43 (s, 1H), 7.21 (s, 1H), 7.06-6.99 (m, 2H), 6.75-6.73 (m, 1H), 4.20-4.16 (m, 1H), 3.49-3.39 (m, 2H), 3.37-3.29 (m, 1H), 3.10-3.05 (m, 1H), 1.93 (s, 3H), 1.90-1.80 (m, 2H), 1.79-1.70 (m, 1H), 1.29-1.19 (m, 1H); Mass (ESI): 367 [M+1]; LCMS: 367 (M+1); (column; X-Select CSH C-18 (50×3.0 mm, 3.5 µm); RT 2.02 min. 0.05% Aq TFA: ACN; 0.80 mL/min); UPLC (column; Acquity UPLC BEH C-18, 2.1× 50 mm, 1.7 µm); RT 1.30 min. ACN: 0.025% Aq TFA; 0.5 mL/min; Chiral HPLC: 98.7% RT=13.04 min (Chiralpak-IA (250×4.6 mm, 5 µm; mobile phase (A) 0.1% DEA in n-hexane (B) CH$_2$Cl$_2$:MeOH (50:50) (A:B: 70:30); flow Rate: 1.0 mL/min); Optical rotation [α]$_D^{19.99}$: +34.60 (c=0.25, CH$_2$Cl$_2$).

Example 289B

Synthesis of (−)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine

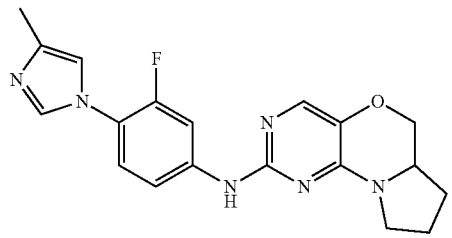

The compound of Example 289B was produced as described in Example 289. Analytical data for Fraction II (−): $^1$H-NMR (CD$_3$OD, 400 MHz): δ 7.72-7.69 (m, 1H), 7.43 (s, 1H), 7.21 (s, 1H), 7.06-6.99 (m, 2H), 6.75-6.73 (m, 1H), 4.20-4.16 (m, 1H), 3.49-3.39 (m, 2H), 3.37-3.29 (m, 1H), 3.10-3.05 (m, 1H), 1.93 (s, 3H), 1.90-1.80 (m, 2H), 1.79-1.70 (m, 1H), 1.29-1.19 (m, 1H); Mass (ESI): 367 [M+1]; LCMS: 367 (M+1); (column; X-Select CSH C-18 (50×3.0 mm, 3.5 µm); RT 2.02 min. 0.05% Aq TFA: ACN; 0.80 mL/min); UPLC (column; Acquity UPLC BEH C-18, 2.1×50 mm, 1.7 µm); RT 1.30 min. ACN: 0.025% Aq TFA;

0.5 mL/min; Chiral HPLC: 99.1% RT=15.31 min (Chiralpak-IA (250×4.6 mm, 5 μm; mobile phase (A) 0.1% DEA in n-hexane (B) CH$_2$Cl$_2$:MeOH (50:50) (A:B: 70:30); flow Rate: 1.0 mL/min); Optical rotation [α]$_D^{20.00}$: -33.39 (c=0.25, CH$_2$Cl$_2$).

Example 290

Synthesis of N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine

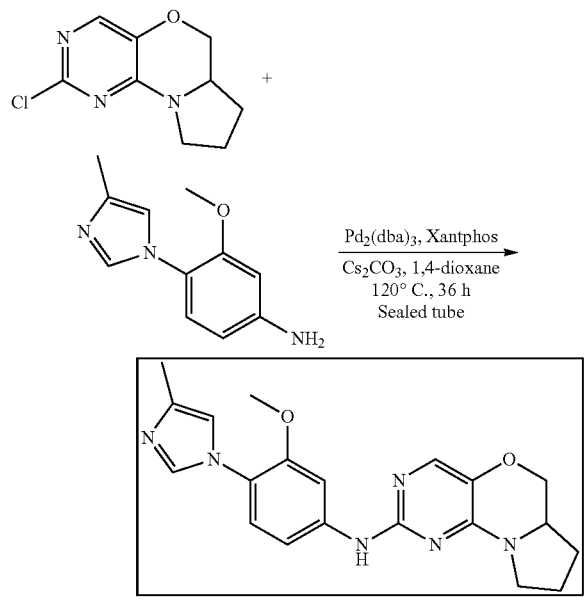

Synthesis of N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine To a dry vial was added a suspension of Pd$_2$(dba)$_3$ (54 mg, 0.05 mmol) and Xantphos (110 mg, 0.19 mmol) in 1, 4-dioxane (2.5 mL) at room temperature. The suspension was degassed with argon, heated to 120° C., and stirred for 3 min. A mixture of 2-chloro-6a, 7, 8, 9-tetrahydro-6H-pyrimido [5, 4-b] pyrrolo [1, 2-d] [1, 4] oxazine (250 mg, 0.12 mmol), 3-methoxy-4-(4-methyl-1H-imidazol-1-yl) aniline (264 mg, 0.13 mmol) and cesium carbonate (530 mg, 1.65 mmol) in 1, 4-dioxane (2.5 mL) was degassed and the catalyst premixture was added. The resultant mixture was stirred at 120° C. for 36 h in a sealed tube. After consumption of the starting material (monitored by TLC and LCMS), the reaction mixture was filtered and the filtrate was concentrated in vacuo. The crude material was purified by column chromatography using 8% MeOH: CH$_2$Cl$_2$ to afford N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine (160 mg, 38%) as an off-white solid. LCMS: 379.4 (M+1); (column; X-Select CSH C-18 (50×3.0 mm, 3.5 μm); RT 3.88 min 5 mM Aq NH$_4$OAc: ACN; 0.80 mL/min); UPLC (column; Acquity UPLC BEH C-18 2.1×50 mm, 1.7 μm); RT 1.28 min. ACN: 0.025% Aq TFA; 0.5 mL/min); TLC: 10% MeOH/CH$_2$Cl$_2$ (R$_f$: 0.3).

Racemic Example 290 was purified by (Chiralpak IC (250×4.6 mm, 5 μm (25 mg loading; 0.1% DEA in n-hexane: CH$_2$Cl$_2$ (A:B: 55:45) as mobile phase) to obtain pure Example 290A (Fraction I (-)) and pure Example 290B (Fraction II (+)).

Example 290A

Synthesis of (-)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine

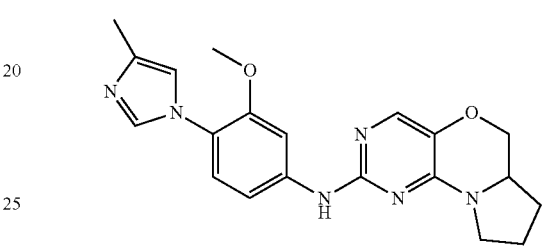

The compound of Example 290A was produced as described in Example 290. Analytical data for Fraction I (-): $^1$H-NMR (CD$_3$OD, 400 MHz): δ 7.82 (s, 1H), 7.65 (s, 1H), 7.52 (s, 1H), 7.19-7.12 (m, 2H), 6.96 (s, 1H), 4.50-4.48 (m, 1H), 3.87 (s, 3H), 3.79-3.70 (m, 2H), 3.69-3.60 (m, 1H), 3.40-3.35 (m, 1H), 2.25 (s, 3H), 2.23-2.11 (m, 2H), 2.10-2.00 (m, 1H), 1.60-1.50 (m, 1H); Mass (ESI): 471.5 [M+1]; LCMS: 378.9 (M+1); (column; X-Select CSH C-18 (50×3.0 mm, 3.5 μm); RT 1.99 min. 0.05% Aq TFA: ACN; 0.80 mL/min); UPLC (column; Acquity UPLC BEH C-18, 2.1× 50 mm, 1.7 μm); RT 1.30 min. ACN: 0.025% Aq TFA; 0.5 mL/min; Chiral HPLC: 99.3% RT=15.93 min (chiralpak-IC (250×4.6 mm, 5 μm; mobile phase (A) 0.1% DEA in n-hexane (B) CH$_2$Cl$_2$:MeOH (90:10) (A:B: 55:45); flow Rate: 1.0 mL/min); Optical rotation [α]$_D^{19.99}$: -34.28 (c=0.25, CH$_2$Cl$_2$).

Example 290B

Synthesis of (+)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine

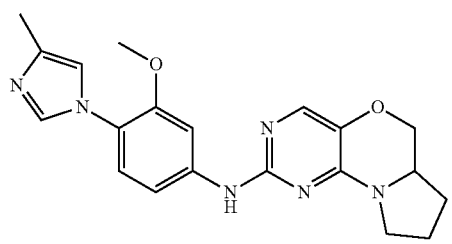

The compound of Example 290B was produced as described in Example 290. Analytical data for Fraction II (+): $^1$H-NMR (CD$_3$OD, 400 MHz): δ 7.82 (s, 1H), 7.65 (s, 1H), 7.52 (s, 1H), 7.19-7.12 (m, 2H), 6.96 (s, 1H), 4.50-4.48 (m, 1H), 3.87 (s, 3H), 3.79-3.70 (m, 2H), 3.69-3.60 (m, 1H), 3.40-3.35 (m, 1H), 2.25 (s, 3H), 2.23-2.11 (m, 2H), 2.10-2.00 (m, 1H), 1.60-1.50 (m, 1H); Mass (ESI): 378.9 [M+1]; LCMS: 379 (M+1); (column; X-Select CSH C-18 (50×3.0 mm, 3.5 µm); RT 2.00 min. 0.05% Aq TFA: ACN; 0.80 mL/min); UPLC (column; Acquity UPLC BEH C-18, 2.1× 50 mm, 1.7 µm); RT 1.30 min. ACN: 0.025% Aq TFA; 0.5 mL/min; Chiral HPLC: 99.4% RT=17.20 min (chiralpak-IC (250×4.6 mm, 5 µm; mobile phase (A) 0.1% DEA in n-hexane (B) CH$_2$Cl$_2$:MeOH (90:10) (A:B: 55:45); flow Rate: 1.0 mL/min); Optical rotation [α]$_D^{20.00}$: +46.40 (c=0.25, CH$_2$Cl$_2$).

Example 291

Synthesis of (S)—N-(3-methoxy-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine

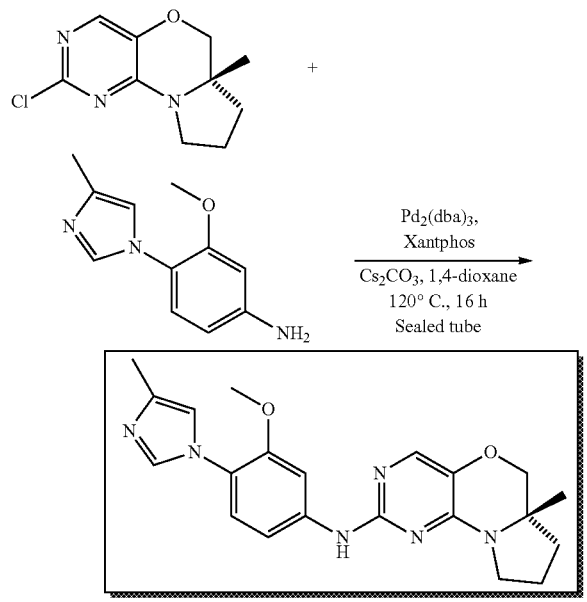

Synthesis of (S)—N-(3-methoxy-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine To a dry vial was added a suspension of Pd$_2$(dba)$_3$ (26 mg, 0.02 mmol) and Xantphos (49 mg, 0.08 mmol) in 1, 4-dioxane (0.65 mL) at room temperature. The suspension was degassed with argon, heated to 120° C., and stirred for 3 min. A mixture of (S)-2-chloro-6a-methyl-6a, 7, 8, 9-tetrahydro-6H-pyrimido [5, 4-b] pyrrolo [1, 2-d] [1, 4] oxazine (130 mg, 0.57 mmol), 3-methoxy-4-(4-methyl-1H-imidazol-1-yl) aniline (233 mg, 1.15 mmol) and cesium carbonate (262 mg, 0.85 mmol) in 1, 4-dioxane (0.65 mL) was degassed and the catalyst premixture was added. The resultant mixture was stirred at 120° C. for 16 h in a sealed tube. After consumption of the starting material (monitored by TLC and LCMS), the volatile components were evaporated in vacuo. The residue was diluted with water (20 mL) and extracted with EtOAc (2×20 mL). The combined organic extracts were dried over sodium sulfate, filtered and concentrated in vacuo. The crude material was purified by column chromatography using 3% MeOH: CH$_2$Cl$_2$ to afford (S)—N-(3-methoxy-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine (40 mg, 17%) as an off-white solid. $^1$H-NMR (DMSO-d$_6$, 500 MHz): δ 9.09 (s, 1H), 7.95 (s, 1H), 7.65 (s, 1H), 7.60 (s, 1H), 7.29 (d, 1H), 7.13 (d, 1H), 7.00 (s, 1H), 4.28 (d, 1H), 3.78 (s, 3H), 3.71-3.66 (m, 1H), 3.60-3.54 (m, 1H), 3.36 (s, 1H), 2.10 (s, 3H), 2.04-1.98 (m, 2H), 1.87-1.80 (m, 1H), 1.69-1.60 (m, 1H), 1.19 (s, 3H); Mass (ESI): 393.4 [M+1]; LCMS: 393.1 (M+1); (column; X-Select CSH C-18 (50×3.0 mm, 3.5 µm); RT 2.11 min 0.05% Aq TFA: ACN; 0.80 mL/min); UPLC (column; Acquity UPLC BEH C-18 2.1×50 mm, 1.7 µm); RT 1.39 min. ACN: 0.025% Aq TFA; 0.5 mL/min; Chiral HPLC: 99.3% RT=8.99 min (chiralpak-IA (250×4.6 mm, 5 µm; mobile phase (A) 0.1% DEA in n-hexane (B) CH$_2$Cl$_2$: MeOH (50:50) (A:B; 75:25); flow Rate: 1.0 mL/min); Optical rotation [α]$_D^{20.00}$: +26.56 (c=0.25, CH$_2$Cl$_2$); TLC: 5% MeOH/CH$_2$Cl$_2$ (R$_f$: 0.3).

Example 292

Synthesis of (S)—N-(3-fluoro-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine

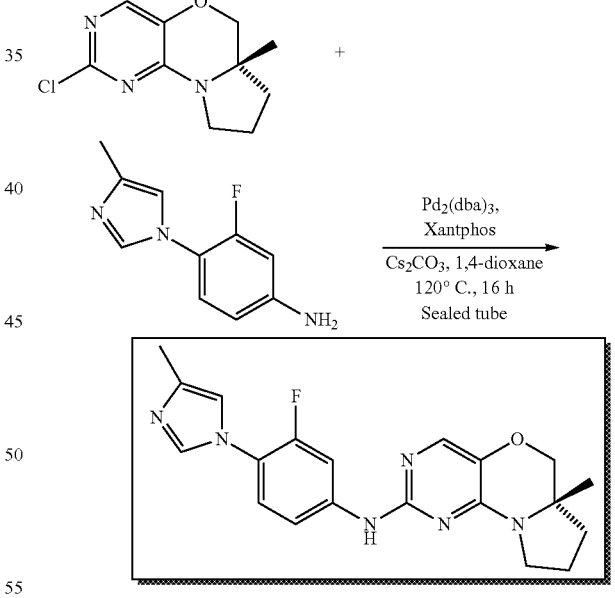

Synthesis of (S)—N-(3-fluoro-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine To a dry vial was added a suspension of Pd$_2$(dba)$_3$ (26 mg, 0.03 mmol) and Xantphos (49 mg, 0.08 mmol) in 1, 4-dioxane (0.65 mL) at room temperature. The suspension was degassed with argon, heated to 120° C., and stirred for 3 min. A mixture of (S)-2-chloro-6a-methyl-6a, 7, 8, 9-tetrahydro-6H-pyrimido [5, 4-b] pyrrolo [1, 2-d] [1, 4] oxazine (130 mg, 0.57 mmol), 3-fluoro-4-(4-methyl-1H-imidazol-1-yl) aniline (219 mg, 1.15 mmol) and cesium carbonate (262 mg, 0.80 mmol) in 1, 4-dioxane (0.65 mL) was degassed and the catalyst premixture was added. The resultant mixture was stirred at 120° C. for 16 h in a sealed tube. After consumption of the starting material (monitored by TLC and LCMS), the volatile components were evaporate in vacuo. The residue was diluted with water (20 mL) and extracted with EtOAc (2×20 mL). The combined organic extracts were dried over sodium sulfate, filtered and concentrated in vacuo. The crude material was purified by column chromatography using 1% MeOH: $CH_2Cl_2$ to afford (S)—N-(3-fluoro-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine (46 mg, 21%) as a brown solid. $^1$H-NMR ($CD_3OD$, 400 MHz): δ 8.05-8.00 (m, 1H), 7.75 (s, 1H), 7.59 (s, 1H), 7.39-7.30 (m, 2H), 7.06 (s, 1H), 4.30-4.28 (m, 1H), 3.79-3.72 (m, 1H), 3.70-3.60 (m, 1H), 3.38 (s, 1H), 2.23 (s, 3H), 2.12-2.10 (m, 1H), 2.15-2.10 (m, 1H), 2.00-1.92 (m, 1H), 1.74-1.69 (m, 1H), 1.25 (s, 3H); Mass (ESI): 381.4 [M+1]; LCMS: 381 (M+1); (column; X-Select CSH C-18 (50×3.0 mm, 3.5 μm); RT 2.08 min 0.05% Aq TFA: ACN; 0.80 mL/min); UPLC (column; Eclipse XDB C-18 150×4.6 mm, 5.0 μm); RT 10.29 min. ACN: 5 mM Aq $NH_4OAc$; 1.0 mL/min; Chiral HPLC: 99.2% RT=21.46 min (chiralpak-IA (250×4.6 mm, 5 μm; mobile phase (A) 0.1% DEA in n-hexane (B) $CH_2Cl_2$:MeOH (50:50) (A:B; 80:20); flow Rate: 1.0 mL/min); Optical rotation $[\alpha]_D^{19.99}$: +40.27 (c=0.25, $CH_2Cl_2$); TLC: 5% MeOH/$CH_2Cl_2$ ($R_f$: 0.3).

Example 293

Synthesis of (R)—N-(3-fluoro-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine Synthesis of (R)—N-(3-fluoro-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine To a dry vial was added a suspension of $Pd_2(dba)_3$ (20 mg, 0.02 mmol) and Xantphos (40 mg, 0.06 mmol) in 1, 4-dioxane (0.5 mL) at room temperature. The suspension was degassed with argon, heated to 120° C., and stirred for 3 min. A mixture of (R)-2-chloro-6a-methyl-6a, 7, 8, 9-tetrahydro-6H-pyrimido [5, 4-b] pyrrolo [1, 2-d] [1, 4] oxazine (100 mg, 0.44 mmol), 3-fluoro-4-(4-methyl-1H-imidazol-1-yl) aniline (125 mg, 0.66 mmol) and cesium carbonate (200 mg, 0.62 mmol) in 1, 4-dioxane (0.5 mL) was degassed and the catalyst premixture was added. The resultant mixture was stirred at 130° C. for 12 h in a sealed tube. After consumption of the starting material (monitored by TLC and LCMS), the volatile components were concentrated in vacuo. The crude material was purified by column chromatography using 4% MeOH: $CH_2Cl_2$ to afford (R)—N-(3-fluoro-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine (32 mg, 20%) as an off-white solid. $^1$H-NMR ($CD_3OD$, 400 MHz): δ 8.07-8.00 (m, 1H), 7.76 (s, 1H), 7.59 (s, 1H), 7.40-7.28 (m, 2H), 7.06 (s, 1H), 4.30-4.25 (m, 1H), 3.79-3.72 (m, 1H), 3.69-3.61 (m, 1H), 3.37-3.30 (m, 1H), 2.23 (s, 3H), 2.22-2.20 (m, 1H), 2.17-2.10 (m, 1H), 1.99-1.92 (m, 1H), 1.74-1.65 (m, 1H), 1.27 (s, 3H); Mass (ESI): 381.4 [M+1]; LCMS: 381 (M+); (column; X-Select CSH C-18 (50×3.0 mm, 3.5 μm); RT 2.08 min 0.05% Aq TFA: ACN; 0.80 mL/min); HPLC (column; Eclipse XDB C-18, 150×4.6 mm, 5.0μ); RT 10.03 min. ACN: 5 mM Aq $NH_4OAc$; 1.0 mL/min; Chiral HPLC: 98.5% RT=20.61 min (chiralpak-IA (250×4.6 mm, 5 μm; mobile phase (A) 0.1% DEA in n-hexane (B) $CH_2Cl_2$:MeOH (50:50) (A:B: 85:15); flow Rate: 1.0 mL/min); Optical rotation $[\alpha]_D^{20.01}$: −31.47 (c=0.25, $CH_2Cl_2$); TLC: 5% MeOH/$CH_2Cl_2$ ($R_f$: 0.2).

Example 294

Synthesis of (R)—N-(3-methoxy-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine

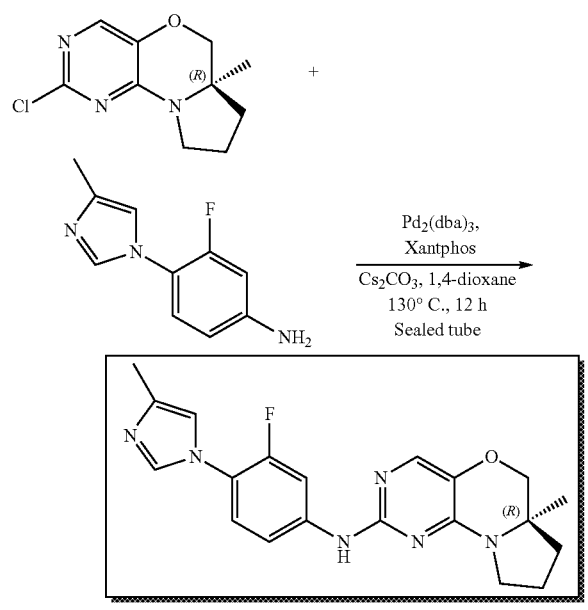

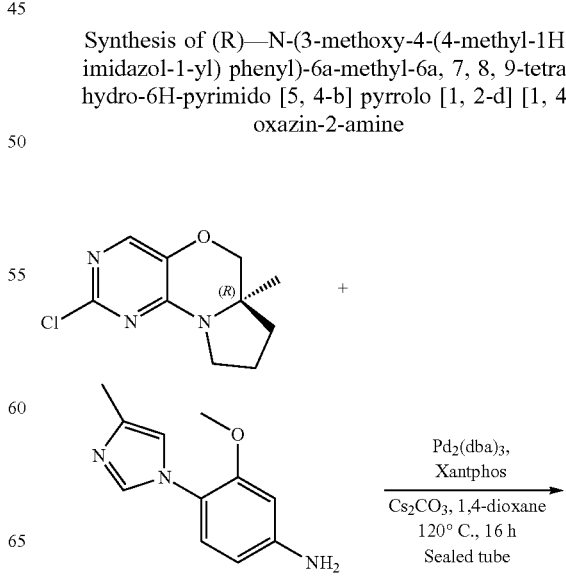

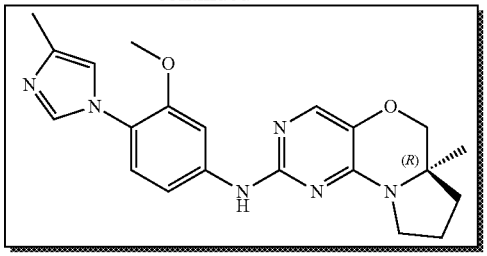

Synthesis of (R)—N-(3-methoxy-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine To a dry vial was added a suspension of Pd$_2$(dba)$_3$ (20 mg, 0.02 mmol) and Xantphos (38 mg, 0.06 mmol) in 1, 4-dioxane (1 mL) at room temperature. The suspension was degassed with argon, heated to 120° C., and stirred for 3 min. A mixture of (R)-2-chloro-6a-methyl-6a, 7, 8, 9-tetrahydro-6H-pyrimido [5, 4-b] pyrrolo [1, 2-d] [1, 4] oxazine (100 mg, 0.44 mmol), 3-methoxy-4-(4-methyl-1H-imidazol-1-yl) aniline (134 mg, 0.66 mmol) and cesium carbonate (200 mg, 0.68 mmol) in 1, 4-dioxane (1 mL) was degassed and the catalyst premixture was added. The resultant mixture was stirred at 120° C. for 16 h in a sealed tube. After consumption of the starting material (monitored by TLC and LCMS), the volatile components were concentrated in vacuo. The crude material was purified by column chromatography using 3% MeOH: CH$_2$Cl$_2$ to afford (R)—N-(3-methoxy-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine (35 mg, 21%) as an off-white solid. $^1$H-NMR (CD$_3$OD, 400 MHz): δ 7.82 (s, 1H), 7.65 (s, 1H), 7.57 (s, 1H), 7.19-7.15 (m, 2H), 6.95 (s, 1H), 4.29-4.25 (m, 1H), 3.85 (s, 3H), 3.80-3.72 (m, 1H), 3.70-3.61 (m, 1H), 3.36-3.31 (m, 1H), 2.25-2.22 (m, 1H), 2.21 (s, 3H), 2.13-2.09 (m, 1H), 1.99-1.93 (m, 1H), 1.75-1.68 (m, 1H), 1.25 (s, 3H); Mass (ESI): 393.4 [M+1]; LCMS: 393.1 (M+); (column; X-Select CSH C-18 (50×3.0 mm, 3.5 μm); RT 2.12 min 0.05% Aq TFA: ACN; 0.80 mL/min); UPLC (column; Acquity BEH C-18, 50×2.1 mm, 1.7 μm); RT 1.43 min. ACN: 0.025% Aq TFA; 0.5 mL/min; Chiral HPLC: 98.5% RT=13.54 min (chiralpak-IA (250×4.6 mm, 5 μm; mobile phase (A) 0.1% DEA in n-hexane (B) CH$_2$Cl$_2$:MeOH (50:50) (A:B: 80:20); flow Rate: 1.0 mL/min); Optical rotation [α]$_D^{19.99}$: −32.12 (c=0.25, CH$_2$Cl$_2$); TLC: 5% MeOH/CH$_2$Cl$_2$ (R$_f$: 0.3).

Example 295

Synthesis of (S)—N-(3-methoxy-4-(4-methyl-1H-imidazol-1-yl) phenyl)-6a, 7, 9, 10-tetrahydro-6H-[1, 4] oxazino [4, 3-d] pyrimido [5, 4-b] [1, 4] oxazin-2-amine

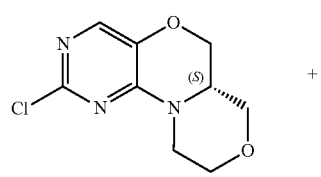 +

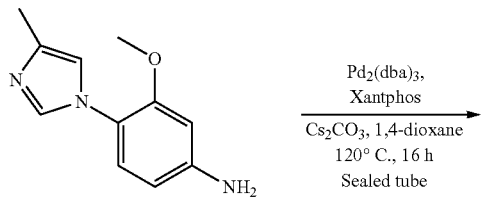

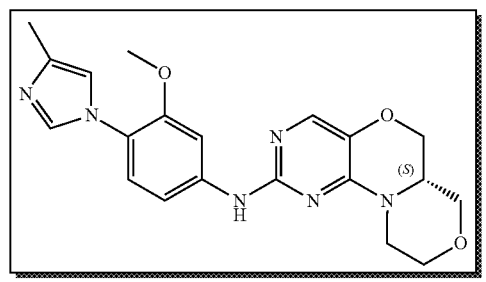

Synthesis of (S)—N-(3-methoxy-4-(4-methyl-1H-imidazol-1-yl) phenyl)-6a, 7, 9, 10-tetrahydro-6H-[1, 4] oxazino [4, 3-d] pyrimido [5, 4-b] [1, 4] oxazin-2-amine To a dry vial was added a suspension of Pd$_2$(dba)$_3$ (60 mg, 0.06 mmol) and Xantphos (13 mg, 0.02 mmol) in 1, 4-dioxane (0.5 mL) at room temperature. The suspension was degassed with argon, heated to 120° C., and stirred for 3 min. A mixture of (S)-2-chloro-6a, 7, 9, 10-tetrahydro-6H-[1, 4] oxazino [4, 3-d] pyrimido [5, 4-b] [1, 4] oxazine (100 mg, 0.44 mmol), 3-methoxy-4-(4-methyl-1H-imidazol-1-yl) aniline (178 mg, 0.88 mmol) and cesium carbonate (200 mg, 0.61 mmol) in 1, 4-dioxane (0.5 mL) was degassed and the catalyst premixture was added. The resultant mixture was stirred at 120° C. for 16 h in a sealed tube. After consumption of the starting material (monitored by TLC and LCMS), the reaction mixture was filtered and the filtrate was concentrated in vacuo. The crude was purified by preparative HPLC (Ascentis C18 (250×21.2 mm: 5μ; (50 mg loading; CH$_3$CN: 0.05% TFA (0.1/90, 2/85, 15/70, 25/20, 30/10, 35/10) as mobile phase) to afford (S)—N-(3-methoxy-4-(4-methyl-1H-imidazol-1-yl) phenyl)-6a, 7, 9, 10-tetrahydro-6H-[1, 4] oxazino [4, 3-d] pyrimido [5, 4-b] [1, 4] oxazin-2-amine (25 mg, 14%) as an off-white solid. $^1$H-NMR (CD$_3$OD, 400 MHz): δ 7.67 (s, 1H), 7.66 (s, 1H), 7.59 (s, 1H), 7.20-7.16 (m, 2H), 6.97 (s, 1H), 4.47-4.40 (m, 1H), 4.27-4.21 (m, 1H), 4.04-4.00 (m, 1H), 3.97-3.90 (m, 1H), 3.84 (s, 3H), 3.83-3.80 (m, 2H), 3.70-3.60 (m, 1H), 3.32-3.30 (m, 1H), 3.11-3.03 (m, 1H), 2.12 (s, 3H); Mass (ESI): 395.1 [M+1]; LCMS: 395.1 (M+1); (column; X-Select CSH C-18 (50×3.0 mm, 3.5 μm); RT 1.86 min 0.05% Aq TFA: ACN; 0.8 mL/min); UPLC (column; Acquity BEH-C-18 50×2.1 mm, 1.7 μm); RT 1.29 min. ACN: 0.025% Aq TFA; 0.5 mL/min; Chiral HPLC: 98.6% RT=21.29 min (Chiralpak-IA (250×4.6 mm, 5μ; mobile phase (A) 0.1% DEA in n-hexane (B) CH$_2$Cl$_2$ (50:50) (A:B; 80:20); flow Rate: 1.0 mL/min); Optical rotation [α]$_D^{20.00}$: +9.66 (c=0.25, CH$_2$Cl$_2$); TLC: 10% MeOH/CH$_2$Cl$_2$ (R$_f$: 0.3).

Example 296

Synthesis of (R)—N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine

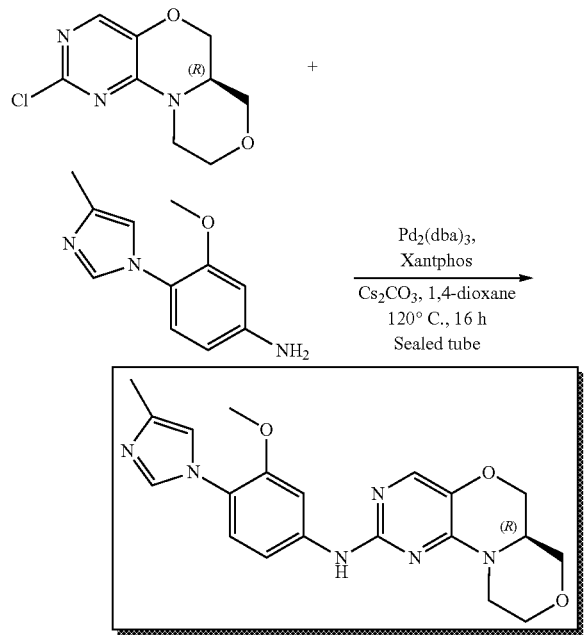

Synthesis of (R)—N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine To a dry vial was added a suspension of $Pd_2(dba)_3$ (60 mg, 0.06 mmol) and Xantphos (13 mg, 0.02 mmol) in 1, 4-dioxane (0.5 mL) at room temperature. The suspension was degassed with argon, heated to 120° C., and stirred for 3 min. A mixture of (R)-2-chloro-6a, 7, 9, 10-tetrahydro-6H-[1, 4] oxazino [4, 3-d] pyrimido [5, 4-b] [1, 4] oxazine (100 mg, 0.44 mmol), 3-methoxy-4-(4-methyl-1H-imidazol-1-yl) aniline (178 mg, 0.88 mmol) and cesium carbonate (200 mg, 0.61 mmol) in 1, 4-dioxane (0.5 mL) was degassed and the catalyst premixture was added. The resultant mixture was stirred at 120° C. for 16 h in a sealed tube. After consumption of the starting material (monitored by TLC and LCMS), the reaction mixture was filtered and the filtrate was concentrated in vacuo. The crude was purified by preparative HPLC (Ascentis C18 (250×21.2 mm: 5μ; (50 mg loading; $CH_3CN$: 0.05% TFA (0.1/90, 2/85, 15/70, 25/20, 30/10, 35/10) as mobile phase) to afford (R)—N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine (23 mg, 13%) as an off-white solid. $^1$H-NMR ($CD_3OD$, 400 MHz): δ 7.67 (s, 1H), 7.66 (s, 1H), 7.58 (s, 1H), 7.20-7.13 (m, 2H), 6.98 (s, 1H), 4.45-4.40 (m, 1H), 4.25-4.20 (m, 1H), 4.01-3.99 (m, 1H), 3.91-3.89 (m, 1H), 3.83 (s, 3H), 3.82-3.80 (m, 2H), 3.69-3.60 (m, 1H), 3.30-3.28 (m, 1H), 3.10-3.01 (m, 1H), 2.20 (s, 3H); Mass (ESI): 395.1 [M+1]; LCMS: 395.2 (M+1); (column; X-Select CSH C-18 (50×3.0 mm, 3.5 μm); RT 1.89 min 0.05% Aq TFA: ACN; 0.8 mL/min); UPLC (column; Acquity BEH-C-18 50×2.1 mm, 1.7 μm); RT 1.26 min. ACN: 0.025% Aq TFA; 0.5 mL/min; Chiral HPLC: 99.0% RT=28.44 min (Chiralpak-IA (250×4.6 mm, 5μ; mobile phase (A) 0.1% DEA in n-hexane (B) $CH_2Cl_2$:MeOH (50:50) (A:B; 80:20); flow Rate: 1.0 mL/min); Optical rotation $[\alpha]_D^{20.00}$: −7.45 (c=0.25, $CH_2Cl_2$); TLC: 5% MeOH/$CH_2Cl_2$ ($R_f$: 0.1).

Example 297

Synthesis of (S)-8, 8-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine

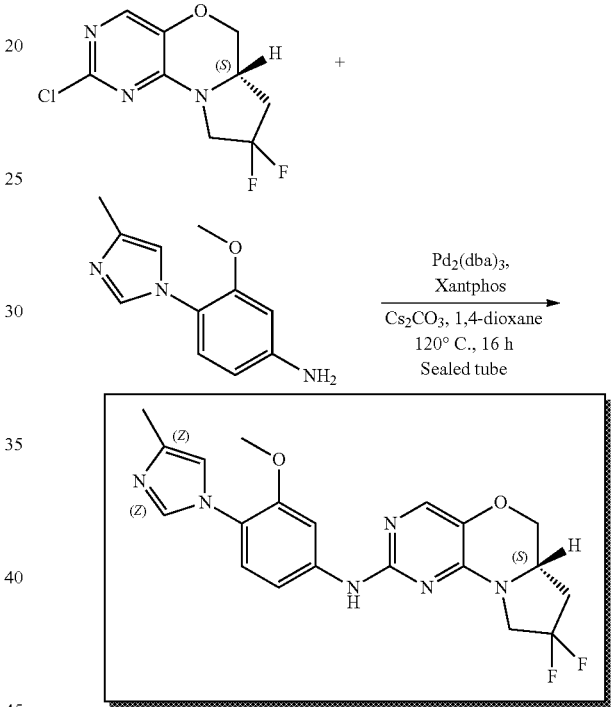

Synthesis of (S)-8, 8-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine To a dry vial was added a suspension of $Pd_2(dba)_3$ (46 mg, 0.05 mmol) and Xantphos (88 mg, 0.15 mmol) in 1, 4-dioxane (1 mL) at room temperature. The suspension was degassed with argon, heated to 120° C., and stirred for 3 min. A mixture of (S)-2-chloro-8, 8-difluoro-6a, 7, 8, 9-tetrahydro-6H-pyrimido [5, 4-b] pyrrolo [1, 2-d] [1, 4] oxazine (250 mg, 1.01 mmol), 3-methoxy-4-(4-methyl-1H-imidazol-1-yl) aniline (411 mg, 2.02 mmol) and cesium carbonate (460 mg, 1.41 mmol) in 1, 4-dioxane (1 mL) was degassed and the catalyst premixture was added. The resultant mixture was stirred at 120° C. for 16 h in a sealed tube. After consumption of the starting material (monitored by TLC and LCMS), the reaction mixture was diluted with a saturated sodium carbonate solution (20 mL) and extracted with EtOAc (2×20 mL). The combined organic extracts were dried over sodium sulfate, filtered and concentrated in vacuo. The crude material was purified by column chromatography using 4% MeOH: $CH_2Cl_2$ to obtain 100 mg of compound which was further purified by preparative HPLC (Ascentis C18 (250×21.2 mm: 5µ; (70 mg loading; $CH_3CN$: 0.05% TFA (0.1/90, 2/85, 15/70, 25/25, 30/10, 35/10) as mobile phase) to afford (S)-8, 8-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine (60 mg, 14%) as an off-white solid. $^1$H-NMR ($CD_3OD$, 400 MHz): δ 7.71-7.70 (m, 1H), 7.66-7.65 (m, 1H), 7.63 (s, 1H), 7.24-7.19 (m, 2H), 6.96 (s, 1H), 4.52 (dd, 1H), 4.23-4.14 (m, 2H), 3.98-3.80 (m, 1H), 3.86 (s, 3H), 3.58 (t, 1H), 2.67-2.56 (m, 1H), 2.34-2.27 (m, 1H), 2.23 (s, 3H); Mass (ESI): 415.4 [M+1]; LCMS: 415.1 (M+1); (column; X-Select CSH C-18 (50×3.0 mm, 3.5 µm); RT 2.04 min. 0.05% Aq TFA: ACN; 0.80 mL/min); UPLC (column; Acquity BEH C-18, 50×2.1 mm, 1.7 µm); RT 1.41 min. ACN: 0.025% Aq TFA; 0.5 mL/min; Chiral HPLC: 100% RT=9.25 min (Chiralpak-IA (250×4.6 mm, 5 µm; mobile phase (A) 0.1% DEA in n-hexane (B) $CH_2Cl_2$:MeOH (50:50) (A:B; 70:30); flow Rate: 1.0 mL/min); Optical rotation $[α]_D^{19.99}$: +16.60 (c=0.25, $CH_2Cl_2$). TLC: 5% MeOH/$CH_2Cl_2$ ($R_f$: 0.4).

Example 298

Synthesis of (S)-8, 8-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine

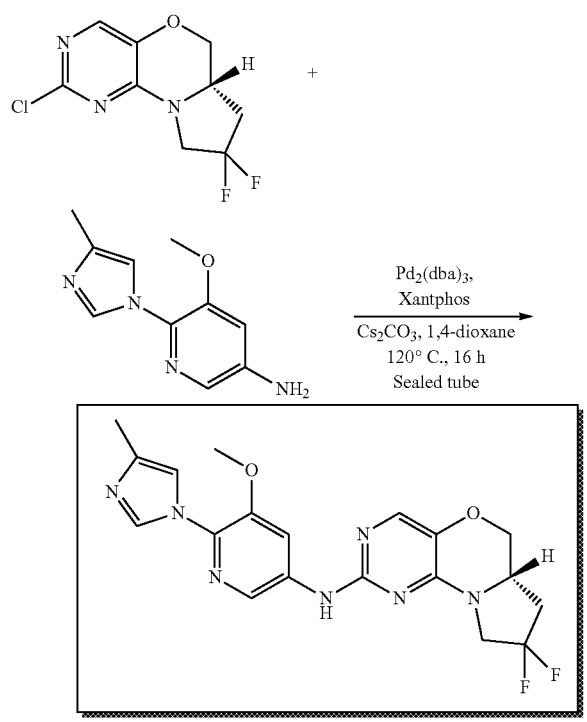

Synthesis of (S)-8, 8-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine To a dry vial was added a suspension of $Pd_2(dba)_3$ (46 mg, 0.05 mmol) and Xantphos (88 mg, 0.15 mmol) in 1, 4-dioxane (1 mL) at room temperature. The suspension was degassed with argon, heated to 120° C., and stirred for 3 min. A mixture of (S)-2-chloro-8, 8-difluoro-6a, 7, 8, 9-tetrahydro-6H-pyrimido [5, 4-b] pyrrolo [1, 2-d] [1, 4] oxazine (250 mg, 1.01 mmol), 5-methoxy-6-(4-methyl-1H-imidazol-1-yl) pyridin-3-amine (413 mg, 2.02 mmol) and cesium carbonate (461 mg, 1.41 mmol) in 1, 4-dioxane (1 mL) was degassed and the catalyst premixture was added. The resultant mixture was stirred at 120° C. for 16 h in a sealed tube. After consumption of the starting material (monitored by TLC and LCMS), the reaction mixture was diluted with a saturated sodium carbonate solution (20 mL) and extracted with EtOAc (2×20 mL). The combined organic extracts were dried over sodium sulfate, filtered and concentrated in vacuo. The crude material was purified by column chromatography using 8% MeOH: $CH_2Cl_2$ to afford (S)-8, 8-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine (100 mg, 23%) as an off-white solid. $^1$H-NMR ($CD_3OD$, 400 MHz): δ 8.25 (s, 2H), 8.12 (s, 1H), 7.67 (s, 1H), 7.40 (s, 1H), 4.52-4.50 (m, 1H), 4.20-4.10 (m, 2H), 3.98 (s, 3H), 3.97-3.90 (m, 1H), 3.59 (t, 1H), 2.68-2.56 (m, 1H), 2.30-2.25 (m, 1H), 2.22 (s, 3H); Mass (ESI): 416.3 [M+1]; LCMS: 416 (M+1); (column; X-Select CSH C-18 (50×3.0 mm, 3.5 µm); RT 2.41 min. 0.05% Aq TFA: ACN; 0.80 mL/min); UPLC (column; Acquity BEH C-18, 50×2.1 mm, 1.7 µm); RT 1.41 min. ACN: 0.025% Aq TFA; 0.5 mL/min; Chiral HPLC: 100% RT=10.74 min (Chiralpak-IA (250×4.6 mm, 5 µm; mobile phase (A) 0.1% DFA in n-hexane (B) $CH_2Cl_2$:MeOH (50:50) (A:B; 70:30); flow Rate: 1.0 mL/min); Optical rotation $[α]_D^{20.00}$: +5.29 (c=0.25, $CH_2Cl_2$); TLC: 10% MeOH/$CH_2Cl_2$ ($R_f$: 0.4).

Example 299

Synthesis of (S)—N-(3-fluoro-4-(4-methyl-1H-imidazol-1-yl) phenyl)-6a, 7, 9, 10-tetrahydro-6H-[1, 4] oxazino [4, 3-d] pyrimido [5, 4-b] [1, 4] oxazin-2-amine

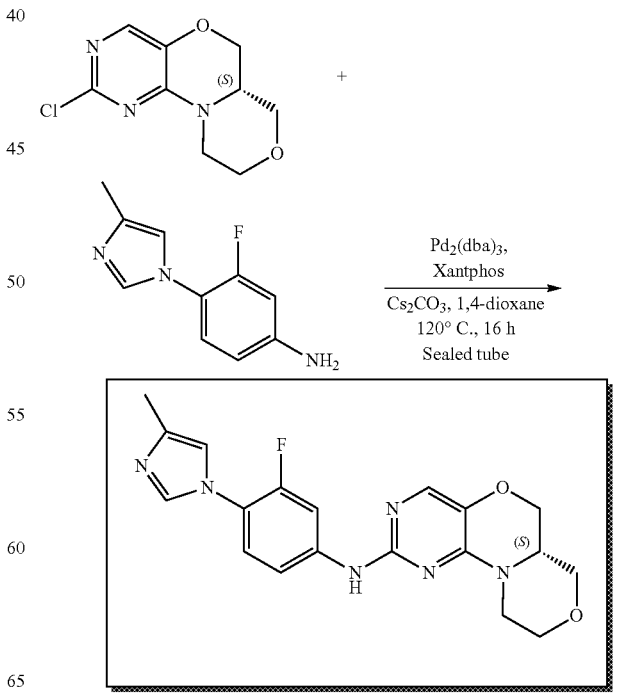

Synthesis of (S)—N-(3-fluoro-4-(4-methyl-1H-imidazol-1-yl) phenyl)-6a, 7, 9, 10-tetrahydro-6H-[1, 4] oxazino [4, 3-d] pyrimido [5, 4-b] [1, 4] oxazin-2-amine To a dry vial was added a suspension of Pd$_2$(dba)$_3$ (20 mg, 0.02 mmol) and Xantphos (38 mg, 0.06 mmol) in 1, 4-dioxane (0.25 mL) at room temperature. The suspension was degassed with argon, heated to 120° C., and stirred for 3 min. A mixture of (S)-2-chloro-6a, 7, 9, 10-tetrahydro-6H-[1, 4] oxazino [4, 3-d] pyrimido [5, 4-b] [1, 4] oxazine (100 mg, 0.44 mmol), 3-fluoro-4-(4-methyl-1H-imidazol-1-yl) aniline (173 mg, 0.88 mmol) and cesium carbonate (200 mg, 0.61 mmol) in 1, 4-dioxane (0.25 mL) was degassed and the catalyst premixture was added. The resultant mixture was stirred at 120° C. for 16 h in a sealed tube. After consumption of the starting material (monitored by TLC and LCMS), the reaction mixture was diluted with water (50 mL) and extracted with EtOAc (2×50 mL). The combined organic extracts were washed with brine (20 mL), dried over sodium sulfate, filtered and concentrated in vacuo. The crude material was purified by preparative HPLC (Ascentis C18 (250× 21.2 mm: 5µ; (50 mg loading; CH$_3$CN: 5 mM NH$_4$OAc (0.1/80, 2/80, 10/50, 25/20, 30/10, 35/10) as mobile phase) to afford (S)—N-(3-fluoro-4-(4-methyl-1H-imidazol-1-yl) phenyl)-6a, 7, 9, 10-tetrahydro-6H-[1, 4] oxazino [4, 3-d] pyrimido [5, 4-b] [1, 4] oxazin-2-amine (24 mg, 21%) as a white solid. $^1$H NMR (CD$_3$OD, 400 MHz): δ 7.90 (d, 1H), 7.76 (s, 1H), 7.61 (s, 1H), 7.40-7.30 (m, 2H), 7.07 (s, 1H), 4.40 (dd, 1H), 4.25 (dd, 1H), 4.04 (dd, 1H), 3.94 (dd, 1H), 3.86-3.81 (m, 1H), 3.71-3.58 (m, 2H), 3.26 (s, 1H), 3.14-3.03 (m, 1H), 2.25 (s, 3H): Mass (ESI): 383.4 [M+1]; LCMS: 383.4 (M+1); (column; X-Select CSH C-18 (50×3.0 mm, 3.5 µm); RT 3.23 min 5 mM NH$_4$OAc in water: ACN; 0.8 mL/min); UPLC (column; Eclipse XDBC-18 150×4.6 mm, 5.0 µm); RT 9.15 min. ACN: 5 mM Aq NH$_4$OAc; 0.5 mL/min; Chiral HPLC: 98.7% RT=10.32 min (Chiralpak-IA (250×4.6 mm, 5µ; mobile phase (A) 0.1% DEA in n-hexane (B) CH$_2$Cl$_2$:MeOH (50:50) (A:B; 70:30); flow Rate: 1.0 mL/min); Optical rotation [α]$_D^{20.00}$: +5.82 (c=0.25, CH$_2$Cl$_2$); TLC: 5% MeOH/CH$_2$Cl$_2$ (R$_f$: 0.1).

Example 300

Synthesis of (R)—N-(3-fluoro-4-(4-methyl-1H-imidazol-1-yl) phenyl)-6a, 7, 9, 10-tetrahydro-6H-[1, 4] oxazino [4, 3-d] pyrimido [5, 4-b] [1, 4] oxazin-2-amine

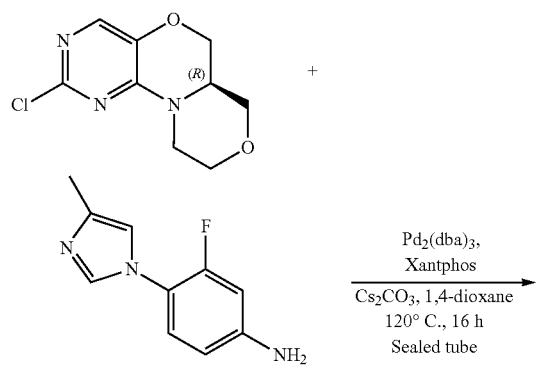

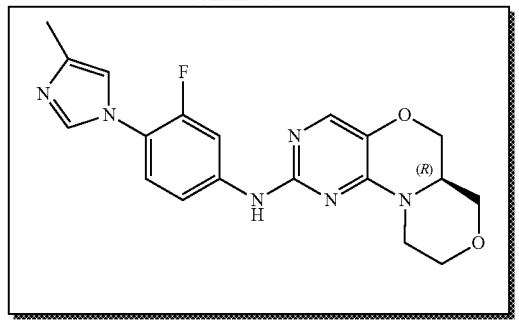

Synthesis of (R)—N-(3-fluoro-4-(4-methyl-1H-imidazol-1-yl) phenyl)-6a, 7, 9, 10-tetrahydro-6H-[1, 4] oxazino [4, 3-d] pyrimido [5, 4-b] [1, 4] oxazin-2-amine To a dry vial was added a suspension of Pd$_2$(dba)$_3$ (20 mg, 0.02 mmol) and Xantphos (38 mg, 0.06 mmol) in 1, 4-dioxane (0.25 mL) at room temperature. The suspension was degassed with argon, heated to 120° C., and stirred for 3 min. A mixture of (R)-2-chloro-6a, 7, 9, 10-tetrahydro-6H-[1, 4] oxazino [4, 3-d] pyrimido [5, 4-b] [1, 4] oxazine (100 mg, 0.44 mmol), 3-fluoro-4-(4-methyl-1H-imidazol-1-yl) aniline (173 mg, 0.88 mmol) and cesium carbonate (200 mg, 0.61 mmol) in 1, 4-dioxane (0.25 mL) was degassed and the catalyst premixture was added. The resultant mixture was stirred at 120° C. for 16 h in a sealed tube. After consumption of the starting material (monitored by TLC and LCMS), the reaction mixture was filtered, the filtrate was concentrated in vacuo. The crude material was purified by preparative HPLC (Chiralpak IC (250×4.6 mm: 5 µm; (35 mg loading; 0.1% DEA in n-hexane: CH$_2$Cl$_2$:MeOH (50:50); (A:B: 70:30) as mobile phas30e) to afford (R)—N-(3-fluoro-4-(4-methyl-1H-imidazol-1-yl) phenyl)-6a, 7, 9, 10-tetrahydro-6H-[1, 4] oxazino [4, 3-d] pyrimido [5, 4-b] [1, 4] oxazin-2-amine (35 mg, 21%) as a white solid. $^1$H NMR (CD$_3$OD, 400 MHz): δ 7.88 (d, 1H), 7.76 (s, 1H), 7.60 (s, 1H), 7.40-7.33 (m, 2H), 7.07 (s, 1H), 4.41 (dd, 1H), 4.24 (dd, 1H), 4.04 (dd, 1H), 3.93 (dd, 1H), 3.84-3.82 (m, 1H), 3.70-3.60 (m, 2H), 3.28 (s, 1H), 3.14-3.02 (m, 1H), 2.26 (s, 3H): Mass (ESI): 383.4 [M+1]; LCMS: 383.4 (M+1); (column; X-Select CSH C-18 (50×3.0 mm, 3.5 µm); RT 3.22 min 5 mM Aq NH$_4$OAc: ACN; 0.8 mL/min); HPLC (column; Eclipse XDB-C-18 150×4.6 mm, 5.0 µm); RT 9.15 min. ACN: 5 mM Aq NH$_4$OAc; 1.0 mL/min; Chiral HPLC: 99.0% RT=14.32 min (Chiralpak-IA (250×4.6 mm, 5µ; mobile phase (A) 0.1% DEA in n-hexane (B) CH$_2$Cl$_2$: MeOH (50:50) (A:B; 70:30); flow Rate: 1.0 mL/min); Optical rotation [α]$_D^{20.01}$: −4.28 (c=0.25, CH$_2$Cl$_2$); TLC: 5% MeOH/CH$_2$Cl$_2$ (R$_f$: 0.1).

Example 301

Synthesis of N-(5-methoxy-6-(4-methyl-1H-imidazol-1-yl) pyridin-3-yl)-8'-methyl-2, 3, 5, 6-tetrahydro-6'H, 8'H-spiro [pyran-4, 7'-pyrimido [5, 4-b] [1, 4] oxazin]-2'-amine

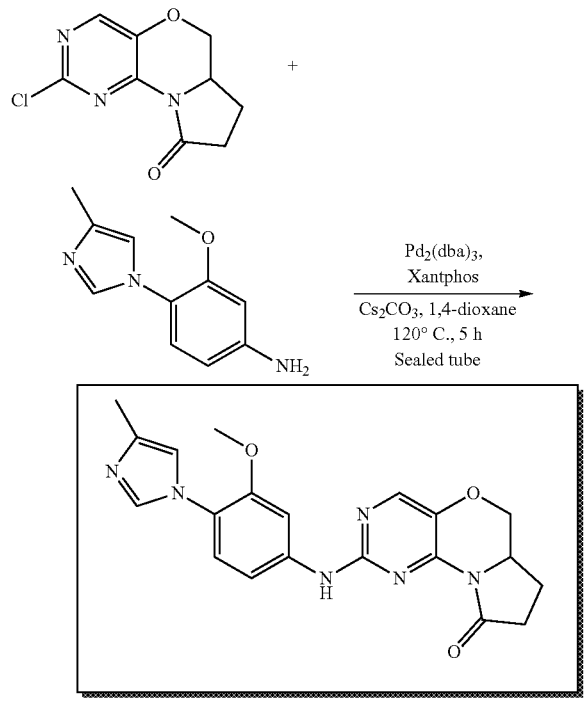

Synthesis of 2-((3-methoxy-4-(4-methyl-1H-imidazol-1-yl) phenyl) amino)-6, 6a, 7, 8-tetrahydro-9H-pyrimido [5, 4-b] pyrrolo [1, 2-d] [1, 4] oxazin-9-one To a dry vial was added a suspension of Pd$_2$(dba)$_3$ (26 mg, 0.03 mmol) and Xantphos (50 mg, 0.08 mmol) in 1, 4-dioxane (0.75 mL) at room temperature. The suspension was degassed with argon, heated to 120° C., and stirred for 3 min. A mixture of 2-chloro-6, 6a, 7, 8-tetrahydro-9H-pyrimido [5, 4-b] pyrrolo [1, 2-d] [1, 4] oxazin-9-one (130 mg, 0.57 mmol), 3-methoxy-4-(4-methyl-1H-imidazol-1-yl) aniline (116 mg, 0.57 mmol) and cesium carbonate (262 mg, 0.80 mmol) in 1, 4-dioxane (0.75 mL) was degassed and the catalyst premixture was added. The resultant mixture was stirred at 120° C. for 5 h in a sealed tube. After consumption of the starting material (monitored by TLC and LCMS), the reaction mixture was filtered and the filtrate was concentrated in vacuo. The residue was diluted with water (20 mL) and extracted with CH$_2$Cl$_2$ (2×20 mL). The combined organic extracts were dried over sodium sulfate, filtered and concentrated in vacuo. The crude material was purified by preparative HPLC (Ascentis C18 (250×21.2 mm: 5μ; (55 mg loading; CH$_3$CN: 0.05% TFA (0.1/90, 2/80, 15/70, 25/20, 30/10, 35/10) to afford 2-((3-methoxy-4-(4-methyl-1H-imidazol-1-yl) phenyl) amino)-6, 6a, 7, 8-tetrahydro-9H-pyrimido [5, 4-b] pyrrolo [1, 2-d] [1, 4] oxazin-9-one (30 mg, 11%) as an off-white solid. LCMS: 393 (M+1); (column; X-select CSH C-18 (50×3.0 mm, 3.5 μm); RT 2.24 min. 0.05% Aq TFA: ACN; 0.8 mL/min); TLC: 5% MeOH/CH$_2$Cl$_2$ (R$_f$: 0.5).

Racemic compound of Example 301 was separated using a Chiralpak-IC column (250×20 mm, 5 μm (10 mg loading; 0.1% DEA in n-hexane: CH$_2$Cl$_2$:MeOH (50:50) (A:B: 70:30) as mobile phase) to provide the compound of Example 301A (Fraction I (+)) the compound of Example 301B (Fraction II (−)).

Example 301A

Synthesis of (+)-N-(5-methoxy-6-(4-methyl-1H-imidazol-1-yl) pyridin-3-yl)-8'-methyl-2, 3, 5, 6-tetrahydro-6'H, 8'H-spiro [pyran-4, 7'-pyrimido [5, 4-b] [1, 4] oxazin]-2'-amine

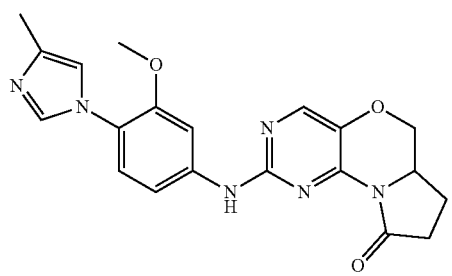 [SMILES: COc1cc(Nc2ncc3c(n2)N2C(=O)CCC2CO3)ccc1-n1cnc(C)c1]

The compound of Example 301A was produced as described in Example 301. Analytical data for product Fraction I (+): $^1$H NMR (CD$_3$OD, 400 MHz): δ 8.11 (s, 1H), 7.98 (s, 1H), 7.69 (s, 1H), 7.20-7.18 (m, 2H), 6.97 (s, 1H), 4.55-4.51 (m, 1H), 4.22-4.19 (m, 1H), 3.91 (s, 3H), 3.78 (t, 1H), 2.75-2.70 (m, 1H), 2.52-2.49 (m, 1H), 2.40-2.30 (m, 1H), 2.22 (s, 3H), 1.83-1.78 (m, 1H); Mass (ESI): 393.4 [M+1]; LCMS: 392.9 (M+1); (column; X-select CSH C-18 (50×3.0 mm, 3.5 μm); RT 2.24 min. 0.05% Aq TFA: ACN; 0.8 mL/min); UPLC (column; Acquity BEH C-18, 50×2.1 mm, 1.7 μm); RT 1.54 min. ACN: 0.025% Aq TFA; 0.5 mL/min; Chiral HPLC: 99.1% RT=15.09 min (Chiralpak-IA (250×4.6 mm, 5 μm; mobile phase (A) 0.1% DEA in n-hexane (B) CH$_2$Cl$_2$:MeOH (80:20) (A:B; 70:30); flow Rate: 1.0 mL/min); Optical rotation [α]$_D^{20.02}$: +63.66 (c=0.25, CH$_2$Cl$_2$).

Example 301B

Synthesis of (−)-N-(5-methoxy-6-(4-methyl-1H-imidazol-1-yl) pyridin-3-yl)-8'-methyl-2, 3, 5, 6-tetrahydro-6'H, 8'H-spiro [pyran-4, 7'-pyrimido [5, 4-b] [1, 4] oxazin]-2'-amine

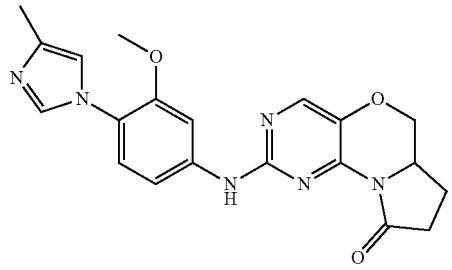 [SMILES: COc1cc(Nc2ncc3c(n2)N2C(=O)CCC2CO3)ccc1-n1cnc(C)c1]

The compound of Example 301B was produced as described in Example 301. Analytical data for product Fraction II (−): $^1$H NMR (CD$_3$OD, 400 MHz): δ 8.11 (s, 1H), 7.98 (s, 1H), 7.69 (s, 1H), 7.20-7.18 (m, 2H), 6.97 (s, 1H), 4.55-4.51 (m, 1H), 4.22-4.19 (m, 1H), 3.91 (s, 3H), 3.78 (t, 1H), 2.75-2.70 (m, 1H), 2.52-2.49 (m, 1H), 2.40-2.30 (m, 1H), 2.22 (s, 3H), 1.83-1.78 (m, 1H); Mass (ESI): 393.4 [M+1]; LCMS: 393 (M+1); (column; X-select CSH C-18 (50×3.0 mm, 3.5 μm); RT 2.24 min. 0.05% Aq TFA: ACN; 0.8 mL/min); UPLC (column; Acquity BEH C-18, 50×2.1 mm, 1.7 μm); RT 1.54 min. ACN: 0.025% Aq TFA; 0.5 mL/min; Chiral HPLC: 99.5% RT=18.96 min (Chiralpak-IA (250×4.6 mm, 5 μm; mobile phase (A) 0.1% DEA in n-hexane (B) CH$_2$Cl$_2$:MeOH (80:20) (A:B; 70:30); flow Rate: 1.0 mL/min); Optical rotation [α]$_D^{20.01}$: −61.98 (c=0.25, CH$_2$Cl$_2$).

Example 302

Synthesis of 2-((5-methoxy-6-(4-methyl-1H-imidazol-1-yl) pyridin-3-yl) amino)-6, 6a, 7, 8-tetrahydro-9H-pyrimido [5, 4-b] pyrrolo [1, 2-d] [1, 4] oxazin-9-one

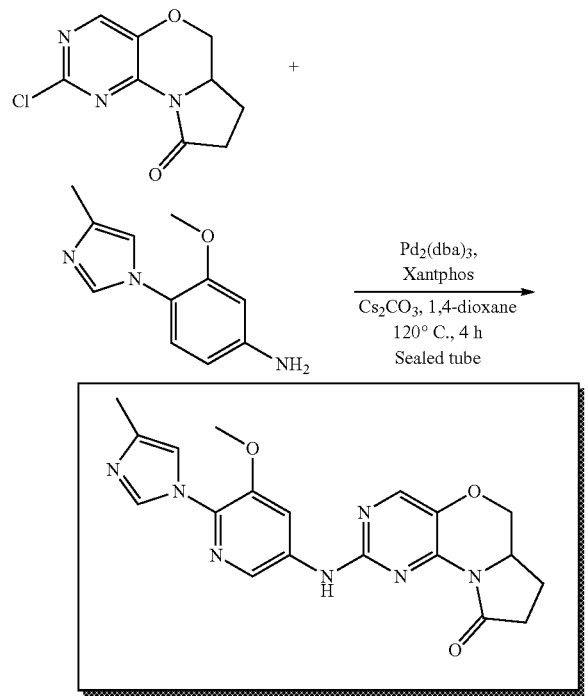

Synthesis of 2-((5-methoxy-6-(4-methyl-1H-imidazol-1-yl) pyridin-3-yl)amino)-6, 6a, 7, 8-tetrahydro-9H-pyrimido [5, 4-b] pyrrolo [1, 2-d] [1, 4] oxazin-9-one To a dry vial was added a suspension of Pd$_2$(dba)$_3$ (20 mg, 0.02 mmol) and Xantphos (38 mg, 0.06 mmol) in 1, 4-dioxane (1 mL) at room temperature. The suspension was degassed with argon, heated to 120° C., and stirred for 3 min. A mixture of 2-chloro-6, 6a, 7, 8-tetrahydro-9H-pyrimido [5, 4-b] pyrrolo [1, 2-d] [1, 4] oxazin-9-one (100 mg, 0.44 mmol), 5-methoxy-6-(4-methyl-1H-imidazol-1-yl) pyridin-3-amine (91 mg, 0.44 mmol) and cesium carbonate (202 mg, 0.62 mmol) in 1, 4-dioxane (1 mL) was degassed and the catalyst premixture was added. The resultant mixture was stirred at 120° C. for 4 h in a sealed tube. After consumption of the starting material (monitored by TLC and LCMS), the reaction mixture was diluted with water (20 mL) and extracted with CH$_2$Cl$_2$ (2×20 mL). The combined organic extracts were dried over sodium sulfate, filtered and concentrated in vacuo. The crude material was purified by preparative HPLC (Column X-select CSH C18 column (250×19 mm, 5 μm (75 mg loading; CH$_3$CN: 005% TFA (0.01/95, 15/70, 25/50, 35/10 to afford 2-((5-methoxy-6-(4-methyl-1H-imidazol-1-yl) pyridin-3-yl) amino)-6, 6a, 7, 8-tetrahydro-9H-pyrimido [5, 4-b] pyrrolo [1, 2-d] [1, 4] oxazin-9-one (65 mg, 37%) as an off-white solid. LCMS: 394 (M+1); (column; X-select CSH C-18 (50×3.0 mm, 3.5 μm); RT 2.20 min. 0.05% Aq TFA: ACN; 0.8 mL/min); TLC: 5% MeOH/CH$_2$Cl$_2$ (R$_f$: 0.3).

Racemic compound of Example 302 was separated using a Chiralpak-IA column (250×20 mm, 5 μm (20 mg loading; 0.1% DEA in n-hexane: CH$_2$Cl$_2$:MeOH (50:50) (A:B; 70:30) as mobile phase) to provide the compound of Example 302A (Fraction I (+)) the compound of Example 302B (Fraction II (−)).

Example 302A

Synthesis of (+)-2-((5-methoxy-6-(4-methyl-1H-imidazol-1-yl) pyridin-3-yl) amino)-6, 6a, 7, 8-tetrahydro-9H-pyrimido [5, 4-b] pyrrolo [1, 2-d] [1, 4] oxazin-9-one

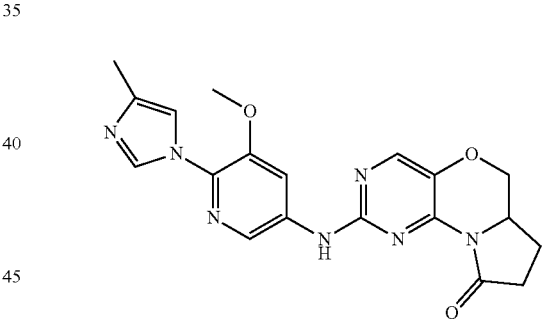

The compound of Example 302A was produced as described in Example 302. Analytical data for product Fraction I (+): $^1$H NMR (CD$_3$OD, 400 MHz): δ 8.81-8.77 (m, 1H), 8.14 (s, 2H), 8.08-8.06 (m, 1H), 7.40 (s, 1H), 4.55 (dd, 1H), 4.28-4.18 (m, 1H), 4.08 (s, 3H), 3.75 (t, 1H), 2.78-2.73 (m, 1H), 2.56-2.50 (m, 1H), 2.40-2.31 (m, 1H), 2.26 (s, 3H), 1.88-1.80 (m, 1H); Mass (ESI): 394.4 [M+1]; LCMS: 394.3 (M+1); (column; X-Select CSH C-18 (50×3.0 mm, 3.5 μm); RT 2.87 min 0.05% Aq TFA: ACN; 0.80 mL/min); UPLC (column; Acquity BEH C-18, 50×2.1 mm, 1.7 μm); RT 1.51 min. ACN: 0.025% Aq TFA; 0.5 mL/min; Chiral HPLC: 99.3% RT=13.44 min (Chiralpak-IA (150×4.6 mm, 5μ; mobile phase (A) 0.1% DEA in n-hexane (B) CH$_2$Cl$_2$:MeOH (50:50) (A:B; 70:30); flow Rate: 1.0 mL/min); Optical rotation [α]$_D^{19.98}$: +61.92 (c=0.25, CH$_2$Cl$_2$).

Example 302B

Synthesis of (−)-2-((5-methoxy-6-(4-methyl-1H-imidazol-1-yl) pyridin-3-yl) amino)-6, 6a, 7, 8-tetrahydro-9H-pyrimido [5, 4-b] pyrrolo [1, 2-d] [1, 4] oxazin-9-one

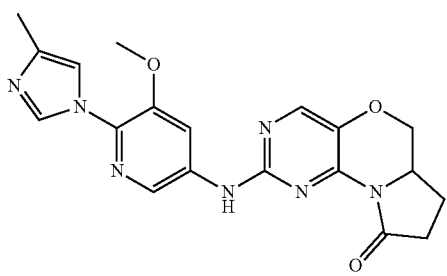 [SMILES: COc1cc(Nc2ncc3c(n2)N2C(=O)CCC2CO3)cnc1-n1cnc(C)c1]

The compound of Example 302B was produced as described in Example 302. Analytical data for product Fraction II (−): ¹H NMR (CD$_3$OD, 400 MHz): δ 8.81-8.77 (m, 1H), 8.14 (s, 2H), 8.08-8.06 (m, 1H), 7.40 (s, 1H), 4.55 (dd, 1H), 4.28-4.18 (m, 1H), 4.08 (s, 3H), 3.75 (t, 1H), 2.78-2.73 (m, 1H), 2.56-2.50 (m, 1H), 2.40-2.31 (m, 1H), 2.26 (s, 3H), 1.88-1.80 (m, 1H); Mass (ESI): 394.4 [M+1]; LCMS: 394.3 (M+1); (column; X-Select CSH C-18 (50×3.0 mm, 3.5 µm); RT 2.86 min 0.05% Aq TFA: ACN; 0.80 mL/min); UPLC (column; Acquity BEH C-18, 50×2.1 mm, 1.7 µm); RT 1.50 min. ACN: 0.025% Aq TFA; 0.5 mL/min; Chiral HPLC: 98.0% RT=15.98 min (Chiralpak-IA (150×4.6 mm, 5µ; mobile phase (A) 0.1% DEA in n-hexane (B) CH$_2$Cl$_2$:MeOH (50:50) (A:B; 70:30); flow Rate: 1.0 mL/min); Optical rotation $[\alpha]_D^{20.01}$: −58.51 (c=0.25, CH$_2$Cl$_2$).

Example 303

Synthesis of (R)-8, 8-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine

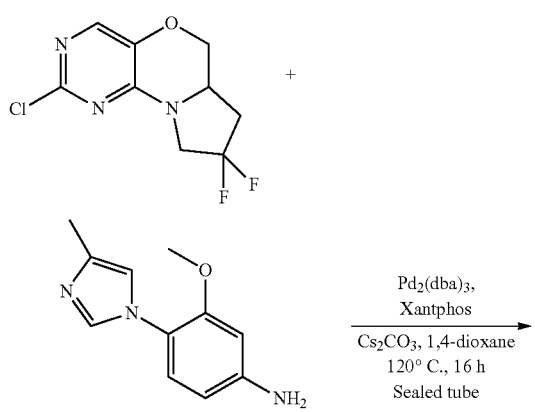

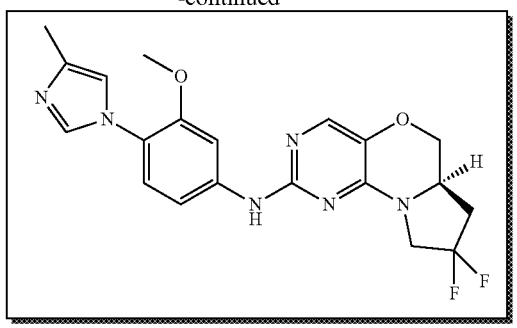

Synthesis of (R)-8, 8-difluoro-N-(3-methoxy-4-(4-methyl-1H-imidazol-1-yl)phenyl)-6a, 7, 8, 9-tetrahydro-6H-pyrimido [5, 4-b] pyrrolo [1, 2-d] [1, 4] oxazin-2-amine To a dry vial was added a suspension of Pd$_2$(dba)$_3$ (46 mg, 0.05 mmol) and Xantphos (88 mg, 0.15 mmol) in 1, 4-dioxane (1.5 mL) at room temperature. The suspension was degassed with argon, heated to 120° C., and stirred for 3 min. A mixture of (R)-2-chloro-8, 8-difluoro-6a, 7, 8, 9-tetrahydro-6H-pyrimido [5, 4-b] pyrrolo [1, 2-d] [1, 4] oxazine (250 mg, 1.01 mmol), 3-methoxy-4-(4-methyl-1H-imidazol-1-yl) aniline (411 mg, 2.02 mmol) and cesium carbonate (460 mg, 1.41 mmol) in 1, 4-dioxane (1.5 mL) was degassed and the catalyst premixture was added. The resultant mixture was stirred at 120° C. for 16 h in a sealed tube. After consumption of the starting material (monitored by TLC and LCMS), the reaction mixture was diluted with water (20 mL) and extracted with CH$_2$Cl$_2$ (2×20 mL). The combined organic extracts were dried over sodium sulfate, filtered and concentrated in vacuo. The crude material was purified by preparative HPLC (Ascentis C18 (250×21.2 mm: 5µ; (70 mg loading; CH$_3$CN: 0.05% TFA (0.1/90, 2/85, 15/70, 25/25, 30/10, 35/10) as mobile phase) to afford (R)-8, 8-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine (140 mg, 33%) as an off-white solid. ¹H-NMR (CD$_3$OD, 400 MHz): δ 7.71-7.70 (m, 1H), 7.66-7.65 (m, 1H), 7.63 (s, 1H), 7.24-7.19 (m, 2H), 6.96 (s, 1H), 4.52 (dd, 1H), 4.23-4.14 (m, 2H), 3.98-3.80 (m, 1H), 3.86 (s, 3H), 3.58 (t, 1H), 2.67-2.56 (m, 1H), 2.34-2.27 (m, 1H), 2.23 (s, 3H); Mass (ESI): 415.5 [M+1]; LCMS: 415.5 (M+1); (column; X-Select CSH C-18 (50×3.0 mm, 3.5 µm); RT 2.03 min. 0.05% Aq TFA: ACN; 0.80 mL/min); UPLC (column; Acquity BEH C-18, 50×2.1 mm, 1.7 µm); RT 1.40 min. ACN: 0.025% Aq TFA; 0.5 mL/min; Chiral HPLC: 98.1% RT=22.40 min (Chiralpak-ADH (250×4.6 mm, 5 µm; mobile phase (A) n-hexane (B) EtOH (70:30); flow Rate: 1.0 mL/min); Optical rotation $[\alpha]_D^{21.00}$: −14 4 (c=0.25, CH$_2$Cl$_2$). TLC: 5% MeOH/CH$_2$Cl$_2$ (R$_f$: 0.4).

Example 304

Synthesis of 7, 7-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine

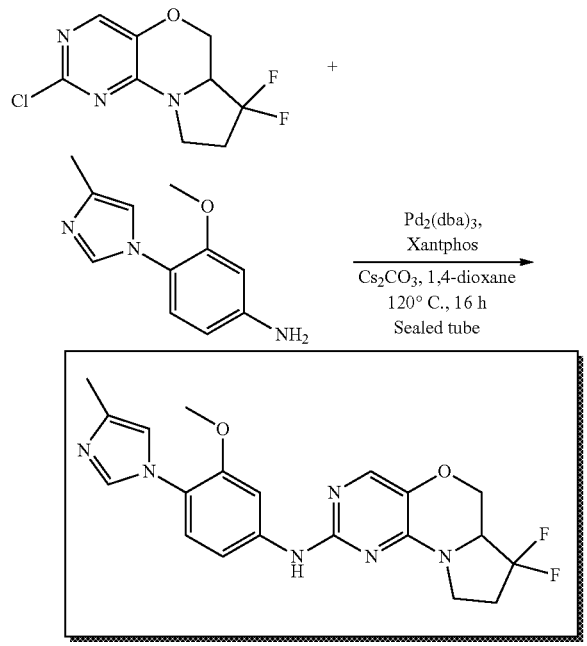

Synthesis of 7, 7-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine To a dry vial was added a suspension of Pd$_2$(dba)$_3$ (37 mg, 0.04 mmol) and Xantphos (70 mg, 0.12 mmol) in 1, 4-dioxane (2 mL) at room temperature. The suspension was degassed with argon, heated to 120° C., and stirred for 3 min. A mixture of 2-chloro-7, 7-difluoro-6a, 7, 8, 9-tetrahydro-6H-pyrimido [5, 4-b] pyrrolo [1, 2-d] [1, 4] oxazine (200 mg, 0.80 mmol), 3-methoxy-4-(4-methyl-1H-imidazol-1-yl) aniline (328 mg, 1.61 mmol) and cesium carbonate (368 mg, 1.13 mmol) in 1, 4-dioxane (2 mL) was degassed and the catalyst premixture was added. The resultant mixture was stirred at 120° C. for 16 h in a sealed tube. After consumption of the starting material (monitored by TLC and LCMS), the reaction mixture was diluted with water (50 mL) and extracted with CH$_2$Cl$_2$ (2×50 mL). The combined organic extracts were dried over sodium sulfate, filtered and concentrated in vacuo. The crude material was purified by column chromatography using 4% MeOH/CH$_2$Cl$_2$ to afford 7, 7-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine (120 mg, 36%) as an off-white solid. LCMS: 415 (M+1); (column; Ascentis Express C-18 (50×3.0 mm, 2.7 µm); RT 1.54 min. 0.025% Aq TFA+5% ACN: ACN+5% 0.025% Aq TFA; 1.2 mL/min); TLC: 5% MeOH/CH$_2$Cl$_2$ (R$_f$: 0.5).

Racemic compound of Example 304 was separated using a Chiralpak-IC column (250×20 mm, 5 µm (50 mg loading; 0.1% DEA in n-hexane: CH$_2$Cl$_2$:MeOH (50:50) (A:B: 70:30) as mobile phase) to provide the compound of Example 304A (Fraction I (−)) the compound of Example 304B (Fraction II (+)).

Example 304A

Synthesis of (−)-7, 7-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine

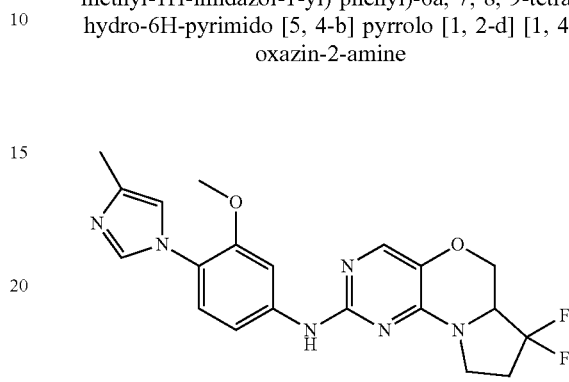

The compound of Example 304A was produced as described in Example 304. Analytical data for product Fraction I (−): $^1$H NMR (CD$_3$OD, 400 MHz): δ 7.79 (s, 1H), 7.67 (s, 1H), 7.66 (s, 1H), 7.24-7.16 (m, 2H), 6.97 (s, 1H), 4.59 (dd, 1H), 4.20-4.11 (m, 1H), 3.95-3.90 (m, 2H), 3.86 (s, 3H), 3.78-3.70 (m, 1H), 2.70-2.51 (m, 2H), 2.24 (s, 3H); Mass (ESI): 415.4 [M+1]; LCMS: 415 (M+1); (column; Ascentis Express C-18 (50×3.0 mm, 2.7 µm); RT 1.53 min. 0.025% Aq TFA+5% ACN: ACN+5% 0.025% Aq TFA; 1.2 mL/min); HPLC (column; Eclipse XDB-C-18, 150×4.6 mm, 5.0 µm); RT 6.31 min. ACN: 0.05% Aq TFA; 1.0 mL/min; Chiral HPLC: 99.6% RT=12.58 min (Chiralpak-IC (250×4.6 mm, 5 µm; mobile phase (A) 0.1% DEA in n-hexane (B) EtOH:MeOH (50:50) (A:B; 70:30); flow Rate: 1.0 mL/min); Optical rotation [α]$_D^{20.03}$: −30.80 (c=0.25, CH$_2$Cl$_2$).

Example 304B

Synthesis of (+)-7, 7-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine

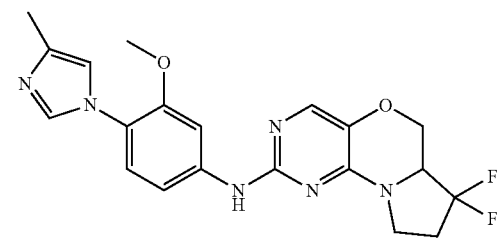 [SMILES: COc1cc(Nc2ncc3c(n2)N2CCC(F)(F)C2CO3)ccc1-n1cnc(C)c1]

The compound of Example 304B was produced as described in Example 304. Analytical data for product Fraction II (+): $^1$H NMR (CD$_3$OD, 400 MHz): δ 7.79 (s, 1H), 7.67 (s, 1H), 7.66 (s, 1H), 7.24-7.16 (m, 2H), 6.97 (s, 1H), 4.59 (dd, 1H), 4.20-4.11 (m, 1H), 3.95-3.90 (m, 2H), 3.86 (s, 3H), 3.78-3.70 (m, 1H), 2.70-2.51 (m, 2H), 2.24 (s, 3H); Mass (ESI): 415.4 [M+1]; LCMS: 415 (M+1); (column; Ascentis Express C-18 (50×3.0 mm, 2.7 μm); RT 1.53 min. 0.025% Aq TFA+5% ACN: ACN+5% 0.025% Aq TFA; 1.2 mL/min); HPLC (column; Eclipse XDB-C-18, 150×4.6 mm, 5.0 μm); RT 6.31 min. ACN: 0.05% Aq TFA; 1.0 mL/min; Chiral HPLC: 96.8% RT=13.81 min (Chiralpak-IC (250×4.6 mm, 5 μm; mobile phase (A) 0.1% DEA in n-hexane (B) EtOH:MeOH (50:50) (A:B; 70:30); flow Rate: 1.0 mL/min); Optical rotation $[\alpha]_D^{20.00}$: +38.27 (c=0.25, CH$_2$Cl$_2$).

Example 305

Synthesis of 7, 7-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine

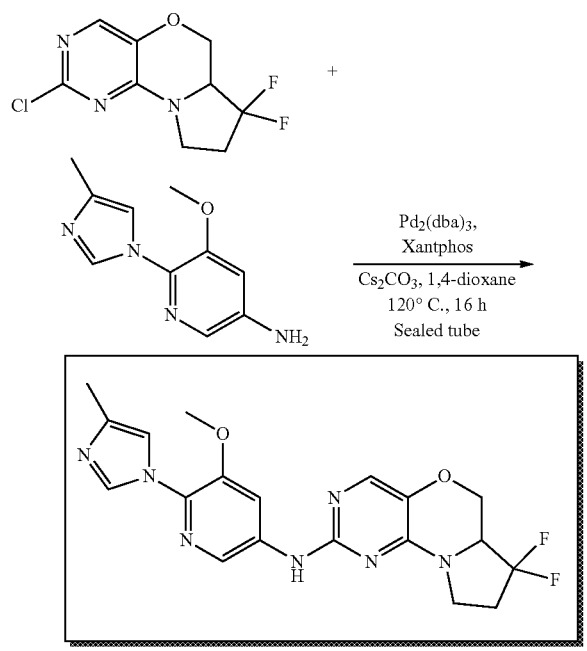

Synthesis of 7, 7-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine To a dry vial was added a suspension of Pd$_2$(dba)$_3$ (37 mg, 0.04 mmol) and Xantphos (70 mg, 0.12 mmol) in 1, 4-dioxane (2 mL) at room temperature. The suspension was degassed with argon, heated to 120° C., and stirred for 3 min. A mixture of 2-chloro-7, 7-difluoro-6a, 7, 8, 9-tetrahydro-6H-pyrimido [5, 4-b] pyrrolo [1, 2-d] [1, 4] oxazine (200 mg, 0.80 mmol), 5-methoxy-6-(4-methyl-1H-imidazol-1-yl) pyridin-3-amine (330 mg, 1.61 mmol) and cesium carbonate (368 mg, 1.13 mmol) in 1, 4-dioxane (2 mL) was degassed and the catalyst premixture was added. The resultant mixture was stirred at 120° C. for 16 h in a sealed tube. After consumption of the starting material (monitored by TLC and LCMS), the reaction mixture was diluted with water (50 mL) and extracted with CH$_2$Cl$_2$ (2×50 mL). The combined organic extracts were dried over sodium sulfate, filtered and concentrated in vacuo. The crude material was purified by column chromatography using 4% MeOH/CH$_2$Cl$_2$ to afford 7, 7-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine (110 mg, 33%) as an off-white solid. LCMS: 416.1 (M+1); (column; Ascentis Express C-18 (50×3.0 mm, 2.7 μm); RT 1.55 min. 0.025% Aq TFA+5% ACN: ACN+5% 0.025% Aq TFA; 1.2 mL/min); TLC: 5% MeOH/CH$_2$Cl$_2$ (R$_f$: 0.3).

Racemic compound of Example 305 was separated using a Chiralpak-IC column (250×20 mm, 5 μm (50 mg loading; 0.1% DEA in n-hexane: CH$_2$Cl$_2$:MeOH (50:50) (A:B: 70:30) as mobile phase) to provide the compound of Example 305A (Fraction I (+)) the compound of Example 305B (Fraction II (−)).

Example 305A

Synthesis of (+)-7, 7-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine

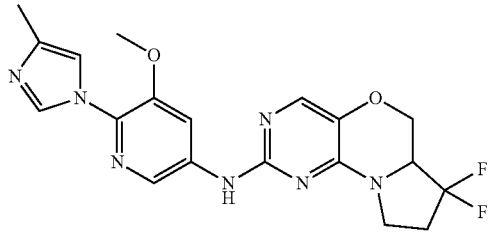 [SMILES: COc1cc(Nc2ncc3c(n2)N2CCC(F)(F)C2CO3)cnc1-n1cnc(C)c1]

The compound of Example 305A was produced as described in Example 305. Analytical data for product Fraction I (+): $^1$H NMR (DMSO-d$_6$, 400 MHz): δ 9.46 (s, 1H), 8.36-8.34 (m, 1H), 8.33-8.31 (m, 1H), 8.05 (s, 1H), 7.77 (s, 1H), 7.37 (s, 1H), 4.65 (dd, 1H), 4.29-4.16 (m, 1H), 3.92 (s, 3H), 3.88-3.83 (m, 2H), 3.67 (t, 1H), 2.70-2.50 (m, 2H), 2.15 (s, 3H); Mass (ESI): 416.4 [M+1]; LCMS: 416 (M+1); (column; Ascentis Express C-18 (50×3.0 mm, 2.7 μm); RT 1.55 min. 0.025% Aq TFA+5% ACN: ACN+5% 0.025% Aq TFA; 1.2 mL/min); HPLC (column; Eclipse XDB-C-18, 150×4.6 mm, 5.0 μm); RT 6.29 min. ACN: 0.05% Aq TFA; 1.0 mL/min; Chiral HPLC: 100% RT=9.66 min (Chiralpak-AD-H (250×4.6 mm, 5 μm; mobile phase (A) 0.1% DEA+MeOH (B) IPA (A:B; 75:25); flow Rate: 1.0 mL/min); Optical rotation $[\alpha]_D^{20.00}$: +36.28 (c=0.25, CH$_2$Cl$_2$).

Example 305B

Synthesis of (−)-7, 7-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine

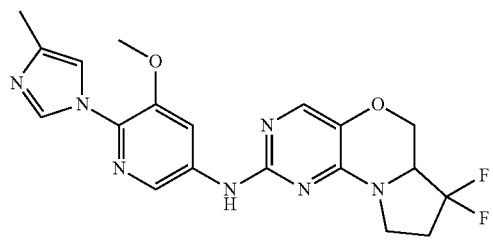 [SMILES: COc1cc(Nc2ncc3c(n2)N2CCC(F)(F)C2CO3)cnc1-n1cnc(C)c1]

The compound of Example 305B was produced as described in Example 305. Analytical data for product Fraction II (−): $^1$H NMR (DMSO-$d_6$, 400 MHz): δ 9.46 (s, 1H), 8.36-8.34 (m, 1H), 8.33-8.31 (m, 1H), 8.05 (s, 1H), 7.77 (s, 1H), 7.37 (s, 1H), 4.65 (dd, 1H), 4.29-4.16 (m, 1H), 3.92 (s, 3H), 3.88-3.83 (m, 2H), 3.67 (t, 1H), 2.70-2.50 (m, 2H), 2.15 (s, 3H); Mass (ESI): 416.4 [M+1]; LCMS: 416 (M+1); (column; Ascentis Express C-18 (50×3.0 mm, 2.7 μm); RT 1.55 min. 0.025% Aq TFA+5% ACN: ACN+5% 0.025% Aq TFA; 1.2 mL/min); HPLC (column; Eclipse XDB-C-18, 150×4.6 mm, 5.0 μm); RT 6.29 min. ACN: 0.05% Aq TFA; 1.0 mL/min; Chiral HPLC: 97.8% RT=13.24 min (Chiralpak-ADH (250×4.6 mm, 5 μm; mobile phase (A) 0.1% DEA+MeOH (B) IPA (A:B; 75:25); flow Rate: 1.0 mL/min); Optical rotation $[\alpha]_D^{19.99}$: −38.15 (c=0.25, $CH_2Cl_2$).

Example 306

In Vitro Cell Screening Assay and Quantification of $A\beta_{(1-x)}$ and $A\beta_{(1-42)}$ Peptides Human neuroglioma H4 cells were transfected with a pcDNA3.1 plasmid expressing human wild type APP751 cDNA and a stable cell line was generated using G418 selection. Cells are plated at 15,000 cells/well in Costar 96-well plates and placed at 37° C. and 5% $CO_2$. Six hours after plating, cells are washed three times with Pro293™ chemically defined medium, followed by addition of compounds (0.003-10 μM, final DMSO concentration of 0.33%). Plates were incubated overnight (16-18 h) and supernatant was removed for quantification of Aβ peptides by sandwich ELISA. Cytotoxicity was evaluated using Cell-Titer 96W AQueous One Solution Cell Proliferation Assay according to the manufacturer's protocol.

ELISA Measurements of Aβ Peptides

Aβ peptide levels were quantified by sandwich ELISA. 96-well plates are coated with C-terminal specific Aβ antibodies recognizing either Aβ37, Aβ38, Aβ40, Aβ42, Aβ43 or a N-terminal specific Aβ antibody to detect Aβ 1-x. Plates are then blocked overnight at 4° C. with 1% bovine serum albumin (BSA) in PBS-T. Plates are washed and 100 μl of cultured cell supernatant or synthetic Aβ peptide standards and a detection antibody (4G8-HRP) are applied to the blocked plate and incubated overnight at 4° C. The next day, wells are washed before the addition the addition of detection substrate (TMB peroxidase). Plates are then read for absorbance at 450 nm on a Molecular Devices SpectraMax M5e Microplate Reader.

Compound-treated samples were normalized to samples treated with DMSO alone (no inhibition) and to samples treated with DAPT. $IC_{50}$ values were calculated from values reported as percent of DMSO controls using nonlinear regression, based on a sigmoidal dose-response (variable slope) model. GraphPAD software from Prism used for calculation.

TABLE III

Biological Assay

| Compound of Example | Structure | Name | Aβ42 H4 Prot Fre IC50 (μM) |
|---|---|---|---|
| 21A | 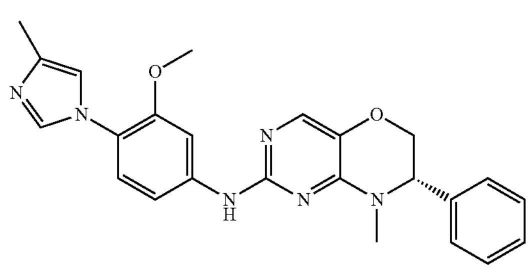 | (S)-N-(3-methoxy-4-(4-methyl-1H-imidazol-1-yl)phenyl)-8-methyl-7-phenyl-7,8-dihydro-6H-pyrimido[5,4-b][1,4]oxazin-2-amine | 0.022 |

TABLE III-continued

Biological Assay

| Compound of Example | Structure | Name | Aβ42 H4 Prot Fre IC50 (μM) |
|---|---|---|---|
| 21B | 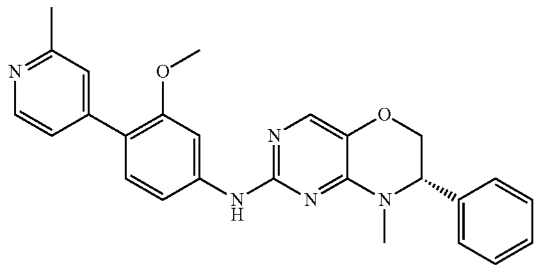 [SMILES: COc1cc(Nc2ncc3c(n2)N(C)[C@@H](c2ccccc2)CO3)ccc1-c1ccnc(C)c1] | (S)-N-(3-methoxy-4-(2-methylpyridin-4-yl)phenyl)-8-methyl-7-phenyl-7,8-dihydro-6H-pyrimido[5,4-b][1,4]oxazin-2-amine | 0.040 |
| 22A | 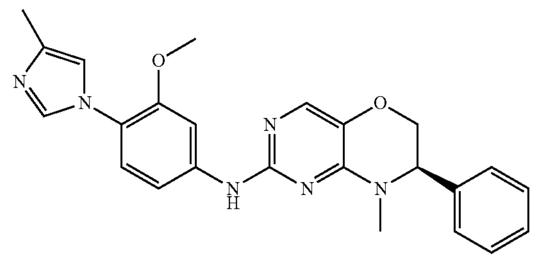 [SMILES: COc1cc(Nc2ncc3c(n2)N(C)[C@H](c2ccccc2)CO3)ccc1-n1cnc(C)c1] | (R)-N-(3-methoxy-4-(4-methyl-1H-imidazol-1-yl)phenyl)-8-methyl-7-phenyl-7,8-dihydro-6H-pyrimido[5,4-b][1,4]oxazin-2-amine | 0.087 |
| 22B | 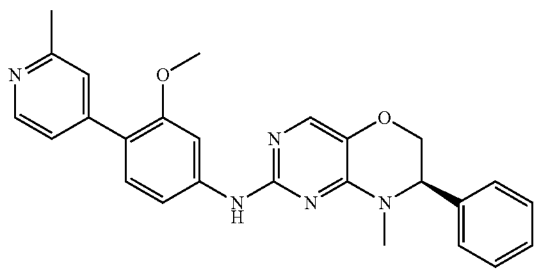 [SMILES: COc1cc(Nc2ncc3c(n2)N(C)[C@H](c2ccccc2)CO3)ccc1-c1ccnc(C)c1] | (R)-N-(3-methoxy-4-(2-methylpyridin-4-yl)phenyl)-8-methyl-7-phenyl-7,8-dihydro-6H-pyrimido[5,4-b][1,4]oxazin-2-amine | 0.168 |
| 23 | 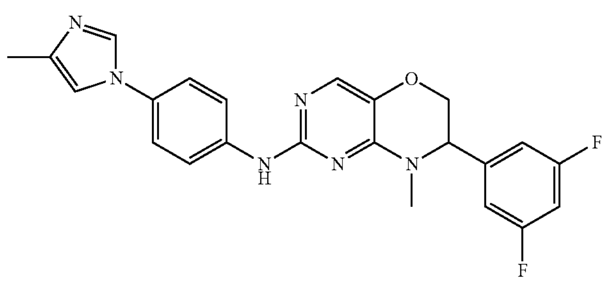 [SMILES: Cc1cn(-c2ccc(Nc3ncc4c(n3)N(C)C(c3cc(F)cc(F)c3)CO4)cc2)cn1] | 7-(3,5-difluorophenyl)-8-methyl-N-(4-(4-methyl-1H-imidazol-1-yl)phenyl)-7,8-dihydro-6H-pyrimido[5,4-b][1,4]oxazin-2-amine (racemic) | 0.0379 |
| 23A | 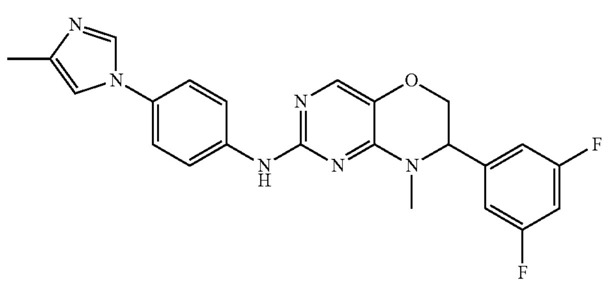 [SMILES: Cc1cn(-c2ccc(Nc3ncc4c(n3)N(C)C(c3cc(F)cc(F)c3)CO4)cc2)cn1] | (−)-7-(3,5-difluorophenyl)-8-methyl-N-(4-(4-methyl-1H-imidazol-1-yl) phenyl)-7,8-dihydro-6H-pyrimido [5, 4-b] [1, 4] oxazin-2-amine | 2.035 |

TABLE III-continued

Biological Assay

| Compound of Example | Structure | Name | Aβ42 H4 Prot Fre IC50 (μM) |
|---|---|---|---|
| 23B | 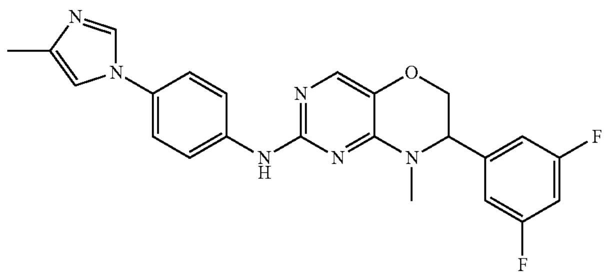 [SMILES: Cc1cn(-c2ccc(Nc3ncc4c(n3)N(C)C(c3cc(F)cc(F)c3)CO4)cc2)cn1] | (+)-7-(3, 5-difluorophenyl)-8-methyl-N-(4-(4-methyl-1H-imidazol-1-yl) phenyl)-7,8-dihydro-6H-pyrimido [5, 4-b] [1, 4] oxazin-2-amine | 0.032 |
| 24 | 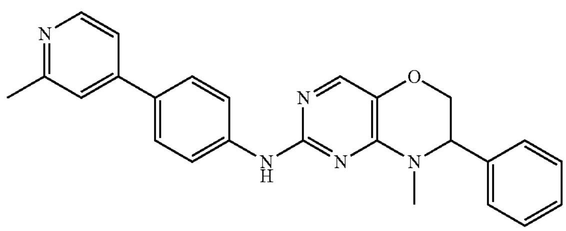 [SMILES: Cc1cc(-c2ccc(Nc3ncc4c(n3)N(C)C(c3ccccc3)CO4)cc2)ccn1] | 8-methyl-N-(4-(2-methylpyridin-4-yl)phenyl)-7-phenyl-7,8-dihydro-6H-pyrimido[5,4-b][1,4]oxazin-2-amine (racemic) | 0.155 |
| 24A | 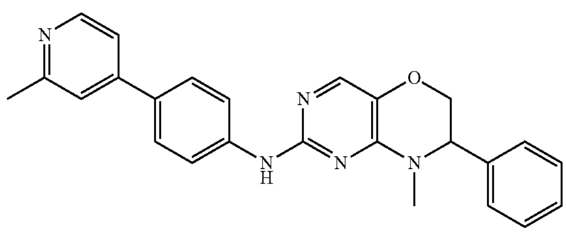 [SMILES: Cc1cc(-c2ccc(Nc3ncc4c(n3)N(C)C(c3ccccc3)CO4)cc2)ccn1] | (+)-8-methyl-N-(4-(2-methylpyridin-4-yl)phenyl)-7-phenyl-7,8-dihydro-6H-pyrimido[5,4-b][1,4]oxazin-2-amine | 0.068 |
| 24B | 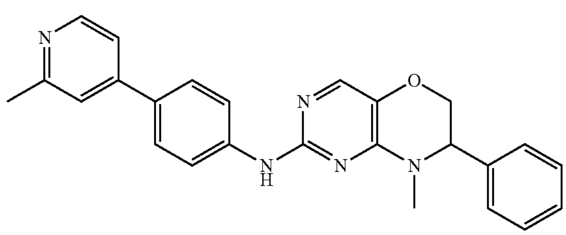 [SMILES: Cc1cc(-c2ccc(Nc3ncc4c(n3)N(C)C(c3ccccc3)CO4)cc2)ccn1] | (−)-8-methyl-N-(4-(2-methylpyridin-4-yl)phenyl)-7-phenyl-7,8-dihydro-6H-pyrimido[5,4-b][1,4]oxazin-2-amine | 1.019 |
| 25 | 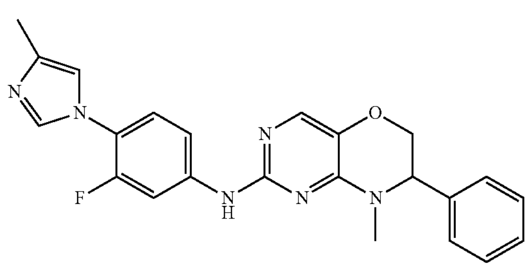 [SMILES: Cc1cn(-c2ccc(Nc3ncc4c(n3)N(C)C(c3ccccc3)CO4)cc2F)cn1] | N-(3-fluoro-4-(4-methyl-1H-imidazol-1-yl)phenyl)-8-methyl-7-phenyl-7,8-dihydro-6H-pyrimido[5,4-b][1,4]oxazin-2-amine (racemic) | 0.101 |

TABLE III-continued

Biological Assay

| Compound of Example | Structure | Name | Aβ42 H4 Prot Fre IC50 (μM) |
|---|---|---|---|
| 25A | 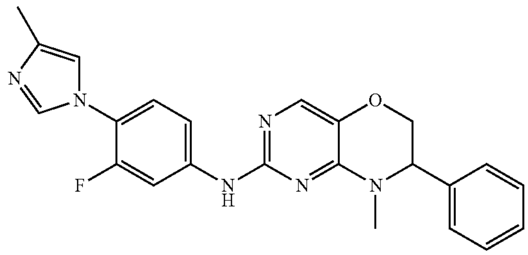 [SMILES: Cc1cn(-c2ccc(Nc3ncc4c(n3)N(C)C(c3ccccc3)CO4)cc2F)cn1] | (+)-N-(3-fluoro-4-(4-methyl-1H-imidazol-1-yl)phenyl)-8-methyl-7-phenyl-7,8-dihydro-6H-pyrimido[5,4-b] [1,4] oxazin-2-amine | 0.014 |
| 25B | 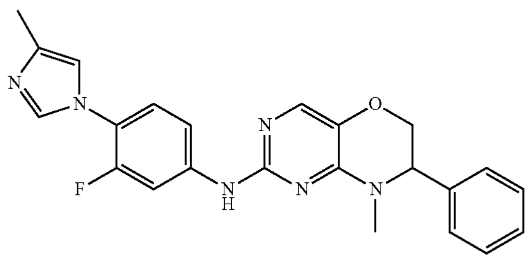 [SMILES: Cc1cn(-c2ccc(Nc3ncc4c(n3)N(C)C(c3ccccc3)CO4)cc2F)cn1] | (−)-N-(3-fluoro-4-(4-methyl-1H-imidazol-1-yl)phenyl)-8-methyl-7-phenyl-7,8-dihydro-6H-pyrimido [5,4-b] [1,4] oxazin-2-amine | 0.334 |
| 26 | 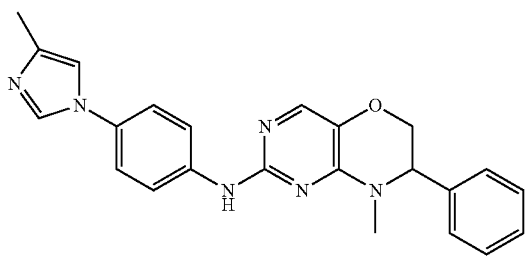 [SMILES: Cc1cn(-c2ccc(Nc3ncc4c(n3)N(C)C(c3ccccc3)CO4)cc2)cn1] | 8-methyl-N-(4-(4-methyl-1H-imidazol-1-yl)phenyl)-7-phenyl-7,8-dihydro-6H-pyrimido [5,4-b] [1,4] oxazin-2-amine (racemic) | 0.121 |
| 26A | 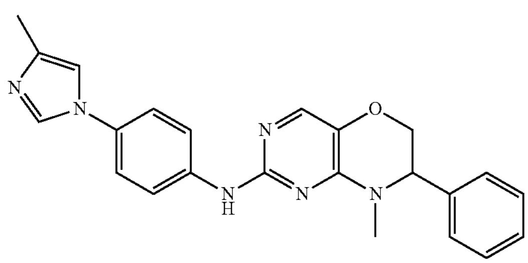 [SMILES: Cc1cn(-c2ccc(Nc3ncc4c(n3)N(C)C(c3ccccc3)CO4)cc2)cn1] | (+)-8-methyl-N-(4-(4-methyl-1H-imidazol-1-yl)phenyl)-7-phenyl-7,8-dihydro-6H-pyrimido [5,4-b] [1,4] oxazin-2-amine | 0.055 |
| 26B | 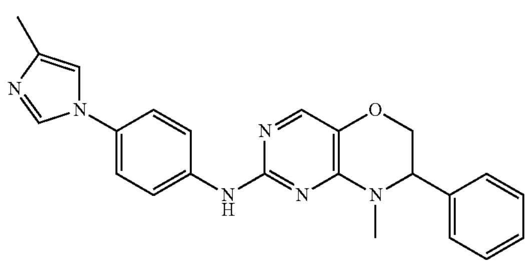 [SMILES: Cc1cn(-c2ccc(Nc3ncc4c(n3)N(C)C(c3ccccc3)CO4)cc2)cn1] | (−)-8-methyl-N-(4-(4-methyl-1H-imidazol-1-yl)phenyl)-7-phenyl-7,8-dihydro-6H-pyrimido [5,4-b] [1,4] oxazin-2-amine | 3.140 |

TABLE III-continued

Biological Assay

| Compound of Example | Structure | Name | Aβ42 H4 Prot Fre IC50 (μM) |
|---|---|---|---|
| 27 | 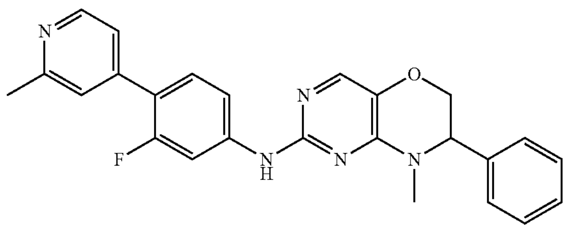 [SMILES: Cc1cc(-c2ccc(Nc3ncc4c(n3)N(C)C(c3ccccc3)CO4)cc2F)ccn1] | N-(3-fluoro-4-(2-methylpyridin-4-yl)phenyl)-8-methyl-7-phenyl-7,8-dihydro-6H-pyrimido [5,4-b] [1,4] oxazin-2-amine (racemic) | 0.374 |
| 27A | 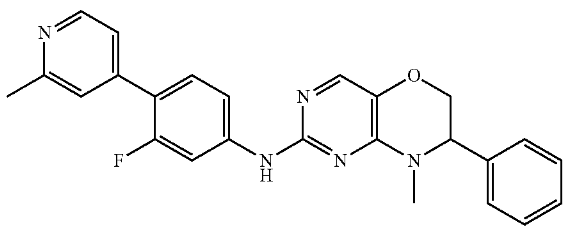 [SMILES: Cc1cc(-c2ccc(Nc3ncc4c(n3)N(C)C(c3ccccc3)CO4)cc2F)ccn1] | (+)-N-(3-fluoro-4-(2-methylpyridin-4-yl)phenyl)-8-methyl-7-phenyl-7,8-dihydro-6H-pyrimido[5,4-b][1,4]oxazin-2-amine | 0.306 |
| 27B | 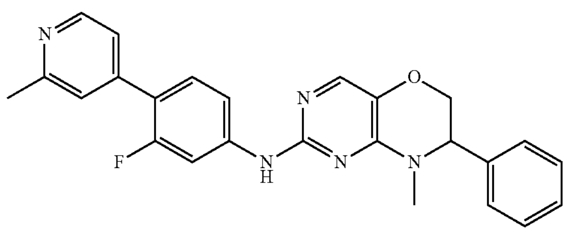 [SMILES: Cc1cc(-c2ccc(Nc3ncc4c(n3)N(C)C(c3ccccc3)CO4)cc2F)ccn1] | (−)-N-(3-fluoro-4-(2-methylpyridin-4-yl)phenyl)-8-methyl-7-phenyl-7,8-dihydro-6H-pyrimido[5,4-b][1,4]oxazin-2-amine | 2.102 |
| 28 | 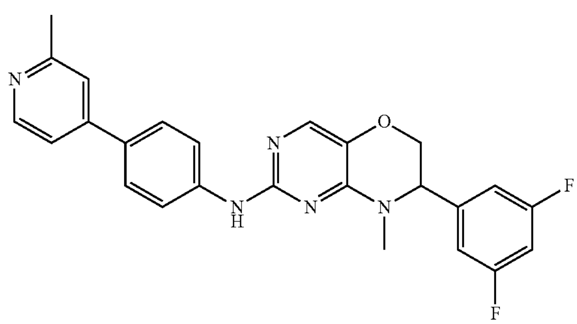 [SMILES: Cc1cc(-c2ccc(Nc3ncc4c(n3)N(C)C(c3cc(F)cc(F)c3)CO4)cc2)ccn1] | 7-(3,5-difluorophenyl)-8-methyl-N-(4-(2-methylpyridin-4-yl)phenyl)-7,8-dihydro-6H-pyrimido[5,4-b][1,4]oxazin-2-amine (racemic) | 0.090 |
| 28A | 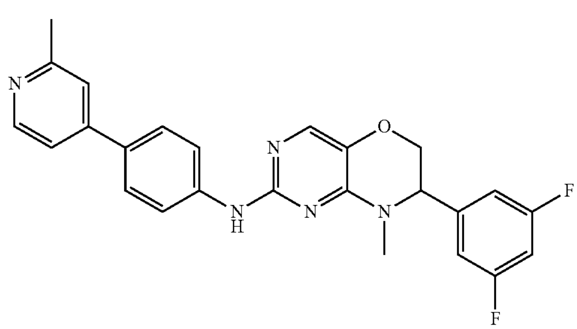 [SMILES: Cc1cc(-c2ccc(Nc3ncc4c(n3)N(C)C(c3cc(F)cc(F)c3)CO4)cc2)ccn1] | (−)-7-(3,5-difluorophenyl)-8-methyl-N-(4-(2-methylpyridin-4-yl)phenyl)-7,8-dihydro-6H-pyrimido[5,4-b][1,4]oxazin-2-amine | 1.957 |

TABLE III-continued

Biological Assay

| Compound of Example | Structure | Name | Aβ42 H4 Prot Fre IC50 (μM) |
|---|---|---|---|
| 28B | 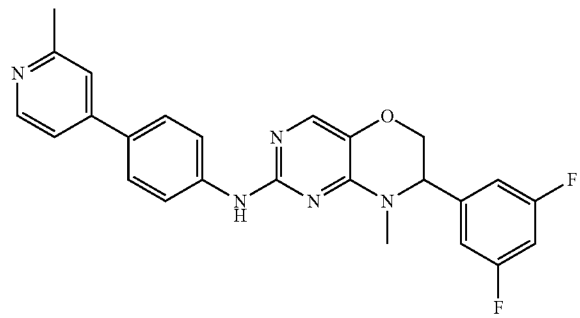 [SMILES: Cc1cc(-c2ccc(Nc3ncc4c(n3)N(C)C(c3cc(F)cc(F)c3)CO4)cc2)ccn1] | (+)-7-(3,5-difluorophenyl)-8-methyl-N-(4-(2-methylpyridin-4-yl)phenyl)-7,8-dihydro-6H-pyrimido[5,4-b][1,4]oxazin-2-amine | 0.060 |
| 29 | 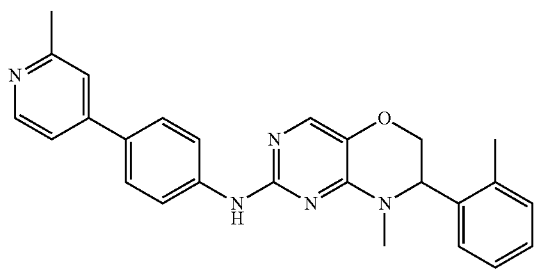 [SMILES: Cc1cc(-c2ccc(Nc3ncc4c(n3)N(C)C(c3ccccc3C)CO4)cc2)ccn1] | 8-methyl-N-(4-(2-methylpyridin-4-yl)phenyl)-7-(o-tolyl)-7,8-dihydro-6H-pyrimido[5,4-b] [1,4]oxazin-2-amine (racemic) | 0.297 |
| 29A | 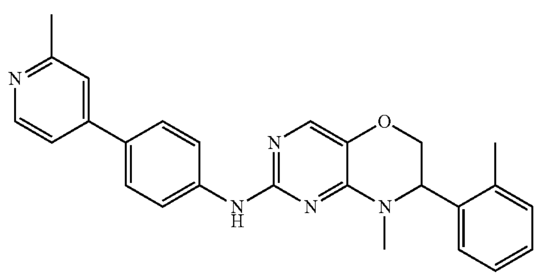 [SMILES: Cc1cc(-c2ccc(Nc3ncc4c(n3)N(C)C(c3ccccc3C)CO4)cc2)ccn1] | (−)-8-methyl-N-(4-(2-methylpyridin-4-yl)phenyl)-7-(o-tolyl)-7,8-dihydro-6H-pyrimido[5,4-b][1,4]oxazin-2-amine | 1.096 |
| 29B | 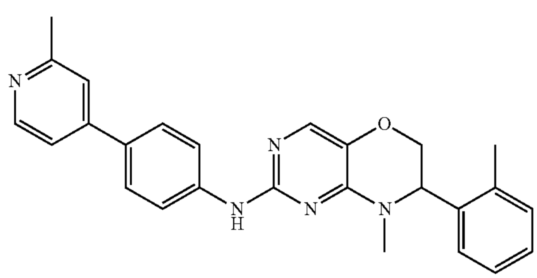 [SMILES: Cc1cc(-c2ccc(Nc3ncc4c(n3)N(C)C(c3ccccc3C)CO4)cc2)ccn1] | (+)-8-methyl-N-(4-(2-methylpyridin-4-yl)phenyl)-7-(o-tolyl)-7,8-dihydro-6H-pyrimido[5,4-b][1,4]oxazin-2-amine | 0.068 |
| 30 | 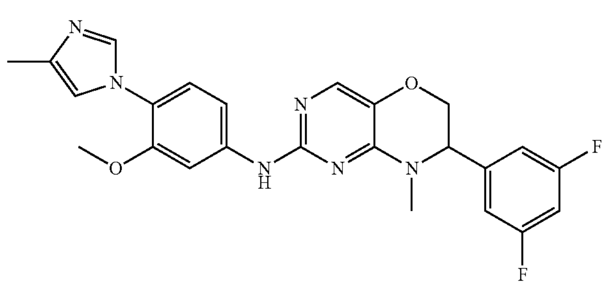 [SMILES: COc1cc(Nc2ncc3c(n2)N(C)C(c2cc(F)cc(F)c2)CO3)ccc1-n1cnc(C)c1] | 7-(3,5-difluorophenyl)-N-(3-methoxy-4-(4-methyl-1H-imidazol-1-yl)phenyl)-8-methyl-7,8-dihydro-6H-pyrimido[5,4-b][1,4]oxazin-2-amine (racemic) | 0.018 |

TABLE III-continued

Biological Assay

| Compound of Example | Structure | Name | Aβ42 H4 Prot Fre IC50 (μM) |
|---|---|---|---|
| 30A | 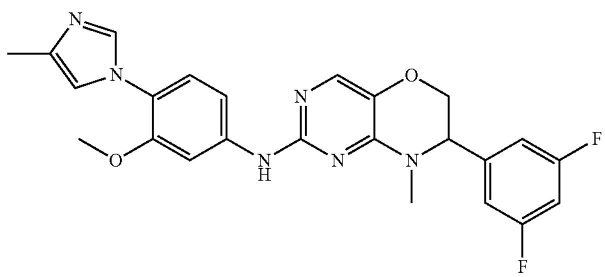 [SMILES: COc1cc(Nc2ncc3c(n2)N(C)C(c2cc(F)cc(F)c2)CO3)ccc1-n1cnc(C)c1] | (−)-7-(3,5-difluorophenyl)-N-(3-methoxy-4-(4-methyl-1H-imidazol-1-yl)phenyl)-8-methyl-7,8-dihydro-6H-pyrimido[5,4-b][1,4]oxazin-2-amine | 0.177 |
| 30B | 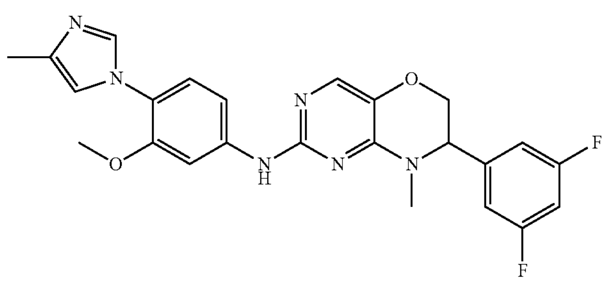 [SMILES: COc1cc(Nc2ncc3c(n2)N(C)C(c2cc(F)cc(F)c2)CO3)ccc1-n1cnc(C)c1] | (+)-7-(3,5-difluorophenyl)-N-(3-methoxy-4-(4-methyl-1H-imidazol-1-yl)phenyl)-8-methyl-7,8-dihydro-6H-pyrimido [5,4-b] [1,4] oxazin-2-amine | 0.023 |
| 31 | 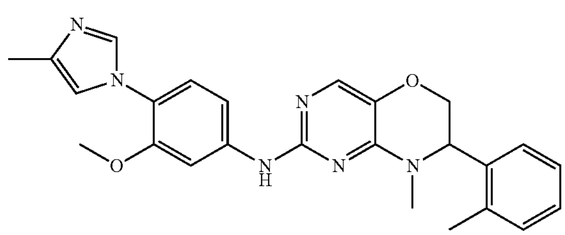 [SMILES: COc1cc(Nc2ncc3c(n2)N(C)C(c2ccccc2C)CO3)ccc1-n1cnc(C)c1] | N-(3-methoxy-4-(4-methyl-1H-imidazol-1-yl)phenyl)-8-methyl-7-(o-tolyl)-7,8-dihydro-6H-pyrimido [5,4-b] [1,4] oxazin-2-amine (racemic) | 0.025 |
| 31A | 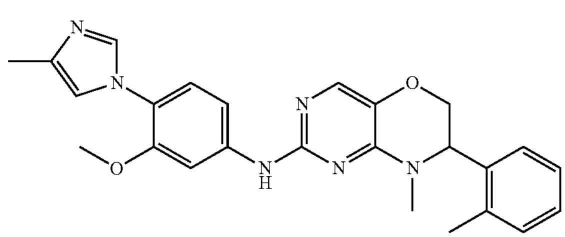 [SMILES: COc1cc(Nc2ncc3c(n2)N(C)C(c2ccccc2C)CO3)ccc1-n1cnc(C)c1] | (−)-N-(3-methoxy-4-(4-methyl-1H-imidazol-1-yl)phenyl)-8-methyl-7-(o-tolyl)-7,8-dihydro-6H-pyrimido [5,4-b] [1,4] oxazin-2-amine | 0.1382 |
| 31B | 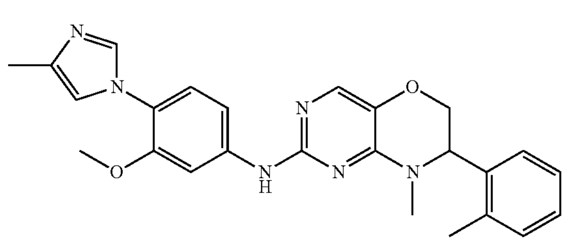 [SMILES: COc1cc(Nc2ncc3c(n2)N(C)C(c2ccccc2C)CO3)ccc1-n1cnc(C)c1] | (+)-N-(3-methoxy-4-(4-methyl-1H-imidazol-1-yl)phenyl)-8-methyl-7-(o-tolyl)-7,8-dihydro-6H-pyrimido [5,4-b] [1,4] oxazin-2-amine | 0.0296 |

TABLE III-continued

Biological Assay

| Compound of Example | Structure | Name | Aβ42 H4 Prot Fre IC50 (μM) |
|---|---|---|---|
| 32 | 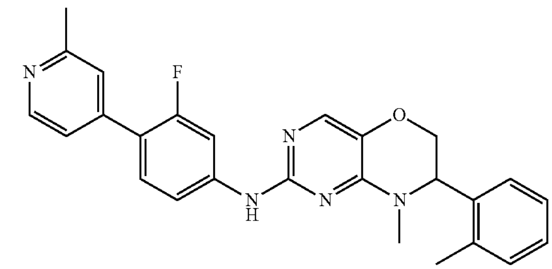 [SMILES: Cc1cc(-c2ccc(Nc3ncc4c(n3)N(C)C(c3ccccc3C)CO4)cc2F)ccn1] | N-(3-fluoro-4-(2-methylpyridin-4-yl)phenyl)-8-methyl-7-(o-tolyl)-7,8-dihydro-6H-pyrimido [5,4-b] [1,4] oxazin-2-amine (racemic) | 0.168 |
| 32A | 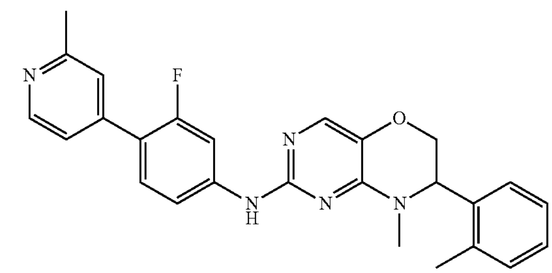 [SMILES: Cc1cc(-c2ccc(Nc3ncc4c(n3)N(C)C(c3ccccc3C)CO4)cc2F)ccn1] | (−)-N-(3-fluoro-4-(2-methylpyridin-4-yl)phenyl)-8-methyl-7-(o-tolyl)-7,8-dihydro-6H-pyrimido[5,4-b][1,4]oxazin-2-amine | 0.888 |
| 32B | 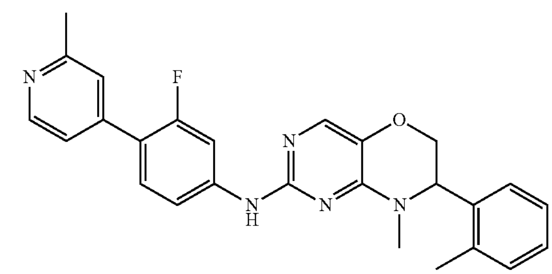 [SMILES: Cc1cc(-c2ccc(Nc3ncc4c(n3)N(C)C(c3ccccc3C)CO4)cc2F)ccn1] | (+)-N-(3-fluoro-4-(2-methylpyridin-4-yl)phenyl)-8-methyl-7-(o-tolyl)-7,8-dihydro-6H-pyrimido[5,4-b][1,4]oxazin-2-amine | 0.131 |
| 33 | 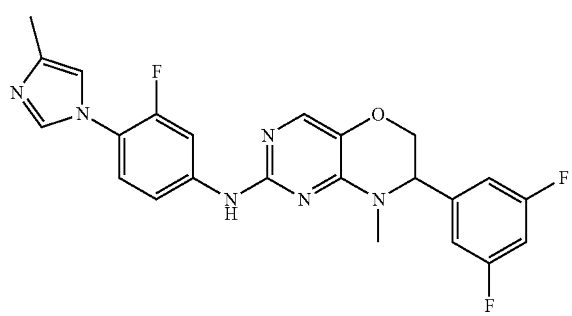 [SMILES: Cc1cn(-c2ccc(Nc3ncc4c(n3)N(C)C(c3cc(F)cc(F)c3)CO4)cc2F)cn1] | 7-(3,5-difluorophenyl)-N-(3-fluoro-4-(4-methyl-1H-imidazol-1-yl)phenyl)-8-methyl-7,8-dihydro-6H-pyrimido[5,4-b][1,4]oxazin-2-amine (racemic) | 0.038 |
| 33A | 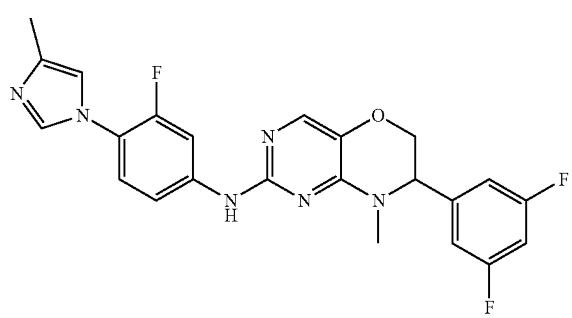 [SMILES: Cc1cn(-c2ccc(Nc3ncc4c(n3)N(C)C(c3cc(F)cc(F)c3)CO4)cc2F)cn1] | (+)-7-(3,5-difluorophenyl)-N-(3-fluoro-4-(4-methyl-1H-imidazol-1-yl)phenyl)-8-methyl-7,8-dihydro-6H-pyrimido[5,4-b][1,4]oxazin-2-amine | 0.014 |

TABLE III-continued

Biological Assay

| Compound of Example | Structure | Name | Aβ42 H4 Prot Fre IC50 (μM) |
|---|---|---|---|
| 33B | 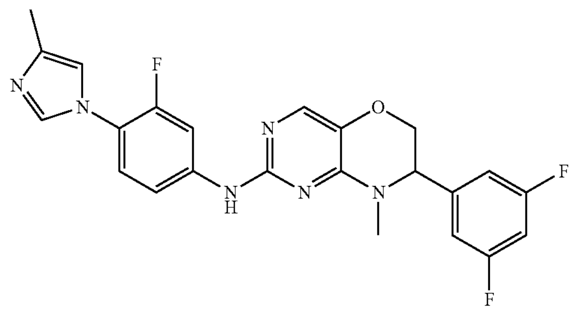 | (−)-7-(3,5-difluorophenyl)-N-(3-fluoro-4-(4-methyl-1H-imidazol-1-yl)phenyl)-8-methyl-7,8-dihydro-6H-pyrimido[5,4-b][1,4]oxazin-2-amine | 0.389 |
| 34 | 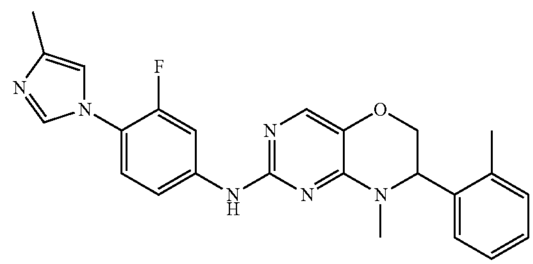 [SMILES: Cc1cn(-c2ccc(Nc3ncc4c(n3)N(C)C(c3ccccc3C)CO4)cc2F)cn1] | N-(3-fluoro-4-(4-methyl-1H-imidazol-1-yl)phenyl)-8-methyl-7-(o-tolyl)-7,8-dihydro-6H-pyrimido[5,4-b][1,4]oxazin-2-amine (racemic) | 0.044 |
| 34A | 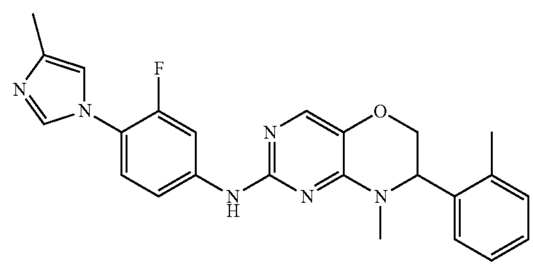 | (+)-N-(3-fluoro-4-(4-methyl-1H-imidazol-1-yl)phenyl)-8-methyl-7-(o-tolyl)-7,8-dihydro-6H-pyrimido[5,4-b][1,4]oxazin-2-amine | 0.020 |
| 34B | 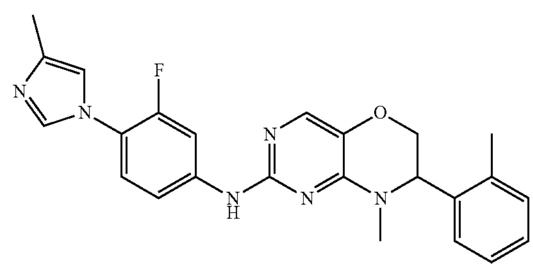 [SMILES: Cc1cn(-c2ccc(Nc3ncc4c(n3)N(C)C(c3ccccc3C)CO4)cc2F)cn1] | (−)-N-(3-fluoro-4-(4-methyl-1H-imidazol-1-yl)phenyl)-8-methyl-7-(o-tolyl)-7,8-dihydro-6H-pyrimido[5,4-b][1,4]oxazin-2-amine | 0.460 |
| 35 | 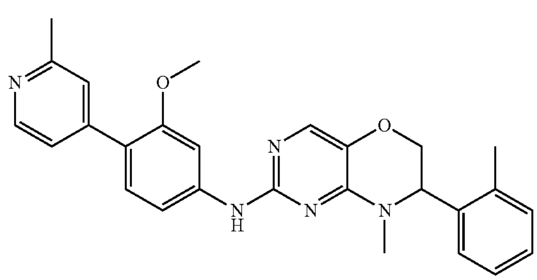 [SMILES: COc1cc(Nc2ncc3c(n2)N(C)C(c2ccccc2C)CO3)ccc1-c1ccnc(C)c1] | N-(3-methoxy-4-(2-methylpyridin-4-yl)phenyl)-8-methyl-7-(o-tolyl)-7,8-dihydro-6H-pyrimido[5,4-b][1,4]oxazin-2-amine (racemic) | 0.087 |

TABLE III-continued

Biological Assay

| Compound of Example | Structure | Name | Aβ42 H4 Prot Fre IC50 (μM) |
|---|---|---|---|
| 35A | 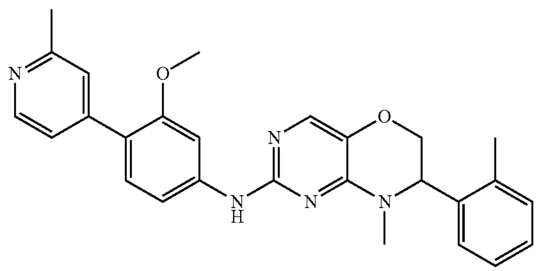 [SMILES: COc1cc(Nc2ncc3c(n2)N(C)C(c2ccccc2C)CO3)ccc1-c1ccnc(C)c1] | (−)-N-(3-methoxy-4-(2-methylpyridin-4-yl)henyl)-8-methyl-7-(o-tolyl)-7,8-dihydro-6H-pyrimido[5,4-b][1,4]oxazin-2-amine | 0.355 |
| 35B | 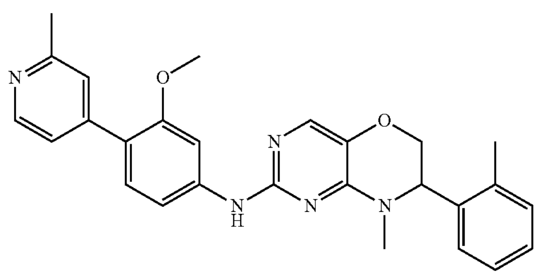 [SMILES: COc1cc(Nc2ncc3c(n2)N(C)C(c2ccccc2C)CO3)ccc1-c1ccnc(C)c1] | (+)-N-(3-methoxy-4-(2-methylpyridin-4-yl)phenyl)-8-methyl-7-(o-tolyl)-7,8-dihydro-6H-pyrimido[5,4-b][1,4]oxazin-2-amine | 0.035 |
| 36 | 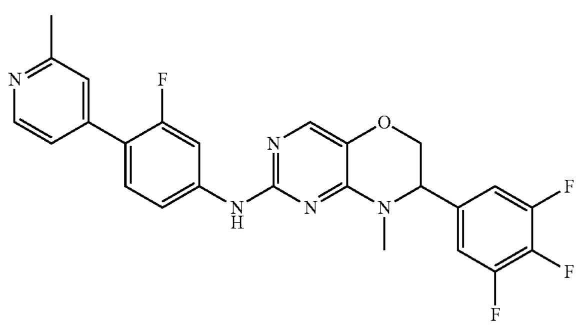 [SMILES: Cc1cc(-c2ccc(Nc3ncc4c(n3)N(C)C(c3cc(F)c(F)c(F)c3)CO4)cc2F)ccn1] | N-(3-fluoro-4-(2-methylpyridin-4-yl)phenyl)-8-methyl-7-(3,4,5-trifluorophenyl)-7,8-dihydro-6H-pyrimido[5,4-b][1,4]oxazin-2-amine (racemic) | 0.162 |
| 36A | 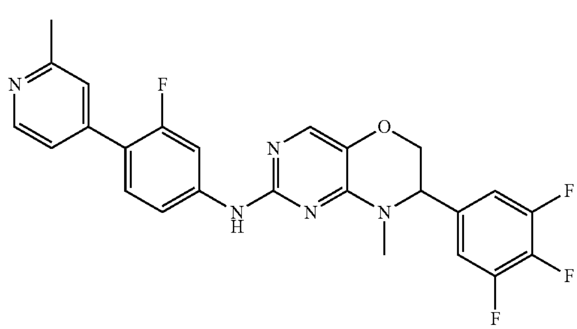 [SMILES: Cc1cc(-c2ccc(Nc3ncc4c(n3)N(C)C(c3cc(F)c(F)c(F)c3)CO4)cc2F)ccn1] | (+)-N-(3-fluoro-4-(2-methylpyridin-4-yl)phenyl)-8-methyl-7-(3,4,5-trifluorophenyl)-7,8-dihydro-6H-pyrimido[5,4-b][1,4]oxazin-2-amine | 0.107 |

TABLE III-continued

Biological Assay

| Compound of Example | Structure | Name | Aβ42 H4 Prot Fre IC50 (μM) |
|---|---|---|---|
| 36B | 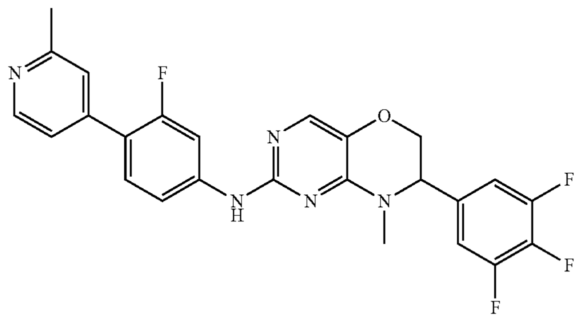 [SMILES: Cc1cc(-c2ccc(Nc3ncc4c(n3)N(C)C(c3cc(F)c(F)c(F)c3)CO4)cc2F)ccn1] | (−)-N-(3-fluoro-4-(2-methylpyridin-4-yl)phenyl)-8-methyl-7-(3,4,5-trifluorophenyl)-7,8-dihydro-6H-pyrimido[5,4-b][1,4]xazin-2-amine | 1.250 |
| 37 | 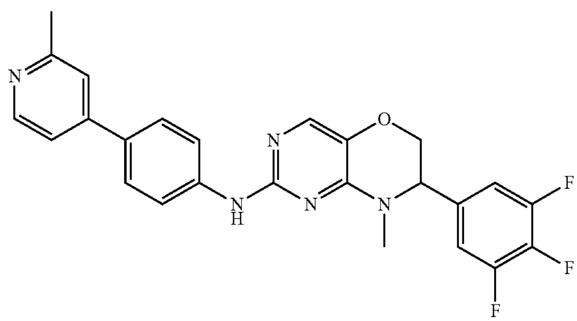 | 8-methyl-N-(4-(2-methylpyridin-4-yl)phenyl)-7-(3,4,5-trifluorophenyl)-7,8-dihydro-6H-pyrimido[5,4-b][1,4]oxazin-2-amine (racemic) | 0.103 |
| 37A | 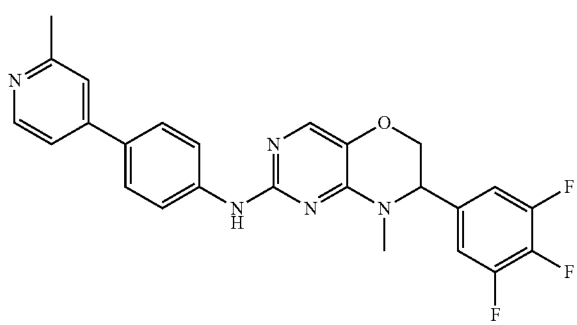 | (+)-8-methyl-N-(4-(2-methylpyridin-4-yl)phenyl)-7-(3,4,5-trifluorophenyl)-7,8-dihydro-6H-pyrimido [5,4-b][1,4]oxazin-2-amine | 0.059 |
| 37B | 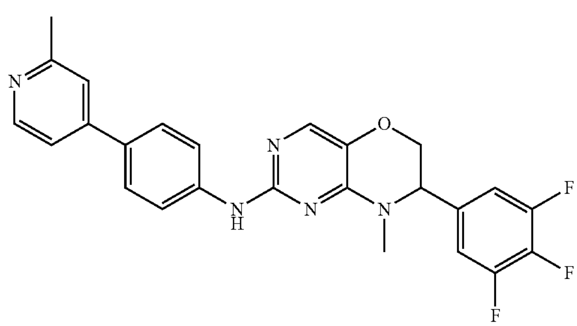 [SMILES: Cc1cc(-c2ccc(Nc3ncc4c(n3)N(C)C(c3cc(F)c(F)c(F)c3)CO4)cc2)ccn1] | (−)-8-methyl-N-(4-(2-methylpyridin-4-yl)phenyl)-7-(3,4,5-trifluorophenyl)-7,8-dihydro-6H-pyrimido [5,4-b][1,4]oxazin-2-amine | 1.539 |

TABLE III-continued

Biological Assay

| Compound of Example | Structure | Name | Aβ42 H4 Prot Fre IC50 (μM) |
|---|---|---|---|
| 38 | 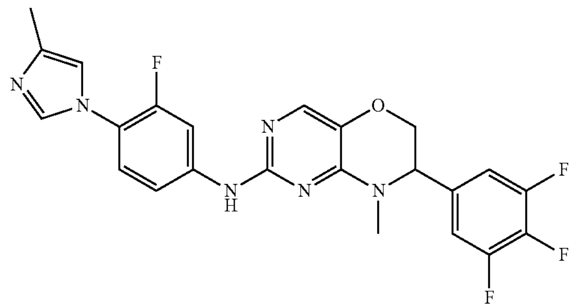 [SMILES: Cc1cn(-c2ccc(Nc3ncc4c(n3)N(C)C(c3cc(F)c(F)c(F)c3)CO4)cc2F)cn1] | N-(3-fluoro-4-(4-methyl-1H-imidazol-1-yl)phenyl)-8-methyl-7-(3,4,5-trifluorophenyl)-7,8-dihydro-6H-pyrimido [5,4-b][1,4]oxazin-2-amine (racemic) | 0.032 |
| 39 | 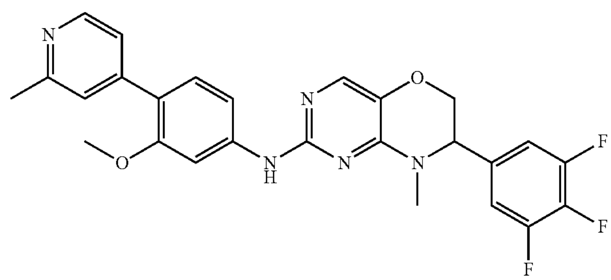 [SMILES: COc1cc(Nc2ncc3c(n2)N(C)C(c2cc(F)c(F)c(F)c2)CO3)ccc1-c1ccnc(C)c1] | N-(3-methoxy-4-(2-methylpyridin-4-yl)phenyl)-8-methyl-7-(3,4,5-trifluorophenyl)-7,8-dihydro-6H-pyrimido [5,4-b][1,4]oxazin-2-amine (racemic) | 0.035 |
| 39A | 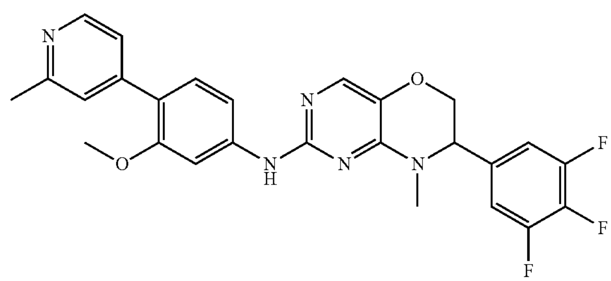 [SMILES: COc1cc(Nc2ncc3c(n2)N(C)C(c2cc(F)c(F)c(F)c2)CO3)ccc1-c1ccnc(C)c1] | (+)-N-(3-methoxy-4-(2-(methylpyridin-4-yl)phenyl)-8-methyl-7-(3,4,5-trifluorophenyl)-7,8-dihydro-6H-pyrimido [5,4-b] [1,4] oxazin-2-amine | 0.041 |
| 39B | 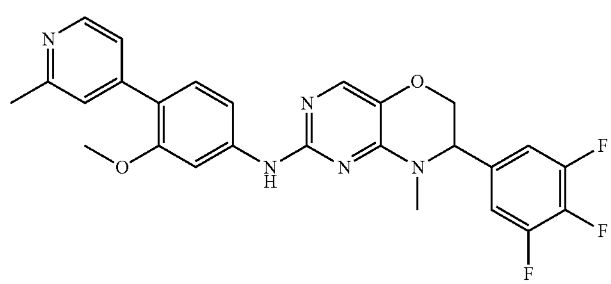 [SMILES: COc1cc(Nc2ncc3c(n2)N(C)C(c2cc(F)c(F)c(F)c2)CO3)ccc1-c1ccnc(C)c1] | (−)-N-(3-methoxy-4-(2-methylpyridin-4-yl)phenyl)-8-methyl-7-(3,4,5-trifluorophenyl)-7,8-dihydro-6H-pyrimido [5,4-b] [1,4] oxazin-2-amine | 0.984 |
| 40 | 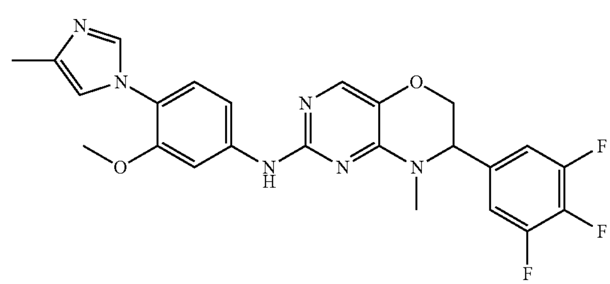 [SMILES: COc1cc(Nc2ncc3c(n2)N(C)C(c2cc(F)c(F)c(F)c2)CO3)ccc1-n1cnc(C)c1] | N-(3-methoxy-4-(4-methyl-1H-imidazol-1-yl)phenyl)-8-methyl-7-(3,4,5-trifluorophenyl)-7,8-dihydro-6H-pyrimido [5,4-b] [1,4] oxazin-2-amine (racemic) | 0.020 |

TABLE III-continued

Biological Assay

| Compound of Example | Structure | Name | Aβ42 H4 Prot Fre IC50 (μM) |
|---|---|---|---|
| 40A | 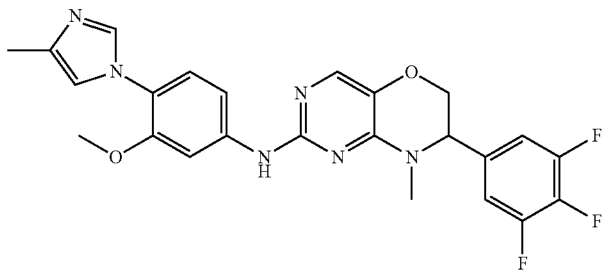 [SMILES: COc1cc(Nc2ncc3c(n2)N(C)C(c2cc(F)c(F)c(F)c2)CO3)ccc1-n1cnc(C)c1] | (−)-N-(3-methoxy-4-(4-methyl-1H-imidazol-1-yl)phenyl)-8-methyl-7-(3,4,5-trifluorophenyl)-7,8-dihydro-6H-pyrimido [5,4-b] [1,4] oxazin-2-amine | 0.279 |
| 40B | 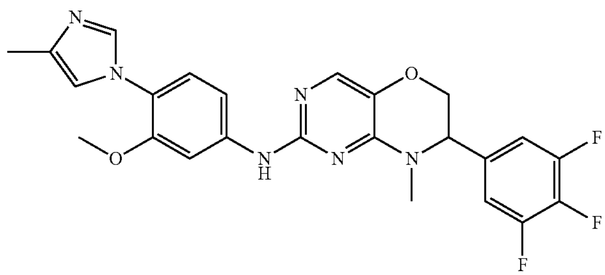 [SMILES: COc1cc(Nc2ncc3c(n2)N(C)C(c2cc(F)c(F)c(F)c2)CO3)ccc1-n1cnc(C)c1] | (+)-N-(3-methoxy-4-(4-methyl-1H-imidazol-1-yl)phenyl)-8-methyl-7-(3,4,5-trifluorophenyl)-7,8-dihydro-6H-pyrimido [5,4-b] [1,4] oxazin-2-amine | 0.011 |
| 41 | 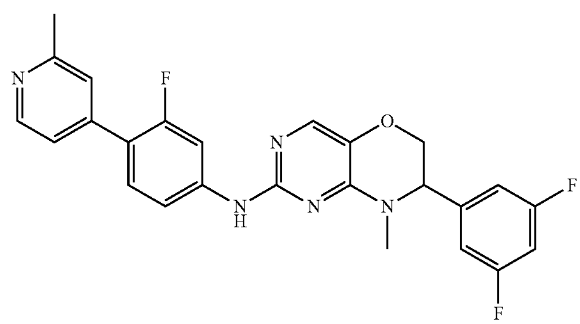 [SMILES: Cc1cc(-c2ccc(Nc3ncc4c(n3)N(C)C(c3cc(F)cc(F)c3)CO4)cc2F)ccn1] | 7-(3,5-difluorophenyl)-N-(3-fluoro-4-(2-methylpyridin-4-yl)phenyl)-8-methyl-7,8-dihydro-6H-pyrimido [5,4-b] [1,4] oxazin-2-amine (racemic) | 0.063 |
| 41A | 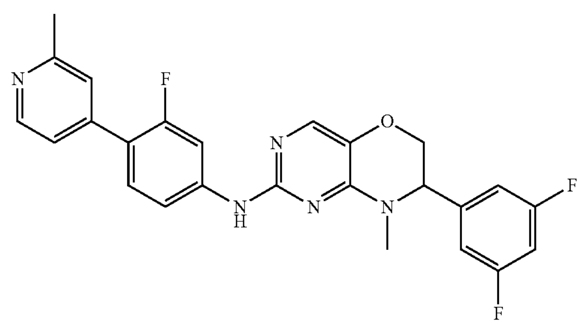 [SMILES: Cc1cc(-c2ccc(Nc3ncc4c(n3)N(C)C(c3cc(F)cc(F)c3)CO4)cc2F)ccn1] | (+)-7-(3,5-difluorophenyl)-N-(3-fluoro-4-(2-methylpyridin-4-yl)phenyl)-8-methyl-7,8-dihydro-6H-pyrimido[5,4-b][1,4]oxazin-2-amine | 0.077 |

TABLE III-continued

Biological Assay

| Compound of Example | Structure | Name | Aβ42 H4 Prot Fre IC50 (μM) |
|---|---|---|---|
| 41B | 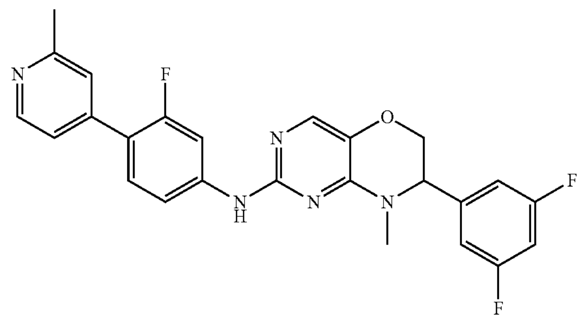 [SMILES: Cc1cc(-c2ccc(Nc3ncc4c(n3)N(C)C(c3cc(F)cc(F)c3)CO4)cc2F)ccn1] | (−)-7-(3,5-difluorophenyl)-N-(3-fluoro-4-(2-methylpyridin-4-yl)phenyl)-8-methyl-7,8-dihydro-6H-pyrimido[5,4-b][1,4]oxazin-2-amine | 1.264 |
| 42 | 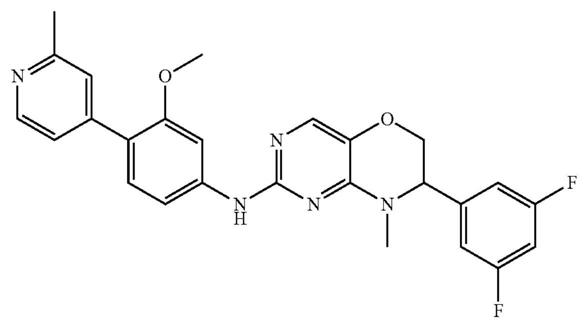 [SMILES: COc1cc(Nc2ncc3c(n2)N(C)C(c2cc(F)cc(F)c2)CO3)ccc1-c1ccnc(C)c1] | 7-(3,5-difluorophenyl)-N-(3-methoxy-4-(2-methylpyridin-4-yl)phenyl)-8-methyl-7,8-dihydro-6H-pyrimido[5,4-b][1,4]oxazin-2-amine (racemic) | 0.047 |
| 42A | 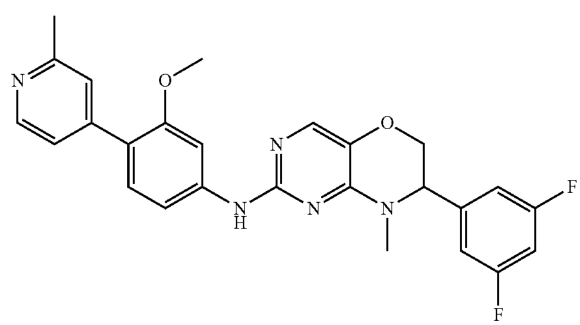 [SMILES: COc1cc(Nc2ncc3c(n2)N(C)C(c2cc(F)cc(F)c2)CO3)ccc1-c1ccnc(C)c1] | (+)-7-(3,5-difluorophenyl)-N-(3-methoxy-4-(2-methylpyridin-4-yl)phenyl)-8-methyl-7,8-dihydro-6H-pyrimido[5,4-b][1,4]oxazin-2-amine | 0.036 |
| 42B | 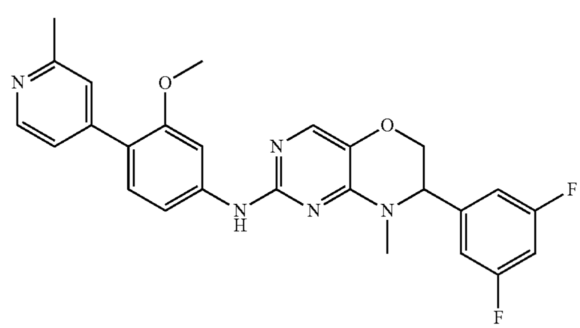 [SMILES: COc1cc(Nc2ncc3c(n2)N(C)C(c2cc(F)cc(F)c2)CO3)ccc1-c1ccnc(C)c1] | (−)-7-(3,5-difluorophenyl)-N-(3-methoxy-4-(2-methylpyridin-4-yl)phenyl)-8-methyl-7,8-dihydro-6H-pyrimido[5,4-b][1,4]oxazin-2-amine | 0.801 |

TABLE III-continued

Biological Assay

| Compound of Example | Structure | Name | Aβ42 H4 Prot Fre IC50 (μM) |
|---|---|---|---|
| 43 | 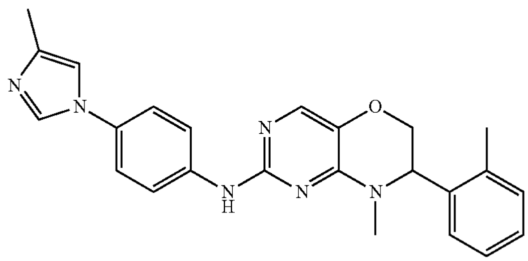 [SMILES: Cc1cn(-c2ccc(Nc3ncc4c(n3)N(C)C(c3ccccc3C)CO4)cc2)cn1] | 8-methyl-N-(4-(4-methyl-1H-imidazol-1-yl)phenyl)-7-(o-tolyl)-7,8-dihydro-6H-pyrimido[5,4-b][1,4]oxazin-2-amine (racemic) | 0.216 |
| 43A | 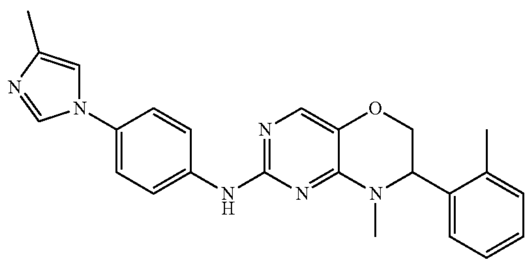 [SMILES: Cc1cn(-c2ccc(Nc3ncc4c(n3)N(C)C(c3ccccc3C)CO4)cc2)cn1] | (+)-8-methyl-N-(4-(4-methyl-1H-imidazol-1-yl)phenyl)-7-(o-tolyl)-7,8-dihydro-6H-pyrimido [5,4-b] [1,4] oxazin-2-amine | 0.031 |
| 43B | 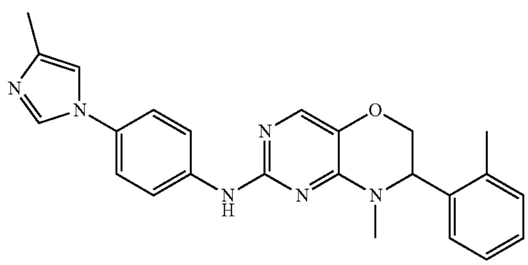 [SMILES: Cc1cn(-c2ccc(Nc3ncc4c(n3)N(C)C(c3ccccc3C)CO4)cc2)cn1] | (−)-8-methyl-N-(4-(4-methyl-1H-imidazol-1-yl)phenyl)-7-(o-tolyl)-7,8-dihydro-6H-pyrimido [5,4-b] [1,4] oxazin-2-amine | >0.300 |
| 44 | 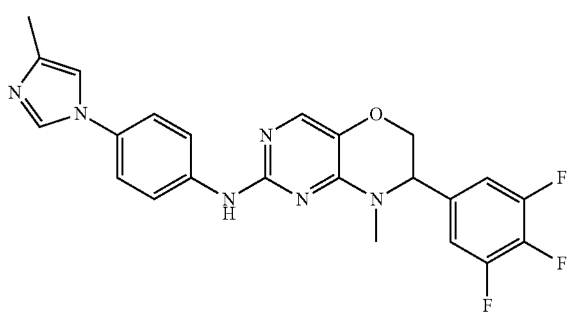 [SMILES: Cc1cn(-c2ccc(Nc3ncc4c(n3)N(C)C(c3cc(F)c(F)c(F)c3)CO4)cc2)cn1] | 8-methyl-N-(4-(4-methyl-1H-imidazol-1-yl)phenyl)-7-(3,4,5-trifluorophenyl)-7,8-dihydro-6H-pyrimido[5,4-b][1,4]oxazin-2-amine (racemic) | 0.075 |
| 45 | 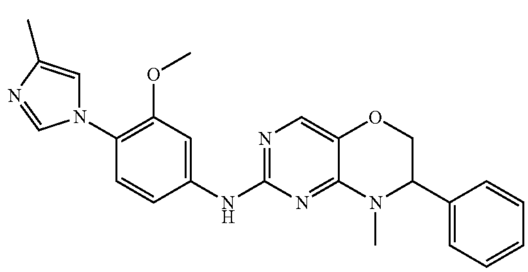 [SMILES: COc1cc(Nc2ncc3c(n2)N(C)C(c2ccccc2)CO3)ccc1-n1cnc(C)c1] | N-(3-methoxy-4-(4-methyl-1H-imidazol-1-yl)phenyl)-8-methyl-7-phenyl-7,8-dihydro-6H-pyrimido [5,4-b][1,4]oxazin-2-amine (racemic) | 0.058 |

TABLE III-continued

Biological Assay

| Compound of Example | Structure | Name | Aβ42 H4 Prot Fre IC50 (μM) |
|---|---|---|---|
| 46 | 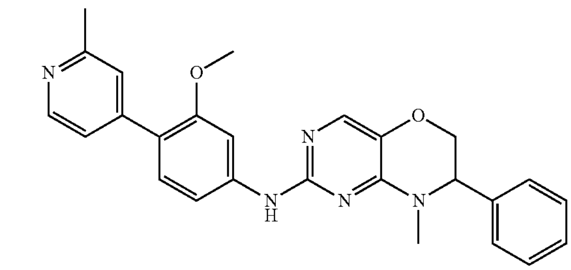 [SMILES: COc1cc(Nc2ncc3c(n2)N(C)C(c2ccccc2)CO3)ccc1-c1ccnc(C)c1] | N-(3-methoxy-4-(2-methylpyridin-4-yl)phenyl)-8-methyl-7-phenyl-7,8-dihydro-6H-pyrimido[5,4-b][1,4]oxazin-2-amine (racemic) | 0.048 |
| 47 | 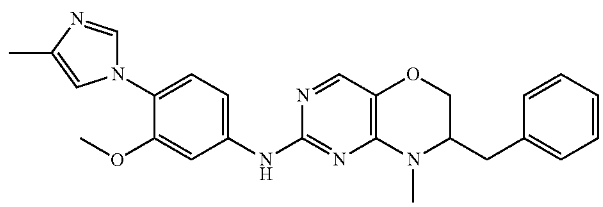 [SMILES: COc1cc(Nc2ncc3c(n2)N(C)C(Cc2ccccc2)CO3)ccc1-n1cnc(C)c1] | 7-benzyl-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) | 0.041 |
| 47A | 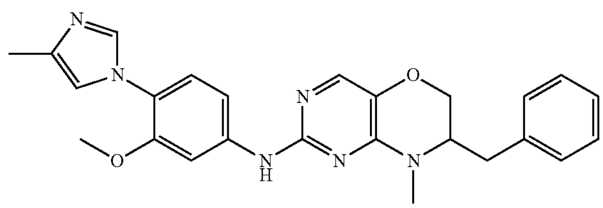 [SMILES: COc1cc(Nc2ncc3c(n2)N(C)C(Cc2ccccc2)CO3)ccc1-n1cnc(C)c1] | (+)-7-benzyl-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.023 |
| 47B | 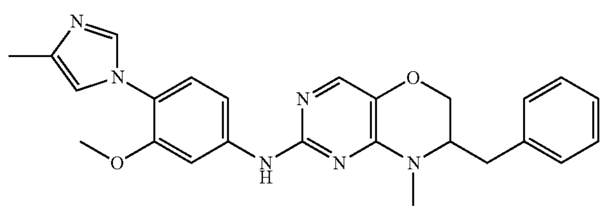 [SMILES: COc1cc(Nc2ncc3c(n2)N(C)C(Cc2ccccc2)CO3)ccc1-n1cnc(C)c1] | (−)-7-benzyl-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.065 |
| 48 | 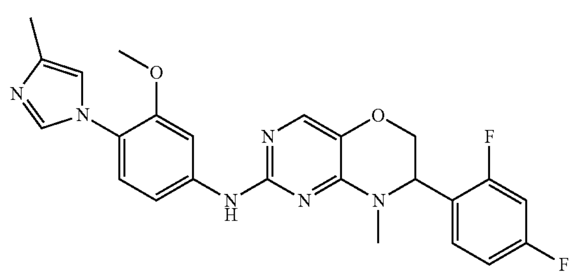 | 7-(2, 4-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) | 0.036 |
| 48A | 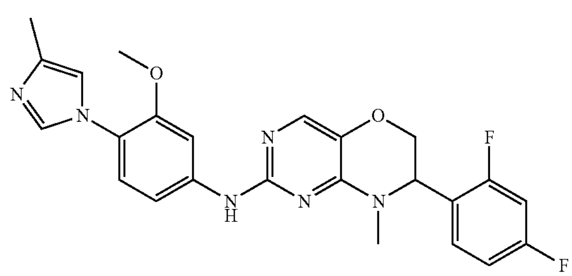 | (−)-7-(2, 4-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.328 |

TABLE III-continued

Biological Assay

| Compound of Example | Structure | Name | Aβ42 H4 Prot Fre IC50 (μM) |
|---|---|---|---|
| 48B | 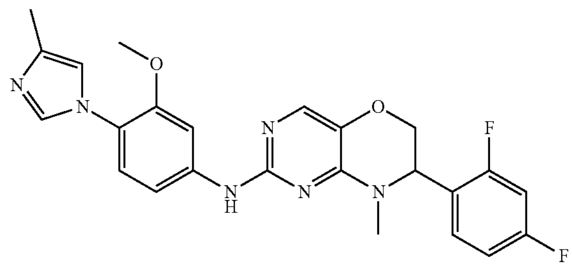 [SMILES: COc1cc(Nc2ncc3c(n2)N(C)C(c2ccc(F)cc2F)CO3)ccc1-n1cnc(C)c1] | (+)-7-(2, 4-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.020 |
| 49 | 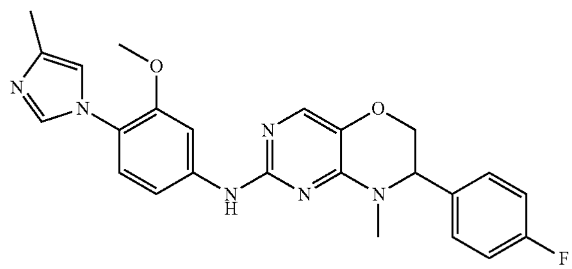 [SMILES: COc1cc(Nc2ncc3c(n2)N(C)C(c2ccc(F)cc2)CO3)ccc1-n1cnc(C)c1] | 7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) | 0.036 |
| 49A | 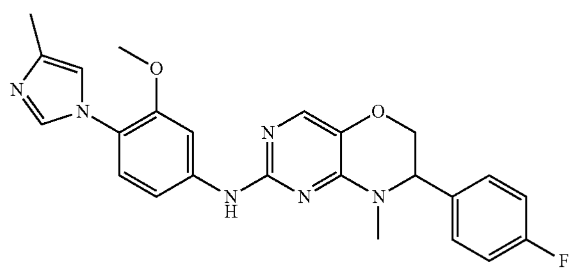 [SMILES: COc1cc(Nc2ncc3c(n2)N(C)C(c2ccc(F)cc2)CO3)ccc1-n1cnc(C)c1] | (−)-7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.191 |
| 49B | 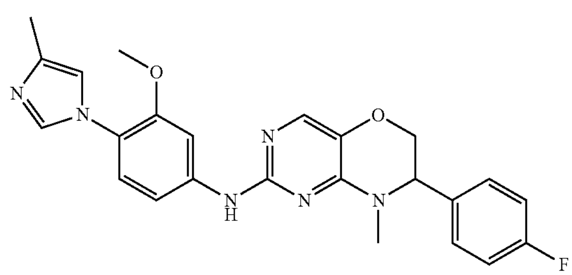 [SMILES: COc1cc(Nc2ncc3c(n2)N(C)C(c2ccc(F)cc2)CO3)ccc1-n1cnc(C)c1] | (+)-7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.009 |
| 50 | 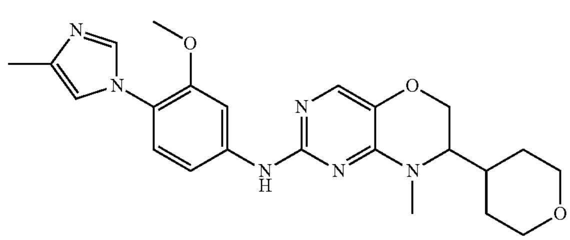 [SMILES: COc1cc(Nc2ncc3c(n2)N(C)C(C2CCOCC2)CO3)ccc1-n1cnc(C)c1] | N-(3-methoxy-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine (racemic) | 0.173 |

TABLE III-continued

Biological Assay

| Compound of Example | Structure | Name | Aβ42 H4 Prot Fre IC50 (μM) |
|---|---|---|---|
| 51 | 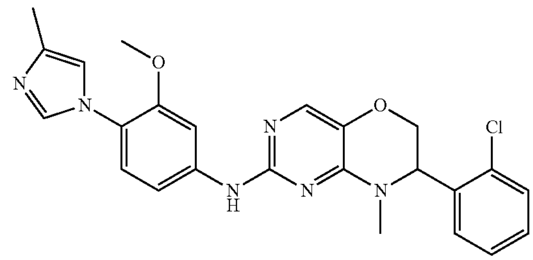 [SMILES: COc1cc(Nc2ncc3c(n2)N(C)C(c2ccccc2Cl)CO3)ccc1-n1cnc(C)c1] | 7-(2-chlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) | 0.032 |
| 51A | 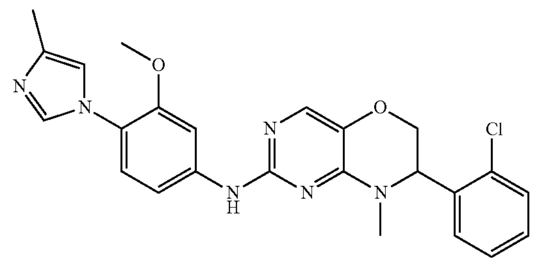 [SMILES: COc1cc(Nc2ncc3c(n2)N(C)C(c2ccccc2Cl)CO3)ccc1-n1cnc(C)c1] | (−)-7-(2-chlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.028 |
| 51B | 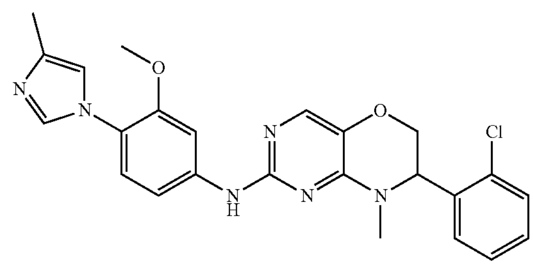 [SMILES: COc1cc(Nc2ncc3c(n2)N(C)C(c2ccccc2Cl)CO3)ccc1-n1cnc(C)c1] | (+)-7-(2-chlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.058 |
| 52 | 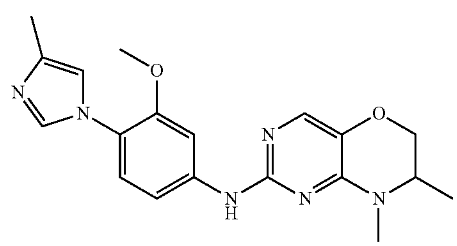 | N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine (racemic) | 0.205 |
| 53 | 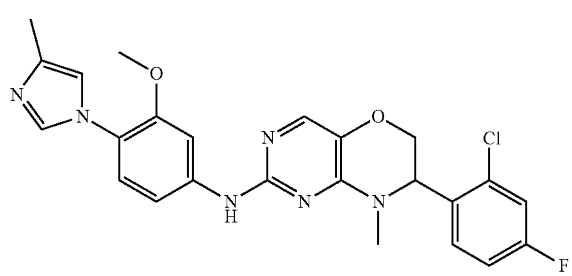 [SMILES: COc1cc(Nc2ncc3c(n2)N(C)C(c2ccc(F)cc2Cl)CO3)ccc1-n1cnc(C)c1] | 7-(2-chloro-4-fluorophenyl)-N-(3-methoxy-4-(4-methyl-1H-imidazol-1-yl) phenyl)-8-methyl-7,8-dihydro-6H-pyrimido [5, 4-b] [1,4] oxazin-2-amine (racemic) | 0.037 |

TABLE III-continued

Biological Assay

| Compound of Example | Structure | Name | Aβ42 H4 Prot Fre IC50 (μM) |
|---|---|---|---|
| 54 | 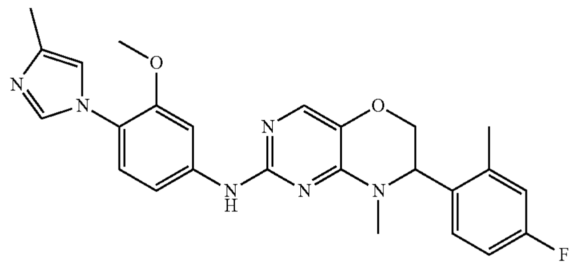 [SMILES: COc1cc(Nc2ncc3c(n2)N(C)C(c2ccc(F)cc2C)CO3)ccc1-n1cnc(C)c1] | 7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) | 0.075 |
| 55 | 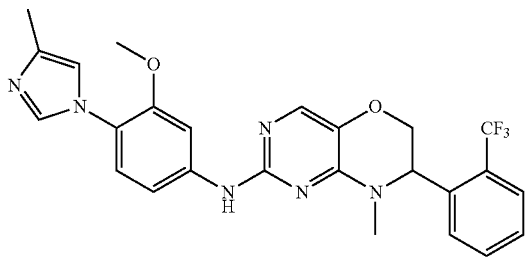 [SMILES: COc1cc(Nc2ncc3c(n2)N(C)C(c2ccccc2C(F)(F)F)CO3)ccc1-n1cnc(C)c1] | N-(3-methoxy-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine (racemic) | 0.037 |
| 55A | 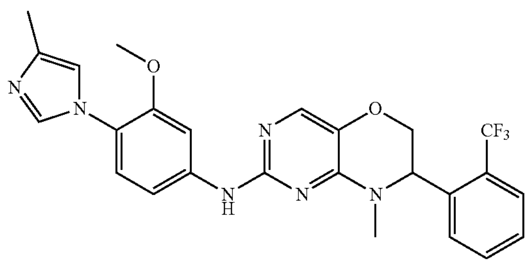 [SMILES: COc1cc(Nc2ncc3c(n2)N(C)C(c2ccccc2C(F)(F)F)CO3)ccc1-n1cnc(C)c1] | (−)-N-(3-methoxy-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine | 0.102 |
| 55B | 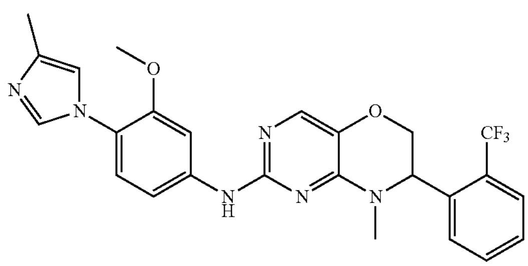 [SMILES: COc1cc(Nc2ncc3c(n2)N(C)C(c2ccccc2C(F)(F)F)CO3)ccc1-n1cnc(C)c1] | (+)-N-(3-methoxy-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine | 0.066 |
| 56A | 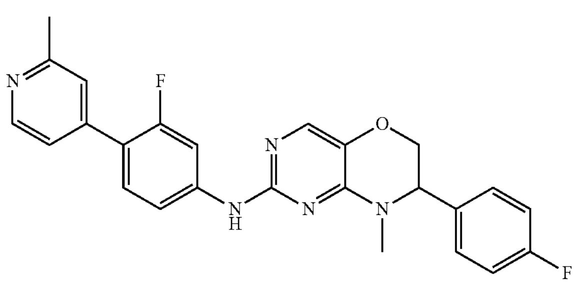 [SMILES: Cc1cc(-c2ccc(Nc3ncc4c(n3)N(C)C(c3ccc(F)cc3)CO4)cc2F)ccn1] | (+)-N-(3-fluoro-4-(2-methylpyridin-4-yl) phenyl)-7-(4-fluorophenyl)-8-methyl-7, 8-dihydro-6H-pyrimido [5, 4-b] [1, 4] oxazin-2-amine | 0.071 |

TABLE III-continued

Biological Assay

| Compound of Example | Structure | Name | Aβ42 H4 Prot Fre IC50 (μM) |
|---|---|---|---|
| 56B | 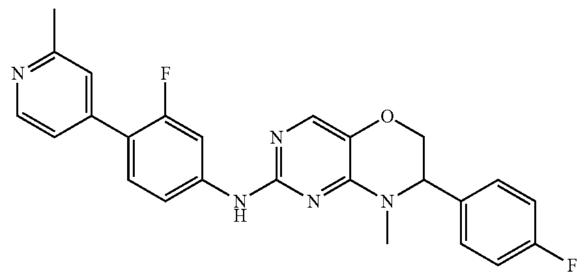 [SMILES: Cc1cc(-c2ccc(Nc3ncc4c(n3)N(C)C(c3ccc(F)cc3)CO4)cc2F)ccn1] | (−)-N-(3-fluoro-4-(2-methylpyridin-4-yl)phenyl)-7-(4-fluorophenyl)-8-methyl-7,8-dihydro-6H-pyrimido [5, 4-b] [1, 4] oxazin-2-amine | 3.464 |
| 57A | 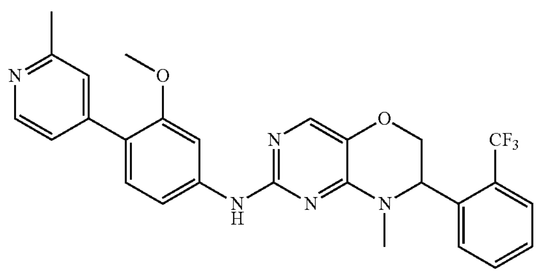 | (+)-7-benzyl-N-(3-fluoro-4-(2-methylpyridin-4-yl)phenyl)-8-methyl-7, 8-dihydro-6H-pyrimido [5, 4-b] [1, 4] oxazin-2-amine | 0.118 |
| 57B | 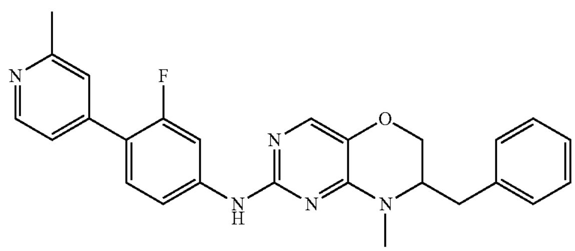 [SMILES: Cc1cc(-c2ccc(Nc3ncc4c(n3)N(C)C(Cc3ccccc3)CO4)cc2F)ccn1] | (−)-7-benzyl-N-(3-fluoro-4-(2-methylpyridin-4-yl)phenyl)-8-methyl-7, 8-dihydro-6H-pyrimido [5, 4-b] [1, 4] oxazin-2-amine | 0.880 |
| 58A | 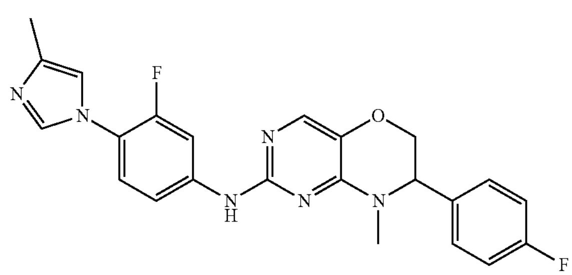 [SMILES: Cc1cn(-c2ccc(Nc3ncc4c(n3)N(C)C(c3ccc(F)cc3)CO4)cc2F)cn1] | (+)-N-(3-fluoro-4-(4-methyl-1H-imidazol-1-yl)phenyl)-7-(4-fluorophenyl)-8-methyl-7,8-dihydro-6H-pyrimido [5, 4-b] [1, 4] oxazin-2-amine | 0.028 |
| 58B | 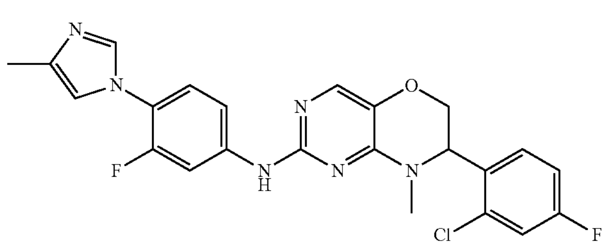 [SMILES: Cc1cn(-c2ccc(Nc3ncc4c(n3)N(C)C(c3ccc(F)cc3Cl)CO4)cc2F)cn1] | (−)-N-(3-fluoro-4-(4-methyl-1H-imidazol-1-yl)phenyl)-7-(4-fluorophenyl)-8-methyl-7,8-dihydro-6H-pyrimido [5, 4-b] [1, 4] oxazin-2-amine | 1.951 |

TABLE III-continued

Biological Assay

| Compound of Example | Structure | Name | Aβ42 H4 Prot Fre IC50 (µM) |
|---|---|---|---|
| 59A | 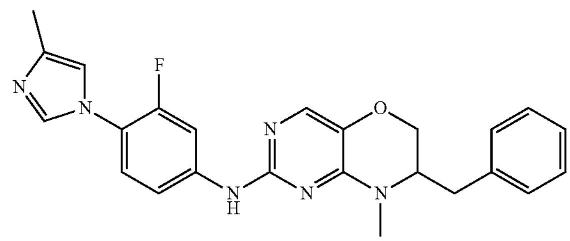 [SMILES: Cc1cn(-c2ccc(Nc3ncc4c(n3)N(C)C(Cc3ccccc3)CO4)cc2F)cn1] | (+)-7-benzyl-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.081 |
| 59B | 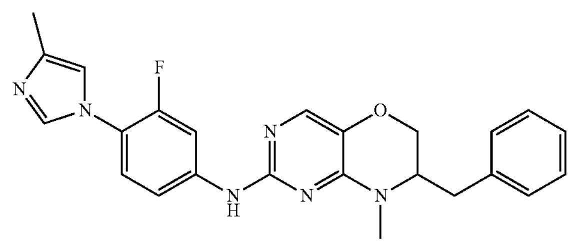 [SMILES: Cc1cn(-c2ccc(Nc3ncc4c(n3)N(C)C(Cc3ccccc3)CO4)cc2F)cn1] | (−)-7-benzyl-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.452 |
| 60A | 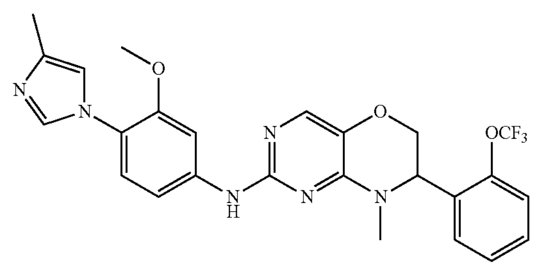 [SMILES: COc1cc(Nc2ncc3c(n2)N(C)C(c2ccccc2OC(F)(F)F)CO3)ccc1-n1cnc(C)c1] | (−)-N-(3-methoxy-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine | 0.092 |
| 60B | 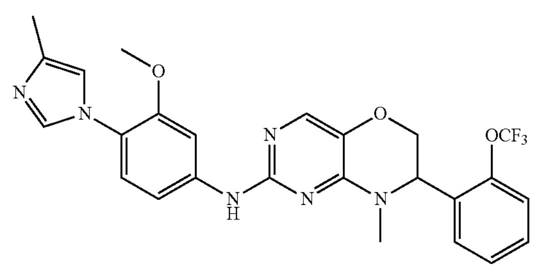 [SMILES: COc1cc(Nc2ncc3c(n2)N(C)C(c2ccccc2OC(F)(F)F)CO3)ccc1-n1cnc(C)c1] | (+)-N-(3-methoxy-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine | 0.078 |
| 61A | 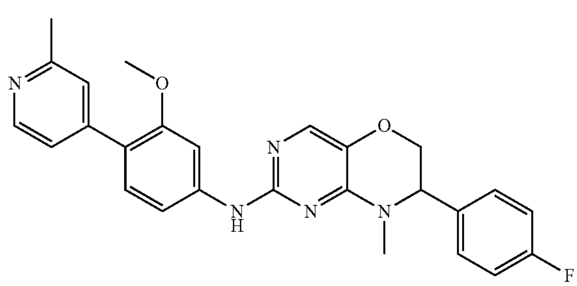 [SMILES: COc1cc(Nc2ncc3c(n2)N(C)C(c2ccc(F)cc2)CO3)ccc1-c1ccnc(C)c1] | (−)-7-(4-fluorophenyl)-N-(3-methoxy-4-(2-methylpyridin-4-yl) phenyl)-8-methyl-7, 8-dihydro-6H-pyrimido [5, 4-b] [1, 4] oxazin-2-amine | 1.007 |

TABLE III-continued

Biological Assay

| Compound of Example | Structure | Name | Aβ42 H4 Prot Fre IC50 (μM) |
|---|---|---|---|
| 61B | 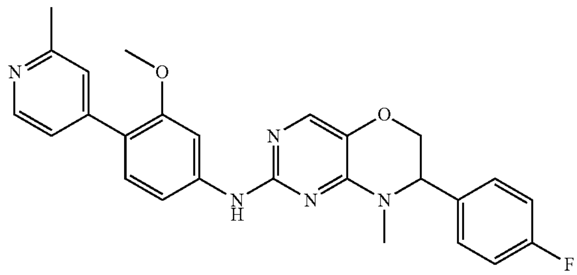 [SMILES: COc1cc(Nc2ncc3c(n2)N(C)C(c2ccc(F)cc2)CO3)ccc1-c1ccnc(C)c1] | (+)-7-(4-fluorophenyl)-N-(3-methoxy-4-(2-methylpyridin-4-yl)phenyl)-8-methyl-7, 8-dihydro-6H-pyrimido [5, 4-b] [1, 4] oxazin-2-amine | 0.058 |
| 62A | 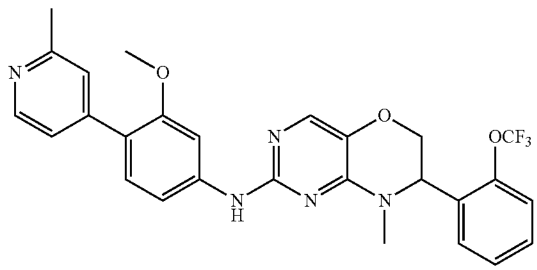 [SMILES: COc1cc(Nc2ncc3c(n2)N(C)C(c2ccccc2OC(F)(F)F)CO3)ccc1-c1ccnc(C)c1] | (−)-N-(3-methoxy-4-(2-methylpyridin-4-yl)phenyl)-8-methyl-7-(2-(trifluoromethoxy)phenyl)-7, 8-dihydro-6H-pyrimido [5, 4-b] [1, 4] oxazin-2-amine | 0.339 |
| 62B | 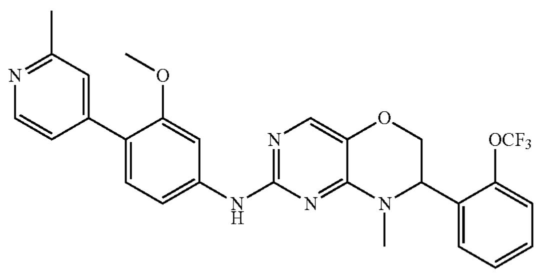 [SMILES: COc1cc(Nc2ncc3c(n2)N(C)C(c2ccccc2OC(F)(F)F)CO3)ccc1-c1ccnc(C)c1] | (+)-N-(3-methoxy-4-(2-methylpyridin-4-yl)phenyl)-8-methyl-7-(2-(trifluoromethoxy)phenyl)-7, 8-dihydro-6H-pyrimido [5, 4-b] [1, 4] oxazin-2-amine | 0.165 |
| 63A | 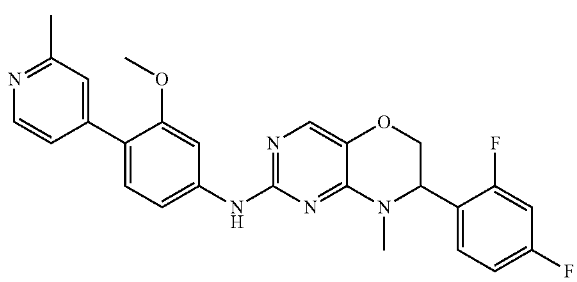 [SMILES: COc1cc(Nc2ncc3c(n2)N(C)C(c2ccc(F)cc2F)CO3)ccc1-c1ccnc(C)c1] | (−)-7-(2, 4-difluorophenyl)-N-(3-methoxy-4-(2-methylpyridin-4-yl)phenyl)-8-methyl-7, 8-dihydro-6H-pyrimido [5, 4-b] [1, 4] oxazin-2-amine | 0.543 |
| 63B | 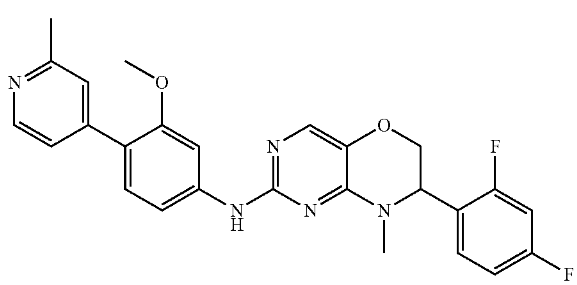 [SMILES: COc1cc(Nc2ncc3c(n2)N(C)C(c2ccc(F)cc2F)CO3)ccc1-c1ccnc(C)c1] | (+)-7-(2, 4-difluorophenyl)-N-(3-methoxy-4-(2-methylpyridin-4-yl)phenyl)-8-methyl-7, 8-dihydro-6H-pyrimido [5, 4-b] [1, 4] oxazin-2-amine | 0.064 |

TABLE III-continued

Biological Assay

| Compound of Example | Structure | Name | Aβ42 H4 Prot Fre IC50 (μM) |
|---|---|---|---|
| 64A | 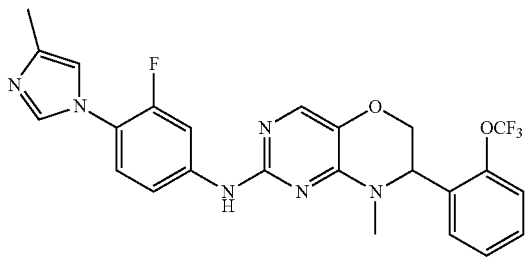 [SMILES: Cc1cn(-c2ccc(Nc3ncc4c(n3)N(C)C(c3ccccc3OC(F)(F)F)CO4)cc2F)cn1] | (+)-N-(3-fluoro-4-(4-methyl-1H-imidazol-1-yl)phenyl)-8-methyl-7-(2-(trifluoromethoxy)phenyl)-7, 8-dihydro-6H-pyrimido [5, 4-b] [1, 4] oxazin-2-amine | 0.402 |
| 64B | 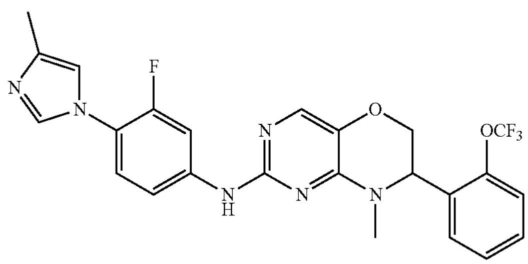 [SMILES: Cc1cn(-c2ccc(Nc3ncc4c(n3)N(C)C(c3ccccc3OC(F)(F)F)CO4)cc2F)cn1] | (−)-N-(3-fluoro-4-(4-methyl-1H-imidazol-1-yl)phenyl)-8-methyl-7-(2-(trifluoromethoxy)phenyl)-7, 8-dihydro-6H-pyrimido [5, 4-b] [1, 4] oxazin-2-amine | 0.741 |
| 65 | 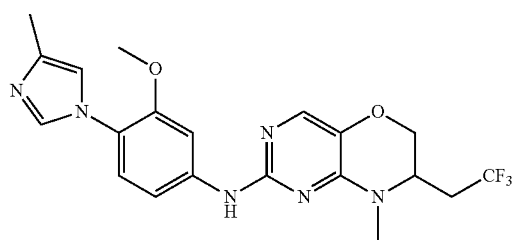 [SMILES: COc1cc(Nc2ncc3c(n2)N(C)C(CC(F)(F)F)CO3)ccc1-n1cnc(C)c1] | N-(3-methoxy-4-(4-methyl-1H-imidazol-1-yl)phenyl)-1-methyl-2-(2, 2, 2-trifluoroethyl)-2, 3-dihydro-1H-pyrido [3, 4-b] [1, 4] oxazin-7-amine (racemic) | 0.092 |
| 66A | 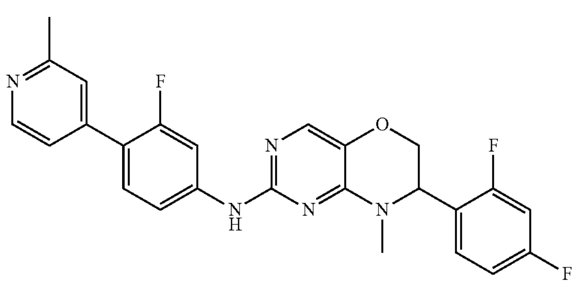 | (+)-7-(2, 4-difluorophenyl)-N-(3-fluoro-4-(2-methylpyridin-4-yl)phenyl)-8-methyl-7, 8-dihydro-6H-pyrimido [5, 4-b] [1, 4] oxazin-2-amine | 0.488 |
| 66B | 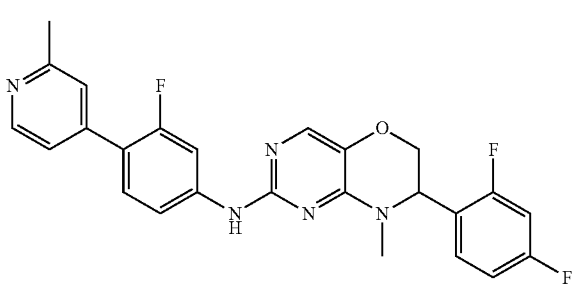 | (−)-7-(2, 4-difluorophenyl)-N-(3-fluoro-4-(2-methylpyridin-4-yl)phenyl)-8-methyl-7, 8-dihydro-6H-pyrimido [5, 4-b] [1, 4] oxazin-2-amine | 1.100 |

TABLE III-continued

Biological Assay

| Compound of Example | Structure | Name | Aβ42 H4 Prot Fre IC50 (μM) |
|---|---|---|---|
| 67A | 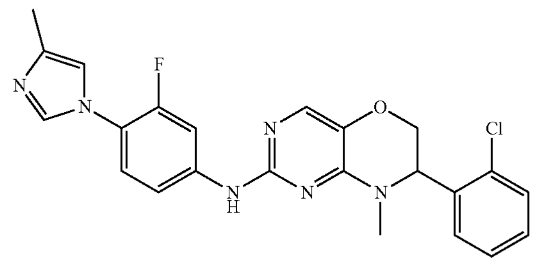 [SMILES: Cc1cn(-c2ccc(Nc3ncc4c(n3)N(C)C(c3ccccc3Cl)CO4)cc2F)cn1] | (+)-7-(2-chlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.124 |
| 67B | 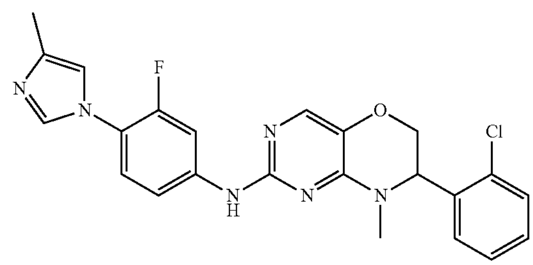 [SMILES: Cc1cn(-c2ccc(Nc3ncc4c(n3)N(C)C(c3ccccc3Cl)CO4)cc2F)cn1] | (−)-7-(2-chlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.643 |
| 68A | 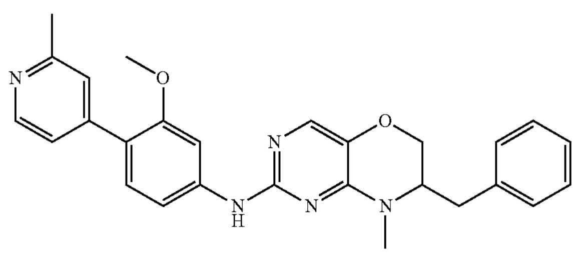 [SMILES: COc1cc(Nc2ncc3c(n2)N(C)C(Cc2ccccc2)CO3)ccc1-c1ccnc(C)c1] | (+)-7-benzyl-N-(3-methoxy-4-(2-methylpyridin-4-yl) phenyl)-8-methyl-7, 8-dihydro-6H-pyrimido [5, 4-b] [1, 4] oxazin-2-amine | 0.050 |
| 68B | 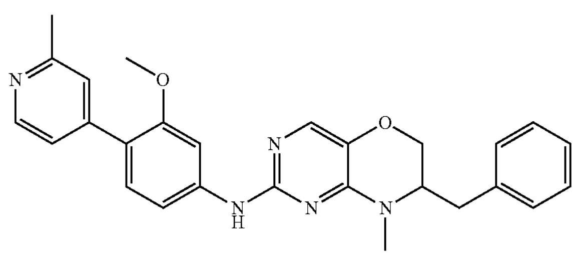 [SMILES: COc1cc(Nc2ncc3c(n2)N(C)C(Cc2ccccc2)CO3)ccc1-c1ccnc(C)c1] | (−)-7-benzyl-N-(3-methoxy-4-(2-methylpyridin-4-yl) phenyl)-8-methyl-7, 8-dihydro-6H-pyrimido [5, 4-b] [1, 4] oxazin-2-amine | 0.229 |
| 69A | 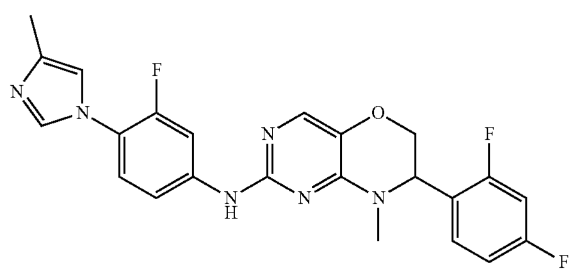 [SMILES: Cc1cn(-c2ccc(Nc3ncc4c(n3)N(C)C(c3ccc(F)cc3F)CO4)cc2F)cn1] | (+)-7-(2, 4-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.069 |

TABLE III-continued

Biological Assay

| Compound of Example | Structure | Name | Aβ42 H4 Prot Fre IC50 (μM) |
|---|---|---|---|
| 69B | 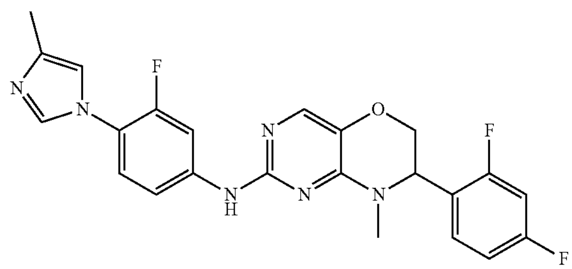 [SMILES: Cc1cn(-c2ccc(Nc3ncc4c(n3)N(C)C(c3ccc(F)cc3F)CO4)cc2F)cn1] | (−)-7-(2, 4-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | >3 |
| 70A | 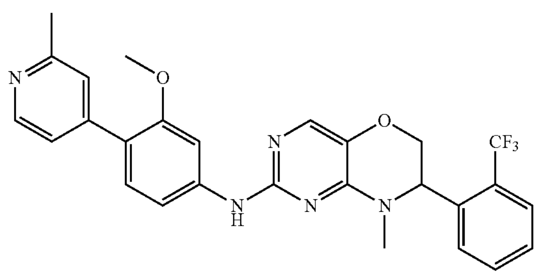 | (−)-N-(3-methoxy-4-(2-methylpyridin-4-yl) phenyl)-8-methyl-7-(2-(trifluoromethyl) phenyl)-7, 8-dihydro-6H-pyrimido [5, 4-b] [1, 4] oxazin-2-amine | 0.339 |
| 70B | 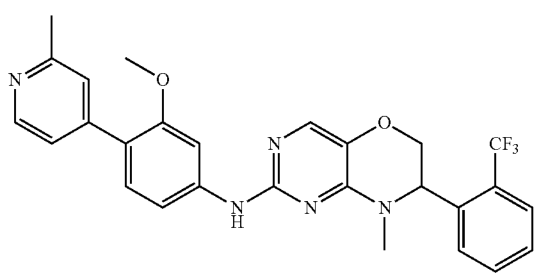 | (+)-N-(3-methoxy-4-(2-methylpyridin-4-yl) phenyl)-8-methyl-7-(2-(trifluoromethyl) phenyl)-7, 8-dihydro-6H-pyrimido [5, 4-b] [1, 4] oxazin-2-amine | 0.151 |
| 84A | 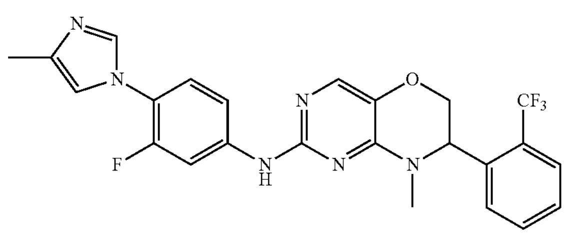 [SMILES: Cc1cn(-c2ccc(Nc3ncc4c(n3)N(C)C(c3ccccc3C(F)(F)F)CO4)cc2F)cn1] | (+)-N-(3-fluoro-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine | 0.203 |
| 84B | 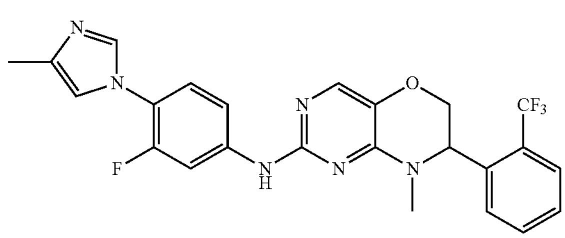 [SMILES: Cc1cn(-c2ccc(Nc3ncc4c(n3)N(C)C(c3ccccc3C(F)(F)F)CO4)cc2F)cn1] | (−)-N-(3-fluoro-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine | 0.421 |

TABLE III-continued

Biological Assay

| Compound of Example | Structure | Name | Aβ42 H4 Prot Fre IC50 (μM) |
|---|---|---|---|
| 85A | 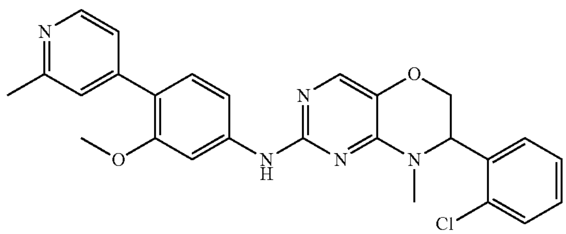 [SMILES: COc1cc(Nc2ncc3c(n2)N(C)C(c2ccccc2Cl)CO3)ccc1-c1ccnc(C)c1] | (−)-2-(2-chlorophenyl)-N-(3-methoxy-4-(2-methylpyridin-4-yl) phenyl)-1-methyl-2, 3-dihydro-1H-pyrido [3, 4-b] [1, 4] oxazin-7-amine | 0.292 |
| 85B | 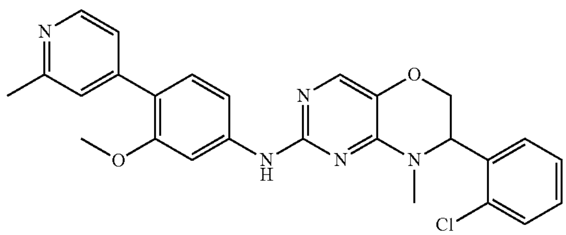 [SMILES: COc1cc(Nc2ncc3c(n2)N(C)C(c2ccccc2Cl)CO3)ccc1-c1ccnc(C)c1] | (+)-2-(2-chlorophenyl)-N-(3-methoxy-4-(2-methylpyridin-4-yl) phenyl)-1-methyl-2, 3-dihydro-1H-pyrido [3, 4-b] [1, 4] oxazin-7-amine | 0.130 |
| 86 | 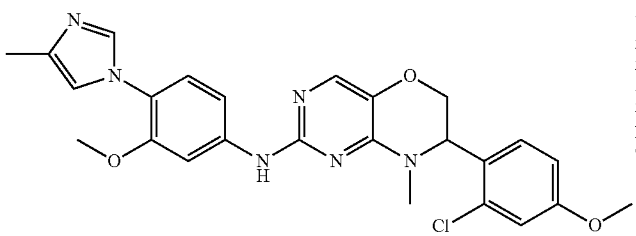 | 7-(2-chloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) | 0.038 |
| 87 | 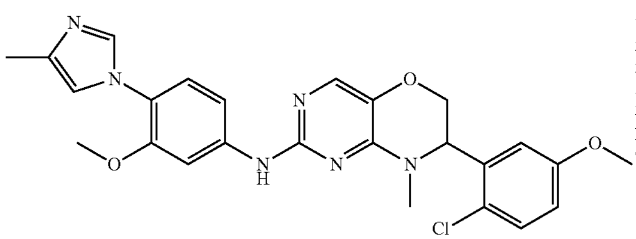 | 7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) | 0.042 |
| 88 | 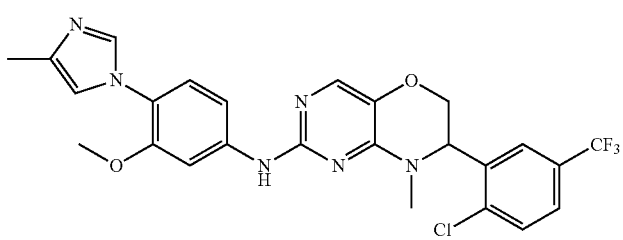 [SMILES: COc1cc(Nc2ncc3c(n2)N(C)C(c2cc(C(F)(F)F)ccc2Cl)CO3)ccc1-n1cnc(C)c1] | 7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) | 0.039 |
| 88A | 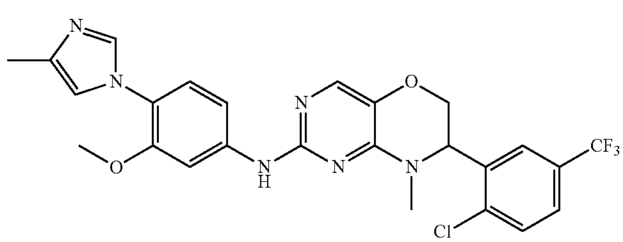 [SMILES: COc1cc(Nc2ncc3c(n2)N(C)C(c2cc(C(F)(F)F)ccc2Cl)CO3)ccc1-n1cnc(C)c1] | (+)-7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.037 |

TABLE III-continued

Biological Assay

| Compound of Example | Structure | Name | Aβ42 H4 Prot Fre IC50 (μM) |
|---|---|---|---|
| 88B | 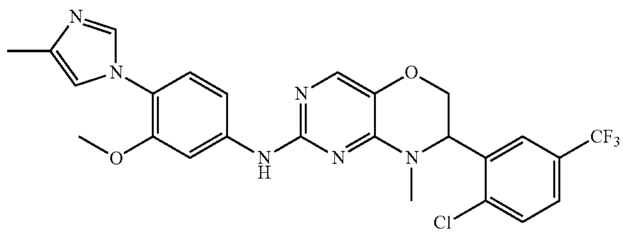 [SMILES: COc1cc(Nc2ncc3c(n2)N(C)C(c2cc(C(F)(F)F)ccc2Cl)CO3)ccc1-n1cnc(C)c1] | (−)-7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.286 |
| 89 | 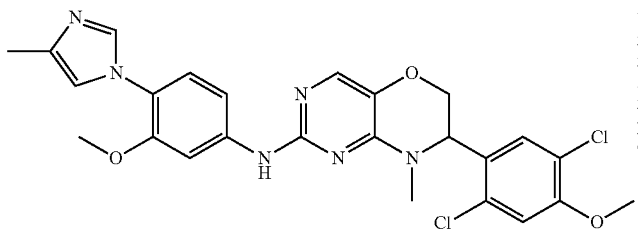 | 7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) | 0.023 |
| 90 | 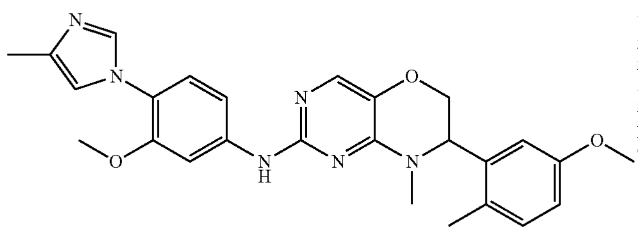 | 7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) | 0.027 |
| 91 | 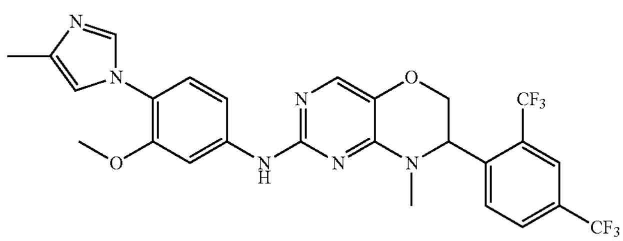 [SMILES: COc1cc(Nc2ncc3c(n2)N(C)C(c2ccc(C(F)(F)F)cc2C(F)(F)F)CO3)ccc1-n1cnc(C)c1] | 7-(2, 4-bis (trifluoromethyl) phenyl)-N-(3-methoxy-4-(4-methyl-1H-imidazol-1-yl) phenyl)-8-methyl-7, 8-dihydro-6H-pyrimido 4-b] [1, 4] oxazin-2-amine (racemic) | 0.110 |
| 92 | 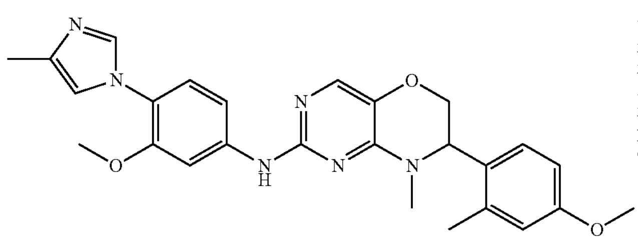 | 7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine (racemic) | 0.027 |
| 93A | 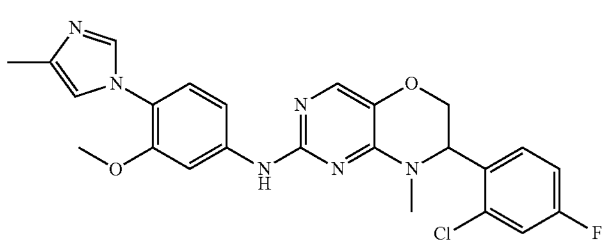 [SMILES: COc1cc(Nc2ncc3c(n2)N(C)C(c2ccc(F)cc2Cl)CO3)ccc1-n1cnc(C)c1] | (−)-7-(2-chloro-4-fluorophenyl)-N-(3-methoxy-4-(4-methyl-1H-imidazol-1-yl) phenyl)-8-methyl-7,8-dihydro-6H-pyrimido [5, 4-b] [1,4] oxazin-2-amine | 0.189 |

TABLE III-continued

Biological Assay

| Compound of Example | Structure | Name | Aβ42 H4 Prot Fre IC50 (μM) |
|---|---|---|---|
| 93B | 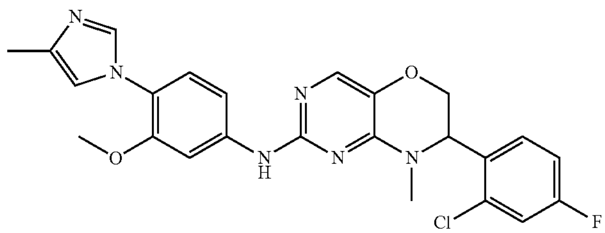 [SMILES: COc1cc(Nc2ncc3c(n2)N(C)C(c2ccc(F)cc2Cl)CO3)ccc1-n1cnc(C)c1] | (+)-7-(2-chloro-4-fluorophenyl)-N-(3-methoxy-4-(4-methyl-1H-imidazol-1-yl) phenyl)-8-methyl-7,8-dihydro-6H-pyrimido [5, 4-b] [1,4] oxazin-2-amine | 0.032 |
| 94A | 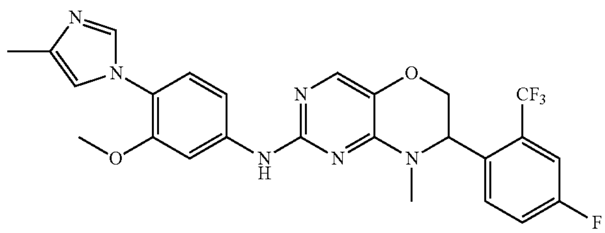 [SMILES: COc1cc(Nc2ncc3c(n2)N(C)C(c2ccc(F)cc2C(F)(F)F)CO3)ccc1-n1cnc(C)c1] | (−)-7-(4-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.078 |
| 94B | 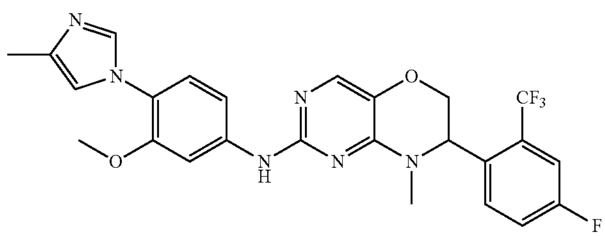 [SMILES: COc1cc(Nc2ncc3c(n2)N(C)C(c2ccc(F)cc2C(F)(F)F)CO3)ccc1-n1cnc(C)c1] | (+)-7-(4-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.029 |
| 95A | 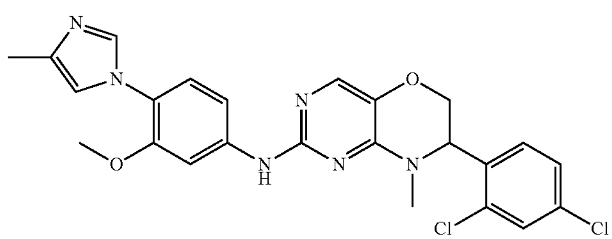 [SMILES: COc1cc(Nc2ncc3c(n2)N(C)C(c2ccc(Cl)cc2Cl)CO3)ccc1-n1cnc(C)c1] | (−)-7-(2, 4-dichlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.116 |
| 95B | 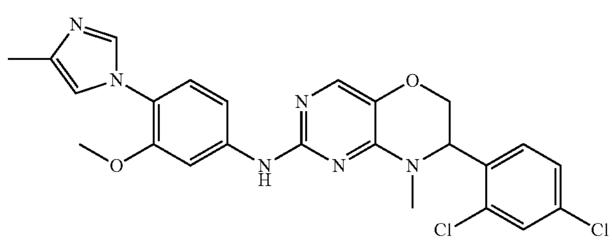 [SMILES: COc1cc(Nc2ncc3c(n2)N(C)C(c2ccc(Cl)cc2Cl)CO3)ccc1-n1cnc(C)c1] | (+)-7-(2, 4-dichlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.015 |
| 96A | 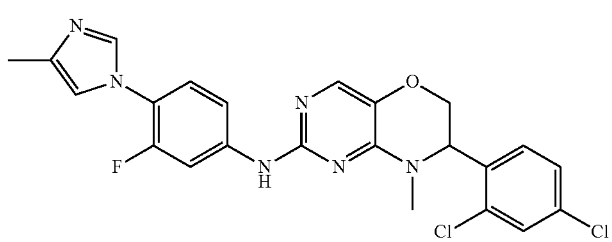 [SMILES: Cc1cn(-c2ccc(Nc3ncc4c(n3)N(C)C(c3ccc(Cl)cc3Cl)CO4)cc2F)cn1] | (+)-7-(2, 4-dichlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.076 |

TABLE III-continued

Biological Assay

| Compound of Example | Structure | Name | Aβ42 H4 Prot Fre IC50 (μM) |
|---|---|---|---|
| 96B | 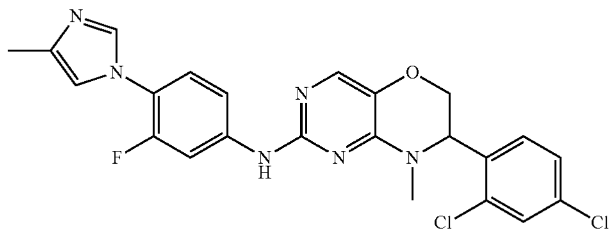 [SMILES: Cc1cn(-c2ccc(Nc3ncc4c(n3)N(C)C(c3ccc(Cl)cc3Cl)CO4)cc2F)cn1] | (−)-7-(2, 4-dichlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.879 |
| 97A | 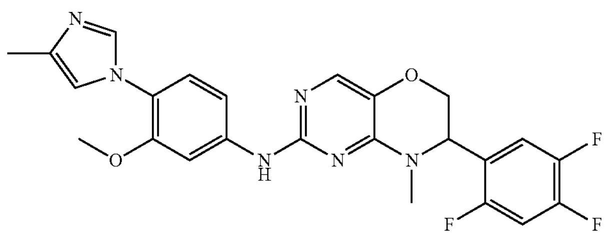 [SMILES: COc1cc(Nc2ncc3c(n2)N(C)C(c2cc(F)c(F)cc2F)CO3)ccc1-n1cnc(C)c1] | (−)-N-(3-methoxy-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine | 0.244 |
| 97B | 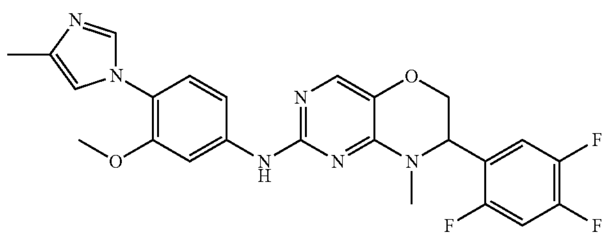 [SMILES: COc1cc(Nc2ncc3c(n2)N(C)C(c2cc(F)c(F)cc2F)CO3)ccc1-n1cnc(C)c1] | (+)-N-(3-methoxy-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine | 0.013 |
| 98A | 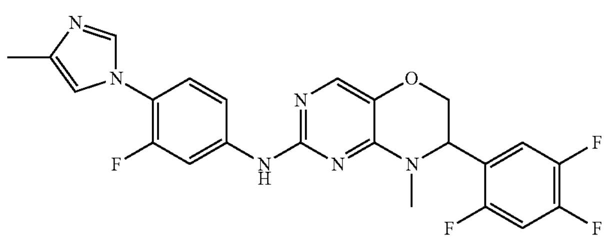 [SMILES: Cc1cn(-c2ccc(Nc3ncc4c(n3)N(C)C(c3cc(F)c(F)cc3F)CO4)cc2F)cn1] | (+)-N-(3-fluoro-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine | 0.020 |
| 98B | 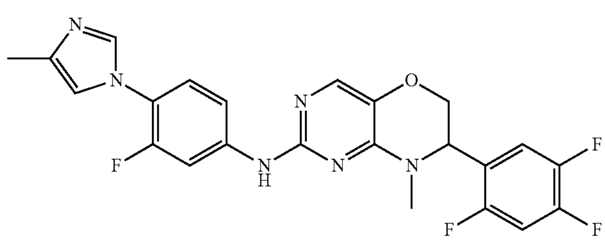 [SMILES: Cc1cn(-c2ccc(Nc3ncc4c(n3)N(C)C(c3cc(F)c(F)cc3F)CO4)cc2F)cn1] | (−)-N-(3-fluoro-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine | 2.103 |
| 99A | 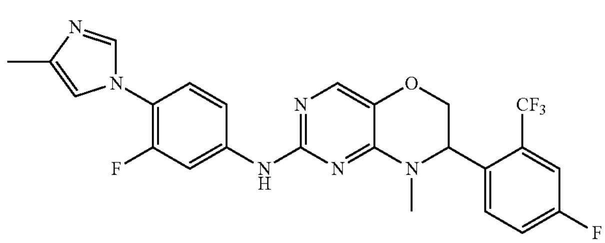 [SMILES: Cc1cn(-c2ccc(Nc3ncc4c(n3)N(C)C(c3ccc(F)cc3C(F)(F)F)CO4)cc2F)cn1] | (+)-7-(4-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.206 |

TABLE III-continued

Biological Assay

| Compound of Example | Structure | Name | Aβ42 H4 Prot Fre IC50 (μM) |
|---|---|---|---|
| 99B | 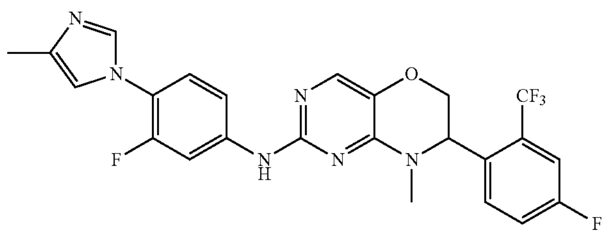 [SMILES: Cc1cn(-c2ccc(Nc3ncc4c(n3)N(C)C(c3ccc(F)cc3C(F)(F)F)CO4)cc2F)cn1] | (−)-7-(4-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 1.039 |
| 100A | 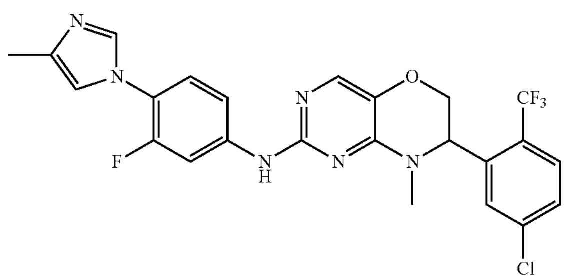 [SMILES: Cc1cn(-c2ccc(Nc3ncc4c(n3)N(C)C(c3cc(Cl)ccc3C(F)(F)F)CO4)cc2F)cn1] | (+)-7-(5-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.101 |
| 100B | 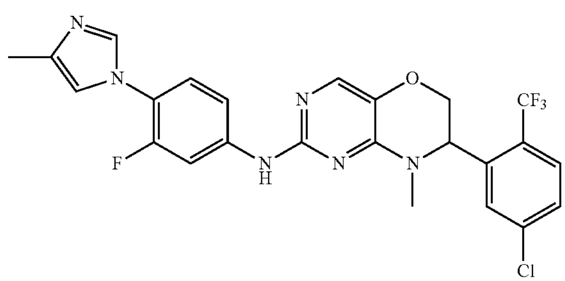 [SMILES: Cc1cn(-c2ccc(Nc3ncc4c(n3)N(C)C(c3cc(Cl)ccc3C(F)(F)F)CO4)cc2F)cn1] | (−)-7-(5-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.588 |
| 101A | 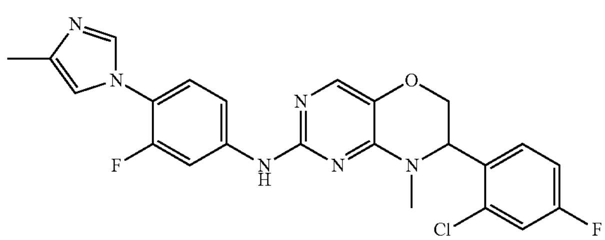 [SMILES: Cc1cn(-c2ccc(Nc3ncc4c(n3)N(C)C(c3ccc(F)cc3Cl)CO4)cc2F)cn1] | (+)-7-(2-chloro-4-fluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.075 |
| 101B | 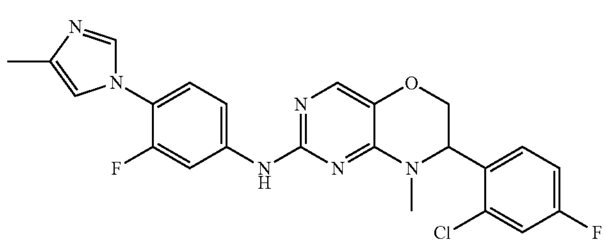 [SMILES: Cc1cn(-c2ccc(Nc3ncc4c(n3)N(C)C(c3ccc(F)cc3Cl)CO4)cc2F)cn1] | (−)-7-(2-chloro-4-fluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.685 |

TABLE III-continued

Biological Assay

| Compound of Example | Structure | Name | Aβ42 H4 Prot Fre IC50 (μM) |
|---|---|---|---|
| 102A | 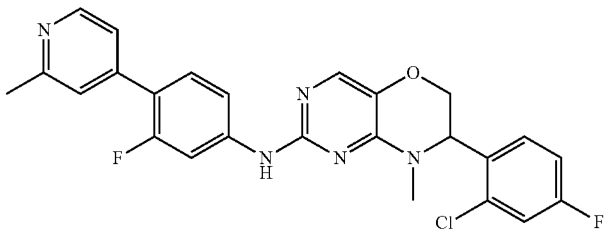 [SMILES: Cc1cc(-c2ccc(Nc3ncc4c(n3)N(C)C(c3ccc(F)cc3Cl)CO4)cc2F)ccn1] | (+)-7-(2-chloro-4-fluorophenyl)-N-(3-fluoro-4-(2-methylpyridin-4-yl) phenyl)-8-methyl-7, 8-dihydro-6H-pyrimido [5 4-b] [1, 4] oxazin-2-amine | 0.415 |
| 102B | 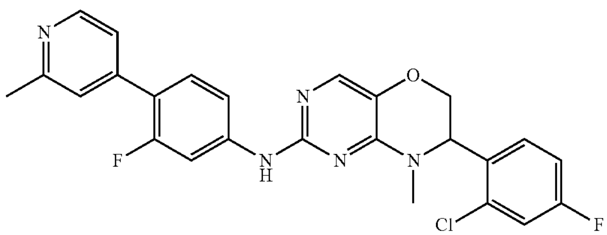 [SMILES: Cc1cc(-c2ccc(Nc3ncc4c(n3)N(C)C(c3ccc(F)cc3Cl)CO4)cc2F)ccn1] | (−)-7-(2-chloro-4-fluorophenyl)-N-(3-fluoro-4-(2-methylpyridin-4-yl) phenyl)-8-methyl-7, 8-dihydro-6H-pyrimido [5, 4-b] [1, 4] oxazin-2-amine | 1.353 |
| 103A | 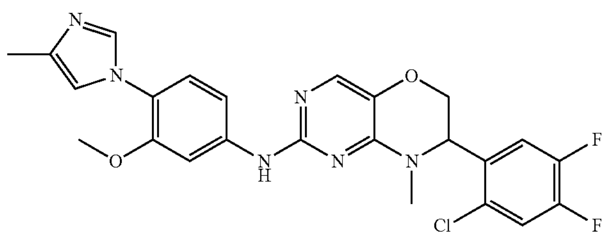 [SMILES: COc1cc(Nc2ncc3c(n2)N(C)C(c2cc(F)c(F)cc2Cl)CO3)ccc1-n1cnc(C)c1] | (+)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.019 |
| 103B | 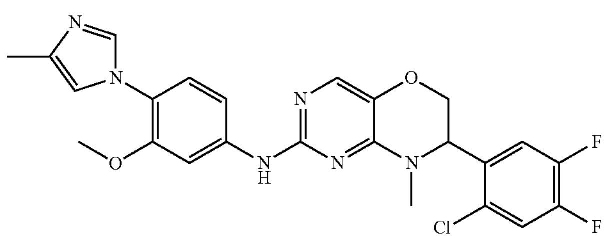 [SMILES: COc1cc(Nc2ncc3c(n2)N(C)C(c2cc(F)c(F)cc2Cl)CO3)ccc1-n1cnc(C)c1] | (−)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.219 |
| 104A | 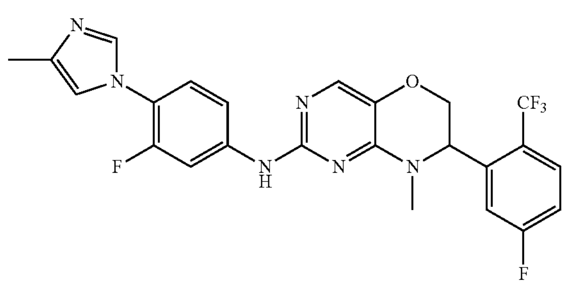 [SMILES: Cc1cn(-c2ccc(Nc3ncc4c(n3)N(C)C(c3cc(F)ccc3C(F)(F)F)CO4)cc2F)cn1] | (−)-7-(5-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.526 |

TABLE III-continued

Biological Assay

| Compound of Example | Structure | Name | Aβ42 H4 Prot Fre IC50 (μM) |
|---|---|---|---|
| 104B | 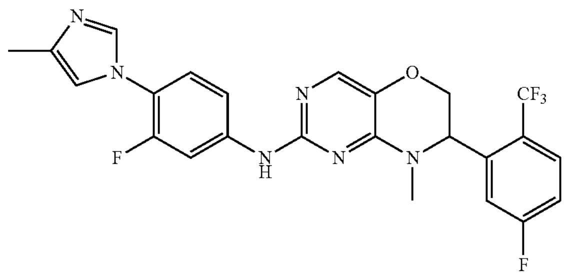 | (+)-7-(5-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.077 |
| 105A | 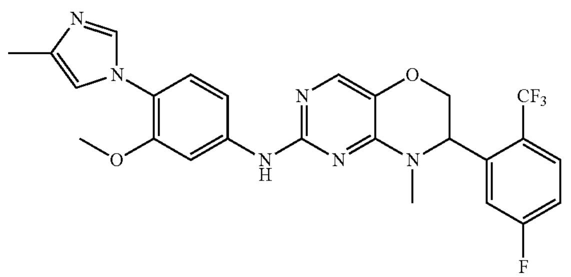 [SMILES: COc1cc(Nc2ncc3c(n2)N(C)C(c2cc(F)ccc2C(F)(F)F)CO3)ccc1-n1cnc(C)c1] | (−)-7-(5-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.088 |
| 105B | 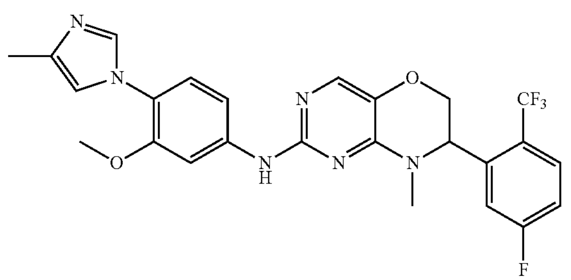 [SMILES: COc1cc(Nc2ncc3c(n2)N(C)C(c2cc(F)ccc2C(F)(F)F)CO3)ccc1-n1cnc(C)c1] | (+)-7-(5-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.051 |
| 106A | 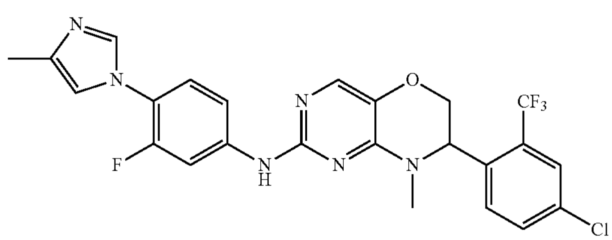 [SMILES: Cc1cn(-c2ccc(Nc3ncc4c(n3)N(C)C(c3ccc(Cl)cc3C(F)(F)F)CO4)cc2F)cn1] | (+)-7-(4-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.154 |
| 106B | 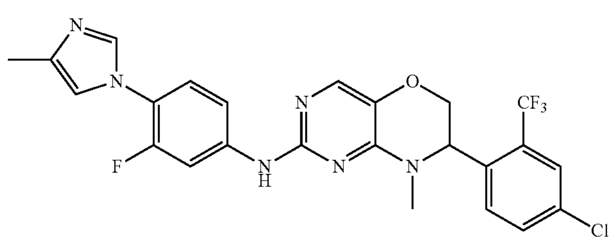 [SMILES: Cc1cn(-c2ccc(Nc3ncc4c(n3)N(C)C(c3ccc(Cl)cc3C(F)(F)F)CO4)cc2F)cn1] | (−)-7-(4-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 1.023 |

TABLE III-continued

Biological Assay

| Compound of Example | Structure | Name | Aβ42 H4 Prot Fre IC50 (μM) |
|---|---|---|---|
| 107A | 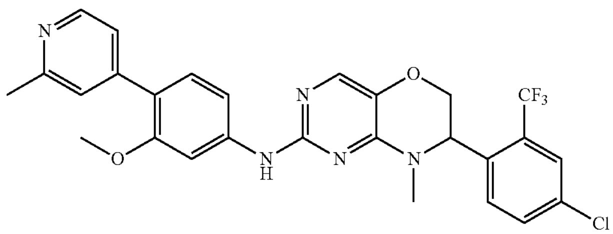 [SMILES: COc1cc(Nc2ncc3c(n2)N(C)C(c2ccc(Cl)cc2C(F)(F)F)CO3)ccc1-c1ccnc(C)c1] | (−)-7-(4-chloro-2-(trifluoromethyl) phenyl)-N-(3-methoxy-4-(2-methylpyridin-4-yl) phenyl)-8-methyl-7, 8-dihydro-6H-pyrimido [5, 4-b] [1, 4] oxazin-2-amine | 0.422 |
| 107B | 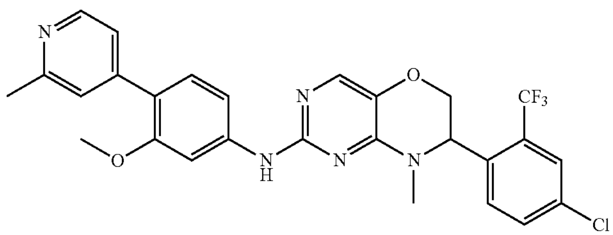 [SMILES: COc1cc(Nc2ncc3c(n2)N(C)C(c2ccc(Cl)cc2C(F)(F)F)CO3)ccc1-c1ccnc(C)c1] | (+)-7-(4-chloro-2-(trifluoromethyl) phenyl)-N-(3-methoxy-4-(2-methylpyridin-4-yl) phenyl)-8-methyl-7, 8-dihydro-6H-pyrimido [5, 4-b] [1, 4] oxazin-2-amine | 0.174 |
| 108A | 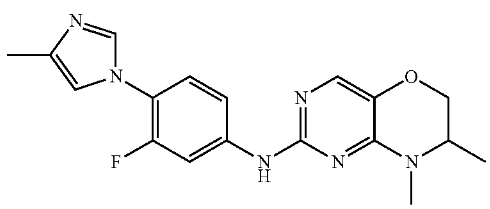 | (−)-N-(3-fluoro-4-(4-methyl-1H-imidazol-1-yl) phenyl)-7, 8-dimethyl-7, 8-dihydro-6H-pyrimido [5, 4-b] [1, 4] oxazin-2-amine | 0.567 |
| 108B | 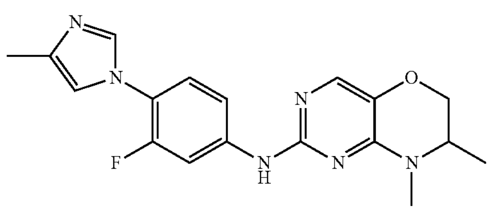 | (+)-N-(3-fluoro-4-(4-methyl-1H-imidazol-1-yl) phenyl)-7, 8-dimethyl-7, 8-dihydro-6H-pyrimido [5, 4-b] [1, 4] oxazin-2-amine | 0.108 |
| 109A | 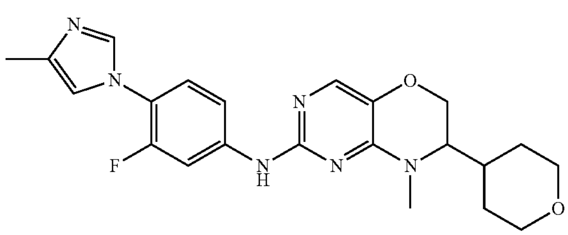 [SMILES: Cc1cn(-c2ccc(Nc3ncc4c(n3)N(C)C(C3CCOCC3)CO4)cc2F)cn1] | (+)-N-(3-fluoro-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine | 0.212 |
| 109B | 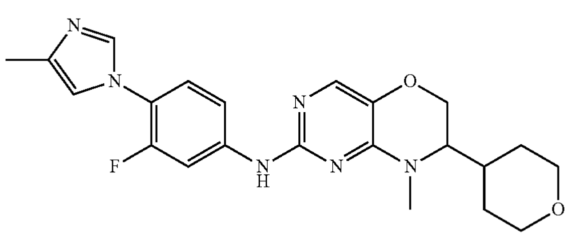 [SMILES: Cc1cn(-c2ccc(Nc3ncc4c(n3)N(C)C(C3CCOCC3)CO4)cc2F)cn1] | (−)-N-(3-fluoro-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine | >3 |

TABLE III-continued

Biological Assay

| Compound of Example | Name | Aβ42 H4 Prot Fre IC50 (μM) |
|---|---|---|
| 110A | (−)-N-(3-methoxy-4-(2-methylpyridin-4-yl)phenyl)-7, 8-dimethyl-7, 8-dihydro-6H-pyrimido [5, 4-b] [1, 4] oxazin-2-amine | 0.199 |
| 110B | (+)-N-(3-methoxy-4-(2-methylpyridin-4-yl)phenyl)-7, 8-dimethyl-7, 8-dihydro-6H-pyrimido [5, 4-b] [1, 4] oxazin-2-amine | 0.091 |
| 111 | (S)-N-(3-methoxy-4-(4-methyl-1H-imidazol-1-yl)phenyl)-7-(methoxymethyl)-8-methyl-7, 8-dihydro-6H-pyrimido [5, 4-b] [1, 4] oxazin-2-amine | 0.120 |
| 112A | (−)-7-(4-chloro-2-(trifluoromethyl) phenyl)-N-(3-methoxy-4-(4-methyl-1H-imidazol-1-yl)phenyl)-8-methyl-7, 8-dihydro-6H-pyrimido [5, 4-b] [1, 4] oxazin-2-amine | 0.231 |
| 112B | (+)-7-(4-chloro-2-(trifluoromethyl) phenyl)-N-(3-methoxy-4-(4-methyl-1H-imidazol-1-yl)phenyl)-8-methyl-7, 8-dihydro-6H-pyrimido [5, 4-b] [1, 4] oxazin-2-amine | 0.064 |
| 113 | (S)-N-(3-fluoro-4-(4-methyl-1H-imidazol-1-yl)phenyl)-7-(methoxymethyl)-8-methyl-7, 8-dihydro-6H-pyrimido [5, 4-b] [1, 4] oxazin-2-amine | 0.331 |

TABLE III-continued

Biological Assay

| Compound of Example | Structure | Name | Aβ42 H4 Prot Fre IC50 (μM) |
|---|---|---|---|
| 114A | 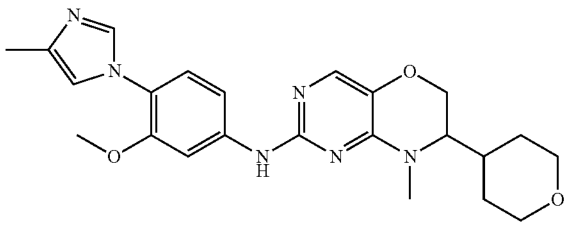 [SMILES: COc1cc(Nc2ncc3c(n2)N(C)C(C2CCOCC2)CO3)ccc1-n1cnc(C)c1] | (−)-N-(3-methoxy-4-(4-methyl-1H-imidazol-1-yl)phenyl)-8-methyl-7-(tetrahydro-2H-pyran-4-yl)-7, 8-dihydro-6H-pyrimido [5, 4-b] [1, 4] oxazin-2-amine | 0.494 |
| 114B | 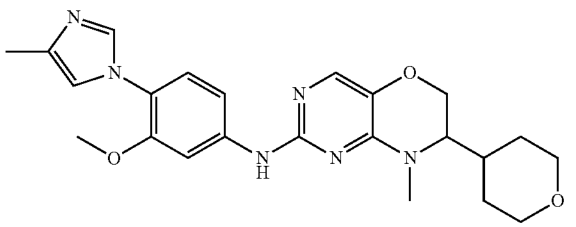 [SMILES: COc1cc(Nc2ncc3c(n2)N(C)C(C2CCOCC2)CO3)ccc1-n1cnc(C)c1] | (+)-N-(3-methoxy-4-(4-methyl-1H-imidazol-1-yl)phenyl)-8-methyl-7-(tetrahydro-2H-pyran-4-yl)-7, 8-dihydro-6H-pyrimido [5, 4-b] [1, 4] oxazin-2-amine | 0.077 |
| 115A | 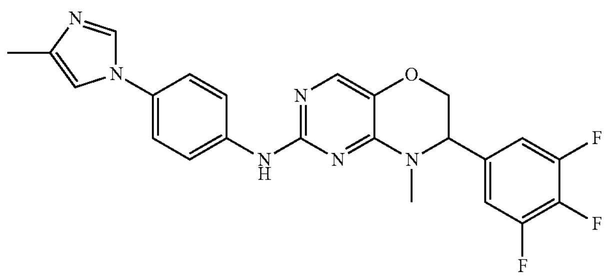 [SMILES: Cc1cn(-c2ccc(Nc3ncc4c(n3)N(C)C(c3cc(F)c(F)c(F)c3)CO4)cc2)cn1] | (−)-8-methyl-N-(4-(4-methyl-1H-imidazol-1-yl)phenyl)-7-(3, 4, 5-trifluorophenyl)-7, 8-dihydro-6H-pyrimido [5, 4-b] [1, 4] oxazin-2-amine | 2.858 |
| 115B | 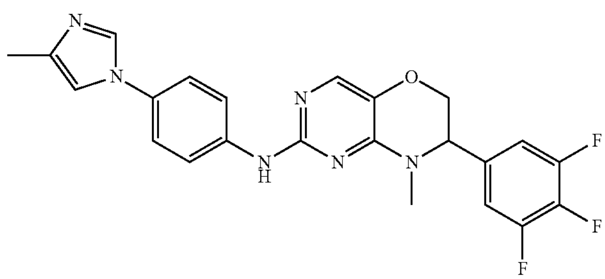 [SMILES: Cc1cn(-c2ccc(Nc3ncc4c(n3)N(C)C(c3cc(F)c(F)c(F)c3)CO4)cc2)cn1] | (+)-8-methyl-N-(4-(4-methyl-1H-imidazol-1-yl)phenyl)-7-(3, 4, 5-trifluorophenyl)-7, 8-dihydro-6H-pyrimido [5, 4-b] [1, 4] oxazin-2-amine | 0.022 |
| 116A | 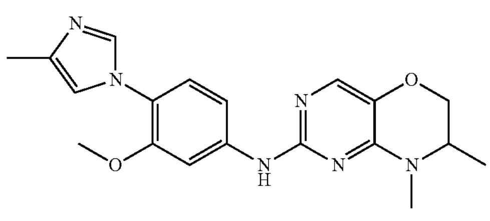 | (−)-N-(3-methoxy-4-(4-methyl-1H-imidazol-1-yl)phenyl)-7, 8-dimethyl-7, 8-dihydro-6H-pyrimido [5, 4-b] [1, 4] oxazin-2-amine | 0.148 |
| 116B | 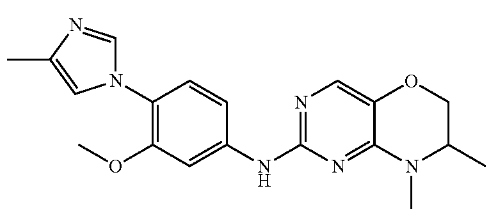 | (+)-N-(3-methoxy-4-(4-methyl-1H-imidazol-1-yl)phenyl)-7, 8-dimethyl-7, 8-dihydro-6H-pyrimido [5, 4-b] [1, 4] oxazin-2-amine | 0.063 |

TABLE III-continued

Biological Assay

| Compound of Example | Structure | Name | Aβ42 H4 Prot Fre IC50 (μM) |
|---|---|---|---|
| 117A | 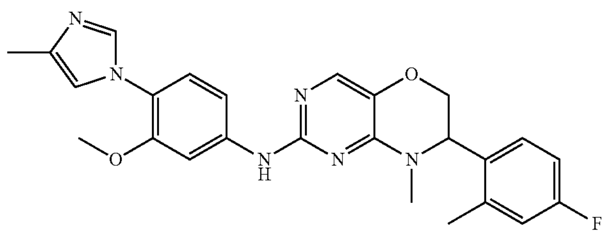 [SMILES: COc1cc(Nc2ncc3c(n2)N(C)C(c2ccc(F)cc2C)CO3)ccc1-n1cnc(C)c1] | (−)-7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.140 |
| 117B | 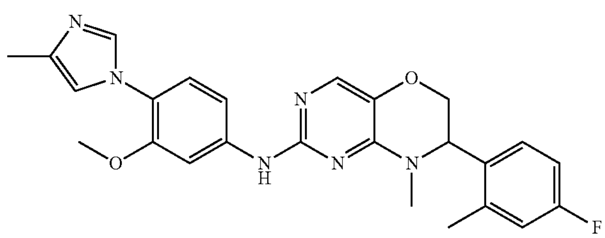 [SMILES: COc1cc(Nc2ncc3c(n2)N(C)C(c2ccc(F)cc2C)CO3)ccc1-n1cnc(C)c1] | (+)-7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.022 |
| 118A | 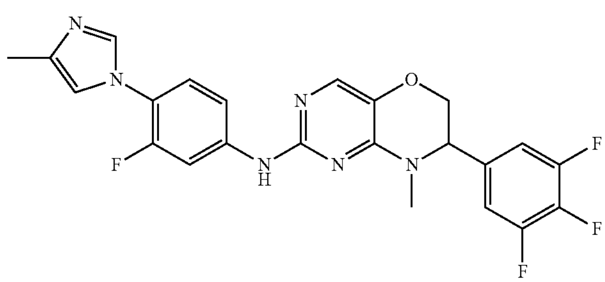 [SMILES: Cc1cn(-c2ccc(Nc3ncc4c(n3)N(C)C(c3cc(F)c(F)c(F)c3)CO4)cc2F)cn1] | (+)-N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine | 0.029 |
| 118B | 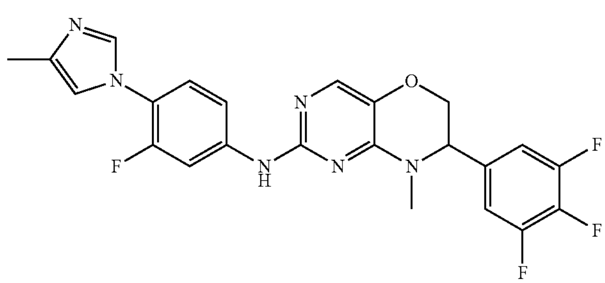 [SMILES: Cc1cn(-c2ccc(Nc3ncc4c(n3)N(C)C(c3cc(F)c(F)c(F)c3)CO4)cc2F)cn1] | (−)-N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine | 1.341 |
| 164 | 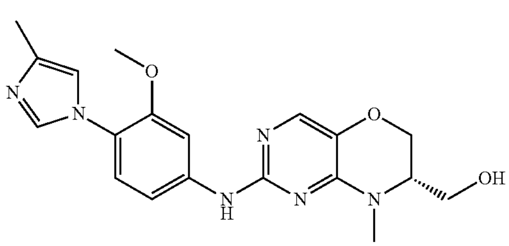 [SMILES: COc1cc(Nc2ncc3c(n2)N(C)[C@@H](CO)CO3)ccc1-n1cnc(C)c1] | (S)-N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine | 0.411 |

TABLE III-continued

Biological Assay

| Compound of Example | Structure | Name | Aβ42 H4 Prot Fre IC50 (µM) |
|---|---|---|---|
| 165A | 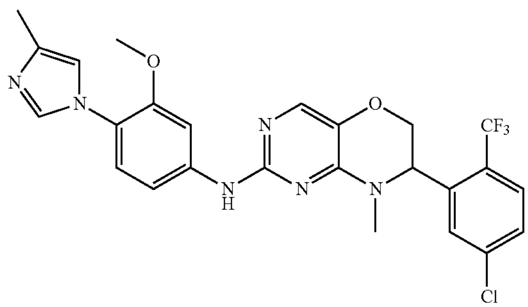 | (+)-7-(5-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.089 |
| 165B | 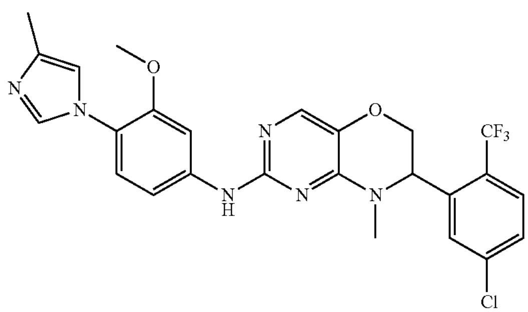 [SMILES: COc1cc(Nc2ncc3c(n2)N(C)C(c2cc(Cl)ccc2C(F)(F)F)CO3)ccc1-n1cnc(C)c1] | (−)-7-(5-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.079 |
| 166A | 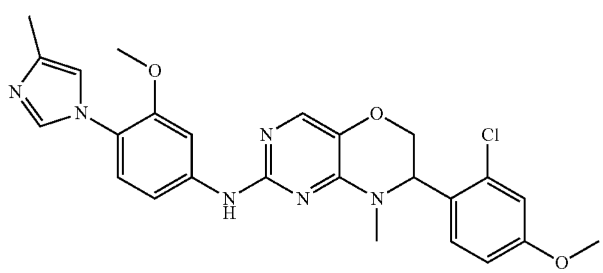 | (+)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.031 |
| 166B | 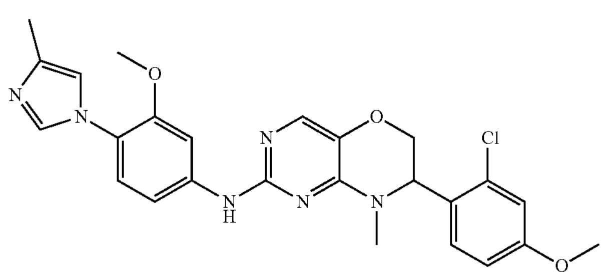 | (−)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.090 |

TABLE III-continued

Biological Assay

| Compound of Example | Structure | Name | Aβ42 H4 Prot Fre IC50 (μM) |
|---|---|---|---|
| 167A | 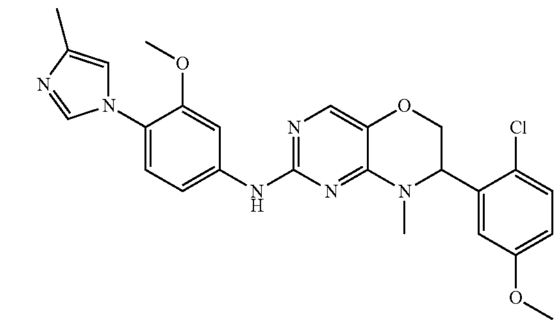 | (+)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.022 |
| 167B | 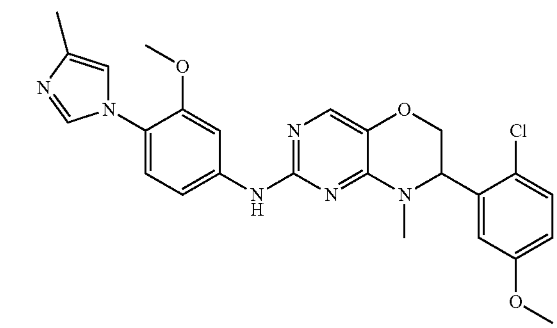 | (−)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.075 |
| 168A | 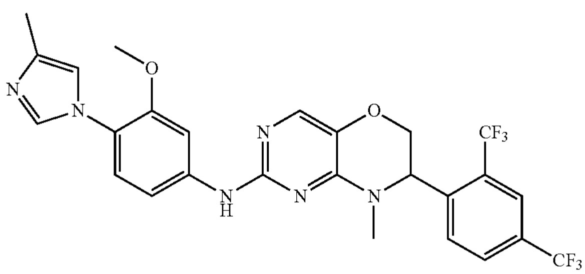 [SMILES: COc1cc(Nc2ncc3c(n2)N(C)C(c2ccc(C(F)(F)F)cc2C(F)(F)F)CO3)ccc1-n1cnc(C)c1] | (−)-7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.566 |
| 168B | 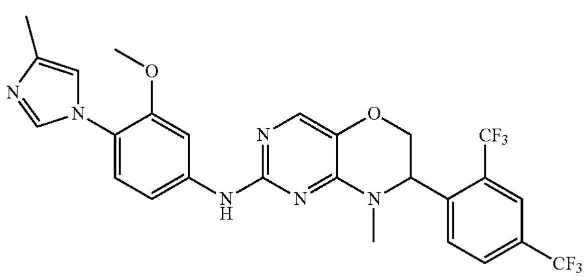 [SMILES: COc1cc(Nc2ncc3c(n2)N(C)C(c2ccc(C(F)(F)F)cc2C(F)(F)F)CO3)ccc1-n1cnc(C)c1] | (+)-7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.076 |

TABLE III-continued

Biological Assay

| Compound of Example | Structure | Name | Aβ42 H4 Prot Fre IC50 (μM) |
|---|---|---|---|
| 169A | 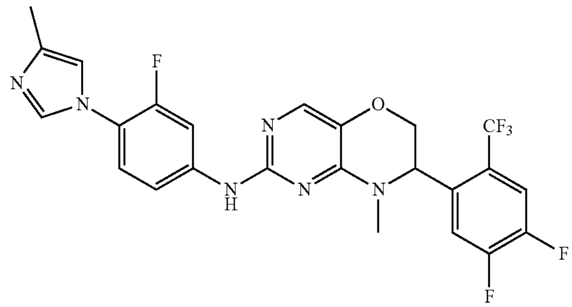 [SMILES: Cc1cn(-c2ccc(Nc3ncc4c(n3)N(C)C(c3cc(F)c(F)cc3C(F)(F)F)CO4)cc2F)cn1] | (+)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.045 |
| 169B | 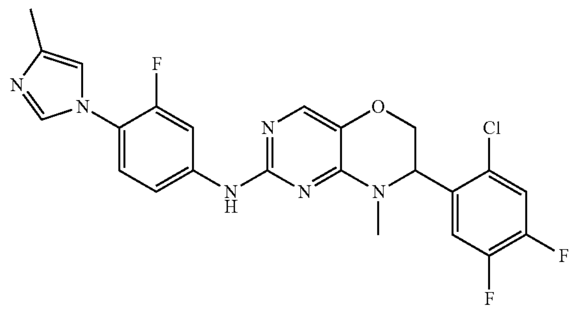 [SMILES: Cc1cn(-c2ccc(Nc3ncc4c(n3)N(C)C(c3cc(F)c(F)cc3Cl)CO4)cc2F)cn1] | (−)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 2.264 |
| 170 | 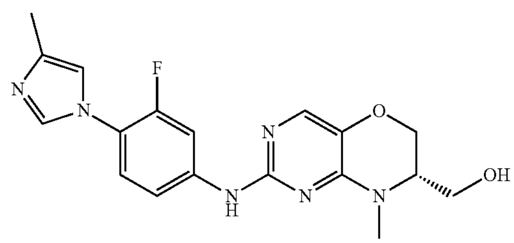 [SMILES: Cc1cn(-c2ccc(Nc3ncc4c(n3)N(C)[C@@H](CO)CO4)cc2F)cn1] | (S)-(2-((3-fluoro-4-(4-methyl-1H-imidazol-1-yl) phenyl) amino)-8-methyl-7, 8-dihydro-6H-pyrimido [5, 4-b] [1, 4] oxazin-7-yl) methanol | 1.243 |
| 171A | 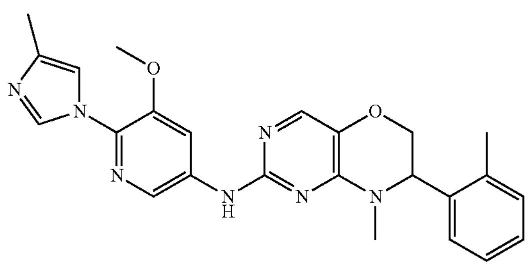 [SMILES: COc1cc(Nc2ncc3c(n2)N(C)C(c2ccccc2C)CO3)cnc1-n1cnc(C)c1] | (+)-N-(5-methoxy-6-(4-methyl-1H-imidazol-1-yl) pyridin-3-yl)-8-methyl-7-(o-tolyl)-7, 8-dihydro-6H-pyrimido [5, 4-b] [1, 4] oxazin-2-amine | 0.011 |
| 171B | 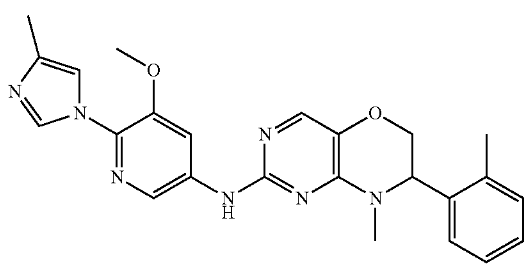 [SMILES: COc1cc(Nc2ncc3c(n2)N(C)C(c2ccccc2C)CO3)cnc1-n1cnc(C)c1] | (−)-N-(5-methoxy-6-(4-methyl-1H-imidazol-1-yl) pyridin-3-yl)-8-methyl-7-(o-tolyl)-7, 8-dihydro-6H-pyrimido [5, 4-b] [1, 4] oxazin-2-amine | 0.067 |

TABLE III-continued

Biological Assay

| Compound of Example | Structure | Name | Aβ42 H4 Prot Fre IC50 (μM) |
|---|---|---|---|
| 172A | 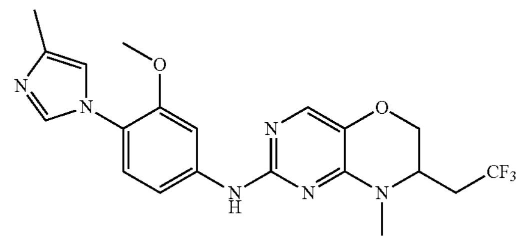 [SMILES: COc1cc(Nc2ncc3c(n2)N(C)C(CC(F)(F)F)CO3)ccc1-n1cnc(C)c1] | (−)-N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine | 0.207 |
| 172B | 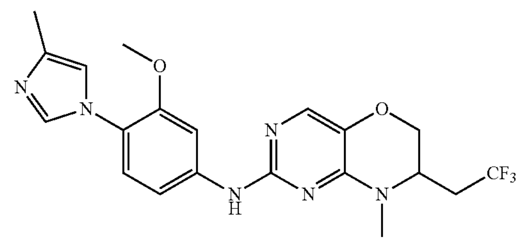 [SMILES: COc1cc(Nc2ncc3c(n2)N(C)C(CC(F)(F)F)CO3)ccc1-n1cnc(C)c1] | (+)-N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4l oxazin-7-amine | 0.054 |
| 173A | 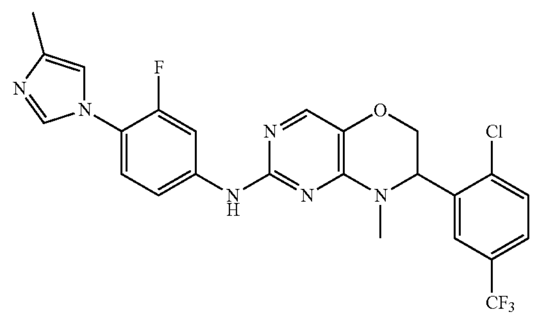 [SMILES: Cc1cn(-c2ccc(Nc3ncc4c(n3)N(C)C(c3cc(C(F)(F)F)ccc3Cl)CO4)cc2F)cn1] | (+)-7-(2-chloro-5-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.072 |
| 173B | 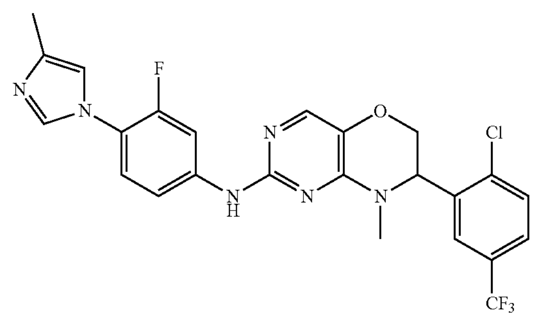 [SMILES: Cc1cn(-c2ccc(Nc3ncc4c(n3)N(C)C(c3cc(C(F)(F)F)ccc3Cl)CO4)cc2F)cn1] | (−)-7-(2-chloro-5-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine | 0.831 |
| 174A | 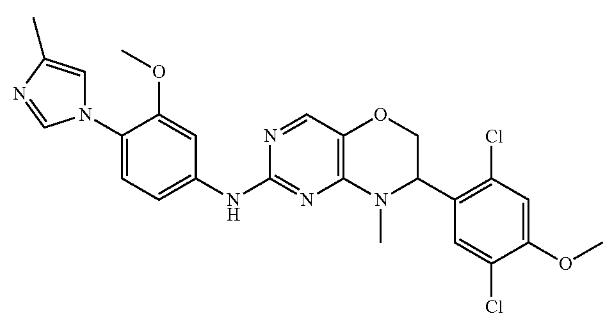 [SMILES: COc1cc(Cl)c(C2COc3cnc(Nc4ccc(-n5cnc(C)c5)c(OC)c4)nc3N2C)cc1Cl] | (−)-7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.150 |

TABLE III-continued

Biological Assay

| Compound of Example | Structure | Name | Aβ42 H4 Prot Fre IC50 (μM) |
|---|---|---|---|
| 174B | 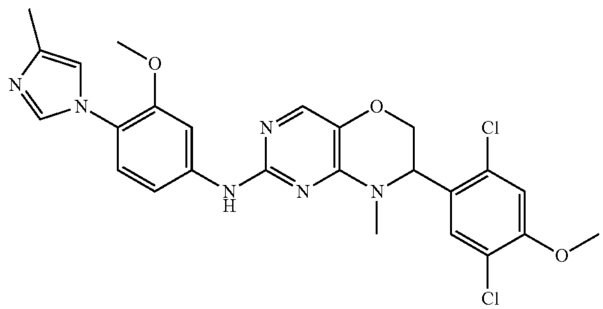 [SMILES: COc1cc(Cl)c(C2COc3cnc(Nc4ccc(-n5cnc(C)c5)c(OC)c4)nc3N2C)cc1Cl] | (+)-7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.032 |
| 175A | 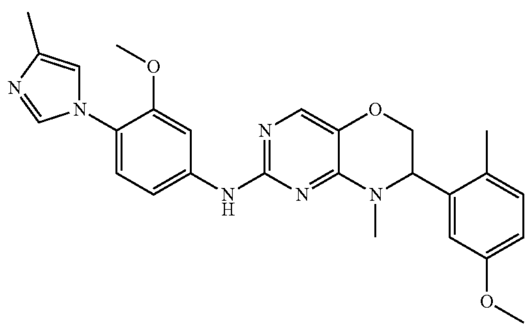 [SMILES: COc1ccc(C)c(C2COc3cnc(Nc4ccc(-n5cnc(C)c5)c(OC)c4)nc3N2C)c1] | (+)-7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.011 |
| 175B | 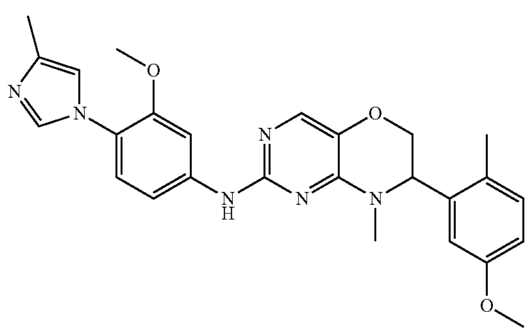 [SMILES: COc1ccc(C)c(C2COc3cnc(Nc4ccc(-n5cnc(C)c5)c(OC)c4)nc3N2C)c1] | (−)-7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.095 |
| 176 | 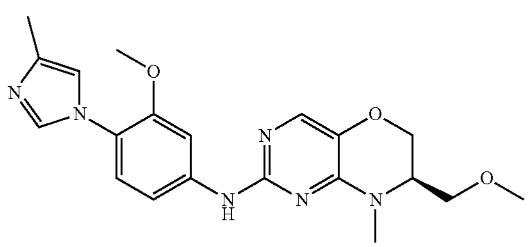 [SMILES: COC[C@@H]1COc2cnc(Nc3ccc(-n4cnc(C)c4)c(OC)c3)nc2N1C] | (R)-N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine | 0.369 |
| 177 | 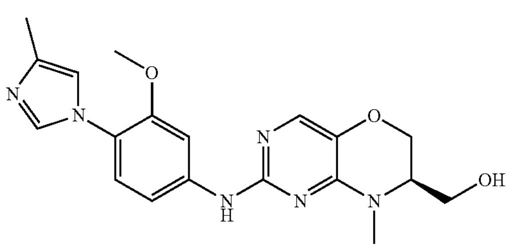 [SMILES: COc1cc(Nc2ncc3c(n2)N(C)[C@H](CO)CO3)ccc1-n1cnc(C)c1] | (R)-(24(3-methoxy-4-(4-methyl- 1H-imidazol-1-yl) phenyl) amino)-8-methyl-7, 8-dihydro-6H-pyrimido [5, 4-b] [1, 4] oxazin-7-yl) methanol | 0.262 |

TABLE III-continued

Biological Assay

| Compound of Example | Structure | Name | Aβ42 H4 Prot Fre IC50 (μM) |
|---|---|---|---|
| 178A | 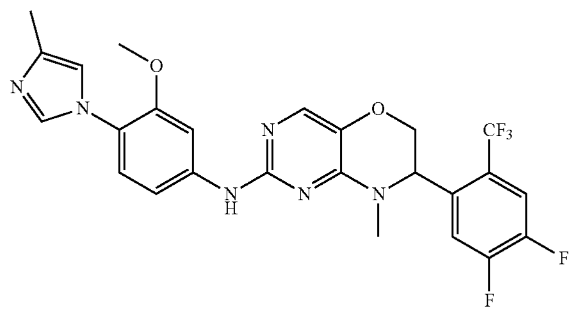 [SMILES: COc1cc(Nc2ncc3c(n2)N(C)C(c2cc(F)c(F)cc2C(F)(F)F)CO3)ccc1-n1cnc(C)c1] | (+)-7-(4, 5-difluoro-2-(trifluoromethyl)phenyl)-N-(1-(2-methoxypyridin-4-yl)piperidin-4-yl)-8-methyl-7, 8-dihydro-6H-pyrimido [5, 4-b] [1, 4] oxazin-2-amine | 0.025 |
| 178B | 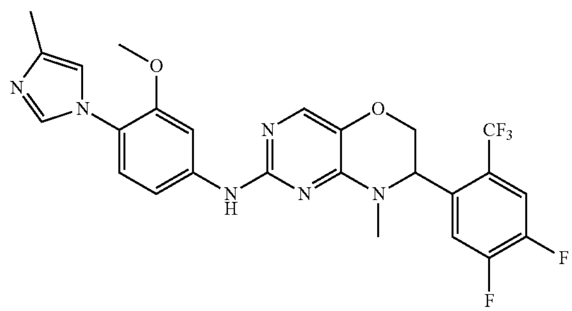 [SMILES: COc1cc(Nc2ncc3c(n2)N(C)C(c2cc(F)c(F)cc2C(F)(F)F)CO3)ccc1-n1cnc(C)c1] | (−)-7-(4, 5-difluoro-2-(trifluoromethyl)phenyl)-N-(1-(2-methoxypyridin-4-yl)piperidin-4-yl)-8-methyl-7, 8-dihydro-6H-pyrimido [5, 4-b] [1, 4] oxazin-2-amine | 0.136 |
| 179A | 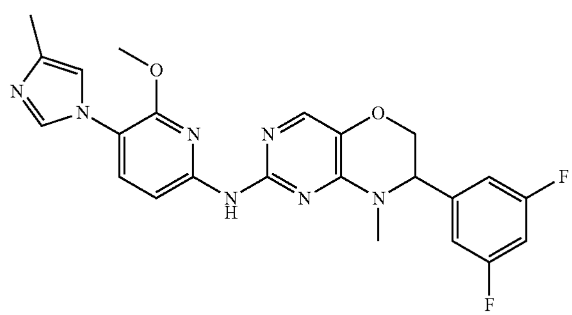 [SMILES: COc1nc(Nc2ncc3c(n2)N(C)C(c2cc(F)cc(F)c2)CO3)ccc1-n1cnc(C)c1] | (−)-7-(3, 5)-difluorophenyl)-N-(6-methoxy-5-(4-methyl-1H-imidazol-1-yl)pyridin-2-yl)-8-methyl-7, 8-dihydro-6H-pyrimido [5, 4-b] [1, 4] oxazin-2-amine | >3 |
| 179B | 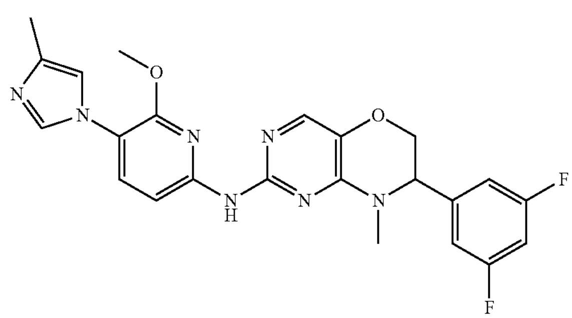 [SMILES: COc1nc(Nc2ncc3c(n2)N(C)C(c2cc(F)cc(F)c2)CO3)ccc1-n1cnc(C)c1] | (+)-7-(3, 5-difluorophenyl)-N-(6-methoxy-5-(4-methyl-1H-imidazol-1-yl)pyridin-2-yl)-8-methyl-7, 8-dihydro-6H-pyrimido [5, 4-b] [1, 4] oxazin-2-amine | 0.287 |

TABLE III-continued

Biological Assay

| Compound of Example | Structure | Name | Aβ42 H4 Prot Fre IC50 (μM) |
|---|---|---|---|
| 180A | 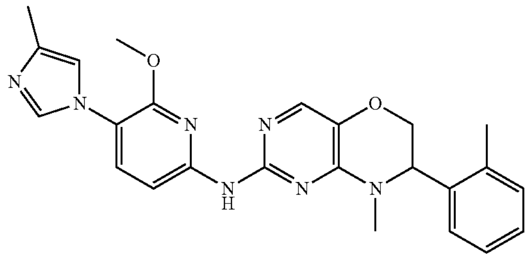 [SMILES: COc1nc(Nc2ncc3c(n2)N(C)C(c2ccccc2C)CO3)ccc1-n1cnc(C)c1] | (−)-N-(6-methoxy-5-(4-methyl-1H-imidazol-1-yl) pyridin-2-yl)-8-methyl-7-(o-tolyl)-7, 8-dihydro-6H-pyrimido [5, 4-b] [1, 4] oxazin-2-amine | >3 |
| 180B | 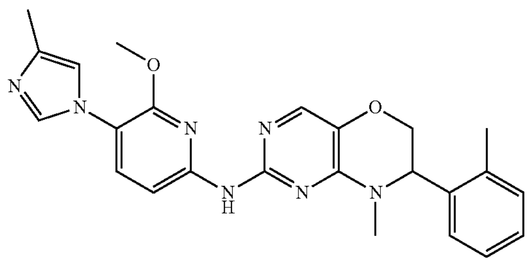 [SMILES: COc1nc(Nc2ncc3c(n2)N(C)C(c2ccccc2C)CO3)ccc1-n1cnc(C)c1] | (+)-N-(6-methoxy-5-(4-methyl-1H-imidazol-1-yl) pyridin-2-yl)-8-methyl-7-(o-tolyl)-7, 8-dihydro-6H-pyrimido [5, 4-b] [1, 4] oxazin-2-amine | 0.374 |
| 181A | 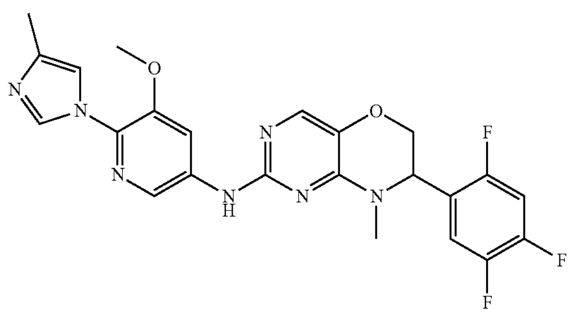 [SMILES: COc1cc(Nc2ncc3c(n2)N(C)C(c2cc(F)c(F)cc2F)CO3)cnc1-n1cnc(C)c1] | (−)-N-(5-methoxy-6-(4-methyl-1H-imidazol-1-yl) pyridin-3-yl)-8-methyl-7-(2, 4, 5-trifluorophenyl)-7, 8-dihydro-6H-pyrimido [5, 4-b] [1, 4] oxazin-2-amine | 0.009 |
| 181B | 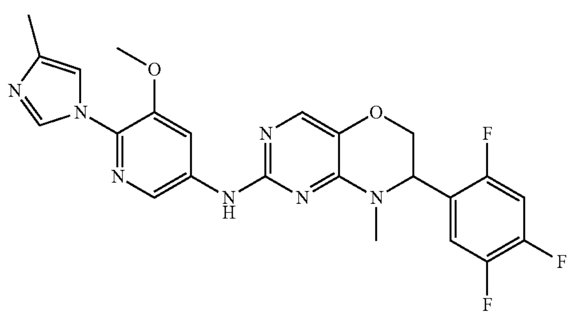 [SMILES: COc1cc(Nc2ncc3c(n2)N(C)C(c2cc(F)c(F)cc2F)CO3)cnc1-n1cnc(C)c1] | (+)-N-(5-methoxy-6-(4-methyl-1H-imidazol-1-yl) pyridin-3-yl)-8-methyl-7-(2, 4, 5-trifluorophenyl)-7, 8-dihydro-6H-pyrimido [5, 4-b] [1, 4] oxazin-2-amine | 0.392 |
| 182A | 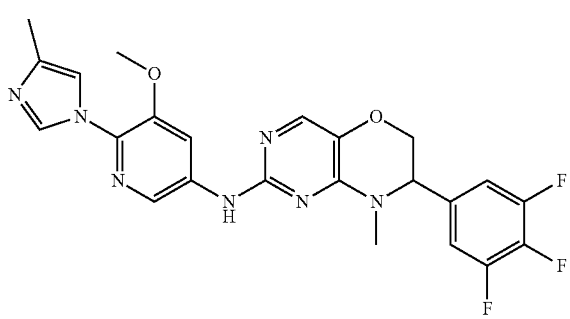 [SMILES: COc1cc(Nc2ncc3c(n2)N(C)C(c2cc(F)c(F)c(F)c2)CO3)cnc1-n1cnc(C)c1] | (+)-N-(5-methoxy-6-(4-methyl-1H-imidazol-1-yl) pyridin-3-yl)-8-methyl-7-(3, 4, 5-trifluorophenyl)-7, 8-dihydro-6H-pyrimido [5, 4-b] [1, 4] oxazin-2-amine | 0.013 |

TABLE III-continued

Biological Assay

| Compound of Example | Structure | Name | Aβ42 H4 Prot Fre IC50 (μM) |
|---|---|---|---|
| 182B | 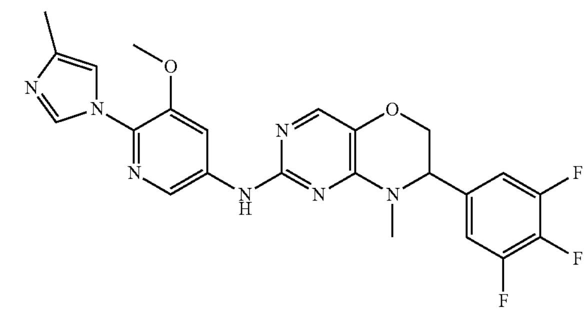 [SMILES: COc1cc(Nc2ncc3c(n2)N(C)C(c2cc(F)c(F)c(F)c2)CO3)cnc1-n1cnc(C)c1] | (−)-N-(5-methoxy-6-(4-methyl-1H-imidazol-1-yl) pyridin-3-yl)-8-methyl-7-(3, 4, 5-trifluorophenyl)-7, 8-dihydro-6H-pyrimido [5, 4-b] [1, 4] oxazin-2-amine | 0.176 |
| 183A | 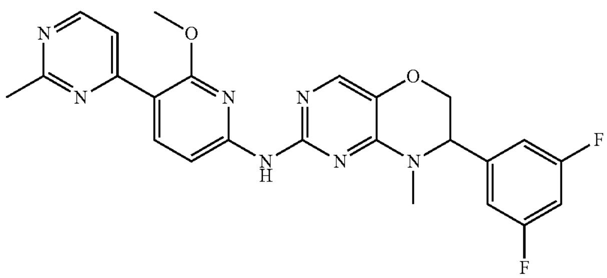 [SMILES: COc1nc(Nc2ncc3c(n2)N(C)C(c2cc(F)cc(F)c2)CO3)ccc1-c1ccnc(C)n1] | (+)-7-(3, 5-difluorophenyl)-N-(6-methoxy-5-(2-methylpyrimidin-4-yl) pyridin-2-yl)-8-methyl-7, 8-dihydro-6H-pyrimido [5, 4-b] [1, 4] oxazin-2-amine | >3 |
| 183B | 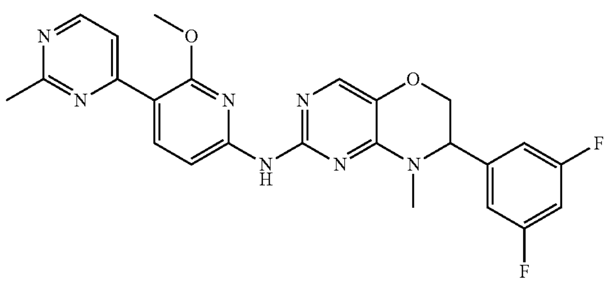 [SMILES: COc1nc(Nc2ncc3c(n2)N(C)C(c2cc(F)cc(F)c2)CO3)ccc1-c1ccnc(C)n1] | (−)-7-(3, 5-difluorophenyl)-N-(6-methoxy-5-(2-methylpyrimidin-4-yl) pyridin-2-yl)-8-methyl-7, 8-dihydro-6H-pyrimido [5, 4-b] [1, 4] oxazin-2-amine | >3 |
| 184A | 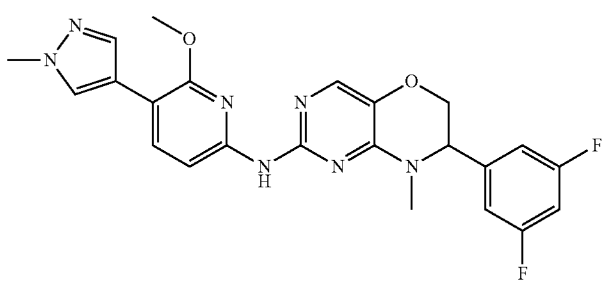 [SMILES: COc1nc(Nc2ncc3c(n2)N(C)C(c2cc(F)cc(F)c2)CO3)ccc1-c1cnn(C)c1] | (−)-7-(3, 5-difluorophenyl)-N-(6-methoxy-5-(1-methyl-1H-pyrazol-4-yl) pyridin-2-yl)-8-methyl-7, 8-dihydro-6H-pyrimido [5, 4-b] [1, 4] oxazin-2-amine | >3 |
| 184B | 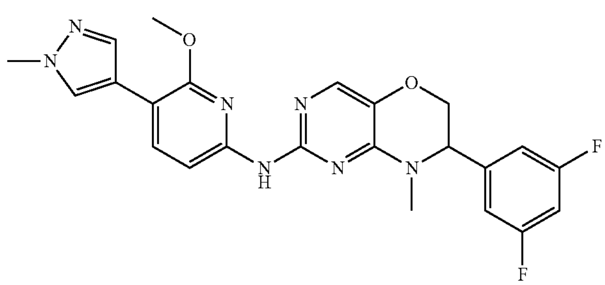 [SMILES: COc1nc(Nc2ncc3c(n2)N(C)C(c2cc(F)cc(F)c2)CO3)ccc1-c1cnn(C)c1] | (+)-7-(3, 5-difluorophenyl)-N-(6-methoxy-5-(1-methyl-1H-pyrazol-4-yl) pyridin-2-yl)-8-methyl-7, 8-dihydro-6H-pyrimido [5, 4-b] [1, 4] oxazin-2-amine | >3 |

TABLE III-continued

Biological Assay

| Compound of Example | Structure | Name | Aβ42 H4 Prot Fre IC50 (μM) |
|---|---|---|---|
| 185A | 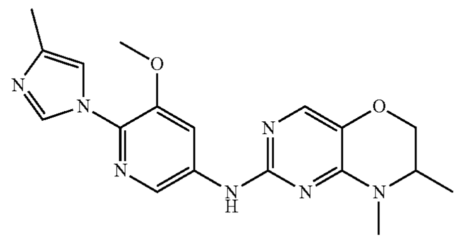 [SMILES: COc1cc(Nc2ncc3c(n2)N(C)C(C)CO3)cnc1-n1cnc(C)c1] | (+)-N-(5-methoxy-6-(4-methyl-1H-imidazol-1-yl) pyridin-3-yl)-7, 8-dimethyl-7, 8-dihydro-6H-pyrimido [5, 4-b] [1, 4] oxazin-2-amine | 0.241 |
| 185B | 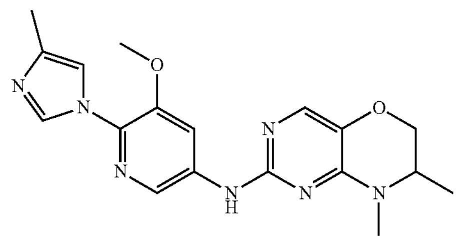 [SMILES: COc1cc(Nc2ncc3c(n2)N(C)C(C)CO3)cnc1-n1cnc(C)c1] | (−)-N-(5-methoxy-6-(4-methyl-1H-imidazol-1-yl) pyridin-3-yl)-7, 8-dimethyl-7, 8-dihydro-6H-pyrimido [5, 4-b] [1, 4] oxazin-2-amine | 0.540 |
| 186A | 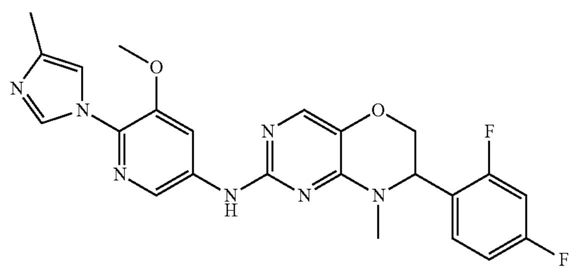 | (+)-7-(2, 4-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine | 0.018 |
| 186B | 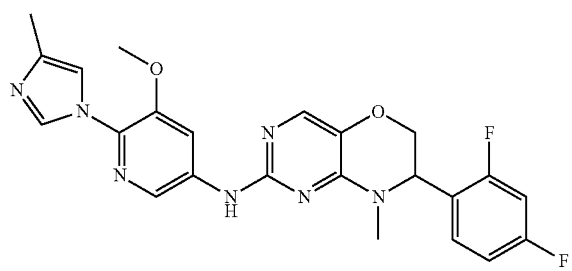 | (−)-7-(2, 4-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine | 0.328 |
| 187A | 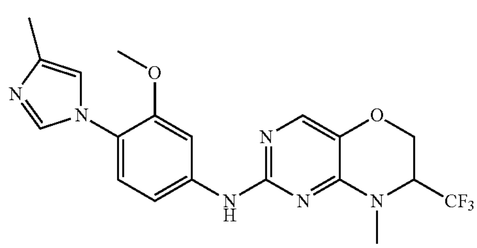 [SMILES: COc1cc(Nc2ncc3c(n2)N(C)C(C(F)(F)F)CO3)ccc1-n1cnc(C)c1] | (+)-N-(3-methoxy-4-(4-methyl-1H-imidazol-1-yl) phenyl)-8-methyl-7-(trifluoromethyl)-7, 8-dihydro-6H-pyrimido [5, 4-b] [1, 4] oxazin-2-amine | 0.419 |

TABLE III-continued

Biological Assay

| Compound of Example | Structure | Name | Aβ42 H4 Prot Fre IC50 (µM) |
|---|---|---|---|
| 187B | 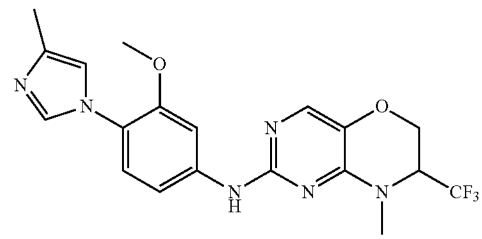 [SMILES: COc1cc(Nc2ncc3c(n2)N(C)C(C(F)(F)F)CO3)ccc1-n1cnc(C)c1] | (−)-N-(3-methoxy-4-(4-methyl-1H-imidazol-1-yl) phenyl)-8-methyl-7-(trifluoromethyl)-7, 8-dihydro-6H-pyrimido [5, 4-b] [1, 4] oxazin-2-amine | 0.033 |
| 188A | 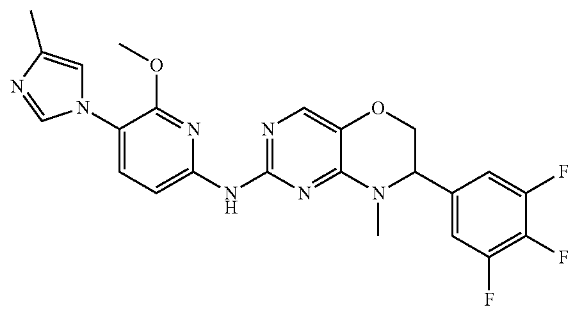 [SMILES: COc1nc(Nc2ncc3c(n2)N(C)C(c2cc(F)c(F)c(F)c2)CO3)ccc1-n1cnc(C)c1] | (−)-N-(6-methoxy-5-(4-methyl-1H-imidazol-1-yl) pyridin-2-yl)-8-methyl-7-(3, 4, 5-trifluorophenyl)-7, 8-dihydro-6H-pyrimido [5, 4-b] [1, 4]oxazin-2-amine | >3 |
| 188B | 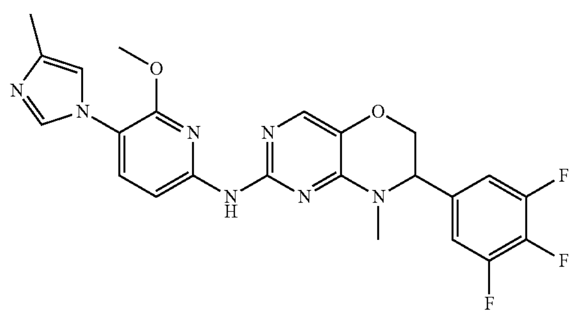 [SMILES: COc1nc(Nc2ncc3c(n2)N(C)C(c2cc(F)c(F)c(F)c2)CO3)ccc1-n1cnc(C)c1] | (+)-N-(6-methoxy-5-(4-methyl-1H-imidazol-1-yl) pyridin-2-yl)-8-methyl-7-(3, 4, 5-trifluorophenyl)-7, 8-dihydro-6H-pyrimido [5, 4-b] [1, 4]oxazin-2-amine | 0.275 |
| 189A | 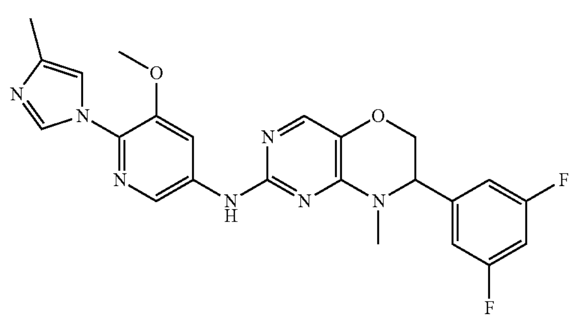 [SMILES: COc1cc(Nc2ncc3c(n2)N(C)C(c2cc(F)cc(F)c2)CO3)cnc1-n1cnc(C)c1] | (+)-7-(3, 5-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine | 0.013 |

TABLE III-continued

Biological Assay

| Compound of Example | Structure | Name | Aβ42 H4 Prot Fre IC50 (μM) |
|---|---|---|---|
| 189B | 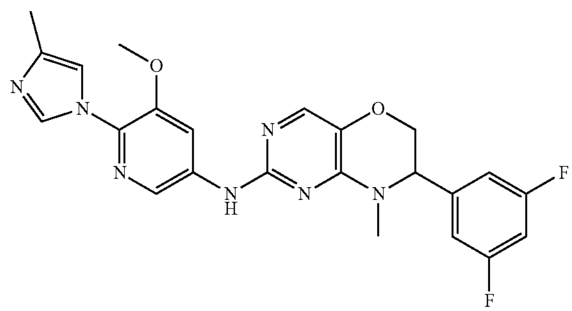 [SMILES: COc1cc(Nc2ncc3c(n2)N(C)C(c2cc(F)cc(F)c2)CO3)cnc1-n1cnc(C)c1] | (−)-7-(3, 5-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine | 0.655 |
| 190 | 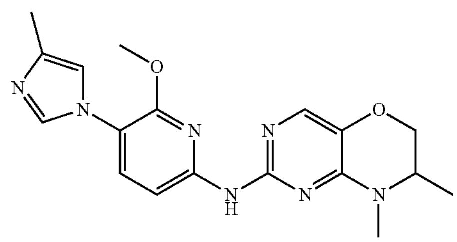 [SMILES: COc1nc(Nc2ncc3c(n2)N(C)C(C)CO3)ccc1-n1cnc(C)c1] | N-(6-methoxy-5-(4-methyl-1H-imidazol-1-yl) pyridin-2-yl)-7, 8-dimethyl-7, 8-dihydro-6H-pyrimido [5, 4-b] [1, 4] oxazin-2-amine (racemic) | >3 |
| 191 | 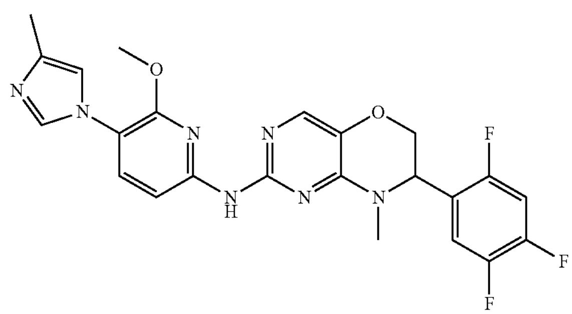 [SMILES: COc1nc(Nc2ncc3c(n2)N(C)C(c2cc(F)c(F)cc2F)CO3)ccc1-n1cnc(C)c1] | N-(6-methoxy-5-(4-methyl-1H-imidazol-1-yl) pyridin-2-yl)-8-methyl-7-(2, 4, 5-trifluorophenyl)-7, 8-dihydro-6H-pyrimido [5, 4-b] [1, 4] oxazin-2-amine (racemic) | 2.252 |
| 192A | 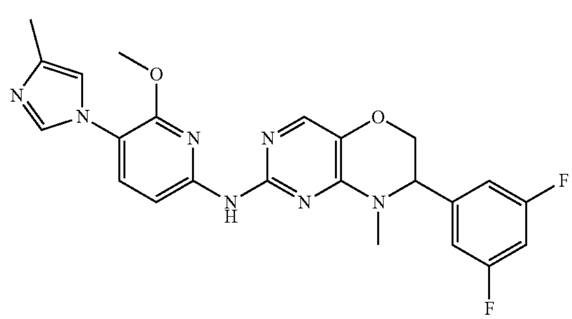 [SMILES: COc1nc(Nc2ncc3c(n2)N(C)C(c2cc(F)cc(F)c2)CO3)ccc1-n1cnc(C)c1] | (−)-6-((7-(3, 5-difluorophenyl)-8-methyl-7, 8-dihydro-6H-pyrimido [5, 4-b] [1, 4] oxazin-2-yl) amino)-3-(4-methyl-1H-imidazol-1-yl) picolinonitrile | >3 |

TABLE III-continued

Biological Assay

| Compound of Example | Structure | Name | Aβ42 H4 Prot Fre IC50 (μM) |
|---|---|---|---|
| 192B | 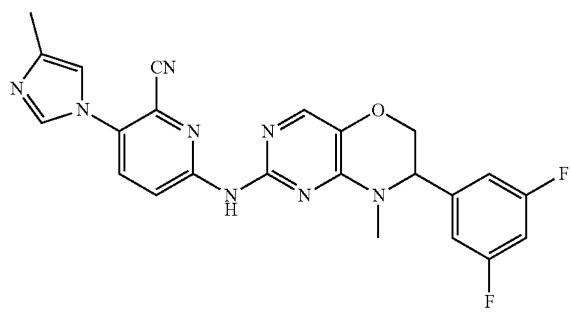 [SMILES: Cc1cn(-c2ccc(Nc3ncc4c(n3)N(C)C(c3cc(F)cc(F)c3)CO4)nc2C#N)cn1] | (+)-6-((7-(3, 5-difluorophenyl)-8-methyl-7, 8-dihydro-6H-pyrimido [5, 4-b] [1, 4] oxazin-2-yl) amino)-3-(4-methyl-1H-imidazol-1-yl) picolinonitrile | 0.576 |
| 193A | 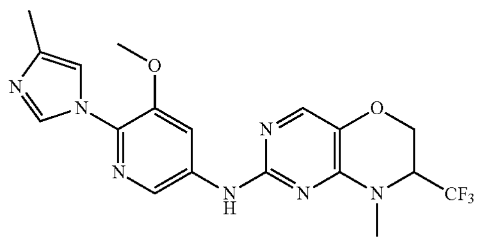 [SMILES: COc1cc(Nc2ncc3c(n2)N(C)C(C(F)(F)F)CO3)cnc1-n1cnc(C)c1] | (+)-N-(5-methoxy-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine | 0.908 |
| 193B | 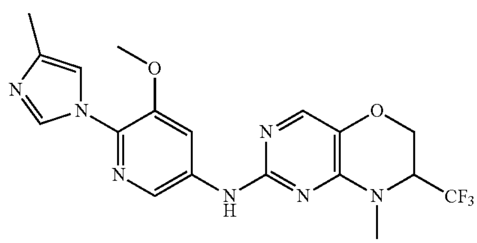 [SMILES: COc1cc(Nc2ncc3c(n2)N(C)C(C(F)(F)F)CO3)cnc1-n1cnc(C)c1] | (−)-N-(5-methoxy-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine | 0.035 |
| 194A | 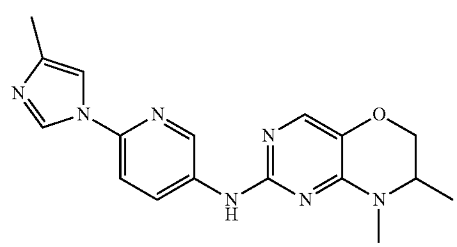 [SMILES: Cc1cn(-c2ccc(Nc3ncc4c(n3)N(C)C(C)CO4)cn2)cn1] | (+)-7, 8-dimethyl-N-(6-(4-methyl-1H-imidazol-1-yl) pyridin-3-yl)-7, 8-dihydro-6H-pyrimido [5, 4-b] [1, 4] oxazin-2-amine | 0.970 |
| 194B | 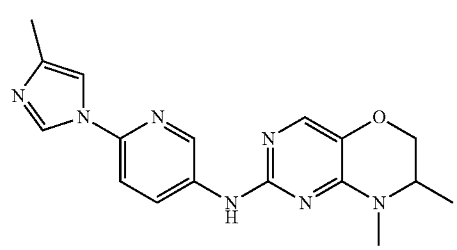 [SMILES: Cc1cn(-c2ccc(Nc3ncc4c(n3)N(C)C(C)CO4)cn2)cn1] | (−)-7, 8-dimethyl-N-(6-(4-methyl-1H-imidazol-1-yl) pyridin-3-yl)-7, 8-dihydro-6H-pyrimido [5, 4-b] [1, 4] oxazin-2-amine | >3 |

TABLE III-continued

Biological Assay

| Compound of Example | Structure | Name | Aβ42 H4 Prot Fre IC50 (µM) |
|---|---|---|---|
| 195 | 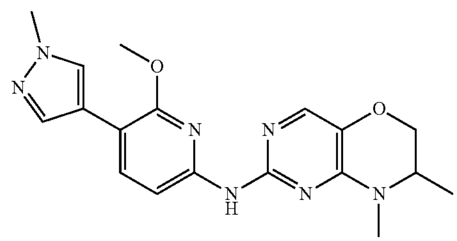 [SMILES: COc1nc(Nc2ncc3c(n2)N(C)C(C)CO3)ccc1-c1cnn(C)c1] | N-(6-methoxy-5-(1-methyl-1H-pyrazol-4-yl) pyridin-2-yl)-7, 8-dimethyl-7, 8-dihydro-6H-pyrimido [5, 4-b] [1, 4] oxazin-2-amine (racemic) | >3 |
| 196 | 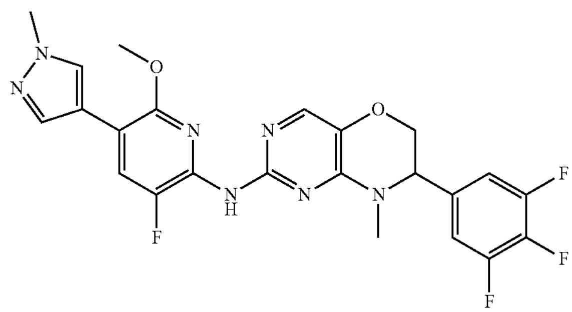 [SMILES: COc1nc(Nc2ncc3c(n2)N(C)C(c2cc(F)c(F)c(F)c2)CO3)c(F)cc1-c1cnn(C)c1] | N-(3-fluoro-6-methoxy-5-(1-methyl-1H-pyrazol-4-yl) pyridin-2-yl)-8-methyl-7-(3, 4, 5-trifluorophenyl)-7, 8-dihydro-6H-pyrimido [5, 4-b] [1, 4] oxazin-2-amine (racemic) | 0.544 |
| 197 | 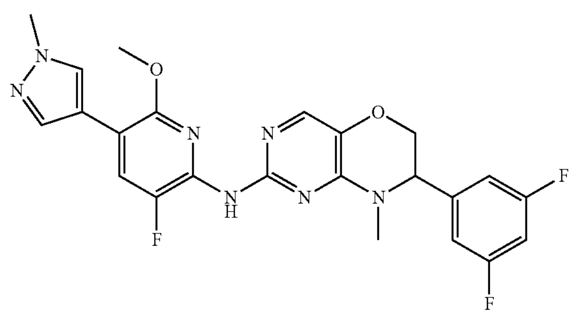 [SMILES: COc1nc(Nc2ncc3c(n2)N(C)C(c2cc(F)cc(F)c2)CO3)c(F)cc1-c1cnn(C)c1] | 7-(3, 5-difluorophenyl)-N-(3-fluoro-6-methoxy-5-(1-methyl-1H-pyrazol-4-yl) pyridin-2-yl)-8-methyl-7, 8-dihydro-6H-pyrimido [5, 4-b] [1, 4] oxazin-2-amine (racemic) | >3 |
| 198A | 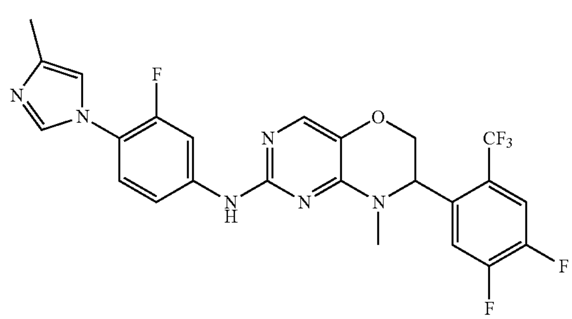 [SMILES: Cc1cn(-c2ccc(Nc3ncc4c(n3)N(C)C(c3cc(F)c(F)cc3C(F)(F)F)CO4)cc2F)cn1] | (−)-N-(5-methoxy-6-(4-methyl-1H-imidazol-1-yl) pyridin-3-yl)-7, 7, 8-trimethyl-7, 8-dihydro-6H-pyrimido [5, 4-b] [1, 4] oxazin-2-amine | 1.114 |

US 9,771,378 B2

889 890

TABLE III-continued

Biological Assay

| Compound of Example | Structure | Name | Aβ42 H4 Prot Fre IC50 (μM) |
|---|---|---|---|
| 198B | 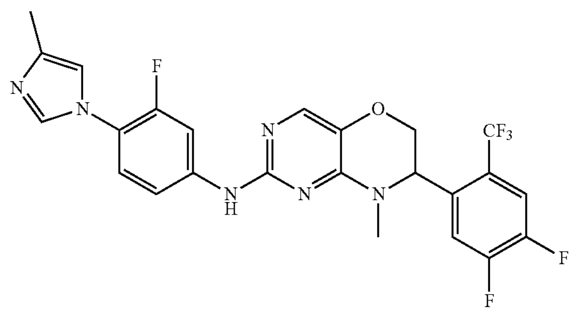 [SMILES: Cc1cn(-c2ccc(Nc3ncc4c(n3)N(C)C(c3cc(F)c(F)cc3C(F)(F)F)CO4)cc2F)cn1] | (+)-N-(5-methoxy-6-(4-methyl-1H-imidazol-1-yl) pyridin-3-yl)-7, 7, 8-trimethyl-7, 8-dihydro-6H-pyrimido? [5, 4-b] [1, 4] oxazin-2-amine | 0.101 |
| 199A | 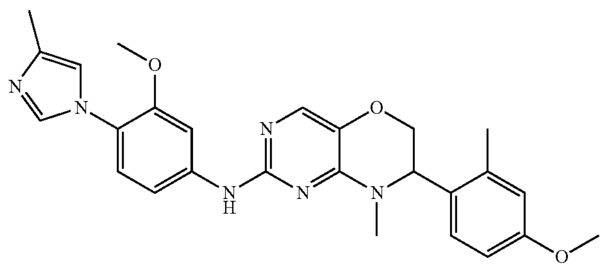 [SMILES: COc1ccc(C2COc3cnc(Nc4ccc(-n5cnc(C)c5)c(OC)c4)nc3N2C)c(C)c1] | (+)-7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.025 |
| 199B | 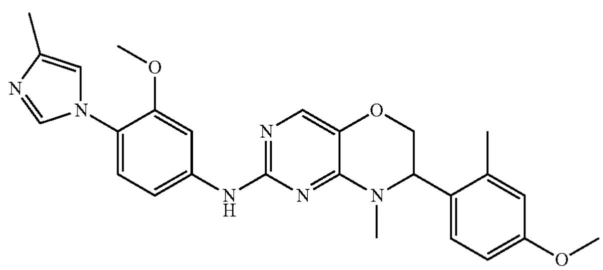 | (−)7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.095 |
| 200 | 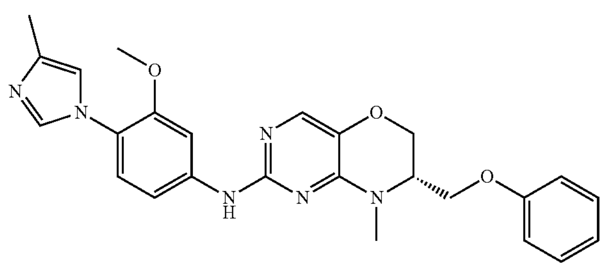 [SMILES: COc1cc(Nc2ncc3c(n2)N(C)[C@@H](COc2ccccc2)CO3)ccc1-n1cnc(C)c1] | (S)-N-(3-methoxy-4-(4-methyl-1H-imidazol-1-yl) phenyl)-8-methyl-7-(phenoxymethyl)-7, 8-dihydro-6H-pyrimido [5, 4-b] [1, 4] oxazin-2-amine | 0.030 |
| 201 | 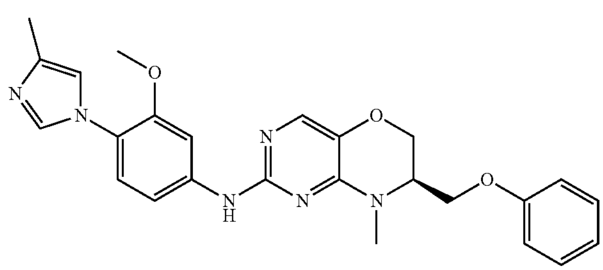 [SMILES: COc1cc(Nc2ncc3c(n2)N(C)[C@H](COc2ccccc2)CO3)ccc1-n1cnc(C)c1] | (R)-N-(3-methoxy-4-(4-methyl-1H-imidazol-1-yl) phenyl)-8-methyl-7-(phenoxymethyl)-7, 8-dihydro-6H-pyrimido [5, 4-b] [1, 4] oxazin-2-amine | 0.143 |

TABLE III-continued

Biological Assay

| Compound of Example | Structure | Name | Aβ42 H4 Prot Fre IC50 (μM) |
|---|---|---|---|
| 202A | 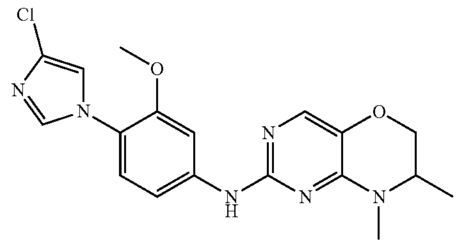 [SMILES: COc1cc(Nc2ncc3c(n2)N(C)C(C)CO3)ccc1-n1cnc(Cl)c1] | (−)-N-(4-(4-chloro-1H-imidazol-1-yl)-3-methoxyphenyl)-7, 8-dimethyl-7, 8-dihydro-6H-pyrimido [5, 4-b] [1, 4] oxazin-2-amine | 0.167 |
| 202B | 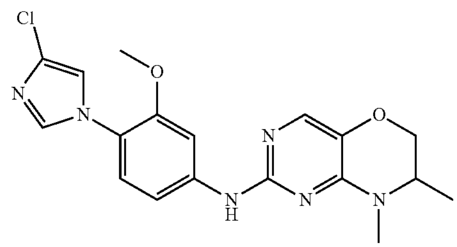 [SMILES: COc1cc(Nc2ncc3c(n2)N(C)C(C)CO3)ccc1-n1cnc(Cl)c1] | (+)-N-(4-(4-chloro-1H-imidazol-1-yl)-3-methoxyphenyl)-7, 8-dimethyl-7, 8-dihydro-6H-pyrimido [5, 4-b] [1, 4] oxazin-2-amine | 0.063 |
| 203A | 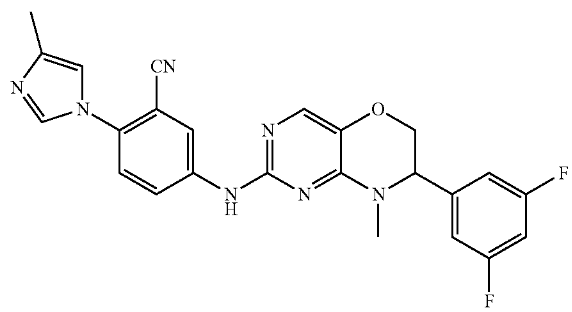 [SMILES: Cc1cn(-c2ccc(Nc3ncc4c(n3)N(C)C(c3cc(F)cc(F)c3)CO4)cc2C#N)cn1] | (+)-5-((7-(3, 5-difluorophenyl)-8-methyl-7, 8-dihydro-6H-pyrimido [5, 4-b] [1, 4] oxazin-2-yl) amino)-2-(4-methyl-1H-imidazol-1-yl) benzonitrile | 0.016 |
| 203B | 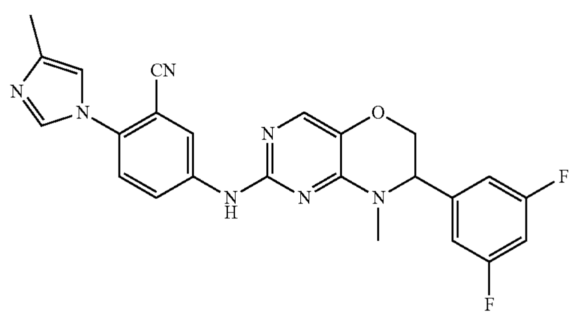 [SMILES: Cc1cn(-c2ccc(Nc3ncc4c(n3)N(C)C(c3cc(F)cc(F)c3)CO4)cc2C#N)cn1] | (−)-5-((7-(3, 5-difluorophenyl)-8-methyl-7, 8-dihydro-6H-pyrimido [5, 4-b] [1, 4] oxazin-2-yl) amino)-2-(4-methyl-1H-imidazol-1-yl) benzonitrile | 0.210 |
| 204A | 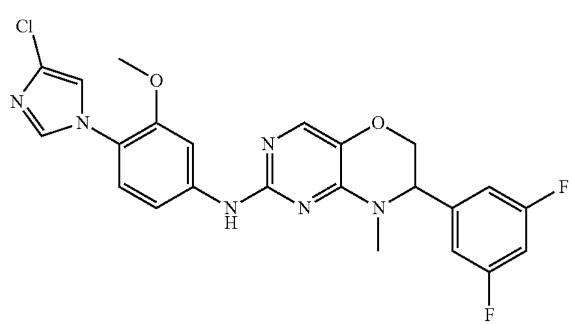 [SMILES: COc1cc(Nc2ncc3c(n2)N(C)C(c2cc(F)cc(F)c2)CO3)ccc1-n1cnc(Cl)c1] | (−)-N-(4-(4-chloro-1H-imidazol-1-yl)-3-methoxyphenyl)-7-(3, 5-difluorophenyl)-8-methyl-7, 8-dihydro-6H-pyrimido [5, 4-b] [1, 4] oxazin-2-amine | 0.433 |

TABLE III-continued

Biological Assay

| Compound of Example | Structure | Name | Aβ42 H4 Prot Fre IC50 (μM) |
|---|---|---|---|
| 204B | 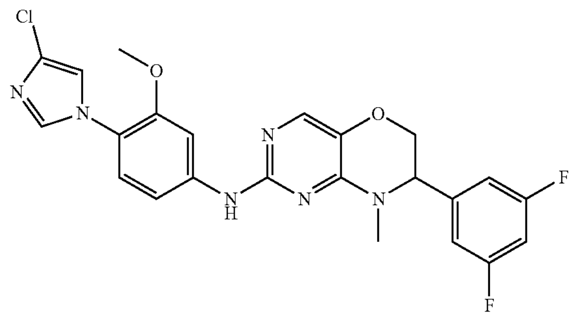 [SMILES: COc1cc(Nc2ncc3c(n2)N(C)C(c2cc(F)cc(F)c2)CO3)ccc1-n1cnc(Cl)c1] | (+)-N-(4-(4-chloro-1H-imidazol-1-yl)-3-methoxyphenyl)-7-(3, 5-difluorophenyl)-8-methyl-7, 8-dihydro-6H-pyrimido [5, 4-b] [1, 4] oxazin-2-amine | 0.019 |
| 205A | 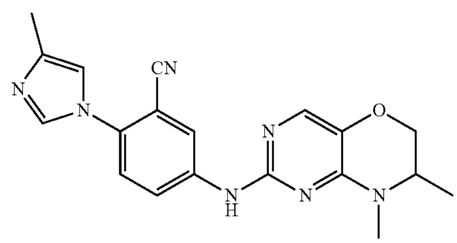 [SMILES: Cc1cn(-c2ccc(Nc3ncc4c(n3)N(C)C(C)CO4)cc2C#N)cn1] | (+)-5-((7, 8-dimethyl-7, 8-dihydro-6H-pyrimido [5, 4-b] [1, 4] oxazin-2-yl) amino)-2-(4-methyl-1H-imidazol-1-yl) benzonitrile | 0.231 |
| 205B | 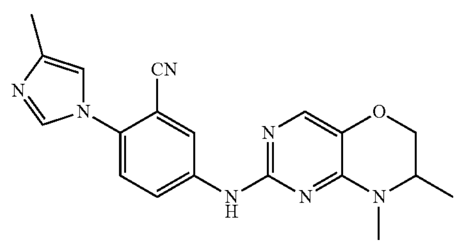 [SMILES: Cc1cn(-c2ccc(Nc3ncc4c(n3)N(C)C(C)CO4)cc2C#N)cn1] | (−)-5-((7, 8-dimethyl-7, 8-dihydro-6H-pyrimido [5, 4-b] [1, 4] oxazin-2-yl) amino)-2-(4-methyl-1H-imidazol-1-yl) benzonitrile | 0.259 |
| 206A | 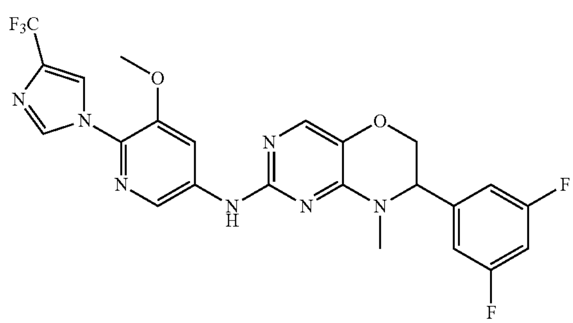 [SMILES: COc1cc(Nc2ncc3c(n2)N(C)C(c2cc(F)cc(F)c2)CO3)cnc1-n1cnc(C(F)(F)F)c1] | (+)-7-(3, 5-difluorophenyl)-N-(5-methoxy-6-(4-(trifluoromethyl)-1H-imidazol-1-yl) pyridin-3-yl)-8-methyl-7, 8-dihydro-6H-pyrimido [5, 4-b] [1, 4] oxazin-2-amine | 0.027 |
| 206B | 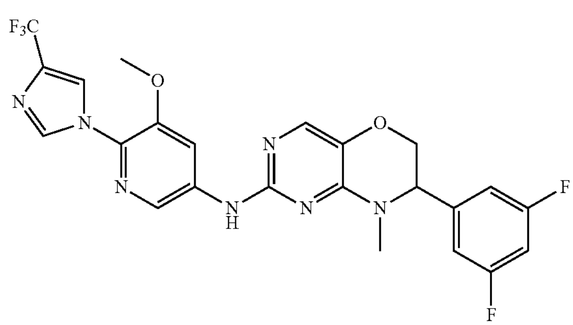 [SMILES: COc1cc(Nc2ncc3c(n2)N(C)C(c2cc(F)cc(F)c2)CO3)cnc1-n1cnc(C(F)(F)F)c1] | (−)-7-(3, 5-difluorophenyl)-N-(5-methoxy-6-(4-(trifluoromethyl)-1H-imidazol-1-yl) pyridin-3-yl)-8-methyl-7, 8-dihydro-6H-pyrimido [5, 4-b] [1, 4] oxazin-2-amine | 0.704 |

TABLE III-continued

Biological Assay

| Compound of Example | Structure | Name | Aβ42 H4 Prot Fre IC50 (μM) |
|---|---|---|---|
| 207A | 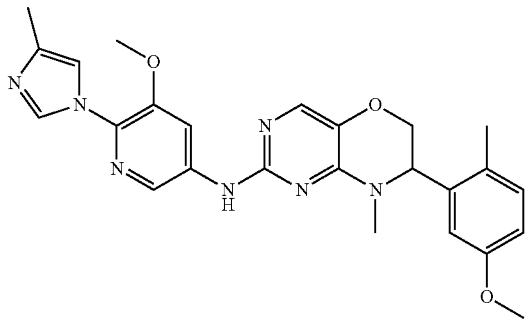 [SMILES: COc1ccc(C)c(C2COc3cnc(Nc4cnc(-n5cnc(C)c5)c(OC)c4)nc3N2C)c1] | (+)-7-(5-methoxy-2-methylphenyl)-N-(5-methoxy-6-(4-methyl-1H-imidazol-1-yl)pyridin-3-yl)-8-methyl-7,8-dihydro-6H-pyrimido[5,4-b][1,4]oxazin-2-amine | 0.010 |
| 207B | 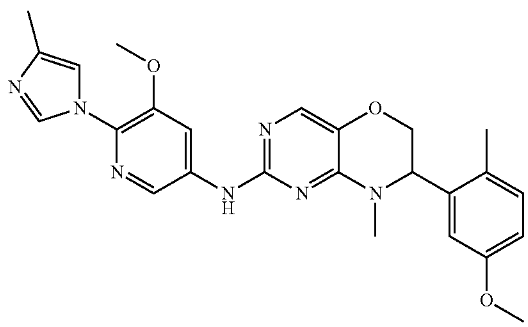 [SMILES: COc1ccc(C)c(C2COc3cnc(Nc4cnc(-n5cnc(C)c5)c(OC)c4)nc3N2C)c1] | (−)-7-(5-methoxy-2-methylphenyl)-N-(5-methoxy-6-(4-methyl-1H-imidazol-1-yl)pyridin-3-yl)-8-methyl-7,8-dihydro-6H-pyrimido[5,4-b][1,4]oxazin-2-amine | 0.096 |
| 208A | 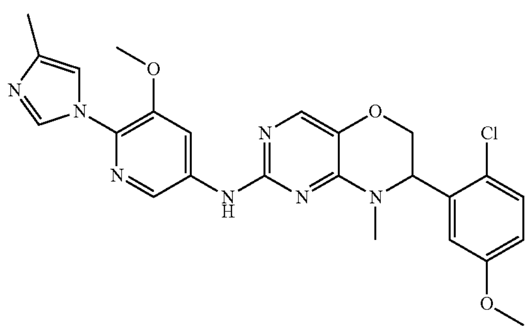 [SMILES: COc1ccc(Cl)c(C2COc3cnc(Nc4cnc(-n5cnc(C)c5)c(OC)c4)nc3N2C)c1] | (+)-7-(2-chloro-5-methoxyphenyl)-N-(5-methoxy-6-(4-methyl-1H-imidazol-1-yl)pyridin-3-yl)-8-methyl-7,8-dihydro-6H-pyrimido[5,4-b][1,4]oxazin-2-amine | 0.020 |
| 208B | 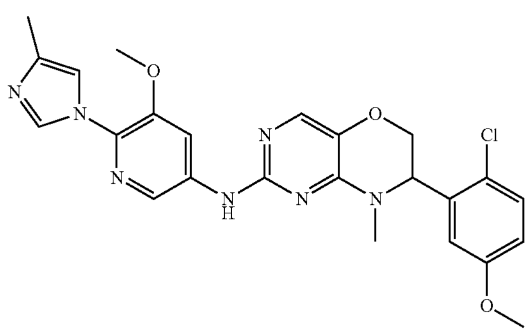 | (−)-7-(2-chloro-5-methoxyphenyl)-N-(5-methoxy-6-(4-methyl-1H-imidazol-1-yl)pyridin-3-yl)-8-methyl-7,8-dihydro-6H-pyrimido[5,4-b][1,4]oxazin-2-amine | 0.136 |

TABLE III-continued

Biological Assay

| Compound of Example | Structure | Name | Aβ42 H4 Prot Fre IC50 (μM) |
|---|---|---|---|
| 209A | 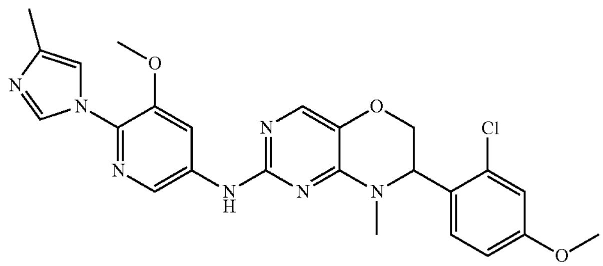 [SMILES: COc1ccc(C2COc3cnc(Nc4cnc(-n5cnc(C)c5)c(OC)c4)nc3N2C)c(Cl)c1] | (+)-7-(2-chloro-4-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine | 0.021 |
| 209B | 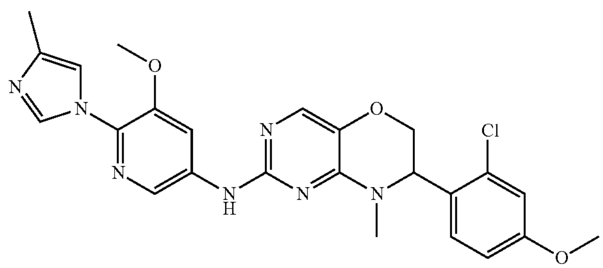 [SMILES: COc1ccc(C2COc3cnc(Nc4cnc(-n5cnc(C)c5)c(OC)c4)nc3N2C)c(Cl)c1] | (−)-7-(2-chloro-4-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine | 0.055 |
| 210A | 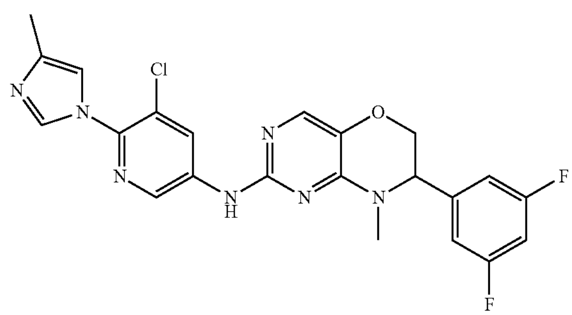 | (+)-N-(5-chloro-6-(4-methyl-1H-imidazol-1-yl) pyridin-3-yl)-7-(3, 5-difluorophenyl)-8-methyl-7, 8-dihydro-6H-pyrimido [5, 4-b] [1, 4] oxazin-2-amine | 0.041 |
| 210B | 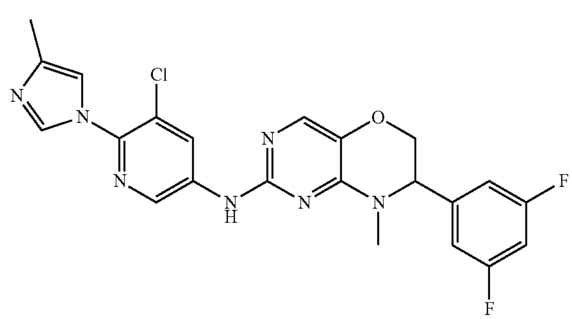 [SMILES: Cc1cn(-c2ncc(Nc3ncc4c(n3)N(C)C(c3cc(F)cc(F)c3)CO4)cc2Cl)cn1] | (−)-N-(5-chloro-6-(4-methyl-1H-imidazol-1-yl) pyridin-3-yl)-7-(3, 5-difluorophenyl)-8-methyl-7, 8-dihydro-6H-pyrimido [5, 4-b] [1, 4] oxazin-2-amine | 2.342 |

TABLE III-continued

Biological Assay

| Compound of Example | Structure | Name | Aβ42 H4 Prot Fre IC50 (μM) |
|---|---|---|---|
| 211A | 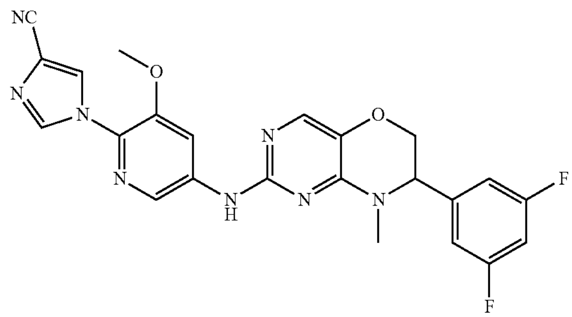 [SMILES: COc1cc(Nc2ncc3c(n2)N(C)C(c2cc(F)cc(F)c2)CO3)cnc1-n1cnc(C#N)c1] | (+)-1-(5-((7-(3, 5-difluorophenyl)-8-methyl-7, 8-dihydro-6H-pyrimido [5, 4-b] [1, 4] oxazin-2-yl) amino)-3-methoxypyridin-2-yl)-1H-imidazole-4-carbonitrile | 0.179 |
| 211B | 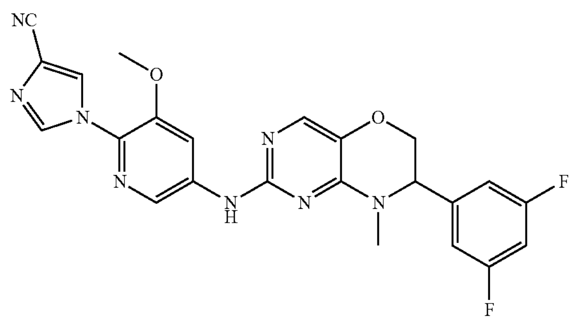 [SMILES: COc1cc(Nc2ncc3c(n2)N(C)C(c2cc(F)cc(F)c2)CO3)cnc1-n1cnc(C#N)c1] | (−)-1-(5-((7-(3, 5-difluorophenyl)-8-methyl-7, 8-dihydro-6H-pyrimido [5, 4-b] [1, 4] oxazin-2-yl) amino)-3-methoxypyridin-2-yl)-1H-imidazole-4-carbonitrile | >3 |
| 212A | 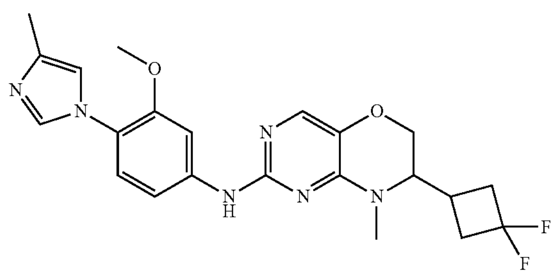 [SMILES: COc1cc(Nc2ncc3c(n2)N(C)C(C2CC(F)(F)C2)CO3)ccc1-n1cnc(C)c1] | (−)-7-(3, 3-difluorocyclobutyl)-N-(3-methoxy-4-(4-methyl- 1H-imidazol-1-yl) phenyl)-8-methyl-7, 8-dihydro-6H-pyrimido [5, 4-b] [1, 4] oxazin-2-amine | 0.348 |
| 212B | 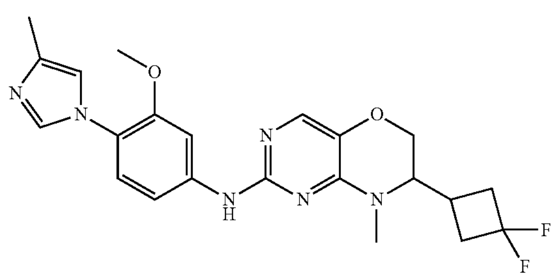 [SMILES: COc1cc(Nc2ncc3c(n2)N(C)C(C2CC(F)(F)C2)CO3)ccc1-n1cnc(C)c1] | (+)-7-(3, 3-difluorocyclobutyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.061 |
| 213A | 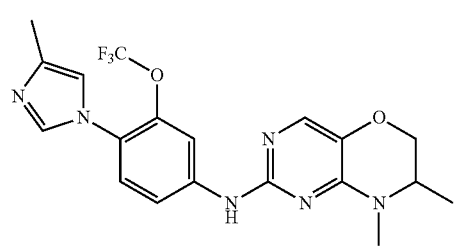 [SMILES: Cc1cn(-c2ccc(Nc3ncc4c(n3)N(C)C(C)CO4)cc2OC(F)(F)F)cn1] | (−)-7, 8-dimethyl-N-(4-(4-methyl- 1H-imidazol-1-yl)-3-(trifluoromethoxy) phenyl)-7, 8-dihydro-6H-pyrimido [5, 4-b] [1, 4] oxazin-2-amine | >3 |

TABLE III-continued

Biological Assay

| Compound of Example | Structure | Name | Aβ42 H4 Prot Fre IC50 (μM) |
|---|---|---|---|
| 213B | 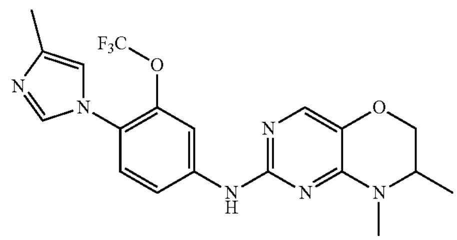 [SMILES: Cc1cn(-c2ccc(Nc3ncc4c(n3)N(C)C(C)CO4)cc2OC(F)(F)F)cn1] | (+)-7, 8-dimethyl-N-(4-(4-methyl-1H-imidazol-1-yl)-3-(trifluoromethoxy)phenyl)-7, 8-dihydro-6H-pyrimido [5, 4-b][1, 4] oxazin-2-amine | >3 |
| 214A | 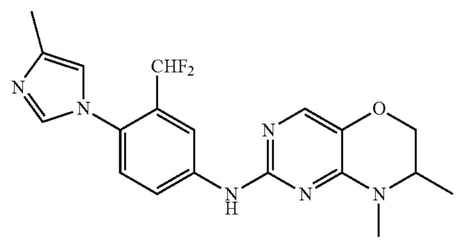 [SMILES: Cc1cn(-c2ccc(Nc3ncc4c(n3)N(C)C(C)CO4)cc2C(F)F)cn1] | (+)-N-(3-(difluoromethyl)-4-(4-methyl-1H-imidazol-1-yl) phenyl)-7, 8-dimethyl-7, 8-dihydro-6H-pyrimido [5, 4-b][1, 4] oxazin-2-amine | >3 |
| 214B | 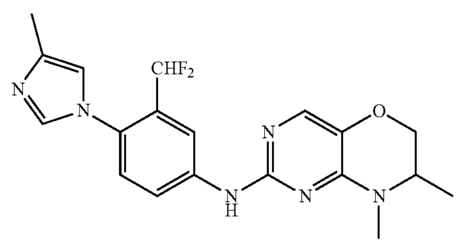 | (−)-N-(3-(difluoromethyl)-4-(4-methyl-1H-imidazol-1-yl) phenyl)-7, 8-dimethyl-7, 8-dihydro-6H-pyrimido [5, 4-b][1, 4] oxazin-2-amine | 2.255 |
| 215A | 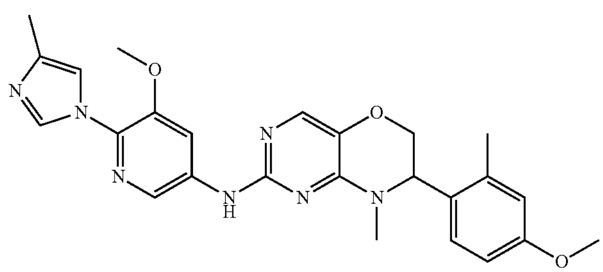 [SMILES: COc1ccc(C2COc3cnc(Nc4cnc(-n5cnc(C)c5)c(OC)c4)nc3N2C)c(C)c1] | (+)-7-(4-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine | 0.016 |
| 215B | 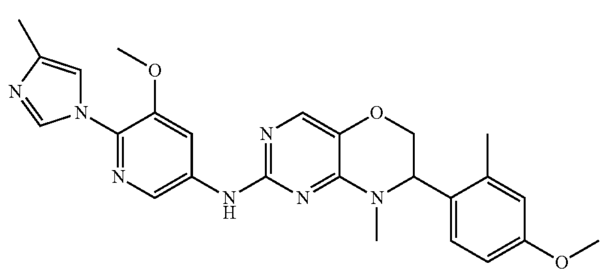 | (−)-7-(4-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine | 0.096 |

TABLE III-continued

Biological Assay

| Compound of Example | Structure | Name | Aβ42 H4 Prot Fre IC50 (μM) |
|---|---|---|---|
| 216A | 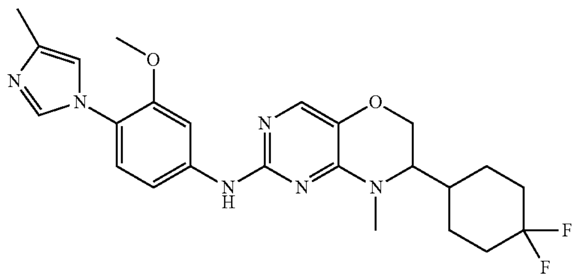 | (−)-7-(4, 4-difluorocyclohexyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.320 |
| 216B | 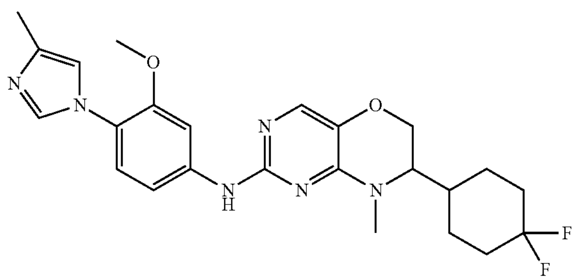 | (+)-7-(4, 4-difluorocyclohexyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.033 |
| 217 | 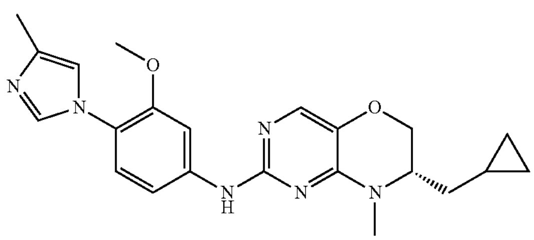 [SMILES: COc1cc(Nc2ncc3c(n2)N(C)[C@@H](CC2CC2)CO3)ccc1-n1cnc(C)c1] | (S)-7-(cyclopropylmethyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.053 |
| 218 | 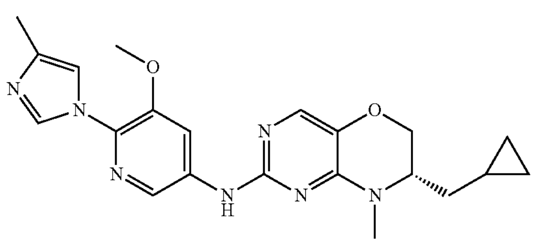 | (S)-7-(cyclopropylmethyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine | 0.039 |
| 219A | 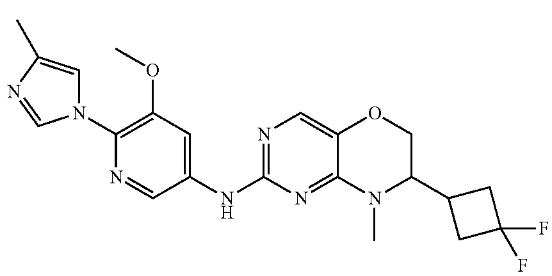 | (+)-7-(3, 3-difluorocyclobutyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine | 0.025 |

TABLE III-continued

Biological Assay

| Compound of Example | Structure | Name | Aβ42 H4 Prot Fre IC50 (μM) |
|---|---|---|---|
| 219B | 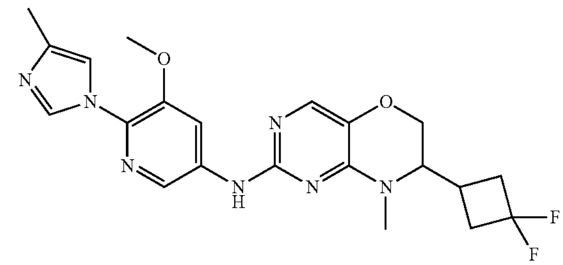 | (−)-7-(3, 3-difluorocyclobutyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine | 0.398 |
| 220A | 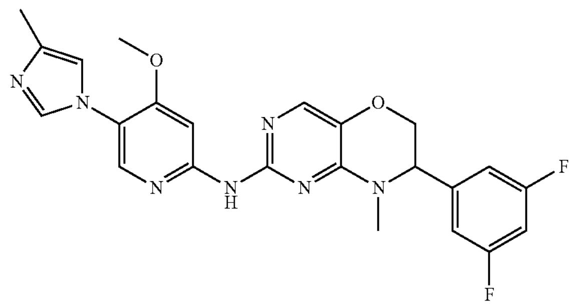 [SMILES: COc1cc(Nc2ncc3c(n2)N(C)C(c2cc(F)cc(F)c2)CO3)ncc1-n1cnc(C)c1] | (−)-7-(3, 5-difluorophenyl)-N-(4-methoxy-5-(4-methyl-1H-imidazol-1-yl) pyridin-2-yl)-8-methyl-7, 8-dihydro-6H-pyrimido [5, 4-b] [1, 4] oxazin-2-amine | >3 |
| 220B | 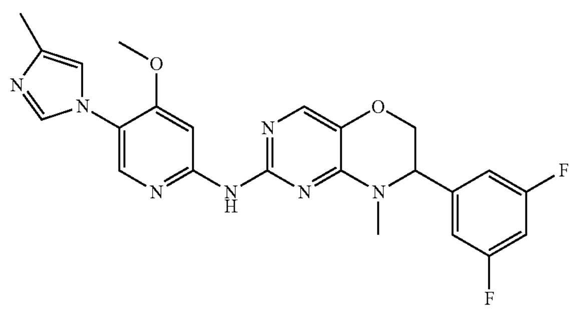 [SMILES: COc1cc(Nc2ncc3c(n2)N(C)C(c2cc(F)cc(F)c2)CO3)ncc1-n1cnc(C)c1] | (+)-7-(3, 5-difluorophenyl)-N-(4-methoxy-5-(4-methyl-1H-imidazol-1-yl) pyridin-2-yl)-8-methyl-7, 8-dihydro-6H-pyrimido [5, 4-b] [1, 4] oxazin-2-amine | 0.044 |
| 221A | 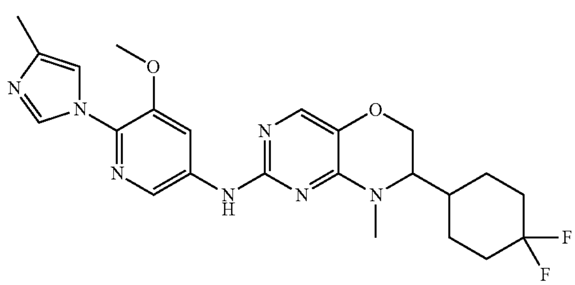 | (+)-7-(4, 4-difluorocyclohexyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine | 0.024 |
| 221B | 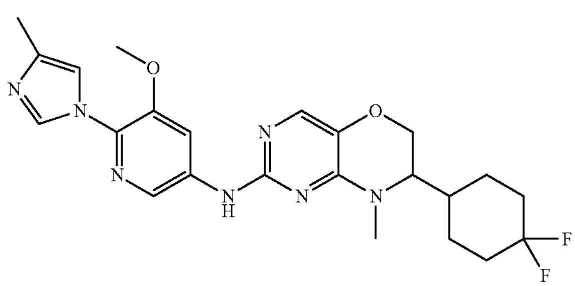 [SMILES: COc1cc(Nc2ncc3c(n2)N(C)C(C2CCC(F)(F)CC2)CO3)cnc1-n1cnc(C)c1] | (−)-7-(4, 4-difluorocyclohexyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine | 0.325 |

TABLE III-continued

Biological Assay

| Compound of Example | Structure | Name | Aβ42 H4 Prot Fre IC50 (μM) |
|---|---|---|---|
| 222A | 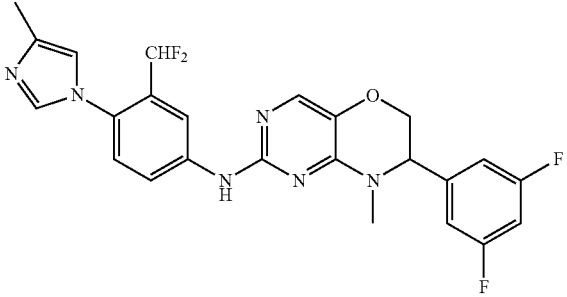 [SMILES: Cc1cn(-c2ccc(Nc3ncc4c(n3)N(C)C(c3cc(F)cc(F)c3)CO4)cc2OC(F)(F)F)cn1] | (+)-N-(3-(difluoromethyl)-4-(4-methyl-1H-imidazol-1-yl) phenyl)-7-(3, 5-difluorophenyl)-8-methyl-7, 8-dihydro-6H-pyrimido [5, 4-b] [1, 4] oxazin-2-amine | 0.361 |
| 222B | 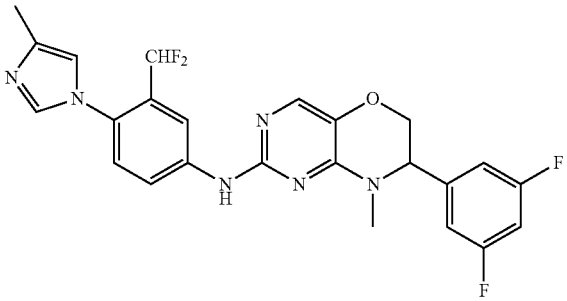 | (−)-N-(3-(difluoromethyl)-4-(4-methyl-1H-imidazol-1-yl) phenyl)-7-(3, 5-difluorophenyl)-8-methyl-7, 8-dihydro-6H-pyrimido [5, 4-b] [1, 4] oxazin-2-amine | >3 |
| 223A | 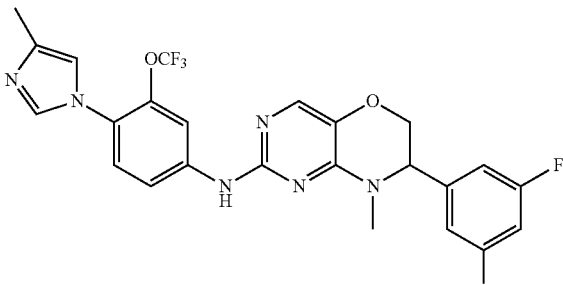 | (−)-7-(3, 5-difluorophenyl)-8-methyl-N-(4-(4-methyl-1H-imidazol-1-yl)-3-(trifluoromethoxy) phenyl)-7, 8-dihydro-6H-pyrimido [5, 4-b] [1, 4] oxazin-2-amine | >3 |
| 223B | 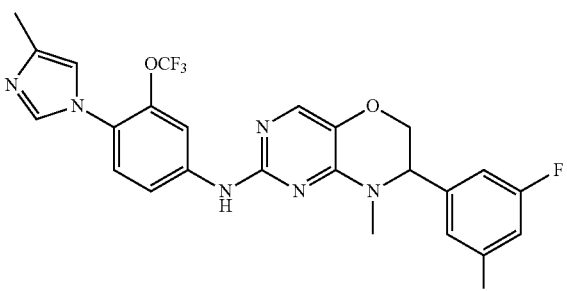 | (+)-7-(3, 5-difluorophenyl)-8-methyl-N-(4-(4-methyl-1H-imidazol-1-yl)-3-(trifluoromethoxy) phenyl)-7, 8-dihydro-6H-pyrimido [5, 4-b] [1, 4] oxazin-2-amine | >3 |
| 224 | 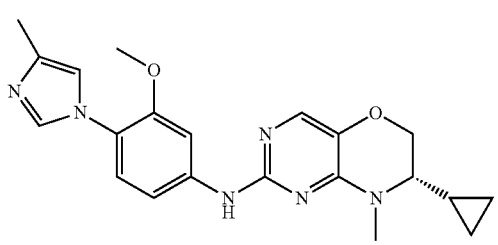 | (S)-7-cyclopropyl-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.022 |

TABLE III-continued

Biological Assay

| Compound of Example | Structure | Name | Aβ42 H4 Prot Fre IC50 (μM) |
|---|---|---|---|
| 225 | 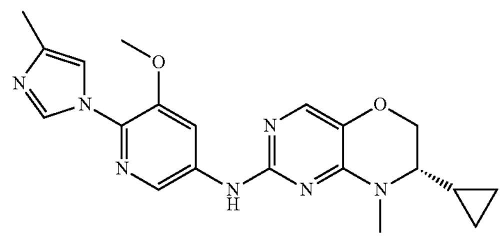 [SMILES: COc1cc(Nc2ncc3c(n2)N(C)[C@@H](C2CC2)CO3)ccc1-n1cnc(C)c1] | (S)-7-cyclopropyl-N-(5-methoxy-6-(4-methyl-1H-imidazol-1-yl)pyridin-3-yl)-8-methyl-7,8-dihydro-6H-pyrimido [5, 4-b] [1, 4] oxazin-2-amine | 0.033 |
| 226A | 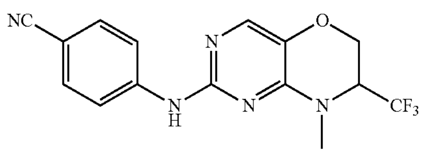 [SMILES: CN1c2nc(Nc3ccc(C#N)cc3)ncc2OCC1C(F)(F)F] | (+)-4-((8-methyl-7-(trifluoromethyl)-7, 8-dihydro-6H-pyrimido [5, 4-b] [1, 4] oxazin-2-yl) amino) benzonitrile | >3 |
| 226B | 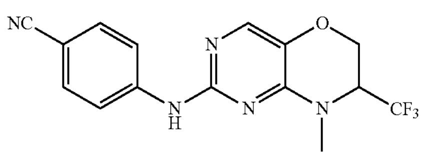 [SMILES: CN1c2nc(Nc3ccc(C#N)cc3)ncc2OCC1C(F)(F)F] | (−)-4-((8-methyl-7-(trifluoromethyl)-7, 8-dihydro-6H-pyrimido [5, 4-b] [1, 4] oxazin-2-yl) amino) benzonitrile | >3 |
| 227 | 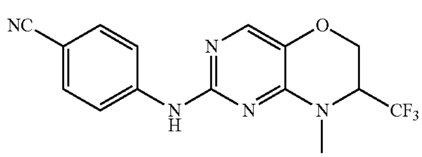 [SMILES: CN1c2nc(Nc3ccc(C#N)cc3)ncc2OCC1C(F)(F)F] | (S)-7-cyclobutyl-N-(3-methoxy-4-(4-methyl-1H-imidazol-1-yl)phenyl)-8-methyl-7, 8-dihydro-6H-pyrimido 5, 4-b] [1, 4] oxazin-2-amine | 0.019 |
| 228A | 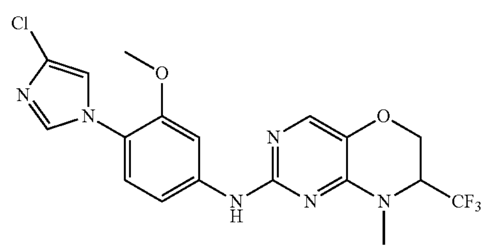 [SMILES: COc1cc(Nc2ncc3c(n2)N(C)C(C(F)(F)F)CO3)ccc1-n1cnc(Cl)c1] | (+)-N-(4-(4-chloro-1H-imidazol-1-yl)-3-methoxyphenyl)-8-methyl-7-(trifluoromethyl)-7, 8-dihydro-6H-pyrimido [5, 4-b] [1, 4] oxazin-2-amine | 0.331 |
| 228B | 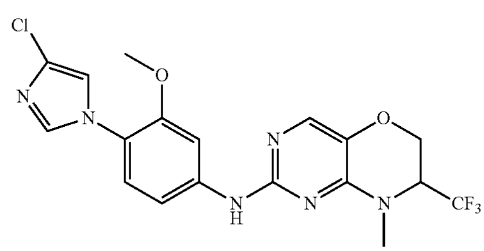 [SMILES: COc1cc(Nc2ncc3c(n2)N(C)C(C(F)(F)F)CO3)ccc1-n1cnc(Cl)c1] | (−)-N-(4-(4-chloro-1H-imidazol-1-yl)-3-methoxyphenyl)-8-methyl-7-(trifluoromethyl)-7, 8-dihydro-6H-pyrimido [5, 4-b] [1, 4] oxazin-2-amine | 0.014 |
| 229A | 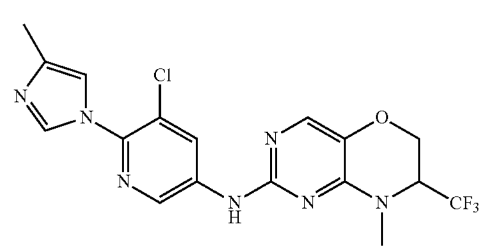 [SMILES: Cc1cn(-c2ncc(Nc3ncc4c(n3)N(C)C(C(F)(F)F)CO4)cc2Cl)cn1] | (−)-N-(5-chloro-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine | 0.215 |

TABLE III-continued

Biological Assay

| Compound of Example | Structure | Name | Aβ42 H4 Prot Fre IC50 (μM) |
|---|---|---|---|
| 229B | 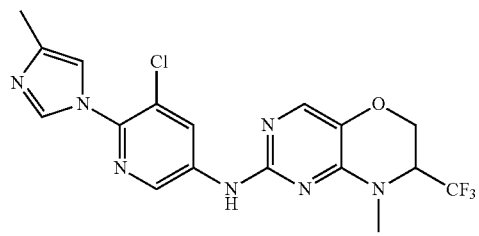 [SMILES: Cc1cn(-c2ncc(Nc3ncc4c(n3)N(C)C(C(F)(F)F)CO4)cc2Cl)cn1] | (+)-N-(5-chloro-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine | 2.848 |
| 230A | 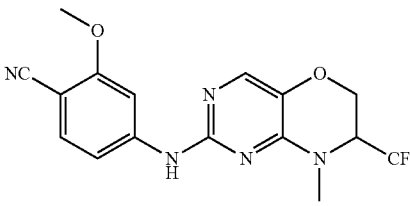 | (+)-2-methoxy-4-((8-methyl-7-?-(trifluoromethyl)-7, 8-dihydro-6H-pyrimido [5, 4-b] [1, 4] oxazin-2-yl) amino) benzonitrile | >3 |
| 230B | 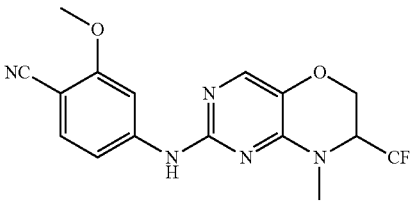 | (−)-2-methoxy-4-((8-methyl-7-(trifluoromethyl)-7, 8-dihydro-6H-pyrimido [5, 4-b] [1, 4] oxazin-2-yl) amino) benzonitrile | 0.717 |
| 231A | 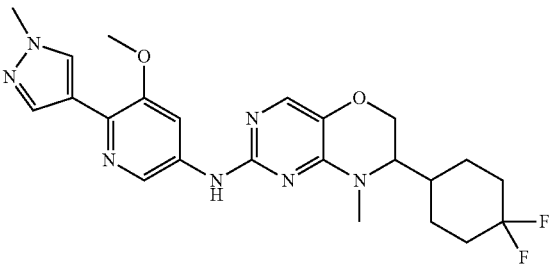 [SMILES: COc1cc(Nc2ncc3c(n2)N(C)C(C2CCC(F)(F)CC2)CO3)cnc1-c1cnn(C)c1] | (+)-7-(4, 4-difluorocyclohexyl)-N-(5-methoxy-6-(1-methyl-1H-pyrazol-4-yl) pyridin-3-yl)-8-methyl-7, 8-dihydro-6H-pyrimido [5, 4-b] [1, 4] oxazin-2-amine | 0.342 |
| 231B | 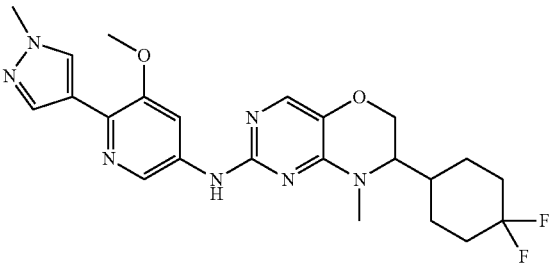 [SMILES: COc1cc(Nc2ncc3c(n2)N(C)C(C2CCC(F)(F)CC2)CO3)cnc1-c1cnn(C)c1] | (−)-7-(4, 4-difluorocyclohexyl)-N-(5-methoxy-6-(1-methyl-1H-pyrazol-4-yl) pyridin-3-yl)-8-methyl-7, 8-dihydro-6H-pyrimido [5, 4-b] [1, 4] oxazin-2-amine | >3 |
| 232A | 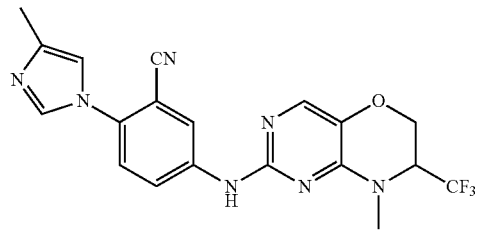 [SMILES: Cc1cn(-c2ccc(Nc3ncc4c(n3)N(C)C(C(F)(F)F)CO4)cc2C#N)cn1] | (+)-2-(4-methyl-1H-imidazol-1-yl)-5-((8-methyl-7-(trifluoromethyl)-7, 8-dihydro-6H-pyrimido [5, 4-b] [1, 4] oxazin-2-yl) amino) benzonitrile | 0.280 |

TABLE III-continued

Biological Assay

| Compound of Example | Structure | Name | Aβ42 H4 Prot Fre IC50 (μM) |
|---|---|---|---|
| 232B | 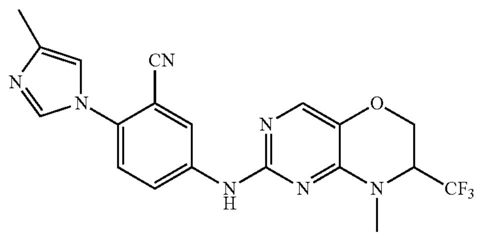 [SMILES: Cc1cn(-c2ccc(Nc3ncc4c(n3)N(C)C(C(F)(F)F)CO4)cc2C#N)cn1] | (−)-2-(4-methyl-1H-imidazol-1-yl)-5-((8-methyl-7-(trifluoromethyl)-7, 8-dihydro-6H-pyrimido [5, 4-b] [1, 4] oxazin-2-yl) amino) benzonitrile | 0.017 |
| 233A | 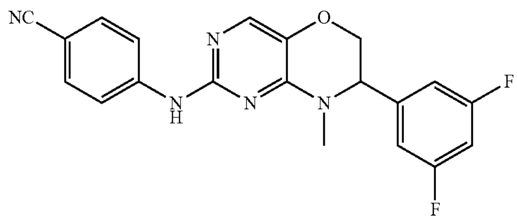 [SMILES: CN1c2nc(Nc3ccc(C#N)cc3)ncc2OCC1c1cc(F)cc(F)c1] | (+)-4-((7-(3, 5-difluorophenyl)-8-methyl-7, 8-dihydro-6H-pyrimido [5, 4-b] [1, 4] oxazin-2-yl) amino) benzonitrile | 0.888 |
| 233B | 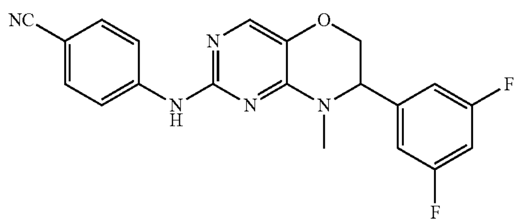 [SMILES: CN1c2nc(Nc3ccc(C#N)cc3)ncc2OCC1c1cc(F)cc(F)c1] | (−)-4-((7-(3, 5-difluorophenyl)-8-methyl-7, 8-dihydro-6H-pyrimido [5, 4-b] [1, 4] oxazin-2-yl) amino) benzonitrile | >3 |
| 234 | 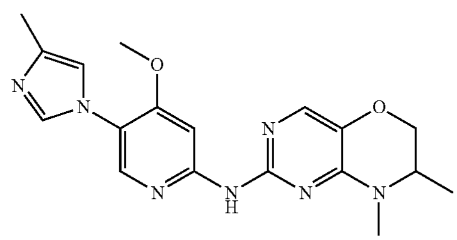 [SMILES: COc1cc(Nc2ncc3c(n2)N(C)C(C)CO3)ncc1-n1cnc(C)c1] | N-(4-methoxy-5-(4-methyl-1H-imidazol-1-yl) pyridin-2-yl)-7, 8-dimethyl-7, 8-dihydro-6H-pyrimido [5, 4-b] [1, 4] oxazin-2-amine (racemic) | 1.771 |
| 235 | 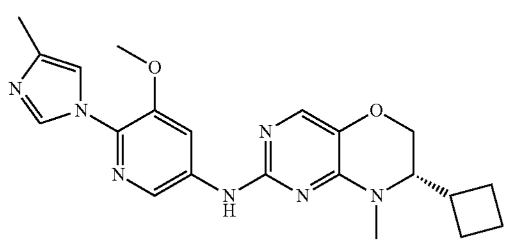 [SMILES: COc1cc(Nc2ncc3c(n2)N(C)[C@@H](C2CCC2)CO3)cnc1-n1cnc(C)c1] | (S)-7-cyclobutyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine | 0.017 |
| 236A | 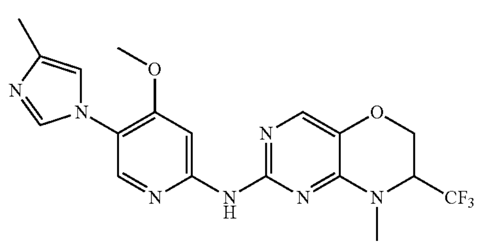 [SMILES: COc1cc(Nc2ncc3c(n2)N(C)C(C(F)(F)F)CO3)ncc1-n1cnc(C)c1] | (+)-N-(4-methoxy-5-(4-methyl-1H-imidazol-1-yl) pyridin-2-yl)-8-methyl-7-(trifluoromethyl)-7, 8-dihydro-6H-pyrimido [5, 4-b] [1, 4] oxazin-2-amine | >3 |

TABLE III-continued

Biological Assay

| Compound of Example | Structure | Name | Aβ42 H4 Prot Fre IC50 (μM) |
|---|---|---|---|
| 236B | 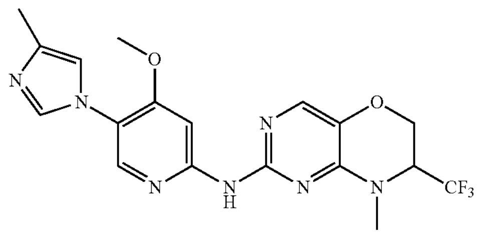 [SMILES: COc1cc(Nc2ncc3c(n2)N(C)C(C(F)(F)F)CO3)ncc1-n1cnc(C)c1] | (−)-N-(4-methoxy-5-(4-methyl-1H-imidazol-1-yl) pyridin-2-yl)-8-methyl-7-(trifluoromethyl)-7, 8-dihydro-6H-pyrimido [5, 4-b] [1, 4] oxazin-2-amine | 0.245 |
| 237A | 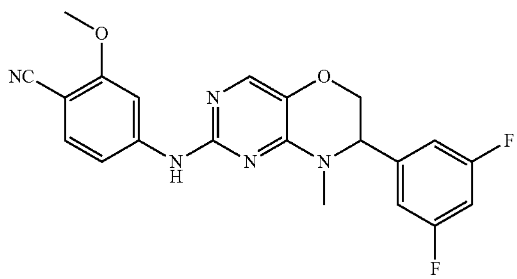 [SMILES: COc1cc(Nc2ncc3c(n2)N(C)C(c2cc(F)cc(F)c2)CO3)ccc1C#N] | (−)-4-((7-(3, 5-difluorophenyl)-8-methyl-7, 8-dihydro-6H-pyrimido [5, 4-b] [1, 4] oxazin-2-yl) amino)-2-methoxybenzonitrile | >3 |
| 237B | 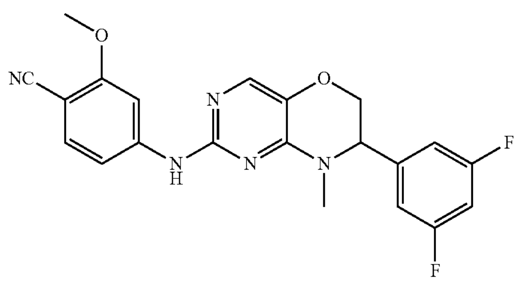 [SMILES: COc1cc(Nc2ncc3c(n2)N(C)C(c2cc(F)cc(F)c2)CO3)ccc1C#N] | (+)-4-((7-(3, 5-difluorophenyl)-8-methyl-7, 8-dihydro-6H-pyrimido [5, 4-b] [1, 4] oxazin-2-yl) amino)-2-methoxybenzonitrile | 0.226 |
| 238A | 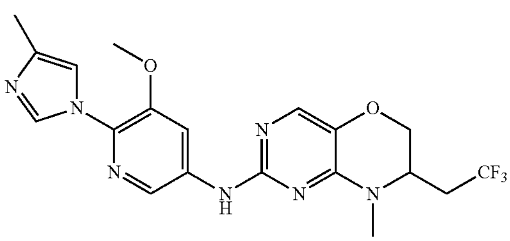 [SMILES: COc1cc(Nc2ncc3c(n2)N(C)C(CC(F)(F)F)CO3)cnc1-n1cnc(C)c1] | (−)-N-(5-methoxy-6-(4-methyl-1H-imidazol-1-yl) pyridin-3-yl)-8-methyl-7-(2, 2, 2-trifluoroethyl)-7, 8-dihydro-6H-pyrimido [5, 4-6] [1, 41 oxazin-2-amine | 0.648 |
| 238B | 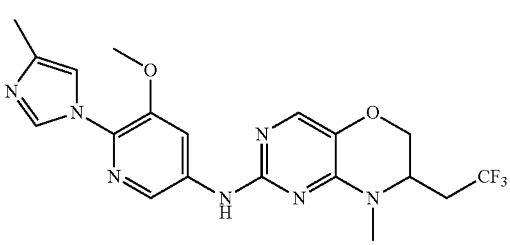 [SMILES: COc1cc(Nc2ncc3c(n2)N(C)C(CC(F)(F)F)CO3)cnc1-n1cnc(C)c1] | (+)-N-(5-methoxy-6-(4-methyl-1H-imidazol-1-yl) pyridin-3-yl)-8-methyl-7-(2, 2, 2-trifluoroethyl)-7, 8-dihydro-6H-pyrimido [5, 4-b] [1, 4] oxazin-2-amine | 0.066 |

TABLE III-continued

Biological Assay

| Compound of Example | Structure | Name | Aβ42 H4 Prot Fre IC50 (μM) |
|---|---|---|---|
| 239A | 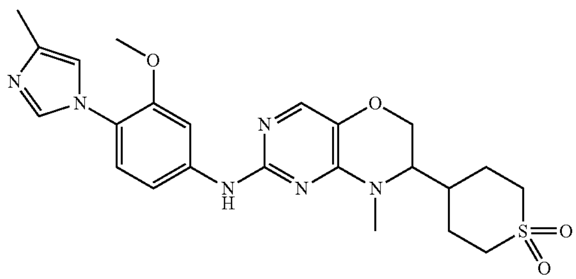 [SMILES: COc1cc(Nc2ncc3c(n2)N(C)C(C2CCS(=O)(=O)CC2)CO3)ccc1-n1cnc(C)c1] | (−)-4-(2-((3 -methoxy-4-(4-methyl-1H-imidazol-1-yl) phenyl) amino)-8-methyl-7, 8-dihydro-6H-pyrimido [5, 4-b] [1, 4] oxazin-7-yl) tetrahydro-2H-thiopyran 1, 1-dioxide | 0.407 |
| 239B | 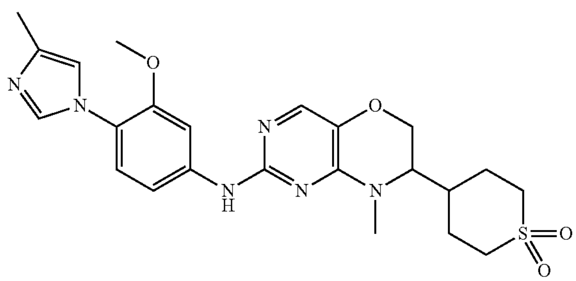 [SMILES: COc1cc(Nc2ncc3c(n2)N(C)C(C2CCS(=O)(=O)CC2)CO3)ccc1-n1cnc(C)c1] | (+)-4-(2-((3 -methoxy-4-(4-methyl- 1H-imidazol-1-yL) phenyl) amino)-8-methyl-7, 8-dihydro-6H-pyrimido [5, 4-b] [1, 4] oxazin-7-yl) tetrahydro-2H-thiopyran 1, 1-dioxide | 0.380 |
| 240 | 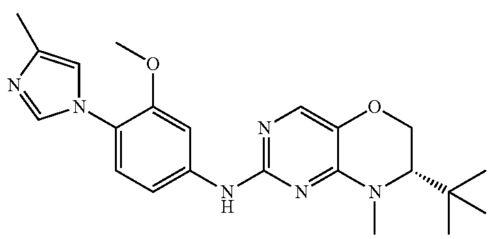 | (S)-7-(tert-butyl)-N-(3-methoxy-4-(4-methyl-1H-imidazol-1-yl) phenyl)-8-methyl-7, 8-dihydro-6H-pyrimido [5, 4-b] [1, 4] oxazin-2-amine | 0.021 |
| 241A | 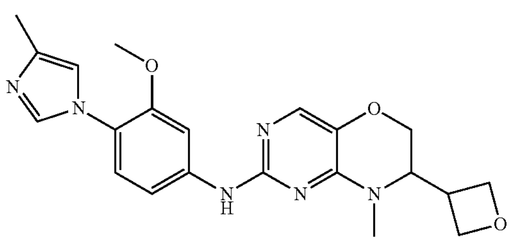 [SMILES: COc1cc(Nc2ncc3c(n2)N(C)C(C2COC2)CO3)ccc1-n1cnc(C)c1] | (−)-N-(3-methoxy-4-(4-methyl-1H-imidazol-1-yl) phenyl)-8-methyl-7-(oxetan-3-yl)-7, 8-dihydro-6H-pyrimido [5, 4-b] [1, 4] oxazin-2-amine | 0.390 |
| 241B | 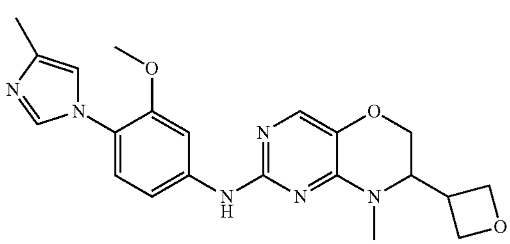 | (+)-N-(3-methoxy-4-(4-methyl-1H-imidazol-1-yl) phenyl)-8-methyl-7-(oxetan-3-yl)-7, 8-dihydro-6H-pyrimido [5, 4-b] [1, 4] oxazin-2-amine | 0.342 |

TABLE III-continued

Biological Assay

| Compound of Example | Structure | Name | Aβ42 H4 Prot Fre IC50 (μM) |
|---|---|---|---|
| 242A | 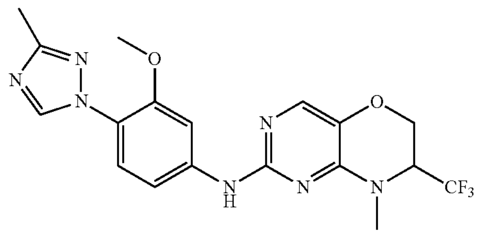 [SMILES: COc1cc(Nc2ncc3c(n2)N(C)C(C(F)(F)F)CO3)ccc1-n1cnc(C)n1] | (−)-N-(3-methoxy-4-(3-methyl-1H-1, 2, 4-triazol-1-yl) phenyl)-8-methyl-7-(trifluoromethyl)-7, 8-dihydro-6H-pyrimido [5, 4-b] [1, 4] oxazin-2-amine | 0.078 |
| 242B | 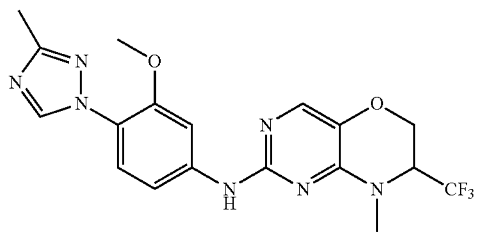 [SMILES: COc1cc(Nc2ncc3c(n2)N(C)C(C(F)(F)F)CO3)ccc1-n1cnc(C)n1] | (+)-N-(3-methoxy-4-(3-methyl-1H-1, 2, 4-triazol-1-yl) phenyl)-8-methyl-7-(trifluoromethyl)-7, 8-dihydro-6H-pyrimido [5, 4-b] [1, 4] oxazin-2-amine | 1.862 |
| 243A | 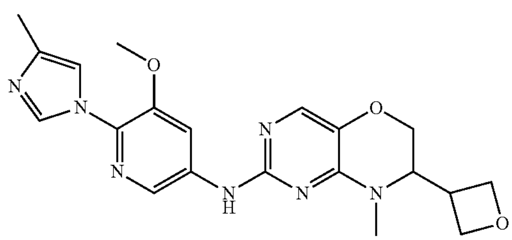 | (+)-N-(5-methoxy-6-(4-methyl-1H-imidazol-1-yl) pyridin-3-yl)-8-methyl-7-(oxetan-3-yl)-7, 8-dihydro-6H-pyrimido [5, 4-b] [1, 4] oxazin-2-amine | 0.601 |
| 243B | 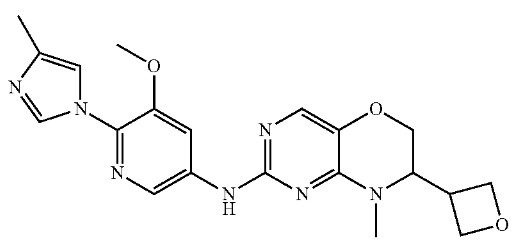 [SMILES: COc1cc(Nc2ncc3c(n2)N(C)C(C2COC2)CO3)cnc1-n1cnc(C)c1] | (−)-N-(5-methoxy-6-(4-methyl-1H-imidazol-1-yl) pyridin-3-yl)-8-methyl-7-(oxetan-3-yl)-7, 8-dihydro-6H-pyrimido [5, 4-b] [1, 4] oxazin-2-amine | 0.814 |
| 244A | 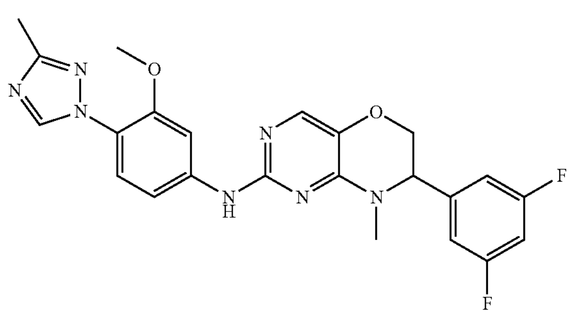 [SMILES: COc1cc(Nc2ncc3c(n2)N(C)C(c2cc(F)cc(F)c2)CO3)ccc1-n1cnc(C)n1] | (+)-7-(3, 5-difluorophenyl)-N-(3 methoxy-4-(3-methyl-1H-1, 2, 4-triazol-1-yl) phenyl)-8-methyl-7, 8-dihydro-6H-pyrimido [5, 4-b] [1, 4] oxazin-2-amine | 0.023 |

TABLE III-continued

Biological Assay

| Compound of Example | Structure | Name | Aβ42 H4 Prot Fre IC50 (μM) |
|---|---|---|---|
| 244B | 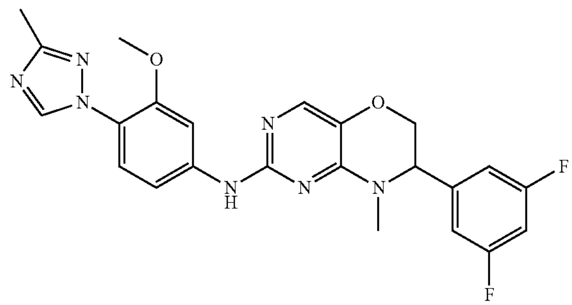 [SMILES: COc1cc(Nc2ncc3c(n2)N(C)C(c2cc(F)cc(F)c2)CO3)ccc1-n1cnc(C)n1] | (−)-7-(3, 5-difluorophenyl)-N-(3-methoxy-4-(3-methyl-1H-1, 2, 4-triazol-1-yl) phenyl)-8-methyl-7, 8-dihydro-6H-pyrimido [5, 4-b] [1, 4] oxazin-2-amine | 0.935 |
| 245A | 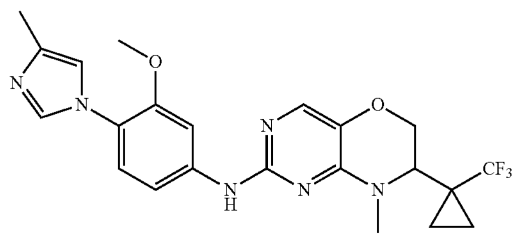 [SMILES: COc1cc(Nc2ncc3c(n2)N(C)C(C2(C(F)(F)F)CC2)CO3)ccc1-n1cnc(C)c1] | (−)-N-(3-methoxy-4-(4-methyl-1H-imidazol-1-yl) phenyl)-8-methyl-7-(1-(trifluoromethyl) cyclopropyl)-7, 8-dihydro-6H-pyrimido [5, 4-b] [1, 4] oxazin-2-amine | 0.216 |
| 245B | 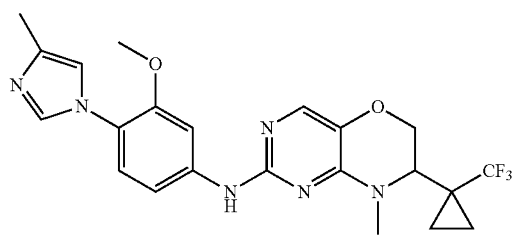 [SMILES: COc1cc(Nc2ncc3c(n2)N(C)C(C2(C(F)(F)F)CC2)CO3)ccc1-n1cnc(C)c1] | (+)-N-(3-methoxy-4-(4-methyl-1H-imidazol-1-yl) phenyl)-8-methyl-7-(1-(trifluoromethyl) cyclopropyl)-7, 8-dihydro-6H-pyrimido [5, 4-b] [1, 4] oxazin-2-amine | 0.022 |
| 246 | 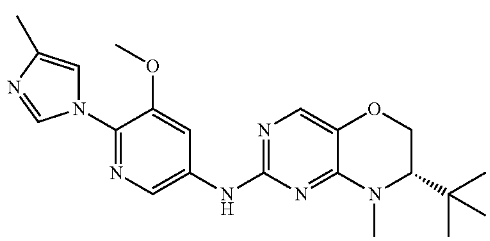 | (S)-7-(tert-butyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine | 0.024 |
| 247A | 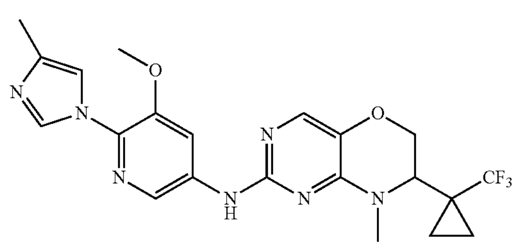 | (−)-N-(5-methoxy-6-(4-methyl-1H-imidazol-1-yl) pyridin-3-yl)-8-methyl-7-(1-(trifluoromethyl) cyclopropyl)-7, 8-dihydro-6H-pyrimido [5, 4-b] [1, 4] oxazin-2-amine | 0.252 |

TABLE III-continued

Biological Assay

| Compound of Example | Structure | Name | Aβ42 H4 Prot Fre IC50 (μM) |
|---|---|---|---|
| 247B | 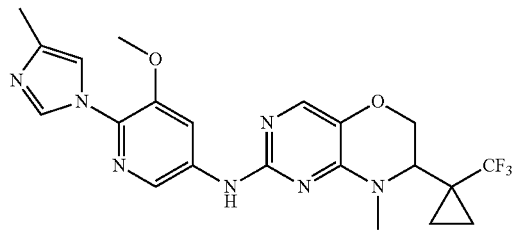 | (+)-N-(5-methoxy-6-(4-methyl-1H-imidazol-1-yl) pyridin-3-yl)-8-methyl-7-(1-(trifluoromethyl) cyclopropyl)-7, 8-dihydro-6H-pyrimido [5, 4-b] [1, 4] oxazin-2-amine | 0.005 |
| 254 | 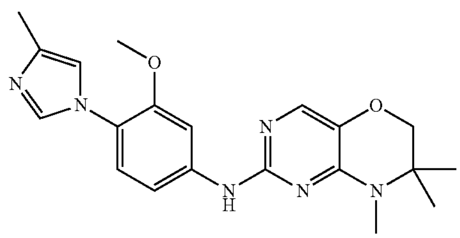 [SMILES: COc1cc(Nc2ncc3c(n2)N(C)C(C)(C)CO3)ccc1-n1cnc(C)c1] | N-(3-methoxy-4-(4-methyl-1H-imidazol-1-yl) phenyl)-7, 7, 8-trimethyl-7, 8-dihydro-6H-pyrimido [5, 4-b] [1, 4] oxazin-2-amine | 0.054 |
| 255 | 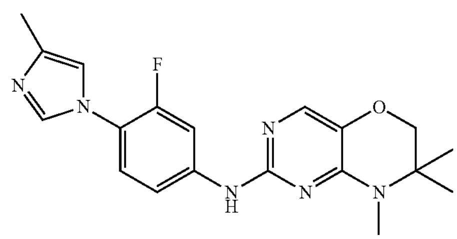 [SMILES: Cc1cn(-c2ccc(Nc3ncc4c(n3)N(C)C(C)(C)CO4)cc2F)cn1] | N-(3-fluoro-4-(4-methyl-1H-imidazol-1-yl) phenyl)-7, 7, 8-trimethyl-7, 8-dihydro-6H-pyrimido [5, 4-b] [1, 4] oxazin-2-amine | 0.488 |
| 256 | 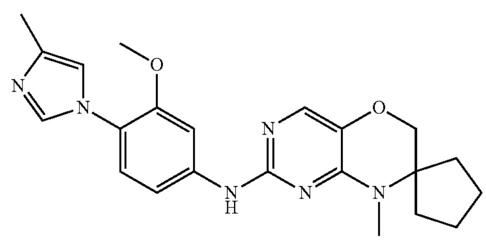 | N-(3-fluoro-4-(4-methyl-1H-imidazol-1-yl) phenyl)-7, 7, 8-trimethyl-7, 8-dihydro-6H-pyrimido [5, 4-b] [1, 4] oxazin-2-amine | 0.025 |
| 257 | 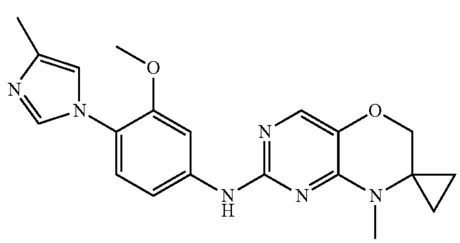 [SMILES: COc1cc(Nc2ncc3c(n2)N(C)C2(CC2)CO3)ccc1-n1cnc(C)c1] | N-(3-methoxy-4-(4-methyl-1H-imidazol-1-yl) phenyl)-8'-methyl-6'H, 8'H-spiro cyclopropane-1, 7'-pyrimido [5, 4-b] [1, 4] oxazin]-2'-amine | 0.049 |
| 258 | 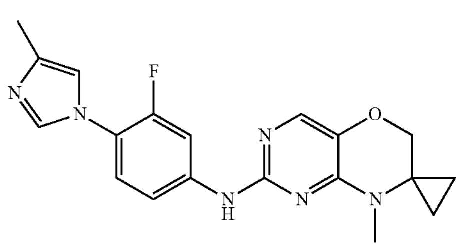 [SMILES: Cc1cn(-c2ccc(Nc3ncc4c(n3)N(C)C3(CC3)CO4)cc2F)cn1] | N-(3-fluoro-4-(4-methyl-1H-imidazol-1-yl) phenyl)-8'-methyl-6'H, 8'H-spiro cyclopropane-1, 7'-pyrimido [5, 4-b] [1, 4] oxazin]-2'-amine | 0.324 |

TABLE III-continued

Biological Assay

| Compound of Example | Structure | Name | Aβ42 H4 Prot Fre IC50 (μM) |
|---|---|---|---|
| 259 | 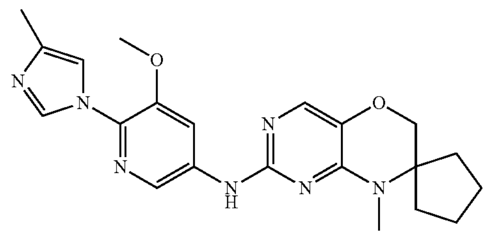 | N-(5-methoxy-6-(4-methyl-1H-imidazol-1-yl) pyridin-3-yl)-8'-methyl-6'H, 8'H-spiro [cyclopentane-1, 7'-pyrimido [5, 4-b] [1, 4] oxazin]-2'-amine | 0.073 |
| 260 | 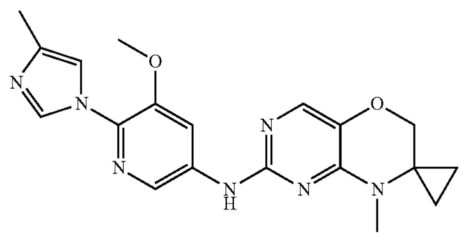 [SMILES: COc1cc(Nc2ncc3c(n2)N(C)C2(CC2)CO3)cnc1-n1cnc(C)c1] | N-(5-methoxy-6-(4-methyl-1H-imidazol-1-yl) pyridin-3-yl)-8'-methyl-6'H, 8'H-spiro [cyclopropane-1, 7'-pyrimido [5, 4-b] [1, 4] oxazin]-2'-amine | 0.213 |
| 261 | 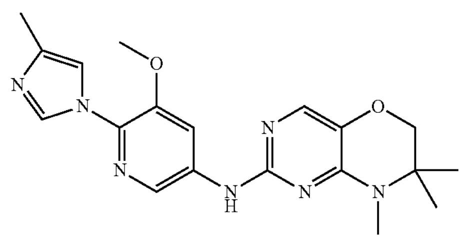 [SMILES: COc1cc(Nc2ncc3c(n2)N(C)C(C)(C)CO3)cnc1-n1cnc(C)c1] | N-(5-methoxy-6-(4-methyl-1H-imidazol-1-yl) pyridin-3-yl)-7, 7, 8-trimethyl-7, 8-dihydro-6H-pyrimido [5, 4-b] [1, 4] oxazin-2-amine | 0.139 |
| 262 | 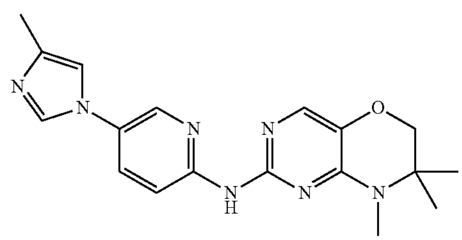 [SMILES: Cc1cn(-c2ccc(Nc3ncc4c(n3)N(C)C(C)(C)CO4)nc2)cn1] | 7, 7, 8-trimethyl-N-(5-(4-methyl-1H-imidazol-1-yl) pyridin-2-yl)-7, 8-dihydro-6H-pyrimido [5, 4-b] [1, 41 oxazin-2-amine | >3 |
| 263 | 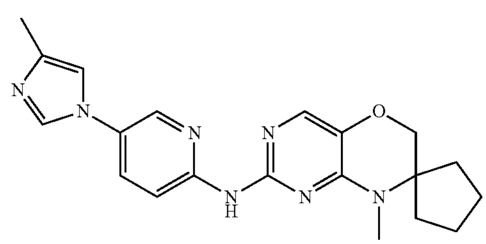 [SMILES: Cc1cn(-c2ccc(Nc3ncc4c(n3)N(C)C3(CCCC3)CO4)nc2)cn1] | 8'-methyl-N-(5-(4-methyl-1H-imidazol-1-yl) pyridin-2-yl)-6'H, 8'H-spiro [cyclopentane-1, 7'-pyrimido [5, 4-b] [1, 4] oxazin]-2'-amine | >3 |
| 264 | 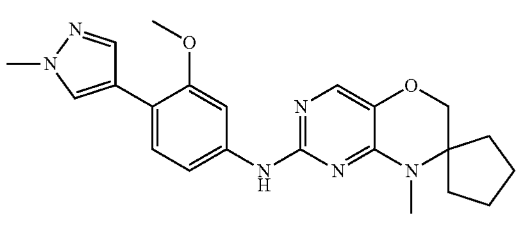 [SMILES: COc1cc(Nc2ncc3c(n2)N(C)C2(CCCC2)CO3)ccc1-c1cnn(C)c1] | N-(3-methoxy-4-(1-methyl-1H-pyrazol-4-yl) phenyl)-8'-methyl-6'H, 8'H-spiro [cyclopentane-1, 7'-pyrimido [5, 4-b] [1, 4] oxazin]-2'-amine | 0.260 |

TABLE III-continued

Biological Assay

| Compound of Example | Structure | Name | Aβ42 H4 Prot Fre IC50 (μM) |
|---|---|---|---|
| 265 | 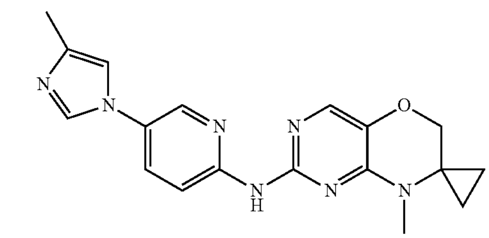 [SMILES: Cc1cn(-c2ccc(Nc3ncc4c(n3)N(C)C3(CC3)CO4)nc2)cn1] | N-(5-(4-methyl-1H-imidazol-1-yl) pyridin-2-yl)-6'H, 8'H-spiro cyclopropane-1, 7'-pyrimido [5, 4-b] [1, 4] oxazin]-2'-amine | >3 |
| 266 | 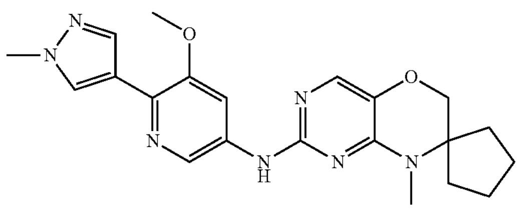 | N-(5-methoxy-6-(1-methyl-1H-pyrazol-4-yl) pyridin-3-yl)-8'-methyl-6'H, 8'H-spiro [cyclopentane-1, 7'-pyrimido [5, 4-b] [1, 4] oxazin]-2'-amine | >3 |
| 267 | 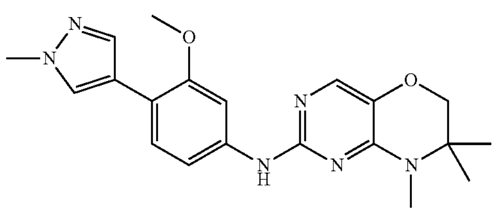 | N-(3-methoxy-4-(1-methyl-1H-pyrazol-4-yl phenyl)-7, 7, 8-trimethyl-7, 8-dihydro-6H-pyrimido [5, 4-b] [1, 4] oxazin-2-amine | 0.822 |
| 268 | 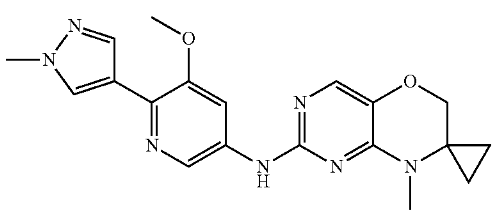 [SMILES: COc1cc(Nc2ncc3c(n2)N(C)C2(CC2)CO3)cnc1-c1cnn(C)c1] | N-(5-methoxy-6-(1-methyl-1H-pyrazol-4-yl) pyridin-3-yl)-8'-methyl-6'H, 8'H-spiro [cyclopropane-1, 7'-pyrimido [5, 4-b] [1, 4] oxazin]-2'-amine | 2.784 |
| 269 | 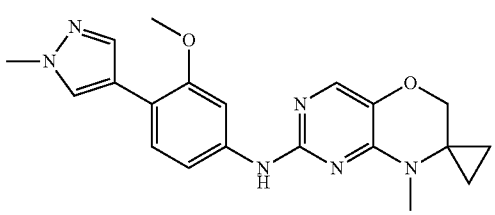 | N-(3-methoxy-4-(1-methyl-1H-pyrazol-4-yl) phenyl)-8'-methyl-6'H, 8'H-spiro [cyclopropane-1, 7'-pyrimido [5, 4-b] [1, 4] oxazin]-2'-amine | 0.703 |
| 270 | 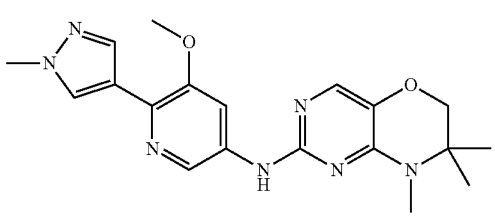 | N-(5-methoxy-6-(1-methyl-1H-pyrazol-4-yl) pyridin-3-yl)-7, 7, 8-trimethyl-7, 8-dihydro-6H-pyrimido [5, 4-b] [1, 4] oxazin-2-amine | >3 |

TABLE III-continued

Biological Assay

| Compound of Example | Structure | Name | Aβ42 H4 Prot Fre IC50 (μM) |
|---|---|---|---|
| 271 | 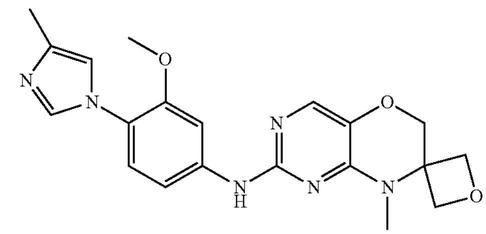 [SMILES: COc1cc(Nc2ncc3c(n2)N(C)C2(COC2)CO3)ccc1-n1cnc(C)c1] | N-(3-methoxy-4-(4-methyl-1H-imidazol-1-yl) phenyl)-8'-methyl-6'H, 8'H-spiro [oxetane-3, 7'-pyrimido [5, 4-b] [1, 4] oxazin]-2'-amine | 0.364 |
| 272 | 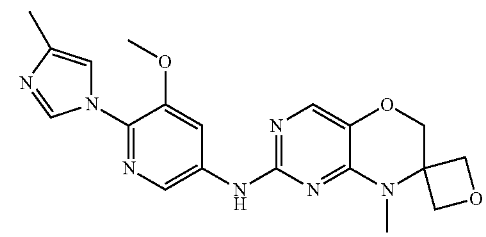 [SMILES: COc1cc(Nc2ncc3c(n2)N(C)C2(COC2)CO3)cnc1-n1cnc(C)c1] | N-(5-methoxy-6-(4-methyl-1H-imidazol-1-yl) pyridin-3-yl)-8'-methyl-6'H, 8'H-spiro [oxetane-3,7'-pyrimido [5, 4-b] [1,4] oxazin]-2'-amine | 0.537 |
| 273 | 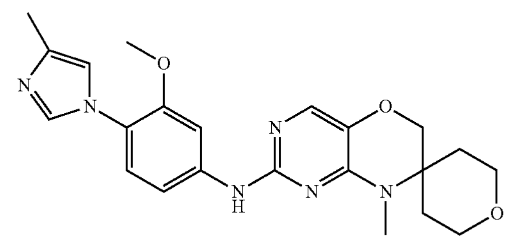 | N-(3-methoxy-4-(4-methyl-1H-imidazol-1-yl) phenyl)-8'-methyl-2, 3, 5, 6-tetrahydro-6'H, 8'H-spiro [pyran-4, 7'-pyrimido [5, 4-b] [1, 4] oxazin]-2'-amine | 0.111 |
| 274 | 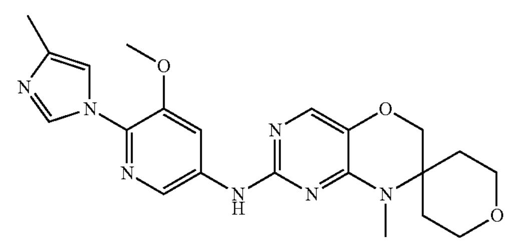 | N-(5-methoxy-6-(4-methyl-1H-imidazol-1-yl) pyridin-3-yl)-8'-methyl-2, 3, 5, 6-tetrahydro-6'H, 8'H-spiro [pyran-4, 7'-pyrimido [5, 4-b] [1, 4] oxazin]-2'-amine | 0.295 |
| 275 | 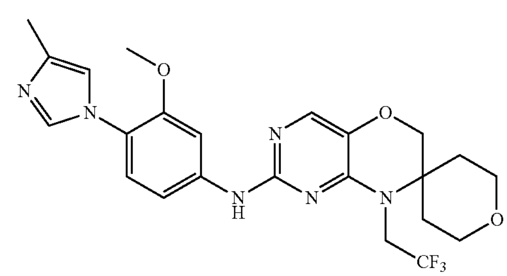 | N-(3-methoxy-4-(4-methyl-1H-imidazol-1-yl) phenyl)-8-(2, 2, 2-trifluoroethyl)-2, 3, 5, 6-tetrahydro-6'H, 8'H-spiro [pyran-4, 7'-pyrimido [5, 4-b] [1, 4] oxazin]-2'-amine | 0.351 |

TABLE III-continued

Biological Assay

| Compound of Example | Structure | Name | Aβ42 H4 Prot Fre IC50 (μM) |
|---|---|---|---|
| 276 | 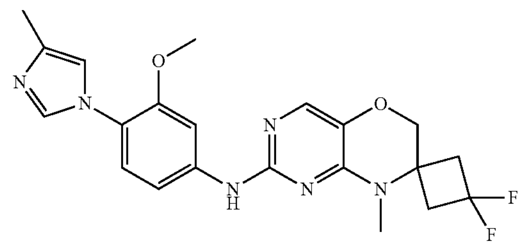 [SMILES: COc1cc(Nc2ncc3c(n2)N(C)C2(CO3)CC(F)(F)C2)ccc1-n1cnc(C)c1] | 3, 3-difluoro-N-(3-methoxy-4-(4-methyl-1H-imidazol-1-yl) phenyl)-8-methyl-6'H, 8'H-spiro [cyclobutane-1, 7'-pyrimido [5, 4-b] [1, 4] oxazin]-2'-amine | 0.056 |
| 277 | 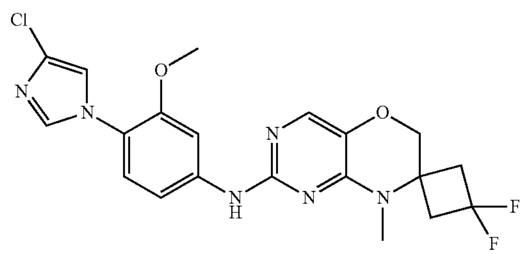 [SMILES: COc1cc(Nc2ncc3c(n2)N(C)C2(CO3)CC(F)(F)C2)ccc1-n1cnc(Cl)c1] | N-(4-(4-chloro-1H-imidazol-1-yl)-3-methoxyphenyl)-3, 3-difluoro-8'-methyl-6'H, 8'H-spiro [cyclobutane-1, 7'-pyrimido [5, 4-b] [1, 4] oxazin]-2'-amine | 0.097 |
| 278 | 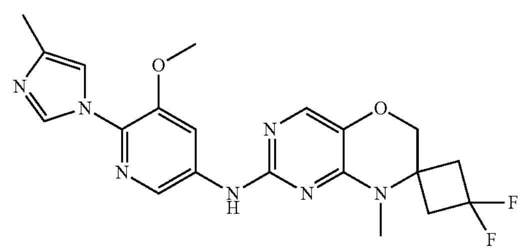 | 3, 3-difluoro-N-(5-methoxy-6-(4-methyl-1H-imidazol-1-yl) pyridin-3-yl)-8'-methyl-6'H, 8'H-spiro [cyclobutane-1, 7'-pyrimido [5, 4-b] [1, 4] oxazin]-2'-amine | 0.092 |
| 279 | 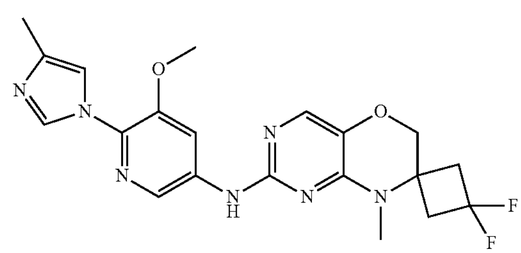 | N-(3-fluoro-4-(4-methyl-1H-imidazol-1-yl) phenyl)-8'-methyl-6'H, 8'H-spiro [cyclopentane-1, 7'-pyrimido [5, 4-b] [1, 4] oxazin]-2'-amine | 0.254 |
| 289A | 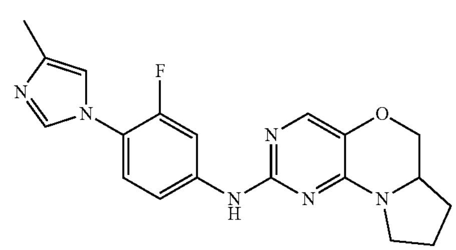 [SMILES: Cc1cn(-c2ccc(Nc3ncc4c(n3)N3CCCC3CO4)cc2F)cn1] | (+)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine | 0.235 |

TABLE III-continued

Biological Assay

| Compound of Example | Structure | Name | Aβ42 H4 Prot Fre IC50 (μM) |
|---|---|---|---|
| 289B | 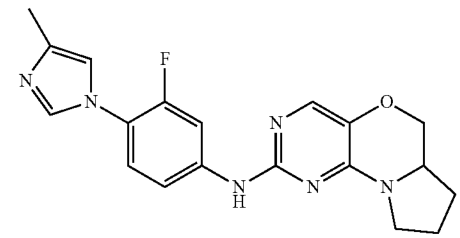 [SMILES: Cc1cn(-c2ccc(Nc3ncc4c(n3)N3CCCC3CO4)cc2F)cn1] | (−)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine | 0.157 |
| 290A | 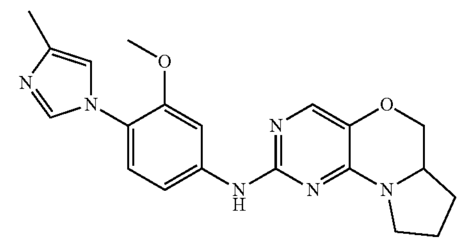 [SMILES: COc1cc(Nc2ncc3c(n2)N2CCCC2CO3)ccc1-n1cnc(C)c1] | (−)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine | 0.071 |
| 290B | 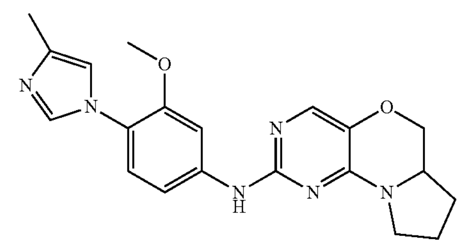 [SMILES: COc1cc(Nc2ncc3c(n2)N2CCCC2CO3)ccc1-n1cnc(C)c1] | (+)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine | 0.151 |
| 291 | 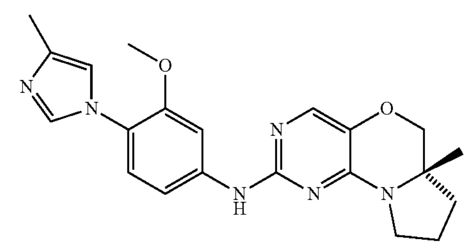 | (S)-N-(3-methoxy-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine | 0.131 |
| 292 | 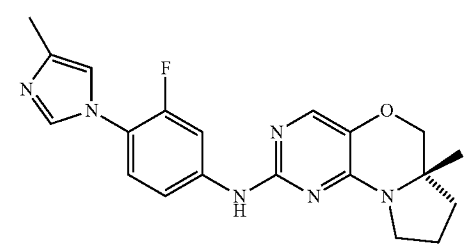 | (S)-N-(3-fluoro-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine | 0.438 |
| 293 | 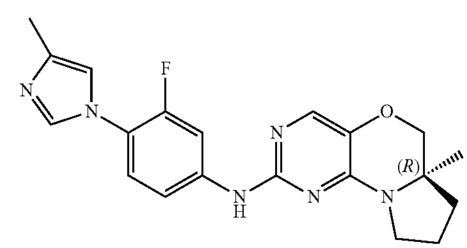 | (R)-N-(3-fluoro-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine | 0.276 |

TABLE III-continued

Biological Assay

| Compound of Example | Structure | Name | Aβ42 H4 Prot Fre IC50 (μM) |
|---|---|---|---|
| 294 | 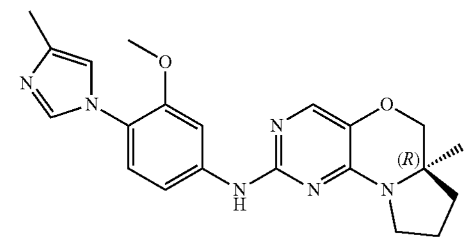 | (R)-N-(3-methoxy-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine | 0.080 |
| 295 | 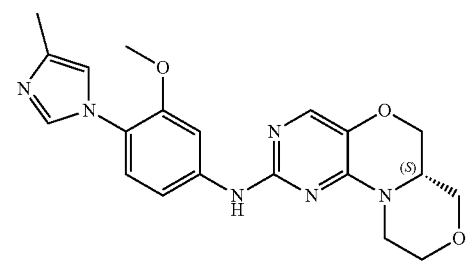 | (S)-N-(3-methoxy-4-(4-methyl-1H-imidazol-1-yl) phenyl)-6a, 7, 9, 10-tetrahydro-6H-[1, 4] oxazino [4, 3-d] pyrimido [5, 4-b] [1, 4] oxazin-2-amine | 0.496 |
| 296 | 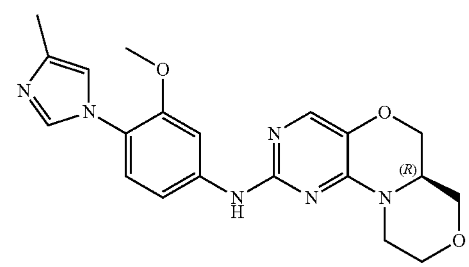 | (R)-N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine | 0.759 |
| 297 | 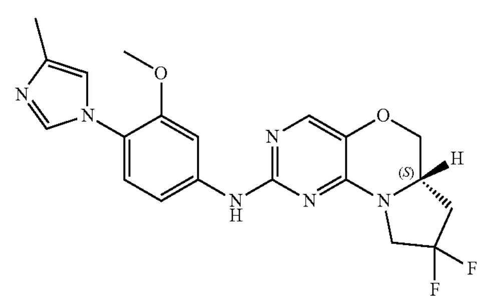 | (S)-8, 8-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine | 0.099 |
| 298 | 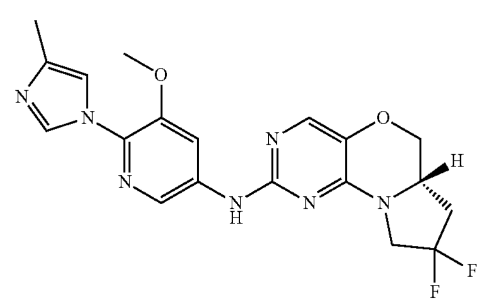 [SMILES: COc1cc(Nc2ncc3c(n2)N2CC(F)(F)C[C@H]2CO3)cnc1-n1cnc(C)c1] | (S)-8, 8-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine | 0.177 |

TABLE III-continued

Biological Assay

| Compound of Example | Structure | Name | Aβ42 H4 Prot Fre IC50 (μM) |
|---|---|---|---|
| 299 | 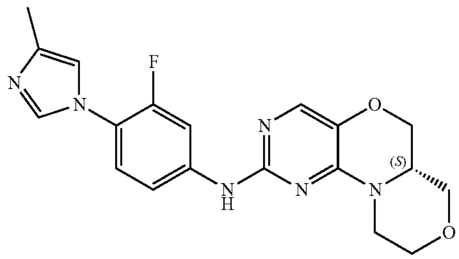 | (S)-N-(3-fluoro-4-(4-methyl-1H-imidazol-1-yl) phenyl)-6a, 7, 9, 10-tetrahydro-6H-[1, 4] oxazino [4, 3-d] pyrimido [5, 4-b] [1, 4] oxazin-2-amine | >3 |
| 300 | 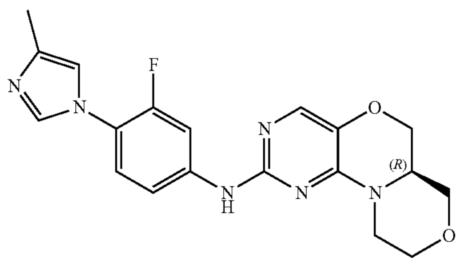 | (R)-N-(3-fluoro-4-(4-methyl-1H-imidazol-1-yl) phenyl)-6a, 7, 9, 10-tetrahydro-6H-[1, 4] oxazino [4, 3-d] pyrimido [5, 4-b] [1, 4] oxazin-2-amine | 0.781 |
| 301A | 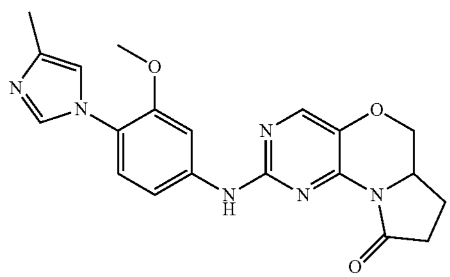 [SMILES: COc1cc(Nc2ncc3c(n2)N2C(=O)CCC2CO3)ccc1-n1cnc(C)c1] | (+)-N-(5-methoxy-6-(4-methyl-1H-imidazol-1-yl) pyridin-3-yl)-8'-methyl-2, 3, 5, 6-tetrahydro-6'H, 8'H-spiro [pyran-4, 7'-pyrimido [5, 4-b] [1, 4] oxazin]-2'-amine | 2.735 |
| 301B | 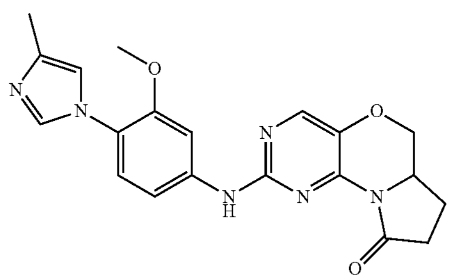 [SMILES: COc1cc(Nc2ncc3c(n2)N2C(=O)CCC2CO3)ccc1-n1cnc(C)c1] | (−)-N-(5-methoxy-6-(4-methyl-1H-imidazol-1-yl) pyridin-3-yl)-8'-methyl-2, 3, 5, 6-tetrahydro-6'H, 8'H-spiro [pyran-4, 7'-pyrimido [5, 4-b] [1, 4] oxazin]-2'-amine | 1.162 |
| 302A | 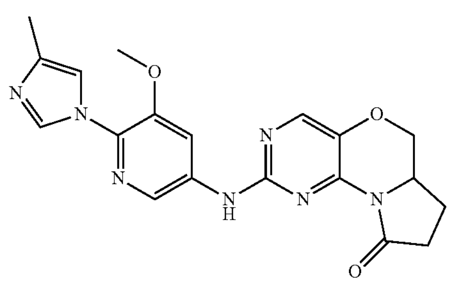 [SMILES: COc1cc(Nc2ncc3c(n2)N2C(=O)CCC2CO3)cnc1-n1cnc(C)c1] | (+)-2-((5-methoxy-6-(4-methyl-1H-imidazol-1-yl) pyridin-3-yl) amino)-6, 6a, 7, 8-tetrahydro-9H-pyrimido [5, 4-b] pyrrolo [1, 2-d] [1, 4] oxazin-9-one | >3 |

TABLE III-continued

Biological Assay

| Compound of Example | Structure | Name | Aβ42 H4 Prot Fre IC50 (μM) |
|---|---|---|---|
| 302B | 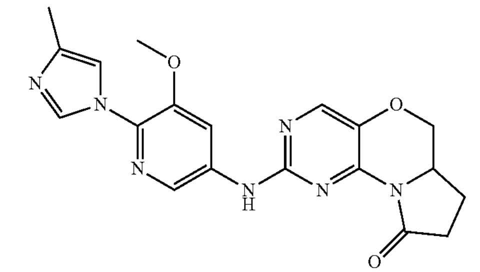 [SMILES: COc1cc(Nc2ncc3c(n2)N2C(=O)CCC2CO3)cnc1-n1cnc(C)c1] | (−)-2-((5-methoxy-6-(4-methyl-1H-imidazol-1-yl) pyridin-3-yl) amino)-6, 6a, 7, 8-tetrahydro-9H-pyrimido [5, 4-b] pyrrolo [1, 2-d] [1, 4] oxazin-9-one | 2.904 |
| 303 | 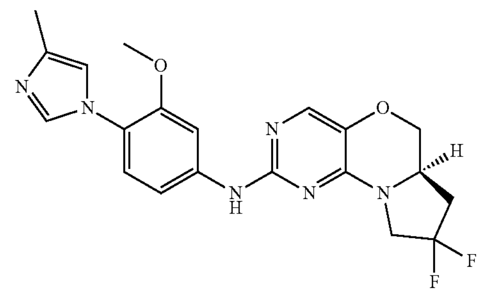 [SMILES: COc1cc(Nc2ncc3c(n2)N2CC(F)(F)C[C@@H]2CO3)ccc1-n1cnc(C)c1] | (R)-8, 8-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine | 0.131 |
| 304A | 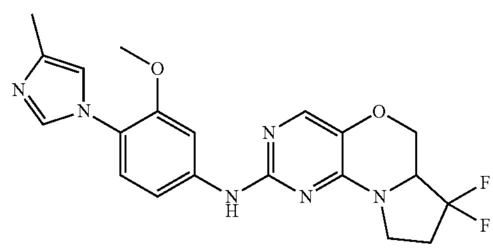 [SMILES: COc1cc(Nc2ncc3c(n2)N2CCC(F)(F)C2CO3)ccc1-n1cnc(C)c1] | (−)-7, 7-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine | 0.274 |
| 304B | 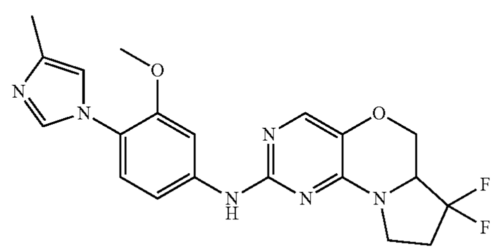 [SMILES: COc1cc(Nc2ncc3c(n2)N2CCC(F)(F)C2CO3)ccc1-n1cnc(C)c1] | (+)-7, 7-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine | 0.075 |
| 305A | 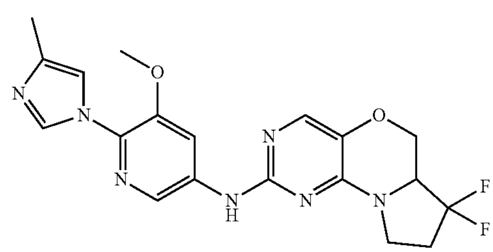 [SMILES: COc1cc(Nc2ncc3c(n2)N2CCC(F)(F)C2CO3)cnc1-n1cnc(C)c1] | (+)-7, 7-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine | 0.132 |

TABLE III-continued

Biological Assay

| Compound of Example | Structure | Name | Aβ42 H4 Prot Fre IC50 (μM) |
|---|---|---|---|
| 305B | 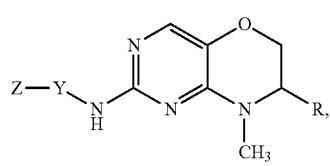 | (−)-7, 7-difluoro-N-(5-methoxy-6-(4-methyl-1H-imidazol-1-yl)pyridin-3-yl)-6a, 7, 8, 9-tetrahydro-6H-pyrimido [5, 4-b] pyrrolo [1, 2-d] [1, 4] oxazin-2-amine | 0.582 |

We claim:

1. A compound of Formula (I)

$$(I)$$

or a pharmaceutically acceptable salt thereof, wherein:

R is phenyl, —C1-C4 alkylene-phenyl, oxetanyl, C1-C6 alkyl, —C3-C8 monocyclic cycloalkyl, —C1-C4 alkylene-C3-C8 monocyclic cycloalkyl, 3- to 7-membered monocyclic heterocycle, —C1-C4 alkylene 3- to 7-membered monocyclic heterocycle, each of which is unsubstituted or substituted with one or more substituents independently selected from the group consisting of -halo, —CN, —NH2, —OH, oxo, —C1-C4 alkyl, halo-substituted C1-C4 alkyl, amino-substituted C1-C4 alkyl, —NH—C1-C4 alkyl, —NHC(O)—C1-C4 alkyl, —C(O)NH—C1-C4 alkyl, —C(O)N(C1-C4 alkyl)2, hydroxy-substituted C1-C4 alkyl, —S(O)2-C1-C4 alkyl, —S(O)2-halo-substituted C1-C4 alkyl, —S(O)2-NH—C1-C4 alkyl, —S(O)2-N(C1-C4 alkyl)2, —NH—S(O)2-C1-C4 alkyl, —N(C1-C4 alkyl)-S(O)2-C1-C4 alkyl, C1-C4 alkoxy, halo-substituted C1-C4 alkoxy, 3- to 7-membered monocyclic heterocycle, —C3-C8 monocyclic cycloalkyl, —C(O)NH2 and -phenoxy, provided that phenyl is not substituted with one or more oxo;

Y is phenyl or pyridinyl which is unsubstituted or substituted with one or more substituents independently selected from the group consisting of -halo, —C1-C4 alkoxy, halo-substituted C1-C4 alkoxy, —C1-C4 alkyl, halo-substituted C1-C4 alkyl, amino-substituted C1-C4 alkoxy, —CN, (C1-C4 alkyl)2N—C1-C4-alkoxy, —NH—C1-C4 alkyl, —OH and —NH2; and Z is —CN or nitrogen-containing 3- to 7-membered monocyclic heterocycle which is unsubstituted or substituted with one or more substituents independently selected from the group consisting of -halo, —CN, —NH2, —OH, —C1-C4 alkyl, halo-substituted C1-C4 alkyl, —C1-C4 alkoxy, —OCF3 and 3- to 7-membered monocyclic heterocycle.

2. A compound of claim 1, wherein:

R is phenyl, —C1-C4 alkylene-phenyl, oxetanyl, C1-C6 alkyl, —C3-C8 monocyclic cycloalkyl, 3- to 7-membered monocyclic heterocycle, —C1-C4 alkylene 3- to 7-membered monocyclic heterocycle or —C1-C4 alkylene-C3-C8 monocyclic cycloalkyl, each of which is unsubstituted or substituted with one or more substituents independently selected from the group consisting of -halo, —CN, —NH2, —OH, —C1-C4 alkyl, halo-substituted C1-C4 alkyl, amino-substituted C1-C4 alkyl, —NH—C1-C4 alkyl, —NHC(O)—C1-C4 alkyl, —C(O)NH—C1-C4 alkyl, —C(O)N(C1-C4 alkyl)2, hydroxy-substituted C1-C4 alkyl, —S(O)2-C1-C4 alkyl, —S(O)2-halo-substituted C1-C4 alkyl, —S(O)2-NH—C1-C4 alkyl, —S(O)2-N(C1-C4 alkyl)2, —NH—S(O)2-C1-C4 alkyl, —N(C1-C4 alkyl)-S(O)2-C1-C4 alkyl, C1-C4 alkoxy, halo-substituted C1-C4 alkoxy, 3- to 7-membered monocyclic heterocycle, —C3-C8 monocyclic cycloalkyl, —C(O)NH2;

Y is phenyl which is unsubstituted or substituted with one or more substituents independently selected from the group consisting of -halo, —C1-C4 alkoxy, halo-substituted C1-C4 alkoxy, —C1-C4 alkyl, halo-substituted C1-C4 alkyl, amino-substituted C1-C4 alkoxy, —CN, (C1-C4 alkyl)2N—C1-C4 alkoxy, —NH—C1-C4 alkyl, —OH and —NH2; and Z is pyridinyl or imidazolyl, each of which is unsubstituted or substituted with one or more substituents independently selected from the group consisting of -halo, —NH2, —OH, —C1-C4 alkyl, halo-substituted C1-C4 alkyl, —C1-C4 alkoxy, —OCF3 and 3- to 7-membered monocyclic heterocycle;

or a pharmaceutically acceptable salt thereof.

3. The compound of claim 2, wherein:

R is phenyl, tetrahydropyranyl, —C1-C4 alkyl, —C1-C4 alkylene-phenyl, each of which is unsubstituted or substituted with one or more substituents independently selected from the group consisting of halo, —C1-C4 alkyl, halo-substituted C1-C4 alkyl and halo-substituted C1-C4 alkoxy;

Y is phenyl which is unsubstituted or substituted with one or more substituents independently selected from the group consisting of halo and —C1-C4 alkoxy; and Z is pyridinyl or imidazolyl, each of which is substituted with one —C1-C4 alkyl or halo;
or a pharmaceutically acceptable salt thereof.

4. The compound of claim 2, wherein:
R is phenyl which is unsubstituted or substituted with one or more substituents independently selected from the group consisting of halo and —C1-C4 alkyl;
Y is phenyl substituted with one or more substituents independently selected from the group consisting of halo and —C1-C4 alkoxy; and
Z is imidazolyl substituted with methyl or halo;
or a pharmaceutically acceptable salt thereof.

5. The compound of claim 2, wherein:
R is phenyl which is unsubstituted or substituted with one or more substituents independently selected from the group consisting of halo and —C1-C4 alkyl;
Y is phenyl substituted with one or more substituents independently selected from the group consisting of halo and —C1-C4 alkoxy; and
Z is pyridinyl substituted with methyl or chloro;
or a pharmaceutically acceptable salt thereof.

6. A compound selected from the group consisting of:
(S)—N-(3-methoxy-4-(4-methyl-1H-imidazol-1-yl)phenyl)-8-methyl-7-phenyl-7,8-dihydro-6H-pyrimido[5,4-b][1,4]oxazin-2-amine;
(S)—N-(3-methoxy-4-(2-methylpyridin-4-yl)phenyl)-8-methyl-7-phenyl-7,8-dihydro-6H-pyrimido[5,4-b][1,4]oxazin-2-amine;
(R)—N-(3-methoxy-4-(4-methyl-1H-imidazol-1-yl)phenyl)-8-methyl-7-phenyl-7,8-dihydro-6H-pyrimido[5,4-b][1,4]oxazin-2-amine;
(R)—N-(3-methoxy-4-(2-methylpyridin-4-yl)phenyl)-8-methyl-7-phenyl-7,8-dihydro-6H-pyrimido[5,4-b][1,4]oxazin-2-amine;
7-(3,5-difluorophenyl)-8-methyl-N-(4-(4-methyl-1H-imidazol-1-yl)phenyl)-7,8-dihydro-6H-pyrimido[5,4-b][1,4]oxazin-2-amine;
(+)-7-(3, 5-difluorophenyl)-8-methyl-N-(4-(4-methyl-1H-imidazol-1-yl) phenyl)-7, 8-dihydro-6H-pyrimido [5, 4-b] [1, 4] oxazin-2-amine;
8-methyl-N-(4-(2-methylpyridin-4-yl)phenyl)-7-phenyl-7,8-dihydro-6H-pyrimido[5,4-b][1,4]oxazin-2-amine;
(+)-8-methyl-N-(4-(2-methylpyridin-4-yl)phenyl)-7-phenyl-7,8-dihydro-6H-pyrimido[5,4-b][1,4]oxazin-2-amine;
N-(3-fluoro-4-(4-methyl-1H-imidazol-1-yl)phenyl)-8-methyl-7-phenyl-7,8-dihydro-6H-pyrimido[5,4-b][1,4]oxazin-2-amine;
(+)-N-(3-fluoro-4-(4-methyl-1H-imidazol-1-yl)phenyl)-8-methyl-7-phenyl-7,8-dihydro-6H-pyrimido[5,4-b][1,4]oxazin-2-amine;
8-methyl-N-(4-(4-methyl-1H-imidazol-1-yl)phenyl)-7-phenyl-7,8-dihydro-6H-pyrimido[5,4-b][1,4]oxazin-2-amine;
(+)-8-methyl-N-(4-(4-methyl-1H-imidazol-1-yl)phenyl)-7-phenyl-7,8-dihydro-6H-pyrimido[5,4-b][1,4]oxazin-2-amine;
7-(3,5-difluorophenyl)-8-methyl-N-(4-(2-methylpyridin-4-yl)phenyl)-7,8-dihydro-6H-pyrimido[5,4-b][1,4]oxazin-2-amine;
(+)-7-(3,5-difluorophenyl)-8-methyl-N-(4-(2-methylpyridin-4-yl)phenyl)-7,8-dihydro-6H-pyrimido[5,4-b][1,4]oxazin-2-amine;
(+)-8-methyl-N-(4-(2-methylpyridin-4-yl)phenyl)-7-(o-tolyl)-7,8-dihydro-6H-pyrimido[5,4-b][1,4]oxazin-2-amine;
7-(3,5-difluorophenyl)-N-(3-methoxy-4-(4-methyl-1H-imidazol-1-yl)phenyl)-8-methyl-7,8-dihydro-6H-pyrimido[5,4-b][1,4]oxazin-2-amine;
(−)-7-(3,5-difluorophenyl)-N-(3-methoxy-4-(4-methyl-1H-imidazol-1-yl)phenyl)-8-methyl-7,8-dihydro-6H-pyrimido[5,4-b][1,4]oxazin-2-amine;
(+)-7-(3,5-difluorophenyl)-N-(3-methoxy-4-(4-methyl-1H-imidazol-1-yl)phenyl)-8-methyl-7,8-dihydro-6H-pyrimido[5,4-b][1,4]oxazin-2-amine;
N-(3-methoxy-4-(4-methyl-1H-imidazol-1-yl)phenyl)-8-methyl-7-(o-tolyl)-7,8-dihydro-6H-pyrimido[5,4-b][1,4]oxazin-2-amine;
(−)-N-(3-methoxy-4-(4-methyl-1H-imidazol-1-yl)phenyl)-8-methyl-7-(o-tolyl)-7,8-dihydro-6H-pyrimido[5,4-b][1,4]oxazin-2-amine;
(+)-N-(3-methoxy-4-(4-methyl-1H-imidazol-1-yl)phenyl)-8-methyl-7-(o-tolyl)-7,8-dihydro-6H-pyrimido[5,4-b][1,4]oxazin-2-amine;
N-(3-fluoro-4-(2-methylpyridin-4-yl)phenyl)-8-methyl-7-(o-tolyl)-7,8-dihydro-6H-pyrimido[5,4-b][1,4]oxazin-2-amine;
(+)-N-(3-fluoro-4-(2-methylpyridin-4-yl)phenyl)-8-methyl-7-(o-tolyl)-7,8-dihydro-6H-pyrimido[5,4-b][1,4]oxazin-2-amine;
7-(3,5-difluorophenyl)-N-(3-fluoro-4-(4-methyl-1H-imidazol-1-yl)phenyl)-8-methyl-7,8-dihydro-6H-pyrimido[5,4-b][1,4]oxazin-2-amine;
(+)-7-(3,5-difluorophenyl)-N-(3-fluoro-4-(4-methyl-1H-imidazol-1-yl)phenyl)-8-methyl-7,8-dihydro-6H-pyrimido[5,4-b][1,4]oxazin-2-amine;
N-(3-fluoro-4-(4-methyl-1H-imidazol-1-yl)phenyl)-8-methyl-7-(o-tolyl)-7,8-dihydro-6H-pyrimido[5,4-b][1,4]oxazin-2-amine;
(+)-N-(3-fluoro-4-(4-methyl-1H-imidazol-1-yl)phenyl)-8-methyl-7-(o-tolyl)-7,8-dihydro-6H-pyrimido[5,4-b][1,4]oxazin-2-amine;
N-(3-methoxy-4-(2-methylpyridin-4-yl)phenyl)-8-methyl-7-(o-tolyl)-7,8-dihydro-6H-pyrimido[5,4-b][1,4]oxazin-2-amine;
(+)-N-(3-methoxy-4-(2-methylpyridin-4-yl)phenyl)-8-methyl-7-(o-tolyl)-7,8-dihydro-6H-pyrimido[5,4-b][1,4]oxazin-2-amine;
N-(3-fluoro-4-(2-methylpyridin-4-yl)phenyl)-8-methyl-7-(3,4,5-trifluorophenyl)-7,8-dihydro-6H-pyrimido[5,4-b][1,4]oxazin-2-amine;
(+)-N-(3-fluoro-4-(2-methylpyridin-4-yl)phenyl)-8-methyl-7-(3,4,5-trifluorophenyl)-7,8-dihydro-6H-pyrimido[5,4-b][1,4]oxazin-2-amine;
8-methyl-N-(4-(2-methylpyridin-4-yl)phenyl)-7-(3,4,5-trifluorophenyl)-7,8-dihydro-6H-pyrimido[5,4-b][1,4]oxazin-2-amine;
(+)-8-methyl-N-(4-(2-methylpyridin-4-yl)phenyl)-7-(3,4,5-trifluorophenyl)-7,8-dihydro-6H-pyrimido[5,4-b][1,4]oxazin-2-amine;
N-(3-fluoro-4-(4-methyl-1H-imidazol-1-yl)phenyl)-8-methyl-7-(3,4,5-trifluorophenyl)-7,8-dihydro-6H-pyrimido[5,4-b][1,4]oxazin-2-amine;
N-(3-methoxy-4-(2-methylpyridin-4-yl)phenyl)-8-methyl-7-(3,4,5-trifluorophenyl)-7,8-dihydro-6H-pyrimido[5,4-b][1,4]oxazin-2-amine;
(+)-N-(3-methoxy-4-(2-methylpyridin-4-yl)phenyl)-8-methyl-7-(3,4,5-trifluorophenyl)-7,8-dihydro-6H-pyrimido[5,4-b][1,4]oxazin-2-amine;
N-(3-methoxy-4-(4-methyl-1H-imidazol-1-yl)phenyl)-8-methyl-7-(3,4,5-trifluorophenyl)-7,8-dihydro-6H-pyrimido[5,4-b][1,4]oxazin-2-amine;

(+)-N-(3-methoxy-4-(4-methyl-1H-imidazol-1-yl)phenyl)-8-methyl-7-(3,4,5-trifluorophenyl)-7,8-dihydro-6H-pyrimido[5,4-b][1,4]oxazin-2-amine;
7-(3,5-difluorophenyl)-N-(3-fluoro-4-(2-methylpyridin-4-yl)phenyl)-8-methyl-7,8-dihydro-6H-pyrimido[5,4-b][1,4]oxazin-2-amine;
(+)-7-(3,5-difluorophenyl)-N-(3-fluoro-4-(2-methylpyridin-4-yl)phenyl)-8-methyl-7,8-dihydro-6H-pyrimido[5,4-b][1,4]oxazin-2-amine;
7-(3,5-difluorophenyl)-N-(3-methoxy-4-(2-methylpyridin-4-yl)phenyl)-8-methyl-7,8-dihydro-6H-pyrimido[5,4-b][1,4]oxazin-2-amine;
(+)-7-(3,5-difluorophenyl)-N-(3-methoxy-4-(2-methylpyridin-4-yl)phenyl)-8-methyl-7,8-dihydro-6H-pyrimido[5,4-b][1,4]oxazin-2-amine;
8-methyl-N-(4-(4-methyl-1H-imidazol-1-yl)phenyl)-7-(o-tolyl)-7,8-dihydro-6H-pyrimido[5,4-b][1,4]oxazin-2-amine;
(+)-8-methyl-N-(4-(4-methyl-1H-imidazol-1-yl)phenyl)-7-(o-tolyl)-7,8-dihydro-6H-pyrimido[5,4-b][1,4]oxazin-2-amine;
8-methyl-N-(4-(4-methyl-1H-imidazol-1-yl)phenyl)-7-(3,4,5-trifluorophenyl)-7,8-dihydro-6H-pyrimido[5,4-b][1,4]oxazin-2-amine;
N-(3-methoxy-4-(4-methyl-1H-imidazol-1-yl)phenyl)-8-methyl-7-phenyl-7,8-dihydro-6H-pyrimido[5,4-b][1,4]oxazin-2-amine;
N-(3-methoxy-4-(2-methylpyridin-4-yl)phenyl)-8-methyl-7-phenyl-7,8-dihydro-6H-pyrimido[5,4-b][1,4]oxazin-2-amine;
7-benzyl-N-(3-methoxy-4-(4-methyl-1H-imidazol-1-yl)phenyl)-8-methyl-7,8-dihydro-6H-pyrimido [5, 4-b] [1, 4] oxazin-2-amine;
(+)-7-benzyl-N-(3-methoxy-4-(4-methyl-1H-imidazol-1-yl) phenyl)-8-methyl-7, 8-dihydro-6H-pyrimido [5, 4-b] [1, 4] oxazin-2-amine;
(−)-7-benzyl-N-(3-methoxy-4-(4-methyl-1H-imidazol-1-yl) phenyl)-8-methyl-7, 8-dihydro-6H-pyrimido [5, 4-b] [1, 4] oxazin-2-amine;
7-(2, 4-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;
(+)-7-(2, 4-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;
7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;
(−)-7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;
(+)-7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;
N-(3-methoxy-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine;
7-(2-chlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;
(−)-7-(2-chlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;
(+)-7-(2-chlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;
N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine;
7-(2-chloro-4-fluorophenyl)-N-(3-methoxy-4-(4-methyl-1H-imidazol-1-yl) phenyl)-8-methyl-7,8-dihydro-6H-pyrimido [5, 4-b] [1,4] oxazin-2-amine;
7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;
N-(3-methoxy-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine;
(−)-N-(3-methoxy-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine;
(+)-N-(3-methoxy-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine;
(+)-N-(3-fluoro-4-(2-methylpyridin-4-yl) phenyl)-7-(4-fluorophenyl)-8-methyl-7, 8-dihydro-6H-pyrimido [5, 4-b] [1, 4] oxazin-2-amine;
(+)-7-benzyl-N-(3-fluoro-4-(2-methylpyridin-4-yl) phenyl)-8-methyl-7, 8-dihydro-6H-pyrimido [5, 4-b] [1, 4] oxazin-2-amine;
(+)-N-(3-fluoro-4-(4-methyl-1H-imidazol-1-yl) phenyl)-7-(4-fluorophenyl)-8-methyl-7, 8-dihydro-6H-pyrimido [5, 4-b] [1, 4] oxazin-2-amine;
(+)-7-benzyl-N-(3-fluoro-4-(4-methyl-1H-imidazol-1-yl) phenyl)-8-methyl-7, 8-dihydro-6H-pyrimido [5, 4-b] [1, 4] oxazin-2-amine;
(−)-N-(3-methoxy-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine;
(+)-N-(3-methoxy-4-(4-methyl-1H-imidazol-1-yl) phenyl)-8-methyl-7-(2-(trifluoromethoxy) phenyl)-7, 8-dihydro-6H-pyrimido [5, 4-b] [1, 4] oxazin-2-amine;
(+)-7-(4-fluorophenyl)-N-(3-methoxy-4-(2-methylpyridin-4-yl) phenyl)-8-methyl-7, 8-dihydro-6H-pyrimido [5, 4-b] [1, 4] oxazin-2-amine;
(+)-N-(3-methoxy-4-(2-methylpyridin-4-yl) phenyl)-8-methyl-7-(2-(trifluoromethoxy) phenyl)-7, 8-dihydro-6H-pyrimido [5, 4-b] [1, 4] oxazin-2-amine;
(+)-7-(2, 4-difluorophenyl)-N-(3-methoxy-4-(2-methylpyridin-4-yl) phenyl)-8-methyl-7, 8-dihydro-6H-pyrimido [5, 4-b] [1, 4] oxazin-2-amine;
N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine;
(+)-7-(2-chlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine;
(+)-7-benzyl-N-(3-methoxy-4-(2-methylpyridin-4-yl) phenyl)-8-methyl-7, 8-dihydro-6H-pyrimido [5, 4-b] [1, 4] oxazin-2-amine;
(−)-7-benzyl-N-(3-methoxy-4-(2-methylpyridin-4-yl) phenyl)-8-methyl-7, 8-dihydro-6H-pyrimido [5, 4-b] [1, 4] oxazin-2-amine;
(+)-7-(2, 4-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine;
(+)-N-(3-methoxy-4-(2-methylpyridin-4-yl) phenyl)-8-methyl-7-(2-(trifluoromethyl) phenyl)-7, 8-dihydro-6H-pyrimido [5, 4-b] [1, 4] oxazin-2-amine;
(+)-N-(3-fluoro-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine;

(+)-2-(2-chlorophenyl)-N-(3-methoxy-4-(2-methylpyridin-4-yl) phenyl)-1-methyl-2, 3-dihydro-1H-pyrido [3, 4-b] [1, 4] oxazin-7-amine;

7-(2-chloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(−)-7-(2-chloro-4-fluorophenyl)-N-(3-methoxy-4-(4-methyl-1H-imidazol-1-yl) phenyl)-8-methyl-7,8-dihydro-6H-pyrimido [5, 4-b] [1,4] oxazin-2-amine;

(+)-7-(2-chloro-4-fluorophenyl)-N-(3-methoxy-4-(4-methyl-1H-imidazol-1-yl) phenyl)-8-methyl-7,8-dihydro-6H-pyrimido [5, 4-b] [1,4] oxazin-2-amine;

(−)-7-(4-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(4-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(−)-7-(2, 4-dichlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(2, 4-dichlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(2, 4-dichlorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine;

(−)-N-(3-methoxy-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine;

(+)-N-(3-methoxy-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine;

(+)-N-(3-fluoro-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine;

(+)-7-(4-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine;

(+)-7-(5-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine;

(+)-7-(2-chloro-4-fluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine;

(+)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine;

(−)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine;

(+)-7-(5-fluoro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine;

(−)-7-(5-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(5-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(4-chloro-2-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine;

(+)-7-(4-chloro-2-(trifluoromethyl) phenyl)-N-(3-methoxy-4-(2-methylpyridin-4-yl) phenyl)-8-methyl-7, 8-dihydro-6H-pyrimido [5, 4-b] [1, 4] oxazin-2-amine;

(+)-N-(3-fluoro-4-(4-methyl-1H-imidazol-1-yl) phenyl)-7, 8-dimethyl-7, 8-dihydro-6H-pyrimido [5, 4-b] [1, 4] oxazin-2-amine;

(+)-N-(3-fluoro-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine;

(−)-N-(3-methoxy-4-(2-methylpyridin-4-yl) phenyl)-7, 8-dimethyl-7, 8-dihydro-6H-pyrimido [5, 4-b] [1, 4] oxazin-2-amine;

(+)-N-(3-methoxy-4-(2-methylpyridin-4-yl) phenyl)-7, 8-dimethyl-7, 8-dihydro-6H-pyrimido [5, 4-b] [1, 4] oxazin-2-amine;

(S)—N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine;

(−)-7-(4-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(4-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-N-(3-methoxy-4-(4-methyl-1H-imidazol-1-yl) phenyl)-8-methyl-7-(tetrahydro-2H-pyran-4-yl)-7, 8-dihydro-6H-pyrimido [5, 4-b] [1, 4] oxazin-2-amine;

(+)-8-methyl-N-(4-(4-methyl-1H-imidazol-1-yl) phenyl)-7-(3, 4, 5-trifluorophenyl)-7, 8-dihydro-6H-pyrimido [5, 4-b] [1, 4] oxazin-2-amine;

(−)-N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine;

(+)-N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine;

(−)-7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine;

(+)-7-(5-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(−)-7-(5-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(−)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(−)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(2, 4-bis (trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine;

(+)-N-(5-methoxy-6-(4-methyl-1H-imidazol-1-yl) pyridin-3-yl)-8-methyl-7-(o-tolyl)-7, 8-dihydro-6H-pyrimido [5, 4-b] [1, 4] oxazin-2-amine;

(−)-N-(5-methoxy-6-(4-methyl-1H-imidazol-1-yl) pyridin-3-yl)-8-methyl-7-(o-tolyl)-7, 8-dihydro-6H-pyrimido [5, 4-b] [1, 4] oxazin-2-amine;

(−)-N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine;

(+)-N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine;

(+)-7-(2-chloro-5-(trifluoromethyl) phenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine;

(−)-7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(−)-7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(4, 5-difluoro-2-(trifluoromethyl) phenyl)-N-(1-(2-methoxypyridin-4-yl) piperidin-4-yl)-8-methyl-7, 8-dihydro-6H-pyrimido [5, 4-b] [1, 4] oxazin-2-amine;

(−)-7-(4, 5-difluoro-2-(trifluoromethyl) phenyl)-N-(1-(2-methoxypyridin-4-yl) piperidin-4-yl)-8-methyl-7, 8-dihydro-6H-pyrimido [5, 4-b] [1, 4] oxazin-2-amine;

(+)-N-(5-methoxy-6-(4-methyl-1H-imidazol-1-yl) pyridin-3-yl)-8-methyl-7-(2, 4, 5-trifluorophenyl)-7, 8-dihydro-6H-pyrimido [5, 4-b] [1, 4] oxazin-2-amine;

(+)-N-(5-methoxy-6-(4-methyl-1H-imidazol-1-yl) pyridin-3-yl)-8-methyl-7-(3, 4, 5-trifluorophenyl)-7, 8-dihydro-6H-pyrimido [5, 4-b] [1, 4] oxazin-2-amine;

(−)-N-(5-methoxy-6-(4-methyl-1H-imidazol-1-yl) pyridin-3-yl)-8-methyl-7-(3, 4, 5-trifluorophenyl)-7, 8-dihydro-6H-pyrimido [5, 4-b] [1, 4] oxazin-2-amine;

(+)-N-(5-methoxy-6-(4-methyl-1H-imidazol-1-yl) pyridin-3-yl)-7, 8-dimethyl-7, 8-dihydro-6H-pyrimido [5, 4-b] [1, 4] oxazin-2-amine;

(+)-7-(2, 4-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(−)-N-(3-methoxy-4-(4-methyl-1H-imidazol-1-yl) phenyl)-8-methyl-7-(trifluoromethyl)-7, 8-dihydro-6H-pyrimido [5, 4-b] [1, 4] oxazin-2-amine;

(+)-7-(3, 5-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(−)-N-(5-methoxy-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine;

(+)-N-(5-methoxy-6-(4-methyl-1H-imidazol-1-yl) pyridin-3-yl)-7, 7, 8-trimethyl-7, 8-dihydro-6H-pyrimido [5, 4-b] [1, 4] oxazin-2-amine;

(+)-7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(−)-7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(S)—N-(3-methoxy-4-(4-methyl-1H-imidazol-1-yl) phenyl)-8-methyl-7-(phenoxymethyl)-7, 8-dihydro-6H-pyrimido [5, 4-b] [1, 4] oxazin-2-amine;

(R)—N-(3-methoxy-4-(4-methyl-1H-imidazol-1-yl) phenyl)-8-methyl-7-(phenoxymethyl)-7, 8-dihydro-6H-pyrimido [5, 4-b] [1, 4] oxazin-2-amine;

(−)-N-(4-(4-chloro-1H-imidazol-1-yl)-3-methoxyphenyl)-7, 8-dimethyl-7, 8-dihydro-6H-pyrimido [5, 4-b] [1, 4] oxazin-2-amine;

(+)-N-(4-(4-chloro-1H-imidazol-1-yl)-3-methoxyphenyl)-7, 8-dimethyl-7, 8-dihydro-6H-pyrimido [5, 4-b] [1, 4] oxazin-2-amine;

(+)-5-((7-(3, 5-difluorophenyl)-8-methyl-7, 8-dihydro-6H-pyrimido [5, 4-b] [1, 4] oxazin-2-yl) amino)-2-(4-methyl-1H-imidazol-1-yl) benzonitrile;

(−)-5-((7-(3, 5-difluorophenyl)-8-methyl-7, 8-dihydro-6H-pyrimido [5, 4-b] [1, 4] oxazin-2-yl) amino)-2-(4-methyl-1H-imidazol-1-yl) benzonitrile;

(+)-N-(4-(4-chloro-1H-imidazol-1-yl)-3-methoxyphenyl)-7-(3, 5-difluorophenyl)-8-methyl-7, 8-dihydro-6H-pyrimido [5, 4-b] [1, 4] oxazin-2-amine;

(+)-5-((7, 8-dimethyl-7, 8-dihydro-6H-pyrimido [5, 4-b] [1, 4] oxazin-2-yl) amino)-2-(4-methyl-1H-imidazol-1-yl) benzonitrile;

(+)-7-(3, 5-difluorophenyl)-N-(5-methoxy-6-(4-(trifluoromethyl)-1H-imidazol-1-yl) pyridin-3-yl)-8-methyl-7, 8-dihydro-6H-pyrimido [5, 4-b] [1, 4] oxazin-2-amine;

(+)-7-(5-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(−)-7-(5-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(+)-7-(2-chloro-5-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(−)-7-(2-chloro-5-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(+)-7-(2-chloro-4-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(−)-7-(2-chloro-4-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(+)-N-(5-chloro-6-(4-methyl-1H-imidazol-1-yl) pyridin-3-yl)-7-(3, 5-difluorophenyl)-8-methyl-7, 8-dihydro-6H-pyrimido [5, 4-b] [1, 4] oxazin-2-amine;

(+)-1-(5-((7-(3, 5-difluorophenyl)-8-methyl-7, 8-dihydro-6H-pyrimido [5, 4-b] [1, 4] oxazin-2-yl) amino)-3-methoxypyridin-2-yl)-1H-imidazole-4-carbonitrile;

(+)-7-(3, 3-difluorocyclobutyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(4-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(−)-7-(4-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(+)-7-(4, 4-difluorocyclohexyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(S)-7-(cyclopropylmethyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(S)-7-(cyclopropylmethyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(+)-7-(3, 3-difluorocyclobutyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(+)-7-(3, 5-difluorophenyl)-N-(4-methoxy-5-(4-methyl-1H-imidazol-1-yl) pyridin-2-yl)-8-methyl-7, 8-dihydro-6H-pyrimido [5, 4-b] [1, 4] oxazin-2-amine;

(+)-7-(4, 4-difluorocyclohexyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(S)-7-cyclopropyl-N-(3-methoxy-4-(4-methyl-1H-imidazol-1-yl) phenyl)-8-methyl-7, 8-dihydro-6H-pyrimido [5, 4-b] [1, 4] oxazin-2-amine;

(S)-7-cyclopropyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(S)-7-cyclobutyl-N-(3-methoxy-4-(4-methyl-1H-imidazol-1-yl) phenyl)-8-methyl-7, 8-dihydro-6H-pyrimido [5, 4-b] [1, 4] oxazin-2-amine;

(−)-N-(4-(4-chloro-1H-imidazol-1-yl)-3-methoxyphenyl)-8-methyl-7-(trifluoromethyl)-7, 8-dihydro-6H-pyrimido [5, 4-b] [1, 4] oxazin-2-amine;

(−)-N-(5-chloro-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine;

(−)-2-(4-methyl-1H-imidazol-1-yl)-5-((8-methyl-7-(trifluoromethyl)-7, 8-dihydro-6H-pyrimido [5, 4-b] [1, 4] oxazin-2-yl) amino) benzonitrile;

(S)-7-cyclobutyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(−)-N-(4-methoxy-5-(4-methyl-1H-imidazol-1-yl) pyridin-2-yl)-8-methyl-7-(trifluoromethyl)-7, 8-dihydro-6H-pyrimido [5, 4-b] [1, 4] oxazin-2-amine;

(+)-4-((7-(3, 5-difluorophenyl)-8-methyl-7, 8-dihydro-6H-pyrimido [5, 4-b] [1, 4] oxazin-2-yl) amino)-2-methoxybenzonitrile;

(+)-N-(5-methoxy-6-(4-methyl-1H-imidazol-1-yl) pyridin-3-yl)-8-methyl-7-(2, 2, 2-trifluoroethyl)-7, 8-dihydro-6H-pyrimido [5, 4-b] [1, 4] oxazin-2-amine;

(S)-7-(tert-butyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(−)-N-(3-methoxy-4-(3-methyl-1H-1, 2, 4-triazol-1-yl) phenyl)-8-methyl-7-(trifluoromethyl)-7, 8-dihydro-6H-pyrimido [5, 4-b] [1, 4] oxazin-2-amine;

(+)-7-(3, 5-difluorophenyl)-N-(3-methoxy-4-(3-methyl-1H-1, 2, 4-triazol-1-yl) phenyl)-8-methyl-7, 8-dihydro-6H-pyrimido [5, 4-b] [1, 4] oxazin-2-amine;

(−)-N-(3-methoxy-4-(4-methyl-1H-imidazol-1-yl) phenyl)-8-methyl-7-(1-(trifluoromethyl) cyclopropyl)-7, 8-dihydro-6H-pyrimido [5, 4-b] [1, 4] oxazin-2-amine;

(+)-N-(3-methoxy-4-(4-methyl-1H-imidazol-1-yl) phenyl)-8-methyl-7-(1-(trifluoromethyl) cyclopropyl)-7, 8-dihydro-6H-pyrimido [5, 4-b] [1, 4] oxazin-2-amine;

(S)-7-(tert-butyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(S)—N-(3-methoxy-4-(4-methyl-1H-imidazol-1-yl) phenyl)-7-(methoxymethyl)-8-methyl-7, 8-dihydro-6H-pyrimido [5, 4-b] [1, 4] oxazin-2-amine (−)-N-(5-methoxy-6-(4-methyl-1H-imidazol-1-yl) pyridin-3-yl)-8-methyl-7-(1-(trifluoromethyl) cyclopropyl)-7, 8-dihydro-6H-pyrimido [5, 4-b] [1, 4] oxazin-2-amine; and (+)-N-(5-methoxy-6-(4-methyl-1H-imidazol-1-yl) pyridin-3-yl)-8-methyl-7-(1-(trifluoromethyl) cyclopropyl)-7, 8-dihydro-6H-pyrimido [5, 4-b] [1, 4] oxazin-2-amine;

or a pharmaceutically acceptable salt thereof.

7. The compound of claim 6, selected from the group consisting of:

(S)—N-(3-methoxy-4-(4-methyl-1H-imidazol-1-yl)phenyl)-8-methyl-7-phenyl-7,8-dihydro-6H-pyrimido[5,4-b][1,4]oxazin-2-amine;

(S)—N-(3-methoxy-4-(2-methylpyridin-4-yl)phenyl)-8-methyl-7-phenyl-7,8-dihydro-6H-pyrimido[5,4-b][1,4]oxazin-2-amine;

7-(3,5-difluorophenyl)-8-methyl-N-(4-(4-methyl-1H-imidazol-1-yl)phenyl)-7,8-dihydro-6H-pyrimido[5,4-b][1,4]oxazin-2-amine;

(+)-7-(3, 5-difluorophenyl)-8-methyl-N-(4-(4-methyl-1H-imidazol-1-yl) phenyl)-7, 8-dihydro-6H-pyrimido [5, 4-b] [1, 4] oxazin-2-amine;

(+)-N-(3-fluoro-4-(4-methyl-1H-imidazol-1-yl)phenyl)-8-methyl-7-phenyl-7,8-dihydro-6H-pyrimido[5,4-b][1,4]oxazin-2-amine;

(+)-8-methyl-N-(4-(4-methyl-1H-imidazol-1-yl)phenyl)-7-phenyl-7,8-dihydro-6H-pyrimido[5,4-b][1,4]oxazin-2-amine;

7-(3,5-difluorophenyl)-N-(3-methoxy-4-(4-methyl-1H-imidazol-1-yl)phenyl)-8-methyl-7,8-dihydro-6H-pyrimido[5,4-b][1,4]oxazin-2-amine;

(+)-7-(3,5-difluorophenyl)-N-(3-methoxy-4-(4-methyl-1H-imidazol-1-yl)phenyl)-8-methyl-7,8-dihydro-6H-pyrimido[5,4-b][1,4]oxazin-2-amine;

N-(3-methoxy-4-(4-methyl-1H-imidazol-1-yl)phenyl)-8-methyl-7-(o-tolyl)-7,8-dihydro-6H-pyrimido[5,4-b][1,4]oxazin-2-amine;

(+)-N-(3-methoxy-4-(4-methyl-1H-imidazol-1-yl)phenyl)-8-methyl-7-(o-tolyl)-7,8-dihydro-6H-pyrimido[5,4-b][1,4]oxazin-2-amine;

7-(3,5-difluorophenyl)-N-(3-fluoro-4-(4-methyl-1H-imidazol-1-yl)phenyl)-8-methyl-7,8-dihydro-6H-pyrimido[5,4-b][1,4]oxazin-2-amine;

(+)-7-(3,5-difluorophenyl)-N-(3-fluoro-4-(4-methyl-1H-imidazol-1-yl)phenyl)-8-methyl-7,8-dihydro-6H-pyrimido[5,4-b][1,4]oxazin-2-amine;

N-(3-fluoro-4-(4-methyl-1H-imidazol-1-yl)phenyl)-8-methyl-7-(o-tolyl)-7,8-dihydro-6H-pyrimido[5,4-b][1,4]oxazin-2-amine;

(+)-N-(3-fluoro-4-(4-methyl-1H-imidazol-1-yl)phenyl)-8-methyl-7-(o-tolyl)-7,8-dihydro-6H-pyrimido[5,4-b][1,4]oxazin-2-amine;

(+)-N-(3-methoxy-4-(2-methylpyridin-4-yl)phenyl)-8-methyl-7-(o-tolyl)-7,8-dihydro-6H-pyrimido[5,4-b][1,4]oxazin-2-amine;

N-(3-fluoro-4-(4-methyl-1H-imidazol-1-yl)phenyl)-8-methyl-7-(3,4,5-trifluorophenyl)-7,8-dihydro-6H-pyrimido[5,4-b][1,4]oxazin-2-amine;

N-(3-methoxy-4-(2-methylpyridin-4-yl)phenyl)-8-methyl-7-(3,4,5-trifluorophenyl)-7,8-dihydro-6H-pyrimido[5,4-b][1,4]oxazin-2-amine;

(+)-N-(3-methoxy-4-(2-methylpyridin-4-yl)phenyl)-8-methyl-7-(3,4,5-trifluorophenyl)-7,8-dihydro-6H-pyrimido[5,4-b][1,4]oxazin-2-amine;

N-(3-methoxy-4-(4-methyl-1H-imidazol-1-yl)phenyl)-8-methyl-7-(3,4,5-trifluorophenyl)-7,8-dihydro-6H-pyrimido[5,4-b][1,4]oxazin-2-amine;

(+)-N-(3-methoxy-4-(4-methyl-1H-imidazol-1-yl)phenyl)-8-methyl-7-(3,4,5-trifluorophenyl)-7,8-dihydro-6H-pyrimido[5,4-b][1,4]oxazin-2-amine;

7-(3,5-difluorophenyl)-N-(3-methoxy-4-(2-methylpyridin-4-yl)phenyl)-8-methyl-7,8-dihydro-6H-pyrimido[5,4-b][1,4]oxazin-2-amine;

(+)-7-(3,5-difluorophenyl)-N-(3-methoxy-4-(2-methylpyridin-4-yl)phenyl)-8-methyl-7,8-dihydro-6H-pyrimido[5,4-b][1,4]oxazin-2-amine;

(+)-8-methyl-N-(4-(4-methyl-1H-imidazol-1-yl)phenyl)-7-(o-tolyl)-7,8-dihydro-6H-pyrimido[5,4-b][1,4]oxazin-2-amine;

N-(3-methoxy-4-(2-methylpyridin-4-yl)phenyl)-8-methyl-7-phenyl-7,8-dihydro-6H-pyrimido[5,4-b][1,4]oxazin-2-amine;

7-benzyl-N-(3-methoxy-4-(4-methyl-1H-imidazol-1-yl)phenyl)-8-methyl-7,8-dihydro-6H-pyrimido [5, 4-b] [1, 4] oxazin-2-amine;

(+)-7-benzyl-N-(3-methoxy-4-(4-methyl-1H-imidazol-1-yl) phenyl)-8-methyl-7, 8-dihydro-6H-pyrimido [5, 4-b] [1, 4] oxazin-2-amine;

7-(2, 4-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(2, 4-difluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(4-fluorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

7-(2-chlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(−)-7-(2-chlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

7-(2-chloro-4-fluorophenyl)-N-(3-methoxy-4-(4-methyl-1H-imidazol-1-yl) phenyl)-8-methyl-7,8-dihydro-6H-pyrimido [5, 4-b] [1,4] oxazin-2-amine;

N-(3-methoxy-4-(4-methyl-1H-imidazol-1-yl) phenyl)-8-methyl-7-(2-(trifluoromethyl) phenyl)-7, 8-dihydro-6H-pyrimido [5, 4-b] [1, 4] oxazin-2-amine;

(+)-N-(3-fluoro-4-(4-methyl-1H-imidazol-1-yl) phenyl)-7-(4-fluorophenyl)-8-methyl-7, 8-dihydro-6H-pyrimido [5, 4-b] [1, 4] oxazin-2-amine;

(+)-7-benzyl-N-(3-methoxy-4-(2-methylpyridin-4-yl) phenyl)-8-methyl-7, 8-dihydro-6H-pyrimido [5, 4-b] [1, 4] oxazin-2-amine;

7-(2-chloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(2-chloro-5-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(2-chloro-4-fluorophenyl)-N-(3-methoxy-4-(4-methyl-1H-imidazol-1-yl) phenyl)-8-methyl-7,8-dihydro-6H-pyrimido [5, 4-b] [1,4] oxazin-2-amine;

(+)-7-(4-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(2, 4-dichlorophenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-N-(3-methoxy-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine;

(+)-N-(3-fluoro-4-(4-methyl-1H-imidazol-1-yl) phenyl)-8-methyl-7-(2, 4, 5-trifluorophenyl)-7, 8-dihydro-6H-pyrimido [5, 4-b] [1, 4] oxazin-2-amine;

(+)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine;

(+)-7-(5-fluoro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(4-chloro-2-(trifluoromethyl) phenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-8-methyl-N-(4-(4-methyl-1H-imidazol-1-yl) phenyl)-7-(3, 4, 5-trifluorophenyl)-7, 8-dihydro-6H-pyrimido [5, 4-b] [1, 4] oxazin-2-amine;

(+)-N-(3-methoxy-4-(4-methyl-1H-imidazol-1-yl) phenyl)-7, 8-dimethyl-7, 8-dihydro-6H-pyrimido [5, 4-b] [1, 4] oxazin-2-amine;

(+)-7-(4-fluoro-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-N-(3-fluoro-4-(4-methyl-1H-imidazol-1-yl) phenyl)-8-methyl-7-(3, 4, 5-trifluorophenyl)-7, 8-dihydro-6H-pyrimido [5, 4-b] [1, 4] oxazin-2-amine;

(+)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(2-chloro-5-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(2-chloro-4, 5-difluorophenyl)-N-(3-fluoro-4-(4-methyl-1H-imidazol-1-yl) phenyl)-8-methyl-7, 8-dihydro-6H-pyrimido [5, 4-b] [1, 4] oxazin-2-amine;

(+)-N-(5-methoxy-6-(4-methyl-1H-imidazol-1-yl) pyridin-3-yl)-8-methyl-7-(o-tolyl)-7, 8-dihydro-6H-pyrimido [5, 4-b] [1, 4] oxazin-2-amine;

(+)-N-(3-methoxy-4-(4-methyl-1H-imidazol-1-yl) phenyl)-1-methyl-2-(2, 2, 2-trifluoroethyl)-2, 3-dihydro-1H-pyrido [3, 4-b] [1, 4] oxazin-7-amine;

(+)-7-(2, 5-dichloro-4-methoxyphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(5-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(4, 5-difluoro-2-(trifluoromethyl) phenyl)-N-(1-(2-methoxypyridin-4-yl) piperidin-4-yl)-8-methyl-7, 8-dihydro-6H-pyrimido [5, 4-b] [1, 4] oxazin-2-amine;

(+)-N-(5-methoxy-6-(4-methyl-1H-imidazol-1-yl) pyridin-3-yl)-8-methyl-7-(2, 4, 5-trifluorophenyl)-7, 8-dihydro-6H-pyrimido [5, 4-b] [1, 4] oxazin-2-amine;

(+)-N-(5-methoxy-6-(4-methyl-1H-imidazol-1-yl) pyridin-3-yl)-8-methyl-7-(3, 4, 5-trifluorophenyl)-7, 8-dihydro-6H-pyrimido [5, 4-b] [1, 4] oxazin-2-amine;

(+)-7-(2, 4-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(−)-N-(3-methoxy-4-(4-methyl-1H-imidazol-1-yl) phenyl)-8-methyl-7-(trifluoromethyl)-7, 8-dihydro-6H-pyrimido [5, 4-b] [1, 4] oxazin-2-amine;

(+)-7-(3, 5-difluorophenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(−)-N-(5-methoxy-6-(4-methyl-1H-imidazol-1-yl) pyridin-3-yl)-8-methyl-7-(trifluoromethyl)-7, 8-dihydro-6H-pyrimido [5, 4-b] [1, 4] oxazin-2-amine;

(+)-7-(4-methoxy-2-methylphenyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(S)—N-(3-methoxy-4-(4-methyl-1H-imidazol-1-yl) phenyl)-8-methyl-7-(phenoxymethyl)-7, 8-dihydro-6H-pyrimido [5, 4-b] [1, 4] oxazin-2-amine;

(+)-N-(4-(4-chloro-1H-imidazol-1-yl)-3-methoxyphenyl)-7, 8-dimethyl-7, 8-dihydro-6H-pyrimido [5, 4-b] [1, 4] oxazin-2-amine;

(+)-5-((7-(3, 5-difluorophenyl)-8-methyl-7, 8-dihydro-6H-pyrimido [5, 4-b] [1, 4] oxazin-2-yl) amino)-2-(4-methyl-1H-imidazol-1-yl) benzonitrile;

(+)-N-(4-(4-chloro-1H-imidazol-1-yl)-3-methoxyphenyl)-7-(3, 5-difluorophenyl)-8-methyl-7, 8-dihydro-6H-pyrimido [5, 4-b] [1, 4] oxazin-2-amine;

(+)-7-(3, 5-difluorophenyl)-N-(5-methoxy-6-(4-(trifluoromethyl)-1H-imidazol-1-yl) pyridin-3-yl)-8-methyl-7, 8-dihydro-6H-pyrimido [5, 4-b] [1, 4] oxazin-2-amine;

(+)-7-(5-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(+)-7-(2-chloro-5-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(+)-7-(2-chloro-4-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(−)-7-(2-chloro-4-methoxyphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(+)-N-(5-chloro-6-(4-methyl-1H-imidazol-1-yl) pyridin-3-yl)-7-(3, 5-difluorophenyl)-8-methyl-7, 8-dihydro-6H-pyrimido [5, 4-b] [1, 4] oxazin-2-amine;

(+)-7-(3, 3-difluorocyclobutyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(4-methoxy-2-methylphenyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(+)-7-(4, 4-difluorocyclohexyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(S)-7-(cyclopropylmethyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(S)-7-(cyclopropylmethyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(+)-7-(3, 3-difluorocyclobutyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(+)-7-(3, 5-difluorophenyl)-N-(4-methoxy-5-(4-methyl-1H-imidazol-1-yl) pyridin-2-yl)-8-methyl-7, 8-dihydro-6H-pyrimido [5, 4-b] [1, 4] oxazin-2-amine;

(+)-7-(4, 4-difluorocyclohexyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(S)-7-cyclopropyl-N-(3-methoxy-4-(4-methyl-1H-imidazol-1-yl) phenyl)-8-methyl-7, 8-dihydro-6H-pyrimido [5, 4-b] [1, 4] oxazin-2-amine;

(S)-7-cyclopropyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(S)-7-cyclobutyl-N-(3-methoxy-4-(4-methyl-1H-imidazol-1-yl) phenyl)-8-methyl-7, 8-dihydro-6H-pyrimido [5, 4-b] [1, 4] oxazin-2-amine;

(−)-N-(4-(4-chloro-1H-imidazol-1-yl)-3-methoxyphenyl)-8-methyl-7-(trifluoromethyl)-7, 8-dihydro-6H-pyrimido [5, 4-b] [1, 4] oxazin-2-amine;

(−)-2-(4-methyl-1H-imidazol-1-yl)-5-((8-methyl-7-(trifluoromethyl)-7, 8-dihydro-6H-pyrimido [5, 4-b] [1, 4] oxazin-2-yl) amino) benzonitrile;

(S)-7-cyclobutyl-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine;

(+)-N-(5-methoxy-6-(4-methyl-1H-imidazol-1-yl) pyridin-3-yl)-8-methyl-7-(2, 2, 2-trifluoroethyl)-7, 8-dihydro-6H-pyrimido [5, 4-b] [1, 4] oxazin-2-amine;

(S)-7-(tert-butyl)-N-(3-methoxy-4-(4-methyl-1H-imidazol-1-yl) phenyl)-8-methyl-7, 8-dihydro-6H-pyrimido [5, 4-b] [1, 4] oxazin-2-amine;

(+)-7-(3, 5-difluorophenyl)-N-(3-methoxy-4-(3-methyl-1H-1, 2, 4-triazol-1-yl) phenyl)-8-methyl-7, 8-dihydro-6H-pyrimido [5, 4-b] [1, 4] oxazin-2-amine;

(+)-N-(3-methoxy-4-(4-methyl-1H-imidazol-1-yl) phenyl)-8-methyl-7-(1-(trifluoromethyl) cyclopropyl)-7, 8-dihydro-6H-pyrimido [5, 4-b] [1, 4] oxazin-2-amine;

(S)-7-(tert-butyl)-N-(5-methoxy-6-(4-methyl-1H-imidazol-1-yl) pyridin-3-yl)-8-methyl-7, 8-dihydro-6H-pyrimido [5, 4-b] [1, 4] oxazin-2-amine; and (+)-N-(5-methoxy-6-(4-methyl-1H-imidazol-1-yl) pyridin-3-yl)-8-methyl-7-(1-(trifluoromethyl) cyclopropyl)-7, 8-dihydro-6H-pyrimido [5, 4-b] [1, 4] oxazin-2-amine;

or a pharmaceutically acceptable salt thereof.

8. A compound of Formula (II)

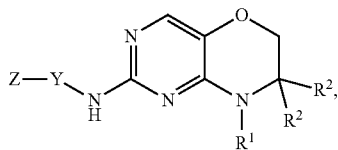

or a pharmaceutically acceptable salt thereof, wherein:

R1 is —C1-C4 alkyl which is unsubstituted or substituted with one or more -halo;

each R2 is independently C1-C6 alkyl, or R1 and one R2 together with the intervening atoms form a nitrogen-containing 4- to 6-membered nonaromatic heterocycle and the other R2 is hydrogen or C1-C4 alkyl, or both R2 together with the intervening atom form a —C3-C8 monocyclic cycloalkyl or an oxygen-containing 3- to 6-membered nonaromatic heterocycle, wherein the nitrogen-containing 4- to 6-membered nonaromatic heterocycle, the —C3-C8 monocyclic cycloalkyl or the oxygen-containing 3- to 6-membered nonaromatic heterocycle is unsubstituted or substituted with one or more substituents independently selected from the group consisting of -halo, —CN, —C1-C4 alkyl, halo-substituted C1-C4 alkyl, —C1-C4 alkoxy and oxo;

Y is phenyl or pyridinyl, each of which is unsubstituted or substituted with one or more substituents independently selected from the group consisting of -halo, —C1-C4 alkoxy, halo-substituted C1-C4 alkoxy, —C1-C4 alkyl and halo-substituted C1-C4 alkyl; and Z is imidazolyl or pyrazolyl, each of which is unsubstituted or substituted with one or more substituents independently selected from the group consisting of -halo and —C1-C4 alkyl.

9. The compound of claim 8, wherein:

R1 is methyl;

R2 is independently C1-C6 alkyl, or R1 and one R2 together with the intervening atoms form a nitrogen-containing 4- to 6-membered nonaromatic heterocycle and the other R2 is hydrogen or C1-C4 alkyl, or both R2 together with the intervening atom form a —C3-C8 monocyclic cycloalkyl or an oxygen-containing 3- to 6-membered nonaromatic heterocycle, wherein the nitrogen-containing 4- to 6-membered nonaromatic heterocycle, the —C3-C8 monocyclic cycloalkyl or the oxygen-containing 3- to 6-membered nonaromatic heterocycle is unsubstituted or substituted with one or more substituents independently selected from the group consisting of -halo and oxo;

Y is phenyl or pyridinyl, each of which is substituted with one or more substituent independently selected from the group consisting of -halo and —C1-C4 alkoxy; and Z is imidazolyl or pyrazolyl, each of which is substituted with one or more substituents independently selected from the group consisting of -halo and —C1-C4 alkyl;

or a pharmaceutically acceptable salt thereof.

10. The compound of claim 8, wherein:

R1 is methyl;

R2 is independently C1-C6 alkyl, or R1 and one R2 together with the intervening atoms form a nitrogen-containing 4- to 6-membered nonaromatic heterocycle and the other R2 is hydrogen or C1-C4 alkyl, or both R2 together with the intervening atom form a —C3-C8 monocyclic cycloalkyl or an oxygen-containing 3- to 6-membered nonaromatic heterocycle, wherein the nitrogen-containing 4- to 6-membered nonaromatic heterocycle, the —C3-C8 monocyclic cycloalkyl or the oxygen-containing 3- to 6-membered nonaromatic heterocycle is unsubstituted or substituted with one or more -halo;

Y is phenyl or pyridinyl, each of which is substituted with one or more substituents independently selected from the group consisting of -halo and —C1-C4 alkoxy; and Z is imidazolyl or pyrazolyl, each of which is substituted with one or more substituents independently selected from the group consisting of -halo and —C1-C4 alkyl;

or a pharmaceutically acceptable salt thereof.

11. The compound of claim 8 selected from the group consisting of:

N-(3-methoxy-4-(4-methyl-1H-imidazol-1-yl) phenyl)-7, 7, 8-trimethyl-7, 8-dihydro-6H-pyrimido [5, 4-b] [1, 4] oxazin-2-amine;

N-(3-fluoro-4-(4-methyl-1H-imidazol-1-yl) phenyl)-7, 7, 8-trimethyl-7, 8-dihydro-6H-pyrimido [5, 4-b] [1, 4] oxazin-2-amine;

N-(3-methoxy-4-(4-methyl-1H-imidazol-1-yl) phenyl)-8'-methyl-6'H, 8'H-spiro [cyclopropane-1, 7'-pyrimido [5, 4-b] [1, 4] oxazin]-2'-amine;

N-(3-fluoro-4-(4-methyl-1H-imidazol-1-yl) phenyl)-8'-methyl-6'H, 8'H-spiro [cyclopentane-1, 7'-pyrimido [5, 4-b] [1, 4] oxazin]-2'-amine;

N-(5-methoxy-6-(4-methyl-1H-imidazol-1-yl) pyridin-3-yl)-8'-methyl-6'H, 8'H-spiro [cyclopentane-1, 7'-pyrimido [5, 4-b] [1, 4] oxazin]-2'-amine;

N-(5-methoxy-6-(4-methyl-1H-imidazol-1-yl) pyridin-3-yl)-8'-methyl-6'H, 8'H-spiro [cyclopropane-1, 7'-pyrimido [5, 4-b] [1, 4] oxazin]-2'-amine;

N-(5-methoxy-6-(4-methyl-1H-imidazol-1-yl) pyridin-3-yl)-7, 7, 8-trimethyl-7, 8-dihydro-6H-pyrimido [5, 4-b] [1, 4] oxazin-2-amine;

N-(3-methoxy-4-(1-methyl-1H-pyrazol-4-yl) phenyl)-8'-methyl-6'H, 8'H-spiro [cyclopentane-1, 7'-pyrimido [5, 4-b] [1, 4] oxazin]-2'-amine;

N-(3-methoxy-4-(4-methyl-1H-imidazol-1-yl) phenyl)-8'-methyl-2, 3, 5, 6-tetrahydro-6'H, 8'H-spiro [pyran-4, 7'-pyrimido [5, 4-b] [1, 4] oxazin]-2'-amine;

3, 3-difluoro-N-(3-methoxy-4-(4-methyl-1H-imidazol-1-yl) phenyl)-8'-methyl-6'H, 8'H-spiro [cyclobutane-1, 7'-pyrimido [5, 4-b] [1, 4] oxazin]-2'-amine;

N-(4-(4-chloro-1H-imidazol-1-yl)-3-methoxyphenyl)-3, 3-difluoro-8'-methyl-6'H, 8'H-spiro [cyclobutane-1, 7'-pyrimido [5, 4-b] [1, 4] oxazin]-2'-amine;

3, 3-difluoro-N-(5-methoxy-6-(4-methyl-1H-imidazol-1-yl) pyridin-3-yl)-8'-methyl-6'H, 8'H-spiro [cyclobutane-1, 7'-pyrimido [5, 4-b] [1, 4] oxazin]-2'-amine;

(+)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine;

(−)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine;

(−)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine;

(+)-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine;

(S)—N-(3-methoxy-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine;

(R)—N-(3-fluoro-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine;

(R)—N-(3-methoxy-4-(4-methyl-1H-imidazol-1-yl) phenyl)-6a-methyl-6a, 7, 8, 9-tetrahydro-6H-pyrimido [5, 4-b] pyrrolo [1, 2-d] [1, 4] oxazin-2-amine;

(S)-8, 8-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine;

(S)-8, 8-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine;

(R)-8, 8-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine;

(+)-7, 7-difluoro-N-(3-methoxy-4-(4-methyl-1H-imidazol-1-yl) phenyl)-6a, 7, 8, 9-tetrahydro-6H-pyrimido [5, 4-b] pyrrolo [1, 2-d] [1, 4] oxazin-2-amine; and (+)-7, 7-difluoro-N-(5-methoxy-6-(4-methyl-1H-imidazol-1-yl) pyridin-3-yl)-6a, 7, 8, 9-tetrahydro-6H-pyrimido [5, 4-b] pyrrolo [1, 2-d] [1, 4] oxazin-2-amine;

or a pharmaceutically acceptable salt thereof.

12. The compound of claim 11, selected from the group consisting of:

N-(3-methoxy-4-(4-methyl-1H-imidazol-1-yl) phenyl)-7, 7, 8-trimethyl-7, 8-dihydro-6H-pyrimido [5, 4-b] [1, 4] oxazin-2-amine;

N-(3-fluoro-4-(4-methyl-1H-imidazol-1-yl) phenyl)-7, 7, 8-trimethyl-7, 8-dihydro-6H-pyrimido [5, 4-b] [1, 4] oxazin-2-amine;

N-(3-methoxy-4-(4-methyl-1H-imidazol-1-yl) phenyl)-8'-methyl-6'H, 8'H-spiro [cyclopropane-1, 7'-pyrimido [5, 4-b] [1, 4] oxazin]-2'-amine; and 3, 3-difluoro-N-(3-methoxy-4-(4-methyl-1H-imidazol-1-yl) phenyl)-8'-methyl-6'H, 8'H-spiro [cyclobutane-1, 7'-pyrimido [5, 4-b] [1, 4] oxazin]-2'-amine;

or a pharmaceutically acceptable salt thereof.

13. A pharmaceutical composition comprising a pharmaceutically acceptable carrier or vehicle and an effective amount of a compound or a pharmaceutically acceptable salt of a compound of claim 1.

14. A method for treating a neurodegenerative disease, comprising administering to a subject in need thereof an effective amount of a compound or a pharmaceutically acceptable salt of a compound of claim 1.

15. The method of claim 14, wherein the neurodegenerative disease is panic disorder, obsessive compulsive disorder, delusional disorder, drug-induced psychosis, post-traumatic stress disorder, age-related cognitive decline, attention deficit/hyperactivity disorder, personality disorder of the paranoid type, personality disorder of the schizoid type, dyskinesia, choreiform condition, psychosis associated with Parkinson's disease, psychotic symptoms associated with Alzheimer's disease, mood disorder, or dementia.

16. A method for improving an impaired cognitive function, comprising administering to a subject having impaired cognitive function an effective amount of a compound or a pharmaceutically acceptable salt of claim 1.

17. A pharmaceutical composition comprising a pharmaceutically acceptable carrier or vehicle and an effective amount of a compound or a pharmaceutically acceptable salt of a compound of claim 8.

18. A method for treating a neurodegenerative disease, comprising administering to a subject in need thereof an effective amount of a compound or a pharmaceutically acceptable salt of a compound of claim 8.

19. The method of claim 17, wherein the neurodegenerative disease is panic disorder, obsessive compulsive disorder, delusional disorder, drug-induced psychosis, post-traumatic stress disorder, age-related cognitive decline, attention deficit/hyperactivity disorder, personality disorder of the paranoid type, personality disorder of the schizoid type, dyskinesia, choreiform condition, psychosis associated with Parkinson's disease, psychotic symptoms associated with Alzheimer's disease, mood disorder, or dementia.

20. A method for improving an impaired cognitive function, comprising administering to a subject having impaired cognitive function an effective amount of a compound or a pharmaceutically acceptable salt of a compound of claim 8.

* * * * *

UNITED STATES PATENT AND TRADEMARK OFFICE
CERTIFICATE OF CORRECTION

PATENT NO. : 9,771,378 B2
APPLICATION NO. : 15/210927
DATED : September 26, 2017
INVENTOR(S) : Duane A. Burnett, Matthew Gregory Bursavich and Andrew J. McRiner Page 1 of 1

It is certified that error appears in the above-identified patent and that said Letters Patent is hereby corrected as shown below:

In the Claims

Column 952, Line 30, Claim 6, please delete "-amine" and insert -- -amine; --;

Column 958, Line 5, Claim 9, please delete "one or more substituent independently" and insert -- one or more substituents independently -- therefor.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*